US009963746B2

(12) United States Patent
Park et al.

(10) Patent No.: US 9,963,746 B2
(45) Date of Patent: May 8, 2018

(54) COMPOSITION OR KIT FOR MAKING A PROGNOSIS OF LIVER CANCER, AND METHOD FOR MAKING A PROGNOSIS OF LIVER CANCER

(75) Inventors: Jin Young Park, Seoul (KR); Seok Joo Hong, Daejeon (KR); Jong Min Kim, Seoul (KR)

(73) Assignee: CBS BIOSCIENCES, CO., LTD. (KR)

( * ) Notice: Subject to any disclaimer, the term of this patent is extended or adjusted under 35 U.S.C. 154(b) by 794 days.

(21) Appl. No.: 13/823,718

(22) PCT Filed: Sep. 16, 2010

(86) PCT No.: PCT/KR2010/006357
§ 371 (c)(1),
(2), (4) Date: Sep. 23, 2013

(87) PCT Pub. No.: WO2012/036329
PCT Pub. Date: Mar. 22, 2012

(65) Prior Publication Data

US 2014/0162889 A1 Jun. 12, 2014

(51) Int. Cl.

| | |
|---|---|
| ***C12Q 1/68*** | (2006.01) |
| ***G01N 33/574*** | (2006.01) |
| ***C07K 16/18*** | (2006.01) |

(52) U.S. Cl.
CPC ............ *C12Q 1/6886* (2013.01); *C07K 16/18* (2013.01); *G01N 33/57438* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

FOREIGN PATENT DOCUMENTS

| | | |
|---|---|---|
| CN | 101509035 A | 8/2009 |
| KR | 100964193 B1 | 6/2010 |
| WO | 2009/147537 A2 | 12/2009 |

OTHER PUBLICATIONS

Määttä et al.; Differential expression of Matrix Metalloproteinase (MMP)-2, MMP-9, and Membrane Type 1-MMP in Hepatocellular and Pancreatic Adenocarcinoma: Implications for Tumor Progression and Clinical Prognosis; Clinical Cancer Research; vol. 6, 2726-2734, Jul. 2000.*

Wang et al., "Overexpression of aspartyl-(asparaginyl)-beta-hydroxylase in hepatocellular carcinoma is associated with worse surgical outcome," *Hepatology*, vol. 52(1), pp. 164-173 (Jul. 2010).

Zhang et al., "Prognosis evaluation in alpha-fetoprotein negative hepatocellular carcinoma after hepatectomy: comparison of five staging systems," *European Journal of Surgical Oncology*, vol. 36(8), pp. 718-724 (Jun. 9, 2010).

Xu et al., "Expression and prognostic significance of placental growth factor in hepatocellular carcinoma and peritumoral liver tissue," *International Journal of Cancer*, vol. 128(7), pp. 1559-1569 (Jun. 2, 2010).

Villanueva et al., "New strategies in hepatocellular carcinoma: genomic prognostic markers," *Clinical Cancer Research*, vol. 16(19), pp. 4688-4694 (Aug. 16, 2010).

Kim et al., "Expression of nicotinamide N-methyltransferase in hepatocellular carcinoma is associated with poor prognosis," *Journal of Experimental & Clinical Cancer Research*, vol. 28(20), pp. 1-9 (2009).

Kim et al., "Epithelial-mesenchymal transition gene signature to predict clinical outcome of hepatocellular carcinoma," *Cancer Science*, vol. 101(6), pp. 1521-1528 (2010).

Suzuki et al., "High mobility group box associated with cell proliferation appears to play an important role in hepatocellular carcinogenesis in rats and humans", Toxicology, vol. 255 (2009) pp. 160-170.

* cited by examiner

*Primary Examiner* — Antonio Galisteo Gonzalez
(74) *Attorney, Agent, or Firm* — Riverside Law LLP

(57) ABSTRACT

The present disclosure provides a marker for predicting prognosis of liver cancer, a composition or kit for predicting prognosis of liver cancer, preferably, a composition or kit for predicting prognosis of liver cancer for predicting the prognosis according to the stage of liver cancer. The marker, composition or kit, and method of the present disclosure make it possible to effectively predict prognosis of liver cancer, preferably, prognosis of liver cancer according to stage.

17 Claims, 106 Drawing Sheets

| Barcelona Clinic Liver Cancer(BCLC) staging Classification | | | | | | |
|---|---|---|---|---|---|---|
| Tumor stage | | | Tumor status | PST | Okuda stage | Liver function |
| very early HCC | 0 | | single <2cm (CIS) | 0 | I | No portal hypertension and normal bilirubin |
| early HCC | A | | | | | |
| | | A1 | single | 0 | I | No portal hypertension and normal bilirubin |
| | | A2 | single | 0 | I | portal hypertension and normal bilirubin |
| | | A3 | single | 0 | I | portal hypertension and abnormal bilirubin |
| | | A4 | 3 tumors, <3cm | 0 | I | Child-Pugh A-B |
| intermediate HCC | B | | large multinodular | 0 | I-II | Child-Pugh A-B |
| advanced HCC | C | | vascular invasion or extrahepatic spread | 1~2 | I-II | Child-Pugh A-B |
| end-stage HCC | D | | any | 3~4 | III | Child-Pugh C |

Fig. 1

SEQUENCE LISTING

```
<160> NUMBER OF SEQ ID NOS: 243

<210> SEQ ID NO 1
<211> LENGTH: 5166
<212> TYPE: DNA
<213> ORGANISM: Homo sapiens

<400> SEQUENCE: 1

aatgagcgct ccgggtctca gcggggtgga ggggttgcac tgcggtaata tggctcttcc      60

ttagccagcg gcggcaacgg cggcagcggc ggcagcggcg gcggctactg tctgggctga     120

gcagtagtgc ctctcgggtg gcgggtttct aggctgcagg ggcttggtag gtggtggcaa     180

gggggcggcg gcggatgccg gaagagtgcc cgcccccgccg cttggcggcc cctggatcga     240

gatgagcgcc tccgcgtcgg tcgggggccc cgtcccccag ccacccccgg gcccggccgc     300

tgctctgcct cccggttctg ccgcgcgggc cctgcatgtg gagctgccgt ctcagcagcg     360

gcgtcttcga catcttcgga acattgctgc ccggaacatt gttaatagaa atggccatca     420

gctccttgat acctacttta cacttcactt gtgtagtact gaaaagatat ataaagaatt     480

ttatagaagt gaagtgatta agaattcctt gaatcccacg tggcgaagtc tcgattttgg     540

aattatgcca gaccgtcttg atacatctgt gtcttgtttc gtggtgaaga tatggggtgg     600

aaaggagaac atctaccagc tgttgattga atggaaagtc tgtttggatg ggctgaaata     660
```

-continued

```
cttgggtcag cagattcatg cccgaaacca aaatgaaata atttttgggc tgaatgatgg    720
atactatggt gctccatttg aacataaggg ttattcaaat gctcagaaga ctattcttct    780
gcaggtggat cagaactgtg ttcgcaattc ttacgatgtc ttctctttgc tacggcttca    840
tagagcccag tgtgcaatta aacagactca ggtaactgtt cagaaaattg gaaaggaaat    900
tgaagaaaaa ctaagactca catctacaag caatgaactg aaaaaaaaaa gtgaatgcct    960
gcagttaaaa attttggtgc ttcagaatga actggaacgg cagaagaaag ctttgggacg   1020
ggaggtggca ttactgcata agcaacaaat tgcattacaa gacaaaggaa gtgcattttc   1080
agctgagcac ctcaaacttc aactccagaa ggaatcccta aatgagctga ggaaggagtg   1140
cactgcaaaa agagaactct tcttgaagac taatgctcag ttgacaattc gttgcaggca   1200
gttactctct gagctttcct acatttaccc tattgatttg aatgaacata aggattactt   1260
tgtatgcggt gtcaagttgc ctaattctga ggacttccaa gcaaaagatg atggaagcat   1320
tgctgttgcc cttggttata ctgcacatct ggtctccatg atttcctttt tcctacaagt   1380
gcccctcaga tatcctataa ttcataaggg gtctagatca acaatcaaag acaatatcaa   1440
tgacaaactg acggaaaagg agagagagtt tccactgtat ccaaaaggag gggagaagtt   1500
gcagtttgat tatggtgtct atcttctgaa caaaaatata gcacagctaa gatatcaaca   1560
tggactaggg actccagact tgcggcaaac ccttcccaac ctgaaaaact tcatggagca   1620
tggactaatg gtcaggtgtg acagacatca cacctccagt gcaatccctg ttcctaagag   1680
acaaagctcc atatttgggg gtgcagatgt aggcttctct ggggggatcc cttcaccaga   1740
caaaggacat cgaaaacggg ccagctctga gaatgagaga cttcagtaca aaacccctcc   1800
tcccagttac aactcagcat tagcccagcc tgtgaccacc gtcccctcca tgggagagac   1860
cgagagaaag ataacatctc tatcctcctc cttggatacc tccttggact tctccaaaga   1920
aaacaagaaa aaaggagagg atctagttgg cagcttaaac ggaggccacg cgaatgtgca   1980
ccctagccaa gaacaaggag aagccctctc cgggcaccgg gccacagtca atggcactct   2040
cctacccagc gagcaggccg ggtccgccag tgtccagctt ccaggcgagt tccacccagt   2100
ctcagaagct gagctctgct gtactgtgga gcaagcagaa gaaatcatcg ggctggaagc   2160
cacaggtttc gcctcaggtg atcagctaga agcatttaac tgcatcccag tggacagtgc   2220
tgtggcagta gagtgtgacg aacaagttct gggagaattt gaagagttct cccgaaggat   2280
ctatgcactg aatgaaaacg tatccagctt ccgccggccg cgcaggagtt ccgataagtg   2340
aagtgagcag gtcaacagta ggactggggc agaagctctg cctaaaatga agtgaaagct   2400
gcacttaacc ctttgtgata atgatgacac aaaatgaata ttaatggagg atattcctcg   2460
gaaaaacaga ctttgggaat gaaggaggga ctcaggatca ttgttatcag tgggccaaag   2520
ttagattttg ctttcaagat ttgcttttcg ggcctgatga ttttaaagca aaaatcaccc   2580
tctagttgaa agagcttaca gctcgagtca ccttttagct atttgtctgc tttttattta   2640
cccttgtatg ttatcctcag agggaagatg ataatatata aataatataa tgaacacacc   2700
cttagtttct cataagcatt tgccctcacc atggtttata aaactttggg aaaacggaat   2760
attcagaaat aggtttccgc catgtactga aaggtctgtg gccatctgtg aggtagatga   2820
agaagcagca tagtggtctc cttacatcta ggcctaactg tccctcttcc tgcccccggg   2880
taccacagtc cacctttaga ccctactgtc gccccatctt ctccgtggat gggccatgcg   2940
tcctgaaaac aggacatcag attcactggt tctgtaaccc agtagctgtg acgttccatc   3000
tcttctaacc agccatggcc ttcccctcct ctgccatacc cttaatgcgg ccctcagatt   3060
```

```
agatgaaaaa cttgctcctg gtggatccca agggaccctc aaggacctcg aggttactgc   3120
agtcagatgc catctcatcc cctgtggggg ccaaagtttt tatgtgggca gatgctgtgg   3180
tcaggaacta ggcatgcttt ctggcaatgc actcaccaga caaaaatccc ttgatgtaaa   3240
tcccatgtta atttattaaa tttcagtcag aaggtcagca tttacatgac agaatgtatg   3300
tagagagttg gggtgtctgg taggcaaact gcaaggcagt tgagatagtt ggattaagag   3360
gctagacgag acatagaata ctattggtat gtgtgcaatt tcatgaatat taaattatgt   3420
ttcgaagtcc agttgtcatt cccgcattca gatttcattt gctgttgctt tatacgttac   3480
gtacccaagg acattgcctc agggttgcaa actctttaaa ggaaaattta tccatatatc   3540
catgtattat atagaagaat aaaaattgag tttacttcac ccgacctgat tttttttac    3600
cagcttggaa attcctcttg aacctacgtc tccatatgtc acatcatgac aggactagcc   3660
tgaacaaaag ccatgtctat ctaagcggag gctgttgact tcattcagtt tgcatattgt   3720
atatagcaac acaaacactt gacaggtata tactccagtc gccacatttg tcctgcataa   3780
cagcttcact cacaggcctc accgtcactt tattttgtgt ccaagcattc ctgggctcaa   3840
gtttaatgta tagctacatt gttgttttcc atgtagagaa ctcacaggat gactacatca   3900
caaataaacc caactctcag gcagtcgaaa gctttaactg gatctgcaga agcccatctt   3960
cctccacatg aagaagtggg gctccttcac ctagagcagg agcttctctg cagtgtactg   4020
tctgtcgctc attttggagt cagtgtgggt ggagacagca tcgtggatat gcacgtgctg   4080
cggggccctc cagggaagta acatttacca aaaaaaaaga aaagttctga agggcagtgt   4140
taggattgca gaatggaagg tcaaccccgt gggacttacg attgccccag gtgcgggatg   4200
gacttaaatg tcacaccaaa ctcaaagtag gtacactggg ttgcagggca tccagcctgg   4260
cgctggcacc accaaggagc aggactcctc atgattacag tgtccatctc aggcccacac   4320
aaccatgaga gcctggactc tggggtctac ccgtcagtgc cccccaccgc tgtgcagact   4380
ccctggttga tcctgggctt gtggcttttc accgcacggc ggggagccct gctcttgaat   4440
gtcatcgggc tgctcagagc tgattgctag gtgcctacac atttgcctcg acccacacag   4500
ccccgtggtg atgcctcaaa acaccactta ggtttgggtt cgtttagttc gagtttgggg   4560
ttttcatttg aacttgtttg atgtctgcag tttctgccat gacctgggta gaacctatgg   4620
gattacccgt ctcctggaat aactgtttga cgttttccaa agttgtagag ttagtatggc   4680
ctctgtttaa agtggctggg gccaaaataa gggatgagtt attatctcct actaaccttt   4740
tagttttgta aatcactaag aaaattgttt gcttggaaga tataagttga attggaaact   4800
cattactatc tatttctgaa ctgctaagaa ccctttcagt tttcttacag ctgagacact   4860
tttaaacagc gggcaaatgt tatcaaatga atatttgatt gtgttttttc tcttcacttc   4920
cccttaacca ctttagaaat tccagagatt tttttcccct cagaatatta gttttggaag   4980
attgtgccca gctatatatt ttttagcagt tctaatggtg cccatttatc ctgacctaac   5040
cagttattta aataattttt taaaccacca cgaataataa atggcatgtg aaactgatct   5100
gttggtaact ggaagaaaac tcagcatctg tatttataca ataaaattga ttagtattta   5160
ttttga                                                              5166
```

<210> SEQ ID NO 2
<211> LENGTH: 4593
<212> TYPE: DNA
<213> ORGANISM: Homo sapiens

<400> SEQUENCE: 2

```
gctgccgcgc cccgcccttt ctcggccccc ggagggtgac ggggtgaagg cgggggaacc     60
gaggtgggga gtccgccaga gctcccagac tgcgagcacg cgagccgccg cagccgtcac    120
ccgcgccgcg tcacggctcc cgggcccgcc ctcctctgac ccctcccctc tctccgtttc    180
cccctctccc cctcctccgc cgaccgagca gtgacttaag caacggagcg cggtgaagct    240
catttttctc cttcctcgca gccgcgccag ggagctcgcg gcgcgcggcc cctgtcctcc    300
ggcccgagat gaatcctgcg gcagaagccg agttcaacat cctcctggcc accgactcct    360
acaaggttac tcactataaa caatatccac ccaacacaag caaagtttat tcctactttg    420
aatgccgtga aaagaagaca gaaaactcca aattaaggaa ggtgaaatat gaggaaacag    480
tattttatgg gttgcagtac attcttaata agtacttaaa aggtaaagta gtaaccaaag    540
agaaaatcca ggaagccaaa gatgtctaca aagaacattt ccaagatgat gtctttaatg    600
aaaagggatg gaactacatt cttgagaagt atgatgggca tcttccaata gaaataaaag    660
ctgttcctga gggctttgtc attcccagag gaaatgttct cttcacggtg gaaaacacag    720
atccagagtg ttactggctt acaaattgga ttgagactat tcttgttcag tcctggtatc    780
caatcacagt ggccacaaat tctagagagc agaagaaaat attggccaaa tatttgttag    840
aaacttctgg taacttagat ggtctggaat acaagttaca tgattttggc tacagaggag    900
tctcttccca agagactgct ggcataggag catctgctca cttggttaac ttcaaaggaa    960
cagatacagt agcaggactt gctctaatta aaaaatatta tggaacgaaa gatcctgttc   1020
caggctattc tgttccagca gcagaacaca gtaccataac agcttggggg aaagaccatg   1080
aaaaagatgc ttttgaacat attgtaacac agttttcatc agtgcctgta tctgtggtca   1140
gcgatagcta tgacatttat aatgcgtgtg agaaaatatg ggtgaagat ctaagacatt   1200
taatagtatc aagaagtaca caggcaccac taataatcag acctgattct ggaaaccctc   1260
ttgacactgt gttaaaggtt ttggagattt taggtaagaa gtttcctgtt actgagaact   1320
caaagggtta caagttgctg ccaccttatc ttagagttat tcaaggggat ggagtagata   1380
ttaatacctt acaagagatt gtagaaggca tgaaacaaaa aatgtggagt attgaaaata   1440
ttgccttcgg ttctggtgga ggtttgctac agaagttgac aagagatctc ttgaattgtt   1500
ccttcaagtg tagctatgtt gtaactaatg gccttgggat taacgtcttc aaggacccag   1560
ttgctgatcc caacaaaagg tccaaaaagg gccgattatc tttacatagg acgccagcag   1620
ggaattttgt tacactggag gaaggaaaag gagaccttga ggaatatggt caggatcttc   1680
tccatactgt cttcaagaat ggcaaggtga caaaaagcta ttcatttgat gaaataagaa   1740
aaaatgcaca gctgaatatt gaactggaag cagcacatca ttaggcttta tgactgggtg   1800
tgtgttgtgt gtatgtaata cataatgttt attgtacaga tgtgtggggt ttgtgtttta   1860
tgatacatta cagccaaatt atttgttggt ttatggacat actgcccttt catttttttt   1920
cttttccagt gtttaggtga tctcaaatta ggaaatgcat ttaaccatgt aaaagatgag   1980
tgctaaagta agctttttag ggccctttgc caataggtag tcattcaatc tggtattgat   2040
cttttcacaa ataacagaac tgagaaactt ttatatataa ctgatgatca cataaaacag   2100
atttgcataa aattaccatg attgctttat gtttatattt aacttgtatt tttgtacaaa   2160
caagattgtg taagatatat ttgaagtttc agtgatttaa cagtctttcc aacttttcat   2220
gatttttatg agcacagact ttcaagaaaa tacttgaaaa taaattacat tgccttttgt   2280
ccattaatca gcaaataaaa catggcctta acaaagttgt ttgtgttatt gtacaatttg   2340
```

```
aaaattatgt cgggacatac cctatagaat tactaacctt actgcccctt gtagaatatg   2400
tattaatcat tctacattaa agaaaataat ggttcttact ggaatgtcta ggcactgtac   2460
agttattata tatcttggtt gttgtattgt accagtgaaa tgccaaattt gaaaggcctg   2520
tactgcaatt ttatatgtca gagattgcct gtggctctaa tatgcacctc aagattttaa   2580
ggagataatg tttttagaga gaatttctgc ttccactata gaatatatac ataaatgtaa   2640
aatacttaca aaagtggaag tagtgtattt taaagtaatt acacttctga atttattttt   2700
catattctat agttggtatg acttaaatga attactggag tgggtagtga gtgtacttaa   2760
atgtttcaat tctgttatat tttttattaa gtttttaaaa aattaaattg gatattaaat   2820
tgtatggaca tcatttatta attttaaact gaatgccctc aataagtaat actgaagcac   2880
attcttaaat gaagataaat tatctccaat gaaaagcatg acatgtgttt caatagaaga   2940
atcttaagtt ggctaaattc aaagtgcttg acatcaaaat gttctagagt gattagctac   3000
tagattctga atcatacatc acatctgact agagaccagt ttctttcgaa tgattctttt   3060
atgtatgtag atctgttctt ctgaggcagc ggttggccaa ctatagccca aaggccaaat   3120
ttggacttct ttttataaat gcagattgtc tatggctgct ttcccactac tccagcctaa   3180
ggtaaacagc tgcaatagaa gccaaatgag aatcgcaaag cccaaaatgt ttattaacct   3240
gccctttaca caaaattaca caaaaagttt cctgatctct gttctaagaa aaggagtgtg   3300
ccttgcattt aaaaggaaat gttggtttct agggaaggga ggaggctaaa taattgatac   3360
ggaattttcc tcttttgtct tctttttttct cacttaagaa tccgatactg gaagactgat   3420
ttagaaaagt ttttaacatg acattaaatg tgaaatttta aaaattgaaa agccataaat   3480
catctgtttt aaatagttac atgagaaaat gatcactaga ataacctaat tagaagtgtt   3540
atcttcatta aatgtttttt gtaagtggta ttagaaagaa tatgtttttc agatggttct   3600
ttaaacatgt agtgagaaca ataagcatta ttcactttta gtaagtcttc tgtaatccat   3660
gatataaaat aattttaaaa tgattttttta atgtatttga gtaaagatga gtagtattaa   3720
gaaaaacaca catttcttca caaaatgtgc taaggggcgt gtaaagaatc aaaagaaact   3780
attaccaata atagttttga taatcaccca taattttgtg tttaaacatt gaaattatag   3840
tacagacagt attctctgtg ttctgtgaat ttcagcagct tcagaataga gtttaattta   3900
gaaatttgca gtgaaaaaag ctatctcttt gttcacaacc ataaatcagg agatggagat   3960
taattctatt ggctcttagt cacttggaac tgattaattc tgactttctg tcactaagca   4020
cttggtattt ggccatctcc attctgagca ccaaacggtt aacacgaatg tccactagaa   4080
ctctgctgtg tgtcaccctt aaatcagtct aaatcttcca gacaaaagca aatggcattt   4140
atggatttaa gtcattagat tttcaactga cattaattaa tccctcttga ttgattatat   4200
catcaagtat ttatatctta aataggaggt aggatttctg tgttaagact cttatttgta   4260
ccctataatt aaagtaaaat gtttttttatg agtatccctt gttttccctt cttaaattgt   4320
tatcaaacaa tttttataat gaaatctatc ttggaaaatt agaaagaaaa atggcaaggt   4380
atttattgtt ctgtttgcca taatttagaa ctcacactta agtattttgt agttttacat   4440
tcctttttaa cccattcagt ggagaatgtc agcttttctc ccaagttgta tgttaagtct   4500
attctaatat gtactcaaca tcaagttata aacatgtaat aaacatggaa ataaagttta   4560
gctctattag tgaagtgtta aaaaaaaaaa aaa                               4593
```

<210> SEQ ID NO 3

<211> LENGTH: 4953
<212> TYPE: DNA
<213> ORGANISM: Homo sapiens

<400> SEQUENCE: 3
ggtttccgga gctgcggcgg cgcagactgg gagggggagc cgggggttcc gacgtcgcag 60
ccgagggaac aagccccaac cggatcctgg acaggcaccc cggcttggcg ctgtctctcc 120
ccctcggctc ggagaggccc ttcggcctga gggagcctcg ccgcccgtcc ccggcacacg 180
cgcagccccg gcctctcggc ctctgccgga gaaacaggat ggcccaatgg aatcagctac 240
agcagcttga cacacggtac ctggagcagc tccatcagct ctacagtgac agcttcccaa 300
tggagctgcg gcagtttctg gccccttgga ttgagagtca agattgggca tatgcggcca 360
gcaaagaatc acatgccact ttggtgtttc ataatctcct gggagagatt gaccagcagt 420
atagccgctt cctgcaagag tcgaatgttc tctatcagca caatctacga agaatcaagc 480
agtttcttca gagcaggtat cttgagaagc caatggagat tgcccggatt gtggcccggt 540
gcctgtggga agaatcacgc cttctacaga ctgcagccac tgcggcccag caagggggcc 600
aggccaacca ccccacagca gccgtggtga cggagaagca gcagatgctg gagcagcacc 660
ttcaggatgt ccggaagaga gtgcaggatc tagaacagaa aatgaaagtg gtagagaatc 720
tccaggatga ctttgatttc aactataaaa ccctcaagag tcaaggagac atgcaagatc 780
tgaatggaaa caaccagtca gtgaccaggc agaagatgca gcagctggaa cagatgctca 840
ctgcgctgga ccagatgcgg agaagcatcg tgagtgagct ggcggggctt ttgtcagcga 900
tggagtacgt gcagaaaact ctcacggacg aggagctggc tgactggaag aggcggcaac 960
agattgcctg cattggaggc ccgcccaaca tctgcctaga tcggctagaa aactggataa 1020
cgtcattagc agaatctcaa cttcagaccc gtcaacaaat taagaaactg gaggagttgc 1080
agcaaaaagt ttcctacaaa ggggacccca ttgtacagca ccggccgatg ctggaggaga 1140
gaatcgtgga gctgtttaga aacttaatga aaagtgcctt tgtggtggag cggcagccct 1200
gcatgcccat gcatcctgac cggcccctcg tcatcaagac cggcgtccag ttcactacta 1260
aagtcaggtt gctggtcaaa ttccctgagt tgaattatca gcttaaaatt aaagtgtgca 1320
ttgacaaaga ctctggggac gttgcagctc tcagaggatc ccggaaattt aacattctgg 1380
gcacaaacac aaaagtgatg aacatggaag aatccaacaa cggcagcctc tctgcagaat 1440
tcaaacactt gaccctgagg gagcagagat gtgggaatgg gggccgagcc aattgtgatg 1500
cttccctgat tgtgactgag gagctgcacc tgatcacctt tgagaccgag gtgtatcacc 1560
aaggcctcaa gattgaccta gagacccact ccttgccagt tgtggtgatc tccaacatct 1620
gtcagatgcc aaatgcctgg gcgtccatcc tgtggtacaa catgctgacc aacaatccca 1680
agaatgtaaa ctttttttacc aagcccccaa ttggaacctg ggatcaagtg gccgaggtcc 1740
tgagctggca gttctcctcc accaccaagc gaggactgag catcgagcag ctgactacac 1800
tggcagagaa actcttggga cctggtgtga attattcagg gtgtcagatc acatgggcta 1860
aattttgcaa agaaaacatg gctggcaagg gcttctcctt ctgggtctgg ctggacaata 1920
tcattgacct tgtgaaaaag tacatcctgg ccctttggaa cgaagggtac atcatgggct 1980
ttatcagtaa ggagcgggag cgggccatct tgagcactaa gcctccaggc accttcctgc 2040
taagattcag tgaaagcagc aaagaaggag gcgtcacttt cacttgggtg gagaaggaca 2100
tcagcggtaa gacccagatc cagtccgtgg aaccatacac aaagcagcag ctgaacaaca 2160
tgtcatttgc tgaaatcatc atgggctata agatcatgga tgctaccaat atcctggtgt 2220
ctccactggt ctatctctat cctgacattc ccaaggagga ggcattcgga aagtattgtc 2280
ggccagagag ccaggagcat cctgaagctg acccaggcgc tgccccatac ctgaagacca 2340
agtttatctg tgtgacacca acgacctgca gcaataccat tgacctgccg atgtccccc 2400 gcactttaga ttcattgatg cagtttggaa ataatggtga aggtgctgaa ccctcagcag 2460
gagggcagtt tgagtccctc acctttgaca tggagttgac ctcggagtgc gctacctccc 2520
ccatgtgagg agctgagaac ggaagctgca gaaagatacg actgaggcgc ctacctgcat 2580
tctgccaccc ctcacacagc caaaccccag atcatctgaa actactaact ttgtggttcc 2640
agattttttt taatctccta cttctgctat ctttgagcaa tctgggcact tttaaaaata 2700
gagaaatgag tgaatgtggg tgatctgctt ttatctaaat gcaaataagg atgtgttctc 2760
tgagacccat gatcagggga tgtggcgggg ggtggctaga gggagaaaaa ggaaatgtct 2820
tgtgttgttt tgttcccctg ccctcctttc tcagcagctt tttgttattg ttgttgttgt 2880
tcttagacaa gtgcctcctg gtgcctgcgg catccttctg cctgtttctg taagcaaatg 2940
ccacaggcca cctatagcta catactcctg gcattgcact ttttaacctt gctgacatcc 3000
aaatagaaga taggactatc taagccctag gtttcttttt aaattaagaa ataataacaa 3060
ttaaagggca aaaaacactg tatcagcata gcctttctgt atttaagaaa cttaagcagc 3120
cgggcatggt ggctcacgcc tgtaatccca gcactttggg aggccgaggc ggatcataag 3180
gtcaggagat caagaccatc ctggctaaca cggtgaaacc ccgtctctac taaaagtaca 3240
aaaaattagc tgggtgtggt ggtgggcgcc tgtagtccca gctactcggg aggctgaggc 3300
aggagaatcg cttgaacctg agaggcggag gttgcagtga gccaaaattg caccactgca 3360
cactgcactc catcctgggc gacagtctga gactctgtct caaaaaaaaa aaaaaaaaaa 3420
agaaacttca gttaacagcc tccttggtgc tttaagcatt cagcttcctt caggctggta 3480
atttatataa tccctgaaac gggcttcagg tcaaaccctt aagacatctg aagctgcaac 3540
ctggcctttg gtgttgaaat aggaaggttt aaggagaatc taagcatttt agactttttt 3600
ttataaatag acttattttc ctttgtaatg tattggcctt ttagtgagta aggctgggca 3660
gagggtgctt acaaccttga ctccctttct ccctggactt gatctgctgt ttcagaggct 3720
aggttgtttc tgtgggtgcc ttatcagggc tgggatactt ctgattctgg cttccttcct 3780
gccccaccct cccgacccca gtccccctga tcctgctaga ggcatgtctc cttgcgtgtc 3840
taaaggtccc tcatcctgtt tgttttagga atcctggtct caggacctca tggaagaaga 3900
gggggagaga gttacaggtt ggacatgatg cacactatgg ggccccagcg acgtgtctgg 3960
ttgagctcag ggaatatggt tcttagccag tttcttggtg atatccagtg gcacttgtaa 4020
tggcgtcttc attcagttca tgcagggcaa aggcttactg ataaacttga gtctgccctc 4080
gtatgagggt gtatacctgg cctccctctg aggctggtga ctcctccctg ctggggcccc 4140
acaggtgagg cagaacagct agagggcctc cccgcctgcc cgccttggct ggctagctcg 4200
cctctcctgt gcgtatggga acacctagca cgtgctggat gggctgcctc tgactcagag 4260
gcatggccgg atttggcaac tcaaaaccac cttgcctcag ctgatcagag tttctgtgga 4320
attctgtttg ttaaatcaaa ttagctggtc tctgaattaa gggggagacg accttctcta 4380
agatgaacag ggttcgcccc agtcctcctg cctggagaca gttgatgtgt catgcagagc 4440
tcttacttct ccagcaacac tcttcagtac ataataagct taactgataa acagaatatt 4500
tagaaaggtg agacttgggc ttaccattgg gtttaaatca tagggaccta gggcgagggt 4560

-continued

```
tcagggcttc tctggagcag atattgtcaa gttcatggcc ttaggtagca tgtatctggt   4620

cttaactctg attgtagcaa aagttctgag aggagctgag ccctgttgtg gcccattaaa   4680

gaacagggtc ctcaggccct gcccgcttcc tgtccactgc cccctcccca tccccagccc   4740

agccgaggga atcccgtggg ttgcttacct acctataagg tggtttataa gctgctgtcc   4800

tggccactgc attcaaattc caatgtgtac ttcatagtgt aaaaatttat attattgtga   4860

ggttttttgt cttttttttt ttttttttt tttggtatat tgctgtatct actttaactt   4920

ccagaaataa acgttatata ggaaccgtaa aaa                              4953
```

<210> SEQ ID NO 4
<211> LENGTH: 5243
<212> TYPE: DNA
<213> ORGANISM: Homo sapiens

<400> SEQUENCE: 4

```
agcgtgagac tcgcgccctc cggcacggaa aaggccaggc gacaggtgtc gcttgaaaag     60

actgggcttg tccttgctgg tgcatgcgtc gtcggcctct gggcagcagg tttacaaagg    120

aggaaaacga cttcttctag attttttttt cagtttcttc tataaatcaa aacatctcaa    180

aatggagacc taaaatcctt aaagggactt agtctaatct cgggaggtag ttttgtgcat    240

gggtaaacaa attaagtatt aactggtgtt ttactatcca aagaatgcta attttataaa    300

catgatcgag ttatataagg tataccataa tgagtttgat tttgaatttg atttgtggaa    360

ataaaggaaa agtgattcta gctggggcat attgttaaag cattttttttc agagttggcc    420

aggcagtctc ctactggcac attctcccat tatgtagaat agaaatagta cctgtgtttg    480

ggaaagattt taaaatgagt gacagttatt tggaacaaag agctaataat caatccactg    540

caaattaaag aaacatgcag atgaaagttt tgacacatta aaatacttct acagtgacaa    600

agaaaaatca agaacaaagc tttttgatat gtgcaacaaa tttagaggaa gtaaaaagat    660

aaatgtgatg attggtcaag aaattatcca gttatttaca aggccactga tattttaaac    720

gtccaaaagt ttgtttaaat gggctgttac cgctgagaat gatgaggatg agaatgatgg    780

ttgaaggtta cattttagga aatgaagaaa cttagaaaat taatataaag acagtgatga    840

atacaaagaa gatttttata acaatgtgta aaatttttgg ccagggaaag gaatattgaa    900

gttagataca attacttacc tttgagggaa ataattgttg gtaatgagat gtgatgtttc    960

tcctgccacc tggaaacaaa gcattgaagt ctgcagttga aaagcccaac gtctgtgaga   1020

tccaggaaac catgcttgca aaccactggt aaaaaaaaaa aaaaaaaaaa aaaaaagcca   1080

cagtgacttg cttattggtc attgctagta ttatcgactc agaacctctt tactaatggc   1140

tagtaaatca taattgagaa attctgaatt ttgacaaggt ctctgctgtt gaaatggtaa   1200

atttattatt ttttttgtca tgataaattc tggttcaagg tatgctatcc atgaaataat   1260

ttctgaccaa aactaaattg atgcaatttg attatccatc ttagcctaca gatggcatct   1320

ggtaactttt gactgtttta aaaaataaat ccactatcag agtagatttg atgttggctt   1380

cagaaacatt tagaaaaaca aaagttcaaa aatgttttca ggaggtgata agttgaataa   1440

ctctacaatg ttagttcttt gagggggaca aaaaatttaa aatctttgaa aggtcttatt   1500

ttacagccat atctaaatta tcttaagaaa atttttaaca aagggaatga aatatatatc   1560

atgattctgt tttccaaaa gtaacctgaa tatagcaatg aagttcagtt ttgttattgg   1620

tagtttgggc agagtctctt tttgcagcac ctgttgtcta ccataattac agaggacatt   1680

tccatgttct agccaagtat actattagaa taaaaaaact taacattgag ttgcttcaac   1740
```

-continued

```
agcatgaaac tgagtccaaa agaccaaatg aacaaacaca ttaatctctg attatttatt   1800
ttaaatagaa tatttaattg tgtaagatct aatagtatca ttatacttaa gcaatcatat   1860
tcctgatgat ctatgggaaa taactattat ttaattaata ttgaaaccag gttttaagat   1920
gtgttagcca gtcctgttac tagtaaatct ctttatttgg agagaaattt tagattgttt   1980
tgttctcctt attagaagga ttgtagaaag aaaaaaatga ctaattggag aaaaattggg   2040
gatatatcat atttcactga attcaaaatg tcttcagttg taaatcttac cattatttta   2100
cgtacctcta agaaataaaa gtgcttctaa ttaaaatatg atgtcattaa ttatgaaata   2160
cttcttgata acagaagttt taaaatagcc atcttagaat cagtgaaata tggtaatgta   2220
ttattttcct cctttgagtt aggtcttgtg ctttttttc ctggccacta aatttcacaa   2280
tttccaaaaa gcaaaataaa catattctga atatttttgc tgtgaaacac ttgacagcag   2340
agctttccac catgaaaaga agcttcatga gtcacacatt acatctttgg gttgattgaa   2400
tgccactgaa acattctagt agcctggaga agttgaccta cctgtggaga tgcctgccat   2460
taaatggcat cctgatggct taatacacat cactcttctg tgaagggttt taattttcaa   2520
cacagcttac tctgtagcat catgtttaca ttgtatgtat aaagattata caaaggtgca   2580
attgtgtatt tcttccttaa aatgtatcag tataggattt agaatctcca tgttgaaact   2640
ctaaatgcat agaaataaaa ataataaaaa atttttcatt ttggcttttc agcctagtat   2700
taaaactgat aaaagcaaag ccatgcacaa aactacctcc ctagagaaag gctagtccct   2760
tttcttcccc attcatttca ttatgaacat agtagaaaac agcatattct tatcaaattt   2820
gatgaaaagc gccaacacgt ttgaactgaa atacgacttg tcatgtgaac tgtaccgaat   2880
gtctacgtat tccacttttc ctgctggggt tcctgtctca gaaaggagtc ttgctcgtgc   2940
tggtttctat tacactggtg tgaatgacaa ggtcaaatgc ttctgttgtg gcctgatgct   3000
ggataactgg aaaagaggag acagtcctac tgaaaagcat aaaaagttgt atcctagctg   3060
cagattcgtt cagagtctaa attccgttaa caacttggaa gctacctctc agcctacttt   3120
tccttcttca gtaacaaatt ccacacactc attacttccg ggtacagaaa acagtggata   3180
tttccgtggc tcttattcaa actctccatc aaatcctgta aactccagag caaatcaaga   3240
tttttctgcc ttgatgagaa gttcctacca ctgtgcaatg aataacgaaa atgccagatt   3300
acttactttt cagacatggc cattgacttt tctgtcgcca acagatctgg caaaagcagg   3360
cttttactac ataggacctg gagacagagt ggcttgcttt gcctgtggtg gaaaattgag   3420
caattgggaa ccgaaggata atgctatgtc agaacacctg agacattttc ccaaatgccc   3480
atttatagaa aatcagcttc aagacacttc aagatacaca gtttctaatc tgagcatgca   3540
gacacatgca gcccgcttta aacattcttt taactggccc tctagtgttc tagttaatcc   3600
tgagcagctt gcaagtgcgg gtttttatta tgtgggtaac agtgatgatg tcaaatgctt   3660
ttgctgtgat ggtggactca ggtgttggga atctggagat gatccatggg ttcaacatgc   3720
caagtggttt ccaaggtgtg agtacttgat aagaattaaa ggacaggagt tcatccgtca   3780
agttcaagcc agttaccctc atctacttga acagctgcta tccacatcag acagcccagg   3840
agatgaaaat gcagagtcat caattatcca ttttgaacct ggagaagacc attcagaaga   3900
tgcaatcatg atgaatactc ctgtgattaa tgctgccgtg gaaatgggct ttagtagaag   3960
cctggtaaaa cagacagttc agagaaaaat cctagcaact ggagagaatt atagactagt   4020
caatgatctt gtgttagact tactcaatgc agaagatgaa ataagggaag aggagagaga   4080
```

aagagcaact gaggaaaaag aatcaaatga tttattatta atccggaaga atagaatggc 4140
actttttcaa catttgactt gtgtaattcc aatcctggat agtctactaa ctgccggaat 4200
tattaatgaa caagaacatg atgttattaa acagaagaca cagacgtctt tacaagcaag 4260
agaactgatt gatacgattt tagtaaaagg aaatattgca gccactgtat tcagaaactc 4320
tctgcaagaa gctgaagctg tgttatatga gcatttattt gtgcaacagg acataaaata 4380
tattcccaca gaagatgttt cagatctacc agtggaagaa caattgcgga gactacaaga 4440
agaaagaaca tgtaaagtgt gtatggacaa agaagtgtcc atagtgttta ttccttgtgg 4500
tcatctagta gtatgcaaag attgtgctcc ttctttaaga aagtgtccta tttgtaggag 4560
tacaatcaag ggtacagttc gtacatttct ttcatgaaga agaaccaaaa catcgtctaa 4620
actttagaat taatttatta aatgtattat aactttaact tttatcctaa tttggtttcc 4680
ttaaaatttt tatttattta caactcaaaa aacattgttt tgtgtaacat atttatatat 4740
gtatctaaac catatgaaca tatatttttt agaaactaag agaatgatag gcttttgttc 4800
ttatgaacga aaaagaggta gcactacaaa cacaatattc aatcaaaatt tcagcattat 4860
tgaaattgta agtgaagtaa aacttaagat atttgagtta acctttaaga attttaaata 4920
ttttggcatt gtactaatac cgggaacatg aagccaggtg tggtggtatg tgcctgtagt 4980
cccaggctga ggcaagagaa ttacttgagc ccaggagttt gaatccatcc tgggcagcat 5040
actgagaccc tgcctttaaa aacaaacaga acaaaaacaa aacaccaggg acacatttct 5100
ctgtcttttt tgatcagtgt cctatacatc gaaggtgtgc atatatgttg aatgacattt 5160
tagggacatg gtgtttttat aaagaattct gtgagaaaaa atttaataaa gcaacaaaaa 5220
ttactcttaa aaaaaaaaaa aaa 5243

<210> SEQ ID NO 5
<211> LENGTH: 3796
<212> TYPE: DNA
<213> ORGANISM: Homo sapiens

<400> SEQUENCE: 5
ctggtctggc cggcgacgcg cgtgccctgt ggccaaacac tgcctggagt gagagcaaac 60
taccagcgca gtggggccgg cgcgagtgtg cgtgtgtgtg cgtgtgtgtg tgcgagcgcg 120
gtggaggggg gggaccaact gcttcacact ttcaacactg cactgaagag ggagagcgag 180
agagagactg gagacgcaca gatcccccca aggtctccca agcctaccgt cccacagatt 240
attgtacaga gccccaaaaa tcgaaacaga ggaaacgaac agcagttgaa catggacgaa 300
ggaattcctc atttgcaaga gagacagtta ctggaacata gagattttat aggactggac 360
tattcctctt tgtatatgtg taaacccaaa aggagcatga aacgagacga caccaaggat 420
acctacaaat taccgcacag attaatagaa aagaaaagaa gagaccgaat taatgaatgc 480
attgctcagc tgaaagattt actgcctgaa catctgaaat tgacaactct gggacatctg 540
gagaaagctg tagtcttgga attaactttg aaacacttaa aagctttaac cgccttaacc 600
gagcaacagc atcagaagat aattgcttta cagaatgggg agcgatctct gaaatcgccc 660
attcagtccg acttggatgc gttccactcg ggatttcaaa catgcgccaa agaagtcttg 720
caatacctct cccggtttga gagctggaca cccagggagc cgcggtgtgt ccagctgatc 780
aaccacttgc acgccgtggc cacccagttc ttgcccaccc cgcagctgtt gactcaacag 840
gtccctctga gcaaaggcac cggcgctccc tcggccgccg ggtccgcggc cgccccctgc 900
ctggagcgcg cggggcagaa gctggagccc ctcgcctact gcgtgcccgt catccagcgg 960

```
actcagccca gcgccgagct cgccgccgag aacgacacgg acaccgacag cggctacggc   1020
ggcgaagccg aggcccggcc ggaccgcgag aaaggcaaag gcgcgggggc gagccgcgtc   1080
accatcaagc aggagcctcc cggggaggac tcgccggcgc ccaagaggat gaagctggat   1140
tcccgcggcg gcggcagcgg cggcggcccg gggggcggcg cggcggcggc ggcagccgcg   1200
cttctggggc ccgaccctgc cgccgcggcc gcgctgctga gacccgacgc cgccctgctc   1260
agctcgctgg tggcgttcgg cggaggcgga ggcgcgccct tcccgcagcc cgcggccgcc   1320
gcggccccct tctgcctgcc cttctgcttc ctctcgcctt ctgcagctgc cgcctacgtg   1380
cagcccttcc tggacaagag cggcctggag aagtatctgt acccggcggc ggctgccgcc   1440
ccgttcccgc tgctataccc cggcatcccc gccccggcgg cagccgcggc agccgccgcc   1500
gccgctgccg ccgccgccgc cgcgttcccc tgcctgtcct cggtgttgtc gccccctccc   1560
gagaaggcgg gcgccgccgc cgcgaccctc ctgccgcacg aggtggcgcc ccttggggcg   1620
ccgcaccccc agcacccgca cggccgcacc cacctgccct tcgccgggcc ccgcgagccg   1680
gggaacccgg agagctctgc tcaggaagat ccctcgcagc caggaaagga agctccctga   1740
atccttgcgt cccgaaggac ggaggttcaa gcagagtgag aagttaaaat acccttaagg   1800
aggttcaagc agagtgagaa gttaaaatac ccttaaggtc tttaagggag gaagtgtaat   1860
agatgcacga caggcataaa caagaacaac aaaacaggtg ttatgtgtac attcggagtt   1920
cctgttttgc tcatcccgca ccaccccacc ctccacacac taacatccct ttcttccccc   1980
caccagctgt aaaagatcct atgcgaaaga cactggctct ttttttaat cccccaaata   2040
aattttgccc ccttttaggc catgttccat tatctcttaa aattggaacc taattcgaga   2100
ggaagtaaga agggtctgtt ctgtggctga gctaggtgaa ccccggggta ggggaaagat   2160
gttaacacct ttgacgtctt tggagttgac atggaacagc aggtagttgt tatgtagagc   2220
tagttctcaa agctgccctg cctgttttag gaggcgttcc acaaacagat tgaggctctt   2280
ttagaattga atttactctt cagtattttc taatgttcag ctttctaaaa ggcatatatt   2340
tttcaaagaa gtgaggatgc agtttctcac gttgcaacct attctgaagt ggtttaaatg   2400
gtatctctta gtaacttgca ctcgttaaag aaacacggag ctgggccatc gtcagaacta   2460
agtcagggaa ggagatggat gagaaggcca gaatcattcc tagtacattt gctaacactt   2520
tattgagaaa ttgaccatga attaatggac tcatcttaat ttcttctaag tccatatata   2580
gatagatatc tatctgtaca gatttctatt tatccataga taggtatcta tacatacaca   2640
tctcaagtgc atctattccc actctcatta atccatcatg ttcctaaatt tttgtaatct   2700
tactgtaaaa aaaagtgcac tgaacttcaa aacaaaacaa aaaacaacaa caacaaaaaa   2760
caagtccaaa ctgatatatc ctatattctg ttaaaattca aaagtgaacg aaagcattta   2820
actggccagt tttgattgca aatgctgtaa agatatagaa tgaagtcctg tgaggccttc   2880
ctatctccaa gtctatgtat tttctggaga ccaaaccaga taccagataa tcacaaagaa   2940
agctttttta ataaggctta aaccaagacc ttgtctagat atttttagtt tgttgccaag   3000
gtagcactgt gagaaatctc acttggatgt tatgtaaggg gtgagacaca acagtctgac   3060
tatgagtgag gaaaatatct gggtcttttc gtcagtttgg tgcatttgct gctgctgttg   3120
ctactgtttg cctcaaacgc tgtgtttaaa caacgttaaa ctcttagcct acaaggtggc   3180
tcttatgtac atagttgtta atacatccaa ttaatgatgt ctgacatgct atttttgtag   3240
ggagaaaata tgtgctaatg atattttgag ttaaaatatc ttttggggag gatttgctga   3300
```

-continued

```
aaagttgcac ttttgttaca atgcttatgc ttggtacaag cttatgctgt cttaaattat   3360

tttaaaaaaa taaatactgt ctgtgagaaa ccagctggtt tagaaaagtt tagtatgtga   3420

cgataaacta gaaattacct ttatattcta gtattttcag cactccataa attctattac   3480

ctaaatattg ccacactatt ttgtgattta aaaattctta ctaaggaata aaaactttaa   3540

tatacgatat gatattgtct aataattaaa aaagacataa tggatgctca attagtttta   3600

agatatctat aactataggg atacaaatca ctacagttct cagatttaca gcttttttt   3660

gtcattggct tgatgtcaca catttccaat ctcttgcaag cctccaggct ctggctttgt   3720

ctacctgctc gttcccaatg tatcttaatg aaaagtgcaa aagaaaaacc taccaattaa   3780

aaaaaaaaaa aaaaaa                                                  3796


<210> SEQ ID NO 6
<211> LENGTH: 3549
<212> TYPE: DNA
<213> ORGANISM: Homo sapiens

<400> SEQUENCE: 6

acatctggcg gctgccctcc cttgtttccg ctgcatccag acttcctcag gcggtggctg     60

gaggctgcgc atctggggct ttaaacatac aaagggattg ccaggacctg cggcggcggc    120

ggcggcggcg ggggctgggg cgcgggggcc ggaccatgag ccgctgagcc gggcaaaccc    180

caggccaccg agccagcgga ccctcggagc gcagccctgc gccgcggagc aggctccaac    240

caggcggcga ggcggccaca cgcaccgagc cagcgacccc cgggcgacgc gcggggccag    300

ggagcgctac gatggaggcg ctaatggccc ggggcgcgct cacgggtccc ctgagggcgc    360

tctgtctcct gggctgcctg ctgagccacg ccgccgccgc gccgtcgccc atcatcaagt    420

tccccggcga tgtcgccccc aaaacggaca aagagttggc agtgcaatac ctgaacacct    480

tctatggctg ccccaaggag agctgcaacc tgtttgtgct gaaggacaca ctaaagaaga    540

tgcagaagtt ctttggactg ccccagacag gtgatcttga ccagaatacc atcgagacca    600

tgcggaagcc acgctgcggc aacccagatg tggccaacta caacttcttc cctcgcaagc    660

ccaagtggga caagaaccag atcacataca ggatcattgg ctacacacct gatctggacc    720

cagagacagt ggatgatgcc tttgctcgtg ccttccaagt ctggagcgat gtgaccccac    780

tgcggttttc tcgaatccat gatggagagg cagacatcat gatcaacttt ggccgctggg    840

agcatggcga tggatacccc tttgacggta aggacggact cctggctcat gccttcgccc    900

caggcactgg tgttggggga gactcccatt ttgatgacga tgagctatgg accttgggag    960

aaggccaagt ggtccgtgtg aagtatggga acgccgatgg ggagtactgc aagttcccct   1020

tcttgttcaa tggcaaggag tacaacagct gcactgatac cggccgcagc gatggcttcc   1080

tctggtgctc caccacctac aactttgaga aggatggcaa gtacggcttc tgtccccatg   1140

aagccctgtt caccatgggc ggcaacgctg aaggacagcc ctgcaagttt ccattccgct   1200

tccagggcac atcctatgac agctgcacca ctgagggccg cacggatggc taccgctggt   1260

gcggcaccac tgaggactac gaccgcgaca agaagtatgg cttctgccct gagaccgcca   1320

tgtccactgt tggtgggaac tcagaaggtg ccccctgtgt cttccccttc actttcctgg   1380

gcaacaaata tgagagctgc accagcgccg gccgcagtga cggaaagatg tggtgtgcga   1440

ccacagccaa ctacgatgat gaccgcaagt ggggcttctg ccctgaccaa gggtacagcc   1500

tgttcctcgt ggcagcccac gagtttggcc acgccatggg gctggagcac tcccaagacc   1560

ctggggccct gatggcaccc atttacacct acaccaagaa cttccgtctg tcccaggatg   1620
```

acatcaaggg cattcaggag ctctatgggg cctctcctga cattgacctt ggcaccggcc 1680
ccacccccac gctgggccct gtcactcctg agatctgcaa acaggacatt gtatttgatg 1740
gcatcgctca gatccgtggt gagatcttct tcttcaagga ccggttcatt tggcggactg 1800
tgacgccacg tgacaagccc atggggcccc tgctggtggc cacattctgg cctgagctcc 1860
cggaaaagat tgatgcggta tacgaggccc cacaggagga gaaggctgtg ttctttgcag 1920
ggaatgaata ctggatctac tcagccagca ccctggagcg agggtacccc aagccactga 1980
ccagcctggg actgccccct gatgtccagc gagtggatgc cgcctttaac tggagcaaaa 2040
acaagaagac atacatcttt gctggagaca aattctggag atacaatgag gtgaagaaga 2100
aaatggatcc tggcttcccc aagctcatcg cagatgcctg gaatgccatc cccgataacc 2160
tggatgccgt cgtggacctg cagggcggcg gtcacagcta cttcttcaag ggtgcctatt 2220
acctgaagct ggagaaccaa agtctgaaga gcgtgaagtt tggaagcatc aaatccgact 2280
ggctaggctg ctgagctggc cctggctccc acaggccctt cctctccact gccttcgata 2340
caccgggcct ggagaactag agaaggaccc ggaggggcct ggcagccgtg ccttcagctc 2400
tacagctaat cagcattctc actcctacct ggtaatttaa gattccagag agtggctcct 2460
cccggtgccc aagaatagat gctgactgta ctcctcccag gcgccccttc cccctccaat 2520
cccaccaacc ctcagagcca ccccctaaaga gatactttga tattttcaac gcagccctgc 2580
tttgggctgc cctggtgctg ccacacttca ggctcttctc ctttcacaac cttctgtggc 2640
tcacagaacc cttggagcca atggagactg tctcaagagg gcactggtgg cccgacagcc 2700
tggcacaggg cagtgggaca gggcatggcc aggtggccac tccagacccc tggcttttca 2760
ctgctggctg ccttagaacc tttcttacat tagcagtttg ctttgtatgc actttgtttt 2820
tttctttggg tcttgttttt tttttccact tagaaattgc atttcctgac agaaggactc 2880
aggttgtctg aagtcactgc acagtgcatc tcagcccaca tagtgatggt tcccctgttc 2940
actctactta gcatgtccct accgagtctc ttctccactg gatggaggaa aaccaagccg 3000
tggcttcccg ctcagccctc cctgcccctc ccttcaacca ttccccatgg gaaatgtcaa 3060
caagtatgaa taaagacacc tactgagtgg ccgtgtttgc catctgtttt agcagagcct 3120
agacaagggc cacagaccca gccagaagcg gaaacttaaa aagtccgaat ctctgctccc 3180
tgcagggcac aggtgatggt gtctgctgga aaggtcagag cttccaaagt aaacagcaag 3240
agaacctcag ggagagtaag ctctagtccc tctgtcctgt agaaagagcc ctgaagaatc 3300
agcaattttg ttgctttatt gtggcatctg ttcgaggttt gcttcctctt taagtctgtt 3360
tcttcattag caatcatatc agttttaatg ctactactaa caatgaacag taacaataat 3420
atccccctca attaatagag tgctttctat gtgcaaggca cttttcacgt gtcacctatt 3480
ttaacctttc caaccacata aataaaaaag gccattatta gttgaaaaaa aaaaaaaaaa 3540
aaaaaaaaa 3549

<210> SEQ ID NO 7
<211> LENGTH: 3503
<212> TYPE: DNA
<213> ORGANISM: Homo sapiens

<400> SEQUENCE: 7
gctggtgtca gagcccggcg agcgctggca gttccgcggc ggggatgctg aggagcgctg 60
ggtccgggag cagccctggc ccctgcggac ttccgaggcc gtgaaaaccc ctgcgctgcg 120

-continued

```
gcccttccca ggcccccgag gccgttcgcc gttcccgaag cccgactggg ggaagagtcc    180
agcaccaaag cggccgttct cggattccgg agcgttctgg agccccgaga gacgccccgg    240
ggttctagaa gctccccggc ggcgcccagt cccggcttca ttcgggcgtc cctccgaaac    300
ccactcgggt gcacgggtcg tcggcgagcc gcgaccgggt cctggcgcgc accatgatcg    360
tggcggactc cgagtgccgc gcagagctca aggactacct gcggttcgcc ccgggcggcg    420
tcggcgactc gggccccgga gaggagcaga gggagagccg ggctcggcga ggccctcgag    480
ggcccagcgc cttcatcccc gtggaggagg tccttcggga gggggctgag agcctcgagc    540
agcacctggg gctggaggca ctgatgtcct ctgggcgagt agacaacctg gcagtggtga    600
tgggcctgca ccctgactac tttaccagct tctggcgcct gcactacctg ctgctgcaca    660
cggatggtcc cttggccagc tcctggcgcc actacattgc catcatggct gccgcccgcc    720
atcagtgttc ttacctggta ggctcccaca tggccgagtt tctgcagact ggtggtgacc    780
ctgagtggct gctgggcctc caccgggccc ccgagaagct gcgcaaactc agcgagatca    840
acaagttgct ggcgcatcgg ccatggctca tcaccaagga acacatccag gccttgctga    900
agaccggcga gcacacttgg tccctggccg agctcattca ggctctggtc ctgctcaccc    960
actgccactc gctctcctcc ttcgtgtttg gctgtggcat cctccctgag gggggatgcag   1020
atggcagccc tgcccccccag gcacctacac cccctagtga acagagcagc cccccaagca   1080
gggacccgtt gaacaactct gggggctttg agtctgcccg cgacgtggag gcgctgatgg   1140
agcgcatgca gcagctgcag gagagcctgc tgcgggatga ggggacgtcc caggaggaga   1200
tggagagccg ctttgagctg gagaagtcag agagcctgct ggtgaccccc tcagctgaca   1260
tcctggagcc ctctccacac ccagacatgc tgtgctttgt ggaagaccct actttcggat   1320
atgaggactt cactcggaga ggggctcagg cacccccctac cttccgggcc caggattata   1380
cctgggaaga ccatggctac tcgctgatcc agcggcttta ccctgagggt gggcagctgc   1440
tggatgagaa gttccaggca gcctatagcc tcacctacaa taccatcgcc atgcacagtg   1500
gtgtggacac ctccgtgctc cgcagggcca tctggaacta tatccactgc gtctttggca   1560
tcagatatga tgactatgat tatggggagg tgaaccagct cctggagcgg aacctcaagg   1620
tctatatcaa gacagtggcc tgctacccag agaagaccac ccgaagaatg tacaacctct   1680
tctggaggca cttccgccac tcagagaagg tccacgtgaa cttgctgctc ctggaggcgc   1740
gcatgcaagc cgctctgctg tacgccctcc gtgccatcac ccgctacatg acctgactcc   1800
tgagcaggac ctgggcccgg ttcagctccc cacaaggact tctctgtctg gagacagccc   1860
cagacccttt tgtgtcccat gcccaccctc cccacgctgc agtgggcttg tgtgtgatgt   1920
gcagtcccga agccacaccc tcccttttcc tcactggaat ggacagttca ttgcactgac   1980
tctgggatct cagccctgct cctgggagct ggaagagcac ttggagatcc taagggacca   2040
caccccttcct ccttcccctg cccacagagg cagagggcac aggaaagaag ccgggccaag   2100
ctcggaatta atgtgccaca agtgttgtgg ccttcctgaa ctgggaagtc cctggctggc   2160
ccccgggggga gaggggcaaa tgcctccggg actgacactc caggcagctt tgccttctct   2220
cccctgtcat ttccagattt cattacctcc tacttgccat tcacccatca atgtgaaagt   2280
cagggtcaca gctggtctgt gtgtccagtt ccctaaaagc ctgttctgtt gggcagcctg   2340
aggctgttgc ccgaatccta gttcagtttt ttgacttcct ttgccctttt tccctttttct   2400
ccatgcttaa tggtgtgagg cgtcaggaga gaggccaagt acataaaaaa aaaaaaagca   2460
gattatctct agagagtttg agcctttgct ggtcacattg ccttctgaag gaggagggagt   2520
```

attagattat aaatcctctt tattttggtc ctttatgctt gaggttccaa cctggagcca 2580
cagtgtgtga gaggaggagg agagggagaa ttctgttctc ccagagctgc acctgcctcg 2640
cagaggccag caccccactc tcctgcctcc agtggccctg ccgcagatgt ctcccaaaaa 2700
gttgagcctt tctagatggc ttaggtggca ccatggctca gcaggagggg cgggaggcac 2760
cagggttctt gtttggaccc tgcccctggg ccatggccag gtgaccatgg ctacattgcc 2820
aaacctctga ctgccacagc tgcagactga gagggtgggt ctgagtcccc acaatgtctg 2880
aagctgcccc tgggattctc aggccaacct gccaacagca agcggatttt cttgcaagat 2940
cagggacccc atttctgcag ccagtgtctc ctgggtgcct tctgaggact cccaccccca 3000
tcccagtatc tcatctgtcc cctctcctgg ggcttaagtg ggttgcttcc aggcagaagc 3060
agccaaggac cgattccagg cactttctgt agcaaatgac tgtgaattac gacttctctt 3120
gcccttcttc tagcagtctg tgcctcctct ctgaccagtt tggagggcac tgaagaaagg 3180
caagggccgt gctgctgctg ggcggggcag gagaggagcc tggccagtgt gccacattaa 3240
atacccgtgc aggcgcggag aagcaaccgg caccccctc cggcctgaaa gccctccctg 3300
caagaaggtg tgcaggagag aagaggcccc ggcatgggga tctgggttct agagggcatg 3360
tgatgactgt aaatgttcac tgggtgggta gggagtggta tccagtgttc aagtgcagaa 3420
atctttggct ttgctaccag ttccatatga tgagaaataa acgttcgctg aggttttgtt 3480
tcataaaaaa aaaaaaaaaa aaa 3503

<210> SEQ ID NO 8
<211> LENGTH: 3428
<212> TYPE: DNA
<213> ORGANISM: Homo sapiens

<400> SEQUENCE: 8
tggagagtaa tgttacagag cggagagagt gaggaggctg cgtctggctc ccgctctcac 60
agccattgca gtacattgag ctccatagag acagcgccgg ggcaagtgag agccggacgg 120
gcactgggcg actctgtgcc tcgctgagga aaaataacta aacatgggca aaggagatcc 180
taagaagccg agaggcaaaa tgtcatcata tgcatttttt gtgcaaactt gtcgggagga 240
gcataagaag aagcacccag atgcttcagt caacttctca gagttttcta agaagtgctc 300
agagaggtgg aagaccatgt ctgctaaaga gaaaggaaaa tttgaagata tggcaaaagc 360
ggacaaggcc cgttatgaaa gagaaatgaa aacctatatc cctcccaaag gggagacaaa 420
aaagaagttc aaggatccca atgcacccaa gaggcctcct tcggccttct tcctcttctg 480
ctctgagtat cgcccaaaaa tcaaaggaga acatcctggc ctgtccattg gtgatgttgc 540
gaagaaactg ggagagatgt ggaataacac tgctgcagat gacaagcagc cttatgaaaa 600
gaaggctgcg aagctgaagg aaaaatacga aaaggatatt gctgcatatc gagctaaagg 660
aaagcctgat gcagcaaaaa agggagttgt caaggctgaa aaaagcaaga aaaagaagga 720
agaggaggaa gatgaggaag atgaagagga tgaggaggag gaggaagatg aagaagatga 780
agatgaagaa gaagatgatg atgatgaata agttggttct agcgcagttt tttttttctt 840
gtctataaag catttaaccc ccctgtacac aactcactcc ttttaaagaa aaaaattgaa 900
atgtaaggct gtgtaagatt tgtttttaaa ctgtacagtg tcttttttttg tatagttaac 960 acactaccga atgtgtcttt agatagccct gtcctggtgg tattttcaat agccactaac 1020
cttgcctggt acagtatggg ggttgtaaat tggcatggaa atttaaagca ggttcttgtt 1080

-continued

```
ggtgcacagc acaaattagt tatatatggg gatggtagtt ttttcatctt cagttgtctc   1140

tgatgcagct tatacgaaat aattgttgtt ctgttaactg aataccactc tgtaattgca   1200

aaaaaaaaaa aaaagttgca gctgttttgt tgacattctg aatgcttcta agtaaataca   1260

attttttta ttagtattgt tgtccttttc ataggtctga aatttttctt cttgagggga   1320

agctagtctt ttgcttttgc ccattttgaa tcacatgaat tattacagtg tttatccttt   1380

catatagtta gctaataaaa agctttttgtc tacacaccct gcatatcata atgggggtaa   1440

agttaagttg agatagtttt catccataac tgaacatcca aaatcttgat cagttaagaa   1500

atttcacata gcccacttac atttacaaac tgaagagtaa tcaatctact caaagcatgg   1560

gattattaga atcaaacatt ttgaaagtct gtccttgaag gactaataga aaagtatgtt   1620

ctaaccttta catgaggact ctattcttta actcccatta ccatgtaatg gcagttatat   1680

tttgcagttc ccacattaaa gaagacctga gaatgtatcc ccaaaagcgt gagcttaaaa   1740

tacaagactg ccatattaaa ttttttgttg acattagtct cagtgaagac tatgaaaatg   1800

ctggctatag atgtcttttc ccatttatct aaatatggac tgctcaggaa acgagacttt   1860

ccattacaag tatttttaat taattgggcc agcttttcaa acaaagatgc cacattcaaa   1920

atagggtata ttttcctata ttacggtttg cccctttata aatccaagta gataggaaga   1980

aagaagacaa actttgcatc tcagtatgaa ttattcaatt tatttgaatg atttttcttt   2040

acaaaacaaa ctcattcatt agtcatgttt atctgcttag gagtttaggg aacaatttgg   2100

caattttgtg gttttcgaga ttatcgtttt cttaaagtgc cagtatttta aaatagcgtt   2160

cttgtaattt tacacgcttt tgtgatggag tgctgttttg ttatataatt tagacttgga   2220

ttctttccat ttgcatttgt ttatgtaatt tcaggaggaa tactgaacat ctgagtcctg   2280

gatgatacta ataaactaat aattgcagag gttttaaata ctagttaaat ggctttcact   2340

taagaactta agattttgtt acatattttt aaatcttgtt tctaataata cctcttagca   2400

gtacctttta aataagtata agggatggca aagtttttcc ctttaaaaat actcacttta   2460

tgcttataaa taggttaatg ggctgataaa aggttttgtc aaacattgca agtattcggt   2520

gctatatata aaggaggaaa aactagtttt actttcagaa tgatttaaac aagattttta   2580

aaaacaagat acatgcaagc gaacagcagg gttagtgata ggctgcaatt gtgtcgaaca   2640

tcagattttt tgttaagagg agcaaatgac tcaatctgat ttagatggaa gtttctactg   2700

tatagaaatc accattaatc accaacatta ataattctga tccatttaaa atgaattctg   2760

gctcaaggag aatttgtaac tttagtaggt acgtcatgac aactaccatt tttttaagat   2820

gttgagaatg ggaacagttt ttttagggtt tattcttgac cacagatctt aagaaaatgg   2880

acaaaacccc tcttcaatct gaagattagt atggtttggt gttctaacag tatcccctag   2940

aagttggatg tctaaaactc aagtaaatgg aagtgggagg caatttagat aagtgtaaag   3000

ccttgtaact gaagatgatt ttttttagaa agtgtataga aactatttta atgccaagat   3060

agttacagtg ctgtggggtt taaagacttt gttgacatca agaaaagact aaatctataa   3120

ttaattgggc caacttttaa aatgaagatg ctttttaaaa ctaatgaact aagatgtata   3180

aatcttagtt tttttgtatt ttaaagatag gcatatggca tattgattaa cgagtcaaat   3240

ttcctaactt tgctgtgcaa aggttgagag ctattgctga ttagttacca cagttctgat   3300

gatcgtccca tcacagtgtt gttaatgttt gctgtattta ttaattttct taaagtgaaa   3360

tctgaaaaat gaaatttgtg tgtcctgtgt acccgagggg taatgattaa atgataaaga   3420

taagaaaa                                                            3428
```

<210> SEQ ID NO 9
<211> LENGTH: 4110
<212> TYPE: DNA
<213> ORGANISM: Homo sapiens

<400> SEQUENCE: 9
gtcgagcggg agcagaggag gcgagggagg agggccagag aggcagttgg aagatggcgg 60
acgaggcggc cctcgccctt cagcccggcg gctccccctc ggcggcgggg gccgacaggg 120
aggccgcgtc gtcccccgcc ggggagccgc tccgcaagag gccgcggaga gatggtcccg 180
gcctcgagcg gagcccgggc gagcccggtg gggcggcccc agagcgtgag gtgccggcgg 240
cggccagggg ctgcccgggt gcggcggcgg cggcgctgtg gcgggaggcg gaggcagagg 300
cggcggcggc aggcggggag caagaggccc aggcgactgc ggcggctggg gaaggagaca 360
atgggccggg cctgcagggc ccatctcggg agccaccgct ggccgacaac ttgtacgacg 420
aagacgacga cgacgagggc gaggaggagg aagaggcggc ggcggcggcg attgggtacc 480
gagataacct tctgttcggt gatgaaatta tcactaatgg ttttcattcc tgtgaaagtg 540
atgaggagga tagagcctca catgcaagct ctagtgactg gactccaagg ccacggatag 600
gtccatatac ttttgttcag caacatctta tgattggcac agatcctcga acaattctta 660
aagatttatt gccggaaaca atacctccac ctgagttgga tgatatgaca ctgtggcaga 720
ttgttattaa tatcctttca gaaccaccaa aaaggaaaaa aagaaaagat attaatacaa 780
ttgaagatgc tgtgaaatta ctgcaagagt gcaaaaaaat tatagttcta actggagctg 840 ggtgtctgt ttcatgtgga atacctgact tcaggtcaag ggatggtatt tatgctcgcc 900
ttgctgtaga cttcccagat cttccagatc ctcaagcgat gtttgatatt gaatatttca 960
gaaaagatcc aagaccattc ttcaagtttg caaaggaaat atatcctgga caattccagc 1020
catctctctg tcacaaattc atagccttgt cagataagga aggaaaacta cttcgcaact 1080
atacccagaa catagacacg ctggaacagg ttgcgggaat ccaaaggata attcagtgtc 1140
atggttcctt tgcaacagca tcttgcctga tttgtaaata caaagttgac tgtgaagctg 1200
tacgaggaga tatttttaat caggtagttc ctcgatgtcc taggtgccca gctgatgaac 1260
cgcttgctat catgaaacca gagattgtgt tttttggtga aaatttacca gaacagtttc 1320
atagagccat gaagtatgac aaagatgaag ttgacctcct cattgttatt gggtcttccc 1380
tcaaagtaag accagtagca ctaattccaa gttccatacc ccatgaagtg cctcagatat 1440
taattaatag agaacctttg cctcatctgc attttgatgt agagcttctt ggagactgtg 1500
atgtcataat taatgaattg tgtcataggt taggtggtga atatgccaaa ctttgctgta 1560
accctgtaaa gctttcagaa attactgaaa aacctccacg aacacaaaaa gaattggctt 1620
atttgtcaga gttgccaccc acacctcttc atgtttcaga agactcaagt tcaccagaaa 1680
gaacttcacc accagattct tcagtgattg tcacactttt agaccaagca gctaagagta 1740
atgatgattt agatgtgtct gaatcaaaag gttgtatgga agaaaaacca caggaagtac 1800
aaacttctag gaatgttgaa agtattgctg aacagatgga aaatccggat ttgaagaatg 1860
ttggttctag tactggggag aaaaatgaaa gaacttcagt ggctggaaca gtgagaaaat 1920
gctggcctaa tagagtggca aaggagcaga ttagtaggcg gcttgatggt aatcagtatc 1980
tgtttttgcc accaaatcgt tacattttcc atggcgctga ggtatattca gactctgaag 2040
atgacgtctt atcctctagt tcttgtggca gtaacagtga tagtgggaca tgccagagtc 2100

-continued caagtttaga agaacccatg gaggatgaaa gtgaaattga agaattctac aatggcttag 2160
aagatgagcc tgatgttcca gagagagctg gaggagctgg atttgggact gatggagatg 2220
atcaagaggc aattaatgaa gctatatctg tgaaacagga agtaacagac atgaactatc 2280
catcaaacaa atcatagtgt aataattgtg caggtacagg aattgttcca ccagcattag 2340
gaactttagc atgtcaaaat gaatgtttac ttgtgaactc gatagagcaa ggaaaccaga 2400
aaggtgtaat atttataggt tggtaaaata gattgttttt catggataat ttttaacttc 2460
attatttctg tacttgtaca aactcaacac taactttttt tttttaaaa aaaaaaaggt 2520 actaagtatc ttcaatcagc tgttggtcaa gactaacttt cttttaaagg ttcatttgta 2580
tgataaattc atatgtgtat atataatttt ttttgttttg tctagtgagt ttcaacattt 2640
ttaaagtttt caaaaagcca tcggaatgtt aaattaatgt aaagggaaca gctaatctag 2700
accaaagaat ggtattttca cttttctttg taacattgaa tggtttgaag tactcaaaat 2760
ctgttacgct aaacttttga ttctttaaca caattatttt taaacactgg cattttccaa 2820
aactgtggca gctaactttt taaaatctca aatgacatgc agtgtgagta gaaggaagtc 2880
aacaatatgt ggggagagca ctcggttgtc tttactttta aaagtaatac ttggtgctaa 2940
gaatttcagg attattgtat ttacgttcaa atgaagatgg cttttgtact tcctgtggac 3000
atgtagtaat gtctatattg gctcataaaa ctaacctgaa aaacaaataa atgctttgga 3060
aatgtttcag ttgctttaga aacattagtg cctgcctgga tccccttagt tttgaaatat 3120
ttgccattgt tgtttaaata cctatcactg tggtagagct tgcattgatc ttttccacaa 3180
gtattaaact gccaaaatgt gaatatgcaa agcctttctg aatctataat aatggtactt 3240
ctactgggga gagtgtaata ttttggactg ctgttttcca ttaatgagga gagcaacagg 3300
cccctgatta tacagttcca aagtaataag atgttaattg taattcagcc agaaagtaca 3360
tgtctcccat tgggaggatt tggtgttaaa taccaaactg ctagccctag tattatggag 3420
atgaacatga tgatgtaact tgtaatagca gaatagttaa tgaatgaaac tagttcttat 3480
aatttatctt tatttaaaag cttagcctgc cttaaaacta gagatcaact ttctcagctg 3540
caaaagcttc tagtctttca agaagttcat actttatgaa attgcacagt aagcatttat 3600
ttttcagacc atttttgaac atcactccta aattaataaa gtattcctct gttgctttag 3660
tatttattac aataaaaagg gtttgaaata tagctgttct ttatgcataa aacacccagc 3720
taggaccatt actgccagag aaaaaaatcg tattgaatgg ccatttccct acttataaga 3780
tgtctcaatc tgaatttatt tggctacact aaagaatgca gtatatttag ttttccattt 3840
gcatgatgtt tgtgtgctat agatgatatt ttaaattgaa aagtttgttt taaattattt 3900
ttacagtgaa gactgttttc agctcttttt atattgtaca tagtctttta tgtaatttac 3960
tggcatatgt tttgtagact gtttaatgac tggatatctt ccttcaactt ttgaaataca 4020
aaaccagtgt tttttacttg tacactgttt taaagtctat taaaattgtc atttgacttt 4080
tttctgttaa cttaaaaaaa aaaaaaaaaa 4110

<210> SEQ ID NO 10
<211> LENGTH: 952
<212> TYPE: DNA
<213> ORGANISM: Homo sapiens

<400> SEQUENCE: 10
ccacgcgtcc ggcacttccg cccatccccc tccggatccc tctgttcggg ctcgggtttc 60
cgccgagacg acagggactg ccaggtcgga agtagtgtga ggctcgtggg cggagccaag 120
cgccgccatg tccgccgccc tgctgcggcg gggcctggag ctgctggcgg cgtccgaggc 180
cccccgggac cctccaggtc aggccaagcc gagaggggct ccggtgaaac ggccccggaa 240
gacgaaggca attcaggccc agaaactgcg gaactcggcc aagggaaagg tgcccaagtc 300
ggcactggac gagtaccgga agcgagagtg tcgagaccac ctcagagtaa acctgaagtt 360
tctgaccagg acgagaagca ccgtggctga gtctgtgagc cagcagattt tgcgccagaa 420
ccggggccgc aaggcctgtg accggcctgt ggccaagacc aagaagaaga aggctgaggg 480
caccgtgttc accgaggaag acttccagaa gttccagcag gaatacttcg gcagctaggc 540
tccctggagg gcacggtgaa gaggccttca agccctgcag cctccgactc ctgctggctc 600
caggaaccgg ccgtgccgcg cggccagcag atggcgatgc aggaccagcc tggctcgagg 660
aagccgcgga gctgagccga gtggaggctg gaatggagct ggtgggccgg aagtcctggg 720
gaggatttac acacagaccg gagctggctt ccgcaggcct gggcagagca tctgcacctg 780
ccggaaagga acgtatctgt tttgtttgct tttgcccagg tggggcctct gggctgtttg 840
ctgtggagca aggctaattc ctgagccctt ggggacgaca gctccaggag taggaagaag 900
ggtgggcttc caagttacaa taaatgtgaa cccaagaaaa aaaaaaaaaa aa 952

<210> SEQ ID NO 11
<211> LENGTH: 6603
<212> TYPE: DNA
<213> ORGANISM: Homo sapiens

<400> SEQUENCE: 11
aagaaagagc cccgccccta gtcttatgac tcgcactgaa gcgccgattc ctggcttttg 60
caaggctgtg gtcggtggtc atcagtgctc ttgacccagg tccagcgagc cttttccctg 120
gtgttgcagc tgttgttgta ccgccgccgt cgccgccgtc gccgcctgct ctgcggggtc 180
atggtgtgct tccgcctctt cccggttccg ggctcagggc tcgttctggt ctgcctagtc 240
ctgggagctg tgcggtctta tgcattggaa cttaatttga cagattcaga aaatgccact 300
tgcctttatg caaaatggca gatgaatttc acagtacgct atgaaactac aaataaaact 360
tataaaactg taaccatttc agaccatggc actgtgacat ataatggaag catttgtggg 420
gatgatcaga atggtcccaa aatagcagtg cagttcggac ctggcttttc ctggattgcg 480
aattttacca aggcagcatc tacttattca attgacagcg tctcattttc ctacaacact 540
ggtgataaca caacatttcc tgatgctgaa gataaaggaa ttcttactgt tgatgaactt 600
ttggccatca gaattccatt gaatgacctt tttagatgca atagtttatc aactttggaa 660
aagaatgatg ttgtccaaca ctactgggat gttcttgtac aagcttttgt ccaaaatggc 720
acagtgagca caaatgagtt cctgtgtgat aaagacaaaa cttcaacagt ggcacccacc 780
atacacacca ctgtgccatc tcctactaca acacctactc caaaggaaaa accagaagct 840
ggaacctatt cagttaataa tggcaatgat acttgtctgc tggctaccat ggggctgcag 900
ctgaacatca ctcaggataa ggttgcttca gttattaaca tcaaccccaa tacaactcac 960
tccacaggca gctgccgttc tcacactgct ctacttagac tcaatagcag caccattaag 1020
tatctagact ttgtctttgc tgtgaaaaat gaaaaccgat tttatctgaa ggaagtgaac 1080
atcagcatgt atttggttaa tggctccgtt ttcagcattg caaataacaa tctcagctac 1140
tgggatgccc ccctgggaag ttcttatatg tgcaacaaag agcagactgt ttcagtgtct 1200
ggagcatttc agataaatac ctttgatcta agggttcagc ctttcaatgt gacacaagga 1260

-continued

```
aagtattcta cagctcaaga ctgcagtgca gatgacgaca acttccttgt gcccatagcg   1320
gtgggagctg ccttggcagg agtacttatt ctagtgttgc tggcttattt tattggtctc   1380
aagcaccatc atgctggata tgagcaattt tagaatctgc aacctgattg attatataaa   1440
aatacatgca aataacaaga ttttcttacc tctcagttgt tgaaacactt tgcttcttaa   1500
aattgatatg ttgaaacttt aattctttta tcaatcccag cattttgaga tcagtcttta   1560
ttaataaaac ctgttctctt taatcagctt aaaatccaaa gtgtcatatt tactggtcct   1620
ggagacaaac ttgttcaaaa gaacatcaac gtgcaatgtt ttaaggtcta tcttaagaag   1680
ccctggccaa attttgatcc taaccttgaa gtatgccttg aacttattaa catggccatt   1740
ataagaataa aatatgtagt tgtgtcttaa tggaattaat aaatgtcatt tcactactgg   1800
tgttctgttt caatgtataa ggactatagt gatttaaact catcaatgtg cctttgcata   1860
aagttcatta aataaatatt gatgtggtat aaatgcccat cagatatgct taaacttggt   1920
tttcagttga atgaagtaga gaatgtcctc aggaccatca gcattttaaa ggttatgtga   1980
cttttgctga tttctctgag ttcaagttaa gcatgaagtt agtacctcaa gcctgtgatt   2040
tttccctagg gatgatacag acccaagagg ctacaacaga acttaaactg gcttcgtaat   2100
tagagttttt aagataattg tttgtttttc agcaatatag actgaaaaga tccaagcata   2160
tttagccact tgctttttttg tttcttgttt tgttcttctt tggatgcctg attagtattg   2220
aaagatagaa atattctatg aactaattag gacagattgt gttgtgtttc tctacctcat   2280
cttgttgatc tctggagcat taaaatctat ttagtgttgt catcagtgtg gtacttatga   2340
aatgtaagct aacagcaatc tcagaaggga ggcagtgaag catagcaact aggctcttgt   2400
ttcttcaaga tggcccctgt ggggcagtgc atagatgggg gtgtaaagag aagctgttgg   2460
cattaaaatg agctagataa tcagcccttg ttgaagcata ttccatggta taagagtagc   2520
acagacatga aacatagata aagaaggaag gcttaataga ctagaagact tccacattga   2580
agtattatta acccattgta tgtatatagg ggcatgatca gagtctctat aacttcctga   2640
ttaacaatac agtgtatctt gttacccagc tgtcagtctt tgagagcttt cagtaaaata   2700
tagtaaattc tttcagcata ggctaatgtg tggttactga gatgagtgtt gtgtactcag   2760
aaccgtagca acatttttat gaatggtaaa agtacaagag gaggaaaagt taaaattaga   2820
agaaaagtac aagttattgc ttaatcataa atcacaccag ataacacatt ttgttaattt   2880
cattagctat tactggaaag gaccttaacg attatttaca gaaaggggag tgaaattcat   2940
tgaggttcca tatcaagtgg gcaacaaaac tattactagc attttgataa aaattgcccc   3000
taatgaaatc tagtcactca acagtaaaac aacagctggt ttacacttga aattatgaga   3060
tcagaattgg gcactttggg cttccgtact atgttttgct taagtttttt ttttaatact   3120
aatatgggct ttttcagtag taatatacca aaacacttct attttaatct ctgtttgcta   3180
cttcaaaacc taatcctcct cagatgggat catgagcata agaggaaaag agaagagaat   3240
gaatacttgt tgacctcttg atgtgtatca gatgctttag aaatgtaatt gtatttaatc   3300
ctcaaatacc ttataggtat tattatcccc ttcttacaga tgaggaaagt gaggcccagt   3360
ttaaataact tgcccaaggt cctttggcta gtactggaag gagtcaagat ttaaacacag   3420
ttctgtctga atccagaact caaaatctac attgcacatg ttgctttcct ggtggttcgg   3480
tggaatggac tgcaacgcat tagatactgc tgttattctt ccaggccacc gctcagctaa   3540
aaataattgt gtgtgtgtgt atatatatat atatgtacac acacacacat atatatacac   3600
acacacatat atatacacat atacatatat atacacatat atatacacac acatatatat   3660
```

-continued

```
gtatatatat actacattct tgatcctaag tcttttttaa cttaaatttt attacttata   3720
cagaattctt atttatactt taattatagg tgtgacgaag agaaagagag tagggaaata   3780
cacaggcagt ggttttaagt gtagatgatg gctccttaac ccagtgtcat tagataatca   3840
aacctaaagt cttcccatat taggcaagcg caattctcta ttttggaccc ttcccattct   3900
tcccttacct tctgcttttc gtactgagga atttcgtgtg attttagata aagtgataat   3960
gagatattga gcaaataaga aaatagaggt aatgctataa aaaactaagc tatgtacact   4020
ttcaaaatgc atgtttcttg catgcttttt actacttaat tgcattcttt gctaatttcc   4080
tttccttgct gtctgttctt ttctaacagc tgaagaatgt tctgctgact ctgacctcaa   4140
ctttcttatt cctgttgcag tgggtgtggc cttgggcttc cttataattg ttgtctttat   4200
ctcttatatg attggaagaa ggaaaagtcg tactggttat cagtctgtgt aatcagttaa   4260
atctagtgtt tgtttgtttt tttcaattag aagttacgtt tccattggct aaaagccagg   4320
acatgctgtg caatagattg tttaagatat gcagactaac ttcagtgagt tcctagctaa   4380
cttgggcatg agtacactta tttaagacaa aatatattag gaccaatttt tttctgtttt   4440
ttttcttcct ttgttaaagt ataattaaaa gaaaaattgt ggcttagaat tttttaagta   4500
aataatgatt ttaagcccct ggatccaatt atgaaagcat ttttgctgat gtgtaatttt   4560
atatgttaca gttacttata ttttactact ttgatgttat ttgcaaaatc aaaggtgtta   4620
aagaatttaa cttgcttcag gaaataaatt caagaacata gtggattcat tttcattggt   4680
ggcagacacg aaatttggtt catgataaga cttcctttcc ccacctcctg atcagcatta   4740
tttaaatctg tatttttctg ttagttaaga aagaaatggc ttcatgatat tgtatttaat   4800
agcaaaagtt tggctgtctt cttcattact gttaatagct actatatttt aacaaggaga   4860
tttctttttt tgttgttgtt gttctagagt ttggaatata ctgattatct cagacttgac   4920
atttatactg aaggatgaag taagacctcc agcttttttt aaaaaaggtg ttgatttgga   4980
acacctgtat gggttatggt ttattaaggt tatggtttag aaagtttttt tccctcagag   5040
ccttaacttg ttaagaaggt tcatttatcc tgcactgaaa acaaaaactc tatatacttt   5100
gtttgtgtgc ctcctgcact ctcccattcc ctatgtgaat atgctctagt tgatattttt   5160
aatatattga tttctttttt ctcacagcaa caagtgctta ctctagaggt tagtgggccc   5220
tgatatgtca tcagtcagat gcctgcctag ccaaagctgg actaagatta ttctgtacat   5280
ttgttgatct tgatatagac ttatatccct gtagggactg ctaatggctc cggcttctgg   5340
agtaaggtac tggagaccac tcatccctgt gtctgcttga ttggttcagc tgttgaattg   5400
cccttttatt tggaagcagt gttgaagttg tctagggttc aaatggctgc tttgtacacc   5460
tgtcattagt ataaggcaga tgtttatttt atcaagctat tttatctcta catttaacta   5520
aaaacaaaag ttcccaaaga tctgccttca cttcagaaat tttttttgga ttaaaaaaat   5580
taagcctgaa ccttaaataa agtgagttgg ttattcattc caaggattaa gtcccaatct   5640
acctctcagc acaatgcaga agctcaccac tgtattgctg ccattaactc atgccagaac   5700
cctttgccaa taactggaat tacaaatttt tgttaaagaa aatttatcaa gatctttctt   5760
tactgccttc tctatatgta catctcaaaa acatgtacat ctcaaaaact ggagtagaaa   5820
gttagattgc tcaactacaa ctcctctaga actctatagc tctgacatac agattcacac   5880
tctcctctat ttgctaagta tgtaaagaat gttttctttt aaaatgttct cttttgagaa   5940
caactgctta tttgttataa aagcatttgg ttaaaatgat gtcatcataa aaaacagtgg   6000
```

-continued

```
ctttgtttca atacatattt ttgagatgat tatctagaag ccagattaat aaaatcagct   6060

tgtgaccttg ctaagcatat aaactggaaa ttcagataca ttcaaaatta tgggttcatt   6120

taaaagtgtt ctaccttttg ggtatgagac taatatcact aattcctcaa tagttatcat   6180

ggctctatct taattaatta gaaaatatgt gtgtttaatt ctttgagaat taaaatagag   6240

aatattaaca gagggttaaa aactgcttca actccaataa gataaaggaa gctcaaaatc   6300

tatgagctga gtgttcaatt agctttgcct actgagttca attttatgtc aatacaacag   6360

tggatcagac agtacgactt tgaactggtg aatgtaaaca attgtttttc acctaagctg   6420

ctttggaaga actgatgctt gctgctaact aaagttttgg atgtatcgat ttagagaacc   6480

aattaatacc tgcaaaataa agcatactgt ggtacttctg tttgatctag tatgtgtgat   6540

tttagattga tggattaaaa attaataaag atcatacatt ccataccaaa aaaaaaaaaa   6600

aaa                                                                 6603
```

<210> SEQ ID NO 12
<211> LENGTH: 1414
<212> TYPE: DNA
<213> ORGANISM: Homo sapiens

<400> SEQUENCE: 12

```
gccaggaccc tggaaggaag caggatggca gccggaacag cagttggagc ctgggtgctg     60

gtcctcagtc tgtggggggc agtagtaggt gctcaaaaca tcacagcccg gattggcgag    120

ccactggtgc tgaagtgtaa gggggccccc aagaaaccac cccagcggct ggaatggaaa    180

ctgaacacag gccggacaga agcttggaag gtcctgtctc cccagggagg aggcccctgg    240

gacagtgtgg ctcgtgtcct tcccaacggc tccctcttcc ttccggctgt cgggatccag    300

gatgagggga ttttccggtg ccaggcaatg aacaggaatg gaaaggagac caagtccaac    360

taccgagtcc gtgtctacca gattcctggg aagccagaaa ttgtagattc tgcctctgaa    420

ctcacggctg gtgttcccaa taaggtgggg acatgtgtgt cagagggaag ctaccctgca    480

gggactctta gctggcactt ggatgggaag cccctggtgc ctaatgagaa gggagtatct    540

gtgaaggaac agaccaggag acaccctgag acagggctct tcacactgca gtcggagcta    600

atggtgaccc cagcccgggg aggagatccc cgtcccacct tctcctgtag cttcagccca    660

ggccttcccc gacaccgggc cttgcgcaca gcccccatcc agccccgtgt ctgggagcct    720

gtgcctctgg aggaggtcca attggtggtg gagccagaag gtggagcagt agctcctggt    780

ggaaccgtaa ccctgacctg tgaagtccct gcccagccct ctcctcaaat ccactggatg    840

aaggatggtg tgcccttgcc ccttcccccc agccctgtgc tgatcctccc tgagataggg    900

cctcaggacc agggaaccta cagctgtgtg gccacccatt ccagccacgg gccccaggaa    960

agccgtgctg tcagcatcag catcatcgaa ccaggcgagg aggggccaac tgcaggctct   1020

gtgggaggat cagggctggg aactctagcc ctggccctgg ggatcctggg aggcctgggg   1080

acagccgccc tgctcattgg ggtcatcttg tggcaaaggc ggcaacgccg aggagaggag   1140

aggaaggccc cagaaaacca ggaggaagag gaggagcgtg cagaactgaa tcagtcggag   1200

gaacctgagg caggcgagag tagtactgga gggccttgag ggcccacag acagatccca   1260

tccatcagct ccctttttctt tttcccttga actgttctgg cctcagacca actctctcct   1320

gtataatctc tctcctgtat aaccccacct tgccaagctt tcttctacaa ccagagcccc   1380

ccacaatgat gattaaacac ctgacacatc ttga                               1414
```

<210> SEQ ID NO 13
<211> LENGTH: 1987
<212> TYPE: DNA
<213> ORGANISM: Homo sapiens

<400> SEQUENCE: 13
agccgccgcc gtctccgccg tcgctggggc agctgccgcg gtggtcgcct ctggcagtgc 60
cgctagcttt caggcagtcg cctctcctcc cgacatcccg ccttgaggag gctgaggcgg 120
aatcgcggct ggcggcgggg ggacggaccg gccctgcagt ggccgcagtg acagcccgga 180
cccggccctc cgcccgctct cgcctcggcg cccgcagcca cgatgaaccg gggcggcggc 240
agcccgtcgg ccgccgccaa ctacctgctc tgtaccaact gccggaaagt gctgcggaag 300
gataaaagaa tcagagtgtc tcaacccttg acaagaggac caagtgcctt tattccagag 360
aaggaagttg tccaagcaaa cacagtggat gaacgtacta actttcttgt ggaagaatac 420
tctacatccg gtcgtctgga caacatcaca caggtcatga gtttacacac tcagtacctg 480
gagtctttct tgcggagcca gttttacatg ttgcgcatgg atggtcccct tcctctacca 540
tacaggcact atattgcaat aatggctgca gctagacatc agtgttctta cttaataaac 600
atgcatgtgg atgaattttt aaagactgga ggtattgctg agtggttgaa tggtttggaa 660
tatgtgccac aaagactgaa aaatcttaat gaaattaata agctgctagc acatcgacct 720
tggctgatca caaaagagca cattcagaaa cttgtcaaaa ctggagaaaa taattggtct 780
ctgcctgaac tggtacatgc tgtggtcctc ctggcacatt atcatgcttt ggcaagcttt 840
gtttttggta gtggtatcaa tccagagaga gatccagaaa tctccaatgg attcaggcta 900
atatcagtca acaatttctg cgtttgtgat cttgctaatg acaacaacat agagaatgca 960
tctctttcag gcagcaactt tgggattgtg gattctctaa gtgagctaga ggccttaatg 1020
gaaaggatga aaagacttca agaagaaagg gaagatgaag aggcgtctca agaagaaatg 1080
agcactcgtt ttgaaaagga gaagaaagaa agtcttttttg tggtctctgg agatactttt 1140
cattcatttc ctcattcaga ttttgaggat gacatgatta taacatctga tgtctctcga 1200
tatattgaag accctggttt tgggtatgaa gactttgcca gacgaggaga agagcatttg 1260
ccaacattcc gagctcagga ctatacctgg gaaaatcatg ggttctccct ggtgaacaga 1320
ctttattctg acattggaca tcttcttgat gaaaagtttc ggatggtcta caatctcaca 1380
tataacacta tggccaccca tgaggatgtt gacacaacca tgctgcgcag agctttattt 1440
aactatgttc actgtatgtt tggaatcagg tatgatgact atgattatgg agaagttaat 1500
caattacttg aaagaagcct gaaggtttac attaagacag tgacctgcta tcctgagaga 1560
actacaaaac gcatgtatga tagttactgg cggcagttca aacactcaga aaaagttcat 1620
gtcaatctac ttttaatgga agcacgaatg caagctgaac ttctttatgc tcttcgtgcc 1680
ataactcggc atttgacctg aagtatcacc caaggaaaat gtcatacatg tgtaaagacc 1740
tttcacataa gataaacatt gaagctattt gtgatatagc atcaaaaatt attcagttct 1800
ctagtgtcaa agtttagccg tttgtttttt tttttttgtt ttttgcggct gtaatgtgca 1860
atgatgtgtt ttattttcct tgatgcttaa cattactaac aattgcaaaa ataatactga 1920
ggagcactac tttgcattgt ttgtagttgg agttttggat actgatcata aatcatgaat 1980
ctggcgt 1987

<210> SEQ ID NO 14
<211> LENGTH: 1402
<212> TYPE: DNA

<213> ORGANISM: Homo sapiens

<400> SEQUENCE: 14

```
gggggacgaag ggaagctcca gcgtgtggcc ccggcgagtg cggataaaag ccgccccgcc      60
gggctcgggc ttcattctga gccgagcccg gtgccaagcg cagctagctc agcaggcggc     120
agcggcggcc tgagcttcag ggcagccagc tccctcccgg tctcgccttc cctcgcggtc     180
agcatgaaag ccttcagtcc cgtgaggtcc gttaggaaaa acagcctgtc ggaccacagc     240
ctgggcatct cccggagcaa aacccctgtg gacgacccga tgagcctgct atacaacatg     300
aacgactgct actccaagct caaggagctg gtgcccagca tcccccagaa caagaaggtg     360
agcaagatgg aaatcctgca gcacgtcatc gactacatct tggacctgca gatcgccctg     420
gactcgcatc ccactattgt cagcctgcat caccagagac ccgggcagaa ccaggcgtcc     480
aggacgccgc tgaccaccct caacacggat atcagcatcc tgtccttgca ggcttctgaa     540
ttcccttctg agttaatgtc aaatgacagc aaagcactgt gtggctgaat aagcggtgtt     600
catgatttct tttattcttt gcacaacaac aacaacaaca aattcacgga atcttttaag     660
tgctgaactt atttttcaac catttcacaa ggaggacaag ttgaatggac ctttttaaaa     720
agaaaaaaaa aatggaagga aaactaagaa tgatcatctt cccagggtgt tctcttactt     780
ggactgtgat attcgttatt tatgaaaaag acttttaaat gccctttctg cagttggaag     840
gttttcttta tatactattc ccaccatggg gagcgaaaac gttaaaatca caaggaattg     900
cccaatctaa gcagactttg ccttttttca aaggtggagc gtgaatacca gaaggatcca     960
gtattcagtc acttaaatga agtcttttgg tcagaaatta ccttttttgac acaagcctac    1020
tgaatgctgt gtatatattt atatataaat atatctattt gagtgaaacc ttgtgaactc    1080
tttaattaga gttttcttgt atagtggcag agatgtctat ttctgcattc aaaagtgtaa    1140
tgatgtactt attcatgcta aactttttat aaaagtttag ttgtaaactt aaccctttta    1200
tacaaaataa atcaagtgtg tttattgaat ggtgattgcc tgctttattt cagaggacca    1260
gtgctttgat ttttattatg ctatgttata actgaaccca aataaataca agttcaaatt    1320
tatgtagact gtataagatt ataataaaac atgtctgaag tcaaaaaaaa aaaaaaaaaa    1380
aaaaaaaaaa aaaaaaaaaa aa                                              1402
```

<210> SEQ ID NO 15
<211> LENGTH: 4462
<212> TYPE: DNA
<213> ORGANISM: Homo sapiens

<400> SEQUENCE: 15

```
gcgccgcgtg cccggccgcg cccagcaggg tttccaggcc tgaggtgccc gccctggccc      60
caggagaatg aaccagccgc agaggatggc gcctgtgggc acagacaagg agctcagtga     120
cctcctggac ttcagcatga tgttcccgct gcctgtcacc aacgggaagg gccggcccgc     180
ctccctggcc ggggcgcagt tcggaggttc aggtcttgag gaccggccca gctcaggctc     240
ctggggcagc ggcgaccaga gcagctcctc ctttgacccc agccggacct tcagcgaggg     300
cacccacttc actgagtcgc acagcagcct ctcttcatcc acattcctgg gaccgggact     360
cggaggcaag agcggtgagc ggggcgccta tgcctccttc gggagagacg caggcgtggg     420
cggcctgact caggctggct tcctgtcagg cgagctggcc ctcaacagcc ccgggcccct     480
gtccccttcg ggcatgaagg ggacctccca gtactacccc tcctactccg gcagctcccg     540
gcggagagcg gcagacggca gcctagacac gcagcccaag aaggtccgga aggtcccgcc     600
```

-continued

```
gggtcttcca tcctcggtgt acccacccag ctcaggtgag gactacggca gggatgccac    660
cgcctacccg tccgccaaga cccccagcag cacctatccc gccccttct acgtggcaga    720
tggcagcctg caccctcag ccgagctctg gagtccccg ggccaggcgg gcttcgggcc    780
catgctgggt gggggctcat ccccgctgcc cctcccgccc ggtagcggcc cggtgggcag    840
cagtggaagc agcagcacgt ttggtggcct gcaccagcac gagcgtatgg gctaccagct    900
gcatggagca gaggtgaacg gtgggctccc atctgcatcc tccttctcct cagcccccgg    960
agccacgtac ggcggcgtct ccagccacac gccgcctgtc agcggggccg acagcctcct   1020
gggctcccga gggaccacag ctggcagctc cggggatgcc ctcggcaaag cactggcctc   1080
gatctactcc ccggatcact caagcaataa cttctcgtcc agcccttcta cccccgtggg   1140
ctccccccag ggcctggcag gaacgtcaca gtggcctcga gcaggagccc ccggtgcctt   1200
atcgcccagc tacgacgggg gtctccacgg cctgcagagt aagatagaag accacctgga   1260
cgaggccatc cacgtgctcc gcagccacgc cgtgggcaca gccggcgaca tgcacacgct   1320
gctgcctggc cacggggcgc tggcctcagg tttcaccggc cccatgtcac tgggcgggcg   1380
gcacgcaggc ctggttggag gcagccaccc cgaggacggc ctcgcaggca gcaccagcct   1440
catgcacaac cacgcggccc tccccagcca gccaggcacc ctccctgacc tgtctcggcc   1500
tcccgactcc tacagtgggc tagggcgagc aggtgccacg gcggccgcca gcgagatcaa   1560
gcgggaggag aaggaggacg aggagaacac gtcagcggct gaccactcgg aggaggagaa   1620
gaaggagctg aaggcccccc gggcccggac cagcccagac gaggacgagg acgaccttct   1680
ccccccagag cagaaggccg agcgggagaa ggagcgccgg gtggccaata acgcccggga   1740
gcggctgcgg gtccgtgaca tcaacgaggc ctttaaggag ctggggcgca tgtgccaact   1800
gcacctcaac agcgagaagc cccagaccaa actgctcatc ctgcaccagg ctgtctcggt   1860
catcctgaac ttggagcagc aagtgcgaga gcggaacctg aatcccaaag cagcctgttt   1920
gaaacggcga gaagaggaaa aggtgtcagg tgtggttgga gacccccaga tggtgctttc   1980
agctccccac ccaggcctga gcgaagccca caaccccgcc gggcacatgt gaaaggtatg   2040
cctccgtggg acgagccacc cgctttcagc cctgtgctct ggccccagaa cggccactcg   2100
agaccccggg cttcatccac atccacacct cacacacctg ttgtcagcat cgagccaaca   2160
ccaacctgac aaggttcgga gtgatggggg cggccaaggt gacactgggt ccaggagctc   2220
cctggggccc tggcctacca ctcactggcc tcgctccccc tgtccccgaa tctcagccac   2280
cgtgtcactc tgtgacctgt cccatggatc ctgaaactgc atcttggccc tgttgcctgg   2340
gctgacagga gcattttttt tttttccagt aaacaaaacc tgaaagcaag caacaaaaca   2400
tacactttgt cagagaagaa aaaaatgcct taactataaa aagcggagaa atggaaacat   2460
atcactcaag gggatgctg tggaaacctg gcttattctt ctaaagccac cagcaaattg   2520
tgcctaagcg aaatattttt tttaaggaaa ataaaaacat tagttacaag attttttttt   2580
tcttaatgta gatgaaaatt agcaaggatg ctgcctttgg tctctggttt ttttaagctt   2640
tttttgcata tgttttgtaa gcaacaaatt tttttgtata aaagtcccgt gtctctcgct   2700
atttctgctg ctgttcctag actgagcatt gcatttcttg atcaaccaga tgattaaacg   2760
ttgtattaaa aagaccccgt gtaaacctga gcccccccgt cccccccccc ccccggaagc   2820
cactgcacac agacagaacg gggacaggcg gcgggtcttt tgttttttttg atgttggggg   2880
ttctcttggt tttgtcatgt ggaaagtgat gcgtgggcgt tccctgatga aggcaccttg   2940
```

gggcttccct gccgcatcct ctcccctcag gaaggggact gacctgggct tgggggaagg 3000
gacgtcagca aggtggctct gaccctccca ggtgactctg ccaagcagct gtggccccca 3060
gggctaccct acacaacgcc ctccccaggc ccccctaagc tgctctccct tggaacctgc 3120
acagctctct gaaatggggc attttgttgg gaccagtgac ccctggcatg ggaccacac 3180 cctggagccc ggtgctgggg acctcctgga caccctgtcc ttcactcctt tgccccaggg 3240
acccaggctc atgctctgaa ctctggctga gaggatgctg ctcaggagcc agcacaggac 3300
accccccacc ccaccccacc atgtccccat tacaccagag ggccatcgtg acgtagacag 3360
gatgccaggg gcctggccag cctcccccaa tgctggggag catccctggg cctggggcca 3420
cacctgctgc cctccctctg tgtggtccaa gggcaagagt ggctggagcc gggggactgt 3480
gctggtctga gccccacgaa ggccttgggc tgtgcgtccg accctgctgc agaaccagca 3540
gggtgtcccc tcgggcccat ctgtgtccca tgtcccagca cccaggcctc tctccaggtc 3600
tccttttctg gtcttttgcc atgagggtaa ccagctcttc ccagctggct ggggactgtc 3660
ttgggtttaa aactgcaagt ctcctaccct gggatcccat ccagttccac acgaactagg 3720
gcagtggtca ctgtggcacc caggtgtggg cctggctagc tgggggcctt catgtgccct 3780
tcatgcccct ccctgcattg aggccttgtg gacccctggg ctggctgtgt tcatccccgc 3840
tgcaggtcgg gcgtctcccc ccgtgccact cctgagactc ccaccgttac ccccaggaga 3900
tcctggactg cctgactccc ctccccagac tggcttggga gcctgggccc catggtagat 3960
gcaagggaaa cctcaaggcc agctcaatgc ctggtatctg cccccagtcc aggccaggcg 4020
gaggggaggg gctgtccggc tgcctctccc ttctcggtgg cttcccctac gccctgggag 4080
tttgatctct taagggaact tgcctctccc tcttgttttg ctcctggccc tgcccctagg 4140
tctgggtggg cagtggcccc atagcctctg gaactgtgcg ttctgcatag aattcaaacg 4200
agattcaccc agcgcgagga ggaagaaaca gcagttcctg ggaaccacaa ttatgggggg 4260
tggggggtgt gatctgagtg cctcaagatg gttttcaaaa aaattttttt aaagaaaata 4320
attgtatacg tgtcaacaca gctggctgga tgattgggac tttaaaacga ccctctttca 4380
ggtggattca gagacctgtc ctgtatataa cagcactgta gcaataaacg tgacatttta 4440
taacgaaaaa aaaaaaaaaa aa 4462

<210> SEQ ID NO 16
<211> LENGTH: 1527
<212> TYPE: DNA
<213> ORGANISM: Homo sapiens

<400> SEQUENCE: 16
ggggatgtgg cccgtggcct agctcgtcaa gttgccgtgg cgcggagaac tctgcaaaac 60
aagaggctga ggattgcgtt agagataaac cagttcacgc cggagccccg tgagggaagc 120
gtctccgttg ggtccggccg ctctgcggga ctctgaggaa aagctcgcac caggtggacg 180
cggatctgtc aacatgggta aaggagaccc caacaagccg cggggcaaaa tgtcctcgta 240
cgccttcttc gtgcagacct gccgggaaga gcacaagaag aaacacccgg actcttccgt 300
caatttcgcg gaattctcca agaagtgttc ggagagatgg aagaccatgt ctgcaaagga 360
gaagtcgaag tttgaagata tggcaaaaag tgacaaagct cgctatgaca gggagatgaa 420
aaattacgtt cctcccaaag gtgataagaa ggggaagaaa aaggacccca atgctcctaa 480
aaggccacca tctgccttct tcctgttttg ctctgaacat cgcccaaaga tcaaaagtga 540
acaccctggc ctatccattg ggatactgc aaagaaattg ggtgaaatgt ggtctgagca 600

```
gtcagccaaa gataaacaac catatgaaca gaaagcagct aagctaaagg agaaatatga    660
aaaggatatt gctgcatatc gtgccaaggg caaaagtgaa gcaggaaaga agggccctgg    720
caggccaaca ggctcaaaga agaagaacga accagaagat gaggaggagg aggaggaaga    780
agaagatgaa gatgaggagg aagaggatga agatgaagaa taaatggcta tcctttaatg    840
atgcgtgtgg aatgtgtgtg tgtgctcagg caattatttt gctaagaatg tgaattcaag    900
tgcagctcaa tactagcttc agtataaaaa ctgtacagat ttttgtatag ctgataagat    960
tctctgtaga gaaaatactt ttaaaaaatg caggttgtag ctttttgatg ggctactcat   1020
acagttagat tttacagctt ctgatgttga atgttcctaa atatttaatg gtttttttaa   1080
tttcttgtgt atggtagcac agcaaacttg taggaattag tatcaatagt aaattttggg   1140
ttttttagga tgttgcattt cgttttttta aaaaaaattt tgtaataaaa ttatgtatat   1200
tatttctatt gtctttgtct taatatgcta agttaatttt cactttaaaa aagccatttg   1260
aagaccagag ctatgttgat ttttttcggt atttctgcct agtagttctt agacacagtt   1320
gacctagtaa aatgtttgag aattaaaacc aaacatgctc atatttgcaa aatgttcttt   1380
aaaagttaca tgttgaactc agtgaacttt ataagaattt atgcagtttt acagaacgtt   1440
aagttttgta cttgacgttt ctgtttatta gctaaattgt tcctcaggtg tgtgtatata   1500
tatatacata tatatatata tatatat                                       1527
```

<210> SEQ ID NO 17
<211> LENGTH: 4927
<212> TYPE: DNA
<213> ORGANISM: Homo sapiens

<400> SEQUENCE: 17

```
cccggcttta tatctatata tacacaggta tatgtgtata ttttatataa ttgttctccg     60
ttcgttgata tcaaagacag ttgaaggaaa tgaattttga aacttcacgg tgtgccaccc    120
tacagtactg ccctgaccct tacatccagc gtttcgtaga aaccccagct catttctctt    180
ggaaagaaag ttattaccga tccaccatgt cccagagcac acagacaaat gaattcctca    240
gtccagaggt tttccagcat atctgggatt ttctggaaca gcctatatgt tcagttcagc    300
ccattgactt gaactttgtg gatgaaccat cagaagatgg tgcgacaaac aagattgaga    360
ttagcatgga ctgtatccgc atgcaggact cggacctgag tgaccccatg tggccacagt    420
acacgaacct ggggctcctg aacagcatgg accagcagat tcagaacggc tcctcgtcca    480
ccagtcccta taacacagac cacgcgcaga acagcgtcac ggcgccctcg ccctacgcac    540
agcccagctc caccttcgat gctctctctc catcacccgc catcccctcc aacaccgact    600
acccaggccc gcacagtttc gacgtgtcct tccagcagtc gagcaccgcc aagtcggcca    660
cctggacgta ttccactgaa ctgaagaaac tctactgcca aattgcaaag acatgcccca    720
tccagatcaa ggtgatgacc ccacctcctc agggagctgt tatccgcgcc atgcctgtct    780
acaaaaaagc tgagcacgtc acggaggtgg tgaagcggtg ccccaaccat gagctgagcc    840
gtgaattcaa cgagggacag attgcccctc ctagtcattt gattcgagta gaggggaaca    900
gccatgccca gtatgtagaa gatcccatca caggaagaca gagtgtgctg gtaccttatg    960
agccacccca ggttggcact gaattcacga cagtcttgta caatttcatg tgtaacagca   1020
gttgtgttgg agggatgaac cgccgtccaa ttttaatcat tgttactctg gaaaccagag   1080
atgggcaagt cctgggccga cgctgctttg aggcccggat ctgtgcttgc ccaggaagag   1140
```

-continued

```
acaggaaggc ggatgaagat agcatcagaa agcagcaagt ttcggacagt acaaagaacg   1200
gtgatggtac gaagcgcccg tttcgtcaga acacacatgg tatccagatg acatccatca   1260
agaaacgaag atccccagat gatgaactgt tatacttacc agtgaggggc cgtgagactt   1320
atgaaatgct gttgaagatc aaagagtccc tggaactcat gcagtacctt cctcagcaca   1380
caattgaaac gtacaggcaa cagcaacagc agcagcacca gcacttactt cagaaacaga   1440
cctcaataca gtctccatct tcatatggta acagctcccc acctctgaac aaaatgaaca   1500
gcatgaacaa gctgccttct gtgagccagc ttatcaaccc tcagcagcgc aacgccctca   1560
ctcctacaac cattcctgat ggcatgggag ccaacattcc catgatgggc acccacatgc   1620
caatggctgg agacatgaat ggactcagcc ccacccaggc actccctccc ccactctcca   1680
tgccatccac ctcccactgc acacccccac ctccgtatcc cacagattgc agcattgtca   1740
gtttcttagc gaggttgggc tgttcatcat gtctggacta tttcacgacc caggggctga   1800
ccaccatcta tcagattgag cattactcca tggatgatct ggcaagtctg aaaatccctg   1860
agcaatttcg acatgcgatc tggaagggca tcctggacca ccggcagctc cacgaattct   1920
cctccccttc tcatctcctg cggaccccaa gcagtgcctc tacagtcagt gtgggctcca   1980
gtgagacccg ggtgagcgt gttattgatg ctgtgcgatt caccctccgc cagaccatct   2040
ctttcccacc ccgagatgag tggaatgact tcaactttga catggatgct cgccgcaata   2100
agcaacagcg catcaaagag gagggggagt gagcctcacc atgtgagctc ttcctatccc   2160
tctcctaact gccagccccc taaaagcact cctgcttaat cttcaaagcc ttctccctag   2220
ctcctcccct tcctcttgtc tgatttctta ggggaaggag aagtaagagg ctacctctta   2280
cctaacatct gacctggcat ctaattctga ttctggcttt aagccttcaa aactatagct   2340
tgcagaactg tagctgccat ggctaggtag aagtgagcaa aaaagagttg ggtgtctcct   2400
taagctgcag agatttctca ttgactttta taaagcatgt tcacccttat agtctaagac   2460
tatatatata aatgtataaa tatacagtat agatttttgg gtgggggca ttgagtattg   2520
tttaaaatgt aatttaaatg aaagaaaatt gagttgcact tattgaccat tttttaattt   2580
acttgttttg gatggcttgt ctatactcct tcccttaagg ggtatcatgt atggtgatag   2640
gtatctagag cttaatgcta catgtgagtg acgatgatgt acagattctt tcagttcttt   2700
ggattctaaa tacatgccac atcaaacctt tgagtagatc catttccatt gcttattatg   2760
taggtaagac tgtagatatg tattcttttc tcagtgttgg tatattttat attactgaca   2820
tttcttctag tgatgatggt tcacgttggg gtgatttaat ccagttataa gaagaagttc   2880
atgtccaaac gtcctcttta gtttttggtt gggaatgagg aaaattctta aaaggcccat   2940
agcagccagt tcaaaaacac ccgacgtcat gtatttgagc atatcagtaa ccccccttaaa   3000
tttaatacca gataccttat cttacaatat tgattgggaa aacatttgct gccattacag   3060
aggtattaaa actaaatttc actactagat tgactaactc aaatacacat ttgctactgt   3120
tgtaagaatt ctgattgatt tgattgggat gaatgccatc tatctagttc taacagtgaa   3180
gttttactgt ctattaatat tcagggtaaa taggaatcat tcagaaatgt tgagtctgta   3240
ctaaacagta agatatctca atgaaccata aattcaactt tgtaaaaatc ttttgaagca   3300
tagataatat tgtttggtaa atgtttcttt tgtttggtaa atgtttcttt taaagaccct   3360
cctattctat aaaactctgc atgtagaggc ttgtttacct ttctctctct aaggtttaca   3420
ataggagtgg tgatttgaaa aatataaaat tatgagattg gttttcctgt ggcataaatt   3480
gcatcactgt atcattttct tttttaaccg gtaagagttt cagtttgttg gaaagtaact   3540
```

-continued

```
gtgagaaccc agtttcccgt ccatctccct tagggactac ccatagacat gaaaggtccc   3600

cacagagcaa gagataagtc tttcatggct gctgttgctt aaaccactta aacgaagagt   3660

tcccttgaaa ctttgggaaa acatgttaat gacaatattc cagatctttc agaaatataa   3720

cacatttttt tgcatgcatg caaatgagct ctgaaatctt cccatgcatt ctggtcaagg   3780

gctgtcattg cacataagct tccattttaa ttttaaagtg caaaagggcc agcgtggctc   3840

taaaaggtaa tgtgtggatt gcctctgaaa agtgtgtata tattttgtgt gaaattgcat   3900

actttgtatt ttgattattt ttttttcttt cttgggatag tgggatttcc agaaccacac   3960

ttgaaacctt tttttatcgt ttttgtattt tcatgaaaat accatttagt aagaatacca   4020

catcaaataa gaaataatgc tacaatttta agaggggagg gaagggaaag ttttttttta   4080

ttattttttt aaaattttgt atgttaaaga gaatgagtcc ttgatttcaa agttttgttg   4140

tacttaaatg gtaataagca ctgtaaactt ctgcaacaag catgcagctt tgcaaaccca   4200

ttaaggggaa gaatgaaagc tgttccttgg tcctagtaag aagacaaact gcttccctta   4260

ctttgctgag ggtttgaata aacctaggac ttccgagcta tgtcagtact attcaggtaa   4320

cactagggcc ttggaaattc ctgtactgtg tctcatggat ttggcactag ccaaagcgag   4380

gcacccttac tggcttacct cctcatggca gcctactctc cttgagtgta tgagtagcca   4440

gggtaagggg taaaaggata gtaagcatag aaaccactag aaagtgggct taatggagtt   4500

cttgtggcct cagctcaatg cagttagctg aagaattgaa aagtttttgt ttggagacgt   4560

ttataaacag aaatggaaag cagagttttc attaaatcct tttacctttt tttttcttg    4620

gtaatcccct aaaataacag tatgtgggat attgaatgtt aaagggatat ttttttctat   4680

tatttttata attgtacaaa attaagcaaa tgttaaaagt tttatatgct ttattaatgt   4740

tttcaaaagg tattatacat gtgatacatt ttttaagctt cagttgcttg tcttctggta   4800

ctttctgtta tgggcttttg gggagccaga agccaatcta caatctcttt ttgtttgcca   4860

ggacatgcaa taaaatttaa aaaataaata aaaactaatt aagaaattga aaaaaaaaaa   4920

aaaaaaa                                                             4927
```

<210> SEQ ID NO 18
<211> LENGTH: 1954
<212> TYPE: DNA
<213> ORGANISM: Homo sapiens

<400> SEQUENCE: 18

```
cgcatgcgca ggcgacagct catggcgttc agggcctgac ggttgctagg gtgacaggga     60

cacaacatgg cggcgggatc tctaacgctc tccttcgagg gaccaccacg gagatcctag    120

tgcgggaccc cgcctcaggg aagtggaaag caggggggaca accttcctgc ttccttcttt   180

tccgtccagt gtcggcaagg ggttgtcacc ggcttccgca tccaagatga agaactataa    240

agcaattggc aaaataggag agggaacgtt ttctgaagtt atgaagatgc aaagcctgag    300

agatggaaac tactatgcat gtaaacaaat gaagcagcgc tttgaaagta ttgagcaagt    360

caacaaccta cgagagatcc aagcactgag gcgcctgaat ccgcacccaa acattcttat    420

gttgcatgaa gtggtttttg acagaaaatc tggttctctt gcactaatat gtgaacttat    480

ggacatgaat atttatgagc taatacgagg gagaagatac ccattatcag aaaaaaaaat    540

tatgcactat atgtaccagt tatgtaagtc cctggatcat attcacagaa atggaatatt    600

tcacagagat gtaaaaccag aaaatatact aataaagcag gatgtcctga aattagggga    660
```

ctttggctcc tgccggagtg tctattccaa gcagccgtac acggaataca tctccacccg 720
ctggtaccgg gccccggagt gtctcctcac tgatgggttc tacacgtaca agatggacct 780
gtggagcgcc ggctgtgtgt tctacgagat cgccagtctg cagcccctct ttcctggagt 840
aaatgaactg gaccaaatct caaaaatcca cgatgtcatc ggcacacccg ctcagaagat 900
cctcaccaag ttcaaacagt cgagagctat gaattttgat tttcctttta aaaagggatc 960
aggaatacct ctactaacaa ccaatttgtc cccacaatgc ctctccctcc tgcacgcaat 1020
ggtggcctat gatcccgatg agagaatcgc cgcccaccag gccctgcagc acccctactt 1080
ccaagaacag aggaaaacag agaagcgggc tctgggcagc cacagaaaag ctggctttcc 1140
ggagcaccct gtggcaccgg aaccactcag taacagctgc cagatttcca aggagggcag 1200
aaagcagaaa cagtccctaa agcaagagga ggaccgtccc aagagacgag gaccggccta 1260
tgtcatggaa ctgcccaaac taaagctttc gggagtggtc agactgtcgt cttactccag 1320
ccccacgctg cagtccgtgc ttggatctgg aacaaatgga agagtgccgg tgctgagacc 1380
cttgaagtgc atccctgcga gcaagaagac agatccgcag aaggacctta agcctgcccc 1440
gcagcagtgt cgcctgccca ccatagtgcg gaaaggcgga agataactga gcagcaccgt 1500
cgtctcgact tcggaggcaa caccaagccc gaccgggcca ggcctgggtg atctgctgct 1560
gagacgccac ggagggctgg ggatgcgcct gcgtccgttt cgcgctggcc ggggctctgg 1620
gtgctgccct gcgccctgcc gcacccgcgg cccgcgcagc tgcctaggat gttctgggct 1680
aatatacttg taaaaccacc gcattctagg gttttctttc attttcgtta agaatttggg 1740
gcaggaaata ctttgtaact ttgtatatga atcaaaacaa acgagcaggc atttctgtga 1800
tgtgttgggc gtggttggaa ggtgggttct gcgtgtccct tcccagcgct gctggtcagt 1860
cgtggagcgc catcatgtct taccagtgac gctgctgaca cccctgactt ttattaaaga 1920
ataagctgtc gttaaaaaaa aaaaaaaaaa aaaa 1954

<210> SEQ ID NO 19
<211> LENGTH: 4031
<212> TYPE: DNA
<213> ORGANISM: Homo sapiens

<400> SEQUENCE: 19
cctcagtcct cccttggtgg cctcgccgcg gctctgctgg gagacccggc gctggcggct 60
gctgaggccg gagcggaggg cccgggagcg tgggagcagg agggtggcgc gcagccggtt 120
tcgcgtttgg tcggccaggg agctgccttc ccaccagccg gtcgaggaaa caacgggtcg 180
ggcttccggg gagagggccc acacagtctc ctcgccggca ccggcctcct ccatttttcc 240
gggccttgcg tggagggttt tggcggatgt ttttgaacga aggaatgtca tcggggctct 300
ctcgagcccc tcaccccgcc agctactctg ggggtggcgt ggcatagtga gaggagcgct 360
aagttgttgg gaggcctggg tccttttccc cacgactctg aaagaggaca gcgttcccaa 420
tgtcccagtt taagcgccag cggatcaacc cgcttccagg gggacgcaac ttctcaggca 480
cagcttcaac atctcttctg ggccctcctc ctggtttgct cactcctcct gtggccacag 540
aactgtccca gaatgccagg caccttcagg gtggggagaa acagcgggtc ttcactggta 600
ttgttaccag cttgcatgac tactttgggg ttgtggatga agaggtcttt tttcagctaa 660
gtgtggtgaa gggccgtctg ccccagctgg gtgagaaggt gctggtgaag gctgcataca 720
acccaggcca ggcagtgccc tggaatgctg tcaaggtgca aacgctctcc aaccagcccc 780
tactgaagtc cccagcacct cctcttctgc atgtagcagc cctgggccag aagcaaggga 840

-continued

```
tcctgggagc tcagcctcag ttgatcttcc agcctcaccg gattccccca ctctttcctc    900
agaagcctct gagtctcttc caaacatccc acacacttca cctgagccac ctgaacagat    960
ttcctgcccg gggccctcat ggacggttgg atcagggccg aagtgatgac tatgactcca   1020
agaaacgcaa acagcgggct ggtggagagc cctggggtgc taagaagcca aggcatgacc   1080
tgcctcctta ccgggtccac ctcactcctt acactgtgga cagccccatc tgtgacttcc   1140
tagaactcca gcgccgttac cgcagcctcc tggtcccctc agattttctg tccgtgcatc   1200
tgagttggct atcagccttc cccctgagcc agcccttttc cctccatcat ccaagccgga   1260
tccaggtctc ttctgaaaag gaggcagctc cagacgctgg tgctgagccc atcactgcag   1320
acagtgaccc cgcttatagt tcgaaggtac tgctgctctc ttccccgggg ttggaggaat   1380
tgtatcgttg ttgcatgctc tttgtggatg acatggctga gccaagggag acgccagagc   1440
atcctctgaa gcagattaag tttttgctgg gcaggaaaga agaggaggca gtgctggttg   1500
ggggtgaatg gtctccttcc ctggatggcc tcgaccccca ggctgacccg caggtgctgg   1560
tgcgtaccgc catccgctgt gcgcaggccc agactggcat tgatttgagc ggctgtacca   1620
agtggtggcg ctttgccgag tttcagtacc tgcagccggg acccccccgg cggcttcaga   1680
cagtggtggt gtacctgccg gatgtctgga ccatcatgcc tactttggag gagtgggagg   1740
ccctgtgcca gcagaaagct gcagaggcag ctcccccaac ccaggaggca caaggggaaa   1800
cggagcctac tgaacaggca cctgatgcct tggagcaagc agcagacact tctagacgga   1860
acgcagaaac tccagaggcc accacacagc aggaaacgga cactgatctc ccagaggccc   1920
ctccaccccc cctagaacct gctgtcatcg cacgccctgg ctgtgtaaac ctgtccctcc   1980
atgggattgt ggaggatcgg aggccaaagg aaaggatctc ttttgaggtg atggtgctgg   2040
ccgagctgtt tctggagatg ctccagaggg attttggcta tagagtttat aagatgctac   2100
tgagccttcc tgaaaaggtc gtgtccccac ctgaacctga gaaggaggag gcggccaagg   2160
aagaagccac caaggaggaa gaagccatca aagaggaggt ggtcaaggag cccaaggatg   2220
aggcacagaa tgagggcccg gctacagagt cagaggcccc gctgaaggag gatgggcttt   2280
tgcccaaacc actctcttct gggggagagg aagaagaaaa accccggggc gaggcttctg   2340
aggacctgtg tgagatggcc ctggacccag aactgttgct tctgagggat gatggagagg   2400
aggagtttgc aggagcaaag ctggaggatt cggaggtccg gtccgttgcc tcaaaccagt   2460
cagagatgga gttctcttca cttcaggaca tgcccaagga gctggatccc tctgctgtgc   2520
tccccttaga ctgtctgctt gcttttgtgt tctttgatgc caactggtgt ggctacttgc   2580
accggcgaga cttagagagg atcctcctta cccttgggat ccggctcagt gcagagcagg   2640
ccaagcagct ggtcagcagg gtggtgaccc agaacatctg ccagtaccgg agccttcagt   2700
acagccgcca ggagggcctg gatggtggcc ttcccgagga ggtgctcttc ggaaacctgg   2760
acctgctgcc ccctcctggg aaaagcacga agccaggtgc tgcccccaca gaacacaaag   2820
ccttggtgtc ccacaatggc agcctgatta acgtggggag cctgctgcag cgcgcggagc   2880
agcaggacag cggccggctc tacctagaga acaagatcca cacactggag ctgaagctgg   2940
aggagagcca taaccgtttc tcagccactg aagtaaccaa taagacgctg gcggcagaga   3000
tgcaggagct gcgagtccgg ctggcggagg ccgaggagac cgcccggacg gcggagcgac   3060
agaagagcca gctccagcgg ctgctgcagg agctccgcag gcgtctgacc cccctgcagc   3120
tggagatcca gcgggtggtg gaaaaggctg acagctgggt ggagaaggag gagccggcac   3180
```

-continued

```
ctagcaactg acggcctcgc acggaactgc catcctgtga gggcagcggt ggcgcccggc   3240
aaagttggag cccttgcggt accagaaagc agcgagagcg agacctggga gccagggcag   3300
gggtggctga ccccatgctc agcctctagg ggacggcagg ccatcaggct gggggctgtg   3360
ctatgtggga tggatgtgtg aggaaccccg gttccactta acaactaaat acaacatctt   3420
ttgcacccct agaatgtcat tttgccctca accttggtat ttctcctggg gcccttttag   3480
tcttgtgctg actttctcct gtcctcttcc agtttagaat aagacagggg agaaaaaggc   3540
ttttcgagtg tgggacaagg tctgatgtca gtgaacggaa ctgaagagca agacatggag   3600
cctggctggg gctaagcagc cccctcctcc ggatggcaca ggctctgcta ggttccggac   3660
acaggcttct gggggaaggg tctcccttgg ccatcacggg aatggagtcc atgctagaaa   3720
gagctcagtg ttgggctggg tttgccagta gaacactgcg ttccagtcac cccggtcttg   3780
ccagaagaaa ccagcacctc tttcccgtgg ctcctgtgtt cagaatgtgg tattggctct   3840
ggcccagcct tctcccctgt tacccataat tcttgcctct ttccataatc cgtggtttca   3900
gtttgacttt gtatataaag ttggggtttt tttttttttt ttttggcttg ttttttaaat   3960
aaaccaaagt caaaaacaaa aaaaaaaaaa aaaaaaaaaa aaaaaaaaaa aaaaaaaaaa   4020
aaaaaaaaaa a                                                        4031
```

<210> SEQ ID NO 20
<211> LENGTH: 5423
<212> TYPE: DNA
<213> ORGANISM: Homo sapiens

<400> SEQUENCE: 20

```
tttctcgctc gctcccgttc cccggacgcg gcggatgagc cggcccccgct ggggaaggct     60
ccgggcggcg gcgggcggcc gggaggaggc tgcgtgctcg gggctggggc tgcgagcggg    120
gtgattttgt attaaaatga ggaggaggaa gaagaggcac ccacagcggc agcggcggcg    180
gcggcggcag cagcagcagg agcagcggcg gagagggctg cagcccgggc ggacgcgcgg    240
agccgagcgg ggcacggcgg cggcagcgac agcggccggg atgagtcaac taataattta    300
atgggggcag agacggcagc gaggggtaga gctagcgagg gagagagcga gagaagcagc    360
cccgtccggg gactcgcgct cacactcacg cacacacaca aacacacaca cacctctccc    420
tgtgccaccc agcaacaccc ggcctcgtca caacaacaac agccgcggcc gccctctatc    480
ctgcccgggg gcccagccga aagccagggc gactctagag gacgctgccc gcccccctct    540
ttcatttcgg gaaactcctg atcagttttg tcggggtttc tgggtttctt ttcccccaaa    600
gtcctagtgc cattgtggtg ctcgttgttt acctcggact ctggacgagt gagagcttgg    660
cgactttttg gggggagggg gcggggagtt tgtcgctgcc taggcggtgg aggtggctgg    720
gggtgccttc tgatcttcct cctcctcccc ctccccccga acctcttctc tcctcacttg    780
ctgggacccc agacgctcac agccccgcgt caatgggcag ggagagggtc cttgcggctg    840
ttgtcagcga gggcagaatc aaaagtggca ttttagtgcc tttccggggc ttttctcgcg    900
accccctgcc ccccaccctc gctgtccccc gctagatgcc ctcgttgggg gtgcgaggct    960
gtggggaaaa gtttaaggtt tgttaatatt agtcgcgatt gttggcgagg ggggtggggg   1020
tgattggaag ggaggcgagg tggccttccc aatgcgcgtt attcggggtt attgaagaat   1080
aatattgcaa gtgacagcca gaagtagact ttctgtcctc acaccgaaga acccgagtga   1140
gcaggaggga gggagagacg cgaagagacc ttttttcctt tttggagacc ttgtccgcag   1200
tgattttttt ttttttaaga gaatcctcag tcaccacgtc gtttccccag caccatcaca   1260
```

-continued

```
gtgtacagct cataacgggt tttgctttgt ttttacgatt tccccccaac gaatcacttg   1320
tcagatcaat tttatcttct tcctcctccc tgcttcccac tctcccctcc tccccatcgc   1380
aaaccctgtt ctctgaggtt agacatttta caaaccccta tatgttggtt ttcgaattgt   1440
gatttttttt ttaaacccct ttctcatggc tactcttcta gacgtttatt tctgcccttc   1500
ccccgcttag gggggcgggg gtaggggaaa ggaaaataat acaatttcag gggaagtcgc   1560
cttcaggtct gctgcttttt tatttttttt tttttaatta aaaaaaaaaa ggacatagaa   1620
aacatcagtc ttgaacttct cttcaagaac ccgggctgca aaggaaatct cctttgtttt   1680
tgttatttat gtgctgtcaa gttttgaagt ggtgatcttt agacagtgac tgagtatgga   1740
tcatttgaac gaggcaactc aggggaaaga acattcagaa atgtctaaca atgtgagtga   1800
tccgaagggt ccaccagcca agattgcccg cctggagcag aacgggagcc cgctaggaag   1860
aggaaggctt gggagtacag gtgcaaaaat gcagggagtg cctttaaaac actcgggcca   1920
tctgatgaaa accaacctta ggaaaggaac catgctgcca gttttctgtg tggtggaaca   1980
ttatgaaaac gccattgaat atgattgcaa ggaggagcat gcagaatttg tgctggtgag   2040
aaaggatatg cttttcaacc agctgatcga aatggcattg ctgtctctag gttattcaca   2100
tagctctgct gcccaggcca aagggctaat ccaggttgga aagtggaatc cagttccact   2160
gtcttacgtg acagatgccc ctgatgctac agtagcagat atgcttcaag atgtgtatca   2220
tgtggtcaca ttgaaaattc agttacacag ttgccccaaa ctagaagact tgcctcccga   2280
acaatggtcg cacaccacag tgaggaatgc tctgaaggac ttactgaaag atatgaatca   2340
gagttcattg gccaaggagt gccccctttc acagagtatg atttcttcca ttgtgaacag   2400
tacttactat gcaaatgtct cagcagcaaa atgtcaagaa tttggaaggt ggtacaaaca   2460
tttcaagaag acaaaagata tgatggttga aatggatagt ctttctgagc tatcccagca   2520
aggcgccaat catgtcaatt ttggccagca accagttcca gggaacacag ccgagcagcc   2580
tccatcccct gcgcagctct cccatggcag ccagccctct gtccggacac ctcttccaaa   2640
cctgcaccct gggctcgtat caacacctat cagtcctcaa ttggtcaacc agcagctggt   2700
gatggctcag ctgctgaacc agcagtatgc agtgaataga cttttagccc agcagtcctt   2760
aaaccaacaa tacttgaacc accctccccc tgtcagtaga tctatgaata agcctttgga   2820
gcaacaggtt tcgaccaaca cagaggtgtc ttccgaaatc taccagtggg tacgcgatga   2880
actgaaacga gcaggaatct cccaggcggt atttgcacgt gtggctttta acagaactca   2940
gggcttgctt tcagaaatcc tccgaaagga agaggacccc aagactgcat cccagtcttt   3000
gctggtaaac cttcgggcta tgcagaattt cttgcagtta ccggaagctg aaagagaccg   3060
aatataccag gacgaaaggg aaaggagctt gaatgctgcc tcggccatgg gtcctgcccc   3120
cctcatcagc acaccaccca gccgtcctcc ccaggtgaaa acagctacta ttgccactga   3180
aaggaatggg aaaccagaga acaataccat gaacattaat gcttccattt atgatgagat   3240
tcagcaggaa atgaagcgtg ctaaagtgtc tcaagcactg tttgcaaagg ttgcagcaac   3300
caaaagccag ggatggttgt gcgagctgtt acgctggaaa gaagatcctt ctccagaaaa   3360
cagaaccctg tgggagaacc tctccatgat ccgaaggttc ctcagtcttc ctcagccaga   3420
acgtgatgcc atttatgaac aggagagcaa cgcggtgcat caccatggcg acaggccgcc   3480
ccacattatc catgttccag cagagcagat tcagcaacag cagcagcaac agcaacagca   3540
gcagcagcag cagcaggcac cgccgcctcc acagccacag cagcagccac agacaggccc   3600
```

-continued tcggctcccc ccacggcaac ccacggtggc ctctccagca gagtcagatg aggaaaaccg 3660
acagaagacc cggccacgaa caaaaatttc agtggaagcc ttgggaatcc tccagagttt 3720
catacaagac gtgggcctgt accctgacga agaggccatc cagactctgt ctgcccagct 3780
cgaccttccc aagtacacca tcatcaagtt ctttcagaac cagcggtact atctcaagca 3840
ccacggcaaa ctgaaggaca attccggttt agaggtcgat gtggcagaat ataaagaaga 3900
ggagctgctg aaggatttgg aagagagtgt ccaagataaa aatactaaca cccttttttc 3960
agtgaaacta gaagaagagc tgtcagtgga aggaaacaca gacattaata ctgatttgaa 4020
agactgagat aaaagtattt gtttcgttca acagtgccac tggtatttac taacaaaatg 4080
aaaagtccac cttgtcttct ctcagaaaac ctttgttgtt cattgtttgg ccaatgaatc 4140
ttcaaaaact tgcacaaaca gaaaagttgg aaaaggataa tacagactgc actaaatgtt 4200
ttcctctgtt ttacaaactg cttggcagcc ccaggtgaag catcaaggat tgtttggtat 4260
taaaatttgt gttcacggga tgcaccaaag tgtgtacccc gtaagcatga aaccagtgtt 4320
ttttgttttt tttttagttc ttattccgga gcctcaaaca agcattatac cttctgtgat 4380
tatgatttcc tctcctataa ttatttctgt agcactccac actgatcttt ggaaacttgc 4440
cccttattta aaaaaaaaaa agaaaaaaaa gagtttgtta ctctattgta tgttacaaaa 4500
gaactataga ctgtggaatg cagtttaaag atgacatatg ccaacaaatg ccttgtatta 4560
tatggcactg ccgtaattca aatttgtttt tattttggaa ataaaagttc actgtacttt 4620
tttttcattc tcattgttac atgatttttt aaaaaaagga aaagaaaatg tgaaacacaa 4680
tttagtcctc attatttatt tgtagatcct gcagcatcat gttgtaatta attttttgga 4740
agtttccgtt aaatgtaata ttgcttctct tgttaccata ctgattcttt tctatttata 4800
aatgtatttt gatgggcagt aaaacaaagt gtcttaaaag ttttaaatag agaaaatgtg 4860
ctttacacag ttgcctataa aaagtgctct atgttatcca agcaattcat actataagct 4920
tcactcttat tgttgtatgc aatttttact atcatgcaaa taagcttagg taaataaaac 4980
taatagatca ccttagaaaa ttatgcaatt aatgtgaaaa taattgatgt ttgcaatgtg 5040
tcttcctttg gtttacaatc aattttaaag ctacatctgt ataaaatttc tgtataaagg 5100
tgtatttctt ttttatgagt ttatggctat gaaaacagct attttgttac agctggctgt 5160
ttttataagt gtatcacaat tttctttatg cagaaatgtt ctgactagga gtggttattg 5220
actgtaacta cacaattaaa attgtttgta tcgtatgaca tggtagggtt tgtctgctta 5280
tgtgaagtaa ctaaaggagt caaaggatgg ccctctcatt taggtgcatg ttaataactt 5340
gttatttcac tgattttaaa aagagcaatt gacaagttac ttgaaacact gtaaatttaa 5400
atcacaaaca catgctcatt ttt 5423

<210> SEQ ID NO 21
<211> LENGTH: 6856
<212> TYPE: DNA
<213> ORGANISM: Homo sapiens

<400> SEQUENCE: 21
cggtgcattc tgggtcctgg caatatggcg tcctccttga tgggctgatg agatgagttt 60
cactgtagct ccaaaccaga gggcaaagct cccatgaccc aataagccca cattgtccct 120
ttcctccgtg gttccgtgtc gcccgtttct caggactcgt tctcaggcag gagagagcct 180
cggggctgaa ggccaggacc agccaggccg cgcggacctg aggttgagga accgggtgca 240
ggcgagcacg atgggccggt cgtggctctg gttgcagcag ctcagacgag tgcgggaccc 300

-continued

```
gcagggctga gagtggctgg aggagaccca gggccctttg aacccgatcc cttggccgga    360
gacctcagcc cagtcggccc agtgggcgaa ccggcaccaa gagcggcctg cctgtcttcg    420
gaactgctga ggcggtggag gccgagagca gggtcatcgt gaggcctgaa gtctcttacg    480
cttttggcag ctcccctcgc agcccctctg gaaacgtaca gcctcaggag cagccagtgg    540
cttgggacct ggggtggtgt gtgtctgcgg agcttcttgg gctgccccat ttcctagcgg    600
cccccacctc cccacttccc gctcagagtt agagataagg atctcagact tttgcctgag    660
taagggtctc cgcactcttt atccatttgg ttttcgattt cccgtttttg tttcttattt    720
caccaattct ggtacacgct agtttttaag gctggaggtt ctcgagcgct tgctgccaag    780
gactccccca ccccctcccc cactgatgga gtccgaaatg ctgcaatcgc ctcttctggg    840
cctgggggag gaagatgagg ctgatcttac agactggaac ctacctttgg cttttatgaa    900
aaagaggcac tgtgagaaaa ttgaaggctc caaatcctta gctcagagct ggaggatgaa    960
ggatcggatg aagacagtca gtgttgcctt agttttgtgc ctgaatgttg gtgtggaccc   1020
tcccgatgtg gtgaagacca cgccctgtgc acgcttggaa tgctggatcg atcctctgtc   1080
gatgggtcct cagaaagctc tggaaaccat cggtgcaaat ttacagaagc agtacgagaa   1140
ctggcagcca agggcccggt acaagcagag ccttgaccca actgtggatg aagtcaagaa   1200
gctctgcacg tccttacgtc gcaacgccaa ggaggagcga gtcctctttc actacaatgg   1260
ccacggggtg ccccggccca cagtcaacgg ggaggtctgg gtcttcaaca agaactacac   1320
gcagtacatc cctctgtcca tatatgacct gcagacgtgg atgggcagcc cgtcgatctt   1380
cgtctacgac tgctccaatg ctggcttgat cgtcaagtcc ttcaagcagt tcgcactaca   1440
gcgggagcag gagctggagg tagctgcaat caacccaaat caccctcttg ctcagatgcc   1500
tttgcctccg tcgatgaaaa actgcatcca gctggcagcc tgcgaggcca ccgagctgct   1560
gcccatgatc cccgacctcc cggctgacct attcacctcc tgcctcacca cccccatcaa   1620
gatcgccctg cgctggtttt gcatgcagaa atgtgtcagt ctggtgcctg gcgtcacact   1680
ggatttgata gaaaagatcc ctggccgcct gaacgacagg aggacgcccc tgggtgaact   1740
gaactggatc ttcacagcca tcacagacac catcgcgtgg aacgtgctcc cccgggatct   1800
cttccaaaag ctcttcagac aggacttgct ggtggctagt ctgtttcgaa atttttttatt   1860
ggcggaaagg attatgaggt cgtataactg cactcccgtc agcagcccgc gtctgccgcc   1920
cacgtacatg cacgccatgt ggcaagcctg ggacctggct gttgacatct gtctgtctca   1980
gctgccgacg atcatcgagg aaggcactgc gtttcggcac agcccgttct tcgccgagca   2040
gctgaccgca ttccaggtgt ggctcaccat gggcgtggag aaccgaaacc cacccgaaca   2100
gctgcccatc gtcctgcagg tgctgttaag ccaagtgcac cggctgagag cattggactt   2160
gcttggaaga tttttggacc tgggtccctg ggcagtgagc ctggccttgt ctgtcggcat   2220
cttcccctac gtgctgaagc tgctccagag ctcggcccga gagctgcggc cacttctcgt   2280
tttcatctgg gccaagatcc tcgcagtgga cagctcgtgc caagcggacc tcgtgaagga   2340
caacggccac aagtacttcc tgtcggtcct ggcggacccc tacatgccag ctgaacaccg   2400
gaccatgacg gctttcattc tcgccgtgat cgtcaacagc tatcacacgg ggcaggaagc   2460
ctgccttcag ggaaacctca ttgccatctg cctggagcag ctcaacgacc cgcacccctt   2520
gctgcgccag tgggtggcca tctgcctcgg caggatctgg cagaacttcg actcggcgag   2580
gtggtgcggc gtgagggaca gcgctcatga gaagctctac agcctcctct ccgaccccat   2640
```

```
tcccgaggtc cgctgcgcag cggtcttcgc ccttggcacg ttcgtgggca actctgcaga   2700
gaggacggac cactccacca ccatcgacca caacgtggcc atgatgctgg cccagctggt   2760
cagcgacggg agccccatgg tccggaagga gctggtggtg gctctgagtc atcttgtggt   2820
tcagtatgaa agcaatttct gcaccgtggc cctgcagttc atagaagagg aaaagaacta   2880
cgccttgcct tctccagcaa ccacagaggg agggagtttg accccagtgc gagacagccc   2940
gtgcaccccc agacttcgtt ctgtgagctc ctatggaaac atccgtgctg tcgccacagc   3000
caggagcctc aacaaatctt tgcagaacct gagtttgaca gaggaatctg gtggcgcggt   3060
ggcgttctcc cccggaaacc tcagcaccag cagcagcgcc agcagcaccc tgggcagccc   3120
cgagaatgag gagcatatcc tgtccttcga gaccatcgac aagatgcgcc gcgccagctc   3180
ctactcctcc ctcaactccc tcatcggagt ttcctttaac agtgtttaca ctcagatttg   3240
gagagtcctg ctgcacctgg ctgctgaccc ctatccagag gtctcggacg tggccatgaa   3300
agtactcaac agcatcgcct acaaggccac cgtgaacgcc cggccgcagc gcgtcctgga   3360
cacctcctcc ctcacgcagt cggcccccgc cagccccacc aacaagggcg tgcacatcca   3420
ccaggcgggg ggctcccctc cggcgtccag caccagcagc tccagcctga ccaacgatgt   3480
ggccaagcag ccggtcagcc gagacttgcc ttctggccgg ccgggcacca caggccccgc   3540
tggggcgcag tacacccctc actcccacca gttcccccgg acacggaaga tgttcgacaa   3600
gggcccagag cagactgcgg acgacgcgga cgatgctgct ggacacaaaa gtttcatctc   3660
cgccacggtg cagacggggt tctgcgactg gagcgcccgc tattttgccc agcccgtcat   3720
gaagatccca gaagagcacg acctggagag tcagatccgc aaggagcggg agtggcggtt   3780
cctgcgaaac agccgtgtca ggaggcaggc ccagcaagtc attcagaagg gcattacgag   3840
attggacgac caaatatttc tgaacaggaa ccccggcgtc ccctctgtgg tgaaattcca   3900
ccccttcacg ccgtgcatcg ccgtagccga caaggacagc atctgctttt gggactggga   3960
gaaaggggag aagctggatt atttccacaa tgggaaccct cggtacacga gggtcactgc   4020
catggagtat ctgaacggcc aggactgctc gcttctgctg acggccacag acgatggtgc   4080
catcagggtc tggaagaatt ttgctgattt ggaaaagaac ccagagatgg tgaccgcgtg   4140
gcaggggctc tcggacatgc tgccaacgac gcgaggagct gggatggtgg tggactggga   4200
gcaggagacc ggcctcctca tgagctcagg agacgtgcgg atcgtccgga tctgggacac   4260
agaccgtgag atgaaggtgc aggacatccc tacgggcgca gacagctgtg tgacgagtct   4320
gtcctgtgat tcccaccgct cactcatcgt ggctggcctc ggtgacggct ccatccgcgt   4380
ctacgacaga aggatggcac tcagcgaatg ccgcgtcatg acgtaccggg agcacacagc   4440
ctgggtggtg aaggcctccc tgcagaagcg tcccgacggc cacatcgtga gtgtgagcgt   4500
caatggagat gtgcgcatct ttgatccccg gatgcctgag tcggtaaatg tgcttcagat   4560
cgtgaagggg ctgacggccc tggacatcca cccccaggcg gacctgatcg catgtggctc   4620
cgtcaatcag ttcaccgcca tctacaacag cagcggagag ctcatcaaca acatcaagta   4680
ctacgacggc ttcatgggcc agcgggtcgg cgccatcagc tgcctggcct tccacccgca   4740
ctggcctcac ctggccgtgg gaagcaacga ctactacatc tccgtgtact cggtggagaa   4800
gcgtgtcaga tagcggcgtg acccgggccc accaggccac ggccgcctgc tgtacatagt   4860
gaagctgtca ctcgccgggg cacggggcgt cggctgctgc ggccccgcag tgtgaacgtt   4920
ggctgctgcc ttagctgctg atgacggcag gagggccctg ctactcgctt ttgtctgtct   4980
tcgctgtcgt gtctggaatg tcagggaagg ggagggctcg ggttgacggt ggcttcccac   5040
```

-continued tgagcaccag catccaggtg cacccccgcg gccacggcgc ctctgtccct ctcctgttct 5100
gtgtttctct gagacgctga aaggggaaac acctcacttt atttccatgt aatcagagca 5160
ttagctgcag aaaaaccccc cgacagagcc ctggcggaga ggcaggcgct ggggctccta 5220
cgggtccctg gggcagctgt ccccatcagg ccaagagcga gcgagaggcg ctgccccagc 5280
caggcccacc acctctcaca gtcagtgcac gcaagcaggg acatttccta gccagctggg 5340
ggacactgga aattcgggaa accaagagag aggaagaagg agacgcccct ccaactggcg 5400
ggtgtgaagg aagccgccca ggggtccggg ctgtccttgg ccgctggcag catcactgag 5460
caggaagcgc acagcccacc ctccccgcac ctccaggtct ctggactcca gttttggccc 5520
ctctcacaca gagctgtcag caggggccgc tgtggcggtg cacaggggag gcaggtcctt 5580
ggcgaggtag cccctgcctt aatccacggg gctcctttcc ctccgaaggg ctgctcttcc 5640
ccacaggcgc ggggacagca gcccgacctg tggtctccat gcctgtgccc tcacacaggt 5700
gtagcacacg catgtgcaga tggcaccacg gccggcacct gggggcacac acatgcaggc 5760
ggcgtggtct ccctgctctg tccccacacg ttcctcacat acaggcaaga ggcactgccg 5820
ggtcccggac ggctccgggt gacaccagcc ccgtctccag ccttgagccg cccatgctga 5880
tgcgacctcg gctgacagct gggcctgtgg tgcagacagg agctgtgtgg acagtcccgc 5940
ccaggagggg ccgcagggcg tgtatgagca gttttgcaaa cagaacacaa ccacaatgat 6000
ggtattttga aaagtgttct ttccgtgttc gtcgggaatc aggattattg agaggtgaag 6060
gagccaggtg gcttcattct ggcggtgaga ggcccacgac cacgggagtg agagctggtg 6120
tggcgaggcc cggctctcct gcggtgtggc tggtggcctg ccgtggccaa gagcatcttc 6180
tgggtggatg gaaccctgcc tggtcacatt tggccagaga cacacctggc cctcaggggg 6240
ctgagctgga gactgagctg gggctggccg ggacgtgaca aggcaggaca gaggcggccc 6300
ctccgctgct cctttttgga atgcgagctc ccaccagaag aaggttccgg cacgaatccc 6360
atccccacgt ctgggccgag aaagcagccc gggtccggaa ggtgtagaga gtcccggcct 6420
cactcagctc acagggcgtg ccaggcggca acaccagaat cttccagaag cccagctcca 6480
cccgcacacg cagcttccca tccagtcctt caactcaatt cttacccaac acgcgtttct 6540
gtttgttttg agacaaaatc accacctgtc aaaaggcagg tggctccaga ggggtcaaga 6600
cccccccccg cccccgctcc accctggagc ccaccccccat gggcaccgcg tgccgcctgc 6660
acgtgggctg tcttcacagg tctgatgtga aaattcaatc acgacgttaa ccggctcgag 6720
agagcgccgg cctagaggct cattatctat ttattttacc aaacgcgaat tgagacggac 6780
tttgacaaaa cacgaaatgg taatgtgaag ctaagagcag agagtgacca acagtaaaca 6840
acacgcgcag actccg 6856

<210> SEQ ID NO 22
<211> LENGTH: 2785
<212> TYPE: DNA
<213> ORGANISM: Homo sapiens

<400> SEQUENCE: 22
gatccgccac catggctgaa ggagagaatg aagtgagatg ggatggactc tgcagcagag 60
attcaactac tagggagaca gcattggaaa acattaggca aaccattttg aggaaaaccg 120
agtatcttcg ttcggtgaaa gaaacacctc atcgtccatc agacgggctt tcaaataccg 180
agtcttcgga tgggttgaat aagctacttg ctcatctgct tatgctttct aagaggtgtc 240

-continued

```
ccttcaaaga tgtgagagag aaaagtgagt ttattctgaa gagcatccag gaacttggca    300
ttagaattcc tcgaccacta ggacagggac caagcagatt catcccagaa aaggagatcc    360
tccaagtggg gagtgaagac gcacagatgc atgctttatt tgcagattct tttgctgctt    420
tgggccgttt ggataacatt acgttagtga tggttttcca cccacaatat ttagaaagtt    480
tcttaaaaac tcagcactat ctactgcaaa tggatgggcc gttacccta cattatcgtc     540
actacattgg aataatggct gcggcaagac atcagtgctc ctacttagtg aacctgcatg    600
taaatgattt ccttcatgtt ggtggggacc ccaagtggct caatggttta gagaatgctc    660
ctcaaaaact acagaattta ggagaactta acaaagtgtt agcccataga ccttggctta    720
ttaccaaaga acacattgag ggacttttaa aagctgaaga gcacagctgg tcccttgcgg    780
aattggtaca tgcagtagtt ttactcacac actatcattc tcttgcctca ttcacattcg    840
gctgtggaat cagtccagaa attcattgtg atggtggcca cacattcaga cctccttctg    900
ttagcaacta ctgcatctgt gacattacaa atggcaatca cagtgtggat gagatgccgg    960
tcaactcagc agaaaatgtt tctgtaagtg attctttctt tgaggttgaa gccctcatgg   1020
aaaagatgag gcagttacag gaatgtcgag atgaagaaga ggcaagtcag gaagagatgg   1080
cttcacgttt tgaaatagaa aaaagagaga gtatgtttgt cttctcttca gatgatgaag   1140
aagttacacc agcaagagct gtatctcgtc attttgagga tactagttat ggctataaag   1200
atttctctag acatgggatg catgttccaa catttcgtgt ccaggactat tgctgggaag   1260
atcatggtta ttctttggta aatcgccttt atccagatgt gggacagttg attgatgaaa   1320
aatttcacat tgcttacaat cttacttata atacaatggc aatgcacaaa gatgttgata   1380
cctcaatgct tagacgggca atttggaact atattcactg catgtttgga ataagatatg   1440
atgattatga ctatggtgaa attaaccagc tattggatcg tagctttaaa gtttatatca   1500
aaactgttgt ttgcactcct gaaaaggtta ccaaaaagaat gtatgatagc ttctggaggc  1560
agttcaagca ctctgagaag gttcatgtta atctgcttct tatagaagct aggatgcaag   1620
cagaactcct ttatgctctg agagccatta cccgctatat gacctgatgc ctttccttca   1680
ttaaagatga ttctggaatg atcagcagat atagtctaca agggggaagg tactaagccc   1740
caggaccaat ggtagacaaa ataattcaga aatccattgt gccatgattc ctttagtttc   1800
tgctattttt ctgtggaaaa ccactgctgg cacaagcagt gactgtttgg cagcttcaag   1860
tttagagctg tgaagacagg ctgccattca cagtattttg ctttttgaca gtacaagatg   1920
ctgtgtaact gttttaatac agcaaatagt aactctccaa atcctgttgc ttttatgtta   1980
aataagataa caagaattgg agcatgcaaa gaatgggact tggataatga cttaagcttt   2040
atatgtaaag aattttagaa gatcttggtg ctgctattcc tgctggagga atgaatagat   2100
ggctgtttca gttaagctat tagtaataaa agtgaacatt gctactatct gagcctacat   2160
acataacttg tgtgatttca aattaaactt gcattatgtg ttaattttct tgcatctaaa   2220
aaagcataga attcctactc acacagctca gcaacaacca ttttgatggt aacagttaat   2280
ttctttcatt agtttttttaa attcagggtt ctggatatta aattaaaatg gcattcttaa  2340
agattttctt caaaaagcaa tcctaaatga aagtgtgtaa attataagaa gctggcgatc   2400
ttttgatatg ctgtttcaca ggatcctgac actggagggc agctgtcttg tgcattactt   2460
gtgttcccag caccaaagtt gtgggacatg ttgctgtaga ctgctgcgca gtcctgggtg   2520
cattcagtct ctctgcctct gcctgcctcc tggtccccac tttaaaggct gtgcagctcc   2580
ttaaataata aagctggaaa atattttag tcgggttatc aaatttgatt tacaaaaacg    2640
```

ctaactttgt ttgaaatgca aacaggtttg aaaatatgta ttaagtactt tgtattctgg 2700
aagcgtgaat tgcttttgaa gtctgtcagt attactggta tttttaaata aagaagaatt 2760
tttctccaaa aaaaaaaaaa aaaaa 2785

<210> SEQ ID NO 23
<211> LENGTH: 5489
<212> TYPE: DNA
<213> ORGANISM: Homo sapiens

<400> SEQUENCE: 23
gaaactctta acaaaaacaa ggggctcggg gaggtttccg ctgaggcggc gggggtgcgg 60
cggtgggctg gtcttccgcg gccggcgttg cgccgcggcg gagggtgggc gcgcggggag 120
cgggatggag ccggggctgt gaggccgagg cggcggtgcc tgggaggaag ggtcggatgc 180
cggaccgggg gcaccgctga ggcggtgggt ccccgacctg cgagacaggt ttggaagccc 240
ccgctgcgcc cagtccgtgc ggaccgcgag gccgcgggcg ggtggaggcg cgtctccggc 300
acgatgaagg atttgggggc agagcacttg gcaggtcatg aaggggtcca acttctcggg 360
ttgttgaacg tctacctgga acaagaagag agattccaac ctcgagaaaa agggctgagt 420
ttgattgagg ctaccccgga gaatgataac actttgtgtc caggattgag aaatgccaaa 480
gttgaagatt taaggagttt agccaacttt tttggatctt gcactgaaac ttttgtcctg 540
gctgtcaata ttttggacag gttcttggct cttatgaagg tgaaacctaa acatttgtct 600
tgcattggag tctgttcttt tttgctggct gctagaatag ttgaagaaga ctgcaatatt 660
ccatccactc atgatgtgat ccggattagt cagtgtaaat gtactgcttc tgacataaaa 720
cggatggaaa aaataatttc agaaaaattg cactatgaat tggaagctac tactgcctta 780
aactttttgc acttatacca tactattata ctttgtcata cttcagaaag gaaagaaata 840
ctgagccttg ataaactaga agctcagctg aaagcttgca actgccgact catcttttca 900
aaagcaaaac catctgtatt agccttgtgc cttctcaatt tggaagtgga aactttgaaa 960
tctgttgaat tactggaaat tctcttgcta gttaaaaaac attccaagat taatgacact 1020
gagttcttct actggagaga gttggtttct aaatgcctag ccgagtattc ttctcctgaa 1080
tgttgcaaac cagatcttaa gaagttggtt tggatcgttt caaggcgcac agcccagaac 1140
ctccacaaca gctactatag tgttcctgag ctgccaacga tacctgaggg gggttgtttt 1200
gatgaaagtg aaagtgagga ctcttgtgaa gatatgagtt gtggagagga gagtctcagc 1260
agctctcctc ccagtgatca agagtgcacc ttcttttca acttcaaagt ggcacaaaca 1320
ctgtgctttc catcttagaa atctgattgt tctgtcagaa tttatattta caggtttcaa 1380
agcaataaat gggggaatag gtagtttcct ggtttagccc ccatctagtc aggaattaat 1440
atactggaat acctaccttc tatttgttat tcagatcaga tctggcctat tttcatattt 1500
atcctaagcc atcaaatggg gtagtgcctc ttaaaccatt aacagtactt tagacattgg 1560
cactttattt ttctcgtaga tctttagcta ctttggggag gagggaaggt gctgatacct 1620
tcaatttgtt acttttcaag atttttaaaa ataactagtg tagcttatct taaacatttt 1680
ataaaacctt cagatgtctt taagcagatt ggaagtatgc aagtgcttcc ttagcaggga 1740
cagtggataa tccttaatgg tttatcatag atttcaccct ccccccttct cagaagagtg 1800
agtatgctct taaatgtcaa acacattttt gttgttttgt tttttaaatg atcagtgtct 1860
atttgatgtg atgcagatct tataaatttg ggaattataa tattgacatt tctgtgattt 1920

```
ttatatatgt aatgtcttaa ttgagatttc tgttaaggca gaaataatta ggctagggct   1980
cttagttttc attcctattg cccaagtatt gtcaaactat ggtattattt taatgttact   2040
ttaaaaatcc ataatctgct agttttgcat gtacttatat gaaaacagtg cagtaagttg   2100
aaaactcagt atctatggaa ttgataaatg ttgatctggt gtagtatatt ttatcgcatt   2160
ttcttatatt aaaaaatgtc tgcatgatta cattttattt cctttgtaat ttacatttca   2220
gaatagtgta ttgctatatg ggtgccaaga ttgaatatga agaacccgag tgtttgtagt   2280
attatagttt taagcaaatc tgtgtggtga tacagccata agaatggggc ttatataaac   2340
tctgtacatg taagatttg tacagagaat ttttaacttt ataaattgta tatgaacatg   2400
taaatctttt aaaatgtaca taaaatactg tattttttta ccttgtgtgt gatagtctag   2460
tcattgcatg taaatataat ttattatgta ttctgtagta taaatcatac attgatgact   2520
tacattttta ctggtaagtc aacatccgtt ggatgttttc tgaagtggct ctttttgaag   2580
tgataataga ttgtaattca aaataaaatt attaatgaat tctccttgtt tgggatcaca   2640
tcttaatttt taatctgtta aaagttcttg atgtatttta atgagaagac tttaggtgag   2700
gctacagtga ttccagagtg agccttctaa ctggctagca gaagttctct aggtttggca   2760
tctgtgcctt ggagatactg aaagagaatc tgtcatttga caattgacct ctttgtggga   2820
tggactcatt aagtatgctc tcagagactg gtatattacc agaatgccta ttaattttca   2880
gtgagaggca acaggtatta agtagaacag aatgctcagg ttggcagatt agaacgatct   2940
ttcaggagac aaagcaagtt ttaatcagtt gtttggttaa taagtatggg gtgttcgctg   3000
tgatagggcc ccgccagctt ctggctcttg tggacctcaa aagtatcagg tggttttgca   3060
agtggtggtc ctttcccctg ccccacccca ataggttccc catctgtcta gtttgatttt   3120
tgtagacctt tgttttctct agttagaaaa tcaggtacac tgaatatggt tttcatgtaa   3180
cacctcttct ctggagatag ggtatgtttt tcctaccctt ctagtggaga atcctacttg   3240
aggatgacct ttcctctctt actaaataat attagtaaat agtgggcaat atattctgct   3300
ttcagatttt gatttgttga gatgtaaaag ttgtttgggg cttaccaaat ctcaagactc   3360
tctttagctc ctgcaggatt gtattgcttt tcttactgga tatttttcct gggtaagcat   3420
ctttgtggct tcatctcttc cccctgtggt tttcagtgta tttagtcgag acctctctgc   3480
tgagcttgca acctgtttat tcacatggcc tgccatgcca cttggaggtt tctgattact   3540
cccaaacctg ctggttcttt atgtctttct cagcgaataa ttccatctat tcatgttgga   3600
aacttaggtg atatgctcat ctccttttgc ctgtttatgg aggtcaccag cctctatcat   3660
ttgtatgatt tcgtttacac tgtttatatc tctctgtccc ccctttttct gccattggca   3720
tggtttagac ctgtactctt tatcagcaga ggtactgtaa tatatttgtg atccctcagc   3780
ttccaggctt actcctggtc tctgccttcc tatctacata tccttttaaa ataaaatttt   3840
aactatctcc tgaaaaattg ttgagtaggt cacgcacaat caggagaaaa atctattcat   3900
gacatacaag tctctgtcta atctgaacac tgcacctgtc tctggccttt ttttcttgtc   3960
atttcctaga ccttaaaaaa tgtgtattga gaaagaactc tgttagctat acagaagatg   4020
aactgggcaa tatagagtag cagcatggag accagtctga ctgaactaag gcagtggaag   4080
tgtggatgag gaagagaggt gaaaattgag aagcgctatc ctttctcttt gggcattatt   4140
aggaggctca cagacaagtc caggagcctg gttataccct cctgtgccat tcaaccaggt   4200
ggctttccca tgactgtgat gaataaaatt gagaagcccc tgccctttte agagcagagg   4260
gtgaggagaa agctaccatt ttgtcctcat ccttaccccc gttgacttgg cgagagattt   4320
```

gacctttcag gttttgatcc tgtcattttc taggatgtgg tgcacgcact ttgctgttgc 4380
gcatggtgaa gtattgtgcc taggtcctgg gtcttcatct gtttggctct gctactgttt 4440
cctcctccca ggaagtgtgg ttagacaaat aatgtgtttt aattacctgt cacactcagg 4500
attaatacat actcaggtta actgtagaga ggcattggct tcagaacact cctcgtgaca 4560
attttaacca ttttctttgt ctagagtctg cctttttctt ttttacaatt tcttttattt 4620
caacactagg tttcaatatg gtgttcctgc tacctcccac ctccctcctc cctcatcaca 4680
catgcaaatt gtcagcttat tgagacaacc cacttagatt catatatgga caaggacaag 4740
gtattttgca tttgttactg gaattcagtt ttcctaacta tttactacca gaaatggtca 4800
ataacttact ttgtgtttag caaatcaaat tgtgtgatag atagtttccc agtatgatgg 4860
ccagtcagtc tttccatccc tgtgcctaca tgctgctctt cccgtccaca agtggagtct 4920
gtttctcttg agttttggct ggccttatga atggctttgc ttactgaagt gcagcagaag 4980
aaatttagta tatgtccaag cctaggcttt aagagactgg cagctttcct tttatccttt 5040
ttggaagcta gccaccatgc tgcaaagaag ctcagctgga ttactgaaag atgagaggcc 5100
atgtggagag agactcttga ggatgagaga ttatcttgga tgttccagcc ttaagctccc 5160
agctgaatgt gggtgtatcc tcagctacac cacagaaaac agaggaacta ctcagtcgat 5220
cccaatcaac ccacagactc actagaaata acaaattatt gttttaagcc acgaggtttt 5280
gggggagggt tgttaaacag taatagataa gtgagacaga ttgcttgtta tttatggtca 5340
aatggtgatt atctctggtg agattacagg tgatgttttt tttaagttat gcctatctgt 5400
agtttccttt ttttcctaaa attgatttga attattagtg tattaacaga ataaagaatg 5460
aactttaaaa cacaaaaaaa aaaaaaaaa 5489

<210> SEQ ID NO 24
<211> LENGTH: 4815
<212> TYPE: DNA
<213> ORGANISM: Homo sapiens

<400> SEQUENCE: 24
agtggcgtcg gaactgcaaa gcacctgtga gcttgcggaa gtcagttcag actccagccc 60
gctccagccc ggcccgaccc gaccgcaccc ggcgcctgcc ctcgctcggc gtccccggcc 120
agccatgggc ccttggagcc gcagcctctc ggcgctgctg ctgctgctgc aggtctcctc 180
ttggctctgc caggagccgg agccctgcca ccctggcttt gacgccgaga gctacacgtt 240
cacggtgccc cggcgccacc tggagagagg ccgcgtcctg ggcagagtga attttgaaga 300
ttgcaccggt cgacaaagga cagcctattt ttccctcgac acccgattca aagtgggcac 360
agatggtgtg attacagtca aaaggcctct acggtttcat aacccacaga tccatttctt 420
ggtctacgcc tgggactcca cctacagaaa gttttccacc aaagtcacgc tgaatacagt 480
ggggcaccac caccgccccc cgccccatca ggcctccgtt tctggaatcc aagcagaatt 540
gctcacattt cccaactcct ctcctggcct cagaagacag aagagagact gggttattcc 600
tcccatcagc tgcccagaaa atgaaaaagg cccatttcct aaaaacctgg ttcagatcaa 660
atccaacaaa gacaaagaag gcaaggtttt ctacagcatc actggccaag gagctgacac 720
accccctgtt ggtgtcttta ttattgaaag agaaacagga tggctgaagg tgacagagcc 780
tctggataga gaacgcattg ccacatacac tctcttctct cacgctgtgt catccaacgg 840
gaatgcagtt gaggatccaa tggagatttt gatcacggta accgatcaga atgacaacaa 900

```
gcccgaattc acccaggagg tctttaaggg gtctgtcatg gaaggtgctc ttccaggaac    960
ctctgtgatg gaggtcacag ccacagacgc ggacgatgat gtgaacacct acaatgccgc   1020
catcgcttac accatcctca gccaagatcc tgagctccct gacaaaaata tgttcaccat   1080
taacaggaac acaggagtca tcagtgtggt caccactggg ctggaccgag agagtttccc   1140
tacgtatacc ctggtggttc aagctgctga ccttcaaggt gaggggttaa gcacaacagc   1200
aacagctgtg atcacagtca ctgacaccaa cgataatcct ccgatcttca atcccaccac   1260
gtacaagggt caggtgcctg agaacgaggc taacgtcgta atcaccacac tgaaagtgac   1320
tgatgctgat gcccccaata ccccagcgtg ggaggctgta tacaccatat tgaatgatga   1380
tggtggacaa tttgtcgtca ccacaaatcc agtgaacaac gatggcattt tgaaaacagc   1440
aaagggcttg gattttgagg ccaagcagca gtacattcta cacgtagcag tgacgaatgt   1500
ggtacctttt gaggtctctc tcaccacctc cacagccacc gtcaccgtgg atgtgctgga   1560
tgtgaatgaa gcccccatct ttgtgcctcc tgaaaagaga gtggaagtgt ccgaggactt   1620
tggcgtgggc caggaaatca catcctacac tgcccaggag ccagacacat ttatggaaca   1680
gaaaataaca tatcggattt ggagagacac tgccaactgg ctggagatta atccggacac   1740
tggtgccatt tccactcggg ctgagctgga cagggaggat tttgagcacg tgaagaacag   1800
cacgtacaca gccctaatca tagctacaga caatggttct ccagttgcta ctggaacagg   1860
gacacttctg ctgatcctgt ctgatgtgaa tgacaacgcc cccataccag aacctcgaac   1920
tatattcttc tgtgagagga atccaaagcc tcaggtcata aacatcattg atgcagacct   1980
tcctcccaat acatctccct tcacagcaga actaacacac ggggcgagtg ccaactggac   2040
cattcagtac aacgacccaa cccaagaatc tatcattttg aagccaaaga tggccttaga   2100
ggtgggtgac tacaaaatca atctcaagct catggataac cagaataaag accaagtgac   2160
caccttagag gtcagcgtgt gtgactgtga aggggccgct ggcgtctgta ggaaggcaca   2220
gcctgtcgaa gcaggattgc aaattcctgc cattctgggg attcttggag gaattcttgc   2280
tttgctaatt ctgattctgc tgctcttgct gtttcttcgg aggagagcgg tggtcaaaga   2340
gcccttactg cccccagagg atgacacccg ggacaacgtt tattactatg atgaagaagg   2400
aggcggagaa gaggaccagg actttgactt gagccagctg cacaggggcc tggacgctcg   2460
gcctgaagtg actcgtaacg acgttgcacc aaccctcatg agtgtccccc ggtatcttcc   2520
ccgccctgcc aatcccgatg aaattggaaa ttttattgat gaaaatctga aagcggctga   2580
tactgacccc acagccccgc cttatgattc tctgctcgtg tttgactatg aaggaagcgg   2640
ttccgaagct gctagtctga gctccctgaa ctcctcagag tcagacaaag accaggacta   2700
tgactacttg aacgaatggg gcaatcgctt caagaagctg gctgacatgt acggaggcgg   2760
cgaggacgac taggggactc gagagaggcg ggccccagac ccatgtgctg ggaaatgcag   2820
aaatcacgtt gctggtggtt tttcagctcc cttcccttga gatgagtttc tggggaaaaa   2880
aaagagactg gttagtgatg cagttagtat agctttatac tctctccact ttatagctct   2940
aataagtttg tgttagaaaa gtttcgactt atttcttaaa gctttttttt ttttcccatc   3000
actctttaca tggtggtgat gtccaaaaga tacccaaatt ttaatattcc agaagaacaa   3060
ctttagcatc agaaggttca cccagcacct tgcagatttt cttaaggaat tttgtctcac   3120
ttttaaaaag aaggggagaa gtcagctact ctagttctgt tgttttgtgt atataatttt   3180
ttaaaaaaaa tttgtgtgct tctgctcatt actacactgg tgtgtccctc tgcctttttt   3240
tttttttaa gacagggtct cattctatcg gccaggctgg agtgcagtgg tgcaatcaca   3300
```

gctcactgca gccttgtcct cccaggctca agctatcctt gcacctcagc ctcccaagta 3360
gctgggacca caggcatgca ccactacgca tgactaattt tttaaatatt tgagacgggg 3420
tctccctgtg ttacccaggc tggtctcaaa ctcctgggct caagtgatcc tcccatcttg 3480
gcctcccaga gtattgggat tacagacatg agccactgca cctgcccagc tccccaactc 3540
cctgccattt tttaagagac agtttcgctc catcgcccag gcctgggatg cagtgatgtg 3600
atcatagctc actgtaacct caaactctgg ggctcaagca gttctcccac cagcctcctt 3660
tttatttttt tgtacagatg gggtcttgct atgttgccca agctggtctt aaactcctgg 3720
cctcaagcaa tccttctgcc ttggcccccc aaagtgctgg gattgtgggc atgagctgct 3780
gtgcccagcc tccatgtttt aatatcaact ctcactcctg aattcagttg ctttgcccaa 3840
gataggagtt ctctgatgca gaaattattg ggctctttta gggtaagaag tttgtgtctt 3900
tgtctggcca catcttgact aggtattgtc tactctgaag acctttaatg gcttccctct 3960
ttcatctcct gagtatgtaa cttgcaatgg gcagctatcc agtgacttgt tctgagtaag 4020
tgtgttcatt aatgtttatt tagctctgaa gcaagagtga tatactccag gacttagaat 4080
agtgcctaaa gtgctgcagc caaagacaga gcggaactat gaaaagtggg cttggagatg 4140
gcaggagagc ttgtcattga gcctggcaat ttagcaaact gatgctgagg atgattgagg 4200
tgggtctacc tcatctctga aaattctgga aggaatggag gagtctcaac atgtgtttct 4260
gacacaagat ccgtggtttg tactcaaagc ccagaatccc caagtgcctg cttttgatga 4320
tgtctacaga aaatgctggc tgagctgaac acatttgccc aattccaggt gtgcacagaa 4380
aaccgagaat attcaaaatt ccaaattttt ttcttaggag caagaagaaa atgtggccct 4440
aaagggggtt agttgagggg tagggggtag tgaggatctt gatttggatc tctttttatt 4500
taaatgtgaa tttcaacttt tgacaatcaa agaaaagact tttgttgaaa tagctttact 4560
gtttctcaag tgttttggag aaaaaaatca accctgcaat cactttttgg aattgtcttg 4620
atttttcggc agttcaagct atatcgaata tagttctgtg tagagaatgt cactgtagtt 4680
ttgagtgtat acatgtgtgg gtgctgataa ttgtgtattt tctttggggg tggaaaagga 4740
aaacaattca agctgagaaa agtattctca aagatgcatt tttataaatt ttattaaaca 4800
attttgttaa accat 4815

<210> SEQ ID NO 25
<211> LENGTH: 1909
<212> TYPE: DNA
<213> ORGANISM: Homo sapiens

<400> SEQUENCE: 25
gaggtgtttc ccttagctat ggaaactcta taagagagat ccagcttgcc tcctcttgag 60
cagtcagcaa cagggtcccg tccttgacac ctcagcctct acaggactga gaagaagtaa 120
aaccgtttgc tggggctggc ctgactcacc agctgccatg cagcagccct tcaattaccc 180
atatccccag atctactggg tggacagcag tgccagctct ccctgggccc ctccaggcac 240
agttcttccc tgtccaacct ctgtgcccag aaggcctggt caaaggaggc caccaccacc 300
accgccaccg ccaccactac cacctccgcc gccgccgcca ccactgcctc cactaccgct 360
gccacccctg aagaagagag ggaaccacag cacaggcctg tgtctccttg tgatgttttt 420
catggttctg gttgccttgg taggattggg cctggggatg tttcagctct tccacctaca 480
gaaggagctg gcagaactcc gagagtctac cagccagatg cacacagcat catctttgga 540
gaagcaaata ggccacccca gtccaccccc tgaaaaaaag gagctgagga aagtggccca 600
tttaacaggc aagtccaact caaggtccat gcctctggaa tgggaagaca cctatggaat 660
tgtcctgctt tctggagtga agtataagaa gggtggcctt gtgatcaatg aaactgggct 720
gtactttgta tattccaaag tatacttccg gggtcaatct tgcaacaacc tgcccctgag 780
ccacaaggtc tacatgagga actctaagta tccccaggat ctggtgatga tggaggggaa 840
gatgatgagc tactgcacta ctgggcagat gtgggcccgc agcagctacc tgggggcagt 900
gttcaatctt accagtgctg atcatttata tgtcaacgta tctgagctct ctctggtcaa 960
ttttgaggaa tctcagacgt tttcggctt atataagctc taagagaagc actttgggat 1020
tctttccatt atgattcttt gttacaggca ccgagaatgt tgtattcagt gagggtcttc 1080
ttacatgcat ttgaggtcaa gtaagaagac atgaaccaag tggaccttga gaccacaggg 1140
ttcaaaatgt ctgtagctcc tcaactcacc taatgtttat gagccagaca aatggaggaa 1200
tatgacggaa gaacatagaa ctctgggctg ccatgtgaag agggagaagc atgaaaaagc 1260
agctaccagg tgttctacac tcatcttagt gcctgagagt atttaggcag attgaaaagg 1320
acacctttta actcacctct caaggtgggc cttgctacct caagggggac tgtctttcag 1380
atacatggtt gtgacctgag gatttaaggg atggaaaagg aagactagag gcttgcataa 1440
taagctaaag aggctgaaag aggccaatgc cccactggca gcatcttcac ttctaaatgc 1500
atatcctgag ccatcggtga aactaacaga taagcaagag agatgttttg ggactcatt 1560 tcattcctaa cacagcatgt gtatttccag tgcaattgta ggggtgtgtg tgtgtgtgtg 1620
tgtgtgtgtg tgtgtatgac taaagagaga atgtagatat tgtgaagtac atattaggaa 1680
aatatgggtt gcatttggtc aagattttga atgcttcctg acaatcaact ctaatagtgc 1740
ttaaaaatca ttgattgtca gctactaatg atgttttcct ataatataat aaatatttat 1800
gtagatgtgc atttttgtga aatgaaaaca tgtaataaaa agtatatgtt aggatacaaa 1860
aaaaaaaaaa aaaaaaaaaa aaaaaaaaaa aaaaaaaaaa aaaaaaaaa 1909

<210> SEQ ID NO 26
<211> LENGTH: 2689
<212> TYPE: DNA
<213> ORGANISM: Homo sapiens

<400> SEQUENCE: 26
acatctcccg gcggcgggcc gcggaagcag tgcagacgcg gctcctagcg gatgggtgct 60
attgtgaggc ggttgtagaa gagtttcgtg agtgctcgca gctcatacct gtggctgtgt 120
atccgtggcc acagctggtt ggcgtcgcct tgaaatccca ggccgtgagg agttagcgag 180
ccctgctcac actcggcgct ctggttttcg gtgggtgtgc cctgcacctg cctcttcccc 240
cattctcatt aataaaggta tccatggaga acactgaaaa ctcagtggat tcaaaatcca 300
ttaaaaattt ggaaccaaag atcatacatg gaagcgaatc aatggactct ggaatatccc 360
tggacaacag ttataaaatg gattatcctg agatgggttt atgtataata attaataata 420
agaattttca taaaagcact ggaatgacat ctcggtctgg tacagatgtc gatgcagcaa 480
acctcaggga aacattcaga aacttgaaat atgaagtcag gaataaaaat gatcttacac 540
gtgaagaaat tgtggaattg atgcgtgatg tttctaaaga agatcacagc aaaaggagca 600
gttttgtttg tgtgcttctg agccatggtg aagaaggaat aatttttgga acaaatggac 660
ctgttgacct gaaaaaaata acaaactttt tcagagggga tcgttgtaga agtctaactg 720
gaaaacccaa acttttcatt attcaggcct gccgtggtac agaactggac tgtggcattg 780

-continued agacagacag tggtgttgat gatgacatgg cgtgtcataa aataccagtg gaggccgact 840
tcttgtatgc atactccaca gcacctggtt attattcttg gcgaaattca aaggatggct 900
cctggttcat ccagtcgctt tgtgccatgc tgaaacagta tgccgacaag cttgaattta 960
tgcacattct tacccgggtt aaccgaaagg tggcaacaga atttgagtcc ttttcctttg 1020
acgctacttt tcatgcaaag aaacagattc catgtattgt ttccatgctc acaaaagaac 1080
tctattttta tcactaaaga aatggttggt tggtggtttt ttttagtttg tatgccaagt 1140
gagaagatgg tatatttggt actgtatttc cctctcattt tgacctactc tcatgctgca 1200
gagggtactt taagacatac tccttccatc aaatagaacc actatgaagc tacctcaaac 1260
ttccagtcag gtagttgcaa ttgaattaaa ttaggaataa ataaaaatgg atactggtgc 1320
agtcattatg agaggcaatg attgttaatt tacagctttc atgattagca agttacagtg 1380
atgctgtgct atgaatttc aagtaattgt gaaaaagtta aacattgaag taatgaattt 1440
ttatgatatt ccccccactt aagactgtgt attctagttt tgtcaaactg tagaaatgat 1500
gatgtggaag aacttaggca tctgtgggca tggtcaaagg ctcaaacctt tattttagaa 1560
ttgatataca cggatgactt aactgcattt ttagaccatt tatctgggat tatggttttg 1620
tgatgtttgt cctgaacact tttgttgtaa aaaaataata ataatgttta atattgagaa 1680
agaaactaat attttatgtg agagaaagtg tgagcaaact aacttgactt ttaaggctaa 1740
aacttaacat tcatagaggg gtggagtttt aactgtaagg tgctacaatg cccctggatc 1800
taccagcata aatatcttct gatttgtccc tatgcatatc agttgagctt catataccag 1860
caatatatct gaagagctat tatataaaaa ccccaaactg ttgattatta gccaggtaat 1920
gtgaataaat tctataggaa catatgaaaa tacaacttaa ataataaaca gtggaatata 1980
aggaaagcaa taaatgaatg ggctgagctg cctgtaactt gagagtagat ggtttgagcc 2040
tgagcagaga catgactcag cctgttccat gaaggcagag ccatggacca cgcaggaagg 2100
gcctacagcc catttctcca tacgcactgg tatgtgtgga tgatgctgcc agggcgccat 2160
cgccaagtaa gaaagtgaag caaatcagaa acttgtgaag tggaaatgtt ctaaaggtgg 2220
tgaggcaata aaaatcatag tactctttgt agcaaaattc ttaagtatgt tattttctgt 2280
tgaagtttac aatcaaagga aaatagtaat gttttatact gtttactgaa agaaaaagac 2340
ctatgagcac ataggactct agacggcatc cagccggagg ccagagctga gccctcagcc 2400
cgggaggcag gctccaggcc tcagcaggtg cggagccgtc actgcaccaa gtctcactgg 2460
ctgtcagtat gacatttcac gggagatttc ttgttgctca aaaaatgagc tcgcatttgt 2520
caatgacagt ttcttttttc ttactagacc tgtaactttt gtaaatacac atagcatgta 2580
atggtatctt aaagtgtgtt tctatgtgac aattttgtac aaatttgtta ttttccattt 2640
ttatttcaaa atatacattc aaacttaaaa ttaaaaaaaa aaaaaaaaa 2689

<210> SEQ ID NO 27
<211> LENGTH: 2143
<212> TYPE: DNA
<213> ORGANISM: Homo sapiens

<400> SEQUENCE: 27
ggaagttttc cggcggctac cgggaagtcg ctgaagacag agcgatggta gttctggagg 60
cctcgctccg gggccgaccc gaggccacag tgcctccgcg gtagaccgga cttgggtgac 120
gggctccggg ctcccgaggt gaagagcatc gggggctgag ggatggaagg gtctaagacg 180

-continued

```
tccaacaaca gcaccatgca ggtgagcttc gtgtgccagc gctgcagcca gcccctgaaa    240
ctggacacga gtttcaagat cctggaccgt gtcaccatcc aggaactcac agctccatta    300
cttaccacag cccaggcgaa accaggagag acccaggagg aagagactaa ctcaggagag    360
gagccattta ttgaaactcc tcgccaggat ggtgtctctc gcagattcat ccccccagcc    420
aggatgatgt ccacagaaag tgccaacagc ttcactctga ttggggaggc atctgatggc    480
ggcaccatgg agaacctcag ccgaagactg aaggtcactg gggacctttt tgacatcatg    540
tcgggccaga cagatgtgga tcacccactc tgtgaggaat gcacagatac tcttttagac    600
cagctggaca ctcagctcaa cgtcactgaa aatgagtgtc agaactacaa acgctgtttg    660
gagatcttag agcaaatgaa tgaggatgac agtgaacagt tacagatgga gctaaaggag    720
ctggcactag aggaggagag gctgatccag gagctggaag acgtggaaaa gaaccgcaag    780
atagtggcag aaaatctcga gaaggtccag gctgaggctg agagactgga tcaggaggaa    840
gctcagtatc agagagaata cagtgaattt aaacgacagc agctggagct ggatgatgag    900
ctgaagagtg ttgaaaacca gatgcgttat gcccagacgc agctggataa gctgaagaaa    960
accaacgtct ttaatgcaac cttccacatc tggcacagtg gacagtttgg cacaatcaat   1020
aacttcaggc tgggtcgcct gcccagtgtt cccgtggaat ggaatgagat taatgctgct   1080
tggggccaga ctgtgttgct gctccatgct ctggccaata agatgggtct gaaatttcag   1140
agataccgac ttgttcctta cggaaaccat tcatatctgg agtctctgac agacaaatct   1200
aaggagctgc cgttatactg ttctgggggg ttgcggtttt tctgggacaa caagtttgac   1260
catgcaatgg tggctttcct ggactgtgtg cagcagttca aagaagaggt tgagaaaggc   1320
gagacacgtt tttgtcttcc ctacaggatg gatgtggaga aaggcaagat tgaagacaca   1380
ggaggcagtg gcggctccta ttccatcaaa acccagttta actctgagga gcagtggaca   1440
aaagctctca agttcatgct gacgaatctt aagtggggtc ttgcttgggt gtcctcacaa   1500
ttttataaca aatgactttt ttccttaggg ggaggtttgc cttaaaggct tttaattttg   1560
ttttgtttgc aaacatgttt taaattaaat tcgggtaata ttaaacagta catgtttaca   1620
ataccaaaaa agaaaaaatc cacaaaagcc actttatttt aaaatatcat gtgacagata   1680
ctttccagag ctacaacatg ccatctatag ttgccagccc tggtcagttt tgattcttaa   1740
ccccatggac tcctttccct ttcttctctg aaaaaaacta atttaaattt gcttttcttt   1800
tttttaactg agttgaattg agattgatgt gttttcactg gatttttatc tctctcaact   1860
tcctgcactt aacaatatga aatagaaact tttgtcttta ctgagatgag gatatgtttg   1920
agatgcacag ttggataatg tgggaaaatg acatctaagc tttacctggt caccatgtga   1980
tgtgatcaga tgcttgaaat ttaacacttt tcacttggtt cttatactga atgccgactc   2040
tgctctgtgt tagagatatg aaatggtgtt tgatactgtt tgagacatta tggagagatt   2100
taattatttg taataaaaga tttgctgcag tctgaaaact gcc                     2143
```

```
<210> SEQ ID NO 28
<211> LENGTH: 4380
<212> TYPE: DNA
<213> ORGANISM: Homo sapiens

<400> SEQUENCE: 28

ggggagcgcc atccgctcca cttccacctc cacatcctcc accggccaag gtccccgccg     60
ctgcatccct cgcggcttcc gctgcgctcc gggccggagc cgagccgcct gcgctgccac    120
agcagccgcc tccacacact cgcagacgct cacacgctct ccctccctgt tcccccgccc    180
```

```
cctccccagc tccttgatct ctgggtctgt tttattactc ctggtgcgag tcccgcggac    240
tccgcggccc gctatttgtc atcagctcgc tctccattgg cggggagcgg agagcagcga    300
agaagggggt ggggagggga ggggaaggga agggggtgga aactgcctgg agccgtttct    360
ccgcgccgct gttggtgctg ccgctgcctc ctcctcctcc gccgccgccg ccgccgccgc    420
cgcctcctcc ggctcttcgc tcggcccctc tccgcctcca tgtgccggat agcgggagcg    480
ctgcggaccc tgctgccgct gctggcggcc ctgcttcagg cgtctgtaga ggcttctggt    540
gaaatcgcat tatgcaagac tggatttcct gaagatgttt acagtgcagt cttatcgaag    600
gatgtgcatg aaggacagcc tcttctcaat gtgaagttta gcaactgcaa tggaaaaaga    660
aaagtacaat atgagagcag tgagcctgca gattttaagg tggatgaaga tggcatggtg    720
tatgccgtga gaagctttcc actctcttct gagcatgcca agttcctgat atatgcccaa    780
gacaaagaga cccaggaaaa gtggcaagtg gcagtaaaat tgagcctgaa gccaacctta    840
actgaggagt cagtgaagga gtcagcagaa gttgaagaaa tagtgttccc aagacaattc    900
agtaagcaca gtggccacct acaaaggcag aagagagact gggtcatccc tccaatcaac    960
ttgccagaaa actccagggg accttttcct caagagcttg tcaggatcag gtctgataga   1020
gataaaaacc tttcactgcg gtacagtgta actgggccag gagctgacca gcctccaact   1080
ggtatcttca ttatcaaccc catctcgggt cagctgtcgg tgacaaagcc cctggatcgc   1140
gagcagatag cccggtttca tttgagggca catgcagtag atattaatgg aaatcaagtg   1200
gagaacccca ttgacattgt catcaatgtt attgacatga atgacaacag acctgagttc   1260
ttacaccagg tttggaatgg gacagttcct gagggatcaa agcctggaac atatgtgatg   1320
accgtaacag caattgatgc tgacgatccc aatgccctca atgggatgtt gaggtacaga   1380
atcgtgtctc aggctccaag caccccttca cccaacatgt ttacaatcaa caatgagact   1440
ggtgacatca tcacagtggc agctggactt gatcgagaaa aagtgcaaca gtatacgtta   1500
ataattcaag ctacagacat ggaaggcaat cccacatatg gcctttcaaa cacagccacg   1560
gccgtcatca cagtgacaga tgtcaatgac aatcctccag agtttactgc catgacgttt   1620
tatggtgaag ttcctgagaa cagggtagac atcatagtag ctaatctaac tgtgaccgat   1680
aaggatcaac cccatacacc agcctggaac gcagtgtaca gaatcagtgg cggagatcct   1740
actggacggt tcgccatcca gaccgaccca aacagcaacg acgggttagt caccgtggtc   1800
aaaccaatcg actttgaaac aaataggatg tttgtcctta ctgttgctgc agaaaatcaa   1860
gtgccattag ccaagggaat tcagcacccg cctcagtcaa ctgcaaccgt gtctgttaca   1920
gttattgacg taaatgaaaa cccttatttt gcccccaatc ctaagatcat tcgccaagaa   1980
gaagggcttc atgccggtac catgttgaca acattcactg ctcaggaccc agatcgatat   2040
atgcagcaaa atattagata cactaaatta tctgatcctg ccaattggct aaaaatagat   2100
cctgtgaatg gacaaataac tacaattgct gttttggacc gagaatcacc aaatgtgaaa   2160
aacaatatat ataatgctac tttccttgct tctgacaatg gaattcctcc tatgagtgga   2220
acaggaacgc tgcagatcta tttacttgat attaatgaca atgcccctca agtgttacct   2280
caagaggcag agacttgcga aactccagac cccaattcaa ttaatattac agcacttgat   2340
tatgacattg atccaaatgc tggaccattt gcttttgatc ttcctttatc tccagtgact   2400
attaagagaa attggaccat cactcggctt aatggtgatt ttgctcagct taatttaaag   2460
ataaaatttc ttgaagctgg tatctatgaa gttcccatca taatcacaga ttcgggtaat   2520
```

-continued

```
cctcccaaat caaatatttc catcctgcgc gtgaaggttt gccagtgtga ctccaacggg   2580

gactgcacag atgtggacag gattgtgggt gcggggcttg gcaccggtgc catcattgcc   2640

atcctgctct gcatcatcat cctgcttatc cttgtgctga tgtttgtggt atggatgaaa   2700

cgccgggata aagaacgcca ggccaaacaa cttttaattg atccagaaga tgatgtaaga   2760

gataatattt taaaatatga tgaagaaggt ggaggagaag aagaccagga ctatgacttg   2820

agccagctgc agcagcctga cactgtggag cctgatgcca tcaagcctgt gggaatccga   2880

cgaatggatg aaagacccat ccacgccgag ccccagtatc cggtccgatc tgcagcccca   2940

caccctggag acattgggga cttcattaat gagggcctta aagcggctga caatgacccc   3000

acagctccac catatgactc cctgttagtg tttgactatg aaggcagtgg ctccactgct   3060

gggtccttga gctcccttaa ttcctcaagt agtggtggtg agcaggacta tgattacctg   3120

aacgactggg ggccacggtt caagaaactt gctgacatgt atggtggagg tgatgactga   3180

acttcagggt gaacttggtt tttggacaag tacaaacaat ttcaactgat attcccaaaa   3240

agcattcaga agctaggctt taactttgta gtctactagc acagtgcttg ctggaggctt   3300

tggcataggc tgcaaaccaa tttgggctca gagggaatat cagtgatcca tactgtttgg   3360

aaaaacactg agctcagtta cacttgaatt ttacagtaca gaagcactgg gattttatgt   3420

gcctttttgt acctttttca gattggaatt agttttctgt ttaaggcttt aatggtactg   3480

atttctgaaa cgataagtaa aagacaaaat attttgtggt gggagcagta agttaaacca   3540

tgatatgctt caacacgctt ttgttacatt gcatttgctt ttattaaaat acaaaattaa   3600

acaaacaaaa aaactcatgg agcgatttta ttatcttggg ggatgagacc atgagattgg   3660

aaaatgtaca ttacttctag ttttagactt tagtttgttt tttttttttt cactaaaatc   3720

ttaaaactta ctcagctggt tgcaaataaa gggagttttc atatcaccaa tttgtagcaa   3780

aattgaattt tttcataaac tagaatgtta gacacatttt ggtcttaatc catgtacact   3840

tttttatttc tgtatttttc cacttcactg taaaaatagt atgtgtacat aatgttttat   3900

tggcatagtc tatggagaag tgcagaaact tcagaacatg tgtatgtatt atttggacta   3960

tggattcagg tttttttgcat gtttatatct ttcgttatgg ataaagtatt tacaaaacag   4020

tgacatttga ttcaattgtt gagctgtagt tagaatactc aatttttaat tttttttaatt   4080

tttttatttt ttattttctt tttggtttgg ggagggagaa aagttcttag cacaaatgtt   4140

ttacataatt tgtaccaaaa aaaaaaaaaa aggaaaggaa agaaaggggt ggcctgacac   4200

tggtggcact actaagtgtg tgttttttta aaaaaaaaat ggaaaaaaaa aagcttttaa   4260

actggagaga cttctgacaa cagctttgcc tctgtattgt gtaccagaat ataaatgata   4320

cacctctgac cccagcgttc tgaataaaat gctaattttg gatctggaaa aaaaaaaaaa   4380
```

<210> SEQ ID NO 29
<211> LENGTH: 1669
<212> TYPE: DNA
<213> ORGANISM: Homo sapiens

<400> SEQUENCE: 29

```
gaggtataag agcctccaag tctgcagctc tcgcccaact cccagacacc tcgcgggctc     60

tgcagcaccg gcaccgtttc caggaggcct ggcggggtgt gcgtccagcc gttgggcgct    120

ttctttttgg acctcggggc catccacacc gtcccctccc cctcccgcct ccctccccgc    180

ctcccccgcg cgccctcccc gcggaggtcc ctcccgtccg tcctcctgct ctctcctccg    240

cgggccgcat cgcccgggcc ggcgccgcgc gcgggggaag ctggcgggct gaggcgcccc    300
```

```
gctcttctcc tctgccccgg gcccgcgagg ccacgcgtcg ccgctcgaga gatgatgcag    360

gacgtgtcca gctcgccagt ctcgccggcc gacgacagcc tgagcaacag cgaggaagag    420

ccagaccggc agcagccgcc gagcggcaag cgcgggggac gcaagcggcg cagcagcagg    480

cgcagcgcgg gcggcggcgc ggggcccggc ggagccgcgg gtgggggcgt cggaggcggc    540

gacgagccgg gcagcccggc ccagggcaag cgcggcaaga agtctgcggg ctgtggcggc    600

ggcggcggcg cgggcggcgg cggcggcagc agcagcggcg gcgggagtcc gcagtcttac    660

gaggagctgc agacgcagcg ggtcatggcc aacgtgcggg agcgccagcg cacccagtcg    720

ctgaacgagg cgttcgccgc gctgcggaag atcatcccca cgctgccctc ggacaagctg    780

agcaagattc agaccctcaa gctggcggcc aggtacatcg acttcctcta ccaggtcctc    840

cagagcgacg agctggactc caagatggca agctgcagct atgtggctca cgagcggctc    900

agctacgcct tctcggtctg gaggatggag ggggcctggt ccatgtccgc gtcccactag    960

caggcggagc cccccacccc ctcagcaggg ccggagacct agatgtcatt gtttccagag   1020

aaggagaaaa tggacagtct agagactctg gagctggata actaaaaata aaaatatatg   1080

ccaaagattt tcttggaaat tagaagagca aaatccaaat tcaaagaaac agggcgtggg   1140

gcgcactttt aaaagagaaa gcgagacagg cccgtggaca gtgattccca gacgggcagc   1200

ggcaccatcc tcacacctct gcattctgat agaagtctga acagttgttt gtgttttttt   1260

ttttttttt tttgacgaag aatgttttta tttttatttt tttcatgcat gcattctcaa    1320

gaggtcgtgc caatcagcca ctgaaaggaa aggcatcact atggactttc tctattttaa   1380

aatggtaaca atcagaggaa ctataagaac acctttagaa ataaaaatac tgggatcaaa   1440

ctggcctgca aaaccatagt cagttaattc ttttttttcat ccttcctctg aggggaaaaa   1500

caaaaaaaaa cttaaaatac aaaaaacaac attctattta tttattgagg acccatggta   1560

aaatgcaaat agatccggtg tctaaatgca ttcatatttt tatgattgtt ttgtaaatat   1620

ctttgtatat ttttctgcaa taaataaata taaaaaattt agagaaaaa               1669
```

<210> SEQ ID NO 30
<211> LENGTH: 2387
<212> TYPE: DNA
<213> ORGANISM: Homo sapiens

<400> SEQUENCE: 30

```
agacacctct gccctcacca tgagcctctg gcagcccctg gtcctggtgc tcctggtgct     60

gggctgctgc tttgctgccc ccagacagcg ccagtccacc cttgtgctct tccctggaga    120

cctgagaacc aatctcaccg acaggcagct ggcagaggaa tacctgtacc gctatggtta    180

cactcgggtg gcagagatgc gtggagagtc gaaatctctg gggcctgcgc tgctgcttct    240

ccagaagcaa ctgtccctgc ccgagaccgg tgagctggat agcgccacgc tgaaggccat    300

gcgaacccca cggtgcgggg tcccagacct gggcagattc caaacctttg agggcgacct    360

caagtggcac caccacaaca tcacctattg gatccaaaac tactcggaag acttgccgcg    420

ggcggtgatt gacgacgcct ttgcccgcgc cttcgcactg tggagcgcgg tgacgccgct    480

caccttcact cgcgtgtaca gccgggacgc agacatcgtc atccagtttg gtgtcgcgga    540

gcacggagac gggtatccct tcgacgggaa ggacgggctc ctggcacacg cctttcctcc    600

tggccccggc attcagggag acgcccattt cgacgatgac gagttgtggt ccctgggcaa    660

gggcgtcgtg gttccaactc ggtttggaaa cgcagatggc gcggcctgcc acttcccctt    720
```

```
catcttcgag ggccgctcct actctgcctg caccaccgac ggtcgctccg acggcttgcc    780

ctggtgcagt accacggcca actacgacac cgacgaccgg tttggcttct gccccagcga    840

gagactctac acccaggacg gcaatgctga tgggaaaccc tgccagtttc cattcatctt    900

ccaaggccaa tcctactccg cctgcaccac ggacggtcgc tccgacggct accgctggtg    960

cgccaccacc gccaactacg accgggacaa gctcttcggc ttctgcccga cccgagctga   1020

ctcgacggtg atgggggca actcggcggg ggagctgtgc gtcttcccct tcactttcct   1080

gggtaaggag tactcgacct gtaccagcga gggccgcgga gatgggcgcc tctggtgcgc   1140

taccacctcg aactttgaca gcgacaagaa gtggggcttc tgcccggacc aaggatacag   1200

tttgttcctc gtggcggcgc atgagttcgg ccacgcgctg ggcttagatc attcctcagt   1260

gccggaggcg ctcatgtacc ctatgtaccg cttcactgag gggcccccct tgcataagga   1320

cgacgtgaat ggcatccggc acctctatgg tcctcgccct gaacctgagc cacggcctcc   1380

aaccaccacc acaccgcagc ccacggctcc cccgacggtc tgccccaccg gaccccccac   1440

tgtccacccc tcagagcgcc ccacagctgg ccccacaggt ccccccctcag ctggccccac   1500

aggtcccccc actgctggcc cttctacggc cactactgtg cctttgagtc cggtggacga   1560

tgcctgcaac gtgaacatct tcgacgccat cgcggagatt gggaaccagc tgtatttgtt   1620

caaggatggg aagtactggc gattctctga gggcaggggg agccggccgc agggcccctt   1680

ccttatcgcc gacaagtggc ccgcgctgcc ccgcaagctg gactcggtct ttgaggagcg   1740

gctctccaag aagcttttct tcttctctgg gcgccaggtg tgggtgtaca caggcgcgtc   1800

ggtgctgggc ccgaggcgtc tggacaagct gggcctggga gccgacgtgg cccaggtgac   1860

cggggccctc cggagtggca gggggaagat gctgctgttc agcgggcggc gcctctggag   1920

gttcgacgtg aaggcgcaga tggtggatcc ccggagcgcc agcgaggtgg accggatgtt   1980

ccccggggtg cctttggaca cgcacgacgt cttccagtac cgagagaaag cctatttctg   2040

ccaggaccgc ttctactggc gcgtgagttc ccggagtgag ttgaaccagg tggaccaagt   2100

gggctacgtg acctatgaca tcctgcagtg ccctgaggac tagggctccc gtcctgcttt   2160

ggcagtgcca tgtaaatccc cactgggacc aaccctgggg aaggagccag tttgccggat   2220

acaaactggt attctgttct ggaggaaagg gaggagtgga ggtgggctgg gccctctctt   2280

ctcacctttg ttttttgttg gagtgtttct aataaacttg gattctctaa cctttaaaaa   2340

aaaaaaaaaa aaaaaaaaaa aaaaaaaaaa aaaaaaaaaa aaaaaaa                 2387
```

<210> SEQ ID NO 31
<211> LENGTH: 3614
<212> TYPE: DNA
<213> ORGANISM: Homo sapiens

<400> SEQUENCE: 31

```
ggcttggggc agccgggtag ctcggaggtc gtggcgctgg gggctagcac cagcgctctg     60

tcgggaggcg cagcggttag gtggaccggt cagcggactc accggccagg gcgctcggtg    120

ctggaatttg atattcattg atccgggttt tatccctctt ctttttctt aaacattttt    180

ttttaaaact gtattgtttc tcgttttaat ttatttttgc ttgccattcc ccacttgaat    240

cgggccgacg gcttggggag attgctctac ttccccaaat cactgtggat tttggaaacc    300

agcagaaaga ggaaagaggt agcaagagct ccagagagaa gtcgaggaag agagagacgg    360

ggtcagagag agcgcgcggg cgtgcgagca gcgaaagcga caggggcaaa gtgagtgacc    420

tgcttttggg ggtgaccgcc ggagcgcggc gtgagccctc ccccttggga tcccgcagct    480
```

```
gaccagtcgc gctgacggac agacagacag acaccgcccc cagccccagc taccacctcc    540
tccccggccg gcggcggaca gtggacgcgg cggcgagccg cgggcagggg ccggagcccg    600
cgcccggagg cggggtggag ggggtcgggg ctcgcggcgt cgcactgaaa cttttcgtcc    660
aacttctggg ctgttctcgc ttcggaggag ccgtggtccg cgcgggggaa gccgagccga    720
gcggagccgc gagaagtgct agctcgggcc gggaggagcc gcagccggag gagggggagg    780
aggaagaaga gaaggaagag gagagggggc cgcagtggcg actcggcgct cggaagccgg    840
gctcatggac gggtgaggcg gcggtgtgcg cagacagtgc tccagccgcg cgcgctcccc    900
aggccctggc ccgggcctcg ggccggggag gaagagtagc tcgccgaggc gccgaggaga    960
gcgggccgcc ccacagcccg agccggagag ggagcgcgag ccgcgccggc cccggtcggg   1020
cctccgaaac catgaacttt ctgctgtctt gggtgcattg gagccttgcc ttgctgctct   1080
acctccacca tgccaagtgg tcccaggctg cacccatggc agaaggagga gggcagaatc   1140
atcacgaagt ggtgaagttc atggatgtct atcagcgcag ctactgccat ccaatcgaga   1200
ccctggtgga catcttccag gagtaccctg atgagatcga gtacatcttc aagccatcct   1260
gtgtgcccct gatgcgatgc gggggctgct gcaatgacga gggcctggag tgtgtgccca   1320
ctgaggagtc caacatcacc atgcagatta tgcggatcaa acctcaccaa ggccagcaca   1380
taggagagat gagcttccta cagcacaaca aatgtgaatg cagaccaaag aaagatagag   1440
caagacaaga aaaaaaatca gttcgaggaa agggaaaggg gcaaaaacga aagcgcaaga   1500
aatcccggta taagtcctgg agcgttccct gtgggccttg ctcagagcgg agaaagcatt   1560
tgtttgtaca agatccgcag acgtgtaaat gttcctgcaa aaacacagac tcgcgttgca   1620
aggcgaggca gcttgagtta aacgaacgta cttgcagatg tgacaagccg aggcggtgag   1680
ccgggcagga ggaaggagcc tccctcaggg tttcgggaac cagatctctc accaggaaag   1740
actgatacag aacgatcgat acagaaacca cgctgccgcc accacaccat caccatcgac   1800
agaacagtcc ttaatccaga aacctgaaat gaaggaagag gagactctgc gcagagcact   1860
ttgggtccgg agggcgagac tccggcggaa gcattcccgg gcgggtgacc cagcacggtc   1920
cctcttggaa ttggattcgc cattttattt ttcttgctgc taaatcaccg agcccggaag   1980
attagagagt tttatttctg ggattcctgt agacacaccc acccacatac atacatttat   2040
atatatatat attatatata tataaaaata aatatctcta ttttatatat ataaaatata   2100
tatattcttt ttttaaatta acagtgctaa tgttattggt gtcttcactg gatgtatttg   2160
actgctgtgg acttgagttg ggaggggaat gttcccactc agatcctgac agggaagagg   2220
aggagatgag agactctggc atgatctttt ttttgtccca cttggtgggg ccagggtcct   2280
ctcccctgcc caggaatgtg caaggccagg gcatgggggc aaatatgacc cagttttggg   2340
aacaccgaca aacccagccc tggcgctgag cctctctacc ccaggtcaga cggacagaaa   2400
gacagatcac aggtacaggg atgaggacac cggctctgac caggagtttg gggagcttca   2460
ggacattgct gtgctttggg gattccctcc acatgctgca cgcgcatctc gcccccaggg   2520
gcactgcctg gaagattcag gagcctgggc ggccttcgct tactctcacc tgcttctgag   2580
ttgcccagga gaccactggc agatgtcccg gcgaagagaa gagacacatt gttggaagaa   2640
gcagcccatg acagctcccc ttcctgggac tcgccctcat cctcttcctg ctccccttcc   2700
tggggtgcag cctaaaagga cctatgtcct cacaccattg aaaccactag ttctgtcccc   2760
ccaggagacc tggttgtgtg tgtgtgagtg gttgaccttc ctccatcccc tggtccttcc   2820
```

-continued cttcccttcc cgaggcacag agagacaggg caggatccac gtgcccattg tggaggcaga 2880
gaaaagagaa agtgttttat atacggtact tatttaatat cccttttttaa ttagaaatta 2940 aaacagttaa tttaattaaa gagtagggtt ttttttcagt attcttggtt aatatttaat 3000
ttcaactatt tatgagatgt atcttttgct ctctcttgct ctcttatttg taccggtttt 3060
tgtatataaa attcatgttt ccaatctctc tctccctgat cggtgacagt cactagctta 3120
tcttgaacag atatttaatt ttgctaacac tcagctctgc cctccccgat cccctggctc 3180
cccagcacac attcctttga aataaggttt caatatacat ctacatacta tatatatatt 3240
tggcaacttg tatttgtgtg tatatatata tatatatgtt tatgtatata tgtgattctg 3300
ataaaataga cattgctatt ctgtttttta tatgtaaaaa caaaacaaga aaaaatagag 3360
aattctacat actaaatctc tctccttttt taattttaat atttgttatc atttatttat 3420
tggtgctact gtttatccgt aataattgtg gggaaaagat attaacatca cgtctttgtc 3480
tctagtgcag tttttcgaga tattccgtag tacatattta tttttaaaca acgacaaaga 3540
aatacagata tatcttaaaa aaaaaaaagc attttgtatt aaagaattta attctgatct 3600
caaaaaaaaa aaaa 3614

<210> SEQ ID NO 32
<211> LENGTH: 2359
<212> TYPE: DNA
<213> ORGANISM: Homo sapiens

<400> SEQUENCE: 32
cgaccgagca cagacacgtt gcccaccgct cctctcccga ggtctgtagt cgcggagaaa 60
cacatgttgc gttactaacg ttcagaggtc tgcgacagct tcgatttgaa tgactagccg 120
ggaacaccaa gtttcactgt gtaattgcgt ccccctactc cggcgcctcc tttgcgacgc 180
tccctggaga aaagcacgcc cactgcacgc gctcagtcgc tacttccgct ctcgagtgtc 240
tccaagcaag atggcggagg agccgcagtc tgtgttgcag cttcctactt caattgctgc 300
tggaggggaa ggacttacgg atgtctcccc agaaacaacc accccggagc ccccgtcttc 360
cgctgcagtt tccccgggaa cagaggaacc tgctggcgac accaagaaaa aaattgacat 420
tttgctaaag gctgtgggag acactcctat tatgaaaaca aagaagtggg cagtagagcg 480
aacacgaacc atccaaggac tcattgactt catcaaaaag tttcttaaac ttgtggcctc 540
agaacagttg tttatttatg tgaatcagtc ctttgctcct tccccagacc aagaagttgg 600
aactctctat gagtgttttg gcagtgatgg taaactggtt ttacattact gcaagtctca 660
ggcgtgggga tgaaccacaa agaaaatcaa cttgctacta catgaaatgg attttcacgg 720
aagagacagc tctgaaaagt tttgatgctt gtggcaagag acttaacaga tgtgatctat 780
ttagtatgtg tctactctat gtttatgcat aagaaaacat ccatagcatg aatggactca 840
gaaaaatgtg atttgtatta atgcaccagt catcataaaa gatggtcatg atagtacacc 900
cattgctcct acttgttact attattgctg cagatctgcc tccaaggttg aaaaggagac 960
taagactgta taaacatctt cattgtcagt tctcaaaatg actgaaattg ttttcatggt 1020
aaaagttaat atactaaagg gttccttttt ttttaatgtt tacatttatc tctatgttta 1080
cctttttagt cacattgacc tgctggctga atacctcaaa tagtccagta gagggcagtc 1140
caccaggcag aaaaggttag gcgttttggt ttcacatctt tgctggggaa taatagggga 1200
aatggctgtt tttgctaatt tttagctaat atctagccag gagagcaagc acataggaca 1260
gactgaaaga ctgtaatttt acacaataca catggcttaa ttattttatt gggatacaga 1320
aaaatataaa ttctggacaa ataagtcata tacctgtttt cagtcctaac atttaaggat 1380
tcttgagtcc caatcacata actgtggtgt tactctgtca tttatatggt gtcaaaagca 1440
cttgatgagt aaacccagta gcatcttttt gagtgtttca taatgcattt tccaacttga 1500
aaacaataat tgaaaaatag ccttattgta tattttatgc catgactaaa agtgccattt 1560
ttactgatgc tattagactg ataatttctt gaagtgaaat ttaacctttt tttctcttta 1620
gtattatgtt tataatgcca tatttttaga aagcattcca gatcaggcat ggtggcttac 1680
acctgtaatc ccagcacttt ggaaggctga ggtgtgggga ttgcgtgaag ccacaagttt 1740
gagaccagcc tggttagcaa ggcaagatcc ccaactctac aaaaaaataa aaattaaaaa 1800
aaaattatta ggctgcagag gcaagaggat cccctgagcc cagaagttca agggtatagt 1860
gagtcgtgat tgtaccactg cattcctgct gagcaacaga gtgagacccc atctcaaaaa 1920
agaaaaaaaa aggcattcta gtaaatcgaa tgtaatgtga atggaatttc aaaacaggat 1980
ctaagatggt atgtagtaga attcaaagta atatcatttt aaagttaaat gagtatggaa 2040
aaggtctgtt ctctagtttt gtccagttca gtttactgaa ggaatatatt taattatatt 2100
catatattta acaaataaaa atatgttgaa ttttcgtatt gtttgccact gagggttcag 2160
atgatagacc tcaaaaaatc gaaaatactg gttgaaattt gtagcatcca tttagttatt 2220
ctttttgacc taaataactt aatagtttat taaatctaag gttagctaaa tatgtagcta 2280
accttatttg ttttctttcc taacaactct gaagaataca taggactttg cacttttttt 2340 ttttttttt ttttttaaa 2359

<210> SEQ ID NO 33
<211> LENGTH: 2265
<212> TYPE: DNA
<213> ORGANISM: Homo sapiens

<400> SEQUENCE: 33
acgcggaggt tgtaattggt ctctagacca cacctagttg ttgagtgccg ctgcttgaaa 60
atctcagttc tgccgagatc gcagaataca cacaagctac ctttgggcac cagagcagac 120
agaaccgcgg agcttcaggg tggaagattc gtggaaactt tgccaaggcc aggacctcgt 180
gtgttcccgt ccgcccctct gggacggcgc cagcccggca ggccgccgac cgtcctgggg 240
ctcccgcgca gcgcgatgcc ggcctcgtcc accgtccacg tgctgcagct gctgcgggag 300
ctgctcgcct tcgtgctcct cagctacacg gtgctcatcg ggcgctgct gctggccggc 360 tggaccactt acttcctggt gctgaagtga cagcgccgtc gccgcgcccg gccccgcctc 420
ccgcccggcc ccgcctcccg cccggccccg cctccctaac tcaccaggaa attcccttca 480
agccctggcc cgaactgagt ccccgcccac ccgccagcgt cacggcgccc gactcagctc 540
cgcgccggac ccacctccgc gccctcaggc cctgcatatg ccccgccccg cgcggaagtt 600
ccggcggttg gttgccttgc gcggccgtta cagcctttgc cctaagcctc gcccccctttc 660 cccctgcctg cccaatcccg actgcttcct tgggtggggg cgtggctatg gggcgaggcg 720
ctctcaggtg gaggccgtgc cccgctccgc gctcacgaag ctgcgtcact tccggcgtgt 780
gcgtctggcg tccgcgcgct gcacaatggc ggctctgaag agttggctgt cgcgcagcgt 840
aacttcattc ttcaggtaca gacagtgttt gtgtgttcct gttgtggcta actttaagaa 900
gcggtgtttc tcagaattga taagaccatg gcacaaaact gtgacgattg gctttggagt 960
aaccctgtgt gcggttccta ttgcacagaa atcagagcct cattccctta gtagtgaagc 1020

```
attgatgagg agagcagtgt ctttggtaac agatagcacc tctacctttc tctctcagac   1080

cacatatgcg ttgattgaag ctattactga atatactaag gctgtttata ccttaacttc   1140

tctttaccga caatatacaa gtttacttgg gaaaatgaat tcagaggagg aagatgaagt   1200

gtggcaggtg atcataggag ccagagctga gatgacttca aaacaccaag agtacttgaa   1260

gctggaaacc acttggatga ctgcagttgg tctttcagag atggcagcag aagctgcata   1320

tcaaactggc gcagatcagg cctctataac cgccaggaat cacattcagc tggtgaaact   1380

gcaggtggaa gaggtgcacc agctctcccg gaaagcagaa accaagctgg cagaagcaca   1440

gatagaagag ctccgtcaga aaacacagga ggaaggggag gagcgggctg agtcggagca   1500

ggaggcctac ctgcgtgagg attgagggcc tgagcacact gccctgtctc cccactcagt   1560

ggggaaagca ggggcagatg ccaccctgcc cagggttggc atgactgtct gtgcaccgag   1620

aagaggcggc agatcctgcc ctggccaatc aggcgagacg cctttgtgag ctgtgagtgc   1680

ctcctgtggt ctcaggcttg cgctggacct ggttcttagc ccttgggcac tgcaccctgt   1740

ttaacatttc accccactct gtacagctgc tcttacccat ttttttacc tcacacccaa   1800

agcattttgc ctacctgggt cagagagagg agtccttttt gtcatgccct taagttcagc   1860

aactgtttaa cctgttttca gtcttattta cgtcgtcaaa aatgatttag tacttgttcc   1920

ctctgttggg atgccagttg tggcaggggg aggggaacct gtccagtttg tacgatttct   1980

ttgtatgtat ttctgatgtg ttctctgatc tgccccccact gtcctgtgag gacagctgag   2040

gccaaggagt gaaaaaccta ttactactaa gagaaggggt gcagagtgtt tacctggtgc   2100

tctcaacagg acttaacatc aacaggactt aacacaggcc tcttgttcct tcctttcttt   2160

ccgtttctct attgtatcca aaggagaaga gtgtaagatt ttgtttgcat ctgaaagaga   2220

aaatgcgtct ctcctggggt cctaaaaaaa aaaaaaaaaa aaaaa                   2265


<210> SEQ ID NO 34
<211> LENGTH: 2722
<212> TYPE: DNA
<213> ORGANISM: Homo sapiens

<400> SEQUENCE: 34

ttggcgcgta aaagtggccg ggactttgca ggcagcggcg gccgggggcg gagcgggatc     60

gagccctcgc cgaggcctgc cgccatgggc ccgcgccgcc gccgccgcct gtcacccggg    120

ccgcgcgggc cgtgagcgtc atggccttgg ccggggcccc tgcgggcggc ccatgcgcgc    180

cggcgctgga ggccctgctc ggggccggcg cgctgcggct gctcgactcc tcgcagatcg    240

tcatcatctc cgccgcgcag gacgccagcg ccccgccggc tcccaccggc cccgcggcgc    300

ccgccgccgg cccctgcgac cctgacctgc tgctcttcgc cacaccgcag gcgccccggc    360

ccacacccag tgcgccgcgg cccgcgctcg gccgcccgcc ggtgaagcgg aggctggacc    420

tggaaactga ccatcagtac ctggccgaga gcagtgggcc agctcggggc agaggccgcc    480

atccaggaaa aggtgtgaaa tccccggggg agaagtcacg ctatgagacc tcactgaatc    540

tgaccaccaa gcgcttcctg gagctgctga gccactcggc tgacggtgtc gtcgacctga    600

actgggctgc cgaggtgctg aaggtgcaga agcggcgcat ctatgacatc accaacgtcc    660

ttgagggcat ccagctcatt gccaagaagt ccaagaacca catccagtgg ctgggcagcc    720

acaccacagt gggcgtcggc ggacggcttg aggggttgac ccaggacctc cgacagctgc    780

aggagagcga gcagcagctg gaccacctga tgaatatctg tactacgcag ctgcgcctgc    840

tctccgagga cactgacagc cagcgcctgg cctacgtgac gtgtcaggac cttcgtagca    900
```

ttgcagaccc tgcagagcag atggttatgg tgatcaaagc ccctcctgag acccagctcc 960
aagccgtgga ctcttcggag aactttcaga tctcccttaa gagcaaacaa ggcccgatcg 1020
atgttttcct gtgccctgag gagaccgtag gtgggatcag ccctgggaag accccatccc 1080
aggaggtcac ttctgaggag gagaacaggg ccactgactc tgccaccata gtgtcaccac 1140
caccatcatc tccccccctca tccctcacca cagatcccag ccagtctcta ctcagcctgg 1200
agcaagaacc gctgttgtcc cggatgggca gcctgcgggc tcccgtggac gaggaccgcc 1260
tgtccccgct ggtggcggcc gactcgctcc tggagcatgt gcgggaggac ttctccggcc 1320
tcctccctga ggagttcatc agcctttccc caccccacga ggccctcgac taccacttcg 1380
gcctcgagga gggcgagggc atcagagacc tcttcgactg tgactttggg gacctcaccc 1440
ccctggattt ctgacagggc ttggagggac cagggtttcc agagatgctc accttgtctc 1500
tgcagccctg gagcccctg tccctggccg tcctcccagc ctgtttggaa acatttaatt 1560
tatacccctc tcctctgtct ccagaagctt ctagctctgg ggtctggcta ccgctaggag 1620
gctgagcaag ccaggaaggg aaggagtctg tgtggtgtgt atgtgcatgc agcctacacc 1680
cacacgtgtg taccgggggt gaatgtgtgt gagcatgtgt gtgtgcatgt accggggaat 1740
gaaggtgaac atacacctct gtgtgtgcac tgcagacacg ccccagtgtg tccacatgtg 1800
tgtgcatgag tccatgtgtg cgcgtggggg ggctctaact gcactttcgg cccttttgct 1860
ctgggggtcc cacaaggccc agggcagtgc ctgctcccag aatctggtgc tctgaccagg 1920
ccaggtgggg aggctttggc tggctgggcg tgtaggacgg tgagagcact tctgtcttaa 1980 aggtttttc tgattgaagc tttaatggag cgttatttat ttatcgaggc ctctttggtg 2040
agcctgggga atcagcaaag gggaggaggg gtgtggggtt gataccccaa ctccctctac 2100
ccttgagcaa gggcaggggt ccctgagctg ttcttctgcc ccatactgaa ggaactgagg 2160
cctgggtgat ttatttattg ggaaagtgag ggagggagac agactgactg acagccatgg 2220
gtggtcagat ggtggggtgg gccctctcca gggggccagt tcagggcccc agctgccccc 2280
caggatggat atgagatggg agaggtgagt gggggacctt cactgatgtg ggcaggaggg 2340
gtggtgaagg cctcccccag cccagaccct gtggtccctc ctgcagtgtc tgaagcgcct 2400
gcctccccac tgctctgccc caccctccaa tctgcacttt gatttgcttc ctaacagctc 2460
tgttccctcc tgctttggtt ttaataaata ttttgatgac gtttgggccg ggttttggga 2520
ctctgttggg aacatttcgg ggcgggagag gccaaggttg ctggggaaat gcccattctc 2580
cacttccctt ctccctgtcc gtgcccgatt tgatttgagc ctcataactc gaagaaaggt 2640
cagcttcctc gctgttttgg tcctaactca aaagcagatc cagtaaaggt ttttgttgta 2700
aaaaaaaaaa aaaaaaaaaa aa 2722

<210> SEQ ID NO 35
<211> LENGTH: 2560
<212> TYPE: DNA
<213> ORGANISM: Homo sapiens

<400> SEQUENCE: 35
tgcggggagc cgagccgccg gcgctcgacg cgcgcgctct cgcgagaccc gcgggatcac 60
gtgacgcccg ggcgcggcgc agctcacgtg acaagcgctg ccggccgcgg tgtcttcttc 120
gtgccggcgt cgcagtggcc gggcctcttg cgtctggtaa cgccgctgtc tctaacgcca 180
gcccttggcg cccgcgcccc gccaccgcag cgcccggcag tccgcggccc aaccgccgcc 240

-continued

```
cgcgcccccg ctccccgcac cgtacccggc cgcctcgcgc catggcggcc cccggcagcg    300
cccggcgacc cctgctgctg ctactgctgt tgctgctgct cggcctcatg cattgtgcgt    360
cagcagcaat gtttatggtg aaaaatggca acgggaccgc gtgcataatg gccaacttct    420
ctgctgcctt ctcagtgaac tacgacacca agagtggccc taagaacatg acctttgacc    480
tgccatcaga tgccacagtg gtgctcaacc gcagctcctg tggaaaagag aacacttctg    540
accccagtct cgtgattgct tttggaagag gacatacact cactctcaat ttcacgagaa    600
atgcaacacg ttacagcgtc cagctcatga gttttgttta taacttgtca gacacacacc    660
ttttccccaa tgcgagctcc aaagaaatca agactgtgga atctataact gacatcaggg    720
cagatataga taaaaaatac agatgtgtta gtggcaccca ggtccacatg aacaacgtga    780
ccgtaacgct ccatgatgcc accatccagg cgtacctttc caacagcagc ttcagcaggg    840
gagagacacg ctgtgaacaa gacaggcctt ccccaaccac agcgcccccct gcgccaccca    900
gcccctcgcc ctcacccgtg cccaagagcc cctctgtgga caagtacaac gtgagcggca    960
ccaacgggac ctgcctgctg gccagcatgg ggctgcagct gaacctcacc tatgagagga   1020
aggacaacac gacggtgaca aggcttctca acatcaaccc caacaagacc tcggccagcg   1080
ggagctgcgg cgcccacctg gtgactctgg agctgcacag cgagggcacc accgtcctgc   1140
tcttccagtt cgggatgaat gcaagttcta gccggttttt cctacaagga atccagttga   1200
atacaattct tcctgacgcc agagaccctg cctttaaagc tgccaacggc tccctgcgag   1260
cgctgcaggc cacagtcggc aattcctaca agtgcaacgc ggaggagcac gtccgtgtca   1320
cgaaggcgtt ttcagtcaat atattcaaag tgtgggtcca ggctttcaag gtggaaggtg   1380
gccagtttgg ctctgtggag gagtgtctgc tggacgagaa cagcatgctg atccccatcg   1440
ctgtgggtgg tgccctggcg gggctggtcc tcatcgtcct catcgcctac ctcgtcggca   1500
ggaagaggag tcacgcaggc taccagacta tctagcctgg tgcacgcagg cacagcagct   1560
gcaggggcct ctgttccttt ctctgggctt agggtcctgt cgaaggggag gcacactttc   1620
tggcaaacgt ttctcaaatc tgcttcatcc aatgtgaagt tcatcttgca gcatttacta   1680
tgcacaacag agtaactatc gaaatgacgg tgttaatttt gctaactggg ttaaatattt   1740
tgctaactgg ttaaacatta atatttacca aagtaggatt ttgagggtgg gggtgctctc   1800
tctgaggggg tgggggtgcc gctgtctctg aggggtgggg gtgccgctgt ctctgagggg   1860
tgggggtgcc gctctctctg agggggtggg ggtgccgctt tctctgaggg ggtgggggtg   1920
ccgctctctc tgagggggtg ggggtgctgc tctctccgag ggtggaatg ccgctgtctc   1980
tgaggggtgg gggtgccgct ctaaattggc tccatatcat ttgagtttag ggttctggtg   2040
tttggtttct tcattcttta ctgcactcag atttaagcct tacaaaggga aagcctctgg   2100
ccgtcacacg taggacgcat gaaggtcact cgtggtgagg ctgacatgct cacacattac   2160
aacagtagag agggaaaatc ctaagacaga ggaactccag agatgagtgt ctggagcgct   2220
tcagttcagc tttaaaggcc aggacgggcc acacgtggct ggcggcctcg ttccagtggc   2280
ggcacgtcct tgggcgtctc taatgtctgc agctcaaggg ctggcacttt tttaaatata   2340
aaaatgggtg ttatttttat ttttttttgt aaagtgattt ttggtcttct gttgacattc   2400
ggggtgatcc tgttctgcgc tgtgtacaat gtgagatcgg tgcgttctcc tgatgttttg   2460
ccgtggcttg ggattgtac acgggaccag ctcacgtaat gcattgcctg taacaatgta   2520
ataaaaagcc tctttctttt aaaaaaaaaa aaaaaaaaaa                         2560
```

<210> SEQ ID NO 36
<211> LENGTH: 1030
<212> TYPE: DNA
<213> ORGANISM: Homo sapiens

<400> SEQUENCE: 36
accgggcgag ttacctcccg cagccgcagc cgccgtgctc agcgcgagcc ccggagccct 60
tgagcgcgag gcgcggagcc cccggagccc ccaaaccgca gacacatccc cgcgccccag 120
agccccggcc tgcgcgccca gccgggcccg cgcgatgccc tcagaccggc ctttcaagca 180
gcggcggagc ttcgccgacc gctgtaagga ggtacagcag atccgcgacc agcaccccag 240
caaaatcccg gtgatcatcg agcgctacaa gggtgagaag cagctgcccg tcctggacaa 300
gaccaagttt ttggtcccgg accatgtcaa catgagcgag ttggtcaaga tcatccggcg 360
ccgcctgcag ctgaacccca cgcaggcctt cttcctgctg gtgaaccagc acagcatggt 420
gagtgtgtcc acgcccatcg cggacatcta cgagcaggag aaagacgagg acggcttcct 480
ctatatggtc tacgcctccc aggaaacctt cggcttctga gccagcagta ggggggctcg 540
gcctgggagt cggggggccc cggtcaggcc ctgcccagag agctcctggt tcctgaactg 600
agctgcctct accgtggtgg gctgggcagg catgtgcccc cctagtcaga gggcaccaac 660
ccacctactc tgcccctggg tggatcctgg gccggtcgtg ttagggttgt ccctctgggt 720
gctggctggt gggatggggg agggtgggga gcagctccca gcacccctgc tgtgtggttc 780
atcttttttt taggcccctg cctgtctgcc catctgcccc tcacccaccc gaggctctgc 840
ccaccgcctg gacctgccca cccctgaaag actggcccct ggctccccgc ccctcggtct 900
ccacgtggtg tatggatctg tggtcattgt ccctctgcag aataaagatt gctcaggcct 960
gcctggcaaa aaaaaaaaaa aaaaaaaaaa aaaaaaaaaa aaaaaaaaaa aaaaaaaaaa 1020
aaaaaaaaaa 1030

<210> SEQ ID NO 37
<211> LENGTH: 5059
<212> TYPE: DNA
<213> ORGANISM: Homo sapiens

<400> SEQUENCE: 37
ctttgcgcac gcgcgccgct tcccagtggc aagcgcgggc aggaccgcgt tgcgtcatcg 60
gggcgcgcgc ctcagagaga gctgtggttg ccggaagttg agcggcggca agaaataatg 120
gcggcagcta cgggggatcc tggactctct aaactgcagt ttgccccttt tagtagtgcc 180
ttggatgttg ggttttggca tgagttgacc cagaagaagc tgaacgagta tcggctggat 240
gaagctccca aggacattaa gggttattac tacaatggtg actctgctgg gctgccagct 300
cgcttaacat tggagttcag tgcttttgac atgagtgctc ccacccccagc ccgttgctgc 360 ccagctattg gaacactgta taacaccaac acactcgagt ctttcaagac tgcagataag 420
aagctccttt tggaacaagc agcaaatgag atatgggaat ccataaaatc aggcactgct 480
cttgaaaacc ctgtactcct caacaagttc ctcctcttga catttgcaga tctaaagaag 540
taccacttct actattggtt ttgctatcct gccctctgtc ttccagagag tttacctctc 600
attcaggggc cagtgggttt ggatcaaagg ttttcactaa aacagattga agcactagag 660
tgtgcatatg ataatctttg tcaaacagaa ggagtcacag ctcttcctta cttcttaatc 720
aagtatgatg agaacatggt gctggtttcc ttgcttaaac actacagtga tttcttccaa 780
ggtcaaagga cgaagataac aattggtgta tatgatccct gtaacttagc ccagtaccct 840

-continued

```
ggatggcctt tgaggaattt tttggtccta gcagcccaca gatggagtag cagtttccag    900
tctgttgaag ttgtttgctt ccgtgaccgt accatgcagg gggcgagaga cgttgcccac    960
agcatcatct tcgaagtgaa gcttccagaa atggcattta gcccagattg tcctaaagca   1020
gttggatggg aaaagaacca gaaaggaggc atgggaccaa ggatggtgaa cctcagtgaa   1080
tgtatggacc ctaaaaggtt agctgagtca tcagtggatc taaatctcaa actgatgtgt   1140
tggagattgg ttcctacttt agacttggac aaggttgtgt ctgtcaaatg tctgctgctt   1200
ggagccggca ccttgggttg caatgtagct aggacgttga tgggttgggg cgtgagacac   1260
atcacatttg tggacaatgc caagatctcc tactccaatc ctgtgaggca gcctctctat   1320
gagtttgaag attgcctagg gggtggtaag cccaaggctc tggcagcagc ggaccggctc   1380
cagaaaatat tccccggtgt gaatgccaga ggattcaaca tgagcatacc tatgcctggg   1440
catccagtga acttctccag tgtcactctg gagcaagccc gcagagatgt ggagcaactg   1500
gagcagctca tcgaaagcca tgatgtcgtc ttcctattga tggacaccag ggagagccgg   1560
tggcttcctg ccgtcattgc tgcaagcaag agaaagctgg tcatcaatgc tgctttggga   1620
tttgacacat ttgttgtcat gagacatggt ctgaagaaac caaagcagca aggagctggg   1680
gacttgtgtc caaaccaccc tgtggcatct gctgacctcc tgggctcatc gctttttgcc   1740
aacatccctg gttacaagct tggctgctac ttctgcaatg atgtggtggc cccaggagat   1800
tcaaccagag accggacctt ggaccagcag tgcactgtga gtcgtccagg actggccgtg   1860
attgcaggag ccctggccgt ggaattgatg gtatctgttt tgcagcatcc agaaggggggc  1920
tatgccattg ccagcagcag tgacgatcgg atgaatgagc ctccaacctc tcttgggctt   1980
gtgcctcacc agatccgggg atttctttca cggtttgata atgtccttcc cgtcagcctg   2040
gcatttgaca aatgtacagc ttgttcttcc aaagttcttg atcaatatga acgagaagga   2100
tttaacttcc tagccaaggt gtttaattct tcacattcct tcttagaaga cttgactggt   2160
cttacattgc tgcatcaaga aacccaagct gctgagatct gggacatgag cgatgatgag   2220
accatctgag atggccccgc tgtggggctg acttctcccc ggccgcctgc tgaggagctc   2280
tccatcgcca gagcaggact gctgacccca ggcctggtga ttctgggccc ctcctccata   2340
ccccgaggtc tgggattccc ccctctgctg cccaggagtg gccagtgttc ggcgttgctc   2400
gggattcaag ataccaccag ttcagagcta aataataacc ttggccttgg ccttgctatt   2460
gacctgggac ttggtcctcc atgcagtttt tatttcttgt cacagtgact gatagccatc   2520
ccccaggatc ctttcccctt ggccctgagg gggtgaccca acacagacca aatggggaaa   2580
tgagcaacca gctcctgccc agagccactg cgggaggtgg caccctcatc cccggaatgt   2640
gctgcccacc gcaccgcagg ctcctcctgt gggggccctg ggcatgggtg agggtgggac   2700
cccgtgagcg cactgcaccc tggccctggt ggagcgggag gaggaggaga gccgagctgg   2760
gtacgagact aaagggccca catgacccag tgacgccaga tttccaccaa ggactgagtg   2820
agctgctcag acatggcttt ctgcctccca gcctgtcctc cactgtgggc atagcatctg   2880
tgcctgcctg cctgcttgag ggagaggagt ttctgctgct gccttgagct gggggggaaga  2940
gcccaggggc agatcctggc agctgcctgg atggggctcc tccctgccct tatgagcagg   3000
ccaggcccag aaaggccgag cctgggctgc cttcctgccc cagccgaggg aggggtcaga   3060
cggctctacc atgggtaact caggcaagag ctggttttcc tctttattct gggtgtgtgc   3120
agctgtgagg ccccaaccca ggagaggcca tggcctaggt acctgtgacc accctgcccc   3180
cgtgtagagg gcatcgtctt tcctgctatt ttattctttc agcttttgtc ttaggcccag   3240
```

aatcaaagtg aaaattgagt cgagctgacc cttacaacag taggatttag tagggtagat 3300
ttcaaatgag gcttcgcttc tcccaaagta gccagtccaa gttccagtgg ctgtcgttca 3360
gctcatggga gcttcatggg gacacagccg gcacaggtgc agggcccgag tccgcccacc 3420
cagcctggcg ctgaaactgc acacgtacac tatgtggttt aagagcactt tattattgtt 3480
cttaaggcta cttttaagta caaaaaaaga tggcctgcca aaccttttt tttcttcttc 3540 caggaaaaac aggccacaga gaatggtata ttacagattt acacacatga agagaaggtc 3600
agagcgcact gcaggcagcg cggctctggg aagaacttca cggagcccct tcttagagca 3660
gggagggggc tttctcagtg aaatgtttgg ttttctgctg cctcctctgc cccaggcccc 3720
cctccagggt actgcctatc ccagataggt cagtgcacca gggacccggc cgccagcacc 3780
gccgacccct cccagagtga cgcccttgtt cactgacaaa gagacctgtc ccaggagtgt 3840
cctccaccga gccggtcagc tgtgggtggt tttcctgtta cgacgctcag tagcctgtag 3900
caataacaaa ctcgtggcta tgaatgcaga tgcagtgttc tcatagaata actgttcctg 3960
cacttttaca gacaaatcta cgacaaaaaa aaagatcaac tttttttttc cgaacaacaa 4020
aaaaaatgaa tgattacaat aggaaaggga aaaattaaat agctacatat cattaacaaa 4080
ttaatgttct tcaaaaaata cctacaaatt tctctgtaca ttctttacgc acagcgtaac 4140
gatggtctca aaatcaccca tatagaaaag tgttctcaac gatttttcct acagaaaata 4200
taggggcctg aatgccaaag cttggaagcc cagtacagtg ggagtgaaat gtgtgcgggg 4260
caaggagaag ggcttttctt tcctccactt ttcaaaggcc tgcagccact ctgtgactac 4320
aagagccagt cctccgacct tttcacccag tgccaatttc caaaattcaa cagctaaaaa 4380
ctgtaaaacc gggggtcata cggtgtgcag agtccacaaa gccttgcagg tgaggtgacc 4440
acgcccacgt cacctggtca ggtgccatcg tcgtgagcct ctggtgggcc aggtgggaca 4500
cagcacaccc caggggggagg ggatagaaac gctcattgac caaaaaggag cagctgtgac 4560
ctccacagct gtgtctgtca tgcttgcttc atctaatttc tagttagtag ctattaatat 4620
agcaaataat aaatgcagta ataacagtat aaagtcagag gaatgtatac tgccttggcc 4680
ccagcgtacg aggaagcgta taaaacacca tatcacagat tgtctgtcag taatctgctg 4740
ttcagccaag agagttcaaa gggagcagtt tctgcatgta gggaagttgg aagacacaaa 4800
ccccacctcc cctgggagct tgtaacaaag cagacaggga tgcaaaaata aatgatgtca 4860
gcctgcagcc aaactccagc atcccacacc gcagctgacc cactgctcat cgcgagggcc 4920
tgccaggagc tggcctcccg cactacttgt gagtaaagtg aatatcaaat accaatctta 4980
gagtacaact gtaccagcag taagtatatc taggactgta actgacaaaa ataaactaat 5040
tctgaaaaga aaaaaaaaa 5059

<210> SEQ ID NO 38
<211> LENGTH: 2117
<212> TYPE: DNA
<213> ORGANISM: Homo sapiens

<400> SEQUENCE: 38
gacttaacgc gcccccgccc cgcgcccggc ctcggcagcc gcctgtcgcc gcgggagcag 60
ccgctatctc tgtgtgtccg cgtgtgcgcc cggtccccgc ctgccgcacc atggagagct 120
accacaagcc tgaccagcag aagctgcagg ccttgaagga cacggccaac cgcctacgta 180
tcagctccat ccaggccacc actgcggcgg gctctggcca ccccacgtca tgctgcagcg 240

```
ccgcagagat catggctgtc ctctttttcc acaccatgcg ctacaagtcc caggaccccc    300

ggaatccgca caatgaccgc tttgtgctct ccaagggcca tgcagctccc atcctctacg    360

cggtctgggc tgaagctggt ttcctggccg aggcggagct gctgaacctg aggaagatca    420

gctccgactt ggacgggcac ccggtcccga aacaagcttt caccgacgtg gccactggct    480

ccctgggcca gggcctcggg gccgcttgtg ggatggccta caccggcaaa tacttcgaca    540

aggccagcta ccgagtctat tgcttgctgg gagacgggga gctgtcagag ggctctgtat    600

gggaggccat ggccttcgcc agcatctata agctggacaa ccttgtggcc attctagaca    660

tcaatcgcct gggccagagt gacccggccc cactgcagca ccagatggac atctaccaga    720

agcggtgcga ggccttcggt tggcatgcca tcatcgtgga tggacacagc gtggaggagc    780

tgtgcaaggc ctttggccag gccaagcacc agccaacagc catcattgcc aagaccttca    840

agggccgagg gatcacgggg gtagaagata aggagtcttg gcatgggaag cccctcccca    900

aaaacatggc tgagcagatc atccaggaga tctacagcca gatccagagc aaaaagaaga    960

tcctggcaac ccctccacag gaggacgcac cctcagtgga cattgccaac atccgcatgc   1020

ccagcctgcc cagctacaaa gttggggaca agatagccac ccgcaaggcc tacgggcagg   1080

cactggccaa gctgggccat gccagtgacc gcatcatcgc cctggatggg gacaccaaaa   1140

attccacctt ctcggagatc ttcaaaaagg agcacccgga ccgcttcatc gagtgctaca   1200

ttgctgagca gaacatggtg agcatcgcgg tgggctgtgc cacccgcaac aggacggtgc   1260

ccttctgcag cacttttgca gccttcttca cgcgggcctt tgaccagatt cgcatggccg   1320

ccatctccga gagcaacatc aacctctgcg gctcccactg cggcgtttcc atcggggaag   1380

acgggccctc ccagatggcc ctagaagatc tggctatgtt tcggtcagtc cccacatcaa   1440

ctgtctttta cccaagtgat ggcgttgcta cagagaaggc agtggaacta gccgccaata   1500

caaagggtat ctgcttcatc cggaccagcc gcccagaaaa tgccatcatc tataacaaca   1560

atgaggactt ccaggtcgga caagccaagg tggtcctgaa gagcaaggat gaccaggtga   1620

ccgttatcgg ggctggggtg accctgcacg aggccttggc cgctgccgaa ctgctgaaga   1680

aagaaaagat caacatccgc gtgctggacc ccttcaccat caagcccctg gacagaaaac   1740

tcattctcga cagcgctcgt gccaccaagg gcaggatcct caccgtggag gaccattatt   1800

atgaaggtgg cattggtgag gctgtgtcca gtgcagtagt gggcgagcct ggcatcactg   1860

tcacccacct ggcagttaac cgggtaccaa gaagtgggaa gccggctgag ctgctgaaga   1920

tgtttggtat cgacagggat gccattgcac aagctgtgag ggcctcatc accaaggcct   1980

agggcgggta tgaagtgtgg ggcgggggtc tatacattcc tgagattctg ggaaaggtgc   2040

tcaaagatgt actgagagga ggggtaaata tatgttttga gaaaaatgaa ttggccctga   2100

aaaaaaaaaa aaaaaaa                                                  2117
```

<210> SEQ ID NO 39
<211> LENGTH: 2215
<212> TYPE: DNA
<213> ORGANISM: Homo sapiens

<400> SEQUENCE: 39

```
ttccccggct ctagcaggcc ggcttctctg tccaatgccc acccggagct gggaggagga     60

gtctgcgtaa tgtgcgtgtg aagagactgg gggagctggc cggggctcac ggtgtttgac    120

ccgtcggtcg tgcgtgagag gaaagggaag gaggaggtcc cgaatagcgg tcgccgaaat    180

gttccggtgt ggaggcctgg cggcgggtgc tttgaagcag aagctggtgc ccttggtgcg    240
```

```
gaccgtgtgc gtccgaagcc cgaggcagag gaaccggctc ccaggcaact tgttccagcg    300
atggcatgtt cctctagaac tccagatgac aagacaaatg gctagctctg gtgcatcagg    360
gggcaaaatc gataattctg tgttagtcct tattgtgggc ttatcaacag taggagctgg    420
tgcctatgcc tacaagacta tgaaagagga tgaaaaaaga tacaatgaaa gaatttcagg    480
gttagggctg acaccagaac agaaacagaa aaaggccgcg ttatctgctt cagaaggaga    540
ggaagttcct caagacaagg cgccaagtca tgttcctttc ctgctaattg gtggaggcac    600
agctgctttt gctgcagcca gatccatccg ggctcgggat cctggggcca gggtactgat    660
tgtatctgaa gatcctgagc tgccgtacat gcgacctcct ctttcaaaag aactgtggtt    720
ttcagatgac ccaaatgtca caaagacact gcgattcaaa cagtggaatg gaaaagagag    780
aagcatatat ttccagccac cttctttcta tgtctctgct caggacctgc ctcatattga    840
gaatggtggt gtggctgtcc tcactgggaa gaaggtagta cagctggatg tgagagacaa    900
catggtgaaa cttaatgatg gctctcaaat aacctatgaa aagtgcttga ttgcaacagg    960
aggtactcca agaagtctgt ctgccattga tagggctgga gcagaggtga agagtagaac   1020
aacgcttttc agaaagattg gagactttag aagcttggag aagatttcac gggaagtcaa   1080
atcaattacg attatcggtg ggggcttcct tggtagcgaa ctggcctgtg ctcttggcag   1140
aaaggctcga gccttgggca cagaagtgat tcaactcttc cccgagaaag gaaatatggg   1200
aaagatcctc cccgaatacc tcagcaactg gaccatggaa aaagtcagac gagagggggt   1260
taaggtgatg cccaatgcta ttgtgcaatc cgttggagtc agcagtggca agttacttat   1320
caagctgaaa gacggcagga aggtagaaac tgaccacata gtggcagctg tgggcctgga   1380
gcccaatgtt gagttggcca agactggtgg cctggaaata gactcagatt ttggtggctt   1440
ccgggtaaat gcagagctac aagcacgctc taacatctgg gtggcaggag atgctgcatg   1500
cttctacgat ataaagttgg gaaggaggcg ggtagagcac catgatcacg ctgttgtgag   1560
tggaagattg gctggagaaa atatgactgg agctgctaag ccgtactggc atcagtcaat   1620
gttctggagt gatttgggcc ccgatgttgg ctatgaagct attggtcttg tggacagtag   1680
tttgcccaca gttggtgttt ttgcaaaagc aactgcacaa gacaacccca aatctgccac   1740
agagcagtca ggaactggta tccgatcaga gagtgagaca gagtccgagg cctcagaaat   1800
tactattcct cccagcaccc cggcagttcc acaggctccc gtccaggggg aggactacgg   1860
caaaggtgtc atcttctacc tcagggacaa agtggtcgtg gggattgtgc tatggaacat   1920
ctttaaccga atgccaatag caaggaagat cattaaggac ggtgagcagc atgaagatct   1980
caatgaagta gccaaactat tcaacattca tgaagactga agccccacag tggaattggc   2040
aaacccactg cagcccctga gaggaggtcg aatgggtaaa ggagcatttt tttattcagc   2100
agactttctc tgtgtatgag tgtgaatgat caagtccttt gtgaatattt tcaactatgt   2160
aggtaaattc ttaatgttca catagtgaaa taaattctga ttcttctaaa ttaaa        2215
```

<210> SEQ ID NO 40
<211> LENGTH: 1535
<212> TYPE: DNA
<213> ORGANISM: Homo sapiens

<400> SEQUENCE: 40

```
cctccgctca gtccgggagc gcacgtgggc cgcggcgctc cgacctccgc tttcccaccg     60
cccgcagctg aagcacatcc cgcagcccgg cgcggactcc gatcgccgca gttgccctct    120
```

```
ggcgccatgt cgcagaacgg agcgcccggg atgcaggagg agagcctgca gggctcctgg    180
gtagaactgc acttcagcaa taatgggaac gggggcagcg ttccagcctc ggtttctatt    240
tataatggag acatggaaaa aatactgctg gacgcacagc atgagtctgg acggagtagc    300
tccaagagct ctcactgtga cagcccacct cgctcgcaga caccacaaga taccaacagg    360
gcttctgaaa cagataccca tagcattgga gagaaaaaca gctcacagtc tgaggaagat    420
gatattgaaa gaaggaaaga agttgaaagc atcttgaaga aaaactcaga ttggatatgg    480
gattggtcaa gtcggccgga aaatattccc cccaaggagt tcctctttaa acacccgaag    540
cgcacggcca ccctcagcat gaggaacacg agcgtcatga agaaaggggg catattctct    600
gcagaatttc tgaaagtttt ccttccatct ctgctgctct ctcatttgct ggccatcgga    660
ttggggatct atattggaag gcgtctgaca acctccacca gcacctttttg atgaagaact    720
ggagtctgac ttggttcgtt agtggattac ttctgagctt gcaacatagc tcactgaaga    780
gctgttagat cctggggtgg ccacgtcact tgtgtttatt tgttctgtaa atgctgcgtt    840
cctaatttag taaaataaaa gaatagacac taaaatcatg ttgatctata attacaccta    900
tgggatcaat aagcatgtca gactgattaa tgtctactgt gaaaatttgg tagtaaattt    960
tcatttgata ttagatataa atatctgaat ataaataatt ttaatatact agtcatgatg   1020
tgtgttgtat tttaaaaatt atctgcaacc ttaattcagc tgaagtactt tatatttcaa   1080
aagaatgaat aacattgata ataaaatcgc tactttaagg ggtttgtcca aaataaatat   1140
tgtggcctta tatatcacac tattgtagaa agtattattt aatttaaatg gatgcaggtt   1200
gtctactaaa gaaagattat atataactat gctaattgtt cataatcaac agaaaccaag   1260
atagagctac aaactcagct gtacagttcg tacactaaac tcttcttgct tttgcattat   1320
aaggaattaa gtctccgatt attaggtgat caccctggat gatcagtttt ctgctgaagg   1380
cacctactca gtatcttttc ctctttatca ctctgcattg gtgaatttaa tcctctcctt   1440
tgtgttcaac ttttgtgtgc ttttaaaatc agctttattc taagcaaatc tgtgtctact   1500
ttaaaaaact ggaaatggaa aaaaaaataa atctt                              1535

<210> SEQ ID NO 41
<211> LENGTH: 1372
<212> TYPE: DNA
<213> ORGANISM: Homo sapiens

<400> SEQUENCE: 41

cgggtgctga tgcgagtcgg tggcagcgag gacattttct gactccctgg cccctgacac     60
ggctgcactt tccatcccgt cgcggggccg gccgctactc cggccccagg atgcagaatg    120
tgattaatac tgtgaaggga aaggcactgg aagtggctga gtacctgacc ccggtcctca    180
aggaatcaaa gtttaaggaa acaggtgtaa ttaccccaga agagtttgtg gcagctggag    240
atcacctagt ccaccactgt ccaacatggc aatgggctac aggggaagaa ttgaaagtga    300
aggcatacct accaacaggc aaacaatttt tggtaaccaa aaatgtgccg tgctataagc    360
ggtgcaaaca gatggaatat tcagatgaat tggaagctat cattgaagaa gatgatggtg    420
atggcggatg ggtagataca tatcacaaca caggtattac aggaataacg gaagccgtta    480
aagagatcac actggaaaat aaggacaata taaggcttca agattgctca gcactatgtg    540
aagaggaaga agatgaagat gaaggagaag ctgcagatat ggaagaatat gaagagagtg    600
gattgttgga aacagatgag gctaccctag atacaaggaa aatagtagaa gcttgtaaag    660
ccaaaactga tgctggcggt gaagatgcta ttttgcaaac cagaacttat gacctttaca    720
```

-continued tcacttatga taaatattac cagactccac gattatggtt gtttggctat gatgagcaac 780
ggcagccttt aacagttgag cacatgtatg aagacatcag tcaggatcat gtgaagaaaa 840
cagtgaccat tgaaaatcac cctcatctgc caccacctcc catgtgttca gttcacccat 900
gcaggcatgc tgaggtgatg aagaaaatca ttgagactgt tgcagaagga gggggagaac 960
ttggagttca tatgtatctt cttattttct tgaaatttgt acaagctgtc attccaacaa 1020
tagaatatga ctacacaaga cacttcacaa tgtaatgaag agagcataaa atctatccta 1080
attattggtt ctgattttta aagaattaac ccatagatgt gaccattgac catattcatc 1140
aatatataca gtttctctaa taagggactt atatgtttat gcattaaata aaaatatgtt 1200
ccactaccag ccttacttgt ttaataaaaa tcagtgcaaa gaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aa 1372

<210> SEQ ID NO 42
<211> LENGTH: 3553
<212> TYPE: DNA
<213> ORGANISM: Homo sapiens

<400> SEQUENCE: 42
gagccagcgc ggtagggcca gagtgggaag gccagagcgg gcgtccccgc cagtgacccc 60
acgccgcccg tccgcgccca acccggcctc cgccgagtgt ccaaaccaaa agcgaaagga 120
acccgacccc gcgtcccctc cggcggctcc gtagtcgcgt ccgcttggag ctcgccgggc 180
gcctccgacc ctgccgggcc gctttgtgac ttcactcgtt tcgcaacaag cccgggcagc 240
ccgcgcccca cccactctgg cccggcagcc tcgccgcccg cagcctcgct ccgctcctcg 300
cgcttcccct ccctccgggg ctgggcctgc cccggccgtc gcggagcctc ccctcccacc 360
gtccgtgagt gtacgcgccc ggccgccgcc tccaggcagc ccggagcaac ccggcgcccg 420
gccccgctgg gcgcagcact ccgtcggcgg cggcggcggc gcgatgctgt gcttcctgag 480
gggaatggct ttcgtcccct tcctcttggt gacctggtcg tcagccgcct tcattatctc 540
ctacgtggtc gccgtgctct ccgggcacgt caacccctte ctcccgtata tcagtgatac 600
gggaacaaca cctccagaga gtggtatttt tggatttatg ataaacttct ctgcatttct 660
tggtgcagcc acgatgtata caagatacaa aatagtacag aagcaaaatc aaacctgcta 720
tttcagcact cctgttttta acttggtgtc tttagtgctt ggattggtgg gatgtttcgg 780
aatgggcatt gtcgccaatt ttcaggagtt agctgtgcca gtggttcatg acgggggcgc 840
tcttttggcc tttgtctgtg gtgtcgtgta cacgctccta cagtccatca tctcttacaa 900
atcatgtccc cagtggaaca gtctctcgac atgccacata cggatggtca tctctgccgt 960
ttcttgcgca gctgtcatcc ccatgattgt ctgtgcttca ctaatttcca taaccaagct 1020
ggagtggaat ccaagagaaa aggattatgt atatcacgta gtgagtgcga tctgtgaatg 1080
gacagtggcc tttggtttta ttttctactt cctaactttc atccaagatt tccagagtgt 1140
caccctaagg atatccacag aaatcaatgg tgatatttga agaaagaaga attcagtctc 1200
actcagtgaa tgtcgcaggc catttctaaa agtgctacag aggacagaca gggttttgag 1260
gccaccctga ttattgggat gcatctgcag cacatccagg acttgaattt cattacgagt 1320
tcctaatagt tgtatttcta aagatgtgtt tcctagagaa tgtacagcct tatgacactg 1380
tagtgatgtt tttataattt tctaagtaga ttttttata ttaacaaatt catatacaga 1440

```
aaaaataagg tgttacaaaa aatggagagc tcttattttt gtacagattc tgtcgttttt   1500
gttttatttg tgtgagattt atggaaatac actaaatgag taattcaggt tcagtacatt   1560
tattacaaag tgaaatcagg ggatattcat ttgtaaattt tattcttagt gaatgaactg   1620
tataattttt tttatcagga gagcacttat aaaattcaat ttataaagat catataccca   1680
aatcataaag atttagttga tacattaaca ctaagatact ctgattttta gccgaactaa   1740
acaaagtgct tctactgaga ggcctttata ccaccatgta cagtaactct aagtgaatac   1800
ggaagacctt ggttttgaaa ttctgccacc ttgtttctcc ctgctcatga ggtcgcacct   1860
tttgctcttg ctgctaattg cccattcgta gtgggtgtaa tgccaggtgg aatggtttca   1920
acaagtcagg tgaaaaccat cctttattgt tgctggcaca acttgatata tagtctgact   1980
cagaactgaa gctcacatct caaattcatt tcatgccagt aaatgtggca aagagaagaa   2040
aggcccaaga gcgagacaag aagaatggag aagggggcag ccaagaagaa cttctgggtt   2100
cagggtactg tttatttgct ccttctcttc atgcctgtgg ctggatgtcc cacaacacta   2160
taagaaatat aagtcaagcc ctttgtgtta agcaagaact acagactcca tcttttcacc   2220
caaatcatga atgaccaata aaaagcaagt tattccagag gaagaagcag cccttgaaat   2280
gttaaggctt aggcttgaaa ggtgaagagc aggaattctc tctttcaaat cctagagcat   2340
aaacccatgt gtggccaagt gagatcagcc ctcaagggca catgccaagg gcagagcagc   2400
ccatgtagac agcttcggag ggcatggggg tgtagggagt tcggggtagc tcctcattaa   2460
ctatttgttg ggtgagtaaa ggggtgaggc tcagtggcag gtacctctgc aatgacaagc   2520
tgcctcccct ctatgtgttt agcatatgtt attagaacat gtccgacacc cctaccgctg   2580
ccatttgggc cctttaataa agccaagtag agaaatctgg caataaaagg caaatgtaag   2640
catgctttct ttaagacgca tcataaatgg ttttctttaa gtgaatggaa gagtttgaca   2700
gagatacacc tttgtaagaa aacattaaga atgctggctg gctgtggtgg ctcacacctg   2760
tattcccagc actttgggag gcctaggcag gaggattgct tgagcctggg acttcgagac   2820
cagactggga aacatggcaa aatcccatct ctacaacaaa aatacaaaaa ttagccaagt   2880
gcggtggtgt gcctgtagtc ctagttactt gggaggctga ggtgggagaa tcacctgagc   2940
ccaggaggtg gaggctgcag tgagccatgc caatgcactc cagtctgggc aacagagtga   3000
gaccctgtct caaaaataaa taaataaata aatgaataaa gagaatgcta atcatttctg   3060
ggttcactgc gactcactgt agtgctgggg atccccccttg taacactgga actgaaagac   3120
agtgatgaaa gctatgtcaa gcattcatta ttctgaagag gaggagaaat gccacatacc   3180
tttcccatgg gacctgtggt ggaatgaatc catacttctg cctcacttcg agcagacttt   3240
tgttctcggc gctcctcacg atggagtttc atgcttcatt ttcacatctc tctgcacaat   3300
tagattggga gctccttgag ggcagagtac gtgccttaat ctttatcttt gtaatgccac   3360
aatgaacaga gtgcctcctg gtacactgta ggagcttaag aaatactcac tgaatgcatg   3420
aatgaatgaa tgaacaaatg aaggaatgac taaggatgtt tgtagtgcta taatatagaa   3480
tgggatttac tctgctttac cagttagttt cataataaac aaatagtctg tatcgcctgg   3540
taaaaaaaaa aaa                                                       3553
```

<210> SEQ ID NO 43
<211> LENGTH: 3244
<212> TYPE: DNA
<213> ORGANISM: Homo sapiens

<400> SEQUENCE: 43

-continued

```
gtgacgtcat ctccgggcgc cgagggtgac tggacttgtg gtgcgctgcc agggctccgc     60
agcgttgccg gttgtattcg ctggatacca gagggcggaa gtgcagcagg gttcagctcc    120
gacctccgcg ccggtgcttt ttgcggctgc gcgggcttcc tggagtcctg ctaccgcgtc    180
cccgcaggac agtgtgtcag gcgggcagct tgccccgccg ccccaccgga gcgcggaatc    240
tgggcgtccc caccagtgcg gggagccgga aggaggagcc atagcttgga gtaggtttgg    300
ctttggttga aataagaatt tagcctgtat gtactgcttt aactcctgga agaatgacag    360
atgacaaaga tgtgcttcga gatgtgtggt ttggacgaat tccaacttgt ttcacgctat    420
atcaggatga gataactgaa agggaagcag aaccatacta tttgcttttg ccaagagtaa    480
gttatttgac gttggtaact gacaaagtga aaaagcactt tcagaaggtt atgagacaag    540
aagacattag tgagatatgg tttgaatatg aaggcacacc actgaaatgg cattatccaa    600
ttggtttgct atttgatctt cttgcatcaa gttcagctct tccttggaac atcacagtac    660
attttaagag ttttccagaa aaagaccttc tgcactgtcc atctaaggat gcaattgaag    720
ctcattttat gtcatgtatg aaagaagctg atgctttaaa acataaaagt caagtaatca    780
atgaaatgca gaaaaaagat cacaagcaac tctggatggg attgcaaaat gacagatttg    840
accagttttg ggccatcaat cggaaactca tggaatatcc tgcagaagaa aatggatttc    900
gttatatccc ctttagaata tatcagacaa cgactgaaag acctttcatt cagaagctgt    960
ttcgtcctgt ggctgcagat ggacagttgc acacactagg agatctcctc aaagaagttt   1020
gtccttctgc tattgatcct gaagatgggg aaaaaaagaa tcaagtgatg attcatggaa   1080
ttgagccaat gttggaaaca cctctgcagt ggctgagtga acatctgagc tacccggata   1140
attttcttca tattagtatc atcccacagc caacagattg aaggatcaac tatttgcctg   1200
aacagaatca tccttaaatg ggatttatca gagcatgtca ccctttttgct tcaatcaggt   1260
ttggtggagg caacctgacc agaaacactt cgctgctgca agccagacag gaaaaagatt   1320
ccatgtcaga taaggcaact gggctggtct tactttgcat cacctctgct ttcctccact   1380
gccatcatta aacctcagct gtgacatgaa agacttaccg gaccactgaa ggtcttctgt   1440
aaaatataat gaagctgaaa cctttggcct aagaagaaaa tggaagtatg tgccactcga   1500
tttgtatttc tgattaacaa ataaacaggg gtatttccta aggtgaccat ggttgaactt   1560
tagctcatga aagtggaaac attggtttaa ttttcaagag aattaagaaa gtaaaagaga   1620
aattctgtta tcaataactt gcaagtaatt ttttgtaaaa gattgaatta cagtaaaccc   1680
atctttcctt aacgaaaatt tcctatgttt acagtctgtc tattggtatg caatcttgta   1740
actttgataa tgaacagtga gagattttta aataaagcct ctaaatatgt tttgtcattt   1800
aataacatac agttttgtca cttttcaagt actttctgac tcacatacag tagatcactt   1860
tttactctgt gttaccattt tgactggtcg tcattggcat ggggtggata tagggcatag   1920
gattacttgt ctcagaagct gtcatagaat ttcttgctgc caattaaaaa acctgtgttc   1980
tttacacact acacgtataa atattgtaac tgttcatctt tgttgtttta tcactgtaag   2040
cctgtcaaat catagtatcc taagcatctg taaatgctaa ttttgcattt ttggaaaaac   2100
ccattccttc caagctagtg tttttcattg gctccaggtc taatttttca ctgtggtccc   2160
tggcagccag tcttttgaag tttaaagatt acctgtctct tgactgcagt accttttctt   2220
taatttttac caaaaatatc cagaggttac tggagttctt attcaatata aggaaagttt   2280
gctgcacttt attaccaagc ctctgggatt ttaccagtca aacatatttg tgcattacat   2340
```

ttcatttctt gtgagctagc tggctgtcca tattgaatgt tgacccattt gagtacgcta 2400
aaaggcttac agtatcagac acgatcatgg ttttagatcc cataataaaa atgaatgttt 2460
ttcttataaa aaattataca aatgctgaag tgagattcta ctattgttca ttgcttcctt 2520
ttctttttcc ttttgcgatt ttcactgatt aatagcacat ttcttcacaa aattagataa 2580
agttggtcaa agaccagata ttctggaatg gaaattgtaa agcttaatca aaaagaatag 2640
ccagtacagc atacaatctc agaaacttag aagcaagtag aaaataattg gttgatgtaa 2700
acgaaagtgc cattttagta aaggcaggaa aaaaatagca atatttgagt tatgtaagga 2760
taaaaaatcc actgacttgt atttttgcac aagaggctgg tctgaatatg attgttcaca 2820
ttaagagtgt ttattcgtcg gttcattttg ggattttcc cccttgatgt tttgacagat 2880
tgaagtgagc tttagtgagc aaaaggatca gaatgcaggg aacactaagc tgtgatgaag 2940
aaagtgtggt aaaaagccag agtagtttta tacagacaaa accagtgtca ggcctttgca 3000
gtaggcttga gtgaacttct gatctagatt tgaaagtaaa ttttatgaag acattgccca 3060
tttttacttc ctcattcatt attgtaccag catcatagct ttattactct aatcccaggt 3120
aagtcaagcc tacaatgccc tagaggaaga gtaaaaccag aaattcatgc tggcttaaat 3180
aatctatttt tgtttctttt catttgaata tttaaatttt atggtttatt aaaaaattaa 3240
ataa 3244

<210> SEQ ID NO 44
<211> LENGTH: 1579
<212> TYPE: DNA
<213> ORGANISM: Homo sapiens

<400> SEQUENCE: 44
gaggaggtgc ttgccagaca ctgggtcatg gcagtggtcg gtgaagctgc agttgcctag 60
ggcagggatg gagagagagt ctgggcatga ggagagggtc tcgggatgtt tggctggact 120
agattttaca gaaagcctta tccaggcttt taaaattact ctttccagac ttcatctgag 180
actccttctt cagccaacat tccttagccc tgaatacatt tcctatcctc atctttccct 240
tctttttttt cctttctttt acatgtttaa atttaaacca ttcttcgtga ccccttttct 300
tgggagattc atggcaagaa cgagaagaat gatggtgctt gttaggggat gtcctgtctc 360
tctgaacttt ggggtcctat gcattaaata attttcctga cgagctcaag tgctccctct 420
ggtctacaat ccctggcggc tggccttcat ccccttgggca agcattgcat acagctcatg 480
gccctccctc taccataccc tccacccccg ttcgcctaag ctcccttctc cgggaatttc 540
atcatttcct agaacagcca gaacatttgt ggtctatttc tctgttagtg tttaaccaac 600
catctgttct aaaagaaggg ctgaactgat ggaaggaatg ctgttagcct gagactcagg 660
aagacaactt ctgcagggtc actccctggc ttctggagga aagagaagga gggcagtgct 720
ccagtggtac agaagtgaga cataatggaa tcaggcttca cctccaagga cacctatcta 780
agccatttta accctcggga ttacctagaa aaatattaca agtttggttc taggcactct 840
gcagaaagcc agattcttaa gcaccttctg aaaaatcttt tcaagatatt ctgcctagac 900
ggtgtgaagg gagacctgct gattgacatc ggctctggcc ccactatcta tcagctcctc 960
tctgcttgtg aatcctttaa ggagatcgtc gtcactgact actcagacca gaacctgcag 1020
gagctggaga agtggctgaa gaaagagcca gaggcctttg actggtcccc agtggtgacc 1080
tatgtgtgtg atcttgaagg gaacagagtc aagggtccag agaaggagga gaagttgaga 1140
caggcggtca agcaggtgct gaagtgtgat gtgactcaga gccagccact gggggccgtc 1200
cccttacccc cggctgactg cgtgctcagc acactgtgtc tggatgccgc ctgcccagac 1260
ctccccacct actgcagggc gctcaggaac ctcggcagcc tactgaagcc agggggcttc 1320
ctggtgatca tggatgcgct caagagcagc tactacatga ttggtgagca gaagttctcc 1380
agcctccccc tgggccggga ggcagtagag gctgctgtga aagaggctgg ctacacaatc 1440
gaatggtttg aggtgatctc gcaaagttat tcttccacca tggccaacaa cgaaggactt 1500
ttctccctgg tggcgaggaa gctgagcaga cccctgtgat gcctgtgacc tcaattaaag 1560
caattccttt gacctgtca 1579

<210> SEQ ID NO 45
<211> LENGTH: 5085
<212> TYPE: DNA
<213> ORGANISM: Homo sapiens

<400> SEQUENCE: 45
agcgccatgc gcagactcag ttcctggaga aagatggcga cagccgagaa gcagaaacac 60
gacgggcggg tgaagatcgg ccactacatt ctgggtgaca cgctgggggt cggcaccttc 120
ggcaaagtga aggttggcaa acatgaattg actgggcata aagtagctgt gaagatactc 180
aatcgacaga agattcggag ccttgatgtg gtaggaaaaa tccgcagaga aattcagaac 240
ctcaagcttt tcaggcatcc tcatataatt aaactgtacc aggtcatcag tacaccatct 300
gatattttca tggtgatgga atatgtctca ggaggagagc tatttgatta tatctgtaag 360
aatggaaggc tggatgaaaa agaaagtcgg cgtctgttcc aacagatcct ttctggtgtg 420
gattattgtc acaggcatat ggtggtccat agagatttga aacctgaaaa tgtcctgctt 480
gatgcacaca tgaatgcaaa gatagctgat tttggtcttt caaacatgat gtcagatggt 540
gaatttttaa gaacaagttg tggctcaccc aactatgctg caccagaagt aatttcagga 600
agattgtatg caggcccaga ggtagatata tggagcagtg ggttattctt ctatgcttta 660
ttatgtggaa cccttccatt tgatgatgac catgtgccaa ctctttttaa gaagatatgt 720
gatgggatct tctatacccc tcaatattta aatccttctg tgattagcct tttgaaacat 780
atgctgcagg tggatcccat gaagagggcc acaatcaaag atatcaggga acatgaatgg 840
tttaaacagg accttccaaa atatctcttt cctgaggatc catcatatag ttcaaccatg 900
attgatgatg aagccttaaa agaagtatgt gaaaagtttg agtgctcaga agaggaagtt 960
ctcagctgtc tttacaacag aaatcaccag gatcctttgg cagttgccta ccatctcata 1020
atagataaca ggagaataat gaatgaagcc aaagatttct atttggcgac aagcccacct 1080
gattcttttc ttgatgatca tcacctgact cggccccatc ctgaaagagt accattcttg 1140
gttgctgaaa caccaagggc acgccatacc cttgatgaat taaatccaca gaaatccaaa 1200
caccaaggtg taaggaaagc aaaatggcat ttaggaatta gaagtcaaag tcgaccaaat 1260
gatattatgg cagaagtatg tagagcaatc aaacaattgg attatgaatg gaaggttgta 1320
aacccatatt atttgcgtgt acgaaggaag aatcctgtga caagcactta ctccaaaatg 1380
agtctacagt tataccaagt ggatagtaga acttatctac tggatttccg tagtattgat 1440
gatgaaatta cagaagccaa atcagggact gctactccac agagatcggg atcagttagc 1500
aactatcgat cttgccaaag gagtgattca gatgctgagg ctcaaggaaa atcctcagaa 1560
gtttctctta cctcatctgt gacctcactt gactcttctc ctgttgacct aactccaaga 1620
cctggaagtc acacaataga attttttgag atgtgtgcaa atctaattaa aattcttgca 1680
caataaacag aaaactttgc ttatttcttt tgcagcaata agcatgcata ataagtcaca 1740
gccaaatgct tccatttgta atcaagttat acataattat aaccgagggc tggcgttttg 1800
gaatgcaatt tgcacaggga ttggaacatg atttatagtt aaaagcctaa tatgcagaaa 1860
tgaattaaga tcattttgtt gttcattgtg cagtatgtat atagcataat atacacagtg 1920
aattataggt ctcaggctta cttgattttt ggctatttta tatttagtgt acacagggct 1980
ttgaaatatt aatttacata aaggccttca tatattatta cgtgttatat attacgtgtt 2040
ataaatttat tcaataaata tttgcctaga attcccaaga cctttatagg tgattttgtt 2100
ttctgggctc cttaacttca taaatagcta gtatcttcca gcagtagtaa cagtctggat 2160
aacttcttcc atatccctcc ctctttgttt ttttgagaca gtgtcacttt gtcacccagg 2220
ctggagtgca atggtgtggt ctcggctcac tgcaacctcc acctcccggg ttcaagtgat 2280
tctcccgcct cagcttcctg agtagctgga actacaggcg tgtgccacca cacccggcta 2340
atttttcgta tttttagtgt agacggggtt tcactatgtt gcccaggctg gtctcgaact 2400
cctgaccgcg tgatccacca cctcagcttc ccaaagtggt gggattacag gcgtgagcca 2460
ccgcacccgg cctccatatc cccttttaa aattctgtag tgtatggtaa gtcatatcag 2520
atatcagacc taatttaaat ttcattttag ctttacaagt ccaaaaacac agaatttata 2580
tattcagata ctctagcact aattttagtc ttaaaatatt cccacgatat tctgtacaca 2640
aaatgttctt tttgttacaa gagctgagtt gcatatactg tagataaatc atattatttt 2700
tgccaatttc acaaattcct ctggcccatc atgtcagtca ttattgagta tatgcacaca 2760
ttgctactta tttgattatg tatcttttaa attgattcag tgcatagaaa actatctctt 2820
acaaacttta agtgctctga tatgacttcc cccccaaatt ttattatgaa catttttaaa 2880
aacagaaaaa ttgaaaaact gtttggtaag cacatgtata tctaccattt agattcagca 2940
gttgttaatg ttttgtcatt tgttttctct atacctatat atgtatagat acagctagtt 3000
atgcatatat atgcatatat gtgtttgttt gtgtatgtat atatgctttt ttccccctga 3060
accatttgga tgttacagac atacttatca ccgtgaaaat acttcaagta tctcctacag 3120
ataatgacat tctcctaaaa atccgtaata ccattgtaaa agtaataatt ccccaatatc 3180
atctaatcaa gccatattta aatttctgaa gttaactcca aatttcttta tagctgatta 3240
tttcaaacta ggatccaatt aaagtttaca tatgacactt ggttataact ctttagttgg 3300
atataacatt attattattt tgataaaata tggaacaaat caattctatt aataagtggt 3360
cacatttgtt ttgggcttaa attactttt aaagatactg gattttccta agatttctga 3420
tttacactga tattttttt tgtcattctt aattgcatca cacaatagat gtaaatgaag 3480
atgtagtcac ctcagataaa attggtatcg tgtatgataa tattgtatca tttatatttg 3540
ccttatgtta actttaagaa attgattttt ttgtattaat cattttccca ttgcaacaga 3600
gctatatttt ttctatttta agaatcatat tttaggatta tttttggcaa atacagtgag 3660
cacttatgta accagatgat aatgaactca aatgtcatga tagcttgcat aaatggtgac 3720
tctagtagat ttgactcaag cacttctaga atcatgcact gaattcaaaa gaaaaatctt 3780
gctgcttttt gtccagggct tgttctattc aacttctaat ttgaaagctg tacaaagtaa 3840
tagaagttcc atttaaatat gagttcaaaa ctgtatttac tttttatgtg gccctctctt 3900
taggggattc taattttact tagggtctct aagtgcagca taatgttcct gatgttaaca 3960
gaagactgta tttttaaagt tacaaatttg tatatggaat taagtaatgg cgctatatac 4020
gctgttgtgg ggagggggga agaaaaggag gaaccaatta aataggacct tttaaaaatt 4080
gttaattttg taaactttgc ttctcttata agttattgtg attcatttta gttactgtgt 4140
tttattttga aaatatttaa atattgcact tctataaata gtatgataaa tgcacagaca 4200
attgcagtaa attcttttt aagctaggat atttgaaatg acaacctttg gttaagtgtg 4260
tcaaggttgc aacagaattt tcacaatttt tttgttgttt gcaaattgtt actaatattg 4320
aagaggtaag ggaggcaatg caaatgattt ttaatctttt tttattatct tttcagcagt 4380
ttatattttt tgtgacttta tgcaaccata tttttacttt gtcttgacaa ctgaaagatg 4440
tataaggttt tttgccagaa atgtactgta tacatagttt taagtataac agattttact 4500
gatatgtaaa aattttgcca ttaaaataaa tgatttctca ctgagaggaa cttttctacc 4560
aggttggggc atatgggagc ttaatatatc atatctaatt taaaataatt tcactgaaat 4620
aaactccatt gcttttacct aattttttc ttgagatgct tttgtagttt ttcagagttt 4680
tagatgattt tatacaaaat cctctgccta gcactgctct ttttgatgtt gtagtgacac 4740
catttacatt gaattaatgc ttggtagcct ggggctagat gtggaactcc atggatctgt 4800
gttctgactg gcacctttgg aatgaaagaa aagtgtgtgc tgtccaaatt ttttcccctt 4860
aattctttcc ctcatcttct cacccataat agaaatttta tttccattgt gagttctgac 4920
aagaatgaaa ttccacatac aacataactg taaattgttg gtaggtagaa gttaatattt 4980
gtggttcatg tatattttga ccagagtata tttaagtata taatttcagc ttccttgatt 5040
tagaaatatg atataataaa gaaaaactcc atttatcatc tgtta 5085

<210> SEQ ID NO 46
<211> LENGTH: 2914
<212> TYPE: DNA
<213> ORGANISM: Homo sapiens

<400> SEQUENCE: 46
gtgctctgag tttttggttt ctgtttcacc ttgtgtctga gctggtctga aggctggttg 60
ttcagactga gcttcctgcc tgcctgtacc ccgccaacag cttcagaaga aggtgactgg 120
tggctgcctg aggaatacca gtgggcaaga gaattagcat ttctggagca tctgctgtct 180
gagcagcccc tgggtgcgtc cactttctgg gcacgtgagg ttgggccttg gccgcctgag 240
cccttgagtt ggtcacttga accttgggaa tattgagatt atattctcct gccttttaaa 300
aagatggact tcagcagaaa tctttatgat attggggaac aactggacag tgaagatctg 360
gcctccctca agttcctgag cctggactac attccgcaaa ggaagcaaga acccatcaag 420
gatgccttga tgttattcca gagactccag gaaaagagaa tgttggagga aagcaatctg 480
tccttcctga aggagctgct cttccgaatt aatagactgg atttgctgat tacctaccta 540
aacactagaa aggaggagat ggaaagggaa cttcagacac caggcagggc tcaaatttct 600
gcctacaggt tccacttctg ccgcatgagc tgggctgaag caaacagcca gtgccagaca 660
cagtctgtac ctttctggcg gagggtcgat catctattaa taagggtcat gctctatcag 720
atttcagaag aagtgagcag atcagaattg aggtctttta agtttctttt gcaagaggaa 780
atctccaaat gcaaactgga tgatgacatg aacctgctgg atattttcat agagatggag 840
aagagggtca tcctgggaga aggaaagttg gacatcctga aaagagtctg tgcccaaatc 900
aacaagagcc tgctgaagat aatcaacgac tatgaagaat tcagcaaagg ggaggagttg 960
tgtggggtaa tgacaatctc ggactctcca agagaacagg atagtgaatc acagactttg 1020
gacaaagttt accaaatgaa aagcaaacct cggggatact gtctgatcat caacaatcac 1080

```
aattttgcaa aagcacggga gaaagtgccc aaacttcaca gcattaggga caggaatgga   1140
acacacttgg atgcaggggc tttgaccacg acctttgaag agcttcattt tgagatcaag   1200
ccccacgatg actgcacagt agagcaaatc tatgagattt tgaaaatcta ccaactcatg   1260
gaccacagta acatggactg cttcatctgc tgtatcctct cccatggaga caagggcatc   1320
atctatggca ctgatggaca ggaggccccc atctatgagc tgacatctca gttcactggt   1380
ttgaagtgcc cttcccttgc tggaaaaccc aaagtgtttt ttattcaggc ttgtcagggg   1440
gataactacc agaaaggtat acctgttgag actgattcag aggagcaacc ctatttagaa   1500
atggatttat catcacctca aacgagatat atcccggatg aggctgactt tctgctgggg   1560
atggccactg tgaataactg tgtttcctac cgaaaccctg cagagggaac ctggtacatc   1620
cagtcacttt gccagagcct gagagagcga tgtcctcgag gcgatgatat tctcaccatc   1680
ctgactgaag tgaactatga agtaagcaac aaggatgaca agaaaaacat ggggaaacag   1740
atgcctcagc ctactttcac actaagaaaa aaacttgtct tcccttctga ttgatggtgc   1800
tattttgttt gttttgtttt gttttgtttt tttgagacag aatctcgctc tgtcgcccag   1860
gctggagtgc agtggcgtga tctcggctca ccgcaagctc cgcctcccgg gttcaggcca   1920
ttctcctgcc tcagcctccc gagtagctgg gactacaggg gcccgccacc acacctggct   1980
aattttttaa aaatattttt agtagagaca gggtttcact gtgttagcca gggtggtctt   2040
gatctcctga cctcgtgatc cacccacctc ggcctcccaa agtgctggga ttacaggcgt   2100
gagccaccgc gcctggccga tggtactatt tagatataac actatgttta tttactaatt   2160
ttctagattt tctactttat taattgtttt gcactttttt ataagagcta aagttaaata   2220
ggatattaac aacaataaca ctgtctcctt tctcttatgc ttaaggcttt gggaatgttt   2280
ttagctggtg gcaataaata ccagacacgt acaaaatcca gctatgaata tagagggctt   2340
atgattcaga ttgttatcta tcaactataa gcccactgtt aatattctat taactttaat   2400
tctctttcaa agctaaattc cacactacca cattaaaaaa attagaaagt agccacgtat   2460
ggtggctcat gtctataatc ccagcacttt gggaggttga ggtgggagga ttgcttgaac   2520
ccaagaggtc aaggctgcag tgagccatgt tcacaccgct gcactcaagc ttgggtgaca   2580
gaacaagacc ccgtctcaaa aaaaattttt tttttaataa aacaaaattt gtttgaaatc   2640
ttttaaaaat tcaaatgatt tttacaagtt ttaaataagc tctccccaaa cttgctttat   2700
gccttcttat tgcttttatg atatatatat gcttggctaa ctatatttgc tttttgctaa   2760
caatgctctg gggtcttttt atgcatttgc atttgctctt tcatctctgc ttggattatt   2820
ttaaatcatt aggaattaag ttatctttaa aatttaagta tctttttttca aaaacatttt   2880
ttaatagaat aaaatataat ttgatcttat taaa                              2914
```

<210> SEQ ID NO 47
<211> LENGTH: 5239
<212> TYPE: DNA
<213> ORGANISM: Homo sapiens

<400> SEQUENCE: 47

```
ggatccggat tcggattagc agcccgggaa gagtgccgtg gcacaggcgc cggagggagc     60
gcgaccctcg gaccccgcct ggcccgcggg gctgggaccc ggccccggcc tgcccgatgg    120
ggcgcgcggc cccggagatg cgccctcgcc cggccccgcg cccccggccc cgcgcccccg    180
gcccgcccgc cccggcccgc gcctccgcct gagtccccccg cgccttggcc cgccaccccc    240
cgccccgcgc ccccggcccg cctgcgccat ggagcccggc cgcggcggca cagagaccgt    300
```

-continued

```
gggcaagttc gagttctccc gcaaggacct gatcggccac ggcgccttcg cggtggtctt    360
caagggccgc caccgcgaga agcacgattt ggaggtcgcc gtcaagtgca ttaacaagaa    420
gaacctcgcc aagtctcaga cgctgctggg gaaggaaatc aaaatcctga aggaactgaa    480
acatgaaaac atcgtggccc tgtacgactt ccaggaaatg gctaattctg tctacctggt    540
tatggagtac tgcaacggtg gggacctggc cgactacctg cacgccatgc gcacgctgag    600
cgaggacacc atcaggctct tcctgcagca gatcgcgggc gccatgcggc ttctgcacag    660
caaaggcatc atccaccgcg acctgaaacc gcagaacatc ctgctgtcca accccgccgg    720
ccgccgcgcc aaccccaaca gcatccgcgt caagatcgct gacttcggct tcgcgcggta    780
cctccagagc aacatgatgg cggccacact ctgcggctcc cccatgtaca tggcccccga    840
ggtcatcatg tcccagcact acgacgggaa ggcggacctg tggagcatcg gcaccatcgt    900
ctaccagtgc ctgacgggga aggcgccctt ccaggccagc agcccccagg acctgcgcct    960
gttctacgag aagaacaaga cgttggtccc caccatcccc cgggagacct cggccccgct   1020
gcggcagctg ctcctggccc tactgcaacg caaccacaag gaccgcatgg acttcgatga   1080
gtttttcat cacccttcc tcgatgccag cccctcggtc aggaaatccc cacccgtgcc   1140
tgtgccctcg tacccaagct cggggtccgg cagcagctcc agcagcagct ccacctccca   1200
cctggcctcc ccgccgtccc tgggcgagat gcagcagctg cagaagaccc tggcctcccc   1260
ggctgacacc gctggcttcc tgcacagctc ccgggactct ggtggcagca aggactcttc   1320
ctgtgacaca gacgacttcg tcatggtccc cgcgcagttt ccaggtgacc tggtggctga   1380
ggcgcccagt gccaaacccc cgccagacag cctgatgtgc agtgggagct cactggtggc   1440
ctctgcgggc ttggagagcc acggccggac cccatctcca tccccaccct gcagcagctc   1500
ccccagtccc tcaggccggg ctggcccgtt ctccagcagc aggtgcggcg cctctgtccc   1560
catcccagtc cccacgcagg tgcagaacta ccagcgcatt gagcgaaacc tgcagtcacc   1620
cacccagttc caaacacctc ggtcctctgc catccgcagg tcaggcagca ccagcccccct   1680
gggctttgca agggccagcc cctcgccccc tgcccacgct gagcatggag gcgtcctggc   1740
caggaagatg tctctgggtg gaggccggcc ctacacgcca tctcctcaag ttggaaccat   1800
ccctgagcgg ccaggctgga gcgggacgcc ctccccacag ggagctgaga tgcggggtgg   1860
caggtcccct cgtccaggct cctctgcacc cgagcactct ccccgcactt ccgggctggg   1920
ctgccgcctg cacagcgccc ccaacctgtc tgacttgcac gtcgtccgcc ccaagctgcc   1980
caaacccccc acggaccccc tgggagctgt gttcagccca ccacaggcca gccctcccca   2040
gccgtcccac ggcctgcagt cctgccggaa cctgcggggc tcacccaagc tgcccgactt   2100
cctgcagcga aacccccctgc cccccatcct gggctccccc accaaggctg tgccctcctt   2160
tgacttcccg aagaccccca gctcccagaa cctgctggcc ctcctagccc ggcagggcgt   2220
ggtgatgacg cccccctcgaa accggacgct gcccgacctc tcggaggtgg gaccccttcca   2280
tggtcagccg ttgggccctg gcctgcggcc aggcgaggac cccaagggcc cctttggccg   2340
gtctttcagc accagccgcc tcactgacct gctccttaag gcggcgtttg ggacacaagc   2400
cccggacccg ggcagcacgg agagcctgca ggagaagccc atggagatcg caccctcagc   2460
tggctttgga gggagcctgc acccaggagc ccgtgctggg ggcaccagca gcccttcccc   2520
ggtggtcttc accgtgggct ctcccccgag cgggagcacg ccccccccagg gcccccgcac   2580
caggatgttc tcagcgggcc ccactggctc tgccagctct tctgcccgcc acctggtgcc   2640
```

-continued

```
tgggccctgc agcgaggccc cagcccctga gctccctgct ccaggacacg gctgcagctt   2700
tgccgacccc attgctgcga acctggaggg ggctgtgacc ttcgaggccc ccgacctccc   2760
tgaggagacc ctcatggagc aagagcacac ggagatcctg cgtggcctgc gcttcacgct   2820
gctgttcgtg cagcacgtcc tggagatcgc agccctgaag ggcagcgcca gtgaggcggc   2880
ggggggccct gagtaccagc tgcaggagag tgtggtggcc gaccagatca gcctgctgag   2940
ccgagaatgg ggcttcgcgg aacagctggt gctgtacctg aaggtggccg agctactgtc   3000
ctccggcctg caaagtgcca tcgaccagat ccgggccggc aagctctgcc tgtcgtccac   3060
tgtgaagcag gtggtgcgca ggctgaatga gctgtacaag gccagcgtgg tgtcctgcca   3120
gggcctgagc ctgcggctgc agcgcttctt cctggacaag cagcggctcc tggaccgcat   3180
tcacagcatc actgccgaga ggctcatctt cagccacgct gtgcagatgg tgcagtcggc   3240
tgccctggac gagatgttcc agcaccgtga gggctgcgtc ccacgctacc acaaggccct   3300
gctgctcctg gaggggctgc agcacatgct ctcggaccag gccgacatcg agaacgtcac   3360
caagtgcaag ctgtgcattg agcggagact ctcggcgctg ctgactggca tctgtgcctg   3420
acctttctgg cctggctggg ccccccgtcc tgccgagccc tgcagagtgg gctctgtgtg   3480
ctggctggac tcctcgggac aagcccatgg cgctgatcgc tggtgctgag ccctgccctg   3540
ggccccacgg acagtcagcc tgccggcctc cctgcagctc acggggcaga accagcacat   3600
ctggagccac acagcttggg gggtgtctcc catcttttac aggtggggat cacagaattt   3660
ctgcccctcc agctgcctgg ctcagcaggc gtgggtgcca ccaccctcta gccccagggc   3720
agccccggag gacaggcaag ggcctgagac cactgccgac tcaaagccaa agcgagctcc   3780
tgcttagggc aggtcagcag gcactgtgcc caggaagagc ctgcggcctc ggcgtccccc   3840
agtctccagg agcctctccc tccgagatac ccacccagct ttgtcaatca cccaagcact   3900
ttatgcatat agagacagaa cctggacctc accagggact gctgggcagc gattcctggc   3960
agtggcctgg tgtttgtaca tacacatatg cagacacatg ccagggcccc ccaagcccga   4020
gcaccggacc acgttgctgc ccaggtctgg acctcagcgg gagaactggc tccgggggga   4080
gtggggccct gcgctagagg cagaggcagt tctttgttca agcgttcctc tggggaccgg   4140
cagcagaggc accgtgttct ctcagccctg gatacgtctt gtaatctttc acactttatt   4200
cctaaaacgt gtcttatttt tatgcagctc atttttttctt taaaggagaa aacttgtagg   4260
tgtttaagaa ttggttttgg gagggcgagg actgggccag gttagaggca gatggcacag   4320
gggcgtgtgg cgggcgggtg aggctgcttt gcacacctgt gttggtggct gtcccctgcc   4380
gcccctccct gtggcagcag caggacaggt gtgtgcccag caccctccct acctgggcct   4440
ggaagcagat gaggggaata cttcatgcaa agaaaaaagt aacatgtgca aaagctcccc   4500
gtccagcttt gacagtcagt tttgatgtca gctcctcggc agggtaggcc tgatgacagc   4560
cctgtccctc cctgcctctg ccttgcccaa ggccacggag ggcatctgca gagaggcctg   4620
ccttccggat tccaggcggg catgccctgc aaaccccgcc tgggcctccc ttggtctgcc   4680
cagccctcgg ttagccctgc ctgaatcagt agatacttga acgagtcccc agtctgcggg   4740
aggcagtggt ggggccatgg acccatgcgg ggggttccag ggtcacacgc cacataacag   4800
acaaaaatac acacacgtgt gtttttcttt gcaatacttg aaatattgcc actgtgcttg   4860
gacttagaag aagaaaatcc ccgtgacttc ttcctcatca ccttgatggc tttattctca   4920
ccttgtgggg catgtttgta tttattgctt catggccgac tggaatcctg agtcctggga   4980
agctggcact gcggggatct tgcccggtgt cctggtcctc ttgcttccgt cgcggccgca   5040
```

-continued

```
tgtgcgtgtg tccaagcagg tcctgggcgc ctcaactgct gcccctggtt gaatgttctc   5100

ttgatagtgc tggacccttt gtctatttta aagcgaattt tgtgtgattt cctgcccttt   5160

gcgttatatt gtataatacc aacgtaagga aataaacctt tggaattgtt gggctggtgt   5220

caaaaaaaaa aaaaaaaaa                                                5239
```

<210> SEQ ID NO 48
<211> LENGTH: 2386
<212> TYPE: DNA
<213> ORGANISM: Homo sapiens

<400> SEQUENCE: 48

```
ggaggaggaa gcaagcgagg gggctggttc ctgagcttcg caattcctgt gtcgccttct     60

gggctcccag cctgccgggt cgcatgatcc ctccggccgg agctggtttt tttgccagcc    120

accgcgaggc cggctgagtt accggcatcc ccgcagccac ctcctctccc gacctgtgat    180

acaaaagatc ttccgggggc tgcacctgcc tgcctttgcc taaggcggat ttgaatctct    240

ttctctccct tcagaatctt atcttggctt tggatcttag aagagaatca ctaaccagag    300

acgagactca gtgagtgagc aggtgttttg gacaatggac tggttgagcc catccctatt    360

ataaaaatgt ctcagagcaa ccgggagctg gtggttgact ttctctccta caagctttcc    420

cagaaaggat acagctggag tcagtttagt gatgtggaag agaacaggac tgaggcccca    480

gaagggactg aatcggagat ggagaccccc agtgccatca atggcaaccc atcctggcac    540

ctggcagaca gccccgcggt gaatggagcc actggccaca gcagcagttt ggatgcccgg    600

gaggtgatcc ccatggcagc agtaaagcaa gcgctgaggg aggcaggcga cgagtttgaa    660

ctgcggtacc ggcgggcatt cagtgacctg acatcccagc tccacatcac cccagggaca    720

gcatatcaga gctttgaaca ggatactttt gtggaactct atgggaacaa tgcagcagcc    780

gagagccgaa agggccagga acgcttcaac cgctggttcc tgacgggcat gactgtggcc    840

ggcgtggttc tgctgggctc actcttcagt cggaaatgac cagacactga ccatccactc    900

taccctccca ccccttctc tgctccacca catcctccgt ccagccgcca ttgccaccag    960

gagaaccact acatgcagcc catgcccacc tgcccatcac agggttgggc ccagatctgg   1020

tcccttgcag ctagttttct agaatttatc acacttctgt gagaccccca cacctcagtt   1080

cccttggcct cagaattcac aaaatttcca caaaatctgt ccaaaggagg ctggcaggta   1140

tggaagggtt tgtggctggg ggcaggaggg ccctacctga ttggtgcaac ccttacccct   1200

tagcctccct gaaaatgttt ttctgccagg gagcttgaaa gttttcagaa cctcttcccc   1260

agaaaggaga ctagattgcc tttgttttga tgtttgtggc ctcagaattg atcattttcc   1320

ccccactctc cccacactaa cctgggttcc ctttccttcc atccctaccc cctaagagcc   1380

atttaggggc cacttttgac tagggattca ggctgcttgg gataaagatg caaggaccag   1440

gactccctcc tcacctctgg actggctaga gtcctcactc ccagtccaaa tgtcctccag   1500

aagcctctgg ctagaggcca gccccaccca ggagggaggg ggctatagct acaggaagca   1560

ccccatgcca aagctagggt ggcccttgca gttcagcacc accctagtcc cttcccctcc   1620

ctggctccca tgaccatact gagggaccaa ctgggcccaa gacagatgcc ccagagctgt   1680

ttatggcctc agctgcctca cttcctacaa gagcagcctg tggcatcttt gccttgggct   1740

gctcctcatg gtgggttcag ggactcagc cctgaggtga aagggagcta tcaggaacag   1800

ctatgggagc cccagggtct tccctacctc aggcaggaag ggcaggaagg agagcctgct   1860
```

-continued gcatggggtg gggtagggct gactagaagg gccagtcctg cctggccagg cagatctgtg 1920
ccccatgcct gtccagcctg ggcagccagg ctgccaaggc cagagtggcc tggccaggag 1980
ctcttcaggc ctccctctct cttctgctcc acccttggcc tgtctcatcc ccaggggtcc 2040
cagccacccc gggctctctg ctgtacatat ttgagactag tttttattcc ttgtgaagat 2100
gatatactat ttttgttaag cgtgtctgta tttatgtgtg aggagctgct ggcttgcagt 2160
gcgcgtgcac gtggagagct ggtgcccgga gattggacgg cctgatgctc cctcccctgc 2220
cctggtccag ggaagctggc cgagggtcct ggctcctgag ggcatctgc ccctccccca 2280 acccccaccc cacacttgtt ccagctcttt gaaatagtct gtgtgaaggt gaaagtgcag 2340
ttcagtaata aactgtgttt actcagtgaa aaaaaaaaaa aaaaaa 2386

<210> SEQ ID NO 49
<211> LENGTH: 2755
<212> TYPE: DNA
<213> ORGANISM: Homo sapiens

<400> SEQUENCE: 49
cctacccgcg cgcaggccaa gttgctgaat caatggagcc ctccccaacc cgggcgttcc 60
ccagcgaggc ttccttccca tcctcctgac caccggggct tttcgtgagc tcgtctctga 120
tctcgcgcaa gagtgacaca caggtgttca aagacgcttc tggggagtga gggaagcggt 180
ttacgagtga cttggctgga gcctcagggg cgggcactgg cacggaacac accctgaggc 240
cagccctggc tgcccaggcg gagctgcctc ttctcccgcg ggttggtgga cccgctcagt 300
acggagttgg ggaagctctt tcacttcgga ggattgctca acaaccatgc tgggcatctg 360
gaccctccta cctctggttc ttacgtctgt tgctagatta tcgtccaaaa gtgttaatgc 420
ccaagtgact gacatcaact ccaagggatt ggaattgagg aagactgtta ctacagttga 480
gactcagaac ttggaaggcc tgcatcatga tggccaattc tgccataagc cctgtcctcc 540
aggtgaaagg aaagctaggg actgcacagt caatggggat gaaccagact gcgtgccctg 600
ccaagaaggg aaggagtaca cagacaaagc ccatttttct tccaaatgca gaagatgtag 660
attgtgtgat gaaggacatg gcttagaagt ggaaataaac tgcacccgga cccagaatac 720
caagtgcaga tgtaaaccaa actttttttg taactctact gtatgtgaac actgtgaccc 780
ttgcaccaaa tgtgaacatg gaatcatcaa ggaatgcaca ctcaccagca acaccaagtg 840
caaagaggaa ggatccagat ctaacttggg gtggctttgt cttcttcttt tgccaattcc 900
actaattgtt tgggtgaaga gaaaggaagt acagaaaaca tgcagaaagc acagaaagga 960
aaaccaaggt tctcatgaat ctccaacctt aaatcctgaa acagtggcaa taaatttatc 1020
tgatgttgac ttgagtaaat atatcaccac tattgctgga gtcatgacac taagtcaagt 1080
taaaggcttt gttcgaaaga atggtgtcaa tgaagccaaa atagatgaga tcaagaatga 1140
caatgtccaa gacacagcag aacagaaagt tcaactgctt cgtaattggc atcaacttca 1200
tggaaagaaa gaagcgtatg acacattgat taaagatctc aaaaaagcca atctttgtac 1260
tcttgcagag aaaattcaga ctatcatcct caaggacatt actagtgact cagaaaattc 1320
aaacttcaga aatgaaatcc aaagcttggt ctagagtgaa aaacaacaaa ttcagttctg 1380
agtatatgca attagtgttt gaaaagattc ttaatagctg gctgtaaata ctgcttggtt 1440
ttttactggg tacattttat catttattag cgctgaagag ccaacatatt tgtagatttt 1500
taatatctca tgattctgcc tccaaggatg tttaaaatct agttgggaaa acaaacttca 1560
tcaagagtaa atgcagtggc atgctaagta cccaaatagg agtgtatgca gaggatgaaa 1620

```
gattaagatt atgctctggc atctaacata tgattctgta gtatgaatgt aatcagtgta   1680
tgttagtaca aatgtctatc cacaggctaa ccccactcta tgaatcaata gaagaagcta   1740
tgaccttttg ctgaaatatc agttactgaa caggcaggcc actttgcctc taaattacct   1800
ctgataattc tagagatttt accatatttc taaactttgt ttataactct gagaagatca   1860
tatttatgta aagtatatgt atttgagtgc agaatttaaa taaggctcta cctcaaagac   1920
ctttgcacag tttattggtg tcatattata caatatttca attgtgaatt cacatagaaa   1980
acattaaatt ataatgtttg actattatat atgtgtatgc attttactgg ctcaaaacta   2040
cctacttctt tctcaggcat caaaagcatt ttgagcagga gagtattact agagctttgc   2100
cacctctcca tttttgcctt ggtgctcatc ttaatggcct aatgcacccc caaacatgga   2160
aatatcacca aaaaatactt aatagtccac caaaaggcaa gactgccctt agaaattcta   2220
gcctggtttg gagatactaa ctgctctcag agaaagtagc tttgtgacat gtcatgaacc   2280
catgtttgca atcaaagatg ataaaataga ttcttatttt tcccccaccc ccgaaaatgt   2340
tcaataatgt cccatgtaaa acctgctaca aatggcagct tatacatagc aatggtaaaa   2400
tcatcatctg gatttaggaa ttgctcttgt catacccccca agtttctaag atttaagatt   2460
ctccttacta ctatcctacg tttaaatatc tttgaaagtt tgtattaaat gtgaatttta   2520
agaaataata tttatatttc tgtaaatgta aactgtgaag atagttataa actgaagcag   2580
atacctggaa ccacctaaag aacttccatt tatggaggat ttttttgccc cttgtgtttg   2640
gaattataaa atataggtaa aagtacgtaa ttaaataatg tttttggtaa aaaaaaaaaa   2700
aaaaaaaaaa aaaaaaaaaa aaaaaaaaaa aaaaaaaaaa aaaaaaaaaa aaaaa        2755
```

```
<210> SEQ ID NO 50
<211> LENGTH: 3579
<212> TYPE: DNA
<213> ORGANISM: Homo sapiens

<400> SEQUENCE: 50
```

```
tcaggctcgc tgtcgcgcca ttttgccggg gtttgaatgt gaggcggagc ggcggcagga     60
gcgggtagtg ccagctacgg tccgcggctg ggttccctc ctccgtttct gtatccccac     120
gagatcctat agcaatggaa ctcagcgatg caaatctgca aacactaaca gaatatttaa    180
agaaaacact tgatcctgat cctgccatcc gacgtccagc tgagaaattt cttgaatctg    240
ttgaaggaaa tcagaattat ccactgttgc ttttgacatt actggagaag tcccaggata    300
atgttatcaa agtatgtgct tcagtaacat tcaaaaacta tattaaaagg aactggagaa    360
ttgttgaaga tgaaccaaac aaaatttgtg aagccgatcg agtggccatt aaagccaaca    420
tagtgcactt gatgcttagc agcccagagc aaattcagaa gcagttaagt gatgcaatta    480
gcattattgg cagagaagat tttccacaga aatggcctga cttgctgaca gaaatggtga    540
atcgctttca gagtggagat ttccatgtta ttaatggagt cctccgtaca gcacattcat    600
tatttaaaag ataccgtcat gaatttaagt caaacgagtt atggactgaa attaagcttg    660
ttctggatgc ctttgctttg cctttgacta atctttttaa ggccactatt gaactctgca    720
gtacccatgc aaatgatgcc tctgccctga ggattctgtt ttcttccctg atcctgatct    780
caaaattgtt ctatagttta aactttcagg atctccctga attttttgaa gataatatgg    840
aaacttggat gaataatttt catactctct taacattgga taataagctt ttacaaactg    900
atgatgaaga ggaagccggc ttattggagc tcttaaaatc ccagatttgt gataatgccg    960
```

-continued

```
cactctatgc acaaaagtac gatgaagaat tccagcgata cctgcctcgt tttgttacag   1020
ccatctggaa tttactagtt acaacgggtc aagaggttaa atatgatttg ttggtaagta   1080
atgcaattca atttctggct tcagtttgtg agagacctca ttataagaat ctatttgagg   1140
accagaacac gctgacaagt atctgtgaaa aggttattgt gcctaacatg gaatttagag   1200
ctgctgatga agaagcattt gaagataatt ctgaggagta cataaggaga gatttggaag   1260
gatctgatat tgatactaga cgcagggctg cttgtgatct ggtacgagga ttatgcaagt   1320
tttttgaggg acctgtgaca ggaatcttct ctggttatgt taattccatg ctgcaggaat   1380
acgcaaaaaa tccatctgtc aactggaaac acaaagatgc agccatctac ctagtgacat   1440
ctttggcatc aaaagcccaa acacagaagc atggaattac acaagcaaat gaacttgtaa   1500
acctaactga gttctttgtg aatcacatcc tccctgattt aaaatcagct aatgtgaatg   1560
aatttcctgt ccttaaagct gacggtatca aatatattat gatttttaga aatcaagtgc   1620
caaaagaaca tcttttagtc tcgattcctc tcttgattaa tcatcttcaa gctgaaagta   1680
ttgttgttca tacttacgca gctcatgctc ttgaacggct ctttactatg cgagggccta   1740
acaatgccac tctctttaca gctgcagaaa tcgcaccgtt tgttgagatt ctgctaacaa   1800
accttttcaa agctctcaca cttcctggct cttcagaaaa tgaatatatt atgaaagcta   1860
tcatgagaag tttttctctc ctacaagaag ccataatccc ctacatccct actctcatca   1920
ctcagcttac acagaagcta ttagctgtta gtaagaaccc aagcaaacct cactttaatc   1980
actacatgtt tgaagcaata tgtttatcca taagaataac ttgcaaagct aaccctgctg   2040
ctgttgtaaa ttttgaggag gctttgtttt tggtgtttac tgaaatctta caaaatgatg   2100
tgcaagaatt tattccatac gtctttcaag tgatgtcttt gcttctggaa acacacaaaa   2160
atgacatccc gtcttcctat atggccttat ttcctcatct ccttcagcca gtgctttggg   2220
aaagaacagg aaatattcct gctctagtga ggcttcttca agcattctta gaacgcggtt   2280
caaacacaat agcaagtgct gcagctgaca aaattcctgg gttactaggt gtctttcaga   2340
agctgattgc atccaaagca aatgaccacc aaggttttta tcttctaaac agtataatag   2400
agcacatgcc tcctgaatca gttgaccaat ataggaaaca aatcttcatt ctgctattcc   2460
agagacttca gaattccaaa acaaccaagt ttatcaagag ttttttagtc tttattaatt   2520
tgtattgcat aaaatatggg gcactagcac tacaagaaat atttgatggt atacaaccaa   2580
aaatgtttgg aatggttttg gaaaaaatta ttattcctga aattcagaag gtatctggaa   2640
atgtagagaa aaagatctgt gcggttggca taaccaaatt actaacagaa tgtcccccaa   2700
tgatggacac tgagtatacc aaactgtgga ctccattatt acagtctttg attggtcttt   2760
ttgagttacc cgaagatgat accattcctg atgaggaaca ttttattgac atagaagata   2820
caccaggata tcagactgcc ttctcacagt tggcatttgc tgggaaaaaa gagcatgatc   2880
ctgtaggtca aatggtgaat aaccccaaaa ttcacctggc acagtcactt cacaagttgt   2940
ctaccgcctg tccaggaagg gttccatcaa tggtgagcac cagcctgaat gcagaagcgc   3000
tccagtatct ccaagggtac cttcaggcag ccagtgtgac actgctttaa actgcatttt   3060
tctaatgggc taaacccaga tggtttccta ggaaatcaca ggcttctgag cacagctgca   3120
ttaaaacaaa ggaagttctc cttttgaact tgtcacgaat tccatcttgt aaaggatatt   3180
aaatgttgct ttaacctgaa ccttgagcaa attagttggt ttgtgtgatc atacagttat   3240
gtgggtggct tctagtttgc aacttcaagg gacaagtatt aatagttcag tgtatggcgt   3300
tggtttgtgt tgagcgtttg cacggtttgg ataatcttaa attttgacgg acactgtgga   3360
```

gactttctgt tactaaatcc ttttgttttg aagctgttgc tatttgtatt tctcttgtcc 3420
tttatatttt ttgtctgttt atttacgctt ttattggaaa tgtgaataag taaagaatta 3480
cttgtgttac ttgccaagca gtgcacattt catagtttca aatctgtaat cagcaataaa 3540
aatcctaaaa tatgtaccta aaaaaaaaaa aaaaaaaaa 3579

<210> SEQ ID NO 51
<211> LENGTH: 8733
<212> TYPE: DNA
<213> ORGANISM: Homo sapiens

<400> SEQUENCE: 51
gctcccggct tagaggacag cggggaaggc gggcggtggg gcaggggggcc tgaagcggcg 60 gtaccggtgc tggcggcggc agctgaggcc ttggccgaag ccgcgcgaac ctcagggcaa 120
gatgcttgga accggacctg ccgccgccac caccgctgcc accacatcta gcaatgtgag 180
cgtcctgcag cagtttgcca gtggcctaaa gagccggaat gaggaaacca gggccaaagc 240
cgccaaggag ctccagcact atgtcaccat ggaactccga gagatgagtc aagaggagtc 300
tactcgcttc tatgaccaac tgaaccatca catttttgaa ttggtttcca gctcagatgc 360
caatgagagg aaaggtggca tcttggccat agctagcctc ataggagtgg aaggtgggaa 420
tgccacccga attggcagat ttgccaacta tcttcggaac ctcctcccct ccaatgaccc 480
agttgtcatg gaaatggcat ccaaggccat tggccgtctt gccatggcag gggacacttt 540
taccgctgag tacgtggaat ttgaggtgaa gcgagccctg gaatggctgg gtgctgaccg 600
caatgagggc cggagacatg cagctgtcct ggttctccgt gagctggcca tcagcgtccc 660
taccttcttc ttccagcaag tgcaaccctt ctttgacaac atttttgtgg ccgtgtggga 720
ccccaaacag gccatccgtg agggagctgt agccgccctt cgtgcctgtc tgattctcac 780
aacccagcgt gagccgaagg agatgcagaa gcctcagtgg tacaggcaca catttgaaga 840
agcagagaag ggatttgatg agaccttggc caaagagaag ggcatgaatc gggatgatcg 900
gatccatgga gccttgttga tccttaacga gctggtccga atcagcagca tggagggaga 960
gcgtctgaga gaagaaatgg aagaaatcac acagcagcag ctggtacacg acaagtactg 1020
caaagatctc atgggcttcg gaacaaaacc tcgtcacatt accccccttca ccagtttcca 1080 ggctgtacag ccccagcagt caaatgcctt ggtggggctg ctggggtaca gctctcacca 1140
aggcctcatg ggatttggga cctcccccag tccagctaag tccaccctgg tggagagccg 1200
gtgttgcaga gacttgatgg aggagaaatt tgatcaggtg tgccagtggg tgctgaaatg 1260
caggaatagc aagaactcgc tgatccaaat gacaatcctt aatttgttgc cccgcttggc 1320
tgcattccga ccttctgcct tcacagatac ccagtatctc caagatacca tgaaccatgt 1380
cctaagctgt gtcaagaagg agaaggaacg tacagcggcc ttccaagccc tggggctact 1440
ttctgtggct gtgaggtctg agtttaaggt ctatttgcct cgcgtgctgg acatcatccg 1500
agcggccctg cccccaaagg acttcgccca taagaggcag aaggcaatgc aggtggatgc 1560
cacagtcttc acttgcatca gcatgctggc tcgagcaatg ggcccaggca tccagcagga 1620
tatcaaggag ctgctggagc ccatgctggc agtgggacta agccctgccc tcactgcagt 1680
gctctacgac ctgagccgtc agattccaca gctaaagaag gacattcaag atgggctact 1740
gaaaatgctg tccctggtcc ttatgcacaa accccttcgc cacccaggca tgcccaaggg 1800
cctggcccat cagctggcct ctcctggcct cacgaccctc cctgaggcca gcgatgtggg 1860

-continued cagcatcact cttgccctcc gaacgcttgg cagctttgaa tttgaaggcc actctctgac 1920
ccaatttgtt cgccactgtg cggatcattt cctgaacagt gagcacaagg agatccgcat 1980
ggaggctgcc cgcacctgct cccgcctgct cacaccctcc atccacctca tcagtggcca 2040
tgctcatgtg gttagccaga ccgcagtgca agtggtggca gatgtgctta gcaaactgct 2100
cgtagttggg ataacagatc ctgaccctga cattcgctac tgtgtcttgg cgtccctgga 2160
cgagcgcttt gatgcacacc tggcccaggc ggagaacttg caggccttgt ttgtggctct 2220
gaatgaccag gtgtttgaga tccgggagct ggccatctgc actgtgggcc gactcagtag 2280
catgaaccct gcctttgtca tgcctttcct gcgcaagatg ctcatccaga ttttgacaga 2340
gttggagcac agtgggattg gaagaatcaa agagcagagt gcccgcatgc tggggcacct 2400
ggtctccaat gccccccgac tcatccgccc ctacatggag cctattctga aggcattaat 2460
tttgaaactg aaagatccag accctgatcc aaacccaggt gtgatcaata atgtcctggc 2520
aacaatagga gaattggcac aggttagtgg cctggaaatg aggaaatggg ttgatgaact 2580
ttttattatc atcatggaca tgctccagga ttcctctttg ttggccaaaa ggcaggtggc 2640
tctgtggacc ctgggacagt tggtggccag cactggctat gtagtagagc cctacaggaa 2700
gtaccctact ttgcttgagg tgctactgaa ttttctgaag actgagcaga accagggtac 2760
acgcagagag gccatccgtg tgttagggct tttaggggct ttggatcctt acaagcacaa 2820
agtgaacatt ggcatgatag accagtcccg ggatgcctct gctgtcagcc tgtcagaatc 2880
caagtcaagt caggattcct ctgactatag cactagtgaa atgctggtca acatgggaaa 2940
cttgcctctg gatgagttct acccagctgt gtccatggtg gccctgatgc ggatcttccg 3000
agaccagtca ctctctcatc atcacaccat ggttgtccag gccatcacct tcatcttcaa 3060
gtccctggga ctcaaatgtg tgcagttcct gccccaggtc atgcccacgt tccttaacgt 3120
cattcgagtc tgtgatgggg ccatccggga atttttgttc cagcagctgg gaatgttggt 3180
gtcctttgtg aagagccaca tcagacctta tatggatgaa atagtcaccc tcatgagaga 3240
attctgggtc atgaacacct caattcagag cacgatcatt cttctcattg agcaaattgt 3300
ggtagctctt gggggtgaat ttaagctcta cctgccccag ctgatcccac acatgctgcg 3360
tgtcttcatg catgacaaca gcccaggccg cattgtctct atcaagttac tggctgcaat 3420
ccagctgttt ggcgccaacc tggatgacta cctgcattta ctgctgcctc ctattgttaa 3480
gttgtttgat gcccctgaag ctccactgcc atctcgaaag gcagcgctag agactgtgga 3540
ccgcctgacg gagtccctgg atttcactga ctatgcctcc cggatcattc accctattgt 3600
tcgaacactg gaccagagcc cagaactgcg ctccacagcc atggacacgc tgtcttcact 3660
tgtttttcag ctggggaaga agtaccaaat tttcattcca atggtgaata aagttctggt 3720
gcgacaccga atcaatcatc agcgctatga tgtgctcatc tgcagaattg tcaagggata 3780
cacacttgct gatgaagagg aggatccttt gatttaccag catcggatgc ttaggagtgg 3840
ccaaggggat gcattggcta gtggaccagt ggaaacagga cccatgaaga aactgcacgt 3900
cagcaccatc aacctccaaa aggcctgggg cgctgccagg agggtctcca aagatgactg 3960
gctggaatgg ctgagacggc tgagcctgga gctgctgaag gactcatcat cgccctccct 4020
gcgctcctgc tgggccctgg cacaggccta caacccgatg gccagggatc tcttcaatgc 4080
tgcatttgtg tcctgctggt ctgaactgaa tgaagatcaa caggatgagc tcatcagaag 4140
catcgagttg gccctcacct cacaagacat cgctgaagtc acacagaccc tcttaaactt 4200
ggctgaattc atggaacaca gtgacaaggg cccccctgcca ctgagagatg acaatggcat 4260

-continued

```
tgttctgctg ggtgagagag ctgccaagtg ccgagcatat gccaaagcac tacactacaa   4320
agaactggag ttccagaaag gccccacccc tgccattcta gaatctctca tcagcattaa   4380
taataagcta cagcagccgg aggcagcggc cggagtgtta gaatatgcca tgaaacactt   4440
tggagagctg gagatccagg ctacctggta tgagaaactg cacgagtggg aggatgccct   4500
tgtggcctat gacaagaaaa tggacaccaa caaggacgac ccagagctga tgctgggccg   4560
catgcgctgc ctcgaggcct tgggggaatg gggtcaactc caccagcagt gctgtgaaaa   4620
gtggaccctg gttaatgatg agacccaagc caagatggcc cggatggctg ctgcagctgc   4680
atggggttta ggtcagtggg acagcatgga agaatacacc tgtatgatcc ctcgggacac   4740
ccatgatggg gcattttata gagctgtgct ggcactgcat caggacctct tctccttggc   4800
acaacagtgc attgacaagg ccagggacct gctggatgct gaattaactg cgatggcagg   4860
agagagttac agtcgggcat atggggccat ggtttcttgc cacatgctgt ccgagctgga   4920
ggaggttatc cagtacaaac ttgtccccga gcgacgagag atcatccgcc agatctggtg   4980
ggagagactg cagggctgcc agcgtatcgt agaggactgg cagaaaatcc ttatggtgcg   5040
gtcccttgtg gtcagccctc atgaagacat gagaacctgg ctcaagtatg caagcctgtg   5100
cggcaagagt ggcaggctgg ctcttgctca taaaacttta gtgttgctcc tgggagttga   5160
tccgtctcgg caacttgacc atcctctgcc aacagttcac cctcaggtga cctatgccta   5220
catgaaaaac atgtggaaga gtgcccgcaa gatcgatgcc ttccagcaca tgcagcattt   5280
tgtccagacc atgcagcaac aggcccagca tgccatcgct actgaggacc agcagcataa   5340
gcaggaactg cacaagctca tggcccgatg cttcctgaaa cttggagagt ggcagctgaa   5400
tctacagggc atcaatgaga gcacaatccc caaagtgctg cagtactaca gcgccgccac   5460
agagcacgac cgcagctggt acaaggcctg gcatgcgtgg gcagtgatga acttcgaagc   5520
tgtgctacac tacaaacatc agaaccaagc ccgcgatgag aagaagaaac tgcgtcatgc   5580
cagcggggcc aacatcacca acgccaccac tgccgccacc acggccgcca ctgccaccac   5640
cactgccagc accgagggca gcaacagtga gagcgaggcc gagagcaccg agaacagccc   5700
caccccatcg ccgctgcaga agaaggtcac tgaggatctg tccaaaaccc tcctgatgta   5760
cacggtgcct gccgtccagg gcttcttccg ttccatctcc ttgtcacgag gcaacaacct   5820
ccaggataca ctcagagttc tcaccttatg gtttgattat ggtcactggc cagatgtcaa   5880
tgaggcctta gtggaggggg tgaaagccat ccagattgat acctggctac aggttatacc   5940
tcagctcatt gcaagaattg atacgcccag acccttggtg ggacgtctca ttcaccagct   6000
tctcacagac attggtcggt accaccccca ggccctcatc tacccactga cagtggcttc   6060
taagtctacc acgacagccc ggcacaatgc agccaacaag attctgaaga acatgtgtga   6120
gcacagcaac accctggtcc agcaggccat gatggtgagc gaggagctga tccgagtggc   6180
catcctctgg catgagatgt ggcatgaagg cctggaagag gcatctcgtt tgtactttgg   6240
ggaaaggaac gtgaaaggca tgtttgaggt gctggagccc ttgcatgcta tgatggaacg   6300
gggcccccag actctgaagg aaacatcctt taatcaggcc tatggtcgag atttaatgga   6360
ggcccaagag tggtgcagga agtacatgaa atcagggaat gtcaaggacc tcacccaagc   6420
ctgggacctc tattatcatg tgttccgacg aatctcaaag cagctgcctc agctcacatc   6480
cttagagctg caatatgttt ccccaaaact tctgatgtgc cgggaccttg aattggctgt   6540
gccaggaaca tatgacccca accagccaat cattcgcatt cagtccatag caccgtcttt   6600
```

```
gcaagtcatc acatccaagc agaggccccg gaaattgaca cttatgggca gcaacggaca   6660
tgagtttgtt ttccttctaa aaggccatga agatctgcgc caggatgagc gtgtgatgca   6720
gctcttcggc ctggttaaca cccttctggc caatgaccca acatctcttc ggaaaaacct   6780
cagcatccag agatacgctg tcatcccttt atcgaccaac tcgggcctca ttggctgggt   6840
tccccactgt gacacactgc acgccctcat ccgggactac agggagaaga agaagatcct   6900
tctcaacatc gagcatcgca tcatgttgcg gatggctccg gactatgacc acttgactct   6960
gatgcagaag gtggaggtgt ttgagcatgc cgtcaataat acagctgggg acgacctggc   7020
caagctgctg tggctgaaaa gccccagctc cgaggtgtgg tttgaccgaa gaaccaatta   7080
tacccgttct ttagcggtca tgtcaatggt tgggtatatt ttaggcctgg gagatagaca   7140
cccatccaac ctgatgctgg accgtctgag tgggaagatc ctgcacattg actttgggga   7200
ctgctttgag gttgctatga cccgagagaa gtttccagag aagattccat ttagactaac   7260
aagaatgttg accaatgcta tggaggttac aggcctggat ggcaactaca gaatcacatg   7320
ccacacagtg atggaggtgc tgcgagagca caaggacagt gtcatggccg tgctggaagc   7380
ctttgtctat gaccccttgc tgaactggag gctgatggac acaaatacca aaggcaacaa   7440
gcgatcccga acgaggacgg attcctactc tgctggccag tcagtcgaaa ttttggacgg   7500
tgtggaactt ggagagccag cccataagaa aacggggacc acagtgccag aatctattca   7560
ttctttcatt ggagacggtt tggtgaaacc agaggcccta aataagaaag ctatccagat   7620
tattaacagg gttcgagata agctcactgg tcgggacttc tctcatgatg acactttgga   7680
tgttccaacg caagttgagc tgctcatcaa acaagcgaca tcccatgaaa acctctgcca   7740
gtgctatatt ggctggtgcc ctttctggta actggaggcc cagatgtgcc catcacgttt   7800
tttctgaggc ttttgtactt tagtaaatgc ttccactaaa ctgaaaccat ggtgagaaag   7860
tttgactttg ttaaatattt tgaaatgtaa atgaaaagaa ctactgtata ttaaaagttg   7920
gtttgaacca actttctagc tgctgttgaa gaatatattg tcagaaacac aaggcttgat   7980
ttggttccca ggacagtgaa acatagtaat accacgtaaa tcaagccatt catttggggg   8040
aacagaagat ccataacttt agaaatacgg gttttgactt aactcacaag agaactcatc   8100
ataagtactt gctgatggaa gaatgaccta gttgctcctc tcaacatggg tacagcaaac   8160
tcagcacagc caagaagcct caggtcgtgg agaacatgga ttaggatcct agactgtaaa   8220
gacacagaag atgctgacct cacccctgcc acctatccca agacctcact ggtctgtgga   8280
cagcagcaga aatgtttgca agataggcca aaatgagtac aaaaggtctg tcttccatca   8340
gacccagtga tgctgcgact cacacgcttc aattcaagac ctgaccgcta gtagggaggt   8400
ttattcagat cgctggcagc ctcggctgag cagatgcaca gaggggatca ctgtgcagtg   8460
ggaccaccct cactggcctt ctgcagcagg gttctgggat gttttcagtg gtcaaaatac   8520
tctgtttaga gcaagggctc agaaaacaga aatactgtca tggaggtgct gaacacaggg   8580
aaggtctggt acatattgga aattatgagc agaacaaata ctcaactaaa tgcacaaagt   8640
ataaagtgta gccatgtcta gacaccatgt tgtatcagaa taatttttgt gccaataaat   8700
gacatcagaa ttttaaacat atgtaaaaaa aaa                                8733
```

<210> SEQ ID NO 52
<211> LENGTH: 3008
<212> TYPE: DNA
<213> ORGANISM: Homo sapiens

<400> SEQUENCE: 52

```
taattatggg tctgtaacca ccctggactg ggtgctcctc actgacggac ttgtctgaac     60
ctctctttgt ctccagcgcc cagcactggg cctggcaaaa cctgagacgc ccggtacatg    120
ttggccaaat gaatgaacca gattcagacc ggcaggggcg ctgtggttta ggaggggcct    180
ggggtttctc ccaggaggtt tttgggcttg cgctggaggg ctctggactc ccgtttgcgc    240
cagtggcctg catcctggtc ctgtcttcct catgtttgaa tttctttgct ttcctagtct    300
ggggagcagg gaggagccct gtgccctgtc ccaggatcca tgggtaggaa caccatggac    360
agggagagca aacggggcca tctgtcacca ggggcttagg gaaggccgag ccagcctggg    420
tcaaagaagt caaaggggct gcctggagga ggcagcctgt cagctggtgc atcagaggct    480
gtggccaggc cagctgggct cggggagcgc cagcctgaga ggagcgcgtg agcgtcgcgg    540
gagcctcggg caccatgagc gacgtggcta ttgtgaagga gggttggctg cacaaacgag    600
gggagtacat caagacctgg cggccacgct acttcctcct caagaatgat ggcaccttca    660
ttggctacaa ggagcggccg caggatgtgg accaacgtga ggctcccctc aacaacttct    720
ctgtggcgca gtgccagctg atgaagacgg agcggccccg gcccaacacc ttcatcatcc    780
gctgcctgca gtggaccact gtcatcgaac gcaccttcca tgtggagact cctgaggagc    840
gggaggagtg gacaaccgcc atccagactg tggctgacgg cctcaagaag caggaggagg    900
aggagatgga cttccggtcg ggctcaccca gtgacaactc aggggctgaa gagatggagg    960
tgtccctggc caagcccaag caccgcgtga ccatgaacga gtttgagtac ctgaagctgc   1020
tgggcaaggg cactttcggc aaggtgatcc tggtgaagga gaaggccaca ggccgctact   1080
acgccatgaa gatcctcaag aaggaagtca tcgtggccaa ggacgaggtg gcccacacac   1140
tcaccgagaa ccgcgtcctg cagaactcca ggcacccctt cctcacagcc ctgaagtact   1200
ctttccagac ccacgaccgc ctctgctttg tcatggagta cgccaacggg ggcgagctgt   1260
tcttccacct gtcccgggag cgtgtgttct ccgaggaccg ggcccgcttc tatggcgctg   1320
agattgtgtc agccctggac tacctgcact cggagaagaa cgtggtgtac cgggacctca   1380
agctggagaa cctcatgctg gacaaggacg ggcacattaa gatcacagac ttcgggctgt   1440
gcaaggaggg gatcaaggac ggtgccacca tgaagacctt ttgcggcaca cctgagtacc   1500
tggcccccga ggtgctggag gacaatgact acggccgtgc agtggactgg tgggggctgg   1560
gcgtggtcat gtacgagatg atgtgcggtc gcctgccctt ctacaaccag gaccatgaga   1620
agctttttga gctcatcctc atggaggaga tccgcttccc gcgcacgctt ggtcccgagg   1680
ccaagtcctt gctttcaggg ctgctcaaga aggaccccaa gcagaggctt ggcgggggct   1740
ccgaggacgc caaggagatc atgcagcatc gcttctttgc cggtatcgtg tggcagcacg   1800
tgtacgagaa gaagctcagc ccacccttca agccccaggt cacgtcggag actgacacca   1860
ggtattttga tgaggagttc acggcccaga tgatcaccat cacaccacct gaccaagatg   1920
acagcatgga gtgtgtggac agcgagcgca ggccccactt cccccagttc tcctactcgg   1980
ccagcggcac ggcctgaggc ggcggtggac tgcgctggac gatagcttgg agggatggag   2040
aggcggcctc gtgccatgat ctgtatttaa tggtttttat ttctcgggtg catttgagag   2100
aagccacgct gtcctctcga gcccagatgg aaagacgttt ttgtgctgtg ggcagcaccc   2160
tcccccgcag cggggtaggg aagaaaacta tcctgcgggt tttaatttat ttcatccagt   2220
ttgttctccg ggtgtggcct cagccctcag aacaatccga ttcacgtagg gaaatgttaa   2280
ggacttctgc agctatgcgc aatgtggcat tgggggccg ggcaggtcct gcccatgtgt   2340
```

```
cccctcactc tgtcagccag ccgccctggg ctgtctgtca ccagctatct gtcatctctc   2400

tggggccctg ggcctcagtt caacctggtg gcaccagatg caacctcact atggtatgct   2460

ggccagcacc ctctcctggg ggtggcaggc acacagcagc cccccagcac taaggccgtg   2520

tctctgagga cgtcatcgga ggctgggccc ctgggatggg accagggatg gggatgggc   2580

cagggtttac ccagtgggac agaggagcaa ggtttaaatt tgttattgtg tattatgttg   2640

ttcaaatgca ttttgggggt ttttaatctt tgtgacagga aagccctccc ccttcccctt   2700

ctgtgtcaca gttcttggtg actgtcccac cgggagcctc cccctcagat gatctctcca   2760

cggtagcact tgaccttttc gacgcttaac ctttccgctg tcgccccagg ccctccctga   2820

ctccctgtgg gggtggccat ccctgggccc ctccacgcct cctggccaga cgctgccgct   2880

gccgctgcac cacggcgttt ttttacaaca ttcaacttta gtatttttac tattataata   2940

taatatggaa ccttccctcc aaattcttca ataaaagttg cttttcaaaa aaaaaaaaaa   3000

aaaaaaaa                                                            3008
```

<210> SEQ ID NO 53
<211> LENGTH: 891
<212> TYPE: DNA
<213> ORGANISM: Homo sapiens

<400> SEQUENCE: 53

```
tcacgtgacc cgggcgcgct gcggccgccc gcgcggaccc ggcgagaggc ggcggcggga     60

gcggcggtga tggacgggtc cggggagcag cccagaggcg gggggcccac cagctctgag    120

cagatcatga agacaggggc ccttttgctt cagggtttca tccaggatcg agcagggcga    180

atgggggggg aggcacccga gctggccctg gacccggtgc ctcaggatgc gtccaccaag    240

aagctgagcg agtgtctcaa gcgcatcggg gacgaactgg acagtaacat ggagctgcag    300

aggatgattg ccgccgtgga cacagactcc ccccgagagg tctttttccg agtggcagct    360

gacatgtttt ctgacggcaa cttcaactgg ggccgggttg tcgccctttt ctactttgcc    420

agcaaactgg tgctcaaggc cctgtgcacc aaggtgccgg aactgatcag aaccatcatg    480

ggctggacat tggacttcct ccgggagcgg ctgttgggct ggatccaaga ccagggtggt    540

tgggtgagac tcctcaagcc tcctcacccc caccaccgcg ccctcaccac cgcccctgcc    600

ccaccgtccc tgccccccgc cactcctctg ggaccctggg ccttctggag caggtcacag    660

tggtgccctc tccccatctt cagatcatca gatgtggtct ataatgcgtt ttccttacgt    720

gtctgatcaa tccccgattc atctaccctg ctgacctccc agtgacccct gacctcactg    780

tgaccttgac ttgattagtg ccttctgccc tccctggagc ctccactgcc tctggaattg    840

ctcaagttca ttgatgaccc tctgacccta gctctttcct tttttttttt t             891
```

<210> SEQ ID NO 54
<211> LENGTH: 6492
<212> TYPE: DNA
<213> ORGANISM: Homo sapiens

<400> SEQUENCE: 54

```
tttctgtgaa gcagaagtct gggaatcgat ctggaaatcc tcctaatttt tactccctct     60

ccccgcgact cctgattcat tgggaagttt caaatcagct ataactggag agtgctgaag    120

attgatggga tcgttgcctt atgcatttgt tttggtttta caaaaaggaa acttgacaga    180

ggatcatgct gtacttaaaa aatacaacat cacagaggaa gtagactgat attaacaata    240

cttactaata ataacgtgcc tcatgaaata aagatccgaa aggaattgga ataaaaattt    300
```

```
cctgcatctc atgccaaggg ggaaacacca gaatcaagtg ttccgcgtga ttgaagacac    360
cccctcgtcc aagaatgcaa agcacatcca ataaaatagc tggattataa ctcctcttct    420
ttctctgggg gccgtggggt gggagctggg gcgagaggtg ccgttggccc ccgttgcttt    480
tcctctggga aggatggcgc acgctgggag aacagggtac gataaccggg agatagtgat    540
gaagtacatc cattataagc tgtcgcagag gggctacgag tgggatgcgg gagatgtggg    600
cgccgcgccc ccgggggccg cccccgcacc gggcatcttc tcctcccagc ccgggcacac    660
gccccatcca gccgcatccc gggacccggt cgccaggacc tcgccgctgc agaccccggc    720
tgcccccggc gccgccgcgg ggcctgcgct cagcccggtg ccacctgtgg tccacctgac    780
cctccgccag gccggcgacg acttctcccg ccgctaccgc cgcgacttcg ccgagatgtc    840
cagccagctg cacctgacgc ccttcaccgc gcggggacgc tttgccacgg tggtggagga    900
gctcttcagg gacggggtga actgggggag gattgtggcc ttctttgagt tcggtggggt    960
catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca cacaacaatt   1380
aacagtcttc aggcaaaacg tcgaatcagc tatttactgc caaagggaaa tatcatttat   1440
tttttacatt attaagaaaa aaagatttat ttatttaaga cagtcccatc aaaactcctg   1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtggggggaa gtccatgcct ccctggcctg aagaagagac tctttgcata   1800
tgactcacat gatgcatacc tggtgggagg aaaagagttg ggaacttcag atggacctag   1860
tacccactga gatttccacg ccgaaggaca gcgatgggaa aaatgccctt aaatcatagg   1920
aaagtatttt tttaagctac caattgtgcc gagaaaagca ttttagcaat ttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340
gtagaggggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
```

-continued

```
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
taaagaagta acaaaagaag tgacatcttc agcaaataaa ctaggaaatt tttttttctt   2880
ccagtttaga atcagccttg aaacattgat ggaataactc tgtggcatta ttgcattata   2940
taccatttat ctgtattaac tttggaatgt actctgttca atgtttaatg ctgtggttga   3000
tatttcgaaa gctgctttaa aaaaatacat gcatctcagc gttttttttgt ttttaattgt   3060
atttagttat ggcctataca ctatttgtga gcaaaggtga tcgttttctg tttgagattt   3120
ttatctcttg attcttcaaa agcattctga gaaggtgaga taagccctga gtctcagcta   3180
cctaagaaaa acctggatgt cactggccac tgaggagctt tgtttcaacc aagtcatgtg   3240
catttccacg tcaacagaat tgtttattgt gacagttata tctgttgtcc ctttgacctt   3300
gtttcttgaa ggtttcctcg tccctgggca attccgcatt taattcatgg tattcaggat   3360
tacatgcatg tttggttaaa cccatgagat tcattcagtt aaaaatccag atggcaaatg   3420
accagcagat tcaaatctat ggtggtttga cctttagaga gttgctttac gtggcctgtt   3480
tcaacacaga cccacccaga gccctcctgc cctccttccg cgggggcttt ctcatggctg   3540
tccttcaggg tcttcctgaa atgcagtggt gcttacgctc caccaagaaa gcaggaaacc   3600
tgtggtatga agccagacct ccccggcggg cctcagggaa cagaatgatc agacctttga   3660
atgattctaa tttttaagca aaatattatt ttatgaaagg tttacattgt caaagtgatg   3720
aatatggaat atccaatcct gtgctgctat cctgccaaaa tcattttaat ggagtcagtt   3780
tgcagtatgc tccacgtggt aagatcctcc aagctgcttt agaagtaaca atgaagaacg   3840
tggacgtttt taatataaag cctgttttgt cttttgttgt tgttcaaacg ggattcacag   3900
agtatttgaa aaatgtatat atattaagag gtcacggggg ctaattgctg gctggctgcc   3960
ttttgctgtg gggttttgtt acctggtttt aataacagta aatgtgccca gcctcttggc   4020
cccagaactg tacagtattg tggctgcact tgctctaaga gtagttgatg ttgcattttc   4080
cttattgtta aaaacatgtt agaagcaatg aatgtatata aaagcctcaa ctagtcattt   4140
ttttctcctc ttcttttttt tcattatatc taattatttt gcagttgggc aacagagaac   4200
catccctatt ttgtattgaa gagggattca catctgcatc ttaactgctc tttatgaatg   4260
aaaaaacagt cctctgtatg tactcctctt tacactggcc agggtcagag ttaaatagag   4320
tatatgcact ttccaaattg gggacaaggg ctctaaaaaa agccccaaaa ggagaagaac   4380
atctgagaac ctcctcggcc ctcccagtcc ctcgctgcac aaatactccg caagagaggc   4440
cagaatgaca gctgacaggg tctatggcca tcgggtcgtc tccgaagatt tggcaggggc   4500
agaaaactct ggcaggctta agatttggaa taaagtcaca gaattaagga agcacctcaa   4560
tttagttcaa acaagacgcc aacattctct ccacagctca cttacctctc tgtgttcaga   4620
tgtggccttc catttatatg tgatctttgt tttattagta aatgcttatc atctaaagat   4680
gtagctctgg cccagtggga aaaattagga agtgattata aatcgagagg agttataata   4740
atcaagatta aatgtaaata atcagggcaa tcccaacaca tgtctagctt tcacctccag   4800
gatctattga gtgaacagaa ttgcaaatag tctctatttg taattgaact tatcctaaaa   4860
caaatagttt ataaatgtga acttaaactc taattaattc caactgtact tttaaggcag   4920
tggctgtttt tagactttct tatcacttat agttagtaat gtacacctac tctatcagag   4980
aaaaacagga aaggctcgaa atacaagcca ttctaaggaa attagggagt cagttgaaat   5040
```

tctattctga tcttattctg tggtgtcttt tgcagcccag acaaatgtgg ttacacactt 5100
tttaagaaat acaattctac attgtcaagc ttatgaaggt tccaatcaga tctttattgt 5160
tattcaattt ggatctttca gggatttttt ttttaaatta ttatgggaca aaggacattt 5220
gttggagggg tgggagggag gaagaatttt taaatgtaaa acattcccaa gtttggatca 5280
gggagttgga agttttcaga ataaccagaa ctaagggtat gaaggacctg tattggggtc 5340
gatgtgatgc ctctgcgaag aaccttgtgt gacaaatgag aaacattttg aagtttgtgg 5400
tacgaccttt agattccaga gacatcagca tggctcaaag tgcagctccg tttggcagtg 5460
caatggtata aatttcaagc tggatatgtc taatgggtat ttaaacaata aatgtgcagt 5520
tttaactaac aggatattta atgacaacct tctggttggt agggacatct gtttctaaat 5580
gtttattatg tacaatacag aaaaaaattt tataaaatta agcaatgtga aactgaattg 5640
gagagtgata atacaagtcc tttagtctta cccagtgaat cattctgttc catgtctttg 5700
gacaaccatg accttggaca atcatgaaat atgcatctca ctggatgcaa agaaaatcag 5760
atggagcatg aatggtactg taccggttca tctggactgc cccagaaaaa taacttcaag 5820
caaacatcct atcaacaaca aggttgttct gcataccaag ctgagcacag aagatgggaa 5880
cactggtgga ggatggaaag gctcgctcaa tcaagaaaat tctgagacta ttaataaata 5940
agactgtagt gtagatactg agtaaatcca tgcacctaaa ccttttggaa aatctgccgt 6000
gggccctcca gatagctcat ttcattaagt ttttccctcc aaggtagaat ttgcaagagt 6060
gacagtggat tgcatttctt ttggggaagc tttcttttgg tggttttgtt tattatacct 6120
tcttaagttt tcaaccaagg tttgcttttg ttttgagtta ctggggttat ttttgtttta 6180
aataaaaata agtgtacaat aagtgttttt gtattgaaag cttttgttat caagattttc 6240
atacttttac cttccatggc tctttttaag attgatactt ttaagaggtg gctgatattc 6300
tgcaacactg tacacataaa aaatacggta aggatacttt acatggttaa ggtaaagtaa 6360
gtctccagtt ggccaccatt agctataatg gcactttgtt tgtgttgttg gaaaaagtca 6420
cattgccatt aaactttcct tgtctgtcta gttaatattg tgaagaaaaa taaagtacag 6480
tgtgagatac tg 6492

<210> SEQ ID NO 55
<211> LENGTH: 5572
<212> TYPE: DNA
<213> ORGANISM: Homo sapiens

<400> SEQUENCE: 55
cctcccctcg cccggcgcgg tcccgtccgc ctctcgctcg cctcccgcct cccctcggtc 60
ttccgaggcg cccgggctcc cggcgcggcg gcggaggggg cgggcaggcc ggcgggcggt 120
gatgtggcgg gactctttat gcgctgcggc aggatacgcg ctcggcgctg ggacgcgact 180
gcgctcagtt ctctcctctc ggaagctgca gccatgatgg aagtttgaga gttgagccgc 240
tgtgaggcga ggccgggctc aggcgaggga gatgagagac ggcggcggcc gcggcccgga 300
gcccctctca gcgcctgtga gcagccgcgg gggcagcgcc ctcggggagc cggccggcct 360
gcggcggcgg cagcggcggc gtttctcgcc tcctcttcgt cttttctaac cgtgcagcct 420
cttcctcggc ttctcctgaa agggaaggtg gaagccgtgg gctcgggcgg gagccggctg 480
aggcgcggcg gcggcggcgg cacctcccgc tcctggagcg ggggggagaa gcggcggcgg 540
cggcggccgc ggcggctgca gctccaggga gggggtctga gtcgcctgtc accatttcca 600
gggctgggaa cgccggagag ttggtctctc cccttctact gcctccaaca cggcggcggc 660
ggcggcggca catccaggga cccgggccgg ttttaaacct cccgtccgcc gccgccgcac 720
cccccgtggc ccgggctccg gaggccgccg gcggaggcag ccgttcggag gattattcgt 780
cttctcccca ttccgctgcc gccgctgcca ggcctctggc tgctgaggag aagcaggccc 840
agtcgctgca accatccagc agccgccgca gcagccatta cccggctgcg gtccagagcc 900
aagcggcggc agagcgaggg gcatcagcta ccgccaagtc cagagccatt tccatcctgc 960
agaagaagcc ccgccaccag cagcttctgc catctctctc ctcctttttc ttcagccaca 1020
ggctcccaga catgacagcc atcatcaaag agatcgttag cagaaacaaa aggagatatc 1080
aagaggatgg attcgactta gacttgacct atatttatcc aaacattatt gctatgggat 1140
ttcctgcaga aagacttgaa ggcgtataca ggaacaatat tgatgatgta gtaaggtttt 1200
tggattcaaa gcataaaaac cattacaaga tatacaatct ttgtgctgaa agacattatg 1260
acaccgccaa atttaattgc agagttgcac aatatccttt tgaagaccat aacccaccac 1320
agctagaact tatcaaaccc ttttgtgaag atcttgacca atggctaagt gaagatgaca 1380
atcatgttgc agcaattcac tgtaaagctg gaaagggacg aactggtgta atgatatgtg 1440
catatttatt acatcggggc aaatttttaa aggcacaaga ggccctagat ttctatgggg 1500
aagtaaggac cagagacaaa aagggagtaa ctattcccag tcagaggcgc tatgtgtatt 1560
attatagcta cctgttaaag aatcatctgg attatagacc agtggcactg ttgtttcaca 1620
agatgatgtt tgaaactatt ccaatgttca gtggcggaac ttgcaatcct cagtttgtgg 1680
tctgccagct aaaggtgaag atatattcct ccaattcagg acccacacga cgggaagaca 1740
agttcatgta ctttgagttc cctcagccgt tacctgtgtg tggtgatatc aaagtagagt 1800
tcttccacaa acagaacaag atgctaaaaa aggacaaaat gtttcacttt tgggtaaata 1860
cattcttcat accaggacca gaggaaacct cagaaaaagt agaaaatgga agtctatgtg 1920
atcaagaaat cgatagcatt tgcagtatag agcgtgcaga taatgacaag gaatatctag 1980
tacttacttt aacaaaaaat gatcttgaca aagcaaataa agacaaagcc aaccgatact 2040
tttctccaaa ttttaaggtg aagctgtact tcacaaaaac agtagaggag ccgtcaaatc 2100
cagaggctag cagttcaact tctgtaacac cagatgttag tgacaatgaa cctgatcatt 2160
atagatattc tgacaccact gactctgatc cagagaatga acctttttgat gaagatcagc 2220
atacacaaat tacaaaagtc tgaatttttt tttatcaaga gggataaaac accatgaaaa 2280
taaacttgaa taaactgaaa atggaccttt tttttttttaa tggcaatagg acattgtgtc 2340
agattaccag ttataggaac aattctcttt tcctgaccaa tcttgtttta ccctatacat 2400
ccacagggtt ttgacacttg ttgtccagtt gaaaaaaggt tgtgtagctg tgtcatgtat 2460
ataccttttt gtgtcaaaag gacatttaaa attcaattag gattaataaa gatggcactt 2520
tcccgtttta ttccagtttt ataaaaagtg gagacagact gatgtgtata cgtaggaatt 2580
ttttcctttt gtgttctgtc accaactgaa gtggctaaag agctttgtga tatactggtt 2640
cacatcctac ccctttgcac ttgtggcaac agataagttt gcagttggct aagagaggtt 2700
tccgaagggt tttgctacat tctaatgcat gtattcgggt taggggaatg gagggaatgc 2760
tcagaaagga aataatttta tgctggactc tggaccatat accatctcca gctatttaca 2820
cacacctttc tttagcatgc tacagttatt aatctggaca ttcgaggaat tggccgctgt 2880
cactgcttgt tgtttgcgca tttttttta aagcatattg gtgctagaaa aggcagctaa 2940
aggaagtgaa tctgtattgg ggtacaggaa tgaaccttct gcaacatctt aagatccaca 3000
aatgaaggga tataaaaata atgtcatagg taagaaacac agcaacaatg acttaaccat 3060
ataaatgtgg aggctatcaa caaagaatgg gcttgaaaca ttataaaaat tgacaatgat 3120
ttattaaata tgttttctca attgtaacga cttctccatc tcctgtgtaa tcaaggccag 3180
tgctaaaatt cagatgctgt tagtacctac atcagtcaac aacttacact tattttacta 3240
gttttcaatc ataatacctg ctgtggatgc ttcatgtgct gcctgcaagc ttcttttttc 3300
tcattaaata taaaatattt tgtaatgctg cacagaaatt ttcaatttga gattctacag 3360
taagcgtttt ttttctttga agatttatga tgcacttatt caatagctgt cagccgttcc 3420
acccttttga ccttacacat tctattacaa tgaattttgc agttttgcac atttttttaaa 3480
tgtcattaac tgttagggaa ttttacttga atactgaata catataatgt ttatattaaa 3540
aaggacattt gtgttaaaaa ggaaattaga gttgcagtaa actttcaatg ctgcacacaa 3600
aaaaaagaca tttgattttt cagtagaaat tgtcctacat gtgctttatt gatttgctat 3660
tgaaagaata gggttttttt tttttttttt tttttttttt ttaaatgtgc agtgttgaat 3720
catttcttca tagtgctccc ccgagttggg actagggctt caatttcact tcttaaaaaa 3780
aatcatcata tatttgatat gcccagactg catacgattt taagcggagt acaactacta 3840
ttgtaaagct aatgtgaaga tattattaaa aaggtttttt tttccagaaa tttggtgtct 3900
tcaaattata ccttcacctt gacatttgaa tatccagcca ttttgtttct taatggtata 3960
aaattccatt ttcaataact tattggtgct gaaattgttc actagctgtg gtctgaccta 4020
gttaatttac aaatacagat tgaataggac ctactagagc agcatttata gagtttgatg 4080
gcaaatagat taggcagaac ttcatctaaa atattcttag taaataatgt tgacacgttt 4140
tccatacctt gtcagtttca ttcaacaatt tttaaatttt taacaaagct cttaggattt 4200
acacatttat atttaaacat tgatatatag agtattgatt gattgctcat aagttaaatt 4260
ggtaaagtta gagacaacta ttctaacacc tcaccattga aatttatatg ccaccttgtc 4320
tttcataaaa gctgaaaatt gttacctaaa atgaaaatca acttcatgtt ttgaagatag 4380
ttataaatat tgttctttgt tacaatttcg ggcaccgcat attaaaacgt aactttattg 4440
ttccaatatg taacatggag ggccaggtca taaataatga cattataatg ggcttttgca 4500
ctgttattat ttttcctttg gaatgtgaag gtctgaatga gggttttgat tttgaatgtt 4560
tcaatgtttt tgagaagcct tgcttacatt ttatggtgta gtcattggaa atggaaaaat 4620
ggcattatat atattatata tataaatata tattatacat actctcctta ctttatttca 4680
gttaccatcc ccatagaatt tgacaagaat tgctatgact gaaaggtttt cgagtcctaa 4740
ttaaaacttt atttatggca gtattcataa ttagcctgaa atgcattctg taggtaatct 4800
ctgagtttct ggaatatttt cttagacttt ttggatgtgc agcagcttac atgtctgaag 4860
ttacttgaag gcatcacttt taagaaagct tacagttggg ccctgtacca tcccaagtcc 4920
tttgtagctc ctcttgaaca tgtttgccat acttttaaaa gggtagttga ataaatagca 4980
tcaccattct ttgctgtggc acaggttata aacttaagtg gagtttaccg gcagcatcaa 5040
atgtttcagc tttaaaaaat aaaagtaggg tacaagttta atgtttagtt ctagaaattt 5100
tgtgcaatat gttcataacg atggctgtgg ttgccacaaa gtgcctcgtt tacctttaaa 5160
tactgttaat gtgtcatgca tgcagatgga aggggtggaa ctgtgcacta aagtgggggc 5220
tttaactgta gtatttggca gagttgcctt ctacctgcca gttcaaaagt tcaacctgtt 5280
ttcatataga atatatatac taaaaaattt cagtctgtta aacagcctta ctctgattca 5340
gcctcttcag atactcttgt gctgtgcagc agtggctctg tgtgtaaatg ctatgcactg 5400
aggatacaca aaaataccaa tatgatgtgt acaggataat gcctcatccc aatcagatgt 5460
ccatttgtta ttgtgtttgt taacaaccct ttatctctta gtgttataaa ctccacttaa 5520
aactgattaa agtctcattc ttgtcaaaaa aaaaaaaaaa aaaaaaaaaa aa 5572

<210> SEQ ID NO 56
<211> LENGTH: 2609
<212> TYPE: DNA
<213> ORGANISM: Homo sapiens

<400> SEQUENCE: 56
acattggccg gcgccggcct ccgcccccgc ctctccgcca atcaccgccc gcctgctccc 60
ctcgccgtgg gtccccgcga ggccgccacc ccggggtcgc cgtctccgcc tcgccgcagt 120
cggggcagcc gctcgcccct cttttccatg tatccgtcca ggatcccatg acagattctg 180
ttgtcacgtc tccttacaga gtttgagcgg tgctgaactg tcagcaccat ctgtccggtc 240
ccagcatgcc ttctgagacc ccccaggcag aagtggggcc cacaggctgc ccccaccgct 300
cagggccaca ctcggcgaag gggagcctgg agaaggggtc cccagaggat aaggaagcca 360
aggagcccct gtggatccgg cccgatgctc cgagcaggtg cacctggcag ctgggccggc 420
ctgcctccga gtccccacat caccacactg ccccggcaaa atctccaaaa atcttgccag 480
atattctgaa gaaaatcggg gacaccccta tggtcagaat caacaagatt gggaagaagt 540
tcggcctgaa gtgtgagctc ttggccaagt gtgagttctt caacgcgggc gggagcgtga 600
aggaccgcat cagcctgcgg atgattgagg atgctgagcg cgacgggacg ctgaagcccg 660
gggacacgat tatcgagccg acatccggga acaccgggat cggcctggcc ctggctgcgg 720
cagtgagggg ctatcgctgc atcatcgtga tgccagagaa gatgagctcc gagaaggtgg 780
acgtgctgcg ggcactgggg gctgagattg tgaggacgcc caccaatgcc aggttcgact 840
ccccggagtc acacgtgggg gtggcctggc ggctgaagaa cgaaatcccc aattctcaca 900
tcctagacca gtaccgcaac gccagcaacc ccctggctca ctacgacacc accgctgatg 960
agatcctgca gcagtgtgat gggaagctgg acatgctggt ggcttcagtg ggcacgggcg 1020
gcaccatcac gggcattgcc aggaagctga aggagaagtg tcctggatgc aggatcattg 1080 ggtggatcc cgaagggtcc atcctcgcag agccggagga gctgaaccag acggagcaga 1140
caacctacga ggtggaaggg atcggctacg acttcatccc cacggtgctg gacaggacgg 1200
tggtggacaa gtggttcaag agcaacgatg aggaggcgtt cacctttgcc cgcatgctga 1260
tcgcgcaaga ggggctgctg tgcggtggca gtgctggcag cacggtggcg gtggccgtga 1320
aggccgcgca ggagctgcag gagggccagc gctgcgtggt cattctgccc gactcagtgc 1380
ggaactacat gaccaagttc ctgagcgaca ggtggatgct gcagaagggc tttctgaagg 1440
aggaggacct cacggagaag aagccctggt ggtggcacct ccgtgttcag gagctgggcc 1500
tgtcagcccc gctgaccgtg ctcccgacca tcacctgtgg gcacaccatc gagatcctcc 1560
gggagaaggg cttcgaccag gcgcccgtgg tggatgaggc gggggtaatc ctgggaatgg 1620
tgacgcttgg gaacatgctc tcgtccctgc ttgccgggaa ggtgcagccg tcagaccaag 1680
ttggcaaagt catctacaag cagttcaaac agatccgcct cacggacacg ctgggcaggc 1740
tctcgcacat cctggagatg gaccacttcg ccctggtggt gcacgagcag atccagtacc 1800
acagcaccgg gaagtccagt cagcggcaga tggtgttcgg ggtggtcacc gccattgact 1860
tgctgaactt cgtggccgcc caggagcggg accagaagtg aagtccggag cgctgggcgg 1920
tgcggagcgg gcccgccacc cttgcccact tctccttcgc tttcctgagc cctaaacaca 1980
cgcgtgattg gtaactgcct ggcctggcac cgttatccct gcacacggca cagagcatcc 2040
gtctcccctc gttaacacat ggcttcctaa atggccctgt ttacggccta tgagatgaaa 2100
tatgtgattt tctctaatgt aacttcctct taggatgttt caccaaggaa atattgagag 2160
agaagtcggc caggtaggat gaacacaggc aatgactgcg cagagtggat taaaggcaaa 2220
agagagaaga gtccaggaag gggcggggag aagcctgggt ggctcagcat cctccacggg 2280
ctgcgccgtc tgctcggggc tgagctggcg ggagcagttt gcgtgtttgg gttttttaat 2340
tgagatgaaa ttcaaataac ctaaaaatca atcacttgaa agtgaacaat cagcggcatt 2400
tagtacatcc agaaagttgt gtaggcacca cctctgtcac gttctggaac attctgtcat 2460
caccccgtga agcaatcatt tcccctcccg tcttcctcct cccctggcaa ctgctgatcg 2520
actttgtgtc tctgttgtct aaaataggtt ttccctgttc tggacatttc atataaatgg 2580
aatcacacaa aaaaaaaaaa aaaaaaaaa 2609

<210> SEQ ID NO 57
<211> LENGTH: 8413
<212> TYPE: DNA
<213> ORGANISM: Homo sapiens

<400> SEQUENCE: 57
tttccagatt ggggctcggg ccgcgcctcc tccgggaccc tccccttgga ccgagccgat 60
cgccgcgggg cagttcgggc cggctgtcct ggcgcgaaaa ggtggacaag tcctattttc 120
aagagaagat gacttttaac agttttgaag gatctaaaac ttgtgtacct gcagacatca 180
ataaggaaga agaatttgta gaagagttta atagattaaa aacttttgct aattttccaa 240
gtggtagtcc tgtttcagca tcaacactgg cacgagcagg gtttctttat actggtgaag 300
gagataccgt gcggtgcttt agttgtcatg cagctgtaga tagatggcaa tatggagact 360
cagcagttgg aagacacagg aaagtatccc caaattgcag atttatcaac ggcttttatc 420
ttgaaaatag tgccacgcag tctacaaatt ctggtatcca gaatggtcag tacaaagttg 480
aaaactatct gggaagcaga gatcattttg ccttagacag gccatctgag acacatgcag 540
actatctttt gagaactggg caggttgtag atatatcaga caccatatac ccgaggaacc 600
ctgccatgta tagtgaagaa gctagattaa agtcctttca gaactggcca gactatgctc 660
acctaacccc aagagagtta gcaagtgctg gactctacta cacaggtatt ggtgaccaag 720
tgcagtgctt ttgttgtggt ggaaaactga aaaattggga accttgtgat cgtgcctggt 780
cagaacacag gcgacacttt cctaattgct tctttgtttt gggccggaat cttaatattc 840
gaagtgaatc tgatgctgtg agttctgata ggaatttccc aaattcaaca aatcttccaa 900
gaaatccatc catggcagat tatgaagcac ggatctttac ttttgggaca tggatatact 960
cagttaacaa ggagcagctt gcaagagctg gattttatgc tttaggtgaa ggtgataaag 1020
taaagtgctt tcactgtgga ggagggctaa ctgattggaa gcccagtgaa gacccttggg 1080
aacaacatgc taaatggtat ccagggtgca aatatctgtt agaacagaag ggacaagaat 1140
atataaacaa tattcattta actcattcac ttgaggagtg tctggtaaga actactgaga 1200
aaacaccatc actaactaga agaattgatg ataccatctt ccaaaatcct atggtacaag 1260
aagctatacg aatggggttc agtttcaagg acattaagaa aataatggag gaaaaaattc 1320
agatatctgg gagcaactat aaatcacttg aggttctggt tgcagatcta gtgaatgctc 1380

-continued

```
agaaagacag tatgcaagat gagtcaagtc agacttcatt acagaaagag attagtactg   1440
aagagcagct aaggcgcctg caagaggaga agctttgcaa aatctgtatg gatagaaata   1500
ttgctatcgt tttgttcct tgtggacatc tagtcacttg taaacaatgt gctgaagcag   1560
ttgacaagtg tcccatgtgc tacacagtca ttactttcaa gcaaaaaatt tttatgtctt   1620
aatctaactc tatagtaggc atgttatgtt gttcttatta ccctgattga atgtgtgatg   1680
tgaactgact ttaagtaatc aggattgaat tccattagca tttgctacca agtaggaaaa   1740
aaaatgtaca tggcagtgtt ttagttggca atataatctt tgaatttctt gatttttcag   1800
ggtattagct gtattatcca ttttttttac tgttatttaa ttgaaaccat agactaagaa   1860
taagaagcat catactataa ctgaacacaa tgtgtattca tagtatactg atttaatttc   1920
taagtgtaag tgaattaatc atctggattt tttattcttt tcagataggc ttaacaaatg   1980
gagctttctg tatataaatg tggagattag agttaatctc cccaatcaca taatttgttt   2040
tgtgtgaaaa aggaataaat tgttccatgc tggtggaaag atagagattg tttttagagg   2100
ttggttgttg tgttttagga ttctgtccat ttcttttaa agttataaac acgtacttgt   2160
gcgaattatt tttttaaagt gatttgccat ttttgaaagc gtatttaatg atagaatact   2220
atcgagccaa catgtactga catggaaaga tgtcaaagat atgttaagtg taaaatgcaa   2280
gtggcaaaac actatgtata gtctgagcca gatcaaagta tgtatgtttt taatatgcat   2340
agaacaaaag atttggaaag atatacacca aactgttaaa tgtggtttct cttcggggag   2400
ggggggattg ggggaggggc cccagagggg ttttataggg gccttttcac tttctacttt   2460
tttcattttg ttctgttcga attttttata agtatgtatt acttttgtaa tcagaatttt   2520
tagaaagtat tttgctgatt taaaggctta ggcatgttca aacgcctgca aaactactta   2580
tcactcagct ttagttttc taatccaaga aggcagggca gttaaccttt ttggtgccaa   2640
tgtgaaatgt aaatgatttt atgtttttcc tgctttgtgg atgaaaaata tttctgagtg   2700
gtagtttttt gacaggtaga ccatgtctta tcttgtttca aaataagtat ttctgatttt   2760
gtaaaatgaa atataaaata tgtctcagat cttccaatta attagtaagg attcatcctt   2820
aatccttgct agtttaagcc tgcctaagtc actttactaa aagatctttg ttaactcagt   2880
attttaaaca tctgtcagct tatgtaggta aaagtagaag catgtttgta cactgcttgt   2940
agttatagtg acagctttcc atgttgagat tctcatatca tcttgtatct taaagtttca   3000
tgtgagtttt taccgttagg atgattaaga tgtatatagg acaaaatgtt aagtctttcc   3060
tctacctaca tttgttttct tggctagtaa tagtagtaga tacttctgaa ataaatgttc   3120
tctcaagatc cttaaaacct cttggaaatt ataaaaatat tggcaagaaa agaagaatag   3180
ttgtttaaat atttttaaa aaacacttga ataagaatca gtagggtata aactagaagt   3240
ttaaaaatgc ttcatagaac gtccagggtt tacattacaa gattctcaca acaaacctat   3300
tgtagaggtg agtaaggcat gttactacag aggaaagttt gagagtaaaa ctgtaaaaaa   3360
ttatattttt gttgtacttt ctaagagaaa gagtattgtt atgttctcct aacttctgtt   3420
gattactact ttaagtgata ttcatttaaa acattgcaaa tttattttat ttatttaatt   3480
ttctttttga gatggagtct tgcttgtcac ccaggctgga gtgcagtgga gtgatctctg   3540
ctcactgcaa cctccgcctt ctgggttcaa gcgattctcg tgcctcagct tcctgagtag   3600
ctggaattac aggcaggtgc caccatgccc gactaatttt tttttatttt tagtagagac   3660
ggggtttcac catgttggcc aggctggtat caaactcctg acctcaagag atccactcgc   3720
cttgccctcc caaagtgctg ggattacagg cttgagccac cacgcccggc taaaacattg   3780
```

-continued

```
caaatttaaa tgagagtttt aaaaattaaa taatgactgc cctgtttctg ttttagtatg   3840
taaatcctca gttcttcacc tttgcactgt ctgccactta gtttggttat atagtcatta   3900
acttgaattt ggtctgtata gtctagactt taaatttaaa gttttctaca aggggagaaa   3960
agtgttaaaa tttttaaaat atgttttcca ggacacttca cttccaagtc aggtaggtag   4020
ttcaatctag ttgttagcca aggactcaag gactgaattg ttttaacata aggcttttcc   4080
tgttctggga gccgcacttc attaaaattc ttctaaaact tgtatgttta gagttaagca   4140
agactttttt tcttcctctc catgagttgt gaaatttaat gcacaacgct gatgtggcta   4200
acaagtttat tttaagaatt gtttagaaat gctgttgctt caggttctta aaatcactca   4260
gcactccaac ttctaatcaa atttttggag acttaacagc atttgtctgt gtttgaacta   4320
taaaaagcac cggatctttt ccatctaatt ccgcaaaaat tgatcatttg caaagtcaaa   4380
actatagcca tatccaaatc ttttccccct cccaagagtt ctcagtgtct acatgtagac   4440
tattcctttt ctgtataaag ttcactctag gatttcaagt caccacttat tttacatttt   4500
agtcatgcaa agattcaagt agttttgcaa taagtactta tctttatttg taataattta   4560
gtctgctgat caaaagcatt gtcttaattt ttgagaactg gttttagcat ttacaaacta   4620
aattccagtt aattaattaa tagctttata ttgcctttcc tgctacattt ggtttttttcc  4680
cctgtccctt tgattacggg ctaaggtagg gtagagtggg tgtagtgagt gtatataatg   4740
tgatttggcc ctgtgtatta tgatattttg ttattttttgt tgttatatta tttacatttc  4800
agtagttgtt ttttgtgttt ccattttagt ggataaaatt tgtattttga actatgaatg   4860
gagactaccg ccccagcatt agtttcacat gatataccct ttaaacccga atcattgttt   4920
tatttcctga ttacacaggt gttgaatggg gaaaggggct agtatatcag taggatatac   4980
tatgggatgt atatatatca ttgctgttag agaaatgaaa taaaatgggg ctgggctcag   5040
tggctcacgc ctgtaatccc agcactttgg gaggctgagg caggtggatc acgaggtcag   5100
gagatcgaga ccatcctggc taacacggtg aaaccccgtc tctactaaaa aacagaaaat   5160
tagccgggcg tggtggcggg cgcctgtagt cccagctact cgggaggctg aggcaggaga   5220
atggtgtgaa cccgggaggc agagcttgca gtgagccgag atctcgccac tgcactccag   5280
cctgggcaac agagcaagac tctgtctcaa aaaaaaaaaa aaaagaaata agaaaatggg   5340
aagcaatatt tgacatagtt ctttttagtc aaatctactt gttaaaaaaa gggtagcagt   5400
ttattcatct gtgaaaggaa aataatactt atcttacaag gttgcaagag ctcaaggaga   5460
ccatgtatgt aaagttcctg ctgtaaatat gaactcccat cctaataccc ttttacctct   5520
ctgtgggttt gtcttgacct ggaaatttgg gctaaaactt agaaaaaatt cttacatgat   5580
aactcagtga tgcttactca tagtttttgg tgtttctcat agataagata taaatcagct   5640
gggcgcggtg gctcatgcct gtaatcccag cactttggga ggccgaggcg ggcagatcac   5700
ctgaggtcgg gaggtcgaga ccagcctgac caacatggag aaaccccgtc tctactaaaa   5760
atacaaaatt agctgggcgt ggtggctcat gcctgtaatc ccagctactt gggaggctga   5820
ggcaggagaa tcgcttgaac ccaggaggcg gaggttgtgg tgagcgaaga tcgtgccatt   5880
gcactccagc ctgggcaaca agagcaaaac tctgtctcaa aaaaaaaaaa agatataaat   5940
cacaataaat aaataggtca atacaaatgt tagccaggcg tggtggcaca tgcccatagt   6000
cgcagctact ctggaggcag aggcaggagg atcacttgag cccatgaatt tgaggcagca   6060
gtgagctatg attgtgccac tgtactccag tctgggtgac agagtgagac cccatctcta   6120
```

-continued

```
aataaatagg tcaaaccctt aaaaatattt aaattcttaa aaaattgaaa agattattct   6180
tctcaaattt agttgagctt tctaagagaa gcaattggct ttttcccact tcaataatca   6240
ttttcagttt gactcataca gttaacacaa tgtgaatttc ttcctcagca taacagagtt   6300
atagaatgac agggctggaa gtgaccttag agagtatcca gttctttcat tttacaggtg   6360
aggcaactga gactcaaagg tgatgtaatt tgtgcaaaga ttatagctaa ttagtagcag   6420
agccctgact gggacatagt ttgaaggtga aaaacttcac caagctacct ttcttgaaag   6480
gtccaaatgt ttatgttttc aactactctt tccactgtac cataactttc actacatatt   6540
aaatgacact ttataactaa tataatagga caatcatcaa tgcatatata gccagccctt   6600
catatctgtg ggttttgcat ccatggattc aaccaaggag gaattgaaaa cactgagaaa   6660
aaaaaaaaag accacacaat aaaaaaaaaa aatacaaaat aatacaaaga aaaagccaaa   6720
attgtcatac tgttgttaag caacagtata acaactattt acatagcatt aaggttggtg   6780
caaaaatgca aaaaaaaaaa aagcaattat ttttaaacca acctaatata ttgtattagg   6840
tattaaagtc atctggacat gaattaaagt atatgatgcc agcctggaca aaaggcaaaa   6900
ccctgtctct acaaaaaata caaaaattag ctgggcatgg tggtgtgtgc ctgtagtcct   6960
ggctactccg gagcctgagg tgggaggatc gcttgagtct gggaggcaga ggctgcattg   7020
agctatgatc atggcactgc attccagcct gggtgacagt gcaagacctt gtctcagaat   7080
aaataaagta tgtgatgaag atgtgcatac attatatgca aatactgttt tttttttttt   7140
taatttaaac agtctcactg tgttgcccag gatggagtgc aatggcacaa tcttggctca   7200
tggcaaactc tgcctcgcaa gcagctggga ctacaggcat gctccacggt gcccagttaa   7260
tttttttgt attcttagta gagacagggt ttcaccatgt tggccaggct agtcttgaat   7320
ttctgacctc aagtgattca tctcccaaag tgctgggatt acaggcgtga gccaccacgg   7380
ccggctaatt tttgtatttt ttagtagtga ctggtttcgc ggtgttgacc aggctggtct   7440
cgaactcctg atctcaggtg atctgcctgc ctcggcctca caaagtgctg ggattacagg   7500
tgtgaaccac tgctcccggc cttgtgtgat tttatctaag ggacttaagc gtcctcaggt   7560
cctagggggt cgtgaaacca aaaccccagg gatagcaagg gacaattgta tcttcaaagt   7620
agacaaatgg cgccgggcac ggtggctcac gcctgtaatc ccagcagttt ccgaggctga   7680
ggcaggcggc tcacctgagg tcaggagttg gagaccagcc tggccaacat gctgaaaccc   7740
tgtctgtaca aaaatacaaa aatagctggg catggtggcg catgcctgta gtcccagcta   7800
ctagagcgac tgaggcagga gaattgcttg aacctgggag gcggaggttg cagggagcca   7860
agatggcgcc accgcactcc agcctaggtg atagagtgag actccctctc aaaaacaaaa   7920
caaaacaaaa aaattagaca aatgctacat taatgtttgg gtggtcagat tctactttga   7980
atctgaagtt tgcagatatg cctatagatt tttggagttt accactttct tattctgtat   8040
cattaatgta atattttaaa ttactatata tgttaccatt tttctggatt tagtaagaaa   8100
tttgcagttt tggtttgatg taacaagggt tttaatgtaa tttatgttag attttgcatt   8160
tttttcatta ctgttatatt ttaacctgac tgactgatct aattgtatta gtattgtgaa   8220
taatcatgtg aaatgttttg agacagagta ctatatttgt gaatataatt ttatggtttt   8280
tttcacttag aacctttctg tgtggaaaac taagaaaatt gctttctgct gtataatctg   8340
gcattcattg tagattaaag cttatttttc tgtgaataaa acgtattcaa taaaatacta   8400
ttctttaaaa tta                                                       8413
```

<210> SEQ ID NO 58
<211> LENGTH: 21
<212> TYPE: DNA
<213> ORGANISM: Artificial Sequence
<220> FEATURE:
<223> OTHER INFORMATION: forward primer

<400> SEQUENCE: 58
aatgtgcacc ctagccaaga a 21

<210> SEQ ID NO 59
<211> LENGTH: 20
<212> TYPE: DNA
<213> ORGANISM: Artificial Sequence
<220> FEATURE:
<223> OTHER INFORMATION: reverse primer

<400> SEQUENCE: 59
tgctcgctgg gtaggagagt 20

<210> SEQ ID NO 60
<211> LENGTH: 21
<212> TYPE: DNA
<213> ORGANISM: Artificial Sequence
<220> FEATURE:
<223> OTHER INFORMATION: probe

<400> SEQUENCE: 60
agaagccctc tccgggcacc g 21

<210> SEQ ID NO 61
<211> LENGTH: 18
<212> TYPE: DNA
<213> ORGANISM: Artificial Sequence
<220> FEATURE:
<223> OTHER INFORMATION: forward primer

<400> SEQUENCE: 61
cggcagaagc cgagttca 18

<210> SEQ ID NO 62
<211> LENGTH: 23
<212> TYPE: DNA
<213> ORGANISM: Artificial Sequence
<220> FEATURE:
<223> OTHER INFORMATION: reverse primer

<400> SEQUENCE: 62
gcttgtgttg ggtggatatt gtt 23

<210> SEQ ID NO 63
<211> LENGTH: 25
<212> TYPE: DNA
<213> ORGANISM: Artificial Sequence
<220> FEATURE:
<223> OTHER INFORMATION: probe

<400> SEQUENCE: 63
catcctcctg gccaccgact cctac 25

<210> SEQ ID NO 64
<211> LENGTH: 19
<212> TYPE: DNA
<213> ORGANISM: Artificial Sequence
<220> FEATURE:
<223> OTHER INFORMATION: forward primer

<400> SEQUENCE: 64
gccagagagc caggagcat 19

<210> SEQ ID NO 65
<211> LENGTH: 26
<212> TYPE: DNA
<213> ORGANISM: Artificial Sequence
<220> FEATURE:
<223> OTHER INFORMATION: reverse primer

<400> SEQUENCE: 65
ggtgtcacac agataaactt ggtctt 26

<210> SEQ ID NO 66
<211> LENGTH: 20
<212> TYPE: DNA
<213> ORGANISM: Artificial Sequence
<220> FEATURE:
<223> OTHER INFORMATION: probe

<400> SEQUENCE: 66
agctgaccca ggcgctgccc 20

<210> SEQ ID NO 67
<211> LENGTH: 24
<212> TYPE: DNA
<213> ORGANISM: Artificial Sequence
<220> FEATURE:
<223> OTHER INFORMATION: forward primer

<400> SEQUENCE: 67
tggtttccaa ggtgtgagta cttg 24

<210> SEQ ID NO 68
<211> LENGTH: 21
<212> TYPE: DNA
<213> ORGANISM: Artificial Sequence
<220> FEATURE:
<223> OTHER INFORMATION: reverse primer

<400> SEQUENCE: 68
gggctgtctg atgtggatag c 21

<210> SEQ ID NO 69
<211> LENGTH: 30
<212> TYPE: DNA
<213> ORGANISM: Artificial Sequence
<220> FEATURE:
<223> OTHER INFORMATION: probe

<400> SEQUENCE: 69
tcatccgtca agttcaagcc agttaccctc 30

<210> SEQ ID NO 70
<211> LENGTH: 20
<212> TYPE: DNA
<213> ORGANISM: Artificial Sequence
<220> FEATURE:
<223> OTHER INFORMATION: forward primer

<400> SEQUENCE: 70
caagcctacc gtcccacaga 20

<210> SEQ ID NO 71
<211> LENGTH: 25

<212> TYPE: DNA
<213> ORGANISM: Artificial Sequence
<220> FEATURE:
<223> OTHER INFORMATION: reverse primer

<400> SEQUENCE: 71
ccagtaactg tctctcttgc aaatg 25

<210> SEQ ID NO 72
<211> LENGTH: 30
<212> TYPE: DNA
<213> ORGANISM: Artificial Sequence
<220> FEATURE:
<223> OTHER INFORMATION: probe

<400> SEQUENCE: 72
cccaaaaatc gaaacagagg aaacgaacag 30

<210> SEQ ID NO 73
<211> LENGTH: 24
<212> TYPE: DNA
<213> ORGANISM: Artificial Sequence
<220> FEATURE:
<223> OTHER INFORMATION: forward primer

<400> SEQUENCE: 73
ggttgtctga agtcactgca cagt 24

<210> SEQ ID NO 74
<211> LENGTH: 25
<212> TYPE: DNA
<213> ORGANISM: Artificial Sequence
<220> FEATURE:
<223> OTHER INFORMATION: reverse primer

<400> SEQUENCE: 74
ctcggtaggg acatgctaag tagag 25

<210> SEQ ID NO 75
<211> LENGTH: 28
<212> TYPE: DNA
<213> ORGANISM: Artificial Sequence
<220> FEATURE:
<223> OTHER INFORMATION: probe

<400> SEQUENCE: 75
catctcagcc cacatagtga tggttccc 28

<210> SEQ ID NO 76
<211> LENGTH: 17
<212> TYPE: DNA
<213> ORGANISM: Artificial Sequence
<220> FEATURE:
<223> OTHER INFORMATION: forward primer

<400> SEQUENCE: 76
tgcctccggg actgaca 17

<210> SEQ ID NO 77
<211> LENGTH: 23
<212> TYPE: DNA
<213> ORGANISM: Artificial Sequence
<220> FEATURE:
<223> OTHER INFORMATION: reverse primer

<400> SEQUENCE: 77
tgaccctgac tttcacattg atg 23

<210> SEQ ID NO 78
<211> LENGTH: 26
<212> TYPE: DNA
<213> ORGANISM: Artificial Sequence
<220> FEATURE:
<223> OTHER INFORMATION: probe

<400> SEQUENCE: 78
tgccttctct cccctgtcat ttccag 26

<210> SEQ ID NO 79
<211> LENGTH: 18
<212> TYPE: DNA
<213> ORGANISM: Artificial Sequence
<220> FEATURE:
<223> OTHER INFORMATION: forward primer

<400> SEQUENCE: 79
cggacaaggc ccgttatg 18

<210> SEQ ID NO 80
<211> LENGTH: 20
<212> TYPE: DNA
<213> ORGANISM: Artificial Sequence
<220> FEATURE:
<223> OTHER INFORMATION: reverse primer

<400> SEQUENCE: 80
agaggaagaa ggccgaagga 20

<210> SEQ ID NO 81
<211> LENGTH: 29
<212> TYPE: DNA
<213> ORGANISM: Artificial Sequence
<220> FEATURE:
<223> OTHER INFORMATION: probe

<400> SEQUENCE: 81
aaaagaagtt caaggatccc aatgcaccc 29

<210> SEQ ID NO 82
<211> LENGTH: 23
<212> TYPE: DNA
<213> ORGANISM: Artificial Sequence
<220> FEATURE:
<223> OTHER INFORMATION: forward primer

<400> SEQUENCE: 82
aaaaacctcc acgaacacaa aaa 23

<210> SEQ ID NO 83
<211> LENGTH: 25
<212> TYPE: DNA
<213> ORGANISM: Artificial Sequence
<220> FEATURE:
<223> OTHER INFORMATION: reverse primer

<400> SEQUENCE: 83
tgcttggtct aaaagtgtga caatc 25

<210> SEQ ID NO 84
<211> LENGTH: 26
<212> TYPE: DNA
<213> ORGANISM: Artificial Sequence
<220> FEATURE:
<223> OTHER INFORMATION: probe

<400> SEQUENCE: 84
tcagagttgc cacccacacc tcttca 26

<210> SEQ ID NO 85
<211> LENGTH: 20
<212> TYPE: DNA
<213> ORGANISM: Artificial Sequence
<220> FEATURE:
<223> OTHER INFORMATION: forward primer

<400> SEQUENCE: 85
cggaagacga aggcaattca 20

<210> SEQ ID NO 86
<211> LENGTH: 18
<212> TYPE: DNA
<213> ORGANISM: Artificial Sequence
<220> FEATURE:
<223> OTHER INFORMATION: reverse primer

<400> SEQUENCE: 86
gccgacttgg gcaccttt 18

<210> SEQ ID NO 87
<211> LENGTH: 23
<212> TYPE: DNA
<213> ORGANISM: Artificial Sequence
<220> FEATURE:
<223> OTHER INFORMATION: probe

<400> SEQUENCE: 87
ccagaaactg cggaactcgg cca 23

<210> SEQ ID NO 88
<211> LENGTH: 18
<212> TYPE: DNA
<213> ORGANISM: Artificial Sequence
<220> FEATURE:
<223> OTHER INFORMATION: forward primer

<400> SEQUENCE: 88
gccccgcccc tagtctta 18

<210> SEQ ID NO 89
<211> LENGTH: 18
<212> TYPE: DNA
<213> ORGANISM: Artificial Sequence
<220> FEATURE:
<223> OTHER INFORMATION: reverse primer

<400> SEQUENCE: 89
accgaccaca gccttgca 18

<210> SEQ ID NO 90
<211> LENGTH: 22
<212> TYPE: DNA
<213> ORGANISM: Artificial Sequence
<220> FEATURE:
<223> OTHER INFORMATION: probe

<400> SEQUENCE: 90
ctcgcactga agcgccgatt cc 22

<210> SEQ ID NO 91
<211> LENGTH: 22
<212> TYPE: DNA
<213> ORGANISM: Artificial Sequence
<220> FEATURE:
<223> OTHER INFORMATION: forward primer

<400> SEQUENCE: 91
ccgagtccgt gtctaccaga tt 22

<210> SEQ ID NO 92
<211> LENGTH: 21
<212> TYPE: DNA
<213> ORGANISM: Artificial Sequence
<220> FEATURE:
<223> OTHER INFORMATION: reverse primer

<400> SEQUENCE: 92
cacatgtccc caccttattg g 21

<210> SEQ ID NO 93
<211> LENGTH: 26
<212> TYPE: DNA
<213> ORGANISM: Artificial Sequence
<220> FEATURE:
<223> OTHER INFORMATION: probe

<400> SEQUENCE: 93
tctgcctctg aactcacggc tggtgt 26

<210> SEQ ID NO 94
<211> LENGTH: 22
<212> TYPE: DNA
<213> ORGANISM: Artificial Sequence
<220> FEATURE:
<223> OTHER INFORMATION: forward primer

<400> SEQUENCE: 94
tctgcctgaa ctggtacatg ct 22

<210> SEQ ID NO 95
<211> LENGTH: 25
<212> TYPE: DNA
<213> ORGANISM: Artificial Sequence
<220> FEATURE:
<223> OTHER INFORMATION: reverse primer

<400> SEQUENCE: 95
tggattgata ccactaccaa aaaca 25

<210> SEQ ID NO 96
<211> LENGTH: 28
<212> TYPE: DNA
<213> ORGANISM: Artificial Sequence
<220> FEATURE:
<223> OTHER INFORMATION: probe

<400> SEQUENCE: 96
tggtcctcct ggcacattat catgcttt 28

<210> SEQ ID NO 97
<211> LENGTH: 23
<212> TYPE: DNA
<213> ORGANISM: Artificial Sequence
<220> FEATURE:
<223> OTHER INFORMATION: forward primer

<400> SEQUENCE: 97
aacgactgct actccaagct caa 23

<210> SEQ ID NO 98
<211> LENGTH: 22
<212> TYPE: DNA
<213> ORGANISM: Artificial Sequence
<220> FEATURE:
<223> OTHER INFORMATION: reverse primer

<400> SEQUENCE: 98
ggatttccat cttgctcacc tt 22

<210> SEQ ID NO 99
<211> LENGTH: 22
<212> TYPE: DNA
<213> ORGANISM: Artificial Sequence
<220> FEATURE:
<223> OTHER INFORMATION: probe

<400> SEQUENCE: 99
tgcccagcat cccccagaac aa 22

<210> SEQ ID NO 100
<211> LENGTH: 21
<212> TYPE: DNA
<213> ORGANISM: Artificial Sequence
<220> FEATURE:
<223> OTHER INFORMATION: forward primer

<400> SEQUENCE: 100
gctgcctttg gtctctggtt t 21

<210> SEQ ID NO 101
<211> LENGTH: 24
<212> TYPE: DNA
<213> ORGANISM: Artificial Sequence
<220> FEATURE:
<223> OTHER INFORMATION: reverse primer

<400> SEQUENCE: 101
agaaatgcaa tgctcagtct agga 24

<210> SEQ ID NO 102
<211> LENGTH: 28
<212> TYPE: DNA
<213> ORGANISM: Artificial Sequence
<220> FEATURE:
<223> OTHER INFORMATION: probe

<400> SEQUENCE: 102
agtcccgtgt ctctcgctat ttctgctg 28

<210> SEQ ID NO 103
<211> LENGTH: 17
<212> TYPE: DNA
<213> ORGANISM: Artificial Sequence
<220> FEATURE:
<223> OTHER INFORMATION: forward primer

<400> SEQUENCE: 103
tgccgggaag agcacaa 17

<210> SEQ ID NO 104

<211> LENGTH: 23
<212> TYPE: DNA
<213> ORGANISM: Artificial Sequence
<220> FEATURE:
<223> OTHER INFORMATION: reverse primer

<400> SEQUENCE: 104
tccatctctc cgaacacttc ttg 23

<210> SEQ ID NO 105
<211> LENGTH: 26
<212> TYPE: DNA
<213> ORGANISM: Artificial Sequence
<220> FEATURE:
<223> OTHER INFORMATION: probe

<400> SEQUENCE: 105
acacccggac tcttccgtca atttcg 26

<210> SEQ ID NO 106
<211> LENGTH: 21
<212> TYPE: DNA
<213> ORGANISM: Artificial Sequence
<220> FEATURE:
<223> OTHER INFORMATION: forward primer

<400> SEQUENCE: 106
gctccacctt cgatgctctc t 21

<210> SEQ ID NO 107
<211> LENGTH: 19
<212> TYPE: DNA
<213> ORGANISM: Artificial Sequence
<220> FEATURE:
<223> OTHER INFORMATION: reverse primer

<400> SEQUENCE: 107
tgctcgactg ctggaagga 19

<210> SEQ ID NO 108
<211> LENGTH: 22
<212> TYPE: DNA
<213> ORGANISM: Artificial Sequence
<220> FEATURE:
<223> OTHER INFORMATION: probe

<400> SEQUENCE: 108
atcacccgcc atcccctcca ac 22

<210> SEQ ID NO 109
<211> LENGTH: 20
<212> TYPE: DNA
<213> ORGANISM: Artificial Sequence
<220> FEATURE:
<223> OTHER INFORMATION: forward primer

<400> SEQUENCE: 109
ccaatttgtc cccacaatgc 20

<210> SEQ ID NO 110
<211> LENGTH: 17
<212> TYPE: DNA
<213> ORGANISM: Artificial Sequence
<220> FEATURE:
<223> OTHER INFORMATION: reverse primer

<400> SEQUENCE: 110
gggcggcgat tctctca 17

<210> SEQ ID NO 111
<211> LENGTH: 21
<212> TYPE: DNA
<213> ORGANISM: Artificial Sequence
<220> FEATURE:
<223> OTHER INFORMATION: probe

<400> SEQUENCE: 111
cctcctgcac gcaatggtgg c 21

<210> SEQ ID NO 112
<211> LENGTH: 21
<212> TYPE: DNA
<213> ORGANISM: Artificial Sequence
<220> FEATURE:
<223> OTHER INFORMATION: forward primer

<400> SEQUENCE: 112
cgttgttgca tgctctttgt g 21

<210> SEQ ID NO 113
<211> LENGTH: 24
<212> TYPE: DNA
<213> ORGANISM: Artificial Sequence
<220> FEATURE:
<223> OTHER INFORMATION: reverse primer

<400> SEQUENCE: 113
ccagcaaaaa cttaatctgc ttca 24

<210> SEQ ID NO 114
<211> LENGTH: 23
<212> TYPE: DNA
<213> ORGANISM: Artificial Sequence
<220> FEATURE:
<223> OTHER INFORMATION: probe

<400> SEQUENCE: 114
ccaagggaga cgccagagca tcc 23

<210> SEQ ID NO 115
<211> LENGTH: 16
<212> TYPE: DNA
<213> ORGANISM: Artificial Sequence
<220> FEATURE:
<223> OTHER INFORMATION: forward primer

<400> SEQUENCE: 115
gacccggcca cgaaca 16

<210> SEQ ID NO 116
<211> LENGTH: 19
<212> TYPE: DNA
<213> ORGANISM: Artificial Sequence
<220> FEATURE:
<223> OTHER INFORMATION: reverse primer

<400> SEQUENCE: 116
gtcgagctgg gcagacaga 19

<210> SEQ ID NO 117
<211> LENGTH: 29
<212> TYPE: DNA

<213> ORGANISM: Artificial Sequence
<220> FEATURE:
<223> OTHER INFORMATION: probe

<400> SEQUENCE: 117
tttcatacaa gacgtgggcc tgtaccctg 29

<210> SEQ ID NO 118
<211> LENGTH: 19
<212> TYPE: DNA
<213> ORGANISM: Artificial Sequence
<220> FEATURE:
<223> OTHER INFORMATION: forward primer

<400> SEQUENCE: 118
gatggcactc agcgaatgc 19

<210> SEQ ID NO 119
<211> LENGTH: 20
<212> TYPE: DNA
<213> ORGANISM: Artificial Sequence
<220> FEATURE:
<223> OTHER INFORMATION: reverse primer

<400> SEQUENCE: 119
atgcgcacat ctccattgac 20

<210> SEQ ID NO 120
<211> LENGTH: 22
<212> TYPE: DNA
<213> ORGANISM: Artificial Sequence
<220> FEATURE:
<223> OTHER INFORMATION: probe

<400> SEQUENCE: 120
ctccctgcag aagcgtcccg ac 22

<210> SEQ ID NO 121
<211> LENGTH: 21
<212> TYPE: DNA
<213> ORGANISM: Artificial Sequence
<220> FEATURE:
<223> OTHER INFORMATION: forward primer

<400> SEQUENCE: 121
tcctgggtgc attcagtctc t 21

<210> SEQ ID NO 122
<211> LENGTH: 22
<212> TYPE: DNA
<213> ORGANISM: Artificial Sequence
<220> FEATURE:
<223> OTHER INFORMATION: reverse primer

<400> SEQUENCE: 122
ggagctgcac agcctttaaa gt 22

<210> SEQ ID NO 123
<211> LENGTH: 22
<212> TYPE: DNA
<213> ORGANISM: Artificial Sequence
<220> FEATURE:
<223> OTHER INFORMATION: probe

<400> SEQUENCE: 123
tgcctctgcc tgcctcctgg tc 22

<210> SEQ ID NO 124
<211> LENGTH: 21
<212> TYPE: DNA
<213> ORGANISM: Artificial Sequence
<220> FEATURE:
<223> OTHER INFORMATION: forward primer

<400> SEQUENCE: 124
tcccagtatg atggccagtc a 21

<210> SEQ ID NO 125
<211> LENGTH: 22
<212> TYPE: DNA
<213> ORGANISM: Artificial Sequence
<220> FEATURE:
<223> OTHER INFORMATION: reverse primer

<400> SEQUENCE: 125
ataaggccag ccaaaactca ag 22

<210> SEQ ID NO 126
<211> LENGTH: 25
<212> TYPE: DNA
<213> ORGANISM: Artificial Sequence
<220> FEATURE:
<223> OTHER INFORMATION: probe

<400> SEQUENCE: 126
atgctgctct tcccgtccac aagtg 25

<210> SEQ ID NO 127
<211> LENGTH: 23
<212> TYPE: DNA
<213> ORGANISM: Artificial Sequence
<220> FEATURE:
<223> OTHER INFORMATION: forward primer

<400> SEQUENCE: 127
aaatctgaaa gcggctgata ctg 23

<210> SEQ ID NO 128
<211> LENGTH: 20
<212> TYPE: DNA
<213> ORGANISM: Artificial Sequence
<220> FEATURE:
<223> OTHER INFORMATION: reverse primer

<400> SEQUENCE: 128
cggaaccgct tccttcatag 20

<210> SEQ ID NO 129
<211> LENGTH: 21
<212> TYPE: DNA
<213> ORGANISM: Artificial Sequence
<220> FEATURE:
<223> OTHER INFORMATION: probe

<400> SEQUENCE: 129
ccccacagcc ccgccttatg a 21

<210> SEQ ID NO 130
<211> LENGTH: 22
<212> TYPE: DNA
<213> ORGANISM: Artificial Sequence
<220> FEATURE:

<223> OTHER INFORMATION: forward primer

<400> SEQUENCE: 130
gagatccagc ttgcctcctc tt 22

<210> SEQ ID NO 131
<211> LENGTH: 26
<212> TYPE: DNA
<213> ORGANISM: Artificial Sequence
<220> FEATURE:
<223> OTHER INFORMATION: reverse primer

<400> SEQUENCE: 131
cggttttact tcttctcagt cctgta 26

<210> SEQ ID NO 132
<211> LENGTH: 24
<212> TYPE: DNA
<213> ORGANISM: Artificial Sequence
<220> FEATURE:
<223> OTHER INFORMATION: probe

<400> SEQUENCE: 132
agcaacaggg tcccgtcctt gaca 24

<210> SEQ ID NO 133
<211> LENGTH: 20
<212> TYPE: DNA
<213> ORGANISM: Artificial Sequence
<220> FEATURE:
<223> OTHER INFORMATION: forward primer

<400> SEQUENCE: 133
cagtggaggc cgacttcttg 20

<210> SEQ ID NO 134
<211> LENGTH: 21
<212> TYPE: DNA
<213> ORGANISM: Artificial Sequence
<220> FEATURE:
<223> OTHER INFORMATION: reverse primer

<400> SEQUENCE: 134
atgaaccagg agccatcctt t 21

<210> SEQ ID NO 135
<211> LENGTH: 29
<212> TYPE: DNA
<213> ORGANISM: Artificial Sequence
<220> FEATURE:
<223> OTHER INFORMATION: probe

<400> SEQUENCE: 135
tccacagcac ctggttatta ttcttggcg 29

<210> SEQ ID NO 136
<211> LENGTH: 22
<212> TYPE: DNA
<213> ORGANISM: Artificial Sequence
<220> FEATURE:
<223> OTHER INFORMATION: forward primer

<400> SEQUENCE: 136
gatggtgtct ctcgcagatt ca 22

<210> SEQ ID NO 137
<211> LENGTH: 20
<212> TYPE: DNA
<213> ORGANISM: Artificial Sequence
<220> FEATURE:
<223> OTHER INFORMATION: reverse primer

<400> SEQUENCE: 137
tcagatgcct ccccaatcag 20

<210> SEQ ID NO 138
<211> LENGTH: 29
<212> TYPE: DNA
<213> ORGANISM: Artificial Sequence
<220> FEATURE:
<223> OTHER INFORMATION: probe

<400> SEQUENCE: 138
atgtccacag aaagtgccaa cagcttcac 29

<210> SEQ ID NO 139
<211> LENGTH: 19
<212> TYPE: DNA
<213> ORGANISM: Artificial Sequence
<220> FEATURE:
<223> OTHER INFORMATION: forward primer

<400> SEQUENCE: 139
gcacccgcct cagtcaact 19

<210> SEQ ID NO 140
<211> LENGTH: 20
<212> TYPE: DNA
<213> ORGANISM: Artificial Sequence
<220> FEATURE:
<223> OTHER INFORMATION: reverse primer

<400> SEQUENCE: 140
caacatggta ccggcatgaa 20

<210> SEQ ID NO 141
<211> LENGTH: 29
<212> TYPE: DNA
<213> ORGANISM: Artificial Sequence
<220> FEATURE:
<223> OTHER INFORMATION: probe

<400> SEQUENCE: 141
aatgaaaacc cttattttgc ccccaatcc 29

<210> SEQ ID NO 142
<211> LENGTH: 17
<212> TYPE: DNA
<213> ORGANISM: Artificial Sequence
<220> FEATURE:
<223> OTHER INFORMATION: forward primer

<400> SEQUENCE: 142
tccgcgtccc actagca 17

<210> SEQ ID NO 143
<211> LENGTH: 27
<212> TYPE: DNA
<213> ORGANISM: Artificial Sequence
<220> FEATURE:
<223> OTHER INFORMATION: reverse primer

<400> SEQUENCE: 143
agttatccag ctccagagtc tctagac 27

<210> SEQ ID NO 144
<211> LENGTH: 19
<212> TYPE: DNA
<213> ORGANISM: Artificial Sequence
<220> FEATURE:
<223> OTHER INFORMATION: probe

<400> SEQUENCE: 144 cacccctca gcagggccg 19

<210> SEQ ID NO 145
<211> LENGTH: 17
<212> TYPE: DNA
<213> ORGANISM: Artificial Sequence
<220> FEATURE:
<223> OTHER INFORMATION: forward primer

<400> SEQUENCE: 145
gggctcccgt cctgctt 17

<210> SEQ ID NO 146
<211> LENGTH: 22
<212> TYPE: DNA
<213> ORGANISM: Artificial Sequence
<220> FEATURE:
<223> OTHER INFORMATION: reverse primer

<400> SEQUENCE: 146
actcctccct ttcctccaga ac 22

<210> SEQ ID NO 147
<211> LENGTH: 25
<212> TYPE: DNA
<213> ORGANISM: Artificial Sequence
<220> FEATURE:
<223> OTHER INFORMATION: probe

<400> SEQUENCE: 147
tgccatgtaa atccccactg ggacc 25

<210> SEQ ID NO 148
<211> LENGTH: 25
<212> TYPE: DNA
<213> ORGANISM: Artificial Sequence
<220> FEATURE:
<223> OTHER INFORMATION: forward primer

<400> SEQUENCE: 148
gcttactctc acctgcttct gagtt 25

<210> SEQ ID NO 149
<211> LENGTH: 19
<212> TYPE: DNA
<213> ORGANISM: Artificial Sequence
<220> FEATURE:
<223> OTHER INFORMATION: reverse primer

<400> SEQUENCE: 149
tgggctgctt cttccaaca 19

<210> SEQ ID NO 150
<211> LENGTH: 23

<212> TYPE: DNA
<213> ORGANISM: Artificial Sequence
<220> FEATURE:
<223> OTHER INFORMATION: probe

<400> SEQUENCE: 150
agaccactgg cagatgtccc ggc 23

<210> SEQ ID NO 151
<211> LENGTH: 22
<212> TYPE: DNA
<213> ORGANISM: Artificial Sequence
<220> FEATURE:
<223> OTHER INFORMATION: forward primer

<400> SEQUENCE: 151
cgacagcttc gatttgaatg ac 22

<210> SEQ ID NO 152
<211> LENGTH: 17
<212> TYPE: DNA
<213> ORGANISM: Artificial Sequence
<220> FEATURE:
<223> OTHER INFORMATION: reverse primer

<400> SEQUENCE: 152
gggagcgtcg caaagga 17

<210> SEQ ID NO 153
<211> LENGTH: 25
<212> TYPE: DNA
<213> ORGANISM: Artificial Sequence
<220> FEATURE:
<223> OTHER INFORMATION: probe

<400> SEQUENCE: 153
tgtaattgcg tccccctact ccggc 25

<210> SEQ ID NO 154
<211> LENGTH: 24
<212> TYPE: DNA
<213> ORGANISM: Artificial Sequence
<220> FEATURE:
<223> OTHER INFORMATION: forward primer

<400> SEQUENCE: 154
aatcacattc agctggtgaa actg 24

<210> SEQ ID NO 155
<211> LENGTH: 20
<212> TYPE: DNA
<213> ORGANISM: Artificial Sequence
<220> FEATURE:
<223> OTHER INFORMATION: reverse primer

<400> SEQUENCE: 155
tgccagcttg gtttctgctt 20

<210> SEQ ID NO 156
<211> LENGTH: 23
<212> TYPE: DNA
<213> ORGANISM: Artificial Sequence
<220> FEATURE:
<223> OTHER INFORMATION: probe

<400> SEQUENCE: 156
aagaggtgca ccagctctcc cgg 23

<210> SEQ ID NO 157
<211> LENGTH: 24
<212> TYPE: DNA
<213> ORGANISM: Artificial Sequence
<220> FEATURE:
<223> OTHER INFORMATION: forward primer

<400> SEQUENCE: 157
ctggaccacc tgatgaatat ctgt 24

<210> SEQ ID NO 158
<211> LENGTH: 22
<212> TYPE: DNA
<213> ORGANISM: Artificial Sequence
<220> FEATURE:
<223> OTHER INFORMATION: reverse primer

<400> SEQUENCE: 158
caatgctacg aaggtcctga ca 22

<210> SEQ ID NO 159
<211> LENGTH: 20
<212> TYPE: DNA
<213> ORGANISM: Artificial Sequence
<220> FEATURE:
<223> OTHER INFORMATION: probe

<400> SEQUENCE: 159
cagctgcgcc tgctctccga 20

<210> SEQ ID NO 160
<211> LENGTH: 25
<212> TYPE: DNA
<213> ORGANISM: Artificial Sequence
<220> FEATURE:
<223> OTHER INFORMATION: forward primer

<400> SEQUENCE: 160
tgcactcaga tttaagcctt acaaa 25

<210> SEQ ID NO 161
<211> LENGTH: 21
<212> TYPE: DNA
<213> ORGANISM: Artificial Sequence
<220> FEATURE:
<223> OTHER INFORMATION: reverse primer

<400> SEQUENCE: 161
tcaccacgag tgaccttcat g 21

<210> SEQ ID NO 162
<211> LENGTH: 24
<212> TYPE: DNA
<213> ORGANISM: Artificial Sequence
<220> FEATURE:
<223> OTHER INFORMATION: probe

<400> SEQUENCE: 162
aagcctctgg ccgtcacacg tagg 24

<210> SEQ ID NO 163
<211> LENGTH: 21
<212> TYPE: DNA
<213> ORGANISM: Artificial Sequence
<220> FEATURE:
<223> OTHER INFORMATION: forward primer

<400> SEQUENCE: 163
aaccagcaca gcatggtgag t 21

<210> SEQ ID NO 164
<211> LENGTH: 22
<212> TYPE: DNA
<213> ORGANISM: Artificial Sequence
<220> FEATURE:
<223> OTHER INFORMATION: reverse primer

<400> SEQUENCE: 164
cctcgtcttt ctcctgctcg ta 22

<210> SEQ ID NO 165
<211> LENGTH: 19
<212> TYPE: DNA
<213> ORGANISM: Artificial Sequence
<220> FEATURE:
<223> OTHER INFORMATION: probe

<400> SEQUENCE: 165
tccacgccca tcgcggaca 19

<210> SEQ ID NO 166
<211> LENGTH: 19
<212> TYPE: DNA
<213> ORGANISM: Artificial Sequence
<220> FEATURE:
<223> OTHER INFORMATION: forward primer

<400> SEQUENCE: 166
cggatgaatg agcctccaa 19

<210> SEQ ID NO 167
<211> LENGTH: 24
<212> TYPE: DNA
<213> ORGANISM: Artificial Sequence
<220> FEATURE:
<223> OTHER INFORMATION: reverse primer

<400> SEQUENCE: 167
ggacattatc aaaccgtgaa agaa 24

<210> SEQ ID NO 168
<211> LENGTH: 25
<212> TYPE: DNA
<213> ORGANISM: Artificial Sequence
<220> FEATURE:
<223> OTHER INFORMATION: probe

<400> SEQUENCE: 168
tcttgggctt gtgcctcacc agatc 25

<210> SEQ ID NO 169
<211> LENGTH: 22
<212> TYPE: DNA
<213> ORGANISM: Artificial Sequence
<220> FEATURE:
<223> OTHER INFORMATION: forward primer

<400> SEQUENCE: 169
gaggctgtgt ccagtgcagt ag 22

<210> SEQ ID NO 170
<211> LENGTH: 22
<212> TYPE: DNA
<213> ORGANISM: Artificial Sequence
<220> FEATURE:
<223> OTHER INFORMATION: reverse primer

<400> SEQUENCE: 170
ccacttcttg gtacccggtt aa 22

<210> SEQ ID NO 171
<211> LENGTH: 24
<212> TYPE: DNA
<213> ORGANISM: Artificial Sequence
<220> FEATURE:
<223> OTHER INFORMATION: probe

<400> SEQUENCE: 171
cctggcatca ctgtcaccca cctg 24

<210> SEQ ID NO 172
<211> LENGTH: 29
<212> TYPE: DNA
<213> ORGANISM: Artificial Sequence
<220> FEATURE:
<223> OTHER INFORMATION: forward primer

<400> SEQUENCE: 172
tgaagatctc aatgaagtag ccaaactat 29

<210> SEQ ID NO 173
<211> LENGTH: 19
<212> TYPE: DNA
<213> ORGANISM: Artificial Sequence
<220> FEATURE:
<223> OTHER INFORMATION: reverse primer

<400> SEQUENCE: 173
ctgcagtggg tttgccaat 19

<210> SEQ ID NO 174
<211> LENGTH: 28
<212> TYPE: DNA
<213> ORGANISM: Artificial Sequence
<220> FEATURE:
<223> OTHER INFORMATION: probe

<400> SEQUENCE: 174
caacattcat gaagactgaa gccccaca 28

<210> SEQ ID NO 175
<211> LENGTH: 19
<212> TYPE: DNA
<213> ORGANISM: Artificial Sequence
<220> FEATURE:
<223> OTHER INFORMATION: forward primer

<400> SEQUENCE: 175
ttccccccaa ggagttcct 19

<210> SEQ ID NO 176
<211> LENGTH: 19
<212> TYPE: DNA
<213> ORGANISM: Artificial Sequence
<220> FEATURE:
<223> OTHER INFORMATION: reverse primer

<400> SEQUENCE: 176
cgctcgtgtt cctcatgct 19

<210> SEQ ID NO 177
<211> LENGTH: 19
<212> TYPE: DNA
<213> ORGANISM: Artificial Sequence
<220> FEATURE:
<223> OTHER INFORMATION: probe

<400> SEQUENCE: 177
acccgaagcg cacggccac 19

<210> SEQ ID NO 178
<211> LENGTH: 23
<212> TYPE: DNA
<213> ORGANISM: Artificial Sequence
<220> FEATURE:
<223> OTHER INFORMATION: forward primer

<400> SEQUENCE: 178
ccattgaaaa tcaccctcat ctg 23

<210> SEQ ID NO 179
<211> LENGTH: 19
<212> TYPE: DNA
<213> ORGANISM: Artificial Sequence
<220> FEATURE:
<223> OTHER INFORMATION: reverse primer

<400> SEQUENCE: 179
cacctcagca tgcctgcat 19

<210> SEQ ID NO 180
<211> LENGTH: 27
<212> TYPE: DNA
<213> ORGANISM: Artificial Sequence
<220> FEATURE:
<223> OTHER INFORMATION: probe

<400> SEQUENCE: 180
caccacctcc catgtgttca gttcacc 27

<210> SEQ ID NO 181
<211> LENGTH: 22
<212> TYPE: DNA
<213> ORGANISM: Artificial Sequence
<220> FEATURE:
<223> OTHER INFORMATION: forward primer

<400> SEQUENCE: 181
cagccgcctt cattatctcc ta 22

<210> SEQ ID NO 182
<211> LENGTH: 21
<212> TYPE: DNA
<213> ORGANISM: Artificial Sequence
<220> FEATURE:
<223> OTHER INFORMATION: reverse primer

<400> SEQUENCE: 182
tggaggtgtt gttcccgtat c 21

<210> SEQ ID NO 183

<211> LENGTH: 21
<212> TYPE: DNA
<213> ORGANISM: Artificial Sequence
<220> FEATURE:
<223> OTHER INFORMATION: probe

<400> SEQUENCE: 183
tgctctccgg gcacgtcaac c 21

<210> SEQ ID NO 184
<211> LENGTH: 22
<212> TYPE: DNA
<213> ORGANISM: Artificial Sequence
<220> FEATURE:
<223> OTHER INFORMATION: forward primer

<400> SEQUENCE: 184
tttcctccac tgccatcatt aa 22

<210> SEQ ID NO 185
<211> LENGTH: 20
<212> TYPE: DNA
<213> ORGANISM: Artificial Sequence
<220> FEATURE:
<223> OTHER INFORMATION: reverse primer

<400> SEQUENCE: 185
ggccaaaggt ttcagcttca 20

<210> SEQ ID NO 186
<211> LENGTH: 29
<212> TYPE: DNA
<213> ORGANISM: Artificial Sequence
<220> FEATURE:
<223> OTHER INFORMATION: probe

<400> SEQUENCE: 186
cctcagctgt gacatgaaag acttaccgg 29

<210> SEQ ID NO 187
<211> LENGTH: 24
<212> TYPE: DNA
<213> ORGANISM: Artificial Sequence
<220> FEATURE:
<223> OTHER INFORMATION: forward primer

<400> SEQUENCE: 187
ttgaggtgat ctcgcaaagt tatt 24

<210> SEQ ID NO 188
<211> LENGTH: 18
<212> TYPE: DNA
<213> ORGANISM: Artificial Sequence
<220> FEATURE:
<223> OTHER INFORMATION: reverse primer

<400> SEQUENCE: 188
ctcgccacca gggagaaa 18

<210> SEQ ID NO 189
<211> LENGTH: 24
<212> TYPE: DNA
<213> ORGANISM: Artificial Sequence
<220> FEATURE:
<223> OTHER INFORMATION: probe

<400> SEQUENCE: 189
ccaccatggc caacaacgaa ggac 24

<210> SEQ ID NO 190
<211> LENGTH: 23
<212> TYPE: DNA
<213> ORGANISM: Artificial Sequence
<220> FEATURE:
<223> OTHER INFORMATION: forward primer

<400> SEQUENCE: 190
ggcagttgcc taccatctca taa 23

<210> SEQ ID NO 191
<211> LENGTH: 20
<212> TYPE: DNA
<213> ORGANISM: Artificial Sequence
<220> FEATURE:
<223> OTHER INFORMATION: reverse primer

<400> SEQUENCE: 191
gccgagtcag gtgatgatca 20

<210> SEQ ID NO 192
<211> LENGTH: 27
<212> TYPE: DNA
<213> ORGANISM: Artificial Sequence
<220> FEATURE:
<223> OTHER INFORMATION: probe

<400> SEQUENCE: 192
tctatttggc gacaagccca cctgatt 27

<210> SEQ ID NO 193
<211> LENGTH: 25
<212> TYPE: DNA
<213> ORGANISM: Artificial Sequence
<220> FEATURE:
<223> OTHER INFORMATION: forward primer

<400> SEQUENCE: 193
ccttctgatt gatggtgcta ttttg 25

<210> SEQ ID NO 194
<211> LENGTH: 18
<212> TYPE: DNA
<213> ORGANISM: Artificial Sequence
<220> FEATURE:
<223> OTHER INFORMATION: reverse primer

<400> SEQUENCE: 194
gcggtgagcc gagatcac 18

<210> SEQ ID NO 195
<211> LENGTH: 24
<212> TYPE: DNA
<213> ORGANISM: Artificial Sequence
<220> FEATURE:
<223> OTHER INFORMATION: probe

<400> SEQUENCE: 195
cagaatctcg ctctgtcgcc cagg 24

<210> SEQ ID NO 196
<211> LENGTH: 14
<212> TYPE: DNA

```
<213> ORGANISM: Artificial Sequence
<220> FEATURE:
<223> OTHER INFORMATION: forward primer

<400> SEQUENCE: 196

tcgcggccgc atgt                                                    14


<210> SEQ ID NO 197
<211> LENGTH: 23
<212> TYPE: DNA
<213> ORGANISM: Artificial Sequence
<220> FEATURE:
<223> OTHER INFORMATION: reverse primer

<400> SEQUENCE: 197

aagggtccag cactatcaag aga                                          23


<210> SEQ ID NO 198
<211> LENGTH: 22
<212> TYPE: DNA
<213> ORGANISM: Artificial Sequence
<220> FEATURE:
<223> OTHER INFORMATION: probe

<400> SEQUENCE: 198

agcaggtcct gggcgcctca ac                                           22


<210> SEQ ID NO 199
<211> LENGTH: 24
<212> TYPE: DNA
<213> ORGANISM: Artificial Sequence
<220> FEATURE:
<223> OTHER INFORMATION: forward primer

<400> SEQUENCE: 199

gattgccttt gttttgatgt ttgt                                         24


<210> SEQ ID NO 200
<211> LENGTH: 22
<212> TYPE: DNA
<213> ORGANISM: Artificial Sequence
<220> FEATURE:
<223> OTHER INFORMATION: reverse primer

<400> SEQUENCE: 200

ggaaagggaa cccaggttag tg                                           22


<210> SEQ ID NO 201
<211> LENGTH: 29
<212> TYPE: DNA
<213> ORGANISM: Artificial Sequence
<220> FEATURE:
<223> OTHER INFORMATION: probe

<400> SEQUENCE: 201

cagaattgat cattttcccc ccactctcc                                    29


<210> SEQ ID NO 202
<211> LENGTH: 23
<212> TYPE: DNA
<213> ORGANISM: Artificial Sequence
<220> FEATURE:
<223> OTHER INFORMATION: forward primer

<400> SEQUENCE: 202

aatggtgtca atgaagccaa aat                                          23
```

<210> SEQ ID NO 203
<211> LENGTH: 25
<212> TYPE: DNA
<213> ORGANISM: Artificial Sequence
<220> FEATURE:
<223> OTHER INFORMATION: reverse primer

<400> SEQUENCE: 203
gtcatacgct tctttctttc catga 25

<210> SEQ ID NO 204
<211> LENGTH: 30
<212> TYPE: DNA
<213> ORGANISM: Artificial Sequence
<220> FEATURE:
<223> OTHER INFORMATION: probe

<400> SEQUENCE: 204
tgacaatgtc caagacacag cagaacagaa 30

<210> SEQ ID NO 205
<211> LENGTH: 23
<212> TYPE: DNA
<213> ORGANISM: Artificial Sequence
<220> FEATURE:
<223> OTHER INFORMATION: forward primer

<400> SEQUENCE: 205
gcatgatcct gtaggtcaaa tgg 23

<210> SEQ ID NO 206
<211> LENGTH: 22
<212> TYPE: DNA
<213> ORGANISM: Artificial Sequence
<220> FEATURE:
<223> OTHER INFORMATION: reverse primer

<400> SEQUENCE: 206
caggcggtag acaacttgtg aa 22

<210> SEQ ID NO 207
<211> LENGTH: 30
<212> TYPE: DNA
<213> ORGANISM: Artificial Sequence
<220> FEATURE:
<223> OTHER INFORMATION: probe

<400> SEQUENCE: 207
aataacccca aaattcacct ggcacagtca 30

<210> SEQ ID NO 208
<211> LENGTH: 21
<212> TYPE: DNA
<213> ORGANISM: Artificial Sequence
<220> FEATURE:
<223> OTHER INFORMATION: forward primer

<400> SEQUENCE: 208
aggccgcatt gtctctatca a 21

<210> SEQ ID NO 209
<211> LENGTH: 24
<212> TYPE: DNA
<213> ORGANISM: Artificial Sequence
<220> FEATURE:

<223> OTHER INFORMATION: reverse primer

<400> SEQUENCE: 209
gcagtaaatg caggtagtca tcca 24

<210> SEQ ID NO 210
<211> LENGTH: 22
<212> TYPE: DNA
<213> ORGANISM: Artificial Sequence
<220> FEATURE:
<223> OTHER INFORMATION: probe

<400> SEQUENCE: 210
tgcaatccag ctgtttggcg cc 22

<210> SEQ ID NO 211
<211> LENGTH: 21
<212> TYPE: DNA
<213> ORGANISM: Artificial Sequence
<220> FEATURE:
<223> OTHER INFORMATION: forward primer

<400> SEQUENCE: 211
tctcgggtgc atttgagaga a 21

<210> SEQ ID NO 212
<211> LENGTH: 22
<212> TYPE: DNA
<213> ORGANISM: Artificial Sequence
<220> FEATURE:
<223> OTHER INFORMATION: reverse primer

<400> SEQUENCE: 212
acagcacaaa aacgtctttc ca 22

<210> SEQ ID NO 213
<211> LENGTH: 22
<212> TYPE: DNA
<213> ORGANISM: Artificial Sequence
<220> FEATURE:
<223> OTHER INFORMATION: probe

<400> SEQUENCE: 213
ccacgctgtc ctctcgagcc ca 22

<210> SEQ ID NO 214
<211> LENGTH: 23
<212> TYPE: DNA
<213> ORGANISM: Artificial Sequence
<220> FEATURE:
<223> OTHER INFORMATION: forward primer

<400> SEQUENCE: 214
ggttgtcgcc cttttctact ttg 23

<210> SEQ ID NO 215
<211> LENGTH: 18
<212> TYPE: DNA
<213> ORGANISM: Artificial Sequence
<220> FEATURE:
<223> OTHER INFORMATION: reverse primer

<400> SEQUENCE: 215
cagttccggc accttggt 18

<210> SEQ ID NO 216
<211> LENGTH: 24
<212> TYPE: DNA
<213> ORGANISM: Artificial Sequence
<220> FEATURE:
<223> OTHER INFORMATION: probe

<400> SEQUENCE: 216
cagcaaactg gtgctcaagg ccct 24

<210> SEQ ID NO 217
<211> LENGTH: 21
<212> TYPE: DNA
<213> ORGANISM: Artificial Sequence
<220> FEATURE:
<223> OTHER INFORMATION: forward primer

<400> SEQUENCE: 217
catgtgtgtg gagagcgtca a 21

<210> SEQ ID NO 218
<211> LENGTH: 21
<212> TYPE: DNA
<213> ORGANISM: Artificial Sequence
<220> FEATURE:
<223> OTHER INFORMATION: reverse primer

<400> SEQUENCE: 218
gccggttcag gtactcagtc a 21

<210> SEQ ID NO 219
<211> LENGTH: 23
<212> TYPE: DNA
<213> ORGANISM: Artificial Sequence
<220> FEATURE:
<223> OTHER INFORMATION: probe

<400> SEQUENCE: 219
cctggtggac aacatcgccc tgt 23

<210> SEQ ID NO 220
<211> LENGTH: 18
<212> TYPE: DNA
<213> ORGANISM: Artificial Sequence
<220> FEATURE:
<223> OTHER INFORMATION: forward primer

<400> SEQUENCE: 220
tggcggaact tgcaatcc 18

<210> SEQ ID NO 221
<211> LENGTH: 24
<212> TYPE: DNA
<213> ORGANISM: Artificial Sequence
<220> FEATURE:
<223> OTHER INFORMATION: reverse primer

<400> SEQUENCE: 221
gctgagggaa ctcaaagtac atga 24

<210> SEQ ID NO 222
<211> LENGTH: 29
<212> TYPE: DNA
<213> ORGANISM: Artificial Sequence
<220> FEATURE:
<223> OTHER INFORMATION: probe

<400> SEQUENCE: 222
atattcctcc aattcaggac ccacacgac 29

<210> SEQ ID NO 223
<211> LENGTH: 23
<212> TYPE: DNA
<213> ORGANISM: Artificial Sequence
<220> FEATURE:
<223> OTHER INFORMATION: forward primer

<400> SEQUENCE: 223
gttggcaaag tcatctacaa gca 23

<210> SEQ ID NO 224
<211> LENGTH: 19
<212> TYPE: DNA
<213> ORGANISM: Artificial Sequence
<220> FEATURE:
<223> OTHER INFORMATION: reverse primer

<400> SEQUENCE: 224
gggcgaagtg gtccatctc 19

<210> SEQ ID NO 225
<211> LENGTH: 21
<212> TYPE: DNA
<213> ORGANISM: Artificial Sequence
<220> FEATURE:
<223> OTHER INFORMATION: probe

<400> SEQUENCE: 225
acgctgggca ggctctcgca c 21

<210> SEQ ID NO 226
<211> LENGTH: 22
<212> TYPE: DNA
<213> ORGANISM: Artificial Sequence
<220> FEATURE:
<223> OTHER INFORMATION: forward primer

<400> SEQUENCE: 226
gacaggccat ctgagacaca tg 22

<210> SEQ ID NO 227
<211> LENGTH: 23
<212> TYPE: DNA
<213> ORGANISM: Artificial Sequence
<220> FEATURE:
<223> OTHER INFORMATION: reverse primer

<400> SEQUENCE: 227
agcatagtct ggccagttct gaa 23

<210> SEQ ID NO 228
<211> LENGTH: 28
<212> TYPE: DNA
<213> ORGANISM: Artificial Sequence
<220> FEATURE:
<223> OTHER INFORMATION: probe

<400> SEQUENCE: 228
agacaccata tacccgagga accctgcc 28

<210> SEQ ID NO 229
<211> LENGTH: 19

<212> TYPE: DNA
<213> ORGANISM: Artificial Sequence
<220> FEATURE:
<223> OTHER INFORMATION: forward primer

<400> SEQUENCE: 229
cattcgggcc gagatgtct 19

<210> SEQ ID NO 230
<211> LENGTH: 24
<212> TYPE: DNA
<213> ORGANISM: Artificial Sequence
<220> FEATURE:
<223> OTHER INFORMATION: reverse primer

<400> SEQUENCE: 230
ctccaggcca gaaagagaga gtag 24

<210> SEQ ID NO 231
<211> LENGTH: 22
<212> TYPE: DNA
<213> ORGANISM: Artificial Sequence
<220> FEATURE:
<223> OTHER INFORMATION: probe

<400> SEQUENCE: 231
ccgtggcctt agctgtgctc gc 22

<210> SEQ ID NO 232
<211> LENGTH: 21
<212> TYPE: DNA
<213> ORGANISM: Artificial Sequence
<220> FEATURE:
<223> OTHER INFORMATION: forward primer

<400> SEQUENCE: 232
cacatggcct ccaaggagta a 21

<210> SEQ ID NO 233
<211> LENGTH: 24
<212> TYPE: DNA
<213> ORGANISM: Artificial Sequence
<220> FEATURE:
<223> OTHER INFORMATION: reverse primer

<400> SEQUENCE: 233
tgagggtctc tctcttcctc ttgt 24

<210> SEQ ID NO 234
<211> LENGTH: 22
<212> TYPE: DNA
<213> ORGANISM: Artificial Sequence
<220> FEATURE:
<223> OTHER INFORMATION: probe

<400> SEQUENCE: 234
ctggaccacc agccccagca ag 22

<210> SEQ ID NO 235
<211> LENGTH: 20
<212> TYPE: DNA
<213> ORGANISM: Artificial Sequence
<220> FEATURE:
<223> OTHER INFORMATION: forward primer

<400> SEQUENCE: 235
ccagggattt gcctcacctt 20

<210> SEQ ID NO 236
<211> LENGTH: 21
<212> TYPE: DNA
<213> ORGANISM: Artificial Sequence
<220> FEATURE:
<223> OTHER INFORMATION: reverse primer

<400> SEQUENCE: 236
aaagagatga agcccccaca t 21

<210> SEQ ID NO 237
<211> LENGTH: 26
<212> TYPE: DNA
<213> ORGANISM: Artificial Sequence
<220> FEATURE:
<223> OTHER INFORMATION: probe

<400> SEQUENCE: 237
ccttgatgac tgccttgcct cctcag 26

<210> SEQ ID NO 238
<211> LENGTH: 23
<212> TYPE: DNA
<213> ORGANISM: Artificial Sequence
<220> FEATURE:
<223> OTHER INFORMATION: forward primer

<400> SEQUENCE: 238
gctcgagatg tgatgaagga gat 23

<210> SEQ ID NO 239
<211> LENGTH: 21
<212> TYPE: DNA
<213> ORGANISM: Artificial Sequence
<220> FEATURE:
<223> OTHER INFORMATION: reverse primer

<400> SEQUENCE: 239
ccagcaggtc agcaaagaat t 21

<210> SEQ ID NO 240
<211> LENGTH: 28
<212> TYPE: DNA
<213> ORGANISM: Artificial Sequence
<220> FEATURE:
<223> OTHER INFORMATION: probe

<400> SEQUENCE: 240
ccatcacatt gtagccctct gtgtgctc 28

<210> SEQ ID NO 241
<211> LENGTH: 20
<212> TYPE: DNA
<213> ORGANISM: Artificial Sequence
<220> FEATURE:
<223> OTHER INFORMATION: forward primer

<400> SEQUENCE: 241
cacctagtgg ctgggagctt 20

<210> SEQ ID NO 242
<211> LENGTH: 24
<212> TYPE: DNA
<213> ORGANISM: Artificial Sequence -continued

```
<220> FEATURE:
<223> OTHER INFORMATION: reverse primer

<400> SEQUENCE: 242

gcccagtttt atcatctcac aaga                                          24


<210> SEQ ID NO 243
<211> LENGTH: 27
<212> TYPE: DNA
<213> ORGANISM: Artificial Sequence
<220> FEATURE:
<223> OTHER INFORMATION: probe

<400> SEQUENCE: 243

tggcacttac ctttgtccct tgcttca                                       27
```

COMPOSITION OR KIT FOR MAKING A PROGNOSIS OF LIVER CANCER, AND METHOD FOR MAKING A PROGNOSIS OF LIVER CANCER

CROSS REFERENCE TO RELATED INTERNATIONAL APPLICATION DATA

This application is a US National Application of International Application No. PCT/KR2010/006357, filed on Sep. 16, 2010. This application hereby incorporates by reference the international priority application enumerated herein.

TECHNICAL FIELD

The present disclosure relates to a biomarker for predicting prognosis of liver cancer. More particularly, the present disclosure relates to a composition or kit for predicting prognosis of liver cancer, and a method for predicting prognosis of liver cancer.

BACKGROUND ART

Liver cancer is known as one of the most fatal cancers in the world. In particular, it is reported that at least about five hundred thousand people die of liver cancer every year in Asia and in Sub-Saharan Africa. Liver cancer can be largely classified into hepatocellular carcinoma which arises from the liver cell itself, and metastatic liver cancer which is cancer from other tissues spread to the liver. About 90% of liver cancer is hepatocellular carcinoma, and the term liver cancer is generally understood to refer to hepatocellular carcinoma.

Prognosis of liver cancer refers to anticipating various conditions of the patient suffering from liver cancer such as possibility of full recovery from liver cancer, possibility of recurrence after treatment, possibility of survival of patient after being diagnosed of liver cancer, etc. This may vary depending on various conditions such as severity of the disease, diagnosis point, treatment progress, etc. Liver cancer can be treated efficiently only when various treatment methods are properly applied according to its prognosis. For example, with regard to patients who are estimated to have good prognosis, it would be necessary to avoid dangerous treatment methods which have a possibility to cause severe side effects to the patients such as aggressive chemical treatment or operations, radiation treatment, and select treatment methods which are relatively moderate, conservative and safe. On the other hand, with regard to patients who are estimated to have bad prognosis, chemical treatment or operations, treatment methods such as radiation treatment should be actively conducted in an attempt to increase the survival period or rate.

According to researchers conducted until now, the prognosis of liver cancer that has already progressed is extremely bad, and shows a high fatal rate of dying within 6 months from diagnosis, which leaves an average duration of life of only 4 months. However, liver cancer having a size of less than 3 cm has good prognosis, and is known to have a survival rate of 90% for a year without any particular treatment and after surgery, the survival rate of five years is about 40~50%. However, it is very difficult to estimate the prognosis of liver cancer patients precisely with prior art technology. In order to estimate prognosis accurately, an analysis method which classifies patients into each risk group is required. However, until now, prognosis has been determined depending only on the clinical pathological liver cancer stage at the time of diagnosis and primary surgical treatment without a means for accurately estimating prognosis of liver cancer.

The conventional analysis methods include the BCLC (Barcelona-Clinic Liver Cancer) staging system. Said system is a system for classifying liver cancer patients to determine a treatment method (liver resection, liver transplantation or radiofrequency ablation, etc. according to the stage of the disease) by determining the stage of a patient's liver cancer before conducting surgery on the patient (Llovert J M, Bru C, Bruix J. Prognosis of hepatocellular carcinoma: the BCLC staging classification. Semin Liver Dis. 1999; 19(3):329-338).

However, unfortunately, the prognosis of each liver cancer patient cannot be precisely determined by the liver cancer stage alone. Thus, it is necessary to develop a technology using gene markers to predict prognosis of liver cancer patients accurately. That is, by selecting patients expected to respond well to a specific treatment method (for example, liver resection) based on the stage and the prognosis result of each individual patient and providing the treatment to the patients, the overall treatment outcomes of liver cancer patients can be improved, and socioeconomic effects such as saving medical cost can be expected.

Meanwhile, with regard to UVRAG, NAMPT, STAT3, CIAP2, BHLHE41, MMP2, SESN2, HMGB1, SIRT1, RPS19BP1, LAMP2, AGER, SESN3, ID2, TCF3, HMGB2, TP63, RAGE, KIAA1967, SATB1, RAPTOR, SESN1, CCNG2, CDH1, FASLG, CASP3, BECN1, CDH2, TWIST1, MMP9, VEGF, ATG12, DIABLO, E2F1, LAMP1, LC3, ATG7, TKT, AIFM1, BNIP3, ATG3, DRAM, ATG5, NNMT, PRKAA1, CASP8, ULK1, BCL2L1, FAS, CSE1L, FRAP1, AKT1, BAX, BCL2, PTEN, CBS, XIAP proteins, it is not known how their expression level or expression pattern in liver cancer tissues changes according to the stage of liver cancer and how they can be used for predicting prognosis of liver cancer according to stage. Although there have been cases using the above proteins or some of the genes encoding the above proteins as a marker for prognosis of liver cancer, there has not been a case using them as a marker for prognosis of liver cancer according to stage.

As a result of conducting a research on predicting prognosis of liver cancer, the present inventors found genes whose expression level and expression pattern vary significantly (according to the stage of liver cancer), and completed the present disclosure.

DETAILED DESCRIPTION

Technical Subject

A technical subject matter to be solved by the present disclosure is to provide a biomarker for predicting prognosis of liver cancer which is capable of predicting prognosis (according to the stage of the cancer).

Another technical subject matter to be solved by the present disclosure is to provide a composition or kit for predicting prognosis of liver cancer which is capable of predicting prognosis (according to the stage of the cancer).

Yet another technical subject matter to be solved by the present disclosure is to provide a method for predicting prognosis of liver cancer which allows to predict prognosis (according to the stage of the cancer).

Means for Achieving the Subject Matter

The present disclosure provides a biomarker for predicting prognosis of liver cancer, preferably, a biomarker for predicting prognosis of liver cancer according to stage, which is at least one selected from the genes described in the following Table 1 and proteins encoded by the genes.

TABLE 1

| Indication of gene | Gene name | Transcriptome | NCBI GI | SEQ ID No. |
|---|---|---|---|---|
| UVRAG | UV radiation resistance-associated gene protein | NM_003369.3 | 111160877 | 1 |
| NAMPT | nicotinamide phosphoribosyltransferase | NM_005746.2 | 111161293 | 2 |
| STAT3 | Signal transducer and activator of transcription 3 | NM_003150.3 | 47080105 | 3 |
| CIAP2 | baculoviral IAP repeat-containing 3 | NM_001165.3 | 33946283 | 4 |
| BHLHE41 | basic helix-loop-helix family, member e41 | NM_030762.2 | 209529713 | 5 |
| MMP2 | matrix metallopeptidase 2 | NM_004530.4 | 189217851 | 6 |
| SESN2 | Sestrin-2 | NM_031459.3 | 32454742 | 7 |
| HMGB1 | high-mobility group box 1 | NM_002128.4 | 118918424 | 8 |
| SIRT1 | sirtuin 1 | NM_012238.4 | 215982795 | 9 |
| RPS19BP1 | ribosomal protein S19 binding protein 1 | NM_194326.2 | 55775474 | 10 |
| LAMP2 | lysosomal-associated membrane protein 2 | NM_002294.2 | 169790830 | 11 |
| AGER | advanced glycosylation end product-specific receptor | NM_001136.3 | 26787960 | 12 |
| SESN3 | Sestrin-3. | NM_144665.2 | 31377590 | 13 |
| ID2 | inhibitor of DNA binding 2 | NM_002166.4 | 33946335 | 14 |
| TCF3 | transcription factor 3 | NM_003200.2 | 209915592 | 15 |
| HMGB2 | high-mobility group box 2 | NM_002129.3 | 194688131 | 16 |
| TP63 | Tumor protein 63 | NM_003722.4 | 169234655 | 17 |
| RAGE | renal tumor antigen | NM_014226.1 | 7657497 | 18 |
| KIAA1967 | Deleted in breast cancer gene 1 protein | NM_021174.4 | 40548406 | 19 |
| SATB1 | SATB homeobox 1 | NM_002971.3 | 196114979 | 20 |
| RAPTOR | Regulatory-associated protein of mTOR | NM_020761.2 | 92373520 | 21 |
| SESN1 | Sestrin-1 | NM_014454.1 | 7657436 | 22 |
| CCNG2 | Cyclin-G2 | NM_004354.2 | 187608552 | 23 |
| CDH1 | cadherin 1, type 1, E-cadherin | NM_004360.3 | 169790842 | 24 |
| FASLG | Fas ligand (TNF superfamily, member 6) | NM_000639.1 | 4557328 | 25 |
| CASP3 | caspase 3, apoptosis-related cysteine peptidase | NM_004346.3 | 73622121 | 26 |
| BECN1 | beclin 1, autophagy related | NM_003766.3 | 187608304 | 27 |
| CDH2 | cadherin 2, type 1, N-cadherin | NM_001792.3 | 215422305 | 28 |
| TWIST1 | twist homolog 1 | NM_000474.3 | 68160957 | 29 |
| MMP9 | matrix metallopeptidase 9 | NM_004994.2 | 74272286 | 30 |
| VEGF | vascular endothelial growth factor A | NM_003376.4 | 71051577 | 31 |
| ATG12 | ATG12 autophagy related 12 homolog | NM_004707.2 | 38261968 | 32 |
| DIABLO | Diablo homolog, mitochondrial | NM_019887.4 | 218505810 | 33 |
| E2F1 | E2F transcription factor 1 | NM_005225.2 | 168480109 | 34 |
| LAMP1 | Lysosome-associated membrane glycoprotein 1 | NM_005561.3 | 112380627 | 35 |
| LC3 | microtubule-associated protein 1 light chain 3 alpha | NM_032514.2 | 31563519 | 36 |
| ATG7 | ATG7 autophagy related 7 homolog | NM_006395.1 | 5453667 | 37 |
| TKT | transketolase | NM_001064.2 | 205277461 | 38 |
| AIFM1 | apoptosis-inducing factor, mitochondrion-associated, 1 | NM_004208.2 | 22202627 | 39 |
| BNIP3 | BCL2/adenovirus E1B 19 kDa interacting protein 3 | NM_004052.2 | 7669480 | 40 |
| ATG3 | ATG3 autophagy related 3 homolog | NM_022488.3 | 34147490 | 41 |
| DRAM | DNA-damage regulated autophagy modulator 1 | NM_018370.2 | 110825977 | 42 |
| ATG5 | ATG5 autophagy related 5 homolog | NM_004849.2 | 92859692 | 43 |
| NNMT | nicotinamide N-methyltransferase | NM_006169.2 | 62953139 | 44 |
| PRKAA1 | protein kinase, AMP-activated, alpha 1 catalytic subunit | NM_006251.5 | 94557300 | 45 |
| CASP8 | caspase 8, apoptosis-related cysteine peptidase | NM_001228.4 | 122056470 | 46 |
| ULK1 | unc-51-like kinase 1 | NM_003565.1 | 4507830 | 47 |
| BCL2L1 | BCL2-like 1 | NM_001191.2 | 20336333 | 48 |
| FAS | Fas (TNF receptor superfamily, member 6) | NM_000043.3 | 23510419 | 49 |
| CSE1L | CSE1 chromosome segregation 1-like | NM_001316.2 | 29029558 | 50 |
| FRAP1 | mechanistic target of rapamycin (serine/threonine kinase) | NM_004958.3 | 206725550 | 51 |
| AKT1 | v-akt murine thymoma viral oncogene homolog 1 | NM_005163.2 | 62241010 | 52 |
| BAX | BCL2-associated X protein | NM_004324.3 | 34335114 | 53 |
| BCL2 | B-cell CLL/lymphoma 2 | NM_000633.2 | 72198188 | 54 |
| PTEN | phosphatase and tensin homolog | NM_000314.4 | 110224474 | 55 |
| CBS | cystathionine beta-synthase | NM_000071.2 | 209862802 | 56 |
| XIAP | X-linked inhibitor of apoptosis | NM_001167.2 | 32528298 | 57 |

In the above table, NCBI GI (Geninfo Identifier) refers to a sequence identification number given by the National Center for Biotechnology Information (NCBI), U.S.A., which consists of accession number and version number.

In the present disclosure, the “liver cancer” includes hepatocellular carcinoma, which arises from liver cells themselves, and metastatic liver cancer, which is a cancer from other tissues spread to the liver. Preferably, the “liver cancer” refers to hepatocellular carcinoma.

In the present disclosure, the “marker for predicting prognosis of liver cancer” means a gene marker as a criterion for predicting prognosis of liver cancer after occurrence the disease. This maker has a significantly low p-value, when the p-value is calculated based on the difference in its expression in the liver cancer cell and/or tissue of patients with different prognosis. Preferably, the p-value of this marker is less than 0.05.

Also, the present disclosure provides a composition or kit for predicting prognosis of liver cancer comprising nucleic acids which are specific to each of one or at least two genes selected from the group described in the above Table 1, or antibodies which are specific to proteins encoded by said genes, and for predicting prognosis of liver according to stage in one or more groups selected from A1 group {a group of portal vein invasion-negative patients in stage 0 or A of BCLC (Barcelona-Clinic Liver Cancer) staging system, having one tumor which is 5 cm or less in size, or 3 or less tumors which are 3 cm or less in size}, A2 group {a group of portal vein invasion-negative patients, having a tumor which is more than 5 cm in size}, B group {a group of portal vein invasion-negative patients in intermediate stage of BCLC staging system, having plural tumors which are more than 3 cm in size or plural tumors which are more than 3 in number}, or C group {a group of portal vein invasion-positive patients regardless of tumors size and number}.

The at least two genes may be at least three, four, five, six, seven or eight or more genes.

Preferably, the group consisting of genes may be a group consisting of the genes described in the following Table 2.

TABLE 2

| Indication of gene | Gene name | Transcriptome | NCBI GI | SEQ ID No. |
|---|---|---|---|---|
| UVRAG | UV radiation resistance-associated gene protein | NM_003369.3 | 111160877 | 1 |
| NAMPT | nicotinamide phosphoribosyltransferase | NM_005746.2 | 111161293 | 2 |
| STAT3 | Signal transducer and activator of transcription 3 | NM_003150.3 | 47080105 | 3 |
| CIAP2 | baculoviral IAP repeat-containing 3 | NM_001165.3 | 33946283 | 4 |
| BHLHE41 | basic helix-loop-helix family, member e41 | NM_030762.2 | 209529713 | 5 |
| MMP2 | matrix metallopeptidase 2 | NM_004530.4 | 189217851 | 6 |
| SESN2 | Sestrin-2 | NM_031459.3 | 32454742 | 7 |
| HMGB1 | high-mobility group box 1 | NM_002128.4 | 118918424 | 8 |
| SIRT1 | sirtuin 1 | NM_012238.4 | 215982795 | 9 |
| RPS19BP1 | ribosomal protein S19 binding protein 1 | NM_194326.2 | 55775474 | 10 |
| LAMP2 | lysosomal-associated membrane protein 2 | NM_002294.2 | 169790830 | 11 |
| AGER | advanced glycosylation end product-specific receptor | NM_001136.3 | 26787960 | 12 |
| SESN3 | Sestrin-3. | NM_144665.2 | 31377590 | 13 |
| ID2 | inhibitor of DNA binding 2 | NM_002166.4 | 33946335 | 14 |
| TCF3 | transcription factor 3 | NM_003200.2 | 209915592 | 15 |
| HMGB2 | high-mobility group box 2 | NM_002129.3 | 194688131 | 16 |
| TP63 | Tumor protein 63 | NM_003722.4 | 169234655 | 17 |
| RAGE | renal tumor antigen | NM_014226.1 | 7657497 | 18 |
| KIAA1967 | Deleted in breast cancer gene 1 protein | NM_021174.4 | 40548406 | 19 |
| SATB1 | SATB homeobox 1 | NM_002971.3 | 196114979 | 20 |
| RAPTOR | Regulatory-associated protein of mTOR | NM_020761.2 | 92373520 | 21 |
| SESN1 | Sestrin-1 | NM_014454.1 | 7657436 | 22 |
| CCNG2 | Cyclin-G2 | NM_004354.2 | 187608552 | 23 |
| CDH1 | cadherin 1, type 1, E-cadherin | NM_004360.3 | 169790842 | 24 |
| FASLG | Fas ligand (TNF superfamily, member 6) | NM_000639.1 | 4557328 | 25 |
| CASP3 | caspase 3, apoptosis-related cysteine peptidase | NM_004346.3 | 73622121 | 26 |
| BECN1 | beclin 1, autophagy related | NM_003766.3 | 187608304 | 27 |
| CDH2 | cadherin 2, type 1, N-cadherin | NM_001792.3 | 215422305 | 28 |
| TWIST1 | twist homolog 1 | NM_000474.3 | 68160957 | 29 |
| MMP9 | matrix metallopeptidase 9 | NM_004994.2 | 74272286 | 30 |
| VEGF | vascular endothelial growth factor A | NM_003376.4 | 71051577 | 31 |

More preferably, the group consisting of genes may further comprise the genes described in the following Table 3.

TABLE 3

| Indication of gene | Gene name | Transcriptome | NCBI GI | SEQ ID No. |
|---|---|---|---|---|
| ATG12 | ATG12 autophagy related 12 homolog | NM_004707.2 | 38261968 | 32 |
| DIABLO | Diablo homolog, mitochondrial | NM_019887.4 | 218505810 | 33 |
| E2F1 | E2F transcription factor 1 | NM_005225.2 | 168480109 | 34 |
| LAMP1 | Lysosome-associated membrane glycoprotein 1 | NM_005561.3 | 112380627 | 35 |
| LC3 | microtubule-associated protein 1 light chain 3 alpha | NM_032514.2 | 31563519 | 36 |
| ATG7 | ATG7 autophagy related 7 homolog | NM_006395.1 | 5453667 | 37 |
| TKT | transketolase | NM_001064.2 | 205277461 | 38 |
| AIFM1 | apoptosis-inducing factor, mitochondrion-associated, 1 | NM_004208.2 | 22202627 | 39 |
| BNIP3 | BCL2/adenovirus E1B 19 kDa interacting protein 3 | NM_004052.2 | 7669480 | 40 |
| ATG3 | ATG3 autophagy related 3 homolog | NM_022488.3 | 34147490 | 41 |
| DRAM | DNA-damage regulated autophagy modulator 1 | NM_018370.2 | 110825977 | 42 |
| ATG5 | ATG5 autophagy related 5 homolog | NM_004849.2 | 92859692 | 43 |
| NNMT | nicotinamide N-methyltransferase | NM_006169.2 | 62953139 | 44 |
| PRKAA1 | protein kinase, AMP-activated, alpha 1 catalytic subunit | NM_006251.5 | 94557300 | 45 |
| CASP8 | caspase 8, apoptosis-related cysteine peptidase | NM_001228.4 | 122056470 | 46 |
| ULK1 | unc-51-like kinase 1 | NM_003565.1 | 4507830 | 47 |
| BCL2L1 | BCL2-like 1 | NM_001191.2 | 20336333 | 48 |
| FAS | Fas (TNF receptor superfamily, member 6) | NM_000043.3 | 23510419 | 49 |
| CSE1L | CSE1 chromosome segregation 1-like | NM_001316.2 | 29029558 | 50 |
| FRAP1 | mechanistic target of rapamycin (serine/threonine kinase) | NM_004958.3 | 206725550 | 51 |
| AKT1 | v-akt murine thymoma viral oncogene homolog 1 | NM_005163.2 | 62241010 | 52 |
| BAX | BCL2-associated X protein | NM_004324.3 | 34335114 | 53 |
| BCL2 | B-cell CLL/lymphoma 2 | NM_000633.2 | 72198188 | 54 |
| PTEN | phosphatase and tensin homolog | NM_000314.4 | 110224474 | 55 |
| CBS | cystathionine beta-synthase | NM_000071.2 | 209862802 | 56 |
| XIAP | X-linked inhibitor of apoptosis | NM_001167.2 | 32528298 | 57 |

Among the genes described in the above Table 2, CDH1, ID2, MMP9, TCF3 may be excluded from Table 2, and may be further included in the group of the genes of Table 3.

The BCLC classification, which is the classification used in FIG. 1, is a system for classifying liver cancer patients to determine the treatment method (liver resection, liver transplantation or radiofrequency ablation, etc. according to stage) by determining the stage of the disease before conducting surgery on liver cancer patients (see Llovert J M, Bru C, Bruix J. Prognosis of hepatocellular carcinoma: the BCLC staging classification. Semin Liver Dis. 1999; 19(3): 329-338). In FIG. 1, the performance status test (PST) is classified into steps 0 to 4. Step 0 means the case where there is no problem in performance; step 1 means the case where the patient can perform light work; step 2 means the case where the patient cannot perform work, but can take care of himself; step 3 means the step where the patient can take care of himself limitedly, and spend at least 50% of everyday life in bed or on a chair; and step 4 means the case where the patient cannot perform activity at all, cannot take care of himself, and stays in bed or on a chair all day. In Okuda stage, stages are determined based on four criteria, and the stages are classified as stages I, II, III based on whether the size of cancer is larger or smaller than 50% of the entire liver; whether there is ascites; and the numerical values for bilirubin (< or >3 mg/dL), and albumin (< or >3 g/dL). Child-Pugh step is an index evaluating the liver function of patients suffering hepatocirrhosis. The albumin value (>3.5 g·dL: 1 point; 2.8-3.5 g/dL: 2 points; <2.8 g/dL: 3 points), bilirubin value (<2.0 mg/dL: 1 point; 2.0-3.0 mg/dL: 2 points; >3.0 mg/dL: 3 points), prothrombin time value (>50%: 1 point; 4050%: 2 points; <40%: 3 points), presence of ascites (none: 1 point; slight: 2 points; moderate: 3 points), encephalopathy step (none: 1 point; uncertain temper change, depression, tremor, drowsiness, inarticulate and slow in speech, asterixis, difficulty in walking: 2 points; muscle stiffness, loss of orientation, confusion, intermittent muscle cramp, nystagmus, coma, dilatation of pupil, decerebrate pose: 3 points), etc. are evaluated. 6 points or below are classified as class A, 7-9 points are classified as class B, and 10 points or higher are classified as class C.

The above prognosis can be predicting of recurrence, survival, or disease-free survival, and can be a prognosis after liver resection for cancer. The "recurrence" means recurrence of liver cancer in those who survived after liver resection for cancer. The "survival" means the survival rate of five years after liver resection for cancer. The disease-free survival means surviving without recurrence after going through liver resection for cancer.

Preferably, the composition or kit is for predicting prognosis of recurrence of the A1 group, and the genes are one or more selected from the genes or groups of genes described in the following Table 4.

TABLE 4

| One type | Combinations of two types | Combinations of three types | Combinations of four types |
|---|---|---|---|
| BCL2L1 | FRAP1__SESN1 | FRAP1__CASP3__CDH2 | ID2__NAMPT__RPS19BP1__SESN3 |
| BECN1 | FRAP1__TWIST1 | ID2__CDH2__SESN3 | FRAP1__LC3__CASP3__CDH2 |
| BAX | FRAP1__CASP3 | FRAP1__CDH2__SESN1 | FRAP1__TKT__CASP3__CDH2 |
| CDH2 | FRAP1__CCNG2 | FRAP1__LC3__CASP3 | BAX__FRAP1__LC3__CDH2 |
| NAMPT | BAX__FRAP1 | FRAP1__LC3__TWIST1 | ID2__CDH2__NAMPT__SESN3 |
| TWIST1 | FRAP1__NNMT | BAX__FRAP1__LC3 | CBS__ID2__CDH2__SESN3 |
| RPS19BP1 | BCL2L1__FRAP1 | FRAP1__CDH2__TWIST1 | FRAP1__LC3__CDH2__KIAA1967 |
| MMP2 | AIFM1__FRAP1 | FRAP1__NNMT__CDH2 | FRAP1__CDH2__SESN1__STAT3 |
| SESN3 | FRAP1__RAGE | FRAP1__LC3__NNMT | FRAP1__LC3__NNMT__CDH2 |
| ID2 | FRAP1__VEGF | BAX__FRAP1__CDH2 | FRAP1__LC3__CDH2__RAPTOR |
| AGER | ID2__CDH2 | FRAP1__SESN1__STAT3 | ID2__CDH2__RPS19BP1__SESN3 |
| ATG12 | FRAP1__PTEN | AIFM1__FRAP1__CDH2 | FRAP1__LC3__CDH2__TWIST1 |
| | NAMPT__SESN3 | FRAP1__LC3__VEGF | FRAP1__LC3__CDH2__VEGF |
| | BCL2__FRAP1 | FRAP1__NNMT__MMP2 | FRAP1__LC3__SESN1__STAT3 |
| | CDH2__SESN3 | FRAP1__LC3__RAGE | FRAP1__LC3__CDH2__RAGE |
| | FRAP1__RAPTOR | FRAP1__CCNG2__CDH2 | FRAP1__LC3__NNMT__STAT3 |
| | FRAP1__KIAA1967 | BCL2L1__FRAP1__CDH2 | ID2__CDH2__MMP2__SESN3 |
| | FRAP1__XIAP | FRAP1__CDH2__VEGF | FRAP1__LC3__CASP3__STAT3 |
| | BECN1__SESN3 | FRAP1__LC3__CCNG2 | AIFM1__FRAP1__LC3__CDH2 |
| | HMGB1__TWIST1 | FRAP1__CASP3__MMP2 | BCL2L1__FRAP1__LC3__CDH2 |
| | ID2__NAMPT | BCL2L1__FRAP1__LC3 | FRAP1__LC3__PTEN__CDH2 |
| | FRAP1__PRKAA1 | FRAP1__LC3__SESN1 | BAX__FRAP1__LC3__BECN1 |
| | ID2__RPS19BP1 | FRAP1__CDH2__KIAA1967 | BAX__FRAP1__LC3__RPS19BP1 |
| | BAX__LC3 | AIFM1__FRAP1__LC3 | FRAP1__CASP3__CDH2__STAT3 |
| | FRAP1__TP63 | FRAP1__LC3__RAPTOR | LC3__HMGB1__STAT3__TWIST1 |
| | ATG12__SESN3 | FRAP1__CDH2__RAGE | BAX__FRAP1__TKT__CDH2 |
| | BAX__TWIST1 | BAX__FRAP1__MMP2 | FRAP1__LC3__CCNG2__CDH2 |
| | RPS19BP1__SESN3 | FRAP1__LC3__PTEN | FRAP1__TKT__CDH2__SESN1 |
| | BAX__MMP2 | FRAP1__TKT__CASP3 | FRAP1__LC3__HMGB1__TWIST1 |
| | SESN1__STAT3 | FRAP1__PTEN__CDH2 | FRAP1__NNMT__TKT__CDH2 |
| | LC3__TWIST1 | FRAP1__TKT__TWIST1 | BAX__FRAP1__LC3__MMP2 |
| | MMP2__NAMPT | FRAP1__LC3__KIAA1967 | FRAP1__LC3__CCNG2__STAT3 |
| | ID2__BECN1 | BAX__FRAP1__TKT | FRAP1__LC3__STAT3__TWIST1 |
| | BCL2L1__LC3 | BCL2__FRAP1__CDH2 | FRAP1__TKT__CDH2__TWIST1 |
| | MMP2__RPS19BP1 | FRAP1__HMGB1__TWIST1 | FRAP1__LC3__NNMT__MMP2 |
| | ATG7__BCL2L1 | FRAP1__RPS19BP1__TWIST1 | BAX__FRAP1__TKT__MMP2 |
| | ID2__TWIST1 | FRAP1__CDH2__RAPTOR | FRAP1__NNMT__CDH2__MMP2 |
| | CDH2__HMGB1 | FRAP1__TKT__SESN1 | FRAP1__LC3__CDH2__SESN1 |
| | CDH2__MMP2 | FRAP1__RPS19BP1__SESN1 | BAX__FRAP1__LC3__TKT |
| | ATG7__TWIST1 | BAX__FRAP1__BECN1 | FAS__FRAP1__CDH2__SESN1 |
| | BAX__SESN3 | ID2__NAMPT__SESN3 | BAX__FAS__FRAP1__LC3 |
| | FASLG__NAMPT | FRAP1__CCNG2__STAT3 | FRAP1__CASP3__CDH2__MMP2 |
| | ATG7__BAX | BCL2L1__FRAP1__MMP2 | ID2__FASLG__NAMPT__SESN3 |
| | TKT__NAMPT | BCL2__FRAP1__LC3 | FRAP1__ID2__CDH2__TWIST1 |

TABLE 4-continued

| | | |
|---|---|---|
| STAT3__TWIST1 | FASLG__NAMPT__SESN3 | FRAP1__CDH2__HMGB1__TWIST1 |
| BCL2L1__MMP2 | AIFM1__FRAP1__MMP2 | BAX__FRAP1__BECN1__CDH2 |
| LC3__KIAA1967 | FRAP1__CCNG2__RPS19BP1 | DRAM__ID2__CDH2__SESN3 |
| BAX__BECN1 | BAX__FRAP1__RPS19BP1 | FRAP1__LC3__RPS19BP1__TWIST1 |
| ATG12__ID2 | FAS__FRAP1__SESN1 | AIFM1__FRAP1__TKT__CDH2 |
| BECN1__MMP2 | BCL2L1__FRAP1__TKT | FRAP1__TKT__CCNG2__CDH2 |
| AKT1__BAX | FRAP1__NNMT__STAT3 | BCL2L1__FRAP1__TKT__CDH2 |
| LC3__RAPTOR | FRAP1__MMP2__SESN1 | DIABLO__ID2__CDH2__SESN3 |
| BAX__RPS19BP1 | FRAP1__ID2__TWIST1 | BCL2__FRAP1__LC3__CDH2 |
| BAX__TKT | FRAP1__CASP3__STAT3 | FRAP1__LC3__CASP3__FASLG |
| BAX__SATB1 | FRAP1__TKT__CCNG2 | FRAP1__CDH2__RPS19BP1__SESN1 |
| LC3__NAMPT | FRAP1__MMP2__VEGF | FRAP1__LC3__CASP3__MMP2 |
| KIAA1967__MMP2 | FRAP1__MMP2__RAPTOR | ID2__CDH2__HMGB2__SESN3 |
| | | CDH1__ID2__MMP9__TCF3 |

| Combinations of five types | Combinations of six types |
|---|---|
| FRAP1__LC3__CASP3__CDH2__STAT3 | FRAP1__LC3__BECN1__CASP3__CDH2__STAT3 |
| ID2__MMP2__NAMPT__RPS19BP1__SESN3 | FRAP1__LC3__NNMT__BECN1__CDH2__STAT3 |
| FRAP1__LC3__CDH2__SESN1__STAT3 | FRAP1__LC3__TKT__CASP3__CDH2__STAT3 |
| ID2__CDH2__MMP2__RPS19BP1__SESN3 | ID2__CDH2__HMGB1__MMP2__RPS19BP1__SESN3 |
| FRAP1__LC3__NNMT__CDH2__STAT3 | FAS__FRAP1__LC3__CDH2__SESN1__STAT3 |
| BAX__FRAP1__LC3__BECN1__CDH2 | ID2__CDH2__FASLG__NAMPT__RPS19BP1__SESN3 |
| ID2__FASLG__NAMPT__RPS19BP1__SESN3 | FRAP1__LC3__CASP3__CDH2__HMGB1__STAT3 |
| BAX__FRAP1__LC3__TKT__CDH2 | FRAP1__LC3__CDH2__RPS19BP1__SESN1__STAT3 |
| FRAP1__LC3__BECN1__CDH2__RAPTOR | FRAP1__LC3__CASP3__CDH2__RPS19BP1__STAT3 |
| FRAP1__LC3__CDH2__STAT3__TWIST1 | FRAP1__LC3__CDH2__HMGB1__STAT3__TWIST1 |
| FRAP1__LC3__CCNG2__CDH2__STAT3 | ID2__HMGB2__MMP2__NAMPT__RPS19BP1__SESN3 |
| ID2__CDH2__FASLG__NAMPT__SESN3 | AIFM1__FRAP1__LC3__BECN1__CDH2__STAT3 |
| LC3__CDH2__HMGB1__STAT3__TWIST1 | ID2__MMP2__NAMPT__RPS19BP1__SESN3__STAT3 |
| ID2__CDH2__HMGB1__RPS19BP1__SESN3 | ID2__FASLG__HMGB2__NAMPT__RPS19BP1__SESN3 |
| ID2__CDH2__MMP2__NAMPT__SESN3 | AKT1__FAS__BECN1__CDH2__STAT3__TP63 |
| FRAP1__LC3__BECN1__CDH2__KIAA1967 | FRAP1__LC3__CCNG2__CDH2__RPS19BP1__STAT3 |
| BAX__FRAP1__LC3__CDH2__RPS19BP1 | AKT1__ATG12__BECN1__CDH2__STAT3__TP63 |
| ID2__HMGB2__NAMPT__RPS19BP1__SESN3 | FRAP1__LC3__NNMT__CDH2__RPS19BP1__STAT3 |
| ID2__NAMPT__RPS19BP1__SESN3__STAT3 | CSE1L__FRAP1__LC3__CASP3__CDH2__STAT3 |
| FRAP1__LC3__CDH2__HMGB1__TWIST1 | FRAP1__LC3__BECN1__CDH2__RAGE__STAT3 |
| FRAP1__TKT__CDH2__SESN1__STAT3 | FAS__FRAP1__LC3__NNMT__CDH2__STAT3 |
| CSE1L__ID2__CDH2__RPS19BP1__SESN3 | ID2__HMGB1__MMP2__NAMPT__RPS19BP1__SESN3 |
| FRAP1__LC3__TKT__CASP3__CDH2 | FRAP1__LC3__TKT__CDH2__SESN1__STAT3 |
| BAX__FAS__FRAP1__LC3__CDH2 | FRAP1__LC3__NNMT__CDH2__MMP2__STAT3 |
| FAS__FRAP1__LC3__CDH2__RAPTOR | FRAP1__LC3__NNMT__TKT__CDH2__STAT3 |
| LC3__CASP3__CDH2__HMGB1__STAT3 | BAX__FRAP1__LC3__BECN1__CDH2__STAT3 |
| FAS__FRAP1__LC3__CDH2__KIAA1967 | FRAP1__LC3__CASP3__CDH2__SIRT1__STAT3 |
| AIFM1__FRAP1__LC3__CDH2__STAT3 | FAS__FRAP1__LC3__CDH2__RAPTOR__RPS19BP1 |
| FRAP1__LC3__BECN1__CASP3__STAT3 | CBS__FRAP1__LC3__CASP3__CDH2__STAT3 |
| FRAP1__BECN1__CASP3__CDH2__STAT3 | FAS__FRAP1__LC3__CASP3__CDH2__STAT3 |
| ID2__CDH2__NAMPT__SESN3__STAT3 | AKT1__ATG12__FAS__CDH2__STAT3__TP63 |
| LC3__ID2__NAMPT__RPS19BP1__SESN3 | LC3__CDH2__HMGB1__RPS19BP1__STAT3__TWIST1 |
| FRAP1__LC3__NNMT__MMP2__STAT3 | FRAP1__LC3__BECN1__CDH2__STAT3__TWIST1 |
| BAX__FRAP1__LC3__CASP3__CDH2 | FRAP1__LC3__CASP3__CDH2__MMP2__STAT3 |
| FRAP1__TKT__CASP3__CDH2__STAT3 | ID2__MMP9__MMP2__NAMPT__RPS19BP1__SESN3 |
| LC3__HMGB1__RPS19BP1__STAT3__TWIST1 | CSE1L__ID2__CDH2__MMP2__RPS19BP1__SESN3 |
| FRAP1__CDH2__RPS19BP1__SESN1__STAT3 | FRAP1__LC3__BECN1__CDH2__STAT3__VEGF |
| CBS__FRAP1__LC3__CASP3__CDH2 | BAX__FRAP1__LC3__TKT__BECN1__CDH2 |
| FRAP1__LAMP1__TKT__CASP3__CDH2 | FRAP1__LC3__NNMT__CASP3__CDH2__STAT3 |
| ID2__CDH2__HMGB1__NAMPT__SESN3 | FRAP1__TKT__BECN1__CASP3__CDH2__STAT3 |
| ID2__HMGB1__NAMPT__RPS19BP1__SESN3 | ID2__FASLG__NAMPT__RPS19BP1__SESN3__STAT3 |
| AKT1__ID2__NAMPT__RPS19BP1__SESN3 | FAS__FRAP1__LC3__CDH2__KIAA1967__RPS19BP1 |
| FRAP1__LC3__TKT__CDH2__KIAA1967 | FRAP1__LC3__BECN1__CDH2__SESN1__STAT3 |
| FRAP1__LC3__CASP3__CDH2__HMGB1 | ID2__CDH2__FASLG__NAMPT__SESN3__STAT3 |
| ATG7__FRAP1__LC3__CASP3__CDH2 | FRAP1__LC3__TKT__CDH2__STAT3__TWIST1 |
| BAX__FRAP1__LC3__TKT__MMP2 | ATG5__FRAP1__LC3__CASP3__CDH2__STAT3 |
| FRAP1__LC3__CDH2__RAPTOR__RPS19BP1 | ID2__CDH2__MMP2__RPS19BP1__SESN3__STAT3 |
| FRAP1__LC3__RPS19BP1__SESN1__STAT3 | FAS__LC3__CDH2__HMGB1__STAT3__TWIST1 |
| BAX__FRAP1__LC3__CDH2__MMP2 | AIFM1__FRAP1__LC3__TKT__CDH2__STAT3 |
| ID2__TCF3__CDH2__RPS19BP1__SESN3 | FRAP1__LC3__TKT__CASP3__CDH2__FASLG |
| FRAP1__TKT__CASP3__CDH2__FASLG | DRAM__ID2__MMP2__NAMPT__RPS19BP1__SESN3 |
| FAS__FRAP1__CDH2__SESN1__STAT3 | FRAP1__LC3__CASP3__CDH2__NAMPT__STAT3 |
| CBS__ID2__NAMPT__RPS19BP1__SESN3 | FAS__FRAP1__LC3__CCNG2__CDH2__STAT3 |
| FRAP1__LC3__CDH2__KIAA1967__MMP2 | BAX__FAS__FRAP1__LC3__CDH2__RPS19BP1 |
| FAS__FRAP1__LC3__CASP3__CDH2 | BNIP3__FRAP1__LC3__CASP3__CDH2__STAT3 |
| BAX__CBS__FRAP1__LC3__CDH2 | FRAP1__LC3__CDH2__RPS19BP1__STAT3__TWIST1 |
| FRAP1__LC3__TKT__CDH2__RAPTOR | FRAP1__LC3__MMP9__CASP3__CDH2__STAT3 |
| CDH1__ID2__MMP9__TCF3__RPS19BP1 | CDH1__ID2__MMP9__TCF3__RPS19BP1__SESN3 |

| Combinations of seven types | Combinations of eight types |
|---|---|
| AKT1__ATG12__FAS__BECN1__CDH2__STAT3__TP63 | AKT1__ATG12__FAS__CDH2__RPS19BP1__SESN2__STAT3__TP63 |
| FRAP1__LC3__TKT__BECN1__CASP3__CDH2__STAT3 | AKT1__FAS__LC3__CDH2__HMGB1__RPS19BP1__STAT3__TP63 |

TABLE 4-continued

| | |
|---|---|
| FAS_FRAP1_LC3_CASP3_CDH2_RPS19BP1_STAT3 | AKT1_ATG12_FAS_BECN1_CDH2_RPS19BP1_STAT3_TP63 |
| FAS_FRAP1_LC3_CDH2_RPS19BP1_SESN1_STAT3 | AKT1_ATG12_CASP8_FAS_BECN1_CDH2_STAT3_TP63 |
| AKT1_FAS_BECN1_CDH2_RPS19BP1_STAT3_TP63 | AKT1_ATG12_FAS_LC3_CDH2_RPS19BP1_STAT3_TP63 |
| ID2_CDH2_FASLG_NAMPT_RPS19BP1_SESN3_STAT3 | AKT1_ATG12_FAS_NNMT_BECN1_CDH2_STAT3_TP63 |
| FRAP1_LC3_NNMT_TKT_BECN1_CDH2_STAT3 | AKT1_ATG12_FAS_BECN1_CDH2_RAPTOR_STAT3_TP63 |
| AKT1_ATG12_FAS_CDH2_RPS19BP1_STAT3_TP63 | AKT1_FAS_LC3_BECN1_CDH2_RPS19BP1_STAT3_TP63 |
| FAS_FRAP1_LC3_NNMT_CDH2_RPS19BP1_STAT3 | FAS_FRAP1_LC3_BECN1_CASP3_CDH2_RPS19BP1_STAT3 |
| FAS_FRAP1_LC3_CCNG2_CDH2_RPS19BP1_STAT3 | AKT1_ATG12_FAS_CDH2_HMGB1_RPS19BP1_STAT3_TP63 |
| FRAP1_LC3_BECN1_CASP3_CDH2_HMGB1_STAT3 | FRAP1_LC3_TKT_BECN1_CASP3_CDH2_FASLG_STAT3 |
| ID2_FASLG_HMGB2_NAMPT_RPS19BP1_SESN3_STAT3 | CSE1L_FAS_FRAP1_LC3_CASP3_CDH2_RPS19BP1_STAT3 |
| FRAP1_LC3_NNMT_BECN1_CASP3_CDH2_STAT3 | AKT1_ATG12_LC3_CDH2_HMGB1_RPS19BP1_STAT3_TP63 |
| CBS_FRAP1_LC3_BECN1_CASP3_CDH2_STAT3 | FAS_FRAP1_LC3_NNMT_BECN1_CDH2_RPS19BP1_STAT3 |
| FRAP1_LC3_BECN1_CASP3_CDH2_SIRT1_STAT3 | AKT1_CASP8_FAS_BECN1_CDH2_RPS19BP1_STAT3_TP63 |
| CSE1L_FRAP1_LC3_CASP3_CDH2_RPS19BP1_STAT3 | FRAP1_LC3_NNMT_TKT_BECN1_CDH2_FASLG_STAT3 |
| FRAP1_LC3_TKT_CASP3_CDH2_HMGB1_STAT3 | AKT1_ATG12_FAS_BECN1_CDH2_LAMP2_STAT3_TP63 |
| FRAP1_LC3_TKT_CDH2_HMGB1_STAT3_TWIST1 | AKT1_FAS_LC3_CDH2_RPS19BP1_SESN2_STAT3_TP63 |
| ATG5_FRAP1_LC3_BECN1_CASP3_CDH2_STAT3 | AKT1_ATG12_FAS_LAMP1_BECN1_CDH2_STAT3_TP63 |
| CSE1L_FRAP1_LC3_BECN1_CASP3_CDH2_STAT3 | ID2_CDH2_FASLG_HMGB1_HMGB2_NAMPT_RPS19BP1_SESN3 |
| FRAP1_LC3_BECN1_CASP3_CDH2_HMGB2_STAT3 | AKT1_ATG12_FAS_BECN1_CDH2_CIAP2_STAT3_TP63 |
| AKT1_LC3_CDH2_HMGB1_RPS19BP1_STAT3_TP63 | AKT1_ATG12_CASP8_FAS_CDH2_RPS19BP1_STAT3_TP63 |
| FAS_FRAP1_LC3_CDH2_MMP2_RAPTOR_RPS19BP1 | ID2_CDH2_FASLG_HMGB2_NAMPT_RPS19BP1_SESN3_STAT3 |
| AKT1_FAS_CDH2_RPS19BP1_SESN2_STAT3_TP63 | AKT1_ATG12_FAS_TCF3_CDH2_RPS19BP1_STAT3_TP63 |
| FRAP1_LC3_BECN1_CASP3_CDH2_FASLG_STAT3 | AKT1_ATG12_E2F1_FAS_BECN1_CDH2_STAT3_TP63 |
| ID2_CDH2_HMGB1_HMGB2_MMP2_RPS19BP1_SESN3 | AKT1_ATG7_FAS_BECN1_CDH2_RPS19BP1_STAT3_TP63 |
| AKT1_CASP8_FAS_BECN1_CDH2_STAT3_TP63 | AKT1_FAS_BECN1_CDH2_RPS19BP1_SESN2_STAT3_TP63 |
| FAS_FRAP1_LC3_TKT_CDH2_SESN1_STAT3 | AKT1_ATG12_FAS_LC3_BECN1_CDH2_STAT3_TP63 |
| CBS_FRAP1_LC3_NNMT_BECN1_CDH2_STAT3 | AKT1_LC3_BECN1_CDH2_HMGB1_RPS19BP1_STAT3_TP63 |
| AKT1_FAS_LC3_CDH2_RPS19BP1_STAT3_TP63 | AKT1_ATG12_ATG7_BECN1_CDH2_RPS19BP1_STAT3_TP63 |
| FRAP1_LC3_BECN1_CDH2_HMGB1_STAT3_TWIST1 | FAS_FRAP1_LC3_CASP3_CDH2_FASLG_RPS19BP1_STAT3 |
| CSE1L_FRAP1_LC3_TKT_CASP3_CDH2_STAT3 | AKT1_ATG12_FAS_BECN1_CASP3_CDH2_STAT3_TP63 |
| FRAP1_LC3_NNMT_BECN1_CDH2_SIRT1_STAT3 | AKT1_ATG12_FAS_BECN1_CDH2_HMGB2_STAT3_TP63 |
| AKT1_ATG12_CDH2_HMGB1_RPS19BP1_STAT3_TP63 | AKT1_ATG12_FAS_LC3_CDH2_HMGB1_STAT3_TP63 |
| ID2_CDH2_FASLG_HMGB1_NAMPT_RPS19BP1_SESN3 | FRAP1_LC3_TKT_CASP3_CDH2_FASLG_HMGB1_STAT3 |
| ID2_CDH2_HMGB1_MMP2_RPS19BP1_SESN3_STAT3 | FAS_FRAP1_LC3_NNMT_CDH2_MMP2_RPS19BP1_STAT3 |
| FRAP1_LC3_CDH2_HMGB1_RPS19BP1_STAT3_TWIST1 | FAS_FRAP1_LC3_BECN1_CDH2_RPS19BP1_SESN1_STAT3 |
| FAS_FRAP1_LC3_CDH2_KIAA1967_MMP2_RPS19BP1 | FAS_FRAP1_LC3_TKT_CDH2_RPS19BP1_SESN1_STAT3 |
| FRAP1_LC3_BECN1_CASP3_CDH2_RPS19BP1_STAT3 | AKT1_ATG12_BECN1_CDH2_HMGB1_RPS19BP1_STAT3_TP63 |
| FRAP1_LC3_TKT_CASP3_CDH2_FASLG_STAT3 | AKT1_ATG12_FAS_CASP3_CDH2_RPS19BP1_STAT3_TP63 |
| BNIP3_FRAP1_LC3_BECN1_CASP3_CDH2_STAT3 | AKT1_ATG12_FAS_CDH2_NAMPT_RPS19BP1_STAT3_TP63 |
| FRAP1_LC3_CASP3_CDH2_HMGB1_MMP2_STAT3 | FAS_FRAP1_LC3_CASP3_CDH2_RPS19BP1_SIRT1_STAT3 |
| FAS_LC3_CDH2_HMGB1_RPS19BP1_STAT3_TWIST1 | FAS_FRAP1_LC3_CDH2_FASLG_RPS19BP1_SESN1_STAT3 |
| ID2_HMGB1_HMGB2_MMP2_NAMPT_RPS19BP1_SESN3 | AKT1_FAS_NNMT_BECN1_CDH2_RPS19BP1_STAT3_TP63 |
| FRAP1_LC3_TKT_BECN1_CDH2_FASLG_RAPTOR | CSE1L_FAS_FRAP1_LC3_NNMT_CDH2_RPS19BP1_STAT3 |
| FRAP1_LC3_NNMT_BECN1_CDH2_FASLG_STAT3 | FAS_FRAP1_LC3_TKT_CDH2_FASLG_RAPTOR_RPS19BP1 |
| FAS_FRAP1_LC3_CDH2_FASLG_RAPTOR_RPS19BP1 | AKT1_FAS_BECN1_CDH2_HMGB1_RPS19BP1_STAT3_TP63 |
| FRAP1_LC3_MMP9_BECN1_CASP3_CDH2_STAT3 | FAS_LC3_CDH2_HMGB1_RPS19BP1_STAT3_TP63_TWIST1 |
| FAS_FRAP1_LC3_NNMT_BECN1_CDH2_STAT3 | FAS_FRAP1_LC3_TKT_CASP3_CDH2_RPS19BP1_STAT3 |
| AIFM1_FAS_FRAP1_LC3_CDH2_RPS19BP1_STAT3 | ID2_CDH2_FASLG_HMGB1_NAMPT_RPS19BP1_SESN3_STAT3 |
| AKT1_ATG12_FAS_LC3_CDH2_STAT3_TP63 | FAS_FRAP1_LC3_BECN1_CDH2_FASLG_RAPTOR_RPS19BP1 |
| AKT1_FAS_CDH2_HMGB1_RPS19BP1_STAT3_TP63 | CSE1L_FRAP1_LC3_TKT_BECN1_CASP3_CDH2_STAT3 |
| ID2_CDH2_HMGB1_MMP2_NAMPT_RPS19BP1_SESN3 | FRAP1_LC3_TKT_BECN1_CASP3_CDH2_HMGB1_STAT3 |
| AKT1_BECN1_CDH2_HMGB1_RPS19BP1_STAT3_TP63 | FAS_FRAP1_LC3_BECN1_CCNG2_CDH2_RPS19BP1_STAT3 |
| AKT1_ATG12_CASP8_FAS_CDH2_STAT3_TP63 | FAS_FRAP1_LC3_TKT_BECN1_CDH2_FASLG_RAPTOR |
| ATG5_FRAP1_LC3_NNMT_BECN1_CDH2_STAT3 | AKT1_ATG12_FAS_TKT_BECN1_CDH2_STAT3_TP63 |
| FRAP1_LC3_CASP3_CDH2_HMGB1_RPS19BP1_STAT3 | FRAP1_LC3_BECN1_CASP3_CDH2_FASLG_HMGB1_STAT3 |
| CDH1_ID2_MMP9_TCF3_CDH2_RPS19BP1_SESN3 | CDH1_ID2_MMP9_TCF3_CDH2_MMP2_RPS19BP1_SESN3 |

Preferably, the composition or kit is for predicting the prognosis of survival of the A1 group, and the genes are one or more selected from the genes or groups of genes described in the following Table 5.

TABLE 5

| One type | Combinations of two types | Combinations of three types | Combinations of four types |
|---|---|---|---|
| ID2 | CDH1_ID2 | ATG12_CDH1_ID2 | ATG12_CDH1_ID2_HMGB2 |
| CDH1 | ATG12_CDH1 | CDH1_ID2_HMGB2 | CDH1_ID2_AGER_HMGB2 |
| LC3 | LAMP1_ID2 | ATG12_CDH1_HMGB2 | ATG12_CDH1_ID2_AGER |
| TKT | BNIP3_ID2 | CDH1_ID2_AGER | ATG12_CDH1_TCF3_HMGB2 |
| AKT1 | ATG12_ID2 | DRAM_CDH1_ID2 | ATG12_DRAM_CDH1_ID2 |
| AIFM1 | CDH1_HMGB2 | E2F1_CDH1_ID2 | AIFM1_CASP8_LC3_CDH1 |
| BNIP3 | ID2_HMGB2 | CDH1_ID2_LAMP2 | ATG12_CDH1_AGER_HMGB2 |
| LAMP1 | E2F1_ID2 | TKT_CDH1_ID2 | ATG12_CDH1_ID2_BECN1 |
| FRAP1 | TKT_ID2 | LAMP1_CDH1_ID2 | ATG12_DRAM_CDH1_HMGB2 |
| | DRAM_ID2 | CDH1_ID2_MMP2 | DRAM_CDH1_ID2_HMGB2 |
| | ATG5_ID2 | ATG12_DRAM_CDH1 | ATG12_CDH1_BHLHE41_HMGB2 |
| | ID2_BECN1 | CSE1L_CDH1_ID2 | CDH1_ID2_HMGB2_LAMP2 |
| | ID2_AGER | CDH1_ID2_MMP9 | ATG12_CDH1_BECN1_HMGB2 |

TABLE 5-continued

| | | |
|---|---|---|
| ID2__MMP2 | BNIP3__CDH1__ID2 | E2F1__CDH1__ID2__HMGB2 |
| ATG3__ID2 | CDH1__ID2__BECN1 | ATG12__DIABLO__CDH1__BHLHE41 |
| ID2__LAMP2 | ATG12__CDH1__BHLHE41 | CDH1__ID2__BECN1__HMGB2 |
| ULK1__CDH1 | ULK1__CDH1__ID2 | ATG12__ATG5__CDH1__HMGB2 |
| CSE1L__ID2 | LC3__CDH1__ID2 | DRAM__CDH1__ID2__AGER |
| TKT__CDH1 | ATG12__CDH1__TCF3 | LAMP1__CDH1__ID2__HMGB2 |
| LC3__CDH1 | ATG5__CDH1__ID2 | ATG12__BNIP3__CDH1__ID2 |
| ID2__MMP9 | ATG3__CDH1__ID2 | ATG12__CSE1L__CDH1__ID2 |
| LC3__ID2 | DIABLO__CDH1__ID2 | ATG12__CDH1__ID2__MMP2 |
| FRAP1__ID2 | CASP8__CDH1__ID2 | ATG12__CASP8__CDH1__ID2 |
| CASP8__ID2 | ATG12__ULK1__CDH1 | ATG12__ATG3__CDH1__HMGB2 |
| ID2__CIAP2 | ATG12__CDH1__BECN1 | ATG12__CDH1__ID2__MMP9 |
| ID2__UVRAG | ATG12__BNIP3__ID2 | CDH1__ID2__HMGB2__MMP2 |
| DIABLO__ID2 | CDH1__ID2__CIAP2 | ATG12__ATG3__CDH1__ID2 |
| DRAM__CDH1 | CBS__CDH1__ID2 | ATG12__CASP8__CDH1__HMGB2 |
| ID2__SIRT1 | CDH1__ID2__HMGB1 | ATG12__LAMP1__CDH1__ID2 |
| FAS__ID2 | CDH1__ID2__SIRT1 | CDH1__ID2__AGER__BECN1 |
| CDH1__AGER | LAMP1__ID2__HMGB2 | ATG12__FAS__CDH1__HMGB2 |
| ID2__STAT3 | CDH1__ID2__UVRAG | ATG12__TKT__CDH1__ID2 |
| CBS__ID2 | AIFM1__LC3__CDH1 | CDH1__ID2__MMP9__HMGB2 |
| CDH1__MMP2 | ATG12__CDH1__AGER | ATG12__CDH1__HMGB1__HMGB2 |
| AKT1__ID2 | CDH1__ID2__STAT3 | ATG12__CDH1__MMP9__HMGB2 |
| ID2__CDH2 | ATG12__LAMP1__ID2 | ATG12__ATG5__CDH1__ID2 |
| ATG7__ID2 | ATG12__LC3__CDH1 | ATG5__CDH1__ID2__HMGB2 |
| ID2__HMGB1 | CDH1__AGER__HMGB2 | ATG3__CDH1__ID2__HMGB2 |
| ULK1__ID2 | FAS__CDH1__ID2 | ATG12__DIABLO__CDH1__ID2 |
| CDH1__LAMP2 | ATG7__CDH1__ID2 | CSE1L__CDH1__ID2__HMGB2 |
| ATG5__CDH1 | ATG12__CDH1__MMP2 | ATG12__CDH1__CIAP2__HMGB2 |
| ID2__SATB1 | ATG12__CASP8__CDH1 | ATG12__CDH1__ID2__UVRAG |
| CDH1__MMP9 | ATG12__TKT__CDH1 | ATG12__CDH1__HMGB2__SESN3 |
| ID2__RPS19BP1 | BNIP3__ID2__HMGB2 | LC3__CDH1__ID2__AGER |
| ID2__TCF3 | E2F1__ID2__HMGB2 | ATG12__CDH1__HMGB2__SIRT1 |
| CSE1L__CDH1 | ATG12__CDH1__MMP9 | ATG12__E2F1__CDH1__ID2 |
| AIFM1__CDH1 | ATG12__CDH1__SESN2 | ATG12__FAS__CDH1__ID2 |
| ID2__SESN3 | CDH1__ID2__CDH2 | AIFM1__ATG3__LC3__CDH1 |
| ID2__SESN2 | AKT1__CDH1__ID2 | ATG12__CDH1__HMGB2__MMP2 |
| LAMP1__CDH1 | LAMP1__ID2__BECN1 | BNIP3__CDH1__ID2__HMGB2 |
| AIFM1__LC3 | CDH1__ID2__TCF3 | ATG12__ULK1__CDH1__HMGB2 |
| E2F1__CDH1 | ATG12__CDH1__UVRAG | TKT__CDH1__ID2__HMGB2 |
| ID2__NAMPT | ATG12__FAS__CDH1 | ATG12__CDH1__ID2__LAMP2 |
| DIABLO__CDH1 | LAMP1__TKT__ID2 | ATG12__LC3__CDH1__ID2 |
| BNIP3__CDH1 | LAMP1__ID2__AGER | ATG12__CDH1__HMGB2__UVRAG |
| AKT1__CDH1 | DRAM__LAMP1__ID2 | CASP8__CDH1__ID2__HMGB2 |
| CASP8__CDH1 | ATG12__DIABLO__CDH1 | DIABLO__CDH1__ID2__HMGB2 |
| | | CDH1__ID2__MMP9__TCF3 |

| Combinations of five types | Combinations of six types |
|---|---|
| ATG12__CDH1__ID2__AGER__HMGB2 | ATG12__DRAM__CDH1__ID2__AGER__HMGB2 |
| ATG12__DRAM__CDH1__ID2__HMGB2 | ATG12__CDH1__ID2__AGER__BECN1__HMGB2 |
| DRAM__CDH1__ID2__AGER__HMGB2 | ATG12__CSE1L__CDH1__ID2__AGER__HMGB2 |
| ATG12__CDH1__ID2__BECN1__HMGB2 | ATG12__CDH1__ID2__AGER__HMGB2__RPS19BP1 |
| ATG12__LAMP1__CDH1__ID2__HMGB2 | ATG12__LAMP1__CDH1__ID2__AGER__HMGB2 |
| ATG12__ATG5__CDH1__ID2__HMGB2 | ATG12__CDH1__ID2__MMP9__AGER__HMGB2 |
| ATG12__E2F1__CDH1__ID2__HMGB2 | ATG12__ATG3__CDH1__ID2__AGER__HMGB2 |
| ATG12__ATG3__CDH1__ID2__HMGB2 | ATG12__LC3__CDH1__ID2__AGER__HMGB2 |
| CDH1__ID2__AGER__BECN1__HMGB2 | ATG12__BNIP3__CDH1__ID2__AGER__HMGB2 |
| ATG12__CDH1__ID2__HMGB2__MMP2 | ATG12__CDH1__ID2__AGER__HMGB2__SIRT1 |
| ATG12__CASP8__CDH1__ID2__HMGB2 | ATG12__CDH1__ID2__AGER__HMGB2__MMP2 |
| ATG12__BNIP3__CDH1__ID2__HMGB2 | ATG12__CASP8__CDH1__ID2__AGER__HMGB2 |
| ATG12__CDH1__ID2__MMP9__HMGB2 | ATG12__CDH1__ID2__AGER__CIAP2__HMGB2 |
| LAMP1__CDH1__ID2__AGER__HMGB2 | ATG12__ATG5__CDH1__ID2__AGER__HMGB2 |
| ATG12__CSE1L__CDH1__ID2__HMGB2 | ATG12__CDH1__ID2__TCF3__AGER__HMGB2 |
| LC3__CDH1__ID2__AGER__HMGB2 | ATG12__DRAM__CDH1__ID2__BECN1__HMGB2 |
| ATG12__DIABLO__CDH1__ID2__HMGB2 | ATG12__FAS__CDH1__ID2__AGER__HMGB2 |
| CSE1L__CDH1__ID2__AGER__HMGB2 | ATG12__CDH1__ID2__AGER__HMGB1__HMGB2 |
| CDH1__ID2__MMP9__AGER__HMGB2 | ATG12__DRAM__LAMP1__CDH1__ID2__HMGB2 |
| CDH1__ID2__AGER__HMGB2__RPS19BP1 | ATG12__ATG3__DRAM__CDH1__ID2__HMGB2 |
| ATG12__CDH1__ID2__CIAP2__HMGB2 | ATG12__ATG5__DRAM__CDH1__ID2__HMGB2 |
| ATG12__CDH1__ID2__HMGB2__UVRAG | ATG12__DIABLO__CDH1__ID2__AGER__HMGB2 |
| ATG12__DRAM__CDH1__ID2__AGER | ATG12__DIABLO__CDH1__TCF3__BHLHE41__HMGB2 |
| ATG12__DRAM__CDH1__TCF3__HMGB2 | ATG12__CASP8__DRAM__CDH1__ID2__HMGB2 |
| ATG12__CDH1__ID2__AGER__BECN1 | ATG12__DRAM__CDH1__ID2__HMGB2__MMP2 |
| ATG12__DIABLO__CDH1__BHLHE41__HMGB2 | ATG12__LAMP1__CDH1__ID2__BECN1__HMGB2 |
| ATG12__DIABLO__CDH1__HMGB2__SESN3 | ATG12__CBS__CDH1__ID2__AGER__HMGB2 |
| ATG12__FAS__CDH1__ID2__HMGB2 | ATG12__DRAM__CDH1__ID2__MMP9__HMGB2 |
| ATG3__CDH1__ID2__AGER__HMGB2 | ATG12__CDH1__ID2__AGER__HMGB2__UVRAG |
| CDH1__ID2__AGER__HMGB2__MMP2 | ATG12__E2F1__CDH1__ID2__AGER__HMGB2 |
| ATG12__CDH1__ID2__TCF3__HMGB2 | ATG12__ATG5__CDH1__ID2__BECN1__HMGB2 |
| ATG12__CDH1__TCF3__AGER__HMGB2 | ATG12__DIABLO__CDH1__CIAP2__HMGB2__SESN3 |

TABLE 5-continued

| | |
|---|---|
| ATG12_CDH1_ID2_HMGB1_HMGB2 | ATG12_CSE1L_DRAM_CDH1_ID2_HMGB2 |
| AIFM1_ATG3_CASP8_LC3_CDH1 | ATG12_DRAM_E2F1_CDH1_ID2_HMGB2 |
| ATG12_CDH1_ID2_HMGB2_SIRT1 | ATG12_DIABLO_CDH1_TCF3_HMGB2_SESN3 |
| ATG12_CDH1_TCF3_BECN1_HMGB2 | AIFM1_ATG3_ATG5_CASP8_LC3_CDH1 |
| ATG12_DIABLO_CDH1_TCF3_BHLHE41 | ATG12_BNIP3_DRAM_CDH1_ID2_HMGB2 |
| BNIP3_CDH1_ID2_AGER_HMGB2 | ATG12_DIABLO_CDH1_ID2_HMGB2_SESN3 |
| AIFM1_CASP8_DRAM_LC3_CDH1 | AIFM1_ATG3_CASP8_LC3_CDH1_MMP9 |
| ATG12_CDH1_ID2_HMGB2_LAMP2 | ATG12_ATG3_CDH1_ID2_BECN1_HMGB2 |
| ATG12_ATG3_CDH1_TCF3_HMGB2 | ATG12_CDH1_ID2_AGER_HMGB2_STAT3 |
| ATG12_LC3_CDH1_ID2_HMGB2 | ATG12_DIABLO_DRAM_CDH1_ID2_HMGB2 |
| ATG12_TKT_CDH1_ID2_HMGB2 | ATG12_DRAM_CDH1_ID2_CIAP2_HMGB2 |
| CASP8_CDH1_ID2_AGER_HMGB2 | DRAM_LAMP1_CDH1_ID2_AGER_HMGB2 |
| ATG12_CDH1_TCF3_BHLHE41_HMGB2 | DRAM_CDH1_ID2_AGER_BECN1_HMGB2 |
| ATG5_CDH1_ID2_AGER_HMGB2 | ATG12_BNIP3_CDH1_ID2_HMGB2_MMP2 |
| ATG12_CSE1L_CDH1_ID2_AGER | ATG12_BNIP3_CDH1_ID2_BECN1_HMGB2 |
| CDH1_ID2_AGER_HMGB2_SIRT1 | ATG12_CSE1L_CDH1_ID2_BECN1_HMGB2 |
| CDH1_ID2_AGER_CIAP2_HMGB2 | LAMP1_LC3_CDH1_ID2_AGER_HMGB2 |
| CDH1_ID2_TCF3_AGER_HMGB2 | ATG12_CDH1_ID2_BECN1_HMGB2_MMP2 |
| AIFM1_CASP8_LC3_CDH1_MMP9 | DRAM_LC3_CDH1_ID2_AGER_HMGB2 |
| ATG12_DRAM_CDH1_ID2_BECN1 | ATG12_DIABLO_CDH1_BHLHE41_HMGB2_SIRT1 |
| AIFM1_CASP8_DIABLO_LC3_CDH1 | ATG12_TKT_CDH1_ID2_AGER_HMGB2 |
| CDH1_ID2_AGER_HMGB1_HMGB2 | DRAM_CDH1_ID2_MMP9_AGER_HMGB2 |
| ATG12_CDH1_ID2_HMGB2_RPS19BP1 | ATG12_CDH1_ID2_MMP9_BECN1_HMGB2 |
| ATG12_LC3_CDH1_AGER_HMGB2 | CSE1L_DRAM_CDH1_ID2_AGER_HMGB2 |
| FAS_CDH1_ID2_AGER_HMGB2 | ATG12_DRAM_FAS_CDH1_ID2_HMGB2 |
| ATG12_CDH1_ID2_MMP9_TCF3 | ATG12_CDH1_ID2_MMP9_TCF3_HMGB2 |

| Combinations of seven types | Combinations of eight types |
|---|---|
| ATG12_DRAM_CDH1_ID2_AGER_BECN1_HMGB2 | ATG12_ATG3_DIABLO_CDH1_TCF3_CIAP2_HMGB2_SESN3 |
| ATG12_CSE1L_DRAM_CDH1_ID2_AGER_HMGB2 | ATG12_DIABLO_DRAM_CDH1_TCF3_CIAP2_HMGB2_SESN3 |
| ATG12_CDH1_ID2_AGER_BECN1_HMGB2_RPS19BP1 | ATG12_BNIP3_DIABLO_CDH1_TCF3_CIAP2_HMGB2_SESN3 |
| ATG12_CSE1L_CDH1_ID2_AGER_BECN1_HMGB2 | ATG12_DRAM_CDH1_ID2_AGER_BECN1_HMGB2_RPS19BP1 |
| ATG12_DRAM_LAMP1_CDH1_ID2_AGER_HMGB2 | ATG12_CSE1L_DRAM_CDH1_ID2_AGER_BECN1_HMGB2 |
| ATG12_DRAM_CDH1_ID2_MMP9_AGER_HMGB2 | ATG12_DIABLO_DRAM_CDH1_TCF3_BHLHE41_HMGB2_SIRT1 |
| ATG12_DRAM_CDH1_ID2_AGER_HMGB2_RPS19BP1 | ATG12_DIABLO_CDH1_TCF3_BECN1_CIAP2_HMGB2_SESN3 |
| ATG12_ATG3_DRAM_CDH1_ID2_AGER_HMGB2 | ATG12_LAMP1_LC3_CDH1_ID2_AGER_BECN1_HMGB2 |
| ATG12_LC3_CDH1_ID2_AGER_BECN1_HMGB2 | ATG12_CSE1L_CDH1_ID2_AGER_BECN1_HMGB2_RPS19BP1 |
| ATG12_DRAM_LC3_CDH1_ID2_AGER_HMGB2 | ATG12_DRAM_LAMP1_CDH1_ID2_AGER_BECN1_HMGB2 |
| ATG12_LAMP1_CDH1_ID2_AGER_BECN1_HMGB2 | ATG12_DRAM_LC3_CDH1_ID2_AGER_BECN1_HMGB2 |
| ATG12_DRAM_CDH1_ID2_AGER_HMGB2_SIRT1 | ATG12_ATG3_DIABLO_CDH1_BECN1_CIAP2_HMGB2_SESN3 |
| ATG12_CDH1_ID2_MMP9_AGER_BECN1_HMGB2 | ATG12_DRAM_CDH1_ID2_MMP9_AGER_BECN1_HMGB2 |
| ATG12_DIABLO_CDH1_TCF3_CIAP2_HMGB2_SESN3 | ATG12_CASP8_DIABLO_CDH1_TCF3_CIAP2_HMGB2_SESN3 |
| ATG12_DIABLO_CDH1_TCF3_BHLHE41_HMGB2_SIRT1 | ATG12_ATG3_DIABLO_CDH1_TCF3_BHLHE41_HMGB2_SIRT1 |
| ATG12_ATG3_CDH1_ID2_AGER_BECN1_HMGB2 | ATG12_DRAM_LAMP1_LC3_CDH1_ID2_AGER_HMGB2 |
| ATG12_BNIP3_DRAM_CDH1_ID2_AGER_HMGB2 | ATG12_DIABLO_CDH1_TCF3_BECN1_BHLHE41_HMGB2_SIRT1 |
| ATG12_DRAM_CDH1_ID2_AGER_CIAP2_HMGB2 | ATG12_CSE1L_LC3_CDH1_ID2_AGER_BECN1_HMGB2 |
| ATG12_LAMP1_LC3_CDH1_ID2_AGER_HMGB2 | ATG12_ATG3_DRAM_CDH1_ID2_AGER_BECN1_HMGB2 |
| ATG12_DRAM_CDH1_ID2_AGER_HMGB2_MMP2 | ATG12_CSE1L_DRAM_CDH1_ID2_AGER_HMGB2_RPS19BP1 |
| ATG12_CASP8_DRAM_CDH1_ID2_AGER_HMGB2 | ATG12_DRAM_CDH1_ID2_TCF3_AGER_BECN1_HMGB2 |
| ATG12_CSE1L_CDH1_ID2_AGER_HMGB2_RPS19BP1 | ATG12_DIABLO_CDH1_TCF3_BHLHE41_HMGB2_SESN2_SIRT1 |
| ATG12_BNIP3_CDH1_ID2_AGER_HMGB2_MMP2 | ATG12_ATG5_DIABLO_CDH1_TCF3_BHLHE41_HMGB2_SIRT1 |
| ATG12_CDH1_ID2_TCF3_AGER_BECN1_HMGB2 | ATG12_ATG3_CSE1L_DRAM_CDH1_ID2_AGER_HMGB2 |
| ATG12_CDH1_ID2_AGER_BECN1_HMGB2_MMP2 | ATG12_ATG3_DIABLO_FAS_CDH1_TCF3_BHLHE41_HMGB2 |
| ATG12_BNIP3_CDH1_ID2_AGER_BECN1_HMGB2 | ATG12_BNIP3_DRAM_CDH1_ID2_AGER_HMGB2_MMP2 |
| ATG12_FAS_CDH1_ID2_AGER_BECN1_HMGB2 | ATG12_CSE1L_DRAM_CDH1_ID2_MMP9_AGER_HMGB2 |
| ATG12_ATG3_CSE1L_CDH1_ID2_AGER_HMGB2 | ATG12_CDH1_ID2_MMP9_AGER_BECN1_HMGB2_RPS19BP1 |
| ATG12_DIABLO_CDH1_BECN1_CIAP2_HMGB2_SESN3 | ATG12_DRAM_CDH1_ID2_MMP9_AGER_HMGB2_RPS19BP1 |
| ATG12_DRAM_CDH1_ID2_TCF3_AGER_HMGB2 | ATG12_CSE1L_CDH1_ID2_MMP9_AGER_BECN1_HMGB2 |
| ATG12_ATG3_DIABLO_CDH1_TCF3_HMGB2_SESN3 | ATG12_DRAM_CDH1_ID2_AGER_HMGB2_MMP2_SIRT1 |
| ATG12_CSE1IL_LC3_CDH1_ID2_AGER_HMGB2 | ATG12_DIABLO_FAS_CDH1_TCF3_BECN1_BHLHE41_HMGB2 |
| ATG12_CSE1IL_CDH1_ID2_MMP9_AGER_HMGB2 | ATG12_CSE1L_DRAM_LC3_CDH1_ID2_AGER_HMGB2 |
| ATG12_ATG5_DRAM_CDH1_ID2_AGER_HMGB2 | ATG12_DRAM_LAMP1_CDH1_ID2_MMP9_AGER_HMGB2 |
| ATG12_DRAM_CDH1_ID2_AGER_HMGB1_HMGB2 | ATG12_DRAM_CDH1_ID2_AGER_BECN1_HMGB2_MMP2 |
| ATG12_DRAM_LAMP1_CDH1_ID2_BECN1_HMGB2 | ATG12_ATG3_CSE1L_CDH1_ID2_AGER_BECN1_HMGB2 |
| ATG12_CDH1_ID2_MMP9_AGER_HMGB2_RPS19BP1 | ATG12_CSE1L_DRAM_LAMP1_CDH1_ID2_AGER_HMGB2 |
| ATG12_DRAM_FAS_CDH1_ID2_AGER_HMGB2 | ATG12_ATG3_DRAM_CDH1_ID2_AGER_HMGB2_RPS19BP1 |
| ATG12_DIABLO_DRAM_CDH1_ID2_AGER_HMGB2 | ATG12_ATG3_DRAM_CDH1_ID2_MMP9_AGER_HMGB2 |
| ATG12_CSE1L_LAMP1_CDH1_ID2_AGER_HMGB2 | ATG12_CSE1L_LAMP1_CDH1_ID2_AGER_BECN1_HMGB2 |
| ATG12_DIABLO_FAS_CDH1_TCF3_BHLHE41_HMGB2 | ATG12_DRAM_FAS_CDH1_ID2_AGER_BECN1_HMGB2 |
| ATG12_LAMP1_CDH1_ID2_MMP9_AGER_HMGB2 | ATG12_DIABLO_CDH1_TCF3_BECN1_HMGB2_SESN3_SIRT1 |
| ATG12_ATG3_DIABLO_CDH1_TCF3_BHLHE41_HMGB2 | ATG12_BNIP3_CDH1_ID2_AGER_BECN1_HMGB2_MMP2 |
| ATG12_ATG3_CDH1_ID2_AGER_HMGB2_RPS19BP1 | ATG12_LC3_CDH1_ID2_MMP9_AGER_BECN1_HMGB2 |
| ATG12_CDH1_ID2_AGER_BECN1_HMGB2_SIRT1 | AIFM1_CASP8_LAMP1_CDH1_AGER_CIAP2_HMGB2_RPS19BP1 |
| ATG12_CDH1_ID2_AGER_HMGB2_MMP2_SIRT1 | ATG12_ATG3_CDH1_ID2_AGER_BECN1_HMGB2_RPS19BP1 |
| AIFM1_ATG3_CASP8_CSE1L_LC3_CDH1_MMP9 | ATG12_ATG3_DIABLO_CDH1_BECN1_HMGB2_SESN3_SIRT1 |
| ATG12_ATG3_CDH1_ID2_MMP9_AGER_HMGB2 | ATG12_ATG3_DIABLO_FAS_CDH1_TCF3_HMGB2_SESN3 |
| ATG12_LC3_CDH1_ID2_MMP9_AGER_HMGB2 | ATG12_DIABLO_FAS_CDH1_TCF3_CIAP2_HMGB2_SESN3 |
| AIFM1_CASP8_LC3_CDH1_AGER_HMGB2_RPS19BP1 | ATG12_CDH1_ID2_TCF3_AGER_BECN1_HMGB2_RPS19BP1 |
| ATG12_ATG5_CDH1_ID2_AGER_BECN1_HMGB2 | ATG12_CSE1L_CDH1_ID2_TCF3_AGER_BECN1_HMGB2 |

TABLE 5-continued

| | |
|---|---|
| ATG12__LAMP1__CDH1__ID2__AGER__HMGB2__MMP2 | ATG12__BNIP3__DRAM__CDH1__ID2__AGER__BECN1__HMGB2 |
| ATG12__LAMP1__CDH1__ID2__AGER__HMGB2__RPS19BP1 | ATG12__FAS__CDH1__ID2__AGER__BECN1__HMGB2__RPS19BP1 |
| AIFM1__ATG3__ATG5__CASP8__LC3__CDH1__MMP9 | ATG12__DRAM__LC3__CDH1__ID2__MMP9__AGER__HMGB2 |
| ATG12__ATG5__DRAM__CDH1__ID2__BECN1__HMGB2 | ATG12__DIABLO__CDH1__TCF3__CIAP2__HMGB2__RPS19BP1__SESN3 |
| ATG12__BNIP3__CDH1__ID2__MMP9__AGER__HMGB2 | ATG12__DRAM__CDH1__ID2__TCF3__AGER__HMGB2__RPS19BP1 |
| ATG12__BNIP3__CSE1L__CDH1__ID2__AGER__HMGB2 | ATG12__LAMP1__CDH1__ID2__TCF3__AGER__BECN1__HMGB2 |
| ATG12__CDH1__ID2__MMP9__TCF3__AGER__HMGB2 | ATG12__CDH1__ID2__MMP9__TCF3__AGER__BECN1__HMGB2 |

Preferably, the composition or kit is for predicting the prognosis of disease-free survival of the A1 group, and the genes are one or more selected from the genes or groups of genes described in the following Table 6.

TABLE 6

| One type | Combinations of two types | Combinations of three types | Combinations of four types |
|---|---|---|---|
| MMP2 | ID2_CDH2 | FRAP1_CASP3_CDH2 | FRAP1_TKT_CASP3_CDH2 |
| ID2 | FRAP1_TWIST1 | ID2_CDH2_SESN3 | ID2_CDH2_MMP2_SESN3 |
| TWIST1 | FRAP1_CASP3 | ID2_CDH2_MMP2 | CBS_ID2_CDH2_SESN3 |
| BECN1 | FRAP1_SESN1 | FRAP1_CDH2_TWIST1 | FRAP1_TKT_CDH2_TWIST1 |
| BAX | BAX_FRAP1 | FRAP1_CDH2_SESN1 | FRAP1_LC3_CASP3_CDH2 |
| BCL2L1 | FRAP1_NNMT | FRAP1_NNMT_CDH2 | FRAP1_NNMT_TKT_CDH2 |
| CDH2 | FRAP1_CCNG2 | AIFM1_FRAP1_CDH2 | ID2_CDH2_RPS19BP1_SESN3 |
| FASLG | BCL2L1_FRAP1 | FRAP1_TKT_TWIST1 | BAX_FRAP1_TKT_CDH2 |
| AGER | FRAP1_RAGE | BAX_FRAP1_CDH2 | BAX_FRAP1_LC3_CDH2 |
| ATG12 | AIFM1_FRAP1 | FRAP1_LC3_TWIST1 | ATG12_ID2_CDH2_SESN3 |
| TKT | BCL2_FRAP1 | AKT1_ID2_CDH2 | ATG12_ID2_MMP2_SESN3 |
| | FRAP1_VEGF | ATG12_ID2_MMP2 | FRAP1_LC3_CDH2_KIAA1967 |
| | FRAP1_PTEN | FRAP1_CDH2_KIAA1967 | AIFM1_FRAP1_TKT_CDH2 |
| | HMGB1_TWIST1 | FRAP1_CCNG2_CDH2 | FRAP1_TKT_CDH2_SESN1 |
| | ATG12_ID2 | FRAP1_NNMT_MMP2 | ID2_MMP2_RPS19BP1_SESN3 |
| | FRAP1_RAPTOR | FRAP1_CDH2_RAGE | FRAP1_CDH2_SESN1_STAT3 |
| | FRAP1_KIAA1967 | BCL2L1_FRAP1_CDH2 | FRAP1_LC3_CDH2_TWIST1 |
| | ID2_BECN1 | FRAP1_TKT_CASP3 | FRAP1_LC3_NNMT_CDH2 |
| | BECN1_SESN3 | ATG12_MMP2_SESN3 | FRAP1_LC3_CDH2_RAPTOR |
| | ATG12_MMP2 | FRAP1_CDH2_VEGF | FRAP1_TKT_CCNG2_CDH2 |
| | CDH2_SESN3 | ID2_CDH2_HMGB1 | DIABLO_ID2_CDH2_SESN3 |
| | ID2_MMP2 | FRAP1_PTEN_CDH2 | ID2_CDH2_HMGB2_SESN3 |
| | FRAP1_XIAP | CDH1_ID2_CDH2 | FRAP1_TKT_CDH2_KIAA1967 |
| | AKT1_CDH2 | FRAP1_CASP3_MMP2 | FRAP1_LC3_CDH2_RAGE |
| | FRAP1_PRKAA1 | FRAP1_LC3_CASP3 | BAX_FRAP1_TKT_MMP2 |
| | ID2_RPS19BP1 | BCL2_FRAP1_CDH2 | BCL2L1_FRAP1_TKT_CDH2 |
| | TKT_MMP2 | BAX_FRAP1_TKT | FRAP1_CASP3_CDH2_STAT3 |
| | BAX_TWIST1 | FRAP1_CDH2_RAPTOR | FRAP1_PTEN_TKT_CDH2 |
| | BECN1_FASLG | BAX_FRAP1_LC3 | FRAP1_ID2_CDH2_TWIST1 |
| | ATG12_SESN3 | BAX_FRAP1_MMP2 | ID2_CDH2_NAMPT_SESN3 |
| | CDH2_MMP2 | FAS_ID2_CDH2 | FRAP1_TKT_CDH2_VEGF |
| | BECN1_MMP2 | FRAP1_RPS19BP1_TWIST1 | FRAP1_LC3_CDH2_VEGF |
| | BAX_MMP2 | FRAP1_LC3_NNMT | FRAP1_NNMT_CDH2_MMP2 |
| | ID2_NAMPT | FRAP1_LC3_RAGE | AIFM1_FRAP1_LC3_CDH2 |
| | CASP8_ID2 | FRAP1_HMGB1_TWIST1 | FRAP1_LC3_PTEN_CDH2 |
| | ID2_TWIST1 | FRAP1_SESN1_STAT3 | FRAP1_TKT_CDH2_RAGE |
| | MMP2_SESN3 | FRAP1_TKT_SESN1 | FRAP1_CDH2_HMGB1_TWIST1 |
| | AKT1_BAX | ATG3_ID2_CDH2 | FAS_FRAP1_CDH2_SESN1 |
| | FRAP1_TP63 | FRAP1_ID2_CDH2 | FRAP1_CASP3_CDH2_MMP2 |
| | BAX_LC3 | FRAP1_TKT_CCNG2 | DRAM_ID2_CDH2_SESN3 |
| | ATG12_FASLG | FAS_FRAP1_TWIST1 | LC3_HMGB1_STAT3_TWIST1 |
| | LC3_TWIST1 | FRAP1_NNMT_TKT | CASP8_ID2_CDH2_SESN3 |
| | AKT1_TWIST1 | AIFM1_FRAP1_MMP2 | FRAP1_TKT_CDH2_RAPTOR |
| | ID2_FASLG | ID2_CDH2_CIAP2 | BCL2L1_FRAP1_LC3_CDH2 |
| | STAT3_TWIST1 | FRAP1_LC3_VEGF | FRAP1_CDH2_KIAA1967_MMP2 |
| | TKT_FASLG | CDH2_MMP2_SESN3 | FRAP1_TKT_CASP3_FASLG |
| | AKT1_ATG12 | ID2_CDH2_FASLG | TKT_ID2_CDH2_MMP2 |
| | MMP2_NAMPT | CBS_ID2_CDH2 | FRAP1_NNMT_TKT_MMP2 |
| | ID2_SIRT1 | FRAP1_LC3_CCNG2 | FRAP1_TKT_CASP3_MMP2 |
| | ID2_AGER | BCL2L1_FRAP1_TKT | ID2_CDH2_CIAP2_SESN3 |
| | ATG7_TWIST1 | FRAP1_ID2_TWIST1 | FRAP1_CDH2_STAT3_TWIST1 |
| | AKT1_BCL2L1 | AIFM1_FRAP1_LC3 | CBS_FRAP1_CASP3_CDH2 |
| | BAX_TKT | AIFM1_FRAP1_TKT | BAX_FRAP1_CDH2_MMP2 |
| | KIAA1967_MMP2 | ATG5_ID2_CDH2 | ATG12_TKT_MMP2_SESN3 |
| | BCL2L1_MMP2 | FRAP1_TKT_RAGE | FRAP1_CDH1_CASP3_CDH2 |
| | ATG7_TP63 | BCL2L1_FRAP1_MMP2 | BAX_FRAP1_BECN1_CDH2 |
| | LC3_BECN1 | FRAP1_CDH2_TP63 | ID2_CDH2_HMGB1_MMP2 |
| | | | CDH1_ID2_MMP9_TCF3 |

TABLE 6-continued

| Combinations of five types | Combinations of six types |
|---|---|
| ID2_CDH2_MMP2_RPS19BP1_SESN3 | AKT1_ATG12_FAS_CDH2_STAT3_TP63 |
| ATG12_ID2_CDH2_MMP2_SESN3 | AKT1_FAS_BECN1_CDH2_STAT3_TP63 |
| FRAP1_LC3_CASP3_CDH2_STAT3 | AKT1_FAS_CDH2_RPS19BP1_STAT3_TP63 |
| ATG12_ID2_MMP2_RPS19BP1_SESN3 | AKT1_FAS_LC3_CDH2_STAT3_TP63 |
| AKT1_FAS_CDH2_STAT3_TP63 | ID2_CDH2_HMGB1_MMP2_RPS19BP1_SESN3 |
| FRAP1_TKT_CASP3_CDH2_STAT3 | AKT1_ATG12_BECN1_CDH2_STAT3_TP63 |
| CASP8_ID2_CDH2_MMP2_SESN3 | AKT1_ATG7_FAS_CDH2_RPS19BP1_TP63 |
| FRAP1_TKT_CASP3_CDH2_FASLG | ATG12_ID2_CDH2_HMGB1_MMP2_SESN3 |
| BAX_FRAP1_LC3_TKT_CDH2 | FRAP1_LC3_BECN1_CASP3_CDH2_STAT3 |
| ID2_CDH2_HMGB2_MMP2_SESN3 | FRAP1_LC3_TKT_CASP3_CDH2_STAT3 |
| DIABLO_ID2_CDH2_MMP2_SESN3 | FRAP1_LC3_NNMT_BECN1_CDH2_STAT3 |
| FRAP1_LAMP1_TKT_CASP3_CDH2 | ID2_CDH2_HMGB2_MMP2_RPS19BP1_SESN3 |
| CBS_ID2_CDH2_MMP2_SESN3 | ATG12_ID2_CDH2_CIAP2_MMP2_SESN3 |
| FRAP1_LC3_NNMT_CDH2_STAT3 | FAS_FRAP1_LC3_CDH2_SESN1_STAT3 |
| FRAP1_TKT_CDH2_SESN1_STAT3 | FRAP1_TKT_BECN1_CASP3_CDH2_STAT3 |
| LC3_CDH2_HMGB1_STAT3_TWIST1 | ATG12_FRAP1_ID2_CDH2_MMP2_SESN3 |
| DRAM_ID2_CDH2_MMP2_SESN3 | FAS_LC3_CDH2_HMGB1_STAT3_TWIST1 |
| FRAP1_LC3_CDH2_SESN1_STAT3 | ATG12_TKT_ID2_CDH2_MMP2_SESN3 |
| CBS_FRAP1_TKT_CASP3_CDH2 | ID2_CDH2_CIAP2_MMP2_RPS19BP1_SESN3 |
| ID2_MMP2_NAMPT_RPS19BP1_SESN3 | AKT1_CASP8_FAS_CDH2_STAT3_TP63 |
| AKT1_ID2_CDH2_RPS19BP1_SESN3 | AKT1_FAS_CASP3_CDH2_STAT3_TP63 |
| ID2_CDH2_MMP2_NAMPT_SESN3 | FAS_FRAP1_LC3_NNMT_CDH2_STAT3 |
| AKT1_BECN1_CDH2_STAT3_TP63 | FAS_FRAP1_TKT_CDH2_SESN1_STAT3 |
| FAS_FRAP1_LC3_CDH2_RAPTOR | ATG12_ID2_CDH2_MMP2_SESN3_STAT3 |
| FRAP1_LC3_CDH2_STAT3_TWIST1 | FRAP1_NNMT_TKT_BECN1_CDH2_STAT3 |
| BAX_FRAP1_TKT_CDH2_MMP2 | ATG12_FAS_FRAP1_CDH2_STAT3_TP63 |
| FAS_FRAP1_LC3_CDH2_KIAA1967 | ATG12_ATG3_ID2_CDH2_MMP2_SESN3 |
| AKT1_ATG7_CDH2_RPS19BP1_TP63 | DRAM_ID2_CDH2_MMP2_RPS19BP1_SESN3 |
| FAS_FRAP1_LC3_CDH2_RAGE | ATG12_CBS_ID2_CDH2_MMP2_SESN3 |
| FAS_LC3_HMGB1_STAT3_TWIST1 | ID2_CDH2_MMP2_RPS19BP1_SESN3_STAT3 |
| FRAP1_LC3_TKT_CASP3_CDH2 | FRAP1_ID2_CDH2_MMP2_RPS19BP1_SESN3 |
| FRAP1_TKT_CASP3_CDH2_CIAP2 | AKT1_ID2_CDH2_MMP2_RPS19BP1_SESN3 |
| TKT_ID2_CDH2_MMP2_SESN3 | FAS_FRAP1_LC3_CASP3_CDH2_STAT3 |
| FRAP1_TKT_CDH2_KIAA1967_MMP2 | ATG5_ID2_CDH2_MMP2_RPS19BP1_SESN3 |
| FRAP1_IKT_CDH2_HMGB1_TWIST1 | AKT1_FAS_CDH2_HMGB1_STAT3_TP63 |
| BAX_FRAP1_LC3_BECN1_CDH2 | CSE1L_ID2_CDH2_MMP2_RPS19BP1_SESN3 |
| FRAP1_TKT_CDH2_STAT3_TWIST1 | ATG3_ID2_CDH2_MMP2_RPS19BP1_SESN3 |
| AKT1_ATG12_ID2_CDH2_SESN3 | FRAP1_LC3_NNMT_TKT_CDH2_STAT3 |
| BAX_FAS_FRAP1_LC3_CDH2 | CBS_ID2_CDH2_MMP2_RPS19BP1_SESN3 |
| ATG12_CBS_ID2_MMP2_SESN3 | AKT1_ATG12_CDH2_HMGB1_STAT3_TP63 |
| FAS_FRAP1_CDH2_SESN1_STAT3 | FAS_FRAP1_LC3_CDH2_RAPTOR_RPS19BP1 |
| FRAP1_BECN1_CASP3_CDH2_STAT3 | AKT1_ATG12_ID2_CDH2_MMP2_SESN3 |
| FAS_FRAP1_TKT_CDH2_SESN1 | ATG12_ATG5_ID2_CDH2_MMP2_SESN3 |
| FRAP1_LC3_CCNG2_CDH2_STAT3 | AKT1_ATG12_FAS_BECN1_STAT3_TP63 |
| ID2_CDH2_MMP2_SESN3_UVRAG | AKT1_FAS_BECN1_RPS19BP1_STAT3_TP63 |
| ATG7_ID2_CDH2_MMP2_SESN3 | FAS_FRAP1_LC3_CDH2_FASLG_RAPTOR |
| ID2_CDH2_HMGB1_RPS19BP1_SESN3 | FAS_ID2_CDH2_MMP2_RPS19BP1_SESN3 |
| FRAP1_TKT_CDH2_MMP2_RAPTOR | ATG12_CDH1_ID2_CDH2_MMP2_SESN3 |
| FRAP1_LC3_BECN1_CDH2_RAPTOR | FRAP1_LC3_TKT_CDH2_STAT3_TWIST1 |
| ATG12_ID2_CDH2_FASLG_SESN3 | CDH1_ID2_CDH2_MMP2_RPS19BP1_SESN3 |
| ATG7_FRAP1_TKT_CASP3_CDH2 | FAS_FRAP1_LC3_CDH2_KIAA1967_RPS19BP1 |
| FRAP1_TKT_CASP3_CDH2_MMP2 | FRAP1_LC3_CDH2_HMGB1_STAT3_TWIST1 |
| FRAP1_LC3_CDH2_HMGB1_TWIST1 | ATG12_ID2_CDH2_HMGB2_MMP2_SESN3 |
| FRAP1_LC3_TKT_CDH2_KIAA1967 | ATG12_FAS_ID2_CDH2_MMP2_SESN3 |
| ATG7_ID2_CDH2_RPS19BP1_TP63 | TKT_ID2_CDH2_MMP2_RPS19BP1_SESN3 |
| BAX_FRAP1_TKT_BECN1_CDH2 | BAX_FAS_FRAP1_LC3_TKT_CDH2 |
| ATG3_FRAP1_TKT_CASP3_CDH2 | ATG12_ID2_CDH2_MMP2_RPS19BP1_SESN3 |
| CDH1_ID2_MMP9_TCF3_CDH2 | CDH1_ID2_MMP9_TCF3_CDH2_SESN3 |

| Combinations of seven types | Combinations of eight types |
|---|---|
| AKT1_ATG12_FAS_CDH2_RPS19BP1_STAT3_TP63 | AKT1_ATG12_FAS_CDH2_RPS19BP1_SESN2_STAT3_TP63 |
| AKT1_ATG12_FAS_BECN1_CDH2_STAT3_TP63 | AKT1_ATG12_FAS_BECN1_CDH2_RAPTOR_STAT3_TP63 |
| AKT1_ATG12_FAS_LC3_CDH2_STAT3_TP63 | AKT1_ATG12_FAS_BECN1_CDH2_LAMP2_STAT3_TP63 |
| AKT1_ATG12_CASP8_FAS_CDH2_STAT3_TP63 | AKT1_ATG12_FAS_LC3_CDH2_RPS19BP1_STAT3_TP63 |
| AKT1_FAS_CDH2_RPS19BP1_SESN2_STAT3_TP63 | AKT1_FAS_LC3_CDH2_HMGB1_RPS19BP1_STAT3_TP63 |
| AKT1_FAS_LC3_CDH2_RPS19BP1_STAT3_TP63 | AKT1_FAS_LC3_CDH2_RPS19BP1_SESN2_STAT3_TP63 |
| AKT1_ATG12_FAS_CASP3_CDH2_STAT3_TP63 | AKT1_ATG12_ATG7_FAS_CDH2_RPS19BP1_STAT3_TP63 |
| AKT1_FAS_BECN1_CDH2_RPS19BP1_STAT3_TP63 | AKT1_ATG7_FAS_BECN1_CDH2_RPS19BP1_STAT3_TP63 |
| AKT1_ATG12_FAS_LAMP1_CDH2_STAT3_TP63 | AKT1_ATG12_CASP8_FAS_CDH2_RPS19BP1_STAT3_TP63 |
| AKT1_ATG12_FAS_CDH2_HMGB2_STAT3_TP63 | AKT1_ATG12_FAS_CDH2_HMGB1_RPS19BP1_STAT3_TP63 |
| AIFM1_AKT1_ATG12_FAS_CDH2_STAT3_TP63 | AKT1_ATG12_FAS_TCF3_CDH2_RPS19BP1_STAT3_TP63 |
| AKT1_ATG12_FAS_CDH2_CIAP2_STAT3_TP63 | AKT1_ATG12_FAS_BECN1_CDH2_KIAA1967_STAT3_TP63 |
| AKT1_ATG12_FAS_CDH2_SESN2_STAT3_TP63 | AKT1_FAS_BECN1_CDH2_RAPTOR_RPS19BP1_STAT3_TP36 |
| AKT1_ATG12_FAS_NNMT_CDH2_STAT3_TP63 | AKT1_ATG12_FAS_CDH2_HMGB2_RPS19BP1_STAT3_TP63 |
| AKT1_FAS_CDH2_HMGB1_RPS19BP1_STAT3_TP63 | AKT1_ATG12_BCL2L1_FAS_BECN1_CDH2_STAT3_TP63 |
| AKT1_ATG12_FAS_CDH2_NAMPT_STAT3_TP63 | AKT1_CASP8_FAS_CDH2_RPS19BP1_SESN2_STAT3_TP63 |
| AKT1_ATG12_FAS_CDH2_SIRT1_STAT3_TP63 | AKT1_ATG12_FAS_LAMP1_LC3_CDH2_STAT3_TP63 |

TABLE 6-continued

| | |
|---|---|
| AKT1_FAS_LC3_BECN1_CDH2_STAT3_TP63 | AKT1_ATG12_CASP8_FAS_LC3_CDH2_STAT3_TP63 |
| AKT1_CASP8_FAS_BECN1_CDH2_STAT3_TP63 | AKT1_ATG12_FAS_CDH2_RAPTOR_RPS19BP1_STAT3_TP63 |
| AKT1_ATG12_DRAM_FAS_CDH2_STAT3_TP63 | AKT1_FAS_LC3_BECN1_CDH2_RPS19BP1_STAT3_TP63 |
| AKT1_ATG7_FAS_CDH2_RPS19BP1_STAT3_TP63 | AKT1_ATG12_FAS_NNMT_CDH2_RPS19BP1_STAT3_TP63 |
| AKT1_ATG12_FAS_BECN1_RPS19BP1_STAT3_TP63 | AKT1_ATG12_CASP8_FAS_BECN1_CDH2_STAT3_TP63 |
| AKT1_CASP8_FAS_CDH2_RPS19BP1_STAT3_TP63 | AKT1_ATG7_FAS_LC3_CDH2_RPS19BP1_STAT3_TP63 |
| AKT1_ATG12_FAS_CDH2_HMGB1_STAT3_TP63 | AKT1_ATG12_FAS_CDH2_NAMPT_RPS19BP1_STAT3_TP63 |
| ATG12_FAS_FRAP1_LC3_CDH2_STAT3_TP63 | AKT1_ATG12_CASP8_FAS_LAMP1_CDH2_STAT3_TP63 |
| AKT1_ATG12_FAS_XIAP_CDH2_STAT3_TP63 | AKT1_ATG12_FAS_NNMT_BECN1_CDH2_STAT3_TP63 |
| AKT1_ATG12_FAS_CDH2_LAMP2_STAT3_TP63 | AKT1_ATG12_FAS_LC3_BECN1_CDH2_STAT3_TP63 |
| AKT1_ATG12_ATG3_FAS_CDH2_STAT3_TP63 | AKT1_ATG12_FAS_LC3_CDH2_HMGB1_STAT3_TP63 |
| AKT1_ATG12_FAS_PTEN_CDH2_STAT3_TP63 | AKT1_ATG12_FAS_BECN1_CDH2_RPS19BP1_STAT3_TP63 |
| AKT1_ATG7_BECN1_CDH2_RPS19BP1_STAT3_TP63 | AKT1_ATG12_E2F1_FAS_BECN1_CDH2_STAT3_TP63 |
| AKT1_FAS_CASP3_CDH2_RPS19BP1_STAT3_TP63 | AKT1_ATG12_FAS_CDH1_BECN1_CDH2_STAT3_TP63 |
| AKT1_ATG7_FAS_LC3_CDH2_RPS19BP1_TP63 | AKT1_CASP8_FAS_LC3_CDH2_RPS19BP1_STAT3_TP63 |
| AKT1_FAS_LC3_CDH2_HMGB1_STAT3_TP63 | AKT1_ATG12_FAS_CASP3_CDH2_RPS19BP1_STAT3_TP63 |
| AKT1_ATG12_FAS_TKT_CDH2_STAT3_TP63 | AKT1_ATG12_FAS_CDH2_CIAP2_RPS19BP1_STAT3_TP63 |
| FAS_FRAP1_LC3_CASP3_CDH2_RPS19BP1_STAT3 | AKT1_FAS_CDH2_HMGB1_HMGB2_RPS19BP1_STAT3_TP63 |
| AKT1_FAS_CDH2_HMGB2_RPS19BP1_STAT3_TP63 | AKT1_ATG12_FAS_LC3_CASP3_CDH2_STAT3_TP63 |
| AKT1_FAS_TCF3_CDH2_RPS19BP1_STAT3_TP63 | AKT1_ATG12_ATG7_BECN1_CDH2_RPS19BP1_STAT3_TP63 |
| FAS_FRAP1_LC3_TKT_CDH2_FASLG_RAPTOR | AKT1_ATG12_E2F1_FAS_CDH2_RPS19BP1_STAT3_TP63 |
| AKT1_ATG12_E2F1_FAS_CDH2_STAT3_TP63 | AKT1_ATG12_DRAM_FAS_CDH2_RPS19BP1_STAT3_TP63 |
| AKT1_FAS_BECN1_CDH2_RAPTOR_STAT3_TP63 | AKT1_FAS_CASP3_CDH2_RPS19BP1_SESN2_STAT3_TP63 |
| AKT1_FAS_NNMT_BECN1_CDH2_STAT3_TP63 | AKT1_FAS_CDH2_HMGB2_RPS19BP1_SESN2_STAT3_TP63 |
| AKT1_ATG12_CDH2_HMGB1_RPS19BP1_STAT3_TP63 | AKT1_FAS_LC3_CASP3_CDH2_RPS19BP1_STAT3_TP63 |
| AKT1_FAS_BECN1_CDH2_LAMP2_STAT3_TP63 | AKT1_ATG12_FAS_LAMP1_BECN1_CDH2_STAT3_TP63 |
| FAS_FRAP1_LC3_CDH2_RPS19BP1_SESN1_STAT3 | AKT1_FAS_TKT_CDH2_RPS19BP1_SESN2_STAT3_TP63 |
| FAS_FRAP1_LC3_NNMT_CDH2_RPS19BP1_STAT3 | AKT1_ATG12_ATG3_FAS_CDH2_RPS19BP1_STAT3_TP63 |
| ID2_CDH2_HMGB1_HMGB2_MMP2_RPS19BP1_SESN3 | AKT1_ATG12_FAS_XIAP_CDH2_RPS19BP1_STAT3_TP63 |
| AKT1_ATG12_FAS_CDH2_RAPTOR_STAT3_TP63 | AKT1_ATG12_CASP8_FAS_NNMT_CDH2_STAT3_TP63 |
| FRAP1_LC3_TKT_BECN1_CASP3_CDH2_STAT3 | AKT1_ATG12_CASP8_FAS_CASP3_CDH2_STAT3_TP63 |
| FAS_FRAP1_LC3_CDH2_FASLG_RAPTOR_RPS19BP1 | AKT1_ATG12_FAS_CDH2_RPS19BP1_SIRT1_STAT3_TP63 |
| FAS_LC3_CDH2_HMGB1_RPS19BP1_STAT3_TWIST1 | AKT1_ATG12_BCL2L1_FAS_CDH2_RPS19BP1_STAT3_TP63 |
| AKT1_FAS_TKT_BECN1_CDH2_STAT3_TP63 | AKT1_ATG12_CASP8_FAS_CDH2_HMGB2_STAT3_TP63 |
| AKT1_CASP8_FAS_LC3_CDH2_STAT3_TP63 | AKT1_ATG12_FAS_LC3_NNMT_CDH2_STAT3_TP63 |
| AKT1_FAS_LC3_CASP3_CDH2_STAT3_TP63 | AIFM1_AKT1_ATG12_CASP8_FAS_CDH2_STAT3_TP63 |
| AKT1_FAS_LAMP1_BECN1_CDH2_STAT3_TP63 | AKT1_ATG7_FAS_CASP3_CDH2_RPS19BP1_STAT3_TP63 |
| AKT1_ATG12_ATG7_FAS_CDH2_RPS19BP1_TP63 | AKT1_ATG12_FAS_PTEN_CDH2_RPS19BP1_STAT3_TP63 |
| AKT1_ATG12_FAS_TCF3_CDH2_STAT3_TP63 | AKT1_ATG12_FAS_LAMP1_CDH2_RPS19BP1_STAT3_TP63 |
| AKT1_FAS_CDH2_NAMPT_RPS19BP1_STAT3_TP63 | AKT1_ATG12_CASP8_FAS_CDH2_CIAP2_STAT3_TP63 |
| CDH1_ID2_MMP9_TCF3_CDH2_RPS19BP1_SESN3 | AKT1_CDH1_ID2_MMP9_TCF3_CDH2_RPS19BP1_SESN3 |

Preferably, the composition or kit is for predicting the prognosis of recurrence of the A2 group, and the genes are one or more selected from the genes or groups of genes described in the following Table 7.

TABLE 7

| One type | Combinations of two types | Combinations of three types | Combinations of four types |
|---|---|---|---|
| TKT | PRKAA1_LAMP2 | LC3_SESN2_SIRT1 | ATG5_LC3_SESN2_SIRT1 |
| SESN2 | TKT_SESN2 | BNIP3_PRKAA1_LAMP2 | ATG3_LC3_SESN2_SIRT1 |
| LAMP2 | ATG7_LAMP2 | ATG5_LC3_SESN2 | CSE1L_LC3_SESN2_SIRT1 |
| | LAMP2_SESN2 | BNIP3_LC3_SESN2 | ATG5_CSE1L_LC3_SESN2 |
| | AKT1_PRKAA1 | ATG7_LC3_SESN2 | BNIP3_LC3_SESN2_SIRT1 |
| | SESN2_SIRT1 | AKT1_PRKAA1_LAMP2 | FRAP1_LC3_SESN2_SIRT1 |
| | TKT_VEGF | ATG7_TKT_SESN2 | AKT1_ATG3_PRKAA1_LAMP2 |
| | ATG7_TKT | DRAM_LC3_SESN2 | ATG3_ATG5_LC3_SESN2 |
| | TKT_LAMP2 | PRKAA1_AGER_LAMP2 | ATG7_LC3_SESN2_SIRT1 |
| | BHLHE41_SESN2 | PRKAA1_TKT_LAMP2 | BNIP3_CSE1L_LC3_SESN2 |
| | TKT_BHLHE41 | ATG7_TKT_LAMP2 | TKT_LAMP2_SESN2_SIRT1 |
| | ATG5_SESN2 | TKT_LAMP2_SESN2 | CIAP2_LAMP2_SESN2_SIRT1 |
| | LAMP1_SESN2 | TKT_LAMP2_VEGF | ATG12_TKT_LAMP2_SESN2 |
| | CSE1L_LAMP2 | ATG12_LC3_SESN2 | ATG7_TKT_LAMP2_SESN2 |
| | ATG12_SESN2 | ATG7_LAMP2_SESN2 | AKT1_ATG7_PRKAA1_LAMP2 |
| | AKT1_TKT | TKT_SESN2_SIRT1 | ATG5_BNIP3_LC3_SESN2 |
| | E2F1_SESN2 | E2F1_LC3_SESN2 | ATG3_BNIP3_LC3_SESN2 |
| | ATG3_LAMP2 | LC3_SESN2_UVRAG | AKT1_PRKAA1_LAMP2_UVRAG |
| | BNIP3_SESN2 | PRKAA1_CCNG2_LAMP2 | DRAM_LC3_SESN2_SIRT1 |
| | LC3_SESN2 | AKT1_ATG7_TKT | ATG7_CSE1L_LC3_SESN2 |
| | TWIST1_VEGF | ATG5_PRKAA1_LAMP2 | ATG7_FRAP1_LC3_SESN2 |
| | ATG7_LC3 | ATG3_LAMP2_SESN2 | BNIP3_PRKAA1_LAMP2_SESN2 |
| | CSE1L_SESN2 | BNIP3_TKT_SESN2 | ATG5_ATG7_LC3_SESN2 |
| | ATG5_LC3 | LAMP2_SESN2_SIRT1 | PRKAA1_TKT_LAMP2_SESN2 |
| | ATG7_SESN2 | ATG7_PRKAA1_LAMP2 | ATG3_ATG7_LC3_SESN2 |
| | LC3_ULK1 | LAMP1_LC3_SESN2 | BNIP3_PRKAA1_AGER_LAMP2 |
| | ATG3_TKT | ATG12_PRKAA1_LAMP2 | E2F1_LC3_SESN2_SIRT1 |
| | DRAM_SESN2 | CASP8_PRKAA1_LAMP2 | LC3_ID2_SESN2_SIRT1 |

TABLE 7-continued

| | | |
|---|---|---|
| PRKAA1_TKT | AIFM1_TKT_SESN2 | LC3_NAMPT_SESN2_SIRT1 |
| BHLHE41_LAMP2 | FRAP1_SESN2_SIRT1 | ATG5_FRAP1_LC3_SESN2 |
| LAMP2_VEGF | PRKAA1_HMGB1_LAMP2 | ATG7_BNIP3_LC3_SESN2 |
| AKT1_VEGF | LC3_BHLHE41_SESN2 | LC3_RPS19BP1_SESN2_SIRT1 |
| TKT_CIAP2 | ATG12_TKT_SESN2 | AKT1_ATG7_TKT_SESN2 |
| CSE1L_BHLHE41 | CSE1L_LAMP2_SESN2 | BCL2L1_BNIP3_PRKAA1_LAMP2 |
| LC3_BHLHE41 | PRKAA1_CASP3_LAMP2 | CSE1L_DRAM_LC3_SESN2 |
| LC3_SIRT1 | PRKAA1_LAMP2_RAGE | DIABLO_LC3_SESN2_SIRT1 |
| CSE1L_LAMP1 | PRKAA1_LAMP2_SESN2 | LC3_SESN2_SIRT1_STAT3 |
| TKT_RPS19BP1 | TKT_CIAP2_SESN2 | ATG12_ATG5_LC3_SESN2 |
| CBS_TKT | BCL2L1_PRKAA1_LAMP2 | BNIP3_PRKAA1_TCF3_LAMP2 |
| CSE1L_BECN1 | DIABLO_PRKAA1_LAMP2 | LC3_SESN2_SIRT1_UVRAG |
| TKT_CDH1 | PRKAA1_CDH1_LAMP2 | BNIP3_PRKAA1_MMP9_LAMP2 |
| TKT_HMGB1 | CBS_PRKAA1_LAMP2 | AKT1_LC3_SESN2_SIRT1 |
| TKT_RAGE | CSE1L_SESN2_SIRT1 | AKT1_PRKAA1_CDH1_LAMP2 |
| AIFM1_SESN2 | ATG3_PRKAA1_LAMP2 | CSE1L_LAMP1_LC3_SESN2 |
| ATG7_TWIST1 | PRKAA1_FASLG_LAMP2 | ATG7_PRKAA1_TKT_LAMP2 |
| BHLHE41_NAMPT | PRKAA1_ID2_LAMP2 | KIAA1967_LAMP2_SESN2_SIRT1 |
| BNIP3_LC3 | PRKAA1_LAMP2_SATB1 | LC3_SESN2_SESN3_SIRT1 |
| PRKAA1_SESN2 | PRKAA1_LAMP2_SESN1 | BNIP3_PRKAA1_HMGB1_LAMP2 |
| ATG7_NAMPT | AKT1_ATG7_PTEN | CSE1L_LC3_SESN2_UVRAG |
| BECN1_SESN2 | ATG7_TKT_BHLHE41 | LC3_MMP9_SESN2_SIRT1 |
| TKT_HMGB2 | PRKAA1_LAMP2_MMP2 | ATG3_LAMP2_SESN2_SIRT1 |
| TKT_SIRT1 | CSE1L_LAMP1_SESN2 | BNIP3_PRKAA1_CCNG2_LAMP2 |
| ATG5_CSE1L | PRKAA1_LAMP2_SESN3 | BNIP3_PRKAA1_LAMP2_SATB1 |
| SESN2_UVRAG | ATG3_TKT_SESN2 | BNIP3_PRKAA1_LAMP2_SESN1 |
| TKT_CASP3 | ATG5_CSE1L_SESN2 | ATG5_DRAM_LC3_SESN2 |
| TKT_CDH2 | ATG5_CSE1L_LC3 | BNIP3_PRKAA1_CASP3_LAMP2 |
| TKT_MMP2 | FRAP1_PRKAA1_LAMP2 | BNIP3_FRAP1_LC3_SESN2 |

| Combinations of five types | Combinations of six types |
|---|---|
| CIAP2_FASLG_LAMP2_SESN2_SIRT1 | LC3_CIAP2_FASLG_LAMP2_SESN2_SIRT1 |
| ATG3_ATG5_LC3_SESN2_SIRT1 | CCNG2_CIAP2_FASLG_LAMP2_SESN2_SIRT1 |
| ATG3_FRAP1_LC3_SESN2_SIRT1 | NNMT_CIAP2_FASLG_LAMP2_SESN2_SIRT1 |
| ATG7_FRAP1_LC3_SESN2_SIRT1 | CIAP2_FASLG_LAMP2_MMP2_SESN2_SIRT1 |
| TKT_CIAP2_LAMP2_SESN2_SIRT1 | AGER_CIAP2_FASLG_LAMP2_SESN2_SIRT1 |
| ATG5_FRAP1_LC3_SESN2_SIRT1 | CIAP2_FASLG_LAMP2_SESN1_SESN2_SIRT1 |
| ATG5_BNIP3_LC3_SESN2_SIRT1 | CIAP2_FASLG_HMGB1_LAMP2_SESN2_SIRT1 |
| TKT_CDH1_LAMP2_SESN2_SIRT1 | CIAP2_FASLG_LAMP2_NAMPT_SESN2_SIRT1 |
| CSE1L_FRAP1_LC3_SESN2_SIRT1 | AKT1_CIAP2_FASLG_LAMP2_SESN2_SIRT1 |
| ATG3_BNIP3_LC3_SESN2_SIRT1 | ID2_CIAP2_FASLG_LAMP2_SESN2_SIRT1 |
| ATG5_CSE1L_LC3_SESN2_SIRT1 | FAS_CIAP2_FASLG_LAMP2_SESN2_SIRT1 |
| ATG3_LC3_LAMP2_SESN2_SIRT1 | CIAP2_FASLG_LAMP2_SESN2_SESN3_SIRT1 |
| BNIP3_FRAP1_LC3_SESN2_SIRT1 | TCF3_CIAP2_FASLG_LAMP2_SESN2_SIRT1 |
| BNIP3_PRKAA1_TKT_LAMP2_SESN2 | ATG3_ATG5_FRAP1_LC3_SESN2_SIRT1 |
| ATG12_TKT_LAMP2_SESN2_SIRT1 | ULK1_CIAP2_FASLG_LAMP2_SESN2_SIRT1 |
| ATG5_ATG7_LC3_SESN2_SIRT1 | BCL2_CIAP2_FASLG_LAMP2_SESN2_SIRT1 |
| ATG7_BNIP3_TKT_LAMP2_SESN2 | CIAP2_FASLG_LAMP2_RAGE_SESN2_SIRT1 |
| AKT1_ATG7_BNIP3_PRKAA1_LAMP2 | ATG5_CIAP2_FASLG_LAMP2_SESN2_SIRT1 |
| ATG3_ATG7_LC3_SESN2_SIRT1 | CASP3_CIAP2_FASLG_LAMP2_SESN2_SIRT1 |
| ATG3_ATG5_BNIP3_LC3_SESN2 | FRAP1_CIAP2_FASLG_LAMP2_SESN2_SIRT1 |
| BNIP3_CSE1L_LC3_SESN2_SIRT1 | MMP9_CIAP2_FASLG_LAMP2_SESN2_SIRT1 |
| ATG5_DRAM_LC3_SESN2_SIRT1 | CIAP2_FASLG_LAMP2_SATB1_SESN2_SIRT1 |
| AIFM1_CIAP2_LAMP2_SESN2_SIRT1 | ATG3_ATG7_FRAP1_LC3_SESN2_SIRT1 |
| ATG7_TKT_LAMP2_SESN2_SIRT1 | CDH2_CIAP2_FASLG_LAMP2_SESN2_SIRT1 |
| ATG5_CSE1L_FRAP1_LC3_SESN2 | LAMP1_CIAP2_FASLG_LAMP2_SESN2_SIRT1 |
| ATG7_LC3_NAMPT_SESN2_SIRT1 | TKT_CIAP2_FASLG_LAMP2_SESN2_SIRT1 |
| ATG5_E2F1_LC3_SESN2_SIRT1 | ATG7_LC3_FASLG_LAMP2_SESN2_SIRT1 |
| BNIP3_CSE1L_FRAP1_LC3_SESN2 | ATG3_ATG7_LC3_LAMP2_SESN2_SIRT1 |
| ATG7_LC3_LAMP2_SESN2_SIRT1 | ATG3_BNIP3_FRAP1_LC3_SESN2_SIRT1 |
| AIFM1_BNIP3_PRKAA1_LAMP2_SESN2 | ATG5_ATG7_FRAP1_LC3_SESN2_SIRT1 |
| ATG12_BNIP3_TKT_LAMP2_SESN2 | ATG3_ATG5_BNIP3_LC3_SESN2_SIRT1 |
| CIAP2_KIAA1967_LAMP2_SESN2_SIRT1 | E2F1_CIAP2_FASLG_LAMP2_SESN2_SIRT1 |
| ATG12_ATG5_BNIP3_LC3_SESN2 | ATG3_BNIP3_LC3_LAMP2_SESN2_SIRT1 |
| ATG3_ATG7_LC3_LAMP2_SESN2 | ATG5_BNIP3_FRAP1_LC3_SESN2_SIRT1 |
| ATG12_TKT_CIAP2_LAMP2_SESN2 | ATG7_BNIP3_FRAP1_LC3_SESN2_SIRT1 |
| ATG5_BNIP3_CSE1L_LC3_SESN2 | TKT_CDH1_CIAP2_LAMP2_SESN2_SIRT1 |
| AKT1_ATG7_PRKAA1_TKT_LAMP2 | ATG5_BNIP3_E2F1_LC3_SESN2_SIRT1 |
| ATG3_LC3_NAMPT_SESN2_SIRT1 | ATG3_ATG7_LC3_NAMPT_SESN2_SIRT1 |
| ATG3_CSE1L_LC3_SESN2_SIRT1 | AIFM1_CIAP2_FASLG_LAMP2_SESN2_SIRT1 |
| ATG3_ATG7_FRAP1_LC3_SESN2 | ATG5_CSE1L_FRAP1_LC3_SESN2_SIRT1 |
| ATG5_LC3_ID2_SESN2_SIRT1 | CBS_TKT_CIAP2_LAMP2_SESN2_SIRT1 |
| BNIP3_E2F1_LC3_SESN2_SIRT1 | ATG3_ATG5_LC3_ID2_SESN2_SIRT1 |
| ATG3_LC3_ID2_SESN2_SIRT1 | AIFM1_TKT_CIAP2_LAMP2_SESN2_SIRT1 |
| ATG7_CSE1L_FRAP1_LC3_SESN2 | ATG3_DRAM_FRAP1_LC3_SESN2_SIRT1 |
| AIFM1_IKT_LAMP2_SESN2_SIRT1 | ATG3_ATG5_E2F1_LC3_SESN2_SIRT1 |

TABLE 7-continued

| | |
|---|---|
| LC3_CIAP2_LAMP2_SESN2_SIRT1 | ATG7_BNIP3_LC3_LAMP2_SESN2_SIRT1 |
| ATG12_TKT_CDH1_LAMP2_SESN2 | ATG3_ATG5_LC3_SESN2_SIRT1_STAT3 |
| ATG5_LC3_SESN2_SIRT1_STAT3 | AIFM1_AKT1_LAMP2_SESN2_SIRT1_UVRAG |
| ATG3_DRAM_LC3_SESN2_SIRT1 | AKT1_ATG7_TKT_LAMP2_SESN2_SIRT1 |
| ATG5_DIABLO_LC3_SESN2_SIRT1 | ATG3_ATG5_LC3_NAMPT_SESN2_SIRT1 |
| ATG7_BNIP3_LC3_SESN2_SIRT1 | ATG3_ATG5_DIABLO_LC3_SESN2_SIRT1 |
| CDH2_CIAP2_LAMP2_SESN2_SIRT1 | TKT_CDH1_HMGB1_LAMP2_SESN2_SIRT1 |
| ATG3_ATG5_FRAP1_LC3_SESN2 | ATG3_ATG5_LC3_LAMP2_SESN2_SIRT1 |
| DRAM_TKT_LAMP2_SESN2_SIRT1 | ATG5_DRAM_FRAP1_LC3_SESN2_SIRT1 |
| ATG12_ATG3_TKT_LAMP2_SESN2 | BNIP3_CSE1L_FRAP1_LC3_SESN2_SIRT1 |
| ATG3_LC3_SESN2_SIRT1_STAT3 | AKT1_ATG3_ATG5_LC3_SESN2_SIRT1 |
| ATG5_LC3_SESN2_SIRT1_UVRAG | AIFM1_BNIP3_PRKAA1_TKT_LAMP2_SESN2 |
| | TKT_CDH1_ID2_MMP9_TCF3_SESN2 |

| Combinations of seven types | Combinations of eight types |
|---|---|
| ATG3_ATG7_LC3_FASLG_LAMP2_SESN2_SIRT1 | ATG3_ATG7_LC3_ID2_FASLG_LAMP2_SESN2_SIRT1 |
| MMP9_CCNG2_CIAP2_FASLG_LAMP2_SESN2_SIRT1 | FRAP1_LC3_CIAP2_FASLG_LAMP2_NAMPT_SESN2_SIRT1 |
| FRAP1_LC3_CIAP2_FASLG_LAMP2_SESN2_SIRT1 | FRAP1_LC3_CIAP2_FASLG_LAMP2_MMP2_SESN2_SIRT1 |
| ATG7_BNIP3_LC3_FASLG_LAMP2_SESN2_SIRT1 | MMP9_CCNG2_CIAP2_FASLG_LAMP2_NAMPT_SESN2_SIRT1 |
| CCNG2_CIAP2_FASLG_LAMP2_NAMPT_SESN2_SIRT1 | FRAP1_LC3_CCNG2_CIAP2_FASLG_LAMP2_SESN2_SIRT1 |
| LC3_CIAP2_FASLG_LAMP2_MMP2_SESN2_SIRT1 | ATG5_FRAP1_LC3_CIAP2_FASLG_LAMP2_SESN2_SIRT1 |
| CCNG2_CIAP2_FASLG_LAMP2_MMP2_SESN2_SIRT1 | FRAP1_LC3_CIAP2_FASLG_HMGB1_LAMP2_SESN2_SIRT1 |
| LC3_NNMT_CIAP2_FASLG_LAMP2_SESN2_SIRT1 | CCNG2_CIAP2_FASLG_LAMP2_MMP2_NAMPT_SESN2_SIRT1 |
| LC3_CCNG2_CIAP2_FASLG_LAMP2_SESN2_SIRT1 | LC3_CCNG2_CIAP2_FASLG_LAMP2_MMP2_SESN2_SIRT1 |
| TCF3_CCNG2_CIAP2_FASLG_LAMP2_SESN2_SIRT1 | LC3_NNMT_CIAP2_FASLG_LAMP2_MMP2_SESN2_SIRT1 |
| LC3_CIAP2_FASLG_LAMP2_NAMPT_SESN2_SIRT1 | FRAP1_LC3_AGER_CIAP2_FASLG_LAMP2_SESN2_SIRT1 |
| FAS_CCNG2_CIAP2_FASLG_LAMP2_SESN2_SIRT1 | LC3_CCNG2_CIAP2_FASLG_LAMP2_NAMPT_SESN2_SIRT1 |
| CIAP2_FASLG_LAMP2_NAMPT_SESN1_SESN2_SIRT1 | ATG3_ATG7_LC3_FASLG_LAMP2_SESN2_SIRT1_STAT3 |
| CIAP2_FASLG_LAMP2_MMP2_SESN1_SESN2_SIRT1 | NNMT_MMP9_CCNG2_CIAP2_FASLG_LAMP2_SESN2_SIRT1 |
| ATG3_ATG5_BNIP3_FRAP1_LC3_SESN2_SIRT1 | FRAP1_AGER_CIAP2_FASLG_LAMP2_NAMPT_SESN2_SIRT1 |
| NNMT_CCNG2_CIAP2_FASLG_LAMP2_SESN2_SIRT1 | FRAP1_CCNG2_CIAP2_FASLG_LAMP2_NAMPT_SESN2_SIRT1 |
| LC3_CIAP2_FASLG_LAMP2_SATB1_SESN2_SIRT1 | CIAP2_FASLG_LAMP2_MMP2_NAMPT_SESN1_SESN2_SIRT1 |
| ATG5_LC3_CIAP2_FASLG_LAMP2_SESN2_SIRT1 | MMP9_CCNG2_CIAP2_FASLG_HMGB1_LAMP2_SESN2_SIRT1 |
| LC3_TCF3_CIAP2_FASLG_LAMP2_SESN2_SIRT1 | TCF3_CCNG2_CIAP2_FASLG_LAMP2_MMP2_SESN2_SIRT1 |
| AGER_CIAP2_FASLG_LAMP2_NAMPT_SESN2_SIRT1 | TCF3_CCNG2_CIAP2_FASLG_LAMP2_NAMPT_SESN2_SIRT1 |
| CCNG2_CIAP2_FASLG_LAMP2_SATB1_SESN2_SIRT1 | CCNG2_CIAP2_FASLG_LAMP2_NAMPT_SATB1_SESN2_SIRT1 |
| AKT1_CCNG2_CIAP2_FASLG_LAMP2_SESN2_SIRT1 | FAS_CCNG2_CIAP2_FASLG_LAMP2_NAMPT_SESN2_SIRT1 |
| LC3_ULK1_CIAP2_FASLG_LAMP2_SESN2_SIRT1 | NNMT_CCNG2_CIAP2_FASLG_LAMP2_MMP2_SESN2_SIRT1 |
| CCNG2_CIAP2_FASLG_LAMP2_SESN2_SESN3_SIRT1 | ATG3_ATG7_BNIP3_LC3_FASLG_LAMP2_SESN2_SIRT1 |
| NNMT_CIAP2_FASLG_HMGB1_LAMP2_SESN2_SIRT1 | AKT1_MMP9_CCNG2_CIAP2_FASLG_LAMP2_SESN2_SIRT1 |
| ATG3_ATG5_ATG7_FRAP1_LC3_SESN2_SIRT1 | LC3_CCNG2_CIAP2_FASLG_LAMP2_SATB1_SESN2_SIRT1 |
| NNMT_CIAP2_FASLG_LAMP2_MMP2_SESN2_SIRT1 | MMP9_CCNG2_CIAP2_FASLG_LAMP2_MMP2_SESN2_SIRT1 |
| LC3_CIAP2_FASLG_HMGB1_LAMP2_SESN2_SIRT1 | FRAP1_LC3_NNMT_CIAP2_FASLG_LAMP2_SESN2_SIRT1 |
| AGER_CIAP2_FASLG_LAMP2_MMP2_SESN2_SIRT1 | FRAP1_MMP9_CCNG2_CIAP2_FASLG_LAMP2_SESN2_SIRT1 |
| BCL2_LC3_CIAP2_FASLG_LAMP2_SESN2_SIRT1 | ATG7_BNIP3_LC3_ID2_FASLG_LAMP2_SESN2_SIRT1 |
| BCL2_CCNG2_CIAP2_FASLG_LAMP2_SESN2_SIRT1 | ATG7_BNIP3_LC3_FASLG_LAMP2_SESN2_SIRT1_STAT3 |
| ULK1_CCNG2_CIAP2_FASLG_LAMP2_SESN2_SIRT1 | LC3_TCF3_CCNG2_CIAP2_FASLG_LAMP2_SESN2_SIRT1 |
| CCNG2_CIAP2_FASLG_HMGB1_LAMP2_SESN2_SIRT1 | CIAP2_FASLG_HMGB1_LAMP2_NAMPT_SESN_1_SESN2_SIRT1 |
| LC3_CDH2_CIAP2_FASLG_LAMP2_SESN2_SIRT1 | CCNG2_CIAP2_FASLG_LAMP2_MMP2_SESN2_SESN3_SIRT1 |
| LC3_CASP3_CIAP2_FASLG_LAMP2_SESN2_SIRT1 | ATG3_ATG7_LC3_BECN1_FASLG_LAMP2_SESN2_SIRT1 |
| AKT1_NNMT_CIAP2_FASLG_LAMP2_SESN2_SIRT1 | ATG3_ATG7_FRAP1_LC3_FASLG_LAMP2_SESN2_SIRT1 |
| FRAP1_CCNG2_CIAP2_FASLG_LAMP2_SESN2_SIRT1 | NNMT_CCNG2_CIAP2_FASLG_LAMP2_NAMPT_SESN2_SIRT1 |
| FRAP1_AGER_CIAP2_FASLG_LAMP2_SESN2_SIRT1 | ATG7_BNIP3_LC3_FASLG_LAMP2_SESN2_SESN3_SIRT1 |
| CASP3_CCNG2_CIAP2_FASLG_LAMP2_SESN2_SIRT1 | FRAP1_LC3_TCF3_CIAP2_FASLG_LAMP2_SESN2_SIRT1 |
| CIAP2_FASLG_HMGB1_LAMP2_SESN_1_SESN2_SIRT1 | FAS_CCNG2_CIAP2_FASLG_LAMP2_MMP2_SESN2_SIRT1 |
| LC3_AGER_CIAP2_FASLG_LAMP2_SESN2_SIRT1 | CCNG2_CIAP2_FASLG_HMGB1_LAMP2_NAMPT_SESN2_SIRT1 |
| CIAP2_FASLG_HMGB1_LAMP2_NAMPT_SESN2_SIRT1 | CCNG2_CIAP2_FASLG_LAMP2_NAMPT_SESN_1_SESN2_SIRT1 |
| ATG5_CCNG2_CIAP2_FASLG_LAMP2_SESN2_SIRT1 | ATG7_BNIP3_LC3_FASLG_LAMP2_SATB1_SESN2_SIRT1 |
| ID2_CCNG2_CIAP2_FASLG_LAMP2_SESN2_SIRT1 | BCL2_MMP9_CCNG2_CIAP2_FASLG_LAMP2_SESN2_SIRT1 |
| TCF3_AGER_CIAP2_FASLG_LAMP2_SESN2_SIRT1 | ULK1_MMP9_CCNG2_CIAP2_FASLG_LAMP2_SESN2_SIRT1 |
| FAS_LC3_CIAP2_FASLG_LAMP2_SESN2_SIRT1 | LC3_NNMT_CIAP2_FASLG_LAMP2_NAMPT_SESN2_SIRT1 |
| NNMT_CIAP2_FASLG_LAMP2_NAMPT_SESN2_SIRT1 | LC3_CIAP2_FASLG_LAMP2_MMP2_NAMPT_SESN2_SIRT1 |
| LAMP1_CCNG2_CIAP2_FASLG_LAMP2_SESN2_SIRT1 | BCL2_FRAP1_LC3_CIAP2_FASLG_LAMP2_SESN2_SIRT1 |
| CIAP2_FASLG_LAMP2_MMP2_SESN2_SESN3_SIRT1 | AKT1_CCNG2_CIAP2_FASLG_LAMP2_MMP2_SESN2_SIRT1 |
| TCF3_CIAP2_FASLG_LAMP2_SESN_1_SESN2_SIRT1 | ATG7_BNIP3_LC3_MMP9_FASLG_LAMP2_SESN2_SIRT1 |
| FRAP1_CIAP2_FASLG_HMGB1_LAMP2_SESN2_SIRT1 | MMP9_AGER_CCNG2_CIAP2_FASLG_LAMP2_SESN2_SIRT1 |
| ATG3_ATG7_BNIP3_FRAP1_LC3_SESN2_SIRT1 | FRAP1_LC3_ULK1_CIAP2_FASLG_LAMP2_SESN2_SIRT1 |
| AKT1_CIAP2_FASLG_LAMP2_MMP2_SESN2_SIRT1 | LC3_NNMT_CIAP2_FASLG_LAMP2_SATB1_SESN2_SIRT1 |
| NNMT_ID2_CIAP2_FASLG_LAMP2_SESN2_SIRT1 | CASP3_CCNG2_CIAP2_FASLG_LAMP2_NAMPT_SESN2_SIRT1 |
| NNMT_AGER_CIAP2_FASLG_LAMP2_SESN2_SIRT1 | LC3_CDH2_CIAP2_FASLG_LAMP2_NAMPT_SESN2_SIRT1 |
| ATG7_LC3_CDH1_FASLG_LAMP2_SESN2_SIRT1 | LC3_NNMT_CCNG2_CIAP2_FASLG_LAMP2_SESN2_SIRT1 |
| MMP9_AGER_CIAP2_FASLG_LAMP2_SESN2_SIRT1 | ATG3_ATG7_LC3_CDH1_FASLG_LAMP2_SESN2_SIRT1 |
| BNIP3_PRKAA1_CDH1_ID2_MMP9_TCF3_LAMP2 | TKT_CDH1_ID2_MMP9_TCF3_LAMP2_SESN2_SIRT1 |

Preferably, the composition or kit is for predicting the prognosis of survival of the A2 group, and the genes are one or more selected from the genes or groups of genes described in the following Table 8.

TABLE 8

| One type | Combinations of two types | Combinations of three types | Combinations of four types |
|---|---|---|---|
| BCL2L1 | BCL2L1_NNMT | BCL2L1_NNMT_PRKAA1 | ATG3_BCL2L1_NNMT_PRKAA1 |
| FAS | BCL2L1_E2F1 | BCL2L1_E2F1_PRKAA1 | BCL2L1_TKT_CASP3_SESN2 |
| LAMP1 | BCL2L1_TKT | ATG3_BCL2L1_PRKAA1 | BCL2L1_ID2_CASP3_SESN2 |
| BHLHE41 | FAS_LAMP1 | ATG3_BCL2L1_NNMT | ATG3_BCL2L1_E2F1_PRKAA1 |
| TKT | BCL2L1_PRKAA1 | ATG3_BCL2L1_E2F1 | BCL2L1_NNMT_PRKAA1_HMGB1 |
| LC3 | FAS_BHLHE41 | FAS_BHLHE41_SESN2 | BCL2L1_NNMT_PRKAA1_MMP2 |
| SESN2 | FAS_TKT | BCL2L1_PRKAA1_HMGB2 | BCL2L1_NNMT_PRKAA1_CDH1 |
| | BCL2L1_CASP3 | BCL2L1_CASP3_SESN2 | FAS_TKT_CASP3_SESN2 |
| | ATG3_BCL2L1 | BCL2L1_PRKAA1_TKT | BCL2L1_NNMT_PRKAA1_VEGF |
| | ATG7_BCL2L1 | FAS_CASP3_SESN2 | ATG7_BCL2L1_NNMT_PRKAA1 |
| | FAS_CASP3 | BCL2L1_TKT_CASP3 | BCL2L1_FRAP1_NNMT_PRKAA1 |
| | TKT_BHLHE41 | FAS_TKT_CASP3 | BCL2L1_NNMT_PRKAA1_ID2 |
| | BCL2L1_KIAA1967 | BCL2L1_E2F1_TKT | AIFM1_BCL2L1_NNMT_PRKAA1 |
| | FAS_PRKAA1 | BCL2L1_NNMT_TKT | BCL2L1_TKT_BHLHE41_CASP3 |
| | FAS_KIAA1967 | FAS_TKT_BHLHE41 | BCL2L1_NNMT_PRKAA1_CDH2 |
| | FAS_SESN2 | FAS_TKT_SESN2 | BCL2L1_CSE1L_NNMT_PRKAA1 |
| | BCL2L1_HMGB2 | FAS_LAMP1_BHLHE41 | BCL2L1_NNMT_PRKAA1_HMGB2 |
| | BCL2L1_VEGF | FAS_LAMP1_SESN2 | BCL2L1_CBS_NNMT_PRKAA1 |
| | BNIP3_FAS | ATG3_BCL2L1_TKT | FAS_TKT_SESN2_TP63 |
| | FAS_TWIST1 | ATG7_BCL2L1_PRKAA1 | BCL2L1_DRAM_NNMT_PRKAA1 |
| | BNIP3_TKT | DIABLO_FAS_BHLHE41 | BCL2L1_NNMT_PRKAA1_ULK1 |
| | BCL2L1_CSE1L | TKT_SESN2_TP63 | BNIP3_TKT_CASP3_SESN2 |
| | TKT_SESN2 | FAS_PRKAA1_TKT | ATG5_BCL2L1_NNMT_PRKAA1 |
| | BCL2L1_FRAP1 | ATG7_BCL2L1_NNMT | BCL2L1_DIABLO_NNMT_PRKAA1 |
| | LAMP1_SESN2 | BCL2L1_BNIP3_TKT | BCL2L1_NNMT_CASP3_SESN2 |
| | LC3_BHLHE41 | BNIP3_FAS_TKT | FAS_TKT_BHLHE41_CASP3 |
| | BCL2L1_BNIP3 | BCL2L1_NNMT_CASP3 | BCL2L1_NNMT_PRKAA1_TKT |
| | BCL2L1_LC3 | TKT_BHLHE41_CASP3 | BNIP3_FAS_TKT_CASP3 |
| | ATG5_BCL2L1 | ATG3_BCL2L1_CASP3 | ATG3_ATG7_BCL2L1_PRKAA1 |
| | BCL2L1_CBS | BCL2L1_PRKAA1_CASP3 | FAS_ID2_CASP3_SESN2 |
| | CSE1L_LAMP1 | BCL2L1_PRKAA1_MMP2 | BCL2L1_NNMT_PRKAA1_CASP3 |
| | E2F1_FAS | FAS_BHLHE41_CASP3 | ATG3_BCL2L1_PRKAA1_HMGB2 |
| | AIFM1_BCL2L1 | FAS_TKT_KIAA1967 | FAS_LC3_BHLHE41_SESN2 |
| | BHLHE41_SESN2 | FAS_TKT_TWIST1 | ATG3_BCL2L1_BNIP3_NNMT |
| | CASP8_FAS | BCL2L1_E2F1_NNMT | BCL2L1_CASP8_NNMT_PRKAA1 |
| | FAS_NAMPT | BCL2L1_FRAP1_NNMT | FAS_BHLHE41_CASP3_SESN2 |
| | FAS_TP63 | BCL2L1_TKT_BHLHE41 | BCL2L1_BNIP3_NNMT_TKT |
| | LAMP1_BHLHE41 | BCL2L1_TKT_SESN2 | DIABLO_FAS_BHLHE41_SESN2 |
| | ATG12_FAS | FAS_KIAA1967_SESN2 | ATG3_BCL2L1_PRKAA1_TKT |
| | BCL2L1_MMP2 | DIABLO_FAS_LAMP1 | BCL2L1_NNMT_PRKAA1_MMP9 |
| | BHLHE41_CASP3 | ATG3_BCL2L1_KIAA1967 | BNIP3_FAS_CASP3_SESN2 |
| | FAS_HMGB1 | ATG7_BCL2L1_E2F1 | FAS_LAMP1_BHLHE41_SESN2 |
| | FAS_VEGF | FAS_BHLHE41_SATB1 | BCL2L1_CASP3_SESN1_SESN2 |
| | LAMP1_TCF3 | ATG3_ATG7_BCL2L1 | BCL2L1_NNMT_PRKAA1_SIRT1 |
| | BCL2L1_ULK1 | ATG7_BCL2L1_TKT | DIABLO_FAS_LAMP1_BHLHE41 |
| | FAS_LC3 | BCL2L1_BNIP3_NNMT | FAS_TKT_CASP3_SIRT1 |
| | NNMT_BHLHE41 | BCL2L1_PRKAA1_VEGF | E2F1_FAS_BHLHE41_SESN2 |
| | BCL2L1_FAS | BCL2L1_BHLHE41_CASP3 | FAS_TKT_CASP3_FASLG |
| | TKT_TP63 | FAS_SESN2_TP63 | FAS_TKT_HMGB1_SESN2 |
| | AKT1_BCL2L1 | TKT_BHLHE41_TP63 | FAS_CASP3_HMGB1_SESN2 |
| | ATG12_BCL2L1 | AIFM1_BCL2L1_NNMT | BAX_BCL2L1_NNMT_PRKAA1 |
| | FAS_HMGB2 | BCL2L1_CSE1L_NNMT | BCL2L1_E2F1_NNMT_PRKAA1 |
| | BCL2L1_ID2 | BCL2L1_E2F1_FRAP1 | ATG3_BCL2L1_PRKAA1_MMP2 |
| | BCL2L1_RPS19BP1 | BNIP3_FAS_CASP3 | FAS_TKT_KIAA1967_SESN2 |
| | TKT_SATB1 | FAS_TKT_SATB1 | BNIP3_FAS_TKT_TWIST1 |
| | FAS_XIAP | BCL2L1_CSE1L_PRKAA1 | ATG3_BCL2L1_BNIP3_TKT |
| | BCL2_BCL2L1 | BCL2L1_NNMT_VEGF | BCL2L1_NNMT_PRKAA1_PTEN |

| Combinations of five types | Combinations of six types |
|---|---|
| BCL2L1_NNMT_ID2_CASP3_SESN2 | BCL2L1_NNMT_ID2_CASP3_RAGE_SESN2 |
| BCL2L1_PTEN_TKT_CASP3_SESN2 | BCL2L1_NNMT_ID2_CASP3_HMGB1_SESN2 |
| ATG3_BCL2L1_NNMT_PRKAA1_HMGB1 | ATG3_BCL2L1_NNMT_PRKAA1_CASP3_SIRT1 |
| BCL2L1_TKT_XIAP_CASP3_SESN2 | BCL2L1_NNMT_ID2_CASP3_SESN1_SESN2 |
| BCL2L1_TKT_CASP3_HMGB1_SESN2 | BCL2L1_NNMT_PRKAA1_ID2_SESN1_SESN2 |
| ATG3_BCL2L1_NNMT_PRKAA1_ID2 | BCL2L1_BNIP3_TKT_XIAP_CASP3_SESN2 |
| BCL2L1_BNIP3_TKT_CASP3_SESN2 | FAS_TKT_CASP3_HMGB1_SESN2_TP63 |
| ATG3_BCL2L1_NNMT_PRKAA1_CDH1 | ATG3_BCL2L1_NNMT_PRKAA1_KIAA1967_SIRT1 |
| BCL2L1_TKT_CASP3_RAGE_SESN2 | ATG3_BCL2L1_NNMT_ID2_CASP3_SESN2 |
| ATG3_BCL2L1_NNMT_PRKAA1_ULK1 | ATG3_BCL2L1_NNMT_PRKAA1_HMGB1_VEGF |
| FAS_TKT_CASP3_HMGB1_SESN2 | BCL2L1_PTEN_TKT_CASP3_SESN1_SESN2 |
| FAS_TKT_CASP3_SESN2_TP63 | BCL2L1_NNMT_ID2_AGER_CASP3_SESN2 |
| ATG3_BCL2L1_FRAP1_NNMT_PRKAA1 | BCL2L1_NNMT_ID2_BECN1_CASP3_SESN2 |
| FAS_TKT_HMGB1_SESN2_TP63 | BCL2L1_PTEN_TKT_CASP3_HMGB1_SESN2 |
| AIFM1_ATG3_BCL2L1_NNMT_PRKAA1 | BCL2L1_PTEN_TKT_XIAP_CASP3_SESN2 |

TABLE 8-continued

| | |
|---|---|
| BCL2L1_ID2_CASP3_SESN1_SESN2 | ATG12_BCL2L1_NNMT_ID2_CASP3_SESN2 |
| ATG3_BCL2L1_NNMT_PRKAA1_MMP2 | BNIP3_TKT_XIAP_CASP3_RAGE_SESN2 |
| BCL2L1_TKT_CASP3_SESN1_SESN2 | BCL2L1_NNMT_ID2_CASP3_CCNG2_SESN2 |
| ATG3_BCL2L1_NNMT_PRKAA1_VEGF | AIFM1_BCL2L1_NNMT_ID2_CASP3_SESN2 |
| BCL2L1_TKT_ID2_CASP3_SESN2 | BCL2L1_PTEN_TKT_CASP3_RAGE_SESN2 |
| ATG3_BCL2L1_ID2_CASP3_SESN2 | BCL2L1_NNMT_ID2_CASP3_CDH2_SESN2 |
| BNIP3_TKT_XIAP_CASP3_SESN2 | BCL2L1_NNMT_ID2_CASP3_LAMP2_SESN2 |
| BCL2L1_NNMT_PRKAA1_ID2_SESN2 | ATG3_BCL2L1_BNIP3_NNMT_PRKAA1_FASLG |
| BCL2L1_NNMT_PRKAA1_HMGB1_VEGF | BCL2L1_NNMT_ID2_CASP3_SESN2_SESN3 |
| ATG3_BCL2L1_NNMT_PRKAA1_CDH2 | BCL2L1_CSE1L_NNMT_ID2_CASP3_SESN2 |
| ATG3_BCL2L1_LAMP1_NNMT_PRKAA1 | BAX_BCL2L1_NNMT_ID2_CASP3_SESN2 |
| BCL2L1_NNMT_ID2_SESN2_UVRAG | BCL2L1_NNMT_ID2_BHLHE41_CASP3_SESN2 |
| ATG3_ATG7_BCL2L1_NNMT_PRKAA1 | BCL2L1_NNMT_ID2_CASP3_MMP2_SESN2 |
| ATG3_BCL2L1_CBS_NNMT_PRKAA1 | BNIP3_PTEN_TKT_XIAP_CASP3_SESN2 |
| BCL2L1_ID2_CASP3_RPS19BP1_SESN2 | BCL2L1_BNIP3_TKT_ID2_CASP3_SESN2 |
| BNIP3_FAS_TKT_CASP3_SESN2 | BCL2L1_BNIP3_TKT_CASP3_SESN1_SESN2 |
| ATG3_BCL2L1_DRAM_NNMT_PRKAA1 | ATG3_ATG7_BCL2L1_NNMT_PRKAA1_HMGB1 |
| ATG7_BCL2L1_NNMT_PRKAA1_HMGB1 | BCL2L1_CASP8_NNMT_ID2_CASP3_SESN2 |
| BCL2L1_NNMT_PRKAA1_HMGB1_HMGB2 | ATG5_BCL2L1_NNMT_ID2_CASP3_SESN2 |
| BCL2L1_FAS_TKT_CASP3_SESN2 | BCL2L1_NNMT_CDH1_ID2_CASP3_SESN2 |
| ATG3_BCL2L1_CSE1L_NNMT_PRKAA1 | ATG3_BCL2L1_NNMT_PRKAA1_ID2_VEGF |
| ATG3_BCL2L1_DIABLO_NNMT_PRKAA1 | BCL2L1_NNMT_PRKAA1_ID2_CASP3_SESN2 |
| ATG3_BCL2L1_NNMT_PRKAA1_SIRT1 | BCL2L1_TKT_XIAP_CASP3_SESN1_SESN2 |
| BCL2L1_CASP8_ID2_CASP3_SESN2 | BCL2L1_NNMT_XIAP_ID2_CASP3_SESN2 |
| BCL2L1_DIABLO_ID2_CASP3_SESN2 | BCL2L1_DIABLO_NNMT_ID2_CASP3_SESN2 |
| BCL2L1_TKT_CASP3_SESN2_STAT3 | BCL2L1_TKT_XIAP_CASP3_HMGB1_SESN2 |
| BCL2L1_NNMT_PRKAA1_ID2_VEGF | BCL2L1_BNIP3_TKT_CASP3_RAGE_SESN2 |
| BCL2L1_ID2_CASP3_HMGB2_SESN2 | BCL2L1_TKT_BHLHE41_CASP3_SESN1_SESN2 |
| BCL2L1_TKT_CASP3_SESN2_SESN3 | BCL2L1_TKT_CASP3_HMGB1_RAGE_SESN2 |
| BCL2L1_TKT_CASP3_CCNG2_SESN2 | BCL2L1_PTEN_TKT_CASP3_CCNG2_SESN2 |
| FAS_TKT_CASP3_FASLG_SESN2 | BCL2L1_PRKAA1_TKT_XIAP_CASP3_SESN2 |
| FAS_TKT_CASP3_SESN2_SIRT1 | BCL2L1_TKT_CASP3_HMGB1_SESN1_SESN2 |
| BCL2L1_NNMT_ID2_KIAA1967_SESN2 | BNIP3_FAS_TKT_CASP3_HMGB1_SESN2 |
| ATG5_BCL2L1_ID2_CASP3_SESN2 | FAS_TKT_XIAP_CASP3_HMGB1_SESN2 |
| BCL2L1_NNMT_PRKAA1_CASP3_SIRT1 | BCL2L1_NNMT_ID2_SESN1_SESN2_UVRAG |
| BCL2L1_TKT_XIAP_BHLHE41_CASP3 | FAS_TKT_HMGB1_KIAA1967_SESN2_TP63 |
| FAS_TKT_XIAP_CASP3_SESN2 | BCL2L1_TKT_ID2_BHLHE41_CASP3_SESN2 |
| BCL2L1_CDH1_ID2_CASP3_SESN2 | BCL2L1_PTEN_TKT_ID2_CASP3_SESN2 |
| BCL2L1_TKT_CASP3_SESN2_SIRT1 | BCL2L1_ID2_CASP3_RAGE_RPS19BP1_SESN2 |
| ATG7_BCL2L1_NNMT_PRKAA1_ID2 | BNIP3_TKT_XIAP_CASP3_HMGB1_SESN2 |
| BCL2_BCL2L1_TKT_CASP3_SESN2 | ATG3_ATG7_BCL2L1_NNMT_PRKAA1_ID2 |
| BCL2L1_ID2_CASP3_CDH2_SESN2 | BCL2L1_BNIP3_NNMT_TKT_CASP3_SESN2 |

| Combinations of seven types | Combinations of eight types |
|---|---|
| BCL2L1_NNMT_PRKAA1_XIAP_ID2_CASP3_SESN2 | BCL2L1_NNMT_PRKAA1_PTEN_XIAP_ID2_CASP3_SESN2 |
| BCL2L1_PRKAA1_PTEN_TKT_XIAP_CASP3_SESN2 | BCL2L1_NNMT_ID2_BHLHE41_CASP3_SESN1_SESN2_SESN3 |
| BCL2L1_NNMT_ID2_BHLHE41_CASP3_SESN1_SESN2 | BCL2L1_PRKAA1_PTEN_TKT_XIAP_CASP3_HMGB1_SESN2 |
| BCL2L1_CASP8_NNMT_XIAP_ID2_CASP3_SESN2 | BCL2L1_PRKAA1_PTEN_TKT_XIAP_CASP3_SESN1_SESN2 |
| ATG3_BCL2L1_NNMT_ID2_CASP3_RAGE_SESN2 | BCL2L1_NNMT_PRKAA1_XIAP_ID2_CASP3_SESN2_SESN3 |
| BCL2L1_TKT_XIAP_BHLHE41_CASP3_SESN1_SESN2 | ATG3_BCL2L1_NNMT_PRKAA1_XIAP_ID2_CASP3_SESN2 |
| BCL2L1_BNIP3_TKT_XIAP_CASP3_SESN1_SESN2 | BCL2L1_NNMT_PRKAA1_XIAP_ID2_CASP3_SESN1_SESN2 |
| ATG3_BCL2L1_NNMT_PRKAA1_ID2_CASP3_SIRT1 | BCL2_BCL2L1_NNMT_ID2_BHLHE41_CASP3_SESN1_SESN2 |
| BCL2L1_CASP8_NNMT_ID2_CASP3_RAGE_SESN2 | BCL2L1_PRKAA1_PTEN_TKT_XIAP_CASP3_RAGE_SESN2 |
| BNIP3_PTEN_TKT_XIAP_CASP3_RAGE_SESN2 | BCL2L1_NNMT_XIAP_ID2_BHLHE41_CASP3_SESN1_SESN2 |
| ATG3_BCL2L1_NNMT_PRKAA1_ID2_SESN1_SESN2 | BCL2L1_NNMT_PRKAA1_XIAP_ID2_CASP3_HMGB1_SESN2 |
| BCL2L1_BNIP3_TKT_XIAP_CASP3_RPS19BP1_SESN2 | BCL2L1_PRKAA1_PTEN_TKT_XIAP_ID2_CASP3_SESN2 |
| BCL2L1_FRAP1_PTEN_TKT_XIAP_CASP3_SESN2 | BCL2L1_NNMT_PRKAA1_XIAP_ID2_CASP3_RAGE_SESN2 |
| BCL2L1_NNMT_ID2_BHLHE41_CASP3_SESN2_SESN3 | BCL2L1_PRKAA1_PTEN_TKT_XIAP_CASP3_SESN2_SESN3 |
| BCL2L1_CASP8_PTEN_TKT_XIAP_CASP3_SESN2 | BCL2L1_BNIP3_TKT_XIAP_CASP3_RPS19BP1_SESN1_SESN2 |
| BNIP3_PTEN_TKT_XIAP_ID2_CASP3_SESN2 | BCL2L1_NNMT_ID2_BHLHE41_CASP3_CCNG2_SESN_1_SESN2 |
| ATG3_BCL2L1_NNMT_PRKAA1_XIAP_CASP3_SIRT1 | BCL2L1_BNIP3_TKT_XIAP_ID2_CASP3_RPS19BP1_SESN2 |
| BCL2L1_BNIP3_NNMT_TKT_XIAP_CASP3_SESN2 | ATG3_BCL2L1_NNMT_PRKAA1_ID2_HMGB1_SESN1_SESN2 |
| BCL2_BCL2L1_TKT_BHLHE41_CASP3_SESN1_SESN2 | BCL2L1_TKT_XIAP_BHLHE41_CASP3_SESN1_SESN2_SESN3 |
| ATG3_BCL2L1_BNIP3_NNMT_PRKAA1_ID2_FASLG | BCL2L1_NNMT_ID2_BHLHE41_CASP3_HMGB1_SESN1_SESN2 |
| ATG3_BCL2L1_NNMT_ID2_CASP3_HMGB1_SESN2 | ATG3_BCL2L1_CASP8_NNMT_XIAP_ID2_CASP3_SESN2 |
| BCL2L1_NNMT_PRKAA1_ID2_CASP3_RAGE_SESN2 | ATG5_BCL2L1_NNMT_PRKAA1_XIAP_ID2_CASP3_SESN2 |
| BCL2L1_PRKAA1_TKT_XIAP_ID2_CASP3_SESN2 | BCL2L1_NNMT_PRKAA1_XIAP_ID2_CASP3_MMP2_SESN2 |
| BCL2L1_NNMT_PRKAA1_ID2_HMGB1_SESN1_SESN2 | BCL2L1_BNIP3_TKT_XIAP_CASP3_RAGE_RPS19BP1_SESN2 |
| BCL2L1_TKT_ID2_BHLHE41_CASP3_SESN1_SESN2 | BCL2L1_NNMT_ID2_BHLHE41_CASP3_CCNG2_SESN2_SESN3 |
| ATG3_BCL2L1_BNIP3_TKT_XIAP_CASP3_SESN2 | BCL2L1_PRKAA1_PTEN_TKT_XIAP_CASP3_MMP2_SESN2 |
| BCL2L1_BNIP3_NNMT_TKT_ID2_CASP3_SESN2 | BCL2L1_PRKAA1_PTEN_TKT_XIAP_CASP3_CCNG2_SESN2 |
| BCL2L1_NNMT_ID2_CASP3_HMGB1_RAGE_SESN2 | BCL2_BCL2L1_PRKAA1_PTEN_TKT_XIAP_CASP3_SESN2 |
| BCL2L1_PRKAA1_TKT_XIAP_CASP3_RAGE_SESN2 | ATG5_BCL2L1_PRKAA1_PTEN_TKT_XIAP_CASP3_SESN2 |
| BCL2L1_PRKAA1_TKT_XIAP_CASP3_HMGB1_SESN2 | BCL2L1_NNMT_PRKAA1_PTEN_TKT_XIAP_CASP3_SESN2 |
| BCL2L1_NNMT_XIAP_ID2_BHLHE41_CASP3_SESN2 | BCL2L1_NNMT_PRKAA1_XIAP_ID2_AGER_CASP3_SESN2 |
| BCL2L1_TKT_BHLHE41_CASP3_RAGE_SESN1_SESN2 | BCL2L1_NNMT_ID2_BHLHE41_CASP3_RAGE_SESN1_SESN2 |
| BCL2L1_NNMT_ID2_BHLHE41_CASP3_CCNG2_SESN2 | BCL2L1_NNMT_PRKAA1_XIAP_ID2_CASP3_LAMP2_SESN2 |
| BCL2L1_NNMT_ID2_BECN1_CASP3_RAGE_SESN2 | BCL2L1_BNIP3_NNMT_TKT_XIAP_ID2_CASP3_SESN2 |
| BCL2L1_BNIP3_TKT_XIAP_ID2_CASP3_SESN2 | ATG12_BCL2L1_NNMT_PRKAA1_XIAP_ID2_CASP3_SESN2 |

TABLE 8-continued

| | |
|---|---|
| BNIP3_TKT_XIAP_ID2_CASP3_RAGE_SESN2 | BCL2L1_NNMT_PRKAA1_XIAP_ID2_BECN1_CASP3_SESN2 |
| BCL2L1_PTEN_TKT_XIAP_CASP3_SESN1_SESN2 | BCL2L1_NNMT_PRKAA1_XIAP_ID2_CASP3_CDH2_SESN2 |
| BCL2L1_PTEN_TKT_CASP3_HMGB1_SESN1_SESN2 | AIFM1_BCL2L1_NNMT_PRKAA1_XIAP_ID2_CASP3_SESN2 |
| BCL2L1_NNMT_ID2_BHLHE41_CASP3_RAGE_SESN2 | ATG12_BCL2L1_PRKAA1_PTEN_TKT_XIAP_CASP3_SESN2 |
| AIFM1_BCL2L1_NNMT_ID2_CASP3_RAGE_SESN2 | BAX_BCL2L1_NNMT_PRKAA1_XIAP_ID2_CASP3_SESN2 |
| BCL2L1_NNMT_ID2_CASP3_CDH2_RAGE_SESN2 | BCL2L1_PRKAA1_PTEN_TKT_XIAP_CASP3_LAMP2_SESN2 |
| BCL2L1_NNMT_CDH1_ID2_CASP3_RAGE_SESN2 | BCL2L1_PRKAA1_PTEN_TKT_XIAP_AGER_CASP3_SESN2 |
| BCL2L1_NNMT_ID2_AGER_CASP3_RAGE_SESN2 | AKT1_BCL2L1_NNMT_PRKAA1_XIAP_ID2_CASP3_SESN2 |
| BNIP3_PTEN_TKT_XIAP_CASP3_SESN1_SESN2 | BAX_BCL2L1_PRKAA1_PTEN_TKT_XIAP_CASP3_SESN2 |
| BNIP3_PTEN_TKT_XIAP_CASP3_HMGB1_SESN2 | BCL2L1_PTEN_TKT_XIAP_BHLHE41_CASP3_SESN1_SESN2 |
| BNIP3_TKT_XIAP_CASP3_HMGB1_RAGE_SESN2 | BCL2L1_PRKAA1_PTEN_TKT_XIAP_BECN1_CASP3_SESN2 |
| BCL2L1_NNMT_ID2_CASP3_MMP2_RAGE_SESN2 | BCL2L1_PRKAA1_PTEN_TKT_XIAP_CASP3_CDH2_SESN2 |
| ATG5_BCL2L1_NNMT_PRKAA1_ID2_SESN1_SESN2 | BCL2L1_CASP8_NNMT_ID2_CASP3_HMGB1_RAGE_SESN2 |
| BCL2L1_BNIP3_TKT_ID2_CASP3_RPS19BP1_SESN2 | BCL2L1_CASP8_PTEN_TKT_XIAP_CASP3_SESN1_SESN2 |
| BCL2L1_NNMT_ID2_CASP3_RAGE_SESN1_SESN2 | ATG3_BCL2L1_BNIP3_NNMT_PRKAA1_ID2_FASLG_KIAA1967 |
| BCL2L1_NNMT_TKT_ID2_BHLHE41_CASP3_SESN2 | BCL2L1_NNMT_XIAP_ID2_BHLHE41_CASP3_SESN2_SESN3 |
| BCL2L1_PTEN_TKT_BHLHE41_CASP3_SESN1_SESN2 | BCL2L1_CSE1L_NNMT_PRKAA1_XIAP_ID2_CASP3_SESN2 |
| BCL2L1_CSE1L_NNMT_ID2_CASP3_RAGE_SESN2 | BCL2L1_NNMT_ID2_BHLHE41_CASP3_SESN1_SESN2_STAT3 |
| BCL2L1_PTEN_TKT_CASP3_RAGE_SESN1_SESN2 | BCL2L1_FRAP1_PTEN_TKT_XIAP_CASP3_HMGB1_SESN2 |
| BNIP3_TKT_XIAP_CASP3_CCNG2_RAGE_SESN2 | BCL2L1_NNMT_XIAP_BHLHE41_CASP3_SESN1_SESN2_SESN3 |
| ATG3_BCL2L1_BNIP3_TKT_CASP3_FASLG_SESN2 | BNIP3_PTEN_TKT_XIAP_CASP3_RAGE_SESN1_SESN2 |
| BCL2L1_BNIP3_E2F1_TKT_XIAP_CASP3_SESN2 | BCL2L1_NNMT_PRKAA1_ID2_HMGB1_HMGB2_SESN1_SESN2 |
| BCL2L1_CDH1_ID2_MMP9_TCF3_CASP3_SESN2 | BCL2L1_TKT_CDH1_ID2_MMP9_TCF3_CASP3_SESN2 |

Preferably, the composition or kit is for predicting the prognosis of disease-free survival of the A2 group, and the genes are one or more selected from the genes or groups of genes described in the following Table 9.

TABLE 9

| One type | Combinations of two types | Combinations of three types | Combinations of four types |
|---|---|---|---|
| SESN2 | TKT_SESN2 | ATG7_TKT_SESN2 | ATG5_CSE1L_FRAP1_SESN2 |
| TKT | BHLHE41_SESN2 | FRAP1_SESN2_SIRT1 | CSE1L_FRAP1_SESN2_SIRT1 |
| LAMP2 | LAMP2_SESN2 | ATG5_LC3_SESN2 | ATG7_TKT_LAMP2_SESN2 |
| BHLHE41 | ATG5_SESN2 | ATG5_FRAP1_SESN2 | ATG5_FRAP1_SESN2_SIRT1 |
| CSE1L | LAMP1_SESN2 | TKT_LAMP2_SESN2 | AKT1_ATG7_TKT_SESN2 |
| | SESN2_SIRT1 | AIFM1_IKT_SESN2 | ATG5_CSE1L_LC3_SESN2 |
| | E2F1_SESN2 | ATG5_CSE1L_SESN2 | FRAP1_LC3_SESN2_SIRT1 |
| | ATG12_SESN2 | LC3_SESN2_SIRT1 | CSE1L_FRAP1_LAMP1_SESN2 |
| | TKT_VEGF | ATG12_TKT_SESN2 | ATG7_TKT_SESN2_SESN3 |
| | CSE1L_BECN1 | CSE1L_LAMP1_SESN2 | ATG5_FRAP1_LC3_SESN2 |
| | CSE1L_SESN2 | TKT_HMGB2_SESN2 | ATG7_CSE1L_FRAP1_SESN2 |
| | ATG7_TKT | ATG5_TKT_SESN2 | CSE1L_LC3_SESN2_SIRT1 |
| | FASLG_SESN2 | TKT_CDH1_SESN2 | ATG5_LC3_SESN2_SIRT1 |
| | PRKAA1_LAMP2 | TKT_SESN2_SESN3 | ATG7_TKT_FASLG_SESN2 |
| | PRKAA1_SESN2 | TKT_SESN2_VEGF | ATG7_TKT_AGER_SESN2 |
| | TKT_BHLHE41 | CSE1L_BHLHE41_SESN2 | ATG7_TKT_HMGB1_SESN2 |
| | CSE1L_BHLHE41 | PRKAA1_TKT_SESN2 | ATG7_TKT_MMP2_SESN2 |
| | ATG7_SESN2 | ATG3_TKT_SESN2 | BNIP3_CSE1L_FRAP1_SESN2 |
| | CSE1L_LAMP2 | TKT_RPS19BP1_SESN2 | ATG5_ATG7_TKT_SESN2 |
| | FAS_SESN2 | CBS_TKT_SESN2 | ATG7_BCL2_TKT_SESN2 |
| | HMGB2_SESN2 | CSE1L_LAMP2_SESN2 | ATG7_BNIP3_TKT_SESN2 |
| | CSE1L_LAMP1 | TKT_SESN2_SIRT1 | FAS_FRAP1_SESN2_SIRT1 |
| | BECN1_SESN2 | AKT1_TKT_SESN2 | AIFM1_ATG7_TKT_SESN2 |
| | NNMT_SESN2 | CSE1L_SESN2_SIRT1 | ATG12_TKT_LAMP2_SESN2 |
| | AIFM1_SESN2 | TKT_CDH2_SESN2 | ATG7_TKT_BHLHE41_SESN2 |
| | BAX_SESN2 | BNIP3_TKT_SESN2 | ATG7_TKT_ID2_SESN2 |
| | DRAM_SESN2 | NNMT_TKT_SESN2 | CSE1L_DRAM_FRAP1_SESN2 |
| | CSE1L_ULK1 | TKT_AGER_SESN2 | CSE1L_FRAP1_SESN2_UVRAG |
| | KIAA1967_SESN2 | TKT_BHLHE41_SESN2 | ATG7_LAMP1_TKT_SESN2 |
| | SESN2_VEGF | TKT_HMGB1_SESN2 | ATG7_BCL2L1_TKT_SESN2 |
| | BNIP3_SESN2 | TKT_MMP2_SESN2 | ATG7_TKT_CCNG2_SESN2 |
| | SESN2_UVRAG | E2F1_TKT_SESN2 | CSE1L_E2F1_FRAP1_SESN2 |
| | TWIST1_VEGF | NAMPT_SESN2_SIRT1 | CSE1L_LAMP1_LC3_SESN2 |
| | PRKAA1_FASLG | TKT_KIAA1967_SESN2 | PRKAA1_TKT_LAMP2_SESN2 |
| | TKT_RPS19BP1 | DRAM_TKT_SESN2 | ATG7_CBS_TKT_SESN2 |
| | PRKAA1_TKT | TKT_CIAP2_SESN2 | ATG7_LC3_TKT_SESN2 |
| | ATG7_LAMP2 | TKT_MMP9_SESN2 | ATG7_NNMT_TKT_SESN2 |
| | AGER_SESN2 | ATG5_NAMPT_SESN2 | ATG7_TKT_CIAP2_SESN2 |
| | CDH2_SESN2 | ATG7_FRAP1_SESN2 | ATG7_TKT_SESN2_STAT3 |
| | AKT1_PRKAA1 | CSE1L_E2F1_SESN2 | ATG7_PTEN_TKT_SESN2 |
| | ULK1_SESN2 | LAMP1_TKT_SESN2 | ATG7_TKT_CASP3_SESN2 |
| | MMP2_SESN2 | LC3_TKT_SESN2 | ATG7_TKT_CDH2_SESN2 |
| | ATG5_CSE1L | TKT_CASP3_SESN2 | ATG7_TKT_HMGB2_SESN2 |
| | HMGB1_SESN2 | TKT_CCNG2_SESN2 | ATG7_TKT_NAMPT_SESN2 |
| | AKT1_TKT | TKT_ID2_SESN2 | ATG7_TKT_RAPTOR_SESN2 |
| | CBS_SESN2 | TKT_RAPTOR_SESN2 | ATG7_TKT_SESN2_SIRT1 |

TABLE 9-continued

| | | |
|---|---|---|
| FRAP1_SESN2 | TKT_XIAP_SESN2 | ATG7_FRAP1_LC3_SESN2 |
| CIAP2_SESN2 | BAX_TKT_SESN2 | ATG7_TKT_BECN1_SESN2 |
| BCL2_SESN2 | BCL2_TKT_SESN2 | ATG7_DIABLO_TKT_SESN2 |
| CCNG2_SESN2 | ATG12_CSE1L_SESN2 | ATG7_FRAP1_SESN2_SIRT1 |
| BCL2L1_SESN2 | BCL2L1_TKT_SESN2 | ATG12_CSE1L_FRAP1_SESN2 |
| CSE1L_UVRAG | CASP8_TKT_SESN2 | ATG7_TKT_XIAP_SESN2 |
| RAPTOR_SESN2 | DIABLO_TKT_SESN2 | ATG7_E2F1_TKT_SESN2 |
| XIAP_SESN2 | FAS_BHLHE41_SESN2 | ATG7_TKT_MMP9_SESN2 |
| CASP3_SESN2 | FRAP1_TKT_SESN2 | ATG7_TKT_RAGE_SESN2 |
| CASP8_SESN2 | PTEN_TKT_SESN2 | ATG3_ATG7_TKT_SESN2 |
| LC3_SESN2 | TKT_RAGE_SESN2 | ATG7_CSE1L_LC3_SESN2 |

| Combinations of five types | Combinations of six types |
|---|---|
| ATG5_CSE1L_FRAP1_LC3_SESN2 | ATG5_CSE1L_FRAP1_LC3_SESN2_SIRT1 |
| CSE1L_FRAP1_LC3_SESN2_SIRT1 | ATG3_ATG5_FRAP1_LC3_SESN2_SIRT1 |
| ATG5_FRAP1_LC3_SESN2_SIRT1 | ATG5_ATG7_FRAP1_LC3_SESN2_SIRT1 |
| ATG5_CSE1L_FRAP1_SESN2_SIRT1 | ATG3_ATG5_CSE1L_FRAP1_LC3_SESN2 |
| ATG7_CSE1L_FRAP1_LC3_SESN2 | ATG3_CSE1L_FRAP1_LC3_SESN2_SIRT1 |
| ATG7_FRAP1_LC3_SESN2_SIRT1 | ATG7_CSE1L_FRAP1_LC3_SESN2_SIRT1 |
| ATG5_CSE1L_FRAP1_LAMP1_SESN2 | ATG5_ATG7_CSE1L_FRAP1_LC3_SESN2 |
| AKT1_ATG7_TKT_LAMP2_SESN2 | ATG5_DRAM_FRAP1_LC3_SESN2_SIRT1 |
| ATG5_FRAP1_LAMP1_SESN2_SIRT1 | ATG5_CSE1L_DIABLO_FRAP1_LC3_SESN2 |
| CSE1L_FRAP1LAMP1SESN2_SIRT1 | CSE1L_FRAP1LC3_SATB1SESN2_SIRT1 |
| ATG3_FRAP1_LC3_SESN2_SIRT1 | AKT1_ATG5_CSE1L_FRAP1_LC3_SESN2 |
| AKT1_ATG5_CSE1L_FRAP1_SESN2 | ATG5_FRAP1_LC3_RPS19BP1_SESN2_SIRT1 |
| ATG5_CSE1L_DIABLO_FRAP1_SESN2 | ATG5_CSE1L_FRAP1_LC3_ID2_SESN2 |
| ATG5_CSE1L_LC3_SESN2_SIRT1 | ATG5_CSE1L_FRAP1_LC3_SESN2_SESN3 |
| CSE1L_FRAP1SESN2_SIRT1_UVRAG | CSE1L_FRAP1_LC3_SESN2_SIRT1_UVRAG |
| ATG7_TKT_LAMP2_SESN2_SESN3 | AKT1_CSE1L_FRAP1_LC3_SESN2_SIRT1 |
| CSE1L_FRAP1SATB1SESN2_SIRT1 | ATG5_DIABLO_FRAP1_LC3_SESN2_SIRT1 |
| CSE1L_FRAP1CDH1_SESN2_SIRT1 | CSE1L_FRAP1_LC3_SESN2_SESN3_SIRT1 |
| ATG7_TKT_FASLG_LAMP2_SESN2 | ATG5_FRAP1_LC3_SESN2_SESN3_SIRT1 |
| ATG5_CSE1L_FRAP1_ID2_SESN2 | CSE1L_DRAM_FRAP1_LC3_SESN2_SIRT1 |
| AKT1_ATG7_TKT_SESN2_SESN3 | CSE1L_DIABLO_FRAP1_LC3_SESN2_SIRT1 |
| ATG7_TKT_LAMP2_MMP2_SESN2 | CSE1L_FRAP1_LC3_ID2_SESN2_SIRT1 |
| AKT1_CSE1L_FRAP1_SESN2_SIRT1 | AKT1_ATG5_FRAP1_LC3_SESN2_SIRT1 |
| BNIP3_CSE1L_FRAP1LC3_SESN2 | ATG5_CSE1L_FRAP1_LC3_SATB1_SESN2 |
| ATG5_CSE1L_FRAP1_SESN2_SESN3 | ATG5_FRAP1_LC3_ID2_SESN2_SIRT1 |
| CSE1L_FRAP1LAMP1LC3_SESN2 | ATG5_CSE1L_FRAP1LAMP1SESN2_SIRT1 |
| ATG3_ATG5_CSE1L_FRAP1_SESN2 | ATG3_ATG7_FRAP1_LC3_SESN2_SIRT1 |
| CSE1L_DRAM_FRAP1_LC3_SESN2 | ATG5_E2F1_FRAP1_LC3_SESN2_SIRT1 |
| ATG3_CSE1L_FRAP1_SESN2_SIRT1 | ATG5_CSE1L_FRAP1_LAMP1_LC3_SESN2 |
| ATG5_ATG7_FRAP1_LC3_SESN2 | ATG5_BNIP3_CSE1L_FRAP1LC3_SESN2 |
| ATG5_FAS_FRAP1_SESN2_SIRT1 | CSE1L_FRAP1_LC3_SESN2_SIRT1_STAT3 |
| CSE1L_FRAP1_SESN2_SESN3_SIRT1 | BNIP3_CSE1L_FRAP1_LC3_SESN2_SIRT1 |
| CSE1L_DRAM_FRAP1_SESN2_SIRT1 | ATG5_CSE1L_FRAP1_SESN2_SIRT1_UVRAG |
| CSE1L_DIABLO_FRAP1_SESN2_SIRT1 | ATG5_CSE1L_DRAM_FRAP1_LC3_SESN2 |
| ATG7_CSE1L_FRAP1_SESN2_SIRT1 | ATG5_FRAP1_LC3_MMP9_SESN2_SIRT1 |
| ATG5_CSE1L_FRAP1CDH1SESN2 | ATG5_ATG7_FRAP1_LAMP1_SESN2_SIRT1 |
| ATG7_TKT_FASLG_SESN2_SESN3 | ATG5_CSE1L_FRAP1CDH1_SESN2_SIRT1 |
| ATG7_TKT_HMGB1_LAMP2_SESN2 | ATG5_FRAP1_LC3_SESN2_SIRT1_STAT3 |
| ATG7_TKT_AGER_LAMP2_SESN2 | ATG12_ATG5_CSE1L_FRAP1_LC3_SESN2 |
| ATG3_ATG5_FRAP1_LC3_SESN2 | ATG5_FRAP1_LC3_SESN2_SIRT1_UVRAG |
| ATG3_ATG5_FRAP1_SESN2_SIRT1 | ATG5_BNIP3_FRAP1_LC3_SESN2_SIRT1 |
| ATG5_CSE1L_FRAP1_SATB1_SESN2 | ATG3_ATG5_FRAP1_LAMP1_SESN2_SIRT1 |
| CSE1L_FRAP1_ID2_SESN2_SIRT1 | CSE1L_FRAP1LC3_CDH1_SESN2_SIRT1 |
| ATG7_BNIP3_TKT_LAMP2_SESN2 | ATG5_CSE1L_FRAP1_LC3_SESN2_STAT3 |
| ATG5_ATG7_CSE1L_FRAP1_SESN2 | AIFM1_ATG12_TKT_FASLG_LAMP2_SESN2 |
| ATG5_LC3_NAMPT_SESN2_SIRT1 | ATG5_CSE1L_FRAP1_LC3_SESN2_UVRAG |
| ATG12_ATG5_CSE1L_FRAP1_SESN2 | CSE1L_FRAP1_LAMP1_LC3_SESN2_SIRT1 |
| CSE1L_FRAP1_SESN2_SIRT1_STAT3 | CSE1L_FRAP1_LC3_MMP9_SESN2_SIRT1 |
| CSE1L_FRAP1_LC3_SESN2_UVRAG | ATG5_CSE1L_FRAP1_LC3_RPS19BP1_SESN2 |
| AKT1_ATG7_TKT_MMP2_SESN2 | AKT1_ATG5_CSE1L_FRAP1_SESN2_SIRT1 |
| ATG5_BNIP3_CSE1L_FRAP1SESN2 | ATG5_CSE1L_E2F1_FRAP1_LC3_SESN2 |
| CSE1L_FRAP1_MMP9_SESN2_SIRT1 | CSE1L_E2F1_FRAP1_LC3_SESN2_SIRT1 |
| BNIP3_CSE1L_FRAP1_SESN2_SIRT1 | ATG5_CSE1L_FRAP1_LC3_CDH1_SESN2 |
| AKT1_ATG7_TKT_HMGB1_SESN2 | ATG3_ATG7_CSE1L_FRAP1_LC3_SESN2 |
| AIFM1_AKT1_ATG7_TKT_SESN2 | ATG5_CSE1L_FRAP1_SATB1_SESN2_SIRT1 |
| AKT1_ATG5_ATG7_TKT_SESN2 | ATG5_CSE1L_FRAP1_SESN2_SESN3_SIRT1 |
| ATG12_ATG7_TKT_LAMP2_SESN2 | ATG7_TKT_FASLG_LAMP2_SESN2_SIRT1 |
| CDH1_ID2_MMP9_TCF3_SESN2 | TKT_CDH1_ID2_MMP9_TCF3_SESN2 |

| Combinations of seven types | Combinations of eight types |
|---|---|
| ATG3_ATG5_ATG7_FRAP1_LC3_SESN2_SIRT1 | ATG3_ATG5_ATG7_FRAP1_LC3_SESN2_SIRT1_STAT3 |
| ATG3_ATG5_CSE1L_FRAP1_LC3_SESN2_SIRT1 | AIFM1_ATG12_TKT_CDH1_FASLG_HMGB1_LAMP2_SESN2 |
| ATG5_CSE1L_FRAP1_LC3_SESN2_SIRT1_UVRAG | ATG3_ATG5_ATG7_DRAM_FRAP1_LC3_SESN2_SIRT1 |
| AKT1_ATG5_CSE1L_FRAP1_LC3_SESN2_SIRT1 | AKT1_ATG3_ATG5_ATG7_FRAP1_LC3_SESN2_SIRT1 |
| ATG5_CSE1L_FRAP1_LC3_SATB1_SESN2_SIRT1 | ATG3_ATG5_ATG7_FRAP1_LC3_SESN2_SESN3_SIRT1 |

TABLE 9-continued

| | |
|---|---|
| ATG5_CSE1L_FRAP1_LC3_SESN2_SESN3_SIRT1 | ATG3_ATG5_CSE1L_FRAP1_LC3_SESN2_SIRT1_UVRAG |
| ATG5_ATG7_CSE1L_FRAP1_LC3_SESN2_SIRT1 | ATG3_ATG5_ATG7_DIABLO_FRAP1_LC3_SESN2_SIRT1 |
| ATG5_CSE1L_DIABLO_FRAP1_LC3_SESN2_SIRT1 | ATG3_ATG5_ATG7_FRAP1_LC3_SESN2_SIRT1_UVRAG |
| ATG5_CSE1L_FRAP1_LC3_ID2_SESN2_SIRT1 | AKT1_ATG3_ATG5_CSE1L_FRAP1_LC3_SESN2_SIRT1 |
| ATG5_CSE1L_DRAM_FRAP1_LC3_SESN2_SIRT1 | ATG3_ATG5_ATG7_FRAP1_LC3_ID2_SESN2_SIRT1 |
| ATG3_ATG5_DRAM_FRAP1_LC3_SESN2_SIRT1 | ATG3_ATG5_CSE1L_FRAP1_LC3_SESN2_SESN3_SIRT1 |
| ATG5_BNIP3_CSE1L_FRAP1_LC3_SESN2_SIRT1 | ATG5_ATG7_CSE1L_FRAP1_LC3_SESN2_SIRT1_UVRAG |
| ATG5_CSE1L_FRAP1_LC3_SESN2_SIRT1_STAT3 | ATG3_ATG5_CSE1L_FRAP1_LC3_SATB1_SESN2_SIRT1 |
| ATG3_ATG5_DIABLO_FRAP1_LC3_SESN2_SIRT1 | AIFM1_ATG12_NNMT_CIAP2_FASLG_LAMP2_SESN2_SIRT1 |
| ATG3_ATG5_FRAP1_LC3_SESN2_SESN3_SIRT1 | ATG5_CSE1L_FRAP1_LC3_SATB1_SESN2_SIRT1_UVRAG |
| AKT1_ATG3_ATG5_FRAP1_LC3_SESN2_SIRT1 | ATG3_ATG5_CSE1L_DIABLO_FRAP1_LC3_SESN2_SIRT1 |
| ATG5_CSE1L_E2F1_FRAP1_LC3_SESN2_SIRT1 | ATG3_ATG5_CSE1L_FRAP1_LC3_ID2_SESN2_SIRT1 |
| ATG3_ATG5_FRAP1_LC3_ID2_SESN2_SIRT1 | AIFM1_ATG12_TKT_CDH1_CIAP2_FASLG_LAMP2_SESN2 |
| ATG5_ATG7_DRAM_FRAP1_LC3_SESN2_SIRT1 | AIFM1_ATG12_NNMT_AGER_CIAP2_FASLG_LAMP2_SESN2 |
| ATG5_CSE1L_FRAP1_LAMP1_LC3_SESN2_SIRT1 | AKT1_ATG5_CSE1L_FRAP1_LC3_SESN2_SIRT1_UVRAG |
| AIFM1_ATG12_TKT_CDH1_FASLG_LAMP2_SESN2 | ATG3_ATG5_CSE1L_DRAM_FRAP1_LC3_SESN2_SIRT1 |
| ATG5_CSE1L_FRAP1_LC3_CDH1_SESN2_SIRT1 | ATG5_CSE1L_FRAP1_LC3_SESN2_SESN3_SIRT1_UVRAG |
| ATG5_ATG7_FRAP1_LC3_SESN2_SIRT1_STAT3 | AKT1_ATG5_CSE1L_FRAP1_LC3_SATB1_SESN2_SIRT1 |
| AKT1_ATG5_ATG7_FRAP1_LC3_SESN2_SIRT1 | AKT1_ATG5_CSE1L_FRAP1_LC3_SESN2_SESN3_SIRT1 |
| ATG5_ATG7_DIABLO_FRAP1_LC3_SESN2_SIRT1 | AKT1_ATG5_ATG7_CSE1L_FRAP1_LC3_SESN2_SIRT1 |
| ATG5_ATG7_FRAP1_LC3_SESN2_SESN3_SIRT1 | AIFM1_ATG12_NNMT_CDH2_CIAP2_FASLG_LAMP2_SESN2 |
| ATG3_ATG5_FRAP1_LC3_SESN2_SIRT1_STAT3 | ATG3_ATG5_ATG7_BNIP3_FRAP1_LC3_SESN2_SIRT1 |
| ATG5_ATG7_FRAP1_LC3_ID2_SESN2_SIRT1 | ATG5_CSE1L_FRAP1_LC3_SATB1_SESN2_SESN3_SIRT1 |
| ATG3_ATG5_FRAP1_LC3_RPS19BP1_SESN2_SIRT1 | ATG5_CSE1L_DRAM_FRAP1_LC3_SESN2_SIRT1_UVRAG |
| ATG3_ATG5_E2F1_FRAP1_LC3_SESN2_SIRT1 | AIFM1_ATG12_TKT_CDH1_AGER_FASLG_LAMP2_SESN2 |
| ATG3_ATG5_FRAP1_LC3_SESN2_SIRT1_UVRAG | ATG3_ATG5_ATG7_CSE1L_FRAP1_LC3_SESN2_SIRT1 |
| ATG12_ATG5_CSE1L_FRAP1_LC3_SESN2_SIRT1 | ATG5_CSE1L_DIABLO_FRAP1_LC3_SESN2_SIRT1_UVRAG |
| ATG3_ATG5_BNIP3_FRAP1_LC3_SESN2_SIRT1 | ATG5_CSE1L_FRAP1_LC3_ID2_SESN2_SIRT1_UVRAG |
| ATG5_ATG7_FRAP1_LC3_SESN2_SIRT1_UVRAG | ATG3_ATG5_BNIP3_CSE1L_FRAP1_LC3_SESN2_SIRT1 |
| ATG5_ATG7_E2F1_FRAP1_LC3_SESN2_SIRT1 | ATG5_ATG7_CSE1L_FRAP1_LC3_SESN2_SESN3_SIRT1 |
| AIFM1_ATG12_TKT_CIAP2_FASLG_LAMP2_SESN2 | ATG3_ATG5_ATG7_FRAP1_LAMP1_LC3_SESN2_SIRT1 |
| ATG5_CSE1L_FRAP1_LC3_MMP9_SESN2_SIRT1 | AKT1_ATG5_CSE1L_DIABLO_FRAP1_LC3_SESN2_SIRT1 |
| ATG3_ATG5_FRAP1_LC3_MMP9_SESN2_SIRT1 | AKT1_ATG5_CSE1L_FRAP1_LC3_ID2_SESN2_SIRT1 |
| ATG7_TKT_FASLG_LAMP2_SESN2_SESN3_SIRT1 | AIFM1_DRAM_TKT_CDH1_FASLG_LAMP2_SESN2_SIRT1 |
| ATG5_ATG7_BNIP3_FRAP1_LC3_SESN2_SIRT1 | AKT1_ATG5_CSE1L_DRAM_FRAP1_LC3_SESN2_SIRT1 |
| ATG3_ATG7_CSE1L_FRAP1_LC3_SESN2_SIRT1 | ATG5_CSE1L_DIABLO_FRAP1_LC3_SATB1_SESN2_SIRT1 |
| ATG3_ATG5_CSE1L_DIABLO_FRAP1_LC3_SESN2 | ATG5_CSE1L_FRAP1_LC3_ID2_SATB1_SESN2_SIRT1 |
| ATG7_CSE1L_FRAP1_LC3_SESN2_SIRT1_UVRAG | ATG3_ATG5_CSE1L_FRAP1_LC3_SESN2_SIRT1_STAT3 |
| AKT1_ATG3_ATG5_CSE1L_FRAP1_LC3_SESN2 | ATG5_CSE1L_DIABLO_FRAP1_LC3_SESN2_SESN3_SIRT1 |
| ATG12_ATG3_ATG5_FRAP1_LC3_SESN2_SIRT1 | ATG5_CSE1L_FRAP1_LC3_ID2_SESN2_SESN3_SIRT1 |
| AIFM1_ATG12_NNMT_CIAP2_FASLG_LAMP2_SESN2 | ATG5_CSE1L_DRAM_FRAP1_LC3_SESN2_SESN3_SIRT12 |
| ATG5_ATG7_FRAP1_LC3_RPS19BP1_SESN2_SIRT1 | ATG5_CSE1L_DRAM_FRAP1_LC3_SATB1_SESN2_SIRT1 |
| ATG3_CSE1L_FRAP1_LC3_SATB1_SESN2_SIRT1 | ATG3_ATG5_ATG7_E2F1_FRAP1_LC3_SESN2_SIRT1 |
| ATG5_ATG7_CSE1L_DIABLO_FRAP1_LC3_SESN2 | ATG5_ATG7_CSE1L_FRAP1_LC3_SESN2_SIRT1_STAT3 |
| ATG3_CSE1L_FRAP1_LC3_SESN2_SIRT1_UVRAG | ATG5_ATG7_CSE1L_DIABLO_FRAP1_LC3_SESN2_SIRT1 |
| ATG3_ATG5_ATG7_CSE1L_FRAP1_LC3_SESN2 | AIFM1_DRAM_TKT_CIAP2_FASLG_LAMP2_SESN2_SIRT1 |
| AKT1_ATG5_ATG7_CSE1L_FRAP1_LC3_SESN2 | ATG5_ATG7_CSE1L_FRAP1_LAMP1_LC3_SESN2_SIRT1 |
| ATG3_ATG5_CSE1L_FRAP1_LC3_ID2_SESN2 | ATG3_ATG5_DIABLO_DRAM_FRAP1_LC3_SESN2_SIRT1 |
| ATG3_ATG5_CSE1L_FRAP1_LC3_SESN2_SESN3 | ATG5_ATG7_CSE1L_FRAP1_LC3_ID2_SESN2_SIRT1 |
| AKT1_ATG7_CSE1L_FRAP1_LC3_SESN2_SIRT1 | AIFM1_ATG12_MMP9_AGER_FASLG_LAMP2_SESN2_SIRT1 |
| AKT1_ATG3_CSE1L_FRAP1_LC3_SESN2_SIRT1 | ATG3_ATG5_DRAM_FRAP1_LC3_SESN2_SESN3_SIRT1 |
| ATG7_CSE1L_FRAP1_LC3_SATB1_SESN2_SIRT1 | ATG5_ATG7_CSE1L_FRAP1_LC3_SATB1_SESN2_SIRT1 |
| ATG7_TKT_CDH1_ID2_MMP9_TCF3_SESN2 | TKT_CDH1_ID2_MMP9_TCF3_FASLG_SESN2_SIRT1 |

Preferably, the composition or kit is for predicting the prognosis of recurrence of the B group, and the genes are one or more selected from the genes or groups of genes described in the following Table 10.

TABLE 10

| One type | Combinations of two types | Combinations of three types | Combinations of four types |
|---|---|---|---|
| HMGB1 | ATG3_HMGB1 | ATG3_BCL2_HMGB1 | ATG3_BCL2_CDH1_HMGB1 |
| TKT | ATG3_BECN1 | ATG3_HMGB1_RAGE | ATG3_CDH1_HMGB1_UVRAG |
| | TKT_HMGB1 | ATG3_TKT_HMGB1 | ATG3_BCL2_TKT_HMGB1 |
| | BCL2L1_TKT | ATG3_CDH1_HMGB1 | ATG3_BCL2_HMGB1_RAGE |
| | ATG3_NAMPT | ATG3_HMGB1_HMGB2 | ATG3_BCL2_HMGB1_HMGB2 |
| | BCL2_HMGB1 | ATG3_HMGB1_UVRAG | ATG3_CDH1_HMGB1_SIRT1 |
| | HMGB1_TWIST1 | ATG3_CASP3_HMGB1 | ATG3_BCL2_HMGB1_MMP2 |
| | ATG12_ATG3 | ATG3_HMGB1_SIRT1 | ATG3_HMGB1_HMGB2_RAGE |
| | CSE1L_DIABLO | ATG3_BECN1_SATB1 | ATG3_BCL2_BNIP3_HMGB1 |
| | ATG3_TKT | ATG3_HMGB1_SATB1 | ATG3_CDH1_CASP3_HMGB1 |
| | LAMP1_HMGB1 | ATG3_LC3_BECN1 | ATG3_CDH1_HMGB1_KIAA1967 |
| | TKT_BECN1 | ATG3_HMGB1_LAMP2 | ATG3_HMGB1_RAGE_UVRAG |
| | CDH1_HMGB1 | ATG3_HMGB1_RAPTOR | ATG3_HMGB1_RAGE_SIRT1 |
| | HMGB1_TP63 | ATG3_HMGB1_KIAA1967 | ATG3_TKT_HMGB1_HMGB2 |
| | TKT_NAMPT | BCL2L1_TKT_CASP3 | ATG3_TKT_HMGB1_UVRAG |
| | BCL2_TKT | ATG12_ATG3_HMGB1 | ATG3_BCL2_LAMP1_HMGB1 |

TABLE 10-continued

| | | |
|---|---|---|
| CSE1L_TKT | BCL2L1_TKT_SIRT1 | ATG3_BCL2_HMGB1_RAPTOR |
| LC3_TKT | ATG3_CIAP2_HMGB1 | AIFM1_ATG3_BCL2_HMGB1 |
| TKT_CASP3 | BCL2L1_TKT_BECN1 | ATG3_CASP3_HMGB1_RAGE |
| FASLG_HMGB1 | BCL2_TKT_HMGB1 | ATG12_ATG3_HMGB1_RAGE |
| CDH2_HMGB1 | ATG3_BECN1_SESN3 | ATG3_TKT_CASP3_HMGB1 |
| ATG5_HMGB1 | ATG3_CASP8_HMGB1 | ATG3_TKT_HMGB1_KIAA1967 |
| HMGB1_SIRT1 | ATG3_CDH2_HMGB1 | ATG3_BCL2L1_TKT_BECN1 |
| ATG12_HMGB1 | ATG3_FRAP1_HMGB1 | ATG12_ATG3_CDH1_HMGB1 |
| HMGB1_RAGE | ATG3_BNIP3_HMGB1 | ATG3_CDH1_HMGB1_RAGE |
| HMGB1_UVRAG | ATG3_BECN1_HMGB1 | ATG3_BCL2_FRAP1_HMGB1 |
| BCL2L1_SIRT1 | ATG3_CBS_HMGB1 | ATG3_BCL2_HMGB1_LAMP2 |
| ATG3_TCF3 | AIFM1_ATG3_HMGB1 | ATG3_BCL2_DIABLO_HMGB1 |
| BCL2L1_HMGB1 | ATG3_HMGB1_STAT3 | ATG3_TKT_HMGB1_SIRT1 |
| TKT_SIRT1 | ATG3_HMGB1_MMP2 | ATG3_BCL2_CBS_HMGB1 |
| HMGB1_LAMP2 | ATG3_LAMP1_HMGB1 | ATG3_BCL2_CASP8_HMGB1 |
| TKT_SESN2 | BCL2L1_TKT_FASLG | ATG3_HMGB1_HMGB2_SATB1 |
| HMGB1_MMP2 | ATG3_DIABLO_HMGB1 | ATG3_BCL2_PTEN_HMGB1 |
| TKT_AGER | BCL2_BCL2L1_TKT | ATG3_HMGB1_RAGE_RAPTOR |
| HMGB1_RAPTOR | TKT_HMGB1_TWIST1 | ATG3_TKT_HMGB1_RAGE |
| E2F1_HMGB1 | ATG3_NNMT_HMGB1 | ATG3_BCL2_CASP3_HMGB1 |
| CASP8_HMGB1 | ATG3_MMP9_HMGB1 | ATG3_BCL2_HMGB1_SATB1 |
| TKT_ID2 | BCL2L1_TKT_HMGB1 | ATG3_HMGB1_LAMP2_RAGE |
| AKT1_TKT | ATG3_LAMP1_BECN1 | ATG3_CDH1_HMGB1_LAMP2 |
| ATG3_SIRT1 | ATG3_BCL2L1_BECN1 | ATG3_HMGB1_HMGB2_UVRAG |
| TKT_RPS19BP1 | ATG5_TKT_HMGB1 | ATG3_BCL2L1_TKT_HMGB1 |
| CSE1L_HMGB1 | ATG3_FASLG_HMGB1 | CDH1_HMGB1_TP63_UVRAG |
| BCL2L1_BECN1 | ATG3_MMP9_BECN1 | ATG3_CDH1_HMGB1_HMGB2 |
| CASP3_HMGB1 | ATG3_ATG7_BECN1 | ATG3_BCL2L1_TKT_CASP3 |
| ATG7_HMGB1 | ATG3_HMGB1_SESN3 | ATG3_HMGB1_KIAA1967_RAGE |
| FRAP1_HMGB1 | ATG3_E2F1_HMGB1 | ATG3_BCL2_DRAM_HMGB1 |
| HMGB1_HMGB2 | HMGB1_RAPTOR_TWIST1 | ATG3_LC3_TKT_HMGB1 |
| HMGB1_SATB1 | AKT1_ATG3_BECN1 | ATG3_BCL2_HMGB1_UVRAG |
| ATG3_ULK1 | ATG3_FAS_HMGB1 | ATG3_CDH1_CDH2_HMGB1 |
| ATG3_SESN1 | ATG3_ULK1_HMGB1 | BCL2_BCL2L1_TKT_CASP3 |
| CBS_HMGB1 | TKT_HMGB1_SIRT1 | ATG3_TKT_BECN1_HMGB1 |
| TKT_KIAA1967 | ATG3_BAX_HMGB1 | ATG3_TKT_HMGB1_LAMP2 |
| ATG12_BCL2L1 | TKT_CDH2_HMGB1 | ATG3_BCL2_PRKAA1_HMGB1 |
| DRAM_HMGB1 | ATG3_PTEN_HMGB1 | BCL2L1_TKT_CASP3_SIRT1 |
| LC3_FASLG | ATG3_TKT_BECN1 | BCL2L1_TKT_CASP3_FASLG |
| HMGB1_KIAA1967 | ATG3_HMGB1_TWIST1 | BCL2L1_TKT_CASP3_CDH2 |
| TKT_SESN1 | BCL2L1_TKT_UVRAG | ATG3_BCL2_NNMT_HMGB1 |

| Combinations of five types | Combinations of six types |
|---|---|
| ATG3_BCL2_CDH1_HMGB1_RAGE | ATG3_BCL2_CDH1_HMGB1_RAGE_RAPTOR |
| ATG3_BCL2_CDH1_HMGB1_UVRAG | ATG3_BCL2_BNIP3_CDH1_HMGB1_RAGE |
| ATG3_BCL2_CDH1_HMGB1_SIRT1 | ATG3_BCL2_CDH1_HMGB1_HMGB2_RAGE |
| ATG3_BCL2_CDH1_HMGB1_RAPTOR | ATG3_BCL2_CDH1_HMGB1_KIAA1967_RAGE |
| ATG3_BCL2_CDH1_HMGB1_HMGB2 | ATG3_BCL2_CDH1_HMGB1_RAGE_SIRT1 |
| ATG3_BCL2_CDH1_HMGB1_KIAA1967 | ATG3_BCL2_CDH1_HMGB1_HMGB2_RAPTOR |
| ATG3_BCL2_BNIP3_CDH1_HMGB1 | ATG3_BCL2_CDH1_CDH2_HMGB1_RAGE |
| ATG3_BCL2_CDH1_HMGB1_LAMP2 | ATG3_BCL2_CDH1_HMGB1_RAGE_UVRAG |
| ATG3_BCL2_CDH1_CDH2_HMGB1 | ATG3_BCL2_CDH1_CASP3_HMGB1_RAGE |
| ATG3_CDH1_HMGB1_RAGE_SIRT1 | AIFM1_ATG3_BCL2_CDH1_HMGB1_SIRT1 |
| ATG3_BCL2_CDH1_CASP3_HMGB1 | ATG3_BCL2_BNIP3_CDH1_HMGB1_UVRAG |
| ATG12_ATG3_BCL2_CDH1_HMGB1 | ATG12_ATG3_BCL2_CDH1_HMGB1_RAGE |
| AIFM1_ATG3_BCL2_CDH1_HMGB1 | ATG3_BCL2_CDH1_HMGB1_HMGB2_UVRAG |
| ATG3_BCL2_CASP8_CDH1_HMGB1 | ATG3_BCL2_CDH1_HMGB1_LAMP2_RAGE |
| ATG3_BCL2_FRAP1_CDH1_HMGB1 | ATG3_BCL2_CDH1_HMGB1_HMGB2_LAMP2 |
| ATG3_BCL2_CBS_CDH1_HMGB1 | ATG3_BCL2_CDH1_CDH2_HMGB1_HMGB2 |
| ATG3_CDH1_HMGB1_RAGE_UVRAG | ATG3_BCL2_BCL2L1_TKT_CASP3_HMGB1 |
| ATG3_BCL2_TKT_HMGB1_HMGB2 | AIFM1_ATG3_BCL2_CDH1_HMGB1_UVRAG |
| ATG3_BCL2_CDH1_HMGB1_MMP2 | ATG3_BCL2_CDH1_HMGB1_HMGB2_KIAA1967 |
| ATG3_BCL2_NNMT_CDH1_HMGB1 | ATG3_BCL2_BNIP3_CDH1_HMGB1_HMGB2 |
| ATG3_BCL2_HMGB1_HMGB2_RAGE | ATG12_ATG3_CDH1_HMGB1_RAGE_SIRT1 |
| ATG3_BCL2_CDH1_MMP9_HMGB1 | ATG3_BCL2_BNIP3_CDH1_HMGB1_RAPTOR |
| ATG12_ATG3_CDH1_HMGB1_RAGE | ATG3_BCL2_DRAM_CDH1_HMGB1_SIRT1 |
| ATG3_CDH1_HMGB1_LAMP2_SIRT1 | ATG3_BCL2_BNIP3_CDH1_HMGB1_LAMP2 |
| ATG3_BCL2_DIABLO_CDH1_HMGB1 | AIFM1_ATG3_BCL2_CDH1_HMGB1_RAGE |
| ATG3_BCL2L1_TKT_BECN1_CASP3 | ATG3_BCL2_BNIP3_CDH1_HMGB1_KIAA1967 |
| ATG3_BCL2_HMGB1_MMP2_RAGE | ATG3_BCL2_CDH1_HMGB1_MMP2_RAGE |
| ATG3_CDH1_HMGB1_HMGB2_UVRAG | AIFM1_ATG3_BCL2_CDH1_HMGB1_HMGB2 |
| ATG3_BCL2_DRAM_CDH1_HMGB1 | ATG3_BCL2_CDH1_HMGB1_HMGB2_SIRT1 |
| ATG3_BCL2_TKT_CDH1_HMGB1 | ATG3_BCL2_CDH1_HMGB1_MMP2_UVRAG |
| ATG3_BCL2_TKT_CASP3_HMGB1 | ATG3_BCL2_CASP8_CDH1_HMGB1_RAGE |
| ATG3_CDH1_HMGB1_KIAA1967_UVRAG | ATG3_CDH1_HMGB1_LAMP2_RAGE_SIRT1 |
| ATG3_CDH1_HMGB1_LAMP2_UVRAG | ATG3_BCL2_DRAM_CDH1_HMGB1_UVRAG |
| ATG3_BCL2_BCL2L1_TKT_HMGB1 | ATG3_BCL2_PTEN_CDH1_HMGB1_SIRT1 |
| ATG3_BCL2_CDH1_HMGB1_SATB1 | ATG3_BCL2_BCL2L1_TKT_HMGB1_SIRT1 |
| ATG3_BCL2L1_TKT_HMGB1_SIRT1 | ATG3_BCL2_BNIP3_CDH1_HMGB1_SIRT1 |

TABLE 10-continued

| | |
|---|---|
| ATG3_BCL2_TKT_ID2_HMGB1 | ATG3_BCL2_FRAP1_CDH1_HMGB1_RAGE |
| ATG3_CDH1_HMGB1_KIAA1967_RAGE | AIFM1_ATG3_BCL2_CDH1_HMGB1_KIAA1967 |
| ATG3_BCL2_PTEN_CDH1_HMGB1 | ATG3_BCL2_CDH1_HMGB1_LAMP2_RAPTOR |
| AIFM1_ATG3_CDH1_HMGB1_SIRT1 | ATG3_CDH1_HMGB1_RAGE_SIRT1_UVRAG |
| ATG3_BCL2_CDH1_HMGB1_STAT3 | ATG3_BCL2_CBS_CDH1_HMGB1_RAGE |
| ATG3_CDH1_CASP3_HMGB1_RAGE | ATG3_BCL2_FRAP1_CDH1_HMGB1_UVRAG |
| ATG3_BCL2_LC3_TKT_HMGB1 | ATG3_BCL2_CBS_CDH1_HMGB1_UVRAG |
| ATG3_CDH1_CASP3_HMGB1_UVRAG | ATG3_CDH1_HMGB1_HMGB2_RAGE_SIRT1 |
| ATG3_BCL2_CDH1_CIAP2_HMGB1 | AIFM1_ATG3_BCL2_CDH1_HMGB1_RAPTOR |
| ATG3_BCL2_BNIP3_HMGB1_RAGE | ATG3_BCL2_CDH1_HMGB1_KIAA1967_RAPTOR |
| ATG3_CDH1_HMGB1_RAPTOR_SIRT1 | ATG3_BCL2_BCL2L1_TKT_ID2_CASP3 |
| ATG3_CDH1_HMGB1_SIRT1_UVRAG | ATG3_BCL2_CDH1_HMGB1_RAPTOR_UVRAG |
| ATG3_CDH1_HMGB1_RAPTOR_UVRAG | ATG3_BCL2_CASP8_CDH1_HMGB1_HMGB2 |
| ATG3_CDH1_HMGB1_KIAA1967_SIRT1 | ATG12_ATG3_BCL2_CDH1_HMGB1_HMGB2 |
| ATG3_BAX_BCL2_CDH1_HMGB1 | ATG3_BCL2_FRAP1_CDH1_HMGB1_SIRT1 |
| ATG3_BCL2_LAMP1_CDH1_HMGB1 | ATG3_BCL2_CDH1_HMGB1_MMP2_SIRT1 |
| ATG3_ATG5_BCL2_CDH1_HMGB1 | AIFM1_ATG3_CDH1_HMGB1_RAGE_SIRT1 |
| ATG3_BCL2_TKT_HMGB1_RAGE | ATG3_BCL2_FRAP1_CDH1_HMGB1_HMGB2 |
| ATG3_CDH1_HMGB1_SATB1_UVRAG | ATG3_BCL2_CBS_CDH1_HMGB1_SIRT1 |
| ATG3_BCL2_CDH1_HMGB1_SESN3 | ATG3_BCL2_CASP8_CDH1_HMGB1_UVRAG |
| ATG3_BCL2_FAS_CDH1_HMGB1 | ATG3_BCL2_PTEN_CDH1_HMGB1_UVRAG |
| CDH1_ID2_MMP9_TCF3_FASLG | ATG12_ATG3_CDH1_ID2_MMP9_TCF3 |

| Combinations of seven types | Combinations of eight types |
|---|---|
| ATG3_BCL2_CDH1_HMGB1_HMGB2_RAGE_RAPTOR | ATG3_BCL2_BCL2L1_TKT_ID2_CASP3_CDH2_HMGB2 |
| ATG3_BCL2_CDH1_CDH2_HMGB1_HMGB2_RAGE | ATG3_BCL2_BNIP3_CDH1_HMGB1_HMGB2_RAGE_RAPTOR |
| ATG3_BCL2_BNIP3_CDH1_HMGB1_RAGE_RAPTOR | ATG3_BCL2L1_TKT_ID2_CDH2_HMGB2_TWIST1_UVRAG |
| ATG3_BCL2_BNIP3_CDH1_HMGB1_HMGB2_RAGE | ATG3_BCL2_BCL2L1_TKT_ID2_CASP3_HMGB2_KIAA1967 |
| ATG3_BCL2_BNIP3_CDH1_HMGB1_KIAA1967_RAGE | ATG3_BCL2_BCL2L1_TKT_ID2_CASP3_HMGB2_SIRT1 |
| AIFM1_ATG3_BCL2_CDH1_HMGB1_RAGE_SIRT1 | ATG3_BCL2_BCL2L1_TKT_CDH1_CASP3_HMGB1_SIRT1 |
| ATG3_BCL2_CDH1_HMGB1_HMGB2_KIAA1967_RAGE | ATG3_BCL2_BNIP3_CDH1_FASLG_HMGB1_HMGB2_RAGE |
| ATG3_BCL2_DRAM_CDH1_HMGB1_RAGE_SIRT1 | ATG3_BCL2_BCL2L1_BNIP3_TKT_ID2_CASP3_HMGB2 |
| ATG3_BCL2_BNIP3_CDH1_HMGB1_RAGE_UVRAG | ATG3_BCL2_BNIP3_CDH1_CASP3_FASLG_HMGB1_RAGE |
| ATG3_BCL2_BCL2L1_TKT_ID2_CASP3_HMGB2 | ATG3_BCL2L1_TKT_ID2_CDH2_HMGB2_SIRT1_TWIST1 |
| ATG3_BCL2_BCL2L1_TKT_ID2_CASP3_SIRT1 | AIFM1_ATG3_BCL2_CDH1_CDH2_HMGB1_HMGB2_RAGE |
| ATG3_BCL2_BCL2L1_TKT_CASP3_HMGB1_SIRT1 | ATG3_BCL2L1_TKT_ID2_CDH2_HMGB2_KIAA1967_TWIST1 |
| ATG3_BCL2_BNIP3_CDH1_HMGB1_LAMP2_RAGE | ATG3_BCL2_DRAM_CDH1_HMGB1_HMGB2_RAGE_SIRT1 |
| ATG3_BCL2_BNIP3_CDH1_CDH2_HMGB1_RAGE | ATG3_BCL2_BCL2L1_TKT_CASP3_CDH2_HMGB1_HMGB2 |
| ATG3_BCL2_BNIP3_CDH1_HMGB1_RAGE_SIRT1 | AIFM1_ATG3_BCL2_CDH1_HMGB1_HMGB2_RAGE_RAPTOR |
| ATG3_BCL2_CDH1_HMGB1_HMGB2_LAMP2_RAGE | ATG3_BCL2_BNIP3_CDH1_CDH2_HMGB1_HMGB2_RAGE |
| ATG12_ATG3_BCL2_CDH1_HMGB1_HMGB2_RAGE | ATG3_BCL2_BCL2L1_TKT_ID2_CASP3_HMGB2_UVRAG |
| ATG3_BCL2_BCL2L1_TKT_ID2_CASP3_KIAA1967 | ATG3_CDH1_CDH2_HMGB1_HMGB2_RAGE_RAPTOR_TWIST1 |
| ATG3_BCL2_BCL2L1_TKT_CASP3_CDH2_HMGB1 | ATG3_BCL2_BCL2L1_BNIP3_TKT_ID2_HMGB2_SIRT1 |
| AIFM1_ATG3_BCL2_CDH1_HMGB1_HMGB2_RAGE | ATG3_BCL2_DRAM_CDH1_CDH2_HMGB1_HMGB2_RAGE |
| ATG3_BCL2_BCL2L1_TKT_CASP3_HMGB1_HMGB2 | ATG3_BCL2_BCL2L1_TKT_CDH1_CASP3_CDH2_HMGB1 |
| ATG12_ATG3_BCL2_BNIP3_CDH1_HMGB1_RAGE | ATG3_BCL2_BCL2L1_TKT_CASP3_HMGB1_HMGB2_RAPTOR |
| ATG3_BCL2_BCL2L1_TKT_CASP3_HMGB1_UVRAG | AIFM1_ATG3_BCL2_BNIP3_CDH1_HMGB1_HMGB2_RAGE |
| ATG3_BCL2_CDH1_HMGB1_KIAA1967_MMP2_RAGE | ATG3_BCL2_BCL2L1_BNIP3_TKT_ID2_CASP3_KIAA1967 |
| AIFM1_ATG3_BCL2_BNIP3_CDH1_HMGB1_RAGE | ATG3_BCL2L1_TKT_HMGB1_RAGE_RAPTOR_TWIST1_UVRAG |
| ATG3_BCL2_BCL2L1_TKT_CASP3_HMGB1_KIAA1967 | AIFM1_ATG3_BCL2_BNIP3_CDH1_HMGB1_RAGE_SIRT1 |
| ATG3_BCL2_BCL2L1_TKT_CASP3_HMGB1_RAPTOR | ATG3_BCL2_BNIP3_CDH1_HMGB1_HMGB2_LAMP2_RAGE |
| AIFM1_ATG3_BCL2_CDH1_HMGB1_KIAA1967_RAGE | ATG3_BCL2_DRAM_CDH1_HMGB1_HMGB2_RAGE_RAPTOR |
| ATG3_BCL2_BCL2L1_TKT_ID2_HMGB2_SIRT1 | ATG3_BCL2_BCL2L1_TKT_ID2_CASP3_HMGB2_RAPTOR |
| ATG3_BCL2_CDH1_HMGB1_MMP2_RAGE_SIRT1 | ATG3_BCL2_BCL2L1_TKT_CASP3_CDH2_HMGB1_RAGE |
| AIFM1_ATG3_BCL2_CDH1_CASP3_HMGB1_RAGE | ATG3_CDH1_CDH2_HMGB1_HMGB2_KIAA1967_RAGE_TWIST1 |
| ATG3_BCL2_CDH1_HMGB1_KIAA1967_RAGE_RAPTOR | ATG3_BCL2_BCL2L1_TKT_CDH1_CASP3_HMGB1_UVRAG |
| ATG3_BCL2_DRAM_CDH1_CASP3_HMGB1_RAGE | ATG3_BCL2_BNIP3_CDH1_HMGB1_HMGB2_KIAA1967_RAGE |
| ATG3_BCL2_BNIP3_CDH1_FASLG_HMGB1_RAGE | ATG3_BCL2_BCL2L1_TKT_CASP3_HMGB1_HMGB2_LAMP2 |
| ATG3_BCL2_CDH1_HMGB1_HMGB2_RAGE_SIRT1 | ATG3_BCL2L1_TKT_ID2_HMGB2_KIAA1967_TWIST1_UVRAG |
| ATG3_TKT_HMGB1_HMGB2_KIAA1967_RAGE_TWIST1 | ATG3_BCL2_BCL2L1_TKT_CASP3_HMGB1_RAGE_SIRT1 |
| ATG3_BCL2_BCL2L1_TKT_ID2_CASP3_CDH2 | ATG3_BCL2_BCL2L1_TKT_CASP3_HMGB1_HMGB2_SIRT1 |
| ATG3_BCL2_DRAM_CDH1_HMGB1_HMGB2_UVRAG | ATG3_BCL2_BCL2L1_TKT_CDH1_CASP3_HMGB1_KIAA1967 |
| AIFM1_ATG3_BCL2_CDH1_CDH2_HMGB1_RAGE | ATG3_BCL2_FRAP1_CDH1_HMGB1_HMGB2_RAGE_RAPTOR |
| ATG3_BCL2_BCL2L1_TKT_CASP3_HMGB1_LAMP2 | AIFM1_ATG3_BCL2_BNIP3_CDH1_HMGB1_KIAA1967_RAGE |
| AIFM1_ATG3_BCL2_CDH1_HMGB1_HMGB2_RAPTOR | ATG3_LC3_TKT_HMGB1_RAGE_RAPTOR_TWIST1_UVRAG |
| AIFM1_ATG3_BCL2_CDH1_HMGB1_RAGE_RAPTOR | ATG3_BCL2_BCL2L1_BNIP3_TKT_ID2_CASP3_SIRT1 |
| ATG3_BCL2_CASP8_CDH1_HMGB1_HMGB2_RAGE | AIFM1_ATG3_BCL2_CDH1_HMGB1_MMP2_RAGE_SIRT1 |
| ATG3_BCL2_CDH1_HMGB1_HMGB2_RAGE_UVRAG | ATG3_BCL2_DRAM_CDH1_HMGB1_HMGB2_RAGE_UVRAG |
| ATG3_BCL2_BNIP3_CDH1_HMGB1_HMGB2_RAPTOR | AIFM1_ATG3_BCL2_CDH1_HMGB1_HMGB2_RAGE_SIRT1 |
| ATG3_BCL2_BNIP3_CASP8_CDH1_HMGB1_RAGE | ATG3_BCL2_CASP8_CDH1_HMGB1_HMGB2_RAGE_RAPTOR |
| ATG3_BCL2_CDH1_HMGB1_MMP2_RAGE_UVRAG | ATG3_BCL2_BNIP3_DRAM_CDH1_HMGB1_RAGE_SIRT1 |
| ATG3_BCL2_BCL2L1_TKT_HMGB1_HMGB2_SIRT1 | ATG3_LC3_TKT_HMGB1_KIAA1967_RAGE_TWIST1_UVRAG |
| ATG3_BCL2_BCL2L1_TKT_CASP3_HMGB1_RAGE | ATG3_BCL2_BCL2L1_TKT_CASP3_HMGB1_HMGB2_KIAA1967 |
| AIFM1_ATG3_BCL2_BNIP3_CDH1_HMGB1_UVRAG | AIFM1_ATG3_BCL2_BNIP3_CDH1_HMGB1_RAGE_RAPTOR |
| ATG3_BCL2_DRAM_CDH1_HMGB1_HMGB2_SIRT1 | AIFM1_ATG3_BCL2_CDH1_HMGB1_HMGB2_KIAA1967_RAGE |
| ATG12_ATG3_BCL2_BCL2L1_TKT_CASP3_HMGB1 | ATG3_BCL2_BCL2L1_TKT_CASP3_HMGB1_RAGE_RAPTOR |
| ATG12_ATG3_BCL2_PTEN_CDH1_HMGB1_RAGE | ATG3_CDH1_CDH2_HMGB1_HMGB2_RAGE_TWIST1_UVRAG |
| ATG3_BCL2_PTEN_CDH1_HMGB1_RAGE_SIRT1 | ATG3_BCL2_DRAM_CDH1_HMGB1_MMP2_RAGE_SIRT1 |
| ATG3_BCL2_CDH1_CASP3_HMGB1_RAGE_RAPTOR | ATG3_BCL2_BCL2L1_TKT_CASP3_HMGB1_HMGB2_UVRAG |

TABLE 10-continued

| | |
|---|---|
| ATG3_BCL2_BNIP3_FRAP1_CDH1_HMGB1_RAGE | ATG3_BCL2_CBS_CDH1_HMGB1_HMGB2_RAGE_RAPTOR |
| ATG3_BCL2_FRAP1_CDH1_HMGB1_HMGB2_RAGE | ATG3_BCL2_BCL2L1_TKT_CASP3_HMGB1_HMGB2_RAGE |
| ATG12_ATG3_CDH1_ID2_MMP9_TCF3_SATB1 | ATG3_TKT_CDH1_ID2_MMP9_TCF3_TWIST1_UVRAG |

Preferably, the composition or kit is for predicting the prognosis of survival of the B group, and the genes are one or more selected from the genes or groups of genes described in the following Table 11.

TABLE 11

| One type | Combinations of two types | Combinations of three types | Combinations of four types |
|---|---|---|---|
| ATG12 | DIABLO_NAMPT | DIABLO_ID2_NAMPT | ATG12_ID2_MMP9_TCF3 |
| DIABLO | ATG12_ID2 | DIABLO_FAS_NAMPT | DIABLO_FAS_ID2_NAMPT |
| UVRAG | ATG12_RPS19BP1 | ATG12_ID2_TCF3 | ATG12_CSE1L_ID2_MMP9 |
| NAMPT | ATG12_DIABLO | DIABLO_FAS_STAT3 | DIABLO_ID2_MMP9_NAMPT |
| STAT3 | ID2_NAMPT | ATG12_ID2_MMP9 | DIABLO_FAS_MMP9_NAMPT |
| E2F1 | DIABLO_STAT3 | ATG12_ID2_SATB1 | DIABLO_ID2_NAMPT_STAT3 |
| BECN1 | DIABLO_FAS | ATG12_ID2_RPS19BP1 | ATG12_FAS_ID2_MMP9 |
| FRAP1 | ATG12_CSE1L | ATG12_CSE1L_ID2 | ATG12_ID2_MMP9_SATB1 |
| ATG7 | ATG12_MMP9 | ATG12_DIABLO_FAS | DIABLO_ID2_NAMPT_SATB1 |
| ID2 | ATG12_ATG3 | ATG12_ID2_SESN2 | ATG12_ID2_MMP9_SESN2 |
| SIRT1 | ATG12_SATB1 | ATG12_ID2_NAMPT | ATG12_ID2_MMP9_RPS19BP1 |
| BCL2 | ATG12_SESN2 | ATG12_CSE1L_DIABLO | CSE1L_DIABLO_ID2_NAMPT |
| BNIP3 | CSE1L_DIABLO | ID2_NAMPT_STAT3 | DIABLO_ID2_TCF3_NAMPT |
| LAMP2 | ATG12_TCF3 | ATG12_ID2_BHLHE41 | DIABLO_FAS_NAMPT_SATB1 |
| TKT | ATG12_FAS | CSE1L_DIABLO_NAMPT | ATG12_DIABLO_FAS_MMP9 |
| | ATG12_STAT3 | DIABLO_LC3_NAMPT | DIABLO_FAS_ID2_STAT3 |
| | ATG12_BHLHE41 | ATG12_FAS_ID2 | ATG12_ATG3_ID2_TCF3 |
| | ATG12_NAMPT | ID2_NAMPT_RPS19BP1 | ATG3_DIABLO_ID2_NAMPT |
| | ATG12_ATG7 | ID2_MMP9_TCF3 | ATG12_ID2_TCF3_STAT3 |
| | ID2_BECN1 | DIABLO_NAMPT_SATB1 | DIABLO_FAS_NAMPT_STAT3 |
| | E2F1_FAS | ATG12_CSE1L_MMP9 | ATG12_CSE1L_DIABLO_MMP9 |
| | ATG12_ATG5 | ATG12_MMP9_RPS19BP1 | ATG12_ID2_TCF3_SATB1 |
| | ID2_STAT3 | ID2_MMP9_BECN1 | DIABLO_FAS_MMP9_STAT3 |
| | ATG12_ULK1 | DIABLO_NAMPT_STAT3 | ATG12_ID2_MMP9_BHLHE41 |
| | DIABLO_BECN1 | ATG12_DIABLO_MMP9 | ATG12_BNIP3_ID2_MMP9 |
| | ATG12_LAMP1 | ATG12_FAS_RPS19BP1 | DIABLO_FAS_SATB1_STAT3 |
| | ATG12_LC3 | DIABLO_FAS_MMP9 | DIABLO_FAS_NAMPT_RPS19BP1 |
| | DIABLO_TCF3 | ID2_MMP9_NAMPT | ATG12_ATG3_ID2_MMP9 |
| | AKT1_ATG12 | ATG12_ID2_STAT3 | ATG12_ID2_MMP9_NAMPT |
| | ATG12_FRAP1 | ATG12_DIABLO_TCF3 | DIABLO_FAS_NAMPT_SESN2 |
| | DIABLO_ID2 | ATG12_ATG3_ID2 | DIABLO_ID2_NAMPT_SESN2 |
| | ID2_TCF3 | ATG12_DIABLO_ID2 | ATG12_ID2_TCF3_RPS19BP1 |
| | DIABLO_SATB1 | CSE1L_DIABLO_STAT3 | ATG12_DIABLO_MMP9_TCF3 |
| | ATG12_BECN1 | DIABLO_ID2_STAT3 | ATG12_CSE1L_ID2_SATB1 |
| | ATG12_SIRT1 | ATG12_ATG3_RPS19BP1 | ATG12_FAS_MMP9_RPS19BP1 |
| | NAMPT_STAT3 | ATG12_DIABLO_SATB1 | ID2_MMP9_TCF3_STAT3 |
| | ATG12_BNIP3 | ATG12_MMP9_TCF3 | ATG12_DIABLO_ID2_NAMPT |
| | DIABLO_MMP9 | ATG3_DIABLO_NAMPT | DIABLO_ID2_TCF3_STAT3 |
| | ATG12_UVRAG | ATG12_DIABLO_NAMPT | ATG12_ULK1_ID2_TCF3 |
| | DIABLO_FRAP1 | ATG12_CSE1L_RPS19BP1 | ATG12_ID2_TCF3_SESN2 |
| | NAMPT_RPS19BP1 | DIABLO_MMP9_NAMPT | BNIP3_CSE1L_DIABLO_MMP9 |
| | AKT1_NAMPT | ATG12_ATG3_DIABLO | ATG12_DIABLO_ID2_TCF3 |
| | E2F1_UVRAG | DIABLO_SATB1_STAT3 | ATG12_ATG5_ID2_MMP9 |
| | ATG3_DIABLO | ID2_TCF3_STAT3 | ATG12_ID2_SATB1_STAT3 |
| | NAMPT_UVRAG | ATG12_RPS19BP1_SATB1 | ATG12_MMP9_TCF3_RPS19BP1 |
| | BNIP3_DIABLO | ATG12_DIABLO_STAT3 | ATG12_DIABLO_FAS_ID2 |
| | DIABLO_LC3 | ATG12_TCF3_RPS19BP1 | ATG12_CSE1L_ID2_SESN2 |
| | DIABLO_SIRT1 | DIABLO_NAMPT_SESN2 | DIABLO_FAS_MMP9_TCF3 |
| | LC3_NAMPT | ATG12_DIABLO_SESN2 | ATG12_ID2_TCF3_BHLHE41 |
| | DIABLO_SESN2 | ATG12_ULK1_ID2 | ATG12_FAS_ID2_STAT3 |
| | FAS_STAT3 | ATG12_ATG5_ID2 | BNIP3_CSE1L_ID2_MMP9 |
| | FAS_NAMPT | AKT1_DIABLO_NAMPT | CSE1L_DIABLO_FAS_NAMPT |
| | E2F1_NAMPT | ATG12_ID2_BECN1 | ATG12_CSE1L_ID2_TCF3 |
| | ATG12_SESN3 | ATG12_FAS_MMP9 | ATG12_ID2_NAMPT_RPS19BP1 |
| | BCL2_TKT | ATG12_DIABLO_BHLHE41 | ATG12_ID2_MMP9_BECN1 |
| | ATG7_NAMPT | ATG12_RPS19BP1_STAT3 | DIABLO_FAS_LC3_NAMPT |
| | ATG7_BECN1 | DIABLO_NAMPT_RPS19BP1 | FAS_ID2_NAMPT_RPS19BP1 |
| | | | CDH1_ID2_MMP9_TCF3 |

| Combinations of five types | Combinations of six types |
|---|---|
| DIABLO_FAS_ID2_MMP9_NAMPT | DIABLO_FAS_ID2_MMP9_TCF3_NAMPT |
| ATG12_ATG3_ID2_MMP9_TCF3 | ATG12_ATG3_BNIP3_ID2_MMP9_TCF3 |
| ATG12_ID2_MMP9_TCF3_SATB1 | ATG12_BNIP3_CSE1L_ID2_MMP9_SATB1 |
| ATG12_CSE1L_ID2_MMP9_TCF3 | ATG12_ATG3_ID2_MMP9_TCF3_SATB1 |
| ATG12_BNIP3_ID2_MMP9_TCF3 | DIABLO_FAS_ID2_MMP9_NAMPT_SATB1 |

TABLE 11-continued

| | |
|---|---|
| ATG12_ID2_MMP9_TCF3_SESN2 | ATG12_ATG3_ULK1_ID2_MMP9_TCF3 |
| ATG12_ULK1_ID2_MMP9_TCF3 | ATG12_BNIP3_CSE1L_ID2_MMP9_SESN2 |
| ATG12_ATG5_ID2_MMP9_TCF3 | DIABLO_FAS_ID2_MMP9_NAMPT_STAT3 |
| ATG12_FAS_ID2_MMP9_TCF3 | ATG12_ATG3_FAS_ID2_MMP9_TCF3 |
| DIABLO_FAS_ID2_NAMPT_STAT3 | ATG12_ATG3_ID2_MMP9_TCF3_SESN2 |
| ATG12_ID2_MMP9_TCF3_RPS19BP1 | ATG12_BNIP3_CSE1L_ID2_MMP9_TCF3 |
| ATG12_BNIP3_ID2_MMP9_RPS19BP1 | CSE1L_DIABLO_FAS_ID2_MMP9_NAMPT |
| ATG12_CSE1L_ID2_MMP9_SATB1 | ATG12_ATG3_CSE1L_ID2_MMP9_TCF3 |
| ATG12_CSE1L_ID2_MMP9_SESN2 | ATG12_BNIP3_ID2_MMP9_TCF3_SATB1 |
| ATG12_LAMP1_ID2_MMP9_TCF3 | DIABLO_FAS_ID2_MMP9_NAMPT_SESN2 |
| DIABLO_FAS_ID2_NAMPT_SATB1 | ATG12_BNIP3_CSE1L_ID2_MMP9_BHLHE41 |
| ATG12_BNIP3_CSE1L_ID2_MMP9 | ATG12_BNIP3_ID2_MMP9_TCF3_RPS19BP1 |
| DIABLO_ID2_MMP9_TCF3_NAMPT | DIABLO_FAS_ID2_MMP9_TCF3_STAT3 |
| ATG12_BNIP3_ID2_MMP9_SATB1 | ATG12_ATG3_BNIP3_FAS_ID2_MMP9 |
| ATG12_ID2_MMP9_TCF3_BHLHE41 | ATG12_ATG3_BNIP3_ID2_MMP9_SATB1 |
| ATG12_ID2_MMP9_TCF3_STAT3 | ATG12_BNIP3_CSE1L_ID2_MMP9_RPS19BP1 |
| ATG12_BNIP3_FAS_ID2_MMP9 | ATG12_BNIP3_DIABLO_FAS_ID2_MMP9 |
| ATG12_BNIP3_ID2_MMP9_SESN2 | ATG12_BNIP3_FAS_ID2_MMP9_RPS19BP1 |
| ATG12_ATG3_FAS_ID2_MMP9 | ATG12_CSE1L_ID2_MMP9_TCF3_SATB1 |
| CSE1L_DIABLO_ID2_MMP9_NAMPT | ATG12_CSE1L_ULK1_ID2_MMP9_TCF3 |
| ATG12_DIABLO_ID2_MMP9_TCF3 | ATG12_FAS_ID2_MMP9_TCF3_RPS19BP1 |
| DIABLO_ID2_NAMPT_SATB1_STAT3 | DIABLO_FAS_ID2_NAMPT_SATB1_STAT3 |
| ATG12_ATG3_CSE1L_ID2_MMP9 | ATG12_ATG5_BNIP3_ID2_MMP9_TCF3 |
| ATG12_FAS_ID2_MMP9_RPS19BP1 | ATG12_BNIP3_ID2_MMP9_TCF3_SESN2 |
| ATG12_DIABLO_FAS_ID2_MMP9 | ATG12_CSE1L_ID2_MMP9_TCF3_SESN2 |
| DIABLO_FAS_ID2_MMP9_STAT3 | ATG12_ID2_MMP9_TCF3_SATB1_SESN2 |
| ATG12_CSE1L_ID2_MMP9_BHLHE41 | ATG12_ULK1_ID2_MMP9_TCF3_SATB1 |
| DIABLO_ID2_MMP9_NAMPT_STAT3 | ATG12_ATG3_ATG5_ID2_MMP9_TCF3 |
| DIABLO_FAS_ID2_NAMPT_SESN2 | ATG12_ATG3_BNIP3_CSE1L_ID2_MMP9 |
| ATG12_CSE1L_FAS_ID2_MMP9 | ATG12_ATG3_LAMP1_ID2_MMP9_TCF3 |
| DIABLO_FAS_ID2_TCF3_NAMPT | ATG12_BNIP3_DIABLO_ID2_MMP9_TCF3 |
| ATG12_ATG3_ID2_MMP9_SATB1 | ATG12_BNIP3_ULK1_ID2_MMP9_TCF3 |
| ATG12_BNIP3_ID2_MMP9_BHLHE41 | ATG12_DIABLO_FAS_ID2_MMP9_TCF3 |
| ATG3_DIABLO_FAS_ID2_NAMPT | ATG12_ULK1_ID2_MMP9_TCF3_SESN2 |
| CSE1L_DIABLO_FAS_ID2_NAMPT | ATG3_DIABLO_FAS_ID2_MMP9_NAMPT |
| ATG12_CSE1L_ID2_MMP9_RPS19BP1 | ATG12_ATG3_BNIP3_ID2_MMP9_SESN2 |
| ATG12_CSE1L_ULKLID2_MMP9 | ATG12_ATG3_ID2_MMP9_TCF3_BHLHE41 |
| DIABLO_FAS_ID2_MMP9_TCF3 | ATG12_BNIP3_CSE1L_FAS_ID2_MMP9 |
| CSE1L_DIABLO_ID2_NAMPT_STAT3 | DIABLO_ID2_MMP9_TCF3_NAMPT_SATB1 |
| ATG12_ATG3_ID2_MMP9_SESN2 | ATG12_ATG3_BNIP3_ID2_MMP9_RPS19BP1 |
| DIABLO_ID2_MMP9_TCF3_STAT3 | ATG12_ATG5_ID2_MMP9_TCF3_SATB1 |
| DIABLO_ID2_TCF3_NAMPT_SATB1 | ATG12_BNIP3_FAS_ID2_MMP9_TCF3 |
| CSE1L_DIABLO_FAS_MMP9_NAMPT | ATG12_ATG3_CSE1L_ID2_MMP9_SATB1 |
| DIABLO_FAS_ID2_NAMPT_RPS19BP1 | ATG12_ATG3_ID2_MMP9_TCF3_STAT3 |
| BNIP3_DIABLO_FAS_ID2_MMP9 | ATG12_ATG5_BNIP3_ID2_MMP9_SATB1 |
| DIABLO_ID2_MMP9_NAMPT_SATB1 | ATG12_BNIP3_ID2_MMP9_TCF3_BHLHE41 |
| ATG12_DIABLO_FAS_MMP9_TCF3 | ATG12_FAS_ID2_MMP9_TCF3_SESN2 |
| ATG12_ATG5_FAS_ID2_MMP9 | DIABLO_FAS_ID2_MMP9_NAMPT_RPS19BP1 |
| ATG12_LC3_ID2_MMP9_TCF3 | ATG12_ATG3_CSE1L_ID2_MMP9_SESN2 |
| ATG12_FAS_ID2_MMP9_STAT3 | ATG12_ATG3_ID2_MMP9_TCF3_RPS19BP1 |
| FAS_ID2_MMP9_NAMPT_RPS19BP1 | ATG12_ATG5_BNIP3_FAS_ID2_MMP9 |
| ATG12_ID2_MMP9_TCF3_BECN1 | ATG12_ATG5_ULK1_ID2_MMP9_TCF3 |
| ATG12_CDH1_ID2_MMP9_TCF3 | E2F1_FAS_CDH1_ID2_MMP9_TCF3 |

| Combinations of seven types | Combinations of eight types |
|---|---|
| DIABLO_FASJD2_MMP9_TCF3_NAMPT_SATB1 | ATG12_ATG3_BNIP3_CSE1L_ID2_MMP9_SATB1_SESN2 |
| ATG12_ATG3_BNIP3_CSE1L_ID2_MMP9_SATB1 | ATG12_ATG3_BNIP3_CSE1L_ID2_MMP9_TCF3_SATB1 |
| ATG12_ATG3_BNIP3_CSE1L_ID2_MMP9_SESN2 | ATG12_ATG3_BNIP3_CSE1L_ULK1_ID2_MMP9_SATB1 |
| ATG12_ATG3_BNIP3_ID2_MMP9_TCF3_SATB1 | ATG12_ATG3_BNIP3_FAS_ID2_MMP9_TCF3_RPS19BP1 |
| ATG12_ATG3_BNIP3_CSE1L_ID2_MMP9_TCF3 | DIABLO_FAS_ID2_MMP9_TCF3_NAMPT_SATB1_STAT3 |
| DIABLO_FASJD2_MMP9_TCF3_NAMPT_SESN2 | DIABLO_FAS_ID2_MMP9_TCF3_NAMPT_SATB1_SESN2 |
| ATG12_ATG3_BNIP3_CSE1L_ID2_MMP9_BHLHE41 | ATG12_ATG3_ATG5_BNIP3_CSE1L_ID2_MMP9_SATB1 |
| ATG12_ATG3_BNIP3_ID2_MMP9_TCF3_SESN2 | ATG12_ATG3_ATG5_BNIP3_ID2_MMP9_TCF3_SATB1 |
| ATG12_ATG3_BNIP3_ULK1_ID2_MMP9_TCF3 | ATG12_ATG3_BNIP3_CSE1L_ULK1_ID2_MMP9_SESN2 |
| ATG12_BNIP3_CSE1L_ULK1_ID2_MMP9_SATB1 | ATG12_ATG3_BNIP3_CSE1L_ULK1_ID2_MMP9_TCF3 |
| ATG12_BNIP3_FAS_ID2_MMP9_TCF3_RPS19BP1 | ATG12_ATG3_BNIP3_DIABLO_FAS_ID2_MMP9_TCF3 |
| DIABLO_FASJD2_MMP9_NAMPT_SATB1_STAT3 | ATG12_ATG3_BNIP3_ID2_MMP9_TCF3_SATB1_SESN2 |
| DIABLO_FASJD2_MMP9_TCF3_NAMPT_STAT3 | ATG12_ATG3_BNIP3_ULK1_ID2_MMP9_TCF3_SATB1 |
| ATG12_ATG3_ATG5_BNIP3_ID2_MMP9_TCF3 | ATG12_ATG3_BNIP3_CSE1L_ID2_MMP9_BHLHE41_SATB1 |
| ATG12_ATG3_BNIP3_FAS_ID2_MMP9_RPS19BP1 | ATG12_ATG3_BNIP3_CSE1L_ID2_MMP9_TCF3_SESN2 |
| ATG12_ATG3_BNIP3_FAS_ID2_MMP9_TCF3 | ATG3_BCL2_E2F1_LAMP1_TKT_MMP9_CASP3_HMGB1 |
| ATG12_ATG3_BNIP3_ID2_MMP9_TCF3_RPS19BP1 | ATG12_ATG3_ATG5_BNIP3_CSE1L_ID2_MMP9_SESN2 |
| ATG12_ATG3_ULK1_ID2_MMP9_TCF3_SATB1 | ATG12_ATG3_BNIP3_CSE1L_DIABLO_FASJD2_MMP9 |
| ATG12_ATG5_BNIP3_CSE1L_ID2_MMP9_SATB1 | ATG12_ATG3_BNIP3_CSE1L_ID2_MMP9_TCF3_BHLHE41 |
| ATG12_BNIP3_CSE1L_ID2_MMP9_SATB1_SESN2 | ATG12_ATG3_BNIP3_CSE1L_ULK1_02_MMP9_BHLHE41 |
| ATG12_BNIP3_CSE1L_ID2_MMP9_TCF3_SATB1 | ATG12_ATG3_BNIP3_FAS_ID2_MMP9_RPS19BP1_SATB1 |
| ATG12_BNIP3_DIABLO_FAS_ID2_MMP9_TCF3 | ATG12_ATG3_BNIP3_FAS_ID2_MMP9_TCF3_SATB1 |
| ATG12_ATG3_ID2_MMP9_TCF3_SATB1_SESN2 | ATG12_ATG3_BNIP3_FAS_ID2_MMP9_TCF3_SESN2 |
| DIABLO_FASJD2_MMP9_TCF3_SATB1_STAT3 | ATG12_ATG3_BNIP3_ID2_MMP9_TCF3_BHLHE41_SATB1 |

TABLE 11-continued

| | |
|---|---|
| ATG12_ATG3_BNIP3_CSE1L_FAS_ID2_MMP9 | ATG12_ATG3_BNIP3_ID2_MMP9_TCF3_RPS19BP1_SATB1 |
| ATG12_ATG3_BNIP3_DIABLO_FAS_ID2_MMP9 | ATG12_ATG3_BNIP3_ULK1_ID2_MMP9_TCF3_SESN2 |
| ATG12_ATG3_BNIP3_ID2_MMP9_TCF3_BHLHE41 | ATG12_BNIP3_CSE1L_ID2_MMP9_TCF3_SATB1_SESN2 |
| ATG12_BNIP3_CSE1L_DIABLO_FAS_ID2_MMP9 | ATG12_BNIP3_DIABLO_FAS_ID2_MMP9_TCF3_SATB1 |
| ATG12_BNIP3_CSE1L_ULK1_02_MMP9_SESN2 | ATG12_BNIP3_FAS_ID2_MMP9_TCF3_RPS19BP1_SATB1 |
| CSE1L_DIABLO_FAS_ID2_MMP9_NAMPT_STAT3 | ATG12_BNIP3_FAS_ULK1_ID2_MMP9_TCF3_RPS19BP1 |
| ATG12_ATG3_ATG5_BNIP3_FAS_ID2_MMP9 | CSE1L_DIABLO_FAS_ID2_MMP9_NAMPT_SATB1_STAT3 |
| ATG12_ATG3_CSE1L_ID2_MMP9_TCF3_SATB1 | ATG12_ATG3_ATG5_BNIP3_FAS_ID2_MMP9_TCF3 |
| ATG12_ATG3_ULK1_ID2_MMP9_TCF3_SESN2 | ATG12_ATG3_ATG5_BNIP3_ID2_MMP9_TCF3_SESN2 |
| ATG12_ATG5_BNIP3_CSE1L_ID2_MMP9_SESN2 | ATG12_ATG3_ATG5_BNIP3_ULK1_ID2_MMP9_TCF3 |
| ATG12_ATG5_BNIP3_ID2_MMP9_TCF3_SATB1 | ATG12_ATG3_BNIP3_CSE1L_FAS_ID2_MMP9_RPS19BP1 |
| ATG12_BNIP3_CSE1L_ID2_MMP9_TCF3_SESN2 | ATG12_ATG3_BNIP3_CSE1L_FAS_ID2_MMP9_SATB1 |
| ATG12_BNIP3_CSE1L_ULK1_02_MMP9_TCF3 | ATG12_ATG3_BNIP3_CSE1L_ID2_MMP9_BHLHE41_SESN2 |
| ATG12_BNIP3_ID2_MMP9_TCF3_RPS19BP1_SATB1 | ATG12_ATG3_BNIP3_DIABLO_FAS_ID2_MMP9_SATB1 |
| ATG12_ATG3_FAS_ID2_MMP9_TCF3_SATB1 | ATG12_ATG3_BNIP3_FAS_ID2_MMP9_RPS19BP1_SESN2 |
| ATG12_ATG3_FAS_ID2_MMP9_TCF3_RPS19BP1 | ATG12_ATG3_BNIP3_FAS_ULK1_ID2_MMP9_RPS19BP1 |
| ATG12_ATG3_FAS_ID2_MMP9_TCF3_SESN2 | ATG12_ATG3_BNIP3_FAS_ULK1_ID2_MMP9_TCF3 |
| ATG12_ATG3_FAS_ULK1_ID2_MMP9_TCF3 | ATG12_ATG5_BNIP3_CSE1L_ID2_MMP9_SATB1_SESN2 |
| ATG12_ATG3_ATG5_BNIP3_ID2_MMP9_SATB1 | ATG12_ATG5_BNIP3_CSE1L_ULK1_ID2_MMP9_SATB1 |
| ATG12_ATG3_BNIP3_CSE1L_ID2_MMP9_RPS19BP1 | ATG12_BNIP3_CSE1L_ULK1_ID2_MMP9_SATB1_SESN2 |
| ATG12_ATG3_CSE1L_ID2_MMP9_TCF3_SESN2 | ATG12_BNIP3_CSE1L_ULK1_ID2_MMP9_TCF3_SATB1 |
| ATG12_ATG3_CSE1L_ULK1_ID2_MMP9_TCF3 | ATG12_BNIP3_DIABLO_FAS_ID2_MMP9_TCF3_SESN2 |
| ATG12_BNIP3_CSE1L_FAS_ID2_MMP9_RPS19BP1 | ATG12_BNIP3_DIABLO_FAS_ULK1_02_MMP9_TCF3 |
| ATG12_BNIP3_CSE1L_ID2_MMP9_BHLHE41_SATB1 | ATG12_BNIP3_FAS_ID2_MMP9_TCF3_RPS19BP1_SESN2 |
| ATG12_BNIP3_CSE1L_ID2_MMP9_TCF3_BHLHE41 | ATG3_DIABLO_FAS_ID2_MMP9_TCF3_NAMPT_SATB1 |
| ATG12_BNIP3_ID2_MMP9_TCF3_SATB1_SESN2 | DIABLO_FAS_ID2_MMP9_TCF3_NAMPT_SESN2_STAT3 |
| ATG12_BNIP3_ULK1_ID2_MMP9_TCF3_SATB1 | DIABLO_FAS_ID2_MMP9_NAMPT_SATB1_SESN2_STAT3 |
| DIABLO_FASJD2_MMP9_NAMPT_SESN2_STAT3 | ATG12_ATG3_ATG5_BNIP3_CSE1L_FAS_ID2_MMP9 |
| CSE1L_DIABLO_FAS_ID2_MMP9_TCF3_NAMPT | ATG12_ATG3_ATG5_BNIP3_CSE1L_ID2_MMP9_BHLHE41 |
| DIABLO_FASJD2_MMP9_NAMPT_SATB1_SESN2 | ATG12_ATG3_ATG5_BNIP3_CSE1L_ID2_MMP9_TCF3 |
| CSE1L_DIABLO_FAS_ID2_MMP9_NAMPT_SATB1 | ATG12_ATG3_ATG5_BNIP3_FAS_ID2_MMP9_RPS19BP1 |
| ATG12_ATG3_BNIP3_DIABLO_ID2_MMP9_TCF3 | ATG12_ATG3_ATG5_BNIP3_FAS_ID2_MMP9_SATB1 |
| ATG12_ATG3_BNIP3_FAS_ID2_MMP9_SATB1 | ATG12_ATG3_BNIP3_CSE1L_FAS_ID2_MMP9_SESN2 |
| ATG3_TKT_CDH1_ID2_MMP9_TCF3_UVRAG | ATG3_TKT_CDH1_ID2_MMP9_TCF3_TP63_UVRAG |

Preferably, the composition or kit is for predicting the prognosis of disease-free survival of the B group, and the genes are one or more selected from the genes or groups of genes described in the following Table 12.

TABLE 12

| One type | Combinations of two types | Combinations of three types | Combinations of four types |
|---|---|---|---|
| DIABLO | ATG3_BECN1 | ATG3_BCL2 HMGB1 | ATG3_BCL2_CDH1_HMGB1 |
| BECN1 | ATG3_HMGB1 | ATG3_HMGB1_RAGE | ATG3_CDH1_HMGB1_UVRAG |
| HMGB1 | BCL2L1_TKT | ATG3_HMGB1_UVRAG | ATG3_BCL2_TKT_HMGB1 |
| | CSE1L_DIABLO | ATG3_CASP3_HMGB1 | ATG3_BCL2_HMGB1_RAGE |
| | BCL2_HMGB1 | ATG3_HMGB1_SIRT1 | ATG3_BCL2_HMGB1_HMGB2 |
| | ATG12_ATG3 | ATG3_BECN1_SATB1 | ATG3_CDH1_HMGB1_SIRT1 |
| | ATG3_NAMPT | ATG3_HMGB1_LAMP2 | ATG3_BCL2_HMGB1_MMP2 |
| | HMGB1_TWIST1 | ATG3_HMGB1_RAPTOR | ATG3_HMGB1_HMGB2_RAGE |
| | TKT_HMGB1 | ATG3_LC3_BECN1 | ATG3_BCL2_BNIP3_HMGB1 |
| | LAMP1_HMGB1 | ATG3_HMGB1_KIAA1967 | ATG3_CDH1_CASP3_HMGB1 |
| | TKT_BECN1 | BCL2L1_TKT_CASP3 | ATG3_CDH1_HMGB1_KIAA1967 |
| | HMGB1_TP63 | ATG12_ATG3_HMGB1 | ATG3_HMGB1_RAGE_UVRAG |
| | BCL2_TKT | BCL2L1_TKT_SIRT1 | ATG3_HMGB1_RAGE_SIRT1 |
| | TKT_CASP3 | BCL2L1_TKT_BECN1 | ATG3_TKT_HMGB1_UVRAG |
| | FASLG_HMGB1 | BCL2_TKT_HMGB1 | ATG3_BCL2_LAMP1_HMGB1 |
| | TKT_NAMPT | ATG3_BECN1_SESN3 | ATG3_BCL2_HMGB1_RAPTOR |
| | ATG5_HMGB1 | ATG3_BNIP3_HMGB1 | AIFM1_ATG3_BCL2_HMGB1 |
| | HMGB1_SIRT1 | ATG3_BECN1_HMGB1 | ATG3_CASP3_HMGB1_RAGE |
| | ATG12_HMGB1 | AIFM1_ATG3_HMGB1 | ATG12_ATG3_HMGB1_RAGE |
| | HMGB1_RAGE | ATG3_LAMP1_HMGB1 | ATG3_TKT_CASP3_HMGB1 |
| | DIABLO_NAMPT | BCL2L1_TKT_FASLG | ATG3_TKT_HMGB1_KIAA1967 |
| | HMGB1_UVRAG | BCL2_BCL2L1_TKT | ATG3_BCL2L1_TKT_BECN1 |
| | DIABLO_BECN1 | TKT_HMGB1_TWIST1 | ATG12_ATG3_CDH1_HMGB1 |
| | BECN1_SATB1 | ATG3_NNMT_HMGB1 | ATG3_CDH1_HMGB1_RAGE |
| | BCL2L1_SIRT1 | BCL2L1_TKT_HMGB1 | ATG3_BCL2_FRAP1_HMGB1 |
| | BCL2L1_HMGB1 | ATG3_BCL2L1_BECN1 | ATG3_BCL2_HMGB1_LAMP2 |
| | TKT_SIRT1 | ATG5_TKT_HMGB1 | ATG3_BCL2_DIABLO_HMGB1 |
| | DIABLO_TCF3 | ATG3_FASLG_HMGB1 | ATG3_TKT_HMGB1_SIRT1 |
| | HMGB1_LAMP2 | ATG3_MMP9_BECN1 | ATG3_BCL2_CBS_HMGB1 |
| | DIABLO_SATB1 | ATG3_LAMP1_BECN1 | ATG3_BCL2_CASP8_HMGB1 |
| | HMGB1_RAPTOR | ATG3_E2F1_HMGB1 | ATG3_BCL2_PTEN_HMGB1 |
| | E2F1_HMGB1 | HMGB1_RAPTOR_TWIST1 | ATG3_HMGB1_RAGE_RAPTOR |
| | ATG5_BECN1 | AKT1_ATG3_BECN1 | ATG3_TKT_HMGB1_RAGE |
| | ATG12_SATB1 | ATG3_ULK1_HMGB1 | ATG3_BCL2_CASP3_HMGB1 |
| | BCL2L1_BECN1 | TKT_HMGB1_SIRT1 | ATG3_BCL2_HMGB1_SATB1 |

TABLE 12-continued

| | | |
|---|---|---|
| CASP3_HMGB1 | ATG3_BAX_HMGB1 | ATG3_HMGB1_LAMP2_RAGE |
| ATG12_CSE1L | ATG3_PTEN_HMGB1 | ATG3_CDH1_HMGB1_LAMP2 |
| ATG7_HMGB1 | ATG3_TKT_HMGB1 | ATG3_HMGB1_HMGB2_UVRAG |
| ATG3_SIRT1 | ATG3_TKT_BECN1 | ATG3_BCL2L1_TKT_HMGB1 |
| CASP8_HMGB1 | ATG3_HMGB1_TWIST1 | CDH1_HMGB1_TP63_UVRAG |
| ATG3_SESN1 | BCL2L1_TKT_UVRAG | ATG3_BCL2L1_TKT_CASP3 |
| TKT_KIAA1967 | TKT_HMGB1_UVRAG | ATG3_HMGB1_KIAA1967_RAGE |
| ATG12_BCL2L1 | BCL2L1_TKT_CDH2 | ATG3_BCL2_DRAM_HMGB1 |
| DRAM_HMGB1 | BCL2L1_TKT_KIAA1967 | ATG3_BCL2_HMGB1_UVRAG |
| LC3_FASLG | ATG3_BCL2L1_HMGB1 | BCL2_BCL2L1_TKT_CASP3 |
| HMGB1_KIAA1967 | ATG3_ATG5_HMGB1 | ATG3_TKT_BECN1_HMGB1 |
| TKT_SESN1 | ATG3_DRAM_HMGB1 | ATG3_TKT_HMGB1_LAMP2 |
| ATG3_DIABLO | ATG3_HMGB1_SATB1 | ATG3_BCL2_PRKAA1_HMGB1 |
| DIABLO_SIRT1 | ATG3_BCL2L1_TKT | BCL2L1_TKT_CASP3_SIRT1 |
| BECN1_HMGB1 | ATG3_PRKAA1_HMGB1 | BCL2L1_TKT_CASP3_FASLG |
| A1FM1_HMGB1 | TKT_CASP3_HMGB1 | BCL2L1_TKT_CASP3_CDH2 |
| ID2_BECN1 | ATG3_XIAP_HMGB1 | ATG3_BCL2_NNMT_HMGB1 |
| CSE1L_BECN1 | TKT_HMGB1_KIAA1967 | ATG3_CDH1_HMGB1_RAPTOR |
| TKT_ULK1 | TKT_HMGB1_LAMP2 | ATG3_BNIP3_HMGB1_RAGE |
| BNIP3_HMGB1 | HMGB1_RAGE_TWIST1 | ATG3_BAX_BCL2_HMGB1 |
| TKT_UVRAG | ATG12_BCL2L1_TKT | ATG3_BCL2_ID2_HMGB1 |
| ATG5_TKT | ATG3_PTEN_BECN1 | ATG3_BCL2_HMGB1_STAT3 |

| Combinations of five types | Combinations of six types |
|---|---|
| ATG3_BCL2_CDH1_HMGB1_RAGE | ATG3_BCL2_CDH1_HMGB1_RAGE_RAPTOR |
| ATG3_BCL2_CDH1_HMGB1_UVRAG | ATG3_BCL2_BNIP3_CDH1_HMGB1_RAGE |
| ATG3_BCL2_CDH1_HMGB1_SIRT1 | ATG3_BCL2_CDH1_HMGB1_HMGB2_RAGE |
| ATG3_BCL2_CDH1_HMGB1_RAPTOR | ATG3_BCL2_CDH1_HMGB1_KIAA1967_RAGE |
| ATG3_BCL2_CDH1_HMGB1_HMGB2 | ATG3_BCL2_CDH1_HMGB1_RAGE_SIRT1 |
| ATG3_BCL2_CDH1_HMGB1_KIAA1967 | ATG3_BCL2_CDH1_HMGB1_HMGB2_RAPTOR |
| ATG3_BCL2_BNIP3_CDH1_HMGB1 | ATG3_BCL2_CDH1_CDH2_HMGB1_RAGE |
| ATG3_BCL2_CDH1_HMGB1_LAMP2 | ATG3_BCL2_CDH1_HMGB1_RAGE_UVRAG |
| ATG3_BCL2_CDH1_CDH2_HMGB1 | ATG3_BCL2_CDH1_CASP3_HMGB1_RAGE |
| ATG3_CDH1_HMGB1_RAGE_SIRT1 | AIFM1_ATG3_BCL2_CDH1_HMGB1_SIRT1 |
| ATG3_BCL2_CDH1_CASP3_HMGB1 | ATG3_BCL2_BNIP3_CDH1_HMGB1_UVRAG |
| ATG12_ATG3_BCL2_CDH1_HMGB1 | ATG12_ATG3_BCL2_CDH1_HMGB1_RAGE |
| AIFM1_ATG3_BCL2_CDH1_HMGB1 | ATG3_BCL2_CDH1_HMGB1_HMGB2_UVRAG |
| ATG3_BCL2_CASP8_CDH1_HMGB1 | ATG3_BCL2_CDH1_HMGB1_LAMP2_RAGE |
| ATG3_BCL2_FRAP1_CDH1_HMGB1 | ATG3_BCL2_CDH1_HMGB1_HMGB2_LAMP2 |
| ATG3_BCL2_CBS_CDH1_HMGB1 | ATG3_BCL2_CDH1_CDH2_HMGB1_HMGB2 |
| ATG3_CDH1_HMGB1_RAGE_UVRAG | ATG3_BCL2_BCL2L1_TKT_CASP3_HMGB1 |
| ATG3_BCL2_TKT_HMGB1_HMGB2 | AIFM1_ATG3_BCL2_CDH1_HMGB1_UVRAG |
| ATG3_BCL2_CDH1_HMGB1_MMP2 | ATG3_BCL2_CDH1_HMGB1_HMGB2_KIAA1967 |
| ATG3_BCL2_NNMT_CDH1_HMGB1 | ATG3_BCL2_BNIP3_CDH1_HMGB1_HMGB2 |
| ATG3_BCL2_HMGB1_HMGB2_RAGE | ATG12_ATG3_CDH1_HMGB1_RAGE_SIRT1 |
| ATG3_BCL2_CDH1_MMP9_HMGB1 | ATG3_BCL2_BNIP3_CDH1_HMGB1_RAPTOR |
| ATG12_ATG3_CDH1_HMGB1_RAGE | ATG3_BCL2_DRAM_CDH1_HMGB1_SIRT1 |
| ATG3_CDH1_HMGB1_LAMP2_SIRT1 | ATG3_BCL2_BNIP3_CDH1_HMGB1_LAMP2 |
| ATG3_BCL2_DIABLO_CDH1_HMGB1 | AIFMLATG3_BCL2_CDH1_HMGB1_RAGE |
| ATG3_BCL2L1_TKT_BECN1_CASP3 | ATG3_BCL2_BNIP3_CDH1_HMGB1_KIAA1967 |
| ATG3_BCL2_HMGB1_MMP2_RAGE | ATG3_BCL2_CDH1_HMGB1_MMP2_RAGE |
| ATG3_CDH1_HMGB1_HMGB2_UVRAG | AIFM1_ATG3_BCL2_CDH1_HMGB1_HMGB2 |
| ATG3_BCL2_DRAM_CDH1_HMGB1 | ATG3_BCL2_CDH1_HMGB1_HMGB2_SIRT1 |
| ATG3_BCL2_TKT_CDH1_HMGB1 | ATG3_BCL2_CDH1_HMGB1_MMP2_UVRAG |
| ATG3_BCL2_TKT_CASP3_HMGB1 | ATG3_BCL2_CASP8_CDH1_HMGB1_RAGE |
| ATG3_CDH1_HMGB1_KIAA1967_UVRAG | ATG3_CDH1_HMGB1_LAMP2_RAGE_SIRT1 |
| ATG3_CDH1_HMGB1_LAMP2_UVRAG | ATG3_BCL2_DRAM_CDH1_HMGB1_UVRAG |
| ATG3_BCL2_BCL2L1_TKT_HMGB1 | ATG3_BCL2_PTEN_CDH1_HMGB1_SIRT1 |
| ATG3_BCL2_CDH1_HMGB1_SATB1 | ATG3_BCL2_BCL2L1_TKT_HMGB1_SIRT1 |
| ATG3_BCL2L1_TKT_HMGB1_SIRT1 | ATG3_BCL2_BNIP3_CDH1_HMGB1_SIRT1 |
| ATG3_BCL2_TKT_ID2_HMGB1 | ATG3_BCL2_FRAP1_CDH1_HMGB1_RAGE |
| ATG3_CDH1_HMGB1_KIAA1967_RAGE | AIFM1_ATG3_BCL2_CDH1_HMGB1_KIAA1967 |
| ATG3_BCL2_PTEN_CDH1_HMGB1 | ATG3_BCL2_CDH1_HMGB1_LAMP2_RAPTOR |
| AIFM1_ATG3_CDH1_HMGB1_SIRT1 | ATG3_CDH1_HMGB1_RAGE_SIRT1_UVRAG |
| ATG3_BCL2_CDH1_HMGB1_STAT3 | ATG3_BCL2_CBS_CDH1_HMGB1_RAGE |
| ATG3_CDH1_CASP3_HMGB1_RAGE | ATG3_BCL2_FRAP1_CDH1_HMGB1_UVRAG |
| ATG3_BCL2_LC3_TKT_HMGB1 | ATG3_BCL2_CBS_CDH1_HMGB1_UVRAG |
| ATG3_CDH1_CASP3_HMGB1_UVRAG | ATG3_CDH1_HMGB1_HMGB2_RAGE_SIRT1 |
| ATG3_BCL2_CDH1_CIAP2_HMGB1 | AIFM1_ATG3_BCL2_CDH1_HMGB1_RAPTOR |
| ATG3_BCL2_BNIP3_HMGB1_RAGE | ATG3_BCL2_CDH1_HMGB1_KIAA1967_RAPTOR |
| ATG3_CDH1_HMGB1_RAPTOR_SIRT1 | ATG3_BCL2_BCL2L1_TKT_ID2_CASP3 |
| ATG3_CDH1_HMGB1_SIRT1_UVRAG | ATG3_BCL2_CDH1_HMGB1_RAPTOR_UVRAG |
| ATG3_CDH1_HMGB1_RAPTOR_UVRAG | ATG3_BCL2_CASP8_CDH1_HMGB1_HMGB2 |
| ATG3_CDH1_HMGB1_KIAA1967_SIRT1 | ATG12_ATG3_BCL2_CDH1_HMGB1_HMGB2 |
| ATG3_BAX_BCL2_CDH1_HMGB1 | ATG3_BCL2_FRAP1_CDH1_HMGB1_SIRT1 |
| ATG3_BCL2_LAMP1_CDH1_HMGB1 | ATG3_BCL2_CDH1_HMGB1_MMP2_SIRT1 |
| ATG3_ATG5_BCL2_CDH1_HMGB1 | AIFM1_ATG3_CDH1_HMGB1_RAGE_SIRT1 |
| ATG3_BCL2_TKT_HMGB1_RAGE | ATG3_BCL2_FRAP1_CDH1_HMGB1_HMGB2 |
| ATG3_CDH1_HMGB1_SATB1_UVRAG | ATG3_BCL2_CBS_CDH1_HMGB1_SIRT1 |

TABLE 12-continued

| | |
|---|---|
| ATG3_BCL2_CDH1_HMGB1_SESN3 | ATG3_BCL2_CASP8_CDH1_HMGB1_UVRAG |
| ATG3_BCL2_FAS_CDH1_HMGB1 | ATG3_BCL2_PTEN_CDH1_HMGB1_UVRAG |
| CDH1_ID2_MMP9_TCF3_FASLG | ATG12_ATG3_CDH1_ID2_MMP9_TCF3 |
| Combinations of seven types | Combinations of eight types |
| ATG3_BCL2_CDH1_HMGB1_HMGB2_RAGE_RAPTOR | ATG3_BCL2_BCL2L1_TKT_ID2_CASP3_CDH2_HMGB2 |
| ATG3_BCL2_CDH1_CDH2_HMGB1_HMGB2_RAGE | ATG3_BCL2_BNIP3_CDH1_HMGB1_HMGB2_RAGE_RAPTOR |
| ATG3_BCL2_BNIP3_CDH1_HMGB1_RAGE_RAPTOR | ATG3_BCL2L1_TKT_ID2_CDH2_HMGB2_TWIST1_UVRAG |
| ATG3_BCL2_BNIP3_CDH1_HMGB1_HMGB2_RAGE | ATG3_BCL2_BCL2L1_TKT_ID2_CASP3_HMGB2_KIAA1967 |
| ATG3_BCL2_BNIP3_CDH1_HMGB1_KIAA1967_RAGE | ATG3_BCL2_BCL2L1_TKT_ID2_CASP3_HMGB2_SIRT1 |
| AIFM1_ATG3_BCL2_CDH1_HMGB1_RAGE_SIRT1 | ATG3_BCL2_BCL2L1_TKT_CDH1_CASP3_HMGB1_SIRT1 |
| ATG3_BCL2_CDH1_HMGB1_HMGB2_KIAA1967_RAGE | ATG3_BCL2_BNIP3_CDH1_FASLG_HMGB1_HMGB2_RAGE |
| ATG3_BCL2_DRAM_CDH1_HMGB1_RAGE_SIRT1 | ATG3_BCL2_BCL2L1_BNIP3_TKT_ID2_CASP3_HMGB2 |
| ATG3_BCL2_BNIP3_CDH1_HMGB1_RAGE_UVRAG | ATG3_BCL2_BNIP3_CDH1_CASP3_FASLG_HMGB1_RAGE |
| ATG3_BCL2_BCL2L1_TKT_ID2_CASP3_HMGB2 | ATG3_BCL2L1_TKT_ID2_CDH2_HMGB2_SIRT1_TWIST1 |
| ATG3_BCL2_BCL2L1_TKT_ID2_CASP3_SIRT1 | AIFM1_ATG3_BCL2_CDH1_CDH2_HMGB1_HMGB2_RAGE |
| ATG3_BCL2_BCL2L1_TKT_CASP3_HMGB1_SIRT1 | ATG3_BCL2L1_TKT_ID2_CDH2_HMGB2_KIAA1967_TWIST1 |
| ATG3_BCL2_BNIP3_CDH1_HMGB1_LAMP2_RAGE | ATG3_BCL2_DRAM_CDH1_HMGB1_HMGB2_RAGE_SIRT1 |
| ATG3_BCL2_BNIP3_CDH1_CDH2_HMGB1_RAGE | ATG3_BCL2_BCL2L1_TKT_CASP3_CDH2_HMGB1_HMGB2 |
| ATG3_BCL2_BNIP3_CDH1_HMGB1_RAGE_SIRT1 | AIFM1_ATG3_BCL2_CDH1_HMGB1_HMGB2_RAGE_RAPTOR |
| ATG3_BCL2_CDH1_HMGB1_HMGB2_LAMP2_RAGE | ATG3_BCL2_BNIP3_CDH1_CDH2_HMGB1_HMGB2_RAGE |
| ATG12_ATG3_BCL2_CDH1_HMGB1_HMGB2_RAGE | ATG3_BCL2_BCL2L1_TKT_ID2_CASP3_HMGB2_UVRAG |
| ATG3_BCL2_BCL2L1_TKT_ID2_CASP3_KIAA1967 | ATG3_CDH1_CDH2_HMGB1_HMGB2_RAGE_RAPTOR_TWIST1 |
| ATG3_BCL2_BCL2L1_TKT_CASP3_CDH2_HMGB1 | ATG3_BCL2_BCL2L1_BNIP3_TKT_ID2_HMGB2_SIRT1 |
| AIFM1_ATG3_BCL2_CDH1_HMGB1_HMGB2_RAGE | ATG3_BCL2_DRAM_CDH1_CDH2_HMGB1_HMGB2_RAGE |
| ATG3_BCL2_BCL2L1_TKT_CASP3_HMGB1_HMGB20000 | ATG3_BCL2_BCL2L1_TKT_CDH1_CASP3_CDH2_HMGB1 |
| ATG12_ATG3_BCL2_BNIP3_CDH1_HMGB1_RAGE | ATG3_BCL2_BCL2L1_TKT_CASP3_HMGB1_HMGB2_RAPTOR |
| ATG3_BCL2_BCL2L1_TKT_CASP3_HMGB1_UVRAG | AIFM1_ATG3_BCL2_BNIP3_CDH1_HMGB1_HMGB2_RAGE |
| ATG3_BCL2_CDH1_HMGB1_KIAA1967_MMP2_RAGE | ATG3_BCL2_BCL2L1_BNIP3_TKT_ID2_CASP3_KIAA1967 |
| AIFM1_ATG3_BCL2_BNIP3_CDH1_HMGB1_RAGE | ATG3_BCL2L1_TKT_HMGB1_RAGE_RAPTOR_TWIST1_UVRAG |
| ATG3_BCL2_BCL2L1_TKT_CASP3_HMGB1_KIAA1967 | AIFM1_ATG3_BCL2_BNIP3_CDH1_HMGB1_RAGE_SIRT1 |
| ATG3_BCL2_BCL2L1_TKT_CASP3_HMGB1_RAPTOR | ATG3_BCL2_BNIP3_CDH1_HMGB1_HMGB2_LAMP2_RAGE |
| AIFM1_ATG3_BCL2_CDH1_HMGB1_KIAA1967_RAGE | ATG3_BCL2_DRAM_CDH1_HMGB1_HMGB2_RAGE_RAPTOR |
| ATG3_BCL2_BCL2L1_TKT_ID2_HMGB2_SIRT1 | ATG3_BCL2_BCL2L1_TKT_ID2_CASP3_HMGB2_RAPTOR |
| ATG3_BCL2_CDH1_HMGB1_MMP2_RAGE_SIRT1 | ATG3_BCL2_BCL2L1_TKT_CASP3_CDH2_HMGB1_RAGE |
| AIFM1_ATG3_BCL2_CDH1_CASP3_HMGB1_RAGE | ATG3_CDH1_CDH2_HMGB1_HMGB2_KIAA1967_RAGE_TWIST1 |
| ATG3_BCL2_CDH1_HMGB1_KIAA1967_RAGE_RAPTOR | ATG3_BCL2_BCL2L1_TKT_CDH1_CASP3_HMGB1_UVRAG |
| ATG3_BCL2_DRAM_CDH1_CASP3_HMGB1_RAGE | ATG3_BCL2_BNIP3_CDH1_HMGB1_HMGB2_KIAA1967_RAGE |
| ATG3_BCL2_BNIP3_CDH1_FASLG_HMGB1_RAGE | ATG3_BCL2_BCL2L1_TKT_CASP3_HMGB1_HMGB2_LAMP2 |
| ATG3_BCL2_CDH1_HMGB1_HMGB2_RAGE_SIRT1 | ATG3_BCL2L1_TKT_ID2_HMGB2_KIAA1967_TWISTLUVRAG |
| ATG3_TKT_HMGB1_HMGB2_KIAA1967_RAGE_TWIST1 | ATG3_BCL2_BCL2L1_TKT_CASP3_HMGB1_RAGE_SIRT1 |
| ATG3_BCL2_BCL2L1_TKT_ID2_CASP3_CDH2 | ATG3_BCL2_BCL2L1_TKT_CASP3_HMGB1_HMGB2_SIRT1 |
| ATG3_BCL2_DRAM_CDH1_HMGB1_HMGB2_UVRAG | ATG3_BCL2_BCL2L1_TKT_CDH1_CASP3_HMGB1_KIAA1967 |
| AIFM1_ATG3_BCL2_CDH1_CDH2_HMGB1_RAGE | ATG3_BCL2_FRAP1_CDH1_HMGB1_HMGB2_RAGE_RAPTOR |
| ATG3_BCL2_BCL2L1_TKT_CASP3_HMGB1_LAMP2 | AIFM1_ATG3_BCL2_BNIP3_CDH1_HMGB1_KIAA1967_RAGE |
| AIFM1_ATG3_BCL2_CDH1_HMGB1_HMGB2_RAPTOR | ATG3_LC3_TKT_HMGB1_RAGE_RAPTOR_TWIST1_UVRAG |
| AIFM1_ATG3_BCL2_CDH1_HMGB1_RAGE_RAPTOR | ATG3_BCL2_BCL2L1_BNIP3_TKT_ID2_CASP3_SIRT1 |
| ATG3_BCL2_CASP8_CDH1_HMGB1_HMGB2_RAGE | AIFM1_ATG3_BCL2_CDH1_HMGB1_MMP2_RAGE_SIRT1 |
| ATG3_BCL2_CDH1_HMGB1_HMGB2_RAGE_UVRAG | ATG3_BCL2_DRAM_CDH1_HMGB1_HMGB2_RAGE_UVRAG |
| ATG3_BCL2_BNIP3_CDH1_HMGB1_HMGB2_RAPTOR | AIFM1_ATG3_BCL2_CDH1_HMGB1_HMGB2_RAGE_SIRT1 |
| ATG3_BCL2_BNIP3_CASP8_CDH1_HMGB1_RAGE | ATG3_BCL2_CASP8_CDH1_HMGB1_HMGB2_RAGE_RAPTOR |
| ATG3_BCL2_CDH1_HMGB1_MMP2_RAGE_UVRAG | ATG3_BCL2_BNIP3_DRAM_CDH1_HMGB1_RAGE_SIRT1 |
| ATG3_BCL2_BCL2L1_TKT_HMGB1_HMGB2_SIRT1 | ATG3_LC3_TKT_HMGB1_KIAA1967_RAGE_TWIST1_UVRAG |
| ATG3_BCL2_BCL2L1_TKT_CASP3_HMGB1_RAGE | ATG3_BCL2_BCL2L1_TKT_CASP3_HMGB1_HMGB2_KIAA1967 |
| AIFM1_ATG3_BCL2_BNIP3_CDH1_HMGB1_UVRAG | AIFM1_ATG3_BCL2_BNIP3_CDH1_HMGB1_RAGE_RAPTOR |
| ATG3_BCL2_DRAM_CDH1_HMGB1_HMGB2_SIRT1 | AIFM1_ATG3_BCL2_CDH1_HMGB1_HMGB2_KIAA1967_RAGE |
| ATG12_ATG3_BCL2_BCL2L1_TKT_CASP3_HMGB1 | ATG3_BCL2_BCL2L1_TKT_CASP3_HMGB1_RAGE_RAPTOR |
| ATG12_ATG3_BCL2_PTEN_CDH1_HMGB1_RAGE | ATG3_CDH1_CDH2_HMGB1_HMGB2_RAGE_TWIST1_UVRAG |
| ATG3_BCL2_PTEN_CDH1_HMGB1_RAGE_SIRT1 | ATG3_BCL2_DRAM_CDH1_HMGB1_MMP2_RAGE_SIRT1 |
| ATG3_BCL2_CDH1_CASP3_HMGB1_RAGE_RAPTOR | ATG3_BCL2_BCL2L1_TKT_CASP3_HMGB1_HMGB2_UVRAG |
| ATG3_BCL2_BNIP3_FRAP1_CDH1_HMGB1_RAGE | ATG3_BCL2_CBS_CDH1_HMGB1_HMGB2_RAGE_RAPTOR |
| ATG3_BCL2_FRAP1_CDH1_HMGB1_HMGB2_RAGE | ATG3_BCL2_BCL2L1_TKT_CASP3_HMGB1_HMGB2_RAGE |
| NNMT_CDH1_ID2_MMP9_TCF3_TP63_UVRAG | ATG3_TKT_CDH1_ID2_MMP9_TCF3_TWIST1_UVRAG |

Preferably, the composition or kit is for predicting the prognosis of recurrence of the C group, and the genes are one or more selected from the genes or groups of genes described in the following Table 13.

TABLE 13

| One type | Combinations of two types | Combinations of three types | Combinations of four types |
|---|---|---|---|
| FASLG | CIAP2_FASLG | FAS_LC3_FASLG | DIABLO_FAS_LC3_FASLG |
| CIAP2 | E2F1_FASLG | DIABLO_FAS_FASLG | FAS_LC3_FASLG_UVRAG |
| CSE1L | LC3_FASLG | E2F1_LC3_FASLG | BNIP3_FAS_LC3_FASLG |
| FAS | DIABLO_FASLG | FAS_FASLG_RPS19BP1 | DRAM_FAS_LC3_FASLG |
| TCF3 | FAS_FASLG | E2F1_FAS_FASLG | E2F1_FAS_LC3_FASLG |

TABLE 13-continued

| | | |
|---|---|---|
| FASLG_RPS19BP1 | FAS_FASLG_UVRAG | ATG3_FAS_LC3_FASLG |
| PIEN_FASLG | DIABLO_LC3_FASLG | ATG7_FAS_LC3_FASLG |
| CASP3_FASLG | ATG7_FAS_FASLG | FAS_LC3_FASLG_STAT3 |
| FASLG_SESN2 | CIAP2_FASLG_SESN3 | FAS_FRAP1_LC3_FASLG |
| FASLG_HMGB1 | CIAP2_FASLG_UVRAG | FAS_LC3_FASLG_SESN3 |
| CDH2_FASLG | BNIP3_LC3_FASLG | FAS_LC3_FASLG_SIRT1 |
| FRAP1_FASLG | LC3_CIAP2_FASLG | FAS_LC3_BECN1_FASLG |
| ATG7_FASLG | LC3_FASLG_SESN2 | ATG5_FAS_LC3_FASLG |
| ATG3_FAS | FRAP1_LC3_FASLG | FAS_LC3_FASLG_RPS19BP1 |
| FASLG_HMGB2 | LC3_FASLG_SESN3 | FAS_LAMP1_LC3_FASLG |
| FASLG_UVRAG | ATG3_FAS_FASLG | FAS_LC3_FASLG_NAMPT |
| DIABLO_FAS | ATG7_LC3_FASLG | AKT1_FAS_LC3_FASLG |
| FASLG_MMP2 | FAS_FRAP1_FASLG | FAS_LC3_FASLG_SESN2 |
| TKT_FASLG | DIABLO_FASLG_SESN2 | FAS_LC3_MMP9_FASLG |
| PIEN_CIAP2 | DRAM_LC3_FASLG | FAS_FASLG_RPS19BP1_SESN3 |
| FAS_LC3 | CIAP2_FASLG_HMGB1 | FAS_FASLG_RPS19BP1_UVRAG |
| CBS_FASLG | FAS_FASLG_SESN3 | FAS_LC3_CDH1_FASLG |
| AIFM1_FASLG | LC3_FASLG_UVRAG | ATG12_FAS_LC3_FASLG |
| CASP3_CIAP2 | CASP3_CIAP2_FASLG | DIABLO_FAS_FASLG_SESN3 |
| FASLG_SESN3 | FAS_FASLG_SESN2 | DIABLO_FAS_FASLG_UVRAG |
| ATG3_FASLG | PTEN_CIAP2_FASLG | FAS_LC3_FASLG_LAMP2 |
| CASP8_FASLG | DIABLO_FASLG_SESN3 | FAS_LC3_ID2_FASLG |
| XIAP_FASLG | ATG7_CIAP2_FASLG | DIABLO_FAS_FASLG_SESN2 |
| AGER_FASLG | LC3_FASLG_SIRT1 | FAS_LC3_BHLHE41_FASLG |
| ATG3_ULK1 | LC3_FASLG_RPS19BP1 | DIABLO_DRAM_FAS_FASLG |
| BNIP3_FASLG | FASLG_SESN2_SESN3 | DIABLO_FAS_FASLG_STAT3 |
| FAS_UVRAG | DRAM_FAS_FASLG | DRAM_FAS_FASLG_RPS19BP1 |
| CIAP2_RAGE | ID2_CIAP2_FASLG | DIABLO_FAS_FRAP1_FASLG |
| ATG3_TCF3 | FAS_FASLG_STAT3 | FAS_FASLG_SESN2_UVRAG |
| FASLG_RAGE | AKT1_CIAP2_FASLG | ATG3_FAS_FASLG_SESN2 |
| E2F1_CIAP2 | DIABLO_FRAP1_FASLG | ATG7_DIABLO_FAS_FASLG |
| FASLG_VEGF | BNIP3_FAS_FASLG | FAS_LC3_TCF3_FASLG |
| E2F1_FAS | FAS_LAMP1_FASLG | ATG7_FAS_FASLG_UVRAG |
| XIAP_CIAP2 | TKT_CIAP2_FASLG | DIABLO_FAS_FASLG_NAMPT |
| BCL2L1_FASLG | ATG7_DIABLO_FASLG | DIABLO_FAS_FASLG_SIRT1 |
| BNIP3_FAS | FRAP1_FASLG_SESN2 | DIABLO_FAS_LAMP1_FASLG |
| FASLG_SESN1 | E2F1_ULK1_FASLG | FAS_FRAP1_FASLG_RPS19BP1 |
| FASLG_KIAA1967 | DRAM_CIAP2_FASLG | CSE1L_FAS_LC3_FASLG |
| AIFM1_CIAP2 | PTEN_CASP3_FASLG | DIABLO_FAS_BECN1_FASLG |
| DRAM_FASLG | LC3_FASLG_NAMPT | E2F1_LC3_ID2_FASLG |
| ATG3_CIAP2 | PTEN_CDH1_CIAP2 | AKT1_DIABLO_FAS_FASLG |
| CSE1L_FASLG | ATG12_CIAP2_FASLG | ATG3_DIABLO_FAS_FASLG |
| FASLG_RAPTOR | FASLG_RPS19BP1_SESN3 | E2F1_FAS_FASLG_SESN3 |
| TCF3_FASLG | MMP9_CIAP2_FASLG | ATG7_FAS_FASLG_SESN2 |
| FASLG_STAT3 | LAMP1_CIAP2_FASLG | DIABLO_FAS_FASLG_RPS19BP1 |
| ULK1_FASLG | LC3_BECN1_FASLG | DRAM_FAS_FASLG_UVRAG |
| PRKAA1_CIAP2 | CDH1_CIAP2_FASLG | LC3_MMP9_FASLG_SESN2 |
| FASLG_SIRT1 | BECN1_CIAP2_FASLG | FAS_FASLG_SESN3_UVRAG |
| ATG12_FASLG | CIAP2_FASLG_HMGB2 | DIABLO_FAS_FASLG_LAMP2 |
| LAMP1_FASLG | E2F1_FASLG_LAMP2 | DIABLO_FAS_ID2_FASLG |
| NNMT_FASLG | CIAP2_FASLG_SIRT1 | E2F1_LC3_FASLG_LAMP2 |
| BCL2L1_CIAP2 | PTEN_XIAP_FASLG | E2F1_LC3_MMP9_FASLG |
| | | CDH1_ID2_MMP9_TCF3 |

| Combinations of five types | Combinations of six types |
|---|---|
| BNIP3_DRAM_FAS_LC3_FASLG | BNIP3_DRAM_FAS_LC3_FASLG_SESN2 |
| DRAM_FAS_LC3_FASLG_UVRAG | BNIP3_DRAM_FAS_LC3_FASLG_SESN3 |
| DIABLO_DRAM_FAS_LC3_FASLG | ATG3_FAS_LC3_MMP9_FASLG_SESN2 |
| ATG3_FAS_LC3_FASLG_SESN3 | ATG3_FAS_LC3_MMP9_FASLG_SESN3 |
| BNIP3_FAS_LC3_FASLG_SESN3 | ATG3_FAS_LC3_FASLG_SESN2_SESN3 |
| BNIP3_FAS_LC3_FASLG_UVRAG | BNIP3_DRAM_FAS_LC3_MMP9_FASLG |
| ATG3_FAS_LC3_FASLG_SESN2 | BNIP3_DRAM_FAS_LC3_FASLG_STAT3 |
| BNIP3_FAS_LC3_FASLG_SESN2 | BNIP3_DRAM_FAS_LC3_FASLG_UVRAG |
| DRAM_FAS_LC3_FASLG_STAT3 | BNIP3_DRAM_FAS_LC3_FASLG_SIRT1 |
| DIABLO_FAS_LC3_BECN1_FASLG | ATG3_DRAM_FAS_LC3_FASLG_SESN2 |
| BNIP3_DIABLO_FAS_LC3_FASLG | BNIP3_DRAM_FAS_LC3_BECN1_FASLG |
| ATG7_DRAM_FAS_LC3_FASLG | DRAM_FAS_LC3_ID2_FASLG_UVRAG |
| DIABLO_FAS_LC3_FASLG_STAT3 | BNIP3_FAS_LC3_MMP9_FASLG_UVRAG |
| DRAM_FAS_LC3_FASLG_SIRT1 | DRAM_FAS_LC3_MMP9_FASLG_RPS19BP1 |
| DRAM_E2F1_FAS_LC3_FASLG | ATG5_DRAM_FAS_LC3_FASLG_UVRAG |
| DRAM_FAS_LC3_FASLG_SESN3 | DRAM_FAS_LC3_FASLG_SIRT1_UVRAG |
| DRAM_FAS_LC3_BECN1_FASLG | DRAM_FAS_LC3_MMP9_FASLG_UVRAG |
| BNIP3_FAS_LC3_FASLG_STAT3 | BNIP3_DRAM_FAS_LC3_ID2_FASLG |
| BNIP3_FAS_LC3_MMP9_FASLG | ATG3_DRAM_FAS_LC3_FASLG_SESN3 |
| DIABLO_FAS_LC3_ID2_FASLG | BNIP3_FAS_LC3_MMP9_FASLG_SESN3 |
| DIABLO_FAS_LC3_MMP9_FASLG | BNIP3_FAS_LC3_MMP9_FASLG_SESN2 |
| ATG5_FAS_LC3_FASLG_UVRAG | DRAM_FAS_LC3_BECN1_FASLG_UVRAG |
| ATG5_DRAM_FAS_LC3_FASLG | BNIP3_DRAM_FAS_FRAP1_LC3_FASLG |
| DIABLO_FAS_LC3_FASLG_SIRT1 | BNIP3_FAS_LC3_FASLG_SESN3_SIRT1 |

TABLE 13-continued

| | |
|---|---|
| FAS_LC3_FASLG_SIRT1_UVRAG | DRAM_FAS_LC3_BHLHE41_FASLG_UVRAG |
| DRAM_FAS_FRAP1_LC3_FASLG | BNIP3_DRAM_FAS_LC3_FASLG_LAMP2 |
| DIABLO_FAS_LC3_FASLG_SESN3 | AKT1_BNIP3_DRAM_FAS_LC3_FASLG |
| FAS_LC3_BECN1_FASLG_UVRAG | DIABLO_DRAM_FAS_LC3_ID2_FASLG |
| ATG3_FAS_LC3_MMP9_FASLG | DRAM_FAS_LC3_FASLG_SESN3_SIRT1 |
| BNIP3_FAS_LC3_FASLG_SIRT1 | ATG3_DIABLO_FAS_LC3_MMP9_FASLG |
| BNIP3_FAS_FRAP1_LC3_FASLG | BNIP3_FAS_LC3_FASLG_SESN3_STAT3 |
| DIABLO_FAS_LC3_FASLG_UVRAG | BNIP3_FAS_LC3_BECN1_FASLG_SESN2 |
| DIABLO_FAS_LC3_FASLG_NAMPT | BNIP3_FAS_LC3_FASLG_SESN2_SIRT1 |
| FAS_LC3_MMP9_FASLG_RPS19BP1 | DIABLO_DRAM_FAS_LC3_MMP9_FASLG |
| BNIP3_FAS_LC3_BECN1_FASLG | BNIP3_FAS_LC3_BECN1_FASLG_SESN3 |
| E2F1_FAS_LC3_MMP9_FASLG | BNIP3_FAS_LC3_FASLG_SESN2_UVRAG |
| FAS_LC3_MMP9_FASLG_UVRAG | DRAM_FAS_LC3_FASLG_LAMP2_UVRAG |
| ATG3_DIABLO_FAS_LC3_FASLG | ATG3_FAS_FRAP1_LC3_MMP9_FASLG |
| DIABLO_FAS_LC3_BHLHE41_FASLG | DRAM_FAS_LC3_BECN1_FASLG_SESN3 |
| FAS_LC3_ID2_FASLG_UVRAG | DIABLO_DRAM_FAS_LC3_BECN1_FASLG |
| DIABLO_FAS_LC3_FASLG_LAMP2 | ATG3_DRAM_FAS_LC3_MMP9_FASLG |
| DRAM_FAS_LC3_FASLG_SESN2 | BNIP3_DRAM_FAS_LC3_CDH1_FASLG |
| DRAM_FAS_LAMP1_LC3_FASLG | DRAM_FAS_LC3_FASLG_SESN2_UVRAG |
| ATG3_FAS_FRAP1_LC3_FASLG | BNIP3_DRAM_FAS_LC3_BHLHE41_FASLG |
| FAS_LC3_FASLG_STAT3_UVRAG | ATG5_DRAM_FAS_LC3_FASLG_SESN3 |
| AKT1_BNIP3_FAS_LC3_FASLG | DRAM_FAS_LC3_FASLG_SESN3_STAT3 |
| FAS_LC3_FASLG_SESN3_UVRAG | BNIP3_FAS_LC3_FASLG_SESN2_STAT3 |
| ATG3_DRAM_FAS_LC3_FASLG | BNIP3_DIABLO_FAS_LC3_MMP9_FASLG |
| AKT1_DRAM_FAS_LC3_FASLG | ATG5_DRAM_FAS_LC3_FASLG_SESN2 |
| FAS_LC3_FASLG_SESN2_UVRAG | ATG5_FAS_LC3_MMP9_FASLG_UVRAG |
| FAS_LC3_BHLHE41_FASLG_UVRAG | DIABLO_DRAM_FAS_LC3_BHLHE41_FASLG |
| DRAM_FAS_LC3_FASLG_NAMPT | DIABLO_DRAM_FAS_LC3_FASLG_STAT3 |
| FAS_LC3_FASLG_LAMP2_UVRAG | ATG3_DIABLO_FAS_LC3_FASLG_SESN3 |
| ATG7_BNIP3_FAS_LC3_FASLG | DRAM_FAS_LC3_TCF3_FASLG_UVRAG |
| AKT1_FAS_LC3_FASLG_UVRAG | BNIP3_FAS_LC3_MMP9_FASLG_RPS19BP1 |
| E2F1_FAS_LC3_ID2_FASLG | ATG5_DRAM_FAS_LC3_FASLG_STAT3 |
| DRAM_FAS_LC3_CDH1_FASLG | ATG7_DRAM_FAS_LC3_MMP9_FASLG |
| PTEN_CDH1_ID2_MMP9_TCF3 | LC3_CDH1_ID2_MMP9_TCF3_FASLG |
| Combinations of seven types | Combinations of eight types |
| ATG3_FAS_LC3_MMP9_FASLG_SESN2_SESN3 | ATG3_DRAM_FAS_LC3_MMP9_FASLG_SESN2_SESN3 |
| BNIP3_DRAM_FAS_LC3_MMP9_FASLG_SESN2 | ATG3_FAS_LC3_ID2_MMP9_FASLG_SESN2_SESN3 |
| ATG3_DRAM_FAS_LC3_MMP9_FASLG_SESN2 | ATG3_FAS_LC3_MMP9_FASLG_SESN2_SESN3_SIRT1 |
| BNIP3_DRAM_FAS_LC3_MMP9_FASLG_SESN3 | ATG3_FAS_LC3_MMP9_TCF3_FASLG_SESN2_SESN3 |
| ATG3_DRAM_FAS_LC3_FASLG_SESN2_SESN3 | ATG3_FAS_LC3_MMP9_BECN1_FASLG_SESN2_SESN3 |
| ATG3_DRAM_FAS_LC3_MMP9_FASLG_SESN3 | ATG3_FAS_LC3_MMP9_BHLHE41_FASLG_SESN2_SESN3 |
| BNIP3_DRAM_FAS_LC3_BECN1_FASLG_SESN2 | BNIP3_DRAM_FAS_LC3_MMP9_FASLG_SESN2_SIRT1 |
| BNIP3_DRAM_FAS_LC3_FASLG_SESN2_SIRT1 | ATG3_FAS_LC3_MMP9_FASLG_LAMP2_SESN2_SESN3 |
| BNIP3_DRAM_FAS_LC3_MMP9_FASLG_UVRAG | BNIP3_DRAM_FAS_LC3_MMP9_BECN1_FASLG_SESN2 |
| BNIP3_DRAM_FAS_LC3_ID2_FASLG_SESN2 | ATG3_DRAM_FAS_LC3_MMP9_TCF3_FASLG_SESN2 |
| ATG3_FAS_LC3_MMP9_TCF3_FASLG_SESN3 | BNIP3_DRAM_FAS_LC3_ID2_MMP9_FASLG_SESN2 |
| BNIP3_DRAM_FAS_LC3_FASLG_SESN3_SIRT1 | ATG3_ATG5_FAS_LC3_MMP9_FASLG_SESN2_SESN3 |
| ATG3_FAS_LC3_MMP9_FASLG_SESN2_UVRAG | ATG3_DRAM_FAS_LC3_MMP9_TCF3_FASLG_SESN3 |
| BNIP3_DRAM_FAS_LC3_FASLG_SESN2_STAT3 | ATG3_BNIP3_FAS_LC3_MMP9_FASLG_SESN2_SESN3 |
| BNIP3_DRAM_FAS_LC3_MMP9_FASLG_SIRT1 | ATG3_DRAM_FAS_LC3_ID2_MMP9_FASLG_SESN2 |
| BNIP3_DRAM_FAS_LC3_MMP9_TCF3_FASLG | ATG3_FAS_LC3_CDH1_MMP9_FASLG_SESN2_SESN3 |
| BNIP3_DRAM_FAS_LC3_FASLG_SESN2_SESN3 | BNIP3_DRAM_FAS_LC3_MMP9_TCF3_FASLG_UVRAG |
| BNIP3_DRAM_FAS_LC3_ID2_FASLG_SESN3 | BNIP3_DRAM_FAS_LC3_MMP9_FASLG_SESN2_SESN3 |
| ATG3_FAS_LC3_MMP9_FASLG_SESN2_SIRT1 | BNIP3_DRAM_FAS_LC3_MMP9_FASLG_SESN3_SIRT1 |
| ATG3_FAS_FRAP1_LC3_MMP9_FASLG_SESN3 | ATG5_BNIP3_DRAM_FAS_LC3_MMP9_FASLG_SESN2 |
| ATG3_DIABLO_FAS_LC3_MMP9_FASLG_SESN2 | ATG3_DRAM_FAS_LC3_MMP9_FASLG_SESN2_SIRT1 |
| BNIP3_DRAM_FAS_LC3_BECN1_FASLG_SESN3 | BNIP3_DRAM_FAS_LC3_MMP9_FASLG_SESN2_UVRAG |
| ATG3_FAS_FRAP1_LC3_MMP9_FASLG_SESN2 | ATG3_DRAM_FAS_LC3_MMP9_FASLG_LAMP2_SESN2 |
| BNIP3_DRAM_FAS_LC3_FASLG_SESN3_STAT3 | BNIP3_DRAM_FAS_LC3_MMP9_FASLG_LAMP2_SESN2 |
| ATG3_FAS_LC3_ID2_FASLG_SESN2_SESN3 | BNIP3_DRAM_FAS_LC3_MMP9_FASLG_SESN2_STAT3 |
| ATG3_FAS_LC3_MMP9_FASLG_SESN3_SIRT1 | BNIP3_DRAM_FAS_LC3_MMP9_TCF3_FASLG_SESN3 |
| ATG5_DRAM_FAS_LC3_MMP9_FASLG_UVRAG | ATG3_DRAM_FAS_LC3_MMP9_BHLHE41_FASLG_SESN2 |
| ATG3_FAS_LC3_ID2_MMP9_FASLG_SESN2 | ATG3_FAS_FRAP1_LC3_MMP9_FASLG_SESN2_SESN3 |
| ATG3_DIABLO_FAS_LC3_MMP9_FASLG_SESN3 | BNIP3_DRAM_FAS_LC3_ID2_MMP9_FASLG_SESN3 |
| BNIP3_DRAM_FAS_LC3_BHLHE41_FASLG_SESN2 | ATG3_FAS_LC3_MMP9_FASLG_SESN2_SESN3_UVRAG |
| ATG3_FAS_LC3_MMP9_TCF3_FASLG_SESN2 | ATG3_DRAM_FAS_LC3_ID2_FASLG_SESN2_SESN3 |
| ATG3_FAS_LC3_ID2_MMP9_FASLG_SESN3 | ATG3_DRAM_FAS_LC3_BHLHE41_FASLG_SESN2_SESN3 |
| ATG3_FAS_LC3_FASLG_SESN2_SESN3_SIRT1 | AKT1_ATG3_FAS_LC3_MMP9_FASLG_SESN2_SESN3 |
| BNIP3_DRAM_FAS_LC3_MMP9_BECN1_FASLG | BNIP3_DRAM_FAS_LC3_MMP9_TCF3_FASLG_SESN2 |
| ATG3_FAS_LC3_BHLHE41_FASLG_SESN2_SESN3 | BNIP3_DRAM_FAS_LC3_ID2_FASLG_SESN2_SIRT1 |
| BNIP3_DRAM_FAS_LC3_FASLG_LAMP2_SESN2 | BNIP3_DRAM_FAS_LC3_ID2_BECN1_FASLG_SESN2 |
| ATG3_FAS_LC3_MMP9_BECNI_FASLG_SESN2 | ATG3_DRAM_FAS_LC3_MMP9_BECNI_FASLG_SESN2 |
| BNIP3_DRAM_FAS_LC3_ID2_MMP9_FASLG | ATG3_DRAM_FAS_LC3_ID2_MMP9_FASLG_SESN3 |
| BNIP3_FAS_LC3_MMP9_FASLG_SESN2_UVRAG | BNIP3_DRAM_FAS_LC3_MMP9_TCF3_FASLG_SIRT1 |
| BNIP3_DRAM_FAS_LC3_BHLHE41_FASLG_SESN3 | ATG3_DIABLO_FAS_LC3_MMP9_FASLG_SESN2_SESN3 |
| ATG3_FAS_LC3_BECN1_FASLG_SESN2_SESN3 | ATG3_DRAM_FAS_FRAP1_LC3_MMP9_FASLG_SESN2 |
| BNIP3_DRAM_FAS_LC3_FASLG_SESN2_UVRAG | BNIP3_DRAM_FAS_LC3_MMP9_BHLHE41_FASLG_SESN2 |
| ATG7_BNIP3_DRAM_FAS_LC3_MMP9_FASLG | ATG3_FAS_LC3_MMP9_FASLG_SESN2_SESN3_STAT3 |

TABLE 13-continued

| | |
|---|---|
| BNIP3_DRAM_FAS_LC3_MMP9_FASLG_STAT3 | ATG3_DRAM_FAS_LC3_MMP9_FASLG_SESN2_UVRAG |
| BNIP3_FAS_LC3_MMP9_FASLG_SESN2_SIRT1 | BNIP3_DRAM_FAS_LC3_MMP9_TCF3_FASLG_STAT3 |
| ATG3_FAS_LC3_MMP9_FASLG_LAMP2_SESN2 | BNIP3_DRAM_FAS_LC3_MMP9_BECNl_FASLG_SESN3 |
| BNIP3_FAS_LC3_MMP9_FASLG_SESN3_SIRT1 | BNIP3_DRAM_FAS_LC3_CDH1_MMP9_FASLG_SESN2 |
| ATG3_FAS_LC3_MMP9_FASLG_LAMP2_SESN3 | ATG3_FAS_LC3_MMP9_TCF3_FASLG_SESN2_UVRAG |
| BNIP3_DRAM_FAS_LC3_FASLG_LAMP2_SESN3 | ATG3_DRAM_FAS_LC3_CDH1_MMP9_FASLG_SESN2 |
| ATG5_DRAM_FAS_LC3_MMP9_FASLG_SESN2 | BNIP3_DRAM_FAS_LC3_MMP9_TCF3_BECNl_FASLG |
| BNIP3_DRAM_FAS_FRAP1_LC3_MMP9_FASLG | BNIP3_CSE1L_DRAM_FAS_LC3_MMP9_FASLG_SESN3 |
| ATG3_FAS_LC3_FASLG_LAMP2_SESN2_SESN3 | ATG3_DRAM_FAS_LC3_ULK1_MMP9_FASLG_SESN3 |
| BNIP3_FAS_LC3_MMP9_TCF3_FASLG_UVRAG | BNIP3_DRAM_FAS_LC3_ID2_FASLG_SESN2_STAT3 |
| BNIP3_FAS_LC3_MMP9_BECNI_FASLG_SESN2 | ATG5_DRAM_FAS_LC3_MMP9_FASLG_SESN2_SIRT1 |
| ATG3_FAS_LC3_MMP9_BECNI_FASLG_SESN3 | ATG3_FAS_LC3_ULK1_MMP9_FASLG_SESN2_SESN3 |
| BNIP3_DRAM_FAS_LC3_MMP9_FASLG_LAMP2 | BNIP3_DRAM_FAS_LC3_ID2_MMP9_FASLG_UVRAG |
| BNIP3_DRAM_FAS_LC3_CDH1_FASLG_SESN2 | ATG3_FAS_LC3_MMP9_TCF3_FASLG_SESN3_SIRT1 |
| FAS_LC3_CDH1_ID2_MMP9_TCF3_FASLG | ATG3_FAS_LC3_CDH1_ID2_MMP9_TCF3_FASLG |

Preferably, the composition or kit is for predicting the prognosis of survival of the C group, and the genes are one or more selected from the genes or groups of genes described in the following Table 14.

TABLE 14

| One type | Combinations of two types | Combinations of three types | Combinations of four types |
|---|---|---|---|
| CSE1L | ID2_CIAP2 | ID2_CIAP2_SESN2 | AIFM1_ID2_CIAP2_SESN2 |
| CIAP2 | CASP3_CIAP2 | ID2_CASP3_CIAP2 | PTEN_ID2_CIAP2_SESN2 |
| TCF3 | ID2_TCF3 | ULK1_ID2_HMGB2 | DIABLO_ID2_CASP3_CIAP2 |
| CDH2 | DIABLO_CDH2 | ULK1_ID2_HMGB1 | DRAM_FRAP1_CIAP2_TP63 |
| FASLG | CSE1L_CDH2 | DIABLO_ID2_CASP3 | BAX_ID2_CIAP2_SESN2 |
| BECN1 | CSE1L_TCF3 | ULK1_ID2_AGER | ID2_CIAP2_SESN2_VEGF |
| CASP3 | CSE1L_CASP3 | ID2_CIAP2_RPS19BP1 | DRAM_ID2_CIAP2_SESN2 |
| CDH1 | CSE1L_RPS19BP1 | CASP8_ULK1_ID2 | ID2_CIAP2_RPS19BP1_SESN2 |
| | CDH2_CIAP2 | ID2_TCF3_CIAP2 | CBS_ID2_CIAP2_SESN2 |
| | ULK1_ID2 | FRAP1_ID2_CIAP2 | ATG3_ID2_CIAP2_SESN2 |
| | CSE1L_ID2 | AIFM1_CDH1_CIAP2 | NNMT_ID2_CIAP2_SESN2 |
| | CDH1_CIAP2 | PTEN_CDH1_CIAP2 | DIABLO_ID2_CIAP2_SESN2 |
| | CSE1L_FASLG | ULK1_ID2_CIAP2 | PRKAA1_ID2_CIAP2_SESN2 |
| | NNMT_CIAP2 | DIABLO_ID2_CDH2 | FRAP1_ID2_CIAP2_SESN2 |
| | CSE1L_MMP9 | CDH1_CIAP2_VEGF | DIABLO_DRAM_ID2_CASP3 |
| | CSE1L_CDH1 | CDH1_CCNG2_CIAP2 | XIAP_ID2_CIAP2_SESN2 |
| | CIAP2_RPS19BP1 | BAX_CDH1_CIAP2 | ID2_CIAP2_RAGE_SESN2 |
| | ID2_CDH2 | ATG3_ID2_TCF3 | DRAM_CIAP2_SESN2_TP63 |
| | CDH2_RPS19BP1 | ULK1_ID2_MMP2 | BNIP3_ID2_CIAP2_SESN2 |
| | CSE1L_STAT3 | CBS_ULK1_ID2 | BCL2L1_ID2_CIAP2_SESN2 |
| | DIABLO_CASP3 | DIABLO_ID2_CIAP2 | AIFM1_DIABLO_CDH1_CIAP2 |
| | CDH1_TCF3 | LC3_ID2_CIAP2 | ID2_CCNG2_CIAP2_SESN2 |
| | CSE1L_SIRT1 | PTEN_ULK1_ID2 | LC3_ID2_CIAP2_SESN2 |
| | CIAP2_SESN2 | BAX_ULK1_ID2 | ID2_CASP3_CIAP2_RPS19BP1 |
| | AIFM1_CIAP2 | DIABLO_PTEN_CDH1 | AIFM1_CDH1_CIAP2_SESN2 |
| | DIABLO_KIAA1967 | CDH1_CASP3_CIAP2 | ATG3_ID2_TCF3_RPS19BP1 |
| | CSE1L_KIAA1967 | ULK1_ID2_CDH2 | DIABLO_FRAP1_ID2_CDH2 |
| | AKT1_CSE1L | CDH1_CIAP2_RAGE | E2F1_ID2_CIAP2_SESN2 |
| | CSE1L_SESN2 | ID2_CDH2_CIAP2 | ID2_CASP3_CIAP2_SESN2 |
| | FRAP1_CDH2 | NNMT_ID2_CIAP2 | DRAM_ID2_CIAP2_RPS19BP1 |
| | FRAP1_CIAP2 | XIAP_CIAP2_SESN2 | ID2_CIAP2_HMGB1_SESN2 |
| | TCF3_FASLG | CSE1L_ID2_CASP3 | PTEN_ID2_CASP3_CIAP2 |
| | FASLG_SESN2 | CSE1L_FRAPLCDH2 | ATG3_ID2_MMP9_TCF3 |
| | CSE1L_DIABLO | BCL2_ID2_SESN2 | LAMP1_ID2_CIAP2_SESN2 |
| | CSE1L_SATB1 | AIFM1_ULK1_ID2 | AIFM1_ID2_CASP3_CIAP2 |
| | MMP9_TCF3 | ULK1_ID2_RAGE | ATG5_ID2_CIAP2_SESN2 |
| | ATG12_CSE1L | DIABLO_CDH1_CCNG2 | DIABLO_PTEN_CDH1_CIAP2 |
| | ATG7_CSE1L | BAX_DIABLO_CDH1 | LAMP1_ID2_CASP3_CIAP2 |
| | CSE1L_BECN1 | CSE1L_ID2_CDH2 | ID2_CIAP2_HMGB2_SESN2 |
| | XIAP_CIAP2 | AIFM1_CIAP2_SESN2 | BCL2L1_CSE1L_ID2_SESN2 |
| | CSE1L_FAS | NNMT_CDH1_CIAP2 | TKT_ID2_CIAP2_SESN2 |
| | TCF3_RPS19BP1 | CBS_ID2_CIAP2 | DIABLO_XIAP_ID2_SESN2 |
| | XIAP_SESN2 | DIABLO_CDH1_VEGF | FRAP1_LC3_ID2_CIAP2 |
| | CIAP2_KIAA1967 | ID2_MMP9_TCF3 | ATG7_ID2_CIAP2_SESN2 |
| | TKT_CIAP2 | AIFM1_DIABLO_CDH1 | ID2_AGER_CIAP2_SESN2 |
| | PRKAA1_CIAP2 | PRKAA1_CIAP2_SESN2 | CSE1L_ID2_CASP3_CIAP2 |
| | CDH2_FASLG | CDH1_ID2_CIAP2 | DRAM_CASP3_CIAP2_TP63 |
| | CSE1L_FRAP1 | CSE1L_CASP3_CIAP2 | PTEN_CDH1_ID2_CIAP2 |
| | CSE1L_CIAP2 | ULK1_ID2_VEGF | CDHLID2_CIAP2_RPS19BP1 |
| | CSE1L_ULK1 | ID2_CIAP2_HMGB1 | ATG3_ULK1_ID2_HMGB1 |
| | PTEN_CIAP2 | BCL2L1_CDH1_CIAP2 | FRAP1_ID2_CIAP2_RPS19BP1 |
| | BCL2L1_CIAP2 | ID2_CIAP2_MMP2 | DIABLO_PTEN_ID2_CASP3 |
| | CIAP2_VEGF | CSE1L_ID2_CIAP2 | ID2_CIAP2_SESN2_TP63 |
| | ATG3_TCF3 | BCL2L1_CSE1L_CDH1 | ID2_TCF3_CIAP2_SESN2 |

TABLE 14-continued

| | | |
|---|---|---|
| AKT1_TCF3 | CSE1L_CDH1_CASP3 | DIABLO_CDH1_CIAP2_VEGF |
| CSE1L_LC3 | CSE1L_XIAP_SESN2 | ATG3_ULK1_ID2_AGER |
| TKT_CDH2 | PRKAA1_CDH1_CIAP2 | ID2_CIAP2_MMP2_SESN2 |
| | | CDH1_ID2_MMP9_TCF3 |

| Combinations of five types | Combinations of six types |
|---|---|
| DRAM_ID2_CIAP2_SESN2_TP63 | ATG12_DRAM_FRAP1_TKT_CIAP2_TP63 |
| AIFM1_DRAM_CIAP2_SESN2_TP63 | AIFM1_DRAM_TKT_CIAP2_SESN2_TP63 |
| DRAM_FRAP1_CDH1_CIAP2_TP63 | AIFM1_ATG12_DRAM_FRAP1_CIAP2_TP63 |
| ATG12_DRAM_FRAP1_CIAP2_TP63 | AIFM1_DRAM_ID2_CIAP2_SESN2_TP63 |
| DRAM_FRAP1_XIAP_CIAP2_TP63 | DRAM_TKT_ID2_CIAP2_SESN2_TP63 |
| DRAM_TKT_CIAP2_SESN2_TP63 | AIFM1_ATG3_DRAM_CIAP2_SESN2_TP63 |
| AIFM1_CDH1_ID2_CIAP2_SESN2 | DRAM_FRAP1_TKT_CDH1_CIAP2_TP63 |
| AIFM1_DRAM_FRAP1_CIAP2_TP63 | ATG3_DRAM_ID2_CIAP2_SESN2_TP63 |
| DRAM_FRAP1_TKT_CIAP2_TP63 | DRAM_PTEN_ID2_CIAP2_SESN2_TP63 |
| PTEN_CDH1_ID2_CIAP2_SESN2 | DRAM_FRAP1_TKT_XIAP_CIAP2_TP63 |
| BAX_CDH1_ID2_CIAP2_SESN2 | DRAM_E2F1_FRAP1_CDH1_CIAP2_TP63 |
| DRAM_FRAP1_ID2_CIAP2_TP63 | ATG3_DRAM_FRAP1_CDH1_CIAP2_TP63 |
| DRAM_TKT_CASP3_CIAP2_TP63 | ATG7_DRAM_ID2_CIAP2_SESN2_TP63 |
| CDH1_ID2_CCNG2_CIAP2_SESN2 | AIFM1_DRAM_FRAP1_CDH1_CIAP2_TP63 |
| AIFM1_PTEN_ID2_CIAP2_SESN2 | ATG5_DRAM_ID2_CIAP2_SESN2_TP63 |
| DIABLO_FRAPLCDH1_ID2_CIAP2 | AIFM1_DIABLO_CDH1_ID2_CIAP2_SESN2 |
| AIFM1_CBS_ID2_CIAP2_SESN2 | AIFM1_BNIP3_DRAM_CIAP2_SESN2_TP63 |
| AIFM1_LAMP1_ID2_CIAP2_SESN2 | BCL2L1_DRAM_ID2_CIAP2_SESN2_TP63 |
| DRAM_ID2_CASP3_CIAP2_TP63 | DRAM_NNMT_ID2_CIAP2_SESN2_TP63 |
| DIABLO_PTEN_CDH1_ID2_CIAP2 | CASP8_DRAM_ID2_CIAP2_SESN2_TP63 |
| CDH1_ID2_CIAP2_SESN2_VEGF | DRAM_ID2_BHLHE41_CIAP2_SESN2_TP63 |
| DIABLO_CDH1_ID2_CASP3_CIAP2 | DRAM_FRAP1_CDH1_CIAP2_RPS19BP1_TP63 |
| AIFM1_ATG3_ID2_CIAP2_SESN2 | DRAM_LAMP1_ID2_CIAP2_SESN2_TP63 |
| AIFM1_BNIP3_ID2_CIAP2_SESN2 | DRAM_FRAP1_CDH1_ID2_CIAP2_TP63 |
| AIFM1_DIABLO_CDH1_ID2_CIAP2 | BNIP3_DRAM_ID2_CIAP2_SESN2_TP63 |
| ATG3_DRAM_ID2_CIAP2_SESN2 | DRAM_ID2_MMP9_CIAP2_SESN2_TP63 |
| AIFM1_BAX_ID2_CIAP2_SESN2 | AKT1_DRAM_ID2_CIAP2_SESN2_TP63 |
| DRAM_E2F1_CASP3_CIAP2_TP63 | DRAM_ID2_CIAP2_RAGE_SESN2_TP63 |
| AIFM1_ID2_CIAP2_HMGB2_SESN2 | ATG12_DRAM_FRAP1_XIAP_CIAP2_TP63 |
| AIFM1_ID2_MMP9_CIAP2_SESN2 | DRAM_PRKAA1_ID2_CIAP2_SESN2_TP63 |
| DIABLO_CDH1_ID2_CIAP2_VEGF | DRAM_XIAP_ID2_CIAP2_SESN2_TP63 |
| DIABLO_DRAM_XIAP_ID2_SESN2 | AIFM1_DRAM_PTEN_CIAP2_SESN2_TP63 |
| AIFM1_ATG5_ID2_CIAP2_SESN2 | ATG3_DRAM_FRAP1_CASP3_CIAP2_TP63 |
| AIFM1_ID2_CIAP2_HMGB1_SESN2 | CASP8_DRAM_FRAP1_CDH1_CIAP2_TP63 |
| BAX_DIABLO_CDH1_ID2_CIAP2 | AIFM1_ATG5_DRAM_CIAP2_SESN2_TP63 |
| DRAM_FRAP1_NNMT_CIAP2_TP63 | AIFM1_CASP8_DRAM_CIAP2_SESN2_TP63 |
| FRAP1_CDH1_ID2_CIAP2_RPS19BP1 | BCL2L1_DRAM_FRAPLIKT_CIAP2_TP63 |
| DRAM_XIAP_CIAP2_SESN2_TP63 | CBS_DRAM_ID2_CIAP2_SESN2_TP63 |
| AIFM1_DIABLO_ID2_CIAP2_SESN2 | DRAM_FRAP1_NNMT_TKT_CIAP2_TP63 |
| AIFM1_DRAM_ID2_CIAP2_SESN2 | AIFM1_AKT1_DRAM_CIAP2_SESN2_TP63 |
| AIFM1_ID2_CIAP2_SESN2_VEGF | DRAM_FRAP1_PTEN_CDH1_CIAP2_TP63 |
| AIFM1_TKT_ID2_CIAP2_SESN2 | DIABLO_PTEN_CDH1_ID2_CIAP2_SESN2 |
| ATG3_ID2_MMP9_TCF3_RPS19BP1 | DRAM_ID2_CIAP2_SESN2_TP63_VEGF |
| ATG5_DRAM_CIAP2_SESN2_TP63 | AIFM1_DRAM_XIAP_CIAP2_SESN2_TP63 |
| CBS_FRAP1_ID2_CIAP2_SESN2 | BNIP3_DRAM_FRAP1_CDH1_CIAP2_TP63 |
| AIFM1_DIABLO_ID2_CASP3_CIAP2 | AIFM1_ATG7_DRAM_CIAP2_SESN2_TP63 |
| AIFM1_NNMT_ID2_CIAP2_SESN2 | AIFM1_DRAM_FRAP1_NNMT_CIAP2_TP63 |
| ATG3_DRAM_CIAP2_SESN2_TP63 | AIFM1_DRAM_MMP9_CIAP2_SESN2_TP63 |
| ATG3_FRAP1_ID2_CIAP2_SESN2 | AIFM1_DRAM_PRKAA1_CIAP2_SESN2_TP63 |
| BAX_DIABLO_DRAM_ID2_CASP3 | AIFM1_DRAM_CIAP2_RAGE_SESN2_TP63 |
| LAMP1_PTEN_ID2_CIAP2_SESN2 | AIFM1_DRAM_FRAP1_XIAP_CIAP2_TP63 |
| CDH1_ID2_CIAP2_RAGE_SESN2 | AIFM1_DRAM_NNMT_CIAP2_SESN2_TP63 |
| CBS_DIABLO_ID2_CIAP2_SESN2 | DRAM_FRAP1_CDH1_CIAP2_TP63_VEGF |
| DIABLO_CDH1_ID2_CCNG2_CIAP2 | AIFM1_DRAM_LAMP1_CIAP2_SESN2_TP63 |
| DIABLO_LAMP1_ID2_CASP3_CIAP2 | DIABLO_DRAM_FRAP1_XIAP_CASP3_HMGB2 |
| AIFM1_DRAM_CASP3_CIAP2_TP63 | DRAM_TKT_XIAP_CIAP2_SESN2_TP63 |
| BCL2L1_DRAM_FRAPLCIAP2_TP63 | AIFM1_BCL2L1_DRAM_CIAP2_SESN2_TP63 |
| CDH1_ID2_MMP9_TCF3_CIAP2 | BAX_CDH1_ID2_MMP9_TCF3_CIAP2 |

| Combinations of seven types | Combinations of eight types |
|---|---|
| AIFM1_ATG12_DRAM_FRAP1_TKT_CIAP2_TP63 | AIFM1_ATG12_DRAM_FRAP1_TKT_MMP9_CIAP2_TP63 |
| ATG12_BCL2L1_DRAM_FRAP1_TKT_CIAP2_TP63 | AIFM1_ATG12_DRAM_FRAP1_NNMT_TKT_CIAP2_TP63 |
| ATG12_DRAM_FRAP1_LAMP1_TKT_CIAP2_TP63 | AIFM1_ATG12_DRAM_FRAP1_PTEN_TKT_CIAP2_TP63 |
| ATG12_DRAM_FRAP1_TKT_XIAP_CIAP2_TP63 | AIFM1_ATG12_DRAM_FRAP1_TKT_CIAP2_TP63_VEGF |
| ATG12_CBS_DRAM_FRAP1_TKT_CIAP2_TP63 | ATG12_DRAM_FRAP1_PTEN_TKT_XIAP_CIAP2_TP63 |
| ATG12_DRAM_FRAP1_TKT_CIAP2_TP63_VEGF | AIFM1_ATG12_BCL2L1_DRAM_FRAP1_TKT_CIAP2_TP63 |
| ATG12_ATG7_DRAM_FRAP1_TKT_CIAP2_TP63 | AIFM1_ATG12_DRAM_FRAP1_TKT_CIAP2_SATBl_TP63 |
| ATG12_DRAM_FRAP1_PTEN_TKT_CIAP2_TP63 | AIFM1_AKTLATG12_DRAM_FRAP1_TKT_CIAP2_TP63 |
| ATG12_DRAM_FRAP1_PRKAA1_TKT_CIAP2_TP63 | AIFM1_ATG12_DRAM_FRAP1_LAMP1_TKT_CIAP2_TP63 |
| ATG12_DRAM_FRAP1_TKT_CIAP2_RAGE_TP63 | ATG12_BCL2L1_DRAM_FRAP1_PTEN_TKT_CIAP2_TP63 |
| ATG12_DRAM_FRAP1_TKT_MMP9_CIAP2_TP63 | AIFM1_ATG12_CBS_DRAM_FRAP1_TKT_CIAP2_TP63 |
| ATG12_BNIP3_DRAM_FRAP1_TKT_CIAP2_TP63 | AIFM1_ATG12_DRAM_FRAP1_PTEN_MMP9_CIAP2_TP63 |

TABLE 14-continued

| | |
|---|---|
| AIFM1_BCL2L1_DRAM_TKT_CIAP2_SESN2_TP63 | ATG12_DRAM_E2F1_FRAP1_IKT_MMP9_CIAP2_TP63 |
| AIFM1_ATG12_DRAM_FRAP1_PTEN_CIAP2_TP63 | ATG12_BCL2L1_CBS_DRAM_FRAP1_TKT_CIAP2_TP63 |
| AIFM1_DRAM_NNMT_TKT_CIAP2_SESN2_TP63 | ATG12_BCL2L1_DRAM_FRAP1_TKT_CIAP2_TP63_VEGF |
| AIFM1_DRAM_PTEN_ID2_CIAP2_SESN2_TP63 | ATG12_DIABLO_DRAM_FRAP1_TKT_CDH1_CIAP2_TP63 |
| AIFM1_DRAM_TKT_MMP9_CIAP2_SESN2_TP63 | AIFM1_ATG3_DRAM_ID2_MMP9_CIAP2_SESN2_TP63 |
| ATG12_DRAM_FRAP1_NNMT_TKT_CIAP2_TP63 | ATG12_CBS_DRAM_FRAP1_LAMP1_TKT_CIAP2_TP63 |
| AKT1_ATG12_DRAM_FRAP1_TKT_CIAP2_TP63 | ATG12_DRAM_FRAP1_LAMP1_TKT_XIAP_CIAP2_TP63 |
| ATG12_DRAM_E2F1_FRAP1_TKT_CIAP2_TP63 | ATG12_BCL2L1_DRAM_FRAP1_LAMP1_TKT_CIAP2_TP63 |
| ATG12_DRAM_FRAP1_TKT_BHLHE41_CIAP2_TP63 | ATG12_DRAM_FRAP1_TKT_XIAP_CIAP2_HMGB1_TP63 |
| AIFM1_ATG12_DRAM_FRAP1_MMP9_CIAP2_TP63 | AIFM1_ATG12_DRAM_FRAP1_PRKAA1_TKT_CIAP2_TP63 |
| AIFM1_ATG3_DRAM_ID2_CIAP2_SESN2_TP63 | AIFM1_DRAM_PTEN_ID2_MMP9_CIAP2_SESN2_TP63 |
| AIFM1_ATG3_DRAM_MMP9_CIAP2_SESN2_TP63 | ATG12_ATG7_BCL2L1_DRAM_FRAP1_TKT_CIAP2_TP63 |
| ATG12_DRAM_FRAP1_TKT_CIAP2_HMGB1_TP63 | ATG12_DRAM_FRAP1_TKT_XIAP_CIAP2_TP63_VEGF |
| AIFM1_ATG12_DRAM_TKT_CIAP2_SESN2_TP63 | AIFM1_ATG12_ATG7_DRAM_FRAP1_TKT_CIAP2_TP63 |
| AIFM1_BNIP3_DRAM_TKT_CIAP2_SESN2_TP63 | AIFM1_ATG12_DRAM_FRAP1_TKT_CIAP2_RAGE_TP63 |
| AIFM1_DRAM_ID2_MMP9_CIAP2_SESN2_TP63 | ATG12_ATG7_DRAM_FRAP1_LAMP1_TKT_CIAP2_TP63 |
| AIFM1_DRAM_LAMP1_TKT_CIAP2_SESN2_TP63 | ATG12_DRAM_FRAP1_LAMP1_TKT_CIAP2_TP63_VEGF |
| DRAM_FRAP1_TKT_CASP3_CIAP2_HMGB2_TP63 | ATG12_DRAM_FRAP1_LAMP1_PTEN_TKT_CIAP2_TP63 |
| AIFM1_AKT1_ATG12_DRAM_FRAP1_CIAP2_TP63 | ATG12_BCL2L1_DRAM_FRAP1_TKT_CIAP2_RAGE_TP63 |
| AIFM1_DRAM_PRKAA1_TKT_CIAP2_SESN2_TP63 | AIFM1_ATG12_BNIP3_DRAM_FRAP1_TKT_CIAP2_TP63 |
| AIFM1_DRAM_TKT_CIAP2_RAGE_SESN2_TP63 | AIFM1_ATG12_DIABLO_DRAM_FRAP1_CDHl_CIAP2_TP63 |
| AIFM1_DRAM_TKT_ID2_CIAP2_SESN2_TP63 | ATG12_BCL2L1_DRAM_FRAP1_PRKAA1_TKT_CIAP2_TP63 |
| ATG12_DRAM_FRAP1_TKT_CIAP2_SATB1_TP63 | ATG12_CBS_DRAM_FRAP1_TKT_XIAP_CIAP2_TP63 |
| AIFM1_AKT1_DRAM_TKT_CIAP2_SESN2_TP63 | ATG12_DRAM_FRAP1_LAMP1_PRKAA1_TKT_CIAP2_TP63 |
| AIFM1_ATG12_DRAM_FRAP1_CIAP2_TP63_VEGF | ATG12_DRAM_FRAP1_LAMP1_TKT_CIAP2_RAGE_TP63 |
| AIFM1_ATG3_DRAM_NNMT_CIAP2_SESN2_TP63 | ATG12_ATG7_DRAM_FRAP1_TKT_XIAP_CIAP2_TP63 |
| AIFM1_BAX_DRAM_ID2_CIAP2_SESN2_TP63 | ATG12_BCL2L1_BNIP3_DRAM_FRAP1_TKT_CIAP2_TP63 |
| AIFM1_DRAM_NNMT_ID2_CIAP2_SESN2_TP63 | ATG12_CBS_DRAM_FRAP1_TKT_CIAP2_TP63_VEGF |
| DRAM_FRAP1_NNMT_TKT_XIAP_CIAP2_TP63 | AIFM1_ATG3_DRAM_NNMTJD2_CIAP2_SESN2_TP63 |
| BCL2L1_DRAM_FRAP1_IKT_XIAP_CIAP2_TP63 | AIFM1_DRAM_NNMT_PTENJD2_CIAP2_SESN2_TP63 |
| AIFM1_ATG12_ATG3_DRAM_FRAP1_CIAP2_TP63 | ATG12_CBS_DRAM_FRAP1_PTEN_TKT_CIAP2_TP63 |
| AIFM1_ATG7_DRAM_ID2_CIAP2_SESN2_TP63 | ATG12_DRAM_FRAP1_PTEN_TKT_MMP9_CIAP2_TP63 |
| AIFM1_DRAM_TKT_CIAP2_SESN2_TP63_VEGF | AIFM1_ATG12_ATG3_DRAM_FRAP1_MMP9_CIAP2_TP63 |
| ATG12_ATG3_DRAM_FRAP1_TKT_CIAP2_TP63 | AIFM1_ATG12_CASP8_DRAM_TKT_CIAP2_SESN2_TP63 |
| AIFM1_AKT1_DRAM_ID2_CIAP2_SESN2_TP63 | ATG12_ATG7_CBS_DRAM_FRAP1_TKT_CIAP2_TP63 |
| AIFM1_ATG12_ATG7_DRAM_FRAP1_CIAP2_TP63 | ATG12_BCL2L1_DRAM_FRAP1_TKT_XIAP_CIAP2_TP63 |
| AIFM1_ATG3_BCL2L1_DRAM_CIAP2_SESN2_TP63 | AIFM1_ATG12_DRAM_PTEN_TKT_CIAP2_SESN2_TP63 |
| AIFM1_ATG7_DRAM_TKT_CIAP2_SESN2_TP63 | AIFM1_BCL2L1_DRAM_NNMT_TKT_CIAP2_SESN2_TP63 |
| AIFM1_BCL2L1_DRAM_ID2_CIAP2_SESN2_TP63 | ATG12_DRAM_E2F1_FRAP1_NNMT_TKT_CIAP2_TP63 |
| AIFM1_CBS_DRAM_TKT_CIAP2_SESN2_TP63 | ATG12_ATG7_DRAM_FRAP1_TKT_CIAP2_TP63_VEGF |
| AIFM1_DRAM_PTEN_TKT_CIAP2_SESN2_TP63 | ATG12_BNIP3_DRAM_FRAP1_LAMP1_TKT_CIAP2_TP63 |
| AIFM1_DRAM_TKT_BHLHE41_CIAP2_SESN2_TP63 | ATG12_CBS_DRAM_FRAP1_PRKAA1_TKT_CIAP2_TP63 |
| ATG12_DIABLO_DRAM_FRAP1_CDH1_CIAP2_TP63 | ATG12_DIABLO_DRAM_FRAP1_CDH1_ID2_CIAP2_TP63 |
| BCL2L1_DRAM_TKT_ID2_CIAP2_SESN2_TP63 | ATG12_DRAM_FRAP1_PRKAA1_TKT_XIAP_CIAP2_TP63 |
| BAX_DRAM_FRAP1_CDH1_ID2_CIAP2_TP63 | ATG12_DRAM_FRAP1_TKT_XIAP_CIAP2_RAGE_TP63 |
| CBS_DIABLO_FRAP1_CDH1_ID2_MMP9_TCF3 | ATG3_DIABLO_FRAP1_CDH1_ID2_MMP9_TCF3_AGER |

Preferably, the composition or kit is for predicting the prognosis of disease-free survival of the C group, and the genes are one or more selected from the genes or groups of genes described in the following Table 15.

TABLE 15

| One type | Combinations of two types | Combinations of three types | Combinations of four types |
|---|---|---|---|
| FASLG | FAS_FASLG | FAS_LC3_FASLG | DIABLO_FAS_LC3_FASLG |
| CIAP2 | LC3_FASLG | DIABLO_FAS_FASLG | FAS_LC3_FASLG_UVRAG |
| FAS | E2F1_FASLG | E2F1_LC3_FASLG | E2F1_FAS_LC3_FASLG |
| CSE1L | CIAP2_FASLG | FAS_FASLG_RPS19BP1 | BNIP3_FAS_LC3_FASLG |
| TCF3 | DIABLO_FASLG | E2F1_FAS_FASLG | DRAM_FAS_LC3_FASLG |
| | FASLG_RPS19BP1 | FAS_FASLG_UVRAG | ATG7_FAS_LC3_FASLG |
| | FASLG_SESN2 | DIABLO_LC3_FASLG | FAS_LAMP1_LC3_FASLG |
| | CASP3_FASLG | ATG7_FAS_FASLG | FAS_FRAP1_LC3_FASLG |
| | FASLG_UVRAG | FAS_FASLG_SESN2 | ATG3_FAS_LC3_FASLG |
| | FRAP1_FASLG | LC3_FASLG_SESN2 | FAS_LC3_FASLG_RPS19BP1 |
| | PIEN_FASLG | FAS_LAMP1_FASLG | FAS_LC3_FASLG_SESN3 |
| | FASLG_HMGB1 | ATG3_FAS_FASLG | FAS_LC3_FASLG_SESN2 |
| | ATG3_FAS | CIAP2_FASLG_SESN3 | ATG5_FAS_LC3_FASLG |
| | CASP3_CIAP2 | FAS_FRAP1_FASLG | FAS_LC3_FASLG_STAT3 |
| | TCF3_FASLG | FRAP1_LC3_FASLG | FAS_LC3_FASLG_SIRT1 |
| | ATG7_FASLG | BNIP3_LC3_FASLG | AKT1_FAS_LC3_FASLG |
| | PIEN_CIAP2 | FAS_FASLG_SESN3 | FAS_LC3_ID2_FASLG |
| | CDH2_FASLG | BNIP3_FAS_FASLG | FAS_LC3_FASLG_NAMPT |
| | FASLG_SESN3 | DIABLO_FASLG_SESN2 | FAS_LC3_BECN1_FASLG |
| | DIABLO_FAS | CIAP2_FASLG_UVRAG | FAS_LC3_MMP9_FASLG |
| | FAS_LC3 | LC3_FASLG_UVRAG | DIABLO_FAS_FASLG_UVRAG |
| | ULK1_FASLG | LC3_CIAP2_FASLG | ATG12_FAS_LC3_FASLG |
| | CSE1L_FASLG | DRAM_FAS_FASLG | FAS_FASLG_RPS19BP1_UVRAG |

TABLE 15-continued

| | | |
|---|---|---|
| CBS_FASLG | LC3_FASLG_SESN3 | DIABLO_FAS_FASLG_SESN2 |
| FASLG_HMGB2 | FAS_FASLG_STAT3 | FAS_LC3_FASLG_LAMP2 |
| FAS_UVRAG | ATG7_LC3_FASLG | FAS_LC3_CDH1_FASLG |
| LAMP1_FASLG | ATG5_FAS_FASLG | DIABLO_FAS_FASLG_SESN3 |
| BNIP3_FASLG | E2F1_FASLG_SESN2 | FAS_LC3_TCF3_FASLG |
| MMP9_FASLG | LC3_ID2_FASLG | E2F1_LC3_ID2_FASLG |
| TKT_FASLG | DRAM_LC3_FASLG | FAS_LC3_BHLHE41_FASLG |
| FASLG_STAT3 | FAS_TCF3_FASLG | DIABLO_FAS_LAMP1_FASLG |
| AKT1_FASLG | AKT1_FAS_FASLG | DIABLO_DRAM_FAS_FASLG |
| FASLG_MMP2 | E2F1_ULK1_FASLG | FAS_FASLG_SESN2_UVRAG |
| DRAM_FASLG | E2F1_TCF3_FASLG | FAS_FASLG_RPS19BP1_SESN3 |
| FASLG_SIRT1 | LC3_FASLG_RPS19BP1 | DIABLO_FAS_FRAP1_FASLG |
| ATG12_FASLG | LC3_MMP9_FASLG | DIABLO_FAS_FASLG_STAT3 |
| CIAP2_RAGE | FAS_FASLG_SIRT1 | ATG7_DIABLO_FAS_FASLG |
| FAS_LAMP1 | FAS_ULK1_FASLG | CSE1L_FAS_LC3_FASLG |
| ATG5_FASLG | FAS_FASLG_NAMPT | E2F1_LC3_MMP9_FASLG |
| ATG3_FASLG | LC3_FASLG_SIRT1 | DRAM_FAS_FASLG_RPS19BP1 |
| E2F1_FAS | CASP3_CIAP2_FASLG | DIABLO_FAS_FASLG_RPS19BP1 |
| BECN1_FASLG | ATG12_FAS_FASLG | FAS_LC3_ULK1_FASLG |
| E2F1_CIAP2 | FAS_BECN1_FASLG | DIABLO_FAS_FASLG_SIRT1 |
| CASP8_FASLG | ATG5_LC3_FASLG | DIABLO_FAS_ID2_FASLG |
| XIAP_CIAP2 | LC3_BECN1_FASLG | AKT1_DIABLO_FAS_FASLG |
| CDH1_FASLG | LC3_FASLG_STAT3 | DIABLO_FAS_FASLG_NAMPT |
| FASLG_NAMPT | E2F1_FASLG_SESN3 | ATG3_FAS_FASLG_SESN2 |
| BNIP3_FAS | AKT1_LC3_FASLG | FAS_FASLG_RPS19BP1_SESN2 |
| FASLG_LAMP2 | FAS_FASLG_LAMP2 | DIABLO_FAS_BECN1_FASLG |
| AGER_FASLG | LC3_TCF3_FASLG | DIABLO_FAS_CDH1_FASLG |
| ID2_FASLG | LC3_FASLG_NAMPT | ATG7_FAS_FASLG_UVRAG |
| AIFM1_FASLG | LC3_CDH1_FASLG | DIABLO_FAS_FASLG_LAMP2 |
| FASLG_SESN1 | ATG12_LC3_FASLG | FAS_FRAP1_FASLG_RPS19BP1 |
| AIFM1_CIAP2 | PTEN_CDH1_CIAP2 | FAS_LAMP1_FASLG_UVRAG |
| PRKAA1_CIAP2 | LC3_FASLG_LAMP2 | E2F1_FAS_LAMP1_FASLG |
| BCL2L1_CIAP2 | DIABLO_FASLG_SESN3 | ATG7_FAS_FASLG_RPS19BP1 |
| XIAP_FASLG | FAS_CDH1_FASLG | E2F1_FAS_FASLG_UVRAG |
| | | CDH1_ID2_MMP9_TCF3 |

| Combinations of five types | Combinations of six types |
|---|---|
| DIABLO_FAS_LC3_ID2_FASLG | BNIP3_DRAM_FAS_LC3_FASLG_SESN2 |
| DRAM_FAS_LC3_FASLG_UVRAG | DIABLO_DRAM_FAS_LC3_ID2_FASLG |
| DIABLO_DRAM_FAS_LC3_FASLG | ATG3_FAS_LC3_MMP9_FASLG_SESN2 |
| BNIP3_FAS_LC3_FASLG_UVRAG | DRAM_FAS_LC3_ID2_FASLG_UVRAG |
| BNIP3_FAS_LC3_FASLG_SESN2 | BNIP3_DRAM_FAS_LC3_FASLG_UVRAG |
| BNIP3_DRAM_FAS_LC3_FASLG | BNIP3_FAS_LC3_FASLG_SESN2_UVRAG |
| BNIP3_DIABLO_FAS_LC3_FASLG | DIABLO_FAS_LC3_ID2_FASLG_UVRAG |
| FAS_LC3_ID2_FASLG_UVRAG | DIABLO_FAS_LC3_ID2_FASLG_STAT3 |
| DIABLO_FAS_LC3_FASLG_UVRAG | DIABLO_FAS_LC3_ID2_FASLG_SESN3 |
| DIABLO_FAS_LC3_FASLG_STAT3 | BNIP3_FAS_LC3_MMP9_FASLG_UVRAG |
| DIABLO_FAS_LC3_FASLG_SESN3 | BNIP3_DRAM_FAS_LC3_FASLG_SESN3 |
| DIABLO_FAS_LC3_FASLG_SIRT1 | BNIP3_FAS_LC3_ID2_FASLG_UVRAG |
| FAS_LC3_MMP9_FASLG_RPS19BP1 | DRAM_FAS_LC3_MMP9_FASLG_RPS19BP1 |
| ATG5_FAS_LC3_FASLG_UVRAG | BNIP3_FAS_LC3_MMP9_FASLG_RPS19BP1 |
| BNIP3_FAS_LC3_FASLG_SESN3 | BNIP3_FAS_LC3_ID2_FASLG_SESN2 |
| DIABLO_FAS_LC3_BECN1_FASLG | BNIP3_DIABLO_FAS_LC3_ID2_FASLG |
| DIABLO_FAS_LC3_CDH1_FASLG | BNIP3_FAS_LC3_MMP9_FASLG_SESN2 |
| ATG3_FAS_LC3_FASLG_SESN2 | DIABLO_FAS_LC3_ID2_FASLG_SIRT1 |
| DRAM_E2F1_FAS_LC3_FASLG | ATG5_DRAM_FAS_LC3_FASLG_UVRAG |
| FAS_LC3_FASLG_SESN2_UVRAG | FAS_LC3_MMP9_FASLG_RPS19BP1_UVRAG |
| DIABLO_FAS_LC3_FASLG_LAMP2 | ATG3_FAS_LC3_FASLG_SESN2_SESN3 |
| E2F1_FAS_LC3_ID2_FASLG | DRAM_FAS_LC3_FASLG_SESN2_UVRAG |
| DIABLO_FAS_LC3_FASLG_NAMPT | DIABLO_FAS_LC3_ID2_BECN1_FASLG |
| DIABLO_FAS_LC3_MMP9_FASLG | DRAM_FAS_LC3_FASLG_SIRT1_UVRAG |
| FAS_LC3_FASLG_SIRT1_UVRAG | FAS_LC3_ID2_FASLG_SESN2_UVRAG |
| FAS_LC3_FASLG_SESN3_UVRAG | DIABLO_FAS_LC3_CDH1_ID2_FASLG |
| FAS_LAMP1_LC3_FASLG_UVRAG | FAS_LC3_ID2_MMP9_FASLG_RPS19BP1 |
| AKT1_DIABLO_FAS_LC3_FASLG | BNIP3_FAS_LC3_FASLG_SESN2_SESN3 |
| DIABLO_FAS_FRAP1_LC3_FASLG | DIABLO_FAS_LC3_ID2_FASLG_NAMPT |
| DIABLO_FAS_LC3_BHLHE41_FASLG | DIABLO_FAS_LC3_ID2_FASLG_SESN2 |
| FAS_LC3_FASLG_STAT3_UVRAG | DIABLO_FAS_LC3_ID2_FASLG_LAMP2 |
| DIABLO_FAS_LC3_FASLG_SESN2 | BNIP3_FAS_LC3_FASLG_SESN2_SIRT1 |
| E2F1_FAS_LC3_MMP9_FASLG | BNIP3_FAS_LC3_FASLG_SESN2_STAT3 |
| BNIP3_FAS_FRAP1_LC3_FASLG | DRAM_FAS_LC3_FASLG_SESN3_UVRAG |
| DIABLO_FAS_LAMP1_LC3_FASLG | DIABLO_DRAM_FAS_LC3_FASLG_STAT3 |
| FAS_LC3_BECN1_FASLG_UVRAG | BNIP3_DRAM_FAS_LC3_MMP9_FASLG |
| AKT1_FAS_LC3_FASLG_UVRAG | ATG5_FAS_LC3_ID2_FASLG_UVRAG |
| BNIP3_FAS_LC3_MMP9_FASLG | BNIP3_FAS_LC3_FASLG_SESN3_UVRAG |
| FAS_FRAP1_LC3_FASLG_UVRAG | DRAM_FAS_LC3_BECN1_FASLG_UVRAG |
| BNIP3_FAS_LC3_FASLG_STAT3 | DIABLO_DRAM_FAS_LC3_CDH1_FASLG |
| FAS_LC3_CDH1_FASLG_UVRAG | AKT1_DIABLO_FAS_LC3_ID2_FASLG |
| FAS_LC3_FASLG_LAMP2_UVRAG | BNIP3_DIABLO_FAS_LC3_MMP9_FASLG |

TABLE 15-continued

| | |
|---|---|
| FAS_LC3_MMP9_FASLG_UVRAG | DRAM_FAS_LC3_CDH1_FASLG_UVRAG |
| ATG7_FAS_LC3_FASLG_UVRAG | DIABLO_FAS_FRAP1_LC3_ID2_FASLG |
| ATG7_DRAM_FAS_LC3_FASLG | BNIP3_DRAM_FAS_LC3_FASLG_STAT3 |
| BNIP3_FAS_LC3_FASLG_SIRT1 | DIABLO_DRAM_FAS_LC3_FASLG_SESN3 |
| DRAM_FAS_LAMP1_LC3_FASLG | BNIP3_DIABLO_DRAM_FAS_LC3_FASLG |
| ATG7_BNIP3_FAS_LC3_FASLG | DIABLO_DRAM_FAS_LC3_FASLG_SIRT1 |
| BNIP3_FAS_LAMP1_LC3_FASLG | BNIP3_DRAM_FAS_FRAP1_LC3_FASLG |
| ATG3_FAS_LC3_MMP9_FASLG | DIABLO_DRAM_FAS_LC3_BECN1_FASLG |
| ATG5_DIABLO_FAS_LC3_FASLG | ATG3_FAS_LC3_MMP9_FASLG_SESN3 |
| BNIP3_FAS_LC3_ID2_FASLG | DIABLO_FAS_LAMP1_LC3_ID2_FASLG |
| ATG12_DIABLO_FAS_LC3_FASLG | DRAM_FAS_LC3_FASLG_LAMP2_UVRAG |
| E2F1_FAS_LC3_FASLG_SESN3 | ATG5_FAS_LC3_FASLG_SESN2_UVRAG |
| AKT1_BNIP3_FAS_LC3_FASLG | FAS_LC3_MMP9_FASLG_RPS19BP1_SESN3 |
| FAS_LC3_FASLG_NAMPT_UVRAG | FAS_LAMP1_LC3_ID2_FASLG_UVRAG |
| ATG12_FAS_LC3_FASLG_UVRAG | BNIP3_DRAM_FAS_LC3_ID2_FASLG |
| PTEN_CDH1_ID2_MMP9_TCF3 | LC3_CDH1_ID2_MMP9_TCF3_FASLG |

| Combinations of seven types | Combinations of eight types |
|---|---|
| ATG3_FAS_LC3_MMP9_FASLG_SESN2_SESN3 | ATG3_FAS_LC3_ID2_MMP9_FASLG_SESN2_SESN3 |
| BNIP3_DRAM_FAS_LC3_ID2_FASLG_SESN2 | BNIP3_DRAM_FAS_LC3_ID2_FASLG_SESN2_UVRAG |
| BNIP3_FAS_LC3_ID2_FASLG_SESN2_UVRAG | ATG3_DRAM_FAS_LC3_MMP9_FASLG_SESN2_SESN3 |
| ATG3_DRAM_FAS_LC3_MMP9_FASLG_SESN2 | BNIP3_FAS_LC3_ID2_MMP9_FASLG_SESN2_UVRAG |
| BNIP3_DRAM_FAS_LC3_FASLG_SESN2_UVRAG | BNIP3_DRAM_FAS_LC3_MMP9_FASLG_SESN2_UVRAG |
| BNIP3_DRAM_FAS_LC3_MMP9_FASLG_SESN2 | ATG3_FAS_LC3_MMP9_TCF3_FASLG_SESN2_SESN3 |
| ATG3_FAS_LC3_MMP9_FASLG_SESN2_UVRAG | BNIP3_DRAM_FAS_LC3_ID2_MMP9_FASLG_SESN2 |
| BNIP3_FAS_LC3_MMP9_FASLG_SESN2_UVRAG | BNIP3_DRAM_FAS_LC3_MMP9_TCF3_FASLG_UVRAG |
| FAS_LC3_ID2_MMP9_FASLG_RPS19BP1_UVRAG | BNIP3_DRAM_FAS_LC3_ID2_FASLG_SESN2_SESN3 |
| BNIP3_DRAM_FAS_LC3_ID2_FASLG_UVRAG | ATG3_FAS_LC3_ID2_MMP9_FASLG_SESN2_UVRAG |
| DRAM_FAS_LC3_ID2_FASLG_SESN2_UVRAG | DRAM_FAS_LC3_ID2_MMP9_FASLG_RPS19BP1_UVRAG |
| DRAM_FAS_LC3_ID2_MMP9_FASLG_RPS19BP1 | ATG5_DRAM_FAS_LC3_ID2_FASLG_SESN2_UVRAG |
| ATG3_FAS_LC3_ID2_MMP9_FASLG_SESN2 | BNIP3_DRAM_FAS_LC3_ID2_FASLG_SESN2_STAT3 |
| BNIP3_DRAM_FAS_LC3_FASLG_SESN2_SIRT1 | ATG3_DRAM_FAS_LC3_ID2_MMP9_FASLG_SESN2 |
| BNIP3_DRAM_FAS_LC3_FASLG_SESN2_SESN3 | BNIP3_DRAM_FAS_LC3_ID2_FASLG_SESN2_SIRT1 |
| BNIP3_DRAM_FAS_LC3_MMP9_FASLG_UVRAG | ATG3_FAS_LC3_MMP9_TCF3_FASLG_SESN2_UVRAG |
| BNIP3_DRAM_FAS_LC3_FASLG_SESN2_STAT3 | ATG3_DRAM_FAS_LC3_MMP9_TCF3_FASLG_SESN2 |
| BNIP3_FAS_LC3_MMP9_TCF3_FASLG_UVRAG | ATG3_FAS_LC3_MMP9_FASLG_SESN2_SESN3_SIRT1 |
| ATG3_FAS_LC3_MMP9_TCF3_FASLG_SESN2 | BNIP3_FAS_LC3_ID2_MMP9_TCF3_FASLG_UVRAG |
| DIABLO_DRAM_FAS_LC3_ID2_FASLG_STAT3 | DRAM_FAS_LC3_ID2_MMP9_FASLG_RPS19BP1_SESN3 |
| ATG3_DIABLO_FAS_LC3_MMP9_FASLG_SESN2 | ATG3_FAS_LC3_CDH1_MMP9_FASLG_SESN2_SESN3 |
| DIABLO_DRAM_FAS_LC3_ID2_FASLG_SESN3 | BNIP3_DRAM_FAS_LC3_ID2_MMP9_FASLG_RPS19BP1 |
| BNIP3_FAS_LC3_ID2_MMP9_FASLG_RPS19BP1 | ATG3_FAS_LC3_MMP9_FASLG_SESN2_SESN3_UVRAG |
| ATG5_DRAM_FAS_LC3_ID2_FASLG_UVRAG | ATG3_FAS_LC3_MMP9_FASLG_LAMP2_SESN2_SESN3 |
| BNIP3_DRAM_FAS_LC3_BECN1_FASLG_SESN2 | ATG3_FAS_LC3_MMP9_BECN1_FASLG_SESN2_SESN3 |
| BNIP3_DRAM_FAS_LC3_MMP9_FASLG_RPS19BP1 | ATG3_DIABLO_FAS_LC3_ID2_MMP9_FASLG_SESN2 |
| ATG5_FAS_LC3_ID2_FASLG_SESN2_UVRAG | BNIP3_DRAM_FAS_LC3_ID2_MMP9_FASLG_UVRAG |
| ATG3_FAS_FRAP1_LC3_MMP9_FASLG_SESN2 | ATG3_DRAM_FAS_LC3_MMP9_FASLG_SESN2_UVRAG |
| DIABLO_DRAM_FAS_LC3_ID2_FASLG_UVRAG | BNIP3_DRAM_FAS_LC3_ID2_BECN1_FASLG_SESN2 |
| DIABLO_DRAM_FAS_LC3_CDH1_ID2_FASLG | BNIP3_DRAM_FAS_LC3_MMP9_FASLG_SESN2_SIRT1 |
| DRAM_FAS_LC3_ID2_FASLG_SIRT1_UVRAG | BNIP3_DRAM_FAS_LC3_MMP9_FASLG_SESN2_SESN3 |
| DIABLO_DRAM_FAS_LC3_ID2_FASLG_SIRT1 | ATG3_FAS_LC3_ID2_MMP9_TCF3_FASLG_SESN2 |
| BNIP3_DRAM_FAS_LC3_CDH1_FASLG_SESN2 | BNIP3_FAS_LC3_ID2_MMP9_FASLG_RPS19BP1_SESN3 |
| FAS_LC3_ID2_MMP9_FASLG_RPS19BP1_SESN3 | ATG3_BNIP3_FAS_LC3_MMP9_FASLG_SESN2_SESN3 |
| BNIP3_FAS_LC3_ID2_MMP9_FASLG_UVRAG | BNIP3_CSE1L_FAS_LC3_MMP9_FASLG_SESN2_UVRAG |
| DIABLO_DRAM_FAS_LC3_ID2_BECN1_FASLG | ATG5_FAS_LC3_ID2_MMP9_FASLG_SESN2_UVRAG |
| DRAM_FAS_LC3_ID2_FASLG_SESN3_UVRAG | BNIP3_FAS_LC3_CDH1_ID2_FASLG_SESN2_UVRAG |
| ATG3_FAS_LC3_MMP9_FASLG_SESN2_SIRT1 | ATG5_BNIP3_DRAM_FAS_LC3_MMP9_FASLG_SESN2 |
| BNIP3_DRAM_FAS_LC3_FASLG_LAMP2_SESN2 | BNIP3_FAS_LC3_ID2_FASLG_SESN2_SIRT1_UVRAG |
| BNIP3_DRAM_FAS_LC3_ID2_FASLG_SESN3 | ATG3_FAS_FRAP1_LC3_MMP9_FASLG_SESN2_SESN3 |
| BNIP3_FAS_LC3_ID2_FASLG_SESN2_SESN3 | BNIP3_DRAM_FAS_LC3_CDH1_ID2_FASLG_SESN2 |
| DIABLO_DRAM_FAS_LC3_ID2_FASLG_LAMP2 | BNIP3_CSE1L_FAS_LC3_MMP9_FASLG_SESN3_UVRAG |
| BNIP3_FAS_LC3_ID2_MMP9_FASLG_SESN2 | AKT1_BNIP3_DRAM_FAS_LC3_ID2_FASLG_SESN2 |
| ATG5_DRAM_FAS_LC3_FASLG_SESN2_UVRAG | BNIP3_DRAM_FAS_LC3_ID2_FASLG_LAMP2_SESN2 |
| DRAM_FAS_LC3_MMP9_FASLG_RPS19BPLUVRAG | ATG3_ATG5_FAS_LC3_MMP9_FASLG_SESN2_SESN3 |
| DRAM_FAS_LAMP1_LC3_ID2_FASLG_UVRAG | BNIP3_DRAM_FAS_LC3_CDHl_FASLG_SESN2_UVRAG |
| DIABLO_DRAM_FAS_LC3_ID2_FASLG_SESN2 | BNIP3_FAS_LC3_ID2_FASLG_LAMP2_SESN2_UVRAG |
| ATG3_FAS_LC3_CDH1_MMP9_FASLG_SESN2 | BNIP3_FAS_LC3_ID2_BECNl_FASLG_SESN2_UVRAG |
| AKT1_BNIP3_DRAM_FAS_LC3_FASLG_SESN2 | BNIP3_FAS_LC3_MMP9_TCF3_FASLG_SESN2_UVRAG |
| DRAM_FAS_LC3_MMP9_FASLG_RPS19BP1_SESN3 | BNIP3_DRAM_FAS_LC3_ID2_TCF3_FASLG_UVRAG |
| ATG3_DRAM_FAS_LC3_FASLG_SESN2_SESN3 | AKT1_ATG3_FAS_LC3_MMP9_FASLG_SESN2_SESN3 |
| ATG3_FAS_LC3_MMP9_BECN1_FASLG_SESN2 | ATG3_DRAM_FAS_LC3_MMP9_FASLG_SESN2_SIRT1 |
| BNIP3_FAS_LC3_MMP9_FASLG_RPS19BP1_SESN3 | ATG5_DRAM_FAS_LC3_MMP9_FASLG_SESN2_UVRAG |
| DRAM_FAS_LC3_ID2_FASLG_STAT3_UVRAG | ATG3_DRAM_FAS_LC3_CDH1_MMP9_FASLG_SESN2 |
| BNIP3_DRAM_FAS_LC3_CDH1_FASLG_UVRAG | BNIP3_DRAM_FAS_LAMP1_LC3_ID2_FASLG_SESN2 |
| ATG3_FAS_LC3_MMP9_FASLG_LAMP2_SESN2 | ATG3_FAS_FRAP1_LC3_ID2_MMP9_FASLG_SESN2 |
| DRAM_FAS_LC3_ID2_BECN1_FASLG_UVRAG | BNIP3_DRAM_FAS_LC3_MMP9_BECN1_FASLG_SESN2 |
| E2F1_LC3_CDH1_ID2_MMP9_TCF3_FASLG | FAS_LC3_CDH1_ID2_MMP9_TCF3_FASLG_UVRAG |

The nucleic acids included in the composition or kit of the present disclosure may be primers or probes.

The nucleic acids may have a sequence complementary to genes such as DNA and/or RNA, etc., or may be hybridized. The "primer" means a nucleic acid sequence having free 3' hydroxyl group that can complementarily bind to a template and that enables the reverse transcriptase or DNA polymerase to initiate reproduction of template. The primer is a nucleotide having a sequence complementary to the nucleic acid sequence of a specific gene, and a primer of a length of about 7 bp~50 bp, preferably about 10 bp~30 bp, can be used. The primer may comprise other base sequences which do not change the basic feature of the primer acting at the initial point of DNA synthesis. The primer can be synthesized chemically using well known methods, and the nucleic acid sequence can be transformed using many means well known in the pertinent art.

The "probe" refers to a nucleic acid strand partly or completely complementary to the target nucleic acid and refers to an oligonucleotide that can bind to the target nucleic acid by a base specific method. Preferably, it is an oligonucleotide completely complementary to the target nucleic acid. The probe includes not only nucleic acid, but any known nucleic acid derivative capable of complementary binding, including peptide nucleic acid. The binding of a probe and target nucleic acid (generally, referred to as "hybridization") is sequence dependent, and can be performed at various conditions. In general, hybridization reaction takes place at specific ion and pH levels at a temperature about 5□ lower than the Tm of a specific sequence. The "Tm" means a condition where 50% of a probe complementary to the target sequence has bound to the sequence. An example of the reaction condition for hybridization may be pH of 7.0~8.3 and Na+ ion concentration of 0.01~1.0 M. Also, in order to increase the specificity between the target nucleic acid and probe, the reaction may be performed under conditions that do not make the binding between the target nucleic acid and probe unstable, for example, under the condition of not high temperature and in the absence of a high concentration of a destabilizing agent (for example, formamide, etc.). The length of the probe may be a length where the probe can be specifically bind to the target nucleic acid, and includes any length of polynucleotide. For example, the length of the probe may be 10~200 nucleotides, 10~150 nucleotides, 10~100 nucleotides, 10~50 nucleotides, or the length of a full gene, but is not limited thereto. The probe may be a labeled by a label that can be detected. The detectable label may be labeled with a fluorescent substance, FAM at the 5' end of SYBR Green I or various probes (TaqMan Probe) and with a quencher, TAMRA, at the 3' end thereof, but is not limited thereto. The detectable label includes fluorescent labels such as Cy3 or Cy5, radioactive substance label, enzyme transforming the substrate into a color former, etc., but are not limited thereto. In the kit of the present disclosure, the probe or probe set may be fixed to a microarray.

The target nucleic acid in a sample is hybridized with the probe in the microarray, and the existence and concentration thereof can be measured by measuring the hybridization result. The target nucleic acid during the hybridization process may be labeled by a detectable label.

The "antibody" means a protein that can specifically bind to epitope of an antigen, and it is a concept including polyclonal antibody, monoclonal antibody and recombinant antibody. The antibody can be easily prepared by using technology widely known in the art. To be specific, the polyclonal antibodies can be prepared by methods widely known in the art of injecting protein antigen encoded by the marker for prognosis of liver cancer of the present disclosure into animals and collecting blood from the animals to obtain serum comprising antibodies. These polyclonal antibodies can be prepared from various hosts of species of animals, such as goats, rabbits, sheep, monkeys, horses, pigs, cattle, dogs, etc.

Monoclonal antibodies can be prepared by using a hybridoma method [Kohler and Milstein (1976) European Journal of Immunology 6:511-519] or phage antibody library technology [Clackson et al, Nature, 352:624-628, 1991; Marks et al, J. Mol. Biol., 222:58, 1-597, 1991], etc. which are widely known in the art.

Conventionally, a hybridoma method uses cells obtained from host animals which are immunologically suitable, such as a mouse, to which protein antigen encoded by the marker for prognosis of liver cancer of the first aspect of the present disclosure has been injected, and a cancer or myeloma cell line as the other population. The tissues obtained from these two populations are fused by a widely known method in the art such as polyethyleneglycol, and then antibody-producing cells are proliferated by a standard tissue cultivation method. After obtaining a homogenous cell population by subcloning according to a limited dilution technique, hybridoma that can produce desired antibodies is cultivated in quantity in vivo or in vitro according to a known technique. A phage antibody library method is a method of producing monoclonal antibodies by obtaining a gene of the desired antibody, expressing the gene in the form of the fusion protein on the surface of phages, and thereby producing an antibody library in vitro, and separating the desired monoclonal antibodies from the library. The monoclonal antibodies prepared by the above method may be separated by using known methods, such as gel electrophoresis, dialysis, salts precipitation, ion exchange chromatography, affinity chromatography, etc.

The antibody comprises functional fragments of an antibody molecule in addition to perfect shapes of two full-length light chains and two full-length heavy chains. The functional fragments of the antibody molecule refer to fragments having antigen-binding functions, and include Fab, F(ab'), F(ab')2, Fv, etc.

The predicting prognosis of liver cancer may be predicting prognosis before liver resection for cancer or after liver resection for cancer.

In addition to nucleic acids or antibodies, the kit may further comprise one or more types of other ingredients, solutions or apparatus, which are suitable for methods of analyzing the expression level or the expression pattern of gene or methods of analyzing the existing level or the existing patter of protein. For example, in the case of the diagnosis kit for detecting the expression level or the expression pattern of gene, the diagnosis kit may comprise essential ingredients required for performing RT-PCR, and in addition to respective primers specific to mRNA of marker genes, this RT-PCR kit may comprise, for example, test tube or other proper container, reaction buffer solution, deoxynucleotide (dNTPs), enzyme such as Taq-polymerase and reverse transcriptase, DNAse, RNAse inhibitor, DEPC-water (DEPCwater), sterile water, gene-specific primer pair that is used as a quantitative control group, according to specific embodiments. Meanwhile, in case where the kit is for detecting the existing level or the existing pattern of protein, the diagnosis kit may comprise, for example, essential ingredients required for performing ELISA. This ELISA kit may comprise ingredients capable of detecting bound antibodies, for example, a labeled secondary antibody, chromopores, enzyme (for example, enzyme connected to antibody) and its substrate, and an antibody specific to protein of the quantitative control group. Further, according to the specific embodiments, the kit may comprise DNA microarray or protein microarray.

Also, the present disclosure provides a composition or kit for predicting prognosis of liver cancer comprising nucleic acids which are specific to each of one or at least two genes selected from the group described in Table 2 (described in the description of the composition or kit for predicting prognosis of liver cancer for predicting the prognosis according to the stage of liver cancer of the present disclosure), or antibodies which are specific to proteins encoded by said genes.

In the composition or kit, the group of genes may further comprise the genes described in Table 3 (described in the description of the composition or kit for predicting prognosis of liver cancer for predicting the prognosis according to the stage of liver cancer of the present disclosure).

The matters mentioned regarding the composition or kit for predicting prognosis of liver cancer for predicting the prognosis according to the stage of liver cancer of the present disclosure equally apply to the composition and the kit unless there is a contradiction.

Also, the present disclosure provides a method for predicting prognosis of liver cancer according to stage comprising: (A) detecting one or more selected from the expression level or expression pattern of one or at least two genes selected from the group consisting of the genes described in Table 1 (described in the description of the composition or kit for predicting prognosis of liver cancer for predicting the prognosis according to stage of liver cancer of the present disclosure) in samples obtained from patients of liver cancer; and (B) comparing the results of the (A) step with the measurement results of the control groups to predict prognosis of liver cancer, wherein the patients of liver cancer are in one or more groups selected from A1 group {a group of portal vein invasion-negative patients in stage 0 or A of BCLC (Barcelona-Clinic Liver Cancer) staging system, having a tumor which is 5 cm or less in size, or 3 or less tumors which are 3 cm or less in size}, A2 group {a group of portal vein invasion-negative patients, having a tumor which is more than 5 cm in size}, B group {a group of portal vein invasion-negative patients in intermediate stage of BCLC staging system, having plural tumors which are more than 3 cm in size or plural tumors which are more than 3 in number}, or C group {a group of portal vein invasion-positive patients regardless of tumors size and number}.

Preferably, the group consisting of the genes may be a group consisting of the genes described in Table 2 (described in the description of the composition or kit for predicting prognosis of liver cancer for predicting the prognosis according to the stage of liver cancer of the present disclosure), and the group consisting of genes may further comprise the genes described in Table 3 (described in the description of the composition or kit for predicting prognosis of liver cancer for predicting the prognosis according to the stage of liver cancer of the present disclosure).

Samples harvested from patients of liver cancers mean a cell, tissue, etc. separated from human body where the expression level or expression pattern of the marker for prognosis of liver cancer, or existing level or existing pattern of protein encoded by the marker for prognosis of liver cancer can be detected. It can be exemplified by urine, blood, plasma, serum, etc., but is not particularly limited thereto. The tissue may be embedded in a paraffin block.

The expression level or expression pattern of the genes can be detected by general biochemical analysis methods which confirm the level or pattern of mRNA generated by transcription of the corresponding gene. As such an analysis method for confirming the level or pattern of mRNA, there are RT-PCR, competitive RT-PCR, real-time RT-PCT, RNase protection assay, Northern blot, DNA microarray, etc. In addition, any method that is generally carried out in the pertinent art can be used.

Through the above analysis methods, the level or pattern of mRNA in the biological sample of liver cancer patient can be compared with the standard level, and the difference in expression level, expression pattern or both of the marker for prognosis of liver cancer of the present disclosure is detected therefrom. This enables estimating the prognosis of liver cancer patients.

The kit for measuring the level or pattern of mRNA by RT-PCR comprises a primer specific to mRNA of the marker for prognosis of liver cancer of the present disclosure. RT-PCR kits may include a test tube or other suitable container, reaction buffer solution, deoxynucleotide (dNTPs), enzyme such as Taq-polymerase and reverse transcriptase, DNAse, RNAse suppresser, DEPC-water, sterile water, etc. according to detailed embodiments. The primer can initiate DNA synthesis in the presence of a reagent for polymerization (i.e., DNA polymerase or reverse transcriptase) and four different nucleoside triphosphates in a suitable buffer solution and temperature.

As a method for measuring the expression level or expression pattern of a protein by using an antibody, there are western blot, ELISA (enzyme linked immunosorbent assay), radioimmunoassay, radioimmunodiffusion, Ouchterlony immunodiffusion, rocket immunoelectrophoresis, tissue immunity staining, immunoprecipitation assay, complement fixation assay, FACS, protein chip, etc. In addition, any method that is generally carried out in the pertinent art can be used.

Through the above analysis methods, the formation level or formation pattern of the antigen-antibody composite in a sample of subject liver cancer patients can be compared with the standard level, and the existing level or existing pattern of the protein encoded by the marker for prognosis of liver cancer of the present disclosure can be determined therefrom, and finally, the prognosis of liver cancer patients can be estimated. Here, "antigen-antibody composite" means a composite of protein encoded by a marker for prognosis of liver cancer and an antibody specific thereto. The formation level or formation pattern of the antigen-antibody composite can generally be measured by detecting the size and pattern of the signal of the detection label associated with a secondary antibody. Such detection label can be exemplified by enzyme, fluorescent substance, ligand, luminescent substance, nanoparticles, redox molecules, radio isotope, etc., but are not limited thereto. When enzyme is used as a detection label, as enzymes that can be used, there are β-glucuronidase, β-D-glucosidase, β-D-galactosidase, urease, peroxidase or alkaline phosphatase, acetylcholinesterase, glucose oxidase, hexokinase and GDPase, RNase, glucose oxidase, luciferase, phosphofructokinase, phosphoenolpyruvate carboxylase, aspartate aminotransferase, phosphoenolpyruvate decarboxylase, β-lactamase, etc., but the enzymes are not limited thereto. When a fluorescent substance is used as a detection label, as fluorescent substances that can be used, there are fluorescein, isothiocyanate, rhodamine, phycoerythrin, phycocyanin, allophycocyanin, o-phthaldehyde, fluorescamine, etc., but the fluorescent substances are not limited thereto. When a ligand is used as a detection label, as a ligand that can be used, there are biotin derivative, etc., but the ligand is not limited thereto. When a luminescent substance is used as a detection label, as luminescent substances that can be used, there are acridium ester, luciferin, luciferase, etc., but the luminescent substances are not limited thereto. When nanoparticles are used as detection label, as nanoparticles that can be used, there are colloidal gold, tinted latex, etc., but the nanoparticles are not limited thereto. When redox molecules are used as detection label, as redox molecules that can be used, there are ferrocene, ruthenium complex, viologen, quinone, Ti ion, Cs ion, diimide, 1,4-benzoquinone, hydroquinone, K4W(CN)8, [Os (bpy)3]2+, [RU(bpy)3]2+, [MO(CN)8]4−, etc., but the redox molecules are not limited thereto. When a radio isotope is used as a detection label, as radio isotopes that can be used, there are 3H, 14C, 32P, 35S, 36Cl, 51Cr, 57Co, 58Co, 59Fe, 90Y, 125I, 131I or 186Re, etc., but the radio isotopes are not limited thereto.

The "measurement results" refers to at least one selected from the expression level or expression pattern of the genes of the (A) step collected from liver cancer tissue, etc., and "the results of the control groups" may refer to the gene expression level having the lowest p-value among the results obtained by subjecting the measurements from groups of liver cancer patients (A1 group, A2 group, B group, C group) whose liver cancer prognosis is known to a regression analysis of continuous variables or a risk score obtained from the expression level (see *N Engl J. Med* 2007; 356: 11-20). The measurement results and the results of the control groups are expression levels or expression patterns (high expression or low expression) obtained according to the same method, and can be determined based on the average expression level of the control genes (group of genes) (B2M, GAPDH, HMBS, HPRT1, SDHA, etc.) expressing a constant expression level regardless of whether the patient is suffering from liver cancer.

The measurement results of liver cancer patients are characterized by being compared with the results of the control groups which are obtained from the above groups of patients to allow detection of a difference therebetween, and any substance allowing detection of such difference can be used as a substance for specifically detecting the expression level or expression pattern of markers for prognosis of liver cancer, or both of them. The result of detecting a difference between the results of the control group and the measurement results is capable of providing information for determining a method for treating liver cancer.

Also, the present disclosure provides a method for predicting prognosis of liver cancer comprising: (A) detecting one or more selected from the expression level or expression pattern of one or at least two genes selected from the group consisting of the genes described in Table 2 above (described in the description of the composition or kit for predicting prognosis of liver cancer for predicting the prognosis according to the stage of liver cancer of the present disclosure) in samples obtained from patients of liver cancer; and (B) comparing the results of the (A) step with the measurement results of the control groups to predict the prognosis of liver cancer.

The group consisting of the genes may further comprise the genes described in Table 3 above (described in the description of the composition or kit for predicting prognosis of liver cancer for predicting the prognosis according to the stage of liver cancer of the present disclosure).

The matters mentioned regarding the method for predicting prognosis of liver cancer for predicting the prognosis according to the stage of liver cancer of the present disclosure equally apply to the method unless there is a contradiction.

Also, the matters mentioned regarding the composition or kit of the present disclosure equally apply to the method of the present disclosure unless there is a contradiction.

The method for predicting prognosis of liver cancer of the present disclosure may be a method for providing information for predicting prognosis of liver cancer.

Also, the present disclosure provides the use of the nucleic acids or antibodies included in the composition of the present disclosure for prediction of the prognosis of liver cancer.

Also, the present disclosure provides nucleic acids or antibodies for predicting prognosis of liver cancer, and the nucleic acids or antibodies are those included in the composition of the present disclosure.

The matters mentioned regarding the marker, composition or kit, method and use of the present disclosure equally apply unless there is a contradiction.

Effect of the Disclosure

The marker, composition or kit, and method of the present disclosure make it possible to effectively predict prognosis of liver cancer, preferably, prognosis of liver cancer according to stage.

BRIEF DESCRIPTION OF THE DRAWINGS

FIG. 1 illustrates a BCLC classification table.

EMBODIMENTS FOR CARRYING OUT THE DISCLOSURE

Figure 2:
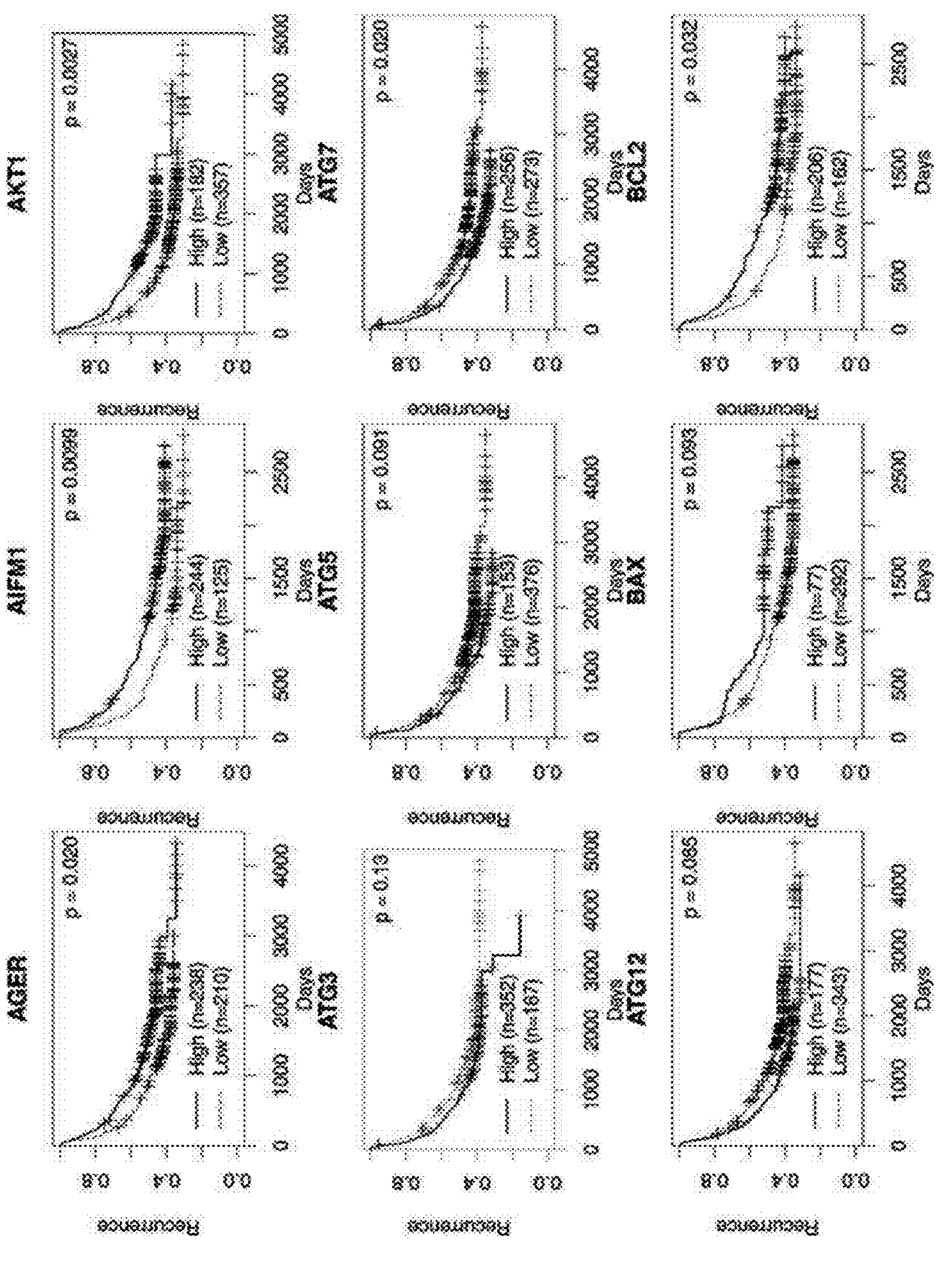
FIGS. 2~106 are Kaplan-Meier curves illustrating the data obtained by measuring the markers for prognosis of liver cancer of the present disclosure in the aspects of recurrence, survival, and disease-free survival.
Figure 3:
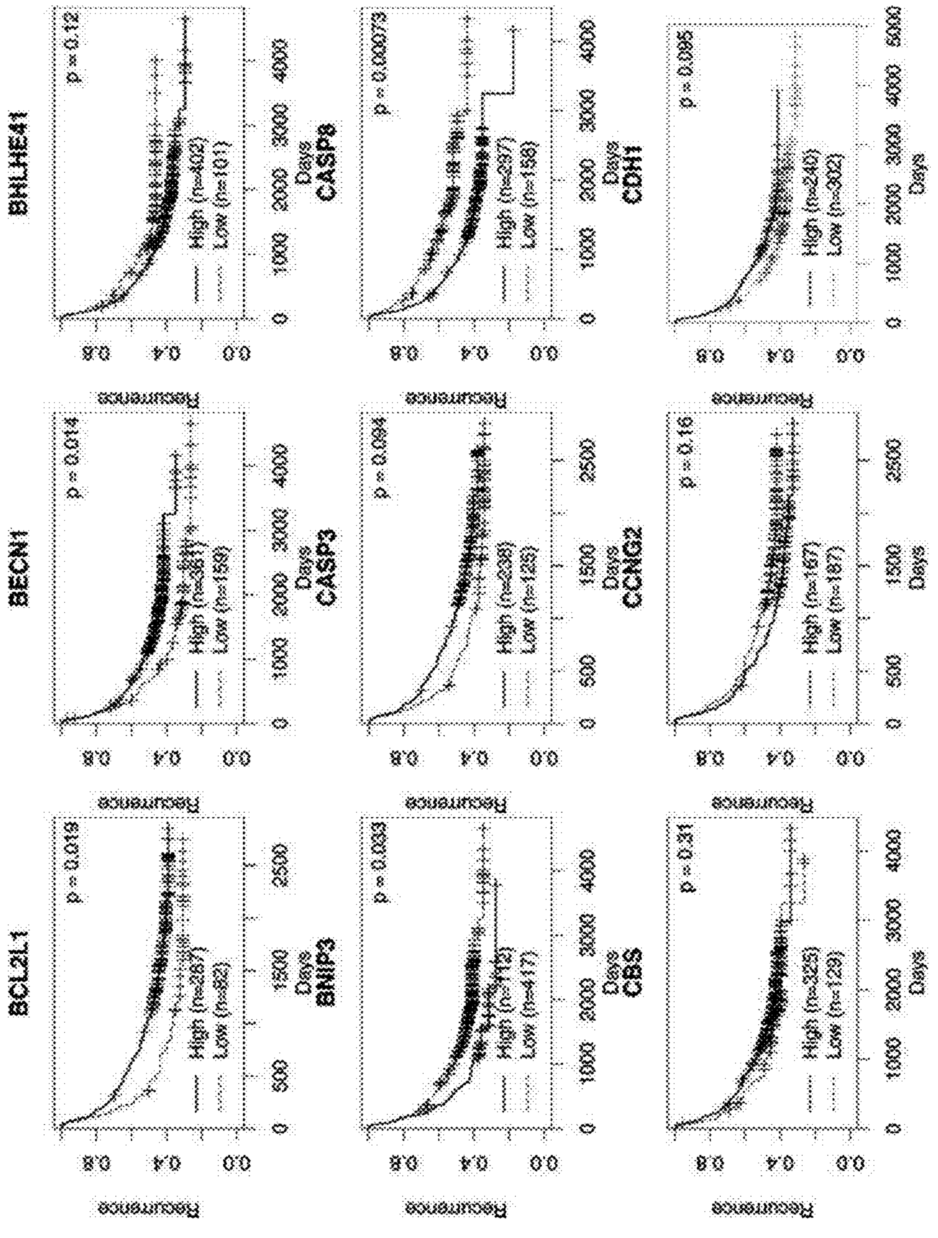
Figure 4:
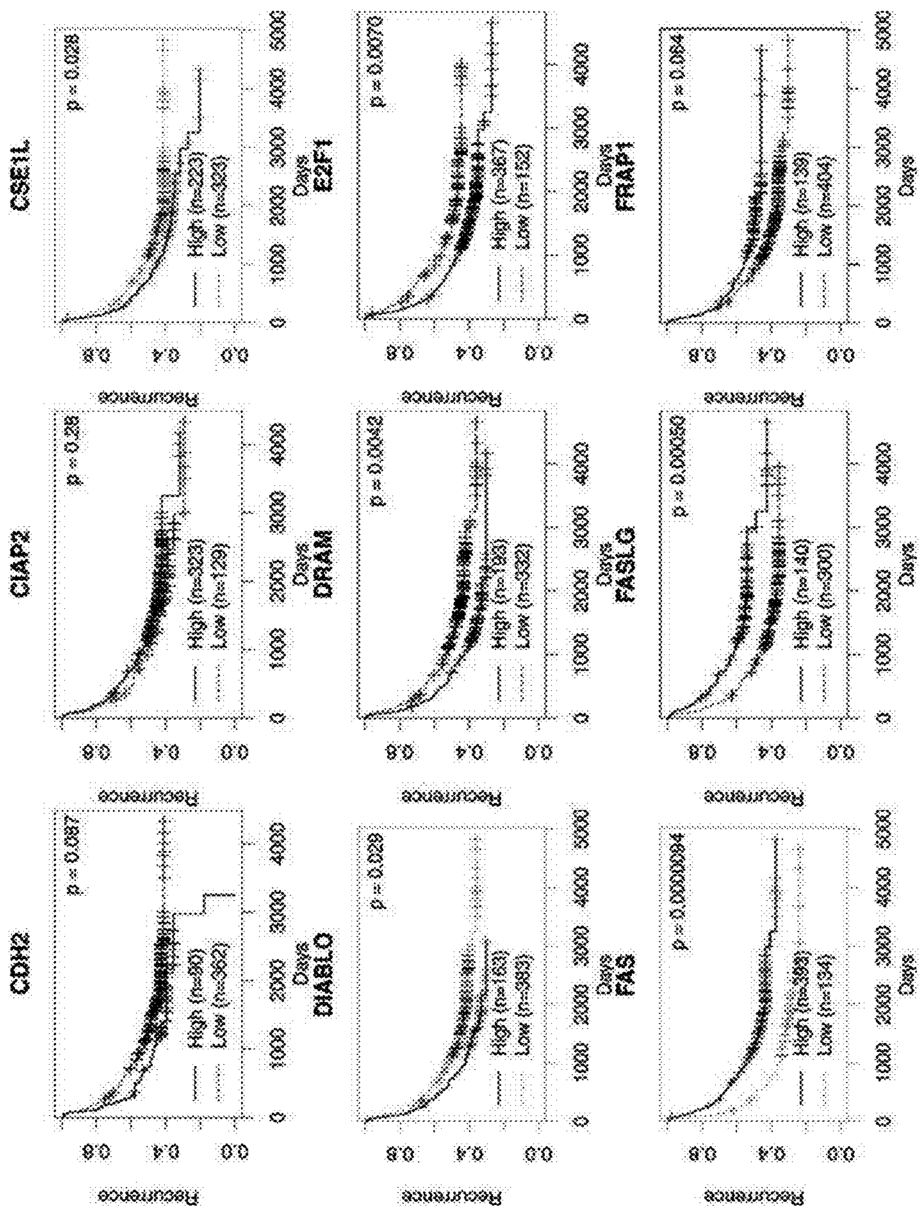
Figure 5:
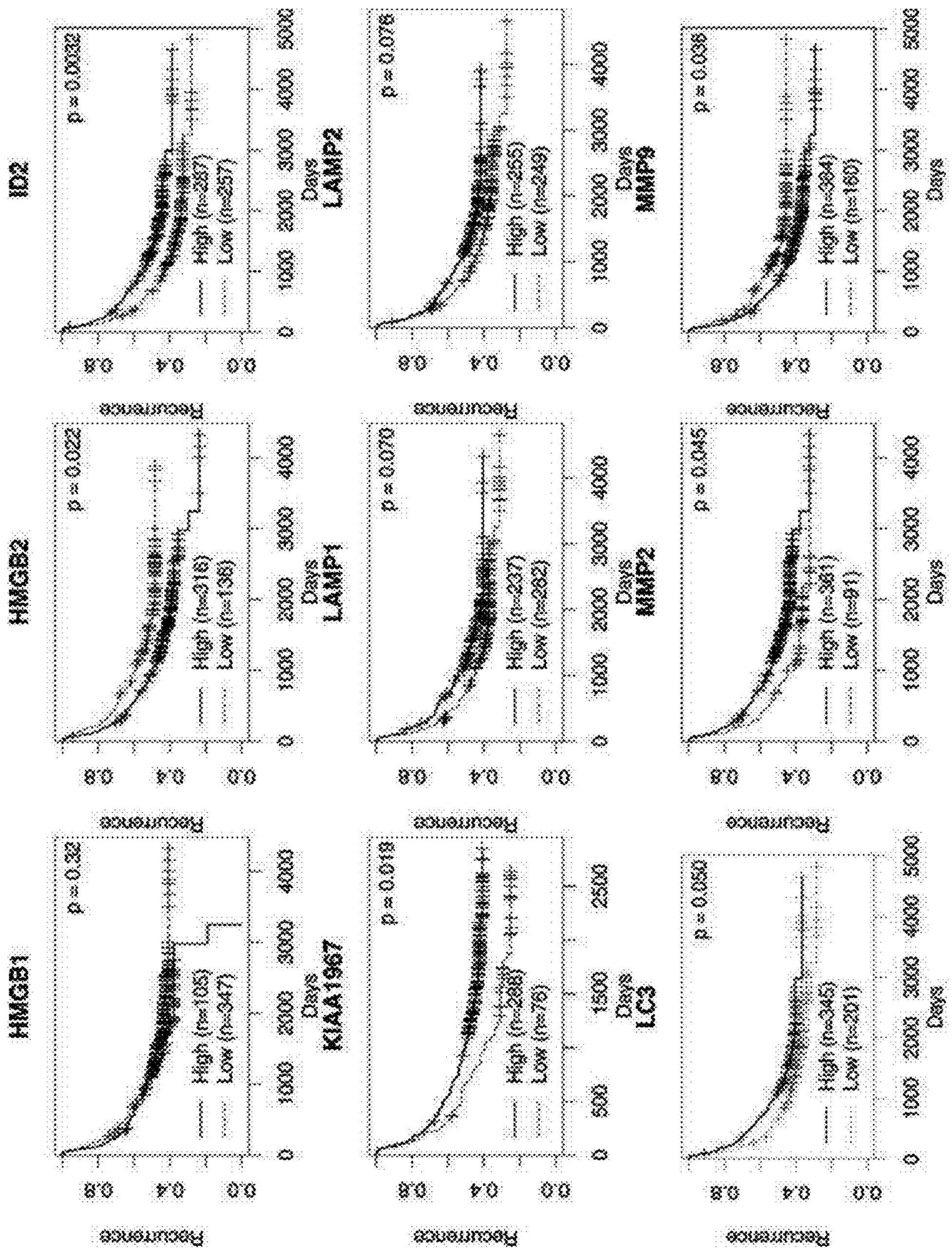
Figure 6:
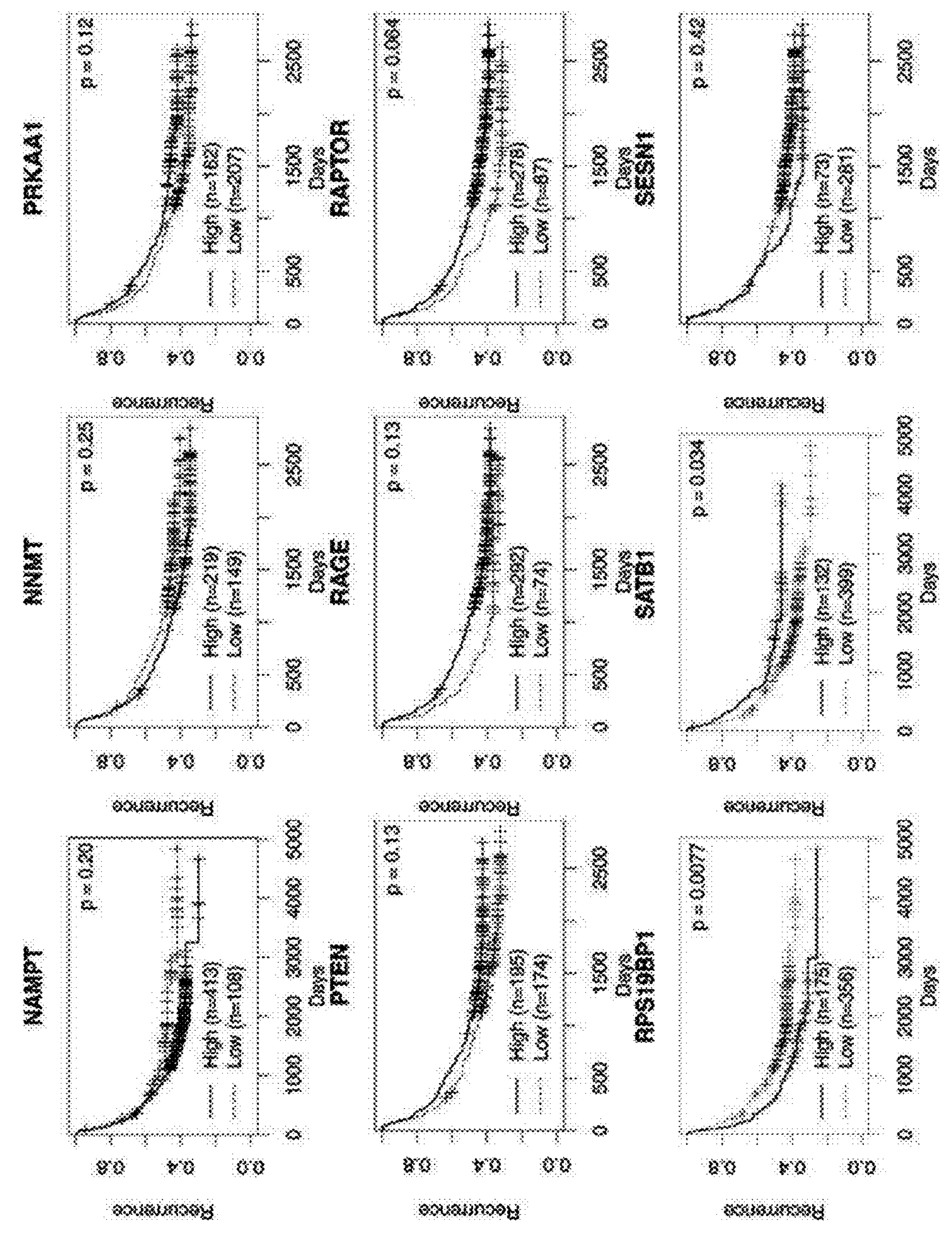
Figure 7:
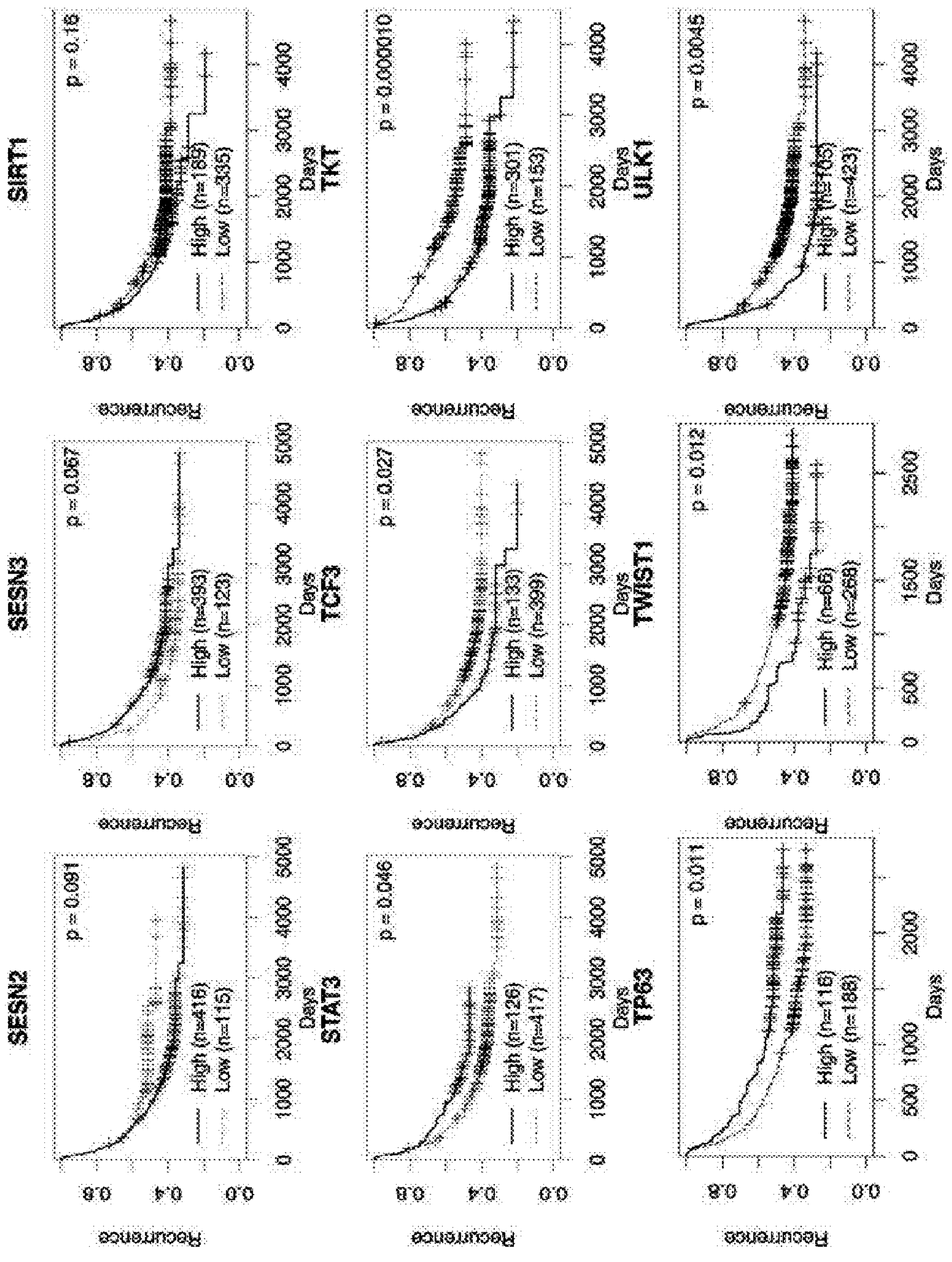
Figure 8:
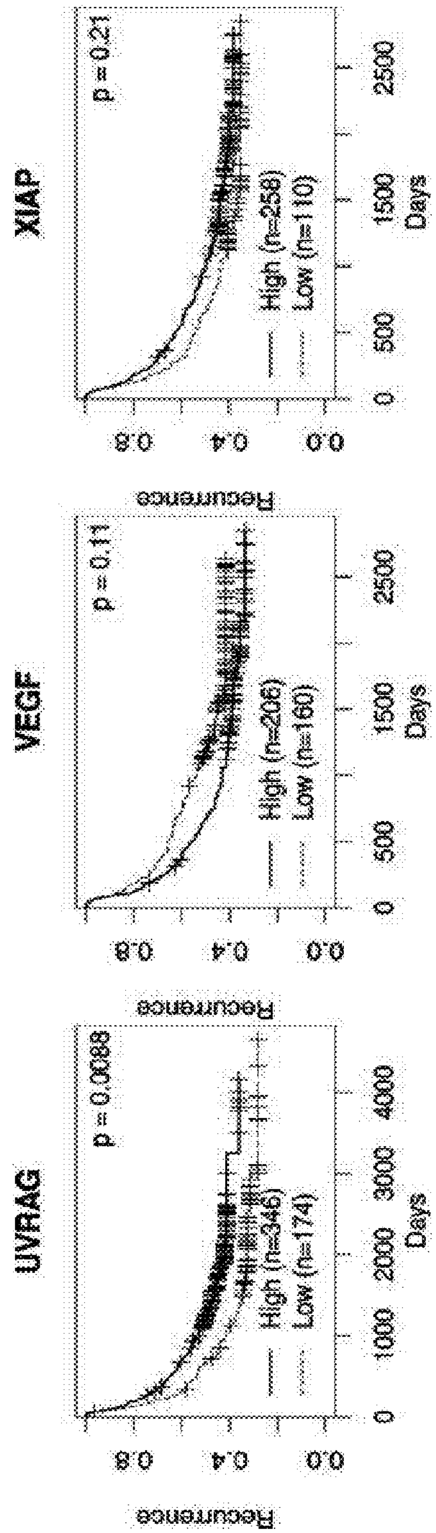
Figure 9:
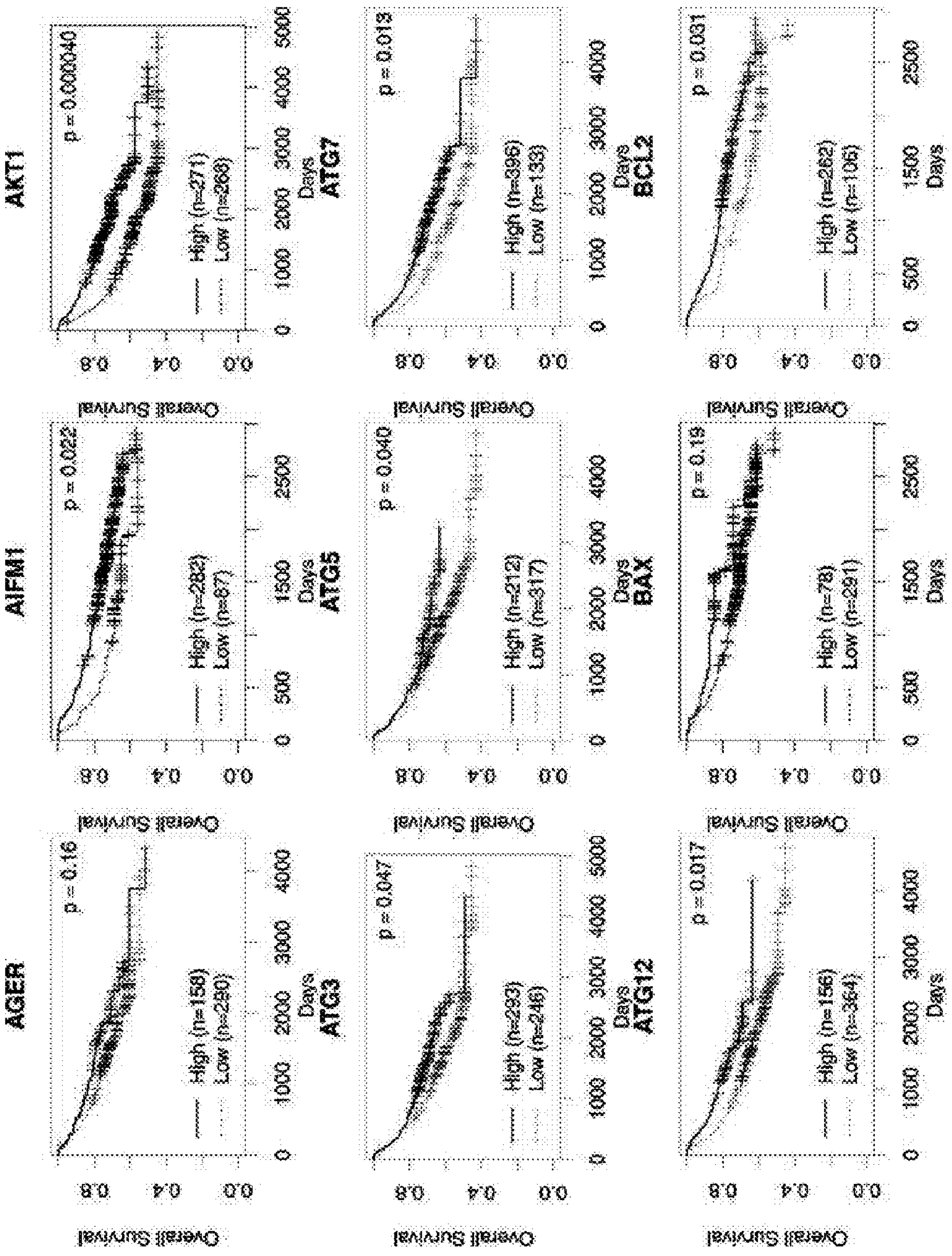
Figure 10:
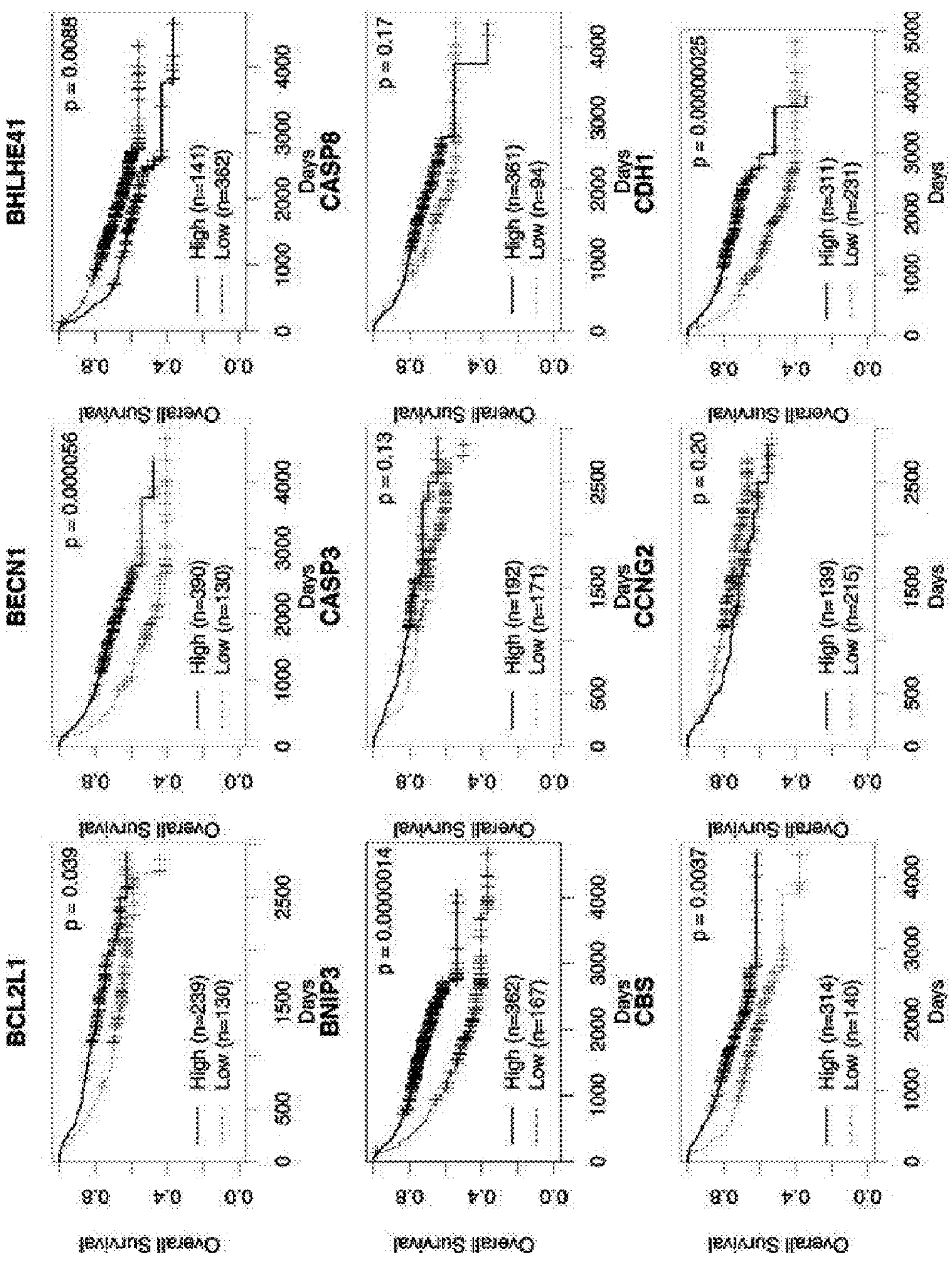
Figure 11:
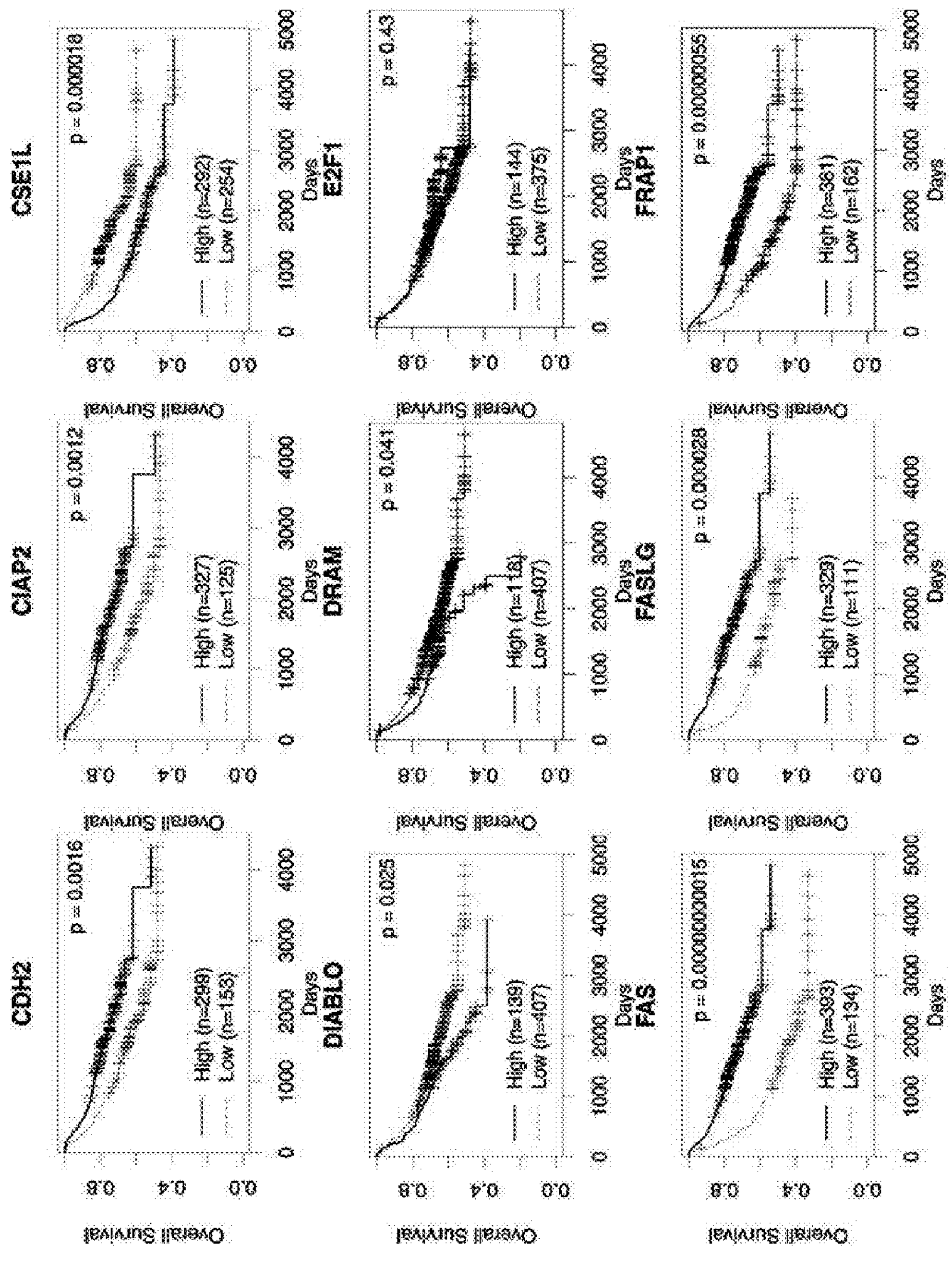
Figure 12:
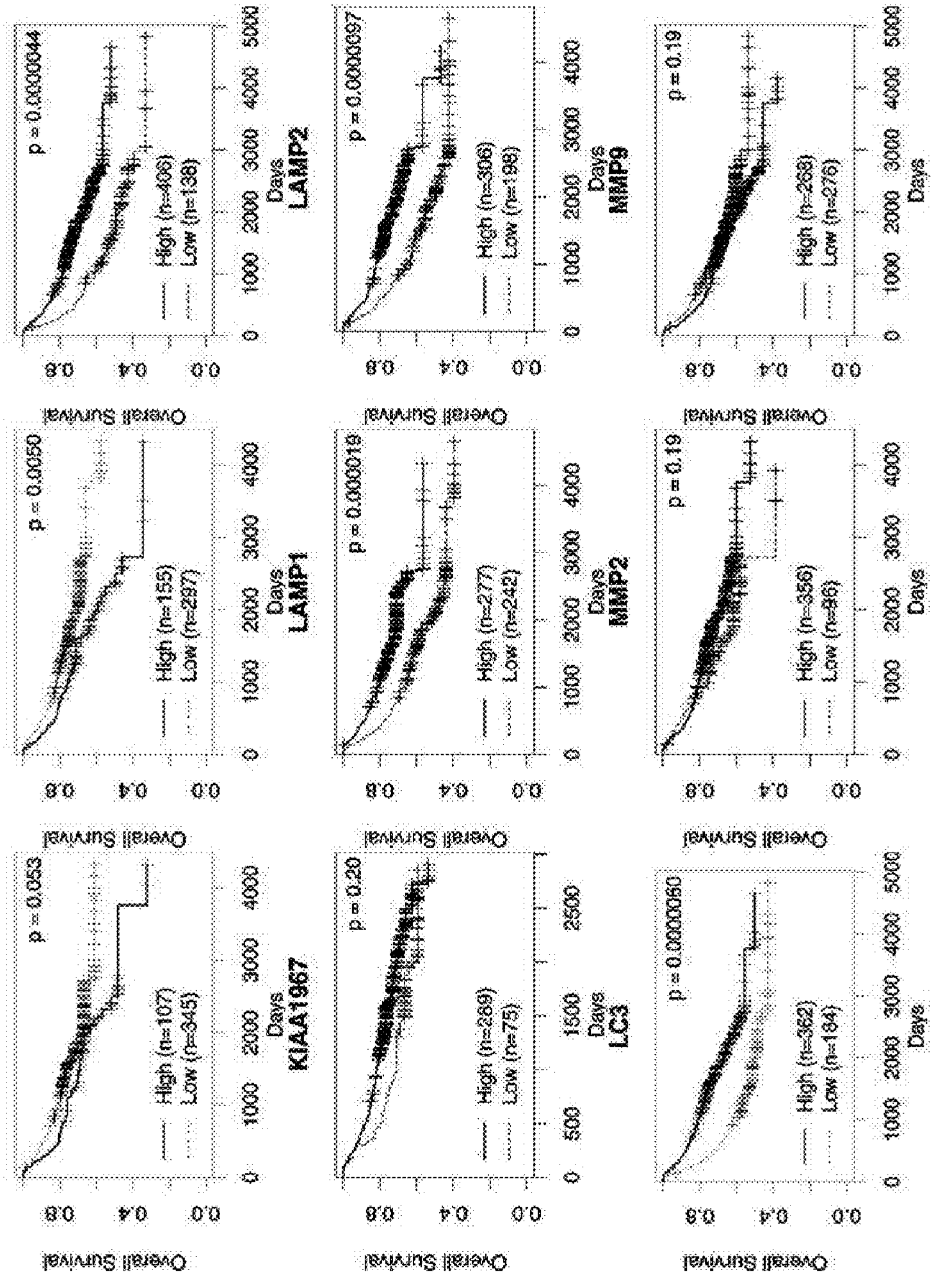
Figure 13:
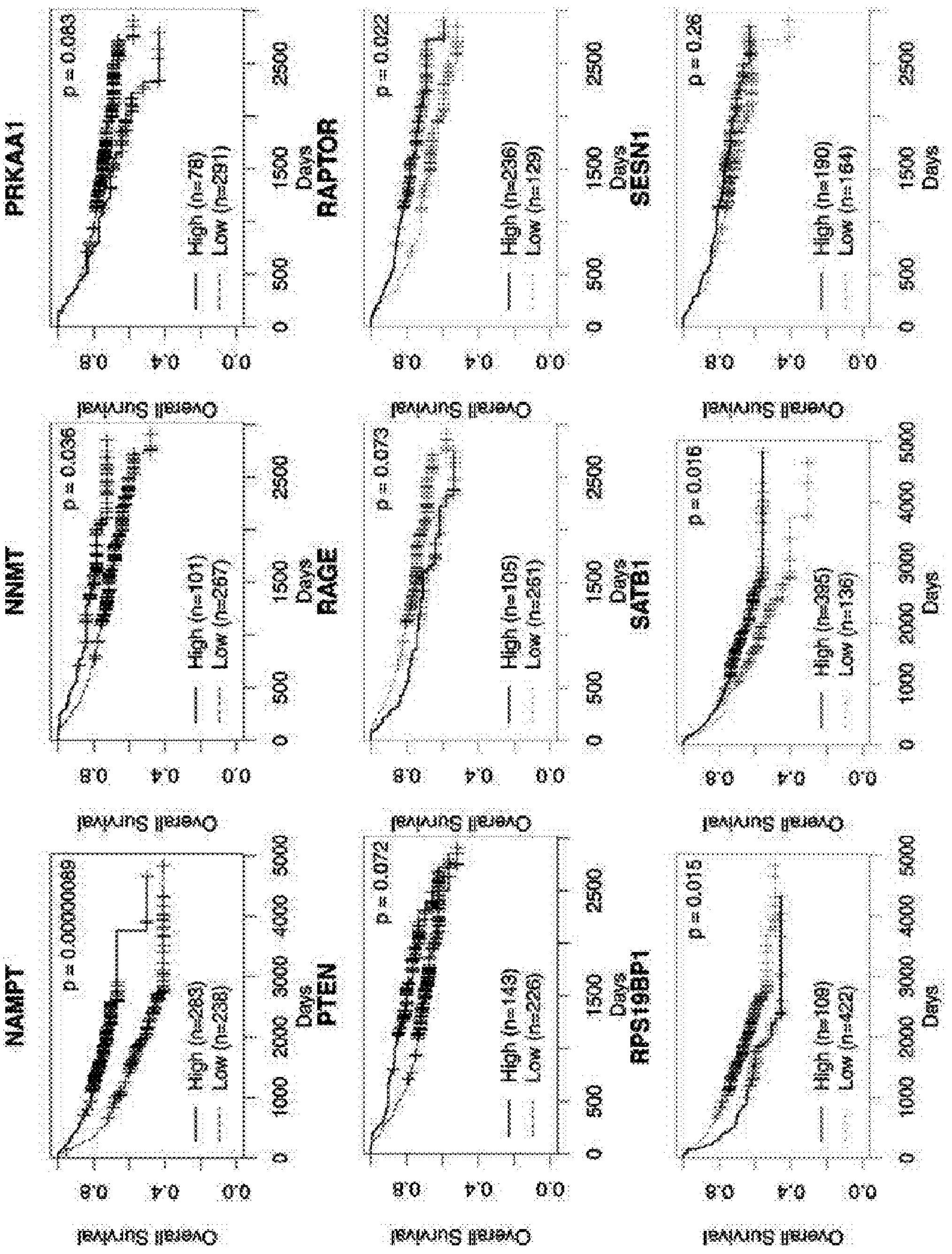
Figure 14:
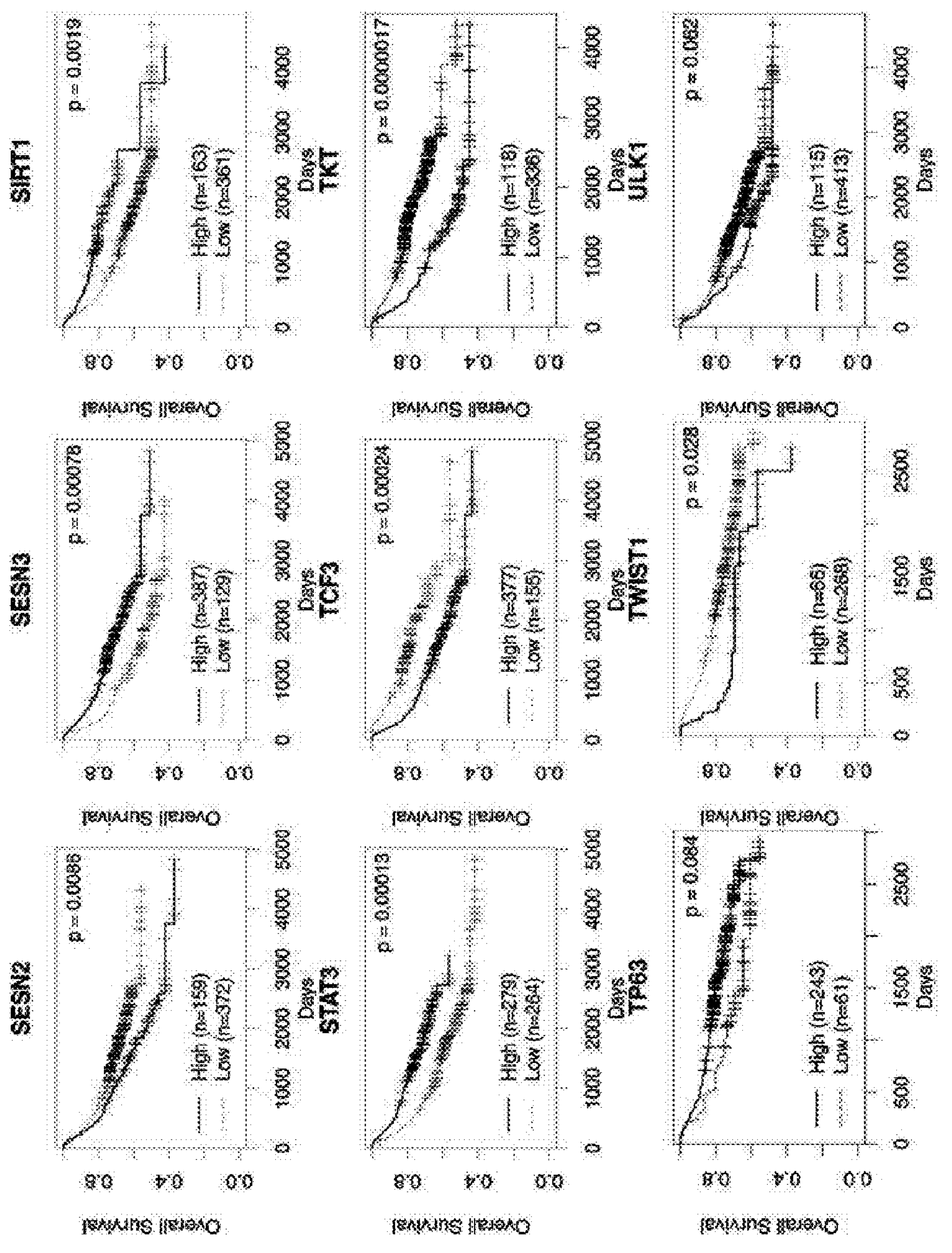
Figure 15:
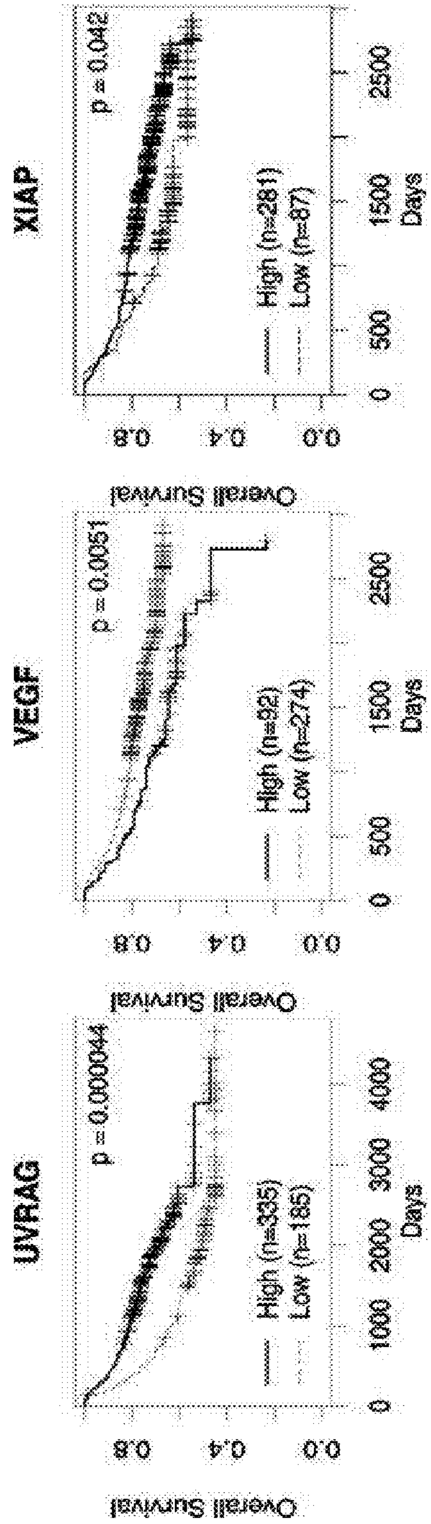
Figure 16:
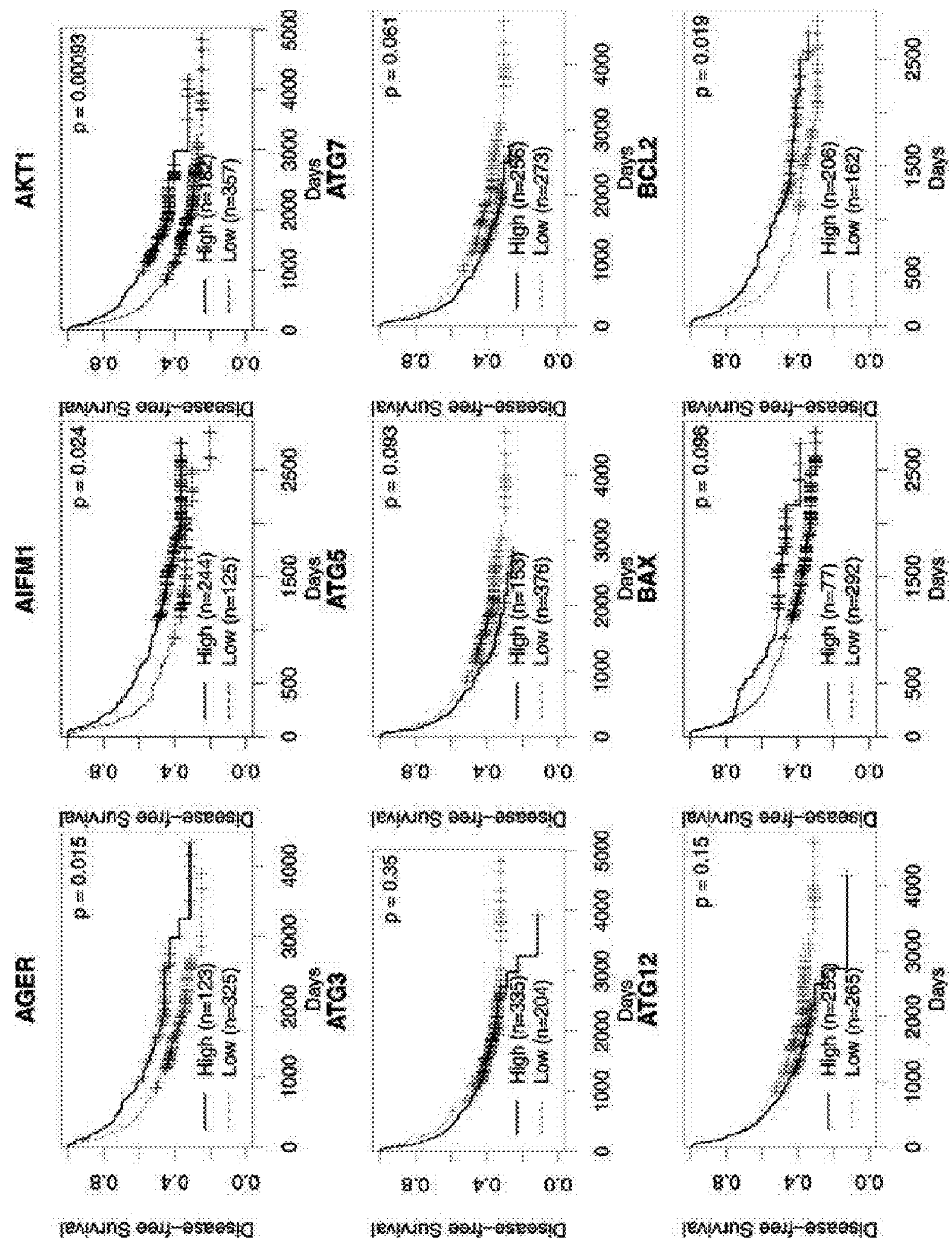
Figure 17:
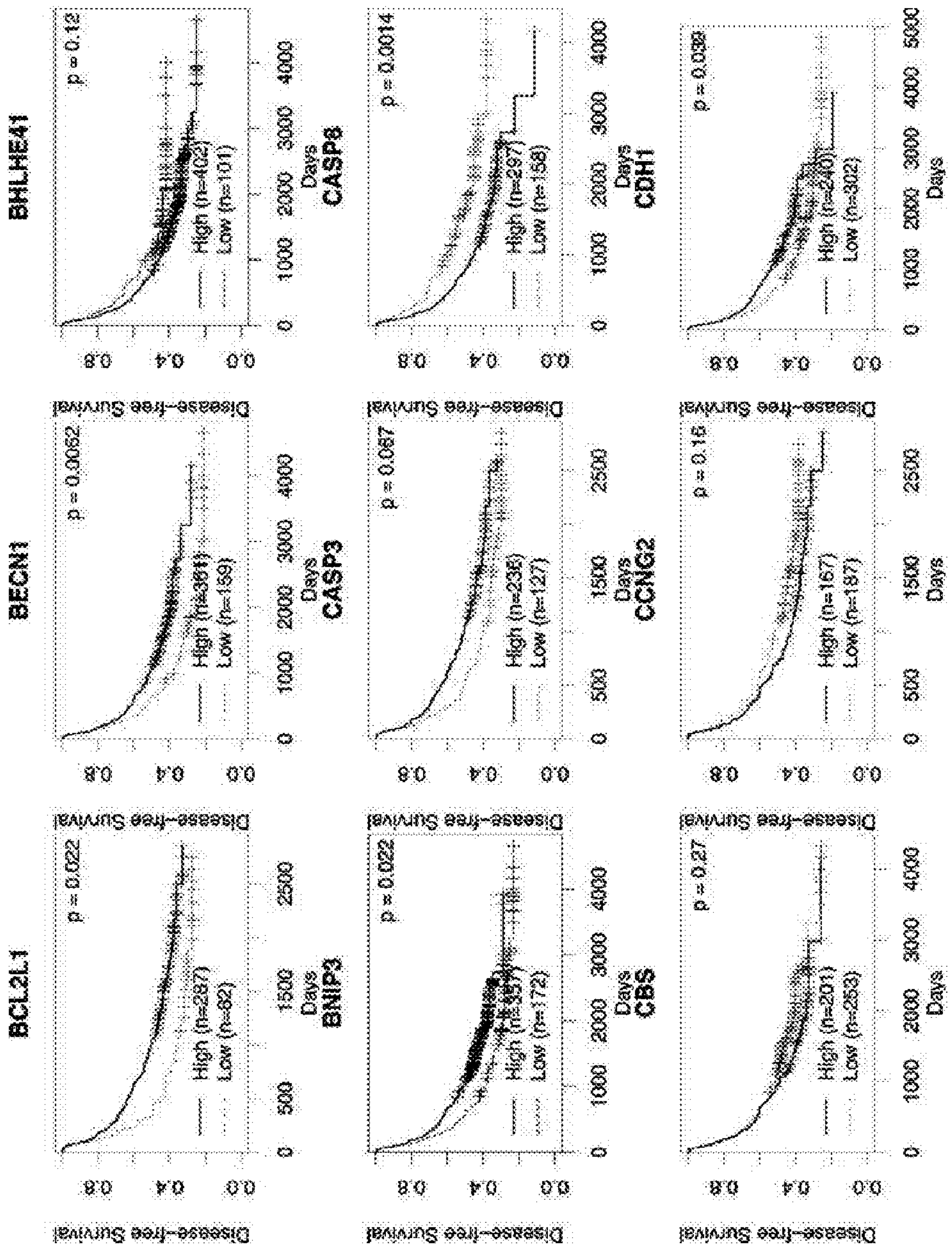
Figure 18:
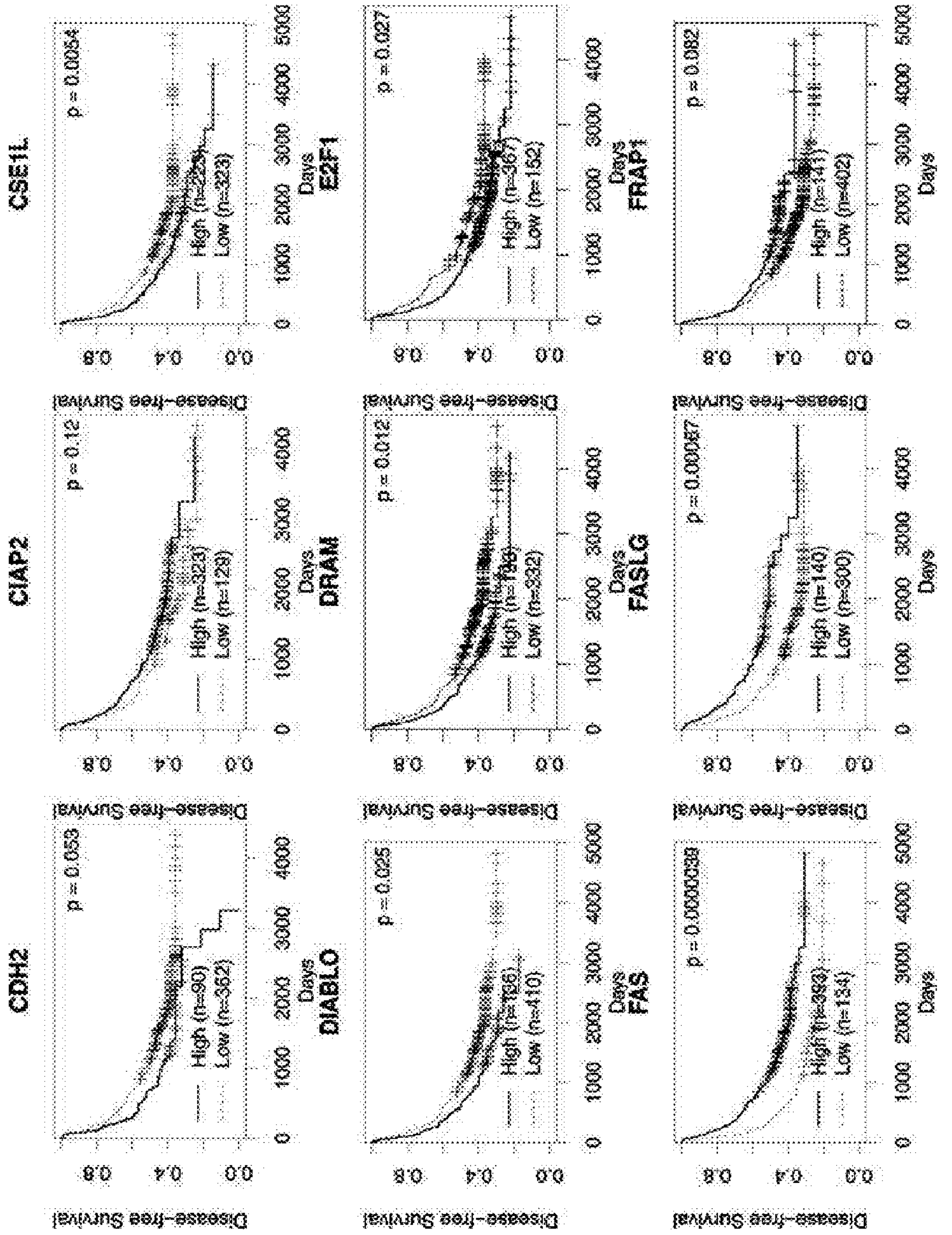
Figure 19:
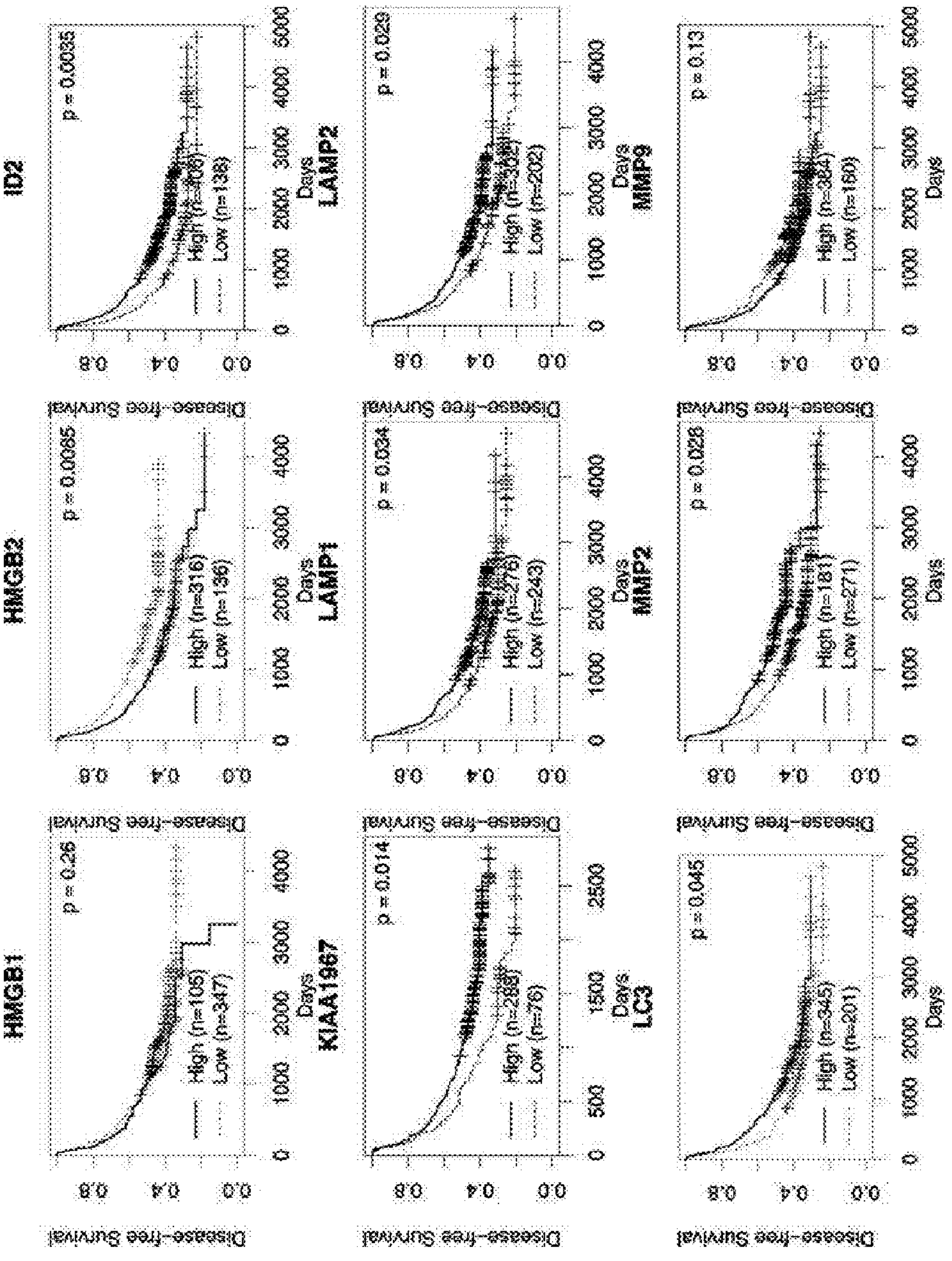
Figure 20:
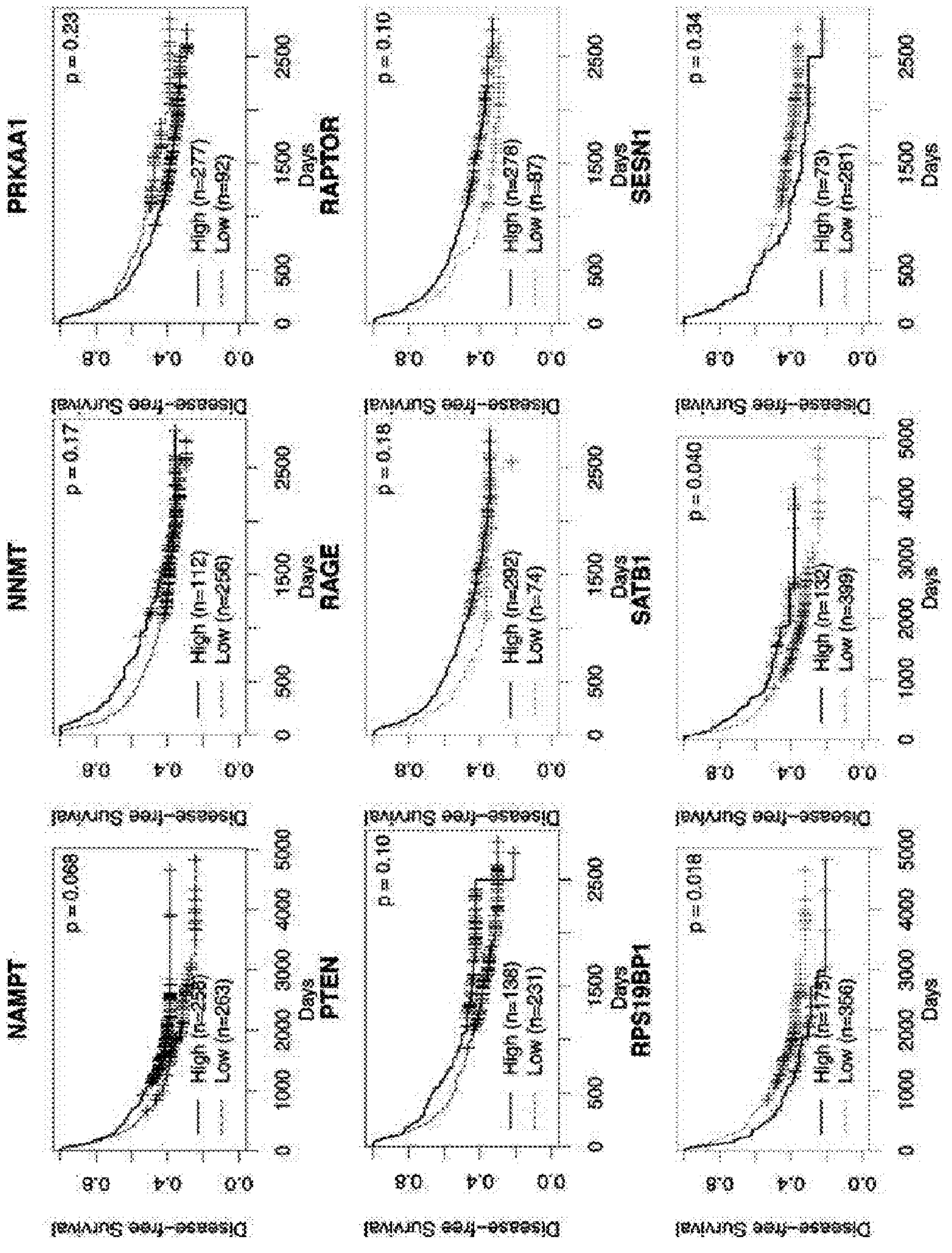
Figure 21:
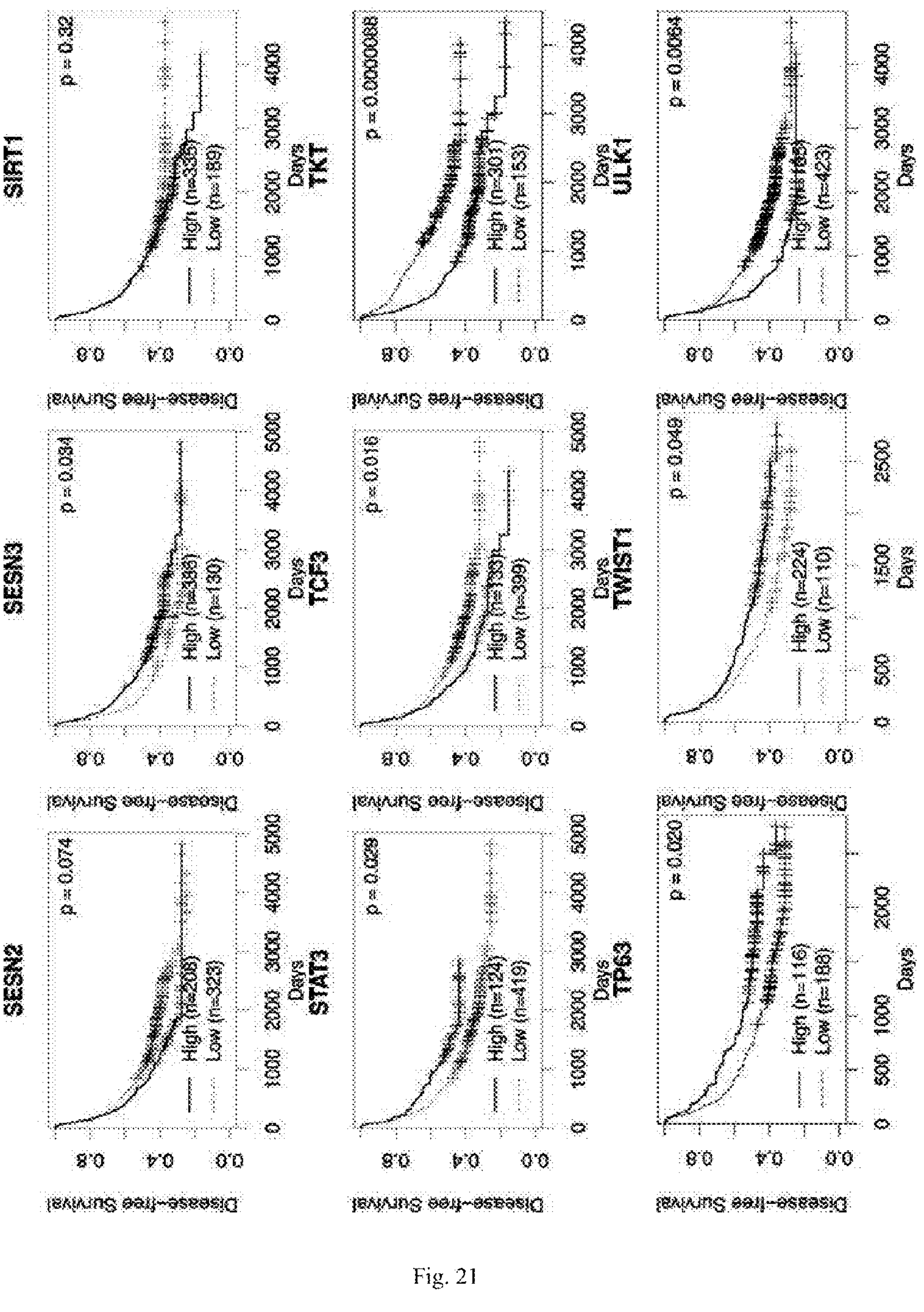
Figure 22:
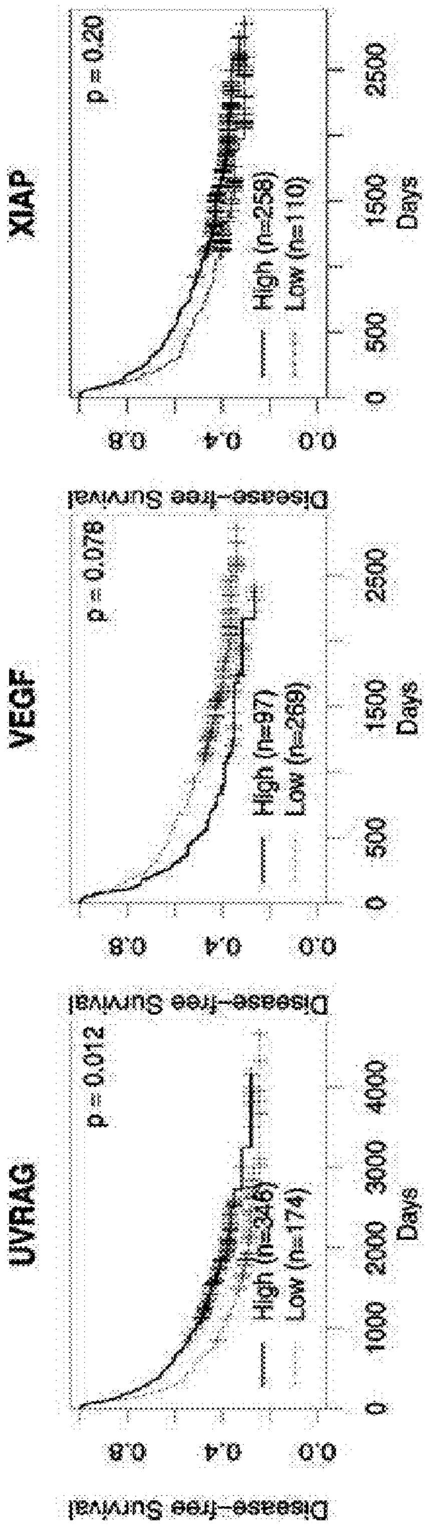
Figure 23:
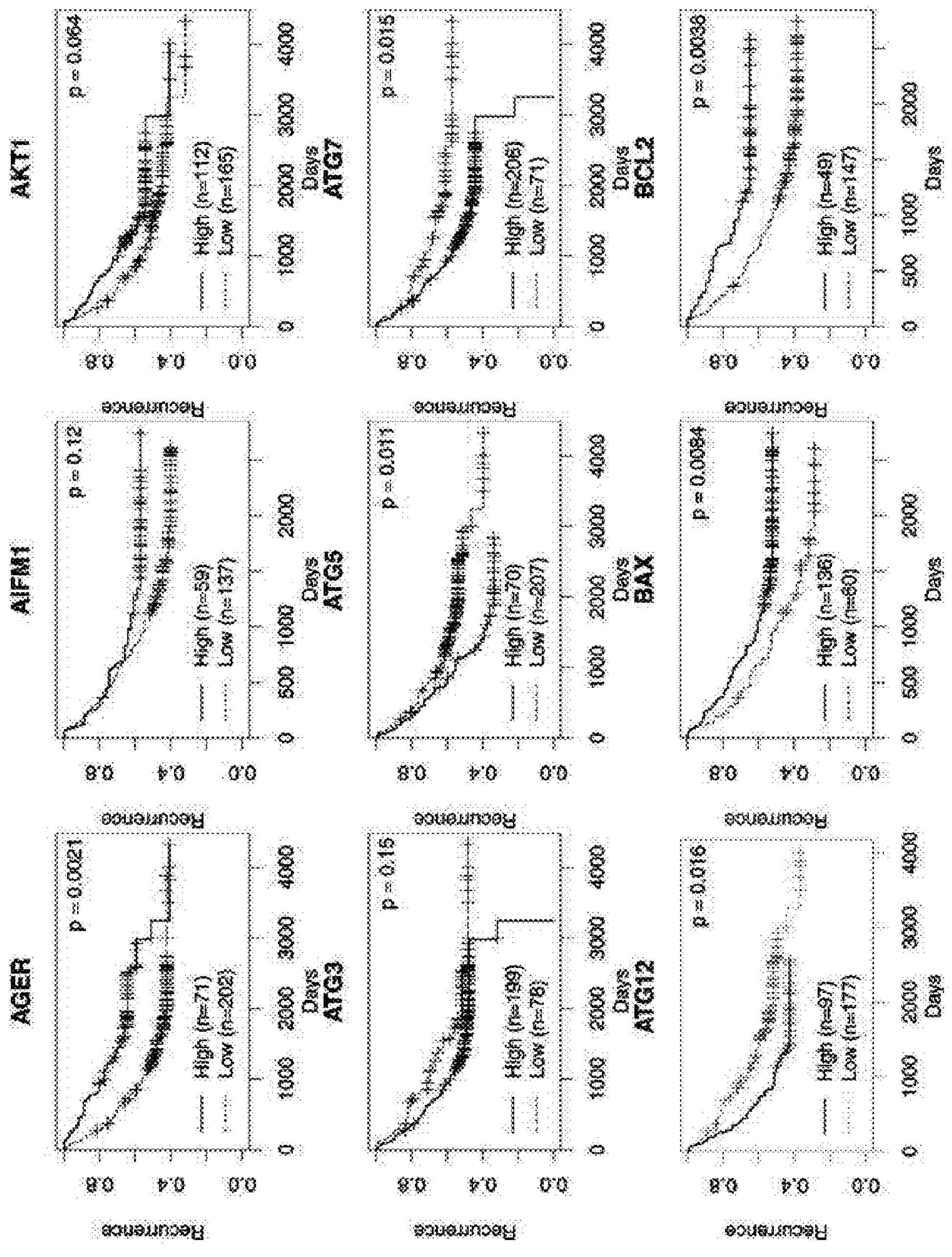
Figure 24:
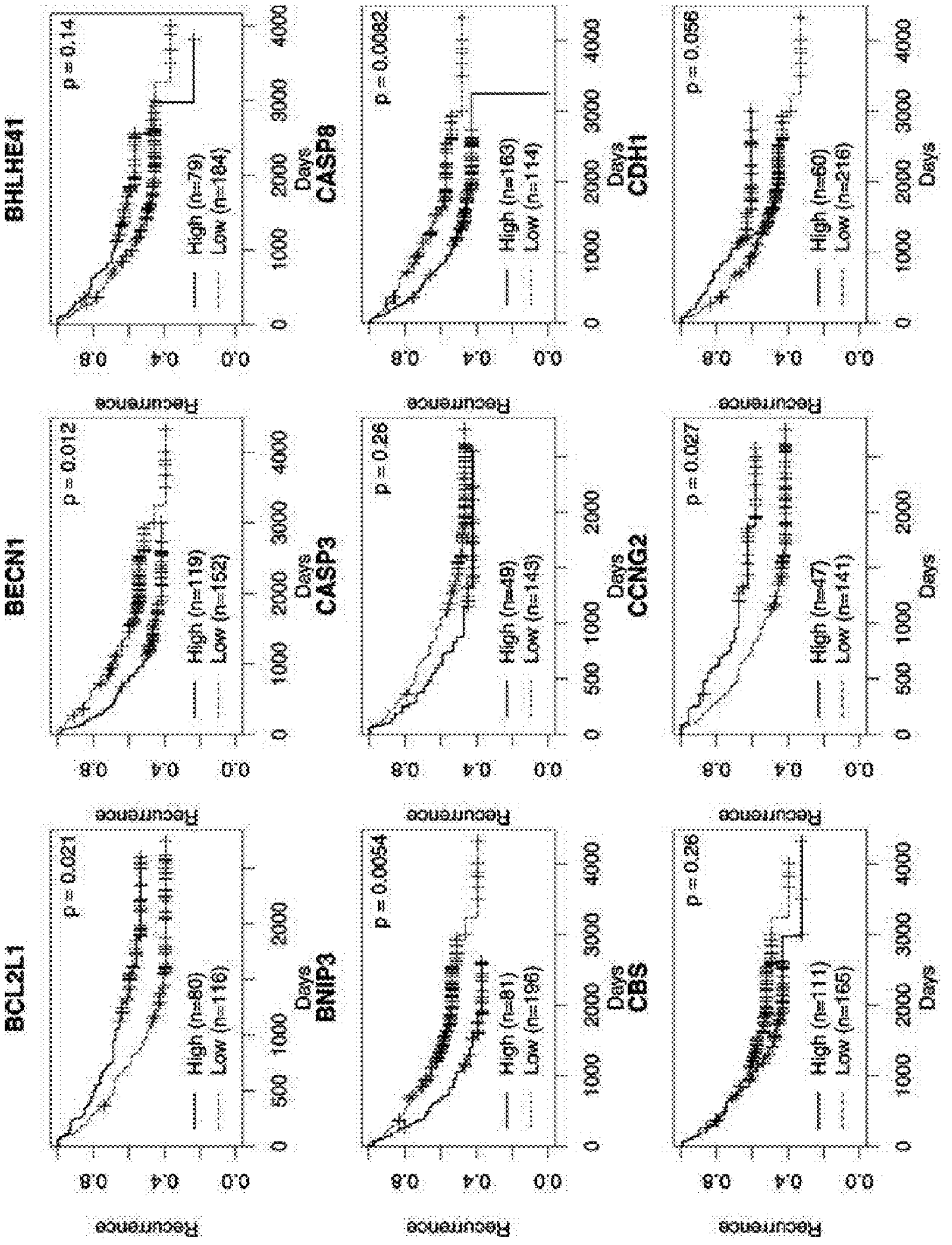
Figure 25:
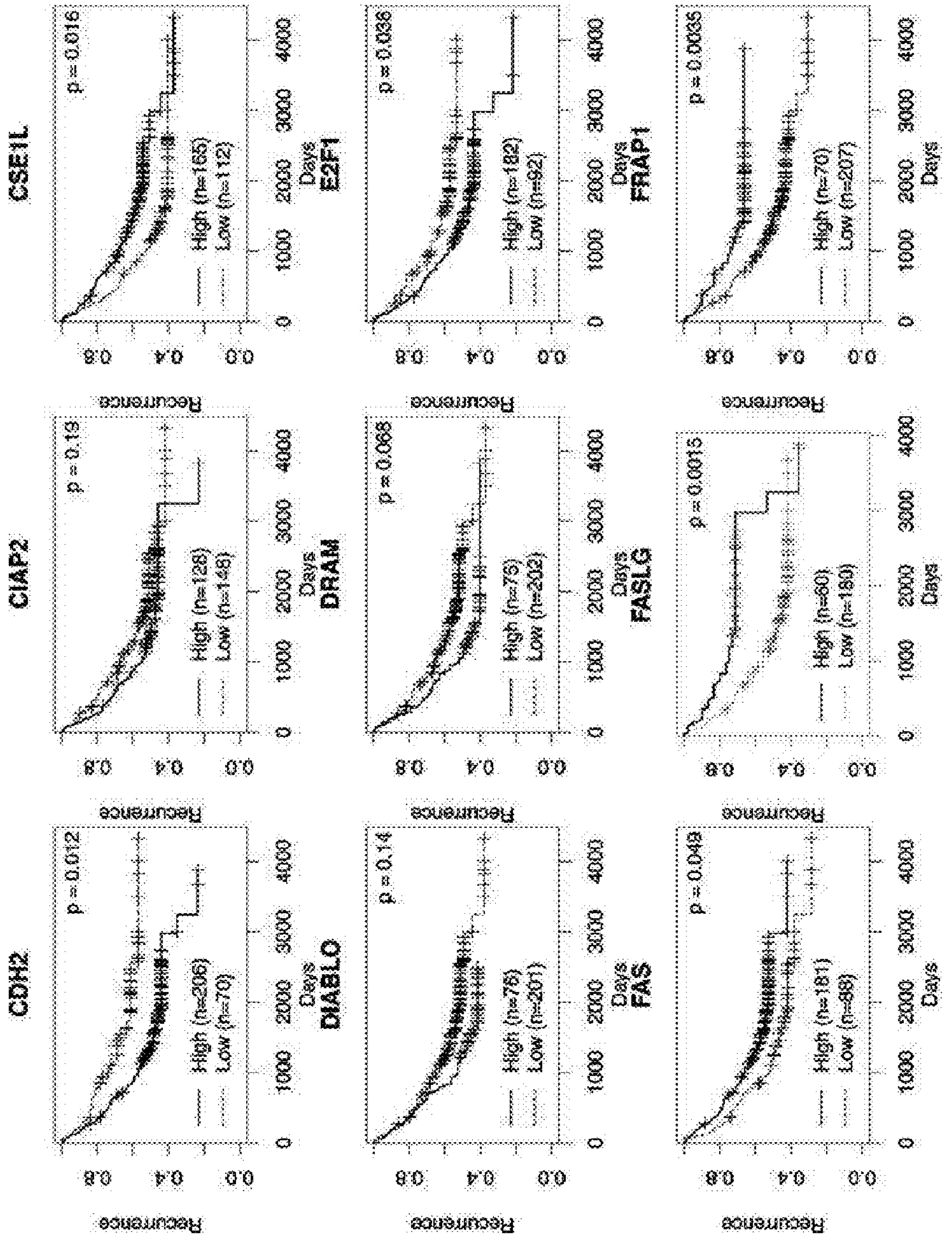
Figure 26:
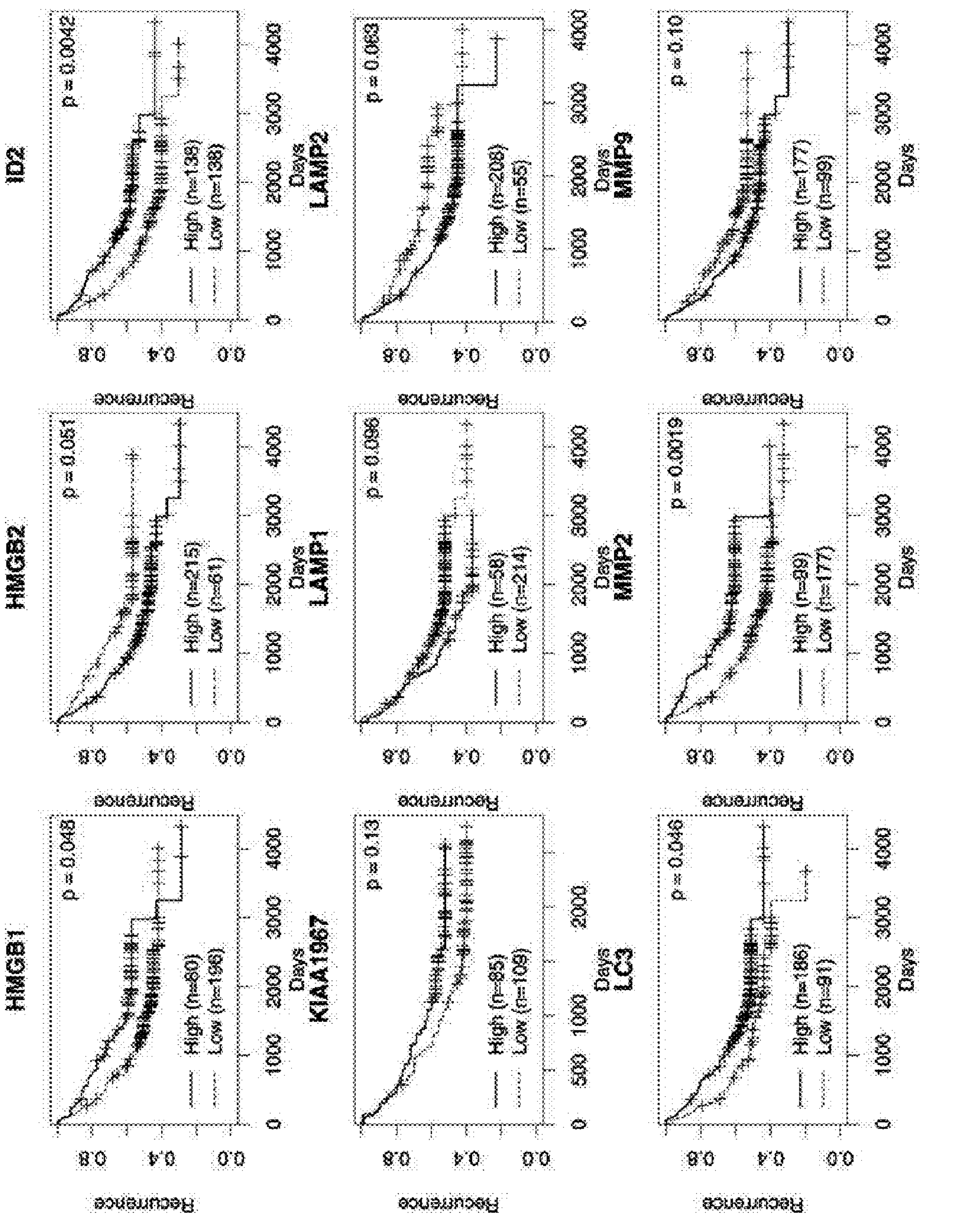
Figure 27:
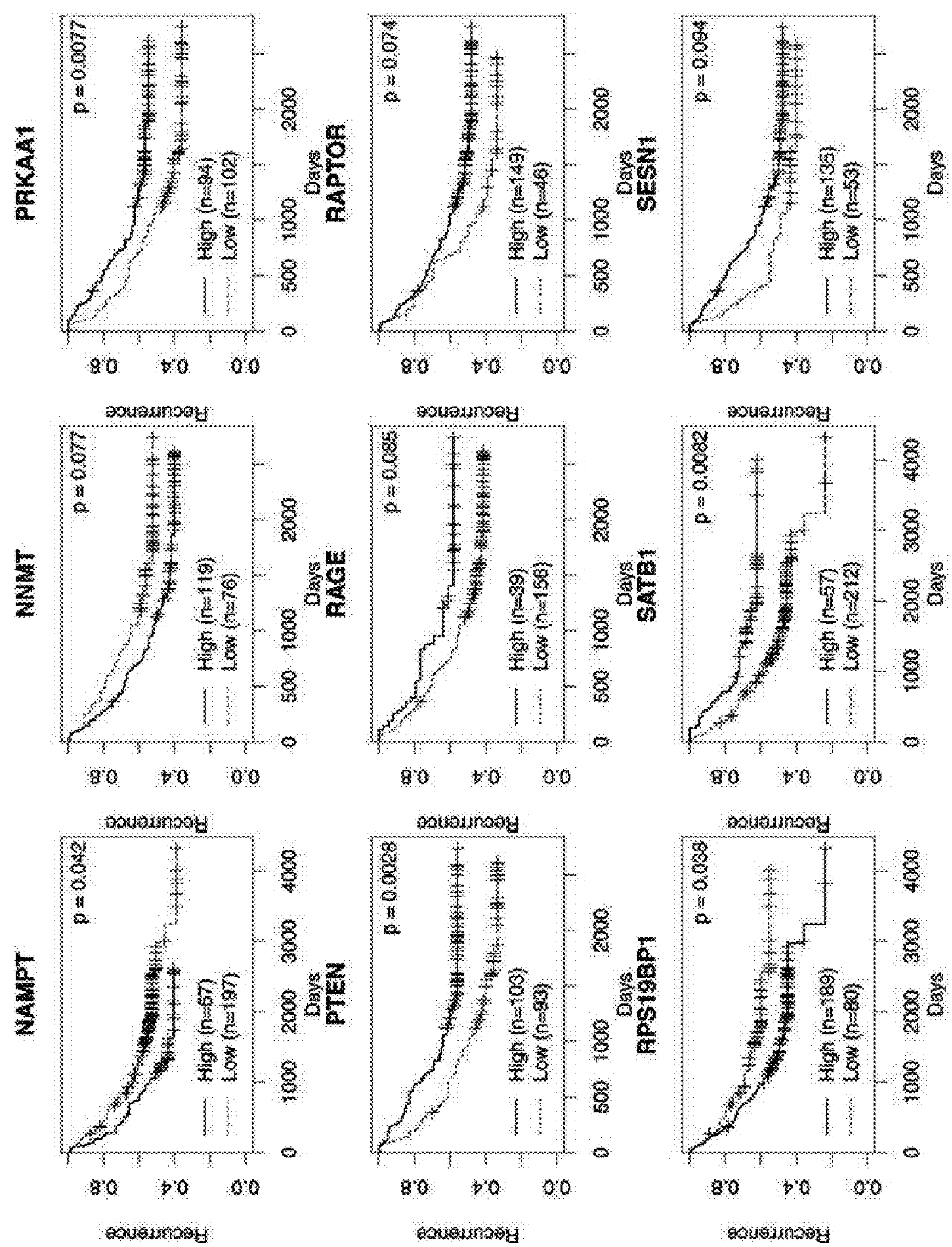
Figure 28:
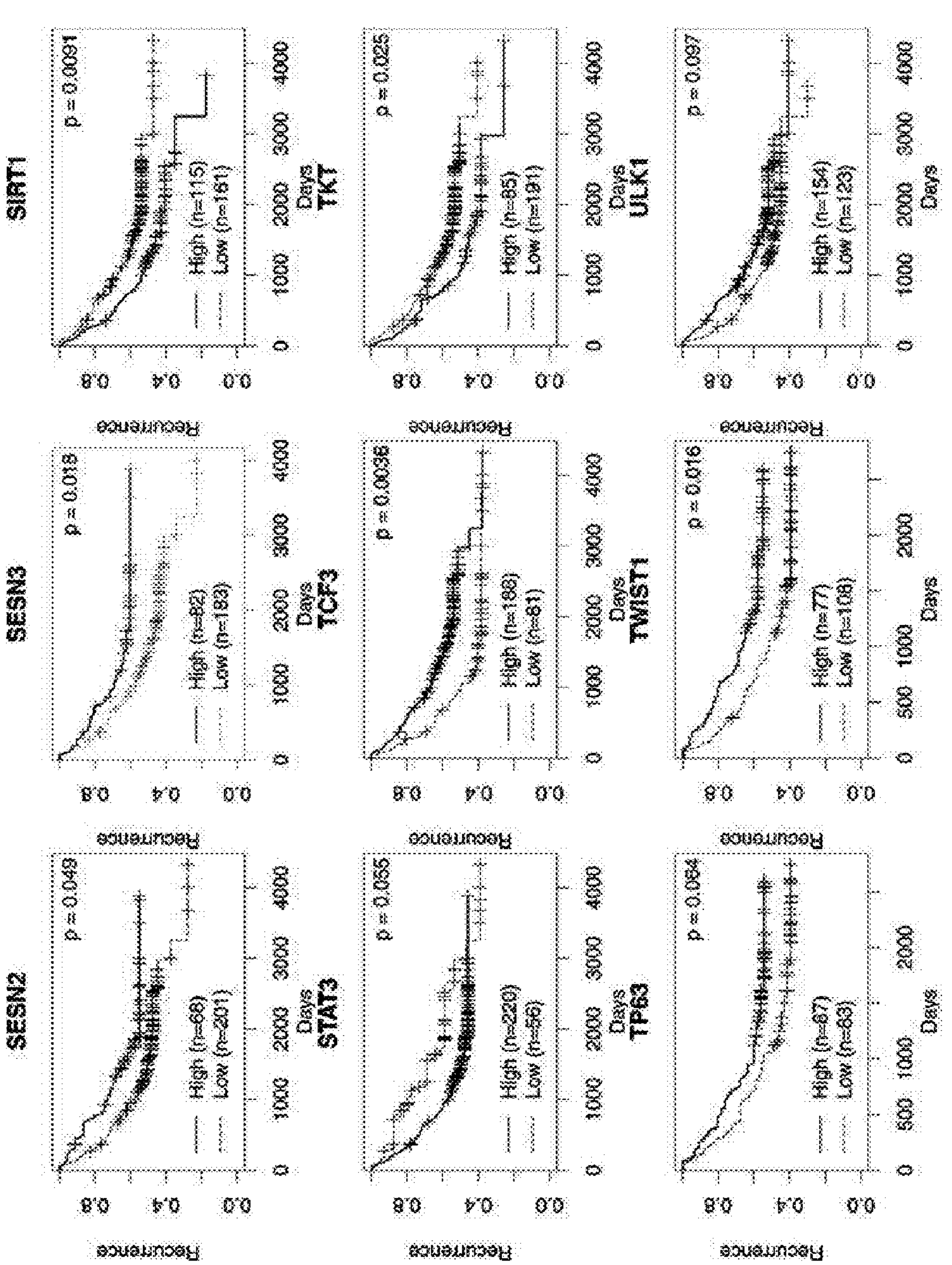
Figure 29:
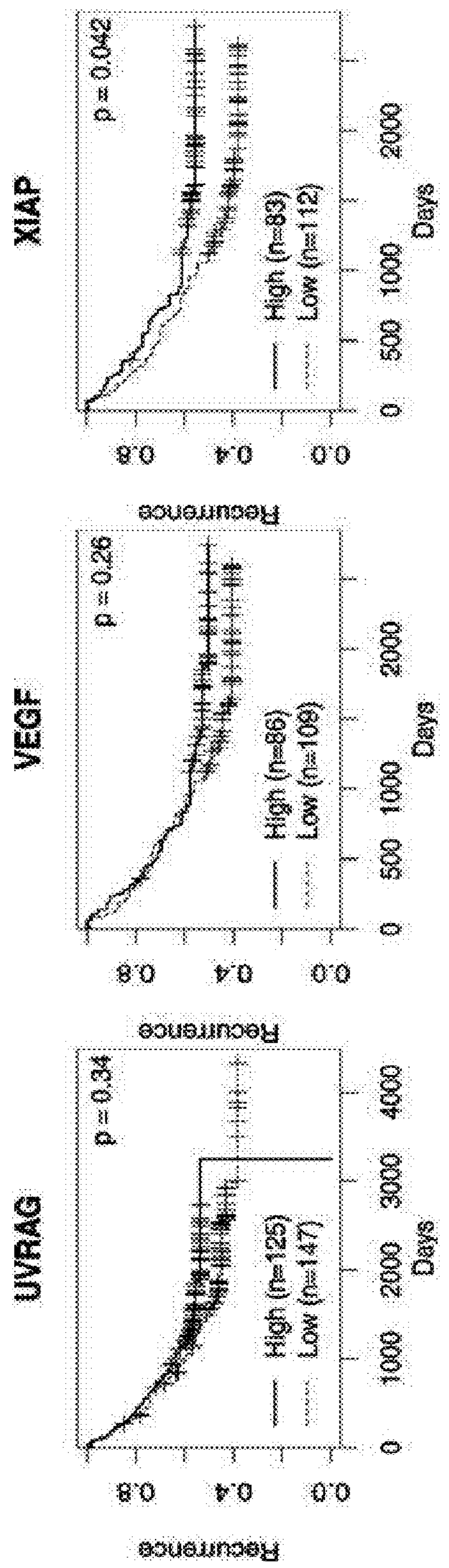
Figure 30:
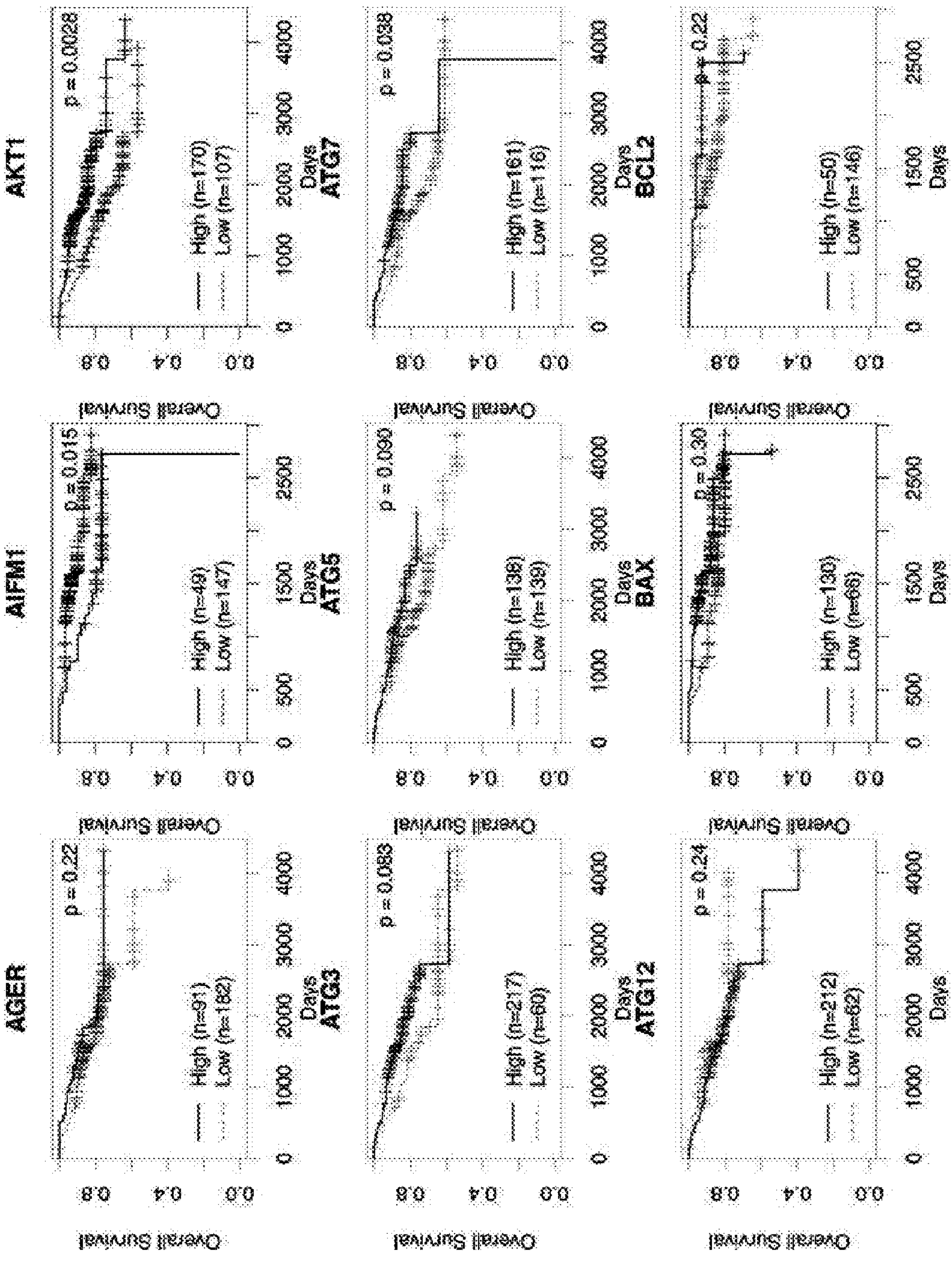
Figure 31:
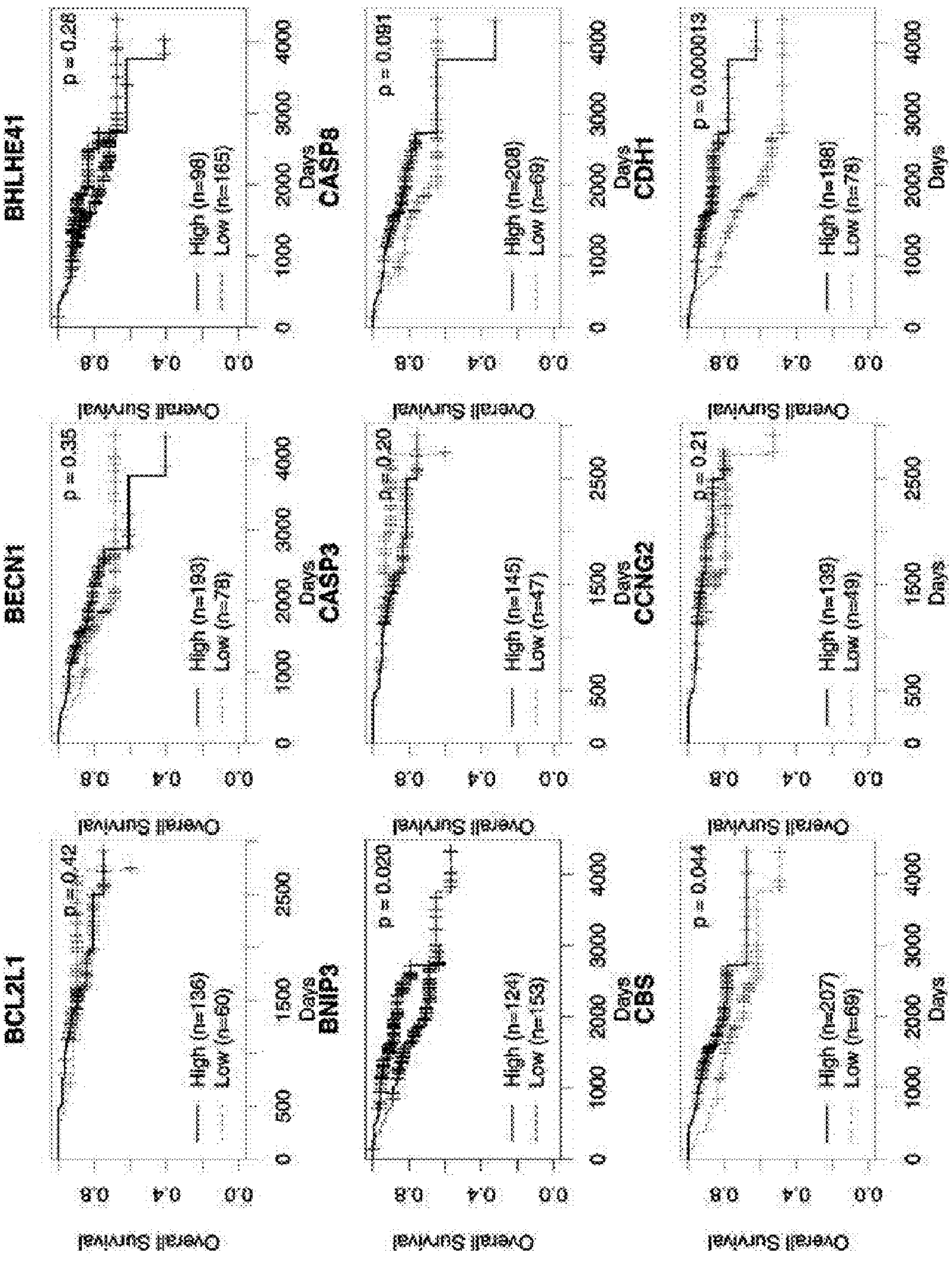
Figure 32:
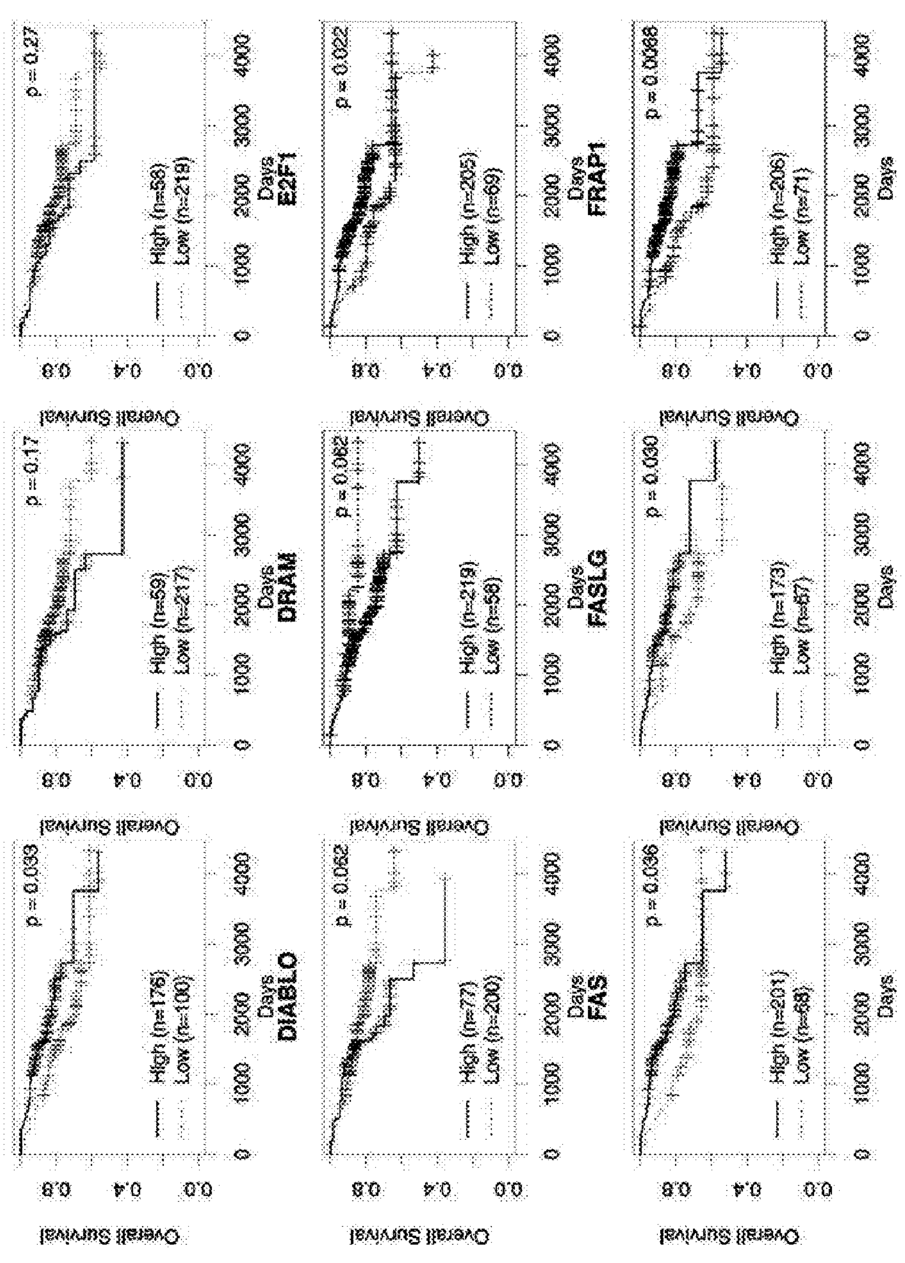
Figure 33:
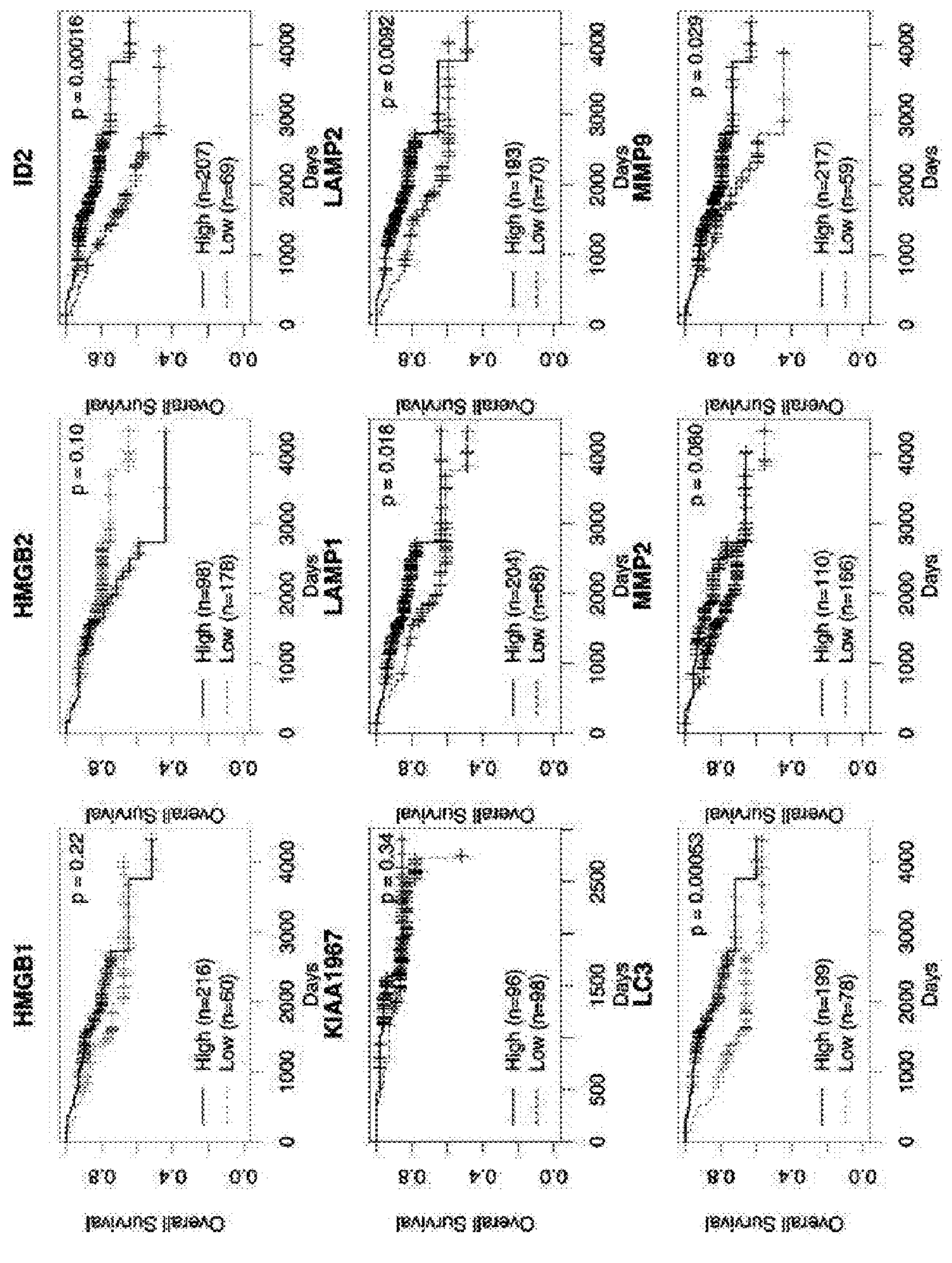
Figure 34:
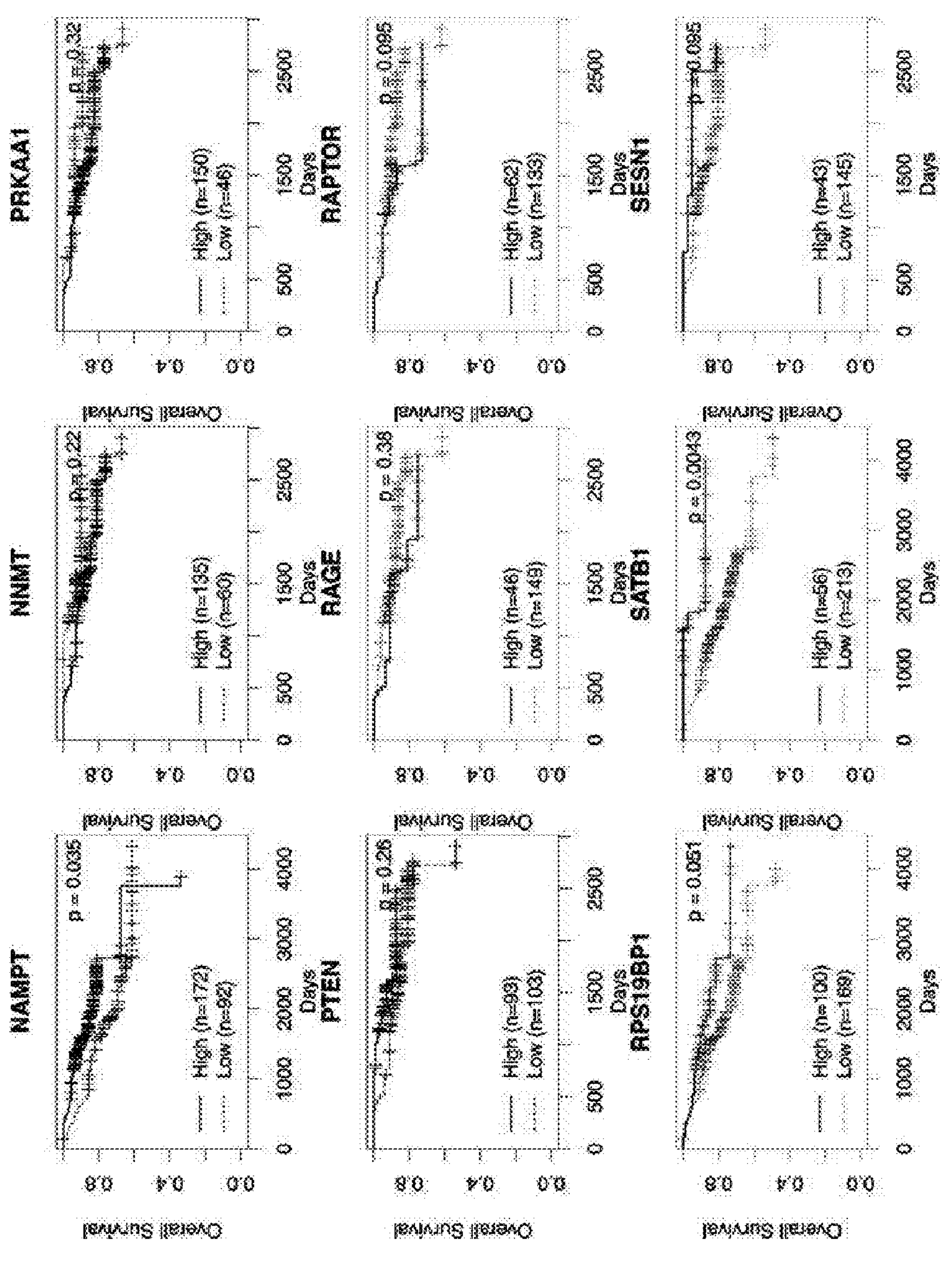
Figure 35:
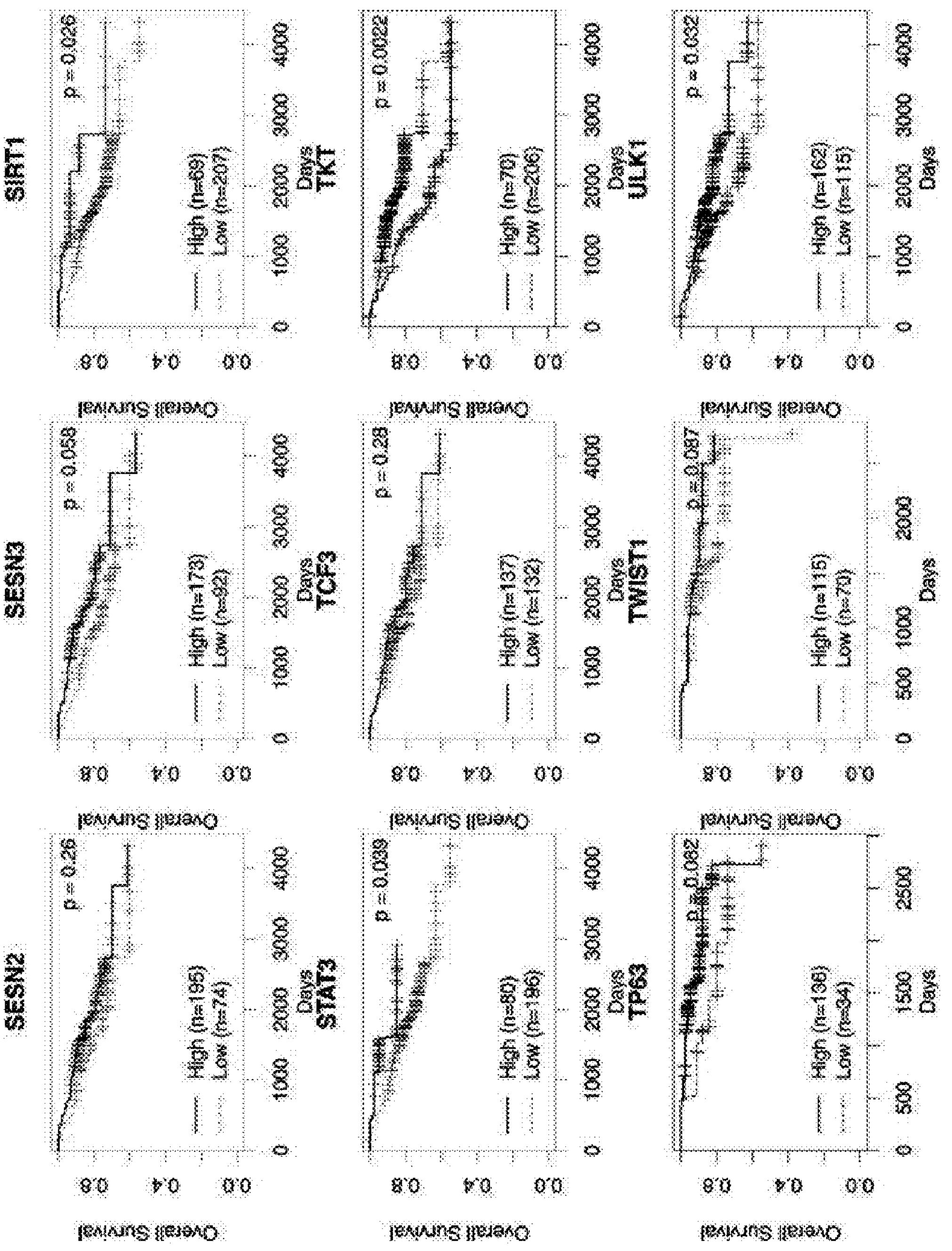
Figure 36:
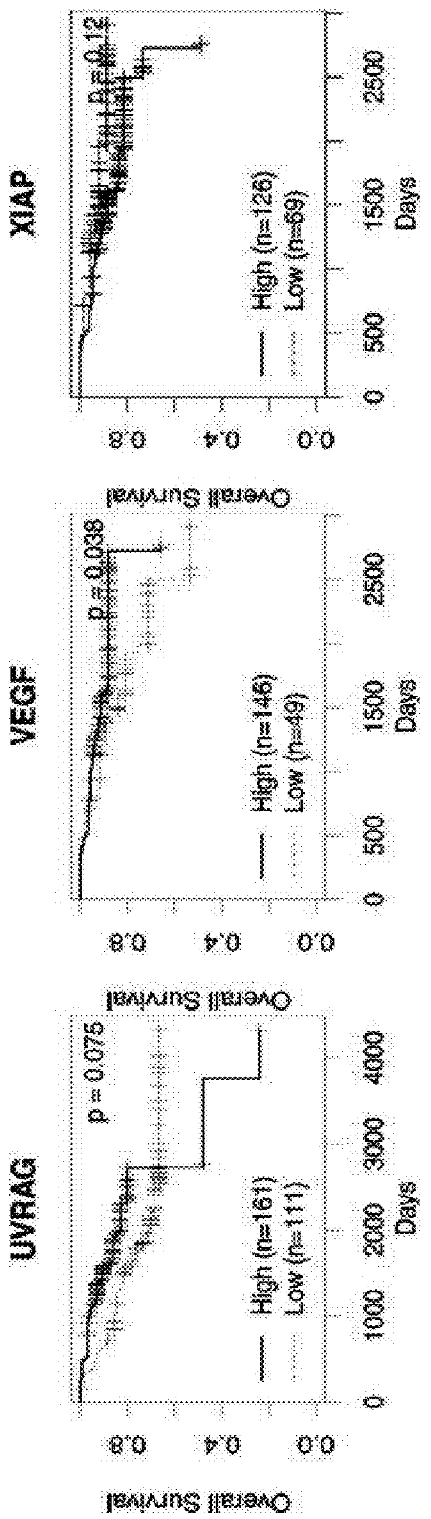
Figure 37:
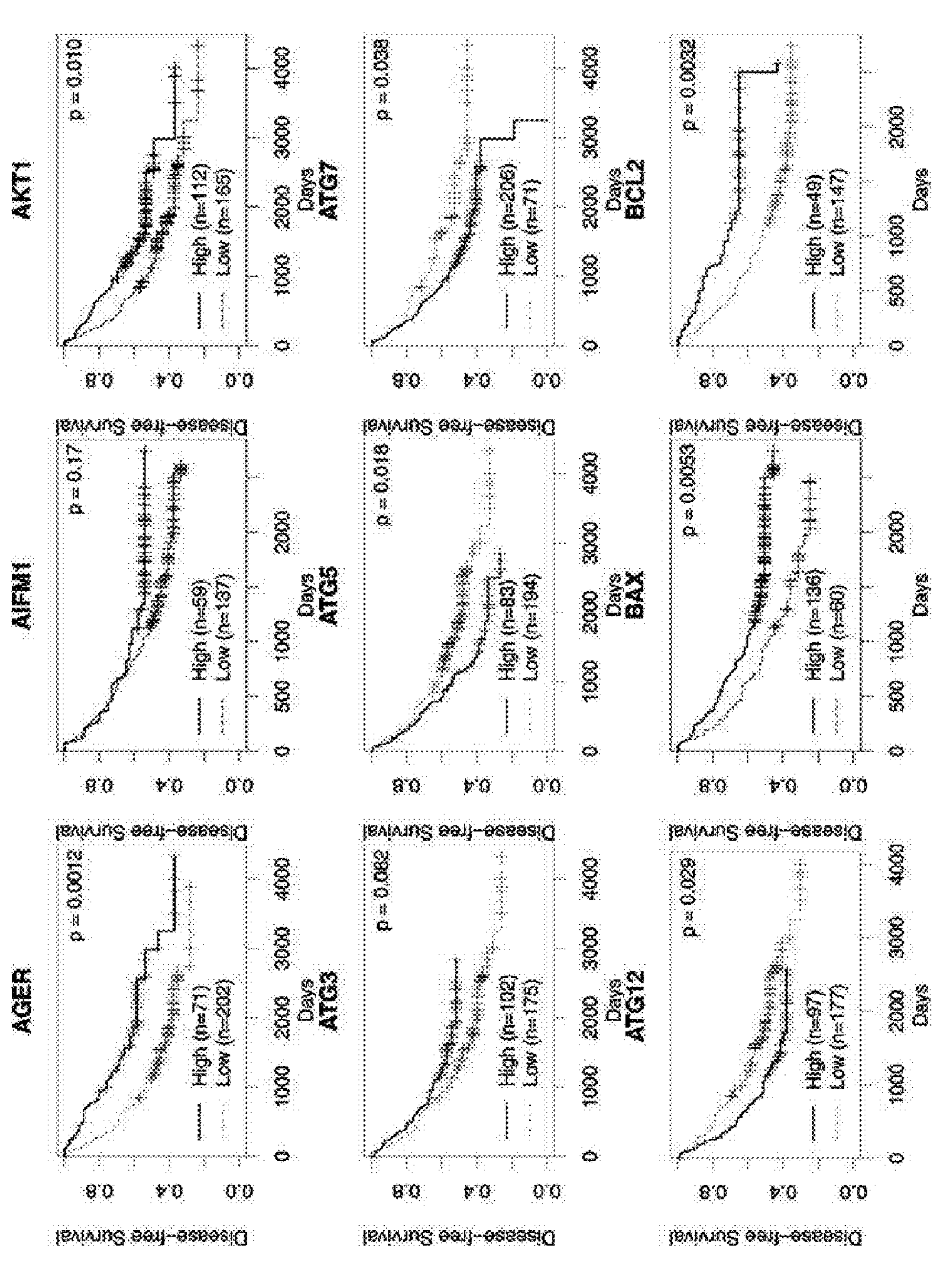
Figure 38:
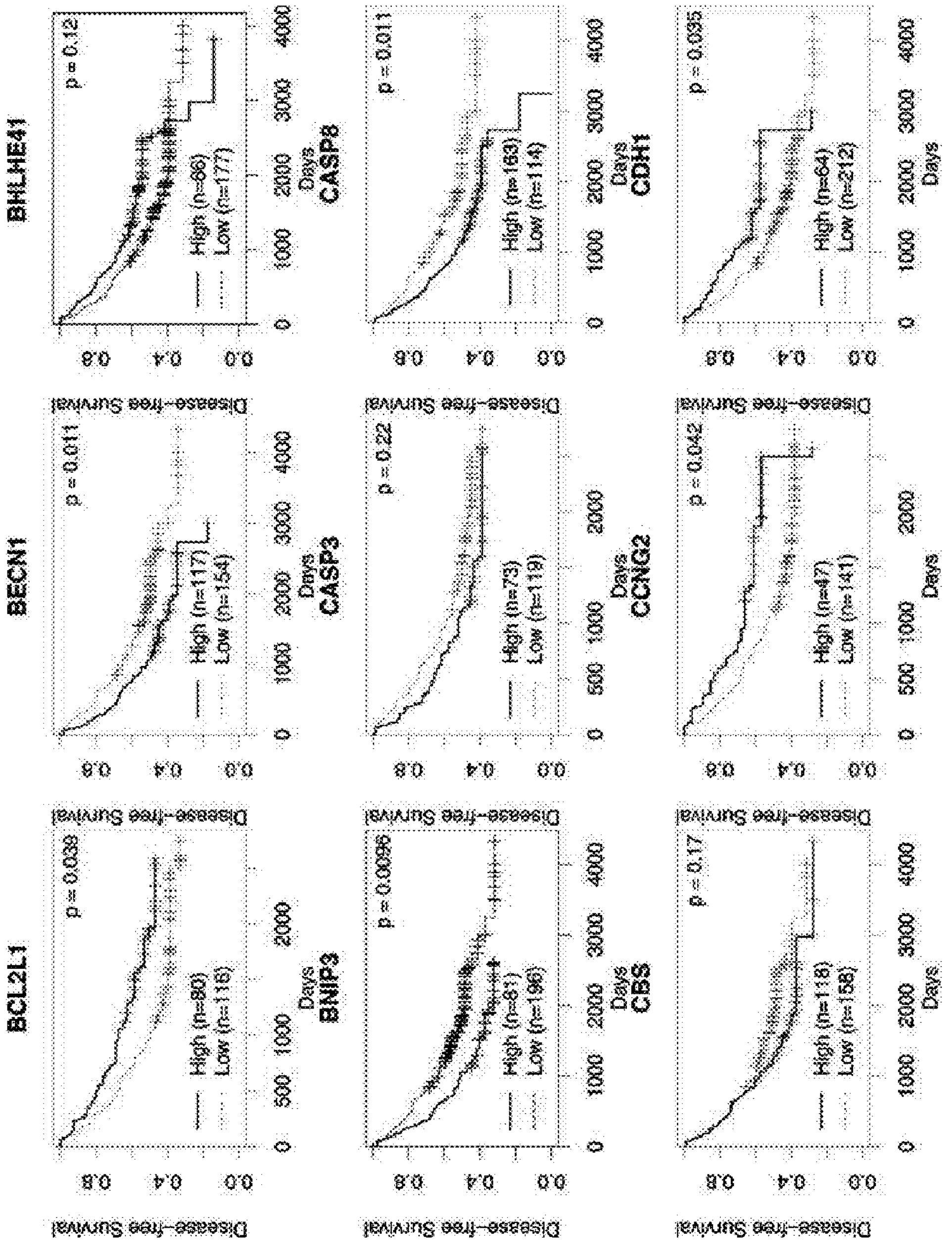
Figure 39:
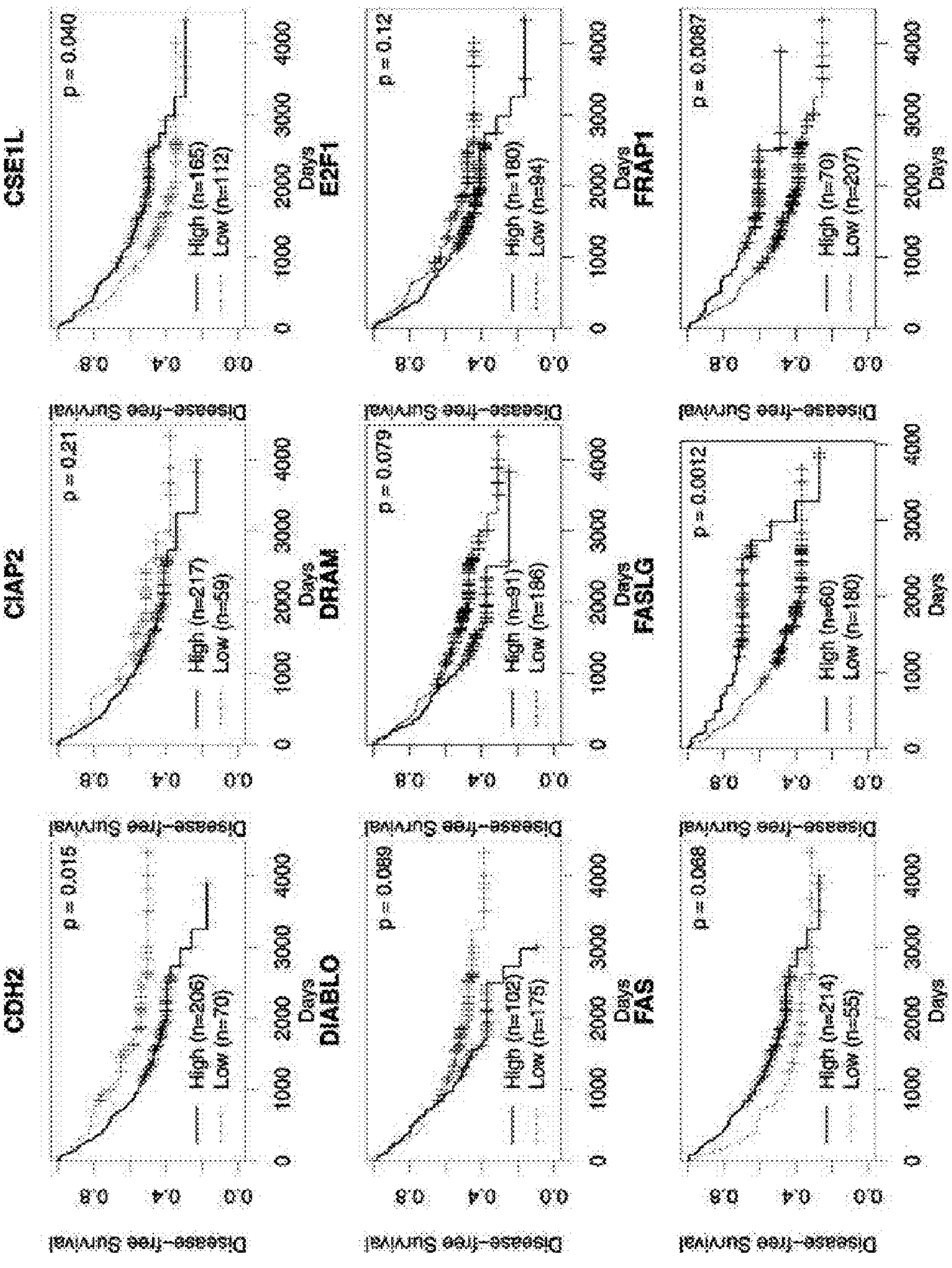
Figure 40:
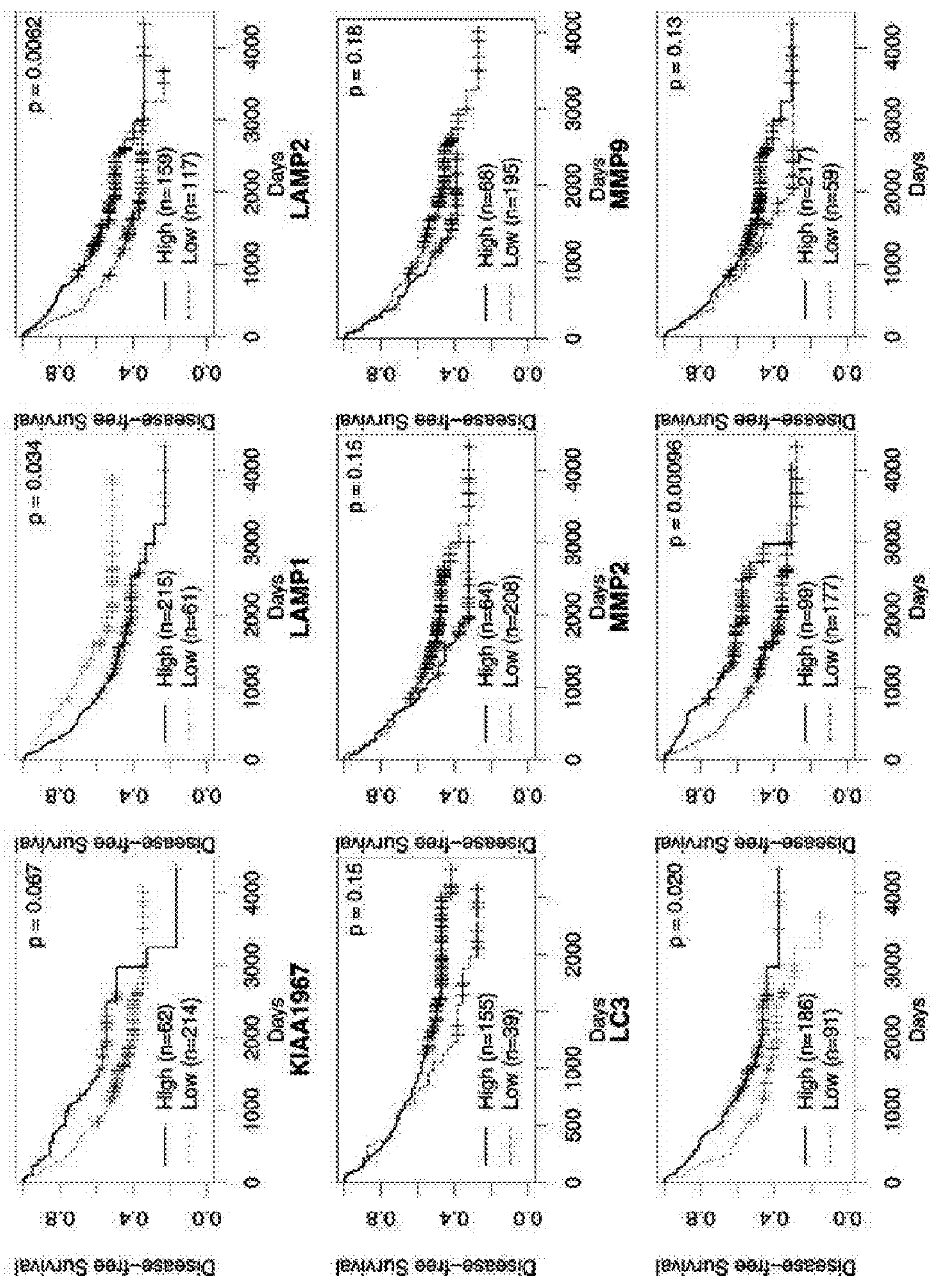
Figure 41:
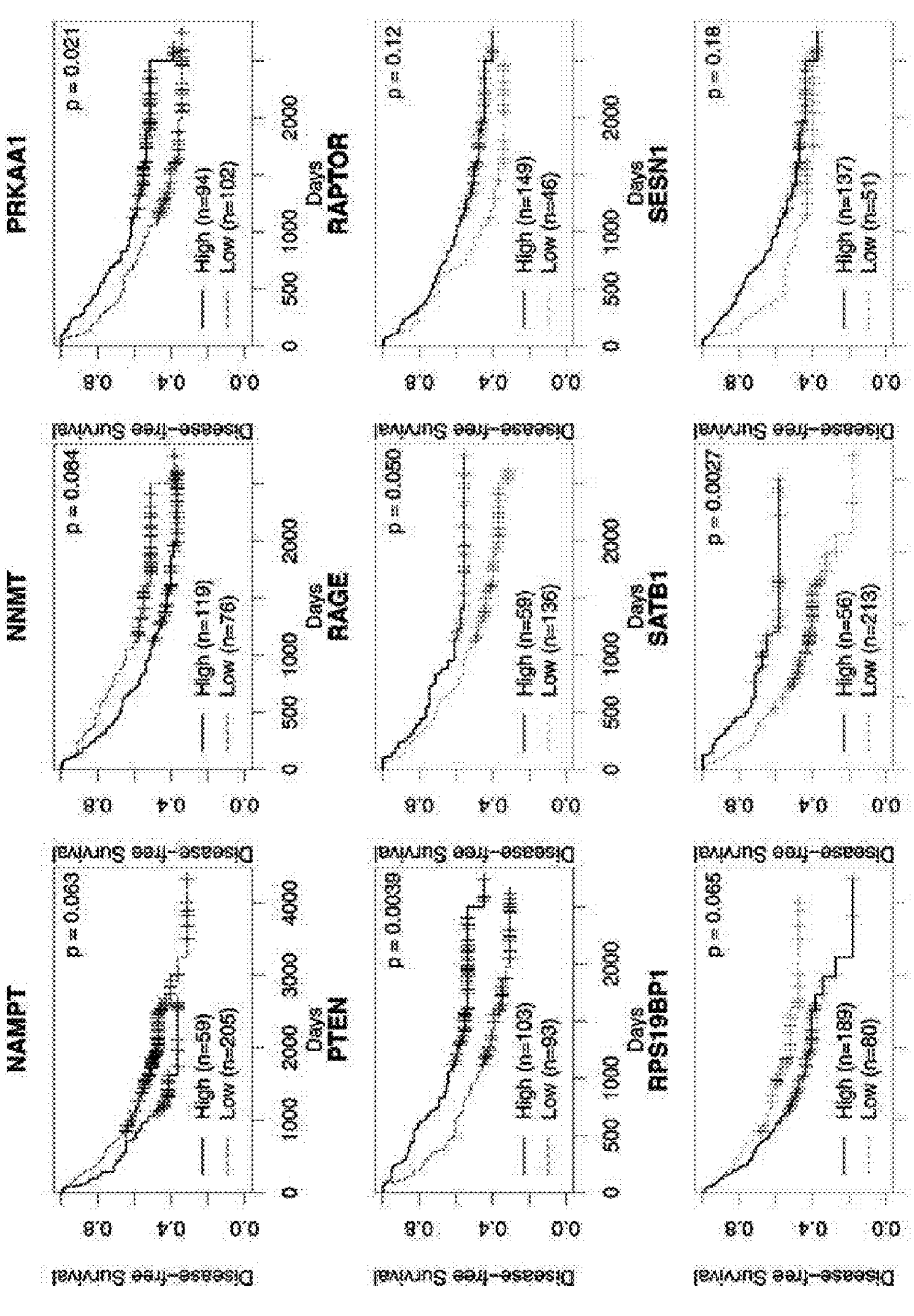
Figure 42:
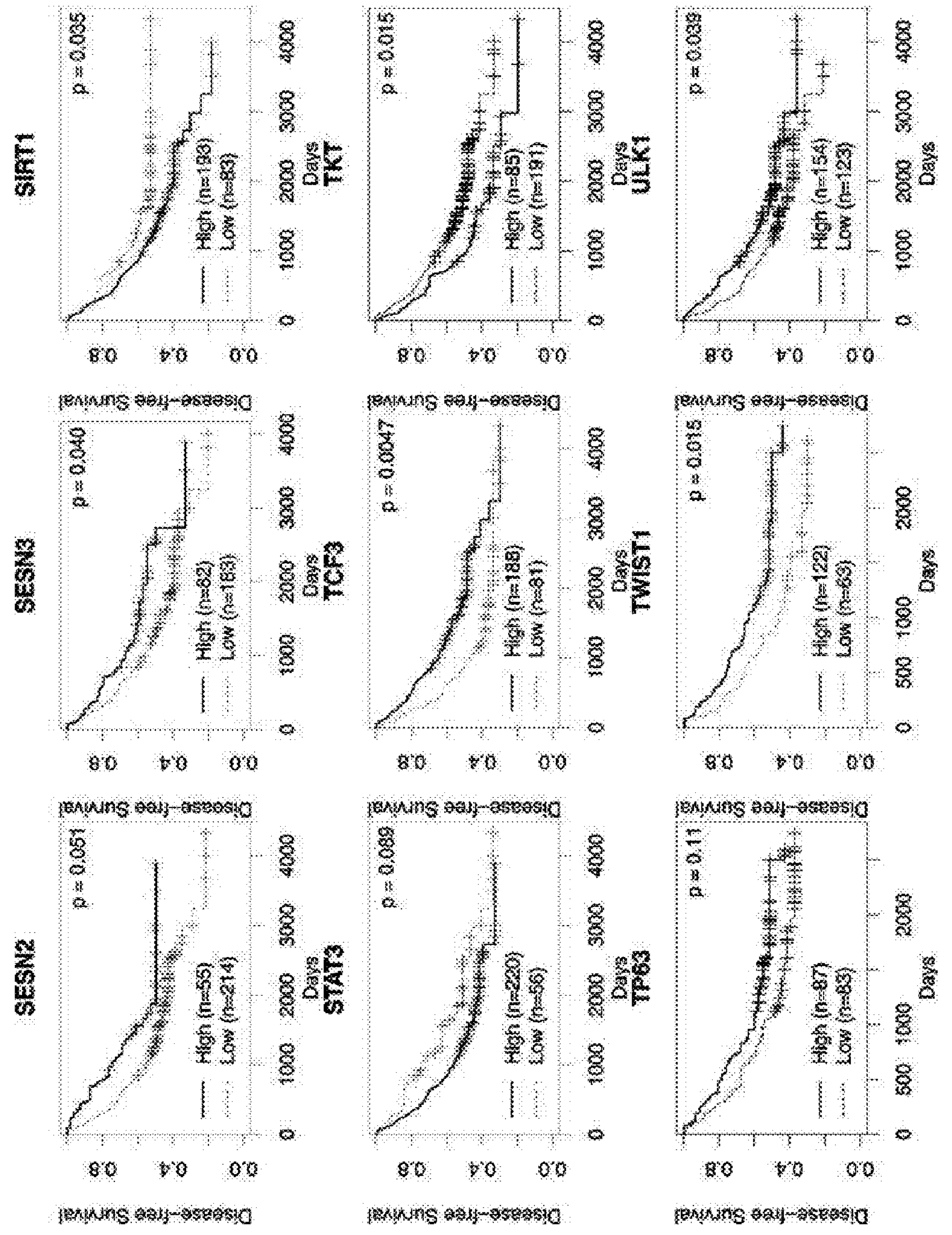
Figure 43:
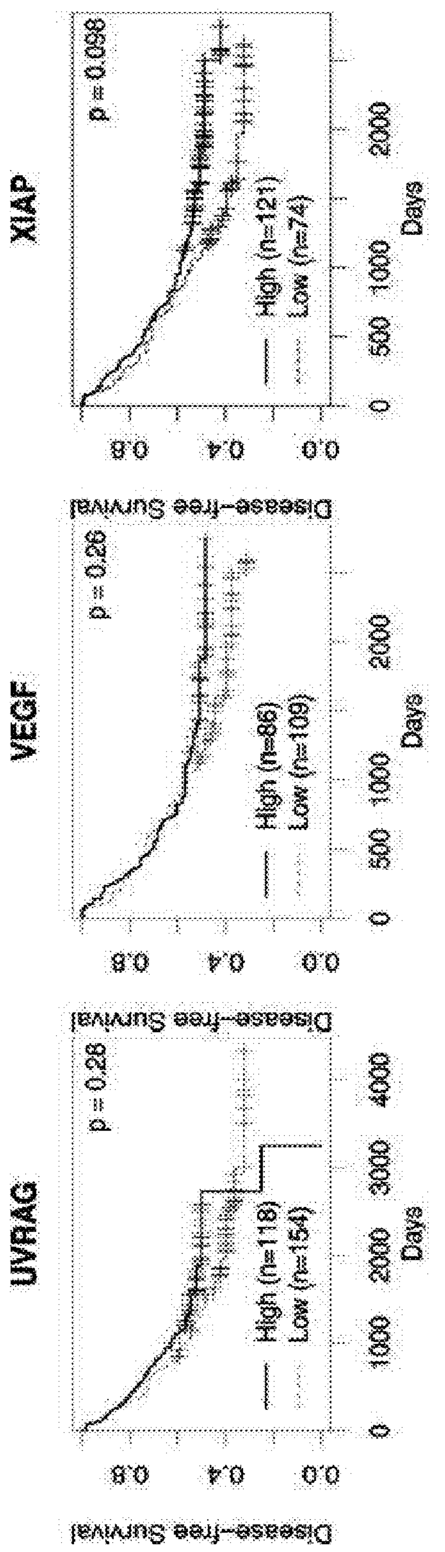

Hereinafter, the present disclosure will be explained in detail by means of examples; however they are described only to help understand the present disclosure, but not to limit the scope of the present disclosure in any way.

Example 1: Predicting Prognosis of Liver Cancer

Markers useful for predicting prognosis of liver cancer were found by the following method, and it was confirmed that it is possible to predict prognosis of liver cancer by using the markers.

1-1. RNA Extraction and cDNA Synthesis

Liver cancer tissue and adjacent normal tissue harvested from 547 patients of liver cancer whose liver cancer occurrence was diagnosed and its development was confirmed were obtained. The liver cancer patients were patients who went through liver resection for cancer without receiving other treatment after diagnosis, and the tissues were tissues harvested and frozen before the liver resection for cancer.

RNA of each of the tissues was extracted and cDNA was synthesized according to the following methods.

Total RNA was extracted from liver cancer tissue and adjacent normal tissue using RNeasy Minikit (Qiagen, Germany) according to the manufacturer's instructions. The total RNA of the obtained RNA extract was weighed using Bioanalyzer 2100 (Agilent Technologies, USA). DNase I treatment was performed in the extraction step to remove contaminated genomic DNA from the RNA extract. The sample containing 4 μg of total RNA was incubated with 2 μl of 10 μM oligo d(T)18 primer (Genotech, Korea) at 70° C. for 7 minutes and cooled down on ice for 5 minutes. An enzyme mix was separately prepared [in a total volume of 11 μl by adding 2 μl of 0.1 M DTT (Duchefa, Netherlands), 2 μl of 10× reverse-transcription buffer, 5 μl of 2 mM dNTP, 1 μl of 200 U/μl MMLV reverse-transcriptase, and 1 μl of 40 U/μl, RNase inhibitor (Enzynomics, Korea)]. After adding the enzyme mix to the samples containing the RNA, they were incubated for 90 minutes at 42° C., and then were incubated at 80° C. for 10 minutes to inactivate reverse-transcriptase. The above samples were brought up to a final volume of 400 μl by adding dimethylpyrocarbonate (DEPC)-treated water.

1-2: Quantitative Real-Time PCR

Real-time PCR amplifications were carried out for each of the cDNA samples obtained from Example 1-1, using PRISM 7900HT (Applied Biosystems, USA) according to the manufacturer's instructions, on the genetic marks described in the following table:

The real-time PCR analysis was performed in a total volume of 10 μl including 5 μl of 2× Taqman gene expression master mix (Applied Biosystems, USA), 1 μl of each of 5 μM forward and reverse primers, 1 μl of 1 μM probe (Genotech, Korea), and 2 μl of cDNA (in the case of a control group, the same amount of water). The amplifications were performed with a cycle of a step of dissociation at 95° C. for 10 minutes, followed by a step of dissociation at 95° C. for 15 seconds; and a step of synthesis at 60° C. for 1 minute. The primer and probe sequences were designed using Primer Express 3.0 (Applied Biosystems, USA) and all the probe sequences were labelled with FAM at the 5' end and with TAMRA at the 3' end. The following primer and probe sequences in the below Table 16 were used for each of the markers:

TABLE 16

| Gene | Forward Primer (SEQ ID NO.) | Reverse Primer (SEQ ID NO.) |
|---|---|---|
| UVRAG | AATGTGCACCCTAGCCAAGAA (58) | TGCTCGCTGGGTAGGAGAGT (59) |
| NAMPT | CGGCAGAAGCCGAGTTCA (61) | GCTTGTGTTGGGTGGATATTGTT (62) |
| STAT3 | GCCAGAGAGCCAGGAGCAT (64) | GGTGTCACACAGATAAACTTGGTCTT (65) |
| CIAP2 | TGGTTTCCAAGGTGTGAGTACTTG (67) | GGGCTGTCTGATGTGGATAGC (68) |
| BHLHE41 | CAAGCCTACCGTCCCACAGA (70) | CCAGTAACTGTCTCTCTTGCAAATG (71) |
| MMP2 | GGTTGTCTGAAGTCACTGCACAGT (73) | CTCGGTAGGGACATGCTAAGTAGAG (74) |
| SESN2 | TGCCTCCGGGACTGACA (76) | TGACCCTGACTTTCACATTGATG (77) |
| HMGB1 | CGGACAAGGCCCGTTATG (79) | AGAGGAAGAAGGCCGAAGGA (80) |
| SIRT1 | AAAAACCTCCACGAACACAAAAA (82) | TGCTTGGTCTAAAAGTGTGACAATC (83) |
| RPS19BP1 | CGGAAGACGAAGGCAATTCA (85) | GCCGACTTGGGCACCTTT (86) |
| LAMP2 | GCCCCGCCCCTAGTCTTA (88) | ACCGACCACAGCCTTGCA (89) |
| AGER | CCGAGTCCGTGTCTACCAGATT (91) | CACATGTCCCCACCTTATTGG (92) |
| SESN3 | TCTGCCTGAACTGGTACATGCT (94) | TGGATTGATACCACTACCAAAAACA (95) |
| ID2 | AACGACTGCTACTCCAAGCTCAA (97) | GGATTTCCATCTTGCTCACCTT (98) |
| TCF3 | GCTGCCTTTGGTCTCTGGTTT (100) | AGAAATGCAATGCTCAGTCTAGGA (101) |
| HMGB2 | TGCCGGGAAGAGCACAA (103) | TCCATCTCTCCGAACACTTCTTG (104) |
| TP63 | GCTCCACCTTCGATGCTCTCT (106) | TGCTCGACTGCTGGAAGGA (107) |
| RAGE | CCAATTTGTCCCCACAATGC (109) | GGGCGGCGATTCTCTCA (110) |
| KIAA1967 | CGTTGTTGCATGCTCTTTGTG (112) | CCAGCAAAAACTTAATCTGCTTCA (113) |
| SATB1 | GACCCGGCCACGAACA (115) | GTCGAGCTGGGCAGACAGA (116) |
| RAPTOR | GATGGCACTCAGCGAATGC (118) | ATGCGCACATCTCCATTGAC (119) |
| SESN1 | TCCTGGGTGCATTCAGTCTCT (121) | GGAGCTGCACAGCCTTTAAAGT (122) |
| CCNG2 | TCCCAGTATGATGGCCAGTCA (124) | ATAAGGCCAGCCAAAACTCAAG (125) |
| CDH1 | AAATCTGAAAGCGGCTGATACTG (127) | CGGAACCGCTTCCTTCATAG (128) |
| FASLG | GAGATCCAGCTTGCCTCCTCTT (130) | CGGTTTTACTTCTTCTCAGTCCTGTA (131) |
| CASP3 | CAGTGGAGGCCGACTTCTTG (133) | ATGAACCAGGAGCCATCCTTT (134) |
| BECN1 | GATGGTGTCTCTCGCAGATTCA (136) | TCAGATGCCTCCCCAATCAG (137) |
| CDH2 | GCACCCGCCTCAGTCAACT (139) | CAACATGGTACCGGCATGAA (140) |
| TWIST1 | TCCGCGTCCCACTAGCA (142) | AGTTATCCAGCTCCAGAGTCTCTAGAC (143) |
| MMP9 | GGGCTCCCGTCCTGCTT (145) | ACTCCTCCCTTTCCTCCAGAAC (146) |
| VEGF | GCTTACTCTCACCTGCTTCTGAGTT (148) | TGGGCTGCTTCTTCCAACA (149) |
| ATG12 | CGACAGCTTCGATTTGAATGAC (151) | GGGAGCGTCGCAAAGGA (152) |
| DIABLO | AATCACATTCAGCTGGTGAAACTG (154) | TGCCAGCTTGGTTTCTGCTT (155) |
| E2F1 | CTGGACCACCTGATGAATATCTGT (157) | CAATGCTACGAAGGTCCTGACA (158) |
| LAMP1 | TGCACTCAGATTTAAGCCTTACAAA (160) | TCACCACGAGTGACCTTCATG (161) |
| LC3 | AACCAGCACAGCATGGTGAGT (163) | CCTCGTCTTTCTCCTGCTCGTA (164) |
| ATG7 | CGGATGAATGAGCCTCCAA (166) | GGACATTATCAAACCGTGAAAGAA (167) |
| TKT | GAGGCTGTGTCCAGTGCAGTAG (169) | CCACTTCTTGGTACCCGGTTA (170) |
| AIFM1 | TGAAGATCTCAATGAAGTAGCCAAACTAT (172) | CTGCAGTGGGTTTGCCAAT (173) |
| BNIP3 | TTCCCCCCAAGGAGTTCCT (175) | CGCTCGTGTTCCTCATGCT (176) |
| ATG3 | CCATTGAAAATCACCCTCATCTG (178) | CACCTCAGCATGCCTGCAT (179) |
| DRAM | CAGCCGCCTTCATTATCTCCTA (181) | TGGAGGTGTTGTTCCCGTATC (182) |
| ATG5 | TTTCCTCCACTGCCATCATTAA (184) | GGCCAAAGGTTTCAGCTTCA (185) |
| NNMT | TTGAGGTGATCTCGCAAAGTTATT (187) | CTCGCCACCAGGGAGAAA (188) |
| PRKAA1 | GGCAGTTGCCTACCATCTCATAA (190) | GCCGAGTCAGGTGATGATCA (191) |
| CASP8 | CCTTCTGATTGATGGTGCTATTTTG (193) | GCGGTGAGCCGAGATCAC (194) |
| ULK1 | TCGCGGCCGCATGT (196) | AAGGGTCCAGCACTATCAAGAGA (197) |
| BCL2L1 | GATTGCCTTTGTTTTGATGTTTGT (199) | GGAAAGGGAACCCAGGTTAGTG (200) |
| FAS | AATGGTGTCAATGAAGCCAAAAT (202) | GTCATACGCTTCTTTCTTTCCATGA (203) |
| CSE1L | GCATGATCCTGTAGGTCAAATGG (205) | CAGGCGGTAGACAACTTGTGAA (206) |
| FRAP1 | AGGCCGCATTGTCTCTATCAA (208) | GCAGTAAATGCAGGTAGTCATCCA (209) |
| AKT1 | TCTCGGGTGCATTTGAGAGAA (211) | ACAGCACAAAAACGTCTTTCCA (212) |
| BAX | GGTTGTCGCCCTTTTCTACTTTG (214) | CAGTTCCGGCACCTTGGT (215) |
| BCL2 | CATGTGTGTGGAGAGCGTCAA (217) | GCCGGTTCAGGTACTCAGTCA (218) |
| PTEN | TGGCGGAACTTGCAATCC (220) | GCTGAGGGAACTCAAAGTACATGA (221) |

TABLE 16-continued

| | | |
|---|---|---|
| CBS | GTTGGCAAAGTCATCTACAAGCA(223) | GGGCGAAGTGGTCCATCTC(224) |
| XIAP | GACAGGCCATCTGAGACACATG(226) | AGCATAGTCTGGCCAGTTCTGAA(227) |

| Gene | Probe (SEQ ID No.) |
|---|---|
| UVRAG | AGAAGCCCTCTCCGGGCACCG(60) |
| NAMPT | CATCCTCCTGGCCACCGACTCCTAC(63) |
| STAT3 | AGCTGACCCAGGCGCTGCCC(66) |
| CIAP2 | TCATCCGTCAAGTTCAAGCCAGTTACCCTC(69) |
| BHLHE41 | CCCAAAAATCGAAACAGAGGAAACGAACAG(72) |
| MMP2 | CATCTCAGCCCACATAGTGATGGTTCCC(75) |
| SESN2 | TGCCTTCTCTCCCCTGTCATTTCCAG(78) |
| HMGB1 | AAAAGAAGTTCAAGGATCCCAATGCACCC(81) |
| SIRT1 | TCAGAGTTGCCACCCACACCTCTTCA(84) |
| RPS19BP1 | CCAGAAACTGCGGAACTCGGCCA(87) |
| LAMP2 | CTCGCACTGAAGCGCCGATTCC(90) |
| AGER | TCTGCCTCTGAACTCACGGCTGGTGT(93) |
| SESN3 | TGGTCCTCCTGGCACATTATCATGCTTT(96) |
| ID2 | TGCCCAGCATCCCCCAGAACAA(99) |
| TCF3 | AGTCCCGTGTCTCTCGCTATTTCTGCTG(102) |
| HMGB2 | ACACCCGGACTCTTCCGTCAATTTCG(105) |
| TP63 | ATCACCCGCCATCCCCTCCAAC(108) |
| RAGE | CCTCCTGCACGCAATGGTGGC(111) |
| KIAA1967 | CCAAGGGAGACGCCAGAGCATCC(114) |
| SATB1 | TTTCATACAAGACGTGGGCCTGTACCCTG(117) |
| RAPTOR | CTCCCTGCAGAAGCGTCCCGAC(120) |
| SESN1 | TGCCTCTGCCTGCCTCCTGGTC(123) |
| CCNG2 | ATGCTGCTCTTCCCGTCCACAAGTG(126) |
| CDH1 | CCCCACAGCCCCGCCTTATGA(129) |
| FAS LG | AGCAACAGGGTCCCGTCCTTGACA(132) |
| CASP3 | TCCACAGCACCTGGTTATTATTCTTGGCG(135) |
| BECN1 | ATGTCCACAGAAAGTGCCAACAGCTTCAC(138) |
| CDH2 | AATGAAAACCCTTATTTTGCCCCCAATCC(141) |
| TWIST1 | CACCCCCTCAGCAGGGCCG(144) |
| MMP9 | TGCCATGTAAATCCCCACTGGGACC(147) |
| VEGF | AGACCACTGGCAGATGTCCCGGC(150) |
| ATG12 | TGTAATTGCGTCCCCCTACTCCGGC(153) |
| DIABLO | AAGAGGTGCACCAGCTCTCCCGG(156) |
| E2F1 | CAGCTGCGCCTGCTCTCCGA(159) |
| LAMP1 | AAGCCTCTGGCCGTCACACGTAGG(162) |
| LC3 | TCCACGCCCATCGCGGACA(165) |
| ATG7 | TCTTGGGCTTGTGCCTCACCAGATC(168) |
| TKT | CCTGGCATCACTGTCACCCACCTG(171) |
| AIFM1 | CAACATTCATGAAGACTGAAGCCCCACA(174) |
| BNIP3 | ACCCGAAGCGCACGGCCAC(177) |
| ATG3 | CACCACCTCCCATGTGTTCAGTTCACC(180) |
| DRAM | TGCTCTCCGGGCACGTCAACC(183) |
| ATG5 | CCTCAGCTGTGACATGAAAGACTTACCGG(186) |
| NNMT | CCACCATGGCCAACAACGAAGGAC(189) |
| PRKAA1 | TCTATTTGGCGACAAGCCCACCTGATT(192) |
| CASP8 | CAGAATCTCGCTCTGTCGCCCAGG(195) |
| ULK1 | AGCAGGTCCTGGGCGCCTCAAC(198) |
| BCL2L1 | CAGAATTGATCATTTTCCCCCCACTCTCC(201) |
| FAS | TGACAATGTCCAAGACACAGCAGAACAGAA(204) |
| CSE1L | AATAACCCCAAAATTCACCTGGCACAGTCA(207) |
| FRAP1 | TGCAATCCAGCTGTTTGGCGCC(210) |
| AKT1 | CCACGCTGTCCTCTCGAGCCCA(213) |
| BAX | CAGCAAACTGGTGCTCAAGGCCCT(216) |
| BCL2 | CCTGGTGGACAACATCGCCCTGT(219) |
| PTEN | ATATTCCTCCAATTCAGGACCCACACGAC(222) |
| CBS | ACGCTGGGCAGGCTCTCGCAC(225) |
| XIAP | AGACACCATATACCCGAGGAACCCTGCC(228) |

Expression of each of the marker genes was measured in triplicate, and then standardized by subtracting the average expression of 5 types of reference genes (B2M, GAPDH, HMBS, HPRT1, and SDHA). The primer and probe sequences in the below Table 17 were used for reference genes.

TABLE 17

| Gene | forward primer (SEQ ID No.) | reverse primer (SEQ ID NO.) |
|---|---|---|
| B2M(beta-2-microglobulin) | CATTCGGGCCGAGATGTCT(229) | CTCCAGGCCAGAAAGAGAGAGTAG(230) |
| GAPDH(glyceraldehyde-3-phosphate dehydrogenase) | CACATGGCCTCCAAGGAGTAA(232) | TGAGGGTCTCTCTCTTCCTCTTGT(233) |
| HMBS(hydroxymethylbilane synthase) | CCAGGGATTTGCCTCACCTT(235) | AAAGAGATGAAGCCCCCACAT(236) |

TABLE 17-continued

| | | |
|---|---|---|
| HPRT1(hypoxanthine phosphoribosyltransferase 1) | GCTCGAGATGTGATGAAGGAGAT(238) | CCAGCAGGTCAGCAAAGAATT(239) |
| SDHA(succinate dehydrogenase complex, subunit A) | CACCTAGTGGCTGGGAGCTT(241) | GCCCAGTTTTATCATCTCACAAGA(242) |

| Gene | Probe (SEQ ID NO.) |
|---|---|
| B2M(beta-2-microglobulin) | CCGTGGCCTTAGCTGTGCTCGC(231) |
| GAPDH(glyceraldehyde-3-phos-phate dehydrogenase) | CTGGACCACCAGCCCCAGCAAG(234) |
| HMBS(hydroxymethylbilane synthase) | CCTTGATGACTGCCTTGCCTCCTCAG(237) |
| HPRT1(hypoxanthine phosphoribosyltransferase 1) | CCATCACATTGTAGCCCTCTGTGTGCTC(240) |
| SDHA(succinate dehydrogenase complex, subunit A) | TGGCACTTACCTTTGTCCCTTGCTTCA(243) |

CT (the number of cycles required to achieve a threshold) of each of the markers was measured, and the ΔCT value (CT of each of the markers minus average CT of the reference genes) was calculated. The mRNA copy number was calculated as $2^{-\Delta CT}$. Standard curves were constructed from the results of simultaneous amplifications of serial dilutions of the cDNA samples.

From the above results, it can be found that the expression level and expression pattern of the markers can be measured by the nucleic acid included in the composition of the present disclosure. Also, since mRNA, a transcriptome, is translated into a protein, it can also be known that the expression level and expression pattern of the markers can also be measured by the antibody included in the composition of the present disclosure.

1-3. Statistical Analysis

In consideration of the standardized expression of each of the markers obtained from Examples 1~2, and the progress of the patients who provided liver cancer tissues, Kaplan-Meier curves were completed, and then significance analysis was performed.

Based on the progress of patients who have provided liver cancer tissues, for the respective cases of recurrence, survival, and disease-free survival, the patients were listed in the ascending order of the period. The interval survival rate (or interval recurrence rate) was calculated by dividing the number of survivors (or patients with recurrence) by the number of patients exposed to a risk. The cumulative survival rate (or cumulative recurrence rate) is conditional probability, which was calculated by multiplying the previous cumulative survival rate (or cumulative recurrence rate) by the current interval survival rate (or interval recurrence rate). Kaplan-Meier curves were constructed as step functions with the horizontal axis of survival time (or observation period) and the vertical axis of cumulative survival rate (or cumulative reoccurrence rate).

For each of the markers, Kaplan-Meier curves with regard to recurrence, survival, and disease-free survival were completed. The expression of each of the markers that was measured in Example 1~2 was classified into high expression and low expression based on statistically significant reference values that were determined experimentally, and the cases of high expression and low expression for each of the markers were separated from each other to complete Kaplan-Meier curves. As the reference values, the gene expression values having the lowest p-value among the results of regression analysis of continuous variables (see *N Engl J Med* 2007; 356: 11-20) were selected. Graphs were prepared by applying them to the Kaplan-Meier curve (*J. Amer. Statist. Assn.* 53:457481, 1958). The criteria for determining significance in the Kaplan-Meier curve was whether the p-value of a single gene or a combination of genes is lower than 0.05.

Kaplan-Meier curves were prepared with regard to prediction of recurrence, survival, and disease-free survival for 57 types of single genes, 31 types of single genes and gene groups consisting of combinations of at least two of them in 547 liver cancer patients whose stage has not been classified. The results for 57 types of single genes are shown in FIGS. 2~22. Kaplan-Meier curves regarding recurrence for 57 types of single genes are shown in FIGS. 2~8, Kaplan-Meier curves regarding survival for 57 types of single genes are shown in FIGS. 9~15, and Kaplan-Meier curves regarding disease-free survival for 57 types of single genes are shown in FIGS. 16~22.

As can be confirmed in the drawings, in the Kaplan-Meier curves completed with respect to recurrence, survival, and disease-free survival, each of the markers forms curves where cases of high expression and low expression are distinctively distinguished from each other. This means that there is remarkable differences in interval recurrence rate or interval survival rate, and cumulative recurrence rate or cumulative survival rate based thereon between the cases where each of the markers shows high expression and low expression, and that consequently, the expression patterns of each of the markers can be an index showing recurrence possibility or survival possibility of patients.

Also, significance tests were performed by log-rank test with respect to each of the markers and their combination by calculating observation values and expected values at every point of recurrence or death to obtain Chi-square test statistics. The results are shown in the following Tables 18~21. The results of 57 markers are shown in Table 18, and the results of 31 markers used alone and in combination are shown in Tables 19~21. Among them, Table 19 shows the result of prediction of recurrence of 31 markers, Table 20 shows the result of prediction of survival of 31 markers, and Table 21 shows the result of prediction of disease-free survival of 31 markers.

TABLE 18

| Marker | p-value |
|---|---|
| Recurrence | |
| FAS | 9.36E−06 |
| TKT | 1.02E−05 |
| FASLG | 4.99E−04 |
| CASP8 | 7.29E−04 |
| AKT1 | 2.67E−03 |
| ID2 | 3.17E−03 |
| DRAM | 4.17E−03 |
| ULK1 | 4.48E−03 |
| E2F1 | 7.03E−03 |
| RPS19BP1 | 7.74E−03 |
| UVRAG | 8.77E−03 |
| AIFM1 | 9.87E−03 |
| TP63 | 1.12E−02 |
| TWIST1 | 1.20E−02 |
| BECN1 | 1.36E−02 |
| BCL2L1 | 1.94E−02 |
| KIAA1967 | 1.95E−02 |
| ATG7 | 2.00E−02 |
| AGER | 2.05E−02 |
| HMGB2 | 2.16E−02 |
| TCF3 | 2.72E−02 |
| CSE1L | 2.77E−02 |
| DIABLO | 2.86E−02 |
| BCL2 | 3.17E−02 |
| BNIP3 | 3.27E−02 |
| SATB1 | 3.42E−02 |
| MMP9 | 3.62E−02 |
| MMP2 | 4.51E−02 |
| STAT3 | 4.61E−02 |
| LC3 | 4.96E−02 |
| RAPTOR | 6.38E−02 |
| FRAP1 | 6.43E−02 |
| SESN3 | 6.70E−02 |
| LAMP1 | 7.01E−02 |
| LAMP2 | 7.55E−02 |
| ATG12 | 8.48E−02 |
| CDH2 | 8.67E−02 |
| ATG5 | 9.08E−02 |
| SESN2 | 9.11E−02 |
| BAX | 9.26E−02 |
| CASP3 | 9.40E−02 |
| CDH1 | 9.49E−02 |
| VEGF | 1.11E−01 |
| PRKAA1 | 1.19E−01 |
| BHLHE41 | 1.23E−01 |
| RAGE | 1.25E−01 |
| ATG3 | 1.31E−01 |
| PTEN | 1.33E−01 |
| CCNG2 | 1.60E−01 |
| SIRT1 | 1.60E−01 |
| NAMPT | 1.96E−01 |
| XIAP | 2.09E−01 |
| NNMT | 2.46E−01 |
| CIAP2 | 2.83E−01 |
| CBS | 3.07E−01 |
| HMGB1 | 3.22E−01 |
| SESN1 | 4.15E−01 |
| Survival | |
| FAS | 1.51E−10 |
| CDH1 | 2.46E−07 |
| FRAP1 | 5.46E−07 |
| NAMPT | 8.91E−07 |
| BNIP3 | 1.42E−06 |
| TKT | 1.66E−06 |
| ID2 | 4.42E−06 |
| LC3 | 5.95E−06 |
| LAMP2 | 9.67E−06 |
| CSE1L | 1.79E−05 |
| LAMP1 | 1.86E−05 |
| FASLG | 2.81E−05 |
| AKT1 | 3.97E−05 |
| UVRAG | 4.45E−05 |
| BECN1 | 5.62E−05 |
| STAT3 | 1.31E−04 |
| TCF3 | 2.39E−04 |

TABLE 18-continued

| Marker | p-value |
|---|---|
| SESN3 | 7.83E−04 |
| CIAP2 | 1.24E−03 |
| CDH2 | 1.63E−03 |
| SIRT1 | 1.91E−03 |
| CBS | 3.72E−03 |
| HMGB2 | 4.96E−03 |
| VEGF | 5.10E−03 |
| SESN2 | 8.63E−03 |
| BHLHE41 | 8.83E−03 |
| ATG7 | 1.29E−02 |
| RPS19BP1 | 1.55E−02 |
| SATB1 | 1.65E−02 |
| ATG12 | 1.66E−02 |
| AIFM1 | 2.17E−02 |
| RAPTOR | 2.19E−02 |
| DIABLO | 2.51E−02 |
| TWIST1 | 2.76E−02 |
| BCL2 | 3.10E−02 |
| NNMT | 3.61E−02 |
| BCL2L1 | 3.88E−02 |
| ATG5 | 3.96E−02 |
| DRAM | 4.10E−02 |
| XIAP | 4.21E−02 |
| ATG3 | 4.68E−02 |
| HMGB1 | 5.33E−02 |
| ULK1 | 6.22E−02 |
| PTEN | 7.19E−02 |
| RAGE | 7.30E−02 |
| PRKAA1 | 8.26E−02 |
| TP63 | 8.38E−02 |
| CASP3 | 1.26E−01 |
| AGER | 1.59E−01 |
| CASP8 | 1.68E−01 |
| BAX | 1.92E−01 |
| MMP9 | 1.93E−01 |
| MMP2 | 1.93E−01 |
| KIAA1967 | 1.99E−01 |
| CCNG2 | 2.05E−01 |
| SESN1 | 2.62E−01 |
| E2F1 | 4.35E−01 |
| Disease-free survival | |
| FAS | 3.86E−06 |
| TKT | 8.83E−06 |
| FASLG | 6.66E−04 |
| AKT1 | 9.30E−04 |
| CASP8 | 1.38E−03 |
| ID2 | 3.46E−03 |
| CSE1L | 5.42E−03 |
| BECN1 | 6.19E−03 |
| ULK1 | 6.39E−03 |
| HMGB2 | 8.45E−03 |
| UVRAG | 1.16E−02 |
| DRAM | 1.21E−02 |
| KIAA1967 | 1.38E−02 |
| AGER | 1.48E−02 |
| TCF3 | 1.59E−02 |
| RPS19BP1 | 1.80E−02 |
| BCL2 | 1.86E−02 |
| TP63 | 1.99E−02 |
| BNIP3 | 2.15E−02 |
| BCL2L1 | 2.18E−02 |
| AIFM1 | 2.42E−02 |
| DIABLO | 2.53E−02 |
| E2F1 | 2.72E−02 |
| MMP2 | 2.77E−02 |
| LAMP2 | 2.86E−02 |
| STAT3 | 2.88E−02 |
| LAMP1 | 3.38E−02 |
| SESN3 | 3.43E−02 |
| CDH1 | 3.87E−02 |
| SATB1 | 4.05E−02 |
| LC3 | 4.47E−02 |
| TWIST1 | 4.94E−02 |
| CDH2 | 5.28E−02 |
| ATG7 | 6.13E−02 |
| CASP3 | 6.69E−02 |
| NAMPT | 6.82E−02 |

TABLE 18-continued

| Marker | p-value |
|---|---|
| SESN2 | 7.38E−02 |
| VEGF | 7.75E−02 |
| FRAP1 | 8.15E−02 |
| ATG5 | 9.29E−02 |
| BAX | 9.60E−02 |
| PTEN | 1.01E−01 |
| RAPTOR | 1.02E−01 |
| CIAP2 | 1.18E−01 |
| BHLHE41 | 1.20E−01 |
| MMP9 | 1.26E−01 |
| ATG12 | 1.53E−01 |
| CCNG2 | 1.61E−01 |
| NNMT | 1.69E−01 |
| RAGE | 1.78E−01 |
| XIAP | 1.99E−01 |
| PRKAA1 | 2.34E−01 |
| HMGB1 | 2.56E−01 |
| CBS | 2.71E−01 |
| SIRT1 | 3.23E−01 |
| SESN1 | 3.41E−01 |
| ATG3 | 3.50E−01 |

TABLE 19

| Marker | p-value |
|---|---|
| One type | |
| FASLG | 8.88E−04 |
| FAS | 4.01E−03 |
| CSE1L | 5.58E−03 |
| ID2 | 7.13E−03 |
| TCF3 | 1.61E−02 |
| LAMP2 | 2.60E−02 |
| RPS19BP1 | 3.32E−02 |
| ULK1 | 4.75E−02 |
| AKT1 | 4.92E−02 |
| DRAM | 5.11E−02 |
| SESN2 | 8.39E−02 |
| SATB1 | 8.55E−02 |
| SESN3 | 8.87E−02 |
| LC3 | 9.38E−02 |
| BECN1 | 1.54E−01 |
| MMP9 | 1.65E−01 |
| BHLHE41 | 2.49E−01 |
| UVRAG | 3.16E−01 |
| ATG5 | 3.43E−01 |
| STAT3 | 3.50E−01 |
| E2F1 | 3.53E−01 |
| ATG3 | 4.00E−01 |
| CDH1 | 4.44E−01 |
| FRAP1 | 5.30E−01 |
| DIABLO | 6.29E−01 |
| ATG12 | 6.44E−01 |
| ATG7 | 7.01E−01 |
| LAMP1 | 7.45E−01 |
| SIRT1 | 7.77E−01 |
| NAMPT | 7.81E−01 |
| BNIP3 | 9.40E−01 |
| Combinations of two types | |
| FASLG_RPS19BP1 | 2.42E−06 |
| ULK1_ID2 | 1.28E−05 |
| DRAM_FASLG | 2.02E−05 |
| FASLG_MMP9 | 2.55E−05 |
| ATG12_FASLG | 3.13E−05 |
| ATG7_FASLG | 3.34E−05 |
| RPS19BP1_LAMP2 | 3.69E−05 |
| CSE1L_ID2 | 5.33E−05 |
| FASLG_ID2 | 5.60E−05 |
| LC3_ULK1 | 5.83E−05 |
| ID2_RPS19BP1 | 7.41E−05 |
| AKT1_CSE1L | 8.20E−05 |
| FASLG_TCF3 | 8.70E−05 |
| ID2_TCF3 | 9.33E−05 |

TABLE 19-continued

| Marker | p-value |
|---|---|
| ID2_SESN2 | 1.01E−04 |
| FAS_ID2 | 1.31E−04 |
| CSE1L_FASLG | 2.12E−04 |
| LC3_FASLG | 2.16E−04 |
| FAS_RPS19BP1 | 2.31E−04 |
| E2F1_FASLG | 2.33E−04 |
| ATG3_FASLG | 2.53E−04 |
| FASLG_BHLHE41 | 2.90E−04 |
| DRAM_FAS | 3.37E−04 |
| FASLG_SESN3 | 3.88E−04 |
| DIABLO_FASLG | 4.27E−04 |
| FASLG_SIRT1 | 4.54E−04 |
| CSE1L_FAS | 4.67E−04 |
| FASLG_STAT3 | 5.37E−04 |
| ULKLFASLG | 5.90E−04 |
| FASLG_SATB1 | 6.01E−04 |
| FASLG_SESN2 | 7.59E−04 |
| Combinations of three types | |
| FASLG_ID2_RPS19BP1 | 8.11E−08 |
| DRAM_FASLG_RPS19BP1 | 2.11E−07 |
| LC3_FASLG_RPS19BP1 | 3.86E−07 |
| FASLG_MMP9_RPS19BP1 | 4.66E−07 |
| ATG12_FASLG_RPS19BP1 | 5.24E−07 |
| ULK1_CSE1L_ID2 | 5.42E−07 |
| FASLG_RPS19BP1_SESN3 | 5.54E−07 |
| FASLG_STAT3_RPS19BP1 | 6.07E−07 |
| FASLG_RPS19BP1_TCF3 | 6.32E−07 |
| FASLG_RPS19BP1_BHLHE41 | 8.13E−07 |
| FASLG_RPS19BP1_SATB1 | 8.65E−07 |
| ATG7_FASLG_ID2 | 1.07E−06 |
| ATG7_FASLG_RPS19BP1 | 1.10E−06 |
| ATG12_FASLG_MMP9 | 1.20E−06 |
| AKT1_FASLG | 1.20E−06 |
| FASLG_FRAPLRPS19BP1 | 1.24E−06 |
| ID2_RPS19BP1_LAMP2 | 1.46E−06 |
| ATG12_FASLG_ID2 | 1.60E−06 |
| DRAM_FASLG_TCF3 | 1.70E−06 |
| FAS_ID2_RPS19BP1 | 1.72E−06 |
| ULK1_FASLG_RPS19BP1 | 1.84E−06 |
| ATG7_FASLG_MMP9 | 1.98E−06 |
| FASLG_RPS19BP1 | 2.00E−06 |
| LC3_ULK1_ID2 | 2.02E−06 |
| DRAM_FASLG_ID2 | 2.07E−06 |
| FASLG_RPS19BP1_SESN2 | 2.14E−06 |
| ULK1_ID2_RPS19BP1 | 2.14E−06 |
| FAS_FASLG_RPS19BP1 | 2.24E−06 |
| ATG12_FASLG_TCF3 | 2.27E−06 |
| FASLG_CDH1_RPS_19BP1 | 2.36E−06 |
| FASLG_RPS19BP1_NAMPT | 2.38E−06 |
| Combinations of four types | |
| DRAM_FASLG_ID2_RPS19BP1 | 6.49E−09 |
| ATG12_FASLG_ID2_RPS19BP1 | 1.07E−08 |
| FASLG_ID2_RPS19BP1_TCF3 | 1.09E−08 |
| ATG7_FASLG_ID2_RPS19BP1 | 1.30E−08 |
| DRAM_FASLG_STAT3_RPS19BP1 | 1.70E−08 |
| FASLG_ID2_MMP9_RPS19BP1 | 2.12E−08 |
| FASLG_ID2_STAT3_RPS19BP1 | 2.78E−08 |
| LC3_ULK1_CSE1L_ID2 | 2.85E−08 |
| DRAM_FASLG_RPS19BP1_SESN3 | 3.03E−08 |
| DRAM_LC3_FASLG_RPS19BP1 | 3.58E−08 |
| FASLG_ID2_RPS19BP1_SESN3 | 3.68E−08 |
| FASLG_ID2_RPS19BP1_SATB1 | 4.01E−08 |
| ULK1_FASLG_ID2_RPS19BP1 | 4.36E−08 |
| FASLG_ID2_RPS19BP1_SESN2 | 4.51E−08 |
| ATG12_FASLG_STAT3_RPS19BP1 | 4.72E−08 |
| DRAM_FASLG_RPS19BP1_SATB1 | 5.03E−08 |
| FASLG_ID2_SIRT1_RPS19BP1 | 5.34E−08 |
| FASLG_ID2_RPS19BP1_BHLHE41 | 5.49E−08 |
| LC3_FASLG_ID2_RPS19BP1 | 6.13E−08 |
| FASLG_ID2_RPS19BP1_UVRAG | 6.21E−08 |
| DRAM_AKT1_FASLG_RPS19BP1 | 6.38E−08 |
| E2F1_FASLG_ID2_RPS19BP1 | 6.45E−08 |
| DRAM_FASLG_RPS19BP1_TCF3 | 6.83E−08 |
| FAS_FASLG_ID2_RPS19BP1 | 7.00E−08 |
| DIABLO_FASLG_ID2_RPS19BP1 | 7.16E−08 |
| ATG12_FASLG_MMP9_STAT3 | 7.44E−08 |

TABLE 19-continued

| Marker | p-value |
|---|---|
| FASLG_ID2_RPS19BP1_NAMPT | 7.49E−08 |
| LC3_ATG12_FASLG_RPS19BP1 | 7.87E−08 |
| ATG12_FASLG_RPS19BP1_SESN | 8.09E−08 |
| LC3_FASLG_RPS19BP1_TCF3 | 8.15E−08 |
| DRAM_FASLG_FRAP1_RPS19BP1 | 8.22E−08 |
| CDH1_ID2_MMP9_TCF3 | 1.61E−03 |
| Combinations of five types | |
| DRAM_FASLG_ID2_STAT3_RPS19BP1 | 7.48E−10 |
| DRAM_FASLG_ID2_RPS19BP1_TCF3 | 1.02E−09 |
| ATG12_FASLG_ID2_STAT3_RPS19BP1 | 1.08E−09 |
| ATG7_FASLG_ID2_STAT3_RPS19BP1 | 1.43E−09 |
| ATG12_FASLG_ID2_RPS19BP1_TCF3 | 1.52E−09 |
| DRAM_FASLG_ID2_RPS19BP1_SATB1 | 2.14E−09 |
| DRAM_FASLG_ID2_RPS19BP1_SESN3 | 2.16E−09 |
| ATG7_FASLG_ID2_RPS19BP1_TCF3 | 2.66E−09 |
| DRAM_FAS_FASLG_ID2_RPS19BP1 | 2.76E−09 |
| DRAM_ULK1_FASLG_ID2_RPS19BP1 | 3.11E−09 |
| ATG7_FASLG_ID2_RPS19BP1_SATB1 | 3.18E−09 |
| DRAM_FASLG_ID2_RPS19BP1_SESN2 | 3.25E−09 |
| ATG12_FASLG_ID2_RPS19BP1_SESN3 | 3.29E−09 |
| DRAM_LC3_FASLG_STAT3_RPS19BP1 | 3.34E−09 |
| ATG12_FASLG_ID2_MMP9_RPS19BP1 | 3.53E−09 |
| DRAM_FASLG_STAT3_RPS19BP1_SESN3 | 3.56E−09 |
| FASLG_ID2_RPS19BP1_SATB1_TCF3 | 3.87E−09 |
| ATG7_FASLG_ID2_RPS19BP1_SESN3 | 3.90E−09 |
| ATG7_DRAM_FASLG_ID2_RPS19BP1 | 4.10E−09 |
| DRAM_FASLG_ID2_MMP9_RPS19BP1 | 4.34E−09 |
| ATG12_FAS_FASLG_ID2_RPS19BP1 | 4.75E−09 |
| DRAM_ATG12_FASLG_ID2_RPS19BP1 | 4.86E−09 |
| ATG12_FASLG_FRAP1_ID2_RPS19BP1 | 4.89E−09 |
| ATG12_FASLG_ID2_RPS19BP1_SATB1 | 4.93E−09 |
| ATG12_FASLG_ID2_RPS19BP1_SESN2 | 5.11E−09 |
| FASLG_ID2_STAT3_RPS19BP1_TCF3 | 5.26E−09 |
| FASLG_ID2_SIRT1_RPS19BP1_TCF3 | 5.29E−09 |
| DRAM_LC3_FASLG_ID2_RPS19BP1 | 5.35E−09 |
| ATG7_LC3_FASLG_ID2_RPS19BP1 | 5.54E−09 |
| DRAM_FASLG_FRAP1_ID2_RPS19BP1 | 5.54E−09 |
| DRAM_AKT1_FASLG_ID2_RPS19BP1 | 5.55E−09 |
| IFASLG_CDH1_ID2_MMP9_TCF3 | 2.18E−06 |
| Combinations of six types | |
| DRAM_FASLG_ID2_STAT3_RPS19BP1_TCF3 | 1.55E−10 |
| ATG12_FASLG_ID2_STAT3_RPS19BP1_TCF3 | 1.72E−10 |
| ATG7_DRAM_FASLG_ID2_STAT3_RPS19BP1 | 1.94E−10 |
| DRAM_FASLG_ID2_RPS19BP1_SATB1_TCF3 | 2.19E−10 |
| DRAM_ATG12_FASLG_ID2_STAT3_RPS19BP1 | 2.70E−10 |
| ATG12_FASLG_ID2_MMP9_STAT3_RPS19BP1 | 3.18E−10 |
| DRAM_FASLG_ID2_STAT3_RPS19BP1_SATB1 | 3.37E−10 |
| DRAM_ULK1_FASLG_ID2_STAT3_RPS19BP1 | 3.54E−10 |
| DRAM_FASLG_ID2_STAT3_RPS19BP1_SESN2 | 3.66E−10 |
| DRAM_FASLG_ID2_STAT3_RPS19BP1_SESN3 | 3.87E−10 |
| ATG7_FASLG_ID2_STAT3_RPS19BP1_TCF3 | 4.01E−10 |
| ATG12_FASLG_ID2_STAT3_RPS19BP1_SESN3 | 4.19E−10 |
| DRAM_FAS_FASLG_ID2_STAT3_RPS19BP1 | 4.19E−10 |
| ATG7_FASLG_ID2_RPS19BP1_SATB1_TCF3 | 4.23E−10 |
| ATG7_FASLG_ID2_STAT3_RPS19BP1_SATB1 | 4.68E−10 |
| DRAM_FASLG_ID2_RPS19BP1_SESN3_TCF3 | 4.97E−10 |
| ATG12_FASLG_ID2_STAT3_RPS19BP1_SESN2 | 4.98E−10 |
| DRAM_FASLG_ID2_MMP9_STAT3_RPS19BP1 | 5.21E−10 |
| ATG12_FASLG_ID2_RPS19BP1_SATB1_TCF3 | 5.22E−10 |
| ULK1_ATG12_FASLG_ID2_STAT3_RPS19BP1 | 5.40E−10 |
| DRAM_FASLG_ID2_STAT3_RPS19BP1_BHLHE41 | 5.59E−10 |
| DRAM_FAS_FASLG_ID2_RPS19BP1_TCF3 | 5.70E−10 |
| ATG12_FASLG_FRAP1_ID2_RPS19BP1_TCF3 | 5.79E−10 |
| ATG12_FASLG_ID2_RPS19BP1_SESN3_TCF3 | 5.88E−10 |
| ATG12_FAS_FASLG_ID2_STAT3_RPS19BP1 | 5.97E−10 |
| ATG7_FASLG_ID2_MMP9_STAT3_RPS19BP1 | 6.05E−10 |
| ATG7_ATG12_FASLG_ID2_STAT3_RPS19BP1 | 6.08E−10 |
| ATG7_DRAM_FASLG_ID2_RPS19BP1_SATB1 | 6.29E−10 |
| ATG12_FASLG_ID2_STAT3_RPS19BP1_BHLHE41 | 6.30E−10 |
| ATG12_FASLG_FRAP1_ID2_STAT3_RPS19BP1 | 6.34E−10 |
| ATG7_DRAM_FASLG_ID2_RPS19BP1_SESN3 | 6.38E−10 |
| IFASLG_CDH1_ID2_MMP9_RPS19BP1_TCF3 | 6.28E−09 |

TABLE 20

| Marker | p-value |
|---|---|
| One type | |
| CDH1 | 7.27E−08 |
| FAS | 2.08E−07 |
| ID2 | 4.37E−07 |
| CSE1L | 9.09E−07 |
| LAMP2 | 2.13E−06 |
| NAMPT | 7.54E−06 |
| BNIP3 | 1.05E−05 |
| BECN1 | 1.56E−05 |
| TCF3 | 2.26E−05 |
| AKT1 | 2.86E−05 |
| LC3 | 5.44E−05 |
| STAT3 | 9.10E−05 |
| FRAP1 | 9.85E−05 |
| FASLG | 3.34E−04 |
| UVRAG | 8.20E−04 |
| LAMP1 | 1.36E−03 |
| BHLHE41 | 7.24E−03 |
| SIRT1 | 8.95E−03 |
| SESN3 | 1.15E−02 |
| ATG7 | 1.61E−02 |
| ATG12 | 1.79E−02 |
| SESN2 | 6.68E−02 |
| SATB1 | 8.42E−02 |
| ULK1 | 1.22E−01 |
| DRAM | 1.63E−01 |
| DIABLO | 2.90E−01 |
| ATG3 | 2.93E−01 |
| RPS19BP1 | 3.00E−01 |
| ATG5 | 3.56E−01 |
| MMP9 | 3.63E−01 |
| E2F1 | 4.93E−01 |
| Combinations of two types | |
| CSE1L_ID2 | 6.55E−15 |
| ID2_TCF3 | 1.74E−13 |
| AKT1_CSE1L | 4.49E−13 |
| FAS_CDH1 | 2.52E−12 |
| FAS_ID2 | 6.73E−12 |
| ID2_BECN1 | 1.19E−11 |
| CDH1_BHLHE41 | 1.37E−11 |
| DRAM_CDH1 | 1.89E−11 |
| CSE1L_CDH1 | 3.44E−11 |
| BNIP3_ID2 | 1.01E−10 |
| BNIP3_CDH1 | 1.02E−10 |
| BNIP3_CSE1L | 1.48E−10 |
| LC3_CSE1L | 1.82E−10 |
| BHLHE41_NAMPT | 2.32E−10 |
| ULK1_CDH1 | 3.30E−10 |
| CSE1L_FAS | 3.60E−10 |
| AKT1_TCF3 | 3.74E−10 |
| BNIP3_FAS | 4.67E−10 |
| ATG5_CDH1 | 5.82E−10 |
| FAS_LAMP2 | 6.81E−10 |
| LC3_BECN1 | 7.00E−10 |
| FAS_FRAP1 | 8.30E−10 |
| CSE1L_FRAP1 | 8.49E−10 |
| CDH1_ID2 | 8.93E−10 |
| FRAP1_BHLHE41 | 9.98E−10 |
| FAS_NAMPT | 1.00E−09 |
| LC3_TCF3 | 1.22E−09 |
| ULK1_ID2 | 1.53E−09 |
| FAS_TCF3 | 1.70E−09 |
| ID2_NAMPT | 1.93E−09 |
| DRAM_NAMPT | 2.01E−09 |
| Combinations of three types | |
| BNIP3_CSE1L_ID2 | <1.0E−16 |
| CSE1L_ID2_BECN1 | <1.0E−16 |
| ULK1_CSE1L_ID2 | 1.11E−16 |
| AKT1_CSE1L_ID2 | 5.55E−16 |
| ATG7_CSE1L_ID2 | 5.55E−16 |
| LAMP1_CSE1L_ID2 | 7.77E−16 |
| CSE1L_FAS_ID2 | 8.88E−16 |
| CSE1L_ID2_TCF3 | 1.33E−15 |
| CSE1L_DIABLO_ID2 | 1.67E−15 |
| LC3_CSE1L_ID2 | 1.78E−15 |

TABLE 20-continued

| | |
|---|---|
| CSE1L_ID2_BHLHE41 | 1.89E−15 |
| CSE1L_ID2_STAT3 | 1.89E−15 |
| FAS_CDH1_BHLHE41 | 1.89E−15 |
| ATG5_CSE1L_ID2 | 2.33E−15 |
| CSE1L_ID2_SESN2 | 2.33E−15 |
| ATG3_CSE1L_ID2 | 2.78E−15 |
| FAS_ID2_TCF3 | 3.00E−15 |
| DRAM_FAS_CDH1 | 3.11E−15 |
| BNIP3_AKTLCSE1L | 5.00E−15 |
| CSE1L_ID2_SIRT1 | 5.44E−15 |
| CSE1L_ID2_RPS19BP1 | 5.88E−15 |
| ATG12_CSE1L_ID2 | 8.33E−15 |
| LC3_ID2_TCF3 | 1.28E−14 |
| BNIP3_LC3_CSE1L | 1.37E−14 |
| CSE1L_ID2_MMP9 | 1.61E−14 |
| LC3_AKT1 | 2.31E−14 |
| ATG7_ID2_TCF3 | 2.32E−14 |
| ID2_RPS19BP1_TCF3 | 2.36E−14 |
| CSE1L_FRAP1_ID2 | 3.18E−14 |
| AKT1_ID2_TCF3 | 3.50E−14 |
| LC3_BHLHE41_NAMPT | 4.36E−14 |
| CDH1_ID2_MMP9_TCF3 | 4.73E−12 |
| Combinations of four types | |
| AKT1_CSE1L_ID2_BHLHE41 | <1.0E−16 |
| AKT1_CSE1L_ID2_TCF3 | <1.0E−16 |
| ATG5_BNIP3_CSE1L_ID2 | <1.0E−16 |
| ATG5_CSE1L_ID2_BECN1 | <1.0E−16 |
| ATG7_BNIP3_CSE1L_ID2 | <1.0E−16 |
| ATG7_CSE1L_ID2_BHLHE41 | <1.0E−16 |
| ATG7_CSE1L_ID2_TCF3 | <1.0E−16 |
| ATG7_LC3_CSE1L_ID2 | <1.0E−16 |
| ATG7_ULK1_CSE1L_ID2 | <1.0E−16 |
| BNIP3_AKT1_CSE1L_ID2 | <1.0E−16 |
| BNIP3_CSE1L_DIABLO_ID2 | <1.0E−16 |
| BNIP3_CSE1L_FAS_ID2 | <1.0E−16 |
| BNIP3_CSE1L_FRAP1_ID2 | <1.0E−16 |
| BNIP3_CSE1L_ID2_BECN1 | <1.0E−16 |
| BNIP3_CSE1L_ID2_RPS19BP1 | <1.0E−16 |
| BNIP3_CSE1L_ID2_SATB1 | <1.0E−16 |
| BNIP3_CSE1L_ID2_SESN2 | <1.0E−16 |
| BNIP3_CSE1L_ID2_STAT3 | <1.0E−16 |
| BNIP3_LC3_CSE1L_ID2 | <1.0E−16 |
| BNIP3_ULK1_CSE1L_ID2 | <1.0E−16 |
| CSE1L_DIABLO_ID2_BECN1 | <1.0E−16 |
| CSE1L_FRAP1_ID2_BHLHE41 | <1.0E−16 |
| CSE1L_ID2_BHLHE41_BECN1 | <1.0E−16 |
| CSE1L_ID2_BHLHE41_NAMPT | <1.0E−16 |
| CSE1L_ID2_RPS19BP1_SESN2 | <1.0E−16 |
| CSE1L_ID2_SESN2_BECN1 | <1.0E−16 |
| CSE1L_ID2_STAT3_BHLHE41 | <1.0E−16 |
| LC3_CSE1L_ID2_BECN1 | <1.0E−16 |
| LC3_CSE1L_ID2_BHLHE41 | <1.0E−16 |
| LC3_CSE1L_ID2_SIRT1 | <1.0E−16 |
| LC3_CSE1L_ID2_TCF3 | <1.0E−16 |
| Combinations of five types | |
| AKT1_ATG12_CSE1L_ID2_TCF3 | <1.0E−16 |
| AKT1_ATG3_CSE1_LID2_TCF3 | <1.0E−16 |
| AKT1_CSE1L_DIABLO_ID2_BHLHE41 | <1.0E−16 |
| AKT1_CSE1L_DIABLO_ID2_TCF3 | <1.0E−16 |
| AKT1_CSE1L_FAS_ID2_BECN1 | <1.0E−16 |
| AKT1_CSE1L_FAS_ID2_TCF3 | <1.0E−16 |
| AKT1_CSE1L_FRAP1_ID2_BHLHE41 | <1.0E−16 |
| AKT1_CSE1L_FRAP1_ID2_TCF3 | <1.0E−16 |
| AKT1_CSE1L_ID2_BHLHE41_BECN1 | <1.0E−16 |
| AKT1_CSE1L_ID2_BHLHE41_NAMPT | <1.0E−16 |
| AKT1_CSE1L_ID2_BHLHE41_SESN2 | <1.0E−16 |
| AKT1_CSE1L_ID2_BHLHE41_TCF3 | <1.0E−16 |
| AKT1_CSE1L_ID2_MMP9_TCF3 | <1.0E−16 |
| AKT1_CSE1L_ID2_NAMPT_TCF3 | <1.0E−16 |
| AKT1_CSE1L_ID2_RPS19BP1_BHLHE41 | <1.0E−16 |
| AKT1_CSE1L_ID2_RPS19BP1_SESN2 | <1.0E−16 |
| AKT1_CSE1L_ID2_RPS19BP1_TCF3 | <1.0E−16 |
| AKT1_CSE1L_ID2_SATB1_TCF3 | <1.0E−16 |
| AKT1_CSE1L_ID2_SESN2_BECN1 | <1.0E−16 |
| AKT1_CSE1L_ID2_SESN2_TCF3 | <1.0E−16 |
| AKT1_CSE1L_ID2_SIRT1_TCF3 | <1.0E−16 |
| AKT1_CSE1L_ID2_STAT3_BHLHE41 | <1.0E−16 |
| AKT1_CSE1L_ID2_STAT3_TCF3 | <1.0E−16 |
| AKT1_CSE1L_ID2_TCF3_BECN1 | <1.0E−16 |
| ATG3_CSE1L_FRAP1_ID2_BHLHE41 | <1.0E−16 |
| ATG3_CSE1L_ID2_RPS19BP1_TCF3 | <1.0E−16 |
| ATG3_CSE1L_ID2_STAT3_BHLHE41 | <1.0E−16 |
| ATG5_AKT1_CSE1L_ID2_TCF3 | <1.0E−16 |
| ATG5_ATG7_CSE1L_ID2_TCF3 | <1.0E−16 |
| ATG5_ATG7_ULK1_CSE1L_ID2 | <1.0E−16 |
| ATG5_BNIP3_AKT1_CSE1L_ID2 | <1.0E−16 |
| FAS_CDH1_ID2_MMP9_TCF3 | 4.00E−15 |
| Combinations of six types | |
| AKT1_ATG12_DIABLO_ID2_TCF3 | <1.0E−16 |
| AKT1_ATG12_CSE1L_FAS_ID2_TCF3 | <1.0E−16 |
| AKT1_ATG12_CSE1L_ID2_BHLHE41_SESN2 | <1.0E−16 |
| AKT1_ATG12_CSE1L_ID2_BHLHE41_TCF3 | <1.0E−16 |
| AKT1_ATG12_CSE1L_ID2_RPS19BP1_TCF3 | <1.0E−16 |
| AKT1_ATG12_CSE1L_ID2_SATB1_TCF3 | <1.0E−16 |
| AKT1_ATG12_CSE1L_ID2_SESN2_TCF3 | <1.0E−16 |
| AKT1_ATG3_CSE1L_DIABLO_ID2_BHLHE41 | <1.0E−16 |
| AKT1_ATG3_CSE1L_DIABLO_ID2_TCF3 | <1.0E−16 |
| AKT1_ATG3_CSE1L_FAS_ID2_TCF3 | <1.0E−16 |
| AKT1_ATG3_CSE1L_FRAP1_ID2_BHLHE41 | <1.0E−16 |
| AKT1_ATG3_CSE1L_ID2_BHLHE41_BECN1 | <1.0E−16 |
| AKT1_ATG3_CSE1L_ID2_BHLHE41_NAMPT | <1.0E−16 |
| AKT1_ATG3_CSE1L_ID2_BHLHE41_SESN2 | <1.0E−16 |
| AKT1_ATG3_CSE1L_ID2_BHLHE41_TCF3 | <1.0E−16 |
| AKT1_ATG3_CSE1L_ID2_MMP9_TCF3 | <1.0E−16 |
| AKT1_ATG3_CSE1L_ID2_RPS19BP1_BHLHE41 | <1.0E−16 |
| AKT1_ATG3_CSE1L_ID2_RPS19BP1_TCF3 | <1.0E−16 |
| AKT1_ATG3_CSE1L_ID2_SATB1_TCF3 | <1.0E−16 |
| AKT1_ATG3_CSE1L_ID2_SESN2_TCF3 | <1.0E−16 |
| AKT1_ATG3_CSE1L_ID2_SIRT1_ICF3 | <1.0E−16 |
| AKT1_ATG3_CSE1L_ID2_STAT3_BHLHE41 | <1.0E−16 |
| AKT1_ATG3_CSE1L_ID2_STAT3_TCF3 | <1.0E−16 |
| AKT1_ATG3_CSE1L_ID2_TCF3_BECN1 | <1.0E−16 |
| AKT1_CSE1L_DIABLO_FAS_CDH1_BHLHE41 | <1.0E−16 |
| AKT1_CSE1L_DIABLO_FAS_ID2_BECN1 | <1.0E−16 |
| AKT1_CSE1L_DIABLO_FAS_ID2_TCF3 | <1.0E−16 |
| AKT1_CSE1L_DIABLO_FRAP1_ID2_BHLHE41 | <1.0E−16 |
| AKT1_CSE1L_DIABLO_ID2_BHLHE41_BECN1 | <1.0E−16 |
| AKT1_CSE1L_DIABLO_ID2_BHLHE41_NAMPT | <1.0E−16 |
| AKT1_CSE1L_DIABLO_ID2_BHLHE41_SATB1 | <1.0E−16 |
| DRAM_FAS_CDH1_ID2_MMP9_TCF3 | <1.0E−16 |

TABLE 21

| Marker | p-value |
|---|---|
| One type | |
| FASLG | 2.12E−04 |
| CSE1L | 1.85E−03 |
| FAS | 3.01E−03 |
| ID2 | 4.85E−03 |
| TCF3 | 8.81E−03 |
| LAMP2 | 1.17E−02 |
| AKT1 | 2.35E−02 |
| ULK1 | 6.69E−02 |
| SESN2 | 7.32E−02 |
| BECN1 | 8.16E−02 |
| SESN3 | 8.49E−02 |
| LC3 | 1.02E−01 |
| SATB1 | 1.10E−01 |
| DRAM | 1.11E−01 |
| RPS19BP1 | 1.24E−01 |
| STAT3 | 1.90E−01 |
| CDH1 | 1.94E−01 |
| FRAP1 | 2.26E−01 |
| UVRAG | 2.61E−01 |
| BHLHE41 | 2.70E−01 |
| ATG5 | 3.41E−01 |
| MMP9 | 3.73E−01 |
| E2F1 | 4.76E−01 |
| BNIP3 | 4.92E−01 |
| LAMP1 | 4.96E−01 |
| NAMPT | 7.13E−01 |
| ATG3 | 7.51E−01 |

TABLE 21-continued

| Marker | p-value |
|---|---|
| DIABLO | 7.99E−01 |
| ATG12 | 8.89E−01 |
| SIRT1 | 9.53E−01 |
| ATG7 | 9.86E−01 |
| Combinations of two types | |
| FASLG_RPS19BP1 | 9.60E−07 |
| FASLG_TCF3 | 4.89E−06 |
| DRAM_FASLG | 1.03E−05 |
| ATG12_FASLG | 1.05E−05 |
| AKT1_CSE1L | 1.17E−05 |
| CSE1L_ID2 | 1.23E−05 |
| FASLG_MMP9 | 1.57E−05 |
| ATG7_FASLG | 1.78E−05 |
| FASLG_ID2 | 2.19E−05 |
| ULK1_ID2 | 2.52E−05 |
| ID2_TCF3 | 2.97E−05 |
| CSE1L_FASLG | 3.13E−05 |
| RPS19BP1_LAMP2 | 3.54E−05 |
| ID2_SESN2 | 5.44E−05 |
| E2F1_FASLG | 7.03E−05 |
| FAS_ID2 | 7.41E−05 |
| LC3_FASLG | 8.16E−05 |
| DIABLO_FASLG | 8.86E−05 |
| FASLG_SESN2 | 1.00E−04 |
| FASLG_SESN3 | 1.02E−04 |
| ATG3_FASLG | 1.03E−04 |
| FASLG_STAT3 | 1.18E−04 |
| FASLG_BHLHE41 | 1.22E−04 |
| FASLG_SATB1 | 1.54E−04 |
| FASLG_SIRT1 | 1.58E−04 |
| CSE1L_FAS | 1.59E−04 |
| AKT1_FASLG | 1.91E−04 |
| ULK1_FASLG | 1.95E−04 |
| FASLG_UVRAG | 2.06E−04 |
| ATG5_FASLG | 2.36E−04 |
| FASLG_BECN1 | 2.37E−04 |
| Combinations of three types | |
| FASLG_ID2_RPS19BP1 | 5.41E−08 |
| FASLG_RPS19BP1_TCF3 | 9.51E−08 |
| DRAM_FASLG_RPS19BP1 | 1.44E−07 |
| ATG12_FASLG_TCF3 | 1.57E−07 |
| DRAM_FASLG_TCF3 | 1.94E−07 |
| FASLG_STATS_RPS19BP1 | 2.04E−07 |
| LC3_FASLG_RPS19BP1 | 2.41E−07 |
| ATG12_FASLG_RPS19BP1 | 2.56E−07 |
| FASLG_MMP9_RPS19BP1 | 2.58E−07 |
| FASLG_RPS19BP1_SESN3 | 2.93E−07 |
| ULK1_CSE1L_ID2 | 3.55E−07 |
| ATG7_FASLG_TCF3 | 4.06E−07 |
| AKT1_FASLG_RPS19BP1 | 4.18E−07 |
| FASLG_RPS19BP1_SATB1 | 4.42E−07 |
| FASLG_FRAP1_RPS19BP1 | 4.76E−07 |
| ATG7_FASLG_RPS19BP1 | 5.24E−07 |
| FASLG_RPS19BP1_BHLHE41 | 6.12E−07 |
| FASLG_RPS19BP1_SESN2 | 6.56E−07 |
| FASLG_ID2_TCF3 | 6.59E−07 |
| ATG12_FASLG_MMP9 | 7.89E−07 |
| FASLG_CDH1_RPS19BP1 | 8.31E−07 |
| FASLG_RPS19BP1_NAMPT | 9.01E−07 |
| ATG12_FASLG_ID2 | 9.27E−07 |
| FASLG_RPS19BP1_LAMP2 | 9.34E−07 |
| FASLG_RPS19BP1_UVRAG | 9.61E−07 |
| FASLG_RPS19BP1_BECN1 | 9.63E−07 |
| ULK1_FASLG_RPS19BP1 | 9.87E−07 |
| FASLG_MMP9_TCF3 | 1.01E−06 |
| CSE1L_ID2_SESN2 | 1.08E−06 |
| FAS_FASLG_RPS19BP1 | 1.12E−06 |
| FASLG_SIRT1_RPS19BP1 | 1.12E−06 |
| Combinations of four types | |
| FASLG_ID2_RPS19BP1_TCF3 | 2.39E−09 |
| DRAM_FASLG_ID2_RPS19BP1 | 7.50E−09 |
| ATG12_FASLG_ID2_RPS19BP1 | 9.10E−09 |
| DRAM_FASLG_STATS_RPS19BP1 | 1.04E−08 |
| ATG12_FASLG_ID2_TCF3 | 1.14E−08 |
| ATG7_FASLG_ID2_RPS19BP1 | 1.22E−08 |

TABLE 21-continued

| Marker | p-value |
|---|---|
| ATG12_FASLG_STATS_TCF3 | 1.48E−08 |
| ATG7_FASLG_ID2_TCF3 | 1.56E−08 |
| FASLG_ID2_STATS_RPS19BP1 | 1.61E−08 |
| ATG12_FASLG_STATS_RPS19BP1 | 1.76E−08 |
| LC3_FASLG_RPS19BP1_TCF3 | 1.86E−08 |
| DRAM_FASLG_RPS19BP1_TCF3 | 1.86E−08 |
| FASLG_ID2_MMP9_RPS19BP1 | 1.87E−08 |
| FASLG_ID2_RPS19BP1_SESN2 | 1.97E−08 |
| FASLG_ID2_RPS19BP1_SESN3 | 2.69E−08 |
| FASLG_RPS19BP1_SATB1_TCF3 | 2.87E−08 |
| ATG12_FASLG_RPS19BP1_TCF3 | 2.90E−08 |
| AKT1_FASLG_RPS19BP1_TCF3 | 2.98E−08 |
| DRAM_FASLG_ID2_TCF3 | 3.15E−08 |
| FASLG_STAT3_RPS19BP1_TCF3 | 3.19E−08 |
| FASLG_ID2_RPS19BP1_SATB1 | 3.20E−08 |
| DRAM_FASLG_RPS19BP1_SESN3 | 3.25E−08 |
| DRAM_AKT1_FASLG_RPS19BP1 | 3.70E−08 |
| DRAM_LC3_FASLG_RPS19BP1 | 3.73E−08 |
| LC3_ULK1_CSE1L_ID2 | 3.84E−08 |
| ATG12_FASLG_MMP9_TCF3 | 3.99E−08 |
| AKT1_ATG12_FASLG_TCF3 | 4.05E−08 |
| FASLG_ID2_RPS19BP1_UVRAG | 4.12E−08 |
| CSE1L_FASLG_ID2_RPS19BP1 | 4.19E−08 |
| DIABLO_FASLG_ID2_RPS19BP1 | 4.19E−08 |
| FASLG_FRAP1_RPS19BP1_TCF3 | 4.28E−08 |
| CDH1_ID2_MMP9_TCF3_ | 7.94E−04 |
| Combinations of five types | |
| DRAM_FASLG_ID2_RPS19BP1_TCF3 | 3.98E−10 |
| ATG12_FASLG_ID2_RPS19BP1_TCF3 | 4.16E−10 |
| ATG12_FASLG_ID2_STAT3_RPS19BP1 | 7.74E−10 |
| DRAM_FASLG_ID2_STAT3_RPS19BP1 | 8.29E−10 |
| ATG7_FASLG_ID2_RPS19BP1_TCF3 | 8.31E−10 |
| FASLG_ID2_RPS19BP1_SATB1_TCF3 | 9.81E−10 |
| FASLG_ID2_STAT3_RPS19BP1_TCF3 | 1.13E−09 |
| ATG7_FASLG_ID2_STAT3_RPS19BP1 | 1.24E−09 |
| FASLG_ID2_RPS19BP1_SESN2_TCF3 | 1.30E−09 |
| FASLG_ID2_MMP9_RPS19BP1_TCF3 | 1.59E−09 |
| FASLG_ID2_SIRT1_RPS19BP1_TCF3 | 1.61E−09 |
| FASLG_ID2_RPS19BP1_TCF3_UVRAG | 1.65E−09 |
| ATG12_FASLG_ID2_SESN2_TCF3 | 1.65E−09 |
| LC3_FASLG_ID2_RPS19BP1_TCF3 | 2.15E−09 |
| FASLG_ID2_RPS19BP1_TCF3_BECN1 | 2.19E−09 |
| DRAM_FASLG_STAT3_RPS19BP1_TCF3 | 2.20E−09 |
| ATG12_FASLG_ID2_STAT3_TCF3 | 2.24E−09 |
| DRAM_FASLG_ID2_RPS19BP1_SESN2 | 2.39E−09 |
| ULK1_FASLG_ID2_RPS19BP1_TCF3 | 2.47E−09 |
| FASLG_ID2_RPS19BP1_SESN3_TCF3 | 2.55E−09 |
| ATG12_FASLG_STAT3_RPS19BP1_TCF3 | 2.62E−09 |
| AKT1_FASLG_ID2_RPS19BP1_TCF3 | 2.70E−09 |
| ATG12_FASLG_ID2_RPS19BP1_SESN2 | 2.72E−09 |
| FASLG_FRAP1_ID2_RPS19BP1_TCF3 | 2.91E−09 |
| DIABLO_FASLG_ID2_RPS19BP1_TCF3 | 2.98E−09 |
| DRAM_ATG12_FASLG_STAT3_TCF3 | 2.99E−09 |
| BNIP3_FASLG_ID2_RPS19BP1_TCF3 | 3.00E−09 |
| DRAM_LC3_FASLG_STAT3_RPS19BP1 | 3.15E−09 |
| ATG7_DRAM_FASLG_ID2_TCF3 | 3.17E−09 |
| DRAM_FASLG_ID2_RPS19BP1_SATB1 | 3.17E−09 |
| ATG12_FASLG_MMP9_STAT3_TCF3 | 3.18E−09 |
| FASLG_CDH1JD2_MMP9_TCF3 | 5.07E−07 |
| Combinations of six types | |
| ATG12_FASLG_ID2_STAT3_RPS19BP1_TCF3 | 4.12E−11 |
| DRAM_FASLG_ID2_STAT3_RPS19BP1_TCF3 | 6.35E−11 |
| DRAM_FASLG_ID2_RPS19BP1_SATB1_TCF3 | 1.02E−10 |
| ATG7_FASLG_ID2_STAT3_RPS19BP1_TCF3 | 1.26E−10 |
| ATG12_FASLG_FRAP1_ID2_RPS19BP1_TCF3 | 1.42E−10 |
| ATG7_ATG12_FASLG_ID2_STAT3_TCF3 | 1.57E−10 |
| ATG12_FASLG_ID2_RPS19BP1_SATB1_TCF3 | 1.68E−10 |
| ATG7_FASLG_ID2_RPS19BP1_SATB1_TCF3 | 1.72E−10 |
| ATG12_FASLG_ID2_RPS19BP1_SESN2_TCF3 | 1.89E−10 |
| DRAM_FASLG_ID2_RPS19BP1_SESN2_TCF3 | 1.95E−10 |
| ATG7_DRAM_FASLG_ID2_STAT3_RPS19BP1 | 1.95E−10 |
| AKT1_ATG12_FASLG_ID2_RPS19BP1_TCF3 | 2.08E−10 |
| ATG12_FASLG_ID2_STAT3_RPS19BP1_SESN2 | 2.20E−10 |
| DRAM_ATG12_FASLG_ID2_STAT3_RPS19BP1 | 2.23E−10 |
| ATG12_FASLG_ID2_RPS19BP1_SESN3_TCF3 | 2.29E−10 |
| DRAM_FASLG_ID2_STAT3_RPS19BP1_SESN2 | 2.58E−10 |

TABLE 21-continued

| Marker | p-value |
|---|---|
| ATG7_DRAM_FASLG_ID2_STAT3_TCF3 | 2.63E−10 |
| DRAM_AKT1_FASLG_ID2_RPS19BP1_TCF3 | 2.68E−10 |
| ATG12_FASLG_ID2_MMP9_STAT3_RPS19BP1 | 2.70E−10 |
| DRAM_FASLG_ID2_RPS19BP1_SESN3_TCF3 | 2.94E−10 |
| DRAM_ATG12_FASLG_ID2_STAT3_TCF3 | 3.16E−10 |
| LC3_ATG12_FASLG_ID2_RPS19BP1_TCF3 | 3.20E−10 |
| ATG12_FASLG_ID2_MMP9_RPS19BP1_TCF3 | 3.24E−10 |
| ATG12_FASLG_ID2_RPS19BP1_TCF3_LAMP2 | 3.30E−10 |
| DRAM_FASLG_FRAP1_ID2_RPS19BP1_TCF3 | 3.38E−10 |
| DRAM_FAS_FASLG_ID2_RPS19BP1_TCF3 | 3.39E−10 |
| ATG12_FAS_FASLG_ID2_RPS19BP1_TCF3 | 3.40E−10 |
| ATG12_FASLG_ID2_STAT3_SESN2_TCF3 | 3.46E−10 |
| ATG12_FASLG_CDH1_ID2_RPS19BP1_TCF3 | 3.57E−10 |
| DRAM_ATG12_FASLG_ID2_RPS19BP1_TCF3 | 3.63E−10 |
| ATG12_FASLG_ID2_STAT3_RPS19BP1_SESN3 | 3.71E−10 |
| FASLG_CDH1_ID2_MMP9_RPS19BP1_TCF3 | 2.21E−09 |

Each of the markers or their combination shows p-values low enough to be considered significant in terms of all of recurrence, survival, and disease-free survival. In particular, in the case of the combination of the two or more markers, all the p-values for recurrence, survival, and disease-free survival were less than 0.05, which is desirable. As a p-value becomes lower, the statistical significance becomes higher. Thus, the low p-values suggest that the estimation for prognosis of liver cancer by each of the markers or their combination is highly accurate.

From the above results, it can be found that as more markers of the present disclosure are combined, the p-value is lower. This means that the more markers of the present disclosure are combined, the lower p-values, which means higher significance, are shown, which means that the more improved accuracy would be achieved in the estimation for prognosis based on the combinations of the markers.

Also, it can be found that the prognosis of liver cancer of the A2 group can be predicted effectively by the method for predicting prognosis of liver cancer of the present disclosure, which is targeted at the markers.

Further, cross-validation was performed for 31 genes. In the cross-validation, patients not classified according to stage were randomly divided into two groups (positive group: 274 patients; test group: 273 patients). With the reference value which was considered statistically significant for the positive group fixed, for the test group, the accuracy of estimation was calculated to be the level of $p<0.05$ or $p<0.001$ with respect to recurrence, survival and disease-free survival.

Among the results of cross-validation of the prediction of recurrence, survival and disease-free survival for a combination of two or more of the 31 genes in all patients not classified according to stage, representative examples showing the excellent accuracy of prognosis in each aspect are as follows:

Recurrence: ATG3_FASLG_ID2_RPS19BP1_SESN3_TCF3 (94% at the level of $p<0.05$)

Survival: CSE1L_FAS_FRAP1_CDH1_BHLHE41_SESN2 (95% at the level of $p<0.0001$)

Disease-free survival: ATG12_FASLG_ID2_STAT3_RPS19BP1_TCF3 (95.0% at the level of $p<0.05$)

Example 2: Predicting Prognosis of Liver Cancer in the A1 Group

An experiment was performed in the same manner as in Example 1, except for experimenting on a patient group determined as the A1 group {a group of portal vein invasion-negative patients in stage 0 or A of BCLC (Barcelona-Clinic Liver Cancer) staging system, having a tumor which is 5 cm or less in size, or 3 or less tumors which are 3 cm or less in size} (277 patients). Kaplan-Meier curves were prepared with respect to the prediction of recurrence, survival, and disease-free survival and the results are shown in FIGS. 23~43. Kaplan-Meier curves for recurrence are shown in FIGS. 23~29, Kaplan-Meier curves for survival are shown in FIGS. 30~36, and Kaplan-Meier curves for disease-free survival are shown in FIGS. 37~43.

As can be seen from the drawings, in Kaplan-Meier curves completed with respect to recurrence, survival, and disease-free survival, the above markers form curves where cases of high expression and low expression are distinctively distinguished from each other. This means that there are remarkable differences in interval recurrence rate or interval survival rate and cumulative recurrence rate or cumulative survival rate based thereon between the cases where the marker is in high expression and low expression, and that consequently, the expression pattern of the marker can be an index showing recurrence possibility or survival possibility of patients.

Also, significance tests were performed by log-rank test with respect to each of the markers and their combination by calculating observation values and expected values at every point of recurrence or death to obtain p-values. The results are shown in the following Tables 22~29. The results of using a marker alone are shown in Table 22, the results of a combination of two markers are shown in Table 23, the results of a combination of three markers are shown in Table 24, the results of a combination of four markers are shown in Table 25, the results of a combination of five markers are shown in Table 26, the results of a combination of six markers are shown in Table 27, the results of a combination of seven markers are shown in Table 28, and the results of a combination of eight markers are shown in Table 29.

TABLE 22

| Marker | p-value |
|---|---|
| Recurrence | |
| BCL2L1 | 1.38E−02 |
| BECN1 | 1.50E−02 |
| BAX | 1.60E−02 |
| CDH2 | 1.67E−02 |
| NAMPT | 1.71E−02 |
| TWIST1 | 2.19E−02 |
| RPS19BP1 | 2.77E−02 |
| MMP2 | 2.88E−02 |
| SESN3 | 3.89E−02 |
| ID2 | 3.92E−02 |
| AGER | 4.00E−02 |
| ATG12 | 4.67E−02 |
| KIAA1967 | 5.73E−02 |
| FASLG | 6.51E−02 |
| TCF3 | 7.55E−02 |
| TKT | 7.85E−02 |
| RAPTOR | 8.57E−02 |
| PRKAA1 | 1.07E−01 |
| SIRT1 | 1.15E−01 |
| CCNG2 | 1.17E−01 |
| CSE1L | 1.17E−01 |
| CASP8 | 1.32E−01 |
| BNIP3 | 1.40E−01 |
| SESN1 | 1.56E−01 |
| BCL2 | 1.65E−01 |
| LC3 | 1.79E−01 |

TABLE 22-continued

| Marker | p-value |
|---|---|
| RAGE | 1.84E−01 |
| PTEN | 1.84E−01 |
| BHLHE41 | 2.06E−01 |
| LAMP1 | 2.36E−01 |
| HMGB1 | 2.59E−01 |
| DRAM | 2.74E−01 |
| XIAP | 2.94E−01 |
| TP63 | 3.11E−01 |
| AKT1 | 3.66E−01 |
| CBS | 3.74E−01 |
| HMGB2 | 3.75E−01 |
| LAMP2 | 3.85E−01 |
| SATB1 | 3.90E−01 |
| UVRAG | 4.60E−01 |
| DIABLO | 4.65E−01 |
| E2F1 | 4.78E−01 |
| ATG7 | 4.83E−01 |
| NNMT | 5.04E−01 |
| AIFM1 | 5.60E−01 |
| CDH1 | 6.66E−01 |
| ULK1 | 6.68E−01 |
| STAT3 | 7.17E−01 |
| FAS | 7.34E−01 |
| FRAP1 | 7.36E−01 |
| VEGF | 7.64E−01 |
| ATG5 | 7.79E−01 |
| CASP3 | 7.93E−01 |
| ATG3 | 8.36E−01 |
| CIAP2 | 9.33E−01 |
| SESN2 | 9.35E−01 |
| MMP9 | 9.53E−01 |
| Survival | |
| ID2 | 5.13E−06 |
| CDH1 | 2.19E−05 |
| LC3 | 1.09E−02 |
| TKT | 1.29E−02 |
| AKT1 | 1.54E−02 |
| AIFM1 | 2.16E−02 |
| BNIP3 | 3.10E−02 |
| LAMP1 | 3.57E−02 |
| FRAP1 | 3.86E−02 |
| FASLG | 6.14E−02 |
| SESN3 | 7.42E−02 |
| NAMPT | 8.01E−02 |
| E2F1 | 9.08E−02 |
| MMP2 | 9.50E−02 |
| SESN1 | 9.58E−02 |
| ATG5 | 1.11E−01 |
| LAMP2 | 1.14E−01 |
| HMGB2 | 1.81E−01 |
| ULK1 | 1.96E−01 |
| SATB1 | 2.07E−01 |
| SIRT1 | 2.12E−01 |
| TWIST1 | 2.36E−01 |
| ATG12 | 2.46E−01 |
| CDH2 | 2.62E−01 |
| CIAP2 | 3.66E−01 |
| FAS | 3.97E−01 |
| RPS19BP1 | 4.40E−01 |
| CBS | 4.45E−01 |
| ATG7 | 4.76E−01 |
| STAT3 | 4.76E−01 |
| HMGB1 | 5.14E−01 |
| ATG3 | 5.18E−01 |
| TCF3 | 6.06E−01 |
| DRAM | 6.07E−01 |
| BAX | 6.19E−01 |
| KIAA1967 | 6.38E−01 |
| BCL2 | 6.46E−01 |
| SESN2 | 6.73E−01 |
| CCNG2 | 6.93E−01 |
| VEGF | 7.04E−01 |
| NNMT | 7.15E−01 |
| XIAP | 7.17E−01 |
| AGER | 7.37E−01 |
| CSE1L | 7.51E−01 |
| RAGE | 7.69E−01 |

TABLE 22-continued

| Marker | p-value |
|---|---|
| MMP9 | 8.11E−01 |
| BCL2L1 | 8.29E−01 |
| DIABLO | 8.59E−01 |
| RAPTOR | 8.62E−01 |
| CASP3 | 8.69E−01 |
| BHLHE41 | 8.77E−01 |
| CASP8 | 9.03E−01 |
| PTEN | 9.31E−01 |
| BECN1 | 9.42E−01 |
| TP63 | 9.68E−01 |
| PRKAA1 | 9.85E−01 |
| UVRAG | 9.90E−01 |
| Disease-free survival | |
| MMP2 | 1.13E−02 |
| ID2 | 1.37E−02 |
| TWIST1 | 1.53E−02 |
| BECN1 | 1.76E−02 |
| BAX | 2.47E−02 |
| BCL2L1 | 2.61E−02 |
| CDH2 | 2.77E−02 |
| FASLG | 3.64E−02 |
| AGER | 3.70E−02 |
| ATG12 | 3.72E−02 |
| TKT | 3.91E−02 |
| NAMPT | 6.77E−02 |
| SESN3 | 7.09E−02 |
| TCF3 | 7.71E−02 |
| KIAA1967 | 8.14E−02 |
| LC3 | 1.15E−01 |
| AKT1 | 1.29E−01 |
| BCL2 | 1.35E−01 |
| PRKAA1 | 1.36E−01 |
| RAGE | 1.36E−01 |
| RAPTOR | 1.39E−01 |
| CCNG2 | 1.41E−01 |
| CASP8 | 1.56E−01 |
| RPS19BP1 | 1.65E−01 |
| SIRT1 | 1.73E−01 |
| BHLHE41 | 1.94E−01 |
| HMGB2 | 2.01E−01 |
| CSE1L | 2.43E−01 |
| SESN1 | 2.46E−01 |
| BNIP3 | 2.64E−01 |
| HMGB1 | 2.66E−01 |
| XIAP | 2.70E−01 |
| DRAM | 2.99E−01 |
| PTEN | 3.10E−01 |
| ULK1 | 3.65E−01 |
| UVRAG | 4.00E−01 |
| CBS | 4.27E−01 |
| SATB1 | 4.52E−01 |
| LAMP1 | 4.72E−01 |
| NNMT | 5.37E−01 |
| TP63 | 5.47E−01 |
| MMP9 | 5.64E−01 |
| ATG7 | 5.80E−01 |
| ATG3 | 5.99E−01 |
| DIABLO | 6.01E−01 |
| AIFM1 | 6.11E−01 |
| VEGF | 6.84E−01 |
| CDH1 | 6.87E−01 |
| ATG5 | 7.08E−01 |
| E2F1 | 7.46E−01 |
| STAT3 | 7.47E−01 |
| SESN2 | 8.00E−01 |
| CASP3 | 8.05E−01 |
| CIAP2 | 8.12E−01 |
| LAMP2 | 8.19E−01 |
| FRAP1 | 8.43E−01 |
| FAS | 9.39E−01 |

TABLE 23

| Marker | p-value |
|---|---|
| Recurrence | |
| FRAP1_SESN1 | 5.25E−05 |
| FRAP1_TWIST1 | 5.74E−05 |
| FRAP1_CASP3 | 6.05E−05 |
| FRAP1_CCNG2 | 8.19E−05 |
| BAX_FRAP1 | 8.19E−05 |
| FRAPLNNMT | 8.59E−05 |
| BCL2L1_FRAP1 | 8.75E−05 |
| AIFM1_FRAP1 | 1.04E−04 |
| FRAP1_RAGE | 1.21E−04 |
| FRAP1_VEGF | 1.21E−04 |
| ID2_CDH2 | 1.27E−04 |
| FRAPLPTEN | 1.43E−04 |
| NAMPT_SESN3 | 1.45E−04 |
| BCL2_FRAP1 | 1.50E−04 |
| CDH2_SESN3 | 1.96E−04 |
| FRAP1_RAPTOR | 2.02E−04 |
| FRAP1_KIAA1967 | 2.25E−04 |
| FRAP1_XIAP | 3.24E−04 |
| BECN1_SESN3 | 3.45E−04 |
| HMGB1_TWIST1 | 4.29E−04 |
| ID2_NAMPT | 4.55E−04 |
| FRAP1_PRKAA1 | 4.65E−04 |
| ID2_RPS19BP1 | 4.97E−04 |
| BAX_LC3 | 6.40E−04 |
| FRAP1_TP63 | 7.32E−04 |
| ATG12_SESN3 | 8.72E−04 |
| BAX_TWIST1 | 9.07E−04 |
| RPS19BP1_SESN3 | 1.04E−03 |
| BAX_MMP2 | 1.06E−03 |
| SESN1_STAT3 | 1.15E−03 |
| LC3_TWIST1 | 1.36E−03 |
| MMP2_NAMPT | 1.37E−03 |
| ID2_BECN1 | 1.40E−03 |
| BCL2L1_LC3 | 1.42E−03 |
| MMP2_RPS19BP1 | 1.47E−03 |
| ATG7_BCL2L1 | 1.55E−03 |
| ID2_TWIST1 | 1.55E−03 |
| CDH2_HMGB1 | 1.60E−03 |
| CDH2_MMP2 | 1.61E−03 |
| ATG7_TWIST1 | 1.71E−03 |
| BAX_SESN3 | 1.73E−03 |
| FASLG_NAMPT | 1.79E−03 |
| ATG7_BAX | 1.83E−03 |
| TKT_NAMPT | 1.84E−03 |
| STAT3_TWIST_1 | 1.85E−03 |
| BCL2L1_MMP2 | 1.92E−03 |
| LC3_KIAA1967 | 1.96E−03 |
| BAX_BECN1 | 1.99E−03 |
| ATG12_ID2 | 2.08E−03 |
| BECNLM_MP2 | 2.10E−03 |
| AKT1_BAX | 2.22E−03 |
| LC3_RAPTOR | 2.25E−03 |
| BAX_RPS19BP1 | 2.26E−03 |
| BAX_TKT | 2.27E−03 |
| BAX_SATB1 | 2.31E−03 |
| LC3_NAMPT | 2.34E−03 |
| KIAA1967_MMP2 | 2.35E−03 |
| Survival | |
| CDH1_ID2 | 3.21E−08 |
| ATG12_CDH1 | 1.73E−07 |
| LAMP1_ID2 | 5.08E−07 |
| BNIP3_ID2 | 7.33E−07 |
| ATG12_ID2 | 1.08E−06 |
| CDH1_HMGB2 | 1.19E−06 |
| ID2_HMGB2 | 1.38E−06 |
| E2F1_ID2 | 1.56E−06 |
| TKT_ID2 | 2.54E−06 |
| DRAM_ID2 | 2.72E−06 |
| ATG5_ID2 | 2.80E−06 |
| ID2_BECN1 | 3.13E−06 |
| ID2_AGER | 3.32E−06 |
| ID2_MMP2 | 3.56E−06 |
| ATG3_ID2 | 3.82E−06 |
| ID2_LAMP2 | 4.03E−06 |
| ULK1_CDH1 | 4.24E−06 |

TABLE 23-continued

| Marker | p-value |
|---|---|
| CSE1L_ID2 | 4.25E−06 |
| TKT_CDH1 | 4.29E−06 |
| LC3_CDH1 | 4.77E−06 |
| ID2_MMP9 | 4.89E−06 |
| LC3_ID2 | 5.03E−06 |
| FRAP1_ID2 | 5.51E−06 |
| CASP8_ID2 | 6.05E−06 |
| ID2_CIAP2 | 6.10E−06 |
| ID2_UVRAG | 6.34E−06 |
| DIABLO_ID2 | 6.59E−06 |
| DRAM_CDH1 | 6.97E−06 |
| ID2_SIRT1 | 6.99E−06 |
| FAS_ID2 | 7.15E−06 |
| CDH_LAGER | 7.80E−06 |
| ID2_STAT3 | 7.83E−06 |
| CBS_ID2 | 8.12E−06 |
| CDH1_MMP2 | 9.00E−06 |
| AKT1_ID2 | 9.11E−06 |
| ID2_CDH2 | 1.03E−05 |
| ATG7_ID2 | 1.05E−05 |
| ID2_HMGB1 | 1.21E−05 |
| ULK1_ID2 | 1.25E−05 |
| CDH1_LAMP2 | 1.32E−05 |
| ATG5_CDH1 | 1.89E−05 |
| ID2_SATB1 | 1.95E−05 |
| CDH1_MMP9 | 2.14E−05 |
| ID2_RPS19BP1 | 2.31E−05 |
| ID2_TCF3 | 2.32E−05 |
| CSE1L_CDH1 | 2.42E−05 |
| AI_FM1_CDH1 | 2.48E−05 |
| ID2_SESN3 | 2.49E−05 |
| ID2_SESN2 | 2.83E−05 |
| LAM_PLCDH1 | 2.88E−05 |
| AIFM1_LC3 | 2.99E−05 |
| E2F1_CDH1 | 3.08E−05 |
| ID2_NAMPT | 3.23E−05 |
| DIABLO_CDH1 | 3.24E−05 |
| BNIP3_CDH1 | 3.29E−05 |
| AKT1_CDH1 | 3.31E−05 |
| CASP8_CDH1 | 3.34E−05 |
| Disease-free survival | |
| ID2_CDH2 | 4.81E−05 |
| FRAP1_TWIST1 | 9.28E−05 |
| FRAP1_CASP3 | 1.56E−04 |
| FRAP1_SESN1 | 1.64E−04 |
| BAX_FRAP1 | 2.04E−04 |
| FRAP1_NNMT | 2.08E−04 |
| FRAP1_CCNG2 | 2.09E−04 |
| BCL2L1_FRAP1 | 2.47E−04 |
| FRAPLRAGE | 2.47E−04 |
| AIFM1_FRAP1 | 2.48E−04 |
| BCL2_FRAP1 | 3.14E−04 |
| FRAP1_VEGF | 3.35E−04 |
| FRAP1_PTEN | 3.46E−04 |
| HMGB1_TWIST1 | 4.38E−04 |
| ATG12_ID2 | 4.68E−04 |
| FRAP1_RAPTOR | 4.80E−04 |
| FRAP1_KIAA1967 | 5.28E−04 |
| ID2_BECN1 | 5.71E−04 |
| BECN1_SESN3 | 6.61E−04 |
| ATG12_MMP2 | 6.71E−04 |
| CDH2_SESN3 | 6.88E−04 |
| ID2_MMP2 | 6.88E−04 |
| FRAPLXIAP | 7.02E−04 |
| AKT1_CDH2 | 8.14E−04 |
| FRAP1_PRKAA1 | 9.50E−04 |
| ID2_RPS19BP1 | 9.90E−04 |
| TKT_MMP2 | 9.99E−04 |
| BAX_TWIST1 | 1.01E−03 |
| BECNI_FASLG | 1.03E−03 |
| ATG12_SESN3 | 1.05E−03 |
| CDH2_MMP2 | 1.08E−03 |
| BECNLMMP2 | 1.10E−03 |
| BAX_MMP2 | 1.12E−03 |
| ID2_NAMPT | 1.15E−03 |
| CASP8_ID2 | 1.15E−03 |
| ID2_TWIST1 | 1.21E−03 |

TABLE 23-continued

| Marker | p-value |
|---|---|
| MMP2_SESN3 | 1.26E−03 |
| AKT1_BAX | 1.31E−03 |
| FRAP1_TP63 | 1.31E−03 |
| BAX_LC3 | 1.33E−03 |
| ATG12_FASLG | 1.33E−03 |
| LC3_TWIST1 | 1.36E−03 |
| AKT1_TWIST1 | 1.41E−03 |
| ID2_FASLG | 1.46E−03 |
| STAT3_TWIST1 | 1.59E−03 |
| TKT_FASLG | 1.61E−03 |
| AKT1_ATG12 | 1.64E−03 |
| MMP2_NAMPT | 1.68E−03 |
| ID2_SIRT1 | 1.70E−03 |
| ID2_AGER | 1.73E−03 |
| ATG7_TWIST1 | 1.83E−03 |
| AKT1_BCL2L1 | 1.95E−03 |
| BAX_TKT | 2.00E−03 |
| KIAA1967_MMP2 | 2.24E−03 |
| BCL2L1_MMP2 | 2.26E−03 |
| ATG7_TP63 | 2.29E−03 |
| LC3_BECN1 | 2.33E−03 |

TABLE 24

| Marker | p-value |
|---|---|
| Recurrence | |
| FRAP1_CASP3_CDH2 | 3.52E−06 |
| ID2_CDH2_SESN3 | 4.61E−06 |
| FRAP1_CDH2_SESN1 | 5.74E−06 |
| FRAP1_LC3_CASP3 | 6.25E−06 |
| FRAP1_LC3_TWIST1 | 6.56E−06 |
| BAX_FRAP1_LC3 | 7.41E−06 |
| FRAP1_CDH2_TWIST1 | 7.58E−06 |
| FRAP1_NNMT_CDH2 | 7.85E−06 |
| FRAP1_LC3_NNMT | 8.70E−06 |
| BAX_FRAP1_CDH2 | 9.08E−06 |
| FRAP1_SESN1_STAT3 | 9.21E−06 |
| AIFM1_FRAP1_CDH2 | 9.30E−06 |
| FRAP1_LC3_VEGF | 9.92E−06 |
| FRAP1_NNMT_MMP2 | 9.99E−06 |
| FRAP1_LC3_RAGE | 1.01E−05 |
| FRAP1_CCNG2_CDH2 | 1.02E−05 |
| BCL2L1_FRAP1_CDH2 | 1.04E−05 |
| FRAP1_CDH2_VEGF | 1.09E−05 |
| FRAP1_LC3_CCNG2 | 1.12E−05 |
| FRAP1_CASP3_MMP2 | 1.18E−05 |
| BCL2L1_FRAP1_LC3 | 1.21E−05 |
| FRAP1_LC3_SESN1 | 1.22E−05 |
| FRAP1_CDH2_KIAA1967 | 1.25E−05 |
| AIFM1_FRAP1_LC3 | 1.28E−05 |
| FRAP1_LC3_RAPTOR | 1.29E−05 |
| FRAP1_CDH2_RAGE | 1.30E−05 |
| BAX_FRAP1_MMP2 | 1.32E−05 |
| FRAP1_LC3_PTEN | 1.36E−05 |
| FRAP1_TKT_CASP3 | 1.38E−05 |
| FRAP1_PTEN_CDH2 | 1.49E−05 |
| FRAP1_TKT_TWIST1 | 1.51E−05 |
| FRAP1_LC3_KIAA1967 | 1.60E−05 |
| BAX_FRAP1_TKT | 1.70E−05 |
| BCL2_FRAP1_CDH2 | 1.72E−05 |
| FRAP1_HMGB1_TWIST1 | 1.72E−05 |
| FRAP1_RPS19BP1_TWIST1 | 1.74E−05 |
| FRAP1_CDH2_RAPTOR | 1.80E−05 |
| FRAP1_TKT_SESN1 | 1.81E−05 |
| FRAP1_RPS19BP1_SESN1 | 1.91E−05 |
| BAX_FRAP1_BECN1 | 1.94E−05 |
| ID2_NAMPT_SESN3 | 1.96E−05 |
| FRAP1_CCNG2_STAT3 | 2.02E−05 |
| BCL2L1_FRAP1_MMP2 | 2.02E−05 |
| BCL2_FRAP1_LC3 | 2.05E−05 |
| FASLG_NAMPT_SESN3 | 2.09E−05 |
| AIFM1_FRAP1_MMP2 | 2.10E−05 |
| FRAP1_CCNG2_RPS19BP1 | 2.14E−05 |

TABLE 24-continued

| Marker | p-value |
|---|---|
| BAX_FRAP1_RPS19BP1 | 2.15E−05 |
| FAS_FRAP1_SESN1 | 2.18E−05 |
| BCL2L1_FRAP1_TKT | 2.23E−05 |
| FRAP1_NNMT_STAT3 | 2.28E−05 |
| FRAP1_MMP2_SESN1 | 2.38E−05 |
| FRAP1_ID2_TWIST1 | 2.39E−05 |
| FRAP1_CASP3_STAT3 | 2.39E−05 |
| FRAP1_TKT_CCNG2 | 2.47E−05 |
| FRAP1_MMP2_VEGF | 2.47E−05 |
| FRAP1_MMP2_RAPTOR | 2.56E−05 |
| Survival | |
| ATG12_CDH1_ID2 | 2.54E−09 |
| CDH1_ID2_HMGB2 | 3.03E−09 |
| ATG12_CDH1_HMGB2 | 3.32E−09 |
| CDH1_ID2_AGER | 5.59E−09 |
| DRAM_CDHLID2 | 1.18E−08 |
| E2F1_CDH1_ID2 | 1.82E−08 |
| CDH1_ID2_LAMP2 | 1.95E−08 |
| TKT_CDHLID2 | 2.47E−08 |
| LAMP1_CDH1_ID2 | 2.58E−08 |
| CDH1_ID2_MMP2 | 2.61E−08 |
| ATG12_DRAM_CDH1 | 2.66E−08 |
| CSE1L_CDH1_ID2 | 3.01E−08 |
| CDH1_ID2_MMP9 | 3.13E−08 |
| BNIP3_CDH1_ID2 | 3.16E−08 |
| CDH1_ID2_BECN1 | 3.21E−08 |
| ATG12_CDH1_BHLHE41 | 3.44E−08 |
| ULK1_CDH1_ID2 | 3.60E−08 |
| LC3_CDH1_ID2 | 3.74E−08 |
| ATG12_CDH1_TCF3 | 3.87E−08 |
| ATG5_CDH1_ID2 | 3.90E−08 |
| ATG3_CDH1_ID2 | 3.97E−08 |
| DIABLO_CDHLID2 | 4.47E−08 |
| CASP8_CDHID2 | 4.50E−08 |
| ATG12_ULK1_CDH1 | 4.71E−08 |
| ATG12_CDH1_BECN1 | 4.84E−08 |
| ATG12_BNIP3_ID2 | 5.54E−08 |
| CDH1_ID2_CIAP2 | 6.23E−08 |
| CBS_CDHLID2 | 6.43E−08 |
| CDHLI_D2_HMGB1 | 7.57E−08 |
| CDH1_ID2_SIRT1 | 8.34E−08 |
| LAMP1_ID2_HMGB2 | 8.59E−08 |
| CDH1_ID2_UVRAG | 8.93E−08 |
| AIFM1_LC3_CDH1 | 9.09E−08 |
| ATG12_CDH_LAGER | 9.55E−08 |
| CDH1_ID2_STAT3 | 9.74E−08 |
| ATG12_LAMP1_ID2 | 9.98E−08 |
| ATG12_LC3_CDH1 | 1.01E−07 |
| CDH1_AGER_HMGB2 | 1.05E−07 |
| FAS_CDHLID2 | 1.19E−07 |
| ATG7_CDH1_ID2 | 1.21E−07 |
| ATG12_CDH1_MMP2 | 1.28E−07 |
| ATG12_CASP8_CDH1 | 1.32E−07 |
| ATG12_TKT_CDH1 | 1.32E−07 |
| BNIP3_ID2_HMGB2 | 1.37E−07 |
| E2F1_ID2_1MGB2 | 1.44E−07 |
| ATG12_CDH1_MMP9 | 1.69E−07 |
| ATG12_CDH1_SESN2 | 1.73E−07 |
| CDH1_ID2_CDH2 | 1.84E−07 |
| AKT1_CDH1_ID2 | 1.84E−07 |
| LAMP1_ID2_BECN1 | 1.93E−07 |
| CDH1_ID2_TCF3 | 1.94E−07 |
| ATG12_CDH1_UVRAG | 1.99E−07 |
| ATG12_FAS_CDH1 | 1.99E−07 |
| LAMP1_TKT_ID2 | 2.09E−07 |
| LAMP1_ID2_AGER | 2.41E−07 |
| DRAM_LAMP1_ID2 | 2.42E−07 |
| ATG12_DIABLO_CDH1 | 2.43E−07 |
| Disease-free survival | |
| FRAP1_CASP3_CDH2 | 5.47E−06 |
| ID2_CDH2_SESN3 | 5.70E−06 |
| ID2_CDH2_MMP2 | 8.25E−06 |
| FRAP1_CDH2_TWIST1 | 9.04E−06 |
| FRAP1_CDH2_SESN1 | 1.10E−05 |
| FRAP1_NNMT_CDH2 | 1.10E−05 |
| AIFM1_FRAP1_CDH2 | 1.32E−05 |

TABLE 24-continued

| Marker | p-value |
|---|---|
| FRAP1_TKT_TWIST1 | 1.34E−05 |
| BAX_FRAP1_CDH2 | 1.44E−05 |
| FRAP1_LC3_TWIST1 | 1.45E−05 |
| AKT1_ID2_CDH2 | 1.54E−05 |
| ATG12_ID2_MMP2 | 1.66E−05 |
| FRAP1_CDH2_KIAA1967 | 1.68E−05 |
| FRAP1_CCNG2_CDH2 | 1.68E−05 |
| FRAP1_NNMT_MMP2 | 1.71E−05 |
| FRAP1_CDH2_RAGE | 1.71E−05 |
| BCL2L1_FRAP1_CDH2 | 1.80E−05 |
| FRAP1_TKT_CASP3 | 1.85E−05 |
| ATG12_MMP2_SESN3 | 1.89E−05 |
| FRAP1_CDH2_VEGF | 1.90E−05 |
| ID2_CDF12_L1MGB1 | 1.92E−05 |
| FRAP1_PTEN_CDH2 | 2.01E−05 |
| CDH1_ID2_CDH2 | 2.03E−05 |
| FRAP1_CASP3_MMP2 | 2.03E−05 |
| FRAP1_LC3_CASP3 | 2.07E−05 |
| BCL2_FRAP1_CDH2 | 2.38E−05 |
| BAX_FRAP1_TKT | 2.39E−05 |
| FRAP1_CDH2_RAPTOR | 2.40E−05 |
| BAX_FRAPLLC3 | 2.41E−05 |
| BAX_FRAPLMMP2 | 2.41E−05 |
| FAS_ID2_CDH2 | 2.57E−05 |
| FRAP1_RPS19BP1_TWIST1 | 2.74E−05 |
| FRAP1_LC3_NNMT | 2.75E−05 |
| FRAP1_LC3_RAGE | 2.75E−05 |
| FRAP1_HMGB1_TWIST1 | 2.96E−05 |
| FRAP1_SESN1_STAT3 | 3.07E−05 |
| FRAP1_TKT_SESN1 | 3.14E−05 |
| ATG3_ID2_CDH2 | 3.31E−05 |
| FRAP1_ID2_CDH2 | 3.42E−05 |
| FRAP1_TKT_CCNG2 | 3.43E−05 |
| FAS_FRAP1_TWIST1 | 3.43E−05 |
| FRAP1_NNMT_TKT | 3.45E−05 |
| AIFM1_FRAP1_MMP2 | 3.50E−05 |
| ID2_CDH2_CIAP2 | 3.53E−05 |
| FRAP1_LC3_VEGF | 3.53E−05 |
| CDH2_MMP2_SESN3 | 3.54E−05 |
| ID2_CDH2_FASLG | 3.63E−05 |
| CBS_ID2_CDH2 | 3.69E−05 |
| FRAP1_LC3_CCNG2 | 3.70E−05 |
| BCL2L1_FRAP1_TKT | 3.72E−05 |
| FRAP1_ID2_TWIST1 | 3.77E−05 |
| AIFM1_FRAP1_LC3 | 3.82E−05 |
| AIFM1_FRAP1_TKT | 3.82E−05 |
| ATG5_ID2_CDH2 | 3.94E−05 |
| FRAP1_TKT_RAGE | 4.03E−05 |
| BCL2L1_FRAP1_MMP2 | 4.04E−05 |
| FRAP1_CDH2_TP63 | 4.05E−05 |

TABLE 25

| Marker | p-value |
|---|---|
| Recurrence | |
| ID2_NAMPT_RPS19BP1_SESN3 | 5.76E−07 |
| FRAP1_LC3_CASP3_CDH2 | 5.78E−07 |
| FRAP1_TKT_CASP3_CDH2 | 6.32E−07 |
| BAX_FRAP1_LC3_CDH2 | 6.71E−07 |
| ID2_CDH2_NAMPT_SESN3 | 7.55E−07 |
| CBS_ID2_CDH2_SESN3 | 8.34E−07 |
| FRAP1_LC3_CDH2_KIAA1967 | 8.40E−07 |
| FRAP1_CDH2_SESN1_STAT3 | 9.25E−07 |
| FRAP1_LC3_NNMT_CDH2 | 9.26E−07 |
| FRAP1_LC3_CDH2_RAPTOR | 9.80E−07 |
| ID2_CDH2_RPS19BP1_SESN3 | 1.03E−06 |
| FRAP1_LC3_CDH2_TWIST1 | 1.10E−06 |
| FRAP1_LC3_CDH2_VEGF | 1.12E−06 |
| FRAP1_LC3_SESN1_STAT3 | 1.15E−06 |
| FRAP1_LC3_CDH2_RAGE | 1.20E−06 |
| FRAP1_LC3_NNMT_STAT3 | 1.37E−06 |
| ID2_CDH2_MMP2_SESN3 | 1.37E−06 |
| FRAP1_LC3_CASP3_STAT3 | 1.38E−06 |

TABLE 25-continued

| Marker | p-value |
|---|---|
| AIFM1_FRAP1_LC3_CDH2 | 1.39E−06 |
| BCL2L1_FRAP1_LC3_CDH2 | 1.40E−06 |
| FRAP1_LC3_PTEN_CDH2 | 1.43E−06 |
| BAX_FRAP1_LC3_BECN1 | 1.46E−06 |
| BAX_FRAP1_LC3_RPS19BP1 | 1.54E−06 |
| FRAP1_CASP3_CDH2_STAT3 | 1.58E−06 |
| LC3_HMGB1_STAT3_TWIST1 | 1.69E−06 |
| BAX_FRAP1_TKT_CDH2 | 1.71E−06 |
| FRAP1_LC3_CCNG2_CDH2 | 1.71E−06 |
| FRAP1_TKT_CDH2_SESN1 | 1.72E−06 |
| FRAP1_LC3HMGB1_TWIST1 | 1.78E−06 |
| FRAP1_NNMT_TKT_CDH2 | 1.78E−06 |
| BAX_FRAP1_LC3_MMP2 | 1.80E−06 |
| FRAP1_LC3_CCNG2_STAT3 | 1.83E−06 |
| FRAP1_LC3_STAT3_TWIST1 | 1.85E−06 |
| FRAP1_TKT_CDH2_TWIST1 | 1.91E−06 |
| FRAP1_LC3_NNMT_MMP2 | 1.92E−06 |
| BAX_FRAP1_TKT_MMP2 | 2.09E−06 |
| FRAP1_NNMT_CDH2_MMP2 | 2.10E−06 |
| FRAP1_LC3_CDH2_SESN1 | 2.10E−06 |
| BAX_FRAP1_LC3_TKT | 2.14E−06 |
| FAS_FRAP1_CDH2_SESN1 | 2.16E−06 |
| BAX_FAS_FRAP1_LC3 | 2.18E−06 |
| FRAP1_CASP3_CDH2_MMP2 | 2.21E−06 |
| ID2_FASLG_NAMPT_SESN3 | 2.22E−06 |
| FRAP1_ID2_CDH2_TWIST1 | 2.33E−06 |
| FRAP1_CDH2_HMGB1_TWIST1 | 2.38E−06 |
| BAX_FRAP1_BECN1_CDH2 | 2.38E−06 |
| DRAM_ID2_CDH2_SESN3 | 2.38E−06 |
| FRAP1_LC3_RPS19BP1_TWIST1 | 2.39E−06 |
| AIFM1_FRAP1_TKTCDH2 | 2.45E−06 |
| FRAP1_TKT_CCNG2_CDH2 | 2.45E−06 |
| BCL2L1_FRAP1_TKT_CDH2 | 2.50E−06 |
| DIABLO_ID2_CDH2_SESN3 | 2.50E−06 |
| BCL2_FRAP1_LC3_CDH2 | 2.51E−06 |
| FRAP1_LC3_CASP3_FASLG | 2.52E−06 |
| FRAP1_CDH2_RPS19BP1_SESN1 | 2.53E−06 |
| FRAP1_LC3_CASP3_MMP2 | 2.56E−06 |
| ID2_CDH2_HMGB2_SESN3 | 2.60E−06 |
| CDH1_ID2_MMP9_TCF3 | 8.98E−03 |
| Survival | |
| ATG12_CDH1_ID2_HMGB2 | 1.06E−10 |
| CDH1_ID2_AGER_HMGB2 | 1.45E−10 |
| ATG12_CDH1_ID2_AGER | 4.15E−10 |
| ATG12_CDH1_TCF3_HMGB2 | 5.35E−10 |
| ATG12_DRAM_CDH1_ID2 | 6.42E−10 |
| AIFM1_CASP8_LC3_CDH1 | 7.92E−10 |
| ATG12_CDH1_AGER_HMGB2 | 8.22E−10 |
| ATG12_CDH1_ID2_BECN1 | 9.07E−10 |
| ATG12_DRAM_CDH1_HMGB2 | 1.11E−09 |
| DRAM_CDH1_ID2_HMGB2 | 1.12E−09 |
| ATG12_CDH1_BHLHE41_HMGB2 | 1.24E−09 |
| CDH1_ID2_HMGB2_LAMP2 | 1.34E−09 |
| ATG12_CDH1_BECN1_HMGB2 | 1.36E−09 |
| E2F1_CDH1_ID2_HMGB2 | 1.37E−09 |
| ATG12_DIABLO_CDH1_BHLHE41 | 1.89E−09 |
| CDH1_ID2_BECN1_HMGB2 | 1.93E−09 |
| ATG12_ATG5_CDH1_HMGB2 | 1.95E−09 |
| DRAM_CDH1_ID2_AGER | 2.00E−09 |
| LAMP1_CDH1_ID2_HMGB2 | 2.03E−09 |
| ATG12_BNIP3_CDH1_ID2 | 2.04E−09 |
| ATG12_CSE1L_CDH1_ID2 | 2.04E−09 |
| ATG12_CDH1_ID2_MMP2 | 2.05E−09 |
| ATG12_CASP8_CDH1_ID2 | 2.20E−09 |
| ATG12_ATG3_CDH1_HMGB2 | 2.43E−09 |
| ATG12_CDH1_ID2_MMP9 | 2.51E−09 |
| CDH1_ID2_HMGB2_MMP2 | 2.61E−09 |
| ATG12_ATG3_CDH1_ID2 | 2.61E−09 |
| ATG12_CASP8_CDH1_HMGB2 | 2.62E−09 |
| ATG12_LAMP1_CDH1_ID2 | 2.74E−09 |
| CDH1_ID2_AGER_BECN1 | 2.80E−09 |
| ATG12_FAS_CDH1_HMGB2 | 2.80E−09 |
| ATG12_TKT_CDH1_ID2 | 2.84E−09 |
| CDH1_ID2_MMP9_HMGB2 | 2.88E−09 |
| ATG12_CDH1_HMGB1_HMGB2 | 2.98E−09 |
| ATG12_CDH1_MMP9_HMGB2 | 3.05E−09 |
| ATG12_ATG5_CDH1_ID2 | 3.06E−09 |

TABLE 25-continued

| Marker | p-value |
|---|---|
| ATG5_CDH1_ID2_HMGB2 | 3.07E−09 |
| ATG3_CDH1_ID2_HMGB2 | 3.08E−09 |
| ATG12_DIABLO_CDHLID2 | 3.09E−09 |
| CSE1L_CDH1_ID2_HMGB2 | 3.13E−09 |
| ATG12_CDH1_CIAP2HMGB2 | 3.16E−09 |
| ATG12_CDH1_ID2_UVRAG | 3.35E−09 |
| ATG12_CDH1_HMGB2_SESN3 | 3.37E−09 |
| LC3_CDH1_ID2_AGER | 3.42E−09 |
| ATG12_CDH1_HMGB2_SIRT1 | 3.58E−09 |
| ATG12_E2F1_CDH1_ID2 | 3.64E−09 |
| ATG12_FAS_CDH1_ID2 | 3.65E−09 |
| AIFM1_ATG3_LC3_CDH1 | 3.70E−09 |
| ATG12_CDH1_HMGB2_MMP2 | 3.77E−09 |
| BNIP3_CDH1_ID2_HMGB2 | 3.78E−09 |
| ATG12_ULK1_CDH1_HMGB2 | 4.01E−09 |
| TKT_CDH1_ID2_HMGB2 | 4.06E−09 |
| ATG12_CDH1_ID2_LAMP2 | 4.07E−09 |
| ATG12_LC3_CDH1_ID2 | 4.14E−09 |
| ATG12_CDH1_HMGB2_UVRAG | 4.16E−09 |
| CASP8_CDH1_ID2_HMGB2 | 4.30E−09 |
| DIABLO_CDH1_ID2_HMGB2 | 4.40E−09 |
| CDH1_ID2_MMP9_TCF3 | 1.86E−07 |
| Disease-free survival | |
| FRAP1_TKT_CASP3_CDH2 | 5.04E−07 |
| ID2_CDH2_MMP2_SESN3 | 6.57E−07 |
| CBS_ID2_CDH2_SESN3 | 1.15E−06 |
| FRAP1_TKT_CDH2_TWIST1 | 1.24E−06 |
| FRAP1_LC3_CASP3_CDH2 | 1.27E−06 |
| FRAP1_NNMT_TKT_CDH2 | 1.28E−06 |
| ID2_CDH2_RPS19BP1_SESN3 | 1.35E−06 |
| BAX_FRAP1_TKT_CDH2 | 1.37E−06 |
| BAX_FRAP1_LC3_CDH2 | 1.47E−06 |
| ATG12_ID2_CDH2_SESN3 | 1.62E−06 |
| ATG12_ID2_MMP2_SESN3 | 1.67E−06 |
| FRAP1_LC3_CDH2_KIAA1967 | 1.68E−06 |
| AIFM1_FRAP1_TKT_CDH2 | 1.75E−06 |
| FRAP1_TKT_CDH2_SESN1 | 1.75E−06 |
| ID2_MMP2_RPS19BP1_SESN3 | 1.83E−06 |
| FRAP1_CDH2_SESN1_STAT3 | 1.87E−06 |
| FRAP1_LC3_CDH2_TWIST1 | 1.87E−06 |
| FRAP1_LC3_NNMT_CDH2 | 1.91E−06 |
| FRAP1_LC3_CDH2_RAPTOR | 1.94E−06 |
| FRAP1_TKT_CCNG2_CDH2 | 2.00E−06 |
| DIABLO_ID2_CDH2_SESN3 | 2.02E−06 |
| ID2_CDH2_HMGB2_SESN3 | 2.09E−06 |
| FRAP1_TKT_CDH2_KIAA1967 | 2.19E−06 |
| FRAP1_LC3_CDH2_RAGE | 2.20E−06 |
| BAX_FRAP1_TKT_MMP2 | 2.24E−06 |
| BCL2L1_FRAP1_TKT_CDH2 | 2.24E−06 |
| FRAP1_CASP3_CDH2_STAT3 | 2.30E−06 |
| FRAP1_PTEN_TKT_CDH2 | 2.33E−06 |
| FRAP1_ID2_CDH2_TWIST1 | 2.43E−06 |
| ID2_CDH2_NAMPT_SESN3 | 2.50E−06 |
| FRAP1_TKT_CDH2_VEGF | 2.55E−06 |
| FRAP1_LC3_CDH2_VEGF | 2.65E−06 |
| FRAP1_NNMT_CDH2_MMP2 | 2.73E−06 |
| AIFM1_FRAP1_LC3_CDH2 | 2.73E−06 |
| FRAP1_LC3_PTEN_CDH2 | 2.86E−06 |
| FRAP1_TKT_CDH2_RAGE | 2.90E−06 |
| FRAP1_CDH2_HMGB1_TWIST1 | 2.91E−06 |
| FAS_FRAP1_CDH2_SESN1 | 2.95E−06 |
| FRAP1_CASP3_CDH2_MMP2 | 3.01E−06 |
| DRAM_ID2_CDH2_SESN3 | 3.09E−06 |
| LC3_HMGB1_STAT3_TWIST1 | 3.10E−06 |
| CASP8_ID2_CDH2_SESN3 | 3.10E−06 |
| FRAP1_TKT_CDH2_RAPTOR | 3.10E−06 |
| BCL2L1_FRAP1_LC3CDH2 | 3.25E−06 |
| FRAP1_CDH2_KIAA1967_MMP2 | 3.35E−06 |
| FRAP1_TKT_CASP3_FASLG | 3.42E−06 |
| TKT_ID2_CDH2_MMP2 | 3.42E−06 |
| FRAP1_NNMT_TKT_MMP2 | 3.43E−06 |
| FRAP1_TKT_CASP3_MMP2 | 3.52E−06 |
| ID2_CDH2_CIAP2_SESN3 | 3.59E−06 |
| FRAP1_CDH2_STAT3_TWIST1 | 3.61E−06 |
| CBS_FRAP1_CASP3_CDH2 | 3.71E−06 |
| BAX_FRAP1_CDH2_MMP2 | 3.74E−06 |
| ATG12_TKT_MMP2_SESN3 | 3.75E−06 |
| FRAP1_CDH1_CASP3_CDH2 | 3.81E−06 |
| BAX_FRAP1_BECN1_CDH2 | 3.92E−06 |
| ID2_CDH2_HMGB1_MMP2 | 3.94E−06 |
| CDH1_ID2_MMP9_TCF3 | 5.11E−03 |

TABLE 26

| Marker | p-value |
|---|---|
| Recurrence | |
| FRAP1_LC3_CASP3_CDH2_STAT3 | 8.29E−08 |
| ID2_MMP2_NAMPT_RPS19BP1_SESN3 | 9.47E−08 |
| FRAP1_LC3_CDH2_SESN1_STAT3 | 1.26E−07 |
| ID2_CDH2_MMP2_RPS19BP1_SESN3 | 1.44E−07 |
| FRAP1_LC3_NNMT_CDH2_STAT3 | 1.46E−07 |
| BAX_FRAP1_LC3_BECN1_CDH2 | 1.75E−07 |
| ID2_FASLG_NAMPT_RPS19BP1_SESN3 | 1.83E−07 |
| BAX_FRAP1_LC3_TKT_CDH2 | 1.91E−07 |
| FRAP1_LC3_BECN1_CDH2_RAPTOR | 2.06E−07 |
| FRAP1_LC3_CDH2_STAT3_TWIST1 | 2.12E−07 |
| FRAP1_LC3_CCNG2_CDH2_STAT3 | 2.14E−07 |
| ID2_CDH2_FASLG_NAMPT_SESN3 | 2.14E−07 |
| LC3_CDH2_HMGB1_STAT3_TWIST1 | 2.18E−07 |
| ID2_CDH2_HMGB1_RPS19BP1_SESN3 | 2.24E−07 |
| ID2_CDH2_MMP2_NAMPT_SESN3 | 2.36E−07 |
| FRAP1_LC3_BECN1_CDH2_KIAA1967 | 2.45E−07 |
| BAX_FRAP1_LC3_CDH2_RPS19BP1 | 2.48E−07 |
| ID2_HMGB2_NAMPT_RPS19BP1_SESN3 | 2.54E−07 |
| ID2_NAMPT_RPS19BP1_SESN3_STAT3 | 2.56E−07 |
| FRAP1_LC3_CDH2_HMGB1_TWIST1 | 2.68E−07 |
| FRAP1_TKT_CDH2_SESN1_STAT3 | 2.78E−07 |
| CSE1L_ID2_CDH2_RPS19BP1_SESN3 | 2.79E−07 |
| FRAP1_LC3_TKT_CASP3_CDH2 | 2.83E−07 |
| BAX_FAS_FRAP1_LC3_CDH2 | 2.91E−07 |
| FAS_FRAP1_LC3_CDH2_RAPTOR | 2.97E−07 |
| LC3_CASP3_CDH2_HMGB1_STAT3 | 3.07E−07 |
| FAS_FRAP1_LC3_CDH2_KIAA1967 | 3.24E−07 |
| AIFM1_FRAP1_LC3_CDH2_STAT3 | 3.25E−07 |
| FRAP1_LC3_BECN1_CASP3_STAT3 | 3.27E−07 |
| FRAP1_BECN1_CASP3_CDH2_STAT3 | 3.27E−07 |
| ID2_CDH2_NAMPT_SESN3_STAT3 | 3.31E−07 |
| LC3_ID2_NAMPT_RPS19BP1_SESN3 | 3.34E−07 |
| FRAP1_LC3_NNMT_MMP2_STAT3 | 3.35E−07 |
| BAX_FRAP1_LC3_CASP3_CDH2 | 3.37E−07 |
| FRAP1_TKT_CASP3_CDH2_STAT3 | 3.37E−07 |
| LC3_HMGB1_RPS19BP1_STAT3_TWIST1 | 3.49E−07 |
| FRAP1_CDH2_RPS19BP1_SESN1_STAT3 | 3.50E−07 |
| CBS_FRAP1_LC3_CASP3_CDH2 | 3.56E−07 |
| FRAP1_LAMP1_TKT_CASP3_CDH2 | 3.58E−07 |
| ID2_CDH2_HMGB1_NAMPT_SESN3 | 3.64E−07 |
| ID2_HMGB1_NAMPT_RPS19BP1_SESN3 | 3.78E−07 |
| AKT1_ID2_NAMPT_RPS19BP1_SESN3 | 3.78E−07 |
| FRAP1_LC3_TKT_CDH2_KIAA1967 | 3.83E−07 |
| FRAP1_LC3_CASP3_CDH2_HMGB1 | 3.84E−07 |
| ATG7_FRAP1_LC3_CASP3_CDH2 | 3.85E−07 |
| BAX_FRAP1_LC3_TKT_MMP2 | 3.89E−07 |
| FRAP1_LC3_CDH2_RAPTOR_RPS19BP1 | 3.90E−07 |
| FRAP1_LC3_RPS19BP1_SESN1_STAT3 | 3.94E−07 |
| BAX_FRAP1_LC3_CDH2_MMP2 | 3.95E−07 |
| ID2_TCF3_CDH2_RPS19BP1_SESN3 | 3.95E−07 |
| FRAP1_TKT_CASP3_CDH2_FASLG | 3.95E−07 |
| FAS_FRAP1_CDH2_SESN1_STAT3 | 3.96E−07 |
| CBS_ID2_NAMPT_RPS19BP1_SESN3 | 3.97E−07 |
| FRAP1_LC3_CDH2_KIAA1967_MMP2 | 4.00E−07 |
| FAS_FRAP1_LC3_CASP3_CDH2 | 4.04E−07 |
| BAX_CBS_FRAP1_LC3_CDH2 | 4.07E−07 |
| FRAP1_LC3_TKT_CDH2_RAPTOR | 4.10E−07 |
| CDH1_ID2_MMP9_TCF3_RPS19BP1 | 1.84E−04 |
| Survival | |
| ATG12_CDH1_ID2_AGER_HMGB2 | 9.20E−12 |
| ATG12_DRAM_CDH1_ID2_HMGB2 | 3.10E−11 |
| DRAM_CDH1_ID2_AGER_HMGB2 | 5.16E−11 |
| ATG12_CDH1_ID2_BECN1_HMGB2 | 5.30E−11 |

TABLE 26-continued

| Marker | p-value |
|---|---|
| ATG12_LAMP1_CDH1_ID2_HMGB2 | 7.40E−11 |
| ATG12_ATG5_CDH1_ID2_HMGB2 | 7.70E−11 |
| ATG12_E2F1_CDH1_ID2_HMGB2 | 7.80E−11 |
| ATG12_ATG3_CDH1_ID2_HMGB2 | 7.90E−11 |
| CDH1_ID2_AGER_BECN1_HMGB2 | 8.92E−11 |
| ATG12_CDH1_ID2_HMGB2_MMP2 | 9.10E−11 |
| ATG12_CASP8_CDH1_ID2_HMGB2 | 9.30E−11 |
| ATG12_BNIP3_CDH1_ID2_HMGB2 | 1.00E−10 |
| ATG12_CDH1_ID2_MMP9_HMGB2 | 1.00E−10 |
| LAMP1_CDH1_ID2_AGER_HMGB2 | 1.06E−10 |
| ATG12_CSE1L_CDH1_ID2_HMGB2 | 1.10E−10 |
| LC3_CDH1_ID2_AGER_HMGB2 | 1.21E−10 |
| ATG12_DIABLO_CDH1_ID2_HMGB2 | 1.30E−10 |
| CSE1L_CDH1_ID2_AGER_HMGB2 | 1.40E−10 |
| CDH1_ID2_MMP9_AGER_HMGB2 | 1.43E−10 |
| CDH1_ID2_AGER_HMGB2_RPS19BP1 | 1.54E−10 |
| ATG12_CDH1_ID2_CIAP2_HMGB2 | 1.60E−10 |
| ATG12_CDH1_ID2_HMGB2_UVRAG | 1.60E−10 |
| ATG12_DRAM_CDH1_ID2_AGER | 1.60E−10 |
| ATG12_DRAM_CDH1_TCF3_HMGB2 | 1.70E−10 |
| ATG12_CDH1_ID2_AGER_BECN1 | 1.80E−10 |
| ATG12_DIABLO_CDH1_BHLHE41_HMGB2 | 1.80E−10 |
| ATG12_DIABLO_CDH1_HMGB2_SESN3 | 1.80E−10 |
| ATG12_FAS_CDH1_ID2_HMGB2 | 1.80E−10 |
| ATG3_CDH1_ID2_AGER_HMGB2 | 1.80E−10 |
| CDH1_ID2_AGER_HMGB2_MMP2 | 1.82E−10 |
| ATG12_CDH1_ID2_TCF3_HMGB2 | 1.90E−10 |
| ATG12_CDH1_TCF3_AGER_HMGB2 | 1.90E−10 |
| ATG12_CDH1_ID2_HMGB1_HMGB2 | 2.00E−10 |
| AIFM1_ATG3_CASP8_LC3_CDH1 | 2.10E−10 |
| ATG12_CDH1_ID2_HMGB2_SIRT1 | 2.10E−10 |
| ATG12_CDH1_TCF3_BECN1_HMGB2 | 2.10E−10 |
| ATG12_DIABLO_CDH1_TCF3_BHLHE41 | 2.20E−10 |
| BNIP3_CDH1_ID2_AGER_HMGB2 | 2.24E−10 |
| AIFM1_CASP8_DRAM_LC3_CDH1 | 2.30E−10 |
| ATG12_CDH1_ID2_HMGB2_LAMP2 | 2.30E−10 |
| ATG12_ATG3_CDH1_TCF3_HMGB2 | 2.50E−10 |
| ATG12_LC3_CDH1_ID2_HMGB2 | 2.50E−10 |
| ATG12_TKT_CDH1_ID2_HMGB2 | 2.60E−10 |
| CASP8_CDH1_ID2_AGER_HMGB2 | 2.64E−10 |
| ATG12_CDH1_TCF3_BHLHE41_HMGB2 | 2.70E−10 |
| ATG5_CDH1_ID2_AGER_HMGB2 | 2.70E−10 |
| ATG12_CSE1L_CDH1_ID2_AGER | 2.80E−10 |
| CDH1_ID2_AGER_HMGB2_SIRT1 | 2.84E−10 |
| CDH1_ID2_AGER_CIAP2_HMGB2 | 2.91E−10 |
| CDH1_ID2_TCF3_AGER_HMGB2 | 2.91E−10 |
| AIFM1_CASP8_LC3_CDH1_MMP9 | 3.00E−10 |
| ATG12_DRAM_CDH1_ID2_BECN1 | 3.00E−10 |
| AIFM1_CASP8_DIABLO_LC3_CDH1 | 3.10E−10 |
| CDH1_ID2_AGER_HMGB1_HMGB2 | 3.12E−10 |
| ATG12_CDH1_ID2_HMGB2_RPS19BP1 | 3.20E−10 |
| ATG12_LC3_CDH1_AGER_HMGB2 | 3.20E−10 |
| FAS_CDH1_ID2_AGER_HMGB2 | 3.35E−10 |
| ATG12_CDH1_ID2_MMP9_TCF3 | 5.60E−09 |
| Disease-free survival | |
| ID2_CDH2_MMP2_RPS19BP1_SESN3 | 8.23E−08 |
| ATG12_ID2_CDH2_MMP2_SESN3 | 8.47E−08 |
| FRAP1_LC3_CASP3_CDH2_STAT3 | 1.62E−07 |
| ATG12_ID2_MMP2_RPS19BP1_SESN3 | 1.67E−07 |
| AKT1_FAS_CDH2_STAT3_TP63 | 1.86E−07 |
| FRAP1_TKT_CASP3_CDH2_STAT3 | 2.31E−07 |
| CASP8_ID2_CDH2_MMP2_SESN3 | 2.43E−07 |
| FRAP1_TKT_CASP3_CDH2_FASLG | 2.44E−07 |
| BAX_FRAP1_LC3_TKT_CDH2 | 2.53E−07 |
| ID2_CDH2_HMGB2_MMP2_SESN3 | 2.55E−07 |
| DIABLO_ID2_CDH2_MMP2_SESN3 | 2.57E−07 |
| FRAP1_LAMP1_TKT_CASP3_CDH2 | 2.61E−07 |
| CBS_ID2_CDH2_MMP2_SESN3 | 2.64E−07 |
| FRAP1_LC3_NNMT_CDH2_STAT3 | 2.78E−07 |
| FRAP1_TKT_CDH2_SESN1_STAT3 | 2.89E−07 |
| LC3_CDH2_HMGB1_STAT3_TWIST1 | 2.93E−07 |
| DRAM_ID2_CDH2_MMP2_SESN3 | 2.96E−07 |
| FRAP1_LC3_CDH2_SESN1_STAT3 | 3.00E−07 |
| CBS_FRAP1_TKT_CASP3_CDH2 | 3.07E−07 |
| ID2_MMP2_NAMPT_RPS19BP1_SESN3 | 3.10E−07 |
| AKT1_ID2_CDH2_RPS19BP1_SESN3 | 3.16E−07 |
| ID2_CDH2_MMP2_NAMPT_SESN3 | 3.32E−07 |

TABLE 26-continued

| Marker | p-value |
|---|---|
| AKT1_BECN1_CDH2_STAT3_TP63 | 3.37E−07 |
| FAS_FRAP1_LC3_CDH2_RAPTOR | 3.42E−07 |
| FRAP1_LC3_CDH2_STAT3_TWIST1 | 3.44E−07 |
| BAX_FRAP1_TKT_CDH2_MMP2 | 3.51E−07 |
| FAS_FRAP1_LC3_CDH2_KIAA1967 | 3.53E−07 |
| AKT1_ATG7_CDH2_RPS19BP1_TP63 | 3.56E−07 |
| FAS_FRAP1_LC3_CDH2_RAGE | 3.79E−07 |
| FAS_LC3_HMGB1_STAT3_TWIST1 | 3.93E−07 |
| FRAP1_LC3_TKT_CASP3_CDH2 | 3.94E−07 |
| FRAP1_TKT_CASP3_CDH2_CIAP2 | 3.98E−07 |
| TKT_ID2_CDH2_MMP2_SESN3 | 3.99E−07 |
| FRAP1_TKT_CDH2_KIAA1967_MMP2 | 4.02E−07 |
| FRAP1_TKT_CDH2_HMGB1_TWIST1 | 4.07E−07 |
| BAX_FRAP1_LC3_BECN1_CDH2 | 4.15E−07 |
| FRAP1_TKT_CDH2_STAT3_TWIST1 | 4.17E−07 |
| AKT1_ATG12_ID2_CDH2_SESN3 | 4.20E−07 |
| BAX_FAS_FRAP1_LC3_CDH2 | 4.24E−07 |
| ATG12_CBS_ID2_MMP2_SESN3 | 4.28E−07 |
| FAS_FRAP1_CDH2_SESN1_STAT3 | 4.33E−07 |
| FRAP1_BECN1_CASP3_CDH2_STAT3 | 4.35E−07 |
| FAS_FRAP1_TKT_CDH2_SESN1 | 4.37E−07 |
| FRAP1_LC3_CCNG2_CDH2_STAT3 | 4.41E−07 |
| ID2_CDH2_MMP2_SESN3_UVRAG | 4.42E−07 |
| ATG7_ID2_CDH2_MMP2_SESN3 | 4.45E−07 |
| ID2_CDH2_HMGB1_RPS19BP1_SESN3 | 4.51E−07 |
| FRAP1_TKT_CDH2_MMP2_RAPTOR | 4.57E−07 |
| FRAP1_LC3_BECN1_CDH2_RAPTOR | 4.61E−07 |
| ATG12_ID2_CDH2_FASLG_SESN3 | 4.64E−07 |
| ATG7_FRAP1_TKT_CASP3_CDH2 | 4.65E−07 |
| FRAP1_TKT_CASP3_CDH2_MMP2 | 4.66E−07 |
| FRAP1_LC3_CDH2_HMGB1_TWIST1 | 4.66E−07 |
| FRAP1_LC3_TKT_CDH2_KIAA1967 | 4.72E−07 |
| ATG7_ID2_CDH2_RPS19BP1_TP63 | 4.72E−07 |
| BAX_FRAP1_TKT_BECN1_CDH2 | 4.73E−07 |
| ATG3_FRAP1_TKT_CASP3_CDH2 | 4.76E−07 |
| CDH1_ID2_MMP9_TCF3_CDH2 | 1.17E−04 |

TABLE 27

| Marker | p-value |
|---|---|
| Recurrence | |
| FRAP1_LC3_BECN1_CASP3_CDH2_STAT3 | 1.90E−08 |
| FRAP1_LC3_NNMT_BECN1_CDH2_STAT3 | 2.38E−08 |
| FRAP1_LC3_TKT_CASP3_CDH2_STAT3 | 3.39E−08 |
| ID2_CDH2_HMG131_MMP2_RPS19BP1_SESN3 | 3.43E−08 |
| FAS_FRAP1_LC3_CDH2_SESN1_STAT3 | 4.04E−08 |
| ID2_CDH2_FASLG_NAMPT_RPS19BP1_SESN3 | 4.30E−08 |
| FRAP1_LC3_CASP3_CDH2_HMG131_STAT3 | 4.31E−08 |
| FRAP1_LC3_CDH2_RPS19BP1_SESN1_STAT3 | 4.41E−08 |
| FRAP1_LC3_CASP3_CDH2_RPS19BP1_STAT3 | 4.45E−08 |
| FRAP1_LC3_CDH2_HMGI31_STAT3_TWIST1 | 4.53E−08 |
| ID2_HMGB2_MMP2_NAMPT_RPS1913P1_SESN3 | 4.81E−08 |
| AIFM1_FRAP1_LC3_BECN1_CDH2_STAT3 | 4.86E−08 |
| ID2_MMP2_NAMPT_RPS1913P1_SESN3_STAT3 | 4.92E−08 |
| ID2_FASLG_HMGB2_NAMPT_RPS1913P1_SESN3 | 4.93E−08 |
| AKT1_FAS_BECN1_CDH2_STAT3_TP63 | 5.40E−08 |
| FRAP1_LC3_CCNG2_CDH2_RPS1913P1_STAT3 | 5.43E−08 |
| AKT1_ATG12_BECN1_CDH2_STAT3_TP63 | 5.69E−08 |
| FRAP1_LC3_NNMT_CDH2_RPS1913P1_STAT3 | 5.80E−08 |
| CSE1L_FRAP1_LC3_CASP3_CDH2_STAT3 | 5.93E−08 |
| FRAP1_LC3_BECN1_CDH2_RAGE_STAT3 | 5.94E−08 |
| FAS_FRAP1_LC3_NNMT_CDH2_STAT3 | 5.97E−08 |
| ID2_HMGB1_MMP2_NAMPT_RPS1913P1_SESN3 | 5.98E−08 |
| FRAP1_LC3_TKT_CDH2_SESNLSTAT3 | 6.02E−08 |
| FRAP1_LC3_NNMT_CDH2_MMP2_STAT3 | 6.07E−08 |
| FRAP1_LC3_NNMT_TKT_CDH2_STAT3 | 6.10E−08 |
| BAX_FRAP1_LC3_BECNLCDH2_STAT3 | 6.30E−08 |
| FRAP1_LC3_CASP3_CDH2_31RT1_STAT3 | 6.41E−08 |
| FAS_FRAP1_LC3_CDH2_RAPTOR_RPS1913P1 | 6.48E−08 |
| CBS_FRAP1_LC3_CASP3_CDH2_STAT3 | 6.53E−08 |
| FAS_FRAP1_LC3_CASP3_CDH2_STAT3 | 6.53E−08 |
| AKT1_ATG12_FAS_CDH2_STAT3_TP63 | 6.67E−08 |
| LC3_CDH2_HMGB1_RPS1913P1_STAT3_TWIST1 | 6.69E−08 |

TABLE 27-continued

| Marker | p-value |
|---|---|
| FRAP1_LC3_BECN1_CDH2_STAT3_TWIST1 | 6.71E−08 |
| FRAP1_LC3_CASP3_CDH2_MMP2_STAT3 | 6.77E−08 |
| ID2_MMP9_MMP2_NAMPT_RPS1913P1_SESN3 | 6.97E−08 |
| CSE1L_ID2_CDH2_MMP2_RPS1913P1_SESN3 | 6.97E−08 |
| FRAP1_LC3_BECN1_CDH2_STAT3_VEGF | 7.00E−08 |
| BAX_FRAP1_LC3_TKT_BECN1_CDH2 | 7.10E−08 |
| FRAP1_LC3_NNMT_CASP3_CDH2_STAT3 | 7.38E−08 |
| FRAP1_TKT_BECN1_CASP3_CDH2_STAT3 | 7.40E−08 |
| ID2_FASLG_NAMPT_RPS1913P1_SESN3_STAT3 | 7.57E−08 |
| FAS_FRAP1_LC3_CDH2_KIAA1967_RPS1913P1 | 7.62E−08 |
| FRAP1_LC3_BECN1_CDH2_SESN1_STAT3 | 7.73E−08 |
| ID2_CDH2_FASLG_NAMPT_SESN3_STAT3 | 7.81E−08 |
| FRAP1_LC3_TKT_CDH2_STAT3_TWIST1 | 7.91E−08 |
| ATG5_FRAP1_LC3_CASP3_CDH2_STAT3 | 7.93E−08 |
| ID2_CDH2_MMP2_RPS1913P1_SESN3_STAT3 | 7.96E−08 |
| FAS_LC3_CDH2_HMGB1_STAT3_TWIST1 | 8.02E−08 |
| AIFM1_FRAP1_LC3_TKT_CDH2_STAT3 | 8.09E−08 |
| FRAP1_LC3_TKT_CASP3_CDH2_FASLG | 8.17E−08 |
| DRAM_ID2_MMP2_NAMPT_RPS19BP1_SESN3 | 8.35E−08 |
| FRAP1_LC3_CASP3_CDH2_NAMPT_STAT3 | 8.40E−08 |
| FAS_FRAP1_LC3_CCNG2_CDH2_STAT3 | 8.40E−08 |
| BAX_FAS_FRAP1_LC3_CDH2_RPS19BP1 | 8.40E−08 |
| BNIP3_FRAP1_LC3_CASP3_CDH2_STAT3 | 8.59E−08 |
| FRAP1_LC3_CDH2_RPS19BP1_STAT3_TWIST1 | 8.60E−08 |
| FRAP1_LC3_MMP9_CASP3_CDH2_STAT3 | 8.66E−08 |
| CDH1_ID2_MMP9_TCF3_RPS19BP1_SESN3 | 4.58E−06 |
| Survival | |
| ATG12_DRAM_CDH1_ID2_AGER_HMGB2 | 3.90E−12 |
| ATG12_CDH1_ID2_AGER_BECN1_HMGB2 | 5.00E−12 |
| ATG12_CSE1L_CD1_ID2_AGER_HMGB2 | 8.30E−12 |
| ATG12_CDH1_ID2_AGER_HMGB2_RPS19BP1 | 8.90E−12 |
| ATG12_LAMP1_CDH1_ID2_AGER_HMGB2 | 9.00E−12 |
| ATG12_CDH1_ID2_MMP9_AGER_HMGB2 | 9.30E−12 |
| ATG12_ATG3_CDH1_ID2_AGER_HMGB2 | 9.80E−12 |
| ATG12_LC3_CDH1_ID2_AGER_HMGB2 | 1.00E−11 |
| ATG12_BNIP3_CDH1_ID2_AGER_HMGB2 | 1.10E−11 |
| ATG12_CDH1_ID2_AGER_HMGB2_31RT1 | 1.30E−11 |
| ATG12_CDH1_ID2_AGER_HMGB2_MMP2 | 1.40E−11 |
| ATG12_CASP8_CDH1_ID2_AGER_HMGB2 | 1.60E−11 |
| ATG12_CDH1_ID2_AGER_CIAP2_HMGB2 | 1.60E−11 |
| ATG12_ATG5_CDH1_ID2_AGER_HMGB2 | 1.90E−11 |
| ATG12_CDH1_ID2_TCF3_AGER_HMGB2 | 1.90E−11 |
| ATG12_DRAM_CDH1_ID2_BECN1_HMGB2 | 1.90E−11 |
| ATG12_FAS_CDH1_ID2_AGER_HMGB2 | 1.90E−11 |
| ATG12_CDH1_ID2_AGER_HMGB1_HMGB2 | 2.00E−11 |
| ATG12_DRAM_LAMP1_CDH1_ID2_HMGB2 | 2.00E−11 |
| ATG12_ATG3_DRAM_CDH1_ID2_HMGB2 | 2.10E−11 |
| ATG12_ATG5_DRAM_CDH1_ID2_HMGB2 | 2.20E−11 |
| ATG12_DIABLO_CDH1_ID2_AGER_HMGB2 | 2.30E−11 |
| ATG12_DIABLO_CDH1_TCF3_BHLHE41_HMGB2 | 2.50E−11 |
| ATG12_CASP8_DRAM_CDH1_ID2_HMGB2 | 2.70E−11 |
| ATG12_DRAM_CDH1_ID2_HMGB2_MMP2 | 2.70E−11 |
| ATG12_LAMP1_CDH1_ID2_BECN1_HMGB2 | 2.70E−11 |
| ATG12_CBS_CDH1_ID2_AGER_HMGB2 | 2.90E−11 |
| ATG12_DRAM_CDH1_ID2_MMP9_HMGB2 | 2.90E−11 |
| ATG12_CDH1_ID2_AGER_HMGB2_UVRAG | 3.00E−11 |
| ATG12_E2F1_CDH1_ID2_AGER_HMGB2 | 3.00E−11 |
| ATG12_ATG5_CDH1_ID2_BECN1_HMGB2 | 3.20E−11 |
| ATG12_DIABLO_CDH1_CIAP2_HMGB2_SESN3 | 3.20E−11 |
| ATG12_CSE1L_DRAM_CDH1_ID2_HMGB2 | 3.30E−11 |
| ATG12_DRAM_E2F1_CDH1_ID2_HMGB2 | 3.30E−11 |
| ATG12_DIABLO_CDH1_TCF3_HMGB2_SESN3 | 3.50E−11 |
| AIFM1_ATG3_ATG5_CASP8_LC3_CDH1 | 3.60E−11 |
| ATG12_BNIP3_DRAM_CDH1_ID2_HMGB2 | 3.60E−11 |
| ATG12_DIABLO_CDH1_ID2_HMGB2_SESN3 | 3.60E−11 |
| AIFMLATG3_CASP8_LC3_CDH1_MMP9 | 3.70E−11 |
| ATG12_ATG3_CDH1_ID2_BECN1_HMGB2 | 3.70E−11 |
| ATG12_CDH1_ID2_AGER_HMGB2_STAT3 | 3.70E−11 |
| ATG12_DIABLO_DRAM_CDH1_ID2_HMGB2 | 3.80E−11 |
| ATG12_DRAM_CDH1_ID2_CIAP2_HMGB2 | 3.80E−11 |
| DRAM_LAMPLCDHLID2_AGER_HMGB2 | 3.95E−11 |
| DRAM_CDHLID2_AGER_BECN1_HMGB2 | 3.97E−11 |
| ATG12_BNIP3_CDH1_ID2_HMGB2_MMP2 | 4.00E−11 |
| ATG12_BNIP3_CDH1_ID2_BECN1_HMGB2 | 4.60E−11 |
| ATG12_CSE1L_CDH1_ID2_BECN1_HMGB2 | 4.60E−11 |
| LAMP1_LC3_CDH1_ID2_AGER_HMGB2 | 4.75E−11 |
| ATG12_CDH1_ID2_BECN1_HMGB2_MMP2 | 4.80E−11 |

TABLE 27-continued

| Marker | p-value |
|---|---|
| DRAM_LC3_CDH1_ID2_AGER_HMGB2 | 4.83E−11 |
| ATG12_DIABLO_CDH1_BHLHE41_HMGB2_SIRT1 | 4.90E−11 |
| ATG12_TKT_CDH1_ID2_AGER_HMGB2 | 4.90E−11 |
| DRAM_CDH1_ID2_MMP9_AGER_HMGB2 | 4.94E−11 |
| ATG12_CDH1_ID2_MMP9_BECN1_HMGB2 | 5.10E−11 |
| CSE1L_DRAM_CDH1_ID2_AGER_HMGB2 | 5.13E−11 |
| ATG12_DRAM_FAS_CDH1_ID2_HMGB2 | 5.30E−11 |
| ATG12_CDH1_ID2_MMP9_TCF3_HMGB2 | 1.80E−10 |
| Disease-free survival | |
| AKT1_ATG12_FAS_CDH2_STAT3_TP63 | 5.94E−09 |
| AKT1_FAS_BECN1_CDH2_STAT3_TP63 | 1.41E−08 |
| AKT1_FAS_CDH2_RPS19BP1_STAT3_TP63 | 1.86E−08 |
| AKT1_FAS_LC3_CDH2_STAT3_TP63 | 2.97E−08 |
| ID2_CDH2_HMG131_MMP2_RPS19BP1_SESN3 | 3.01E−08 |
| AKT1_ATG12_BECN1_CDH2_STAT3_TP63 | 3.23E−08 |
| AKT1_ATG7_FAS_CDH2_RPS19BP1_TP63 | 3.33E−08 |
| ATG12_ID2_CDH2_HMGB1_MMP2_SESN3 | 3.48E−08 |
| FRAP1_LC3_BECN1_CASP3_CDH2_STAT3 | 3.58E−08 |
| FRAP1_LC3_TKT_CASP3_CDH2_STAT3 | 3.93E−08 |
| FRAP1_LC3_NNMT_BECN1_CDH2_STAT3 | 4.23E−08 |
| ID2_CDH2_HMGB2_MMP2_RPS1913P1_SESN3 | 4.26E−08 |
| ATG12_ID2_CDH2_CIAP2_MMP2_SESN3 | 4.44E−08 |
| FAS_FRAP1_LC3_CDH2_SESN1_STAT3 | 4.57E−08 |
| FRAP1_TKT_BECN1_CASP3_CDH2_STAT3 | 4.71E−08 |
| ATG12_FRAP1_ID2_CDH2_MMP2_SESN3 | 4.88E−08 |
| FAS_LC3_CDH2_HMGB1_STAT3_TWIST1 | 5.21E−08 |
| ATG12_TKT_ID2_CDH2_MMP2_SESN3 | 5.23E−08 |
| ID2_CDH2_CIAP2_MMP2_RPS1913P1_SESN3 | 5.31E−08 |
| AKT1_CASP8_FAS_CDH2_STAT3_TP63 | 5.49E−08 |
| AKT1_FAS_CASP3_CDH2_STAT3_TP63 | 5.76E−08 |
| FAS_FRAP1_LC3_NNMT_CDH2_STAT3 | 5.85E−08 |
| FAS_FRAP1_TKT_CDH2_SESN1_STAT3 | 5.91E−08 |
| ATG12_ID2_CDH2_MMP2_SESN3_STAT3 | 6.09E−08 |
| FRAPLNNMT_TKT_BECN1_CDH2_STAT3 | 6.10E−08 |
| ATG12_FAS_FRAP1_CDH2_STAT3_TP63 | 6.16E−08 |
| ATG12_ATG3_ID2_CDH2_MMP2_SESN3 | 6.17E−08 |
| DRAM_ID2_CDH2_MMP2_RPS1913P1_SESN3 | 6.22E−08 |
| ATG12_CBS_ID2_CDH2_MMP2_SESN3 | 6.22E−08 |
| ID2_CDH2_MMP2_RPS1913P1_SESN3_STAT3 | 6.31E−08 |
| FRAP1_ID2_CDH2_MMP2_RPS1913P1_SESN3 | 6.33E−08 |
| AKT1_02_CDH2_MMP2_RPS1913P1_SESN3 | 6.36E−08 |
| FAS_FRAP1_LC3_CASP3_CDH2_STAT3 | 6.57E−08 |
| ATG5_ID2_CDH2_MMP2_RPS1913P1_SESN3 | 6.57E−08 |
| AKT1_FAS_CDH2_HMGB1_STAT3_TP63 | 6.60E−08 |
| CSE1L_ID2_CDH2_MMP2_RPS1913P1_SESN3 | 6.70E−08 |
| ATG3_ID2_CDH2_MMP2_RPS1913P1_SESN3 | 6.76E−08 |
| FRAP1_LC3_NNMT_TKT_CDH2_STAT3 | 6.90E−08 |
| CBS_ID2_CDH2_MMP2_RPS1913P1_SESN3 | 7.00E−08 |
| AKT1_ATG12_CDH2_HMGB1_STAT3_TP63 | 7.01E−08 |
| FAS_FRAP1_LC3_CDH2_RAPTOR_RPS1913P1 | 7.17E−08 |
| AKT1_ATG12_02_CDH2_MMP2_SESN3 | 7.23E−08 |
| ATG12_ATG5_ID2_CDH2_MMP2_SESN3 | 7.25E−08 |
| AKT1_ATG12_FAS_BECN1_STAT3_TP63 | 7.25E−08 |
| AKT1_FAS_BECN1_RPS1913P1_STAT3_TP63 | 7.27E−08 |
| FAS_FRAP1_LC3_CDH2_FASLG_RAPTOR | 7.34E−08 |
| FAS_ID2_CDH2_MMP2_RPS1913P1_SESN3 | 7.34E−08 |
| ATG12_CDH1_ID2_CDH2_MMP2_SESN3 | 7.49E−08 |
| FRAP1_LC3_TKT_CDH2_STAT3_TWIST1 | 7.55E−08 |
| CDH1_ID2_CDH2_MMP2_RPS19BP1_SESN3 | 7.66E−08 |
| FAS_FRAP1_LC3_CDH2_KIAA1967_RPS19BP1 | 7.69E−08 |
| FRAP1_LC3_CDH2_HMGB1_STAT3_TWIST1 | 7.87E−08 |
| ATG12_ID2_CDH2_HMGB2_MMP2_SESN3 | 7.98E−08 |
| ATG12_FAS_ID2_CDH2_MMP2_SESN3 | 7.98E−08 |
| TKT_ID2_CDH2_MMP2_RPS19BP1_SESN3 | 8.12E−08 |
| BAX_FAS_FRAP1_LC3_TKT_CDH2 | 8.37E−08 |
| ATG12_ID2_CDH2_MMP2_RPS19BP1_SESN3 | 8.37E−08 |
| CDH1_ID2_MMP9_TCF3_CDH2_SESN3 | 8.42E−06 |

TABLE 28

| Marker | p-value |
|---|---|
| Recurrence | |
| AKT1_ATG12_FAS_BECN1_CDH2_STAT3_TP63 | 5.95E−09 |
| FRAP1_LC3_TKT_BECN1_CASP3_CDH2_STAT3 | 9.04E−09 |
| FAS_FRAP1_LC3_CASP3_CDH2_RPS19BP1_STAT3 | 9.51E−09 |
| FAS_FRAP1_LC3_CDH2_RPS19BP1_SESN1_STAT3 | 9.55E−09 |
| AKT1_FAS_BECN1_CDH2_RPS19BP1_STAT3_TP63 | 9.89E−09 |
| ID2_CDH2_FASLG_NAMPT_RPS19BP1_SESN3_STAT3 | 1.11E−08 |
| FRAP1_LC3_NNMT_TKT_BECN1_CDH2_STAT3 | 1.15E−08 |
| AKT1_ATG12_FAS_CDH2_RPS19BP1_STAT3_TP63 | 1.17E−08 |
| FAS_FRAP1_LC3_NNMT_CDH2_RPS19BP1_STAT3 | 1.23E−08 |
| FAS_FRAP1_LC3_CCNG2_CDH2_RPS19BP1_STAT3 | 1.39E−08 |
| FRAP1_LC3_BECN1_CASP3_CDH2_HMGB1_STAT3 | 1.44E−08 |
| ID2_FASLG_HMGB2_NAMPT_RPS19BP1_SESN3_STAT3 | 1.50E−08 |
| FRAP1_LC3_NNMT_BECN1_CASP3_CDH2_STAT3 | 1.52E−08 |
| CBS_FRAP1_LC3_BECN1_CASP3_CDH2_STAT3 | 1.52E−08 |
| FRAP1_LC3_BECN1_CASP3_CDH2_SIRT1_STAT3 | 1.62E−08 |
| CSE1L_FRAP1_LC3_CASP3_CDH2_RPS19BP1_STAT3 | 1.63E−08 |
| FRAP1_LC3_TKT_CASP3_CDH2_HMGB1_STAT3 | 1.70E−08 |
| FRAP1_LC3_TKT_CDH2_HMGB1_STAT3_TWIST1 | 1.71E−08 |
| ATG5_FRAP1_LC3_BECN1_CASP3_CDH2_STAT3 | 1.76E−08 |
| CSE1L_FRAP1_LC3_BECN1_CASP3_CDH2_STAT3 | 1.77E−08 |
| FRAP1_LC3_BECN1_CASP3_CDH2_HMGB2_STAT3 | 1.81E−08 |
| AKT1_LC3_CDH2_HMGB1_RPS19BP1_STAT3_TP63 | 1.81E−08 |
| FAS_FRAP1_LC3_CDH2_MMP2_RAPTOR_RPS19BP1 | 1.84E−08 |
| AKT1_FAS_CDH2_RPS19BP1_SESN2_STAT3_TP63 | 1.86E−08 |
| FRAP1_LC3_BECN1_CASP3_CDH2_FASLG_STAT3 | 1.87E−08 |
| ID2_CDH2_HMGB1_HMGB2_MMP2_RPS19BP1_SESN3 | 1.88E−08 |
| AKT1_CASP8_FAS_BECN1_CDH2_STAT3_TP63 | 1.90E−08 |
| FAS_FRAP1_LC3_TKT_CDH2_SESN1_STAT3 | 1.91E−08 |
| CBS_FRAP1_LC3_NNMT_BECN1_CDH2_STAT3 | 1.91E−08 |
| AKT1_FAS_LC3_CDH2_RPS19BP1_STAT3_TP63 | 1.91E−08 |
| FRAP1_LC3_BECN1_CDH2_HMGB1_STAT3_TWIST1 | 1.91E−08 |
| CSE1L_FRAP1_LC3_TKT_CASP3_CDH2_STAT3 | 1.91E−08 |
| FRAP1_LC3_NNMT_BECN1_CDH2_SIRT1_STAT3 | 1.95E−08 |
| AKT1_ATG12_CDH2_HMGB1_RPS19BP1_STAT3_TP63 | 1.96E−08 |
| ID2_CDH2_FASLG_HMGB1_NAMPT_RPS19BP1_SESN3 | 1.96E−08 |
| ID2_CDH2_HMGB1_MMP2_RPS19BP1_SESN3_STAT3 | 1.99E−08 |
| FRAP1_LC3_CDH2_HMGB1_RPS19BP1_STAT3_TWIST1 | 2.00E−08 |
| FAS_FRAP1_LC3_CDH2_KIAA1967_MMP2_RPS19BP1 | 2.01E−08 |
| FRAP1_LC3_BECN1_CASP3_CDH2_RPS19BP1_STAT3 | 2.02E−08 |
| FRAP1_LC3_TKT_CASP3_CDH2_FASLG_STAT3 | 2.04E−08 |
| BNIP3_FRAP1_LC3_BECN1_CASP3_CDH2_STAT3 | 2.05E−08 |
| FRAP1_LC3_CASP3_CDH2_HMGB1_MMP2_STAT3 | 2.05E−08 |
| FAS_LC3_CDH2_HMGB1_RPS19BP1_STAT3_TWIST1 | 2.05E−08 |
| ID2_HMGB1_HMGB2_MMP2_NAMPT_RPS19BP1_SESN3 | 2.06E−08 |
| FRAP1_LC3_TKT_BECN1_CDH2_FASLG_RAPTOR | 2.07E−08 |
| FRAP1_LC3_NNMT_BECN1_CDH2_FASLG_STAT3 | 2.12E−08 |
| FAS_FRAP1_LC3_CDH2_FASLG_RAPTOR_RPS19BP1 | 2.13E−08 |
| FRAP1_LC3_MMP9_BECN1_CASP3_CDH2_STAT3 | 2.15E−08 |
| FAS_FRAP1_LC3_NNMT_BECN1_CDH2_STAT3 | 2.17E−08 |
| AIFM1_FAS_FRAP1_LC3_CDH2_RPS19BP1_STAT3 | 2.18E−08 |
| AKT1_ATG12_FAS_LC3_CDH2_STAT3_TP63 | 2.18E−08 |
| AKT1_FAS_CDH2_HMGB1_RPS19BP1_STAT3_TP63 | 2.18E−08 |
| ID2_CDH2_HMGB1_MMP2_NAMPT_RPS19BP1_SESN3 | 2.22E−08 |
| AKT1_BECN1_CDH2_HMGB1_RPS19BP1_STAT3_TP63 | 2.23E−08 |
| AKT1_ATG12_CASP8_FAS_CDH2_STAT3_TP63 | 2.24E−08 |
| ATG5_FRAP1_LC3_NNMT_BECN1_CDH2_STAT3 | 2.25E−08 |
| FRAP1_LC3_CASP3_CDH2_HMGB1_RPS19BP1_STAT3 | 2.27E−08 |
| CDH1_ID2_MMP9_TCF3_CDH2_RPS19BP1_SESN3 | 6.86E−07 |
| Survival | |
| ATG12_DRAM_CDH1_ID2_AGER_BECN1_HMGB2 | 2.60E−12 |
| ATG12_CSE1L_DRAM_CDH1_ID2_AGER_HMGB2 | 3.62E−12 |
| ATG12_CDH1_ID2_AGER_BECN1_HMGB2_RPS19BP1 | 3.70E−12 |
| ATG12_CSE1L_CDH1_ID2_AGER_BECN1_HMGB2 | 3.76E−12 |
| ATG12_DRAM_LAMP1_CDH1_ID2_AGER_HMGB2 | 3.77E−12 |
| ATG12_DRAM_CDH1_ID2_MMP9_AGER_HMGB2 | 3.85E−12 |
| ATG12_DRAM_CDH1_ID2_AGER_HMGB2_RPS19BP1 | 3.92E−12 |
| ATG12_ATG3_DRAM_CDH1_ID2_AGER_HMGB2 | 4.10E−12 |
| ATG12_LC3_CDH1_ID2_AGER_BECN1_HMGB2 | 4.34E−12 |
| ATG12_DRAM_LC3_CDH1_ID2_AGER_HMGB2 | 4.68E−12 |
| ATG12_LAMP1_CDH1_ID2_AGER_BECN1_HMGB2 | 4.72E−12 |
| ATG12_DRAM_CDH1_ID2_AGER_HMGB2_SIRT1 | 4.96E−12 |
| ATG12_CDH1_ID2_MMP9_AGER_BECN1_HMGB2 | 5.00E−12 |
| ATG12_DIABLO_CDH1_TCF3_CIAP2_HMGB2_SESN3 | 5.29E−12 |
| ATG12_DIABLO_CDH1_TCF3_BHLHE41_HMGB2_SIRT1 | 5.66E−12 |
| ATG12_ATG3_CDH1_ID2_AGER_BECN1_HMGB2 | 5.70E−12 |

TABLE 28-continued

| Marker | p-value |
|---|---|
| ATG12_BNIP3_DRAM_CDH1_ID2_AGER_HMGB2 | 5.90E−12 |
| ATG12_DRAM_CDH1_ID2_AGER_CIAP2_HMGB2 | 6.12E−12 |
| ATG12_LAMP1_LC3_CDH1_ID2_AGER_HMGB2 | 6.14E−12 |
| ATG12_DRAM_CDH1_ID2_AGER_HMGB2_MMP2 | 6.19E−12 |
| ATG12_CASP8_DRAM_CDH1_ID2_AGER_HMGB2 | 6.50E−12 |
| ATG12_CSE1L_CDH1_ID2_AGER_HMGB2_RPS19BP1 | 6.69E−12 |
| ATG12_BNIP3_CDH1_ID2_AGER_HMGB2_MMP2 | 6.80E−12 |
| ATG12_CDH1_ID2_TCF3_AGER_BECN1_HMGB2 | 6.90E−12 |
| ATG12_CDH1_ID2_AGER_BECN1_HMGB2_MMP2 | 7.10E−12 |
| ATG12_BNIP3_CDH1_ID2_AGER_BECN1_HMGB2 | 7.20E−12 |
| ATG12_FAS_CDH1_ID2_AGER_BECN1_HMGB2 | 7.28E−12 |
| ATG12_ATG3_CSE1L_CDH1_ID2_AGER_HMGB2 | 8.00E−12 |
| ATG12_DIABLO_CDH1_BECN1_CIAP2_HMGB2_SESN3 | 8.02E−12 |
| ATG12_DRAM_CDH1_ID2_TCF3_AGER_HMGB2 | 8.06E−12 |
| ATG12_ATG3_DIABLO_CDH1_TCF3_HMGB2_SESN3 | 8.10E−12 |
| ATG12_CSE1L_LC3_CDH1_ID2_AGER_HMGB2 | 8.13E−12 |
| ATG12_CSE1L_CDH1_ID2_MMP9_AGER_HMGB2 | 8.26E−12 |
| ATG12_ATG5_DRAM_CDH1_ID2_AGER_HMGB2 | 8.40E−12 |
| ATG12_DRAM_CDH1_ID2_AGER_HMGB1_HMGB2 | 8.48E−12 |
| ATG12_DRAM_LAMP1_CDH1_ID2_BECN1_HMGB2 | 8.67E−12 |
| ATG12_CDH1_ID2_MMP9_AGER_HMGB2_RPS19BP1 | 8.80E−12 |
| ATG12_DRAM_FAS_CDH1_ID2_AGER_HMGB2 | 8.86E−12 |
| ATG12_DIABLO_DRAM_CDH1_ID2_AGER_HMGB2 | 8.99E−12 |
| ATG12_CSE1L_LAMP1_CDH1_ID2_AGER_HMGB2 | 8.99E−12 |
| ATG12_DIABLO_FAS_CDH1_TCF3_BHLHE41_HMGB2 | 9.11E−12 |
| ATG12_LAMP1_CDH1_ID2_MMP9_AGER_HMGB2 | 9.14E−12 |
| ATG12_ATG3_DIABLO_CDH1_TCF3_BHLHE41_HMGB2 | 9.20E−12 |
| ATG12_ATG3_CDH1_ID2_AGER_HMGB2_RPS19BP1 | 9.40E−12 |
| ATG12_CDH1_ID2_AGER_BECN1_HMGB2_SIRT1 | 9.40E−12 |
| ATG12_CDH1_ID2_AGER_HMGB2_MMP2_SIRT1 | 9.60E−12 |
| AIFM1_ATG3_CASP8_CSE1L_LC3_CDH1_MMP9 | 9.70E−12 |
| ATG12_ATG3_CDH1_ID2_MMP9_AGER_HMGB2 | 9.70E−12 |
| ATG12_LC3_CDH1_ID2_MMP9_AGER_HMGB2 | 9.86E−12 |
| AIFM1_CASP8_LC3_CDH1_AGER_HMGB2_RPS19BP1 | 1.00E−11 |
| ATG12_ATG5_CDH1_ID2_AGER_BECN1_HMGB2 | 1.00E−11 |
| ATG12_LAMP1_CDH1_ID2_AGER_HMGB2_MMP2 | 1.06E−11 |
| ATG12_LAMP1_CDH1_ID2_AGER_HMGB2_RPS19BP1 | 1.07E−11 |
| AIFM1_ATG3_ATG5_CASP8_LC3_CDH1_MMP9 | 1.10E−11 |
| ATG12_ATG5_DRAM_CDH1_ID2_BECN1_HMGB2 | 1.10E−11 |
| ATG12_BNIP3_CDH1_ID2_MMP9_AGER_HMGB2 | 1.10E−11 |
| ATG12_BNIP3_CSE1L_CDH1_ID2_AGER_HMGB2 | 1.10E−11 |
| ATG12_CDH1_ID2_MMP9_TCF3_AGER_HMGB2 | 1.90E−11 |
| Disease-free survival | |
| AKT1_ATG12_FAS_CDH2_RPS19BP1_STAT3_TP63 | 1.25E−09 |
| AKT1_ATG12_FAS_BECN1_CDH2_STAT3_TP63 | 1.62E−09 |
| AKT1_ATG12_FAS_LC3_CDH2_STAT3_TP63 | 1.77E−09 |
| AKT1_ATG12_CASP8_FAS_CDH2_STAT3_TP63 | 1.89E−09 |
| AKT1_FAS_CDH2_RPS19BP1_SESN2_STAT3_TP63 | 2.32E−09 |
| AKT1_FAS_LC3_CDH2_RPS19BP1_STAT3_TP63 | 2.46E−09 |
| AKT1_ATG12_FAS_CASP3_CDH2_STAT3_TP63 | 3.14E−09 |
| AKT1_FAS_BECN1_CDH2_RPS19BP1_STAT3_TP63 | 3.17E−09 |
| AKT1_ATG12_FAS_LAMP1_CDH2_STAT3_TP63 | 3.43E−09 |
| AKT1_ATG12_FAS_CDH2_HMGB2_STAT3_TP63 | 3.66E−09 |
| AIFM1_AKT1_ATG12_FAS_CDH2_STAT3_TP63 | 4.18E−09 |
| AKT1_ATG12_FAS_CDH2_CIAP2_STAT3_TP63 | 4.33E−09 |
| AKT1_ATG12_FAS_CDH2_SESN2_STAT3_TP63 | 4.34E−09 |
| AKT1_ATG12_FAS_NNMT_CDH2_STAT3_TP63 | 4.41E−09 |
| AKT1_FAS_CDH2_HMGB1_RPS19BP1_STAT3_TP63 | 4.69E−09 |
| AKT1_ATG12_FAS_CDH2_NAMPT_STAT3_TP63 | 5.00E−09 |
| AKT1_ATG12_FAS_CDH2_SIRT1_STAT3_TP63 | 5.09E−09 |
| AKT1_FAS_LC3_BECN1_CDH2_STAT3_TP63 | 5.11E−09 |
| AKT1_CASP8_FAS_BECN1_CDH2_STAT3_TP63 | 5.38E−09 |
| AKT1_ATG12_DRAM_FAS_CDH2_STAT3_TP63 | 5.54E−09 |
| AKT1_ATG7_FAS_CDH2_RPS19BP1_STAT3_TP63 | 6.04E−09 |
| AKT1_ATG12_FAS_BECN1_RPS19BP1_STAT3_TP63 | 6.22E−09 |
| AKT1_CASP8_FAS_CDH2_RPS19BP1_STAT3_TP63 | 6.23E−09 |
| AKT1_ATG12_FAS_CDH2_HMGB1_STAT3_TP63 | 6.53E−09 |
| ATG12_FAS_FRAP1_LC3_CDH2_STAT3_TP63 | 6.78E−09 |
| AKT1_ATG12_FAS_XIAP_CDH2_STAT3_TP63 | 6.99E−09 |
| AKT1_ATG12_FAS_CDH2_LAMP2_STAT3_TP63 | 7.29E−09 |
| AKT1_ATG12_ATG3_FAS_CDH2_STAT3_TP63 | 7.32E−09 |
| AKT1_ATG12_FAS_PTEN_CDH2_STAT3_TP63 | 7.70E−09 |
| AKT1_ATG7_BECN1_CDH2_RPS19BP1_STAT3_TP63 | 7.80E−09 |
| AKT1_FAS_CASP3_CDH2_RPS19BP1_STAT3_TP63 | 7.81E−09 |
| AKT1_ATG7_FAS_LC3_CDH2_RPS19BP1_TP63 | 7.97E−09 |
| AKT1_FAS_LC3_CDH2_HMGB1_STAT3_TP63 | 8.01E−09 |
| AKT1_ATG12_FAS_TKT_CDH2_STAT3_TP63 | 8.05E−09 |

TABLE 28-continued

| Marker | p-value |
|---|---|
| FAS_FRAP1_LC3_CASP3_CDH2_RPS19BP1_STAT3 | 8.10E−09 |
| AKT1_FAS_CDH2_HMGB2_RPS19BP1_STAT3_TP63 | 8.20E−09 |
| AKT1_FAS_TCF3_CDH2_RPS19BP1_STAT3_TP63 | 8.24E−09 |
| FAS_FRAP1_LC3_TKT_CDH2_FASLG_RAPTOR | 8.41E−09 |
| AKT1_ATG12_E2F1_FAS_CDH2_STAT3_TP63 | 8.55E−09 |
| AKT1_FAS_BECN1_CDH2_RAPTOR_STAT3_TP63 | 8.57E−09 |
| AKT1_FAS_NNMT_BECN1_CDH2_STAT3_TP63 | 9.44E−09 |
| AKT1_ATG12_CDH2_HMGB1_RPS19BP1_STAT3_TP63 | 9.58E−09 |
| AKT1_FAS_BECN1_CDH2_LAMP2_STAT3_TP63 | 9.77E−09 |
| FAS_FRAP1_LC3_CDH2_RPS19BP1_SESN1_STAT3 | 9.79E−09 |
| FAS_FRAP1_LC3_NNMT_CDH2_RPS19BP1_STAT3 | 9.88E−09 |
| ID2_CDH2_HMGB1_HMGB2_MMP2_RPS19BP1_SESN3 | 9.90E−09 |
| AKT1_ATG12_FAS_CDH2_RAPTOR_STAT3_TP63 | 1.03E−08 |
| FRAP1_LC3_TKT_BECN1_CASP3_CDH2_STAT3 | 1.06E−08 |
| FAS_FRAP1_LC3_CDH2_FASLG_RAPTOR_RPS19BP1 | 1.07E−08 |
| FAS_LC3_CDH2_HMGB1_RPS19BP1_STAT3_TWIST1 | 1.07E−08 |
| AKT1_FAS_TKT_BECN1_CDH2_STAT3_TP63 | 1.10E−08 |
| AKT1_CASP8_FAS_LC3_CDH2_STAT3_TP63 | 1.10E−08 |
| AKT1_FAS_LC3_CASP3_CDH2_STAT3_TP63 | 1.10E−08 |
| AKT1_FAS_LAMP1_BECN1_CDH2_STAT3_TP63 | 1.13E−08 |
| AKT1_ATG12_ATG7_FAS_CDH2_RPS19BP1_TP63 | 1.15E−08 |
| AKT1_ATG12_FAS_TCF3_CDH2_STAT3_TP63 | 1.16E−08 |
| AKT1_FAS_CDH2_NAMPT_RPS19BP1_STAT3_TP63 | 1.17E−08 |
| CDH1_ID2_MMP9_TCF3_CDH2_RPS19BP1_SESN3 | 7.02E−07 |

TABLE 29

| Marker | p-value |
|---|---|
| Recurrence | |
| AKT1_ATG12_FAS_CDH2_RPS19BP1_SESN2_STAT3_TP63 | 2.03E−09 |
| AKT1_FAS_LC3_CDH2_HMGB1_RPS19BP1_STAT3_TP63 | 2.06E−09 |
| AKT1_ATG12_FAS_BECN1_CDH2_RPS19BP1_STAT3_TP63 | 2.35E−09 |
| AKT1_ATG12_CASP8_FAS_BECN1_CDH2_STAT3_TP63 | 2.49E−09 |
| AKT1_ATG12_FAS_LC3_CDH2_RPS19BP1_STAT3_TP63 | 3.36E−09 |
| AKT1_ATG12_FAS_NNMT_BECN1_CDH2_STAT3_TP63 | 3.42E−09 |
| AKT1_ATG12_FAS_BECN1_CDH2_RAPTOR_STAT3_TP63 | 3.50E−09 |
| AKT1_FAS_LC3_BECN1_CDH2_RPS19BP1_STAT3_TP63 | 3.74E−09 |
| FAS_FRAP1_LC3_BECN1_CASP3_CDH2_RPS19BP1_STAT3 | 3.80E−09 |
| AKT1_ATG12_FAS_CDH2_HMGB1_RPS19BP1_STAT3_TP63 | 3.80E−09 |
| FRAP1_LC3_TKT_BECN1_CASP3_CDH2_FASLG_STAT3 | 3.83E−09 |
| CSE1L_FAS_FRAP1_LC3_CASP3_CDH2_RPS19BP1_STAT3 | 3.94E−09 |
| AKT1_ATG12_LC3_CDH2_HMGB1_RPS19BP1_STAT3_TP63 | 4.08E−09 |
| FAS_FRAP1_LC3_NNMT_BECN1_CDH2_RPS19BP1_STAT3 | 4.36E−09 |
| AKT1_CASP8_FAS_BECN1_CDH2_RPS19BP1_STAT3_TP63 | 4.39E−09 |
| FRAP1_LC3_NNMT_TKT_BECN1_CDH2_FASLG_STAT3 | 4.42E−09 |
| AKT1_ATG12_FAS_BECN1_CDH2_LAMP2_STAT3_TP63 | 4.50E−09 |
| AKT1_FAS_LC3_CDH2_RPS19BP1_SESN2_STAT3_TP63 | 4.53E−09 |
| AKT1_ATG12_FAS_LAMP1_BECN1_CDH2_STAT3_TP63 | 4.56E−09 |
| ID2_CDH2_FASLG_HMGB1_HMGB2_NAMPT_RPS19BP1_SESN3 | 4.69E−09 |
| AKT1_ATG12_FAS_BECN1_CDH2_CIAP2_STAT3_TP63 | 4.77E−09 |
| AKT1_ATG12_CASP8_FAS_CDH2_RPS19BP1_STAT3_TP63 | 4.88E−09 |
| ID2_CDH2_FASLG_HMGB2_NAMPT_RPS19BP1_SESN3_STAT3 | 5.10E−09 |
| AKT1_ATG12_FAS_TCF3_CDH2_RPS19BP1_STAT3_TP63 | 5.17E−09 |
| AKT1_ATG12_E2F1_FAS_BECN1_CDH2_STAT3_TP63 | 5.17E−09 |
| AKT1_ATG7_FAS_BECN1_CDH2_RPS19BP1_STAT3_TP63 | 5.22E−09 |
| AKT1_FAS_BECN1_CDH2_RPS19BP1_SESN2_STAT3_TP63 | 5.26E−09 |
| AKT1_ATG12_FAS_LC3_BECN1_CDH2_STAT3_TP63 | 5.29E−09 |
| AKT1_LC3_BECN1_CDH2_HMGB1_RPS19BP1_STAT3_TP63 | 5.33E−09 |
| AKT1_ATG12_ATG7_BECN1_CDH2_RPS19BP1_STAT3_TP63 | 5.39E−09 |
| FAS_FRAP1_LC3_CASP3_CDH2_FASLG_RPS19BP1_STAT3 | 5.55E−09 |
| AKT1_ATG12_FAS_BECN1_CASP3_CDH2_STAT3_TP63 | 5.62E−09 |
| AKT1_ATG12_FAS_BECN1_CDH2_HMGB2_STAT3_TP63 | 5.68E−09 |
| AKT1_ATG12_FAS_LC3_CDH2_HMGB1_STAT3_TP63 | 5.75E−09 |
| FRAP1_LC3_TKT_CASP3_CDH2_FASLG_HMGB1_STAT3 | 5.85E−09 |
| FAS_FRAP1_LC3_NNMT_CDH2_MMP2_RPS19BP1_STAT3 | 5.93E−09 |
| FAS_FRAP1_LC3_BECN1_CDH2_RPS19BP1_SESN1_STAT3 | 5.93E−09 |
| FAS_FRAP1_LC3_TKT_CDH2_RPS19BP1_SESN1_STAT3 | 5.97E−09 |
| AKT1_ATG12_BECN1_CDH2_HMGB1_RPS19BP1_STAT3_TP63 | 5.98E−09 |
| AKT1_ATG12_FAS_CASP3_CDH2_RPS19BP1_STAT3_TP63 | 6.02E−09 |
| AKT1_ATG12_FAS_CDH2_NAMPT_RPS19BP1_STAT3_TP63 | 6.04E−09 |
| FAS_FRAP1_LC3_CASP3_CDH2_RPS19BP1_SIRT1_STAT3 | 6.06E−09 |
| FAS_FRAP1_LC3_CDH2_FASLG_RPS19BP1_SESN1_STAT3 | 6.10E−09 |
| AKT1_FAS_NNMT_BECN1_CDH2_RPS19BP1_STAT3_TP63 | 6.17E−09 |

TABLE 29-continued

| Marker | p-value |
|---|---|
| CSE1L_FAS_FRAP1_LC3_NNMT_CDH2_RPS19BP1_STAT3 | 6.17E−09 |
| FAS_FRAP1_LC3_TKT_CDH2_FASLG_RAPTOR_RPS19BP1 | 6.23E−09 |
| AKT1_FAS_BECN1_CDH2_HMGB1_RPS19BP1_STAT3_TP63 | 6.28E−09 |
| FAS_LC3_CDH2_HMGB1_RPS19BP1_STAT3_TP63_TWIST1 | 6.29E−09 |
| FAS_FRAP1_LC3_TKT_CASP3_CDH2_RPS19BP1_STAT3 | 6.35E−09 |
| ID2_CDH2_FASLG_HMGB1_NAMPT_RPS19BP1_SESN3_STAT3 | 6.36E−09 |
| FAS_FRAP1_LC3_BECN1_CDH2_FASLG_RAPTOR_RPS19BP1 | 6.40E−09 |
| CSE1L_FRAP1_LC3_TKT_BECN1_CASP3_CDH2_STAT3 | 6.45E−09 |
| FRAP1_LC3_TKT_BECN1_CASP3_CDH2_HMGB1_STAT3 | 6.46E−09 |
| FAS_FRAP1_LC3_BECN1_CCNG2_CDH2_RPS19BP1_STAT3 | 6.47E−09 |
| FAS_FRAP1_LC3_TKT_BECN1_CDH2_FASLG_RAPTOR | 6.49E−09 |
| AKT1_ATG12_FAS_TK1_BECN1_CDH2_STAT3_TP63 | 6.56E−09 |
| FRAP1_LC3_BECN1_CASP3_CDH2_FASLG_HMGB1_STAT3 | 6.58E−09 |
| CDH1_ID2_MMP9_TCF3_CDH2_MMP2_RPS19BP1_SESN3 | 2.57E−07 |
| Survival | |
| ATG12_ATG3_DIABLO_CDH1_TCF3_CIAP2_HMGB2_SESN3 | 1.60E−12 |
| ATG12_DIABLO_DRAM_CDH1_TCF3_CIAP2_HMGB2_SESN3 | 1.68E−12 |
| ATG12_BNIP3_DIABLO_CDH1_TCF3_CIAP2_HMGB2_SESN3 | 1.71E−12 |
| ATG12_DRAM_CDH1_ID2_AGER_BECN1_HMGB2_RPS19BP1 | 1.76E−12 |
| ATG12_CSE1L_DRAM_CDH1_ID2_AGER_BECN1_HMGB2 | 2.00E−12 |
| ATG12_DIABLO_DRAM_CDH1_TCF3_BHLHE41_HMGB2_SIRT1 | 2.01E−12 |
| ATG12_DIABLO_CDH1_TCF3_BECN1_CIAP2_HMGB2_SESN3 | 2.17E−12 |
| ATG12_LAMP1_LC3_CDH1_ID2_AGER_BECN1_HMGB2 | 2.31E−12 |
| ATG12_CSE1L_CDH1_ID2_AGER_BECN1_HMGB2_RPS19BP1 | 2.31E−12 |
| ATG12_DRAM_LAMP1_CDH1_ID2_AGER_BECN1_HMGB2 | 2.37E−12 |
| ATG12_DRAM_LC3_CDH1_ID2_AGER_BECN1_HMGB2 | 2.40E−12 |
| ATG12_ATG3_DIABLO_CDH1_BECN1_CIAP2_HMGB2_SESN3 | 2.50E−12 |
| ATG12_DRAM_CDH1_ID2_MMP9_AGER_BECN1_HMGB2 | 2.54E−12 |
| ATG12_CASP8_DIABLO_CDH1_TCF3_CIAP2_HMGB2_SESN3 | 2.59E−12 |
| ATG12_ATG3_DIABLO_CDH1_TCF3_BHLHE41_HMGB2_SIRT1 | 2.70E−12 |
| ATG12_DRAM_LAMP1_LC3_CDH1_ID2_AGER_HMGB2 | 2.71E−12 |
| ATG12_DIABLO_CDH1_TCF3_BECN1_BHLHE41_HMGB2_SIRT1 | 2.73E−12 |
| ATG12_CSE1L_LC3_CDH1_ID2_AGER_BECN1_HMGB2 | 2.88E−12 |
| ATG12_ATG3_DRAM_CDH1_ID2_AGER_BECN1_HMGB2 | 2.90E−12 |
| ATG12_CSE1L_DRAM_CDH1_ID2_AGER_HMGB2_RPS19BP1 | 3.04E−12 |
| ATG12_DRAM_CDH1_ID2_TCF3_AGER_BECN1_HMGB2 | 3.11E−12 |
| ATG12_DIABLO_CDH1_TCF3_BHLHE41_HMGB2_SESN2_SIRT1 | 3.17E−12 |
| ATG12_ATG5_DIABLO_CDH1_TCF3_BHLHE41_HMGB2_SIRT1 | 3.20E−12 |
| ATG12_ATG3_CSE1L_DRAM_CDH1_ID2_AGER_HMGB2 | 3.40E−12 |
| ATG12_ATG3_DIABLO_FAS_CDH1_TCF3_BHLHE41_HMGB2 | 3.40E−12 |
| ATG12_BNIP3_DRAM_CDH1_ID2_AGER_HMGB2_MMP2 | 3.51E−12 |
| ATG12_CSE1L_DRAM_CDH1_ID2_MMP9_AGER_HMGB2 | 3.55E−12 |
| ATG12_CDH1_ID2_MMP9_AGER_BECN1_HMGB2_RPS19BP1 | 3.61E−12 |
| ATG12_DRAM_CDH1_ID2_MMP9_AGER_HMGB2_RPS19BP1 | 3.64E−12 |
| ATG12_CSE1L_CDH1_ID2_MMP9_AGER_BECN1_HMGB2 | 3.75E−12 |
| ATG12_DRAM_CDH1_ID2_AGER_HMGB2_MMP2_SIRT1 | 3.79E−12 |
| ATG12_DIABLO_FAS_CDH1_TCF3_BECN1_BHLHE41_HMGB2 | 3.80E−12 |
| ATG12_CSE1L_DRAM_LC3_CDH1_ID2_AGER_HMGB2 | 3.81E−12 |
| ATG12_DRAM_LAMP1_CDH1_ID2_MMP9_AGER_HMGB2 | 3.87E−12 |
| ATG12_DRAM_CDH1_ID2_AGER_BECN1_HMGB2_MMP2 | 3.90E−12 |
| ATG12_ATG3_CSE1L_CDH1_ID2_AGER_BECN1_HMGB2 | 3.90E−12 |
| ATG12_CSE1L_DRAM_LAMP1_CDH1_ID2_AGER_HMGB2 | 3.93E−12 |
| ATG12_ATG3_DRAM_CDH1_ID2_AGER_HMGB2_RPS19BP1 | 4.00E−12 |
| ATG12_ATG3_DRAM_CDH1_ID2_MMP9_AGER_HMGB2 | 4.00E−12 |
| ATG12_CSE1L_LAMP1_CDH1_ID2_AGER_BECN1_HMGB2 | 4.03E−12 |
| ATG12_DRAM_FAS_CDH1_ID2_AGER_BECN1_HMGB2 | 4.06E−12 |
| ATG12_DIABLO_CDH1_TCF3_BECN1_HMGB2_SESN3_SIRT1 | 4.09E−12 |
| ATG12_BNIP3_CDH1_ID2_AGER_BECN1_HMGB2_MMP2 | 4.09E−12 |
| ATG12_LC3_CDH1_ID2_MMP9_AGER_BECN1_HMGB2 | 4.09E−12 |
| AIFM1_CASP8_LAMP1_CDH1_AGER_CIAP2_HMGB2_RPS19BP1 | 4.10E−12 |
| ATG12_ATG3_CDH1_ID2_AGER_BECN1_HMGB2_RPS19BP1 | 4.10E−12 |
| ATG12_ATG3_DIABLO_CDH1_BECN1_HMGB2_SESN3_SIRT1 | 4.10E−12 |
| ATG12_ATG3_DIABLO_FAS_CDH1_TCF3_HMGB2_SESN3 | 4.20E−12 |
| ATG12_DIABLO_FAS_CDH1_TCF3_CIAP2_HMGB2_SESN3 | 4.22E−12 |
| ATG12_CDH1_ID2_TCF3_AGER_BECN1_HMGB2_RPS19BP1 | 4.23E−12 |
| ATG12_CSE1L_CDH1_ID2_TCF3_AGER_BECN1_HMGB2 | 4.25E−12 |
| ATG12_BNIP3_DRAM_CDH1_ID2_AGER_BECN1_HMGB2 | 4.37E−12 |
| ATG12_FAS_CDH1_ID2_AGER_BECN1_HMGB2_RPS19BP1 | 4.39E−12 |
| ATG12_DRAM_LC3_CDH1_ID2_MMP9_AGER_HMGB2 | 4.47E−12 |
| ATG12_DIABLO_CDH1_TCF3_CIAP2_HMGB2_RPS19BP1_SESN3 | 4.56E−12 |
| ATG12_DRAM_CDH1_ID2_TCF3_AGER_HMGB2_RPS19BP1 | 4.59E−12 |
| ATG12_LAMP1_CDH1_ID2_TCF3_AGER_BECN1_HMGB2 | 4.63E−12 |
| ATG12_CDH1_ID2_MMP9_TCF3_AGER_BECN1_HMGB2 | 7.12E−12 |
| Disease-free survival | |
| AKT1_ATG12_FAS_CDH2_RPS19BP1_SESN2_STAT3_TP63 | 1.76E−10 |
| AKT1_ATG12_FAS_BECN1_CDH2_RAPTOR_STAT3_TP63 | 1.84E−10 |

TABLE 29-continued

| Marker | p-value |
|---|---|
| AKT1_ATG12_FAS_BECN1_CDH2_LAMP2_STAT3_TP63 | 2.81E−10 |
| AKT1_ATG12_FAS_LC3_CDH2_RPS19BP1_STAT3_TP63 | 2.84E−10 |
| AKT1_FAS_LC3_CDH2_HMGB1_RPS19BP1_STAT3_TP63 | 4.35E−10 |
| AKT1_FAS_LC3_CDH2_RPS19BP1_SESN2_STAT3_TP63 | 4.86E−10 |
| AKT1_ATG12_ATG7_FAS_CDH2_RPS19BP1_STAT3_TP63 | 5.42E−10 |
| AKT1_ATG7_FAS_BECN1_CDH2_RPS19BP1_STAT3_TP63 | 5.54E−10 |
| AKT1_ATG12_CASP8_FAS_CDH2_RPS19BP1_STAT3_TP63 | 5.65E−10 |
| AKT1_ATG12_FAS_CDH2_HMGB1_RPS19BP1_STAT3_TP63 | 5.69E−10 |
| AKT1_ATG12_FAS_TCF3_CDH2_RPS19BP1_STAT3_TP63 | 6.64E−10 |
| AKT1_ATG12_FAS_BECN1_CDH2_KIAA1967_STAT3_TP63 | 6.89E−10 |
| AKT1_FAS_BECN1_CDH2_RAPTOR_RPS19BP1_STAT3_TP63 | 7.14E−10 |
| AKT1_ATG12_FAS_CDH2_HMGB2_RPS19BP1_STAT3_TP63 | 7.18E−10 |
| AKT1_ATG12_BCL2L1_FAS_BECN1_CDH2_STAT3_TP63 | 7.38E−10 |
| AKT1_CASP8_FAS_CDH2_RPS19BP1_SESN2_STAT3_TP63 | 7.42E−10 |
| AKT1_ATG12_FAS_LAMP1_LC3_CDH2_STAT3_TP63 | 7.69E−10 |
| AKT1_ATG12_CASP8_FAS_LC3_CDH2_STAT3_TP63 | 7.83E−10 |
| AKT1_ATG12_FAS_CDH2_RAPTOR_RPS19BP1_STAT3_TP63 | 7.90E−10 |
| AKT1_FAS_LC3_BECN1_CDH2_RPS19BP1_STAT3_TP63 | 8.27E−10 |
| AKT1_ATG12_FAS_NNMT_CDH2_RPS19BP1_STAT3_TP63 | 8.45E−10 |
| AKT1_ATG12_CASP8_FAS_BECN1_CDH2_STAT3_TP63 | 8.83E−10 |
| AKT1_ATG7_FAS_LC3_CDH2_RPS19BP1_STAT3_TP63 | 8.96E−10 |
| AKT1_ATG12_FAS_CDH2_NAMPT_RPS19BP1_STAT3_TP63 | 9.10E−10 |
| AKT1_ATG12_CASP8_FAS_LAMP1_CDH2_STAT3_TP63 | 9.24E−10 |
| AKT1_ATG12_FAS_NNMT_BECN1_CDH2_STAT3_TP63 | 9.33E−10 |
| AKT1_ATG12_FAS_LC3_BECN1_CDH2_STAT3_TP63 | 9.38E−10 |
| AKT1_ATG12_FAS_LC3_CDH2_HMGB1_STAT3_TP63 | 9.72E−10 |
| AKT1_ATG12_FAS_BECN1_CDH2_RPS19BP1_STAT3_TP63 | 9.81E−10 |
| AKT1_ATG12_E2F1_FAS_BECN1_CDH2_STAT3_TP63 | 9.82E−10 |
| AKT1_ATG12_FAS_CDH1_BECN1_CDH2_STAT3_TP63 | 9.88E−10 |
| AKT1_CASP8_FAS_LC3_CDH2_RPS19BP1_STAT3_TP63 | 9.98E−10 |
| AKT1_ATG12_FAS_CASP3_CDH2_RPS19BP1_STAT3_TP63 | 1.08E−09 |
| AKT1_ATG12_FAS_CDH2_CIAP2_RPS19BP1_STAT3_TP63 | 1.12E−09 |
| AKT1_FAS_CDH2_HMGB1_HMGB2_RPS19BP1_STAT3_TP63 | 1.12E−09 |
| AKT1_ATG12_FAS_LC3_CASP3_CDH2_STAT3_TP63 | 1.12E−09 |
| AKT1_ATG12_ATG7_BECN1_CDH2_RPS19BP1_STAT3_TP63 | 1.15E−09 |
| AKT1_ATG12_E2F1_FAS_CDH2_RPS19BP1_STAT3_TP63 | 1.18E−09 |
| AKT1_ATG12_DRAM_FAS_CDH2_RPS19BP1_STAT3_TP63 | 1.19E−09 |
| AKT1_FAS_CASP3_CDH2_RPS19BP1_SESN2_STAT3_TP63 | 1.19E−09 |
| AKT1_FAS_CDH2_HMGB2_RPS19BP1_SESN2_STAT3_TP63 | 1.23E−09 |
| AKT1_FAS_LC3_CASP3_CDH2_RPS19BP1_STAT3_TP63 | 1.24E−09 |
| AKT1_ATG12_FAS_LAMP1_BECN1_CDH2_STAT3_TP63 | 1.29E−09 |
| AKT1_FAS_TKT_CDH2_RPS19BP1_SESN2_STAT3_TP63 | 1.31E−09 |
| AKT1_ATG12_ATG3_FAS_CDH2_RPS19BP1_STAT3_TP63 | 1.34E−09 |
| AKT1_ATG12_FAS_XIAP_CDH2_RPS19BP1_STAT3_TP63 | 1.36E−09 |
| AKT1_ATG12_CASP8_FAS_NNMT_CDH2_STAT3_TP63 | 1.36E−09 |
| AKT1_ATG12_CASP8_FAS_CASP3_CDH2_STAT3_TP63 | 1.38E−09 |
| AKT1_ATG12_FAS_CDH2_RPS19BP1_SIRT1_STAT3_TP63 | 1.39E−09 |
| AKT1_ATG12_BCL2L1_FAS_CDH2_RPS19BP1_STAT3_TP63 | 1.40E−09 |
| AKT1_ATG12_CASP8_FAS_CDH2_HMGB2_STAT3_TP63 | 1.41E−09 |
| AKT1_ATG12_FAS_LC3_NNMT_CDH2_STAT3_TP63 | 1.41E−09 |
| AIFM1_AKT1_ATG12_CASP8_FAS_CDH2_STAT3_TP63 | 1.43E−09 |
| AKT1_ATG7_FAS_CASP3_CDH2_RPS19BP1_STAT3_TP63 | 1.44E−09 |
| AKT1_ATG12_FAS_PTEN_CDH2_RPS19BP1_STAT3_TP63 | 1.45E−09 |
| AKT1_ATG12_FAS_LAMP1_CDH2_RPS19BP1_STAT3_TP63 | 1.45E−09 |
| AKT1_ATG12_CASP8_FAS_CDH2_CIAP2_STAT3_TP63 | 1.46E−09 |
| AKT1_CDH1_ID2_MMP9_TCF3_CDH2_RPS19BP1_SESN3 | 2.37E−07 |

As can be confirmed from the above tables, each of the markers or their combination shows p-values low enough to be considered significant in terms of all of recurrence, survival, and disease-free survival. In particular, in the case of the combination of the two or more markers, all the p-values for recurrence, survival, and disease-free survival were low. In particular, it was found that there were cases where the p-value for a single marker was relatively high but the p-value decreased when the marker was used in combination with other marker. As a p-value becomes lower, the statistical significance becomes higher. Thus, the low p-values suggest that the estimation for prognosis of liver cancer by each of the markers or their combination is highly accurate.

This means that the more markers of the present disclosure are combined, the lower p-values, which means higher significance, are shown, which means that the more improved accuracy would be achieved in the estimation for prognosis based on the combinations of the markers.

Thus, it was found that the markers and/or the combinations of markers of Tables 22~29 are effective in predicting prognosis of liver cancer of the A1 group (recurrence, survival, disease-free survival), and that the prognosis of liver cancer of the A1 group can be predicted effectively by nucleic acids and antibodies targeted at the markers.

Also, it can be found that the prognosis of liver cancer of the A1 group can be predicted effectively by the method for predicting prognosis of liver cancer of the present disclosure, which is targeted at the markers.

Further, cross-validation was performed for combinations of markers which were considered statistically significant.

Patients of each patient group were randomly divided into two groups (positive group: 139 patients; test group: 138 patients). With the reference value which was considered statistically significant in the results of the positive group obtained in the same manner as Example 1 fixed, for the test group, the accuracy of estimation was calculated to be the level of $p<0.05$ or $p<0.001$ with respect to recurrence, survival and disease-free survival.

Among the results of cross-validation of the prediction of the recurrence, survival and disease-free survival of the A1 group, representative examples showing the excellent accuracy of prognosis in each aspect are as follows:

Recurrence: ATG7_FRAP1_LC3_NNMT_STAT3 (95% at the level of $p<0.05$)

Survival: AKT1_CDH1_ID2 (98.7% at the level of $p<0.05$)

Disease-free survival: FRAP1_LC3_TKT_HMGB1_STAT3_TWIST1 (84.0% at the level of $p<0.05$)

Example 3: Predicting Prognosis of Liver Cancer in the A2 Group

Figure 44:
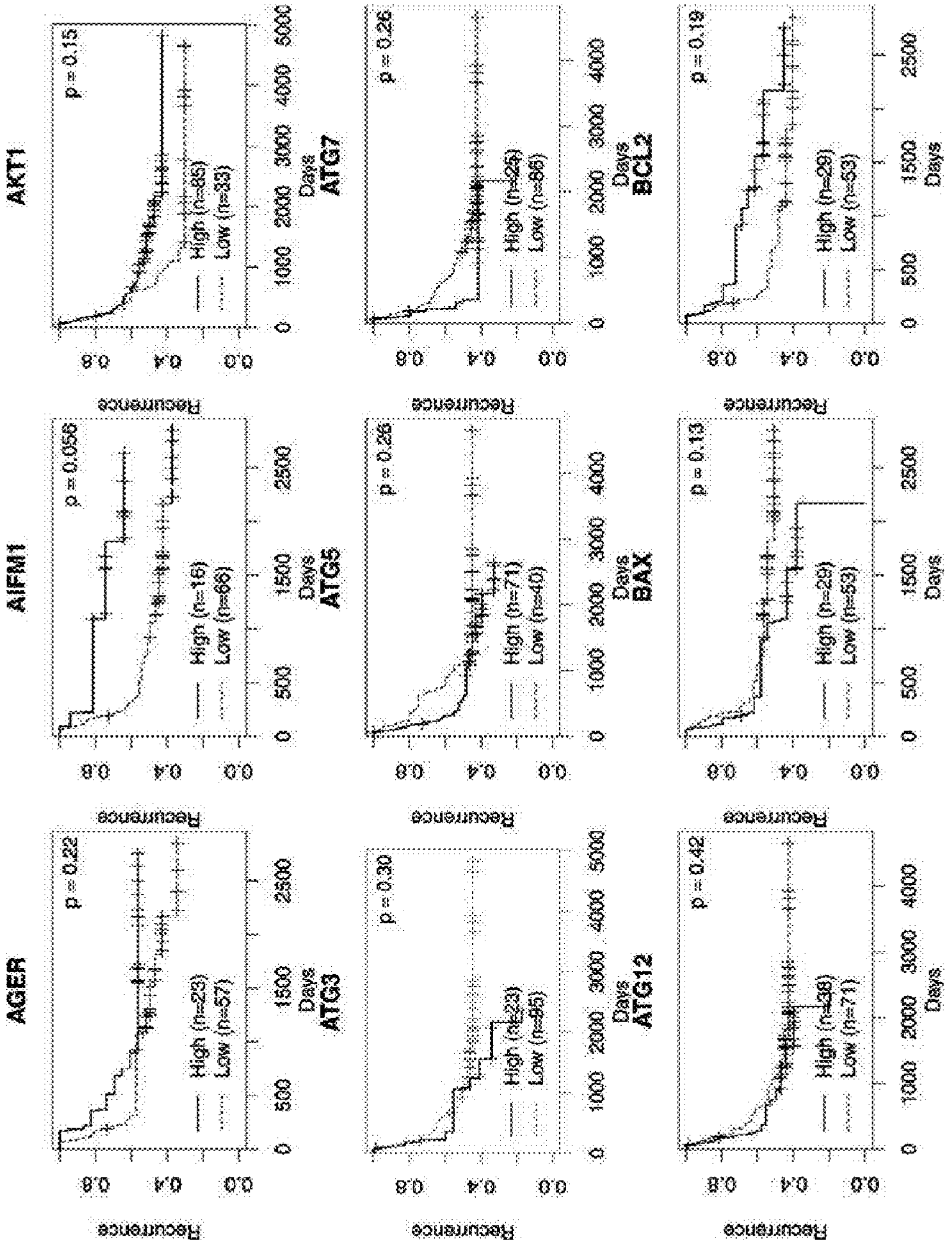
Figure 45:
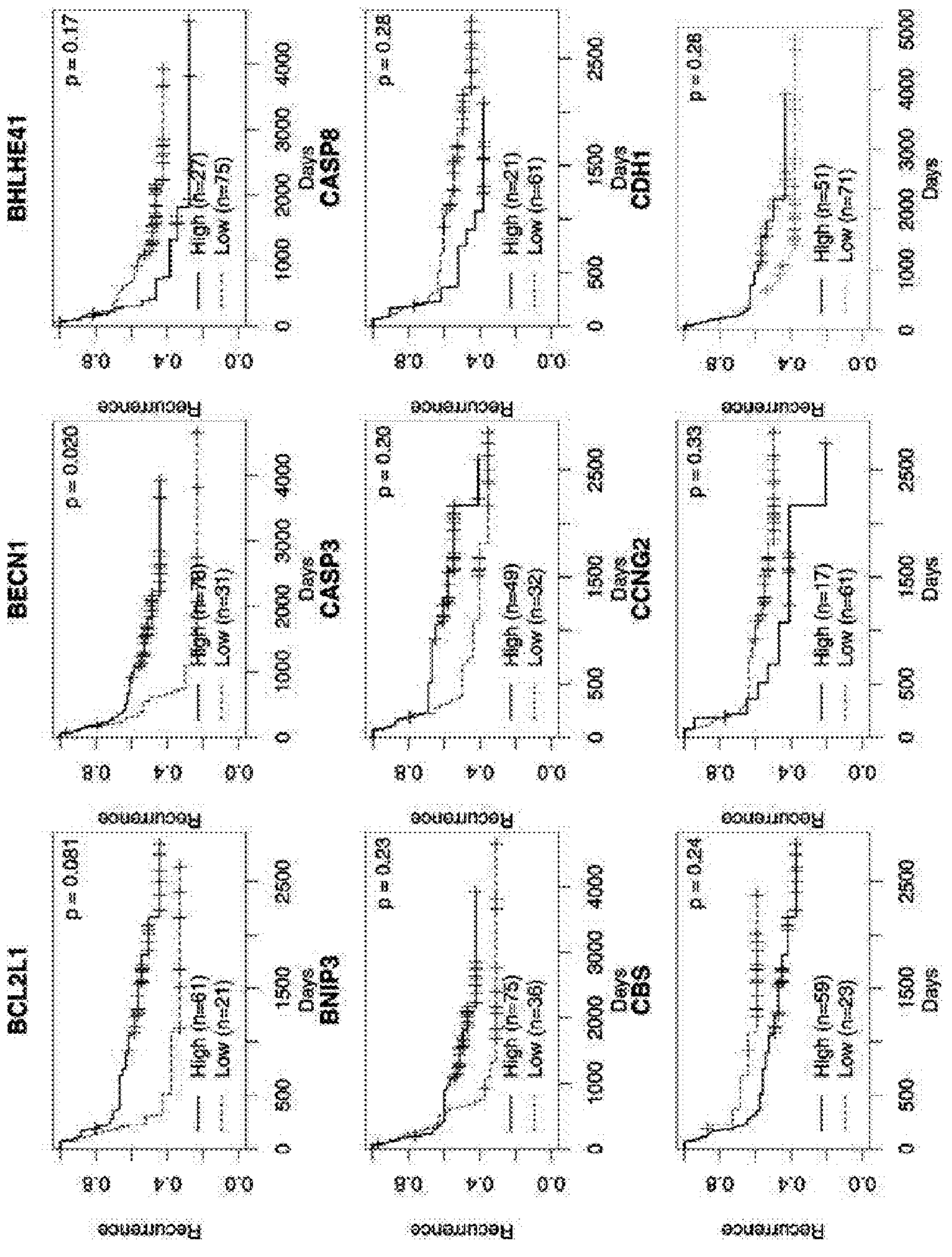
Figure 46:
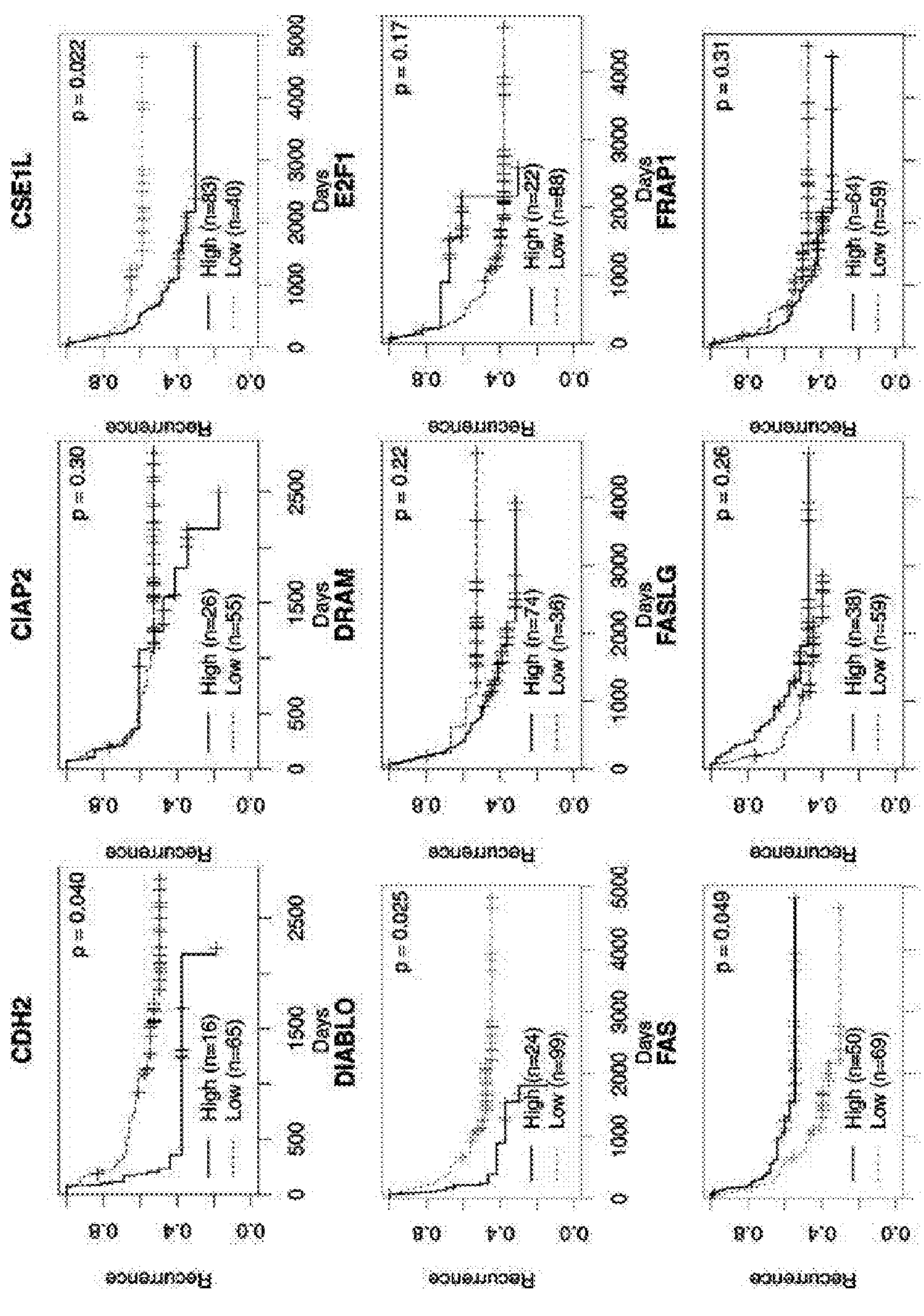
Figure 47:
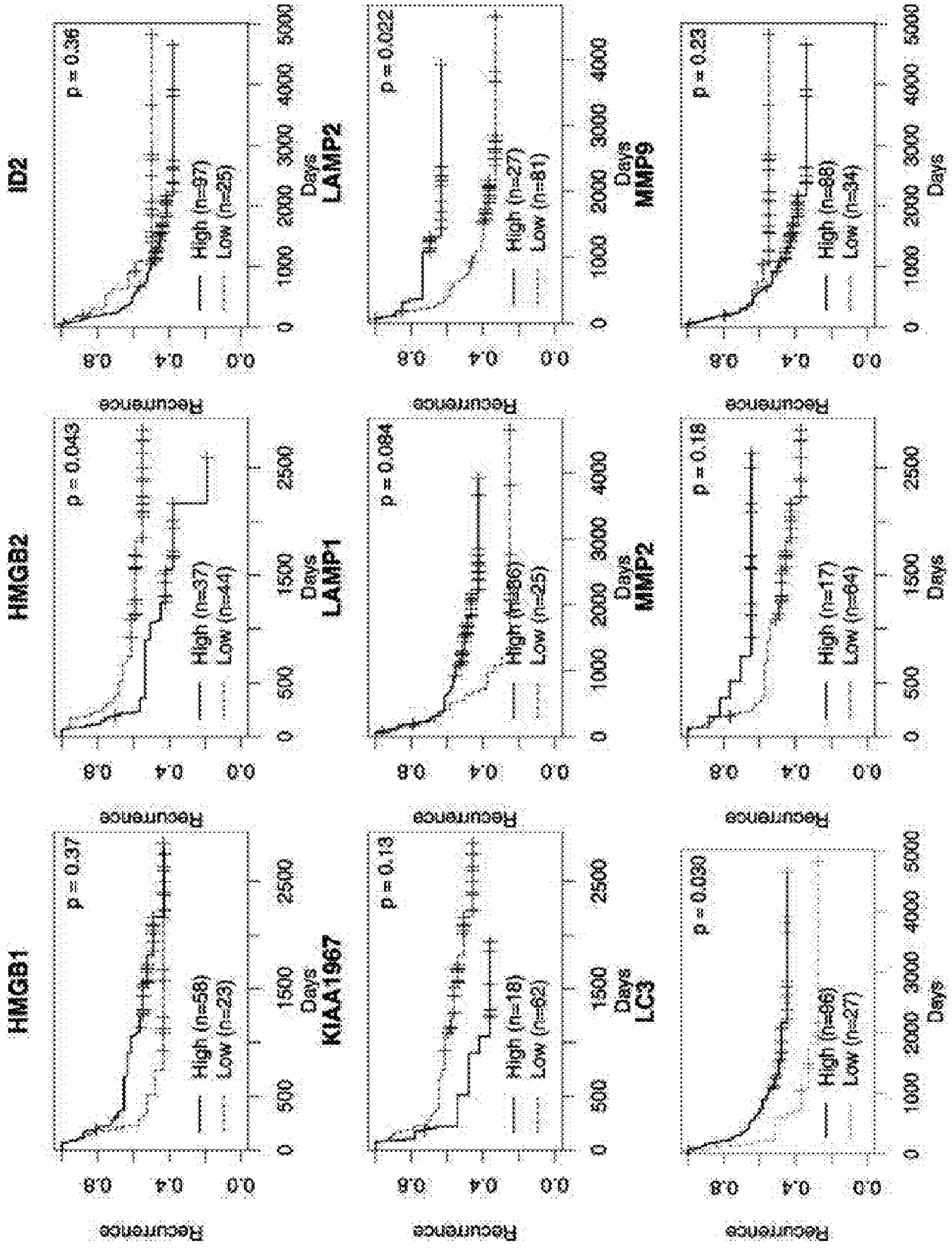
Figure 48:
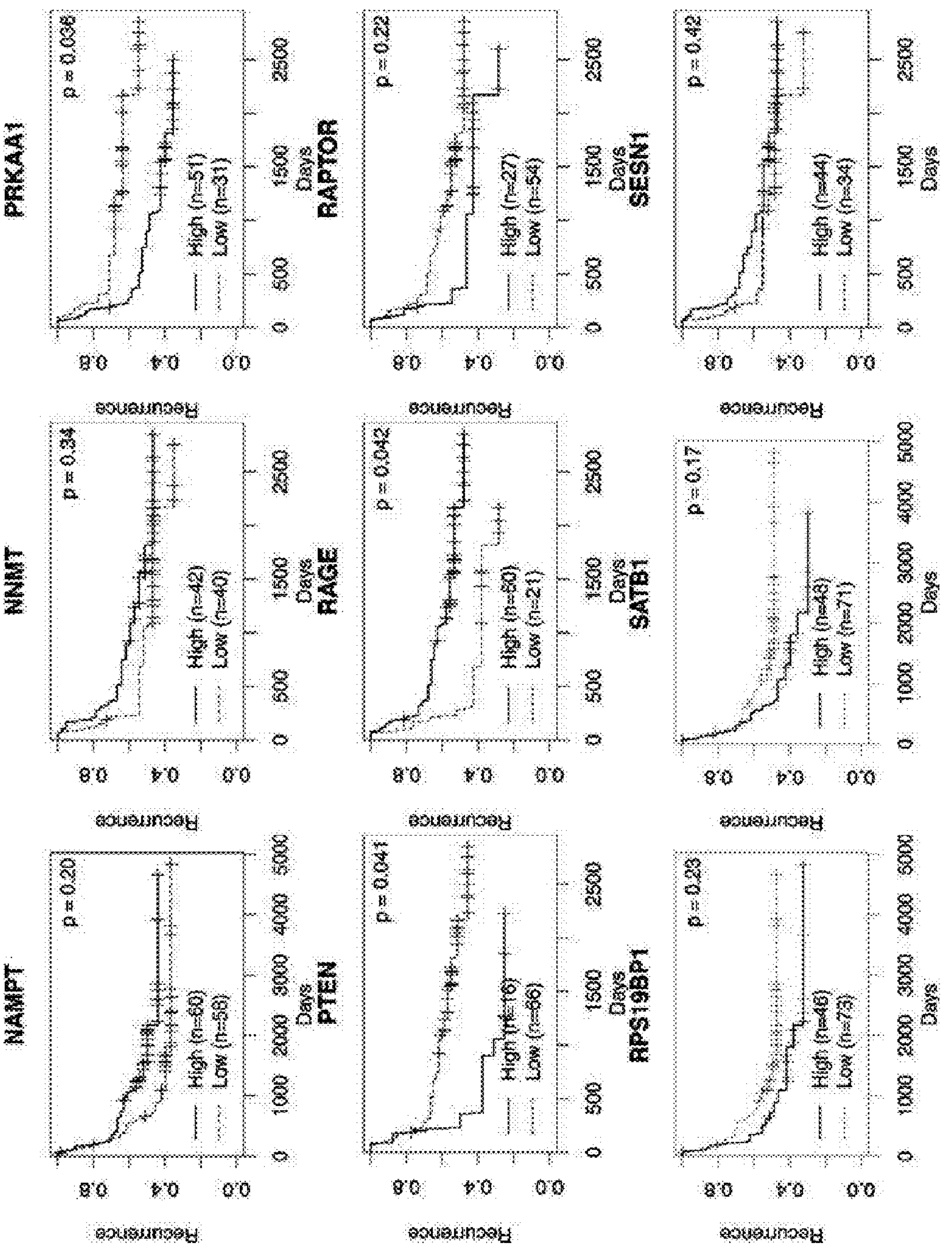
Figure 49:
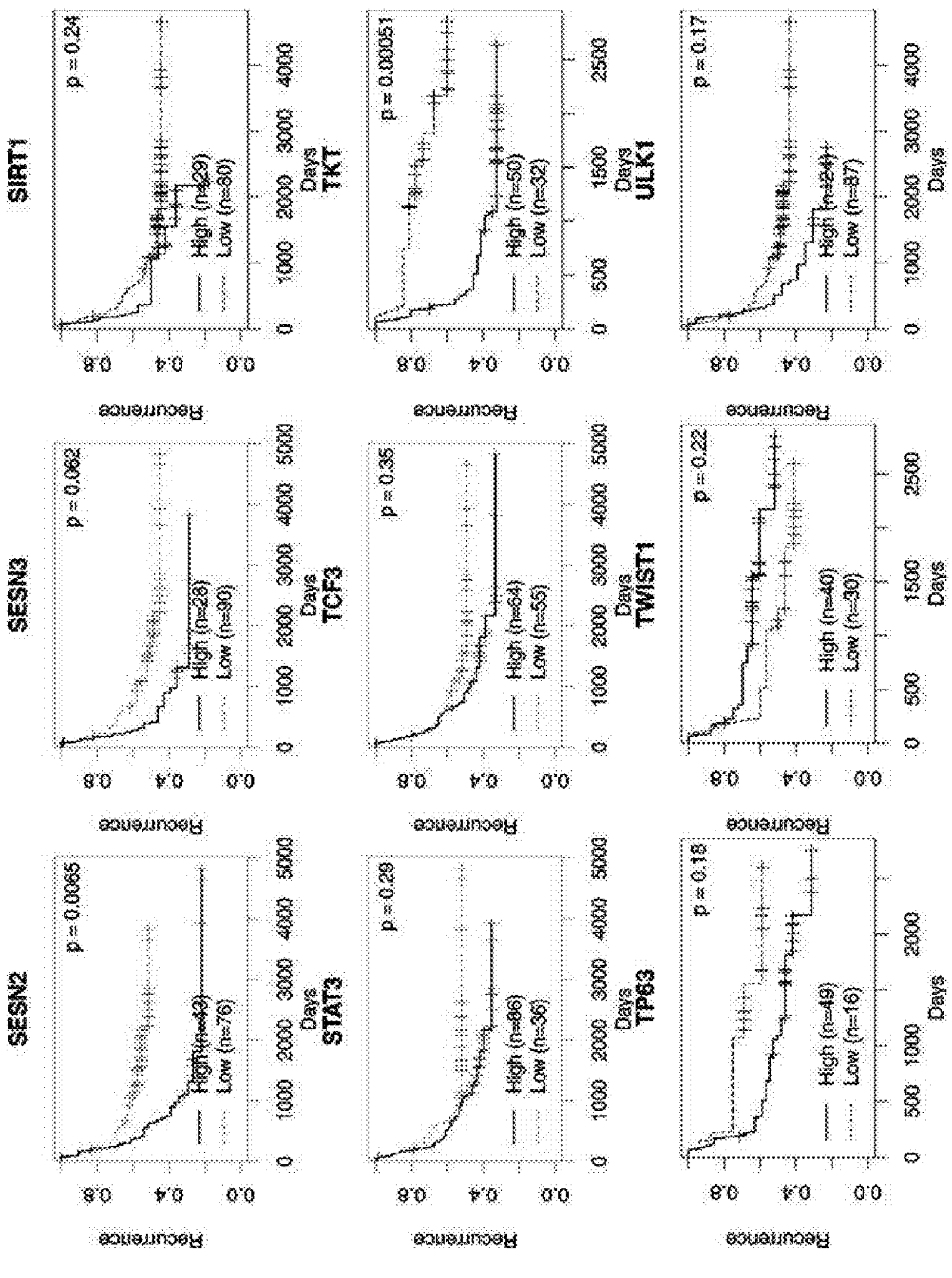
Figure 50:
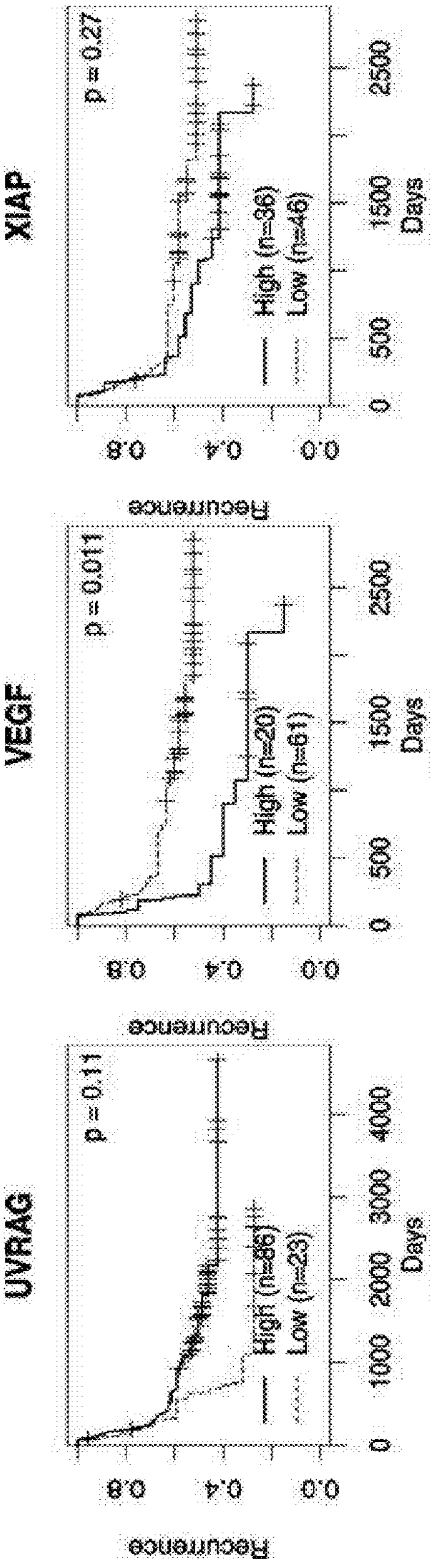
Figure 51:
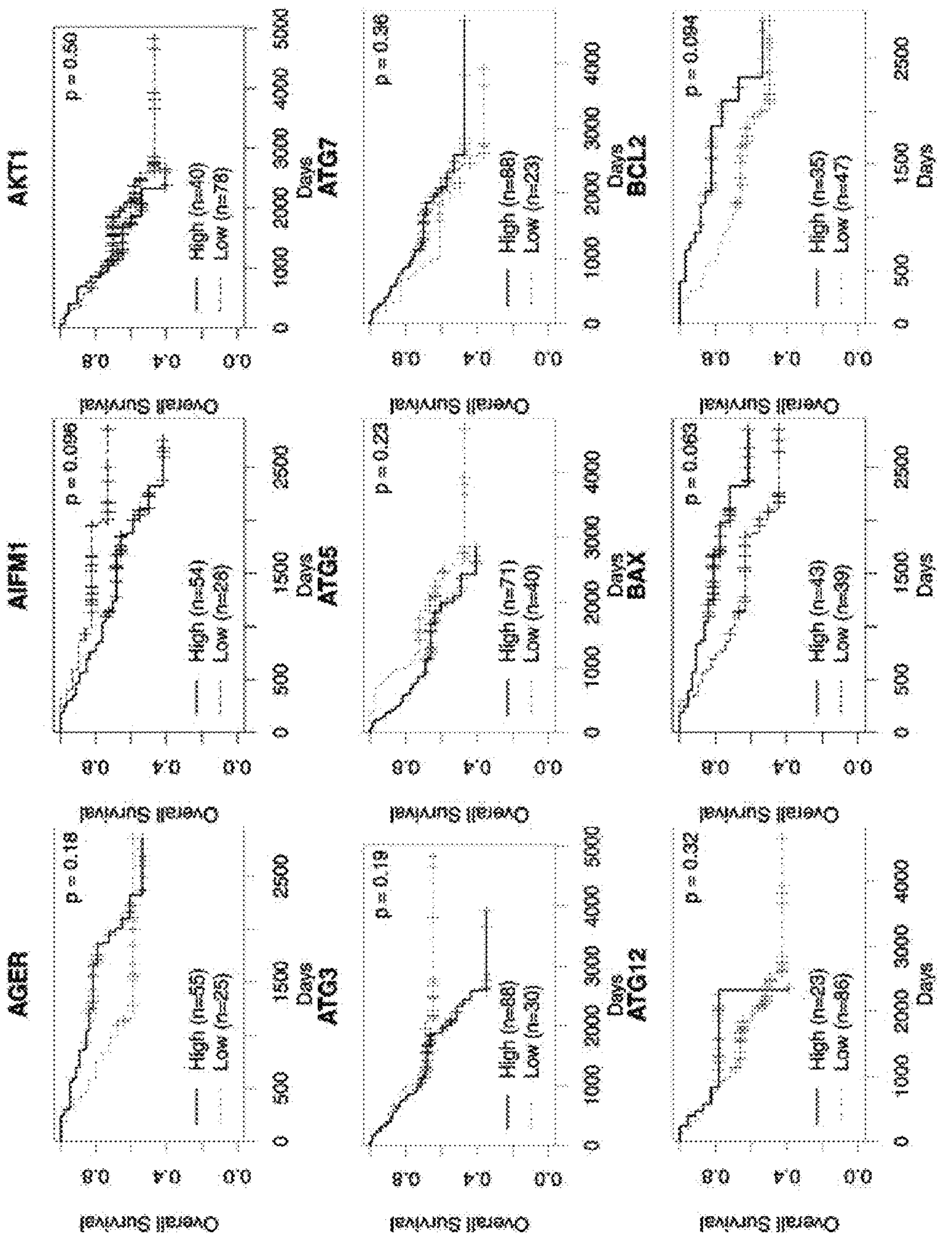
Figure 52:
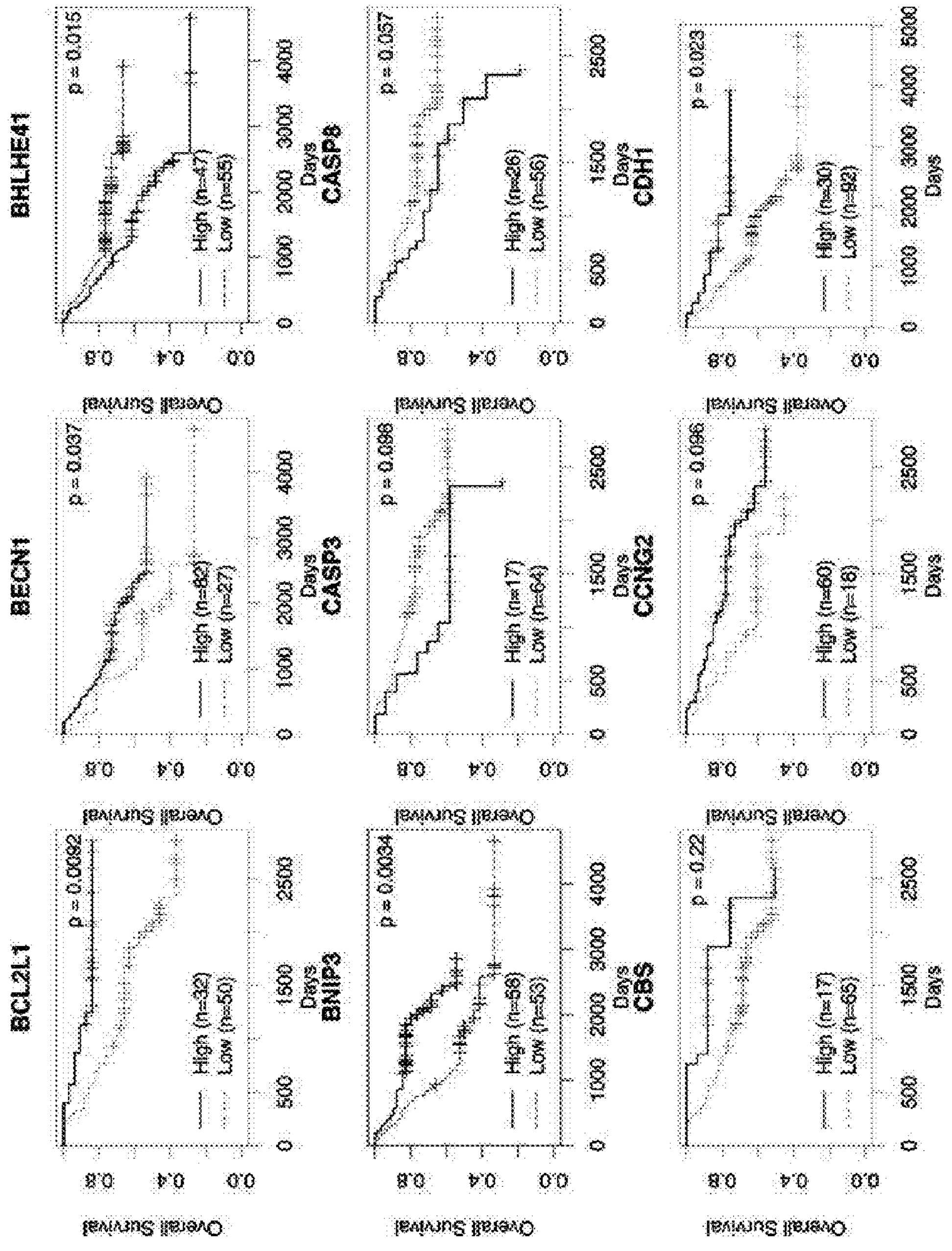
Figure 53:
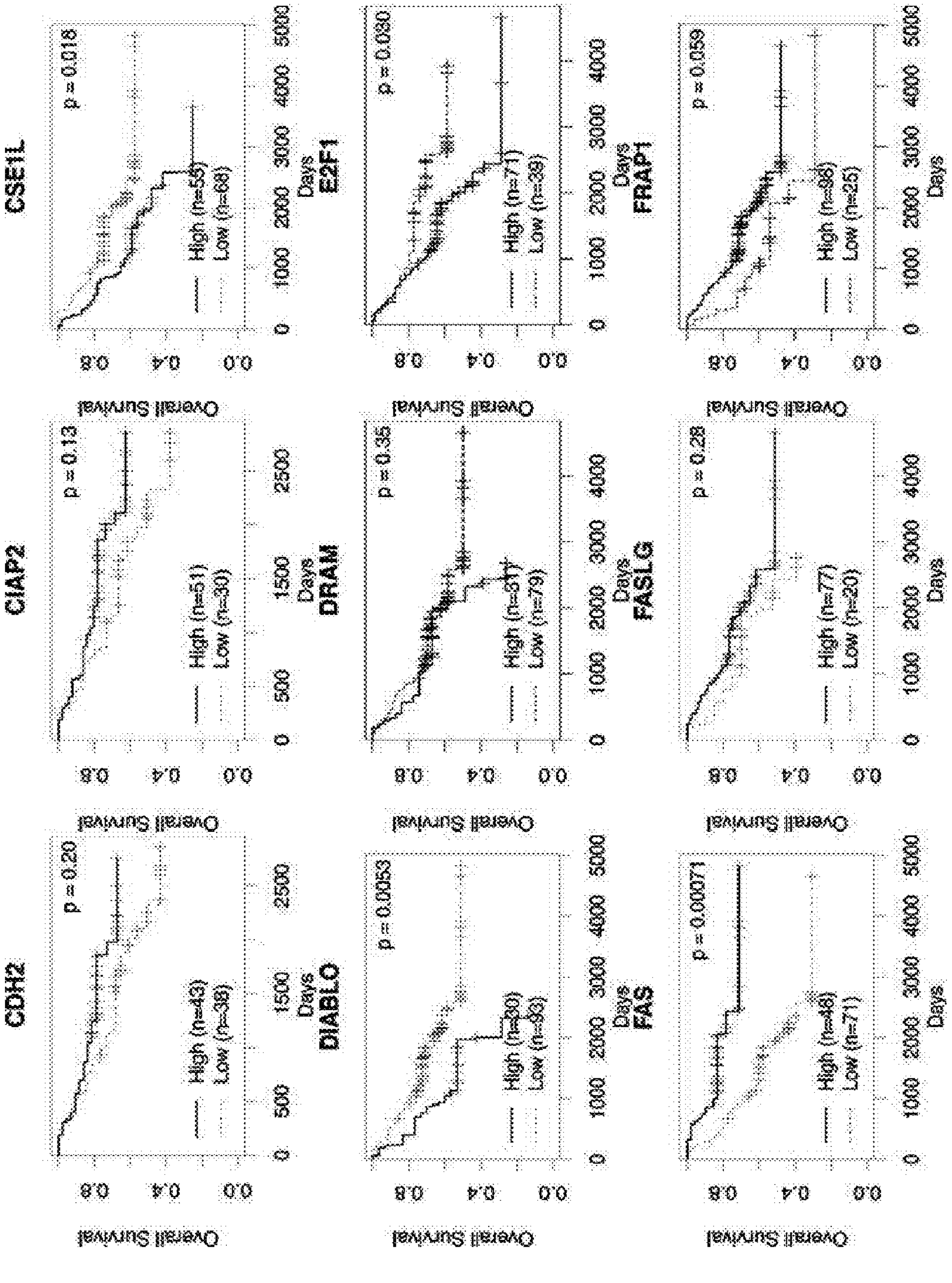
Figure 54:
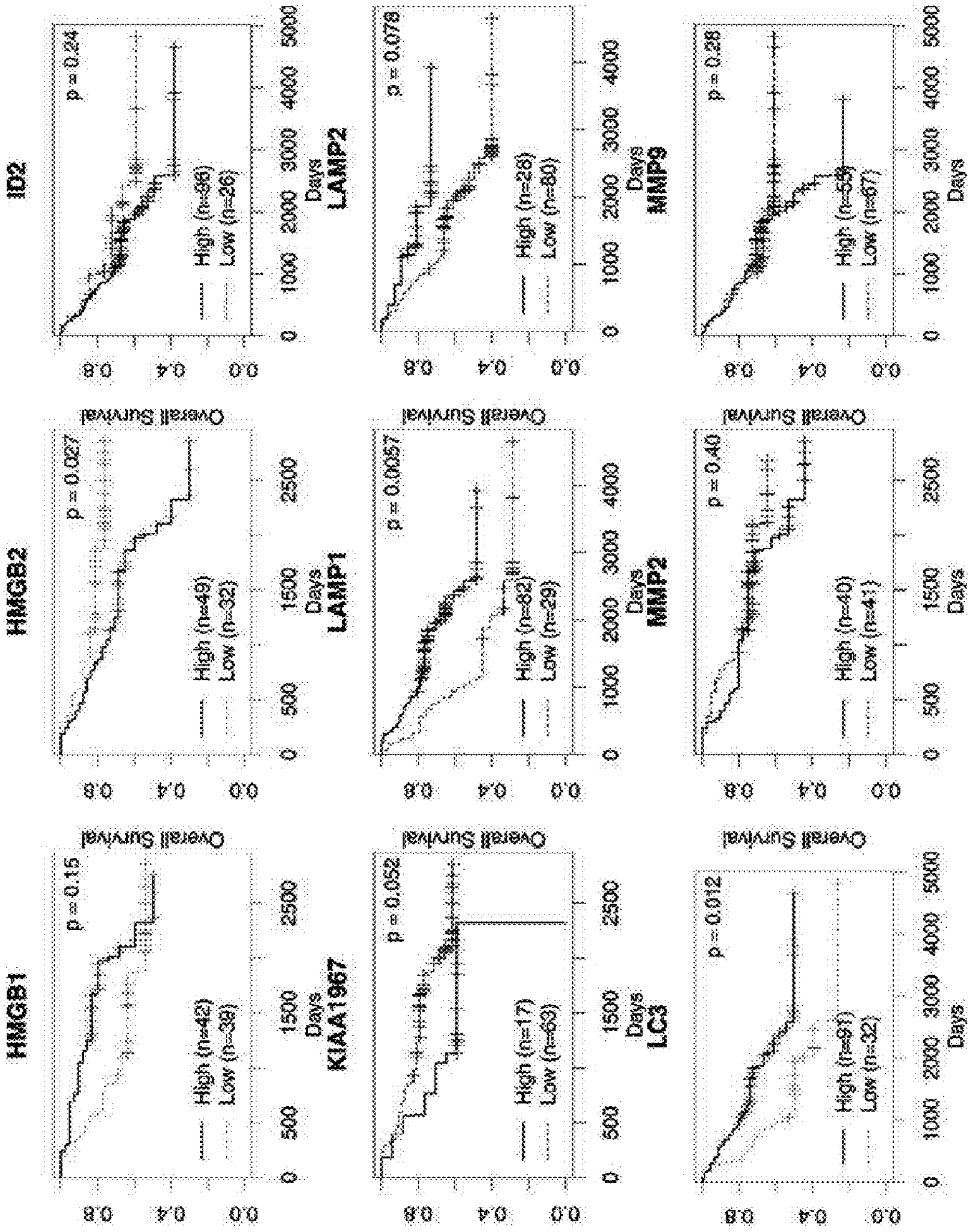
Figure 55:
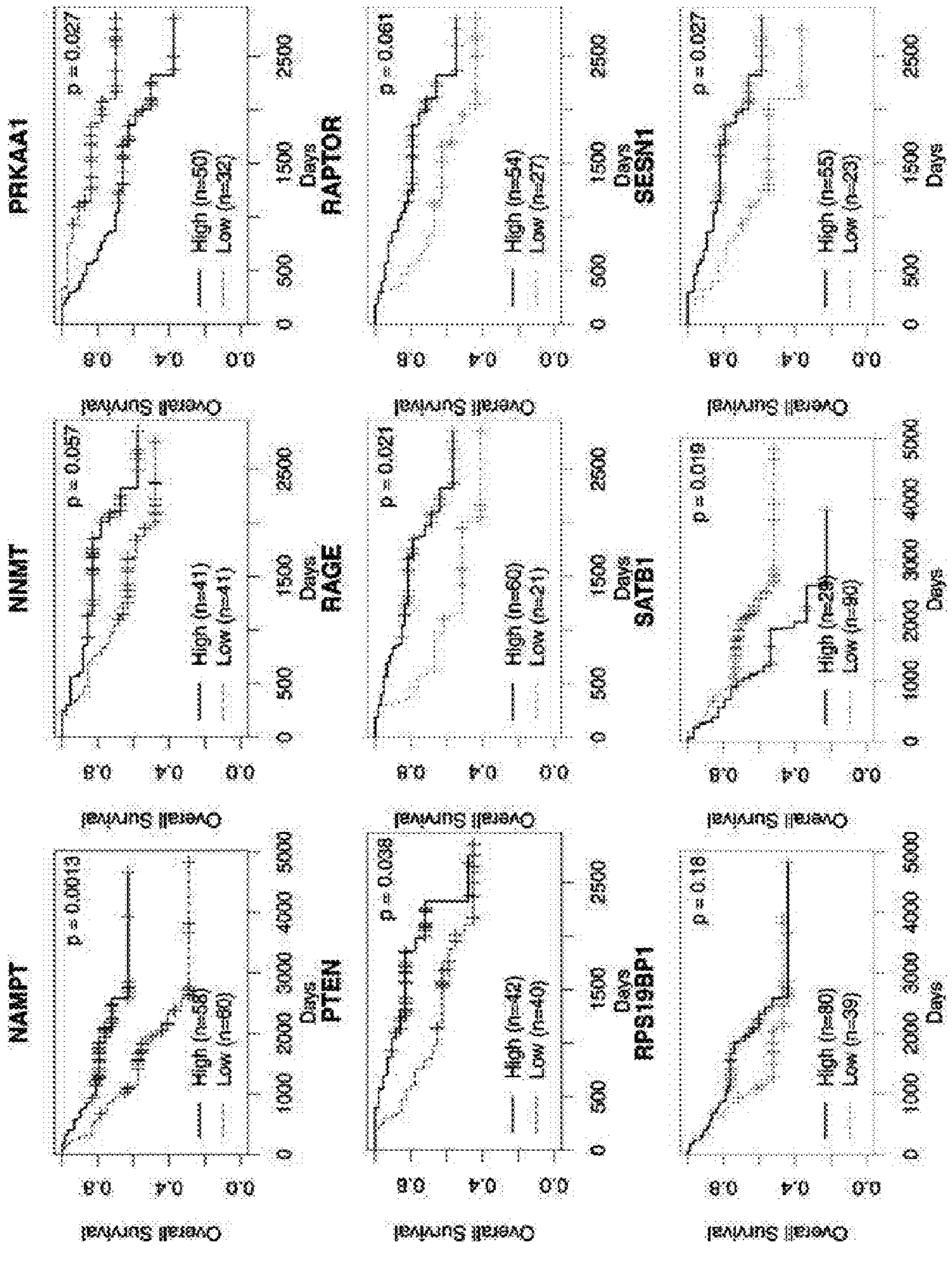
Figure 56:
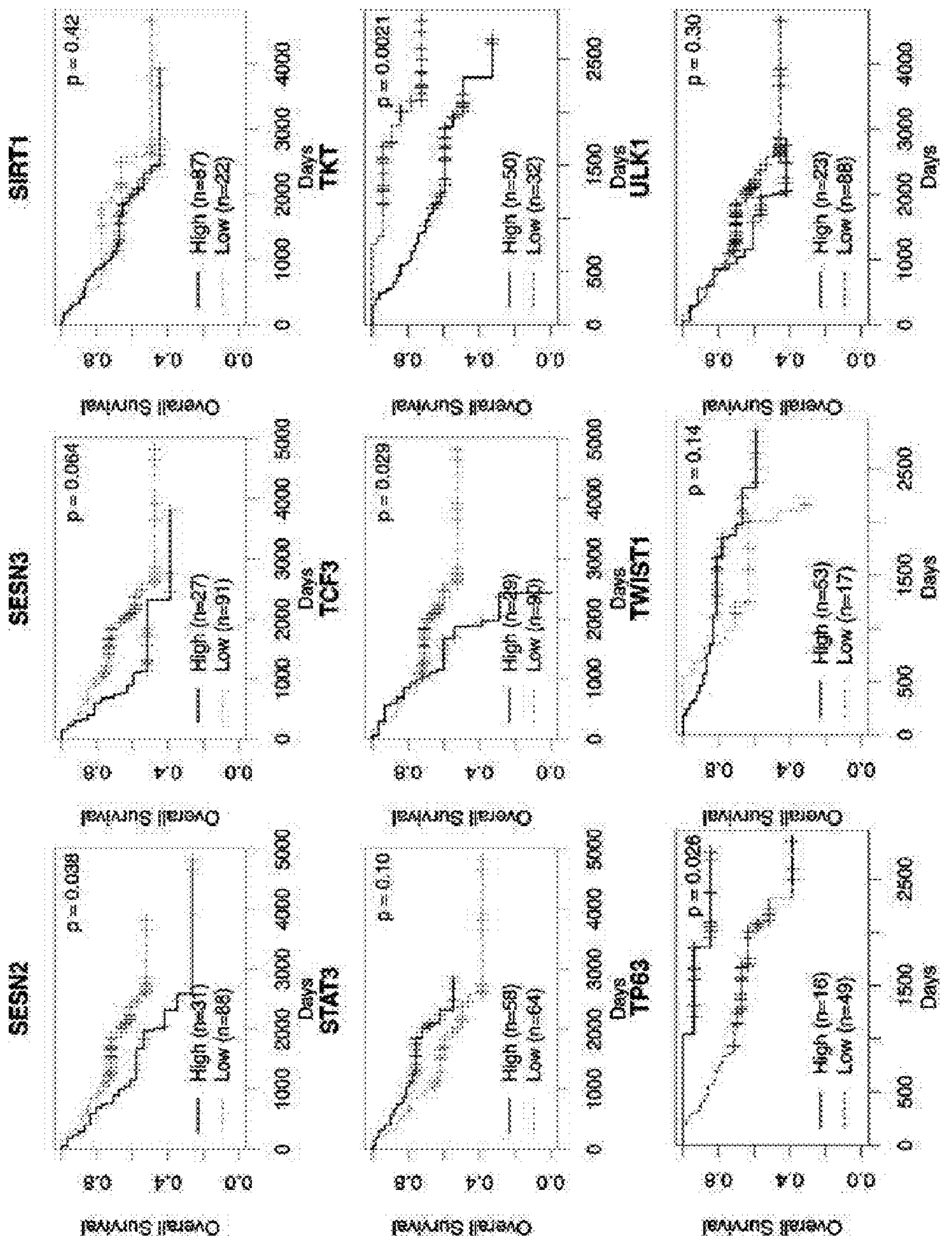
Figure 57:
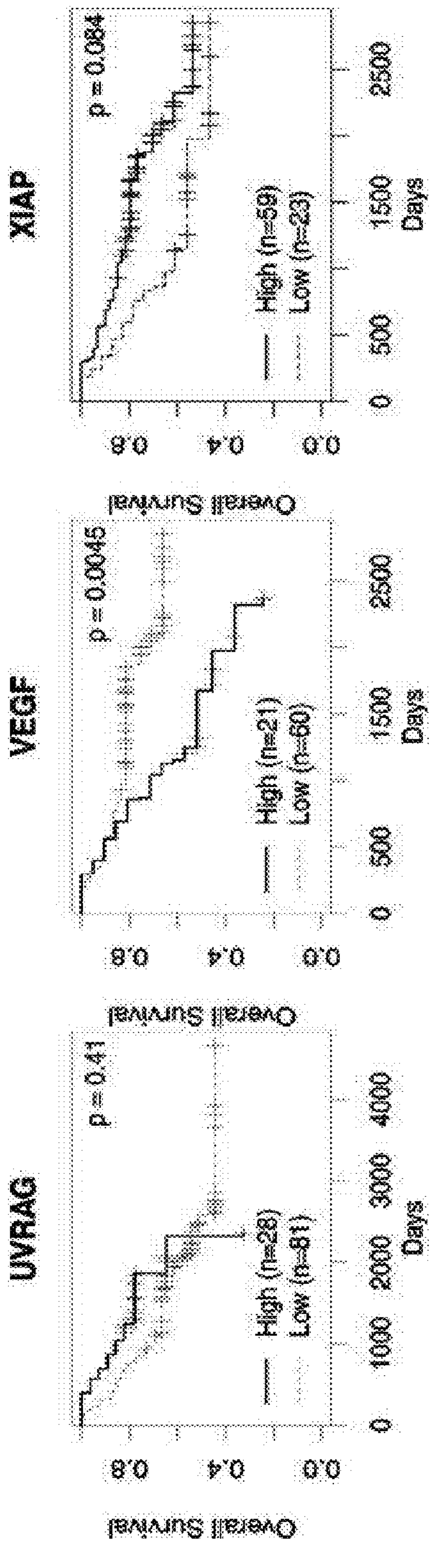
Figure 58:
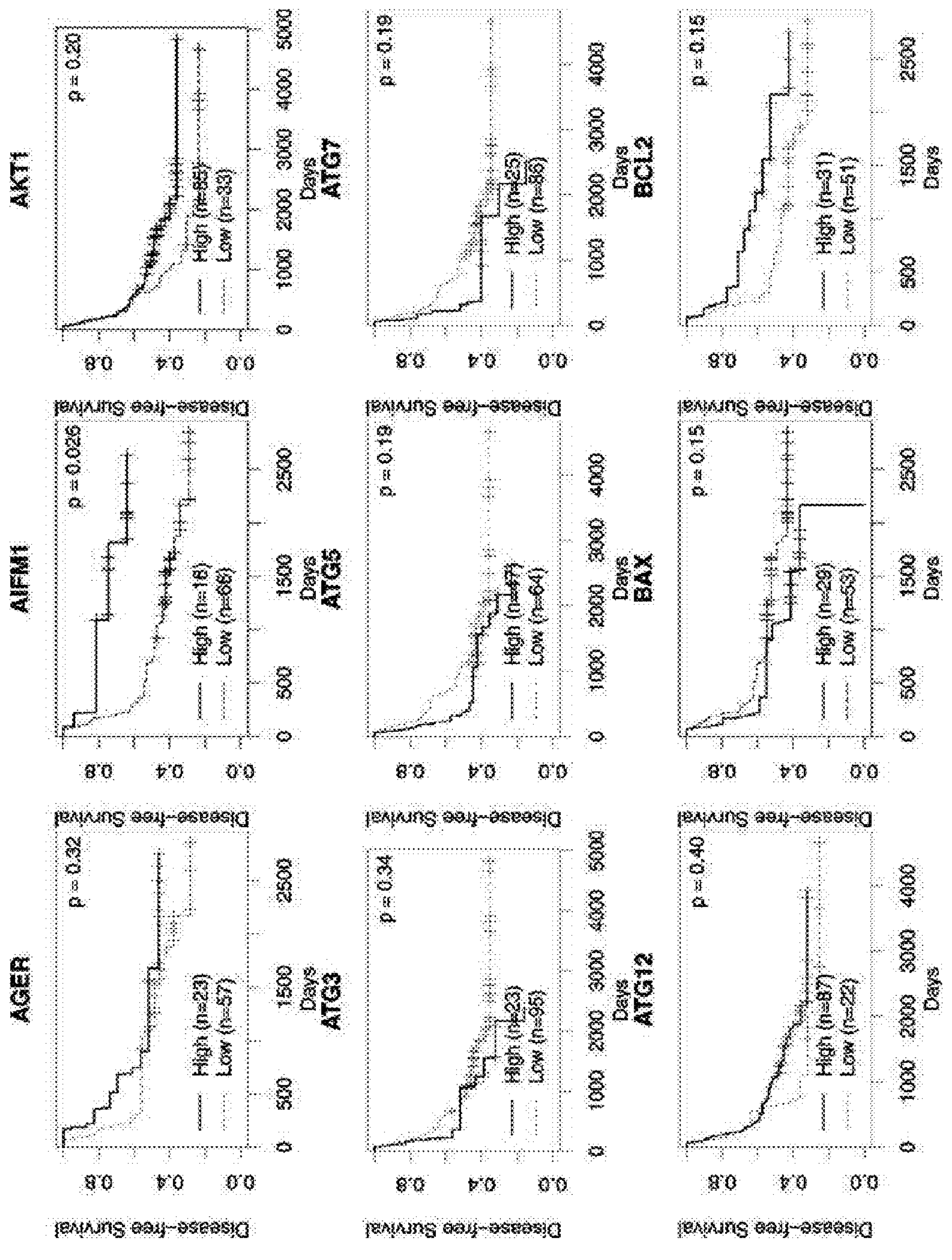
Figure 59:
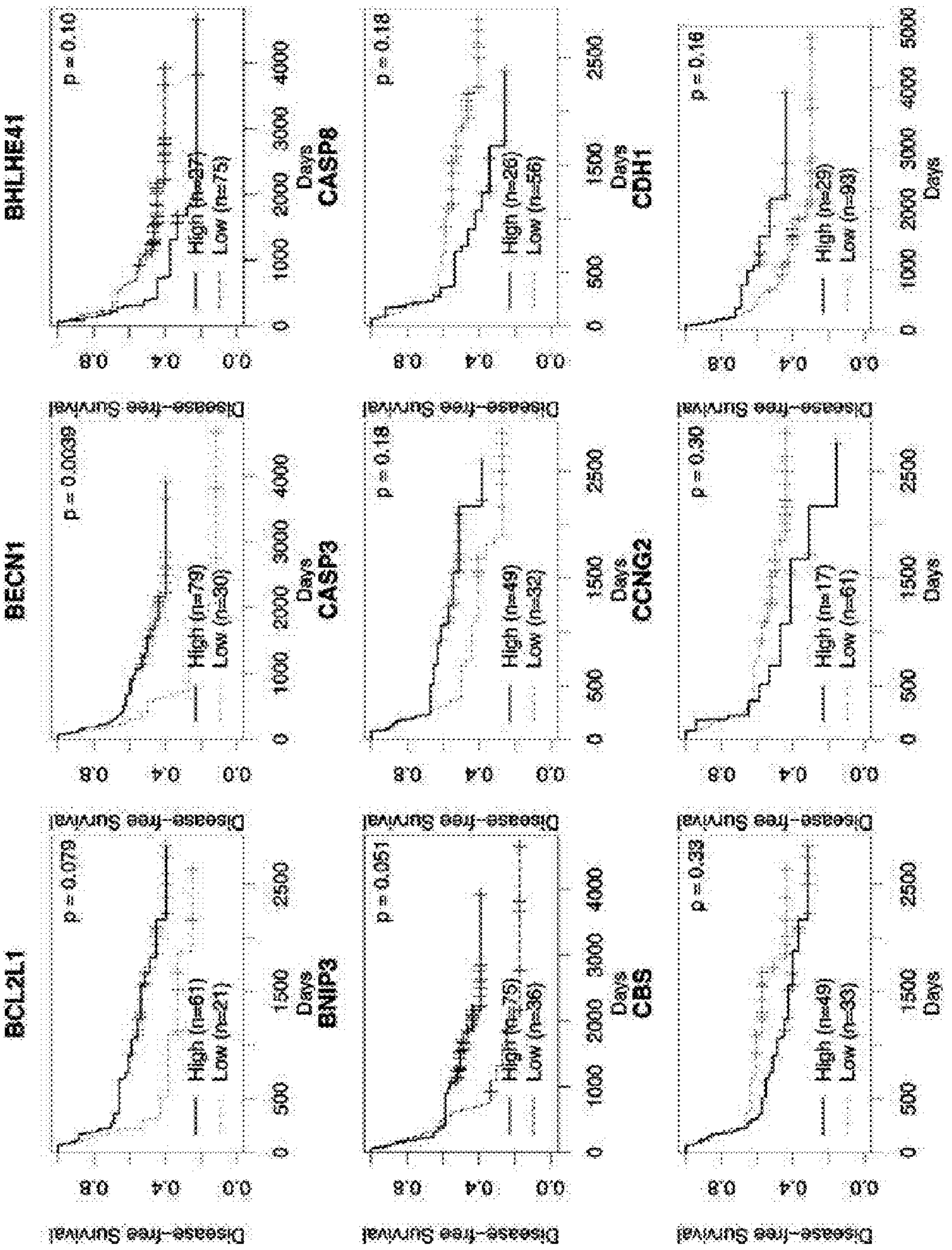
Figure 60:
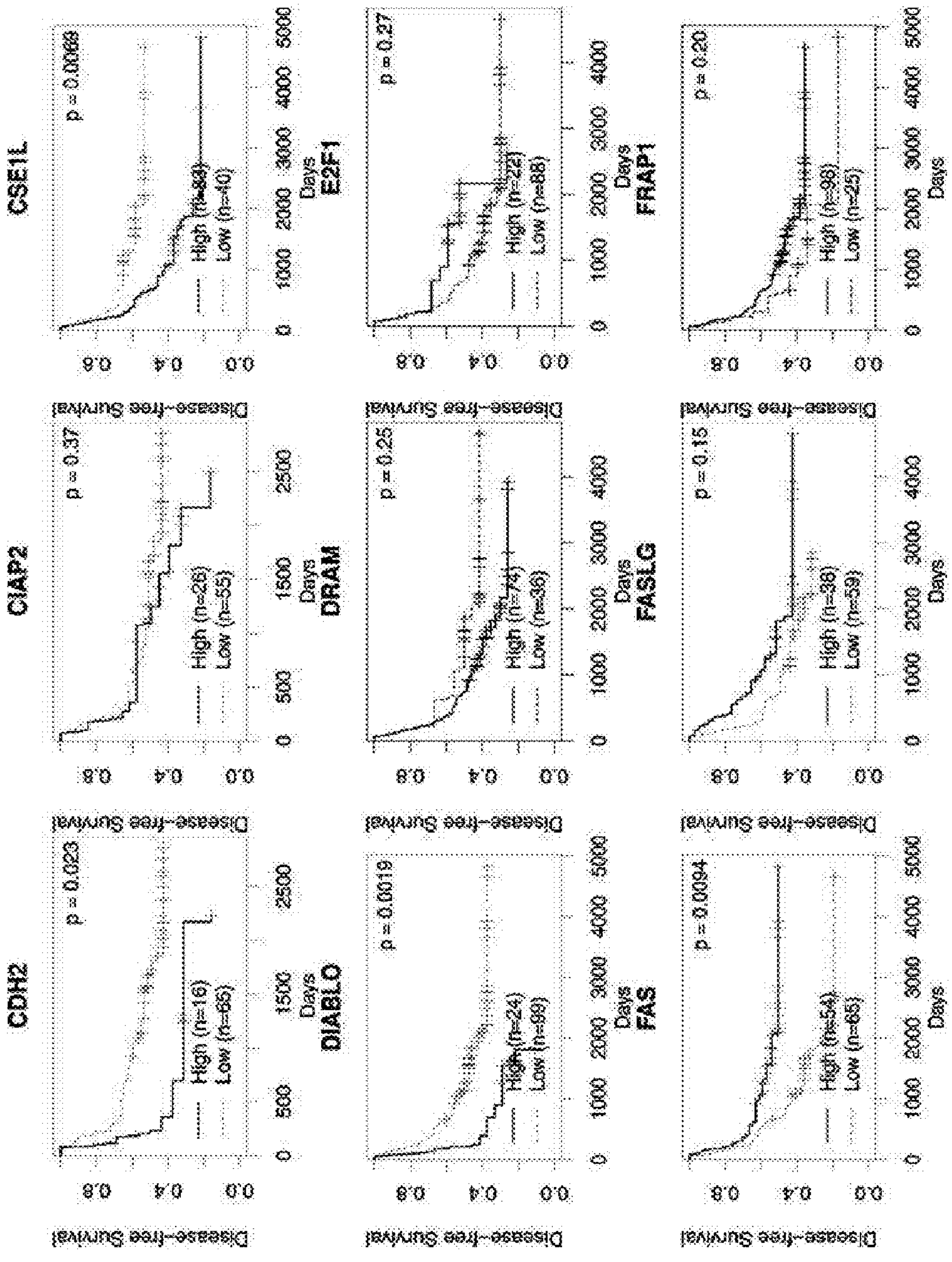
Figure 61:
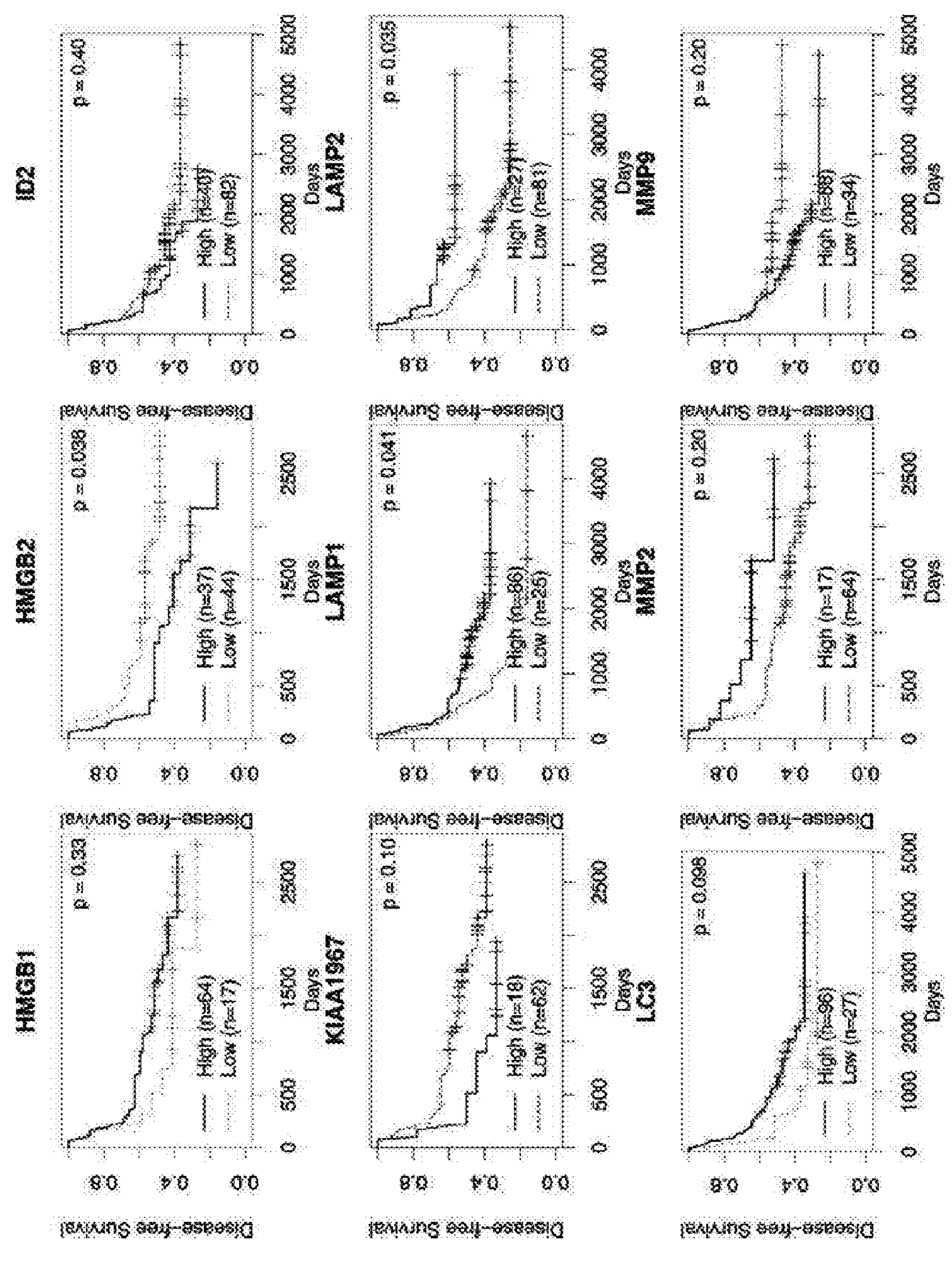
Figure 62:
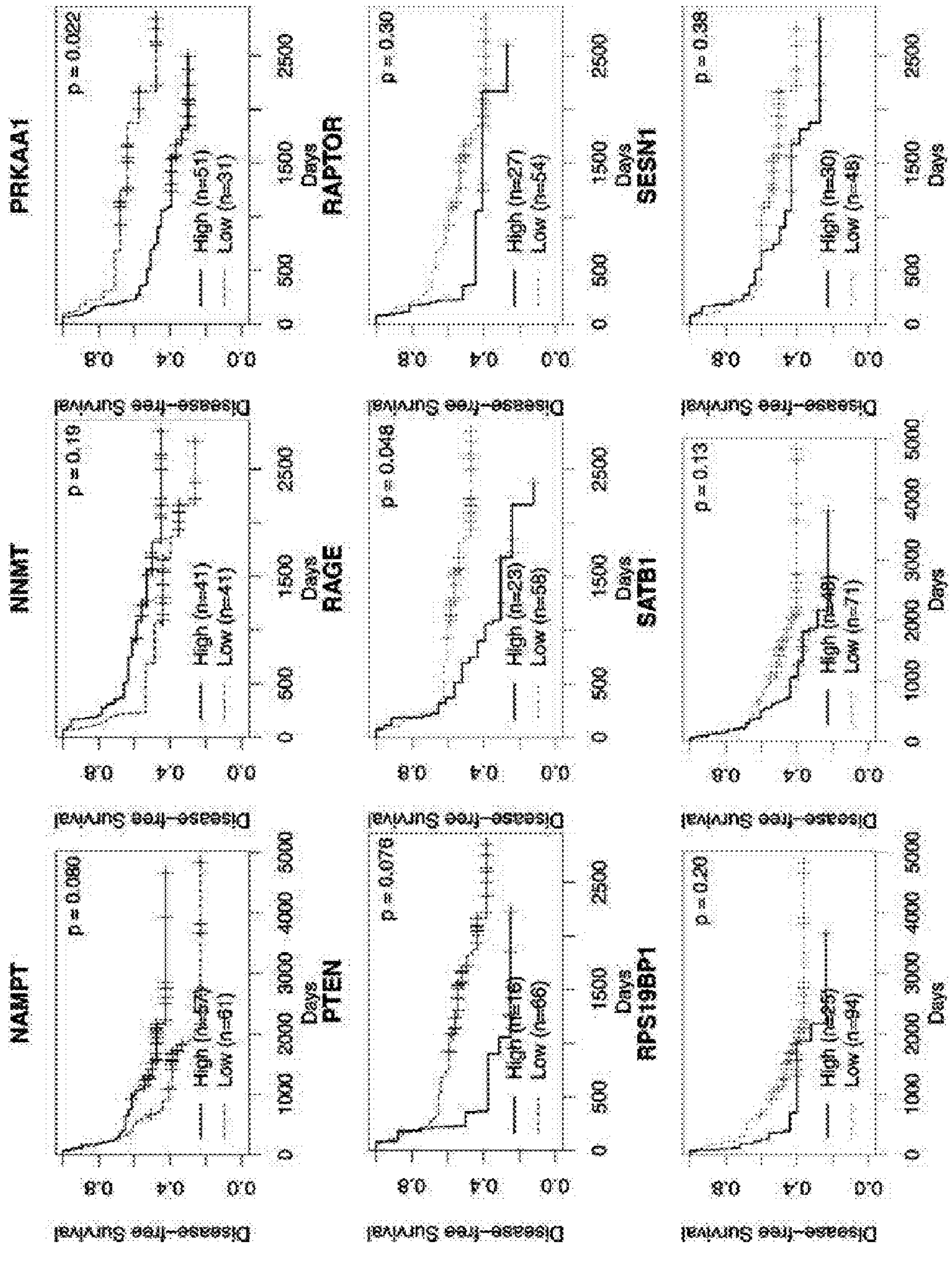
Figure 63:
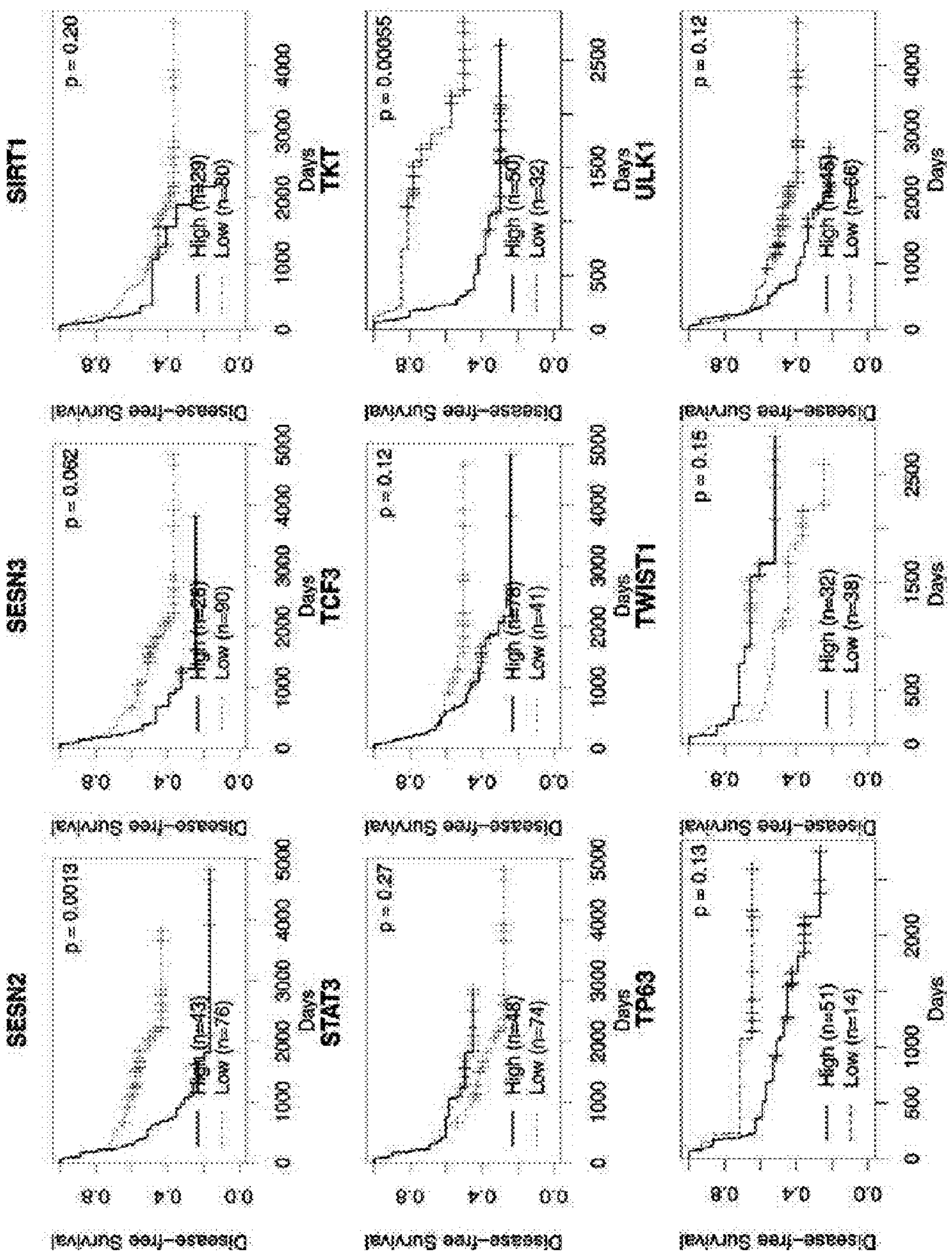
Figure 64:
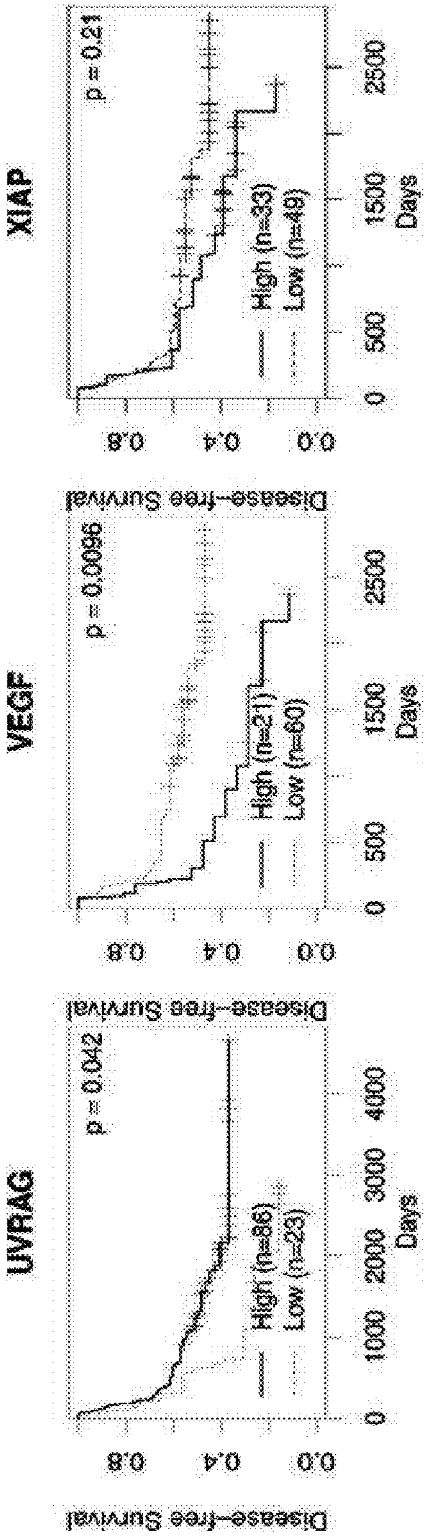
Figure 65:
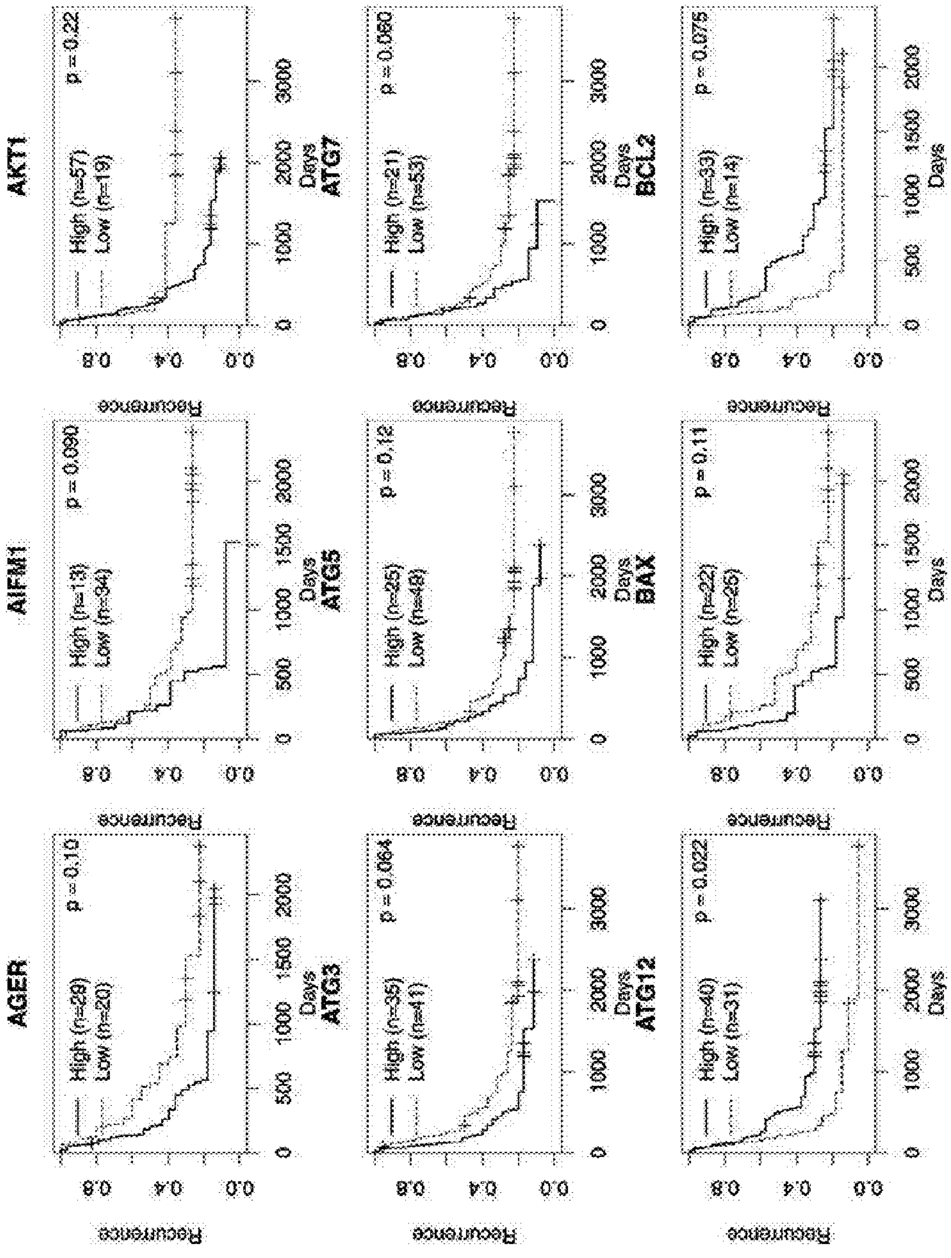
Figure 66:
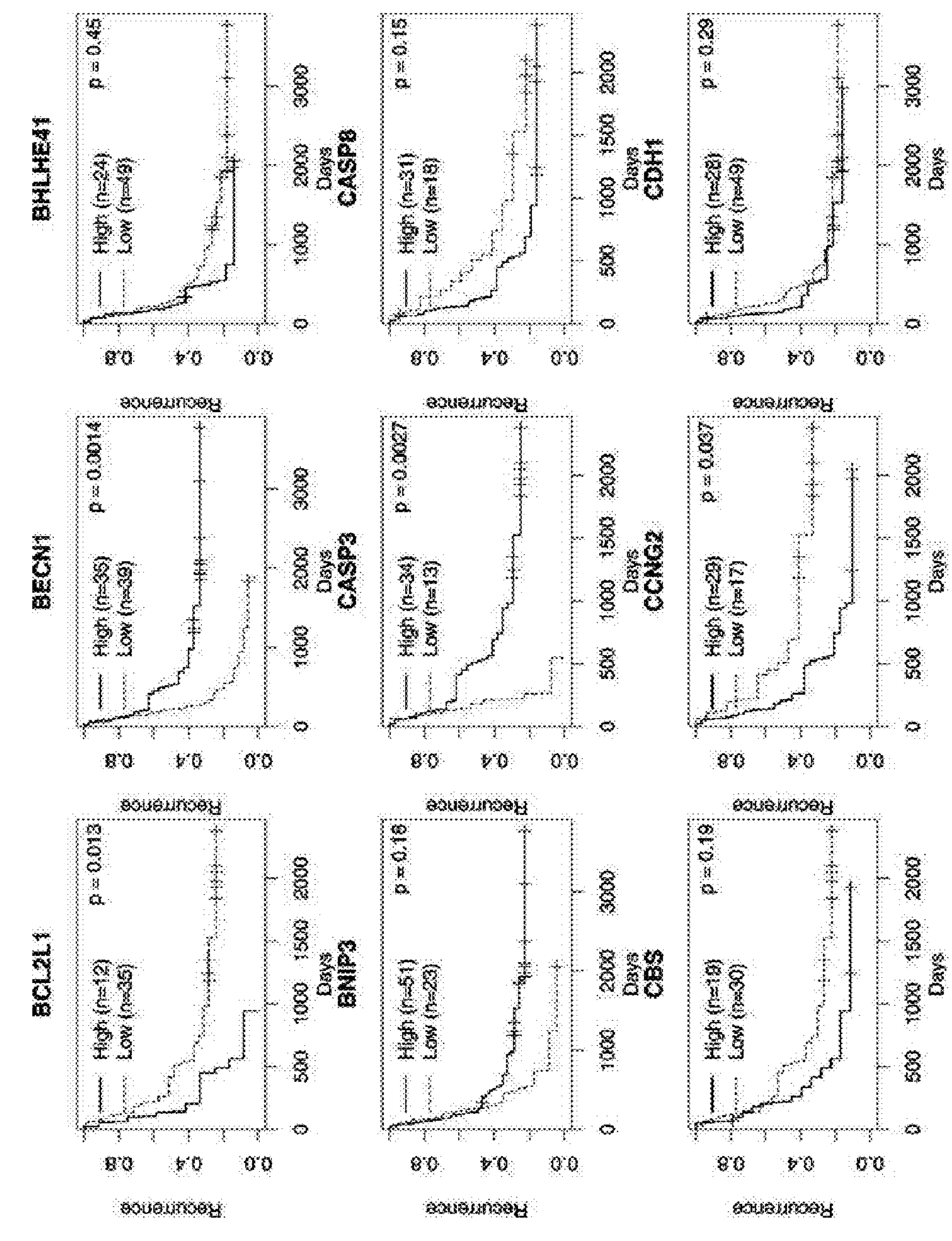
Figure 67:
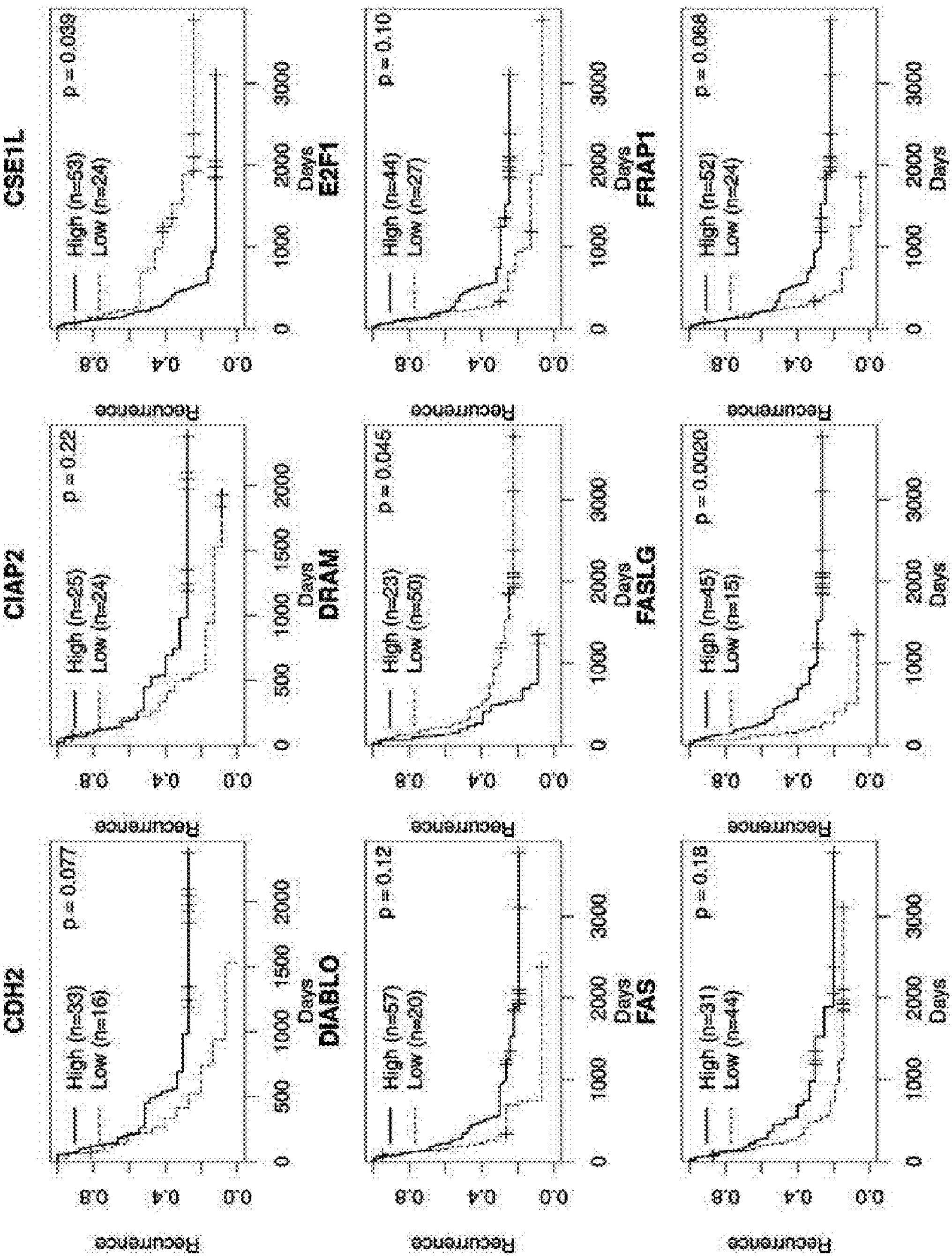
Figure 68:
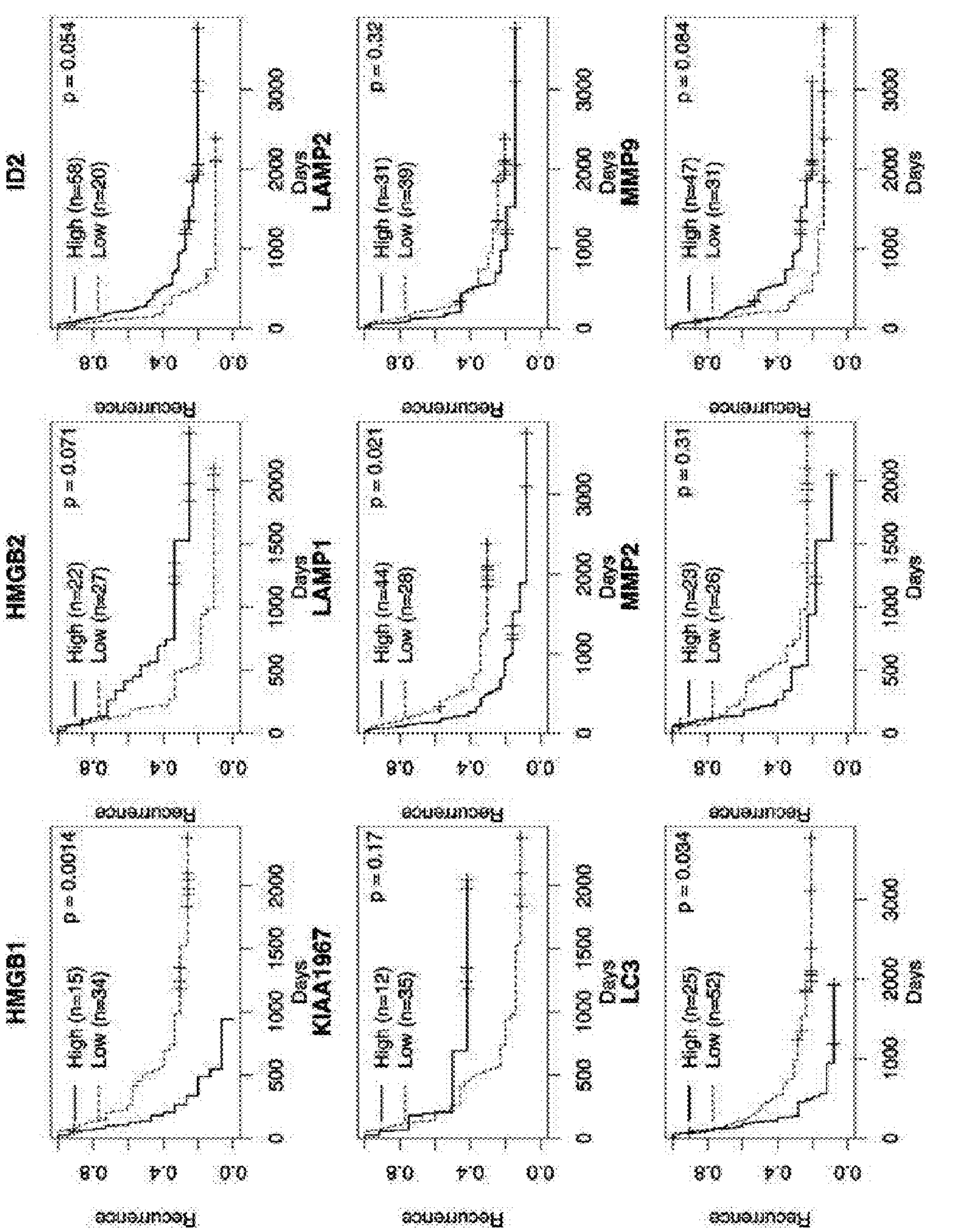
Figure 69:
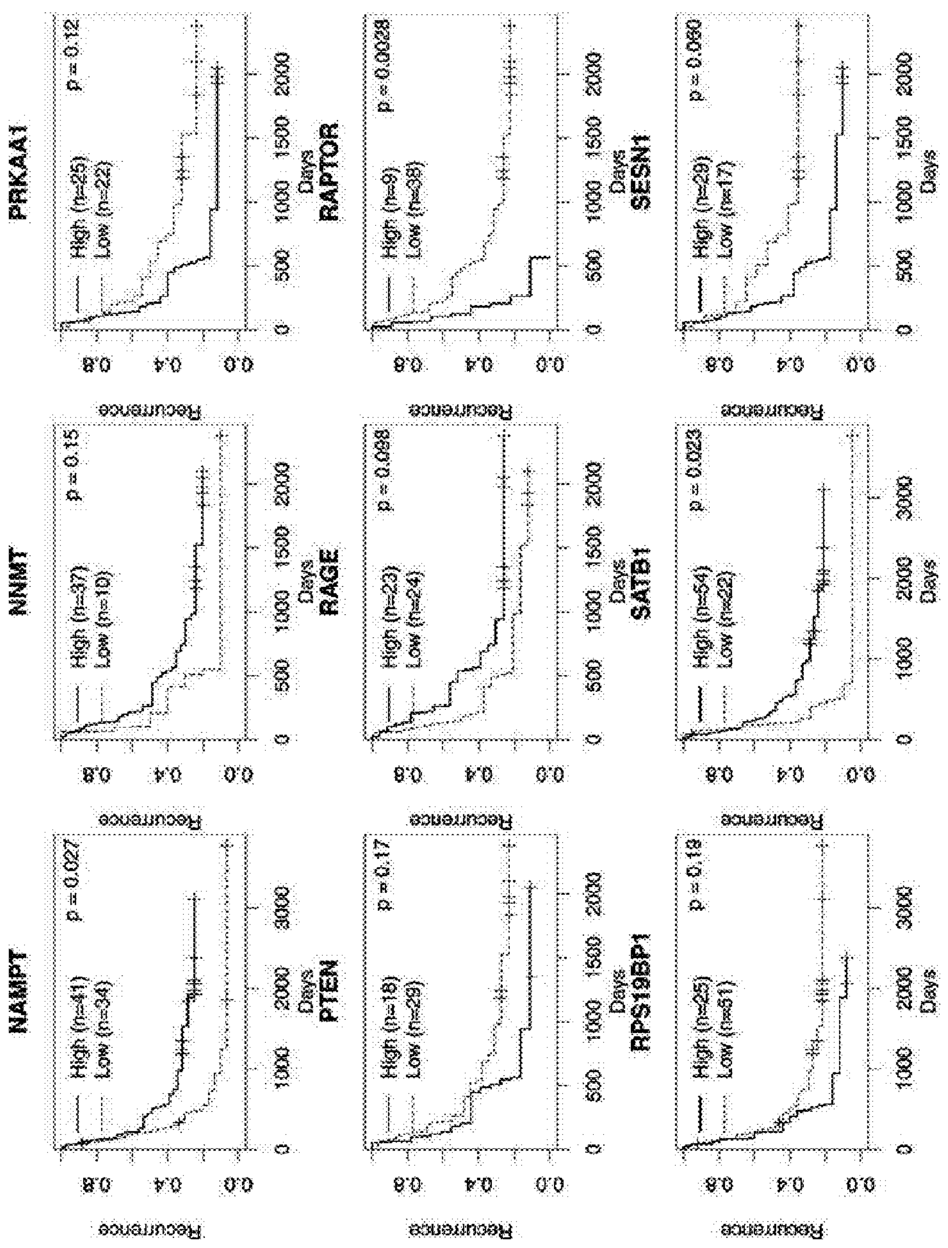
Figure 70:
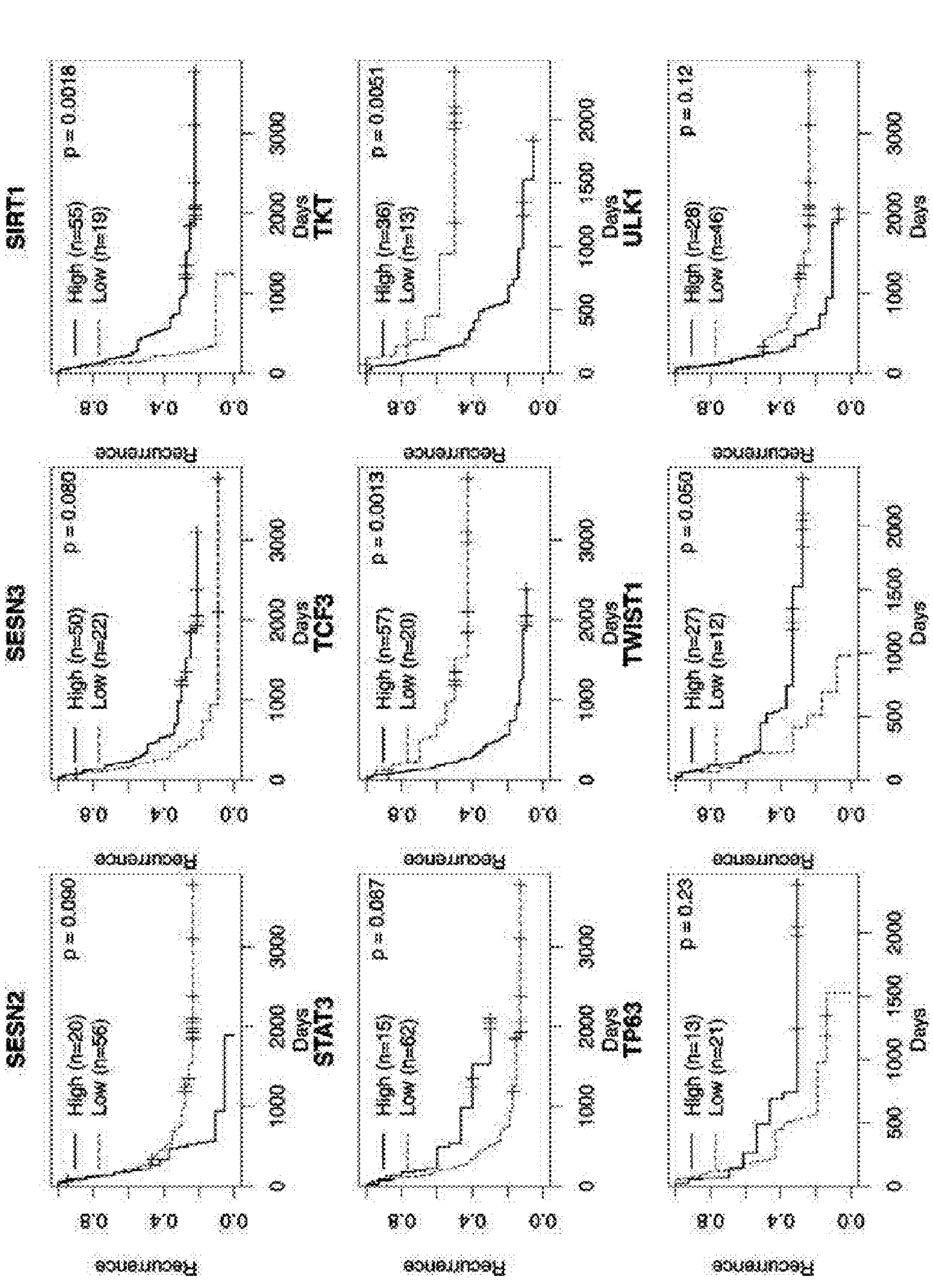
Figure 71:
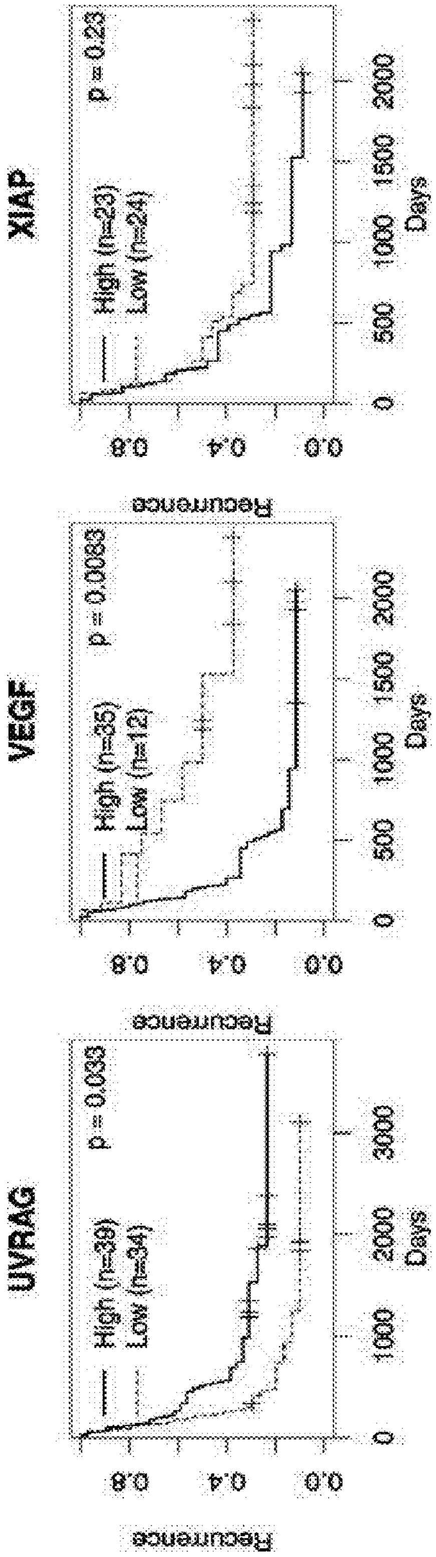
Figure 72:
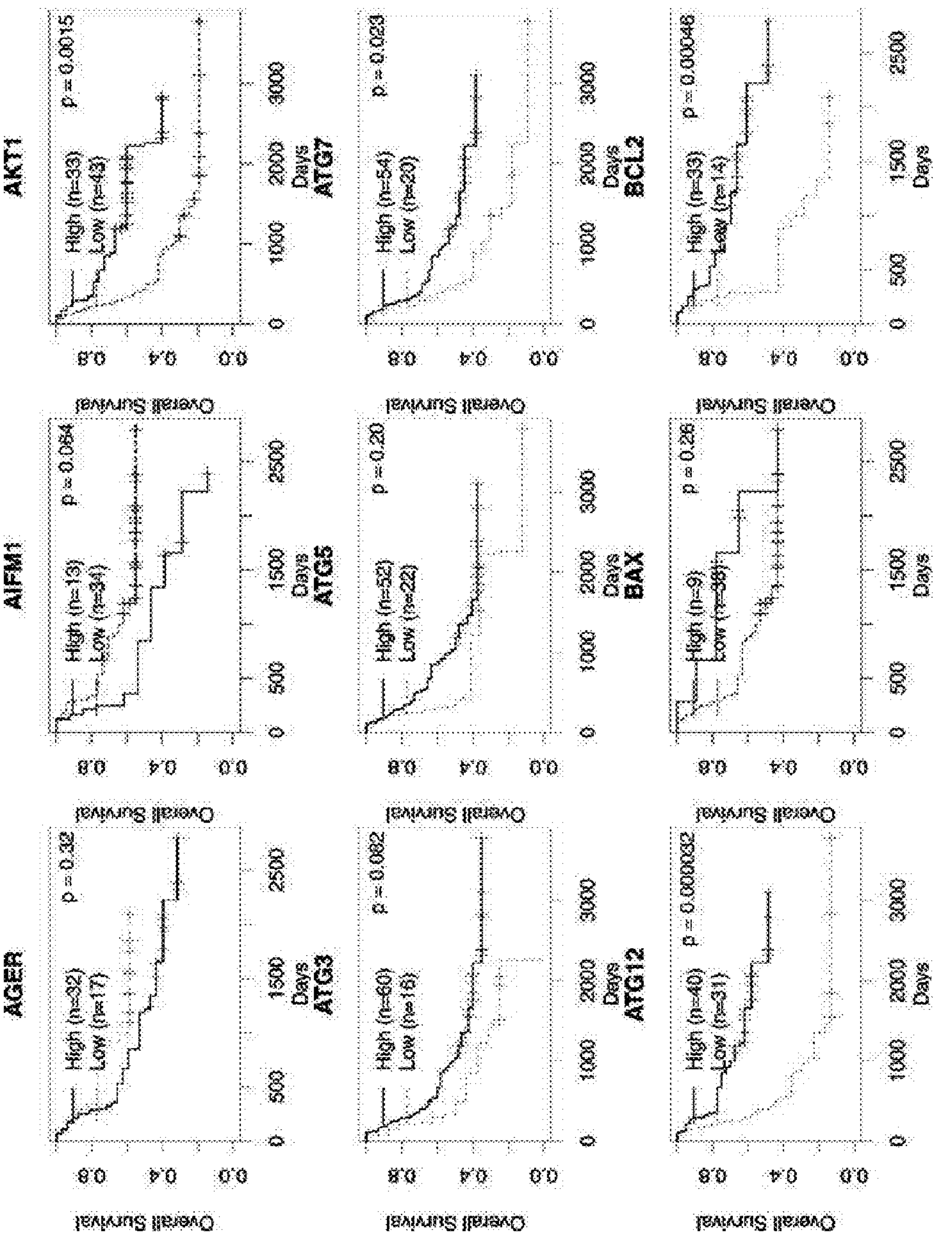
Figure 73:
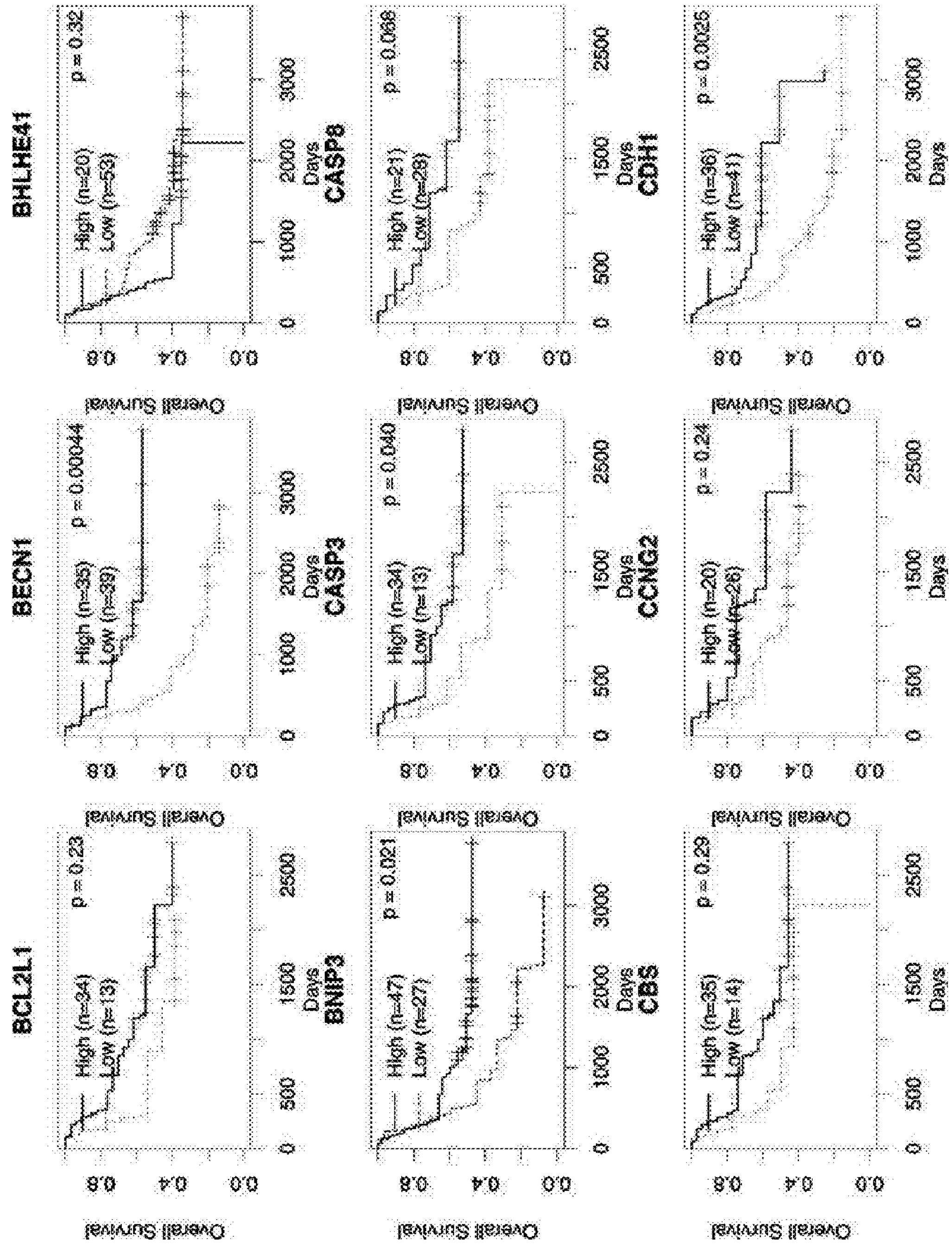
Figure 74:
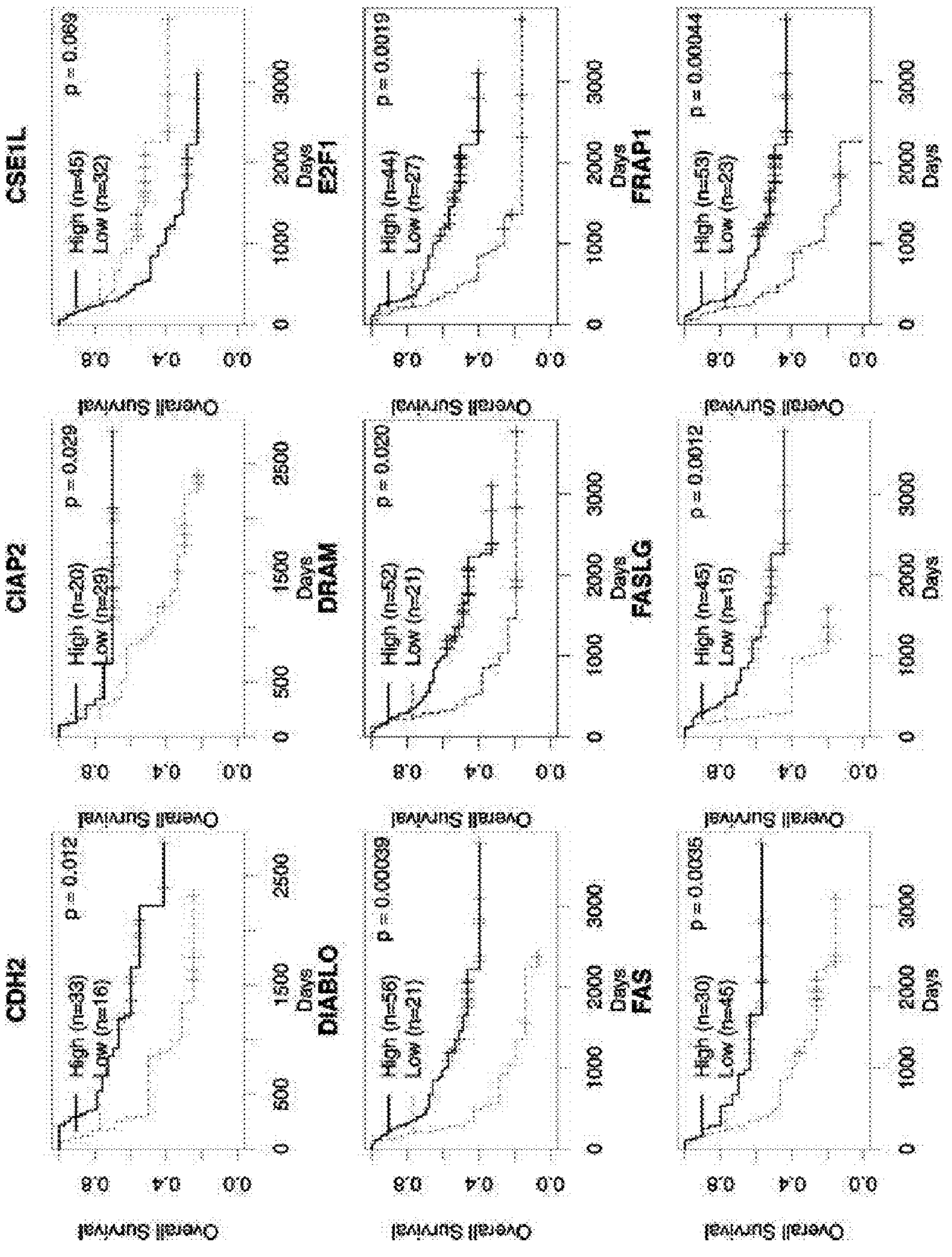
Figure 75:
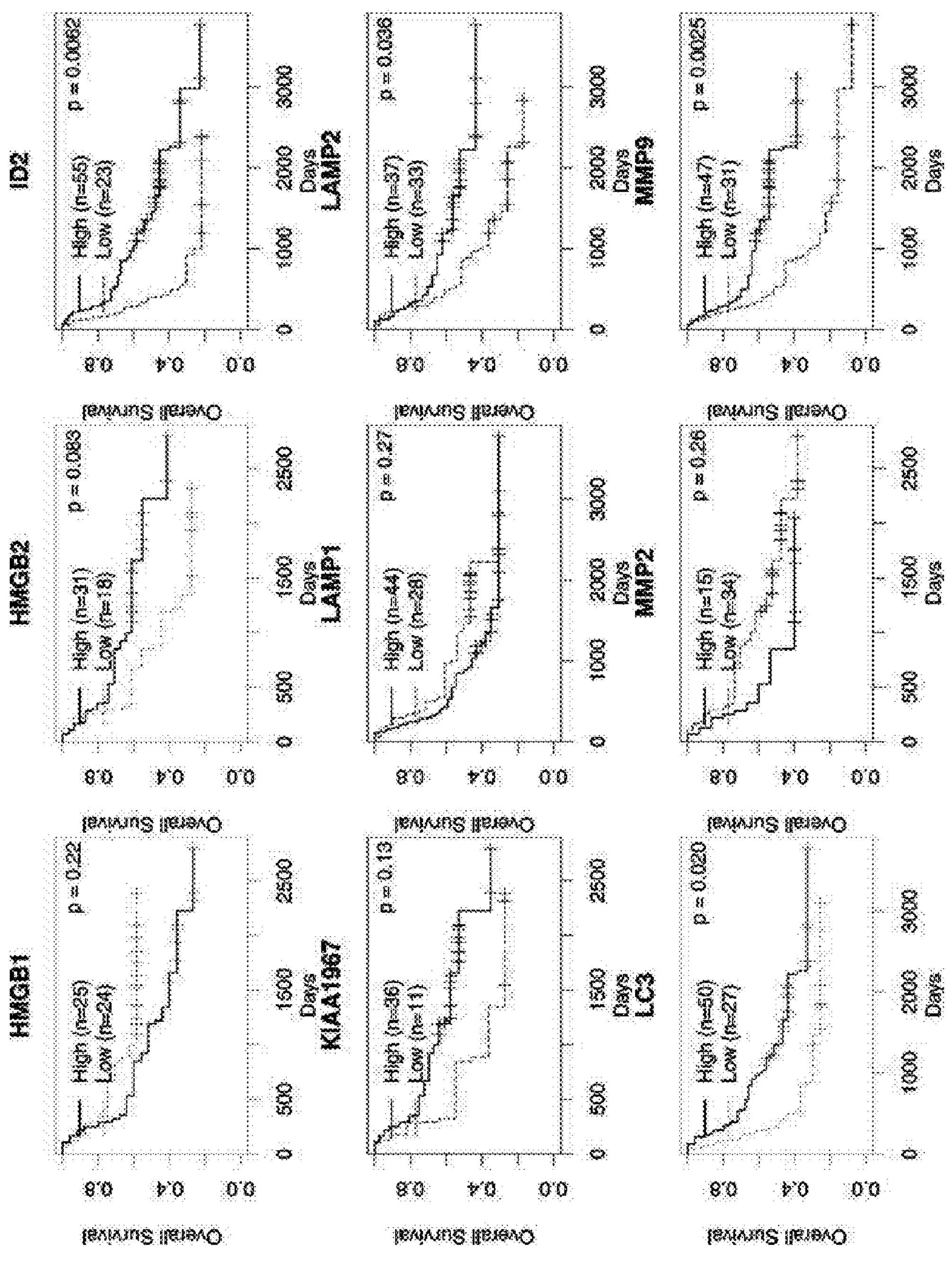
Figure 76:
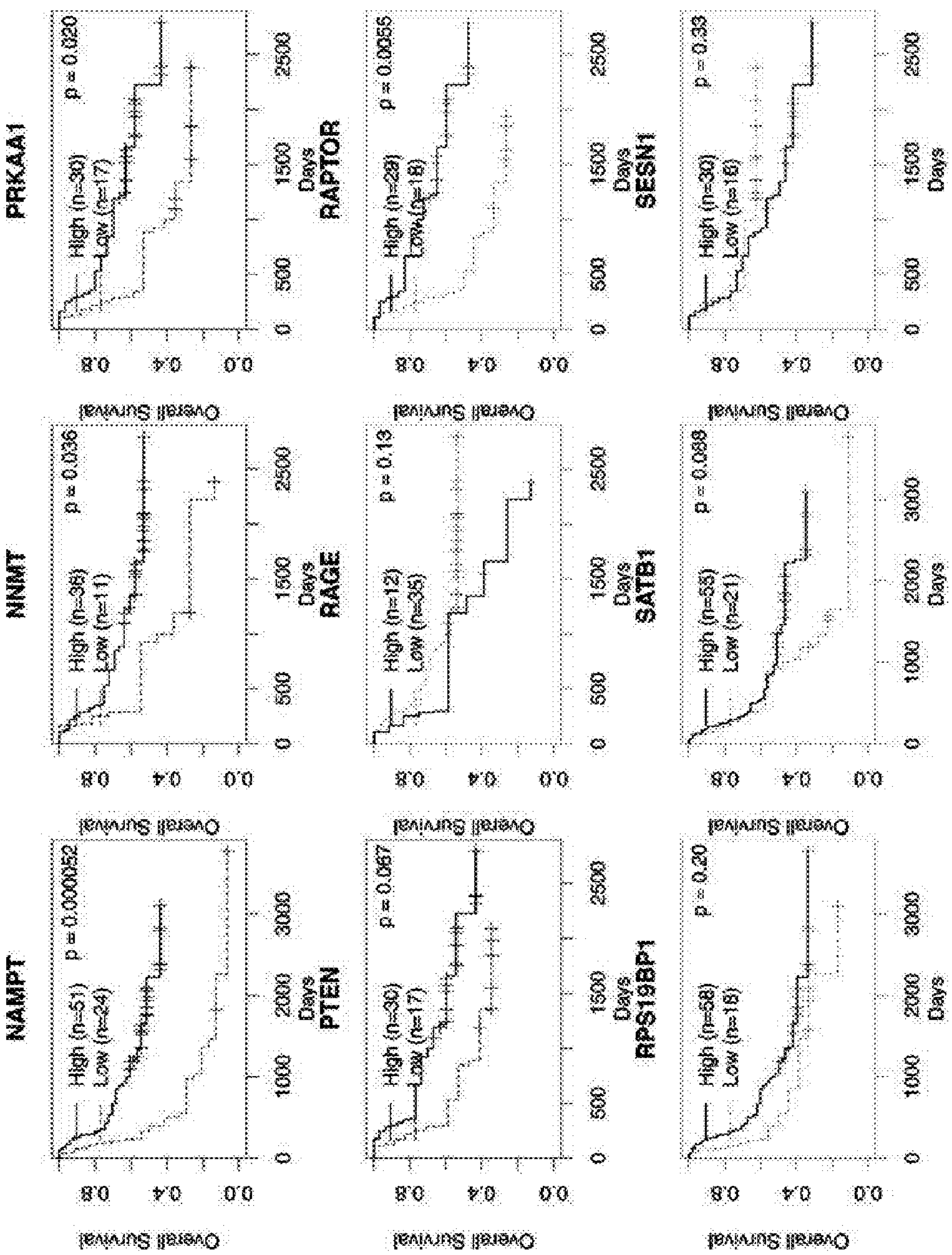
Figure 77:
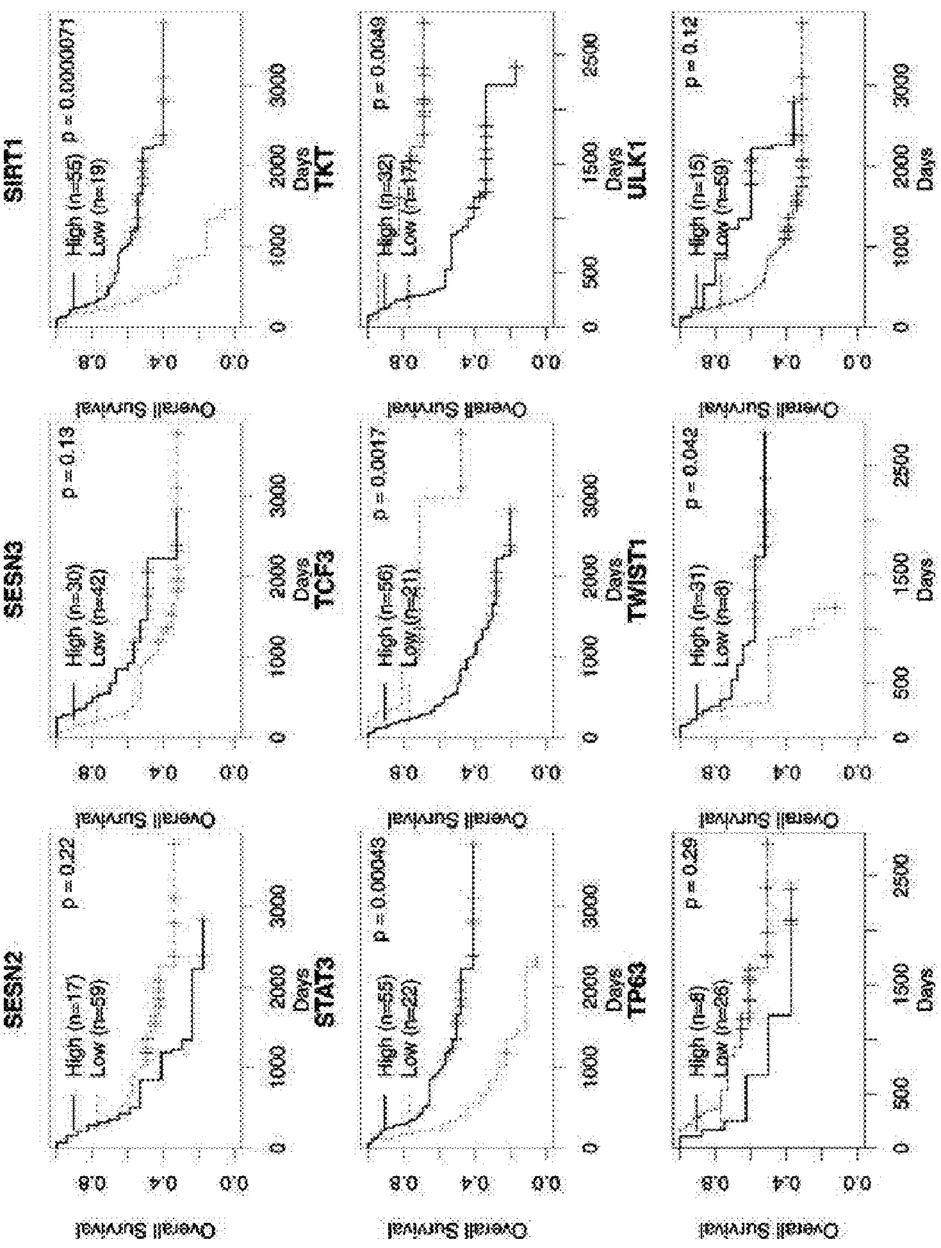
Figure 78:
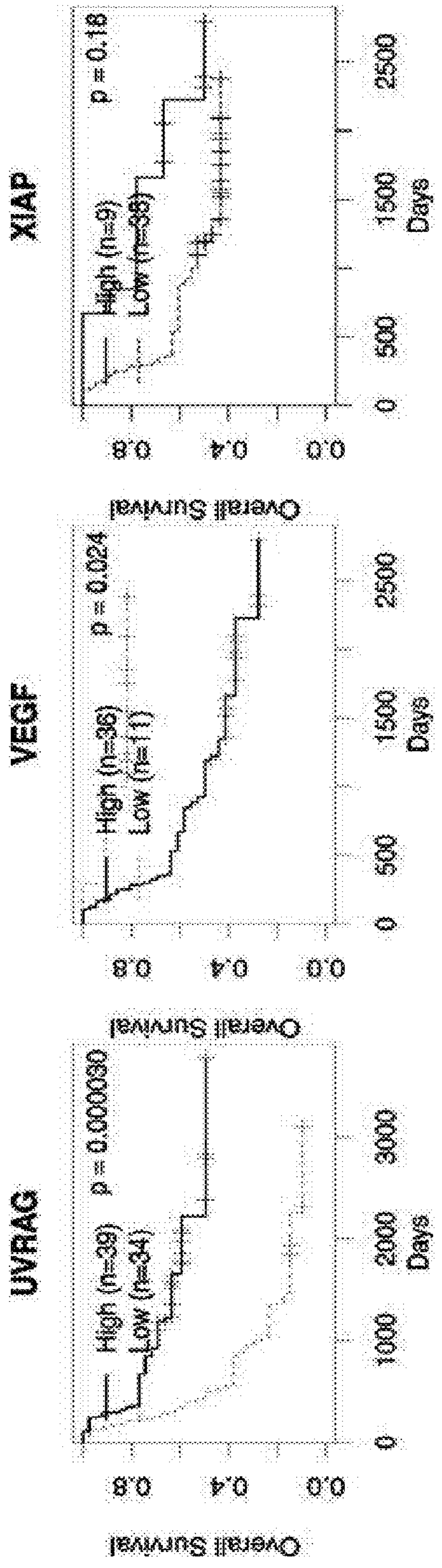
Figure 79:
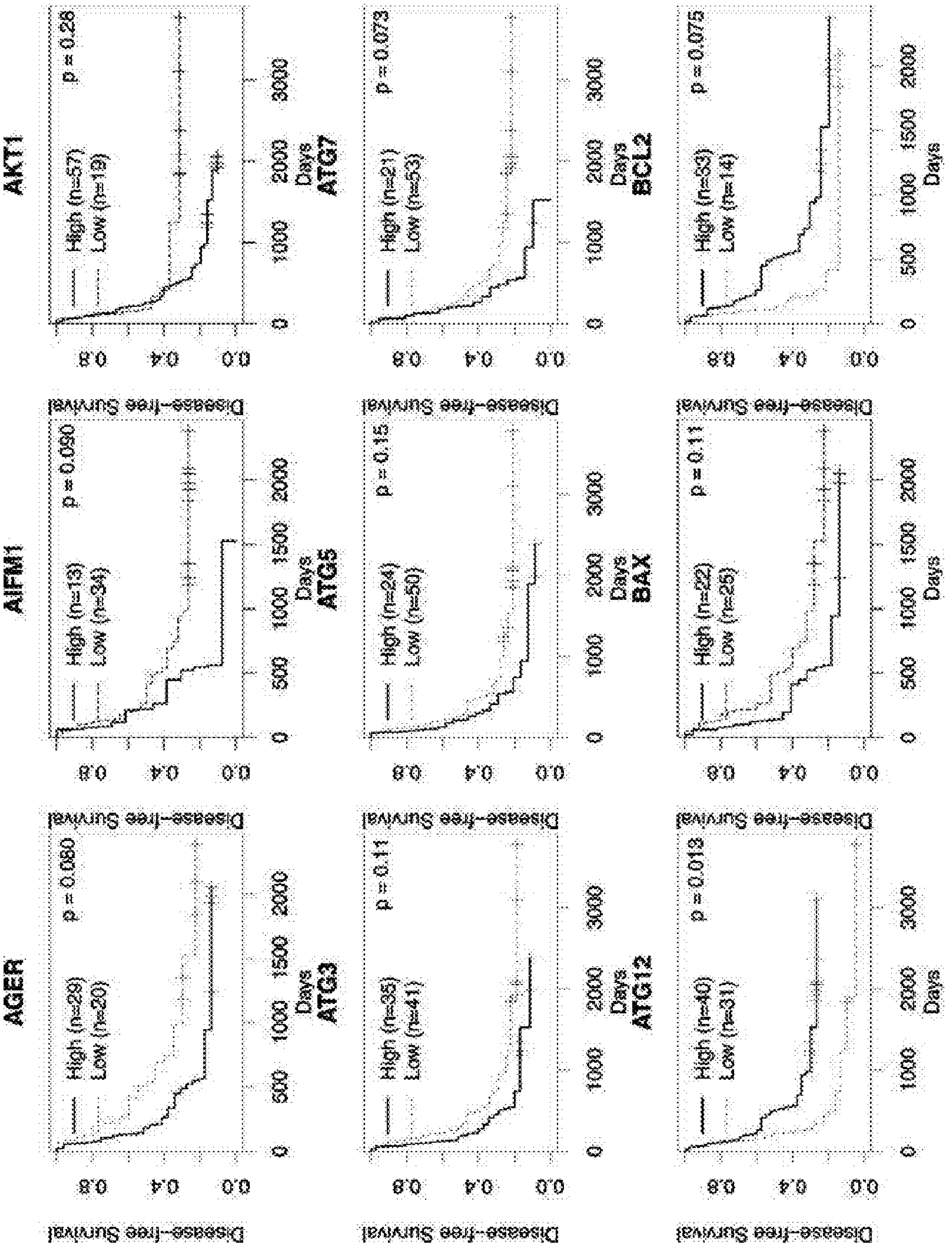
Figure 80:
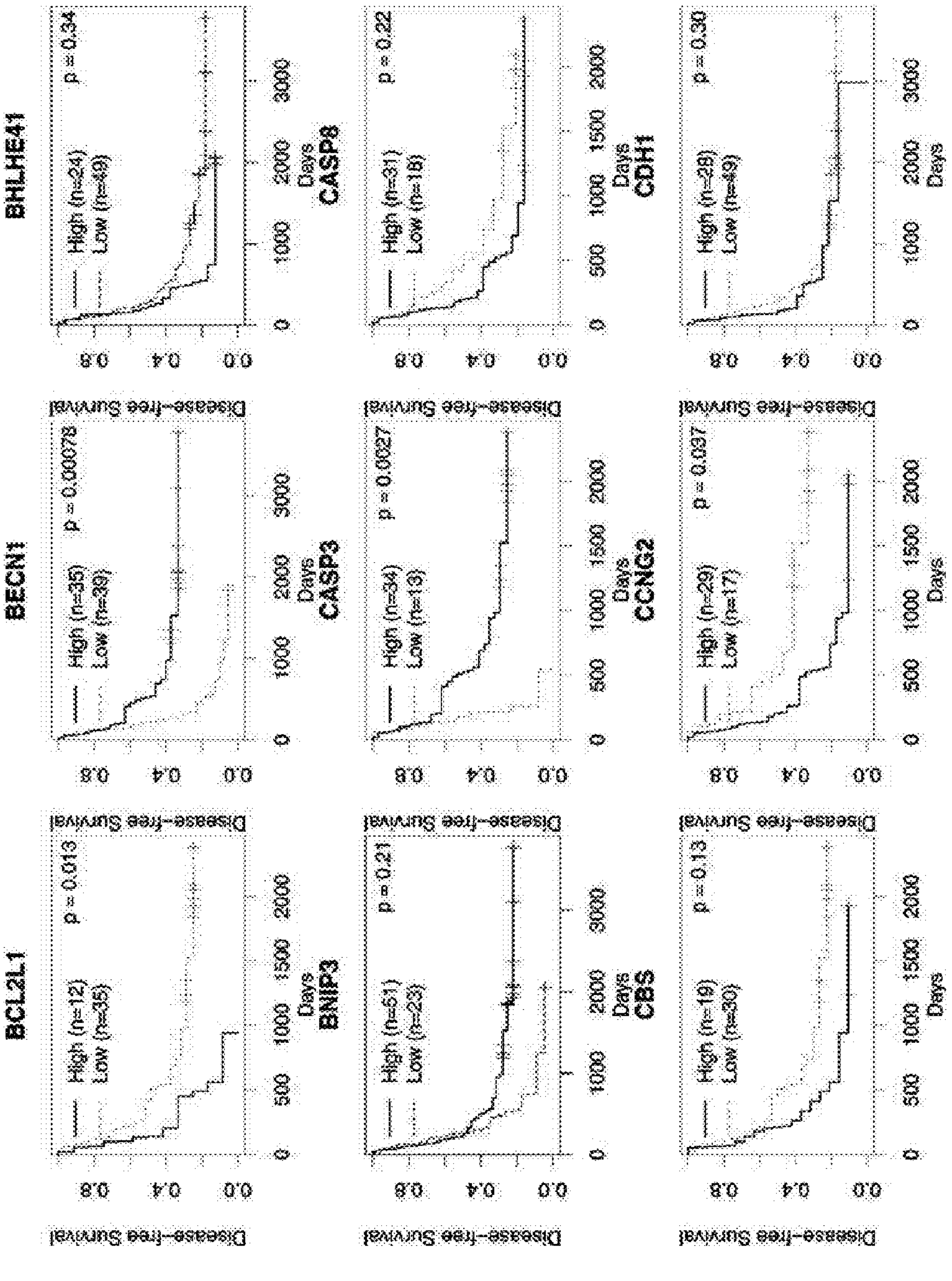
Figure 81:
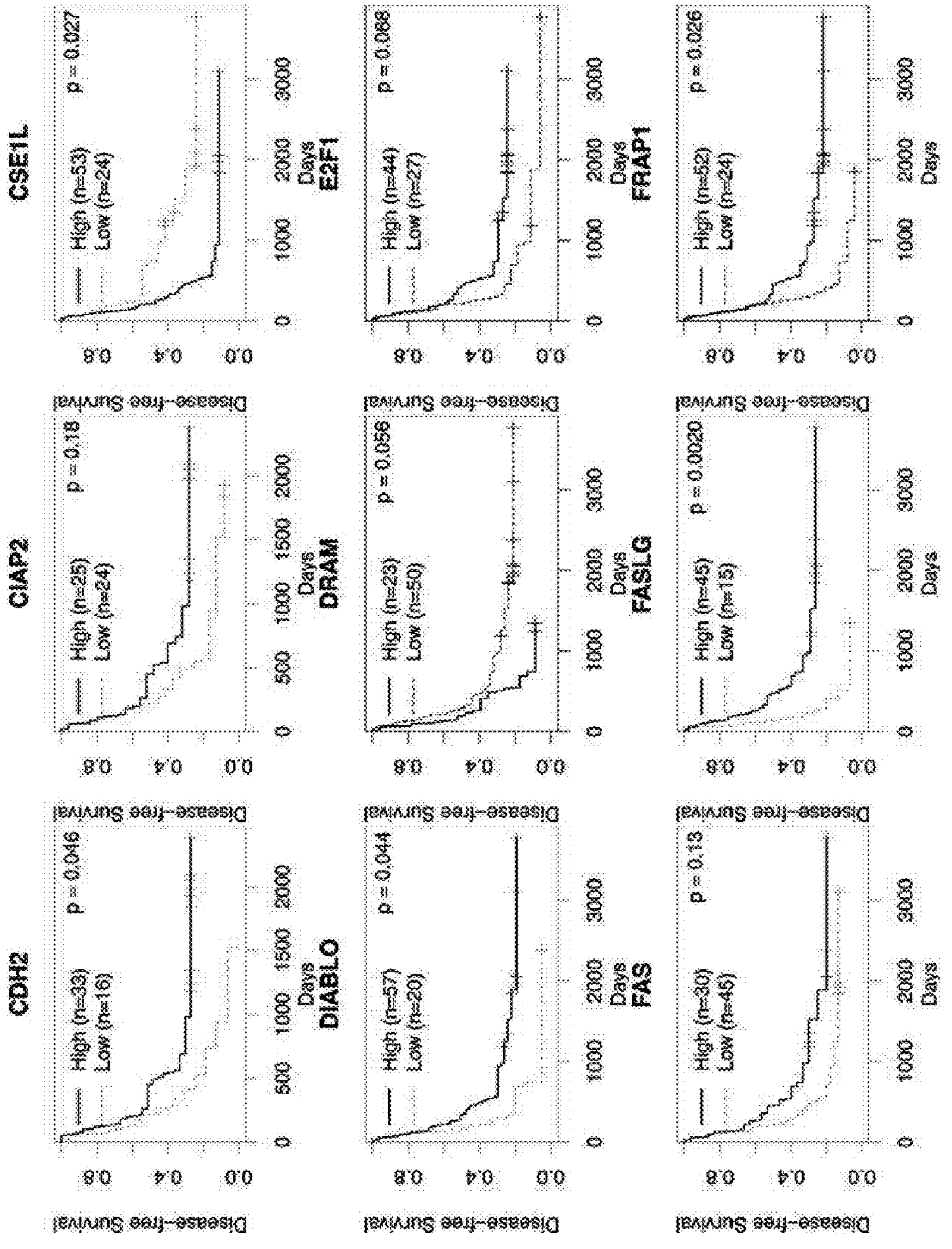
Figure 82:
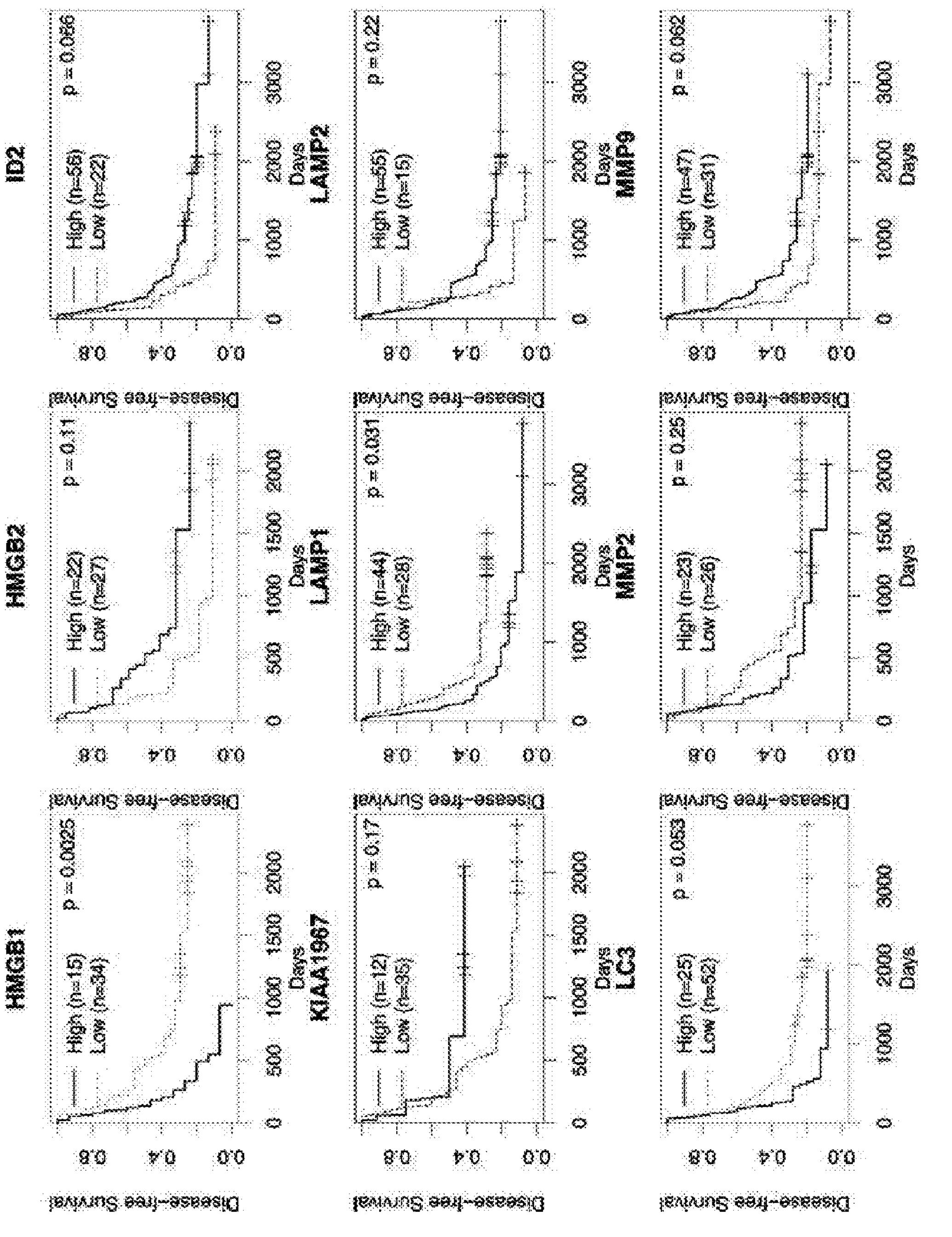
Figure 83:
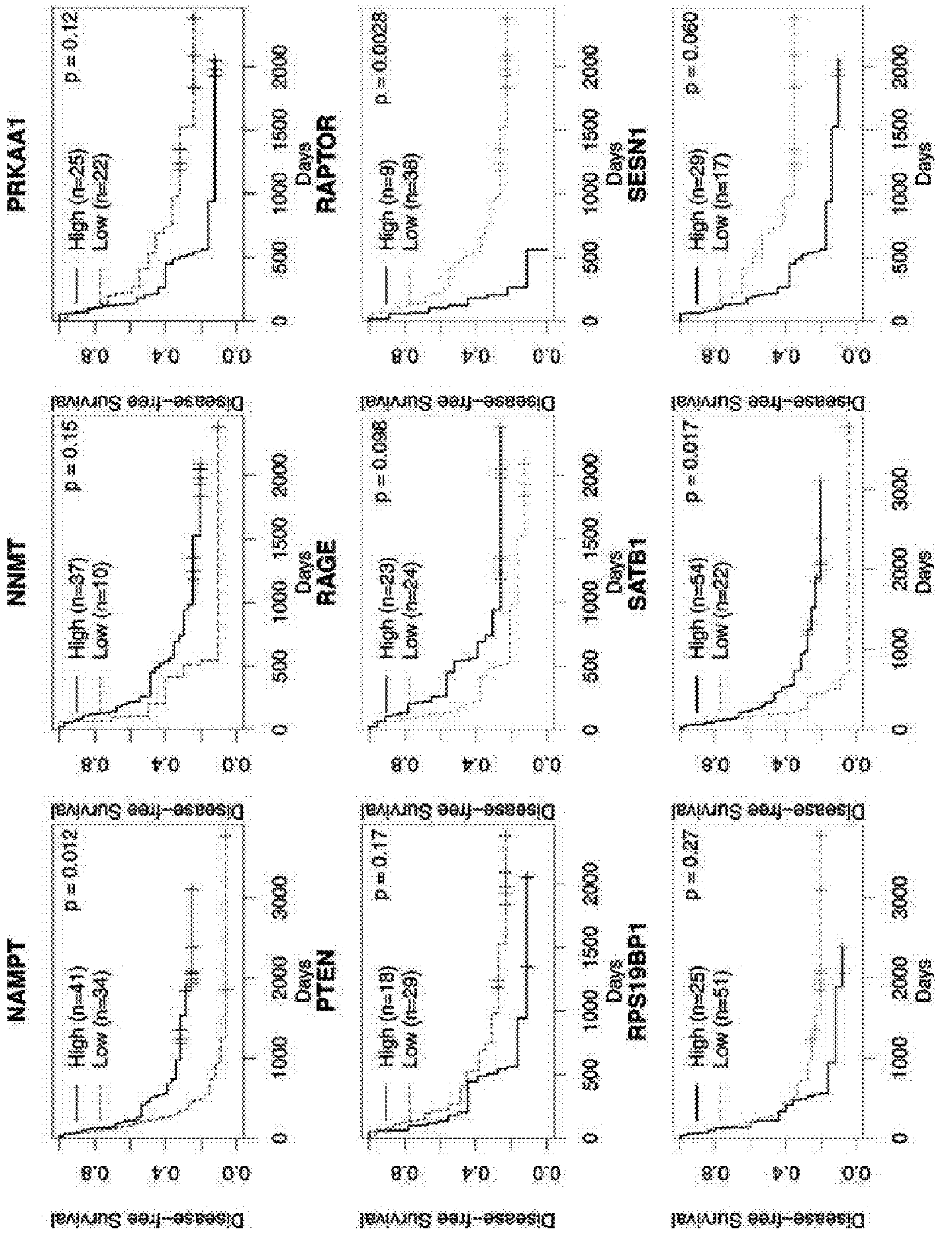
Figure 84:
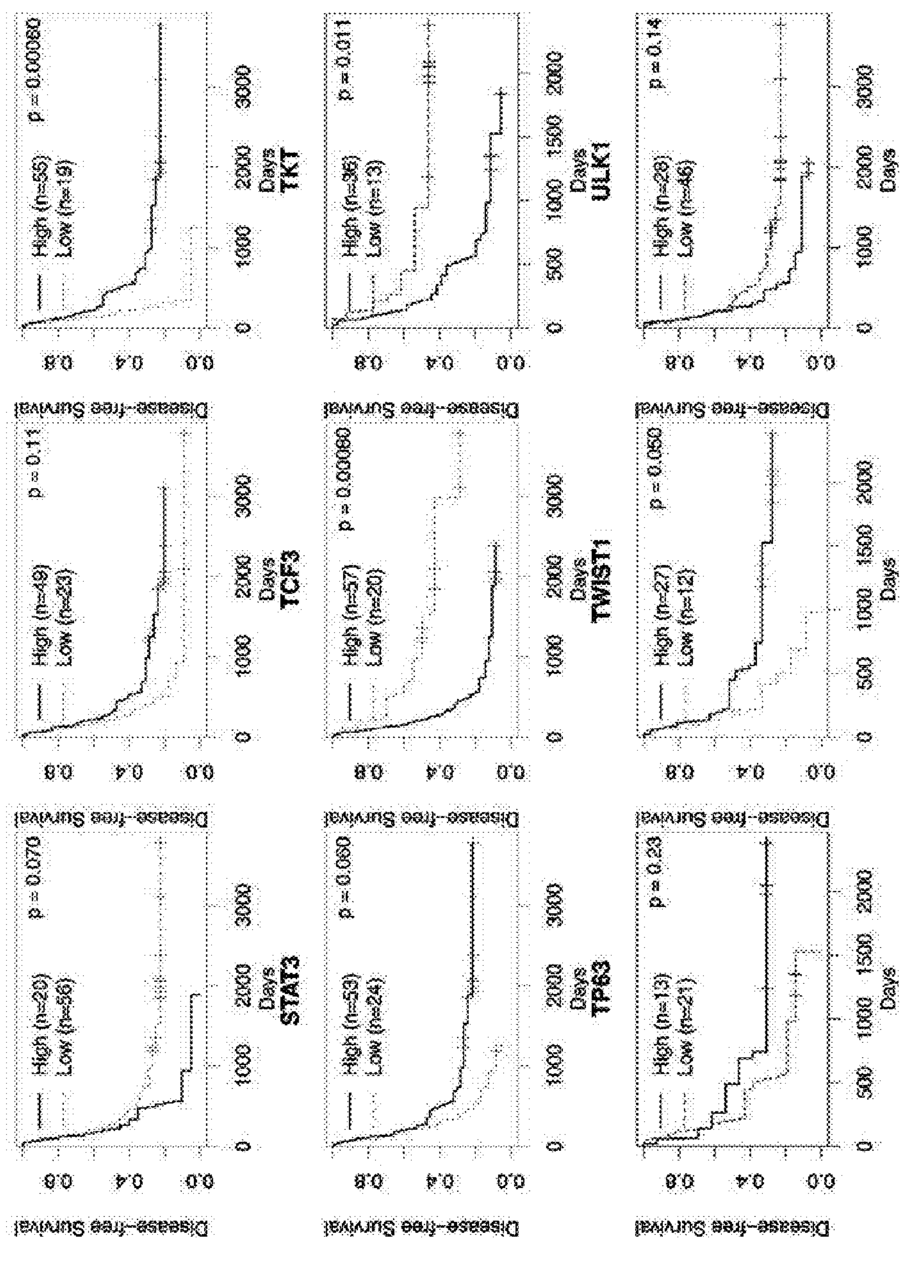
Figure 85:
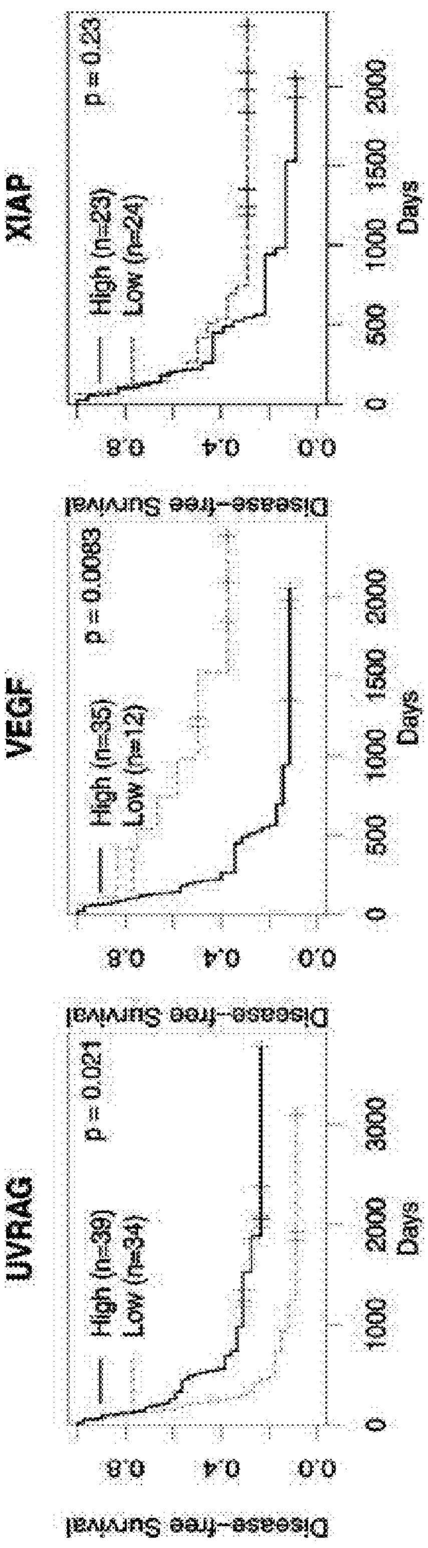
Figure 86:
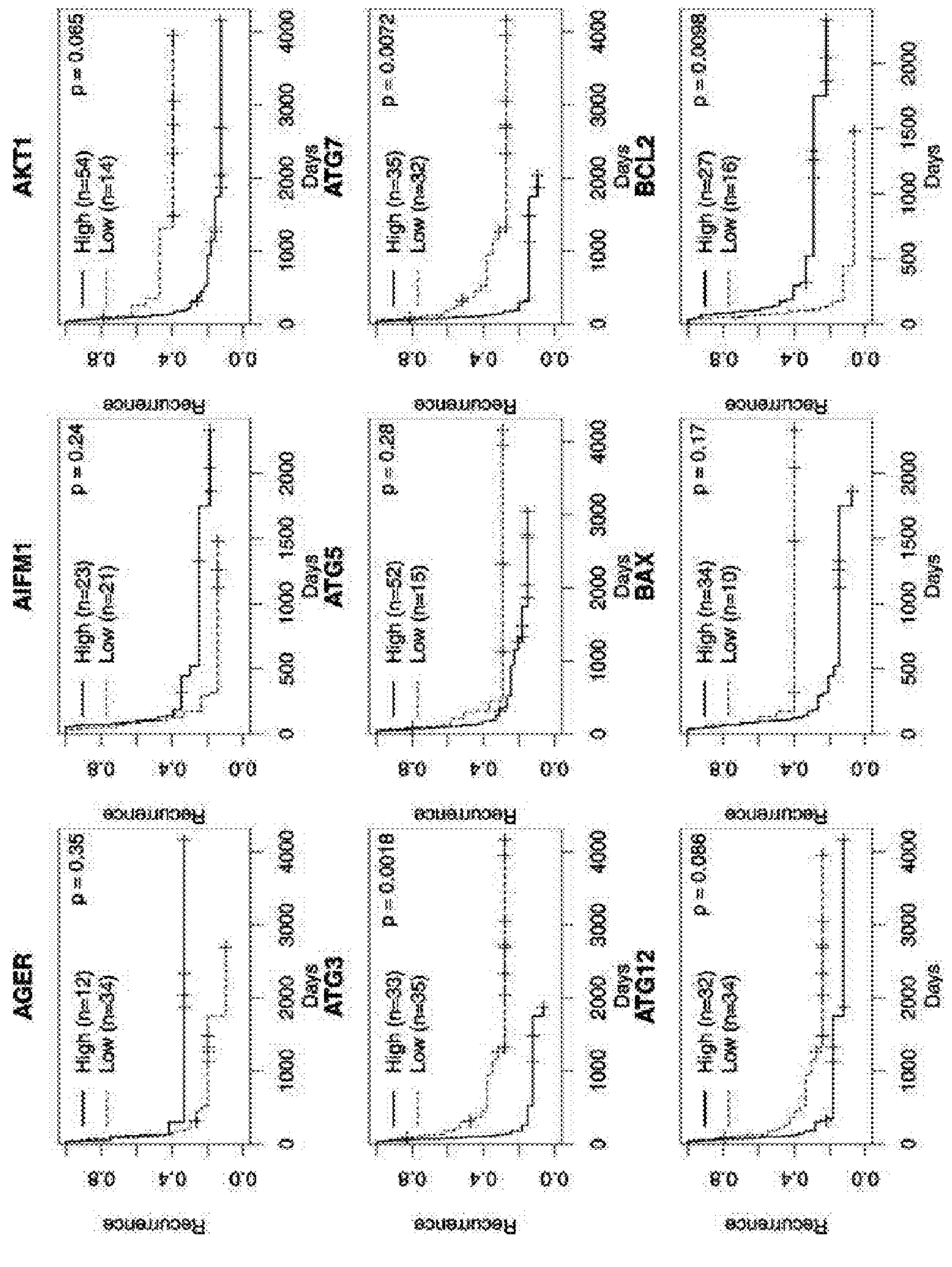
Figure 87:
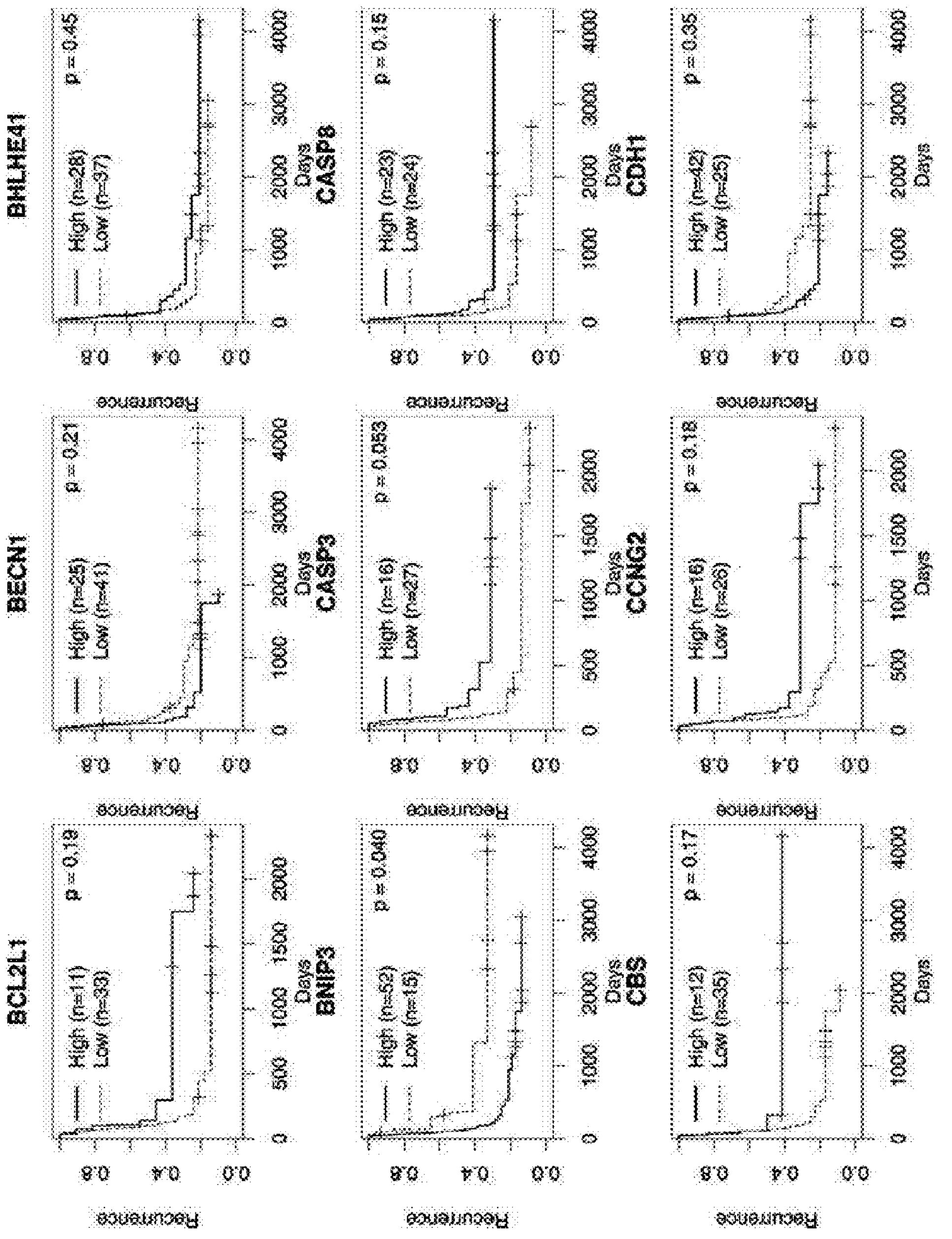
Figure 88:
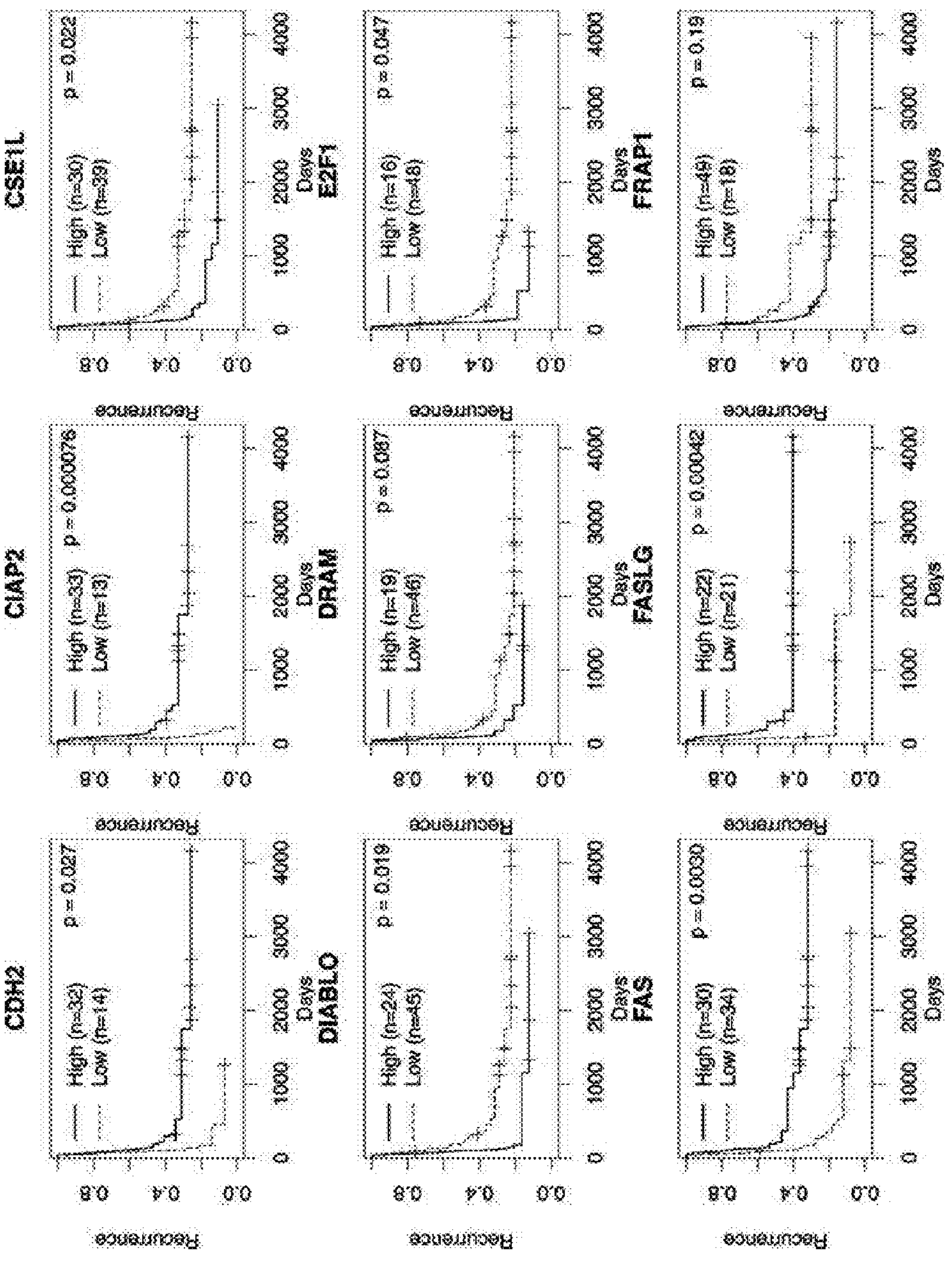
Figure 89:
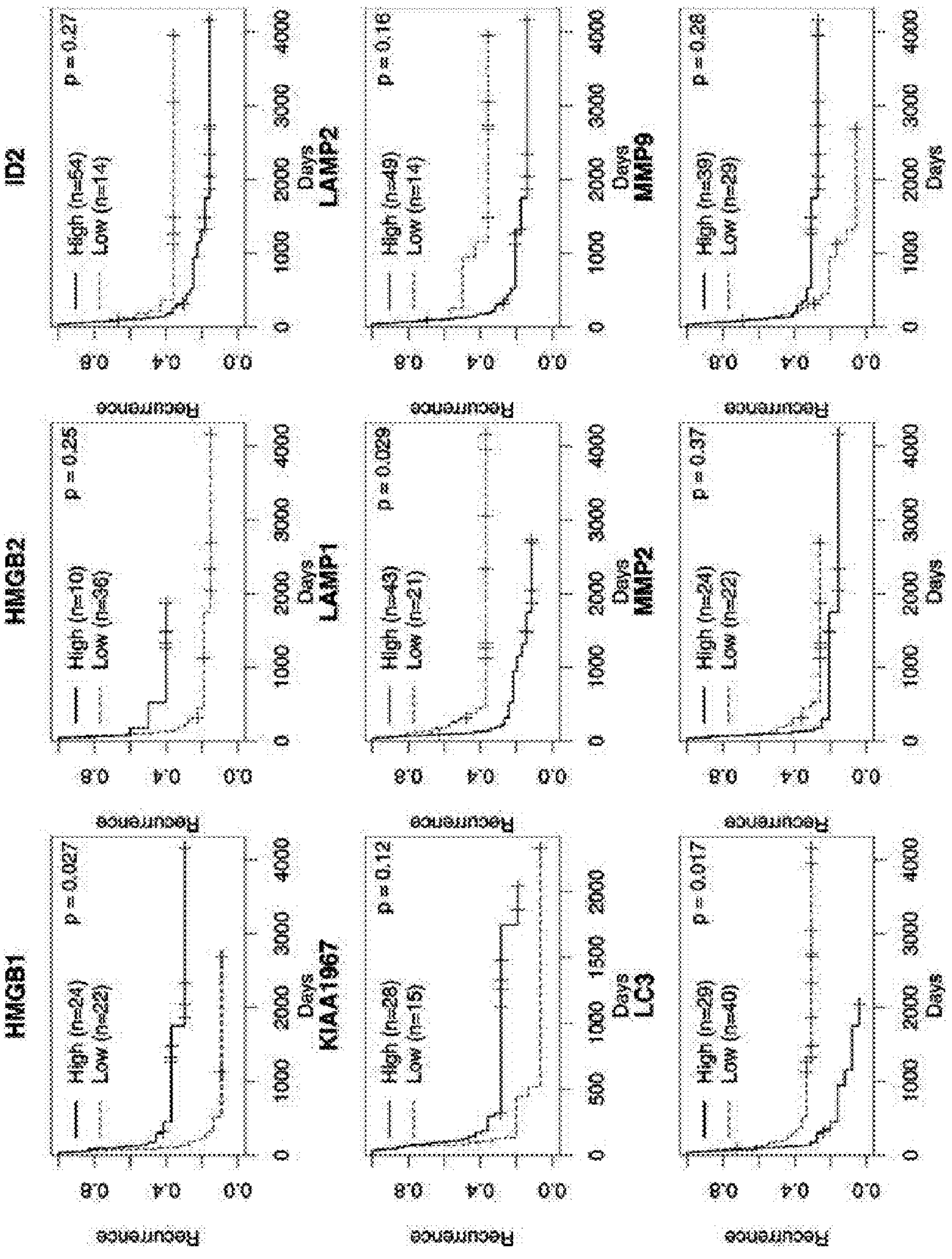
Figure 90:
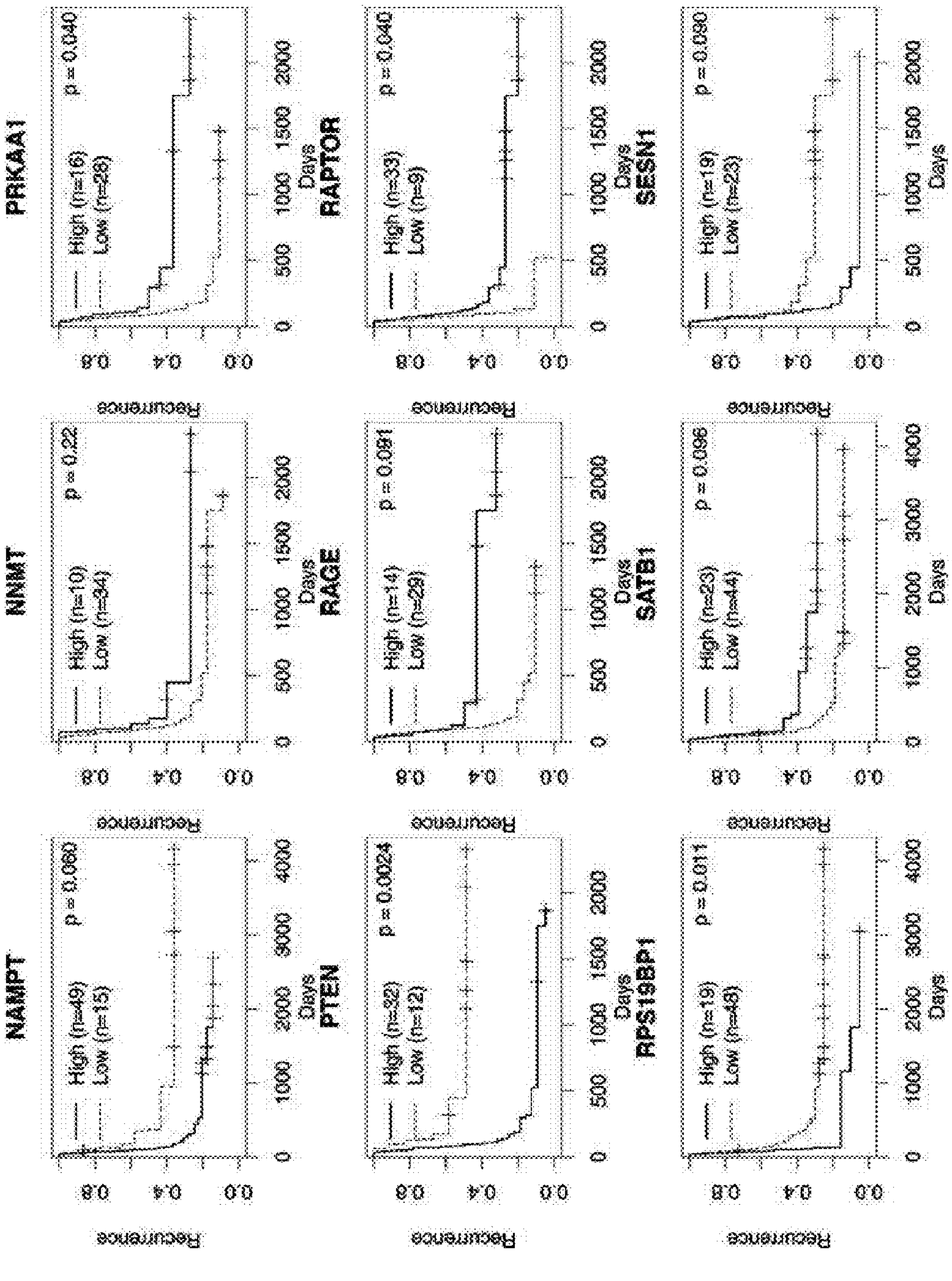
Figure 91:
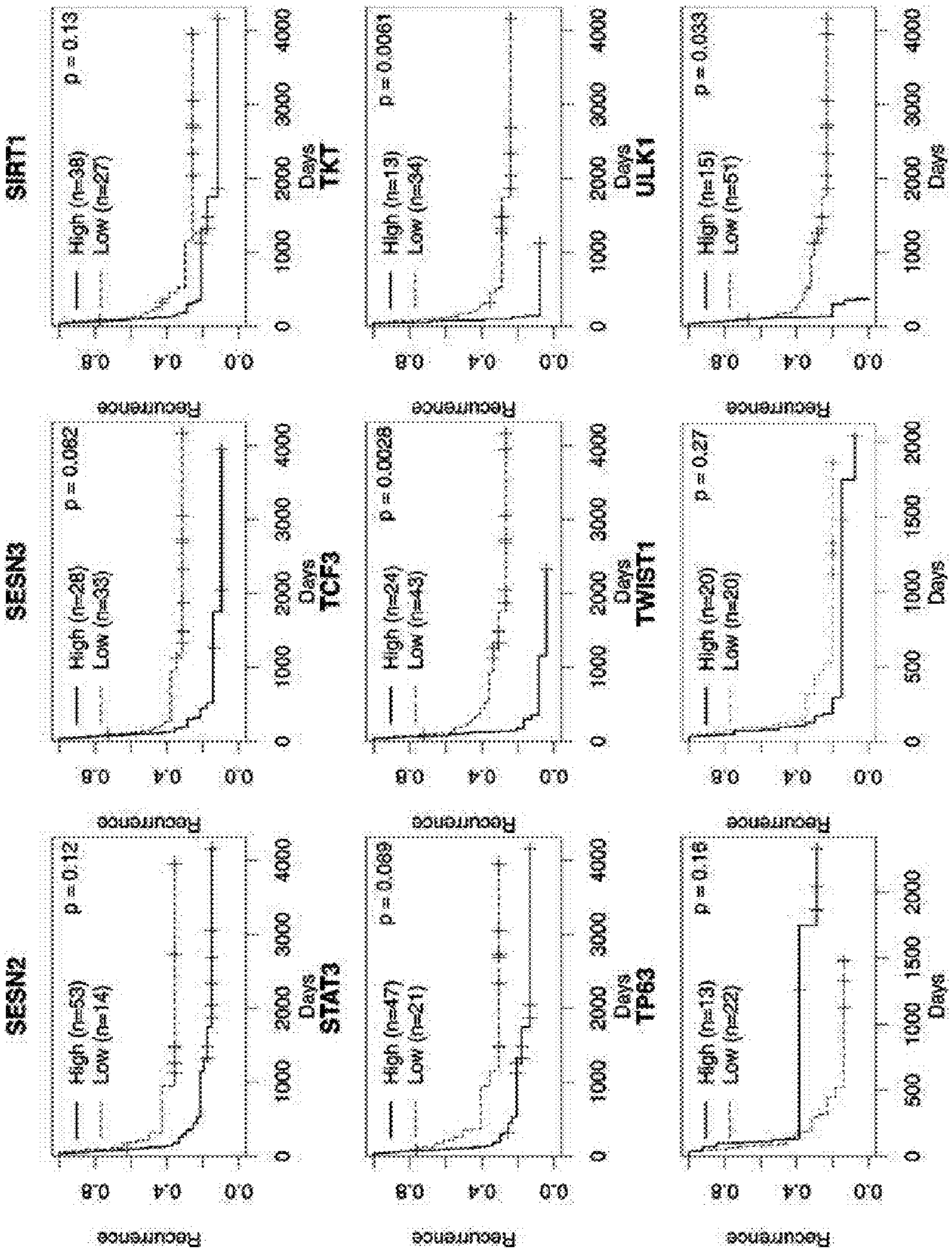
Figure 92:
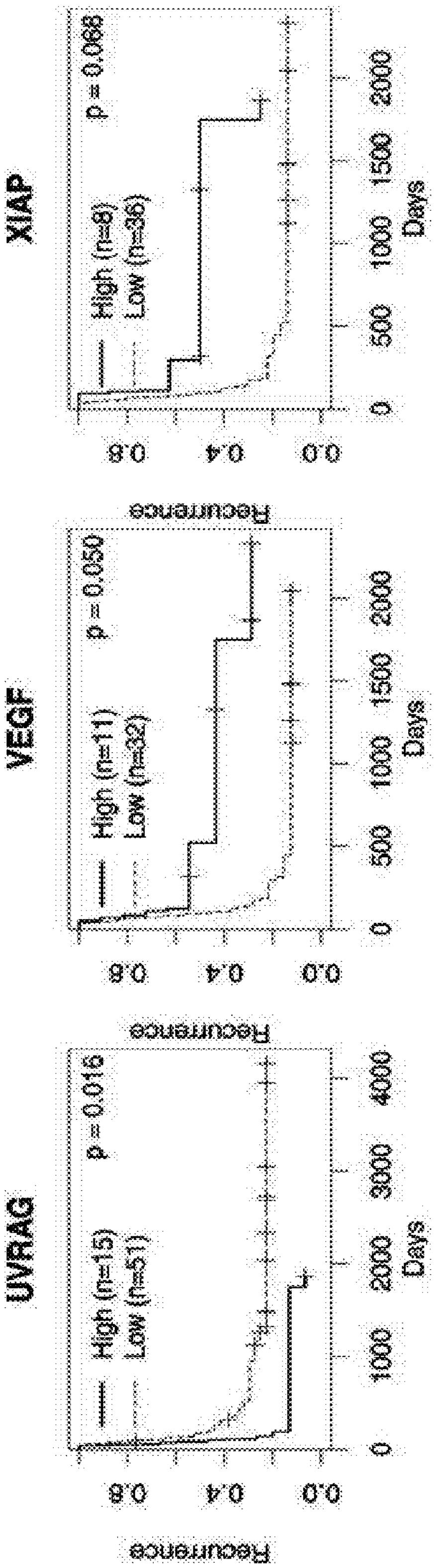
Figure 93:
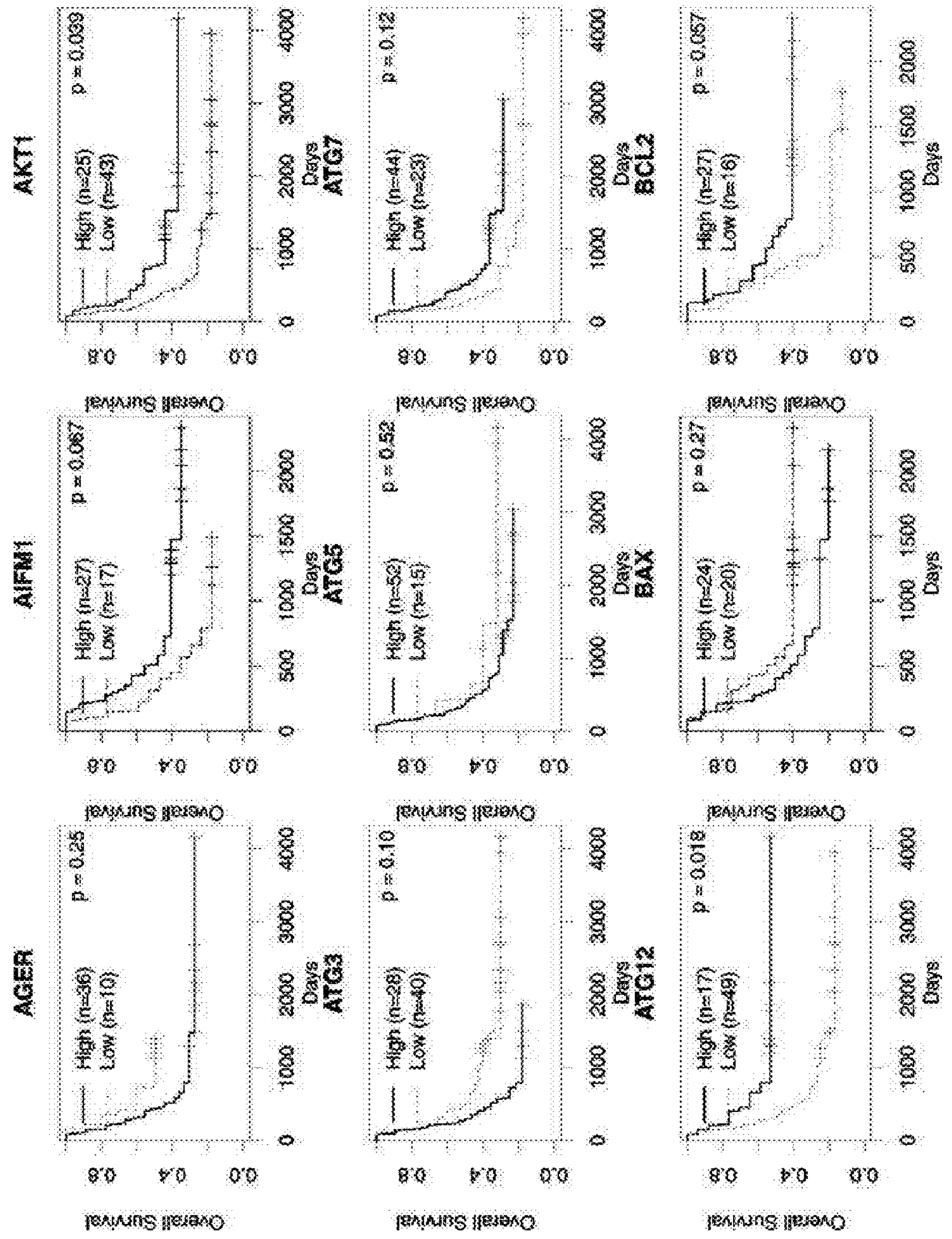
Figure 94:
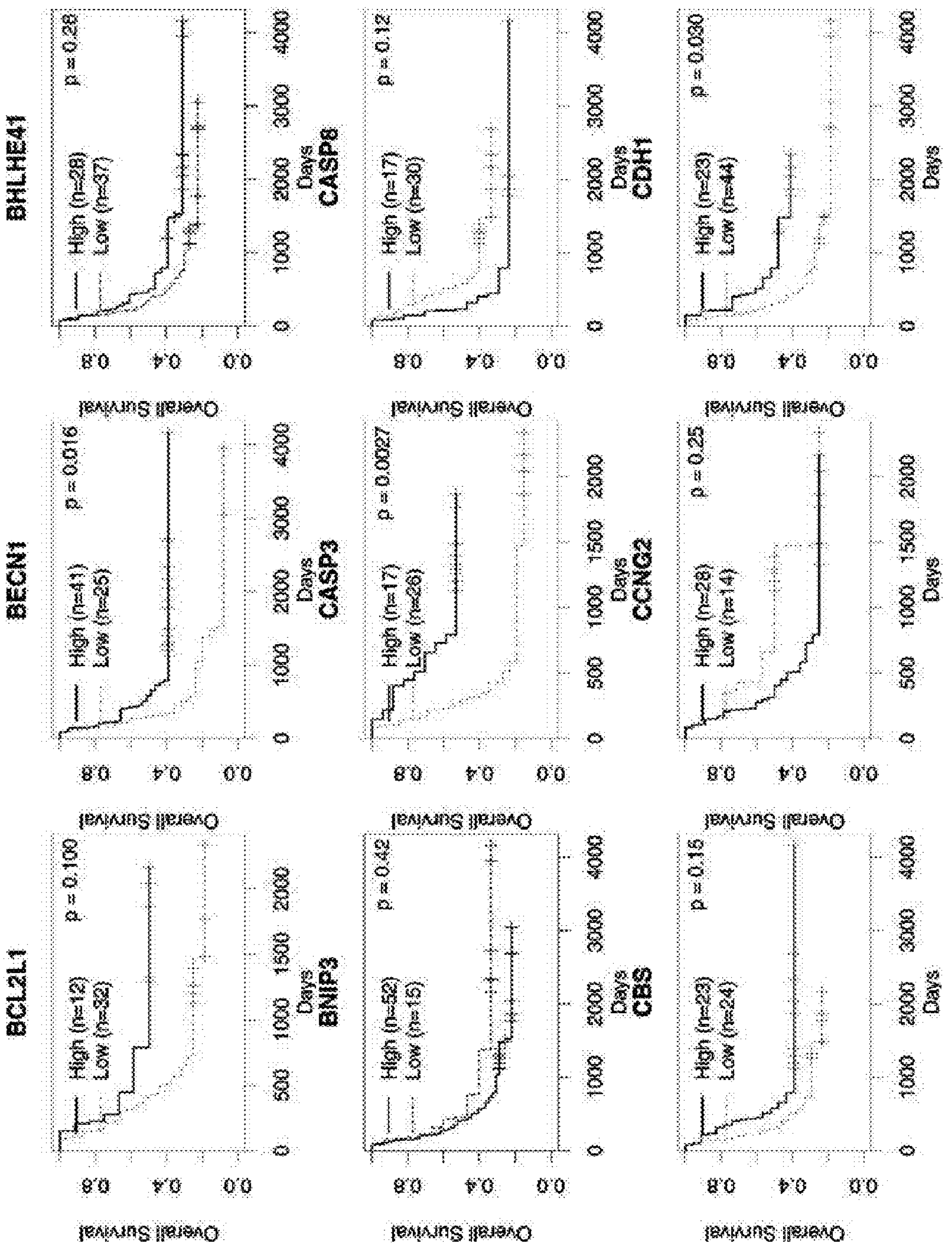
Figure 95:
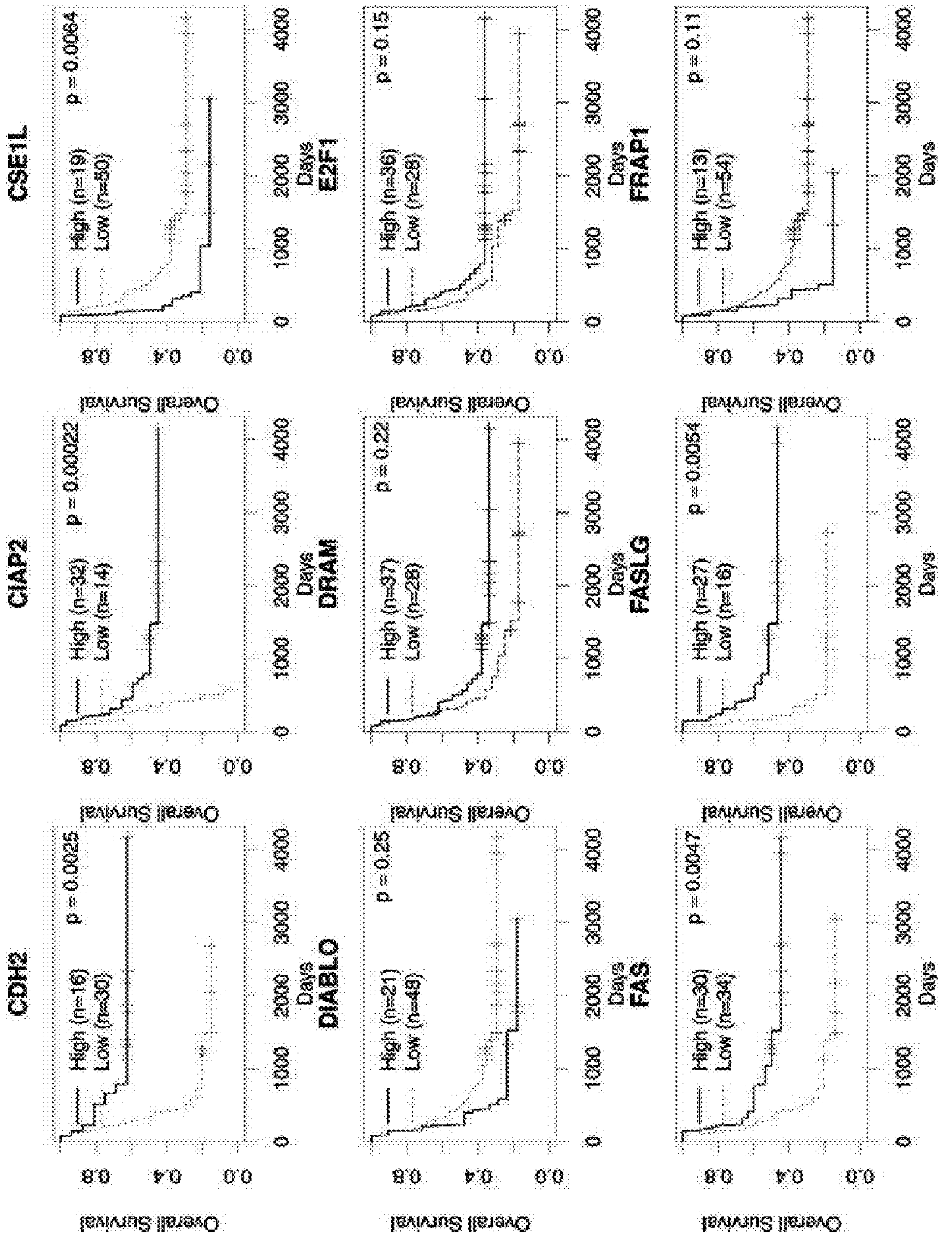
Figure 96:
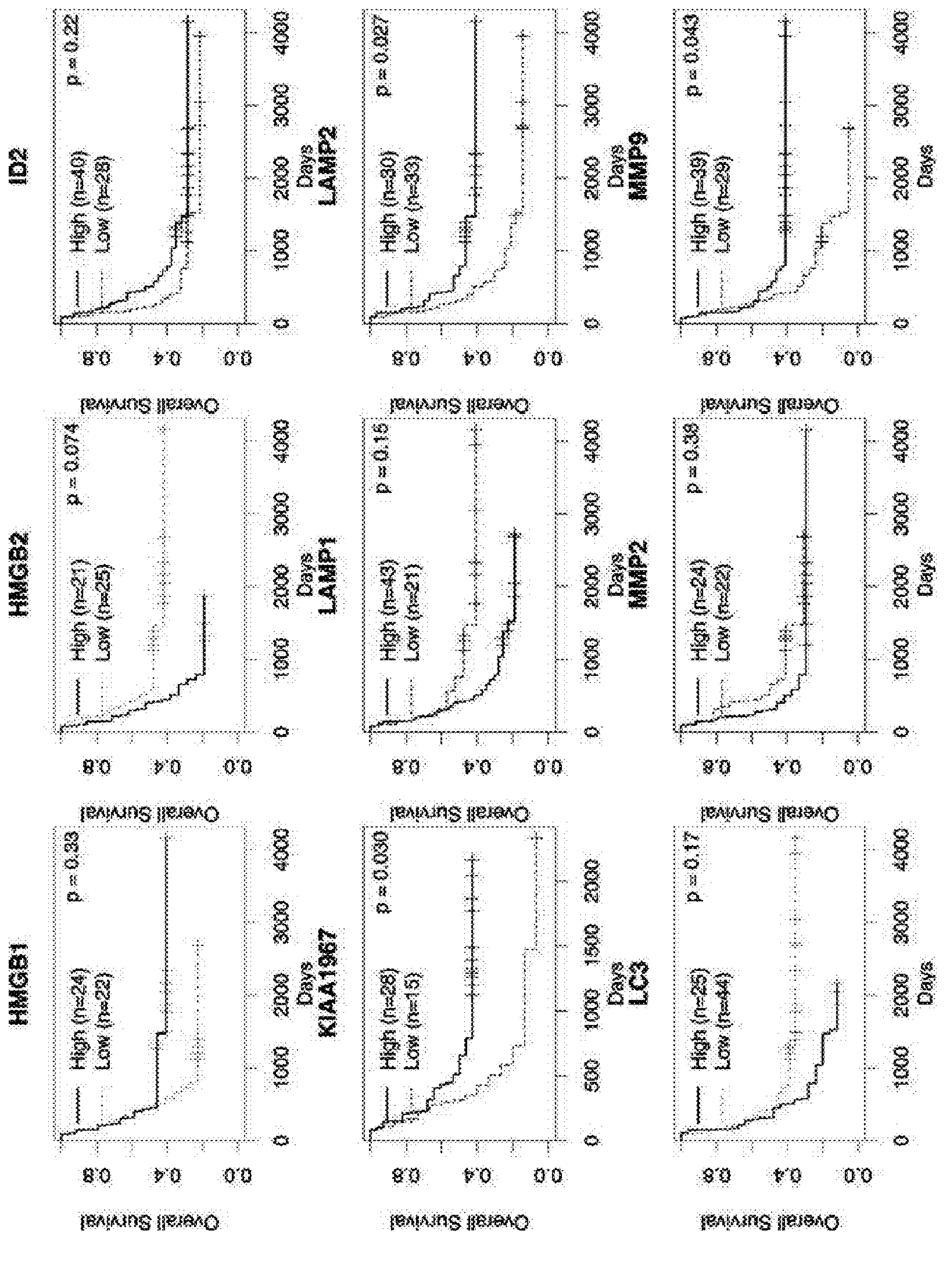
Figure 97:
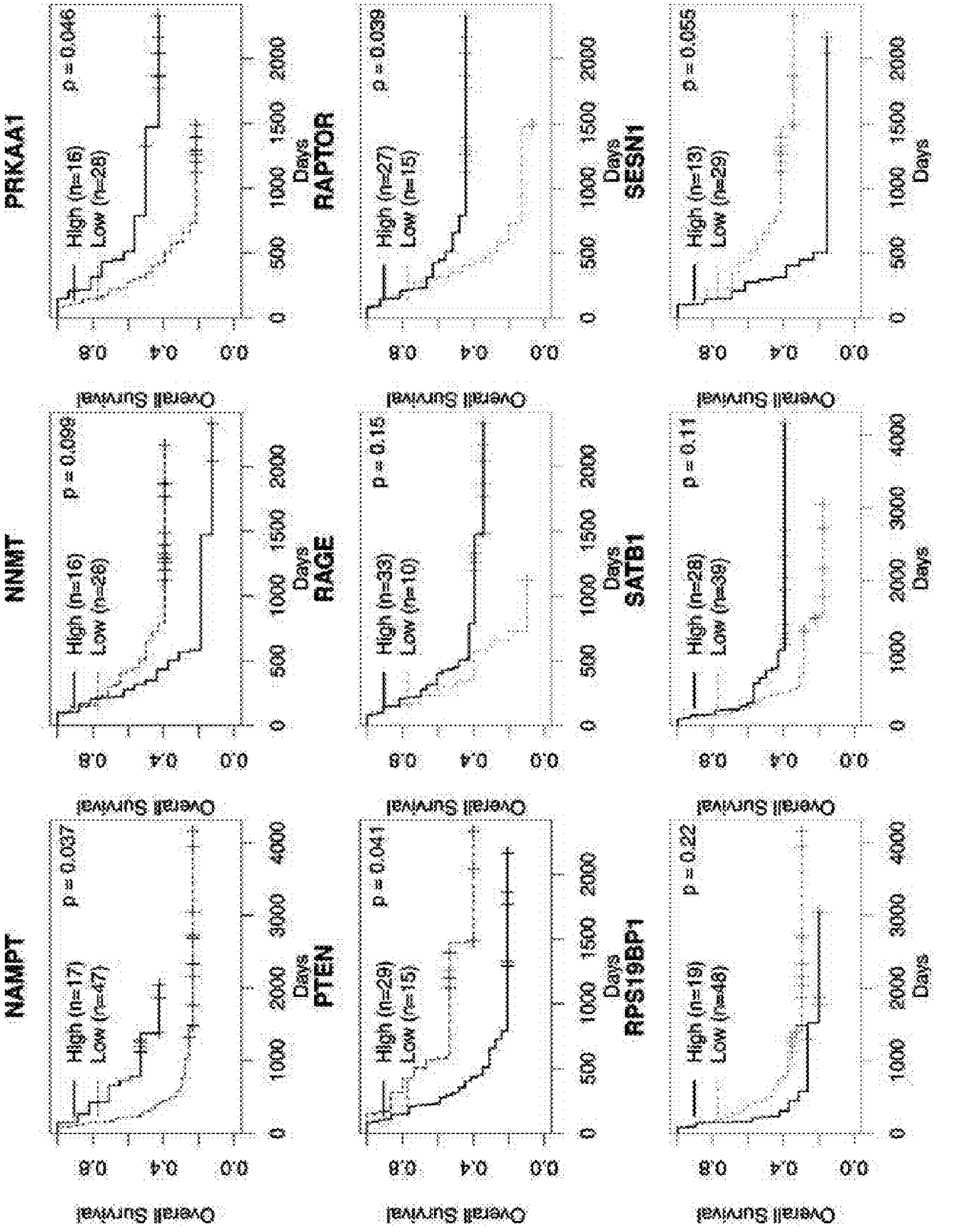
Figure 98:
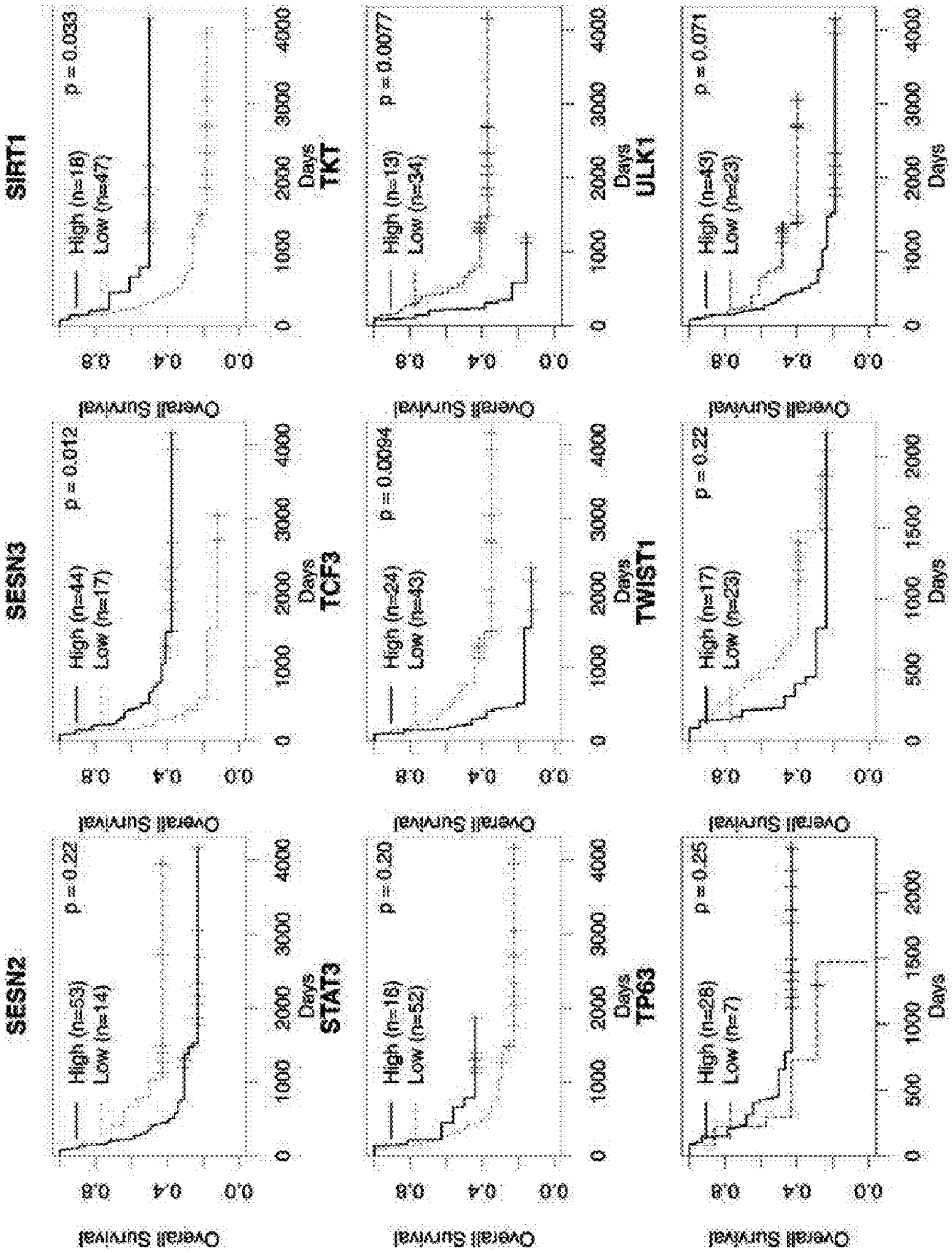
Figure 99:
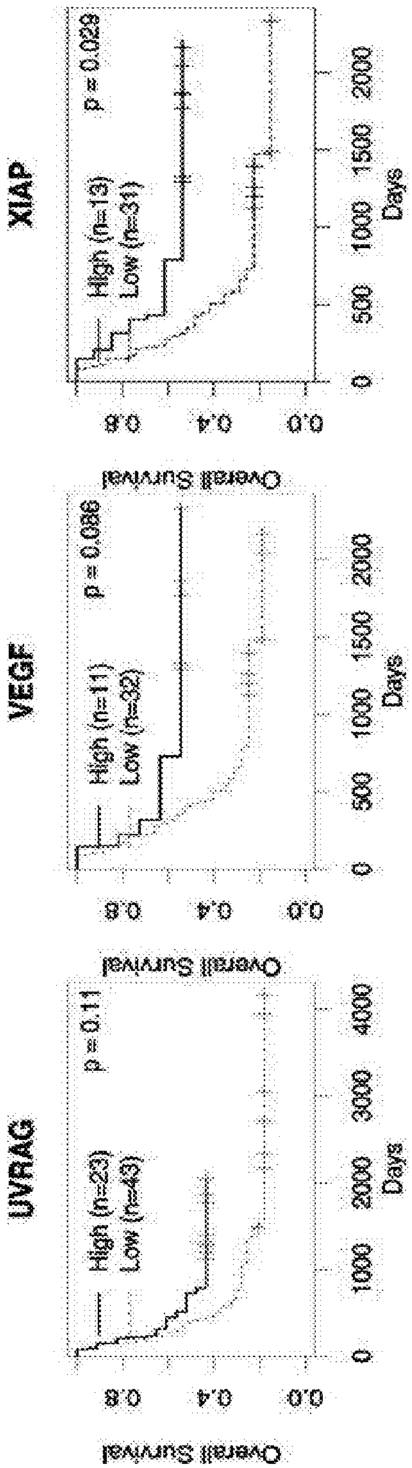
Figure 100:
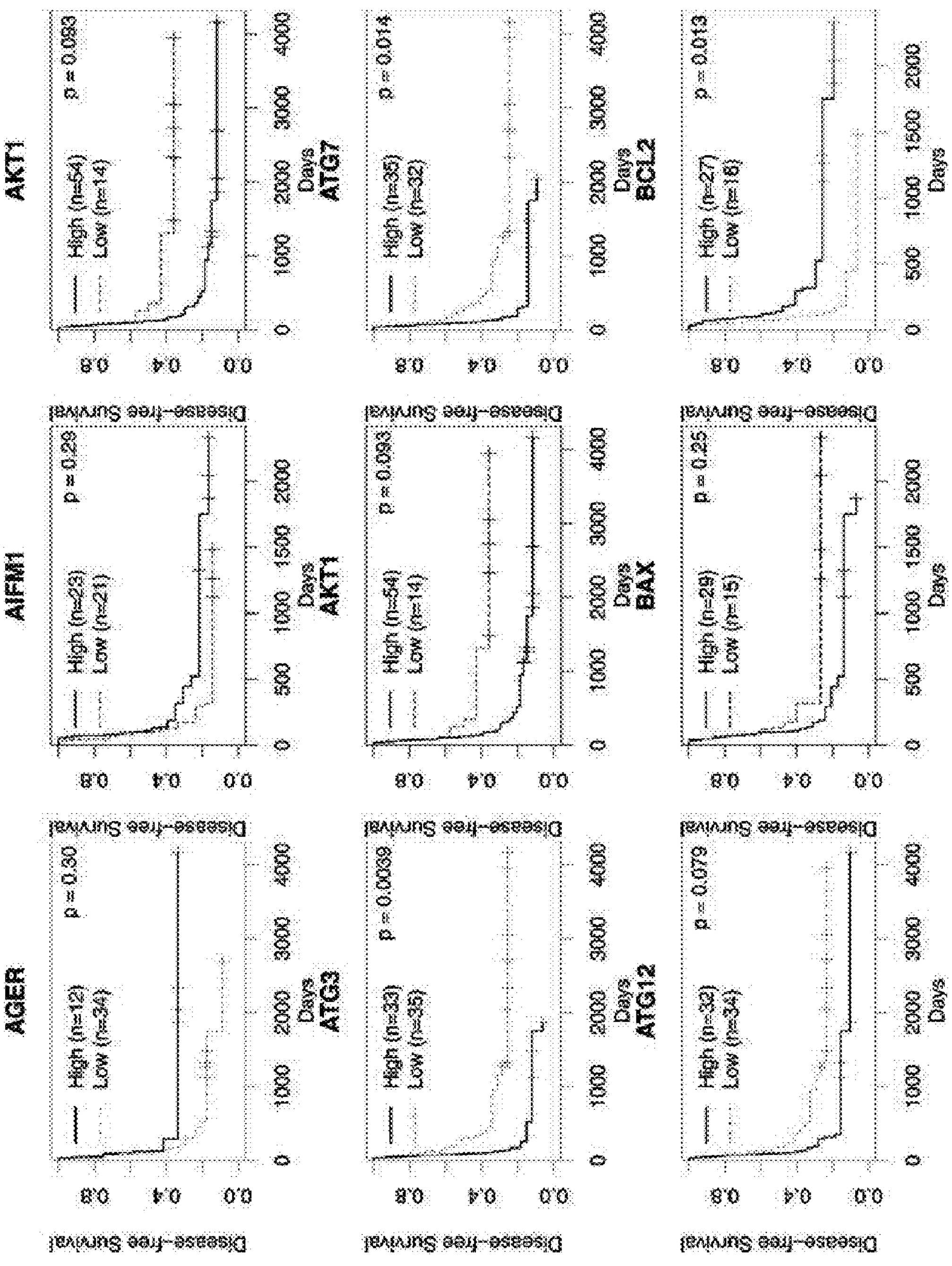
Figure 101:
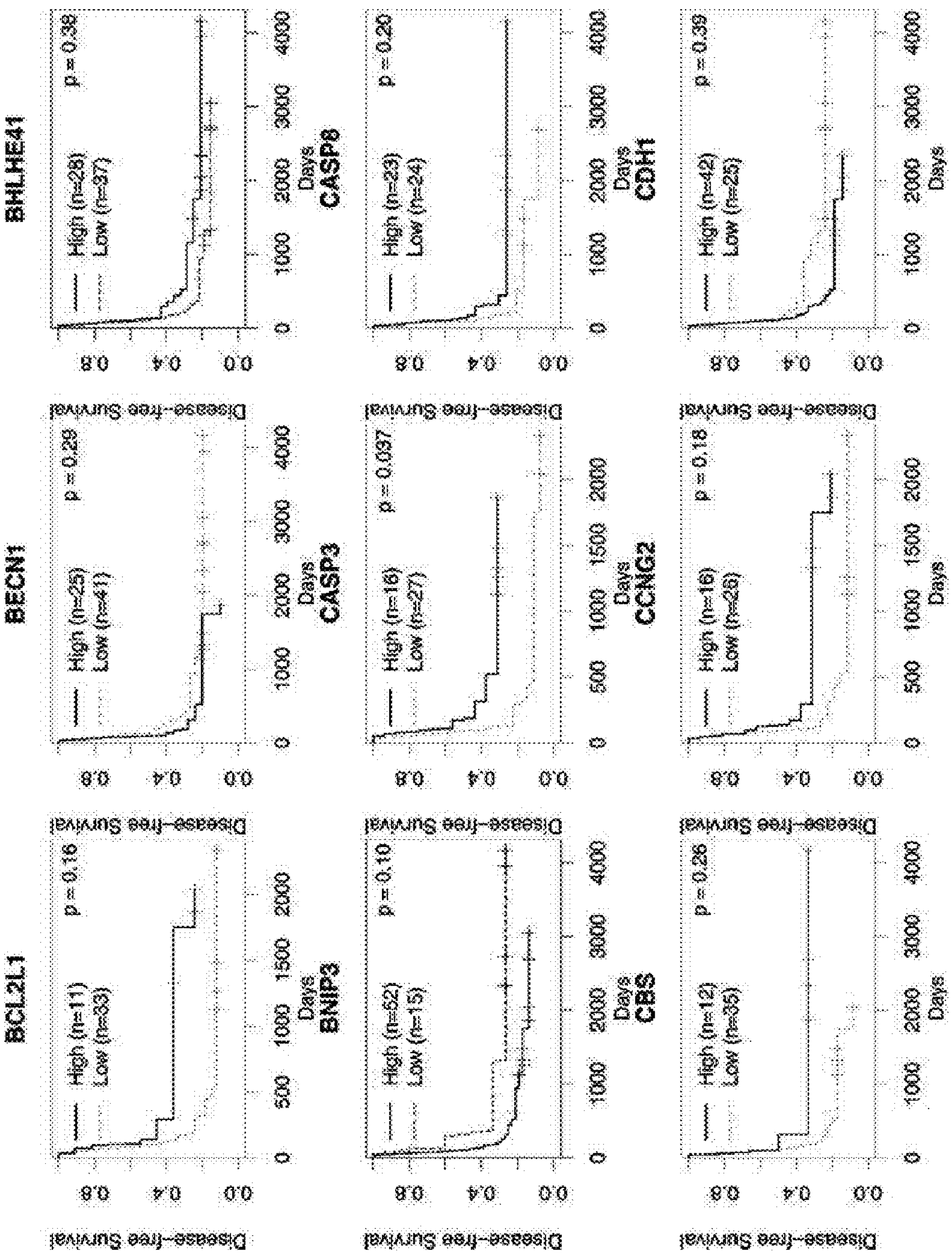
Figure 102:
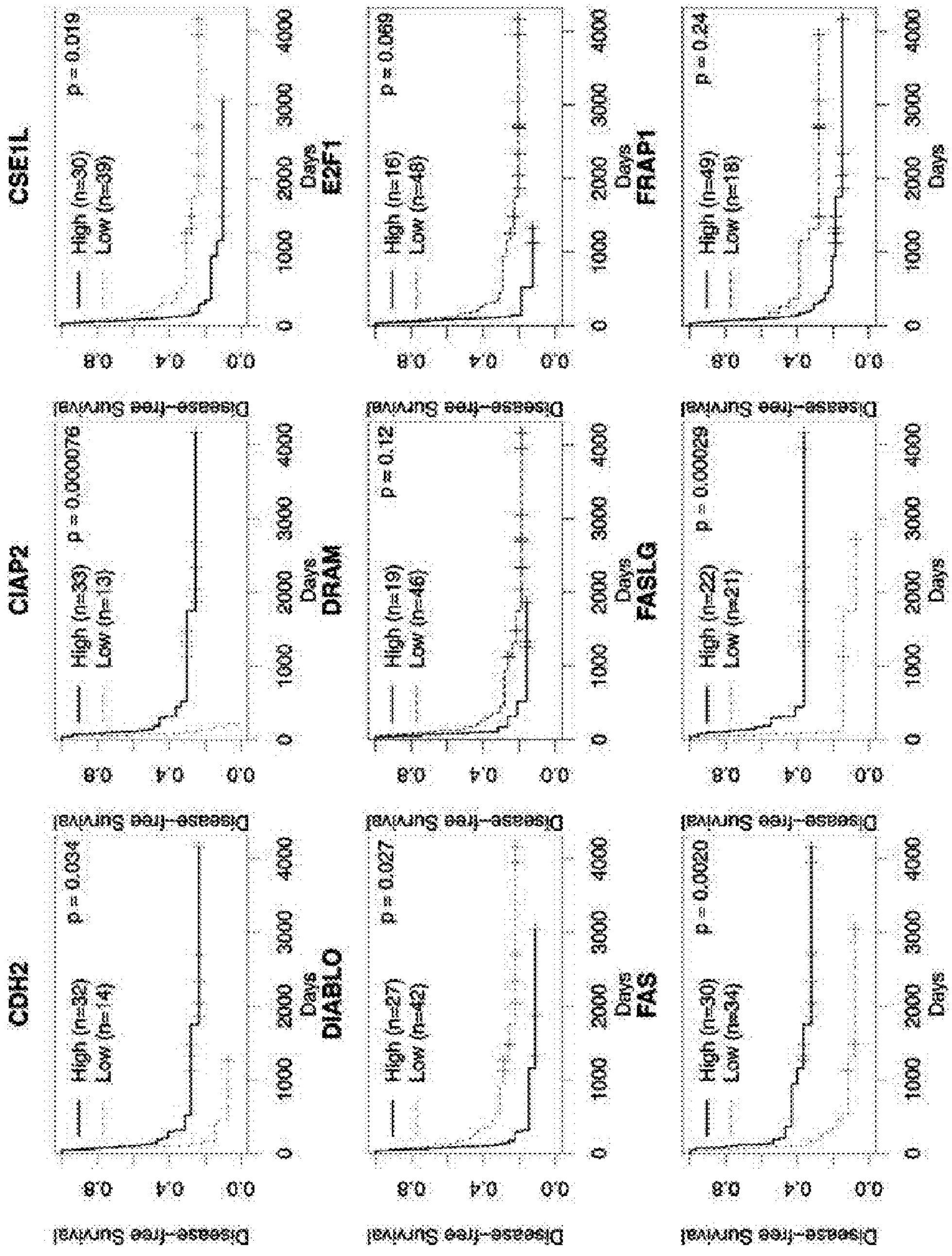
Figure 103:
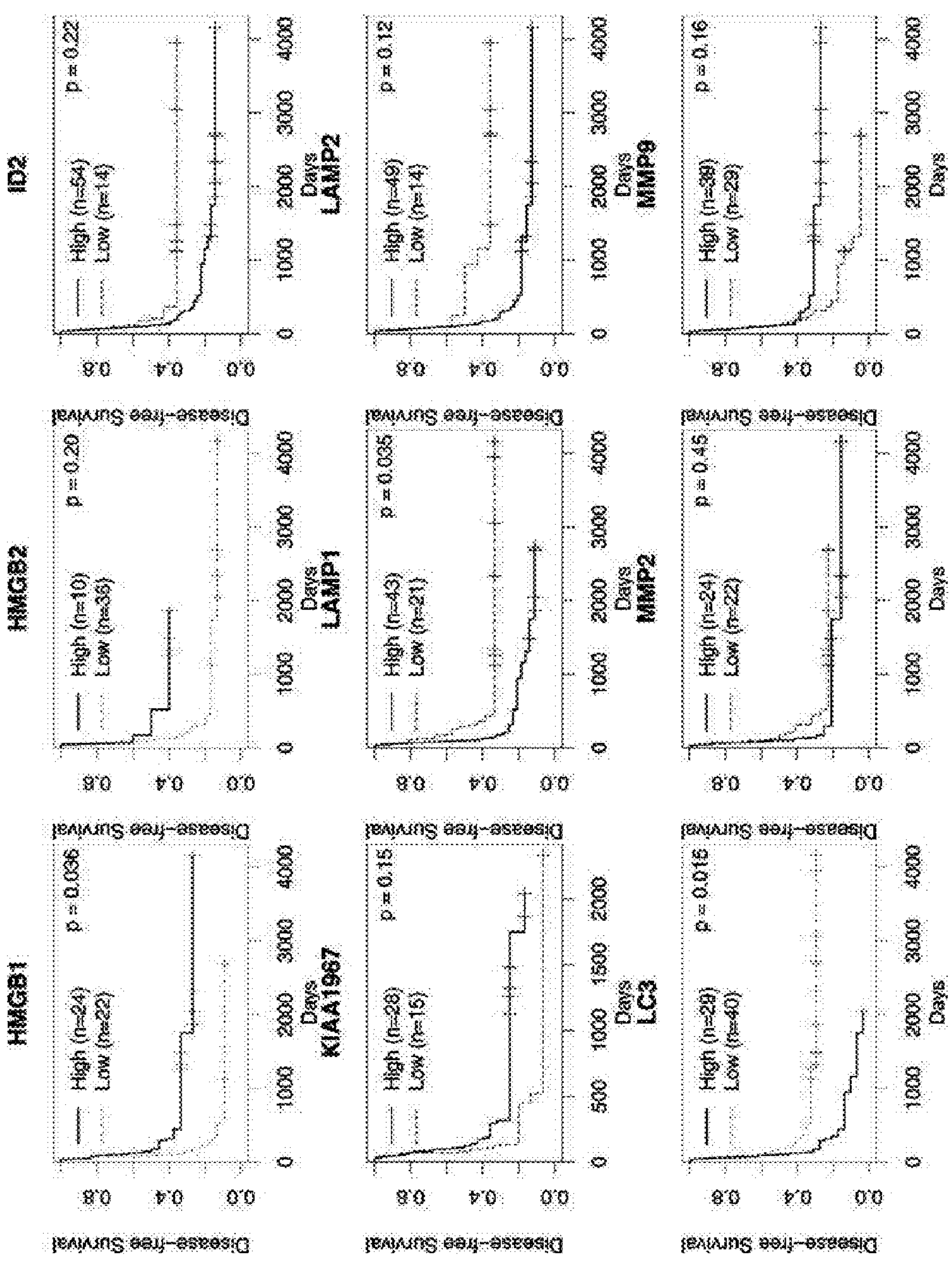
Figure 104:
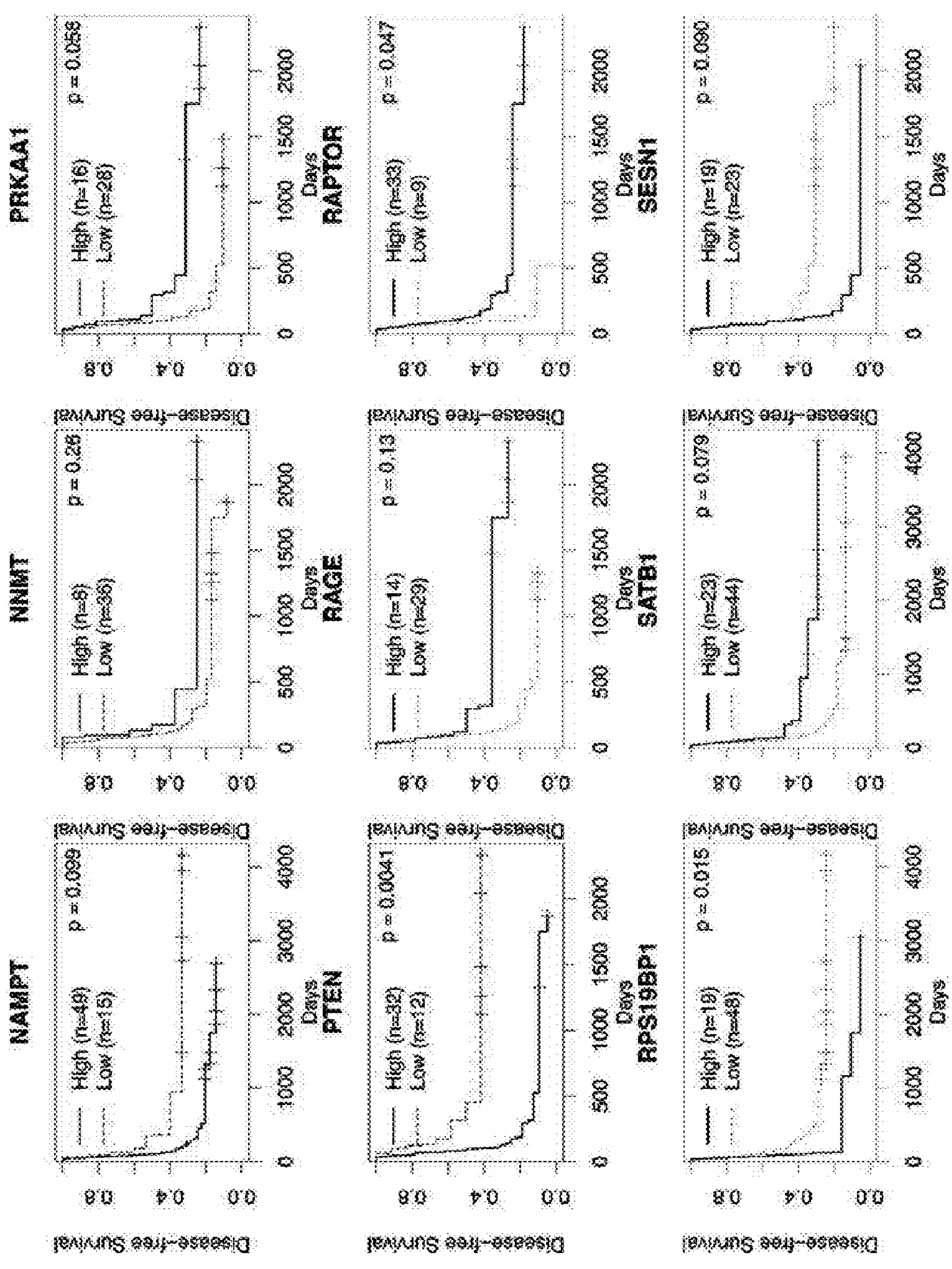
Figure 105:
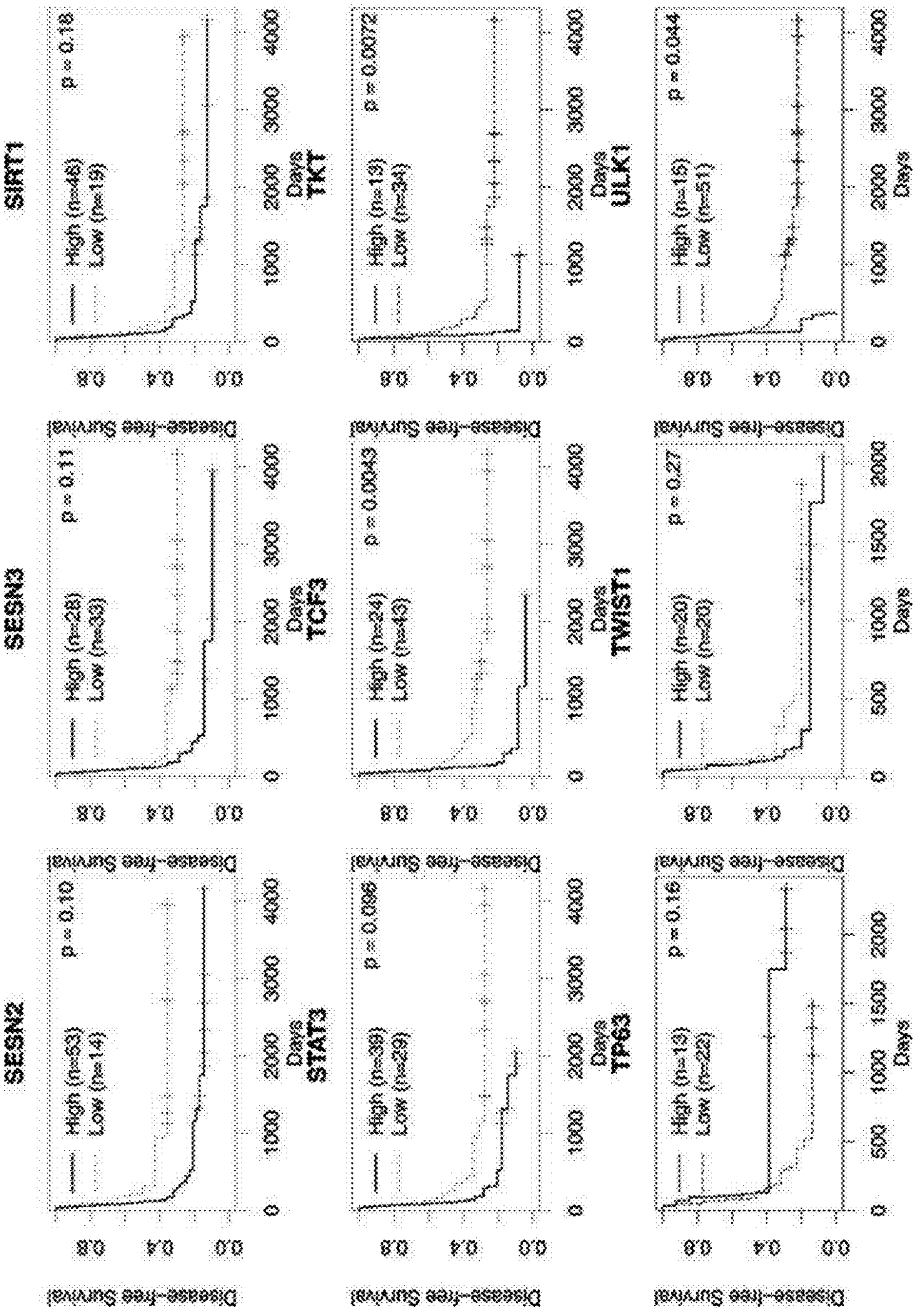
Figure 106:
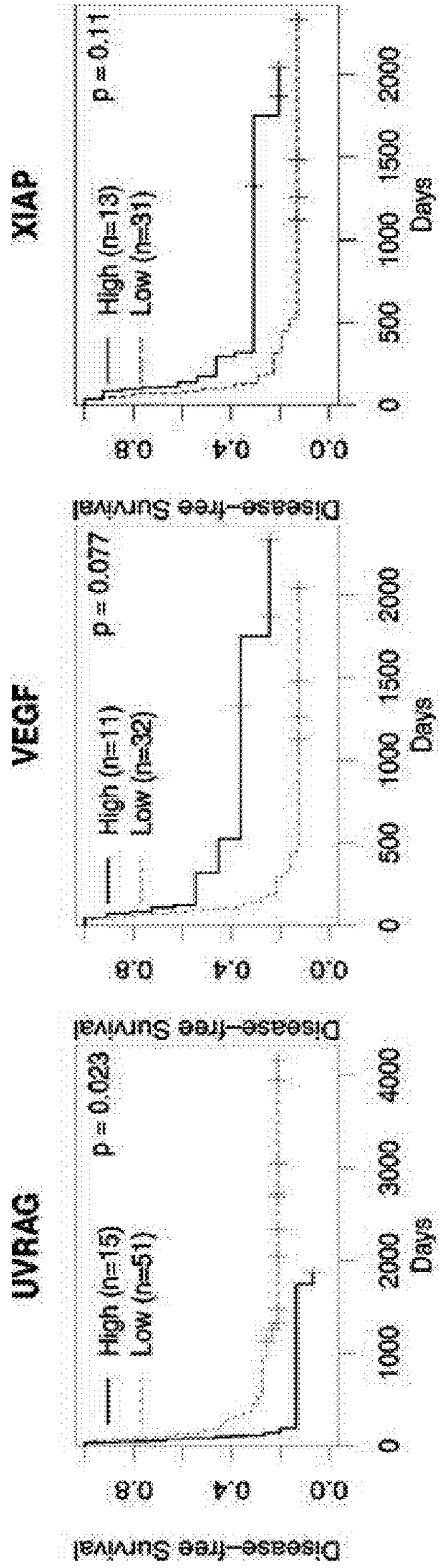

An experiment was performed in the same manner as in Example 1, except for experimenting on a patient group determined as the A2 group {a group of portal vein invasion-negative patients, having a tumor which is more than 5 cm in size} (123 patients), an experiment was performed in the same manner as in Example 1. Kaplan-Meier curves were prepared with respect to the prediction of recurrence, survival, and disease-free survival and the results are shown in FIGS. 44~46. Kaplan-Meier curves for recurrence are shown in FIGS. 44~50, Kaplan-Meier curves for survival are shown in FIGS. 51~57, and Kaplan-Meier curves for disease-free survival are shown in FIGS. 58~64.

As can be seen from the drawings, in Kaplan-Meier curves completed with respect to recurrence, survival, and disease-free survival, the above markers form curves where cases of high expression and low expression are distinctively distinguished from each other. This means that there are remarkable differences in interval recurrence rate or interval survival rate and cumulative recurrence rate or cumulative survival rate based thereon between the cases where the marker is in high expression and low expression, and that consequently, the expression pattern of the marker can be an index showing recurrence possibility or survival possibility of patients.

Also, significance tests were performed by log-rank test with respect to each of the markers and their combination by calculating observation values and expected values at every point of recurrence or death to obtain p-values. The results are shown in the following Tables 30~37. The results of using a marker alone are shown in Table 30, the results of a combination of two markers are shown in Table 31, the results of a combination of three markers are shown in Table 32, the results of a combination of four markers are shown in Table 33, the results of a combination of five markers are shown in Table 34, the results of a combination of six markers are shown in Table 35, the results of a combination of seven markers are shown in Table 36, and the results of a combination of eight markers are shown in Table 37.

TABLE 30

| Marker | p-value |
|---|---|
| Recurrence | |
| TKT | 2.09E−02 |
| SESN | 2.63E−02 |
| LAMP2 | 3.49E−02 |
| BHLHE41 | 5.45E−02 |
| CSE1L | 8.20E−02 |
| LC3 | 1.14E−01 |
| VEGF | 1.68E−01 |
| PRKAA1 | 1.70E−01 |
| BECN1 | 1.86E−01 |
| LAMP1 | 2.14E−01 |
| FAS | 2.80E−01 |
| ATG5 | 3.07E−01 |
| ATG3 | 3.66E−01 |
| ULK1 | 3.48E−01 |
| FASLG | 3.88E−01 |
| RAGE | 4.04E−01 |
| NAMPT | 4.46E−01 |
| SESN3 | 4.48E−01 |
| ATG7 | 4.57E−01 |
| CBS | 4.80E−01 |
| AKT1 | 4.81E−01 |
| BCL2L1 | 4.82E−01 |
| BCL2 | 4.84E−01 |
| CIAP2 | 4.85E−01 |
| TP63 | 4.93E−01 |
| TCF3 | 5.09E−01 |
| CASP8 | 5.36E−01 |
| HMGB2 | 5.51E−01 |
| SIRT1 | 5.52E−01 |
| AIFM1 | 5.72E−01 |
| PTEN | 5.78E−01 |
| DRAM | 6.00E−01 |
| DIABLO | 6.33E−01 |
| BNIP3 | 6.43E−01 |
| CDH1 | 6.55E−01 |
| FRAP1 | 6.84E−01 |
| HMGB1 | 6.85E−01 |
| CDH2 | 6.89E−01 |
| CASP3 | 6.94E−01 |
| SATB1 | 7.11E−01 |
| MMP9 | 7.13E−01 |
| RPS19BP1 | 7.16E−01 |
| KIAA1967 | 7.34E−01 |
| TWIST1 | 7.38E−01 |
| ID2 | 7.63E−01 |
| STAT3 | 7.79E−01 |
| AGER | 7.84E−01 |
| UVRAG | 7.97E−01 |
| CCNG2 | 8.32E−01 |
| MMP2 | 8.38E−01 |
| BAX | 8.66E−01 |
| XIAP | 8.89E−01 |
| RAPTOR | 9.12E−01 |
| ATG12 | 9.21E−01 |
| E2F1 | 9.39E−01 |
| NNMT | 9.67E−01 |
| SESN1 | 9.98E−01 |
| Survival | |
| BCL2L1 | 1.18E−03 |
| FAS | 3.84E−03 |
| LAMP1 | 9.31E−03 |
| BHLHE41 | 1.08E−02 |
| TKT | 1.62E−02 |
| LC3 | 2.80E−02 |
| SESN2 | 4.22E−02 |
| NAMPT | 5.17E−02 |
| BNIP3 | 6.09E−02 |
| CSE1L | 6.82E−02 |
| TCF3 | 7.17E−02 |
| STS3 | 9.89E−02 |
| NNMT | 1.03E−01 |
| TP63 | 1.12E−01 |
| RAGE | 1.21E−01 |
| XIAP | 1.38E−01 |
| BCL2 | 1.38E−01 |

TABLE 30-continued

| Marker | p-value |
|---|---|
| RAPTOR | 1.65E−01 |
| LAMP2 | 2.06E−01 |
| E2F1 | 2.16E−01 |
| FRAP1 | 2.30E−01 |
| CDH1 | 2.34E−01 |
| CASP3 | 2.54E−01 |
| STAB1 | 2.66E−01 |
| BECN1 | 3.08E−01 |
| PTEN | 3.47E−01 |
| PRKAA1 | 3.70E−01 |
| KIAA1967 | 4.07E−01 |
| HMGB1 | 4.07E−01 |
| ATG5 | 4.12E−01 |
| HMGB2 | 4.15E−01 |
| ULK1 | 4.50E−01 |
| AKT1 | 4.50E−01 |
| CIAP2 | 4.66E−01 |
| BAX | 4.83E−01 |
| SESN1 | 5.32E−01 |
| VEGF | 5.48E−01 |
| FASLG | 5.79E−01 |
| RPS19BP1 | 5.81E−01 |
| MMP9 | 5.92E−01 |
| CASP8 | 5.97E−01 |
| MMP2 | 6.02E−01 |
| TWIST1 | 6.04E−01 |
| CDH2 | 6.51E−01 |
| ATG12 | 6.91E−01 |
| CCNG2 | 7.26E−01 |
| CBS | 7.53E−01 |
| ATG3 | 7.61E−01 |
| ATG7 | 7.63E−01 |
| UVRAG | 8.15E−01 |
| SIRT1 | 8.23E−01 |
| SESN3 | 8.58E−01 |
| DRAM | 8.68E−01 |
| DIABLO | 8.80E−01 |
| AIFM1 | 9.34E−01 |
| AGER | 9.81E−01 |
| ID2 | 9.97E−01 |
| Disease-free survival | |
| SESN2 | 1.18E−02 |
| TKT | 1.51E−02 |
| LAMP2 | 3.89E−02 |
| BHLHE41 | 4.38E−02 |
| CSE21L | 4.51E−02 |
| FAS | 6.76E−02 |
| BECN1 | 6.85E−02 |
| TCF3 | 1.13E−01 |
| PRKAA1 | 1.28E−01 |
| VEGF | 1.37E−01 |
| ULK1 | 1.42E−01 |
| LAMP1 | 1.44E−01 |
| FASLG | 2.09E−01 |
| ATG5 | 2.30E−01 |
| NAMPT | 2.58E−01 |
| BCL2L1 | 2.84E−01 |
| LC3 | 3.08E−01 |
| BCL2 | 3.81E−01 |
| STAB1 | 4.47E−01 |
| STAT3 | 4.59E−01 |
| FRAP1 | 4.70E−01 |
| ATG12 | 4.72E−01 |
| HMGB2 | 4.95E−01 |
| ATG3 | 5.13E−01 |
| MMP9 | 5.25E−01 |
| MMP2 | 5.28E−01 |
| SESN1 | 5.39E−01 |
| AKT1 | 5.55E−01 |
| RPS19BP1 | 5.65E−01 |
| TP63 | 5.72E−01 |
| CBS | 5.76E−01 |
| NNMT | 5.82E−01 |
| UVRAG | 5.84E−01 |
| CDH1 | 5.89E−01 |
| ATG7 | 5.98E−01 |
| TWIST1 | 6.16E−01 |

TABLE 30-continued

| Marker | p-value |
|---|---|
| SIRT1 | 6.25E−01 |
| CASP8 | 6.42E−01 |
| SESN3 | 6.72E−01 |
| BAX | 6.80E−01 |
| AIFM1 | 7.29E−01 |
| HMGB1 | 7.40E−01 |
| DIABLO | 7.57E−01 |
| KIAA1967 | 7.85E−01 |
| CASP3 | 8.03E−01 |
| CDH2 | 8.09E−01 |
| BNIP3 | 8.46E−01 |
| RAGE | 8.63E−01 |
| AGER | 8.67E−01 |
| PTEN | 8.79E−01 |
| RAPTOR | 9.04E−01 |
| CCNG2 | 9.23E−01 |
| E2F1 | 9.23E−01 |
| XIAP | 9.27E−01 |
| DRAM | 9.27E−01 |
| CIAP2 | 9.35E−01 |
| ID2 | 9.90E−01 |

TABLE 31

| Marker | p-value |
|---|---|
| Recurrence | |
| PRKAA1_LAMP2 | 5.60E−04 |
| TKT_SESN2 | 1.30E−03 |
| ATG7_LAMP2 | 2.10E−03 |
| LAMP2_SESN2 | 2.30E−03 |
| AKT1_PRKAA1 | 2.90E−03 |
| SESN2_SIRT1 | 3.40E−03 |
| TKT_VEGF | 3.80E−03 |
| ATG7_TKT | 4.10E−03 |
| TKT_LAMP2 | 4.20E−03 |
| BHLHE41_SESN2 | 4.30E−03 |
| TKT_BHLHE41 | 4.30E−03 |
| ATG5_SESN2 | 4.50E−03 |
| LAMP1_SESN2 | 5.00E−03 |
| CSE1L_LAMP2 | 5.30E−03 |
| ATG12_SESN2 | 5.50E−03 |
| AKT1_TKT | 5.60E−03 |
| E2F1_SESN2 | 5.60E−03 |
| ATG3_LAMP2 | 6.30E−03 |
| BNIP3_SESN2 | 6.30E−03 |
| LC3_SESN2 | 6.70E−03 |
| TWIST1_VEGF | 6.80E−03 |
| ATG7_LC3 | 7.10E−03 |
| CSE1L_SESN2 | 7.40E−03 |
| ATG5_LC3 | 7.60E−03 |
| ATG7_SESN2 | 7.70E−03 |
| LC3_ULK1 | 8.00E−03 |
| ATG3_TKT | 8.10E−03 |
| DRAM_SESN2 | 8.10E−03 |
| PRKAA1_TKT | 8.30E−03 |
| BHLHE41_LAMP2 | 8.60E−03 |
| LAMP2_VEGF | 9.10E−03 |
| AKT1_VEGF | 9.20E−03 |
| TKT_CIAP2 | 9.20E−03 |
| CSE1L_NHLHE41 | 9.30E−03 |
| LC3_BHLHE41 | 9.30E−03 |
| LC3_SIRT1 | 9.30E−03 |
| CSE1L_LAMP1 | 1.00E−02 |
| TKT_RPS19BP1 | 1.00E−02 |
| CBS_TKT | 1.10E−02 |
| CSE1L_BECN1 | 1.10E−02 |
| TKT_CDH1 | 1.10E−02 |
| TKT_HMGB1 | 1.10E−02 |
| TKT_RAGE | 1.10E−02 |
| AIFM1_SESN2 | 1.20E−02 |
| ATG7_TWIST1 | 1.20E−02 |
| BHLHE41_NAMPT | 1.20E−02 |
| BNIP3_LC3 | 1.20E−02 |

TABLE 31-continued

| Marker | p-value |
| --- | --- |
| PRKAA1_SESN2 | 1.20E−02 |
| ATG7_NAMPT | 1.30E−02 |
| BECN1_SESN2 | 1.30E−02 |
| TKT_HMGB2 | 1.30E−02 |
| TKT_SIRT1 | 1.30E−02 |
| ATG5_CSE1L | 1.40E−02 |
| SESN2_UVRAG | 1.40E−02 |
| TKT_CASP3 | 1.40E−02 |
| TKT_CDH2 | 1.40E−02 |
| TKT_MMP2 | 1.40E−02 |
| Survival | |
| BCL2L1_NNMT | 5.30E−05 |
| BCL2L1_E2F1 | 7.40E−05 |
| BCL2L1_TKT | 8.10E−05 |
| FAS_LAMP1 | 9.10E−05 |
| BCL2L1_PRKAA1 | 9.50E−05 |
| FAS_BHLHE41 | 1.10E−04 |
| FAS_TKT | 1.30E−04 |
| BCL2L1_CASP3 | 1.60E−04 |
| ATG3_BCL2L1 | 1.70E−04 |
| ATG7_BCL2L1 | 2.30E−04 |
| FAS_CASP3 | 2.50E−04 |
| TKT_BHLHE41 | 3.70E−04 |
| BCL2L1_KIAA1967 | 3.90E−04 |
| FAS_PRKIAA1 | 4.40E−04 |
| FAS_KIAA1967 | 5.00E−04 |
| FAS_SESN2 | 5.50E−04 |
| BCL2L1_HMGB2 | 6.30E−04 |
| BCL2L1_VEGF | 6.40E−04 |
| BNIP3_FAS | 6.70E−04 |
| FAS_TWIST1 | 6.70E−04 |
| BNIP3_TKT | 7.30E−04 |
| BCL2L1_CSE1L | 7.50E−04 |
| TKT_SESN2 | 7.90E−04 |
| BCL2L1_FRAP1 | 8.00E−04 |
| LAMP1_SESN2 | 8.10E−04 |
| LC3_BHLHE41 | 9.40E−04 |
| BCL2L1_BNIP3 | 9.70E−04 |
| BCL2L1_LC3 | 1.00E−03 |
| ATG5_BCL2L1 | 1.10E−03 |
| BCL2L1_CBS | 1.10E−03 |
| CSE1L_LAMP1 | 1.10E−03 |
| E2F1_FAS | 1.10E−03 |
| AIFM1_BCL2L1 | 1.20E−03 |
| BHLHE41_SESN2 | 1.20E−03 |
| BASP8_FAS | 1.30E−03 |
| FAS_NAMPT | 1.30E−03 |
| FAS_TP63 | 1.30E−03 |
| LAMP1_BHLHE41 | 1.30E−03 |
| ATG12_FAS | 1.40E−03 |
| BCL2L1_MMP2 | 1.40E−03 |
| BHLHE41_CASP3 | 1.40E−03 |
| FAS_HMGB1 | 1.40E−03 |
| FAS_VEGF | 1.40E−03 |
| LAMP1_TCF3 | 1.40E−03 |
| BCL2L1_ULK1 | 1.50E−03 |
| FAS_LC3 | 1.50E−03 |
| NNMT_BHLHE41 | 1.50E−03 |
| BCL2L1_FAS | 1.60E−03 |
| TKT_TP63 | 1.60E−03 |
| AKT1_BCL2L1 | 1.70E−03 |
| ATG12_BCL2L1 | 1.70E−03 |
| FAS_HMGB2 | 1.70E−03 |
| BCL2L1_ID2 | 1.80E−03 |
| BCL2L1_RPS19BP1 | 1.80E−03 |
| TKT_SATB1 | 1.80E−03 |
| FAS_XIAP | 1.90E−03 |
| BCL2_NCL2L1 | 2.00E−03 |
| Disease-free survival | |
| TKT_SESN2 | 1.60E−04 |
| BHLHE41_SESN2 | 8.00E−04 |
| LAMP2_SESN2 | 8.80E−04 |
| ATG5_SESN2 | 9.50E−04 |
| LAMP1_SESN2 | 1.30E−03 |
| SESN2_SIRT1 | 1.30E−03 |
| E2F1_SESN2 | 1.70E−03 |

TABLE 31-continued

| Marker | p-value |
| --- | --- |
| ATG12_SESN2 | 1.80E−03 |
| TKT_VEGF | 2.10E−03 |
| CSE1L_BECN1 | 2.20E−03 |
| CSE1L_SESN2 | 2.20E−03 |
| ATG7_TKT | 2.40E−03 |
| FASLG_SESN2 | 2.40E−03 |
| PRKAA1_LAMP2 | 2.50E−03 |
| PRKAA1_SESN2 | 2.50E−03 |
| TKT_BHLHE41 | 2.50E−03 |
| CSE1L_BHLHE41 | 2.90E−03 |
| ATG7_SESN2 | 3.00E−03 |
| CSE1L_LAMP2 | 3.00E−03 |
| FAS_SESN2 | 3.10E−03 |
| HMGB2_SESN2 | 3.10E−03 |
| CSE1L_LAMP1 | 3.40E−03 |
| BECN1_SESN2 | 3.50E−03 |
| NNMT_SESN2 | 3.50E−03 |
| AIFM1_SESN2 | 3.70E−03 |
| BAX_SESN2 | 3.70E−03 |
| DRAM_SESN2 | 3.90E−03 |
| CSE1L_ULK1 | 4.00E−03 |
| KIAA1967_SESN2 | 4.00E−03 |
| SESN2_VEGF | 4.00E−03 |
| BNIP3_SESN2 | 4.10E−03 |
| SESN2_UVRAG | 4.30E−03 |
| TWIST1_VEGF | 4.40E−03 |
| PRKAA1_FASLG | 4.50E−03 |
| TKT_RPS19BP1 | 4.80E−03 |
| PRKAA1_TKT | 4.90E−03 |
| ATG7_LAMP2 | 5.10E−03 |
| AGER_SESN2 | 5.20E−03 |
| CDH2_SESN2 | 5.30E−03 |
| AKT1_PRKAA1 | 5.40E−03 |
| ULK1_SESN2 | 5.40E−03 |
| MMP2_SESN2 | 5.80E−03 |
| ATG5_CSE1L | 6.20E−03 |
| HMGB1_SESN2 | 6.20E−03 |
| AKT1_TKT | 6.30E−03 |
| CBS_SESN2 | 6.30E−03 |
| FRAP1_SESN2 | 6.30E−03 |
| CIAP2_SESN2 | 6.40E−03 |
| BCL2_SESN2 | 6.50E−03 |
| CCNG2_SESN2 | 6.50E−03 |
| BCL2L1_SESN2 | 6.60E−03 |
| CSE1L_UVRAG | 6.60E−03 |
| RAPTOR_SESN2 | 6.60E−03 |
| XIAP_SESN2 | 6.70E−03 |
| CASP3_SESN2 | 6.80E−03 |
| CASP8_SESN2 | 6.80E−03 |
| LC3_SESN2 | 6.80E−03 |

TABLE 32

| Marker | p-value |
| --- | --- |
| Recurrence | |
| LC3_SESN2_SIRT1 | 3.80E−05 |
| BNIP3_PRKAA1_LAMP2 | 6.30E−05 |
| ATG5_LC3_SESN2 | 6.60E−05 |
| BNIP3_LC3_SESN2 | 9.40E−05 |
| ATG7_LC3_SESN2 | 1.00E−04 |
| AKT1_PRKAA1_LAMP2 | 1.70E−04 |
| ATG7_TKT_SESN2 | 1.80E−04 |
| DRAM_LC3_SESN2 | 1.90E−04 |
| PRKAA1_AGER_LAMP2 | 1.90E−04 |
| PRKAA1_TKT_LAMP2 | 1.90E−04 |
| ATG7_TKT_LAMP2 | 2.00E−04 |
| TKT_LAMP2_SESN2 | 2.80E−04 |
| TKT_LAMP2_VEGF | 3.00E−04 |
| ATG12_LC3_SESN2 | 3.10E−04 |
| ATG7_LAMP2_SESN2 | 3.20E−04 |

TABLE 32-continued

| Marker | p-value |
| --- | --- |
| TKT_SESN2_SIRT1 | 3.20E−04 |
| E2F1_LC3_SESN2 | 3.30E−04 |
| LC3_SESN2_UVRAG | 3.30E−04 |
| PRKAA1_CCNG2_LAMP2 | 3.30E−04 |
| AKT1_ATG7_TKT | 3.40E−04 |
| ATG5_PRKAA1_LAMP2 | 3.70E−04 |
| ATG3_LAMP2_SESN2 | 3.80E−04 |
| BNIP3_TKT_SESN2 | 3.80E−04 |
| LAMP2_SESN2_SIRT1 | 3.80E−04 |
| ATG7_PRKAA1_LAMP2 | 3.90E−04 |
| LAMP1_LC3_SESN2 | 3.90E−04 |
| ATG12_PRKAA1_LAMP2 | 4.00E−04 |
| CASP8_PRKAA1_LAMP2 | 4.00E−04 |
| AIFM1_TKT_SESN2 | 4.10E−04 |
| FRAP1_SESN2_SIRT1 | 4.10E−04 |
| PRKAA1_HMGB1_LAMP2 | 4.30E−04 |
| LC3_BHLHE41_SESN2 | 4.50E−04 |
| ATG12_TKT_SESN2 | 4.70E−04 |
| CSE1L_LAMP2_SESN2 | 4.80E−04 |
| PRKAA1_CASP3_LAMP2 | 4.90E−04 |
| PRKAA1_LAMP2_RAGE | 4.90E−04 |
| PRKAA1_LAMP2_SESN2 | 4.90E−04 |
| TKT_CIAP2_SESN2 | 4.90E−04 |
| BCL2L1_PRKAA1_LAMP2 | 5.00E−04 |
| DIABLO_PRKAA1_LAMP2 | 5.00E−04 |
| PRKAA1_CDH1_LAMP2 | 5.00E−04 |
| CBS_PRKAA1_LAMP2 | 5.10E−04 |
| CSE1L_SESN2_SIRT1 | 5.10E−04 |
| ATG3_PRKAA1_LAMP2 | 5.20E−04 |
| PRKAA1_FASLG_LAMP2 | 5.20E−04 |
| PRKAA1_ID2_LAMP2 | 5.20E−04 |
| PRKAA1_LAMP2_SATB1 | 5.40E−04 |
| PRKAA1_LAMP2_SESN1 | 5.40E−04 |
| AKT1_ATG7_PTEN | 5.70E−04 |
| ATG7_TKT_BHLHE41 | 5.70E−04 |
| PRKAA1_LAMP2_MMP2 | 5.70E−04 |
| CSE1L_LAMP1_SESN2 | 5.80E−04 |
| PRKAA1_LAMP2_SESN3 | 5.90E−04 |
| ATG3_TKT_SESN2 | 6.00E−04 |
| ATG5_CSE1L_SESN2 | 6.00E−04 |
| ATG5_CSE1L_LC3 | 6.10E−04 |
| FRAP1_PRKAA1_LAMP2 | 6.10E−04 |
| Survival | |
| BCL2L1_NNMT_PRKAA1 | 1.30E−06 |
| BCL2L1_E2F1_PRKAA1 | 7.50E−06 |
| ATG3_BCL2L1_PRKAA1 | 8.10E−06 |
| ATG3_BCL2L1_NNMT | 8.70E−06 |
| ATG3_BCL2L1_E2F1 | 9.40E−06 |
| FAS_BHLHE41_SESN2 | 1.20E−05 |
| BCL2L1_PRKAA1_HMGB2 | 1.30E−05 |
| BCL2L1_CASP3_SESN2 | 1.40E−05 |
| BCL2L1_PRKAA1_TKT | 1.40E−05 |
| FAS_CASP3_SESN2 | 1.40E−05 |
| BCL2L1_TKT_CASP3 | 1.60E−05 |
| FAS_TKT_CASP3 | 1.60E−05 |
| BCL2L1_E2F1_TKT | 1.80E−05 |
| BCL21_NNMT_TKT | 1.80E−05 |
| FAS_TKT_BHLHE41 | 1.80E−05 |
| FAS_TKT_SESN2 | 1.80E−05 |
| FAS_LAMP1_BHLHE41 | 1.90E−05 |
| FAS_LAMP1_SESN2 | 2.00E−05 |
| ATG3_BCL2L1_TKT | 2.20E−05 |
| ATG7_BCL2L1_PRKAA1 | 2.20E−05 |
| DIABLO_FAS_BHLHE41 | 2.20E−05 |
| TKT_SESN2_TP63 | 2.20E−05 |
| FAS_PRKAA1_TKT | 2.30E−05 |
| ATG7_BCL21_NNMT | 2.40E−05 |
| BCL2L1_BNIP3_TKT | 2.70E−05 |
| BNIP3_FAS_TKT | 2.80E−05 |
| BCL2L1_NNMT_CASP3 | 2.90E−05 |
| TKT_BHLHE41_CASP3 | 3.00E−05 |
| ATG3_BCL2L1_CASP3 | 3.30E−05 |
| BCL2L1_PRKAA1_CASP3 | 3.30E−05 |
| BCL2L1_PRKAA1_MMP2 | 3.30E−05 |
| FAS_BHLHE41_CASP3 | 3.30E−05 |
| FAS_TKT_KIAA1967 | 3.30E−05 |
| FAS_TKT_TWIST1 | 3.40E−05 |

TABLE 32-continued

| Marker | p-value |
| --- | --- |
| BCL2L1_E2F1_NNMT | 3.60E−05 |
| BCL2L1_FRAP1_NNMT | 3.60E−05 |
| BCL2L1_TKT_BHLHE41 | 3.60E−05 |
| BCL2L1_TKT_SESN2 | 3.60E−05 |
| FAS_KIAA1967_SESN2 | 3.60E−05 |
| DIABLO_FAS_LAMP1 | 3.80E−05 |
| ATG3_BCL2L1_KIAA1967 | 3.90E−05 |
| ATG7_BCL2L1_E2F1 | 3.90E−05 |
| FAS_BHLHE41_SATB1 | 3.90E−05 |
| ATG3_ATG7_BCL2L1 | 4.00E−05 |
| ATG7_BCL2L1_TKT | 4.00E−05 |
| BCL2L1_BNIP3_NNMT | 4.10E−05 |
| BCL2L1_PRKAA1_VEGF | 4.10E−05 |
| BCL2L1_BHLHE41_CASP3 | 4.30E−05 |
| FAS_SESN2_TP63 | 4.30E−05 |
| TKT_BHLHE41_TP63 | 4.50E−05 |
| AIFM1_BCL2L1_NNMT | 4.70E−05 |
| BCL2L1_CSE1L_NNMT | 4.90E−05 |
| BCL2L1_E2F1_FRAP1 | 5.00E−05 |
| BNIP3_FAS_CASP3 | 5.00E−05 |
| FAS_TKT_SATB1 | 5.00E−05 |
| BCL2L1_CSE1L_PRKAA1 | 5.10E−05 |
| BCL2L1_NNMT_VEGF | 5.10E−05 |
| Disease-free survival | |
| ATG7_TKT_SESN2 | 1.90E−05 |
| FRAP1_SESN2_SIRT1 | 4.60E−05 |
| ATG5_LC3_SESN2 | 5.60E−05 |
| ATG5_FRAP1_SESN2 | 5.80E−05 |
| TKT_LAMP2_SESN2 | 7.20E−05 |
| AIFM1_TKT_SESN2 | 7.40E−05 |
| ATG5_CSE1L_SESN2 | 7.90E−05 |
| LC3_SESN2_SIRT1 | 8.00E−05 |
| ATG12_TKT_SESN2 | 8.20E−05 |
| CSE1L_LAMP1_SESN2 | 8.20E−05 |
| TKT_HNGB2_SESN2 | 8.40E−05 |
| ATG5_TKT_SESN2 | 8.90E−05 |
| TKT_CDH1_SESN2 | 9.10E−05 |
| TKT_SESN2_SESN3 | 9.20E−05 |
| TKT_SESN2_VEGF | 9.40E−05 |
| CSE1L_NHLHE41_SESN2 | 9.50E−05 |
| PRKAA1_TKT_SESN2 | 9.60E−05 |
| ATG3_TKT_SESN2 | 9.90E−05 |
| TKT_RPS19BP1_SESN2 | 9.90E−05 |
| CBS_TKT_SESN2 | 1.00E−04 |
| CSE1L_LAMP2_SESN2 | 1.00E−04 |
| TKT_SESN2_SIRT1 | 1.00E−04 |
| AKT1_TKT_SESN2 | 1.10E−04 |
| CSE1L_SESN2_SIRT1 | 1.10E−04 |
| TKT_CDH2_SESN2 | 1.10E−04 |
| BNIP3_TKT_SESN2 | 1.20E−04 |
| NNMT_TKT_SESN2 | 1.20E−04 |
| TKT_AGER_SESN2 | 1.20E−04 |
| TKT_BHLHE41_SESN2 | 1.20E−04 |
| TKT_HMGB1_SESN2 | 1.20E−04 |
| TKT_MMP2_SESN2 | 1.20E−04 |
| E2F1_TKT_SESN2 | 1.30E−04 |
| NAMPT_SESN2_SIRT1 | 1.30E−04 |
| TKT_KIAA1967_SESN2 | 1.30E−04 |
| DRAM_TKT_SESN2 | 1.40E−04 |
| TKT_CIAP2_SESN2 | 1.40E−04 |
| TKT_MMP9_SESN2 | 1.40E−04 |
| ATG5_NAMPT_SESN2 | 1.50E−04 |
| ATG7_FRAP1_SESN2 | 1.50E−04 |
| CSE1L_E2F1_SESN2 | 1.50E−04 |
| LAMP1_TKT_SESN2 | 1.50E−04 |
| LC3_TKT_SESN2 | 1.50E−04 |
| TKT_CASP3_SESN2 | 1.50E−04 |
| TKT_CCNG2_SESN2 | 1.50E−04 |
| TKT_IS2_SESN2 | 1.50E−04 |
| TKT_RAPTOR_SESN2 | 1.50E−04 |
| TKT_XIAP_SESN2 | 1.50E−04 |
| BAX_TKT_SESN2 | 1.60E−04 |
| BCL2_TKT_SESN2 | 1.60E−04 |
| ATG12_CSE1L_SESN2 | 1.70E−04 |
| BCL2L1_TKT_SESN2 | 1.70E−04 |
| CASP8_TKT_SESN2 | 1.70E−04 |
| DIABLO_TKT_SESN2 | 1.70E−04 |

TABLE 32-continued

| Marker | p-value |
|---|---|
| FAS_BHLHE41_SESN2 | 1.70E−04 |
| FRAP1_TKT_SESN2 | 1.70E−04 |
| PTEN_TKT_SESN2 | 1.70E−04 |
| TKT_RAGE_SESN2 | 1.70E−04 |

TABLE 33

| Marker | p-value |
|---|---|
| Recurrence | |
| ATG5_LC3_SESN2_SIRT1 | 6.90E−06 |
| ATG3_LC3_SESN2_SIRT1 | 7.60E−06 |
| CSE1L_LC3_SESN2_SIRT1 | 8.80E−06 |
| ATG5_CSE1L_LC3_SESN2 | 1.30E−05 |
| BNIP3_LC3_SESN2_SIRT1 | 1.30E−05 |
| FRAP1_LC3_SESN2_SIRT1 | 1.30E−05 |
| AKT1_ATG3_PRKAA1_LAMP2 | 1.40E−05 |
| ATG3_ATG5_LC3_SESN2 | 1.50E−05 |
| ATG7_LC3_SESN2_SIRT1 | 1.50E−05 |
| BNIP3_CSE1L_LC3_SESN2 | 1.50E−05 |
| TKT_LAMP2_SESN2_SIRT1 | 1.50E−05 |
| CIAP2_LAMP2_SESN2_SIRT1 | 1.80E−05 |
| ATG12_TKT_LAMP2_SESN2 | 1.90E−05 |
| ATG7_TKT_LAMP2_SESN2 | 1.90E−05 |
| AKT1_ATG7_PRKAA1_LAMP2 | 2.00E−05 |
| ATG5_BNIP3_LC3_SESN2 | 2.00E−05 |
| ATG3_BNIP3_LC3_SESN2 | 2.30E−05 |
| AKT1_PRKAA1_LAMP2_UVRAG | 2.50E−05 |
| DRAM_LC3_SESN2_SIRT1 | 2.60E−05 |
| ATG7_CSE1L_LC3_SESN2 | 2.70E−05 |
| ATG7_FRAP1_LC3_SESN2 | 2.70E−05 |
| BNIP3_PRKAA1_LAMP2_SESN2 | 2.70E−05 |
| ATG5_ATG7_LC3_SESN2 | 3.10E−05 |
| PRKAA1_TKT_LAMP2_SESN2 | 3.20E−05 |
| ATG3_ATG7_LC3_SESN2 | 3.30E−05 |
| BNIP3_PRKAA1_AGER_LAMP2 | 3.40E−05 |
| E2F1_LC3_SESN2_SIRT1 | 3.40E−05 |
| LC3_ID2_SESN2_SIRT1 | 3.50E−05 |
| LC3_NAMPT_SESN2_SIRT1 | 3.50E−05 |
| ATG5_FRAP1_LC3_SESN2 | 3.60E−05 |
| ATG7_BNIP3_LC3_SESN2 | 3.60E−05 |
| LC3_RPS19BP1_SESN2_SIRT1 | 3.60E−05 |
| AKT1_ATG7_TKT_SESN2 | 3.70E−05 |
| BCL2L1_BNIP3_PRKAA1_LAMP2 | 3.70E−05 |
| CSE1L_DRAM_LC3_SESN2 | 3.70E−05 |
| DIABLO_LC3_SESN2_SIRT1 | 3.70E−05 |
| LC3_SESN2_SIRT1_STAT3 | 3.70E−05 |
| ATG12_ATG5_LC3_SESN2 | 3.80E−05 |
| BNIP3_PRKAA1_TCF3_LAMP2 | 3.80E−05 |
| LC3_SESN2_SIRT1_UVRAG | 3.80E−05 |
| BNIP3_PRKAA1_MMP9_LAMP2 | 3.90E−05 |
| AKT1_LC3_SESN2_SIRT1 | 4.00E−05 |
| AKT1_PRKAA1_CDH1_LAMP2 | 4.00E−05 |
| CSE1L_LAMP1_LC3_SESN2 | 4.00E−05 |
| ATG7_PRKAA1_TKT_LAMP2 | 4.10E−05 |
| KIAA1967_LAMP2_SESN2_SIRT1 | 4.10E−05 |
| LC3_SESN2_SESN3_SIRT1 | 4.20E−05 |
| BNIP3_PRKAA1_HMGB1_LAMP2 | 4.30E−05 |
| CSE1l-LC3_SESN2_UVRAG | 4.30E−05 |
| LC3_MMP9_SESN2_SIRT1 | 4.30E−05 |
| ATG3_LAMP2_SESN2_SIRT1 | 4.40E−05 |
| BNIP3_PRKAA1_CCNG2_LAMP2 | 4.40E−05 |
| BNIP3_PRKAA1_LAMP2_SATB1 | 4.40E−05 |
| BNIP3_PRKAA1_LAMP2_SESN1 | 4.40E−05 |
| ATG5_DRAM_LC3_SESN2 | 4.50E−05 |
| BNIP3_PRKAA1_CASP3_LAMP2 | 4.50E−05 |
| BNIP3_FRAP1_LC3_SESN2 | 4.60E−05 |
| Survival | |
| ATG3_BCL2L1_NNMT_PRKAA1 | 1.80E−07 |
| BCL2L1_TKT_CASP3_SESN2 | 4.10E−07 |
| BCL2L1_ID2_CASP3_SESN2 | 4.20E−07 |
| ATG3_BCL2L1_E2F1_PRKAA1 | 5.80E−07 |
| BCL2L1_NNMT_PRKAA1_HMGB1 | 6.40E−07 |

TABLE 33-continued

| Marker | p-value |
|---|---|
| BCL2L1_NNMT_PRKAA1_MMP2 | 7.40E−07 |
| BCL2L1_NNMT_PRKAA1_CDH1 | 8.20E−07 |
| FAS_TKT_CASP3_SESN2 | 9.00E−07 |
| BCL2L1_NNMT_PRKAA1_VEGF | 9.30E−07 |
| ATG7_BCL2L1_NNMT_PRKAA1 | 1.00E−06 |
| BCL2L1_FRAP1_NNMT_PRKAA1 | 1.00E−06 |
| BCL2L1_NNMT_PRKAA1_ID2 | 1.00E−06 |
| AIFM1_BCL2L1_NNMT_PRKAA1 | 1.10E−06 |
| BCL2L1_TKT_BHLHE41_CASP3 | 1.10E−06 |
| BCL2L1_NNMT_PRKAA1_CDH2 | 1.20E−06 |
| BCL2L1_CSE1L_NNMT_PRKAA1 | 1.30E−06 |
| BCL2L1_NNMT_PRKAA1_HMGB2 | 1.30E−06 |
| BCL2L1_CBS_NNMT_PRKAA1 | 1.40E−06 |
| FAS_TKT_SESN2_TP63 | 1.40E−06 |
| BCL2L1_DRAM_NNMT_PRKAA1 | 1.70E−06 |
| BCL2L1_NNMT_PRKAA1_ULK1 | 1.70E−06 |
| BNIP3_TKT_CASP3_SESN2 | 1.90E−06 |
| ATG5_BCL2L1_NNMT_PRKAA1 | 2.00E−06 |
| BCL2L1_DIABLO_NNMT_PRKAA1 | 2.00E−06 |
| BCL2L1_NNMT_CASP3_SESN2 | 2.10E−06 |
| FAS_TKT_BHLHE41_CASP3 | 2.10E−06 |
| BCL2L1_NNMT_PRKAA1_TKT | 2.20E−06 |
| BNIP3_FAS_TKT_CASP3 | 2.20E−06 |
| ATG3_ATG7_BCL2L1_PRKAA1 | 2.30E−06 |
| FAS_ID2_CASP3_SESN2 | 2.30E−06 |
| BCL2L1_NNMT_PRKAA1_CASP3 | 2.60E−06 |
| ATG3_BCL2L1_PRKAA1_HMGB2 | 2.70E−06 |
| FAS_LC3_BHLHE41_SESN2 | 2.80E−06 |
| ATG3_BCL2L1_BNIP3_NNMT | 2.90E−06 |
| BCL2L1_CASP8_NNMT_PRKAA1 | 3.00E−06 |
| FAS_BHLHE41_CASP3_SESN2 | 3.00E−06 |
| BCL2L1_BNIP3_NNMT_TKT | 3.10E−06 |
| DIABLO_FAS_BHLHE41_SESN2 | 3.10E−06 |
| ATG3_BCL2L1_PRKAA1_TKT | 3.20E−06 |
| BCL2L1_NNMT_PRKAA1_MMP9 | 3.20E−06 |
| BNIP3_FAS_CASP3_SESN2 | 3.20E−06 |
| FAS_LAMP1_BHLHE41_SESN2 | 3.30E−06 |
| BCL2L1_CASP3_SESN1_SESN2 | 3.50E−06 |
| BCL2L1_NNMT_PRKAA1_SIRT1 | 3.50E−06 |
| DIABLO_FAS_LAMP1_BHLHE41 | 3.50E−06 |
| FAS_TKT_CASP3_SIRT1 | 3.50E−05 |
| E2F1_FAS_BHLHE41_SESN2 | 3.60E−06 |
| FAS_TKT_CASP3_FASLG | 3.60E−06 |
| FAS_TKT_HMGB1_SESN2 | 3.60E−06 |
| FAS_CASP3_HMGB1_SESN2 | 3.70E−06 |
| BAX_BCL2L1_NNMT_PRKAA1 | 3.80E−06 |
| BCL2L1_E2F1_NNMT_PRKAA1 | 3.90E−06 |
| ATG3_BCL2L1_PRKAA1_MMP2 | 4.00E−06 |
| FAS_TKT_KIAA1967_SESN2 | 4.00E−06 |
| BNIP3FAS_TKT_TWIST1 | 4.20E−06 |
| ATG3_BCL2L1_BNIP3_TKT | 4.30E−06 |
| BCL2L1_NNMT_PRKAA1_PTEN | 4.40E−06 |
| Disease-free survival | |
| ATG5_CSE1L_FRAP1_SESN2 | 3.00E−06 |
| CSE1L_FRAP1_SESN2_SIRT1 | 3.10E−06 |
| ATG7_TKT_LAMP2_SESN2 | 5.10E−06 |
| ATG5_FRAP1_SESN2_SIRT1 | 5.40E−06 |
| AKT1_ATG7_TKT_SESN2 | 5.70E−06 |
| ATG5_CSE1L_LC3_SESN2 | 6.30E−06 |
| FRAP1_LC3_SESN2_SIRT1 | 7.30E−06 |
| CSE1L_FRAP1_LAMP1_SESN2 | 7.40E−06 |
| ATG7_TKT_SESN2_SESN3 | 8.20E−06 |
| ATG5_FRAP1_LC3_SESN2 | 8.40E−06 |
| ATG7_CSE1L_FRAP1_SESN2 | 8.40E−06 |
| CSE1L_LC3_SESN2_SIRT1 | 8.60E−06 |
| ATG5_LC3_SESN2_SIRT1 | 8.80E−06 |
| ATG7_TKT_FASLG_SESN2 | 9.70E−06 |
| ATG7_TKT_AGER_SESN2 | 1.30E−05 |
| ATG7_TKT_HMGB1_SESN2 | 1.30E−05 |
| ATG7_TKT_MMP2_SESN2 | 1.30E−05 |
| BNIP3_CSE1L_FRAP1_SESN2 | 1.30E−05 |
| ATG5_ATG7_TKT_SESN2 | 1.40E−06 |
| ATG7_BCL2_TKT_SESN2 | 1.40E−05 |
| ATG7_BNIP3_TKT_SESN2 | 1.40E−05 |
| FAS_FRAP1_SESN2_SIRT1 | 1.40E−05 |
| AIFM1_ATG7_TKT_SESN2 | 1.50E−05 |
| ATG12_TKT_LAMP2_SESN2 | 1.50E−05 |

TABLE 33-continued

| Marker | p-value |
|---|---|
| ATG7_TKT_BHLHE41_SESN2 | 1.50E−05 |
| ATG7_TKT_ID2_SESN2 | 1.50E−05 |
| CSE1L_DRAM_FRAP1_SESN2 | 1.50E−05 |
| CSE1L_FRAP1_SESN2_UVRAG | 1.50E−05 |
| ATG7_LAMP1_TKT_SESN2 | 1.60E−05 |
| ATG7_BCL2L1_TKT_SESN2 | 1.70E−05 |
| ATG7_TKT_CCNG2_SESN2 | 1.70E−05 |
| CSE1L_E2F1_FRAP1_SESN2 | 1.70E−05 |
| CSE1L_LAMP1_LC3_SESN2 | 1.70E−05 |
| PRKAA1_TKT_LAMP2_SESN2 | 1.70E−05 |
| ATG7_CBS_TKT_SESN2 | 1.80E−05 |
| ATG7_LC3_TKT_SESN2 | 1.80E−05 |
| ATG7_NNMT_TKT_SESN2 | 1.80E−05 |
| ATG7_TKT_CIAP2_SESN2 | 1.80E−05 |
| ATG7_TKT_SESN2_STAT3 | 1.80E−05 |
| ATG7_PTEN_TKT_SESN2 | 1.90E−05 |
| ATG7_TKT_CASP3_SESN2 | 1.90E−05 |
| ATG7_TKT_CDH2_SESN2 | 1.90E−05 |
| ATG7_TKT_HMGB2-SESN2 | 1.90E−05 |
| ATG7_TKT_NAMPT_SESN2 | 1.90E−05 |
| ATG7_TKT_RAPTOR_SESN2 | 1.90E−05 |
| ATG7_TKT_SESN2_SIRT1 | 1.90E−05 |
| ATG7_FRAP1_LC3_SESN2 | 2.00E−05 |
| ATG7_TKT_BECN1_SESN2 | 2.00E−06 |
| ATG7_DIABLO_TKT_SESN2 | 2.10E−05 |
| ATG7_FRAP1_SESN2_SIRT1 | 2.10E−05 |
| ATG12_CSE1L_FRAP1_SESN2 | 2.20E−05 |
| ATG7_TKT_XIAP_SESN2 | 2.20E−05 |
| ATG7_E2F1_TKT_SESN2 | 2.30E−05 |
| ATG7_TKT_MMP9_SESN2 | 2.30E−05 |
| ATG7_TKT_RAGE_SESN2 | 2.30E−05 |
| ATG3_ATG7_TKT_SESN2 | 2.40E−05 |
| ATG7_CSE1L_LC3_SESN2 | 2.40E−05 |

TABLE 34

| Marker | p-value |
|---|---|
| Recurrence | |
| CIAP2_FASLG_LAMP2_SESN2_SIRT1 | 2.90E−07 |
| ATG3_ATG5_LC3_SESN2_SIRT1 | 1.32E−06 |
| ATG3_FRAP1_LC3_SESN2_SIRT1 | 1.61E−06 |
| ATG7_FRAP1_LC3_SESN2_SIRT1 | 2.13E−06 |
| TKT_CIAP2_LAMP2_SESN2_SIRT1 | 2.30E−06 |
| ATG5_FRAP1_LC3_SESN2_SIRT1 | 2.32E−06 |
| ATG5_BNIP3_LC3_SESN2_SIRT1 | 2.47E−06 |
| TKT_CDH1_LAMP2_SESN2_SIRT1 | 2.50E−06 |
| CSE1L_FRAP1_LC3_SESN2_SIRT1 | 2.70E−06 |
| ATG3_BNIP3_LC3_SESN2_SIRT1 | 3.03E−06 |
| ATG5_CSE1L_LC3_SESN2_SIRT1 | 3.35E−06 |
| ATG3_LC3_LAMP2_SESN2_SIRT1 | 3.56E−06 |
| BNIP3_FRAP1_LC3_SESN2_SIRT1 | 3.80E−06 |
| BNIP3_PRKAA1_TKT_LAMP2_SESN2 | 3.80E−06 |
| ATG12_TKT_LAMP2_SESN2_SIRT1 | 3.90E−06 |
| ATG5_ATG7_LC3_SESN2_SIRT1 | 4.29E−06 |
| ATG7_BNIP3_TKT_LAMP2_SESN2 | 4.50E−06 |
| AKT1_ATG7_BNIP3_PRKAA1_LAMP2 | 4.51E−06 |
| ATG3_ATG7_LC3_SESN2_SIRT1 | 4.66E−06 |
| ATG3_ATG5_BNIP3_LC3_SESN2 | 4.67E−06 |
| BNIP3_CSE1L_LC3_SESN2_SIRT1 | 4.70E−06 |
| ATG5_DRAM_LC3_SESN2_SIRT1 | 4.84E−06 |
| AIFM1_CIAP2_LAMP2_SESN2_SIRT1 | 4.84E−06 |
| ATG7_TKT_LAMP2_SESN2_SIRT1 | 4.90E−06 |
| ATG5_CSE1L_FRAP1_LC3_SESN2 | 4.96E−06 |
| ATG7_LC3_NAMPT_SESN2_SIRT1 | 5.05E−06 |
| ATG5_E2F1_LC3_SESN2_SIRT1 | 5.06E−06 |
| BNIP3_CSE1L_FRAP1_LC3_SESN2 | 5.20E−06 |
| ATG7_LC3_LAMP2_SESN2_SIRT1 | 5.26E−06 |
| AIFM1_BNIP3_PRKAA1_LAMP2_SESN2 | 5.26E−06 |
| ATG12_BNIP3_TKT_LAMP2_SESN2 | 5.41E−06 |
| CIAP2_KIAA1967_LAMP2_SESN2_SIRT1 | 5.50E−06 |
| ATG12_ATG5_BNIP3_LC3_SESN2 | 5.51E−06 |
| ATG3_ATG7_LC3_LAMP2_SESN2 | 5.57E−06 |
| ATG12_TKT_CIAP2_LAMP2_SESN2 | 5.59E−06 |

TABLE 34-continued

| Marker | p-value |
|---|---|
| ATG5_BNIP3_CSE1L_LC3_SESN2 | 5.71E−06 |
| AKT1_ATG7_PRKAA1_TKT_LAMP2 | 5.85E−06 |
| ATG3_LC3_NAMPT_SESN2_SIRT1 | 5.86E−06 |
| ATG3_CSE1L_LC3_SESN2_SIRT1 | 5.90E−06 |
| ATG3_ATG7_FRAP1_LC3_SESN2 | 5.93E−06 |
| ATG5_LC3_ID2_SESN2_SIRT1 | 5.95E−06 |
| BNIP3_E2F1_LC3_SESN2_SIRT1 | 6.00E−06 |
| ATG3_LC3_ID2_SESN2_SIRT1 | 6.35E−06 |
| ATG7_CSE1L_FRAP1_LC3_SESN2 | 6.37E−06 |
| AIFM1_TKT_LAMP2_SESN2_SIRT1 | 6.38E−06 |
| LC3_CIAP2_LAMP2_SESN2_SIRT1 | 6.50E−06 |
| ATG12_TKT_CDH1_LAMP2_SESN2 | 6.51E−06 |
| ATG5_LC3_SESN2_SIRT1_STAT3 | 6.58E−06 |
| ATG3_DRAM_LC3_SESN2_SIRT1 | 6.63E−06 |
| ATG5_DIABLO_LC3_SESN2_SIRT1 | 6.63E−06 |
| ATG7_BNIP3_LC3_SESN2_SIRT1 | 6.67E−06 |
| CDH2_CIAP2_LAMP2_SESN2_SIRT1 | 6.70E−06 |
| ATG3_ATG5_FRAP1_LC3_SESN2 | 6.73E−06 |
| DRAM_TKT_LAMP2_SESN2_SIRT1 | 6.80E−06 |
| ATG12_ATG3_TKT_LAMP2_SESN2 | 6.84E−06 |
| ATG3_LC3_SESN2_SIRT1_STAT3 | 6.93E−06 |
| ATG5_LC3_SESN2_SIRT1_UVRAG | 6.94E−06 |
| Survival | |
| BCL2L1_NNMT_ID2_CASP3_SESN2 | 3.40E−08 |
| BCL2L1_PTEN_TKT_CASP3_SESN2 | 8.42E−08 |
| ATG3_BCL2L1_NNMT_PRKAA1_HMGB1 | 1.00E−07 |
| BCL2L1_TKT_XIAP_CASP3_SESN2 | 1.19E−07 |
| BCL2L1_TKT_CASP3_HMGB1_SESN2 | 1.20E−07 |
| ATG3_BCL2L1_NNMT_PRKAA1_ID2 | 1.30E−07 |
| BCL2L1_BNIP3_TKT_CASP3_SESN2 | 1.32E−07 |
| ATG3_BCL2L1_NNMT_PRKAA1_CDH1 | 1.35E−07 |
| BCL2L1_TKT_CASP3_RAGE_SESN2 | 1.38E−07 |
| ATG3_BCL2L1_NNMT_PRKAA1_ULK1 | 1.43E−07 |
| FAS_TKT_CASP3_HMGB1_SESN2 | 1.45E−07 |
| FAS_TKT_CASP3_SESN2_TP63 | 1.49E−07 |
| ATG3_BCL2L1_FRAP1_NNMT_PRKAA1 | 1.53E−07 |
| FAS_TKT_HMGB1_SESN2_TP63 | 1.55E−07 |
| AIFM1_ATG3_BCL2L1_NNMT_PRKAA1 | 1.58E−07 |
| BCL2L1_ID2_CASP3_SESN1_SESN2 | 1.63E−07 |
| ATG3_BCL2L1_NNMT_PRKAA1_MMP2 | 1.73E−07 |
| BCL2L1_TKT_CASP3_SESN1_SESN2 | 1.74E−07 |
| ATG3_BCL2L1_NNMT_PRKAA1_VEGF | 1.79E−07 |
| BCL2L1_TKT_ID2_CASP3_SESN2 | 1.81E−07 |
| ATG3_BCL2L1_ID2_CASP3_SESN2 | 1.88E−07 |
| BNIP3_TKT_XIAP_CASP3_SESN2 | 2.07E−07 |
| BCL2L1_NNMT_PRKAA1_ID2_SESN2 | 2.12E−07 |
| BCL2L1_NNMT_PRKAA1_HMGB1_VEGF | 2.16E−07 |
| ATG3_BCL2L1_NNMT_PRKAA1_CDH2 | 2.25E−07 |
| ATG3_BCL2L1_LAMP1_NNMT_PRKAA1 | 2.32E−07 |
| BCL2L1_NNMT_ID2_SESN2_UVRAG | 2.34E−07 |
| ATG3_ATG7_BCL2L1_NNMT_PRKAA1 | 2.41E−07 |
| ATG3_BCL2L1_CBS_NNMT_PRKAA1 | 2.43E−07 |
| BCL2L1_ID2_CASP3_RPS19BP1_SESN2 | 2.44E−07 |
| BNIP3_FAS_TKT_CASP3_SESN2 | 2.48E−07 |
| ATG3_BCL2L1_DRAM_NNMT_PRKAA1 | 2.49E−07 |
| ATG7_BCL2L1_NNMT_PRKAA1_HMGB1 | 2.52E−07 |
| BCL2L1_NNMT_PRKAA1_HMGB1_HMGB2 | 2.54E−07 |
| BCL2L1_FAS_TKT_CASP3_SESN2 | 2.65E−07 |
| ATG3_BCL2L1_CSE1L_NNMT_PRKAA1 | 2.68E−07 |
| ATG3_BCL2L1_DIABLO_NNMT_PRKAA1 | 2.80E−07 |
| ATG3_BCL2L1_NNMT_PRKAA1_SIRT1 | 2.92E−07 |
| BCL2L1_CASP8_ID2_CASP3_SESN2 | 2.93E−07 |
| BCL2L1_DIABLO_ID2_CASP3_SESN2 | 2.96E−07 |
| BCL2L1_TKT_CASP3_SESN2_STAT3 | 2.98E−07 |
| BCL2L1_NNMT_PRKAA1_ID2_VEGF | 3.09E−07 |
| BCL2L1_ID2_CASP3_HMGB2_SESN2 | 3.14E−07 |
| BCL2L1_TKT_CASP3_SESN2_SESN3 | 3.15E−07 |
| BCL2L1_TKT_CASP3_CCNG2_SESN2 | 3.16E−07 |
| FAS_TKT_CASP3_FASLG_SESN2 | 3.20E−07 |
| FAS_TKT_CASP3_SESN2_SIRT1 | 3.22E−07 |
| BCL2L1_NNMT_ID2_KIAA1967_SESN2 | 3.26E−07 |
| ATG5_BCL2L1_ID2_CASP3_SESN2 | 3.28E−07 |
| BCL2L1_NNMT_PRKAA1_CASP3_SIRT1 | 3.35E−07 |
| BCL2L1_TKT_XIAP_BHLHE41_CASP3 | 3.36E−07 |
| FAS_TKT_XIAP_CASP3_SESN2 | 3.40E−07 |
| BCL2L1_CDH1_ID2_CASP3_SESN2 | 3.41E−07 |
| BCL2L1_TKT_CASP3_SESN2_SIRT1 | 3.44E−07 |

TABLE 34-continued

| Marker | p-value |
|---|---|
| ATG7_BCL2L1_NNMT_PRKAA1_ID2 | 3.44E−07 |
| BCL2_BCL2L1_TKT_CASP3_SESN2 | 3.44E−07 |
| BCL2L1_ID2_CASP3_CDH2_SESN2 | 3.54E−07 |
| Disease-free survival | |
| ATG5_CSE1L_FRAP1_LC3_SESN2 | 5.20E−07 |
| CSE1-lFRAP1_LC3_SESN2_SIRT1 | 5.51E−07 |
| ATG5_FRAP1_LC3_SESN2_SIRT1 | 5.70E−07 |
| ATG5_CSE1L_FRAP1_SESN2_SIRT1 | 1.00E−06 |
| ATG7_CSE1L_FRAP1_LC3_SESN2 | 1.39E−06 |
| ATG7_FRAP1_LC3_SESN2_SIRT1 | 1.82E−06 |
| ATG5_CSE1L_FRAP1_LAMP1_SESN2 | 1.90E−06 |
| AKT1_ATG7_TKT_LAMP2_SESN2 | 2.12E−06 |
| ATG5_FRAP1_LAMP1_SESN2_SIRT1 | 2.30E−06 |
| CSE1L_FRAP1_LAMP1_SESN2_SIRT1 | 2.38E−06 |
| ATG3_FRAP1_LC3_SESN2_SIRT1 | 2.40E−06 |
| AKT1_ATG5_CSE1L_FRAP1_SESN2 | 2.47E−06 |
| ATG5_CSE1L_DIABLO_FRAP1_SESN2 | 2.50E−06 |
| ATG5_CSE1L_LC3_SESN2_SIRT1 | 2.50E−06 |
| CSE1L_FRAP1_SESN2_SIRT1_UVRAG | 2.54E−06 |
| ATG7_TKT_LAMP2_SESN2_SESN3 | 2.56E−06 |
| CSE1L_FRAP1_SATB1_SESN2_SIRT1 | 2.72E−06 |
| CSE1L_FRAP1_CDH1_SESN2_SIRT1 | 2.82E−06 |
| ATG6_TKT_FASLG_LAMP2_SESN2 | 2.90E−06 |
| ATG5_CSE1L_FRAP1_ID2_SESN2 | 2.90E−06 |
| AKT1_ATG7_TKT_SESN2_SESN3 | 2.92E−06 |
| ATG7_TKT_LAMP2_MMP2_SESN2 | 2.92E−06 |
| AKT1_CSE1L_FRAP1_SESN2_SIRT1 | 2.98E−06 |
| BNIP3_CSE1L_FRAP1_LC3_SESN2 | 2.99E−06 |
| ATG5_CSE1L_FRAP1_SESN2_SESN3 | 3.00E−06 |
| CSE1L_FRAP1_LAMP1_LC3_SESN2 | 3.10E−06 |
| ATG3_ATG5_CSE1L_FRAP1_SESN2 | 3.10E−06 |
| CSE1L_DRAM_FRAP1_LC3_SESN2 | 3.16E−06 |
| ATG3_CSE1L_FRAP1_SESN2_SIRT1 | 3.20E−06 |
| ATG5_ATG7_FRAP1_LC3_SESN2 | 3.20E−06 |
| ATG5_FAS_FRAP1_SESN2_SIRT1 | 3.20E−06 |
| CSE1L_FRAP1_SESN2_SESN3_SIRT1 | 3.23E−06 |
| CSE1L_DRAM_FRAP1_SESN2_SIRT1 | 3.31E−06 |
| CSE1L_DIABLO_FRAP1_SESN2_SIRT1 | 3.38E−06 |
| ATG7_CSE1L_FRAP1_SESN2_SIRT1 | 3.39E−06 |
| ATG5_CSE1L_FRAP1_CDH1_SESN2 | 3.40E−06 |
| ATG7_TKT_FASLG_SESN2_SESN3 | 3.44E−06 |
| ATG7_TKT_HMGB1_LAMP2_SESN2 | 3.44E−06 |
| ATG7_TKT_AGER_LAMP2_SESN2 | 3.47E−06 |
| ATG3_ATG5_FRAP1_LC3_SESN2 | 3.50E−06 |
| ATG3_ATG5_FRAP1_SESN2_SIRT1 | 3.50E−06 |
| ATG5_CSE1L_FRAP1_SATB1_SESN2 | 3.50E−06 |
| CSE1L_FRAP1_ID2_SESN2_SIRT1 | 3.56E−06 |
| ATG7_BNIP3_TKT_LAMP2_SESN2 | 3.57E−06 |
| ATG5_ATG7_CSE1L_FRAP1_SESN2 | 3.60E−06 |
| ATG5_LC3_NAMPT_SESN2_SIRT1 | 3.60E−06 |
| ATG12_ATG5_CSE1L_FRAP1_SESN2 | 3.60E−06 |
| CSE1L_FRAP1_SESN2_SIRT1_STAT3 | 3.67E−06 |
| CSE1L_FRAP1_LC3_SESN2_UVRAG | 3.67E−06 |
| AKT1_ATG7_TKT_MMP2_SESN2 | 3.80E−06 |
| ATG5_BNIP3_CSE1L_FRAP1_SESN2 | 3.80E−06 |
| CSE1L_FRAP1_MMP9_SESN2_SIRT1 | 3.89E−06 |
| BNIP3_CSE1L_FRAP1_SESN2_SIRT1 | 3.90E−06 |
| AKT1_ATG7_TKT_HMGB1_SESN2 | 3.93E−06 |
| AIFM1_AKT1_ATG7_TKT_SESN2 | 4.07E−06 |
| AKT1_ATG5_ATG7_KT_SESN2 | 4.10E−06 |
| ATG12_ATG7_TKT_LAMP2_SESN2 | 4.14E−06 |
| CDH1_ID2_MMP9_TCF3_SESN2 | 8.41E−03 |

TABLE 35

| Marker | p-value |
|---|---|
| Recurrence | |
| LC3_CIAP2_FASLG_LAMP2_SESN2_SIRT1 | 1.29E−07 |
| CCNG2_CIAP2_FASLG_LAMP2_SESN2_SIRT1 | 1.43E−07 |
| NNMT_CIAP2_FASLG_LAMP2_SESN2_SIRT1 | 2.07E−07 |
| CIAP2_FASLG_LAMP2_MMP2_SESN2_SIRT1 | 2.23E−07 |
| AGER_CIAP2_FASLG_LAMP2_SESN2_SIRT1 | 2.27E−07 |

TABLE 35-continued

| Marker | p-value |
|---|---|
| CIAP2_FASLG_LAMP2_SESN1_SESN2_SIRT1 | 2.29E−07 |
| CIAP2_FASLG_HMGB1_LAMP2_SESN2_SIRT1 | 2.31E−07 |
| CIAP2_FASLG_LAMP2_NAMPT_SESN2_SIRT1 | 2.31E−07 |
| AKT1_CIAP2_FASLG_LAMP2_SESN2_SIRT1 | 2.35E−07 |
| ID2_CIAP2_FASLG_LAMP2_SESN2_SIRT1 | 2.55E−07 |
| FAS_CIAP2_FASLG_LAMP2_SESN2_SIRT1 | 2.62E−07 |
| CIAP2_FASLG_LAMP2_SESN2_SESN3_SIRT1 | 2.69E−07 |
| TCF3_CIAP2_FASLG_LAMP2_SESN2_SIRT1 | 2.77E−07 |
| ATG3_ATG5_FRAP1_LC3_SESN2_SIRT1 | 2.84E−07 |
| ULK1_CIAP2_FASLG_LAMP2_SESN2_SIRT1 | 2.85E−07 |
| BCL2_CIAP2_FASLG_LAMP2_SESN2_SIRT1 | 2.89E−07 |
| CIAP2_FASLG_LAMP2_RAGE_SESN2_SIRT1 | 2.97E−07 |
| ATG5_CIAP2_FASLG_LAMP2_SESN2_SIRT1 | 3.04E−07 |
| CASP3_CIAP2_FASLG_LAMP2_SESN2_SIRT1 | 3.16E−07 |
| FRAP1_CIAP2_FASLG_LAMP2_SESN2_SIRT1 | 3.24E−07 |
| MMP9_CIAP2_FASLG_LAMP2_SESN2_SIRT1 | 3.44E−07 |
| CIAP2_FASLG_LAMP2_SATB1_SESN2_SIRT1 | 3.51E−07 |
| ATG3_ATG7_FRAP1_LC3_SESN2_SIRT1 | 3.70E−07 |
| CDH2_CIAP2_FASLG_LAMP2_SESN2_SIRT1 | 3.78E−07 |
| LAMP1_CIAP2_FASLG_LAMP2_SESN2_SIRT1 | 3.93E−07 |
| TKT_CIAP2_FASLG_LAMP2_SESN2_SIRT1 | 4.02E−07 |
| ATG7_LC3_FASLG_LAMP2_SESN2_SIRT1 | 4.51E−07 |
| ATG3_ATG7_LC3_LAMP2_SESN2_SIRT1 | 4.68E−07 |
| ATG3_BNIP3_FRAP1_LC3_SESN2_SIRT1 | 5.23E−07 |
| ATG5_ATG7_FRAP1_LC3_SESN2_SIRT1 | 5.89E−07 |
| ATG3_ATG5_BNIP3_LC3_SESN2_SIRT1 | 6.24E−07 |
| E2F1_CIAP2_FASLG_LAMP2_SESN2_SIRT1 | 6.56E−07 |
| ATG3_BNIP3_LC3_LAMP2_SESN2_SIRT1 | 6.99E−07 |
| ATG5_BNIP3_FRAP1_LC3_SESN2_SIRT1 | 7.20E−07 |
| ATG7_BNIP3_FRAP1_LC3_SESN2_SIRT1 | 7.32E−07 |
| TKT_CDH1_CIAP2_LAMP2_SESN2_SIRT1 | 8.77E−07 |
| ATG5_BNIP3_E2F1_LC3_SESN2_SIRT1 | 9.14E−07 |
| ATG3_ATG7_LC3_NAMPT_SESN2_SIRT1 | 9.24E−07 |
| AIFM1_CIAP2_FASLG_LAMP2_SESN2_SIRT1 | 9.84E−07 |
| ATG5_CSE1L_FRAP1_LC3_SESN2_SIRT1 | 1.01E−06 |
| CBS_TKT_CIAP2_LAMP2_SESN2_SIRT1 | 1.02E−06 |
| ATG3_ATG5_LC3_ID2_SESN2_SIRT1 | 1.04E−06 |
| AIFM1_TKT_CIAP2_LAMP2_SESN2_SIRT1 | 1.06E−06 |
| ATG3_DRAM_FRAP1_LC3_SESN2_SIRT1 | 1.06E−06 |
| ATG3_ATG5_E2F1_LC3_SESN2_SIRT1 | 1.11E−06 |
| ATG7_BNIP3_LC3_LAMP2_SESN2_SIRT1 | 1.12E−06 |
| ATG3_ATG5_LC3_SESN2_SIRT1_STAT3 | 1.16E−06 |
| AIFM1_AKT1_LAMP2_SESN2_SIRT1_UVRAG | 1.16E−06 |
| AKT1_ATG7_TKT_LAMP2_SESN2_SIRT1 | 1.18E−06 |
| ATG3_ATG5_CS31L_NAMPT_SESN2_SIRT1 | 1.20E−06 |
| ATG3_ATG5_DIABLO_LC3_SESN2_SIRT1 | 1.20E−06 |
| TKT_CDH1_HMGB1_LAMP2_SESN2_SIRT1 | 1.20E−06 |
| ATG3_ATG5_LC3_LAMP2_SESN2_SIRT1 | 1.20E−06 |
| ATG5_DRAM_FRAP1_LC3_SESN2_SIRT1 | 1.23E−06 |
| BNIP3_CSE1L_FRAP1_LC3_SESN2_SIRT1 | 1.23E−06 |
| AKT1_ATG3_ATG5_LC3_SESN2_SIRT1 | 1.24E−06 |
| AIFM1_BNIP3_PRKAA1_TKT_LAMP2_SESN2 | 1.24E−06 |
| TKT_CDH1_ID2_MMP9_TCF3_SESN2 | 7.98E−04 |
| Survival | |
| BCL2L1_NNMT_ID2_CASP3_RAGE_SESN2 | 1.46E−08 |
| BCL2L1_NNMT_ID2_CASP3_HMGB1_SESN2 | 1.89E−08 |
| ATG3_BCL2L1_NNMT_PRKAA1_CASP3_SIRT1 | 2.30E−08 |
| BCL2L1_NNMT_ID2_CASP3_SESN1_SESN2 | 2.42E−08 |
| BCL2L1_NNMT_PRKAA1_ID2_SESN1_SESN2 | 2.46E−08 |
| BCL2L1_BNIP3_TKT_XIAP_CASP3_SESN2 | 2.60E−08 |
| FAS_TKT_CASP3_HMGB1_SESN2_TP63 | 2.64E−08 |
| ATG3_BCL2L1_NNMT_PRKAA1_KIAA1967_SIRT1 | 2.80E−08 |
| ATG3_BCL2L1_NNMT_ID2_CASP3_SESN2 | 3.00E−08 |
| ATG3_BCL2L1_NNMT_PRKAA1_HMGB1_VEGF | 3.10E−08 |
| BCL2L1_PTEN_TKT_CASP3_SESN1_SESN2 | 3.17E−08 |
| BCL2L1_NNMT_ID2_AGER_CASP3_SESN2 | 3.22E−08 |
| BCL2L1_NNMT_ID2_BECN1_CASP3_SESN2 | 3.29E−08 |
| BCL2L1_PTEN_TKT_CASP3_HMGB1_SESN2 | 3.31E−08 |
| BCL2L1_PTEN_TKT_XIAP_CASP3_SESN2 | 3.34E−08 |
| ATG12_BCL2L1_NNMT_ID2_CASP3_SESN2 | 3.40E−08 |
| BNIP3_TKT_XIAP_CASP3_RAGE_SESN2 | 3.42E−08 |
| BCL2L1_NNMT_ID2_CASP3_CCNG2_SESN2 | 3.46E−08 |
| AIFM1_BCL2L1_NNMT_ID2_CASP3_SESN2 | 3.50E−08 |
| BCL2L1_PTEN_TKT_CASP3_RAGE_SESN2 | 3.55E−08 |
| BCL2L1_NNMT_ID2_CASP3_CDH2_SESN2 | 3.61E−08 |
| BCL2L1_NNMT_ID2_CASP3_LAMP2_SESN2 | 3.66E−08 |
| ATG3_BCL2L1_BNIP3_NNMT_PRKAA1_FASLG | 3.70E−06 |

TABLE 35-continued

| Marker | p-value |
|---|---|
| BCL2L1_NNMT_ID2_CASP3_SESN2_SESN3 | 3.78E−08 |
| BCL2L1_CSE1L_NNMT_ID2_CASP2_SESN2 | 3.87E−08 |
| BAX_BCL2L1_NNMT_ID2_CASP3_SESN2 | 3.90E−08 |
| BCL2L1_NNMT_ID2_BHLHE41_CASP3_SESN2 | 3.93E−08 |
| BCL2L1_NNMT_ID2_VASP3_MMP2_SESN2 | 3.93E−08 |
| BNIP3_PTEN_TKT_XIAP_CASP3_SESN2 | 3.97E−08 |
| BCL2L1_BNIP3_TKT_ID2_CASP3_SESN2 | 4.10E−08 |
| BCL2L1_BNIP3_TKT_CASP3_SESN1_SESM2 | 4.20E−08 |
| ATG3_ATG7_BCL2L1_NNMT_PRKAA1_HMGB1 | 4.30E−08 |
| BCL2L1_CASP8_NNMT_ID2_CASP3_SESN2 | 4.30E−08 |
| ATG5_BCL2L1_NNMT_ID2_CASP3_SESN2 | 4.40E−08 |
| BCL2L1_NNMT_CDH1_CASP3_SESN2 | 4.52E−08 |
| ATG3_BCL2L1_NNMT_PRKAA1_ID2_VEGF | 4.60E−08 |
| BCL2L1_NNMT_PRKAA1_ID2_CASP3_SESN2 | 4.65E−08 |
| BCL2L1_TKT_XIAP_CASP3_SESN1_SESN2 | 4.74E−08 |
| BCL2L1_NNMT_XIAP_ID2_CASP3_SESN2 | 4.75E−08 |
| BCL2L1_DIABLO_NNMT_ID2_CASP3_SESN2 | 5.03E−08 |
| BCL2L1_TKT_XIAP_CASP3_HMGB1_SESN2 | 5.21E−08 |
| BCL2L1_BNIP3_TKT_CASP3_RAGE_SESN2 | 5.30E−08 |
| BCL2L1_TKT_BHLHE41_CASP3_SESN1_SESN2 | 5.35E−08 |
| BCL2L1_TKT_CASP3_HMGB1_RAGE_SESN2 | 5.36E−08 |
| BCL2L1_PTEN_TKT_CASP3_CCNG2_SESN2 | 5.37E−08 |
| BCL2L1_PRKAA1_TKT_XIAP_CASP3_SESN2 | 5.38E−08 |
| BCL2L1_TKT_CASP3_HMGB1_SESN1_SESN2 | 5.41E−08 |
| BNIP3_FAS_TKT_CASP3_HMGB1_SESN2 | 5.47E−08 |
| FAS_TKT_XIAP_CASP3_HMGB1_SESN2 | 5.47E−08 |
| BCL2L1_NNMT_ID2_SESN1_SESN2_UVRAG | 5.49E−08 |
| FAS_TKT_HMGB1_KIAA1967_SESN2_TP63 | 5.60E−08 |
| BCL2L1_TKT_ID2_BHLHE41_CASP3_SESN2 | 5.63E−08 |
| BCL2L1_PTAN_TKT_ID2_CASP3_SESN2 | 5.75E−08 |
| BCL2L1_ID2_CASP3_RAGE_RPS19BP1_SESN2 | 5.87E−08 |
| BNIP3_TKT_XIAP_CASP3_HMGB1_SESN2 | 5.89E−08 |
| ATG3_ATG7_BCL2L1_NNMT_PRKAA1_ID2 | 5.90E−08 |
| BCL2L1_BNIP3_NNMT_TKT_CASP3_SESN2 | 5.90E−08 |
| Disease-free survival | |
| ATG5_CSE1L_FRAP1_LC3_SESN2_SIRT1 | 1.28E−07 |
| ATG3_ATG5_FRAP1_LC3_SESN2_SIRT1 | 1.81E−07 |
| ATG5_ATG7_FRAP1_LC3_SESN2_SIRT1 | 2.26E−07 |
| ATG3_ATG5_CSE1L_FRAP1_LC3_SESN2 | 3.87E−07 |
| ATG3_CSE1L_FRAP1_LC3_SESN2_SIRT1 | 4.03E−07 |
| ATG7_CSE1L_FRAP1_LC3_SESN2_SIRT1 | 4.05E−07 |
| ATG5_ATG7_CSE1L_FRAP1_LC3_SESN2 | 4.31E−07 |
| ATG5_DRAM_FRAP1_LC3_SESN2_SIRT1 | 4.39E−07 |
| ATG5_CSE1L_DIABLO_FRAP1_LC3_SESN2 | 4.66E−07 |
| CSE1L_FRAP1_LC3_SATB1_SESN2_SIRT1 | 4.80E−07 |
| AKT1_ATG5_CSE1L_FRAP1_LC3_SESN2 | 4.80E−07 |
| ATG5_FRAP1_LC3_RPS19BP1_SESN2_SIRT1 | 4.87E−07 |
| ATG5_CSE1L_FRAP1_LC3_ID2_SESN2 | 5.13E−07 |
| ATG5_CSE1L_FRAP1_LC3_SESN2_SESN3 | 5.14E−07 |
| CSE1L_FRAP1_LC3_SESN2_SIRT1_UVRAG | 5.36E−07 |
| AKT1_CSE1L_FRAP1_LC3_SESN2_SIRT1 | 5.44E−07 |
| ATG5_DIABLO_FRAP1_LC3_SESN2_SIRT1 | 5.49E−07 |
| CSE1L_FRAP1_LC3_SESN2_SESN3_SIRT1 | 5.50E−07 |
| ATG5_FRAP1_LC3_SESN2_SESN3_SIRT1 | 5.66E−07 |
| CSE1L_DRAM_FRAP1_LC3_SESN2_SIRT1 | 5.70E−07 |
| CSE1L_DIABLO_FRAP1_LC3_SESN2_SIRT1 | 5.76E−07 |
| CSE1L_FRAP1_LC3_ID2_SESN2_SIRT1 | 5.76E−07 |
| AKT1_ATG5_FRAP1_LC3_SESN2_SIRT1 | 5.85E−07 |
| ATG5_CSE1L_FRAP1_LC3_SATB1_SESN2 | 5.95E−07 |
| ATG5_FRAP1_LC3_ID2_SESN2_SIRT1 | 5.96E−07 |
| ATG5_CSE1L_FRAP1_LAMP1_SESN2_SIRT1 | 6.20E−07 |
| ATG3_ATG7_FRAP1_LC3_SESN2_SIRT1 | 6.50E−07 |
| ATG5_E2F1_FRAP1_LC3_SESN2_SIRT1 | 6.69E−07 |
| ATG5_CSE1L_FRAP1_LAMP1_LC3_SESN2 | 6.97E−07 |
| ATG5_BNIP3_CSE1L_FRAP1_LC3_SESN2 | 7.03E−07 |
| CSE1L_FRAP1_LC3_SESN2_SIRT1_STAT3 | 7.19E−07 |
| BNIP3_CSE1L_FRAP1_LC3_SESN2_SIRT1 | 7.24E−07 |
| ATG5_CSE1L_FRAP1_SESN2_SIRT1_UVRAG | 7.96E−07 |
| ATG5_CSE1L_FRAP1_LC3_SESN2 | 8.10E−07 |
| ATG5_FRAP1_LC3_MMP9_SESN2_SIRT1 | 8.11E−07 |
| ATG5_ATG7_FRAP1_LAMP1_SESN2_SIRT1 | 8.50E−07 |
| ATG5_CSE1L_FRAP1_CDH21_SESN2_SIRT1 | 8.54E−07 |
| ATG5_FRAP1_LC3_SESN2_SIRT1_STAT3 | 8.67E−07 |
| ATG12_ATG5_CSE1L_FRAP1_LC3_SESN2 | 8.73E−07 |
| ATG5_FRAP1_LC3_SESN2_SIRT1_UVRAG | 8.73E−07 |
| ATG5_BNIP3_FRAP1_LC3_SESN2_SIRT1 | 8.83E−07 |
| ATG3_ATG5_FRAP1_LAMP1_SESN2_SIRT1 | 8.85E−07 |
| CSE1L_FRAP1_LC3_CDH1_SESN2_SIRT1 | 8.90E−07 |
| ATG5_CSE1L_FRAP1_LC3_SESN2_STAT3 | 8.97E−07 |
| AIFM1_ATG12_TKT_FASLG_LAMP2_SESN2 | 9.06E−07 |
| ATG5_CSE1L_FRAP1_LC3_SESN2_UVRAG | 9.14E−07 |
| CSE1L_FRAP1_LAMP1_LC3_SESN2_SIRT1 | 9.28E−07 |
| CSE1L_FRAP1_LC3_MMP9_SESN2_SIRT1 | 9.50E−07 |
| ATG5_CSE1L_FRAP1_LC3_RPS19BP1_SESN2 | 9.53E−07 |
| AKT1_ATG5_CSE1L_FRAP1_SESN2_SIRT1 | 9.55E−07 |
| ATG5_CSE1L_E2F1_FRAP1_LC3_SESN2 | 9.62E−07 |
| CSE1L_E2F1_FRAP1_SESN2_SIRT1 | 9.90E−07 |
| ATG5_CSE1L_FRAP1_LC3_CDH1_SESN2 | 1.03E−06 |
| ATG3_ATG7_CSE1L_FRAP1_LC3_SESN2 | 1.05E−06 |
| ATG5_CSE1L_FRAP1_SATB1_SESN2_SIRT1 | 1.06E−06 |
| ATG5_CSE1L_FRAP1_SESN2_SESN3_SIRT1 | 1.06E−06 |
| ATG7_TKT_FASLG_LAMP2_SESN2_SIRT1 | 1.07E−06 |
| TKT_CDH1_ID2_MMP9_TCF3_SESN2 | 1.65E−04 |

TABLE 36

| Marker | p-value |
|---|---|
| Recurrence | |
| ATG3_ATG7_LC3_FASLG_LAMP2_SESN2_SIRT1 | 6.31E−08 |
| MMP9_CCNG2_CIAP2_FASLG_LAMP2_SESN2_SIRT1 | 7.01E−08 |
| FRAP1_LC3_CIAP2_FASLG_LAMP2_SESN2_SIRT1 | 7.33E−08 |
| ATG7_BNIP3_LC3_FASLG_LAMP2_SESN2_SIRT1 | 7.57E−08 |
| CCNG2_CIAP2_FASLG_LAMP2_NAMPT_SESN2_SIRT1 | 7.71E−08 |
| LC3_CIAP2_FASLG_LAMP2_MMP2_SESN2_SIRT1 | 8.40E−08 |
| CCNG2_CIAP2_FASLG_MMP2_SESN2_SIRT1 | 8.60E−08 |
| LC3_NNMT_CIAP2_FASLG_LAMP2_SESN2_SIRT1 | 8.97E−08 |
| LC3_CCNG2_CIAP2_FASLG_LAMP2_SESN2_SIRT1 | 9.20E−08 |
| TCF3_CCNG2_CIAP2_FASLG_LAMP2_SESN2_SIRT1 | 9.26E−08 |
| LC3_CIAP2_FASLG_LAMP2_NAMPT_SESN2_SIRT1 | 1.01E−07 |
| FAS_CCNG2_CIAP2_FASLG_LAMP2_SESN2_SIRT1 | 1.09E−07 |
| CIAP2_FASLG_LAMP2_NAMPT_SESN1_SESN2_SIRT1 | 1.10E−07 |
| CIAP2_FASLG_LAMP2_MMP2_SESN1_SESN2_SIRT1 | 1.18E−07 |
| ATG3_ATG5_BNIP3_FRAP1_LC3_SESN2_SIRT1 | 1.18E−07 |
| NNMT_CCNG2_CIAP2_FASLG_LAMP2_SESN2_SIRT1 | 1.19E−07 |
| LC3_CIAP2_FASLG_LAMP2_SATB1_SESN2_SIRT1 | 1.20E−07 |
| ATG5_LC3_CIAP2_FASLG_LAMP2_SESN2_SIRT1 | 1.20E−07 |
| LC3_TCF3_CIAP2_FASLG_LAMP2_SESN2_SIRT1 | 1.23E−07 |
| AGER_CIAP2_FASLG_LAMP2_NAMPT_SESN2_SIRT1 | 1.25E−07 |
| CCNG2_CIAP2_FASLG_LAMP2_SATB1_SESN2_SIRT1 | 1.27E−07 |
| AKT1_CCNG2_CIAP2_FASLG_LAMP2_SESN2_SIRT1 | 1.28E−07 |
| LC3_ULK1_CIAP2_FASLG_LAMP2_SESN2_SIRT1 | 1.29E−07 |
| CCNG2_CIAP2_FASLG_LAMP2_SESN2_SESN3_SIRT1 | 1.29E−07 |
| NNMT_CIAP2_FASLG_HMGB1_LAMP2_SESN2_SIRT1 | 1.31E−07 |
| ATG3_ATG5_ATG7_FRAP1_LC3_SESN2_SIRT1 | 1.33E−07 |
| NNMT_CIAP2_FASLG_LAMP2_MMP2_SESN2_SIRT1 | 1.35E−07 |
| LC3_CIAP2_FASLG_HMGB1_LAMP2_SESN2_SIRT1 | 1.35E−07 |
| AGER_CIAP2_FASLG_LAMP2_MMP2_SESN2_SIRT1 | 1.36E−07 |
| BCL2_LC3_CIAP2_FASLG_LAMP2_SESN2_SIRT1 | 1.36E−07 |
| BCL2_CCNG2_CIAP2_FASLG_LAMP2_SESN2_SIRT1 | 1.42E−07 |
| ULK1_CCNG2_CIAP2_FASLG_LAMP2_SESN2_SIRT1 | 1.44E−07 |
| CCNG2_CIAP2_FASLG_HMGB1_LAMP2_SESN2_SIRT1 | 1.44E−07 |
| LC3_CDH2_CIAP2_FASLG_LAMP2_SESN2_SIRT1 | 1.48E−07 |
| LC3_CASP3_CIAP2_FASLG_LAMP2_SESN2_SIRT1 | 1.48E−07 |
| AKT1_NNMT_CIAP2_FASLG_LAMP2_SESN2_SIRT1 | 1.49E−07 |
| FRAP1_CCNG2_CIAP2_FASLG)LAMP2_SESN2_SIRT1 | 1.50E−07 |
| FRAP1_AGER_CIAP2_FASLG_LAMP2_SESN2_SIRT1 | 1.51E−07 |
| CASP3_CCNG2_CIAP2_FASLG_LAMP2_SESN2_SIRT1 | 1.58E−07 |
| CIAP2_FASLG_HMGB1_LAMP2_SESN1_SESN2_SIRT1 | 1.56E−07 |
| CIAP2_FASLG_HMGB1_LAMP2_SESN1_SESN2_SIRT1 | 1.57E−07 |
| LC3_AGER_CIAP2_FASLG_LAMP2_SESN2_SIRT1 | 1.57E−07 |
| CIAP2_FASLG_HMGB1_LAMP2_NAMPT_SESN2_SIRT1 | 1.58E−07 |
| ATG5_CCNG2_CIAP2_FASLG_LAMP2_SESN2_SIRT1 | 1.58E−07 |
| ID2_CCNG2_CIAP2_FASLG_LAMP2_SESN2_SIRT1 | 1.60E−07 |
| TCF3_AGER_CIAP2_FASLG_LAMP2_SESN2_SIRT1 | 1.60E−07 |
| FAS_LC3_CIAP2_FASLG_LAMP2_SESN2_SIRT1 | 1.60E−07 |
| NNMT_CIAP2_FASLG_LAMP2_NAMPT_SESN2_SIRT1 | 1.62E−07 |
| LAMP1_CCNG2_CIAP2_FASLG_LAMP2_SESN2_SIRT1 | 1.63E−07 |
| CIAP2_FASLG_LAMP2_MMP2_SESN2_SESN3_SIRT1 | 1.66E−07 |
| TCF3_CIAP2_FASLG_LAMP2_SESN1_SESN2_SIRT1 | 1.68E−07 |
| FRAP1_CIAP2_FASLG_HMGB1_LAMP2_SESN2_SIRT1 | 1.69E−07 |

TABLE 36-continued

| Marker | p-value |
|---|---|
| ATG3_ATG7_BNIP3_FRAP1_LC3_SESN2_SIRT1 | 1.72E−07 |
| AKT1_CIAP2_FASLG_LAMP2_MMP2_SESN2_SIRT1 | 1.73E−07 |
| NNMT_ID2_CIAP2_FASLG_LAMP2_SESN2_SIRT1 | 1.78E−07 |
| NNMT_AGER_CIAP2_FASLG_LAMP2_SESN2_SIRT1 | 1.79E−07 |
| ATG7_LC3_CDH1_FASLG_LAMP2_SESN2_SIRT1 | 1.81E−07 |
| MMP9_AGER_CIAP2_FASLG_LAMP2_SESN2_SIRT1 | 1.83E−07 |
| BNIP3_PRKAA1_CDH1_ID2_MMP9_TCF3_LAMP2 | 4.64E−05 |
| Survival | |
| BCL2L1_NNMT_PRKAA1_XIAP_ID2_CASP3_SESN2 | 2.95E−09 |
| BCL2L1_PRKAA1_PTEN_TKT_XIAP_CASP3_SESN2 | 3.28E−09 |
| BCL2L1_NNMT_ID2_BHLHE41_CASP3_SESN1_SESN2 | 4.78E−09 |
| BCL2L1_CASP8_NNMT_XIAP_ID2_CASP3_SESN2 | 7.10E−09 |
| ATG3_BCL2L1_NNMT_ID2_CASP3_RAGE_SESN2 | 7.30E−09 |
| BCL2L1_TKT_XIAP_BHLHE41_CASP3_SESN1_SESN2 | 7.39E−09 |
| BCL2L1_BNIP3_TKT_XIAP_CASP3_SESN1_SESN2 | 7.50E−09 |
| ATG3_BCL2L1_NNMT_PRKAA1_ID2_CASP3_SIRT1 | 7.60E−09 |
| BCL2L1_CASP8_NNMT_ID2_CASP3_RAGE_SESN2 | 7.80E−09 |
| BNIP3_PTEN_TKT_XIAP_CASP3_RAGE_SESN2 | 7.83E−09 |
| ATG3_BCL2L1_NNMT_PRKAA1_ID2_SESN1_SESN2 | 8.10E−09 |
| BCL2L1_BNIP3_TKT_XIAP_CASP3_RPS19BP1_SESN2 | 8.10E−09 |
| BCL2L1_FRAP1_PTEN_TKT_XIAP_CASP3_SESN2 | 8.45E−09 |
| BCL2L1_NNMT_ID2_BHLHE41_CASP3_SESN2_SESN3 | 8.80E−09 |
| BCL2L1_CASP8_PTEN_TKT_XIAP_CASP3_SESN2 | 8.90E−09 |
| BNIP3_PTEN_TKT_XIAP_ID2_CASP3_SESN2 | 9.68E−09 |
| ATG3_BCL2L1_NNMT_PRKAA1_XIAP_CASP3_SIRT1 | 1.00E−08 |
| BCL2L1_BNIP3_NNMT_TKT_XIAP_CASP3_SESN2 | 1.00E−08 |
| BCL2_BCL2L1_BHLHE41_CASP3_SESN1_SESN2 | 1.05E−08 |
| ATG3_BCL2L1_BNIP3_NNMT_PRKAA1_ID2_FASLG | 1.10E−08 |
| ATG3_BCL2L1_NNMT_ID2_CASP3_HMGB1_SESN2 | 1.10E−08 |
| BCL2L1_NNMT_PRKAA1_ID2_CASP3_RAGE_SESN2 | 1.12E−08 |
| BCL2L1_PRKAA1_TKT_XIAP_ID2_CASP3_SESN2 | 1.16E−08 |
| BCL2L1_NNMT_PRKAA1_ID2_HMGB1_SESN1_SESN2 | 1.16E−08 |
| BCL2L1_TKT_ID2_BHLHE41_CASP3_SESN1_SESN2 | 1.17E−08 |
| ATG3_BCL2L1_BNIP3_TKT_XIAP_CASP3_SESN2 | 1.20E−08 |
| BCL2L1_BNIP3_NNMT_TKT_ID2_CASP3_SESN2 | 1.20E−08 |
| BCL2L1_NNMT_ID2_CASP3_HMGB1_RAGE_SESN2 | 1.23E−08 |
| BCL2L1_PRKAA1_TKT_XIAP_CASP3_RAGE_SESN2 | 1.24E−08 |
| BCL2L1_PRKAA1_TKT_XIAP_CASP3_HMGB1_SESN2 | 1.25E−08 |
| BCL2L1_NNMT_XIAP_ID2_BHLHE41_CASP3_SESN2 | 1.26E−08 |
| BCL2L1_TKT_BHLHE4'1_CASP3_RAGE_SESN1_SESN2 | 1.26E−08 |
| BCL2L1_NNMT_ID2_BHLHE41_CASP3_CCNG2_SESN2 | 1.29E−08 |
| BCL2L1_NNMT_BECN1_CASP3_RAGE_SESN2 | 1.29E−08 |
| BCL2L1_BNIP3_TKT_XIAP_ID2_CASP3_SESN2 | 1.30E−08 |
| BNIP3_TKT_XIAP_ID2_CASP3_RAGE_SESN2 | 1.33E−08 |
| BCL2L1_PTEN_TKT_XIAP_CASP3_SESN1_SESN2 | 1.36E−08 |
| BCL2L1_PTEN_TKT_CASP3_HMGB1_SESN1_SESN2 | 1.39E−08 |
| BCL2L1_NNMT_ID2_BHLHE41_CASP3_RAGE_SESN2 | 1.40E−08 |
| BCL2L1_NNMT_ID2_BHLHE41_CASP3_RAGE_SESN2 | 1.40E−08 |
| AIFM1_BCL2L1_NNMT_ID2_CASP3_RAGE_SESN2 | 1.40E−08 |
| BCL2L1_NNMT_ID2_CASP3_CDH2_RAGE_SESN2 | 1.41E−08 |
| BCL2L1_NNMT_CDH1_ID2_CASP3_RAGE_SESN2 | 1.44E−08 |
| BCL2L1_NNMT_ID2_AGER_CASP3_RAGE_SESN2 | 1.44E−08 |
| BNIP3_PTEN_TKT_XIAP_CASP3_SESN1_SESN2 | 1.45E−08 |
| BNIP3_PTEN_TKT_XIAP_CASP3_HMGB1_SESN2 | 1.47E−08 |
| BNIP3_TKT_XIAP_CASP3_HMGB1_RAGE_SESN2 | 1.48E−08 |
| BCL2L1_NNMT_ID2_CASP3_MMP2_RAGE_SESN2 | 1.49E−08 |
| ATG5_BCL2L1_NNMT_PRKAA1_ID2_SESN1_SESN2 | 1.50E−08 |
| BCL2L1_BNIP3_TKT_ID2_CASP3_RPS19BP1_SESN2 | 1.50E−08 |
| BCL2L1_NNMT_ID2_CASP3_RAGE_SESN1_SESN2 | 1.50E−08 |
| BCL2L1_NNMT_TKT_ID2_BHLHE41_CASP3_SESN2 | 1.53E−08 |
| BCL2L1_PTEN_TKT_BHLHE41_CASP3_SESN1_SESN2 | 1.53E−08 |
| BCL2L1_CSE1L_NNMT_ID2_CASP3_RAGE_SESN2 | 1.57E−08 |
| BCL2L1_PTEN_TKT_CASP3_RAGE_SESN1_SESN2 | 1.57E−08 |
| BNIP3_TKT_XIAP_CASP3_CCNG2_RAGE_SESN2 | 1.59E−08 |
| ATG3_BCL2L1_BNIP3_TKT_CASP3_FASLG_SESN2 | 1.60E−08 |
| BCL2L1_BNIP3_E2F1_TKT_XIAP_CASP3_SESN2 | 1.60E−08 |
| BCL2L1_CDH1_ID2_MMP9_TCF3_CASP3_SESN2 | 4.96E−08 |
| Disease-free survival | |
| ATG3_ATG5_ATG7_FRAP1_LC3_SESN2_SIRT1 | 9.03E−08 |
| ATG3_ATG5_CSE1L_FRAP1_LC3_SESN2_SIRT1 | 1.06E−07 |
| ATG5_CSE1L_FRAP1_LC3_SESN2_SIRT1_UVRAG | 1.21E−07 |
| AKT1_ATG5_CSE1L_FRAP1_LC3_SESN2_SIRT1 | 1.24E−07 |
| ATG5_CSE1L_FRAP1_LC3_SATB1_SESN2_SIRT1 | 1.26E−07 |
| ATG5_CSE1L_FRAP1_LC3_SESN2_SESN3_SIRT1 | 1.27E−07 |
| ATG5_ATG7_CSE1L_FRAP1_LC3_SESN2_SIRT1 | 1.31E−07 |
| ATG5_CSE1L_DIABLO_FRAP1_LC3_SESN2_SIRT1 | 1.37E−07 |
| ATG5_CSE1L_RAP1_LC3_ID2_SESN2_SIRT1 | 1.37E−07 |
| ATG5_CSE1L_DRAM_FRAP1_LC3_SESN2_SIRT1 | 1.39E−07 |
| ATG3_ATG5_DRAM_FRAP1_LC3_SESN2_SIRT1 | 1.45E−07 |
| ATG5_BNIP3_CSE1L_FRAP1_LC3_SESN2_SIRT1 | 1.64E−07 |
| ATG5_CSE1L_FRAP1_LC3_SESN2_SIRT1_STAT3 | 1.76E−07 |
| ATG3_ATG5_DIABLO_FRAP1_LC3_SESN2_SIRT1 | 1.78E−07 |
| ATG3_ATG5_FRAP1_LC3_SESN2_SESN3_SIRT1 | 1.80E−07 |
| AKT1_ATG3_ATG5_FRAP1_LC3_SESN2_SIRT1 | 1.84E−07 |
| ATG5_CSE1L_E2F1_LC3_SESN2_SIRT1 | 1.86E−07 |
| ATG3_ATG5_FRAP1_LC3_ID2_SESN2_SIRT1 | 1.94E−07 |
| ATG5_ATG7_DRAM_FRAP1_LC3_SESN2_SIRT1 | 1.96E−07 |
| ATG5_CSE1L_FRAP1_LAMP1_SESN2_SIRT1 | 2.01E−07 |
| AIFM1_ATG12_TKT_CDH1_FASLG_LAMP2_SESN2 | 2.13E−07 |
| ATG5_CSE1L_FRAP1_LC3_CDH1_SESN2_SIRT1 | 2.16E−07 |
| ATG5_ATG7_FRAP1_LC3_SESN2_SIRT1_STAT3 | 2.25E−07 |
| AKT1_ATG5_ATG7_FRAP1_LC3_SESN2_SIRT1 | 2.25E−07 |
| ATG5_ATG7_DIABLO_FRAP1_LC3_SESN2_SIRT1 | 2.26E−07 |
| ATG5_ATG7_FRAP1_LC3_SESN2_SESN3_SIRT1 | 2.28E−07 |
| ATG3_ATG5_FRAP1_LC3_SESN2_SIRT1_STAT3 | 2.47E−07 |
| ATG5_ATG7_FRAP1_LC3_ID2_SESN2_SIRT1 | 2.50E−07 |
| ATG3_ATG5_FRAP1_LC3_RPS19BP1_SESN2_SIRT1 | 2.59E−07 |
| ATG3_ATG5_E2F1_FRAP1_LC3_SESN2_SIRT1 | 2.60E−07 |
| ATG3_ATG5_FRAP1_LC3_SESN2_SIRT1_UVRAG | 2.61E−07 |
| ATG12_ATG5_CSE1L_FRAP1_LC3_SESN2_SIRT1 | 2.61E−07 |
| ATG3_ATG5_BNIP3_FRAP1_LC3_SESN2_SIRT1 | 2.73E−07 |
| ATG5_ATG7_FRAP1_LC3_SESN2_SIRT1_UVRAG | 2.77E−07 |
| ATG5_ATG7_E2F1_FRAP1_LC3_SESN2_SIRT1 | 2.86E−07 |
| AIFM1_ATG12_TKT_CIAP2_FASLG_LAMP2_SESN2 | 2.89E−07 |
| ATG5_CSE1L_FRAP1_LC3_MMP9_SESN2_SIRT1 | 2.94E−07 |
| ATG3_ATG5_FRAP1_LC3_MMP9_SESN2_SIRT1 | 3.12E−07 |
| ATG7_TKT_FASLG_LAMP2_SESN2_SESN3_SIRT1 | 3.20E−07 |
| ATG7_TKT_FASLG_LAMP2_SESN2_SESN3_SIRT1 | 3.20E−07 |
| ATG5_ATG7_BNIP3_FRAP1_LC3_SESN2_SIRT1 | 3.31E−07 |
| ATG3_ATG7_CSE1L_FRAP1_LC3_SESN2_SIRT1 | 3.32E−07 |
| ATG3_ATG5_CSE1L_DIABLO_FRAP1_LC3_SESN2 | 3.35E−07 |
| ATG7_CSE1L_FRAP1_LC3_SESN2_SIRT1_UVRAG | 3.39E−07 |
| AKT1_ATG3_ATG5_CSE1L_FRAP1_LC3_SESN2 | 3.46E−07 |
| ATG12_ATG3_ATG5_FRAP1_LC3_SESN2_SIRT1 | 3.46E−07 |
| AIFM1_ATG12_NNMT_CIAP2_FASLG_LAMP2_SESN2 | 3.48E−07 |
| ATG5_ATG7_FRAP1_LC3_RPS19BP1_SESN2_SIRT1 | 3.52E−07 |
| ATG3_CSE1L_FRAP1_LC3_SATB1_SESN2_SIRT1 | 3.54E−07 |
| ATG5_ATG7_CSE1L_DIABLO_FRAP1_LC3_SESN2 | 3.59E−07 |
| ATG3_CSE1L_FRAP1_LC3_SESN2_SIRT1_UVRAG | 3.63E−07 |
| ATG3_ATG5_ATG7_CSE1L_FRAP1_LC3_SESN2 | 3.64E−07 |
| AKT1_ATG5_ATG7_CSE1L_FRAP1_LC3_SESN2 | 3.75E−07 |
| ATG3_ATG5_CSE1L_FRAP1_LC3_ID2_SESN2 | 3.81E−07 |
| ATG3_ATG5_CSE1L_FRAP1_LC3_SESN2_SESN3 | 3.84E−07 |
| AKT1_ATG7_CSE1L_FRAP1_LC3_SESN2_SIRT1 | 3.92E−07 |
| AKT1_ATG3_CSE1L_FRAP1_LC3_SESN2_SIRT1 | 3.93E−07 |
| ATG7_CSE1L_FRAP1_LC3_SATB1_SESN2_SIRT1 | 3.94E−07 |
| ATG7_TKT_CDH1_ID2_MMP9_TCF3_SESN2 | 5.56E−05 |

TABLE 37

| Marker | p-value |
|---|---|
| Recurrence | |
| ATG3_ATG7_LC3_ID2_FASLG_LAMP2_SESN2_SIRT1 | 3.42E−08 |
| FRAP1_LC3_CIAP2_FASLG_LAMP2_NAMPT_SESN2_SIRT1 | 4.14E−08 |
| FRAP1_LC3_CIAP2_FASLG_LAMP2_MMP2_SESN2_SIRT1 | 4.37E−08 |
| MMP9_CCNG2_CIAP2_FASLG_LAMP2_NAMPT_SESN2_SIRT1 | 4.52E−08 |

TABLE 37-continued

| Marker | p-value |
|---|---|
| FRAP1_LC3_CCNG2_CIAP2_FASLG_LAMP2_SESN2_SIRT1 | 4.53E−08 |
| ATG5_FRAP1_LC3_CIAP2_FASLG_LAMP2_SESN2_SIRT1 | 4.58E−08 |
| FRAP1_LC3_CIAP2_FASLG_HMGB1_LAMP2_SESN2_SIRT1 | 4.90E−08 |
| CCNG2_CIAP2_FASLG_LAMP2_MMP2_NAMPT_SESN2_SIRT1 | 4.94E−08 |
| LC3_CCNG2_CIAP2_FASLG_LAMP2_MMP2_SESN2_SIRT1 | 4.98E−08 |
| LC3_NNMT_CIAP2_FASLG_LAMP2_MMP2_SESN2_SIRT1 | 5.07E−08 |
| FRAP1_LC3_AGER_CIAP2_FASLG_LAMP2_SESN2_SIRT1 | 5.20E−08 |
| LC3_CCNG2_CIAP2_FASLG_LAMP2_NAMPT_SESN2_SIRT1 | 5.31E−08 |
| ATG3_ATG7_LC3_FASLG_LAMP2_SESN2_SIRT1_STAT3 | 5.51E−08 |
| NNMT_MMP9_CCNG2_CIAP2_FASLG_LAMP2_SESN2_SIRT1 | 5.52E−08 |
| FRAP1_AGER_CIAP2_FASLG_LAMP2_NAMPT_SESN2_SIRT1 | 5.78E−08 |
| FRAP1_CCNG2_CIAP2_FASLG_LAMP2_NAMPT_SESN2_SIRT1 | 5.85E−08 |
| CIAP2_FASLG_LAMP2_MMP2_NAMPT_SESN1_SESN2_SIRT1 | 5.86E−08 |
| MMP9_CCNG2_CIAP2_FASLG_HMGB1_LAMP2_SESN2_SIRT1 | 5.98E−08 |
| TCF3_CCNG2_CIAP2_FASLG_LAMP2_MMP2_SESN2_SIRT1 | 6.03E−08 |
| TCF3_CCNG2_CIAP2_FASLG_LAMP2_NAMPT_SESN2_SIRT1 | 6.04E−08 |
| CCNG2_CIAP2_FASLG_LAMP2_NAMPT_SATB1_SESN2_SIRT1 | 6.05E−08 |
| FAS_CCNG2_CIAP2_FASLG_LAMP2_NAMPT_SESN2_SIRT1 | 6.08E−08 |
| NNMT_CCNG2_CIAP2_FASLG_LAMP2_MMP2_SESN2_SIRT1 | 6.08E−08 |
| ATG3_ATG7_BNIP3_LC3_FASLG_LAMP2_SESN2_SIRT1 | 6.10E−08 |
| AKT1_MMP9_CCNG2_CIAP2_FASLG_LAMP2_SESN2_SIRT1 | 6.11E−08 |
| LC3_CCNG2_CIAP2_FASLG_LAMP2_SATB1_SESN2_SIRT1 | 6.12E−08 |
| MMP9_CCNG2_CIAP2_FASLG_LAMP2_MMP2_SESN2_SIRT1 | 6.15E−08 |
| FRAP1_LC3_NNMT_CIAP2_FASLG_LAMP2_SESN2_SIRT1 | 6.16E−08 |
| FRAP1_MMP9_CCNG2_CIAP2_FASLG_LAMP2_SESN2_SIRT1 | 6.19E−08 |
| ATG7_BNIP3_LC3_ID2_FASLG_LAMP2_SESN2_SIRT1 | 6.22E−08 |
| ATG7_BNIP3_LC3_FASLG_LAMP2_SESN2_SIRT1_STAT3 | 6.24E−08 |
| LC3_TCF3_CCNG2_CIAP2_FASLG_LAMP2_SESN2_SIRT1 | 6.25E−08 |
| CIAP2_FASLG_HMGB1_LAMP2_NAMPT_SESN1_SESN2_SIRT1 | 6.30E−08 |
| CCNG2_CIAP2_FASLG_LAMP2_MMP2_SESN2_SESN3_SIRT1 | 6.34E−08 |
| ATG3_ATG7_LC3_BECN1_FASLG_LAMP2_SESN2_SIRT1 | 6.36E−08 |
| ATG3_ATG7_FRAP1_LC3_FASLG_LAMP2_SESN2_SIRT1 | 6.36E−08 |
| NNMT_CCNG2_CIAP2_FASLG_LAMP2_NAMPT_SESN2_SIRT1 | 6.37E−08 |
| ATG7_BNIP3_LC3_FASLG_LAMP2_SESN2_SESN3_SIRT1 | 6.47E−08 |
| FRAP1_LC3_TCF3_CIAP2_FASLG_LAMP2_SESN2_SIRT1 | 6.49E−08 |
| FAS_CCNG2_CIAP2_FASLG_LAMP2_MMP2_SESN2_SIRT1 | 6.53E−08 |
| CCNG2_CIAP2_FASLG_HMGB1_LAMP2_NAMPT_SESN2_SIRT1 | 6.57E−08 |
| CCNG2_CIAP2_FASLG_LAMP2_NAMPT_SESN1_SESN2_SIRT1 | 6.68E−08 |
| ATG7_BNIP3_LC3_FASLG_LAMP2_SATB1_SESN2_SIRT1 | 6.70E−08 |
| BCL2_MMP9_CCNG2_CIAP2_FASLG_LAMP2_SESN2_SIRT1 | 6.93E−08 |
| ULK1_MMP9_CCNG2_CIAP2_FASLG_LAMP2_SESN2_SIRT1 | 6.88E−08 |
| LC3_NNMT_CIAP2_FASLG_LAMP2_NAMPT_SESN2_SIRT1 | 7.02E−08 |
| LC3_CIAP2_FASLG_LAMP2_MMP2_NAMPT_SESN2_SIRT1 | 7.13E−08 |
| BCL2_FRAP1_LC3_CIAP2_FASLG_LAMP2_SESN2_SIRT1 | 7.25E−08 |
| AKT1_CCNG2_CIAP2_FASLG_LAMP2_MMP2_SESN2_SIRT1 | 7.27E−08 |
| ATG7_BNIP3_LC3_MMP9_FASLG_LAMP2_SESN2_SIRT1 | 7.32E−08 |
| MMP9_AGER_CCNG2_CIAP2_FASLG_LAMP2_SESN2_SIRT1 | 7.33E−08 |
| FRAP1_LC3_ULK1_CIAP2_FASLG_LAMP2_SESN2_SIRT1 | 7.38E−08 |
| LC3_NNMT_CIAP2_FASLG_LAMP2_SATB1_SESN2_SIRT1 | 7.51E−08 |
| CASP3_CCNG2_CIAP2_FASLG_LAMP2_NAMPT_SESN2_SIRT1 | 7.52E−08 |
| LC3_CDH2_CIAP2_FASLG_LAMP2_NAMPT_SESN2_SIRT1 | 7.54E−08 |
| LC3_NNMT_CCNG2_CIAP2_FASLG_LAMP2_SESN2_SIRT1 | 7.56E−08 |
| ATG3_ATG7_LC3_CDH1_FASLG_LAMP2_SESN2_SIRT1 | 7.57E−08 |
| TKT_CDH1_ID2_MMP9_TCF3_LAMP2_SESN2_SIRT1 | 4.43E−06 |
| Survival | |
| BCL2L1_NNMT_PRKAA1_PTEN_XIAP_ID2_CASP3_SESN2 | 4.96E−10 |
| BCL2L1_NNMT_ID2_BHLHE41_CASP3_SESN1_SESN2_SESN3 | 9.32E−10 |
| BCL2L1_PRKAA1_PTEN_TKT_XIAP_CASP3_HMGB1_SESN2 | 1.02E−09 |
| BCL2L1_PRKAA1_PTEN_TKT_XIAP_CASP3_SESN1_SESN2 | 1.07E−09 |
| BCL2L1_NNMT_PRKAA1_XIAP_ID2_CASP3_SESN2_SESN3 | 1.17E−09 |
| ATG3_BCL2L1_NNMT_PRKAA1_XIAP_ID2_CASP3_SESN2 | 1.20E−09 |
| BCL2L1_NNMT_PRKAA1_XIAP_ID2_CASP3_SESN1_SESN2 | 1.22E−09 |
| BCL2_BCL2L1_NNMT_ID2_BHLHE41_CASP3_SESN1_SESN2 | 1.32E−09 |
| BCL2L1_PRKAA1_PTEN_TKT_XIAP_CASP3_RAGE_SESN2 | 1.35E−09 |
| BCL2L1_NNMT_XIAP_ID2_BHLHE41_CASP3_SESN1_SESN2 | 1.36E−09 |
| BCL2L1_NNMT_PRKAA1_XIAP_ID2_CASP3_HMGB1_SESN2 | 1.36E−09 |
| BCL2L1_PRKAA1_PTEN_TKT_XIAP_ID2_CASP3_SESN2 | 1.47E−09 |
| BCL2L1_NNMT_PRKAA1_XIAP_ID2_CASP3_RAGE_SESN2 | 1.56E−09 |
| BCL2L1_PRKAA1_PTEN_TKT_XIAP_CASP3_SESN2_SESN3 | 1.84E−09 |
| BCL2L1_BNIP3_TKT_XIAP_CASP3_RPS19BP1_SESN1_SESN2 | 1.86E−09 |
| BCL2L1_NNMT_ID2_BHLHE41_CASP3_CCNG2_SESN1_SESN2 | 1.92E−09 |
| BCL2L1_BNIP3_TKT_XIAP_ID2_CASP3_RPS19BP1_SESN2 | 2.05E−09 |
| ATG3_BCL2L1_NNMT_PRKAA1_ID2_HMGB1_SESN1_SESN2 | 2.10E−09 |
| BCL2L1_TKT_XIAP_BHLHE41_CASP3_SESN1_SESN2_SESN3 | 2.20E−09 |
| BCL2L1_NNMT_ID2_BHLHE41_CASP3_HMGB1_SESN1_SESN2 | 2.24E−09 |
| ATG3_BCL2L1_CASP8_NNMT_XIAP_ID2_CASP3_SESN2 | 2.30E−09 |
| ATG5_BCL2L1_NNMT_PRKAA1_XIAP_ID2_CASP3_SESN2 | 2.40E−09 |

TABLE 37-continued

| Marker | p-value |
|---|---|
| BCL2L1_NNMT_PRKAA1_XIAP_ID2_CASP3_MMP2_SESN2 | 2.41E−09 |
| BCL2L1_BNIP3_TKT_XIAP_CASP3_RAGE_RPS19BP1_SESN2 | 2.46E−09 |
| BCL2L1_NNMT_ID2_BHLHE41_CASP3_CCNG2_SESN2_SESN3 | 2.50E−09 |
| BCL2L1_PRKAA1_PTEN_TKT_XIAP_CASP3_MMP2_SESN2 | 2.52E−09 |
| BCL2L1_PRKAA1_PTEN_TKT_XIAP_CASP3_CCNG2_SESN2 | 2.52E−09 |
| BCL2_BCL2L1_PRKAA1_PTEN_TKT_XIAP_CASP3_SESN2 | 2.54E−09 |
| ATG5_BCL2L1_PRKAA1_PTEN_TKT_XIAP_CASP3_SESN2 | 2.60E−09 |
| BCL2L1_NNMT_PRKAA1_PTEN_TKT_XIAP_CASP3_SESN2 | 2.61E−09 |
| BCL2L1_NNMT_PRKAA1_CIAP_ID2_AGER_CASP3_SESN2 | 2.65E−09 |
| BCL2L1_NNMT_ID2_BHLHE41_CASP3_RAGE_SESN1_SESN2 | 2.67E−09 |
| BCL2L1_NNMT_PRKAA1_XIAP_ID2_CASP3_LAMP2_SESN2 | 2.67E−09 |
| BCL2L1_BNIP3_NNMT_TKT_XIAP_ID2_CASP3_SESN2 | 2.71E−09 |
| ATG12_BCL2L1_NNMT_PRKAA1_XIAP_ID2_CASP3_SESN2 | 2.80E−09 |
| BCL2L1_NNMT_PRKAA1_XIAP_ID2_BECN1_CASP3_SESN2 | 2.85E−09 |
| BCL2L1_NNMT_PRKAA1_XIAP_ID2_CASP3_CDH2_SESN2 | 2.95E−09 |
| AIFM1_BCL2L1_NNMT_PRKAA1_XIAP_ID2_CASP3_SESN2 | 3.00E−09 |
| ATG12_BCL2L1_PRKAA1_PTEN_TKT_XIAP_CASP3_SESN2 | 3.00E−09 |
| BAX_BCL1L2_NNMT_PRKAA1_XIAP_ID2_CASP3_SESN2 | 3.00E−09 |
| BCL2L1_PRKAA1_PTEN_TKT_XIAP_CASP3_LAMP2_SESN2 | 3.02E−09 |
| BCL2L1_PRKAA1_PTEN_TKT_XIAP_AGER_CASP3_SESN2 | 3.03E−09 |
| AKT1_BCL2L1_NNMT_PRKAA1_XIAP_ID2_CASP3_SESN2 | 3.10E−09 |
| BAX_BCL2L1_PRKAA1_PTEN_TKT_XIAP_CASP3_SESN2 | 3.10E−09 |
| BCL2L1_PTEN_TKT_XIAP_BHLHE41_CASP3_SESN1_SESN2 | 3.11E−09 |
| BCL2L1_PRKAA1_PTEN_TKT_XIAP_BECN1_CASP3_SESN2 | 3.15E−09 |
| BCL2L1_PRKAA1_PTEN_TKT_XIAP_CASP3_CDH2_SESN2 | 3.17E−09 |
| BCL2L1_CASP8_NNMT_ID2_CASP3_HMGB1_RAGE_SESN2 | 3.17E−09 |
| BCL2L1_CASP8_PTEN_TKT_XIAP_CASP3_SESN1_SESN2 | 3.18E−09 |
| ATG3_BCL2L1_BNIP3_NNMT_PRKAA1_ID2_FASLG_KIAA1967 | 3.20E−09 |
| BCL2L1_NNMT_XIAP_ID2_BHLHE41_CASP3_SESN2_SESN3 | 3.20E−09 |
| BCL2L1_CSE1L_NNMT_PRKAA1_XIAP_ID2_CASP3_SESN2 | 3.21E−09 |
| BCL2L1_NNMT_ID2_BHLHE41_CASP3_SESN1_SESN2_STAT3 | 3.22E−09 |
| BCL2L1_FRAP1_PTEN_TKT_XIAP_CASP3_HMGB1_SESN2 | 3.30E−09 |
| BCL2L1_NNMT_XIAP_BHLHE41_CASP3_SESN1_SESN2_SESN3 | 3.31E−09 |
| BNIP3_PTEN_TKT_XIAP_CASP3_RAGE_SESN1_SESN2 | 3.33E−09 |
| BCL2L1_NNMT_PRKAA1_ID2_HMGB1_HMGB2_SESN1_SESN2 | 3.34E−09 |
| BCL2L1_TKT_CDH1_ID2_MMP9_TCF3_CASP3_SESN2 | 6.82E−07 |
| Disease-free survival | |
| ATG3_ATG5_ATG7_FRAP1_LC3_SESN2_SIRT1_STAT3 | 7.38E−08 |
| AIFM1_ATG12_TKT_CDH1_FASLG_HMGB1_LAMP2_SESN2 | 8.07E−08 |
| ATG3_ATG5_ATG7_DRAM_FRAP1_LC3_SESN2_SIRT1 | 8.31E−08 |
| AKT1_ATG3_ATG5_ATG7_FRAP1_LC3_SESN2_SIRT1 | 8.83E−08 |
| ATG3_ATG5_ATG7_FRAP1_LC3_SESN2_SESN3_SIRT1 | 9.09E−08 |
| ATG3_ATG5_CSE1L_FRAP1_LC3_SESN2_SIRT1_UVRAG | 9.20E−08 |
| ATG3_ATG5_ATG7_DIABLO_FRAP1_LC3_SESN2_SIRT1 | 9.25E−08 |
| ATG3_ATG5_ATG7_FRAP1_LC3_SESN2_SIRT1_UVRAG | 9.91E−08 |
| AKT1_ATG3_ATG5_CSE1L_FRAP1_LC3_SESN2_SIRT1 | 1.01E−07 |
| ATG3_ATG5_ATG7_FRAP1_LC3_ID2_SESN2_SIRT1 | 1.02E−07 |
| ATG3_ATG5_CSE1L_FRAP1_LC3_SESN2_SESN3_SIRT1 | 1.05E−07 |
| ATG5_ATG7_CSE1L_FRAP1_LC3_SESN2_SIRT1_UVRAG | 1.05E−07 |
| ATG3_ATG5_CSE1L_FRAP1_LC3_SATB1_SESN2_SIRT1 | 1.07E−07 |
| AIFM1_ATG12_NNMT_CIAP2_FASLG_LAMP2_SESN2_SIRT1 | 1.08E−07 |
| ATG5_CSE1L_FRAP1_LC3_SATB1_SESN2_SIRT1_UVRAG | 1.14E−07 |
| ATG3_ATG5_CSE1L_DIABLO_FRAP1_LC3_SESN2_SIRT1 | 1.14E−07 |
| ATG3_ATG5_CSE1L_FRAP1_LC3_ID2_SESN2_SIRT1 | 1.15E−07 |
| AIFM1_ATG12_TKT_CDH1_CIAP2_FASLG_LAMP2_SESN2 | 1.17E−07 |
| AIFM1_ATG12_NNMT_AGER_CIAP2_FASLG_LAMP2_SESN2 | 1.17E−07 |
| AKT1_ATG5_CSE1L_FRAP1_LC3_SESN2_SIRT1_UVRAG | 1.18E−07 |
| ATG3_ATG5_CSE1L_DRAM_FRAP1_LC3_SESN2_SIRT1 | 1.19E−07 |
| ATG5_CSE1L_FRAP1_LC3_SESN2_SESN3_SIRT1_UVRAG | 1.20E−07 |
| AKT1_ATG5_CSE1L_FRAP1_LC3_SATB1_SESN2_SIRT1 | 1.20E−07 |
| AKT1_ATG5_CSE1L_FRAP1_LC3_SESN2_SESN3_SIRT1 | 1.23E−07 |
| AKT1_ATG5_ATG7_CSE1L_FRAP1_LC3_SESN2_SIRT1 | 1.24E−07 |
| AIFM1_ATG12_NNMT_CDH2_CIAP2_FASLG_LAMP2_SESN2 | 1.25E−07 |
| ATG3_ATG5_ATG7_BNIP3_FRAP1_LC3_SESN2_CIRT1 | 1.25E−07 |
| ATG5_CSE1L_FRAP1_LC3_SATB1_SESN2_SESN3_SIRT1 | 1.26E−07 |
| ATG5_CSE1L_DRAM_FRAP1_LC3_SESN2_SIRT1_UVRAG | 1.27E−07 |
| AIFM1_ATG12_TKT_CDH1_AGER_FASLG_LAMP2_SESN2 | 1.27E−07 |
| ATG3_ATG5_ATG7_CSE1L_FRAP1_LC3_SESN2_SIRT1 | 1.27E−07 |
| ATG5_CSE1L_DIABLO_FRAP1_LC3_SESN2_SIRT1_UVRAG | 1.27E−07 |
| ATG5_CSE1L_FRAP1_LC3_ID2_SESN2_SIRT1_UVRAG | 1.27E−07 |
| ATG3_ATG5_BNIP3_CSE1L_FRAP1_LC3_SESN2_SIRT1 | 1.30E−07 |
| ATG5_ATG7_CSE1L_FRAP1_LC3_SESN2_SESN3_SIRT1 | 1.31E−07 |
| ATG3_ATG5_ATG7_FRAP1_LAMP1_LC3_SESN2_SIRT1 | 1.32E−07 |
| AKT1_ATG5_CSE1L_DIABLO_FRAP1_LC3_SESN2_SIRT1 | 1.32E−07 |
| AKT1_ATG5_CSE1L_FRAP1_LC3_ID2_SESN2_SIRT1 | 1.32E−07 |
| AIFM1_DRAM_TKT_CDH1_FASLG_LAMP2_SESN2_SIRT1 | 1.33E−07 |
| AKT1_ATG5_CSE1L_DRAM_FRAP1_LC3_SESN2_SIRT1 | 1.34E−07 |

TABLE 37-continued

| Marker | p-value |
|---|---|
| ATG5_CSE1L_DIABLO_FRAP1_LC3_SATB1_SESN2_SIRT1 | 1.34E−07 |
| ATG5_CSE1L_FRAP1_LC3_ID2_SATB1_SESN2_SIRT1 | 1.35E−07 |
| ATG3_ATG5_CSE1L_FRAP1_LC3_SESN2_SIRT1_STAT3 | 1.35E−07 |
| ATG5_CSE1L_DIABLO_FRAP1_LC3_SESN2_SESN3_SIRT1 | 1.36E−07 |
| ATG5_CSE1L_FRAP1_LC3_ID2_SESN2_SESN3_SIRT1 | 1.36E−07 |
| ATG5_CSE1L_DRAM_FRAP1_LC3_SESN2_SESN3_SIRT1 | 1.38E−07 |
| ATG5_CSE1L_DRAM_FRAP1_LC3_SATB1_SESN2_SIRT1 | 1.40E−07 |
| ATG3_ATG5_ATG7_E2F1_FRAP1_LC3_SESN2_SIRT1 | 1.42E−07 |
| ATG5_ATG7_CSE1L_FRAP1_LC3_SESN2_SIRT1_STAT3 | 1.43E−07 |
| ATG5_ATG7_CSE1L_DIABLO_FRAP1_LC3_SESN2_SIRT1 | 1.43E−07 |
| AIFM1_DRAM_TKT_CIAP2_FASLG_LAMP2_SESN2_SIRT1 | 1.43E−07 |
| ATG5_ATG7_CSE1L_FRAP1_LAMP1_LC3_SESN2_SIRT1 | 1.43E−07 |
| ATG3_ATG5_DIABLO_DRAM_FRAP1_LC3_SESN2_SIRT1 | 1.44E−07 |
| ATG5_ATG7_CSE1L_FRAP1_LC3_ID2_SESN2_SIRT1 | 1.44E−07 |
| AIFM1_ATG12_MMP9_AGER_FASLG_LAMP2_SESN2_SIRT1 | 1.44E−07 |
| ATG3_ATG5_DRAM_FRAP1_LC3_SESN2_SESN3_SIRT1 | 1.45E−07 |
| ATG5_ATG7_CSE1L_FRAP1_LC3_SATB1_SESN2_SIRT1 | 1.45E−07 |
| TKT_CDH1_ID2_MMP9_TCF3_FASLG_SESN2_SIRT1 | 1.20E−05 |

As can be confirmed from the above tables, each of the markers or their combination shows p-values low enough to be considered significant in terms of all of recurrence, survival, and disease-free survival. In particular, in the case of the combination of the two or more markers, all the p-values for recurrence, survival, and disease-free survival were low. In particular, it was found that there were cases where the p-value for a single marker was relatively high but the p-value decreased when the marker was used in combination with other marker. As a p-value becomes lower, the statistical significance becomes higher. Thus, the low p-values suggest that the estimation for prognosis of liver cancer by each of the markers or their combination is highly accurate.

This means that the more markers of the present disclosure are combined, the lower p-values, which means higher significance, are shown, which means that the more improved accuracy would be achieved in the estimation for prognosis based on the combinations of the markers.

Thus, it was found that the markers and/or the combinations of markers of Tables 30~37 are effective in predicting prognosis of liver cancer of the A2 group (recurrence, survival, disease-free survival), and that the prognosis of liver cancer of the A2 group can be predicted effectively by nucleic acids and antibodies targeted at the markers.

Also, it can be found that the prognosis of liver cancer of the A2 group can be predicted effectively by the method for predicting prognosis of liver cancer of the present disclosure, which is targeted at the markers.

Further, cross-validation was performed for combinations of markers which were considered statistically significant. Patients of each patient group were randomly divided into two groups (positive group: 62 patients; test group: 61 patients). With the reference value which was considered statistically significant in the results of the positive group obtained in the same manner as Example 1 fixed, for the test group, the accuracy of estimation was calculated to be the level of $p<0.05$ or $p<0.001$ with respect to recurrence, survival and disease-free survival.

Among the results of cross-validation of the prediction of the recurrence, survival and disease-free survival of the A2 group, representative examples showing the excellent accuracy of prognosis in each aspect are as follows:

Recurrence: TKT_SESN2_VEGF (65.0% at the level of $p<0.05$)

Survival: DIABLO_FAS_LAMP1_BHLHE41_SESN2 (83.3% at the level of $p<0.05$)

Disease-free survival: TKT_SESN2_VEGF (82.0% at the level of $p<0.05$)

Example 4: Predicting Prognosis of Liver Cancer in the B Group

An experiment was performed in the same manner as in Example 1, except for experimenting on a patient group determined as the B group {a group of portal vein invasion-negative patients in intermediate stage of BCLC staging system, having plural tumors which are more than 3 cm in size or plural tumors which are more than 3 in number} (78 patients). Kaplan-Meier curves were prepared with respect to the prediction of recurrence, survival, and disease-free survival and the results are shown in FIGS. 65~85. Kaplan-Meier curves for recurrence are shown in FIGS. 65~71, Kaplan-Meier curves for survival are shown in FIGS. 72~78, and Kaplan-Meier curves for disease-free survival are shown in FIGS. 79~85.

As can be seen from the drawings, in Kaplan-Meier curves completed with respect to recurrence, survival, and disease-free survival, the above markers form curves where cases of high expression and low expression are distinctively distinguished from each other. This means that there are remarkable differences in interval recurrence rate or interval survival rate and cumulative recurrence rate or cumulative survival rate based thereon between the cases where the marker is in high expression and low expression, and that consequently, the expression pattern of the marker can be an index showing recurrence possibility or survival possibility of patients.

Also, significance tests were performed by log-rank test with respect to each of the markers and their combination by calculating observation values and expected values at every point of recurrence or death to obtain p-values. The results are shown in the following Tables 38~45. The results of using a marker alone are shown in Table 38, the results of a combination of two markers are shown in Table 39, the results of a combination of three markers are shown in Table 40, the results of a combination of four markers are shown in Table 41, the results of a combination of five markers are shown in Table 42, the results of a combination of six markers are shown in Table 43, the results of a combination of seven markers are shown in Table 44, and the results of a combination of eight markers are shown in Table 45.

TABLE 38

| Marker | p-value |
|---|---|
| Recurrence | |
| HMGB1 | 2.22E−02 |
| TKT | 3.71E−02 |
| BECN1 | 6.59E−02 |
| DIABLO | 7.11E−02 |
| TCF3 | 8.67E−02 |
| ATG12 | 9.30E−02 |
| CSE1L | 9.76E−02 |
| SIRT1 | 9.92E−02 |
| BCL2L1 | 1.15E−01 |
| NAMPT | 1.26E−01 |
| ATG3 | 1.47E−01 |
| ATG5 | 2.16E−01 |
| STAT3 | 2.52E−01 |
| UVRAG | 2.70E−01 |
| BCL2 | 2.81E−01 |
| BNIP3 | 2.96E−01 |
| STAB1 | 3.11E−01 |
| FASLG | 3.17E−01 |
| ULK1 | 3.23E−01 |
| CASP3 | 3.39E−01 |
| FRAP1 | 3.61E−01 |
| CCNG2 | 3.66E−01 |
| PTEN | 3.67E−01 |
| SESN1 | 3.69E−01 |
| AGER | 4.09E−01 |
| FAS | 4.15E−01 |
| CIAP2 | 4.23E−01 |
| ID2 | 4.28E−01 |
| TWIST1 | 4.50E−01 |
| CDH2 | 4.57E−01 |
| LC3 | 5.41E−01 |
| LAMP1 | 5.61E−01 |
| RPS19BP1 | 5.67E−01 |
| KIAA1967 | 5.68E−01 |
| SESN3 | 5.83E−01 |
| PRKAA1 | 5.93E−01 |
| MMP2 | 6.00E−01 |
| XIAP | 6.17E−01 |
| VEGF | 6.25E−01 |
| LAMP2 | 6.29E−01 |
| RAGE | 6.67E−01 |
| HMGB2 | 6.82E−01 |
| MMP9 | 7.26E−01 |
| TP63 | 7.29E−01 |
| RAPTOR | 7.33E−01 |
| DRAM | 7.87E−01 |
| CDH1 | 7.91E−01 |
| BAX | 7.94E−01 |
| AIFM1 | 8.17E−01 |
| E2F1 | 8.46E−01 |
| NNMT | 8.71E−01 |
| CASP8 | 8.73E−01 |
| AKT1 | 8.74E−01 |
| SESN2 | 8.80E−01 |
| ATG7 | 9.31E−01 |
| BHLHE41 | 9.76E−01 |
| CBS | 9.98E−01 |
| Survival | |
| ATG12 | 2.08E−04 |
| DIABLO | 3.97E−04 |
| UVRAG | 1.53E−03 |
| NAMPT | 1.91E−03 |
| STAT3 | 3.43E−03 |
| E2F1 | 5.12E−03 |
| BECN1 | 5.88E−03 |
| FRAP1 | 7.79E−03 |
| ATG7 | 1.09E−02 |
| ID2 | 1.18E−02 |
| SIRT1 | 2.47E−02 |
| BCL2 | 2.56E−02 |
| BNIP3 | 2.56E−02 |

TABLE 38-continued

| Marker | p-value |
|---|---|
| LAMP2 | 2.97E−02 |
| TKT | 3.95E−02 |
| RPS19BP1 | 5.62E−02 |
| AKT1 | 5.72E−02 |
| FAS | 5.98E−02 |
| FASLG | 6.50E−02 |
| TCF3 | 8.11E−02 |
| CIAP2 | 8.51E−02 |
| RAPTOR | 9.96E−02 |
| LC3 | 1.02E−01 |
| CASP8 | 1.07E−01 |
| CSE1L | 1.48E−01 |
| MMP9 | 1.49E−01 |
| TWIST1 | 1.57E−01 |
| CDH2 | 1.63E−01 |
| CDH1 | 1.94E−01 |
| XIAP | 2.50E−01 |
| DRAM | 3.11E−01 |
| SESN3 | 3.35E−01 |
| PRKAA1 | 3.53E−01 |
| LAMP1 | 4.67E−01 |
| HMGB1 | 4.70E−01 |
| NNMT | 4.96E−01 |
| CASP3 | 5.01E−01 |
| PTEN | 5.30E−01 |
| SATB1 | 5.36E−01 |
| CCNG2 | 5.89E−01 |
| ATG5 | 5.94E−01 |
| BAX | 6.21E−01 |
| TP63 | 6.40E−01 |
| RAGE | 6.77E−01 |
| KIAA1967 | 7.83E−01 |
| CBS | 7.85E−01 |
| BHLHE41 | 8.44E−01 |
| SESN2 | 8.76E−01 |
| ULK1 | 8.82E−01 |
| MMP2 | 8.91E−01 |
| HMGB2 | 8.97E−01 |
| BCL2L1 | 9.37E−01 |
| SESN1 | 9.40E−01 |
| AIFM1 | 9.67E−01 |
| AGER | 9.70E−01 |
| ATG3 | 9.89E−01 |
| VEGF | 9.97E−01 |
| Disease-free survival | |
| DIABLO | 4.18E−02 |
| BECN1 | 4.32E−02 |
| HMGB1 | 4.69E−02 |
| ATG12 | 6.32E−02 |
| TKT | 7.58E−02 |
| SIRT1 | 7.74E−02 |
| NAMPT | 8.06E−02 |
| TCF3 | 9.30E−02 |
| CSE1L | 9.39E−02 |
| BCL2L1 | 1.15E−01 |
| STAT3 | 1.45E−01 |
| UVRAG | 1.98E−01 |
| FRAP1 | 2.31E−01 |
| ATG3 | 2.46E−01 |
| ATG5 | 2.51E−01 |
| SATB1 | 2.60E−01 |
| BNIP3 | 2.65E−01 |
| BCL2 | 2.81E−01 |
| CIAP2 | 3.00E−01 |
| FASLG | 3.17E−01 |
| CASP3 | 3.39E−01 |
| ULK1 | 3.64E−01 |
| CCNG2 | 3.66E−01 |
| PTEN | 3.67E−01 |
| SESN1 | 3.69E−01 |
| ID2 | 3.77E−01 |
| AGER | 3.89E−01 |
| CDH2 | 4.08E−01 |
| FAS | 4.20E−01 |
| TWIST1 | 4.50E−01 |
| RPS19BP1 | 4.59E−01 |
| LAMP2 | 4.82E−01 |

TABLE 38-continued

| Marker | p-value |
|---|---|
| CASP8 | 5.31E−01 |
| MMP2 | 5.53E−01 |
| SESN3 | 5.55E−01 |
| KIAA1967 | 5.68E−01 |
| PRKAA1 | 5.93E−01 |
| XIAP | 6.17E−01 |
| VEGF | 6.25E−01 |
| RAGE | 6.67E−01 |
| MMP9 | 7.01E−01 |
| TP63 | 7.29E−01 |
| RAPTOR | 7.33E−01 |
| LC3 | 7.35E−01 |
| E2F1 | 7.45E−01 |
| SESN2 | 7.76E−01 |
| CDH1 | 7.83E−01 |
| HMGB2 | 7.88E−01 |
| BAX | 7.94E−01 |
| LAMP1 | 7.98E−01 |
| ATG7 | 8.14E−01 |
| AIFM1 | 8.17E−01 |
| CBS | 8.42E−01 |
| NNMT | 8.71E−01 |
| DRAM | 9.18E−01 |
| BHLHE41 | 9.40E−01 |
| AKT1 | 9.88E−01 |

TABLE 39

| Marker | p-value |
|---|---|
| Recurrence | |
| ATG3_HMGB1 | 1.03E−03 |
| ATG3_BECN1 | 1.69E−03 |
| TKT_HMGB1 | 2.65E−03 |
| BCL2L1_TKT | 5.45E−03 |
| ATG3_NAMPT | 6.43E−03 |
| BCL2_HMGB1 | 8.00E−03 |
| HMGB1_TWIST1 | 8.51E−03 |
| ATG12_ATG3 | 8.56E−03 |
| CSE1L_DIABLO | 9.41'E−03 |
| ATG3_TKT | 1.01E−02 |
| LAMP1_HMGB1 | 1.03E−02 |
| TKT_BECN1 | 1.07E−02 |
| CDH1_HMGB1 | 1.13E−02 |
| HMGB1_TP63 | 1.13E−02 |
| TKT_NAMPT | 1.29E−02 |
| BCL2_TKT | 1.35E−02 |
| CSE1L_TKT | 1.35E−02 |
| LC3_TKT | 1.41E−02 |
| TKT_CASP3 | 1.43E−02 |
| FASLG_HMGB1 | 1.43E−02 |
| CDH2_HMGB1 | 1.47E−02 |
| ATG5_HMGB1 | 1.52E−02 |
| HMGB1_SIRT1 | 1.55E−02 |
| ATG12_HMGB1 | 1.57E−02 |
| HMGB1_RAGE | 1.60E−02 |
| HMGB1_UVRAG | 1.66E−02 |
| BCL2L1_SIRT1 | 1.71E−02 |
| ATG3_TCF3 | 1.72E−02 |
| BCL2L1_HMGB1 | 1.73E−02 |
| TKT_SIRT1 | 1.73E−02 |
| HMGB1_LAMP2 | 1.75E−02 |
| TKT_SESN2 | 1.81E−02 |
| HMGB1_MMP2 | 1.84E−02 |
| TKT_AGER | 1.86E−02 |
| HMGB1_RAPTOR | 1.87E−02 |
| E2F1_HMGB1 | 1.87E−02 |
| CASP8_HMGB1 | 1.91E−02 |
| TKT_ID2 | 1.92E−02 |
| AKT1_TKT | 1.93E−02 |
| ATG3_SIRT1 | 1.96E−02 |
| TKT_RPS19BP1 | 1.99E−02 |
| CSE1L_HMGB1 | 2.00E−02 |
| BCL2L1_BECN1 | 2.00E−02 |

TABLE 39-continued

| Marker | p-value |
|---|---|
| CASP3_HMGB1 | 2.03E−02 |
| ATG7_HMGB1 | 2.05E−02 |
| FRAP1_HMGB1 | 2.10E−02 |
| HMGB1_HMGB2 | 2.11E−02 |
| HMGB1_SATB1 | 2.19E−02 |
| ATG3_ULK1 | 2.20E−02 |
| ATG3_SESN1 | 2.21E−02 |
| CBS_HMGB1 | 2.22E−02 |
| TKT_KIAA1967 | 2.23E−02 |
| ATG12_BCL2L1 | 2.23E−02 |
| DRAM_HMGB1 | 2.26E−02 |
| LC3_FASLG | 2.26E−02 |
| HMGB1_KIAA1967 | 2.27E−02 |
| TKT_SESN1 | 2.29E−02 |
| Survival | |
| DIABLO_NAMPT | 3.60E−05 |
| ATG12_ID2 | 4.08E−05 |
| ATG12_RPS19BP1 | 4.47E−05 |
| ATG12_DIABLO | 4.65E−05 |
| ID2_NAMPT | 5.93E−05 |
| DIABLO_STAT3 | 7.01E−05 |
| DIABLO_FAS | 7.40E−05 |
| ATG12_CSE1L | 7.98E−05 |
| ATG12_MMP9 | 1.04E−04 |
| ATG12_ATG3 | 1.05E−04 |
| ATG12_SATB1 | 1.07E−04 |
| ATG12_SESN2 | 1.24E−04 |
| CSE1L_DIABLO | 1.26E−04 |
| ATG12_TCF3 | 1.35E−04 |
| ATG12_FAS | 1.36E−04 |
| ATG12_STAT3 | 1.45E−04 |
| ATG12_NHLHE41 | 1.60E−04 |
| ATG12_NAMPT | 1.61E−04 |
| ATG12_ATG7 | 1.77E−04 |
| ID2_BECN1 | 1.78E−04 |
| E2F1_FAS | 1.81E−04 |
| ATG12_ATG5 | 1.87E−04 |
| ID2_STAT3 | 1.91E−04 |
| ATG12_ULK1 | 2.09E−04 |
| DIABLO_BECN1 | 2.39E−04 |
| ATG12_LAMP1 | 2.42E−04 |
| ATG12_LC3 | 2.50E−04 |
| DIABLO_TCF3 | 2.61E−04 |
| AKT1_ATG12 | 2.71E−04 |
| ATG12_FRAP1 | 2.72E−04 |
| DIABLO_ID2 | 2.88E−04 |
| ID2_TCF3 | 3.27E−04 |
| DIABLLO_SATB1 | 3.48E−04 |
| ATG12_BECN1 | 3.54E−04 |
| ATG12_SITRT1 | 3.57E−04 |
| NAMPT_STAT3 | 3.61E−04 |
| ATG12_BNIP3 | 3.77E−04 |
| DIABLO_MMP9 | 3.89E−04 |
| ATG12_UVRAG | 4.34E−04 |
| DIABLO_FRAP1 | 4.45E−04 |
| NAMPT_RPS19BP1 | 4.56E−04 |
| AKT1_NAMPT | 4.68E−04 |
| E2F1_UVRAG | 5.27E−04 |
| ATG3_DIABLO | 5.44E−04 |
| NAMPT_UVRAG | 5.49E−04 |
| BNIP3_DIABLO | 5.58E−04 |
| DIABLO_LC3 | 5.81E−04 |
| DIABLO_SIRT1 | 5.82E−04 |
| LC3_NAMPT | 6.27E−04 |
| DIABLO_SESN2 | 6.38E−04 |
| FAS_STAT3 | 6.42E−04 |
| FAS_NAMPT | 7.04E−04 |
| E2F1_NAMPT | 7.36E−04 |
| ATG12_SESN3 | 7.46E−04 |
| BCL2_TKT | 8.14E−04 |
| ATG7_NAMPT | 8.22E−04 |
| ATG7_BECN1 | 8.79E−04 |
| Disease-free survival | |
| ATG3_BECN1 | 1.63E−03 |
| ATG3_HNGB1 | 4.45E−03 |
| BCL2L1_TKT | 5.45E−03 |

TABLE 39-continued

| Marker | p-value |
|---|---|
| CSE1L_DIABLO | 5.78E−03 |
| BCL2_HMGB1 | 8.00E−03 |
| ATG12_ATG3 | 8.21E−03 |
| ATG3_NAMPT | 8.42E−03 |
| HMGB1_TWIST1 | 8.51E−03 |
| TKT_HMGB1 | 9.93E−03 |
| LAMP1_HMGB1 | 1.03E−02 |
| TKT_BECN1 | 1.07E−02 |
| HMGB1_TP63 | 1.13E−02 |
| BCL2_TKT | 1.35E−02 |
| TKT_CASP3 | 1.43E−02 |
| FASLG_HMGB1 | 1.43E−02 |
| TKT_NAMPT | 1.49E−02 |
| ATG5_HMGB1 | 1.52E−02 |
| HMGB1_SIRT1 | 1.55E−02 |
| ATG12_HMGB1 | 1.57E−02 |
| HMGB1_RAGE | 1.60E−02 |
| DIABLO_NAMPT | 1.65E−02 |
| HMGB1_UVRAG | 1.66E−02 |
| DIABLO_BECN1 | 1.67E−02 |
| BECN1_SATB1 | 1.70E−02 |
| BCL2L1_SIRT1 | 1.71E−02 |
| BCL2L1_HMGB1 | 1.73E−02 |
| TKT_SIRT1 | 1.73E−02 |
| DIABLO_TCF3 | 1.73E−02 |
| HMGB1_LAMP2 | 1.75E−02 |
| DIABLO_SATB1 | 1.80E−02 |
| HMGB1_RAPTOR | 1.87E−02 |
| E2F1_HMGB1 | 1.87E−02 |
| ATG5_BECN1 | 1.95E−02 |
| ATG12_SATB1 | 1.99E−02 |
| BCL2L1_BECN1 | 2.00E−02 |
| CASP3_HMGB1 | 2.03E−02 |
| ATG12_CSE1L | 2.03E−02 |
| ATG7_HMGB1 | 2.05E−02 |
| ATG3_SIRT1 | 2.05E−02 |
| CASP8_HMGB1 | 2.17E−02 |
| ATG3_SESN1 | 2.21E−02 |
| TKT_KIAA1967 | 2.23E−02 |
| ATG12_BCL2L1 | 2.23E−02 |
| DRAM_HMGB1 | 2.26E−02 |
| LC3_FASLG | 2.26E−02 |
| HMGB1_KIAA1967 | 2.27E−02 |
| TKT_SESN1 | 2.28E−02 |
| ATG3_DIABLO | 2.33E−02 |
| DIABLO_SIRT1 | 2.35E−02 |
| BENC1_HMGB1 | 2.41E−02 |
| AIFM1_HMGB1 | 2.45E−02 |
| ID2_BECN1 | 2.49E−02 |
| CSE1L_BECN1 | 2.52E−02 |
| TKT_ULK1 | 2.52E−02 |
| BNIP3_HMGB1 | 2.52E−02 |
| TKT_UVRAG | 2.54E−02 |
| ATG5_TKT | 2.54E−02 |

TABLE 40

| Marker | p-value |
|---|---|
| Recurrence | |
| ATG3_BCL2_HMGB1 | 1.17E−04 |
| ATG3_HMGB1_RAGE | 2.50E−04 |
| ATG3_TKT_HMGB1 | 2.65E−04 |
| ATG3_CDH1_HMGB1 | 3.47E−04 |
| ATG3_HMGB1_HMGB2 | 3.56E−04 |
| ATG3_HMGB1_UVRAG | 3.65E−04 |
| ATG3_CASP3_HMGB1 | 4.61E−04 |
| ATG3_HMGB1_SIRT1 | 4.72E−04 |
| ATG3_BECN1_SATB1 | 4.93E−04 |
| ATG3_HMGB1_SATB1 | 5.71E−04 |
| ATG3_LC3_BECN1 | 5.77E−04 |
| ATG3_HMGB1_LAMP2 | 5.94E−04 |
| ATG3_HMGB1_RAPTOR | 6.47E−04 |
| ATG3_HMGB1_KIAA1967 | 6.74E−04 |

TABLE 40-continued

| Marker | p-value |
|---|---|
| BCL2L1_TKT_CASP3 | 6.77E−04 |
| ATG12_ATG3_HMGB1 | 7.34E−04 |
| BCL2L1_TKT_SIRT1 | 7.44E−04 |
| ATG3_CIAP2_HMGB1 | 7.53E−04 |
| BCL2L1_TKT_BECN1 | 8.13E−04 |
| BCL2_TKT_HMGB1 | 8.79E−04 |
| ATG3_BECN1_SESN3 | 8.96E−04 |
| ATG3_CASP8_HMGB1 | 9.58E−04 |
| ATG3_CDH2_HMGB1 | 9.62E−04 |
| ATG3_FRAP1_HMGB1 | 9.83E−04 |
| ATG3_BNIP3_HMGB1 | 1.01E−03 |
| ATG3_BECN1_HMGB1 | 1.02E−03 |
| ATG3_CBS_HMGB1 | 1.03E−03 |
| AIFM1_ATG3_HMGB1 | 1.03E−03 |
| ATG3_HMGB1_STAT3 | 1.04E−03 |
| ATG3_HMGB1_MMP2 | 1.06E−03 |
| ATG3_LAMP1_HMGB1 | 1.08E−03 |
| BCL2L1_TKT_FASLG | 1.15E−03 |
| ATG3_IABLO_HMGB1 | 1.17E−03 |
| BCL2_BCL2L1_TKT | 1.18E−03 |
| TKT_HMGB1_TWIST1 | 1.19E−03 |
| ATG3_NNMT_HMGB1 | 1.23E−03 |
| ATG3_MMP9_HMGB1 | 1.24E−03 |
| BCL2L1_TKT_HMGB1 | 1.30E−03 |
| ATG3_LAMP1_BECN1 | 1.39E−03 |
| ATG3_BCL2L1_BECN1 | 1.41E−03 |
| ATG5_TKT_HMGB1 | 1.44E−03 |
| ATG3_FASLG_HMGB1 | 1.45E−03 |
| ATG3_MMP9_BECN1 | 1.48E−03 |
| ATG3_ATG7_BECN1 | 1.51E−03 |
| ATG3_HMGB1_SESN3 | 1.54E−03 |
| ATG3_E2F1_HMGB1 | 1.56E−03 |
| HMGB1_RAPTOR_TWIST1 | 1.56E−03 |
| AKT1_ATG3_BECN1 | 1.57E−03 |
| ATG3_FAS_HMGB1 | 1.59E−03 |
| ATG3_ULK1_HMGB1 | 1.59E−03 |
| TKT_HMGB1_SIRT1 | 1.60E−03 |
| ATG3_BAX_HMGB1 | 1.61E−03 |
| TKT_CDH2_HMGB1 | 1.64E−03 |
| ATG3_PTEN_HMGB1 | 1.65E−03 |
| ATG3_TKT_BECN1 | 1.65E−03 |
| ATG3_HMGB1_TWIST1 | 1.68E−03 |
| BCL2L1_TKT_UVRAG | 1.68E−03 |
| Survival | |
| DIABLO_ID2_NAMPT | 8.10E−06 |
| DIABLO_FAS_NAMPT | 9.84E−04 |
| ATG12_ID2_TCF3 | 1.07E−05 |
| DIABLO_FAS_STAT3 | 1.32E−05 |
| ATG12_ID2_MMP9 | 1.36E−05 |
| ATG12_ID2_SATB1 | 1.63E−05 |
| ATG12_ID2_RPS19BP1 | 1.70E−05 |
| ATG12_CSE1L_ID2 | 1.83E−05 |
| ATG12_DIABLO_FAS | 1.87E−05 |
| ATG12_ID2_SESN2 | 1.92e-05 |
| ATG12_ID2_NAMPT | 2.02E−05 |
| ATG12_CSE1L_DIABLO | 2.06E−05 |
| ID2_NAMP_STAT3 | 2.24E−05 |
| ATG12_ID2_BHLHE41 | 2.27E−05 |
| CSE1L_DIABLO_NAMPT | 2.34E−05 |
| DIABLO_L3_NAMPT | 2.39E−05 |
| ATG12_FAS_ID2 | 2.39E−05 |
| ID2_NAMPT_RPS19BP1 | 2.39E−05 |
| ID2_MMP9_TCF3 | 2.43E−05 |
| DIABLO_NAMPT_SATB1 | 2.43E−05 |
| ATG12_CSE1L_MMP9 | 2.49E−05 |
| ATG12_MMP9_RPS19BP1 | 2.49E−05 |
| ID2_MMP9_BECN1 | 2.56E−05 |
| DIABLO_NAMPT_STAT3 | 2.60E−05 |
| ATG12_DIABLO_MMP9 | 2.65E−05 |
| ATG12_FAS_RPS19BP1 | 2.72E−05 |
| DIABLO_FAS_MMP9 | 2.73E−05 |
| IS2_MMP9_NAMPT | 2.74E−05 |
| ATG12_ID2_STAT3 | 2.79E−05 |
| ATG12_DIABLO_TCF3 | 2.82E−05 |
| ATG12_ATG3_ID2 | 2.97E−05 |
| ATG12_DIABLO_ID2 | 2.98E−05 |
| CSE1L_DIABLO_STAT3 | 2.99E−05 |

TABLE 40-continued

| Marker | p-value |
|---|---|
| DIABLO_ID2_STAT3 | 3.13E−05 |
| ATG12_ATG3_RPS19BP1 | 3.22E−05 |
| ATG12_DIABLO_SATB1 | 3.25E−03 |
| ATG12_MMP9_TCF3 | 3.29E−05 |
| ATG3_DIABLO_NAMPT | 3.32E−05 |
| ATG12_DIABLO_NAMPT | 3.37E−05 |
| ATG12_CSE1L_RPS19BP1 | 3.38E−05 |
| DIABLO_MMP9_NAMPT | 3.42E−05 |
| ATG12_ATG3_DIABLO | 3.56E−05 |
| DIABLO_SATB1_STAT3 | 3.58E−05 |
| ID2_TCF3_STAT3 | 3.70E−05 |
| ATG12_RPS19BP1_SATB1 | 3.72E−05 |
| ATG12_DIABLO_STAT3 | 3.75E−05 |
| ATG12_TCF3_RPS19BP1 | 3.85E−05 |
| IABLO_NAMPT_SESN2 | 3.87E−05 |
| ATG12_DIABLO_SESN2 | 3.90E−05 |
| ATG12_ULK1_ID2 | 4.01E−05 |
| ATG12_ATG5_ID2 | 4.11E−05 |
| AKT1_DIABLO_NAMPT | 4.11E−05 |
| ATG12_ID2_BECN1 | 4.13E−05 |
| ATG12_FAS_MMP9 | 4.16E−05 |
| AG12_DIABLO_BHLHE41 | 4.36E−05 |
| ATG12_RPS19BP1_STAT3 | 4.39E−05 |
| DIABLO_NAMPT_RPS19BP1 | 4.41E−05 |
| Disease-free survival | |
| ATG3_BCL2_HMGB1 | 1.17E−04 |
| ATG3_HMGB1_RAGE | 2.50E−04 |
| ATG3_HMGB1_UVRAG | 3.65E−04 |
| ATG3_CASP3_HMGB1 | 4.61E−04 |
| ATG3_HMGB1_SIRT1 | 4.72E−04 |
| ATG3_BECN1_SATB1 | 4.80E−04 |
| ATG3_HMGB1_LAMP2 | 5.94E−04 |
| ATG3_HMGB1_RAPTOR | 6.47E−04 |
| ATG3_LC3_BECN1 | 6.73E−04 |
| ATG3_HMGB1_KIAA1967 | 6.74E−04 |
| BCL2L1_TKT_CASP3 | 6.77E−04 |
| ATG12_ATG3_HMGB1 | 7.34E−04 |
| BCL2L1_TKT_SIRT1 | 7.44E−04 |
| BCL2L1_TKT_BECN1 | 8.13E−04 |
| BCL2_TKT_HMGB1 | 8.79E−04 |
| ATG3_BECN1_SESN3 | 8.82E−04 |
| ATG3_BNIP3_HMGB1 | 1.01E−03 |
| ATG3_BECN1_HMGB1 | 1.02E−03 |
| AIFM1_ATG3_HMGB1 | 1.03E−03 |
| ATG3_LAMP1_HMGB1 | 1.08E−03 |
| BCL2L1_TKT_FASLG | 1.15E−03 |
| BCL2_BCL2L1_TKT | 1.18E−03 |
| TKT_HMGB1_TWIST1 | 1.19E−03 |
| ATG3_NNMT_HMGB1 | 1.23E−03 |
| BCL2L1_TKT_HMGB1 | 1.30E−03 |
| ATG3_BCL2L1_BECN1 | 1.41E−03 |
| ATG5_TKT_HMGB1 | 1.44E−03 |
| ATG3_FASLG_HMGB1 | 1.45E−03 |
| ATG3_MMP9_BECN1 | 1.46E−03 |
| ATG3_LAMP1_BECN1 | 1.51E−03 |
| ATG3_E2F1_HMGB1 | 1.56E−03 |
| HMGB1_RAPTOR_TWIST1 | 1.56E−03 |
| AKT1_ATG3_BECN1 | 1.57E−03 |
| ATG3_ULK1_HMGB1 | 1.59E−03 |
| TKT_HMGB1_SIRT1 | 1.60E−03 |
| ATG3_BAX_HMGB1 | 1.61E−03 |
| ATG3_PTEN_HMGB1 | 1.65E−03 |
| ATG3_TKT_HMGB1 | 1.65E−03 |
| ATG3_TKT_BECN1 | 1.65E−03 |
| ATG3_HMGB1_TWIST1 | 1.68E−03 |
| BCL2L1_TKT_UVRAG | 1.68E−03 |
| TKT_HMGB1_UVRAG | 1.71E−03 |
| BCL2L1_TKT_CDH2 | 1.72E−03 |
| BCL2L1_TKT_KIAA1967 | 1.72E−05 |
| ATG3_BCL2L1_HMGB1 | 1.79E−03 |
| ATG3_ATG5_HMGB1 | 1.79E−03 |
| ATG3_DRAM_HMGB1 | 1.80E−03 |
| ATG3_HMGB1_SATB1 | 1.82E−03 |
| ATG3_BCL2L1_TKT | 1.82E−03 |
| ATG3_PRKAA1_HMGB1 | 1.83E−03 |
| TKT_CASP3_HMGB1 | 1.85E−03 |
| ATG3_XIAP_HMGB1 | 1.88E−03 |

TABLE 40-continued

| Marker | p-value |
|---|---|
| TKT_HMGB1_KIAA1967 | 1.89E−03 |
| TKT_HMGB1_LAMP2 | 1.92E−03 |
| HMGB1_RAGE_TWIST1 | 1.92E−03 |
| ATG12_BCL2L1_TKT | 1.93E−03 |
| ATG3_PTEN_BECN1 | 1.98E−03 |

TABLE 41

| Marker | p-value |
|---|---|
| Recurrence | |
| ATG3_BCL2_CDH1_HMGB1 | 9.00E−06 |
| ATG3_CDH1_HMGB1_UVRAG | 3.63E−05 |
| ATG3_BCL2_TKT_HMGB1 | 3.74E−05 |
| ATG3_BCL2_HMGB1_RAGE | 3.84E−05 |
| ATG3_BCL2_HMGB1_HMGB2 | 4.08E−05 |
| ATG3_CDH1_HMGB1_SIRT1 | 4.40E−05 |
| ATG3_BCL2_HMGB1_MMP2 | 6.17E−05 |
| ATG3_HMGB1_HMGB2_RAGE | 6.79E−05 |
| ATG3_BCL2_BNIP3_HMGB1 | 7.60E−05 |
| ATG3_CDH1_CASP3_HMGB1 | 7.97E−05 |
| ATG3_CDH1_HMGB1_KIAA1967 | 8.12E−05 |
| ATG3_HMGB1_RAGE_UVRAG | 8.15E−05 |
| ATG3_HMGB1_RAGE_SIRT1 | 8.54E−05 |
| ATG3_TKT_HMGB1_HMGB2 | 8.71E−05 |
| ATG3_TKT_HMGB1_UVRAG | 8.77E−05 |
| ATG3_BCL2_LAMP1_HMGB1 | 8.79E−05 |
| ATG3_BCL2_HMGB1_RAPTOR | 9.44E−05 |
| AIFM1_ATG3_BCL2_HMGB1 | 1.02E−04 |
| ATG3_CASP3_HMGB1_RAGE | 1.03E−04 |
| ATG12_ATG3_HMGB1_RAGE | 1.07E−04 |
| ATG3_TKT_CASP3_HMGB1 | 1.08E−04 |
| ATG3_TKT_HMGB1_KIAA1967 | 1.08E−04 |
| ATG3_BCL2L1_TKT_BECN1 | 1.08E−04 |
| ATG12_ATG3_CDH1_HMGB1 | 1.09E−04 |
| ATG3_CDH1_HMGB1_RAGE | 1.13E−04 |
| ATG3_BCL2_FRAP1_HMGB1 | 1.15E−04 |
| ATG3_BCL2_HMGB1_LAMP2 | 1.16E−04 |
| ATG3_BCL2_DIABLO_HMGB1 | 1.17E−04 |
| ATG3_TKT_HMGB1_SIRT1 | 1.17E−04 |
| ATG3_BCL2_CBS_HMGB1 | 1.20E−04 |
| ATG3_BCL2_CASP8_HMGB1 | 1.24E−04 |
| ATG3_HMGB1_HMGB2_SATB1 | 1.27E−04 |
| ATG3_BCL2_PTEN_HMGB1 | 1.28E−04 |
| ATG3_HMGB1_RAGE_RAPTOR | 1.28E−04 |
| ATG3_TKT_HMGB1_RAGE | 1.28E−04 |
| ATG3_BCL2_CASP3_HMGB1 | 1.35E−04 |
| ATG3_BCL2_HMGB1_SATB1 | 1.37E−04 |
| ATG3_HMGB1_LAMP2_RAGE | 1.39E−04 |
| ATG3_CDH1_HMGB1_LAMP2 | 1.40E−04 |
| ATG3_HMGB1_HMGB2_UVRAG | 1.41E−04 |
| ATG3_BCL2L1_TKT_HMGB1 | 1.42E−04 |
| CDH1_HMGB1_TP63_UVRAG | 1.42E−04 |
| ATG3_CDH1_HMGB1_HMGB2 | 1.43E−04 |
| ATG3_BCL2L1_TKT_CASP3 | 1.44E−04 |
| ATG3_HMGB1_KIAA1967_RAGE | 1.48E−04 |
| ATG3_BCL2_DRAM_HMGB1 | 1.54E−04 |
| ATG3_LC3_TKT_HMGB1 | 1.57E−04 |
| ATG3_BCL2_HMGB1_UVRAG | 1.57E−04 |
| ATG3_CDH1_CDH2_HMGB1 | 1.58E−04 |
| BCL2_BCL2L1_TKT_CASP3 | 1.59E−04 |
| ATG3_TKT_BECN1_HMGB1 | 1.59E−04 |
| ATG3_TKT_HMGB1_LAMP2 | 1.60E−04 |
| ATG3_BCL2_PRKAA1_HMGB1 | 1.64E−04 |
| BCL2L1_TKT_CASP3_SIRT1 | 1.64E−04 |
| BCL2L1_TKT_CASP3_FASLG | 1.64E−04 |
| BCL2L1_TKT_CASP3_CDH2 | 1.68E−04 |
| ATG3_BCL2_NNMT_HMGB1 | 1.68E−04 |
| Survival | |
| ATG12_ID2_MMP9_TCF3 | 2.39E−06 |
| DIABLO_FAS_ID2_NAMPT | 3.68E−06 |
| ATG12_CSE1L_ID2_MMP9 | 4.73E−06 |
| DIABLO_ID2_MMP9_NAMPT | 5.35E−06 |

TABLE 41-continued

| Marker | p-value |
|---|---|
| DIABLO_FAS_MMP9_NAMPT | 5.54E−06 |
| DIABLO_ID2_NAMPT_STAT3 | 5.58E−06 |
| ATG12_FAS_ID2_MMP9 | 5.58E−06 |
| ATG12_ID2_MMP9_SATB1 | 6.11E−06 |
| DIABLO_ID2_NAMPT_SATB1 | 6.14E−06 |
| ATG12_ID2_MMP9_SESN2 | 6.36E−06 |
| ATG12_ID2_MMP9_RPS19BP1 | 6.49E−06 |
| CSE1L_DIABLO_ID2_NAMPT | 6.99E−06 |
| DIABLO_ID2_TCF3_NAMPT | 7.48E−06 |
| DIABLO_FAS_NAMPT_SATB1 | 7.74E−06 |
| ATG12_DIABLO_FAS_MMP9 | 7.81E−06 |
| DIABLO_FAS_ID2_STAT3 | 8.24E−06 |
| ATG12_ATG3_ID2_TCF3 | 8.26E−06 |
| ATG3_DIABLO_ID2_NAMPT | 8.33E−06 |
| ATG12_ID2_TCF3_STAT3 | 8.65E−06 |
| DIABLO_FAS_NAMPT_STAT3 | 8.65E−06 |
| ATG12_CSE1L_DIABLO_MMP9 | 9.06E−06 |
| ATG12_ID2_TCF3_SATB1 | 9.10E−06 |
| DIABLO_FAS_MMP9_STAT3 | 9.14E−06 |
| ATG12_ID2_MMP9_BHLHE41 | 9.26E−06 |
| ATG12_BNIP3_ID2_MMP9 | 9.27E−06 |
| DIABLO_FAS_SATB1_STAT3 | 9.29E−06 |
| DIABLO_FAS_NAMPT_RPS19BP1 | 9.36E−06 |
| ATG12_ATG3_ID2_MMP9 | 9.52E−06 |
| ATG12_ID2_MMP9_NAMPT | 9.68E−06 |
| DIABLO_FAS_NAMPT_SESN2 | 9.81E−06 |
| DIABLO_ID2_NAMPT_SESN2 | 1.00E−05 |
| ATG12_ID2_TCF3_RPS19BP1 | 1.03E−05 |
| ATG12_DIABLO_MMP9_TCF3 | 1.04E−05 |
| ATG12_CSE1L_ID2_SATB1 | 1.05E−05 |
| ATG12_FAS_MMP9_RPS19BP1 | 1.06E−05 |
| ID2_MMP9_TCF3_STAT3 | 1.06E−05 |
| ATG12_DIABLO_ID2_NAMPT | 1.06E−05 |
| DIABLO_ID2_TCF3_STAT3 | 1.07E−05 |
| ATG12_ULK1_ID2_TCF3 | 1.08E−05 |
| ATG12_ID2_TCF3_SESN2 | 1.08E−05 |
| BNIP3_CSE1L_DIABLO_MMP9 | 1.09E−05 |
| ATG12_DIABLO_ID2_TCF3 | 1.13E−05 |
| ATG12_ATG5_ID2_MMP9 | 1.14E−05 |
| ATG12_ID2_SATB1_STAT3 | 1.14E−05 |
| ATG12_MMP9_TCF3_RPS19BP1 | 1.16E−05 |
| ATG12_DIABLO_FAS_ID2 | 1.17E−05 |
| ATG12_CSE1L_ID2_SESN2 | 1.18E−05 |
| DIABLO_FAS_MMP9_TCF3 | 1.18E−05 |
| ATG12_ID2_TCF3_BHLHE41 | 1.19E−05 |
| ATG12_FAS_ID2_STAT3 | 1.19E−05 |
| BNIP3_CSE1L_ID2_MMP9 | 1.20E−05 |
| CSE1L_DIABLO_FAS_NAMPT | 1.20E−05 |
| ATG12_CSE1L_ID2_TCF3 | 1.20E−05 |
| ATG12_ID2_NAMPT_RPS19BP1 | 1.20E−05 |
| ATG12_ID2_MMP9_BECN1 | 1.22E−05 |
| DIABLO_FAS_LC3_NAMPT | 1.25E−05 |
| FAS_ID2_NAMPT_RPS19BP1 | 1.25E−05 |
| CDH1_ID2_MMP9_TCF3 | 1.45E−03 |
| Disease-free survival | |
| ATG3_BCL2_CDH1_HMGB1 | 9.00E−06 |
| ATG3_CDH1_HMGB1_UVRAG | 3.63E−05 |
| ATG3_BCL2_TKT_HMGB1 | 3.74E−05 |
| ATG3_BCL2_HMGB1_RAGE | 3.84E−05 |
| ATG3_BCL2_HMGB1_HMGB2 | 4.08E−05 |
| ATG3_CDH1_HMGB1_SIRT1 | 4.40E−05 |
| ATG3_BCL2_HMGB1_MMP2 | 6.17E−05 |
| ATG3_HMGB1_HMGB2_RAGE | 6.79E−05 |
| ATG3_BCL2_BNIP3_HMGB1 | 7.60E−05 |
| ATG3_CDH1_CASP3_HMGB1 | 7.97E−05 |
| ATG3_CDH1_HMGB1_KIAA1967 | 8.12E−05 |
| ATG3_HMGB1_RAGE_UVRAG | 8.15E−05 |
| ATG3_HMGB1_RAGE_SIRT1 | 8.54E−05 |
| ATG3_TKT_HMGB1_UVRAG | 8.77E−05 |
| ATG3_BCL2_LAMP1_HMGB1 | 8.79E−05 |
| ATG3_BCL2_HMGB1_RAPTOR | 9.44E−05 |
| AIFM1_ATG3_BCL2_HMGB1 | 1.02E−04 |
| ATG3_CASP3_HMGB1_RAGE | 1.03E−04 |
| ATG12_ATG3_HMGB1_RAGE | 1.07E−04 |
| ATG3_TKT_CASP3_HMGB1 | 1.08E−04 |

TABLE 41-continued

| Marker | p-value |
|---|---|
| ATG3_TKT_HMGB1_KIAA1967 | 1.08E−04 |
| ATG3_BCL2L1_TKT_BECN1 | 1.08E−04 |
| ATG12_ATG3_CDH1_HMGB1 | 1.09E−04 |
| ATG3_CDH1_HMGB1_RAGE | 1.13E−04 |
| ATG3_BCL2_FRAP1_HMGB1 | 1.15E−04 |
| ATG3_BCL2_HMGB1_LAMP2 | 1.16E−04 |
| ATG3_BCL2_DIABLO_HMGB1 | 1.17E−04 |
| ATG3_TKT_HMGB1_SIRT1 | 1.17E−04 |
| ATG3_BCL2_CBS_HMGB1 | 1.20E−04 |
| ATG3_BCL2_CASP8_HMGB1 | 1.24E−04 |
| ATG3_BCL2_PTEN_HMGB1 | 1.28E−04 |
| ATG3_HMGB1_RAGE_RAPTOR | 1.28E−04 |
| ATG3_TKT_HMGB1_RAGE | 1.28E−04 |
| ATG3_BCL2_CASP3_HMGB1 | 1.35E−04 |
| ATG3_BCL2_HMGB1_SATB1 | 1.37E−04 |
| ATG3_HMGB1_LAMP2_RAGE | 1.39E−04 |
| ATG3_CDH1_HMGB1_LAMP2 | 1.40E−04 |
| ATG3_HMGB1_HMGB2_UVRAG | 1.41E−04 |
| ATG3_BCL2L1_TKT_HMGB1 | 1.42E−04 |
| CDH1_HMGB1_TP63_UVRAG | 1.42E−04 |
| ATG3_BCL2L1_TKT_CASP3 | 1.44E−04 |
| ATG3_HMGB1_KIAA1967_RAGE | 1.48E−04 |
| ATG3_BCL2_DRAM_HMGB1 | 1.54E−04 |
| ATG3_BCL2_HMGB1_UVRAG | 1.57E−04 |
| BCL2_BCL2L1_TKT_CASP3 | 1.59E−04 |
| ATG3_TKT_BECN1_HMGB1 | 1.59E−04 |
| ATG3_TKT_HMGB1_LAMP2 | 1.60E−04 |
| ATG3_BCL2_PRKAA1_HMGB1 | 1.64E−04 |
| BCL2L1_TKT_CASP3_SIRT1 | 1.64E−04 |
| BCL2L1_TKT_CASP3_FASLG | 1.64E−04 |
| BCL2L1_TKT_CASP3_CDH2 | 1.68E−04 |
| ATG3_BCL2_NNMT_HMGB1 | 1.68E−04 |
| ATG3_CDH1_HMGB1_RAPTOR | 1.72E−04 |
| ATG3_BNIP3_HMGB1_RAGE | 1.76E−04 |
| ATG3_BAX_BCL2_HMGB1 | 1.79E−04 |
| ATG3_BCL2_ID2_HMGB1 | 1.80E−04 |
| ATG3_BCL2_HMGB1_STAT3 | 1.81E−04 |

TABLE 42

| Marker | p-value |
|---|---|
| Recurrence | |
| ATG3_BCL2_CDH1_HMGB1_RAGE | 3.47E−06 |
| ATG3_BCL2_CDH1_HMGB1_UVRAG | 3.54E−06 |
| ATG3_BCL2_CDH1_HMGB1_SIRT1 | 3.82E−06 |
| ATG3_BCL2_CDH1_HMGB1_RAPTOR | 4.19E−06 |
| ATG3_BCL2_CDH1_HMGB1_HMGB2 | 4.20E−06 |
| ATG3_BCL2_CDH1_HMGB1_KIAA1967 | 4.40E−06 |
| ATG3_BCL2_BNIP3_CDH1_HMGB1 | 5.13E−06 |
| ATG3_BCL2_CDH1_HMGB1_LAMP2 | 5.17E−06 |
| ATG3_BCL2_CDH1_CDH2_HMGB1 | 5.94E−06 |
| ATG3_CDH1_HMGB1_RAGE_SIRT1 | 6.16E−06 |
| ATG3_BCL2_CDH1_CASP3_HMGB1 | 6.89E−06 |
| ATG12_ATG3_BCL2_CDH1_HMGB1 | 7.15E−06 |
| AIFM1_ATG3_BCL2_CDH1_HMGB1 | 7.44E−06 |
| ATG3_BCL2_CASP8_CDH1_HMGB1 | 8.17E−06 |
| ATG3_BCL2_FRAP1_CDH1_HMGB1 | 8.58E−06 |
| ATG3_BCL2_CBS_CDH1_HMGB1 | 8.94E−06 |
| ATG3_CDH1_HMGB1_RAGE_UVRAG | 9.37E−06 |
| ATG3_BCL2_TKT_HMGB1_HMGB2 | 9.94E−06 |
| ATG3_BCL2_CDH1_HMGB1_MMP2 | 9.96E−06 |
| ATG3_BCL2_NNMT_CDH1_HMGB1 | 1.21E−05 |
| ATG3_BCL2_HMGB1_HMGB2_RAGE | 1.25E−05 |
| ATG3_BCL2_CDH1_MMP9_HMGB1 | 1.30E−05 |
| ATG12_ATG3_CDH1_HMGB1_RAGE | 1.31E−05 |
| ATG3_CDH1_HMGB1_LAMP2_SIRT1 | 1.38E−05 |
| ATG3_BCL2_DIABLO_CDH1_HMGB1 | 1.42E−05 |
| ATG3_BCL2L1_TKT_BECN1_CASP3 | 1.43E−05 |
| ATG3_BCL2_HMGB1_MMP2_RAGE | 1.50E−05 |
| ATG3_CDH1_HMGB1_HMGB2_UVRAG | 1.53E−05 |
| ATG3_BCL2_DRAM_CDH1_HMGB1 | 1.56E−05 |

TABLE 42-continued

| Marker | p-value |
|---|---|
| ATG3_BCL2_TKT_CDH1_HMGB1 | 1.60E−05 |
| ATG3_BCL2_TKT_CASP3_HMGB1 | 1.60E−05 |
| ATG3_CDH1_HMGB1_KIAA1967_UVRAG | 1.70E−05 |
| ATG3_CDH1_HMGB1_LAMP2_UVRAG | 1.74E−05 |
| ATG3_BCL2_BCL2L1_TKT_HMGB1 | 1.75E−05 |
| ATG3_BCL2_CDH1_HMGB1_SATB1 | 1.75E−05 |
| ATG3_BCL2L1_TKT_HMGB1_SIRT1 | 1.77E−05 |
| ATG3_BCL2_TKT_ID2_HMGB1 | 1.79E−05 |
| ATG3_CDH1_HMGB1_KIAA1967_RAGE | 1.80E−05 |
| ATG3_BCL2_PTEN_CDH1_HMGB1 | 1.88E−05 |
| AIFM1_ATG3_CDH1_HMGB1_SIRT1 | 1.90E−05 |
| ATG3_BCL2_CDH1_HMGB1_STAT3 | 1.91E−05 |
| ATG3_CDH1_CASP3_HMGB1_RAGE | 1.93E−05 |
| ATG3_BCL2_LC3_TKT_HMGB1 | 1.94E−05 |
| ATG3_CDH1_CASP3_HMGB1_UVRAG | 1.95E−05 |
| ATG3_BCL2_CDH1_CIAP2_HMGB1 | 2.00E−05 |
| ATG3_BCL2_BNIP3_HMGB1_RAGE | 2.00E−05 |
| ATG3_CDH1_HMGB1_RAPTOR_SIRT1 | 2.00E−05 |
| ATG3_CDH1_HMGB1_SIRT1_UVRAG | 2.06E−05 |
| ATG3_CDH1_HMGB1_RAPTOR_UVRAG | 2.11E−05 |
| ATG3_CDH1_HMGB1_KIAA1967_SIRT1 | 2.13E−05 |
| ATG3_BAX_BCL2_CDH1_HMGB1 | 2.16E−05 |
| ATG3_BCL2_LAMP1_CDH1_HMGB1 | 2.18E−05 |
| ATG3_ATG5_BCL2_CDH1_HMGB1 | 2.24E−05 |
| ATG3_BCL2_TKT_HMGB1_RAGE | 2.24E−05 |
| ATG3_CDH1_HMGB1_SATB1_UVRAG | 2.32E−05 |
| ATG3_BCL2_CDH1_HMGB1_SESN3 | 2.33E−05 |
| ATG3_BCL2_FAS_CDH1_HMGB1 | 2.34E−05 |
| CDH1_ID2_MMP9_TCF3_FASLG | 7.12E−03 |
| Survival | |
| DIABLO_FAS_ID2_MMP9_NAMPT | 1.76E−06 |
| ATG12_ATG3_ID2_MMP9_TCF3 | 1.80E−06 |
| ATG12_ID2_MMP9_TCF3_SATB1 | 2.20E−06 |
| ATG12_CSE1L_ID2_MMP9_TCF3 | 2.30E−06 |
| ATG12_BNIP3_ID2_MMP9_TCF3 | 2.40E−06 |
| ATG12_ID2_MMP9_TCF3_SESN2 | 2.40E−06 |
| ATG12_ULK1_ID2_MMP9_TCF3 | 2.40E−06 |
| ATG12_ATG5_ID2_MMP9_TCF3 | 2.80E−06 |
| ATG12_FAS_ID2_MMP9_TCF3 | 2.80E−06 |
| DIABLO_FAS_ID2_NAMPT_STAT3 | 2.85E−06 |
| ATG12_ID2_MMP9_TCF3_RPS19BP1 | 3.00E−06 |
| ATG12_BNIP3_ID2_MMP9_RPS19BP1 | 3.10E−06 |
| ATG12_CSE1L_ID2_MMP9_SATB1 | 3.10E−06 |
| ATG12_CSE1L_ID2_MMP9_SESN2 | 3.10E−06 |
| ATG12_LAMP1_ID2_MMP9_TCF3 | 3.10E−06 |
| DIABLO_FAS_ID2_NAMPT_SATB1 | 3.16E−06 |
| ATG12_BNIP3_CSE1L_ID2_MMP9 | 3.20E−06 |
| DIABLO_ID2_MMP9_TCF3_NAMPT | 3.28E−06 |
| ATG12_BNIP3_ID2_MMP9_SATB1 | 3.30E−06 |
| ATG12_ID2_MMP9_TCF3_BHLHE41 | 3.30E−06 |
| ATG12_ID2_MMP9_TCF3_STAT3 | 3.40E−06 |
| ATG12_BNIP3_FAS_ID2_MMP9 | 3.50E−06 |
| ATG12_BNIP3_ID2_MMP9_SESN2 | 3.70E−06 |
| ATG12_ATG3_FAS_ID2_MMP9 | 3.80E−06 |
| CSE1L_DIABLO_ID2_MMP9_NAMPT | 3.80E−06 |
| ATG12_DIABLO_ID2_MMP9_TCF3 | 3.90E−06 |
| DIABLO_ID2_NAMPT_SATB1_STAT3 | 3.95E−06 |
| ATG12_ATG3_CSE1L_ID2_MMP9 | 4.00E−06 |
| ATG12_FAS_ID2_MMP9_RPS19BP1 | 4.00E−06 |
| ATG12_DIABLO_FAS_ID2_MMP9 | 4.10E−06 |
| DIABLO_FAS_ID2_MMP9_STAT3 | 4.15E−06 |
| ATG12_CSE1L_ID2_MMP9_BHLHE41 | 4.20E−06 |
| DIABLO_ID2_MMP9_NAMPT_STAT3 | 4.22E−06 |
| DIABLO_FAS_ID2_NAMPT_SESN2 | 4.26E−06 |
| ATG12_CSE1L_FAS_ID2_MMP9 | 4.30E−06 |
| DIABLO_FAS_ID2_TCF3_NAMPT | 4.36E−06 |
| ATG12_ATG3_ID2_MMP9_SATB1 | 4.50E−06 |
| ATG12_BNIP3_ID2_MMP9_BHLHE41 | 4.50E−06 |
| ATG3_DIABLO_FAS_ID2_NAMPT | 4.60E−06 |
| CSE1L_DIABLO_FAS_ID2_NAMPT | 4.63E−06 |
| ATG12_CSE1L_ID2_MMP9_RPS19BP1 | 4.70E−06 |
| ATG12_CSE1L_ULK1_ID2_MMP9 | 4.70E−06 |
| DIABLO_FAS_ID2_MMP9_TCF3 | 4.73E−06 |
| CSE1L_DIABLO_ID2_NAMPT_STAT3 | 4.75E−06 |
| ATG12_ATG3_ID2_MMP9_SESN2 | 4.80E−06 |
| DIABLO_ID2_MMP9_TCF3_STAT3 | 4.81E−06 |
| DIABLO_ID2_TCF3_NAMPT_SATB1 | 4.84E−06 |

TABLE 42-continued

| Marker | p-value |
|---|---|
| CSE1L_DIABLO_FAS_MMP9_NAMPT | 4.94E−06 |
| DIABLO_FAS_ID2_NAMPT_RPS19BP1 | 4.95E−06 |
| BNIP3_DIABLO_FAS_ID2_MMP9 | 4.97E−06 |
| DIABLO_ID2_MMP9_NAMPT_SATB1 | 4.99E−06 |
| ATG12_DIABLO_FAS_MMP9_TCF3 | 5.00E−06 |
| ATG12_ATG5_FAS_ID2_MMP9 | 5.10E−06 |
| ATG12_LC3_ID2_MMP9_TCF3 | 5.10E−06 |
| ATG12_FAS_ID2_MMP9_STAT3 | 5.20E−06 |
| FAS_ID2_MMP9_NAMPT_RPS19BP1 | 5.21E−06 |
| ATG12_ID2_MMP9_TCF3_BECN1 | 5.40E−06 |
| ATG12_CDH1_ID2_MMP9_TCF3 | 2.10E−04 |
| Disease-free survival | |
| ATG3_BCL2_CDH1_HMGB1_RAGE | 3.47E−06 |
| ATG3_BCL2_CDH1_HMGB1_UVRAG | 3.54E−06 |
| ATG3_BCL2_CDH1_HMGB1_SIRT1 | 3.82E−06 |
| ATG3_BCL2_CDH1_HMGB1_RAPTOR | 4.19E−06 |
| ATG3_BCL2_CDH1_HMGB1_HMGB2 | 4.20E−06 |
| ATG3_BCL2_CDH1_HMGB1_KIAA1967 | 4.40E−06 |
| ATG3_BCL2_BNIP3_CDH1_HMGB1 | 5.13E−06 |
| ATG3_BCL2_CDH1_HMGB1_LAMP2 | 5.17E−06 |
| ATG3_BCL2_CDH1_CDH2_HMGB1 | 5.94E−06 |
| ATG3_CDH1_HMGB1_RAGE_SIRT1 | 6.16E−06 |
| ATG3_BCL2_CDH1_CASP3_HMGB1 | 6.89E−06 |
| ATG12_ATG3_BCL2_CDH1_HMGB1 | 7.15E−06 |
| AIFM1_ATG3_BCL2_CDH1_HMGB1 | 7.44E−06 |
| ATG3_BCL2_CASP8_CDH1_HMGB1 | 8.17E−06 |
| ATG3_BCL2_FRAP1_CDH1_HMGB1 | 8.58E−06 |
| ATG3_BCL2_CBS_CDH1_HMGB1 | 8.94E−06 |
| ATG3_CDH1_HMGB1_RAGE_UVRAG | 9.37E−06 |
| ATG3_BCL2_TKT_HMGB1_HMGB2 | 9.94E−06 |
| ATG3_BCL2_CDH1_HMGB1_MMP2 | 9.96E−06 |
| ATG3_BCL2_NNMT_CDH1_HMGB1 | 1.21E−05 |
| ATG3_BCL2_HMGB1_HMGB2_RAGE | 1.25E−05 |
| ATG3_BCL2_CDH1_MMP9_HMGB1 | 1.30E−05 |
| ATG12_ATG3_CDH1_HMGB1_RAGE | 1.31E−05 |
| ATG3_CDH1_HMGB1_LAMP2_SIRT1 | 1.38E−05 |
| ATG3_BCL2_DIABLO_CDH1_HMGB1 | 1.42E−05 |
| ATG3_BCL2L1_TKT_BECN1_CASP3 | 1.43E−05 |
| ATG3_BCL2_HMGB1_MMP2_RAGE | 1.50E−05 |
| ATG3_CDH1_HMGB1_HMGB2_UVRAG | 1.53E−05 |
| ATG3_BCL2_DRAM_CDH1_HMGB1 | 1.56E−05 |
| ATG3_BCL2_TKT_CDH1_HMGB1 | 1.60E−05 |
| ATG3_BCL2_TKT_CASP3_HMGB1 | 1.60E−05 |
| ATG3_CDH1_HMGB1_KIAA1967_UVRAG | 1.70E−05 |
| ATG3_CDH1_HMGB1_LAMP2_UVRAG | 1.74E−05 |
| ATG3_BCL2_BCL2L1_TKT_HMGB1 | 1.75E−05 |
| ATG3_BCL2_CDH1_HMGB1_SATB1 | 1.75E−05 |
| ATG3_BCL2L1_TKT_HMGB1_SIRT1 | 1.77E−05 |
| ATG3_BCL2_TKT_ID2_HMGB1 | 1.79E−05 |
| ATG3_CDH1_HMGB1_KIAA1967_RAGE | 1.80E−05 |
| ATG3_BCL2_PTEN_CDH1_HMGB1 | 1.88E−05 |
| AIFM1_ATG3_CDH1_HMGB1_SIRT1 | 1.90E−05 |
| ATG3_BCL2_CDH1_HMGB1_STAT3 | 1.91E−05 |
| ATG3_CDH1_CASP3_HMGB1_RAGE | 1.93E−05 |
| ATG3_BCL2_LC3_TKT_HMGB1 | 1.94E−05 |
| ATG3_CDH1_CASP3_HMGB1_UVRAG | 1.95E−05 |
| ATG3_BCL2_CDH1_CIAP2_HMGB1 | 2.00E−05 |
| ATG3_BCL2_BNIP3_HMGB1_RAGE | 2.00E−05 |
| ATG3_CDH1_HMGB1_RAPTOR_SIRT1 | 2.00E−05 |
| ATG3_CDH1_HMGB1_SIRT1_UVRAG | 2.06E−05 |
| ATG3_CDH1_HMGB1_RAPTOR_UVRAG | 2.11E−05 |
| ATG3_CDH1_HMGB1_KIAA1967_SIRT1 | 2.13E−05 |
| ATG3_BAX_BCL2_CDH1_HMGB1 | 2.16E−05 |
| ATG3_BCL2_LAMP1_CDH1_HMGB1 | 2.18E−05 |
| ATG3_ATG5_BCL2_CDH1_HMGB1 | 2.24E−05 |
| ATG3_BCL2_TKT_HMGB1_RAGE | 2.24E−05 |
| ATG3_CDH1_HMGB1_SATB1_UVRAG | 2.32E−05 |
| ATG3_BCL2_CDH1_HMGB1_SESN3 | 2.33E−05 |
| ATG3_BCL2_FAS_CDH1_HMGB1 | 2.34E−05 |
| CDH1_ID2_MMP9_TCF3_FASLG | 7.12E−03 |

TABLE 43

| Marker | p-value |
|---|---|
| Recurrence | |
| ATG3_BCL2_CDH1_HMGB1_RAGE_RAPTOR | 1.52E−06 |
| ATG3_BCL2_BNIP3_CDH1_HMGB1_RAGE | 1.55E−06 |
| ATG3_BCL2_CDH1_HMGB1_HMGB2_RAGE | 1.57E−06 |
| ATG3_BCL2_CDH1_HMGB1_KIAA1967_RAGE | 1.61E−06 |
| ATG3_BCL2_CDH1_HMGB1_RAGE_SIRT1 | 1.62E−06 |
| ATG3_BCL2_CDH1_HMGB1_HMGB2_RAPTOR | 1.81E−06 |
| ATG3_BCL2_CDH1_CDH2_HMGB1_RAGE | 1.82E−06 |
| ATG3_BCL2_CDH1_HMGB1_RAGE_UVRAG | 2.07E−06 |
| ATG3_BCL2_CDH1_CASP3_HMGB1_RAGE | 2.08E−06 |
| AIFM1_ATG3_BCL2_CDH1_HMGB1_SIRT1 | 2.08E−06 |
| ATG3_BCL2_BNIP3_CDH1_HMGB1_UVRAG | 2.08E−06 |
| ATG12_ATG3_BCL2_CDH1_HMGB1_RAGE | 2.28E−06 |
| ATG3_BCL2_CDH1_HMGB1_HMGB2_UVRAG | 2.34E−06 |
| ATG3_BCL2_CDH1_HMGB1_LAMP2_RAGE | 2.42E−06 |
| ATG3_BCL2_CDH1_HMGB1_HMGB2_LAMP2 | 2.48E−06 |
| ATG3_BCL2_CDH1_CDH2_HMGB1_HMGB2 | 2.49E−06 |
| ATG3_BCL2_BCL2L1_TKT_CASP3_HMGB1 | 2.50E−06 |
| AIFM1_ATG3_BCL2_CDH1_HMGB1_UVRAG | 2.57E−06 |
| ATG3_BCL2_CDH1_HMGB1_HMGB2_KIAA1967 | 2.59E−06 |
| ATG3_BCL2_BNIP3_CDH1_HMGB1_HMGB2 | 2.71E−06 |
| ATG12_ATG3_CDH1_HMGB1_RAGE_SIRT1 | 2.73E−06 |
| ATG3_BCL2_BNIP3_CDH1_HMGB1_RAPTOR | 2.75E−06 |
| ATG3_BCL2_DRAM_CDH1_HMGB1_SIRT1 | 2.81E−06 |
| ATG3_BCL2_BNIP3_CDH1_HMGB1_LAMP2 | 2.86E−06 |
| AIFM1_ATG3_BCL2_CDH1_HMGB1_RAGE | 2.94E−06 |
| ATG3_BCL2_BNIP3_CDH1_HMGB1_KIAA1967 | 2.98E−06 |
| ATG3_BCL2_CDH1_HMGB1_MMP2_RAGE | 3.01E−06 |
| AIFM1_ATG3_BCL2_CDH1_HMGB1_HMGB2 | 3.07E−06 |
| ATG3_BCL2_CDH1_HMGB1_HMGB2_SIRT1 | 3.10E−06 |
| ATG3_BCL2_CDH1_HMGB1_MMP2_UVRAG | 3.12E−06 |
| ATG3_BCL2_CASP8_CDH1_HMGB1_RAGE | 3.14E−06 |
| ATG3_CDH1_HMGB1_LAMP2_RAGE_SIRT1 | 3.15E−06 |
| ATG3_BCL2_DRAM_CDH1_HMGB1_UVRAG | 3.17E−06 |
| ATG3_BCL2_PTEN_CDH1_HMGB1_SIRT1 | 3.20E−06 |
| ATG3_BCL2_BCL2L1_TKT_HMGB1_SIRT1 | 3.25E−06 |
| ATG3_BCL2_BNIP3_CDH1_HMGB1_SIRT1 | 3.26E−06 |
| ATG3_BCL2_FRAP1_CDH1_HMGB1_RAGE | 3.33E−06 |
| AIFM1_ATG3_BCL2_CDH1_HMGB1_KIAA1967 | 3.33E−06 |
| ATG3_BCL2_CDH1_HMGB1_LAMP2_RAPTOR | 3.34E−06 |
| ATG3_CDH1_HMGB1_RAGE_SIRT1_UVRAG | 3.37E−06 |
| ATG3_BCL2_CBS_CDH1_HMGB1_RAGE | 3.44E−06 |
| ATG3_BCL2_FRAP1_CDH1_HMGB1_UVRAG | 3.49E−06 |
| ATG3_BCL2_CBS_CDH1_HMGB1_UVRAG | 3.51E−06 |
| ATG3_CDH1_HMGB1_HMGB2_RAGE_SIRT1 | 3.61E−06 |
| AIFM1_ATG3_BCL2_CDH1_HMGB1_RAPTOR | 3.61E−06 |
| ATG3_BCL2_CDH1_HMGB1_KIAA1967_RAPTOR | 3.63E−06 |
| ATG3_BCL2_BCL2L1_TKT_ID2_CASP3 | 3.64E−06 |
| ATG3_BCL2_CDH1_HMGB1_RAPTOR_UVRAG | 3.66E−06 |
| ATG3_BCL2_CASP8_CDH1_HMGB1_HMGB2 | 3.66E−06 |
| ATG12_ATG3_BCL2_CDH1_HMGB1_HMGB2 | 3.70E−06 |
| ATG3_BCL2_FRAP1_CDH1_HMGB1_SIRT1 | 3.71E−06 |
| ATG3_BCL2_CDH1_HMGB1_MMP2_SIRT1 | 3.76E−06 |
| AIFM1_ATG3_CDH1_HMGB1_RAGE_SIRT1 | 3.87E−06 |
| ATG3_BCL2_FRAP1_CDH1_HMGB1_HMGB2 | 3.94E−06 |
| ATG3_BCL2_CBS_CDH1_HMGB1_SIRT1 | 3.98E−06 |
| ATG3_BCL2_CASP8_CDH1_HMGB1_UVRAG | 4.00E−06 |
| ATG3_BCL2_PTEN_CDH1_HMGB1_UVRAG | 4.01E−06 |
| ATG12_ATG3_CDH1_ID2_MMP9_TCF3 | 7.76E−04 |
| Survival | |
| DIABLO_FAS_ID2_MMP9_TCF3_NAMPT | 1.47E−06 |
| ATG12_ATG3_BNIP3_ID2_MMP9_TCF3 | 1.60E−06 |
| ATG12_BNIP3_CSE1L_ID2_MMP9_SATB1 | 1.60E−06 |
| ATG12_ATG3_ID2_MMP9_TCF3_SATB1 | 1.70E−06 |
| DIABLO_FAS_ID2_MMP9_NAMPT_SATB1 | 1.78E−06 |
| ATG12_ATG3_ULK1_ID2_MMP9_TCF3 | 1.80E−06 |
| ATG12_BNIP3_CSE1L_ID2_MMP9_SESN2 | 1.80E−06 |
| DIABLO_FAS_ID2_MMP9_NAMPT_STAT3 | 1.83E−06 |
| ATG12_ATG3_FAS_ID2_MMP9_TCF3 | 1.90E−06 |
| ATG12_ATG3_ID2_MMP9_TCF3_SESN2 | 1.90E−06 |
| ATG12_BNIP3_CSE1L_ID2_MMP9_TCF3 | 1.90E−06 |
| CSE1L_DIABLO_FAS_ID2_MMP9_NAMPT | 1.94E−06 |
| ATG12_ATG3_CSE1L_ID2_MMP9_TCF3 | 2.00E−06 |
| ATG12_BNIP3_ID2_MMP9_TCF3_SATB1 | 2.00E−06 |
| DIABLO_FAS_ID2_MMP9_NAMPT_SESN2 | 2.02E−06 |
| ATG12_BNIP3_CSE1L_ID2_MMP9_BHLHE41 | 2.10E−06 |

TABLE 43-continued

| Marker | p-value |
|---|---|
| ATG12_BNIP3_ID2_MMP9_TCF3_RPS19BP1 | 2.10E−06 |
| DIABLO_FAS_ID2_MMP9_TCF3_STAT3 | 2.10E−06 |
| ATG12_ATG3_BNIP3_FAS_ID2_MMP9 | 2.20E−06 |
| ATG12_ATG3_BNIP3_ID2_MMP9_SATB1 | 2.20E−06 |
| ATG12_BNIP3_CSE1L_ID2_MMP9_RPS19BP1 | 2.20E−06 |
| ATG12_BNIP3_DIABLO_FAS_ID2_MMP9 | 2.20E−06 |
| ATG12_BNIP3_FAS_ID2_MMP9_RPS19BP1 | 2.20E−06 |
| ATG12_CSE1L_ID2_MMP9_TCF3_SATB1 | 2.20E−06 |
| ATG12_CSE1L_ULK1_ID2_MMP9_TCF3 | 2.20E−06 |
| ATG12_FAS_ID2_MMP9_TCF3_RPS19BP1 | 2.20E−06 |
| DIABLO_FAS_ID2_NAMPT_SATB1_STAT3 | 2.27E−06 |
| ATG12_ATG5_BNIP3_ID2_MMP9_TCF3 | 2.30E−06 |
| ATG12_BNIP3_ID2_MMP9_TCF3_SESN2 | 2.30E−06 |
| ATG12_CSE1L_ID2_MMP9_TCF3_SESN2 | 2.30E−06 |
| ATG12_ID2_MMP9_TCF3_SATB1_SESN2 | 2.30E−06 |
| ATG12_ULK1_ID2_MMP9_TCF3_SATB1 | 2.30E−06 |
| ATG12_ATG3_ATG5_ID2_MMP9_TCF3 | 2.40E−06 |
| ATG12_ATG3_BNIP3_CSE1L_ID2_MMP9 | 2.40E−06 |
| ATG12_ATG3_LAMP1_ID2_MMP9_TCF3 | 2.40E−06 |
| ATG12_BNIP3_DIABLO_ID2_MMP9_TCF3 | 2.40E−06 |
| ATG12_BNIP3_ULK1_ID2_MMP9_TCF3 | 2.40E−06 |
| ATG12_DIABLO_FAS_ID2_MMP9_TCF3 | 2.40E−06 |
| ATG12_ULK1_ID2_MMP9_TCF3_SESN2 | 2.40E−06 |
| ATG3_DIABLO_FAS_ID2_MMP9_NAMPT | 2.40E−06 |
| ATG12_ATG3_BNIP3_ID2_MMP9_SESN2 | 2.50E−06 |
| ATG12_ATG3_ID2_MMP9_TCF3_BHLHE41 | 2.50E−06 |
| ATG12_BNIP3_CSE1L_FAS_ID2_MMP9 | 2.50E−06 |
| DIABLO_ID2_MMP9_TCF3_NAMPT_SATB1 | 2.55E−06 |
| ATG12_ATG3_BNIP3_ID2_MMP9_RPS19BP1 | 2.60E−06 |
| ATG12_ATG5_ID2_MMP9_TCF3_SATB1 | 2.60E−06 |
| ATG12_BNIP3_FAS_ID2_MMP9_TCF3 | 2.60E−06 |
| ATG12_ATG3_CSE1L_ID2_MMP9_SATB1 | 2.70E−06 |
| ATG12_ATG3_ID2_MMP9_TCF3_STAT3 | 2.70E−06 |
| ATG12_ATG5_BNIP3_ID2_MMP9_SATB1 | 2.70E−06 |
| ATG12_BNIP3_ID2_MMP9_TCF3_BHLHE41 | 2.70E−06 |
| ATG12_FAS_ID2_MMP9_TCF3_SESN2 | 2.70E−06 |
| DIABLO_FAS_ID2_MMP9_NAMPT_RPS19BP1 | 2.73E−06 |
| ATG12_ATG3_CSE1L_ID2_MMP9_SESN2 | 2.80E−06 |
| ATG12_ATG3_ID2_MMP9_TCF3_RPS19BP1 | 2.80E−06 |
| ATG12_ATG5_BNIP3_FAS_ID2_MMP9 | 2.80E−06 |
| ATG12_ATG5_ULK1_ID2_MMP9_TCF3 | 2.80E−06 |
| E2F1_FAS_CDH1_ID2_MMP9_TCF3 | 7.98E−05 |
| Disease-free survival | |
| ATG3_BCL2_CDH1_HMGB1_RAGE_RAPTOR | 1.52E−06 |
| ATG3_BCL2_BNIP3_CDH1_HMGB1_RAGE | 1.55E−06 |
| ATG3_BCL2_CDH1_HMGB1_HMGB2_RAGE | 1.57E−06 |
| ATG3_BCL2_CDH1_HMGB1_KIAA1967_RAGE | 1.61E−06 |
| ATG3_BCL2_CDH1_HMGB1_RAGE_SIRT1 | 1.62E−06 |
| ATG3_BCL2_CDH1_HMGB1_HMGB2_RAPTOR | 1.81E−06 |
| ATG3_BCL2_CDH1_CDH2_HMGB1_RAGE | 1.82E−06 |
| ATG3_BCL2_CDH1_HMGB1_RAGE_UVRAG | 2.07E−06 |
| ATG3_BCL2_CDH1_CASP3_HMGB1_RAGE | 2.08E−06 |
| AIFM1_ATG3_BCL2_CDH1_HMGB1_SIRT1 | 2.08E−06 |
| ATG3_BCL2_BNIP3_CDH1_HMGB1_UVRAG | 2.08E−06 |
| ATG12_ATG3_BCL2_CDH1_HMGB1_RAGE | 2.28E−06 |
| ATG3_BCL2_CDH1_HMGB1_HMGB2_UVRAG | 2.34E−06 |
| ATG3_BCL2_CDH1_HMGB1_LAMP2_RAGE | 2.42E−06 |
| ATG3_BCL2_CDH1_HMGB1_HMGB2_LAMP2 | 2.48E−06 |
| ATG3_BCL2_CDH1_CDH2_HMGB1_HMGB2 | 2.49E−06 |
| ATG3_BCL2_BCL2L1_TKT_CASP3_HMGB1 | 2.50E−06 |
| AIFM1_ATG3_BCL2_CDH1_HMGB1_UVRAG | 2.57E−06 |
| ATG3_BCL2_CDH1_HMGB1_HMGB2_KIAA1967 | 2.59E−06 |
| ATG3_BCL2_BNIP3_CDH1_HMGB1_HMGB2 | 2.71E−06 |
| ATG12_ATG3_CDH1_HMGB1_RAGE_SIRT1 | 2.73E−06 |
| ATG3_BCL2_BNIP3_CDH1_HMGB1_RAPTOR | 2.75E−06 |
| ATG3_BCL2_DRAM_CDH1_HMGB1_SIRT1 | 2.81E−06 |
| ATG3_BCL2_BNIP3_CDH1_HMGB1_LAMP2 | 2.86E−06 |
| AIFM1_ATG3_BCL2_CDH1_HMGB1_RAGE | 2.94E−06 |
| ATG3_BCL2_BNIP3_CDH1_HMGB1_KIAA1967 | 2.98E−06 |
| ATG3_BCL2_CDH1_HMGB1_MMP2_RAGE | 3.01E−06 |
| AIFM1_ATG3_BCL2_CDH1_HMGB1_HMGB2 | 3.07E−06 |
| ATG3_BCL2_CDH1_HMGB1_HMGB2_SIRT1 | 3.10E−06 |
| ATG3_BCL2_CDH1_HMGB1_MMP2_UVRAG | 3.12E−06 |
| ATG3_BCL2_CASP8_CDH1_HMGB1_RAGE | 3.14E−06 |
| ATG3_CDH1_HMGB1_LAMP2_RAGE_SIRT1 | 3.15E−06 |
| ATG3_BCL2_DRAM_CDH1_HMGB1_UVRAG | 3.17E−06 |
| ATG3_BCL2_PTEN_CDH1_HMGB1_SIRT1 | 3.20E−06 |

TABLE 43-continued

| Marker | p-value |
|---|---|
| ATG3_BCL2_BCL2L1_TKT_HMGB1_SIRT1 | 3.25E−06 |
| ATG3_BCL2_BNIP3_CDH1_HMGB1_SIRT1 | 3.26E−06 |
| ATG3_BCL2_FRAP1_CDH1_HMGB1_RAGE | 3.33E−06 |
| AIFM1_ATG3_BCL2_CDH1_HMGB1_KIAA1967 | 3.33E−06 |
| ATG3_BCL2_CDH1_HMGB1_LAMP2_RAPTOR | 3.34E−06 |
| ATG3_CDH1_HMGB1_RAGE_SIRT1_UVRAG | 3.37E−06 |
| ATG3_BCL2_CBS_CDH1_HMGB1_RAGE | 3.44E−06 |
| ATG3_BCL2_FRAP1_CDH1_HMGB1_UVRAG | 3.49E−06 |
| ATG3_BCL2_CBS_CDH1_HMGB1_UVRAG | 3.51E−06 |
| ATG3_CDH1_HMGB1_HMGB2_RAGE_SIRT1 | 3.61E−06 |
| AIFM1_ATG3_BCL2_CDH1_HMGB1_RAPTOR | 3.61E−06 |
| ATG3_BCL2_CDH1_HMGB1_KIAA1967_RAPTOR | 3.63E−06 |
| ATG3_BCL2_BCL2L1_TKT_ID2_CASP3 | 3.64E−06 |
| ATG3_BCL2_CDH1_HMGB1_RAPTOR_UVRAG | 3.66E−06 |
| ATG3_BCL2_CASP8_CDH1_HMGB1_HMGB2 | 3.66E−06 |
| ATG12_ATG3_BCL2_CDH1_HMGB1_HMGB2 | 3.70E−06 |
| ATG3_BCL2_FRAP1_CDH1_HMGB1_SIRT1 | 3.71E−06 |
| ATG3_BCL2_CDH1_HMGB1_MMP2_SIRT1 | 3.76E−06 |
| AIFM1_ATG3_CDH1_HMGB1_RAGE_SIRT1 | 3.87E−06 |
| ATG3_BCL2_FRAP1_CDH1_HMGB1_HMGB2 | 3.94E−06 |
| ATG3_BCL2_CBS_CDH1_HMGB1_SIRT1 | 3.98E−06 |
| ATG3_BCL2_CASP8_CDH1_HMGB1_UVRAG | 4.00E−06 |
| ATG3_BCL2_PTEN_CDH1_HMGB1_UVRAG | 4.01E−06 |
| ATG12_ATG3_CDH1_ID2_MMP9_TCF3 | 1.32E−03 |

TABLE 44

| Marker | p-value |
|---|---|
| Recurrence | |
| ATG3_BCL2_CDH1_HMGB1_HMGB2_RAGE_RAPTOR | 6.40E−07 |
| ATG3_BCL2_CDH1_CDH2_HMGB1_HMGB2_RAGE | 7.49E−07 |
| ATG3_BCL2_BNIP3_CDH1_HMGB1_RAGE_RAPTOR | 7.69E−07 |
| ATG3_BCL2_BNIP3_CDH1_HMGB1_HMGB2_RAGE | 7.99E−07 |
| ATG3_BCL2_BNIP3_CDH1_HMGB1_KIAA1967_RAGE | 8.59E−07 |
| AIFM1_ATG3_BCL2_CDH1_HMGB1_RAGE_SIRT1 | 8.85E−07 |
| ATG3_BCL2_CDH1_HMGB1_HMGB2_KIAA1967_RAGE | 9.52E−07 |
| ATG3_BCL2_DRAM_CDH1_HMGB1_RAGE_SIRT1 | 9.81E−07 |
| ATG3_BCL2_BNIP3_CDH1_HMGB1_RAGE_UVRAG | 9.88E−07 |
| ATG3_BCL2_BCL2L1_TKT_ID2_CASP3_HMGB2 | 9.95E−07 |
| ATG3_BCL2_BCL2L1_TKT_ID2_CASP3_SIRT1 | 1.01E−06 |
| ATG3_BCL2_BCL2L1_TKT_CASP3_HMGB1_SIRT1 | 1.05E−06 |
| ATG3_BCL2_BNIP3_CDH1_HMGB1_LAMP2_RAGE | 1.06E−06 |
| ATG3_BCL2_BNIP3_CDH1_CDH2_HMGB1_RAGE | 1.08E−06 |
| ATG3_BCL2_BNIP3_CDH1_HMGB1_RAGE_SIRT1 | 1.13E−06 |
| ATG3_BCL2_CDH1_HMGB1_HMGB2_LAMP2_RAGE | 1.15E−06 |
| ATG12_ATG3_BCL2_CDH1_HMGB1_HMGB2_RAGE | 1.15E−06 |
| ATG3_BCL2_BCL2L1_TKT_ID2_CASP3_KIAA1967 | 1.16E−06 |
| ATG3_BCL2_BCL2L1_TKT_CASP3_CDH2_HMGB1 | 1.17E−06 |
| AIFM1_ATG3_BCL2_CDH1_HMGB1_HMGB2_RAGE | 1.18E−06 |
| ATG3_BCL2_BCL2L1_TKT_CASP3_HMGB1_HMGB2 | 1.18E−06 |
| ATG12_ATG3_BCL2_BNIP3_CDH1_HMGB1_RAGE | 1.22E−06 |
| ATG3_BCL2_BCL2L1_TKT_CASP3_HMGB1_UVRAG | 1.22E−06 |
| ATG3_BCL2_CDH1_HMGB1_KIAA1967_MMP2_RAGE | 1.23E−06 |
| AIFM1_ATG3_BCL2_BNIP3_CDH1_HMGB1_RAGE | 1.23E−06 |
| ATG3_BCL2_BCL2L1_TKT_CASP3_HMGB1_KIAA1967 | 1.24E−06 |
| ATG3_BCL2_BCL2L1_TKT_CASP3_HMGB1_RAPTOR | 1.25E−06 |
| AIFM1_ATG3_BCL2_CDH1_HMGB1_KIAA1967_RAGE | 1.25E−06 |
| ATG3_BCL2_BCL2L1_TKT_ID2_HMGB2_SIRT1 | 1.26E−06 |
| ATG3_BCL2_CDH1_HMGB1_MMP2_RAGE_SIRT1 | 1.27E−06 |
| AIFM1_ATG3_BCL2_CDH1_CASP3_HMGB1_RAGE | 1.27E−06 |
| ATG3_BCL2_CDH1_HMGB1_KIAA1967_RAGE_RAPTOR | 1.29E−06 |
| ATG3_BCL2_DRAM_CDH1_CASP3_HMGB1_RAGE | 1.29E−06 |
| ATG3_BCL2_BNIP3_CDH1_FASLG_HMGB1_RAGE | 1.29E−06 |
| ATG3_BCL2_CDH1_HMGB1_HMGB2_RAGE_SIRT1 | 1.30E−06 |
| ATG3_TKT_HMGB1_HMGB2_KIAA1967_RAGE_TWIST1 | 1.30E−06 |
| ATG3_BCL2_BCL2L1_TKT_ID2_CASP3_CDH2 | 1.32E−06 |
| ATG3_BCL2_DRAM_CDH1_HMGB1_HMGB2_UVRAG | 1.33E−06 |
| AIFM1_ATG3_BCL2_CDH1_CDH2_HMGB1_RAGE | 1.34E−06 |
| ATG3_BCL2_BCL2L1_TKT_CASP3_HMGB1_LAMP2 | 1.34E−06 |
| AIFM1_ATG3_BCL2_CDH1_HMGB1_HMGB2_RAPTOR | 1.34E−06 |
| AIFM1_ATG3_BCL2_CDH1_HMGB1_RAGE_RAPTOR | 1.34E−06 |
| ATG3_BCL2_CASP8_CDH1_HMGB1_HMGB2_RAGE | 1.35E−06 |
| ATG3_BCL2_CDH1_HMGB1_HMGB2_RAGE_UVRAG | 1.35E−06 |

TABLE 44-continued

| Marker | p-value |
|---|---|
| ATG3_BCL2_BNIP3_CDH1_HMGB1_HMGB2_RAPTOR | 1.36E−06 |
| ATG3_BCL2_BNIP3_CASP8_CDH1_HMGB1_RAGE | 1.38E−06 |
| ATG3_BCL2_CDH1_HMGB1_MMP2_RAGE_UVRAG | 1.38E−06 |
| ATG3_BCL2_BCL2L1_TKT_HMGB1_HMGB2_SIRT1 | 1.39E−06 |
| ATG3_BCL2_BCL2L1_IKT_CASP3_HMGB1_RAGE | 1.40E−06 |
| AIFM1_ATG3_BCL2_BNIP3_CDH1_HMGB1_UVRAG | 1.42E−06 |
| ATG3_BCL2_DRAM_CDH1_HMGB1_HMGB2_SIRT1 | 1.43E−06 |
| ATG12_ATG3_BCL2_BCL2L1_TKT_CASP3_HMGB1 | 1.44E−06 |
| ATG12_ATG3_BCL2_PTEN_CDH1_HMGB1_RAGE | 1.45E−06 |
| ATG3_BCL2_PTEN_CDH1_HMGB1_RAGE_SIRT1 | 1.46E−06 |
| ATG3_BCL2_CDH1_CASP3_HMGB1_RAGE_RAPTOR | 1.46E−06 |
| ATG3_BCL2_BNIP3_FRAP1_CDH1_HMGB1_RAGE | 1.47E−06 |
| ATG3_BCL2_FRAP1_CDH1_HMGB1_HMGB2_RAGE | 1.47E−06 |
| ATG12_ATG3_CDH1_ID2_MMP9_TCF3_SATB1 | 1.24E−04 |
| Survival | |
| DIABLO_FAS_ID2_MMP9_TCF3_NAMPT_SATB1 | 1.26E−06 |
| ATG12_ATG3_BNIP3_CSE1L_ID2_MMP9_SATB1 | 1.30E−06 |
| ATG12_ATG3_BNIP3_CSE1L_ID2_MMP9_SESN2 | 1.40E−06 |
| ATG12_ATG3_BNIP3_ID2_MMP9_TCF3_SATB1 | 1.40E−06 |
| ATG12_ATG3_BNIP3_CSE1L_ID2_MMP9_TCF3 | 1.50E−06 |
| DIABLO_FAS_ID2_MMP9_TCF3_NAMPT_SESN2 | 1.59E−06 |
| ATG12_ATG3_BNIP3_CSE1L_ID2_MMP9_BHLHE41 | 1.60E−06 |
| ATG12_ATG3_BNIP3_ID2_MMP9_TCF3_SESN2 | 1.60E−06 |
| ATG12_ATG3_BNIP3_ULK1_ID2_MMP9_TCF3 | 1.60E−06 |
| ATG12_BNIP3_CSE1L_ULK1_ID2_MMP9_SATB1 | 1.60E−06 |
| ATG12_BNIP3_FAS_ID2_MMP9_TCF3_RPS19BP1 | 1.60E−06 |
| DIABLO_FAS_ID2_MMP9_NAMPT_SATB1_STAT3 | 1.62E−06 |
| DIABLO_FAS_ID2_MMP9_TCF3_NAMPT_STAT3 | 1.65E−06 |
| ATG12_ATG3_ATG5_BNIP3_ID2_MMP9_TCF3 | 1.68E−06 |
| ATG12_ATG3_BNIP3_FAS_ID2_MMP9_RPS19BP1 | 1.70E−06 |
| ATG12_ATG3_BNIP3_FAS_ID2_MMP9_TCF3 | 1.70E−06 |
| ATG12_ATG3_BNIP3_ID2_MMP9_TCF3_RPS19BP1 | 1.70E−06 |
| ATG12_ATG3_ULK1_ID2_MMP9_TCF3_SATB1 | 1.70E−06 |
| ATG12_ATG5_BNIP3_CSE1L_ID2_MMP9_SATB1 | 1.70E−06 |
| ATG12_BNIP3_CSE1L_ID2_MMP9_SATB1_SESN2 | 1.70E−06 |
| ATG12_BNIP3_CSE1L_ID2_MMP9_TCF3_SATB1 | 1.70E−06 |
| ATG12_BNIP3_DIABLO_FAS_ID2_MMP9_TCF3 | 1.70E−06 |
| ATG12_ATG3_ID2_MMP9_TCF3_SATB1_SESN2 | 1.74E−06 |
| DIABLO_FAS_ID2_MMP9_TCF3_SATB1_STAT3 | 1.79E−06 |
| ATG12_ATG3_BNIP3_CSE1L_FAS_ID2_MMP9 | 1.80E−06 |
| ATG12_ATG3_BNIP3_DIABLO_FAS_ID2_MMP9 | 1.80E−06 |
| ATG12_ATG3_BNIP3_ID2_MMP9_TCF3_BHLHE41 | 1.80E−06 |
| ATG12_BNIP3_CSE1L_DIABLO_FAS_ID2_MMP9 | 1.80E−06 |
| ATG12_BNIP3_CSE1L_ULK1_ID2_MMP9_SESN2 | 1.80E−06 |
| CSE1L_DIABLO_FAS_ID2_MMP9_NAMPT_STAT3 | 1.81E−06 |
| ATG12_ATG3_ATG5_BNIP3_FAS_ID2_MMP9 | 1.89E−06 |
| ATG12_ATG3_CSE1L_ID2_MMP9_TCF3_SATB1 | 1.90E−06 |
| ATG12_ATG3_ULK1_ID2_MMP9_TCF3_SESN2 | 1.90E−06 |
| ATG12_ATG5_BNIP3_CSE1L_ID2_MMP9_SESN2 | 1.90E−06 |
| ATG12_ATG5_BNIP3_ID2_MMP9_TCF3_SATB1 | 1.90E−06 |
| ATG12_BNIP3_CSE1L_ID2_MMP9_TCF3_SESN2 | 1.90E−06 |
| ATG12_BNIP3_CSE1L_ULK1_ID2_MMP9_TCF3 | 1.90E−06 |
| ATG12_BNIP3_ID2_MMP9_TCF3_RPS19BP1_SATB1 | 1.90E−06 |
| ATG12_ATG3_FAS_ID2_MMP9_TCF3_SATB1 | 1.91E−06 |
| ATG12_ATG3_FAS_ID2_MMP9_TCF3_RPS19BP1 | 1.91E−06 |
| ATG12_ATG3_FAS_ID2_MMP9_TCF3_SESN2 | 1.91E−06 |
| ATG12_ATG3_FAS_ULK1_ID2_MMP9_TCF3 | 1.91E−06 |
| ATG12_ATG3_ATG5_BNIP3_ID2_MMP9_SATB1 | 1.93E−06 |
| ATG12_ATG3_BNIP3_CSE1L_ID2_MMP9_RPS19BP1 | 2.00E−06 |
| ATG12_ATG3_CSE1L_ID2_MMP9_TCF3_SESN2 | 2.00E−06 |
| ATG12_ATG3_CSE1L_ULK1_ID2_MMP9_TCF3 | 2.00E−06 |
| ATG12_BNIP3_CSE1L_FASJ_D2_MMP9_RPS19BP1 | 2.00E−06 |
| ATG12_BNIP3_CSE1L_ID2_MMP9_BHLHE41_SATB1 | 2.00E−06 |
| ATG12_BNIP3_CSE1L_ID2_MMP9_TCF3_BHLHE41 | 2.00E−06 |
| ATG12_BNIP3_ID2_MMP9_TCF3_SATB1_SESN2 | 2.00E−06 |
| ATG12_BNIP3_ULK1_ID2_MMP9_TCF3_SATB1 | 2.00E−06 |
| DIABLO_FAS_ID2_MMP9_NAMPT_SESN2_STAT3 | 2.00E−06 |
| CSE1L_DIABLO_FAS_ID2_MMP9_TCF3_NAMPT | 2.04E−06 |
| DIABLO_FAS_ID2_MMP9_NAMPT_SATB1_SESN2 | 2.05E−06 |
| CSE1L_DIABLO_FAS_ID2_MMP9_NAMPT_SATB1 | 2.07E−06 |
| ATG12_ATG3_BNIP3_DIABLO_ID2_MMP9_TCF3 | 2.10E−06 |
| ATG12_ATG3_BNIP3_FAS_ID2_MMP9_SATB1 | 2.10E−06 |
| ATG3_TKT_CDH1_ID2_MMP9_TCF3_UVRAG | 2.52E−05 |
| Disease-free survival | |
| ATG3_BCL2_CDH1_HMGB1_HMGB2_RAGE_RAPTOR | 6.40E−07 |
| ATG3_BCL2_CDH1_CDH2_HMGB1_HMGB2_RAGE | 7.49E−07 |

TABLE 44-continued

| Marker | p-value |
|---|---|
| ATG3_BCL2_BNIP3_CDH1_HMGB1_RAGE_RAPTOR | 7.69E−07 |
| ATG3_BCL2_BNIP3_CDH1_HMGB1_HMGB2_RAGE | 7.99E−07 |
| ATG3_BCL2_BNIP3_CDH1_HMGB1_KIAA1967_RAGE | 8.59E−07 |
| AIFM1_ATG3_BCL2_CDH1_HMGB1_RAGE_SIRT1 | 8.85E−07 |
| ATG3_BCL2_CDH1_HMGB1_HMGB2_KIAA1967_RAGE | 9.52E−07 |
| ATG3_BCL2_DRAM_CDH1_HMGB1_RAGE_SIRT1 | 9.81E−07 |
| ATG3_BCL2_BNIP3_CDH1_HMGB1_RAGE_UVRAG | 9.88E−07 |
| ATG3_BCL2_BCL2L1_TKT_ID2_CASP3_HMGB2 | 9.95E−07 |
| ATG3_BCL2_BCL2L1_TKT_ID2_CASP3_SIRT1 | 1.01E−06 |
| ATG3_BCL2_BCL2L1_TKT_CASP3_HMGB1_SIRT1 | 1.05E−06 |
| ATG3_BCL2_BNIP3_CDH1_HMGB1_LAMP2_RAGE | 1.06E−06 |
| ATG3_BCL2_BNIP3_CDH1_CDH2_HMGB1_RAGE | 1.08E−06 |
| ATG3_BCL2_BNIP3_CDH1_HMGB1_RAGE_SIRT1 | 1.13E−06 |
| ATG3_BCL2_CDH1_HMGB1_HMGB2_LAMP2_RAGE | 1.15E−06 |
| ATG12_ATG3_BCL2_CDH1_HMGB1_HMGB2_RAGE | 1.15E−06 |
| ATG3_BCL2_BCL2L1_TKT_ID2_CASP3_KIAA1967 | 1.16E−06 |
| ATG3_BCL2_BCL2L1_TKT_CASP3_CDH2_HMGB1 | 1.17E−06 |
| AIFM1_ATG3_BCL2_CDH1_HMGB1_HMGB2_RAGE | 1.18E−06 |
| ATG3_BCL2_BCL2L1_TKT_CASP3_HMGB1_HMGB2 | 1.18E−06 |
| ATG12_ATG3_BCL2_BNIP3_CDH1_HMGB1_RAGE | 1.22E−06 |
| ATG3_BCL2_BCL2L1_IKT_CASP3_HMGB1_UVRAG | 1.22E−06 |
| ATG3_BCL2_CDH1_HMGB1_KIAA1967_MMP2_RAGE | 1.23E−06 |
| AIFM1_ATG3_BCL2_BNIP3_CDH1_HMGB1_RAGE | 1.23E−06 |
| ATG3_BCL2_BCL2L1_TKT_CASP3_HMGB1_KIAA1967 | 1.24E−06 |
| ATG3_BCL2_BCL2L1_IKT_CASP3_HMGB1_RAPTOR | 1.25E−06 |
| AIFM1_ATG3_BCL2_CDH1_HMGB1_KIAA1967_RAGE | 1.25E−06 |
| ATG3_BCL2_BCL2L1_TKT_ID2_HMGB2_SIRT1 | 1.26E−06 |
| ATG3_BCL2_CDH1_HMGB1_MMP2_RAGE_SIRT1 | 1.27E−06 |
| AIFM1_ATG3_BCL2_CDH1_CASP3_HMGB1_RAGE | 1.27E−06 |
| ATG3_BCL2_CDH1_HMGB1_KIAA1967_RAGE_RAPTOR | 1.29E−06 |
| ATG3_BCL2_DRAM_CDH1_CASP3_HMGB1_RAGE | 1.29E−06 |
| ATG3_BCL2_BNIP3_CDH1_FASLG_HMGB1_RAGE | 1.29E−06 |
| ATG3_BCL2_CDH1_HMGB1_HMGB2_RAGE_SIRT1 | 1.30E−06 |
| ATG3_TKT_HMGB1_HMGB2_KIAA1967_RAGE_TWIST1 | 1.30E−06 |
| ATG3_BCL2_BCL2L1_TKT_ID2_CASP3_CDH2 | 1.32E−06 |
| ATG3_BCL2_DRAM_CDH1_HMGB1_HMGB2_UVRAG | 1.33E−06 |
| AIFM1_ATG3_BCL2_CDH1_CDH2_HMGB1_RAGE | 1.34E−06 |
| ATG3_BCL2_BCL2L1_IKT_CASP3_HMGB1_LAMP2 | 1.34E−06 |
| AIFM1_ATG3_BCL2_CDH1_HMGB1_HMGB2_RAPTOR | 1.34E−06 |
| AIFM1_ATG3_BCL2_CDH1_HMGB1_RAGE_RAPTOR | 1.34E−06 |
| ATG3_BCL2_CASP8_CDH1_HMGB1_HMGB2_RAGE | 1.35E−06 |
| ATG3_BCL2_CDH1_HMGB1_HMGB2_RAGE_UVRAG | 1.35E−06 |
| ATG3_BCL2_BNIP3_CDH1_HMGB1_HMGB2_RAPTOR | 1.36E−06 |
| ATG3_BCL2_BNIP3_CASP8_CDH1_HMGB1_RAGE | 1.38E−06 |
| ATG3_BCL2_CDH1_HMGB1_MMP2_RAGE_UVRAG | 1.38E−06 |
| ATG3_BCL2_BCL2L1_TKT_HMGB1_HMGB2_SIRT1 | 1.39E−06 |
| ATG3_BCL2_BCL2L1_TKT_CASP3_HMGB1_RAGE | 1.40E−06 |
| AIFM1_ATG3_BCL2_BNIP3_CDH1_HMGB1_UVRAG | 1.42E−06 |
| ATG3_BCL2_DRAM_CDH1_HMGB1_HMGB2_SIRT1 | 1.43E−06 |
| ATG12_ATG3_BCL2_BCL2L1_TKT_CASP3_HMGB1 | 1.44E−06 |
| ATG12_ATG3_BCL2_PTEN_CDH1_HMGB1_RAGE | 1.45E−06 |
| ATG3_BCL2_PTEN_CDH1_HMGB1_RAGE_SIRT1 | 1.46E−06 |
| ATG3_BCL2_CDH1_CASP3_HMGB1_RAGE_RAPTOR | 1.46E−06 |
| ATG3_BCL2_BNIP3_FRAP1_CDH1_HMGB1_RAGE | 1.47E−06 |
| ATG3_BCL2_FRAP1_CDH1_HMGB1_HMGB2_RAGE | 1.47E−06 |
| NNMT_CDH1_ID2_MMP9_TCF3_TP63_UVRAG | 1.87E−04 |

TABLE 45

| Marker | p-value |
|---|---|
| Recurrence | |
| ATG3_BCL2_BCL2L1_TKT_ID2_CASP3_CDH2_HMGB2 | 3.07E−07 |
| ATG3_BCL2_BNIP3_CDH1_HMGB1_HMGB2_RAGE_RAPTOR | 3.75E−07 |
| ATG3_BCL2L1_TKT_ID2_CDH2_HMGB2_TWIST1_UVRAG | 3.78E−07 |
| ATG3_BCL2_BCL2L1_TKT_ID2_CASP3_HMGB2_KIAA1967 | 3.82E−07 |
| ATG3_BCL2_BCL2L1_TKT_ID2_CASP3_HMGB2_SIRT1 | 3.98E−07 |
| ATG3_BCL2_BCL2L1_TKT_CDH1_CASP3_HMGB1_SIRT1 | 4.13E−07 |
| ATG3_BCL2_BNIP3_CDH1_FASLG_HMGB1_HMGB2_RAGE | 4.44E−07 |
| ATG3_BCL2_BCL2L1_BNIP3_TKT_ID2_CASP3_HMGB2 | 4.57E−07 |
| ATG3_BCL2_BNIP3_CDH1_CASP3_FASLG_HMGB1_RAGE | 4.63E−07 |
| ATG3_BCL2L1_TKT_ID2_CDH2_HMGB2_SIRT1_TWIST1 | 4.63E−07 |
| AIFM1_ATG3_BCL2_CDH1_CDH2_HMGB1_HMGB2_RAGE | 4.72E−07 |
| ATG3_BCL2L1_TKT_ID2_CDH2_HMGB2_KIAA1967_TWIST1 | 4.80E−07 |
| ATG3_BCL2_DRAM_CDH1_HMGB1_HMGB2_RAGE_SIRT1 | 4.82E−07 |
| ATG3_BCL2_BCL2L1_TKT_CASP3_CDH2_HMGB1_HMGB2 | 4.89E−07 |
| AIFM1_ATG3_BCL2_CDH1_HMGB1_HMGB2_RAGE_RAPTOR | 4.90E−07 |
| ATG3_BCL2_BNIP3_CDH1_CDH2_HMGB1_HMGB2_RAGE | 4.94E−07 |
| ATG3_BCL2_BCL2L1_TKT_ID2_CASP3_HMGB2_UVRAG | 5.09E−07 |
| ATG3_CDH1_CDH2_HMGB1_HMGB2_RAGE_RAPTOR_TWIST1 | 5.11E−07 |
| ATG3_BCL2_BCL2L1_BNIP3_TKT_ID2_HMGB2_SIRT1 | 5.22E−07 |
| ATG3_BCL2_DRAM_CDH1_CDH2_HMGB1_HMGB2_RAGE | 5.31E−07 |
| ATG3_BCL2_BCL2L1_TKT_CDH1_CASP3_CDH2_HMGB1 | 5.35E−07 |
| ATG3_BCL2_BCL2L1_TKT_CASP3_HMGB1_HMGB2_RAPTOR | 5.51E−07 |
| AIFM1_ATG3_BCL2_BNIP3_CDH1_HMGB1_HMGB2_RAGE | 5.56E−07 |
| ATG3_BCL2_BCL2L1_BNIP3_TKT_ID2_CASP3_KIAA1967 | 5.62E−07 |
| ATG3_BCL2L1_TKT_HMGB1_RAGE_RAPTOR_TWIST1_UVRAG | 5.66E−07 |
| AIFM1_ATG3_BCL2_BNIP3_CDH1_HMGB1_RAGE_SIRT1 | 5.66E−07 |
| ATG3_BCL2_BNIP3_CDH1_HMGB1_HMGB2_LAMP2_RAGE | 5.71E−07 |
| ATG3_BCL2_DRAM_CDH1_HMGB1_HMGB2_RAGE_RAPTOR | 5.82E−07 |
| ATG3_BCL2_BCL2L1_TKT_ID2_CASP3_HMGB2_RAPTOR | 5.82E−07 |
| ATG3_BCL2_BCL2L1_TKT_CASP3_CDH2_HMGB1_RAGE | 5.92E−07 |
| ATG3_CDH1_CDH2_HMGB1_HMGB2_KIAA1967_RAGE_TWIST1 | 5.93E−07 |
| ATG3_BCL2_BCL2L1_TKT_CDH1_CASP3_HMGB1_UVRAG | 5.99E−07 |
| ATG3_BCL2_BNIP3_CDH1_HMGB1_HMGB2_KIAA1967_RAGE | 6.00E−07 |
| ATG3_BCL2_BCL2L1_TKT_CASP3_HMGB1_HMGB2_LAMP2 | 6.03E−07 |
| ATG3_BCL2L1_TKT_ID2_HMGB2_KIAA1967_TWIST1_UVRAG | 6.05E−07 |
| ATG3_BCL2_BCL2L1_TKT_CASP3_HMGB1_RAGE_SIRT1 | 6.05E−07 |
| ATG3_BCL2_BCL2L1_TKT_CASP3_HMGB1_HMGB2_SIRT1 | 6.09E−07 |
| ATG3_BCL2_BCL2L1_TKT_CDH1_CASP3_HMGB1_KIAA1967 | 6.11E−07 |
| ATG3_BCL2_FRAP1_CDH1_HMGB1_HMGB2_RAGE_RAPTOR | 6.14E−07 |
| AIFM1_ATG3_BCL2_BNIP3_CDH1_HMGB1_KIAA1967_RAGE | 6.23E−07 |

TABLE 45-continued

| Marker | p-value |
|---|---|
| ATG3_LC3_TKT_HMGB1_RAGE_RAPTOR_TWIST1_UVRAG | 6.25E−07 |
| ATG3_BCL2_BCL2L1_BNIP3_TKT_ID2_CASP3_SIRT1 | 6.26E−07 |
| AIFM1_ATG3_BCL2_CDH1_HMGB1_MMP2_RAGE_SIRT1 | 6.26E−07 |
| ATG3_BCL2_DRAM_CDH1_HMGB1_HMGB2_RAGE_UVRAG | 6.30E−07 |
| AIFM1_ATG3_BCL2_CDH1_HMGB1_HMGB2_RAGE_SIRT1 | 6.30E−07 |
| ATG3_BCL2_CASP8_CDH1_HMGB1_HMGB2_RAGE_RAPTOR | 6.33E−07 |
| ATG3_BCL2_BNIP3_DRAM_CDH1_HMGB1_RAGE_SIRT1 | 6.38E−07 |
| ATG3_LC3_TKT_HMGB1_KIAA1967_RAGE_TWIST1_UVRAG | 6.38E−07 |
| ATG3_BCL2_BCL2L1_TKT_CASP3_HMGB1_HMGB2_KIAA1967 | 6.42E−07 |
| AIFM1_ATG3_BCL2_BNIP3_CDH1_HMGB1_RAGE_RAPTOR | 6.42E−07 |
| AIFM1_ATG3_BCL2_CDH1_HMGB1_HMGB2_KIAA1967_RAGE | 6.43E−07 |
| ATG3_BCL2_BCL2L1_TKT_CASP3_HMGB1_RAGE_RAPTOR | 6.45E−07 |
| ATG3_CDH1_CDH2_HMGB1_HMGB2_RAGE_TWIST1_UVRAG | 6.46E−07 |
| ATG3_BCL2_DRAM_CDH1_HMGB1_MMP2_RAGE_SIRT1 | 6.46E−07 |
| ATG3_BCL2_BCL2L1_TKT_CASP3_HMGB1_HMGB2_UVRAG | 6.46E−07 |
| ATG3_BCL2_CBS_CDH1_HMGB1_HMGB2_RAGE_RAPTOR | 6.46E−07 |
| ATG3_BCL2_BCL2L1_TKT_CASP3_HMGB1_HMGB2_RAGE | 6.56E−07 |
| ATG3_TKT_CDH1_ID2_MMP9_TCF3_TWIST1_UVRAG | 2.26E−05 |
| Survival | |
| ATG12_ATG3_BNIP3_CSE1L_ID2_MMP9_SATB1_SESN2 | 1.30E−06 |
| ATG12_ATG3_BNIP3_CSE1L_ID2_MMP9_TCF3_SATB1 | 1.30E−06 |
| ATG12_ATG3_BNIP3_CSE1L_ULK1_ID2_MMP9_SATB1 | 1.30E−06 |
| ATG12_ATG3_BNIP3_FAS_ID2_MMP9_TCF3_RPS19BP1 | 1.30E−06 |
| DIABLO_FAS_ID2_MMP9_TCF3_NAMPT_SATB1_STAT3 | 1.34E−06 |
| DIABLO_FAS_ID2_MMP9_TCF3_NAMPT_SATB1_SESN2 | 1.38E−06 |
| ATG12_ATG3_ATG5_BNIP3_CSE1L_ID2_MMP9_SATB1 | 1.40E−06 |
| ATG12_ATG3_ATG5_BNIP3_ID2_MMP9_TCF3_SATB1 | 1.40E−06 |
| ATG12_ATG3_BNIP3_CSE1L_ULK1_ID2_MMP9_SESN2 | 1.40E−06 |
| ATG12_ATG3_BNIP3_CSE1L_ULK1_ID2_MMP9_TCF3 | 1.40E−06 |
| ATG12_ATG3_BNIP3_DIABLO_FAS_ID2_MMP9_TCF3 | 1.40E−06 |
| ATG12_ATG3_BNIP3_ID2_MMP9_TCF3_SATB1_SESN2 | 1.40E−06 |
| ATG12_ATG3_BNIP3_ULK1_ID2_MMP9_TCF3_SATB1 | 1.40E−06 |
| ATG12_ATG3_BNIP3_CSE1L_ID2_MMP9_BHLHE41_SATB1 | 1.50E−06 |
| ATG12_ATG3_BNIP3_CSE1L_ID2_MMP9_TCF3_SESN2 | 1.50E−06 |
| ATG3_BCL2_E2F1_LAMP1_TKT_MMP9_CASP3_HMGB1 | 1.55E−06 |
| ATG12_ATG3_ATG5_BNIP3_CSE1L_ID2_MMP9_SESN2 | 1.60E−06 |
| ATG12_ATG3_BNIP3_CSE1L_DIABLO_FAS_ID2_MMP9 | 1.60E−06 |
| ATG12_ATG3_BNIP3_CSE1L_ID2_MMP9_TCF3_BHLHE41 | 1.60E−06 |
| ATG12_ATG3_BNIP3_CSE1L_ULK1_ID2_MMP9_BHLHE41 | 1.60E−06 |
| ATG12_ATG3_BNIP3_FAS_ID2_MMP9_RPS19BP1_SATB1 | 1.60E−06 |
| ATG12_ATG3_BNIP3_FAS_ID2_MMP9_TCF3_SATB1 | 1.60E−06 |
| ATG12_ATG3_BNIP3_FAS_ID2_MMP9_TCF3_SESN2 | 1.60E−06 |
| ATG12_ATG3_BNIP3_ID2_MMP9_TCF3_BHLHE41_SATB1 | 1.60E−06 |
| ATG12_ATG3_BNIP3_ID2_MMP9_TCF3_SRPS19BP1_ATB1 | 1.60E−06 |
| ATG12_ATG3_BNIP3_ULK1_ID2_MMP9_TCF3_SESN2 | 1.60E−06 |
| ATG12_BNIP3_CSE1L_ID2_MMP9_TCF3_SATB1_SESN2 | 1.60E−06 |
| ATG12_BNIP3_DIABLO_FAS_ID2_MMP9_TCF3_SATB1 | 1.60E−06 |
| ATG12_BNIP3_FAS_ID2_MMP9_TCF3_RPS19BP1_SATB1 | 1.60E−06 |
| ATG12_BNIP3_FAS_ULK1_ID2_MMP9_TCF3_RPS19BP1 | 1.60E−06 |
| CSE1L_DIABLO_FAS_ID2_MMP9_NAMPT_SATB1_STAT3 | 1.69E−06 |
| ATG12_ATG3_ATG5_BNIP3_FAS_ID2_MMP9_TCF3 | 1.70E−06 |
| ATG12_ATG3_ATG5_BNIP3_ID2_MMP9_TCF3_SESN2 | 1.70E−06 |
| ATG12_ATG3_ATG5_BNIP3_ULK1_ID2_MMP9_TCF3 | 1.70E−06 |
| ATG12_ATG3_BNIP3_CSE1L_FAS_ID2_MMP9_RPS19BP1 | 1.70E−06 |
| ATG12_ATG3_BNIP3_CSE1L_FAS_ID2_MMP9_SATB1 | 1.70E−06 |
| ATG12_ATG3_BNIP3_CSE1L_ID2_MMP9_BHLHE41_SESN2 | 1.70E−06 |
| ATG12_ATG3_BNIP3_DIABLO_FAS_ID2_MMP9_SATB1 | 1.70E−06 |
| ATG12_ATG3_BNIP3_FAS_ID2_MMP9_RPS19BP1_SESN2 | 1.70E−06 |
| ATG12_ATG3_BNIP3_FAS_ULK1_ID2_MMP9_RPS19BP1 | 1.70E−06 |
| ATG12_ATG3_BNIP3_FAS_ULK1_ID2_MMP9_TCF3 | 1.70E−06 |
| ATG12_ATG5_BNIP3_CSE1L_ID2_MMP9_SATB1_SESN2 | 1.70E−06 |
| ATG12_ATG5_BNIP3_CSE1L_ULK1_ID2_MMP9_SATB1 | 1.70E−06 |
| ATG12_BNIP3_CSE1L_ULK1_ID2_MMP9_SATB1_SESN2 | 1.70E−06 |
| ATG12_BNIP3_CSE1L_ULK1_ID2_MMP9_TCF3_SATB1 | 1.70E−06 |
| ATG12_BNIP3_DIABLO_FAS_ID2_MMP9_TCF3_SESN2 | 1.70E−06 |
| ATG12_BNIP3_DIABLO_FAS_ULK1_ID2_MMP9_TCF3 | 1.70E−06 |
| ATG12_BNIP3_FAS_ID2_MMP9_TCF3_RPS19BP1_SESN2 | 1.70E−06 |
| ATG3_DIABLO_FAS_ID2_MMP9_TCF3_NAMPT_SATB1 | 1.74E−06 |
| DIABLO_FAS_ID2_MMP9_TCF3_NAMPT_SESN2_STAT3 | 1.75E−06 |
| DIABLO_FAS_ID2_MMP9_NAMPT_SATB1_SESN2_STAT3 | 1.79E−06 |
| ATG12_ATG3_ATG5_BNIP3_CSE1L_FAS_ID2_MMP9 | 1.80E−06 |
| ATG12_ATG3_ATG5_BNIP3_CSE1L_ID2_MMP9_BHLHE41 | 1.80E−06 |
| ATG12_ATG3_ATG5_BNIP3_CSE1L_ID2_MMP9_TCF3 | 1.80E−06 |
| ATG12_ATG3_ATG5_BNIP3_FAS_ID2_MMP9_RPS19BP1 | 1.80E−06 |

TABLE 45-continued

| Marker | p-value |
| --- | --- |
| ATG12_ATG3_ATG5_BNIP3_FAS_ID2_MMP9_SATB1 | 1.80E−06 |
| ATG12_ATG3_BNIP3_CSE1L_FAS_ID2_MMP9_SESN2 | 1.80E−06 |
| ATG3_TKT_CDH1_ID2_MMP9_TCF3_TP63_UVRAG | 1.02E−05 |
| Disease-free survival | |
| ATG3_BCL2_BCL2L1_TKT_ID2_CASP3_CDH2_HMGB2 | 3.07E−07 |
| ATG3_BCL2_BNIP3_CDH1_HMGB1_HMGB2_RAGE_RAPTOR | 3.75E−07 |
| ATG3_BCL2L1_TKT_ID2_CDH2_HMGB2_TWIST1_UVRAG | 3.78E−07 |
| ATG3_BCL2_BCL2L1_TKT_ID2_CASP3_HMGB2_KIAA1967 | 3.82E−07 |
| ATG3_BCL2_BCL2L1_TKT_ID2_CASP3_HMGB2_SIRT1 | 3.98E−07 |
| ATG3_BCL2_BCL2L1_TKT_CDH1_CASP3_HMGB1_SIRT1 | 4.13E−07 |
| ATG3_BCL2_BNIP3_CDH1_FASLG_HMGB1_HMGB2_RAGE | 4.44E−07 |
| ATG3_BCL2_BCL2L1_BNIP3_TKT_ID2_CASP3_HMGB2 | 4.57E−07 |
| ATG3_BCL2_BNIP3_CDH1_CASP3_FASLG_HMGB1_RAGE | 4.63E−07 |
| ATG3_BCL2L1_TKT_ID2_CDH2_HMGB2_SIRT1_TWIST1 | 4.63E−07 |
| AIFM1_ATG3_BCL2_CDH1_CDH2_HMGB1_HMGB2_RAGE | 4.72E−07 |
| ATG3_BCL2L1_TKT_ID2_CDH2_HMGB2_KIAA1967_TWIST1 | 4.80E−07 |
| ATG3_BCL2_DRAM_CDH1_HMGB1_HMGB2_RAGE_SIRT1 | 4.82E−07 |
| ATG3_BCL2_BCL2L1_TKT_CASP3_CDH2_HMGB1_HMGB2 | 4.89E−07 |
| AIFM1_ATG3_BCL2_CDH1_HMGB1_HMGB2_RAGE_RAPTOR | 4.90E−07 |
| ATG3_BCL2_BNIP3_CDH1_CDH2_HMGB1_HMGB2_RAGE | 4.94E−07 |
| ATG3_BCL2_BCL2L1_TKT_ID2_CASP3_HMGB2_UVRAG | 5.09E−07 |
| ATG3_CDH1_CDH2_HMGB1_HMGB2_RAGE_RAPTOR_TWIST1 | 5.11E−07 |
| ATG3_BCL2_BCL2L1_BNIP3_TKT_ID2_HMGB2_SIRT1 | 5.22E−07 |
| ATG3_BCL2_DRAM_CDH1_CDH2_HMGB1_HMGB2_RAGE | 5.31E−07 |
| ATG3_BCL2_BCL2L1_TKT_CDH1_CASP3_CDH2_HMGB1 | 5.35E−07 |
| ATG3_BCL2_BCL2L1_TKT_CASP3_HMGB1_HMGB2_RAPTOR | 5.51E−07 |
| AIFM1_ATG3_BCL2_BNIP3_CDH1_HMGB1_HMGB2_RAGE | 5.56E−07 |
| ATG3_BCL2_BCL2L1_BNIP3_TKT_ID2_CASP3_KIAA1967 | 5.62E−07 |
| ATG3_BCL2L1_TKT_HMGB1_RAGE_RAPTOR_TWIST1_UVRAG | 5.66E−07 |
| AIFM1_ATG3_BCL2_BNIP3_CDH1_HMGB1_RAGE_SIRT1 | 5.66E−07 |
| ATG3_BCL2_BNIP3_CDH1_HMGB1_HMGB2_LAMP2_RAGE | 5.71E−07 |
| ATG3_BCL2_DRAM_CDH1_HMGB1_HMGB2_RAGE_RAPTOR | 5.82E−07 |
| ATG3_BCL2_BCL2L1_TKT_ID2_CASP3_HMGB2_RAPTOR | 5.82E−07 |
| ATG3_BCL2_BCL2L1_TKT_CASP3_CDH2_HMGB1_RAGE | 5.92E−07 |
| ATG3_CDH1_CDH2_HMGB1_HMGB2_KIAA1967_RAGE_TWIST1 | 5.93E−07 |
| ATG3_BCL2_BCL2L1_TKT_CDH1_CASP3_HMGB1_UVRAG | 5.99E−07 |
| ATG3_BCL2_BNIP3_CDH1_HMGB1_HMGB2_KIAA1967_RAGE | 6.00E−07 |
| ATG3_BCL2_BCL2L1_TKT_CASP3_HMGB1_HMGB2_LAMP2 | 6.03E−07 |
| ATG3_BCL2L1_TKT_ID2_HMGB2_KIAA1967_TWIST1_UVRAG | 6.05E−07 |
| ATG3_BCL2_BCL2L1_TKT_CASP3_HMGB1_RAGE_SIRT1 | 6.05E−07 |
| ATG3_BCL2_BCL2L1_TKT_CASP3_HMGB1_HMGB2_SIRT1 | 6.09E−07 |
| ATG3_BCL2_BCL2L1_TKT_CDH1_CASP3_HMGB1_KIAA1967 | 6.11E−07 |
| ATG3_BCL2_FRAP1_CDH1_HMGB1_HMGB2_RAGE_RAPTOR | 6.14E−07 |
| AIFM1_ATG3_BCL2_BNIP3_CDH1_HMGB1_KIAA1967_RAGE | 6.23E−07 |
| ATG3_LC3_TKT_HMGB1_RAGE_RAPTOR_TWIST1_UVRAG | 6.25E−07 |
| ATG3_BCL2_BCL2L1_BNIP3_TKT_ID2_CASP3_SIRT1 | 6.26E−07 |
| AIFM1_ATG3_BCL2_CDH1_HMGB1_MMP2_RAGE_SIRT1 | 6.26E−07 |
| ATG3_BCL2_DRAM_CDH1_HMGB1_HMGB2_RAGE_UVRAG | 6.30E−07 |
| AIFM1_ATG3_BCL2_CDH1_HMGB1_HMGB2_RAGE_SIRT1 | 6.30E−07 |
| ATG3_BCL2_CASP8_CDH1_HMGB1_HMGB2_RAGE_RAPTOR | 6.33E−07 |
| ATG3_BCL2_BNIP3_DRAM_CDH1_HMGB1_RAGE_SIRT1 | 6.38E−07 |
| ATG3_LC3_TKT_HMGB1_KIAA1967_RAGE_TWIST1_UVRAG | 6.38E−07 |
| ATG3_BCL2_BCL2L1_TKT_CASP3_HMGB1_HMGB2_KIAA1967 | 6.42E−07 |
| AIFM1_ATG3_BCL2_BNIP3_CDH1_HMGB1_RAGE_RAPTOR | 6.42E−07 |
| AIFM1_ATG3_BCL2_CDH1_HMGB1_HMGB2_KIAA1967_RAGE | 6.43E−07 |
| ATG3_BCL2_BCL2L1_TKT_CASP3_HMGB1_RAGE_RAPTOR | 6.45E−07 |
| ATG3_CDH1_CDH2_HMGB1_HMGB2_RAGE_TWIST1_UVRAG | 6.46E−07 |
| ATG3_BCL2_DRAM_CDH1_HMGB1_MMP2_RAGE_SIRT1 | 6.46E−07 |
| ATG3_BCL2_BCL2L1_TKT_CASP3_HMGB1_HMGB2_UVRAG | 6.46E−07 |
| ATG3_BCL2_CBS_CDH1_HMGB1_HMGB2_RAGE_RAPTOR | 6.46E−07 |
| ATG3_BCL2_BCL2L1_TKT_CASP3_HMGB1_HMGB2_RAGE | 6.56E−07 |
| ATG3_TKT_CDH1_ID2_MMP9_TCF3_TWIST1_UVRAG | 2.26E−05 |

As can be confirmed from the above tables, each of the markers or their combination shows p-values low enough to be considered significant in terms of all of recurrence, survival, and disease-free survival. In particular, in the case of the combination of the two or more markers, all the p-values for recurrence, survival, and disease-free survival were low. In particular, it was found that there were cases where the p-value for a single marker was relatively high but the p-value decreased when the marker was used in combination with other marker. As a p-value becomes lower, the statistical significance becomes higher. Thus, the low p-values suggest that the estimation for prognosis of liver cancer by each of the markers or their combination is highly accurate.

This means that the more markers of the present disclosure are combined, the lower p-values, which means higher significance, are shown, which means that the more improved accuracy would be achieved in the estimation for prognosis based on the combinations of the markers.

Thus, it was found that the markers and/or the combinations of markers of Tables 38~45 are effective in predicting prognosis of liver cancer of the B group (recurrence, survival, disease-free survival), and that the prognosis of liver cancer of the B group can be predicted effectively by nucleic acids and antibodies targeted at the markers. Also, it can be found that the prognosis of liver cancer of the B group can be predicted effectively by the method for predicting prognosis of liver cancer of the present disclosure, which is targeted at the markers.

Further, cross-validation was performed for combinations of markers which were considered statistically significant. Patients of each patient group were randomly divided into two groups (positive group: 39 patients; test group: 39 patients). With the reference value which was considered statistically significant in the results of the positive group obtained in the same manner as Example 1 fixed, for the test group, the accuracy of estimation was calculated to be the level of $p<0.05$ or $p<0.001$ with respect to recurrence, survival and disease-free survival.

Among the results of cross-validation of the prediction of the survival of the B group, a representative example showing the excellent accuracy of prognosis in each aspect is as follows:

Survival: DIABLO_BECN1_SIRT1 (79.7% at the level of $p<0.05$)

Example 5: Predicting Prognosis of Liver Cancer in the C Group

An experiment was performed in the same manner as in Example 1, except for experimenting on a patient group determined as the C group {a group of portal vein invasion-positive patients regardless of tumors size and number} (69 patients). Kaplan-Meier curves were prepared with respect to the prediction of recurrence, survival, and disease-free survival and the results are shown in FIGS. 86~106. Kaplan-Meier curves for recurrence are shown in FIGS. 86~92, Kaplan-Meier curves for survival are shown in FIGS. 93~99, and Kaplan-Meier curves for disease-free survival are shown in FIGS. 100~106.

As can be seen from the drawings, in Kaplan-Meier curves completed with respect to recurrence, survival, and disease-free survival, the above markers form curves where cases of high expression and low expression are distinctively distinguished from each other. This means that there are remarkable differences in interval recurrence rate or interval survival rate and cumulative recurrence rate or cumulative survival rate based thereon between the cases where the marker is in high expression and low expression, and that consequently, the expression pattern of the marker can be an index showing recurrence possibility or survival possibility of patients.

Also, significance tests were performed by log-rank test with respect to each of the markers and their combination by calculating observation values and expected values at every point of recurrence or death to obtain p-values. The results are shown in the following Tables 46~53. The results of using a marker alone is shown in Table 46, the results of a combination of two markers are shown in Table 47, the results of a combination of three markers are shown in Table 48, the results of a combination of four markers are shown in Table 49, the results of a combination of five markers are shown in Table 50, the results of a combination of six markers are shown in Table 51, the results of a combination of seven markers are shown in Table 52, and the results of a combination of eight markers are shown in Table 53.

TABLE 46

| Marker | p-value |
|---|---|
| Recurrence | |
| FASLG | 3.93E−03 |
| CIAP2 | 1.27E−02 |
| CSE1L | 3.17E−02 |
| FAS | 3.17E−02 |
| TCF3 | 3.65E−02 |
| ATG3 | 5.91E−02 |
| ULK1 | 8.46E−02 |
| LC3 | 9.21E−02 |
| BNIP3 | 9.61E−02 |
| E2F1 | 1.09E−01 |
| CASP3 | 1.16E−01 |
| CDH2 | 1.22E−01 |
| RAPTOR | 1.49E−01 |
| PTEN | 1.50E−01 |
| TKT | 1.89E−01 |
| ATG5 | 1.95E−01 |
| SATB1 | 1.97E−01 |
| BCL2 | 2.03E−01 |
| XIAP | 2.07E−01 |
| DIABLO | 2.24E−01 |
| RAGE | 2.48E−01 |
| LAMP1 | 2.82E−01 |
| SESN2 | 3.03E−01 |
| ATG7 | 3.03E−01 |
| KIAA1967 | 3.34E−01 |
| NAMPT | 3.41E−01 |
| SESN1 | 3.65E−01 |
| FRAP1_ | 4.16E−01 |
| RPS19BP1 | 4.18E−01 |
| SESN3 | 4.21E−01 |
| UVRAG | 4.35E−01 |
| DRAM | 5.20E−01 |
| PRKAA1 | 5.27E−01 |
| HMGB1 | 5.66E−01 |
| CBS | 5.92E−01 |
| ATG12 | 5.93E−01 |
| MMP9 | 6.08E−01 |
| VEGF | 6.72E−01 |
| CASP8 | 7.09E−01 |
| NNMT | 7.11E−01 |
| HMGB2 | 7.12E−01 |
| CCNG2 | 7.23E−01 |
| BAX | 7.32E−01 |
| ID2 | 7.63E−01 |
| BCL2L1 | 7.92E−01 |
| AGER | 7.99E−01 |
| AIFM1 | 8.16E−01 |
| SIRT1 | 8.25E−01 |
| LAMP2 | 8.54E−01 |
| AKT1 | 8.61E−01 |
| STAT3 | 8.91E−01 |
| BHLHE41 | 9.05E−01 |
| CDH1 | 9.08E−01 |
| BECN1 | 9.29E−01 |
| TP63 | 9.37E−01 |
| TWIST1 | 9.94E−01 |
| MMP2 | 9.99E−01 |
| Survival | |
| CSE1L | 5.07E−03 |
| CIAP2 | 8.33E−03 |
| TCF3 | 8.33E−03 |
| CDH2 | 9.89E−03 |
| FASLG | 1.61E−02 |
| BECN1 | 3.48E−02 |
| CASP3 | 3.53E−02 |
| CDH1 | 4.70E−02 |
| FAS | 5.33E−02 |
| KIAA1967 | 6.02E−02 |
| ULK1 | 8.01E−02 |
| STAT3 | 8.62E−02 |
| ATG12 | 9.77E−02 |
| RAPTOR | 1.36E−01 |
| BCL2 | 1.48E−01 |
| SESN3 | 1.75E−01 |
| UVRAG | 2.09E−01 |

TABLE 46-continued

| Marker | p-value |
|---|---|
| SESN1 | 2.11E−01 |
| XIAP | 2.30E−01 |
| SATB1 | 2.46E−01 |
| LAMP2 | 2.51E−01 |
| SESN2 | 2.82E−01 |
| ATG7 | 2.84E−01 |
| ID2 | 3.01E−01 |
| ATG5 | 3.12E−01 |
| SIRT1 | 3.73E−01 |
| NAMPT | 3.90E−01 |
| AKT1 | 4.04E−01 |
| TKT | 4.14E−01 |
| CBS | 4.22E−01 |
| NNMT | 4.35E−01 |
| FRAP1 | 4.69E−01 |
| BCL2L1 | 4.71E−01 |
| RPS19BP1 | 5.16E−01 |
| MMP9 | 5.16E−01 |
| PRKAA1 | 5.35E−01 |
| ATG3 | 5.63E−01 |
| CCNG2 | 5.98E−01 |
| MMP2 | 6.51E−01 |
| RAGE | 6.96E−01 |
| LC3 | 7.14E−01 |
| TP63 | 7.32E−01 |
| AIFM1 | 7.42E−01 |
| LAMP1 | 7.43E−01 |
| BHLHE41 | 7.55E−01 |
| CASP8 | 7.67E−01 |
| TWIST1 | 7.92E−01 |
| PTEN | 8.51E−01 |
| DIABLO | 8.52E−01 |
| HMGB1 | 8.87E−01 |
| AGER | 9.16E−01 |
| HMGB2 | 9.25E−01 |
| BNIP3 | 9.44E−01 |
| VEGF | 9.48E−01 |
| BAX | 9.68E−01 |
| E2F1 | 9.90E−01 |
| DRAM | 9.91E−01 |
| Disease-free survival | |
| FASLG | 2.36E−03 |
| CIAP2 | 1.24E−02 |
| FAS | 2.44E−02 |
| CSE1L | 2.62E−02 |
| TCF3 | 3.79E−02 |
| LC3 | 8.84E−02 |
| CASP3 | 9.68E−02 |
| ATG3 | 1.01E−01 |
| ULK1 | 1.07E−01 |
| RAPTOR | 1.24E−01 |
| E2F1 | 1.32E−01 |
| CDH2 | 1.34E−01 |
| SATB1 | 1.57E−01 |
| PTEN | 1.60E−01 |
| TKT | 1.75E−01 |
| BNIP3 | 1.88E−01 |
| BCL2 | 1.94E−01 |
| DIABLO | 2.52E−01 |
| XIAP | 2.54E−01 |
| ATG5 | 2.64E−01 |
| LAMP1 | 2.86E−01 |
| KIAA1967 | 3.05E−01 |
| SESN2 | 3.46E−01 |
| SESN1 | 3.65E−01 |
| RAGE | 3.70E−01 |
| UVRAG | 4.14E−01 |
| FRAP1_ | 4.25E−01 |
| NAMPT | 4.35E−01 |
| ATG7 | 4.45E−01 |
| MMP9 | 4.75E−01 |
| RPS19BP1 | 4.99E−01 |
| SESN3 | 5.13E−01 |
| HMGB1 | 5.82E−01 |
| PRKAA1 | 6.30E−01 |
| DRAM | 6.45E−01 |
| ATG12 | 6.46E−01 |

TABLE 46-continued

| Marker | p-value |
|---|---|
| CBS | 7.22E−01 |
| CCNG2 | 7.23E−01 |
| HMGB2 | 7.53E−01 |
| LAMP2 | 7.58E−01 |
| BECN1 | 7.60E−01 |
| CASP8 | 7.79E−01 |
| NNMT | 7.92E−01 |
| BCL2L1 | 8.02E−01 |
| ID2 | 8.19E−01 |
| AGER | 8.21E−01 |
| AKT1 | 8.28E−01 |
| VEGF | 8.48E−01 |
| MMP2 | 8.77E−01 |
| AIFM1 | 8.88E−01 |
| STAT3 | 9.28E−01 |
| TP63 | 9.37E−01 |
| CDH1 | 9.54E−01 |
| BAX | 9.64E−01 |
| SIRT1 | 9.77E−01 |
| BHLHE41 | 9.80E−01 |
| TWIST1 | 9.94E−01 |

TABLE 47

| Marker | p-value |
|---|---|
| Recurrence | |
| CIAP2_FASLG | 1.87E−04 |
| E2F1_FASLG | 2.16E−04 |
| LC3_FASLG | 2.38E−04 |
| DIABLO_FASLG | 2.65E−04 |
| FAS_FASLG | 3.89E−04 |
| FASLG_RPS19BP1 | 4.95E−04 |
| PTEN_FASLG | 7.12E−04 |
| CASP3_FASLG | 7.73E−04 |
| FASLG_SESN2 | 7.77E−04 |
| FASLG_HMGB1 | 8.12E−04 |
| CDH2_FASLG | 9.16E−04 |
| FRAP1_FASLG | 9.22E−04 |
| ATG7_FASLG | 1.01E−03 |
| ATG3_FAS | 1.15E−03 |
| FASLG_HMGB2 | 1.16E−03 |
| FASLG_UVRAG | 1.20E−03 |
| DIABLO_FAS | 1.27E−03 |
| FASLG_MMP2 | 1.35E−03 |
| TKT_FASLG | 1.38E−03 |
| PTEN_CIAP2 | 1.38E−03 |
| FAS_LC3 | 1.44E−03 |
| CBS_FASLG | 1.50E−03 |
| AIFM1_FASLG | 1.51E−03 |
| CASP3_CIAP2 | 1.52E−03 |
| FASLG_SESN3 | 1.65E−03 |
| ATG3_FASLG | 1.71E−03 |
| CASP8_FASLG | 1.75E−03 |
| XIAP_FASLG | 1.78E−03 |
| AGER_FASLG | 1.79E−03 |
| ATG3_ULK1 | 1.89E−03 |
| BNIP3_FASLG | 1.90E−03 |
| FAS_UVRAG | 1.96E−03 |
| CIAP2_RAGE | 1.97E−03 |
| ATG3_TCF3 | 2.14E−03 |
| FASLG_RAGE | 2.25E−03 |
| E2F1_CIAP2 | 2.26E−03 |
| FASLG_VEGF | 2.38E−03 |
| E2F1_FAS | 2.40E−03 |
| XIAP_CIAP2 | 2.46E−03 |
| BCL2L1_FASLG | 2.50E−03 |
| BNIP3_FAS | 2.54E−03 |
| FASLG_SESN1 | 2.61E−03 |
| FASLG_KIAA1967 | 2.66E−03 |
| AIFM1_CIAP2 | 2.70E−03 |
| DRAM_FASLG | 2.72E−03 |
| ATG3_CIAP2 | 2.77E−03 |

TABLE 47-continued

| Marker | p-value |
|---|---|
| CSE1L_FASLG | 2.79E−03 |
| FASLG_RAPTOR | 2.83E−03 |
| TCF3_FASLG | 2.84E−03 |
| FASLG_STAT3 | 2.86E−03 |
| ULK1_FASLG | 2.86E−03 |
| PRKAA1_CIAP2 | 2.89E−03 |
| FASLG_SIRT1 | 2.89E−03 |
| ATG12_FASLG | 2.96E−03 |
| LAMP1_FASLG | 2.98E−03 |
| NNMT_FASLG | 3.08E−03 |
| BCL2L1_CIAP2 | 3.12E−03 |
| Survival | |
| ID2_CIAP2 | 5.70E−04 |
| CASP3_CIAP2 | 9.60E−04 |
| ID2_TCF3 | 1.28E−03 |
| DIABLO_CDH2 | 1.58E−03 |
| CSE1L_CDH2 | 1.67E−03 |
| CSE1L_TCF3 | 1.70E−03 |
| CSE1L_CASP3 | 1.86E−03 |
| CSE1L_RPS19BP1 | 1.87E−03 |
| CDH2_CIAP2 | 1.89E−03 |
| ULK1_ID2 | 2.44E−03 |
| CSE1L_ID2 | 2.80E−03 |
| CDH1_CIAP2 | 3.00E−03 |
| CSE1L_FASLG | 3.00E−03 |
| NNMT_CIAP2 | 3.02E−03 |
| CSE1L_MMP9 | 3.02E−03 |
| CSE1L_CDH1 | 3.06E−03 |
| CIAP2_RPS19BP1 | 3.07E−03 |
| ID2_CDH2 | 3.10E−03 |
| CDH2_RPS19BP1 | 3.11E−03 |
| CSE1L_STAT3 | 3.25E−03 |
| DIABLO_CASP3 | 3.29E−03 |
| CDH1_TCF3 | 3.29E−03 |
| CSE1L_SIRT1 | 3.34E−03 |
| CIAP2_SESN2 | 3.36E−03 |
| AIFM1_CIAP2 | 3.56E−03 |
| DIABLO_KIAA1967 | 3.61E−03 |
| CSE1L_KIAA1967 | 3.64E−03 |
| AKT1_CSE1L | 3.75E−03 |
| CSE1L_SESN2 | 3.84E−03 |
| FRAP1_CDH2 | 3.88E−03 |
| FRAP1_CIAP2 | 3.97E−03 |
| TCF3_FASLG | 4.00E−03 |
| FASLG_SESN2 | 4.06E−03 |
| CSE1L_DIABLO | 4.12E−03 |
| CSE1L_SATB1 | 4.13E−03 |
| MMP9_TCF3 | 4.22E−03 |
| ATG12_CSE1L | 4.34E−03 |
| ATG7_CSE1L | 4.35E−03 |
| CSE1L_BECN1 | 4.42E−03 |
| XIAP_CIAP2 | 4.44E−03 |
| CSE1L_FAS | 4.44E−03 |
| TCF3_RPS19BP1 | 4.47E−03 |
| XIAP_SESN2 | 4.67E−03 |
| CIAP2_KIAA1967 | 4.77E−03 |
| TKT_CIAP2 | 4.80E−03 |
| PRKAA1_CIAP2 | 4.81E−03 |
| CDH2_FASLG | 4.84E−03 |
| CSE1L_FRAP1 | 4.87E−03 |
| CSE1L_CIAP2 | 4.87E−03 |
| CSE1L_ULK1 | 4.99E−03 |
| PTEN_CIAP2 | 5.02E−03 |
| BCL2L1_CIAP2 | 5.02E−03 |
| CIAP2_VEGF | 5.07E−03 |
| ATG3_TCF3 | 5.08E−03 |
| AKT1_TCF3 | 5.26E−03 |
| CSE1L_LC3 | 5.35E−03 |
| TKT_CDH2 | 5.40E−03 |
| Disease-free survival | |
| FAS_FASLG | 1.38E−04 |
| LC3_FASLG | 1.39E−04 |
| E2F1_FASLG | 1.79E−04 |
| CIAP2_FASLG | 2.48E−04 |
| DIABLO_FASLG | 2.51E−04 |

TABLE 47-continued

| Marker | p-value |
|---|---|
| FASLG_RPS19BP1 | 3.71E−04 |
| FASLG_SESN2 | 4.41E−04 |
| CASP3_FASLG | 8.51E−04 |
| FASLG_UVRAG | 8.81E−04 |
| FRAP1_FASLG | 9.82E−04 |
| PTEN_FASLG | 1.11E−03 |
| FASLG_HMGB1 | 1.13E−03 |
| ATG3_FAS | 1.13E−03 |
| CASP3_CIAP2 | 1.17E−03 |
| TCF3_FASLG | 1.24E−03 |
| ATG7_FASLG | 1.25E−03 |
| PTEN_CIAP2 | 1.29E−03 |
| CDH2_FASLG | 1.31E−03 |
| FASLG_SESN3 | 1.38E−03 |
| DIABLO_FAS | 1.41E−03 |
| FAS_LC3 | 1.44E−03 |
| ULK1_FASLG | 1.44E−03 |
| CSE1L_FASLG | 1.51E−03 |
| CBS_FASLG | 1.72E−03 |
| FASLG_HMGB2 | 1.73E−03 |
| FAS_UVRAG | 1.76E−03 |
| LAMP1_FASLG | 1.83E−03 |
| BNIP3_FASLG | 1.88E−03 |
| MMP9_FASLG | 1.96E−03 |
| TKT_FASLG | 1.98E−03 |
| FASLG_STAT3 | 2.05E−03 |
| AKT1_FASLG | 2.07E−03 |
| FASLG_MMP2 | 2.08E−03 |
| DRAM_FASLG | 2.12E−03 |
| FASLG_SIRT1 | 2.16E−03 |
| ATG12_FASLG | 2.17E−03 |
| CIAP2_RAGE | 2.19E−03 |
| FAS_LAMP1 | 2.25E−03 |
| ATG5_FASLG | 2.25E−03 |
| ATG3_FASLG | 2.32E−03 |
| E2F1_FAS | 2.32E−03 |
| BECN1_FASLG | 2.39E−03 |
| E2F1_CIAP2 | 2.39E−03 |
| CASP8_FASLG | 2.40E−03 |
| XIAP_CIAP2 | 2.42E−03 |
| CDH1_FASLG | 2.43E−03 |
| FASLG_NAMPT | 2.44E−03 |
| BNIP3_FAS | 2.46E−03 |
| FASLG_LAMP2 | 2.48E−03 |
| AGER_FASLG | 2.50E−03 |
| ID2_FASLG | 2.55E−03 |
| A1FM1_FASLG | 2.57E−03 |
| FASLG_SESN1 | 2.61E−03 |
| AIFM1_CIAP2 | 2.64E−03 |
| PRKAA1_CIAP2 | 2.77E−03 |
| BCL2L1_CIAP2 | 2.80E−03 |
| XIAP_FASLG | 2.82E−03 |

TABLE 48

| Marker | p-value |
|---|---|
| Recurrence | |
| FAS_LC3_FASLG | 1.82E−05 |
| DIABLO_FAS_FASLG | 3.03E−05 |
| E2F1_LC3_FASLG | 3.47E−05 |
| FAS_FASLG_RPS19BP1 | 3.73E−05 |
| E2F1_FAS_FASLG | 4.66E−05 |
| FAS_FASLG_UVRAG | 5.60E−05 |
| DIABLO_LC3_FASLG | 6.35E−05 |
| ATG7_FAS_FASLG | 6.73E−05 |
| CIAP2_FASLG_SESN3 | 6.81E−05 |
| CIAP2_FASLG_UVRAG | 6.91E−05 |
| BNIP3_LC3_FASLG | 7.11E−05 |

TABLE 48-continued

| Marker | p-value |
|---|---|
| LC3_CIAP2_FASLG | 8.25E−05 |
| LC3_FASLG_SESN2 | 8.48E−05 |
| FRAP1_LC3_FASLG | 8.81E−05 |
| LC3_FASLG_SESN3 | 9.71E−05 |
| ATG3_FAS_FASLG | 1.06E−04 |
| ATG7_LC3_FASLG | 1.06E−04 |
| FAS_FRAP1_FASLG | 1.07E−04 |
| DIABLO_FASLG_SESN2 | 1.13E−04 |
| DRAM_LC3_FASLG | 1.15E−04 |
| CIAP2_FASLG_HMGB1 | 1.21E−04 |
| FAS_FASLG_SESN3 | 1.22E−04 |
| LC3_FASLG_UVRAG | 1.24E−04 |
| CASP3_CIAP2_FASLG | 1.26E−04 |
| FAS_FASLG_SESN2 | 1.27E−04 |
| PTEN_CIAP2_FASLG | 1.30E−04 |
| DIABLO_FASLG_SESN3 | 1.31E−04 |
| ATG7_CIAP2_FASLG | 1.37E−04 |
| LC3_FASLG_SIRT1 | 1.38E−04 |
| LC3_FASLG_RPS19BP1 | 1.40E−04 |
| FASLG_SESN2_SESN3 | 1.43E−04 |
| DRAM_FAS_FASLG | 1.46E−04 |
| ID2_CIAP2_FASLG | 1.58E−04 |
| FAS_FASLG_STAT3 | 1.58E−04 |
| AKT1_CIAP2_FASLG | 1.61E−04 |
| DIABLO_FRAP1_FASLG | 1.61E−04 |
| BNIP3_FAS_FASLG | 1.65E−04 |
| FAS_LAMP1_FASLG | 1.65E−04 |
| TKT_CIAP2_FASLG | 1.65E−04 |
| ATG7_DIABLO_FASLG | 1.66E−04 |
| FRAP1_FASLG_SESN2 | 1.67E−04 |
| E2F1_ULK1_FASLG | 1.67E−04 |
| DRAM_CIAP2_FASLG | 1.69E−04 |
| PTEN_CASP3_FASLG | 1.70E−04 |
| LC3_FASLG_NAMPT | 1.73E−04 |
| PTEN_CDH1_CIAP2 | 1.73E−04 |
| ATG12_CIAP2_FASLG | 1.79E−04 |
| FASLG_RPS19BP1_SESN3 | 1.80E−04 |
| MMP9_CIAP2_FASLG | 1.81E−04 |
| LAMP1_CIAP2_FASLG | 1.83E−04 |
| LC3_BECN1_FASLG | 1.85E−04 |
| CDH1_CIAP2_FASLG | 1.85E−04 |
| BECN1_CIAP2_FASLG | 1.88E−04 |
| CIAP2_FASLG_HMGB2 | 1.90E−04 |
| E2F1_FASLG_LAMP2 | 1.93E−04 |
| CIAP2_FASLG_SIRT1 | 1.95E−04 |
| PTEN_XIAP_FASLG | 1.97E−04 |
| Survival | |
| ID2_CIAP2_SESN2 | 7.24E−05 |
| ID2_CASP3_CIAP2 | 9.38E−05 |
| ULK1_ID2_MGB2 | 1.10E−04 |
| ULK1_ID2_MGB1 | 1.22E−04 |
| DIABLO_ID2_CASP3 | 1.29E−04 |
| ULK1_ID2_AGER | 1.29E−04 |
| ID2_CIAP2_RPS19BP1 | 1.40E−04 |
| CASP8_ULK1_ID2 | 1.64E−04 |
| ID2_TCF3_CIAP2 | 1.65E−04 |
| FRAP1_ID2_CIAP2 | 1.73E−04 |
| AIFM1_CDH1_CIAP2 | 1.87E−04 |
| PTEN_CDH1_CIAP2 | 2.06E−04 |
| ULK1_ID2_CIAP2 | 2.36E−04 |
| DIABLO_ID2_CDH2 | 2.42E−04 |
| CDH1_CIAP2_VEGF | 2.43E−04 |
| CDH1_CCNG2_CIAP2 | 2.45E−04 |
| BAX_CDH1_CIAP2 | 2.45E−04 |
| ATG3_ID2_TCF3 | 2.46E−04 |
| ULK1_ID2_MMP2 | 2.60E−04 |
| CBS_ULK1_ID2 | 2.65E−04 |
| DIABLO_ID2_CIAP2 | 2.67E−04 |
| LC3_ID2_CIAP2 | 2.70E−04 |
| PTEN_ULK1_ID2 | 2.92E−04 |
| BAX_ULK1_ID2 | 3.20E−04 |
| DIABLO_PTEN_CDH1 | 3.22E−04 |
| CDH1_CASP3_CIAP2 | 3.24E−04 |
| ULK1_ID2_CDH2 | 3.29E−04 |

TABLE 48-continued

| Marker | p-value |
|---|---|
| CDH1_CIAP2_RAGE | 3.53E−04 |
| ID2_CDH2_CIAP2 | 3.55E−04 |
| NNMT_ID2_CIAP2 | 3.58E−04 |
| XIAP_CIAP2_SESN2 | 3.63E−04 |
| CSE1L_ID2_CASP3 | 3.64E−04 |
| CSE1L_FRAP1_CDH2 | 3.70E−04 |
| BCL2_ID2_SESN2 | 3.79E−04 |
| AIFM1_ULK1_ID2 | 3.83E−04 |
| ULK1_ID2_RAGE | 3.87E−04 |
| DIABLO_CDH1_CCNG2 | 3.89E−04 |
| BAX_DIABLO_CDH1 | 3.94E−04 |
| CSE1L_ID2_CDH2 | 4.05E−04 |
| AIFM1_CIAP2_SESN2 | 4.17E−04 |
| NNMT_CDH1_CIAP2 | 4.20E−04 |
| CBS_ID2_CIAP2 | 4.23E−04 |
| DIABLO_CDH1_VEGF | 4.34E−04 |
| ID2_MMP9_TCF3 | 4.47E−04 |
| AIFM1_DIABLO_CDH1 | 4.48E−04 |
| PRKAA1_CIAP2_SESN2 | 4.56E−04 |
| CDH1_ID2_CIAP2 | 4.57E−04 |
| CSE1L_CASP3_CIAP2 | 4.67E−04 |
| ULK1_ID2_VEGF | 4.72E−04 |
| ID2_CIAP2_HMGB1 | 4.73E−04 |
| BCL2L1_CDH1_CIAP2 | 4.83E−04 |
| ID2_CIAP2_MMP2 | 4.88E−04 |
| CSE1L_ID2_CIAP2 | 4.88E−04 |
| BCL2L1_CSE1L_CDH1 | 4.89E−04 |
| CSE1L_CDH1_CASP3 | 4.92E−04 |
| CSE1L_XIAP_SESN2 | 4.94E−04 |
| PRKAA1_CDH1_CIAP2 | 4.94E−04 |
| Disease-free survival | |
| FAS_LC3_FASLG | 1.06E−05 |
| DIABLO_FAS_FASLG | 1.76E−05 |
| E2F1_LC3_FASLG | 2.26E−05 |
| FAS_FASLG_RPS19BP1 | 2.33E−05 |
| E2F1_FAS_FASLG | 2.65E−05 |
| FAS_FASLG_UVRAG | 3.19E−05 |
| DIABLO_LC3_FASLG | 4.70E−05 |
| ATG7_FAS_FASLG | 4.82E−05 |
| FAS_FASLG_SESN2 | 5.14E−05 |
| LC3_FASLG_SESN2 | 5.39E−05 |
| FAS_LAMP1_FASLG | 5.66E−05 |
| ATG3_FAS_FASLG | 6.21E−05 |
| CIAP2_FASLG_SESN3 | 6.81E−05 |
| FAS_FRAP1_FASLG | 6.84E−05 |
| FRAP1_LC3_FASLG | 7.17E−05 |
| BNIP3_LC3_FASLG | 7.19E−05 |
| FAS_FASLG_SESN3 | 7.28E−05 |
| BNIP3_FAS_FASLG | 7.32E−05 |
| DIABLO_FASLG_SESN2 | 7.63E−05 |
| CIAP2_FASLG_UVRAG | 7.70E−05 |
| LC3_FASLG_UVRAG | 7.80E−05 |
| LC3_CIAP2_FASLG | 8.26E−05 |
| DRAM_FAS_FASLG | 8.27E−05 |
| LC3_FASLG_SESN3 | 8.77E−05 |
| FAS_FASLG_STAT3 | 9.20E−05 |
| ATG7_LC3_FASLG | 9.53E−05 |
| ATG5_FAS_FASLG | 9.63E−05 |
| E2F1_FASLG_SESN2 | 9.94E−05 |
| LC3_ID2_FASLG | 1.01E−04 |
| DRAM_LC3_FASLG | 1.03E−04 |
| FAS_TCF3_FASLG | 1.04E−04 |
| AKT1_FAS_FASLG | 1.05E−04 |
| E2F1_ULK1_FASLG | 1.05E−04 |
| E2F1_TCF3_FASLG | 1.06E−04 |
| LC3_FASLG_RPS19BP1 | 1.06E−04 |
| LC3_MMP9_FASLG | 1.09E−04 |
| FAS_FASLG_SIRT1 | 1.10E−04 |
| FAS_ULK1_FASLG | 1.13E−04 |
| FAS_FASLG_NAMPT | 1.13E−04 |
| LC3_FASLG_SIRT1 | 1.15E−04 |
| CASP3_CIAP2_FASLG | 1.24E−04 |
| ATG12_FAS_FASLG | 1.25E−04 |
| FAS_BECN1_FASLG | 1.29E−04 |
| ATG5_LC3_FASLG | 1.35E−04 |
| LC3_BECN1_FASLG | 1.37E−04 |

TABLE 48-continued

| Marker | p-value |
|---|---|
| LC3_FASLG_STAT3 | 1.37E−04 |
| E2F1_FASLG_SESN3 | 1.39E−04 |
| AKT1_LC3_FASLG | 1.40E−04 |
| FAS_FASLG_LAMP2 | 1.40E−04 |
| LC3_TCF3_FASLG | 1.41E−04 |
| LC3_FASLG_NAMPT | 1.41E−04 |
| LC3_CDH1_FASLG | 1.41E−04 |
| ATG12_LC3_FASLG | 1.42E−04 |
| PTEN_CDH1_CIAP2 | 1.45E−04 |
| LC3_FASLG_LAMP2 | 1.45E−04 |
| DIABLO_FASLG_SESN3 | 1.46E−04 |
| FAS_CDH1_FASLG | 1.46E−04 |

TABLE 49

| Marker | p-value |
|---|---|
| Recurrence | |
| DIABLO_FAS_LC3_FASLG | 4.96E−06 |
| FAS_LC3_FASLG_UVRAG | 5.48E−06 |
| BNIP3_FAS_LC3_FASLG | 6.23E−06 |
| DRAM_FAS_LC3_FASLG | 6.26E−06 |
| E2F1_FAS_LC3_FASLG | 6.40E−06 |
| ATG3_FAS_LC3_FASLG | 8.57E−06 |
| ATG7_FAS_LC3_FASLG | 9.02E−06 |
| FAS_LC3_FASLG_STAT3 | 9.45E−06 |
| FAS_FRAP1_LC3_FASLG | 9.88E−06 |
| FAS_LC3_FASLG_SESN3 | 1.03E−05 |
| FAS_LC3_FASLG_SIRT1 | 1.05E−05 |
| FAS_LC3_BECN1_FASLG | 1.06E−05 |
| ATG5_FAS_LC3_FASLG | 1.10E−05 |
| FAS_LC3_FASLG_RPS19BP1 | 1.22E−05 |
| FAS_LAMP1_LC3_FASLG | 1.27E−05 |
| FAS_LC3_FASLG_NAMPT | 1.30E−05 |
| AKT1_FAS_LC3_FASLG | 1.35E−05 |
| FAS_LC3_FASLG_SESN2 | 1.38E−05 |
| FAS_LC3_MMP9_FASLG | 1.49E−05 |
| FAS_FASLG_RPS19BP1_SESN3 | 1.56E−05 |
| FAS_FASLG_RPS19BP1_UVRAG | 1.57E−05 |
| FAS_LC3_CDH1_FASLG | 1.58E−05 |
| ATG12_FAS_LC3_FASLG | 1.60E−05 |
| DIABLO_FAS_FASLG_SESN3 | 1.66E−05 |
| DIABLO_FAS_FASLG_UVRAG | 1.69E−05 |
| FAS_LC3_FASLG_LAMP2 | 1.71E−05 |
| FAS_LC3_ID2_FASLG | 1.72E−05 |
| DIABLO_FAS_FASLG_SESN2 | 1.88E−05 |
| FAS_LC3_BHLHE41_FASLG | 1.95E−05 |
| DIABLO_DRAM_FAS_FASLG | 1.99E−05 |
| DIABLO_FAS_FASLG_STAT3 | 1.99E−05 |
| DRAM_FAS_FASLG_RPS19BP1 | 2.00E−05 |
| DIABLO_FAS_FRAP1_FASLG | 2.22E−05 |
| FAS_FASLG_SESN2_UVRAG | 2.32E−05 |
| ATG3_FAS_FASLG_SESN2 | 2.35E−05 |
| ATG7_DIABLO_FAS_FASLG | 2.37E−05 |
| FAS_LC3_TCF3_FASLG | 2.38E−05 |
| ATG7_FAS_FASLG_UVRAG | 2.49E−05 |
| DIABLO_FAS_FASLG_NAMPT | 2.61E−05 |
| DIABLO_FAS_FASLG_SIRT1 | 2.62E−05 |
| DIABLO_FAS_LAMP1_FASLG | 2.62E−05 |
| FAS_FRAP1_FASLG_RPS19BP1 | 2.62E−05 |
| CSE1L_FAS_LC3_FASLG | 2.65E−05 |
| DIABLO_FAS_BECN1_FASLG | 2.65E−05 |
| E2F1_LC3_ID2_FASLG | 2.74E−05 |
| AKT1_DIABLO_FAS_FASLG | 2.74E−05 |
| ATG3_DIABLO_FAS_FASLG | 2.77E−05 |
| E2F1_FAS_FASLG_SESN3 | 2.77E−05 |
| ATG7_FAS_FASLG_SESN2 | 2.79E−05 |
| DIABLO_FAS_FASLG_RPS19BP1 | 2.85E−05 |
| DRAM_FAS_FASLG_UVRAG | 2.86E−05 |
| LC3_MMP9_FASLG_SESN2 | 2.90E−05 |
| FAS_FASLG_SESN3_UVRAG | 2.95E−05 |
| DIABLO_FAS_FASLG_LAMP2 | 2.95E−05 |
| DIABLO_FAS_ID2_FASLG | 2.95E−05 |

TABLE 49-continued

| Marker | p-value |
|---|---|
| E2F1_LC3_FASLG_LAMP2 | 2.95E−05 |
| E2F1_LC3_MMP9_FASLG | 2.95E−05 |
| CDH1_ID2_MMP9_TCF3 | 3.71E−02 |
| Survival | |
| AIFM1_ID2_CIAP2_SESN2 | 2.08E−05 |
| PTEN_ID2_CIAP2_SESN2 | 3.00E−05 |
| DIABLO_ID2_CASP3_CIAP2 | 3.38E−05 |
| DRAM_FRAP1_CIAP2_TP63 | 3.54E−05 |
| BAX_ID2_CIAP2_SESN2 | 3.66E−05 |
| ID2_CIAP2_SESN2_VEGF | 4.04E−05 |
| DRAM_ID2_CIAP2_SESN2 | 4.12E−05 |
| ID2_CIAP2_RPS19BP1_SESN2 | 4.18E−05 |
| CBS_ID2_CIAP2_SESN2 | 4.19E−05 |
| ATG3_ID2_CIAP2_SESN2 | 4.27E−05 |
| NNMT_ID2_CIAP2_SESN2 | 4.31E−05 |
| DIABLO_ID2_CIAP2_SESN2 | 4.35E−05 |
| PRKAA1_ID2_CIAP2_SESN2 | 4.41E−05 |
| FRAP1_ID2_CIAP2_SESN2 | 4.44E−05 |
| DIABLO_DRAM_ID2_CASP3 | 4.61E−05 |
| XIAP_ID2_CIAP2_SESN2 | 4.64E−05 |
| ID2_CIAP2_RAGE_SESN2 | 4.72E−05 |
| DRAM_CIAP2_SESN2_TP63 | 5.02E−05 |
| BNIP3_ID2_CIAP2_SESN2 | 5.18E−05 |
| BCL2L1_ID2_CIAP2_SESN2 | 5.28E−05 |
| AIFM1_DIABLO_CDH1_CIAP2 | 5.36E−05 |
| ID2_CCNG2_CIAP2_SESN2 | 5.39E−05 |
| LC3_ID2_CIAP2_SESN2 | 5.46E−05 |
| ID2_CASP3_CIAP2_RPS19BP1 | 5.80E−05 |
| AIFM1_CDH1_CIAP2_SESN2 | 5.98E−05 |
| ATG3_ID2_TCF3_RPS19BP1 | 6.06E−05 |
| DIABLO_FRAP1_ID2_CDH2 | 6.20E−05 |
| E2F1_ID2_CIAP2_SESN2 | 6.45E−05 |
| ID2_CASP3_CIAP2_SESN2 | 6.46E−05 |
| DRAM_ID2_CIAP2_RPS19BP1 | 6.48E−05 |
| ID2_CIAP2_HMGB1_SESN2 | 6.56E−05 |
| PTEN_ID2_CASP3_CIAP2 | 6.84E−05 |
| ATG3_ID2_MMP9_TCF3 | 6.87E−05 |
| LAMP1_ID2_CIAP2_SESN2 | 6.91E−05 |
| AIFM1_ID2_CASP3_CIAP2 | 6.91E−05 |
| ATG5_ID2_CIAP2_SESN2 | 6.93E−05 |
| DIABLO_PTEN_CDH1_CIAP2 | 7.02E−05 |
| LAMP1_ID2_CASP3_CIAP2 | 7.04E−05 |
| ID2_CIAP2_HMGB2_SESN2 | 7.11E−05 |
| BCL2L1_CSE1L_ID2_SESN2 | 7.16E−05 |
| TKT_ID2_CIAP2_SESN2 | 7.17E−05 |
| DIABLO_XIAP_ID2_SESN2 | 7.18E−05 |
| FRAP1_LC3_ID2_CIAP2 | 7.21E−05 |
| ATG7_ID2_CIAP2_SESN2 | 7.36E−05 |
| ID2_AGER_CIAP2_SESN2 | 7.37E−05 |
| CSE1L_ID2_CASP3_CIAP2 | 7.38E−05 |
| DRAM_CASP3_CIAP2_TP63 | 7.39E−05 |
| PTEN_CDH1_ID2_CIAP2 | 7.41E−05 |
| CDH1_ID2_CIAP2_RPS19BP1 | 7.45E−05 |
| ATG3_ULK1_ID2_HMGB1 | 7.54E−05 |
| FRAP1_ID2_CIAP2_RPS19BP1 | 7.63E−05 |
| DIABLO_PTEN_ID2_CASP3 | 7.64E−05 |
| ID2_CIAP2_SESN2_TP63 | 7.74E−05 |
| ID2_TCF3_CIAP2_SESN2 | 7.80E−05 |
| DIABLO_CDH1_CIAP2_VEGF | 7.85E−05 |
| ATG3_ULK1_ID2_AGER | 7.94E−05 |
| ID2_CIAP2_MMP2_SESN2 | 8.02E−05 |
| CDH1_ID2_MMP9_TCF3 | 1.03E−03 |
| Disease-free survival | |
| DIABLO_FAS_LC3_FASLG | 3.51E−06 |
| FAS_LC3_FASLG_UVRAG | 3.97E−06 |
| E2F1_FAS_LC3_FASLG | 4.54E−06 |
| BNIP3_FAS_LC3_FASLG | 4.73E−06 |
| DRAM_FAS_LC3_FASLG | 6.03E−06 |
| ATG7_FAS_LC3_FASLG | 6.51E−06 |
| FAS_LAMP1_LC3_FASLG | 6.58E−06 |
| FAS_FRAP1_LC3_FASLG | 7.21E−06 |
| ATG3_FAS_LC3_FASLG | 7.29E−06 |
| FAS_LC3_FASLG_RPS19BP1 | 7.34E−06 |
| FAS_LC3_FASLG_SESN3 | 7.39E−06 |
| FAS_LC3_FASLG_SESN2 | 7.48E−06 |
| ATG5_FAS_LC3_FASLG | 7.52E−06 |

TABLE 49-continued

| Marker | p-value |
|---|---|
| FAS_LC3_FASLG_STAT3 | 7.79E−06 |
| FAS_LC3_FASLG_SIRT1 | 8.50E−06 |
| AKT1_FAS_LC3_FASLG | 9.12E−06 |
| FAS_LC3_ID2_FASLG | 9.15E−06 |
| FAS_LC3_FASLG_NAMPT | 9.24E−06 |
| FAS_LC3_BECN1_FASLG | 9.71E−06 |
| FAS_LC3_MMP9_FASLG | 9.89E−06 |
| DIABLO_FAS_FASLG_UVRAG | 1.01E−05 |
| ATG12_FAS_LC3_FASLG | 1.03E−05 |
| FAS_FASLG_RPS19BP1_UVRAG | 1.06E−05 |
| DIABLO_FAS_FASLG_SESN2 | 1.07E−05 |
| FAS_LC3_FASLG_LAMP2 | 1.07E−05 |
| FAS_LC3_CDH1_FASLG | 1.09E−05 |
| DIABLO_FAS_FASLG_SESN3 | 1.22E−05 |
| FAS_LC3_TCF3_FASLG | 1.27E−05 |
| E2F1_LC3_ID2_FASLG | 1.31E−05 |
| FAS_LC3_BHLHE41_FASLG | 1.31E−05 |
| DIABLO_FAS_LAMP1_FASLG | 1.33E−05 |
| DIABLO_DRAM_FAS_FASLG | 1.36E−05 |
| FAS_FASLG_SESN2_UVRAG | 1.39E−05 |
| FAS_FASLG_RPS19BP1_SESN3 | 1.39E−05 |
| DIABLO_FAS_FRAP1_FASLG | 1.41E−05 |
| DIABLO_FAS_FASLG_STAT3 | 1.44E−05 |
| ATG7_DIABLO_FAS_FASLG | 1.47E−05 |
| CSE1L_FAS_LC3_FASLG | 1.53E−05 |
| E2F1_LC3_MMP9_FASLG | 1.58E−05 |
| DRAM_FAS_FASLG_RPS19BP1 | 1.59E−05 |
| DIABLO_FAS_FASLG_RPS19BP1 | 1.61E−05 |
| FAS_LC3_ULK1_FASLG | 1.62E−05 |
| DIABLO_FAS_FASLG_SIRT1 | 1.63E−05 |
| DIABLO_FAS_ID2_FASLG | 1.63E−05 |
| AKT1_DIABLO_FAS_FASLG | 1.64E−05 |
| DIABLO_FAS_FASLG_NAMPT | 1.68E−05 |
| ATG3_FAS_FASLG_SESN2 | 1.69E−05 |
| FAS_FASLG_RPS19BP1_SESN2 | 1.70E−05 |
| DIABLO_FAS_BECN1_FASLG | 1.72E−05 |
| DIABLO_FAS_CDH1_FASLG | 1.76E−05 |
| ATG7_FAS_FASLG_UVRAG | 1.77E−05 |
| DIABLO_FAS_FASLG_LAMP2 | 1.77E−05 |
| FAS_FRAP1_FASLG_RPS19BP1 | 1.78E−05 |
| FAS_LAMP1_FASLG_UVRAG | 1.82E−05 |
| E2F1_FAS_LAMP1_FASLG | 1.84E−05 |
| ATG7_FAS_FASLG_RPS19BP1 | 1.89E−05 |
| E2F1_FAS_FASLG_UVRAG | 1.91E−05 |
| CDH1_ID2_MMP9_TCF3 | 3.56E−02 |

TABLE 50

| Marker | p-value |
|---|---|
| Recurrence | |
| BNIP3_DRAM_FAS_LC3_FASLG | 2.75E−06 |
| DRAM_FAS_LC3_FASLG_UVRAG | 2.77E−06 |
| DIABLO_DRAM_FAS_LC3_FASLG | 3.15E−06 |
| ATG3_FAS_LC3_FASLG_SESN3 | 3.60E−06 |
| BNIP3_FAS_LC3_FASLG_SESN3 | 3.69E−06 |
| BNIP3_FAS_LC3_FASLG_UVRAG | 3.69E−06 |
| ATG3_FAS_LC3_FASLG_SESN2 | 3.79E−06 |
| BNIP3_FAS_LC3_FASLG_SESN2 | 3.94E−06 |
| DRAM_FAS_LC3_FASLG_STAT3 | 3.96E−06 |
| DIABLO_FAS_LC3_BECN1_FASLG | 4.05E−06 |
| BNIP3_DIABLO_FAS_LC3_FASLG | 4.11E−06 |
| ATG7_DRAM_FAS_LC3_FASLG | 4.12E−06 |
| DIABLO_FAS_LC3_FASLG_STAT3 | 4.14E−06 |
| DRAM_FAS_LC3_FASLG_SIRT1 | 4.15E−06 |
| DRAM_E2F1_FAS_LC3_FASLG | 4.20E−06 |
| DRAM_FAS_LC3_FASLG_SESN3 | 4.20E−06 |
| DRAM_FAS_LC3_BECN1_FASLG | 4.22E−06 |
| BNIP3_FAS_LC3_FASLG_STAT3 | 4.35E−06 |
| BNIP3_FAS_LC3_MMP9_FASLG | 4.37E−06 |
| DIABLO_FAS_LC3_ID2_FASLG | 4.40E−06 |
| DIABLO_FAS_LC3_MMP9_FASLG | 4.41E−06 |
| ATG5_FAS_LC3_FASLG_UVRAG | 4.43E−06 |
| ATG5_DRAM_FAS_LC3_FASLG | 4.45E−06 |

TABLE 50-continued

| Marker | p-value |
|---|---|
| DIABLO_FAS_LC3_FASLG_SIRT1 | 4.46E−06 |
| FAS_LC3_FASLG_SIRT1_UVRAG | 4.47E−06 |
| DRAM_FAS_FRAP1_LC3_FASLG | 4.49E−06 |
| DIABLO_FAS_LC3_FASLG_SESN3 | 4.54E−06 |
| FAS_LC3_BECN1_FASLG_UVRAG | 4.55E−06 |
| ATG3_FAS_LC3_MMP9_FASLG | 4.58E−06 |
| BNIP3_FAS_LC3_FASLG_SIRT1 | 4.59E−06 |
| BNIP3_FAS_FRAP1_LC3_FASLG | 4.70E−06 |
| DIABLO_FAS_LC3_FASLG_UVRAG | 4.72E−06 |
| DIABLO_FAS_LC3_FASLG_NAMPT | 4.72E−06 |
| FAS_LC3_MMP9_FASLG_RPS19BP1 | 4.73E−06 |
| BNIP3_FAS_LC3_BECN1_FASLG | 4.74E−06 |
| E2F1_FAS_LC3_MMP9_FASLG | 4.74E−06 |
| FAS_LC3_MMP9_FASLG_UVRAG | 4.77E−06 |
| ATG3_DIABLO_FAS_LC3_FASLG | 4.87E−06 |
| DIABLO_FAS_LC3_BHLHE41_FASLG | 4.96E−06 |
| FAS_LC3_ID2_FASLG_UVRAG | 4.96E−06 |
| DIABLO_FAS_LC3_FASLG_LAMP2 | 5.04E−06 |
| DRAM_FAS_LC3_FASLG_SESN2 | 5.17E−06 |
| DRAM_FAS_LAMP1_LC3_FASLG | 5.29E−06 |
| ATG3_FAS_FRAP1_LC3_FASLG | 5.34E−06 |
| FAS_LC3_FASLG_STAT3_UVRAG | 5.37E−06 |
| AKT1_BNIP3_FAS_LC3_FASLG | 5.37E−06 |
| FAS_LC3_FASLG_SESN3_UVRAG | 5.39E−06 |
| ATG3_DRAM_FAS_LC3_FASLG | 5.40E−06 |
| AKT1_DRAM_FAS_LC3_FASLG | 5.42E−06 |
| FAS_LC3_FASLG_SESN2_UVRAG | 5.56E−06 |
| FAS_LC3_BHLHE41_FASLG_UVRAG | 5.58E−06 |
| DRAM_FAS_LC3_FASLG_NAMPT | 5.61E−06 |
| FAS_LC3_FASLG_LAMP2_UVRAG | 5.67E−06 |
| ATG7_BNIP3_FAS_LC3_FASLG | 5.68E−06 |
| AKT1_FAS_LC3_FASLG_UVRAG | 5.78E−06 |
| E2F1_FAS_LC3_ID2_FASLG | 5.85E−06 |
| DRAM_FAS_LC3_CDH1_FASLG | 5.86E−06 |
| PTEN_CDH1_ID2_MMP9_TCF3 | 8.28E−04 |
| Survival | |
| DRAM_ID2_CIAP2_SESN2_TP63 | 4.30E−06 |
| AIFM1_DRAM_CIAP2_SESN2_TP63 | 5.10E−06 |
| DRAM_FRAP1_CDH1_CIAP2_TP63 | 5.59E−06 |
| ATG12_DRAM_FRAP1_CIAP2_TP63 | 7.10E−06 |
| DRAM_FRAP1_XIAP_CIAP2_TP63 | 8.40E−06 |
| DRAM_TKT_CIAP2_SESN2_TP63 | 9.09E−06 |
| AIFM1_CDH1_ID2_CIAP2_SESN2 | 1.00E−05 |
| AIFM1_DRAM_FRAP1_CIAP2_TP63 | 1.00E−05 |
| DRAM_FRAP1_TKT_CIAP2_TP63 | 1.04E−05 |
| PTEN_CDH1_ID2_CIAP2_SESN2 | 1.10E−05 |
| BAX_CDH1_ID2_CIAP2_SESN2 | 1.20E−05 |
| DRAM_FRAP1_ID2_CIAP2_TP63 | 1.37E−05 |
| DRAM_TKT_CASP3_CIAP2_TP63 | 1.39E−05 |
| CDH1_ID2_CCNG2_CIAP2_SESN2 | 1.44E−05 |
| AIFM1_PTEN_ID2_CIAP2_SESN2 | 1.50E−05 |
| DIABLO_FRAP1_CDH1_ID2_CIAP2 | 1.54E−05 |
| AIFM1_CBS_ID2_CIAP2_SESN2 | 1.60E−05 |
| AIFM1_LAMP1_ID2_CIAP2_SESN2 | 1.60E−05 |
| DRAM_ID2_CASP3_CIAP2_TP63 | 1.60E−05 |
| DIABLO_PTEN_CDH1_ID2_CIAP2 | 1.63E−05 |
| CDH1_ID2_CIAP2_SESN2_VEGF | 1.67E−05 |
| DIABLO_CDH1_ID2_CASP3_CIAP2 | 1.70E−05 |
| AIFM1_ATG3_ID2_CIAP2_SESN2 | 1.80E−05 |
| AIFM1_BNIP3_ID2_CIAP2_SESN2 | 1.80E−05 |
| AIFM1_DIABLO_CDH1_ID2_CIAP2 | 1.80E−05 |
| ATG3_DRAM_ID2_CIAP2_SESN2 | 1.80E−05 |
| AIFM1_BAX_ID2_CIAP2_SESN2 | 1.90E−05 |
| DRAM_E2F1_CASP3_CIAP2_TP63 | 1.92E−05 |
| AIFM1_ID2_CIAP2_HMGB2_SESN2 | 2.00E−05 |
| AIFM1_ID2_MMP9_CIAP2_SESN2 | 2.00E−05 |
| DIABLO_CDH1_ID2_CIAP2_VEGF | 2.00E−05 |
| DIABLO_DRAM_XIAP_ID2_SESN2 | 2.09E−05 |
| AIFM1_ATG5_ID2_CIAP2_SESN2 | 2.10E−05 |
| AIFM1_ID2_CIAP2_HMGB1_SESN2 | 2.10E−05 |
| BAX_DIABLO_CDH1_ID2_CIAP2 | 2.10E−05 |
| DRAM_FRAP1_NNMT_CIAP2_TP63 | 2.14E−05 |
| FRAP1_CDH1_ID2_CIAP2_RPS19BP1 | 2.14E−05 |
| DRAM_XIAP_CIAP2_SESN2_TP63 | 2.16E−05 |
| AIFM1_DIABLO_ID2_CIAP2_SESN2 | 2.20E−05 |
| AIFM1_DRAM_ID2_CIAP2_SESN2 | 2.20E−05 |
| AIFM1_ID2_CIAP2_SESN2_ | 2.20E−05 |

TABLE 50-continued

| Marker | p-value |
|---|---|
| AIFM1_TKT_ID2_CIAP2_SESN2 | 2.20E−05 |
| ATG3_ID2_MMP9_TCF3_RPS19BP1 | 2.20E−05 |
| ATG5_DRAM_CIAP2_SESN2_TP63 | 2.20E−05 |
| CBS_FRAP1_ID2_CIAP2_SESN2 | 2.27E−05 |
| AIFM1_DIABLO_ID2_CASP3_CIAP2 | 2.30E−05 |
| AIFM1_NNMT_ID2_CIAP2_SESN2 | 2.30E−05 |
| ATG3_DRAM_CIAP2_SESN2_TP63 | 2.30E−05 |
| ATG3_FRAP1_ID2_CIAP2_SESN2 | 2.30E−05 |
| BAX_DIABLO_DRAM_ID2_CASP3 | 2.30E−05 |
| LAMP1_PTEN_ID2_CIAP2_ | 2.31E−05 |
| CDH1_ID2_CIAP2_RAGE_SESN2 | 2.33E−05 |
| CBS_DIABLO_ID2_CIAP2_SESN2 | 2.35E−05 |
| DIABLO_CDH1_ID2_CCNG2_CIAP2 | 2.39E−05 |
| DIABLO_LAMP1_ID2_CASP3_CIAP2 | 2.39E−05 |
| AIFM1_DRAM_CASP3_CIAP2_TP63 | 2.40E−05 |
| BCL2L1_DRAM_FRAP1_CIAP2_TP63 | 2.40E−05 |
| CDH1_ID2_MMP9_TCF3_CIAP2 | 1.01E−04 |
| Disease-free survival | |
| DIABLO_FAS_LC3_ID2_FASLG | 2.53E−06 |
| DRAM_FAS_LC3_FASLG_UVRAG | 2.65E−06 |
| DIABLO_DRAM_FAS_LC3_FASLG | 2.69E−06 |
| BNIP3_FAS_LC3_FASLG_UVRAG | 2.77E−06 |
| BNIP3_FAS_LC3_FASLG_SESN2 | 2.93E−06 |
| BNIP3_DRAM_FAS_LC3_FASLG | 2.99E−06 |
| BNIP3_DIABLO_FAS_LC3_FASLG | 3.07E−06 |
| FAS_LC3_ID2_FASLG_UVRAG | 3.08E−06 |
| DIABLO_FAS_LC3_FASLG_UVRAG | 3.09E−06 |
| DIABLO_FAS_LC3_FASLG_STAT3 | 3.21E−06 |
| DIABLO_FAS_LC3_FASLG_SESN3 | 3.26E−06 |
| DIABLO_FAS_LC3_FASLG_SIRT1 | 3.32E−06 |
| FAS_LC3_MMP9_FASLG_RPS19BP1 | 3.33E−06 |
| ATG5_FAS_LC3_FASLG_UVRAG | 3.34E−06 |
| BNIP3_FAS_LC3_FASLG_SESN3 | 3.37E−06 |
| DIABLO_FAS_LC3_BECN1_FASLG | 3.39E−06 |
| DIABLO_FAS_LC3_CDH1_FASLG | 3.42E−06 |
| ATG3_FAS_LC3_FASLG_SESN2 | 3.46E−06 |
| DRAM_E2F1_FAS_LC3_FASLG | 3.48E−06 |
| FAS_LC3_FASLG_SESN2_UVRAG | 3.50E−06 |
| DIABLO_FAS_LC3_FASLG_LAMP2 | 3.51E−06 |
| E2F1_FAS_LC3_ID2_FASLG | 3.52E−06 |
| DIABLO_FAS_LC3_FASLG_NAPMT | 3.52E−06 |
| DIABLO_FAS_LC3_MMP9_FASLG | 3.54E−06 |
| FAS_LC3_FASLG_SIRT1_UVRAG | 3.56E−06 |
| FAS_LC3_FASLG_SESN3_UVRAG | 3.64E−06 |
| FAS_LAMP1_LC3_FASLG_UVRAG | 3.65E−06 |
| AKT1_DIABLO_FAS_LC3_FASLG | 3.70E−06 |
| DIABLO_FAS_FRAP1_LC3_FASLG | 3.75E−06 |
| DIABLO_FAS_LC3_BHLHE41_FASLG | 3.75E−06 |
| FAS_LC3_FASLG_STAT3_UVRAG | 3.76E−06 |
| DIABLO_FAS_LC3_FASLG_SESN2 | 3.76E−06 |
| E2F1_FAS_LC3_MMP9_FASLG | 3.77E−06 |
| BNIP3_FAS_FRAP1_LC3_FASLG | 3.81E−06 |
| DIABLO_FAS_LAMP1_LC3_FASLG | 3.81E−06 |
| FAS_LC3_BECN1_FASLG_UVRAG | 3.82E−06 |
| AKT1_FAS_LC3_FASLG_UVRAG | 3.87E−06 |
| BNIP3_FAS_LC3_MMP9_FASLG | 3.87E−06 |
| FAS_FRAP1_LC3_FASLG_UVRAG | 3.90E−06 |
| BNIP3_FAS_LC3_FASLG_STAT3 | 3.92E−06 |
| FAS_LC3_CDH1_FASLG_UVRAG | 3.95E−06 |
| FAS_LC3_FASLG_LAMP2_UVRAG | 3.97E−06 |
| FAS_LC3_MMP9_FASLG_UVRAG | 3.98E−06 |
| ATG7_FAS_LC3_FASLG_UVRAG | 3.99E−06 |
| ATG7_DRAM_FAS_LC3_FASLG | 4.08E−06 |
| BNIP3_FAS_LC3_FASLG_SIRT1 | 4.12E−06 |
| DRAM_FAS_LAMP1_LC3_FASLG | 4.12E−06 |
| ATG7_BNIP3_FAS_LC3_FASLG | 4.12E−06 |
| BNIP3_FAS_LAMP1_LC3_FASLG | 4.13E−06 |
| ATG3_FAS_LC3_MMP9_FASLG | 4.16E−06 |
| ATG5_DIABLO_FAS_LC3_FASLG | 4.20E−06 |
| BNIP3_FAS_LC3_ID2_FASLG | 4.26E−06 |
| ATG12_DIABLO_FAS_LC3_FASLG | 4.26E−06 |
| E2F1_FAS_LC3_FASLG_SESN3 | 4.27E−06 |
| AKT1_BNIP3_FAS_LC3_FASLG | 4.29E−06 |
| FAS_LC3_FASLG_NAMPT_UVRAG | 4.34E−06 |
| ATG12_FAS_LC3_FASLG_UVRAG | 4.37E−06 |
| PTEN_CDH1_ID2_MMP9_TCF3 | 8.28E−04 |

TABLE 51

| Marker | p-value |
|---|---|
| Recurrence | |
| BNIP3_DRAM_FAS_LC3_FASLG_SESN2 | 1.87E−06 |
| BNIP3_DRAM_FAS_LC3_FASLG_SESN3 | 1.96E−06 |
| ATG3_FAS_LC3_MMP9_FASLG_SESN2 | 2.02E−06 |
| ATG3_FAS_LC3_MMP9_FASLG_SESN3 | 2.02E−06 |
| ATG3_FAS_LC3_FASLG_SESN2_SESN3 | 2.03E−06 |
| BNIP3_DRAM_FAS_LC3_MMP9_FASLG | 2.06E−06 |
| BNIP3_DRAM_FAS_LC3_FASLG_STAT3 | 2.33E−06 |
| BNIP3_DRAM_FAS_LC3_FASLG_UVRAG | 2.35E−06 |
| BNIP3_DRAM_FAS_LC3_FASLG_SIRT1 | 2.38E−06 |
| ATG3_DRAM_FAS_LC3_FASLG_SESN2 | 2.48E−06 |
| BNIP3_DRAM_FAS_LC3_BECN1_FASLG | 2.48E−06 |
| DRAM_FAS_LC3_ID2_FASLG_UVRAG | 2.50E−06 |
| BNIP3_FAS_LC3_MMP9_FASLG_UVRAG | 2.54E−06 |
| DRAM_FAS_LC3_MMP9_FASLG_RPS19BP1 | 2.54E−06 |
| ATG5_DRAM_FAS_LC3_FASLG_UVRAG | 2.58E−06 |
| DRAM_FAS_LC3_FASLG_SIRT1_UVRAG | 2.62E−06 |
| DRAM_FAS_LC3_MMP9_FASLG_UVRAG | 2.62E−06 |
| BNIP3_DRAM_FAS_LC3_ID2_FASLG | 2.63E−06 |
| ATG3_DRAM_FAS_LC3_FASLG_SESN3 | 2.65E−06 |
| BNIP3_FAS_LC3_MMP9_FASLG_SESN3 | 2.69E−06 |
| BNIP3_FAS_LC3_MMP9_FASLG_SESN2 | 2.71E−06 |
| DRAM_FAS_LC3_BECN1_FASLG_UVRAG | 2.72E−06 |
| BNIP3_DRAM_FAS_FRAP1_LC3_FASLG | 2.72E−06 |
| BNIP3_FAS_LC3_FASLG_SESN3_SIRT1 | 2.75E−06 |
| DRAM_FAS_LC3_BHLHE41_FASLG_UVRAG | 2.76E−06 |
| BNIP3_DRAM_FAS_LC3_FASLG_LAMP2 | 2.78E−06 |
| AKT1_BNIP3_DRAM_FAS_LC3_FASLG | 2.79E−06 |
| DIABLO_DRAM_FAS_LC3_ID2_FASLG | 2.80E−06 |
| DRAM_FAS_LC3_FASLG_SESN3_SIRT1 | 2.82E−06 |
| ATG3_DIABLO_FAS_LC3_MMP9_FASLG | 2.84E−06 |
| BNIP3_FAS_LC3_FASLG_SESN3_STAT3 | 2.87E−06 |
| BNIP3_FAS_LC3_BECN1_FASLG_SESN2 | 2.89E−06 |
| BNIP3_FAS_LC3_FASLG_SESN2_SIRT1 | 2.92E−06 |
| DIABLO_DRAM_FAS_LC3_MMP9_FASLG | 2.92E−06 |
| BNIP3_FAS_LC3_BECN1_FASLG_SESN3 | 2.94E−06 |
| BNIP3_FAS_LC3_FASLG_SESN2_UVRAG | 2.94E−06 |
| DRAM_FAS_LC3_FASLG_LAMP2_UVRAG | 2.95E−06 |
| ATG3_FAS_FRAP1_LC3_MMP9_FASLG | 2.97E−06 |
| DRAM_FAS_LC3_BECN1_FASLG_SESN3 | 2.98E−06 |
| DIABLO_DRAM_FAS_LC3_BECN1_FASLG | 2.98E−06 |
| ATG3_DRAM_FAS_LC3_MMP9_FASLG | 2.99E−06 |
| BNIP3_DRAM_FAS_LC3_CDH1_FASLG | 3.02E−06 |
| DRAM_FAS_LC3_FASLG_SESN2_UVRAG | 3.04E−06 |
| BNIP3_DRAM_FAS_LC3_BHLHE41_FASLG | 3.05E−06 |
| ATG5_DRAM_FAS_LC3_FASLG_SESN3 | 3.05E−06 |
| DRAM_FAS_LC3_FASLG_SESN3_STAT3 | 3.06E−06 |
| BNIP3_FAS_LC3_FASLG_SESN2_STAT3 | 3.06E−06 |
| BNIP3_DIABLO_FAS_LC3_MMP9_FASLG | 3.07E−06 |
| ATG5_DRAM_FAS_LC3_FASLG_SESN2 | 3.07E−06 |
| ATG5_FAS_LC3_MMP9_FASLG_UVRAG | 3.09E−06 |
| DIABLO_DRAM_FAS_LC3_BHLHE41_FASLG | 3.09E−06 |
| DIABLO_DRAM_FAS_LC3_FASLG_STAT3 | 3.12E−06 |
| ATG3_DIABLO_FAS_LC3_FASLG_SESN3 | 3.13E−06 |
| DRAM_FAS_LC3_TCF3_FASLG_UVRAG | 3.13E−06 |
| BNIP3_FAS_LC3_MMP9_FASLG_RPS19BP1 | 3.14E−06 |
| ATG5_DRAM_FAS_LC3_FASLG_STAT3 | 3.15E−06 |
| ATG7_DRAM_FAS_LC3_MMP9_FASLG | 3.17E−06 |
| LC3_CDH1_ID2_MMP9_TCF3_FASLG | 6.15E−05 |
| Survival | |
| ATG12_DRAM_FRAP1_TKT_CIAP2_TP63 | 8.60E−07 |
| AIFM1_DRAM_TKT_CIAP2_SESN2_TP63 | 1.50E−06 |
| AIFM1_ATG12_DRAM_FRAP1_CIAP2_TP63 | 1.80E−06 |
| AIFM1_DRAM_ID2_CIAP2_SESN2_TP63 | 1.90E−06 |
| DRAM_TKT_ID2_CIAP2_SESN2_TP63 | 2.37E−06 |
| AIFM1_ATG3_DRAM_CIAP2_SESN2_TP63 | 2.40E−06 |
| DRAM_FRAP1_TKT_CDH1_CIAP2_TP63 | 2.50E−06 |
| ATG3_DRAM_ID2_CIAP2_SESN2_TP63 | 2.60E−06 |
| DRAM_PTEN_ID2_CIAP2_SESN2_TP63 | 2.77E−06 |
| DRAM_FRAP1_TKT_XIAP_CIAP2_TP63 | 2.94E−06 |
| DRAM_E2F1_FRAP1_CDH1_CIAP2_TP63 | 3.19E−06 |
| ATG3_DRAM_FRAP1_CDH1_CIAP2_TP63 | 3.30E−06 |
| ATG7_DRAM_ID2_CIAP2_SESN2_TP63 | 3.30E−06 |
| AIFM1_DRAM_FRAP1_CDH1_CIAP2_TP63 | 3.40E−06 |
| ATG5_DRAM_ID2_CIAP2_SESN2_TP63 | 3.40E−06 |
| AIFM1_DIABLO_CDH1_ID2_CIAP2_SESN2 | 3.80E−06 |

TABLE 51-continued

| Marker | p-value |
|---|---|
| AIFM1_BNIP3_DRAM_CIAP2_SESN2_TP63 | 3.90E−06 |
| BCL2L1_DRAM_ID2_CIAP2_SESN2_TP63 | 3.98E−06 |
| DRAM_NNMT_ID2_CIAP2_SESN2_TP63 | 3.99E−06 |
| CASP8_DRAM_ID2_CIAP2_SESN2_TP63 | 4.01E−06 |
| DRAM_ID2_BHLHE41_CIAP2_SESN2_TP63 | 4.02E−06 |
| DRAM_FRAP1_CDH1_CIAP2_RPS19BP1_TP63 | 4.07E−06 |
| DRAM_LAMP1_ID2_CIAP2_SESN2_TP63 | 4.11E−06 |
| DRAM_FRAP1_CDH1_ID2_CIAP2_TP63 | 4.14E−06 |
| BNIP3_DRAM_ID2_CIAP2_SESN2_TP63 | 4.16E−06 |
| DRAM_ID2_MMP9_CIAP2_SESN2_TP63 | 4.20E−06 |
| AKT1_DRAM_ID2_CIAP2_SESN2_TP63 | 4.20E−06 |
| DRAM_ID2_CIAP2_RAGE_SESN2_TP63 | 4.20E−06 |
| ATG12_DRAM_FRAP1_XIAP_CIAP2_TP63 | 4.30E−06 |
| DRAM_PRKAA1_ID2_CIAP2_SESN2_TP63 | 4.31E−06 |
| DRAM_XIAP_ID2_CIAP2_SESN2_TP63 | 4.34E−06 |
| AIFM1_DRAM_PTEN_CIAP2_SESN2_TP63 | 4.40E−06 |
| ATG3_DRAM_FRAP1_CASP3_CIAP2_TP63 | 4.40E−06 |
| CASP8_DRAM_FRAP1_CDH1_CIAP2_TP63 | 4.47E−06 |
| AIFM1_ATG5_DRAM_CIAP2_SESN2_TP63 | 4.50E−06 |
| AIFM1_CASP8_DRAM_CIAP2_SESN2_TP63 | 4.50E−06 |
| BCL2L1_DRAM_FRAP1_TKT_CIAP2_TP63 | 4.53E−06 |
| CBS_DRAM_ID2_CIAP2_SESN2_TP63 | 4.58E−06 |
| DRAM_FRAP1_NNMT_TKT_CIAP2_TP63 | 4.59E−06 |
| AIFM1_AKT1_DRAM_CIAP2_SESN2_TP63 | 4.60E−06 |
| DRAM_FRAP1_PTEN_CDH1_CIAP2_TP63 | 4.61E−06 |
| DIABLO_PTEN_CDH1_ID2_CIAP2_SESN2 | 4.65E−06 |
| DRAM_ID2_CIAP2_SESN2_TP63_VEGF | 4.67E−06 |
| AIFM1_DRAM_XIAP_CIAP2_SESN2_TP63 | 4.70E−06 |
| BNIP3_DRAM_FRAP1_CDH1_CIAP2_TP63 | 4.78E−06 |
| AIFM1_ATG7_DRAM_CIAP2_SESN2_TP63 | 4.80E−06 |
| AIFM1_DRAM_FRAP1_NNMT_CIAP2_TP63 | 4.80E−06 |
| AIFM1_DRAM_MMP9_CIAP2_SESN2_TP63 | 4.80E−06 |
| AIFM1_DRAM_PRKAA1_CIAP2_SESN2_TP63 | 4.80E−06 |
| AIFM1_DRAM_CIAP2_RAGE_SESN2_TP63 | 4.90E−06 |
| AIFM1_DRAM_FRAP1_XIAP_CIAP2_TP63 | 4.90E−06 |
| AIFM1_DRAM_NNMT_CIAP2_SESN2_TP63 | 4.90E−06 |
| DRAM_FRAP1_CDH1_CIAP2_TP63_VEGF | 4.90E−06 |
| AIFM1_DRAM_LAMP1_CIAP2_SESN2_TP63 | 5.00E−06 |
| DIABLO_DRAM_FRAP1_XIAP_CASP3_HMGB2 | 5.01E−06 |
| DRAM_TKT_XIAP_CIAP2_SESN2_TP63 | 5.05E−06 |
| AIFM1_BCL2L1_DRAM_CIAP2_SESN2_TP63 | 5.10E−06 |
| BAX_CDH1_ID2_MMP9_TCF3_CIAP2 | 2.80E−05 |
| Disease-free survival | |
| BNIP3_DRAM_FAS_LC3_FASLG_SESN2 | 1.92E−06 |
| DIABLO_DRAM_FAS_LC3_ID2_FASLG | 1.94E−06 |
| ATG3_FAS_LC3_MMP9_FASLG_SESN2 | 1.99E−06 |
| DRAM_FAS_LC3_ID2_FASLG_UVRAG | 2.04E−06 |
| BNIP3_DRAM_FAS_LC3_FASLG_UVRAG | 2.07E−06 |
| BNIP3_FAS_LC3_FASLG_SESN2_UVRAG | 2.08E−06 |
| DIABLO_FAS_LC3_ID2_FASLG_UVRAG | 2.12E−06 |
| DIABLO_FAS_LC3_ID2_FASLG_STAT3 | 2.24E−06 |
| DIABLO_FAS_LC3_ID2_FASLG_SESN3 | 2.25E−06 |
| BNIP3_FAS_LC3_MMP9_FASLG_UVRAG | 2.26E−06 |
| BNIP3_DRAM_FAS_LC3_FASLG_SESN3 | 2.27E−06 |
| BNIP3_FAS_LC3_ID2_FASLG_UVRAG | 2.28E−06 |
| DRAM_FAS_LC3_MMP9_FASLG_RPS19BP1 | 2.34E−06 |
| BNIP3_FAS_LC3_MMP9_FASLG_RPS19BP1 | 2.34E−06 |
| BNIP3_FAS_LC3_ID2_FASLG_SESN2 | 2.37E−06 |
| BNIP3_DIABLO_FAS_LC3_ID2_FASLG | 2.37E−06 |
| BNIP3_FAS_LC3_MMP9_FASLG_SESN2 | 2.37E−06 |
| DIABLO_FAS_LC3_ID2_FASLG_SIRT1 | 2.38E−06 |
| ATG5_DRAM_FAS_LC3_FASLG_UVRAG | 2.39E−06 |
| FAS_LC3_MMP9_FASLG_RPS19BP1_UVRAG | 2.40E−06 |
| ATG3_FAS_LC3_FASLG_SESN2_SESN3 | 2.41E−06 |
| DRAM_FAS_LC3_FASLG_SESN2_UVRAG | 2.43E−06 |
| DIABLO_FAS_LC3_ID2_BECN1_FASLG | 2.44E−06 |
| DRAM_FAS_LC3_FASLG_SIRT1_UVRAG | 2.46E−06 |
| FAS_LC3_ID2_FASLG_SESN2_UVRAG | 2.47E−06 |
| DIABLO_FAS_LC3_CDH1_ID2_FASLG | 2.48E−06 |
| FAS_LC3_ID2_MMP9_FASLG_RPS19BP1 | 2.48E−06 |
| BNIP3_FAS_LC3_FASLG_SESN2_SESN3 | 2.51E−06 |
| DIABLO_FAS_LC3_ID2_FASLG_NAMPT | 2.52E−06 |
| DIABLO_FAS_LC3_ID2_FASLG_SESN2 | 2.53E−06 |
| DIABLO_FAS_LC3_ID2_FASLG_LAMP2 | 2.54E−06 |
| BNIP3_FAS_LC3_FASLG_SESN2_SIRT1 | 2.56E−06 |
| BNIP3_FAS_LC3_FASLG_SESN2_STAT3 | 2.56E−06 |
| DRAM_FAS_LC3_FASLG_SESN3_UVRAG | 2.58E−06 |

TABLE 51-continued

| Marker | p-value |
|---|---|
| DIABLO_DRAM_FAS_LC3_FASLG_STAT3 | 2.58E−06 |
| BNIP3_DRAM_FAS_LC3_MMP9_FASLG | 2.59E−06 |
| ATG5_FAS_LC3_ID2_FASLG_UVRAG | 2.59E−06 |
| BNIP3_FAS_LC3_FASLG_SESN3_UVRAG | 2.59E−06 |
| DRAM_FAS_LC3_BECN1_FASLG_UVRAG | 2.59E−06 |
| DIABLO_DRAM_FAS_LC3_CDH1_FASLG | 2.60E−06 |
| AKT1_DIABLO_FAS_LC3_ID2_FASLG | 2.60E−06 |
| BNIP3_DIABLO_FAS_LC3_MMP9_FASLG | 2.61E−06 |
| DRAM_FAS_LC3_CDH1_FASLG_UVRAG | 2.61E−06 |
| DIABLO_FAS_FRAP1_LC3_ID2_FASLG | 2.62E−06 |
| BNIP3_DRAM_FAS_LC3_FASLG_STAT3 | 2.62E−06 |
| DIABLO_DRAM_FAS_LC3_FASLG_SESN3 | 2.62E−06 |
| BNIP3_DIABLO_DRAM_FAS_LC3_FASLG | 2.63E−06 |
| DIABLO_DRAM_FAS_LC3_FASLG_SIRT1 | 2.63E−06 |
| BNIP3_DRAM_FAS_FRAP1_LC3_FASLG | 2.63E−06 |
| DIABLO_DRAM_FAS_LC3_BECN1_FASLG | 2.63E−06 |
| ATG3_FAS_LC3_MMP9_FASLG_SESN3 | 2.64E−06 |
| DIABLO_FAS_LAMP1_LC3_ID2_FASLG | 2.64E−06 |
| DRAM_FAS_LC3_FASLG_LAMP2_UVRAG | 2.64E−06 |
| ATG5_FAS_LC3_FASLG_SESN2_UVRAG | 2.65E−06 |
| FAS_LC3_MMP9_FASLG_RPS19BP1_SESN3 | 2.66E−06 |
| FAS_LAMP1_LC3_ID2_FASLG_UVRAG | 2.66E−06 |
| BNIP3_DRAM_FAS_LC3_ID2_FASLG | 2.67E−06 |
| LC3_CDH1_ID2_MMP9_TCF3_FASLG | 3.51E−05 |

TABLE 52

| Marker | p-value |
|---|---|
| Recurrence | |
| ATG3_FAS_LC3_MMP9_FASLG_SESN2_SESN3 | 1.14E−06 |
| BNIP3_DRAM_FAS_LC3_MMP9_FASLG_SESN2 | 1.35E−06 |
| ATG3_DRAM_FAS_LC3_MMP9_FASLG_SESN2 | 1.37E−06 |
| BNIP3_DRAM_FAS_LC3_MMP9_FASLG_SESN3 | 1.55E−06 |
| ATG3_DRAM_FAS_LC3_FASLG_SESN2_SESN3 | 1.56E−06 |
| ATG3_DRAM_FAS_LC3_MMP9_FASLG_SESN3 | 1.56E−06 |
| BNIP3_DRAM_FAS_LC3_BECN1_FASLG_SESN2 | 1.62E−06 |
| BNIP3_DRAM_FAS_LC3_FASLG_SESN2_SIRT1 | 1.62E−06 |
| BNIP3_DRAM_FAS_LC3_MMP9_FASLG_UVRAG | 1.71E−06 |
| BNIP3_DRAM_FAS_LC3_ID2_FASLG_SESN2 | 1.72E−06 |
| ATG3_FAS_LC3_MMP9_TCF3_FASLG_SESN3 | 1.72E−06 |
| BNIP3_DRAM_FAS_LC3_FASLG_SESN3_SIRT1 | 1.72E−06 |
| ATG3_FAS_LC3_MMP9_FASLG_SESN2_UVRAG | 1.75E−06 |
| BNIP3_DRAM_FAS_LC3_FASLG_SESN2_STAT3 | 1.76E−06 |
| BNIP3_DRAM_FAS_LC3_MMP9_FASLG_SIRT1 | 1.76E−06 |
| BNIP3_DRAM_FAS_LC3_MMP9_TCF3_FASLG | 1.80E−06 |
| BNIP3_DRAM_FAS_LC3_FASLG_SESN2_SESN3 | 1.83E−06 |
| BNIP3_DRAM_FAS_LC3_ID2_FASLG_SESN3 | 1.83E−06 |
| ATG3_FAS_LC3_MMP9_FASLG_SESN2_SIRT1 | 1.84E−06 |
| ATG3_FAS_FRAP1_LC3_MMP9_FASLG_SESN3 | 1.85E−06 |
| ATG3_DIABLO_FAS_LC3_MMP9_FASLG_SESN2 | 1.85E−06 |
| BNIP3_DRAM_FAS_LC3_BECN1_FASLG_SESN3 | 1.87E−06 |
| ATG3_FAS_FRAP1_LC3_MMP9_FASLG_SESN2 | 1.88E−06 |
| BNIP3_DRAM_FAS_LC3_FASLG_SESN3_STAT3 | 1.88E−06 |
| ATG3_FAS_LC3_ID2_FASLG_SESN2_SESN3 | 1.90E−06 |
| ATG3_FAS_LC3_MMP9_FASLG_SESN3_SIRT1 | 1.90E−06 |
| ATG5_DRAM_FAS_LC3_MMP9_FASLG_UVRAG | 1.91E−06 |
| ATG3_FAS_LC3_ID2_MMP9_FASLG_SESN2 | 1.92E−06 |
| ATG3_DIABLO_FAS_LC3_MMP9_FASLG_SESN3 | 1.92E−06 |
| BNIP3_DRAM_FAS_LC3_BHLHE41_FASLG_SESN2 | 1.93E−06 |
| ATG3_FAS_LC3_MMP9_TCF3_FASLG_SESN2 | 1.93E−06 |
| ATG3_FAS_LC3_ID2_MMP9_FASLG_SESN3 | 1.93E−06 |
| ATG3_FAS_LC3_FASLG_SESN2_SESN3_SIRT1 | 1.94E−06 |
| BNIP3_DRAM_FAS_LC3_MMP9_BECN1_FASLG | 1.94E−06 |
| ATG3_FAS_LC3_BHLHE41_FASLG_SESN2_SESN3 | 1.94E−06 |
| BNIP3_DRAM_FAS_LC3_FASLG_LAMP2_SESN2 | 1.95E−06 |
| ATG3_FAS_LC3_MMP9_BECN1_FASLG_SESN2 | 1.95E−06 |
| BNIP3_DRAM_FAS_LC3_ID2_MMP9_FASLG | 1.97E−06 |
| BNIP3_FAS_LC3_MMP9_FASLG_SESN2_UVRAG | 1.98E−06 |
| BNIP3_DRAM_FAS_LC3_BHLHE41_FASLG_SESN3 | 1.99E−06 |
| ATG3_FAS_LC3_BECN1_FASLG_SESN2_SESN3 | 2.00E−06 |
| BNIP3_DRAM_FAS_LC3_FASLG_SESN2_UVRAG | 2.00E−06 |
| ATG7_BNIP3_DRAM_FAS_LC3_MMP9_FASLG | 2.00E−06 |
| BNIP3_DRAM_FAS_LC3_MMP9_FASLG_STAT3 | 2.01E−06 |

TABLE 52-continued

| Marker | p-value |
|---|---|
| BNIP3_FAS_LC3_MMP9_FASLG_SESN2_SIRT1 | 2.01E−06 |
| ATG3_FAS_LC3_MMP9_FASLG_LAMP2_SESN2 | 2.03E−06 |
| BNIP3_FAS_LC3_MMP9_FASLG_SESN3_SIRT1 | 2.04E−06 |
| ATG3_FAS_LC3_MMP9_FASLG_LAMP2_SESN3 | 2.05E−06 |
| BNIP3_DRAM_FAS_LC3_FASLG_LAMP2_SESN3 | 2.07E−06 |
| ATG5_DRAM_FAS_LC3_MMP9_FASLG_SESN2 | 2.07E−06 |
| BNIP3_DRAM_FAS_FRAP1_LC3_MMP9_FASLG | 2.07E−06 |
| ATG3_FAS_LC3_FASLG_LAMP2_SESN2_SESN3 | 2.08E−06 |
| BNIP3_FAS_LC3_MMP9_TCF3_FASLG_UVRAG | 2.10E−06 |
| BNIP3_FAS_LC3_MMP9_BECN1_FASLG_SESN2 | 2.10E−06 |
| ATG3_FAS_LC3_MMP9_BECN1_FASLG_SESN3 | 2.12E−06 |
| BNIP3_DRAM_FAS_LC3_MMP9_FASLG_LAMP2 | 2.12E−06 |
| BNIP3_DRAM_FAS_LC3_CDH1_FASLG_SESN2 | 2.14E−06 |
| FAS_LC3_CDH1_ID2_MMP9_TCF3_FASLG | 1.22E−05 |
| Survival | |
| AIFM1_ATG12_DRAM_FRAP1_TKT_CIAP2_TP63 | 6.50E−07 |
| ATG12_BCL2L1_DRAM_FRAP1_TKT_CIAP2_TP63 | 7.10E−07 |
| ATG12_DRAM_FRAP1_LAMP1_TKT_CIAP2_TP63 | 7.20E−07 |
| ATG12_DRAM_FRAP1_TKT_XIAP_CIAP2_TP63 | 7.60E−07 |
| ATG12_CBS_DRAM_FRAP1_TKT_CIAP2_TP63 | 7.80E−07 |
| ATG12_DRAM_FRAP1_TKT_CIAP2_TP63_VEGF | 8.10E−07 |
| ATG12_ATG7_DRAM_FRAP1_TKT_CIAP2_TP63 | 8.20E−07 |
| ATG12_DRAM_FRAP1_PTEN_TKT_CIAP2_TP63 | 8.30E−07 |
| ATG12_DRAM_FRAP1_PRKAA1_TKT_CIAP2_TP63 | 8.60E−07 |
| ATG12_DRAM_FRAP1_TKT_CIAP2_RAGE_TP63 | 8.60E−07 |
| ATG12_DRAM_FRAP1_TKT_MMP9_CIAP2_TP63 | 9.30E−07 |
| ATG12_BNIP3_DRAM_FRAP1_TKT_CIAP2_TP63 | 9.40E−07 |
| AIFM1_BCL2L1_DRAM_TKT_CIAP2_SESN2_TP63 | 9.50E−07 |
| AIFM1_ATG12_DRAM_FRAP1_PTEN_CIAP2_TP63 | 1.00E−06 |
| AIFM1_DRAM_NNMT_TKT_CIAP2_SESN2_TP63 | 1.00E−06 |
| AIFM1_DRAM_PTEN_ID2_CIAP2_SESN2_TP63 | 1.00E−06 |
| AIFM1_DRAM_TKT_MMP9_CIAP2_SESN2_TP63 | 1.00E−06 |
| ATG12_DRAM_FRAP1_NNMT_TKT_CIAP2_TP63 | 1.00E−06 |
| AKT1_ATG12_DRAM_FRAP1_TKT_CIAP2_TP63 | 1.10E−06 |
| ATG12_DRAM_E2F1_FRAP1_TKT_CIAP2_TP63 | 1.10E−06 |
| ATG12_DRAM_FRAP1_TKT_BHLHE41_CIAP2_TP63 | 1.10E−06 |
| AIFM1_ATG12_DRAM_FRAP1_MMP9_CIAP2_TP63 | 1.20E−06 |
| AIFM1_ATG3_DRAM_ID2_CIAP2_SESN2_TP63 | 1.20E−06 |
| AIFM1_ATG3_DRAM_MMP9_CIAP2_SESN2_TP63 | 1.20E−06 |
| ATG12_DRAM_FRAP1_TKT_CIAP2_HMGB1_TP63 | 1.20E−06 |
| AIFM1_ATG12_DRAM_TKT_CIAP2_SESN2_TP63 | 1.30E−06 |
| AIFM1_BNIP3_DRAM_TKT_CIAP2_SESN2_TP63 | 1.30E−06 |
| AIFM1_DRAM_ID2_MMP9_CIAP2_SESN2_TP63 | 1.30E−06 |
| AIFM1_DRAM_LAMP1_TKT_CIAP2_SESN2_TP63 | 1.30E−06 |
| DRAM_FRAP1_TKT_CASP3_CIAP2_HMGB2_TP63 | 1.32E−06 |
| AIFM1_AKT1_ATG12_DRAM_FRAP1_CIAP2_TP63 | 1.40E−06 |
| AIFM1_DRAM_PRKAA1_TKT_CIAP2_SESN2_TP63 | 1.40E−06 |
| AIFM1_DRAM_TKT_CIAP2_RAGE_SESN2_TP63 | 1.40E−06 |
| AIFM1_DRAM_TKT_ID2_CIAP2_SESN2_TP63 | 1.40E−06 |
| ATG12_DRAM_FRAP1_TKT_CIAP2_SATB1_TP63 | 1.40E−06 |
| AIFM1_AKT1_DRAM_TKT_CIAP2_SESN2_TP63 | 1.50E−06 |
| AIFM1_ATG12_DRAM_FRAP1_CIAP2_TP63_VEGF | 1.50E−06 |
| AIFM1_ATG3_DRAM_NNMT_CIAP2_SESN2_TP63 | 1.50E−06 |
| AIFM1_BAX_DRAM_ID2_CIAP2_SESN2_TP63 | 1.50E−06 |
| AIFM1_DRAM_NNMT_ID2_CIAP2_SESN2_TP63 | 1.50E−06 |
| DRAM_FRAP1_NNMT_TKT_XIAP_CIAP2_TP63 | 1.56E−06 |
| BCL2L1_DRAM_FRAP1_TKT_XIAP_CIAP2_TP63 | 1.60E−06 |
| AIFM1_ATG12_ATG3_DRAM_FRAP1_CIAP2_TP63 | 1.60E−06 |
| AIFM1_ATG7_DRAM_ID2_CIAP2_SESN2_TP63 | 1.60E−06 |
| AIFM1_DRAM_TKT_CIAP2_SESN2_TP63_VEGF | 1.60E−06 |
| ATG12_ATG3_DRAM_FRAP1_TKT_CIAP2_TP63 | 1.60E−06 |
| AIFM1_AKT1_DRAM_ID2_CIAP2_SESN2_TP63 | 1.70E−06 |
| AIFM1_ATG12_ATG7_DRAM_FRAP1_CIAP2_TP63 | 1.70E−06 |
| AIFM1_ATG3_BCL2L1_DRAM_CIAP2_SESN2_TP63 | 1.70E−06 |
| AIFM1_ATG7_DRAM_TKT_CIAP2_SESN2_TP63 | 1.70E−06 |
| AIFM1_BCL2L1_DRAM_ID2_CIAP2_SESN2_TP63 | 1.70E−06 |
| AIFM1_CBS_DRAM_TKT_CIAP2_SESN2_TP63 | 1.70E−06 |
| AIFM1_DRAM_PTEN_TKT_CIAP2_SESN2_TP63 | 1.70E−06 |
| AIFM1_DRAM_TKT_BHLHE41_CIAP2_SESN2_TP63 | 1.70E−06 |
| ATG12_DIABLO_DRAM_FRAP1_CDH1_CIAP2_TP63 | 1.70E−06 |
| BCL2L1_DRAM_TKT_ID2_CIAP2_SESN2_TP63 | 1.72E−06 |
| BAX_DRAM_FRAP1_CDH1_ID2_CIAP2_TP63 | 1.74E−06 |
| CBS_DIABLO_FRAP1_CDH1_ID2_MMP9_TCF3 | 1.03E−05 |
| Disease-free survival | |
| ATG3_FAS_LC3_MMP9_FASLG_SESN2_SESN3 | 1.44E−06 |
| BNIP3_DRAM_FAS_LC3_ID2_FASLG_SESN2 | 1.54E−06 |

TABLE 52-continued

| Marker | p-value |
|---|---|
| BNIP3_FAS_LC3_ID2_FASLG_SESN2_UVRAG | 1.56E−06 |
| ATG3_DRAM_FAS_LC3_MMP9_FASLG_SESN2 | 1.60E−06 |
| BNIP3_DRAM_FAS_LC3_FASLG_SESN2_UVRAG | 1.61E−06 |
| BNIP3_DRAM_FAS_LC3_MMP9_FASLG_SESN2 | 1.62E−06 |
| ATG3_FAS_LC3_MMP9_FASLG_SESN2_UVRAG | 1.63E−06 |
| BNIP3_FAS_LC3_MMP9_FASLG_SESN2_UVRAG | 1.65E−06 |
| FAS_LC3_ID2_MMP9_FASLG_RPS19BP1_UVRAG | 1.67E−06 |
| BNIP3_DRAM_FAS_LC3_ID2_FASLG_UVRAG | 1.70E−06 |
| DRAM_FAS_LC3_ID2_FASLG_SESN2_UVRAG | 1.70E−06 |
| DRAM_FAS_LC3_ID2_MMP9_FASLG_RPS19BP1 | 1.72E−06 |
| ATG3_FAS_LC3_ID2_MMP9_FASLG_SESN2 | 1.73E−06 |
| BNIP3_DRAM_FAS_LC3_FASLG_SESN2_SIRT1 | 1.74E−06 |
| BNIP3_DRAM_FAS_LC3_FASLG_SESN2_SESN3 | 1.74E−06 |
| BNIP3_DRAM_FAS_LC3_MMP9_FASLG_UVRAG | 1.75E−06 |
| BNIP3_DRAM_FAS_LC3_FASLG_SESN2_STAT3 | 1.77E−06 |
| BNIP3_FAS_LC3_MMP9_TCF3_FASLG_UVRAG | 1.77E−06 |
| ATG3_FAS_LC3_MMP9_TCF3_FASLG_SESN2 | 1.79E−06 |
| DIABLO_DRAM_FAS_LC3_ID2_FASLG_STAT3 | 1.81E−06 |
| ATG3_DIABLO_FAS_LC3_MMP9_FASLG_SESN2 | 1.81E−06 |
| DIABLO_DRAM_FAS_LC3_ID2_FASLG_SESN3 | 1.82E−06 |
| BNIP3_FAS_LC3_ID2_MMP9_FASLG_RPS19BP1 | 1.83E−06 |
| ATG5_DRAM_FAS_LC3_ID2_FASLG_UVRAG | 1.84E−06 |
| BNIP3_DRAM_FAS_LC3_BECN1_FASLG_SESN2 | 1.84E−06 |
| BNIP3_DRAM_FAS_LC3_MMP9_FASLG_RPS19BP1 | 1.84E−06 |
| ATG5_FAS_LC3_ID2_FASLG_SESN2_UVRAG | 1.86E−06 |
| ATG3_FAS_FRAP1_LC3_MMP9_FASLG_SESN2 | 1.87E−06 |
| DIABLO_DRAM_FAS_LC3_ID2_FASLG_UVRAG | 1.87E−06 |
| DIABLO_DRAM_FAS_LC3_CDH1_ID2_FASLG | 1.88E−06 |
| DRAM_FAS_LC3_ID2_FASLG_SIRT1_UVRAG | 1.88E−06 |
| DIABLO_DRAM_FAS_LC3_ID2_FASLG_SIRT1 | 1.89E−06 |
| BNIP3_DRAM_FAS_LC3_CDH1_FASLG_SESN2 | 1.89E−06 |
| FAS_LC3_ID2_MMP9_FASLG_RPS19BP1_SESN3 | 1.89E−06 |
| BNIP3_FAS_LC3_ID2_MMP9_FASLG_UVRAG | 1.89E−06 |
| DIABLO_DRAM_FAS_LC3_ID2_BECN1_FASLG | 1.90E−06 |
| DRAM_FAS_LC3_ID2_FASLG_SESN3_UVRAG | 1.90E−06 |
| ATG3_FAS_LC3_MMP9_FASLG_SESN2_SIRT1 | 1.90E−06 |
| BNIP3_DRAM_FAS_LC3_FASLG_LAMP2_SESN2 | 1.91E−06 |
| BNIP3_DRAM_FAS_LC3_ID2_FASLG_SESN3 | 1.92E−06 |
| BNIP3_FAS_LC3_ID2_FASLG_SESN2_SESN3 | 1.93E−06 |
| DIABLO_DRAM_FAS_LC3_ID2_FASLG_LAMP2 | 1.93E−06 |
| BNIP3_FAS_LC3_ID2_MMP9_FASLG_SESN2 | 1.94E−06 |
| ATG5_DRAM_FAS_LC3_FASLG_SESN2_UVRAG | 1.95E−06 |
| DRAM_FAS_LC3_MMP9_FASLG_RPS19BP1_UVRAG | 1.95E−06 |
| DRAM_FAS_LAMP1_LC3_ID2_FASLG_UVRAG | 1.97E−06 |
| DIABLO_DRAM_FAS_LC3_ID2_FASLG_SESN2 | 1.97E−06 |
| ATG3_FAS_LC3_CDH1_MMP9_FASLG_SESN2 | 1.97E−06 |
| AKT1_BNIP3_DRAM_FAS_LC3_FASLG_SESN2 | 1.97E−06 |
| DRAM_FAS_LC3_MMP9_FASLG_RPS19BP1_SESN3 | 1.97E−06 |
| ATG3_DRAM_FAS_LC3_FASLG_SESN2_SESN3 | 1.98E−06 |
| ATG3_FAS_LC3_MMP9_BECN1_FASLG_SESN2 | 1.99E−06 |
| BNIP3_FAS_LC3_MMP9_FASLG_RPS19BP1_SESN3 | 1.99E−06 |
| DRAM_FAS_LC3_ID2_FASLG_STAT3_UVRAG | 1.99E−06 |
| BNIP3_DRAM_FAS_LC3_CDH1_FASLG_UVRAG | 1.99E−06 |
| ATG3_FAS_LC3_MMP9_FASLG_LAMP2_SESN2 | 1.99E−06 |
| DRAM_FAS_LC3_ID2_BECN1_FASLG_UVRAG | 1.99E−06 |
| E2F1_LC3_CDH1_ID2_MMP9_TCF3_FASLG | 4.14E−06 |

TABLE 53

| Marker | p-value |
|---|---|
| Recurrence | |
| ATG3_DRAM_FAS_LC3_MMP9_FASLG_SESN2_SESN3 | 9.17E−07 |
| ATG3_FAS_LC3_ID2_MMP9_FASLG_SESN2_SESN3 | 1.07E−06 |
| ATG3_FAS_LC3_MMP9_FASLG_SESN2_SESN3_SIRT1 | 1.07E−06 |
| ATG3_FAS_LC3_MMP9_TCF3_FASLG_SESN2_SESN3 | 1.14E−06 |
| ATG3_FAS_LC3_MMP9_BECN1_FASLG_SESN2_SESN3 | 1.16E−06 |
| ATG3_FAS_LC3_MMP9_BHLHE41_FASLG_SESN2_SESN3 | 1.16E−06 |
| BNIP3_DRAM_FAS_LC3_MMP9_FASLG_SESN2_SIRT1 | 1.16E−06 |
| ATG3_FAS_LC3_MMP9_FASLG_LAMP2_SESN2_SESN3 | 1.18E−06 |
| BNIP3_DRAM_FAS_LC3_MMP9_BECN1_FASLG_SESN2 | 1.22E−06 |
| ATG3_DRAM_FAS_LC3_MMP9_TCF3_FASLG_SESN2 | 1.24E−06 |
| BNIP3_DRAM_FAS_LC3_ID2_MMP9_FASLG_SESN2 | 1.25E−06 |
| ATG3_ATG5_FAS_LC3_MMP9_FASLG_SESN2_SESN3 | 1.26E−06 |

TABLE 53-continued

| Marker | p-value |
| --- | --- |
| ATG3_DRAM_FAS_LC3_MMP9_TCF3_FASLG_SESN3 | 1.26E−06 |
| ATG3_BNIP3_FAS_LC3_MMP9_FASLG_SESN2_SESN3 | 1.29E−06 |
| ATG3_DRAM_FAS_LC3_ID2_MMP9_FASLG_SESN2 | 1.31E−06 |
| ATG3_FAS_LC3_CDH1_MMP9_FASLG_SESN2_SESN3 | 1.31E−06 |
| BNIP3_DRAM_FAS_LC3_MMP9_TCF3_FASLG_UVRAG | 1.32E−06 |
| BNIP3_DRAM_FAS_LC3_MMP9_FASLG_SESN2_SESN3 | 1.33E−06 |
| BNIP3_DRAM_FAS_LC3_MMP9_FASLG_SESN3_SIRT1 | 1.37E−06 |
| ATG5_BNIP3_DRAM_FAS_LC3_MMP9_FASLG_SESN2 | 1.39E−06 |
| ATG3_DRAM_FAS_LC3_MMP9_FASLG_SESN2_SIRT1 | 1.39E−06 |
| BNIP3_DRAM_FAS_LC3_MMP9_FASLG_SESN2_UVRAG | 1.40E−06 |
| ATG3_DRAM_FAS_LC3_MMP9_FASLG_LAMP2_SESN2 | 1.41E−06 |
| BNIP3_DRAM_FAS_LC3_MMP9_FASLG_LAMP2_SESN2 | 1.44E−06 |
| BNIP3_DRAM_FAS_LC3_MMP9_FASLG_SESN2_STAT3 | 1.45E−06 |
| BNIP3_DRAM_FAS_LC3_MMP9_TCF3_FASLG_SESN3 | 1.45E−06 |
| ATG3_DRAM_FAS_LC3_MMP9_BHLHE41_FASLG_SESN2 | 1.45E−06 |
| ATG3_FAS_FRAP1_LC3_MMP9_FASLG_SESN2_SESN3 | 1.45E−06 |
| BNIP3_DRAM_FAS_LC3_ID2_MMP9_FASLG_SESN3 | 1.45E−06 |
| ATG3_FAS_LC3_MMP9_FASLG_SESN2_SESN3_UVRAG | 1.45E−06 |
| ATG3_DRAM_FAS_LC3_ID2_FASLG_SESN2_SESN3 | 1.46E−06 |
| ATG3_DRAM_FAS_LC3_BHLHE41_FASLG_SESN2_SESN3 | 1.46E−06 |
| AKT1_ATG3_FAS_LC3_MMP9_FASLG_SESN2_SESN3 | 1.46E−06 |
| BNIP3_DRAM_FAS_LC3_MMP9_TCF3_FASLG_SESN2 | 1.46E−06 |
| BNIP3_DRAM_FAS_LC3_ID2_FASLG_SESN2_SIRT1 | 1.49E−06 |
| BNIP3_DRAM_FAS_LC3_ID2_BECN1_FASLG_SESN2 | 1.49E−06 |
| ATG3_DRAM_FAS_LC3_MMP9_BECN1_FASLG_SESN2 | 1.49E−06 |
| ATG3_DRAM_FAS_LC3_ID2_MMP9_FASLG_SESN3 | 1.50E−06 |
| BNIP3_DRAM_FAS_LC3_MMP9_TCF3_FASLG_SIRT1 | 1.50E−06 |
| ATG3_DIABLO_FAS_LC3_MMP9_FASLG_SESN2_SESN3 | 1.51E−06 |
| ATG3_DRAM_FAS_FRAP1_LC3_MMP9_FASLG_SESN2 | 1.51E−06 |
| BNIP3_DRAM_FAS_LC3_MMP9_BHLHE41_FASLG_SESN2 | 1.52E−06 |
| ATG3_FAS_LC3_MMP9_FASLG_SESN2_SESN3_STAT3 | 1.53E−06 |
| ATG3_DRAM_FAS_LC3_MMP9_FASLG_SESN2_UVRAG | 1.54E−06 |
| BNIP3_DRAM_FAS_LC3_MMP9_TCF3_FASLG_STAT3 | 1.55E−06 |
| BNIP3_DRAM_FAS_LC3_MMP9_BECN1_FASLG_SESN3 | 1.55E−06 |
| BNIP3_DRAM_FAS_LC3_CDH1_MMP9_FASLG_SESN2 | 1.55E−06 |
| ATG3_FAS_LC3_MMP9_TCF3_FASLG_SESN2_UVRAG | 1.56E−06 |
| ATG3_DRAM_FAS_LC3_CDH1_MMP9_FASLG_SESN2 | 1.56E−06 |
| BNIP3_DRAM_FAS_LC3_MMP9_TCF3_BECN1_FASLG | 1.57E−06 |
| BNIP3_CSE1L_DRAM_FAS_LC3_MMP9_FASLG_SESN3 | 1.57E−06 |
| ATG3_DRAM_FAS_LC3_ULK1_MMP9_FASLG_SESN3 | 1.59E−06 |
| BNIP3_DRAM_FAS_LC3_ID2_FASLG_SESN2_STAT3 | 1.59E−06 |
| ATG5_DRAM_FAS_LC3_MMP9_FASLG_SESN2_SIRT1 | 1.59E−06 |
| ATG3_FAS_LC3_ULK1_MMP9_FASLG_SESN2_SESN3 | 1.60E−06 |
| BNIP3_DRAM_FAS_LC3_ID2_MMP9_FASLG_UVRAG | 1.60E−06 |
| ATG3_FAS_LC3_MMP9_TCF3_FASLG_SESN3_SIRT1 | 1.60E−06 |
| ATG3_FAS_LC3_CDH1_ID2_MMP9_TCF3_FASLG | 3.78E−06 |
| Survival | |
| AIFM1_ATG12_DRAM_FRAP1_IKT_MMP9_CIAP2_TP63 | 3.20E−07 |
| AIFM1_ATG12_DRAM_FRAP1_NNMT_TKT_CIAP2_TP63 | 4.70E−07 |
| AIFM1_ATG12_DRAM_FRAP1_PTEN_TKT_CIAP2_TP63 | 5.00E−07 |
| AIFM1_ATG12_DRAM_FRAP1_IKT_CIAP2_TP63_VEGF | 5.00E−07 |
| ATG12_DRAM_FRAP1_PTEN_TKT_XIAP_CIAP2_TP63 | 5.20E−07 |
| AIFM1_ATG12_BCL2L1_DRAM_FRAP1_TKT_CIAP2_TP63 | 5.40E−07 |
| AIFM1_ATG12_DRAM_FRAP1_TKT_CIAP2_SATB1_TP63 | 5.70E−07 |
| AIFM1_AKT1_ATG12_DRAM_FRAP1_TKT_CIAP2_TP63 | 5.80E−07 |
| AIFM1_ATG12_DRAM_FRAP1_LAMP1_TKT_CIAP2_TP63 | 5.80E−07 |
| ATG12_BCL2L1_DRAM_FRAP1_PTEN_TKT_CIAP2_TP63 | 5.80E−07 |
| AIFM1_ATG12_CBS_DRAM_FRAP1_TKT_CIAP2_TP63 | 6.00E−07 |
| AIFM1_ATG12_DRAM_FRAP1_PTEN_MMP9_CIAP2_TP63 | 6.10E−07 |
| ATG12_DRAM_E2F1_FRAP1_TKT_MMP9_CIAP2_TP63 | 6.10E−07 |
| ATG12_BCL2L1_CBS_DRAM_FRAP1_TKT_CIAP2_TP63 | 6.20E−07 |
| ATG12_BCL2L1_DRAM_FRAP1_TKT_CIAP2_TP63_VEGF | 6.20E−07 |
| ATG12_DIABLO_DRAM_FRAP1_TKT_CDH1_CIAP2_TP63 | 6.20E−07 |
| AIFM1_ATG3_DRAM_ID2_MMP9_CIAP2_SESN2_TP63 | 6.30E−07 |
| ATG12_CBS_DRAM_FRAP1_LAMP1_TKT_CIAP2_TP63 | 6.30E−07 |
| ATG12_DRAM_FRAP1_LAMP1_TKT_XIAP_CIAP2_TP63 | 6.30E−07 |
| ATG12_BCL2L1_DRAM_FRAP1_LAMP1_TKT_CIAP2_TP63 | 6.40E−07 |
| ATG12_DRAM_FRAP1_TKT_XIAP_CIAP2_HMGB1_TP63 | 6.40E−07 |
| AIFM1_ATG12_DRAM_FRAP1_PRKAA1_TKT_CIAP2_TP63 | 6.50E−07 |
| AIFM1_DRAM_PTEN_ID2_MMP9_CIAP2_SESN2_TP63 | 6.50E−07 |
| ATG12_ATG7_BCL2L1_DRAM_FRAP1_TKT_CIAP2_TP63 | 6.50E−07 |
| ATG12_DRAM_FRAP1_TKT_XIAP_CIAP2_TP63_VEGF | 6.50E−07 |
| AIFM1_ATG12_ATG7_DRAM_FRAP1_TKT_CIAP2_TP63 | 6.60E−07 |
| AIFM1_ATG12_DRAM_FRAP1_TKT_CIAP2_RAGE_TP63 | 6.60E−07 |
| ATG12_ATG7_DRAM_FRAP1_LAMP1_TKT_CIAP2_TP63 | 6.70E−07 |
| ATG12_DRAM_FRAP1_LAMP1_TKT_CIAP2_TP63_VEGF | 6.70E−07 |
| ATG12_DRAM_FRAP1_LAMP1_PTEN_TKT_CIAP2_TP63 | 6.90E−07 |

TABLE 53-continued

| Marker | p-value |
| --- | --- |
| ATG12_BCL2L1_DRAM_FRAP1_TKT_CIAP2_RAGE_TP63 | 7.00E−07 |
| AIFM1_ATG12_BNIP3_DRAM_FRAP1_TKT_CIAP2_TP63 | 7.10E−07 |
| AIFM1_ATG12_DIABLO_DRAM_FRAP1_CDH1_CIAP2_TP63 | 7.10E−07 |
| ATG12_BCL2L1_DRAM_FRAP1_PRKAA1_TKT_CIAP2_TP63 | 7.10E−07 |
| ATG12_CBS_DRAM_FRAP1_TKT_XIAP_CIAP2_TP63 | 7.10E−07 |
| ATG12_DRAM_FRAP1_LAMP1_PRKAA1_TKT_CIAP2_TP63 | 7.20E−07 |
| ATG12_DRAM_FRAP1_LAMP1_TKT_CIAP2_RAGE_TP63 | 7.20E−07 |
| ATG12_ATG7_DRAM_FRAP1_TKT_XIAP_CIAP2_TP63 | 7.30E−07 |
| ATG12_BCL2L1_BNIP3_DRAM_FRAP1_TKT_CIAP2_TP63 | 7.30E−07 |
| ATG12_CBS_DRAM_FRAP1_TKT_CIAP2_TP63_VEGF | 7.30E−07 |
| AIFM1_ATG3_DRAM_NNMT_ID2_CIAP2_SESN2_TP63 | 7.40E−07 |
| AIFM1_DRAM_NNMT_PTEN_ID2_CIAP2_SESN2_TP63 | 7.40E−07 |
| ATG12_CBS_DRAM_FRAP1_PTEN_TKT_CIAP2_TP63 | 7.40E−07 |
| ATG12_DRAM_FRAP1_PTEN_TKT_MMP9_CIAP2_TP63 | 7.40E−07 |
| AIFM1_ATG12_ATG3_DRAM_FRAP1_MMP9_CIAP2_TP63 | 7.50E−07 |
| AIFM1_ATG12_CASP8_DRAM_TKT_CIAP2_SESN2_TP63 | 7.50E−07 |
| ATG12_ATG7_CBS_DRAM_FRAP1_TKT_CIAP2_TP63 | 7.50E−07 |
| ATG12_BCL2L1_DRAM_FRAP1_TKT_XIAP_CIAP2_TP63 | 7.50E−07 |
| AIFM1_ATG12_DRAM_PTEN_TKT_CIAP2_SESN2_TP63 | 7.60E−07 |
| AIFM1_BCL2L1_DRAM_NNMT_TKT_CIAP2_SESN2_TP63 | 7.60E−07 |
| ATG12_DRAM_E2F1_FRAP1_NNMT_TKT_CIAP2_TP63 | 7.60E−07 |
| ATG12_ATG7_DRAM_FRAP1_TKT_CIAP2_TP63_VEGF | 7.70E−07 |
| ATG12_BNIP3_DRAM_FRAP1_LAMP1_TKT_CIAP2_TP63 | 7.70E−07 |
| ATG12_CBS_DRAM_FRAP1_PRKAA1_TKT_CIAP2_TP63 | 7.70E−07 |
| ATG12_DIABLO_DRAM_FRAP1_CDH1_ID2_CIAP2_TP63 | 7.70E−07 |
| ATG12_DRAM_FRAP1_PRKAA1_TKT_XIAP_CIAP2_TP63 | 7.70E−07 |
| ATG12_DRAM_FRAP1_TKT_XIAP_CIAP2_RAGE_TP63 | 7.70E−07 |
| ATG3_DIABLO_FRAP1_CDH1_ID2_MMP9_TCF3_AGER | 3.50E−06 |
| Disease-free survival | |
| ATG3_FAS_LC3_ID2_MMP9_FASLG_SESN2_SESN3 | 1.21E−06 |
| BNIP3_DRAM_FAS_LC3_ID2_FASLG_SESN2_UVRAG | 1.21E−06 |
| ATG3_DRAM_FAS_LC3_MMP9_FASLG_SESN2_SESN3 | 1.22E−06 |
| BNIP3_FAS_LC3_ID2_MMP9_FASLG_SESN2_UVRAG | 1.27E−06 |
| BNIP3_DRAM_FAS_LC3_MMP9_FASLG_SESN2_UVRAG | 1.31E−06 |
| ATG3_FAS_LC3_MMP9_TCF3_FASLG_SESN2_SESN3 | 1.32E−06 |
| BNIP3_DRAM_FAS_LC3_ID2_MMP9_FASLG_SESN2 | 1.32E−06 |
| BNIP3_DRAM_FAS_LC3_MMP9_TCF3_FASLG_UVRAG | 1.33E−06 |
| BNIP3_DRAM_FAS_LC3_ID2_FASLG_SESN2_SESN3 | 1.34E−06 |
| ATG3_FAS_LC3_ID2_MMP9_FASLG_SESN2_UVRAG | 1.35E−06 |
| DRAM_FAS_LC3_ID2_MMP9_FASLG_RPS19BP1_UVRAG | 1.36E−06 |
| ATG5_DRAM_FAS_LC3_ID2_FASLG_SESN2_UVRAG | 1.37E−06 |
| BNIP3_DRAM_FAS_LC3_ID2_FASLG_SESN2_STAT3 | 1.37E−06 |
| ATG3_DRAM_FAS_LC3_ID2_MMP9_FASLG_SESN2 | 1.38E−06 |
| BNIP3_DRAM_FAS_LC3_ID2_FASLG_SESN2_SIRT1 | 1.38E−06 |
| ATG3_FAS_LC3_MMP9_TCF3_FASLG_SESN2_UVRAG | 1.38E−06 |
| ATG3_DRAM_FAS_LC3_MMP9_TCF3_FASLG_SESN2 | 1.39E−06 |
| ATG3_FAS_LC3_MMP9_FASLG_SESN2_SESN3_SIRT1 | 1.39E−06 |
| BNIP3_FAS_LC3_ID2_MMP9_TCF3_FASLG_UVRAG | 1.39E−06 |
| DRAM_FAS_LC3_ID2_MMP9_FASLG_RPS19BP1_SESN3 | 1.40E−06 |
| ATG3_FAS_LC3_CDH1_MMP9_FASLG_SESN2_SESN3 | 1.42E−06 |
| BNIP3_DRAM_FAS_LC3_ID2_MMP9_FASLG_RPS19BP1 | 1.43E−06 |
| ATG3_FAS_LC3_MMP9_FASLG_SESN2_SESN3_UVRAG | 1.43E−06 |
| ATG3_FAS_LC3_MMP9_FASLG_LAMP2_SESN2_SESN3 | 1.44E−06 |
| ATG3_FAS_LC3_MMP9_BECN1_FASLG_SESN2_SESN3 | 1.45E−06 |
| ATG3_DIABLO_FAS_LC3_ID2_MMP9_FASLG_SESN2 | 1.45E−06 |
| BNIP3_DRAM_FAS_LC3_ID2_MMP9_FASLG_UVRAG | 1.47E−06 |
| ATG3_DRAM_FAS_LC3_MMP9_FASLG_SESN2_UVRAG | 1.47E−06 |
| BNIP3_DRAM_FAS_LC3_ID2_BECN1_FASLG_SESN2 | 1.47E−06 |
| BNIP3_DRAM_FAS_LC3_MMP9_FASLG_SESN2_SIRT1 | 1.47E−06 |
| BNIP3_DRAM_FAS_LC3_MMP9_FASLG_SESN2_SESN3 | 1.48E−06 |
| ATG3_FAS_LC3_ID2_MMP9_TCF3_FASLG_SESN2 | 1.48E−06 |
| BNIP3_FAS_LC3_ID2_MMP9_FASLG_RPS19BP1_SESN3 | 1.49E−06 |
| ATG3_BNIP3_FAS_LC3_MMP9_FASLG_SESN2_SESN3 | 1.50E−06 |
| BNIP3_CSE1L_FAS_LC3_MMP9_FASLG_SESN2_UVRAG | 1.51E−06 |
| ATG5_FAS_LC3_ID2_MMP9_FASLG_SESN2_UVRAG | 1.51E−06 |
| BNIP3_FAS_LC3_CDH1_ID2_FASLG_SESN2_UVRAG | 1.51E−06 |
| ATG5_BNIP3_DRAM_FAS_LC3_MMP9_FASLG_SESN2 | 1.52E−06 |
| BNIP3_FAS_LC3_ID2_FASLG_SESN2_SIRT1_UVRAG | 1.52E−06 |
| ATG3_FAS_FRAP1_LC3_MMP9_FASLG_SESN2_SESN3 | 1.52E−06 |
| BNIP3_DRAM_FAS_LC3_CDH1_ID2_FASLG_SESN2 | 1.52E−06 |
| BNIP3_CSE1L_FAS_LC3_MMP9_FASLG_SESN3_UVRAG | 1.53E−06 |
| AKT1_BNIP3_DRAM_FAS_LC3_ID2_FASLG_SESN2 | 1.53E−06 |
| BNIP3_DRAM_FAS_LC3_ID2_FASLG_LAMP2_SESN2 | 1.54E−06 |
| ATG3_ATG5_FAS_LC3_MMP9_FASLG_SESN2_SESN3 | 1.54E−06 |
| BNIP3_DRAM_FAS_LC3_CDH1_FASLG_SESN2_UVRAG | 1.54E−06 |
| BNIP3_FAS_LC3_ID2_FASLG_LAMP2_SESN2_UVRAG | 1.55E−06 |
| BNIP3_FAS_LC3_ID2_BECN1_FASLG_SESN2_UVRAG | 1.55E−06 |

TABLE 53-continued

| Marker | p-value |
|---|---|
| BNIP3_FAS_LC3_MMP9_TCF3_FASLG_SESN2_UVRAG | 1.55E−06 |
| BNIP3_DRAM_FAS_LC3_ID2_TCF3_FASLG_UVRAG | 1.56E−06 |
| AKT1_ATG3_FAS_LC3_MMP9_FASLG_SESN2_SESN3 | 1.56E−06 |
| ATG3_DRAM_FAS_LC3_MMP9_FASLG_SESN2_SIRT1 | 1.56E−06 |
| ATG5_DRAM_FAS_LC3_MMP9_FASLG_SESN2_UVRAG | 1.57E−06 |
| ATG3_DRAM_FAS_LC3_CDH1_MMP9_FASLG_SESN2 | 1.57E−06 |
| BNIP3_DRAM_FAS_LAMP1_LC3_ID2_FASLG_SESN2 | 1.57E−06 |
| ATG3_FAS_FRAP1_LC3_ID2_MMP9_FASLG_SESN2 | 1.57E−06 |
| BNIP3_DRAM_FAS_LC3_MMP9_BECN1_FASLG_SESN2 | 1.58E−06 |
| FAS_LC3_CDH1_ID2_MMP9_TCF3_FASLG_UVRAG | 2.48E−06 |

The above tables present the p-value for each of the genes and their combinations.

As can be confirmed from the above tables, each of the markers or their combination shows p-values low enough to be considered significant in terms of all of recurrence, survival, and disease-free survival. In particular, in the case of the combination of the two or more markers, all the p-values for recurrence, survival, and disease-free survival were low. In particular, it was found that there were cases where the p-value for a single marker was relatively high but the p-value decreased when the marker was used in combination with other marker. As a p-value becomes lower, the statistical significance becomes higher. Thus, the low p-values suggest that the estimation for prognosis of liver cancer by each of the markers or their combination is highly accurate.

This means that the more markers of the present disclosure are combined, the lower p-values, which means higher significance, are shown, which means that the more improved accuracy would be achieved in the estimation for prognosis based on the combinations of the markers.

Thus, it was found that the markers and/or the combinations of markers of Tables 41~48 are effective in predicting prognosis of liver cancer of the C group (recurrence, survival, disease-free survival), and that the prognosis of liver cancer of the C group can be predicted effectively by nucleic acids and antibodies targeted at the markers. Also, it can be found that the prognosis of liver cancer of the C group can be predicted effectively by the method for predicting prognosis of liver cancer of the present disclosure, which is targeted at the markers.

Further, cross-validation was performed for combinations of markers which were considered statistically significant. Patients of each patient group were randomly divided into two groups (positive group: 35 patients; test group: 34 patients). With the reference value which was considered statistically significant in the results of the positive group obtained in the same manner as Example 1 fixed, for the test group, the accuracy of estimation was calculated to be the level of $p<0.05$ or $p<0.001$ with respect to recurrence, survival and disease-free survival.

Among the results of cross-validation of the prediction of the recurrence, survival and disease-free survival of the C group, representative examples showing the excellent accuracy of prognosis in each aspect are as follows:

Recurrence: FAS_TCF3_FASLG_RPS19BP1 (69.0% at the level of $p<0.05$)

Survival: CASP3_CDH2_CIAP2 (77.0% at the level of $p<0.05$)

Disease-free survival: FAS_TCF3_FASLG (75.0% at the level of $p<0.05$)

INDUSTRIAL APPLICABILITY

The present disclosure provides a marker for predicting prognosis of liver cancer, a composition or kit for predicting prognosis of liver cancer, preferably a composition or kit for predicting prognosis of liver cancer for predicting liver cancer according to stage, and a method for predicting prognosis of liver cancer. The marker, composition or kit, and method of the present disclosure make it possible to effectively predict prognosis of liver cancer, preferably, prognosis of liver cancer according to stage.

What is claimed are:

1. A method of predicting prognosis of liver cancer according to stage comprising (A) detecting one or more selected from the expression level or expression pattern of one or at least two genes selected from the group consisting of the genes described in Table 1 in at least one liver cancer tissue sample obtained from a patient of liver cancer, wherein the liver cancer tissue sample is from one or more tumor selected from the group consisting of a portal vein invasion-negative tumor which is 5 cm or less in size, a group of 3 or less portal vein invasion-negative tumors which are 3 cm or less in size, a portal vein invasion-negative tumor which is more than 5 cm in size, a group of portal vein invasion-negative tumors which more than 3 cm in size, a group of more than 3 portal vein invasion-negative tumors, and a group of portal vein invasion-positive tumors; and (B) comparing the results of (A) with measurement results of control groups to predict prognosis of liver cancer, wherein the patients of liver cancer are in one or more groups selected from A1 group {a group of portal vein invasion-negative patients in stage 0 or A of BCLC (Barcelona-Clinic Liver Cancer) staging system, having a tumor which is 5 cm or less in size, or 3 or less tumors which are 3 cm or less in size}, A2 group {a group of portal vein invasion-negative patients, having a tumor which is more than 5 cm in size}, B group {a group of portal vein invasion-negative patients in intermediate stage of BCLC staging system, having plural tumors which are more than 3 cm in size or plural tumors which are more than 3 in number}, or C group {a group of portal vein invasion-positive patients regardless of tumors size and number}.

2. The method of claim 1, wherein the group consisting of genes is a group consisting of the genes described in Table 2.

3. The method of claim 1 for predicting the prognosis of recurrence of the A1 group, wherein the genes are one or more selected from the genes or groups of genes described in Table 4.

4. The method of claim 1 for predicting the prognosis of survival of the A1 group, wherein the genes are one or more selected from the genes or groups of genes described in Table 5.

5. The method of claim 1 for predicting the prognosis of disease-free survival of the A1 group, wherein the genes are one or more selected from the genes or groups of genes described in Table 6.

6. The method of claim 1 for predicting the prognosis of recurrence of the A2 group, wherein the genes are one or more selected from the genes or groups of genes described in Table 7.

7. The method of claim 1 for predicting the prognosis of survival of the A2 group, wherein the genes are one or more selected from the genes or groups of genes described in Table 8.

8. The method of claim 1 for predicting the prognosis of disease-free survival of the A2 group, wherein the genes are one or more selected from genes or groups of genes described in Table 9.

9. The method of claim 1 for predicting the prognosis of recurrence of the B group, wherein the genes are one or more selected from the genes or groups of genes described in Table 10.

10. The method of claim 1 for predicting the prognosis of survival of the B group, wherein the genes are one or more selected from the genes or groups of genes described in Table 11.

11. The method of claim 1 for predicting the prognosis of disease-free survival of the B group, wherein the genes are one or more selected from the genes or groups of genes described in Table 12.

12. The method of claim 1 for predicting the prognosis of recurrence of the C group, wherein the genes are one or more selected from the genes or groups of genes described in Table 13.

13. The method of claim 1 for predicting the prognosis of survival of the C group, wherein the genes are one or more selected from the genes or groups of genes described in Table 14.

14. The method of claim 1 for predicting the prognosis of disease-free survival of the C group, wherein the genes are one or more selected from the genes or groups of genes described in Table 15.

15. The method of 1, wherein the expression level or expression pattern of a protein is detected by one or more selected from RT-PCR, competitive RT-PCR, real-time RT-PCT, RNase protection assay, Northern blot, DNA microarray, western bolt, ELISA (enzyme linked immunosorbent assay), radioimmunoassay, radioimmunodiffusion, Ouchterlony immunodiffusion, rocket immunoelectrophoresis, tissue immunity staining, immunoprecipitation assay, complement fixation assay, FACS or protein chip.

16. The method of claim 1, wherein when the method comprises prognosis of the A1 group recurrence, the genes are ATG7, FRAP1, LC3, NNMT, STAT3, wherein the prognosis is determined to be poor when the expression level or expression pattern of FRAP1 and LC3 are determined to be low, and the expression level or expression pattern of ATG7, NNMT, and STAT3 are determined to be high in a sample obtained from a patient having liver cancer, as compared with measurement results of control groups;

wherein when the method comprises prognosis of the A1 group survival, the genes are AKT1, CDH1, ID2, wherein the prognosis is determined to be poor when the expression level or expression pattern of AKT1, CDH1 and ID2 in a sample obtained from a patient having liver cancer are determined to be low as compared with measurement results of control groups;

wherein when the method comprises prognosis of the A1 group disease-free survival, the genes are FRAP1, LC3, TKT, HMGB1, STAT3, TWIST1, wherein the prognosis is determined to be poor when the expression level or expression pattern of FRAP1, LC3 and TWIST1 are determined to be low, and the expression level or expression pattern of HMGB1, STAT3 and TKT are determined to be high in a sample obtained from a patient having liver cancer, as compared with measurement results of control groups;

wherein when the method comprises prognosis of the A2 group recurrence, the genes are TKT, SESN2, VEGF, wherein the prognosis is determined to be poor when the expression level or expression pattern of TKT, SESN2, VEGF in a sample obtained from a patient having liver cancer are determined to be high as compared with measurement results of control groups;

wherein when the method comprises prognosis of the A2 group survival, the genes are DIABLO, FAS, LAMP1, BHLHE41, SESN2, wherein the prognosis is determined to be poor when the expression level or expression pattern of FAS and LAMP1 are determined to be low, and the expression level or expression pattern of DIABLO, BHLHE41 and SESN2 are determined to be high in a sample obtained from a patient having liver cancer, as compared with measurement results of control groups;

wherein when the method comprises prognosis of the A2 group disease-free survival, the genes are TKT, SESN2, VEGF, wherein the prognosis is determined to be poor when the expression level or expression pattern of TKT, SESN2, VEGF in a sample obtained from a patient having liver cancer are determined to be high as compared with measurement results of control groups;

wherein when the method comprises prognosis of the B group recurrence, the genes are ATG3, FASLG, ID2, RPS19BP1, SESN3, TCF3, wherein the prognosis is determined to be poor when the expression level or expression pattern of FASLG, ID2 and SESN3 are determined to be low, and the expression level or expression pattern of ATG3, RPS19BP1, and TCF3 are determined to be high in a sample obtained from a patient having liver cancer, as compared with measurement results of control groups;

wherein when the method comprises prognosis of the B group survival, the genes are DIABLO, BECN1, SIRT1, wherein the prognosis is determined to be poor when the expression level or expression pattern of DIABLO, BECN1 and SIRT1 in a sample obtained from a patient having liver cancer are determined to be low as compared with measurement results of control groups;

wherein when the method comprises prognosis of the B group disease-free survival, the genes are ATG12, FASLG, ID2, STAT3, RPS19BP1, TCF3, wherein the prognosis is determined to be poor when the expression level or expression pattern of ATG12, FASLG, ID2, and STAT3 are determined to be low, and the expression level or expression pattern of RPS19BP1 and TCF3 are determined to be high in a sample obtained from a patient having liver cancer, as compared with measurement results of control groups;

wherein when the method comprises prognosis of the C group recurrence, the genes are FAS, TCF3, FASLG, RPS19BP1, wherein the prognosis is determined to be poor when the expression level or expression pattern of FAS and FASLG are determined to be low, and the expression level or expression pattern of RPS19BP1 and TCF3 are determined to be high in a sample obtained from a patient having liver cancer, as compared with measurement results of control groups;

wherein when the method comprises prognosis of the C group survival, the genes are CASP3, CDH2, CIAP2, wherein the prognosis is determined to be poor when the expression level or expression pattern of CASP3, CDH2, and CIAP2 in a sample obtained from a patient having liver cancer are determined to be low as compared with measurement results of control groups;

wherein when the method comprises prognosis of the C group disease-free survival, the genes are FAS, TCF3, FASLG, wherein the prognosis is determined to be poor when the expression level or expression pattern of FAS and FASLG are determined to be low, and the expression level or expression pattern of TCF3 is determined to be high in a sample obtained from a patient having liver cancer, as compared with measurement results of control groups.

17. The method of claim 16, further comprising providing a treatment to the subject on the basis of a determination of poor prognosis.

* * * * *